(12) United States Patent
Yates et al.

(10) Patent No.: US 10,464,922 B2
(45) Date of Patent: Nov. 5, 2019

(54) METALLOENZYME INHIBITOR COMPOUNDS

(71) Applicant: NQP 1598 LTD., Grand Cayman (KY)

(72) Inventors: Christopher M. Yates, Raleigh, NC (US); Sammy R. Shaver, Chapel Hill, NC (US); William J. Hoekstra, Durham, NC (US)

(73) Assignee: NQP 1598, Ltd., Durham, NC (US)

( * ) Notice: Subject to any disclaimer, the term of this patent is extended or adjusted under 35 U.S.C. 154(b) by 0 days.

(21) Appl. No.: 16/066,763

(22) PCT Filed: Dec. 29, 2016

(86) PCT No.: PCT/US2016/069217
§ 371 (c)(1),
(2) Date: Jun. 28, 2018

(87) PCT Pub. No.: WO2017/117393
PCT Pub. Date: Jul. 6, 2017

(65) Prior Publication Data
US 2019/0016700 A1    Jan. 17, 2019

Related U.S. Application Data

(60) Provisional application No. 62/273,167, filed on Dec. 30, 2015.

(51) Int. Cl.
*C07D 401/06* (2006.01)
*C07D 401/14* (2006.01)
*C07D 409/14* (2006.01)
*C07D 417/14* (2006.01)
*C07F 9/6558* (2006.01)
*A61P 35/00* (2006.01)

(52) U.S. Cl.
CPC ............ *C07D 401/06* (2013.01); *A61P 35/00* (2018.01); *C07D 401/14* (2013.01); *C07D 409/14* (2013.01); *C07D 417/14* (2013.01); *C07F 9/65583* (2013.01)

(58) Field of Classification Search
CPC .................................................. C07D 401/06
USPC ............................................................ 514/85
See application file for complete search history.

(56) References Cited

FOREIGN PATENT DOCUMENTS

| WO | 2002/080678 A1 | 10/2002 |
|---|---|---|
| WO | 2011/133875 A2 | 10/2011 |
| WO | 2013/109998 A1 | 7/2013 |
| WO | 2013/110002 A1 | 7/2013 |
| WO | 2014/201161 A1 | 12/2014 |

OTHER PUBLICATIONS

Extended European Search Report dated May 8, 2019 for EP Application No. 16882663.4 filed Jun. 13, 2018.

*Primary Examiner* — Kahsay Habte
(74) *Attorney, Agent, or Firm* — Brinks Gilson & Lione

(57) ABSTRACT

The instant invention describes compounds having metalloenzyme modulating activity, and methods of treating diseases, disorders or symptoms thereof mediated by such metalloenzymes.

32 Claims, No Drawings

METALLOENZYME INHIBITOR COMPOUNDS

CROSS-REFERENCE TO RELATED APPLICATIONS

This application is the national Phase under 35 U.S.C. § 371 of PCT International Application No. PCT/US2016/069217, filed Dec. 29, 2016, which claims priority to U.S. Provisional Application No. 62/273,167, filed Dec. 30, 2015, each of which is incorporated herein by reference in its entirety.

BACKGROUND

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes.

One example of such clinical toxicity is the unintended inhibition of human drug metabolizing enzymes such as CYP2C9, CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof.

BRIEF SUMMARY OF THE INVENTION

The invention is directed towards compounds (e.g., any of those delineated herein), methods of modulating activity of metalloenzymes, and methods of treating diseases, disorders or symptoms thereof. The methods can comprise the compounds herein.

It is understood that the embodiments of the invention discussed below with respect to the preferred variable selections can be taken alone or in combination with one or more embodiments, or preferred variable selections, of the invention, as if each combination were explicitly listed herein.

A compound of formula (I), or salt, solvate, hydrate or prodrug thereof:

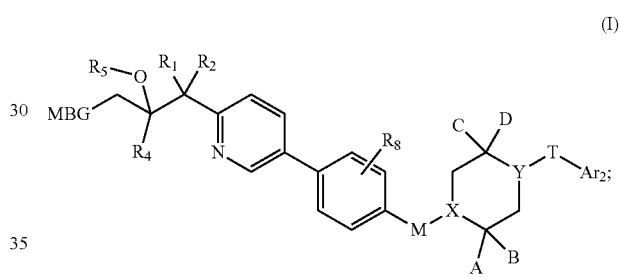

wherein MBG is optionally substituted tetrazolyl, optionally substituted triazolyl, optionally substituted oxazolyl, optionally substituted pyrimidinyl, optionally substituted thiazolyl, or optionally substituted pyrazolyl;

$R_1$ is halo or alkyl;

$R_2$ is halo or alkyl;

or $R_1$, $R_2$, and the carbon atom to which they are attached form an optionally substituted cycloalkyl;

$R_4$ is independently aryl, cycloalkyl, or aralkyl, each substituted with 0, 1, 2 or 3 independent $R_6$;

$R_5$ is H, alkyl, phosphato, phosphito, alkoxyphosphato, or —C(O)alkyl optionally substituted with 1 or 2 $NH_2$;

each $R_6$ is independently optionally substituted alkyl, cyano, haloalkyl, alkoxy, halo, or haloalkoxy;

$R_8$ is hydrogen or halo;

M is —$(CH_2)_o$— or —(C=O)—;

o is 0, 1, 2, or 3;

T is —$(CH_2)_s$— or —(C=O)—;

s is 0, 1, 2, or 3;

each X and Y is independently C or N;

A and B are each hydrogen; or A, B, and the carbon to which they are attached form a carbonyl;

C and D are each hydrogen; or C, D, and the carbon to which they are attached form a carbonyl;

$Ar_2$ is aryl or heteroaryl, each independently substituted with 0, 1, 2, or 3 independent cyano, halo, haloalkyl, $NH_2$, alkoxy, haloalkoxy,

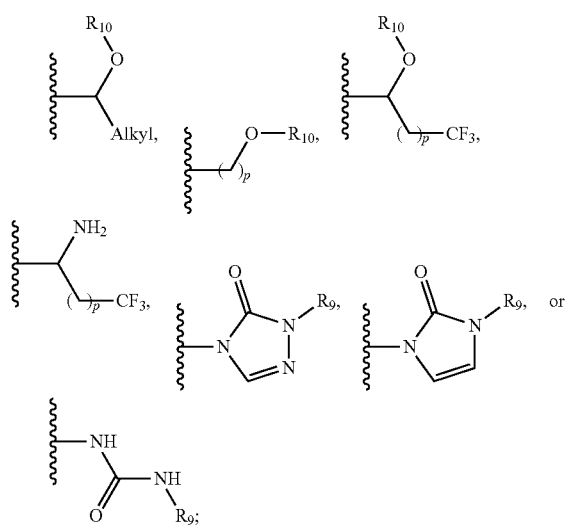

each p is independently 0, 1, 2, or 3;
each $R_9$ is optionally substituted alkyl (e.g., alkyl optionally substituted with 1, 2, or 3 independent OH, halo, $NH_2$, alkoxy, CN, aryl, heteroaryl, aryloxy, or heteroaryloxy) or hydrogen; and
each $R_{10}$ is independently H, alkyl, phosphato, phosphito, alkoxyphosphato, or —C(O)alkyl optionally substituted with 1 or 2 $NH_2$.

A compound of formula (I), or salt, solvate, hydrate or prodrug thereof:

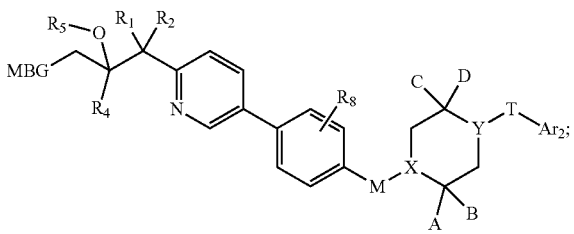

(I)

wherein MBG is optionally substituted tetrazolyl, optionally substituted triazolyl, optionally substituted oxazolyl, optionally substituted pyrimidinyl, optionally substituted thiazolyl, or optionally substituted pyrazolyl;
$R_1$ is halo or alkyl;
$R_2$ is halo or alkyl;
or $R_1$, $R_2$, and the carbon atom to which they are attached form an optionally substituted cycloalkyl;
$R_4$ is independently aryl, cycloalkyl, or aralkyl, each substituted with 0, 1, 2 or 3 independent $R_6$;
$R_5$ is H, alkyl, phosphato, phosphito, alkoxyphosphato, or —C(O)alkyl optionally substituted with 1 or 2 $NH_2$;
each $R_6$ is independently optionally substituted alkyl, cyano, haloalkyl, alkoxy, halo, or haloalkoxy;
$R_5$ is hydrogen or halo;
M is —$(CH_2)_o$— or —(C=O)—;
o is 0, 1, 2, or 3;
T is —$(CH_2)_s$— or —(C=O)—;
s is 0, 1, 2, or 3;
each X and Y is independently $CR_9$ or N;
A and B are each hydrogen; or A, B, and the carbon to which they are attached form a carbonyl;
C and D are each hydrogen; or C, D, and the carbon to which they are attached form a carbonyl;

$Ar_2$ is aryl or heteroaryl, each independently substituted with 0, 1, 2, or 3 independent cyano halo, haloalkyl, $NH_2$, alkoxy, haloalkoxy,

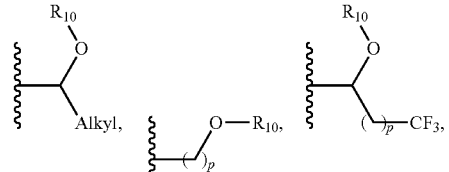

each p is independently 0, 1, 2, or 3;
each $R_9$ is optionally substituted alkyl (e.g., alkyl optionally substituted with 1, 2, or 3 independent OH, halo, $NH_2$, alkoxy, CN, aryl, heteroaryl, aryloxy, or heteroaryloxy) or hydrogen; and
each $R_{10}$ is independently H, alkyl, phosphato, phosphito, alkoxyphosphato, or —C(O)alkyl optionally substituted with 1 or 2 $NH_2$.

Another aspect is a compound of formula (II), or salt, solvate, hydrate or prodrug thereof, wherein:

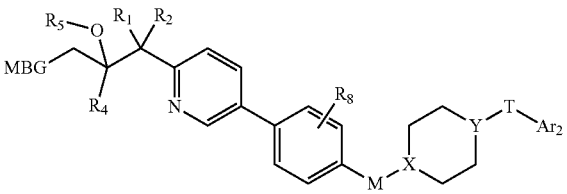

(II)

MBG, $R_1$, $R_2$, $R_4$, $R_5$, $R_8$, M, X, Y, T, and $Ar_2$ are as defined previously.

Another aspect is a compound of formula (III), or salt, solvate, hydrate or prodrug thereof, wherein:

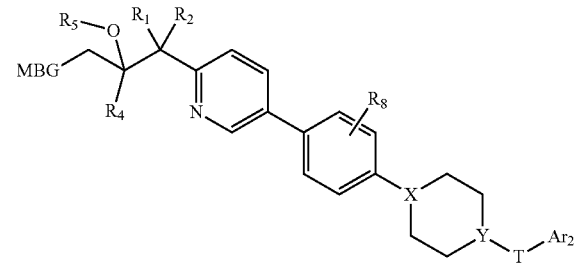

(III)

MBG, $R_1$, $R_2$, $R_4$, $R_5$, $R_8$, X, Y, T, and $Ar_2$ are as defined previously.

Another aspect is a compound of formula (II), or salt, solvate, hydrate or prodrug thereof, wherein $R_1$ is fluoro.

Another aspect is a compound of formula (III), or salt, solvate, hydrate or prodrug thereof, wherein $R_2$ is fluoro.

Another aspect is a compound of formula (III), or salt, solvate, hydrate or prodrug thereof, wherein $R_1$ and $R_2$ are fluoro.

Another aspect is a compound of formula (III), or salt, solvate, hydrate or prodrug thereof, wherein $R_4$ is phenyl optionally substituted with 0, 1, 2 or 3 independent $R_8$.

Another aspect is a compound of formula (III), or salt, solvate, hydrate or prodrug thereof, wherein $R_4$ is phenyl optionally substituted with 0, 1, 2 or 3 independent $R_6$.

Another aspect is a compound of formula (III), or salt, solvate, hydrate or prodrug thereof, wherein $R_4$ is phenyl optionally substituted with 0, 1, 2 or 3 independent halo.

Another aspect is a compound of formula (III), or salt, solvate, hydrate or prodrug thereof, wherein $R_4$ is phenyl optionally substituted with 0, 1, 2 or 3 independent fluoro.

Another aspect is a compound of formula (III), or salt, solvate, hydrate or prodrug thereof, wherein $R_4$ is

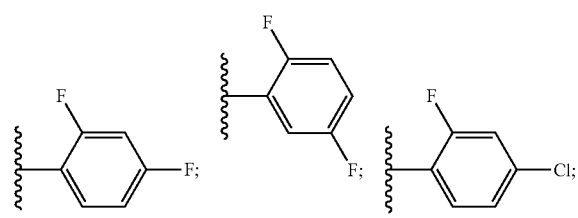

Another aspect is a compound of formula (III), or salt, solvate, hydrate or prodrug thereof, wherein $R_4$ is 2,4-difluorophenyl

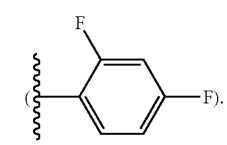

Another aspect is a compound of formula (II), or salt, solvate, hydrate or prodrug thereof, wherein T is $—(CH_2)_s—$ and s is 0.

Another aspect is a compound of formula (III), or salt, solvate, hydrate or prodrug thereof, wherein X is N and Y is C.

Another aspect is a compound of formula (III), or salt, solvate, hydrate or prodrug thereof, wherein X is C and Y is N.

Another aspect is a compound of formula (III), or salt, solvate, hydrate or prodrug thereof, wherein X is N and Y is $CR_9$.

Another aspect is a compound of formula (III), or salt, solvate, hydrate or prodrug thereof, wherein X is $CR_9$ and Y is N.

Another aspect is a compound of formula (III), or salt, solvate, hydrate or prodrug thereof, wherein both X and Y are N.

Another aspect is a compound of formula (III), or salt, solvate, hydrate or prodrug thereof, wherein $R_1$ is fluoro; $R_2$ is fluoro; $R_4$ is

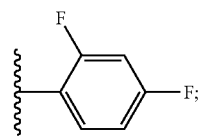 [SMILES: *c1ccc(F)cc1F]

$R_5$ is hydrogen; and MBG is 1-tetrazolyl.

Another aspect is a compound of formula (III), or salt, solvate, hydrate or prodrug thereof, wherein $R_1$ is fluoro; $R_2$ is fluoro; $R_4$ is

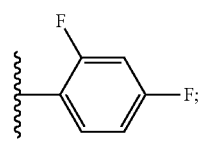 [SMILES: *c1ccc(F)cc1F]

$R_5$ is hydrogen; X and Y are N; and MBG is 1-tetrazolyl.

Another aspect is a compound of formula (III), or salt, solvate, hydrate or prodrug thereof, wherein $R_1$ is fluoro; $R_2$ is fluoro; $R_4$ is

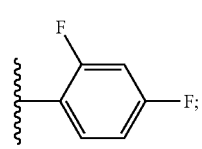 [SMILES: *c1ccc(F)cc1F]

$R_5$ is hydrogen; T is $—(CH_2)_s—$; s is 0; and MBG is 1-tetrazolyl.

Another aspect is a compound of formula (III), or salt, solvate, hydrate or prodrug thereof, wherein $R_1$ is fluoro; $R_2$ is fluoro; $R_4$ is

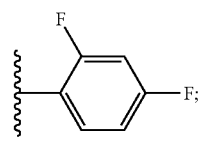

$R_5$ is hydrogen; X and Y are N; T is $—(CH_2)_s—$; s is 0; and MBG is 1-tetrazolyl.

Another aspect is a compound of formula (III), or salt, solvate, hydrate or prodrug thereof, wherein $R_5$ is amino substituted acyl.

Another aspect is a compound of formula (III), or salt, solvate, hydrate or prodrug thereof, wherein $R_5$ is $—C(O)$ alkyl optionally substituted with 1 or 2 $NH_2$.

Another aspect is a compound of formula (III), or salt, solvate, hydrate or prodrug thereof, wherein $R_5$ is phosphato.

Another aspect is a compound of the formulae herein, wherein Ar₂ is:

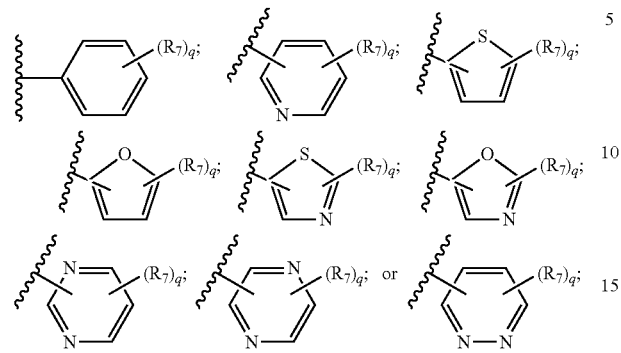

wherein each R₇ is independently cyano, halo, haloalkyl, amino, alkoxy, haloalkoxy,

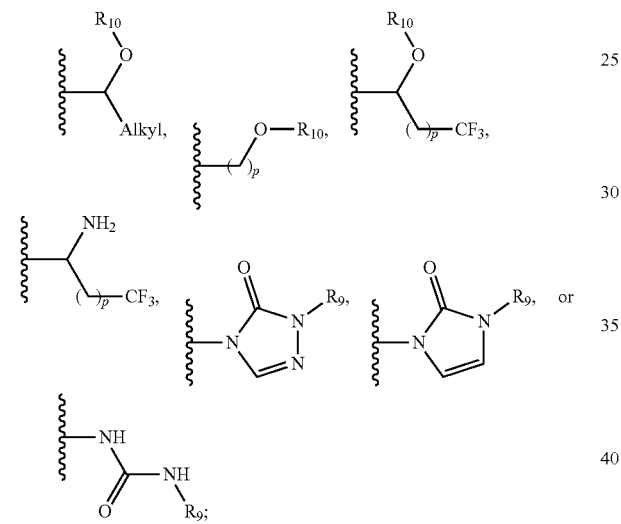

each p is independently 0, 1, 2, or 3;
each q is independently 0, 1, 2, or 3;
each R₉ is optionally substituted alkyl (e.g., alkyl optionally substituted with 1, 2, or 3 independent OH, halo, NH₂, alkoxy, CN, aryl, heteroaryl, aryloxy, or heteroaryloxy) or hydrogen; and
each R₁₀ is independently H, alkyl, phosphato, phosphito, alkoxyphosphato, or —C(O)alkyl optionally substituted with 1 or 2 NH₂.

Another aspect is a compound of the formulae herein, wherein Ar₂ is:

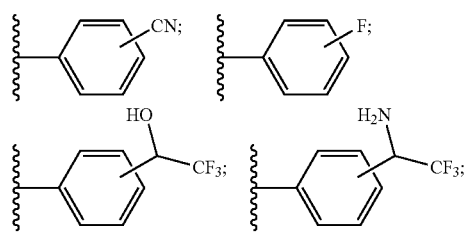

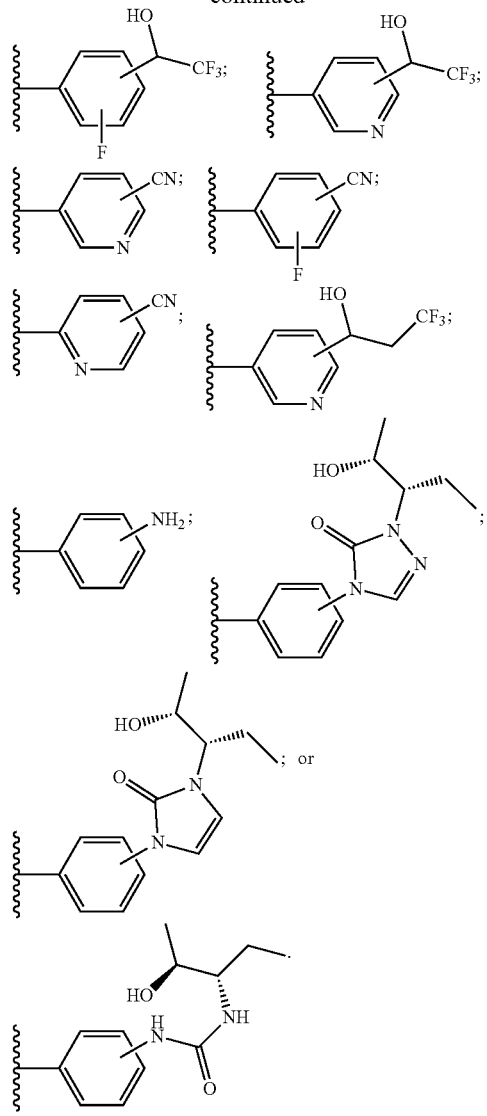

Another aspect is a compound of the formulae herein, wherein Ar₂ is:

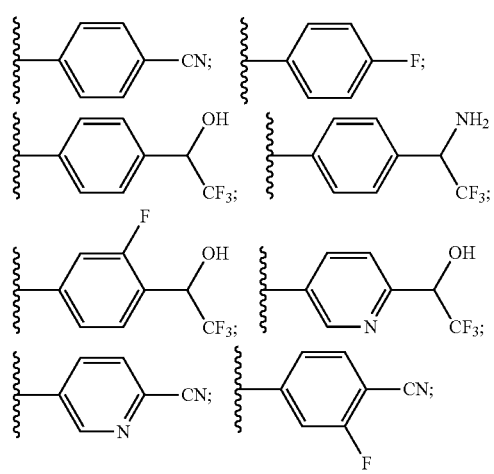

-continued

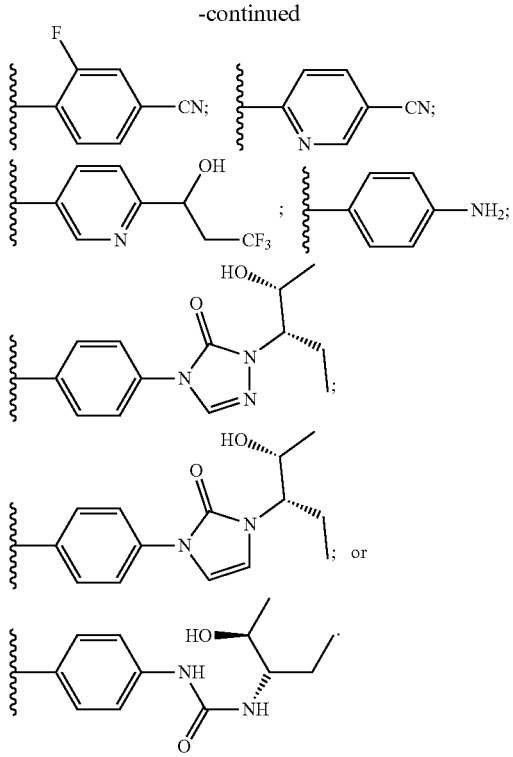

Another aspect is a compound of the formulae herein, wherein $R_1$ is fluoro.

Another aspect is a compound of the formulae herein, wherein $R_2$ is fluoro.

Another aspect is a compound of the formulae herein, wherein $R_1$ and $R_2$ are fluoro.

Another aspect is a compound of the formulae herein, wherein $R_4$ is phenyl optionally substituted with 0, 1, 2 or 3 independent $R_8$.

Another aspect is a compound of the formulae herein, wherein $R_4$ is phenyl optionally substituted with 0, 1, 2 or 3 independent halo.

Another aspect is a compound of the formulae herein, wherein $R_4$ is phenyl optionally substituted with 0, 1, 2 or 3 independent fluoro.

Another aspect is a compound of the formulae herein, wherein $R_4$ is

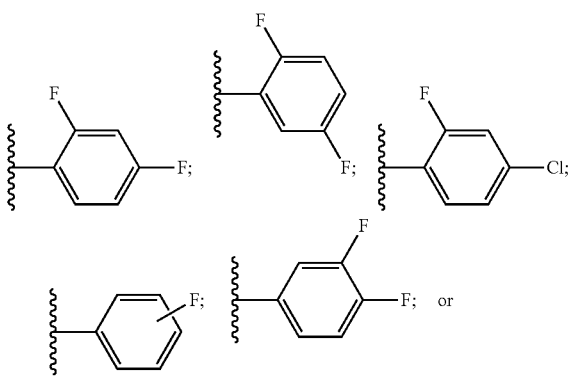

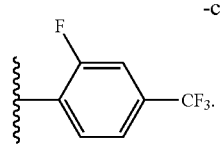

Another aspect is a compound of the formulae herein, wherein $R_4$ is 2,4-difluorophenyl

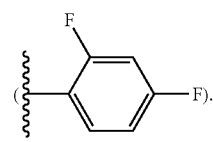

Another aspect is a compound of the formulae herein, wherein X is N and Y is C.

Another aspect is a compound of the formulae herein, wherein X is C and Y is N.

Another aspect is a compound of the formulae herein, wherein X is N and Y is $CR_9$.

Another aspect is a compound of the formulae herein, wherein X is $CR_9$ and Y is N.

Another aspect is a compound of the formulae herein, wherein both X and Y are N.

Another aspect is a compound of the formulae herein, wherein $R_1$ is fluoro; $R_2$ is fluoro; $R_4$ is

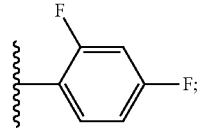

$R_5$ is hydrogen; and MBG is 1-tetrazolyl.

Another aspect is a compound of the formulae herein, wherein $R_1$ is fluoro; $R_2$ is fluoro; $R_4$ is

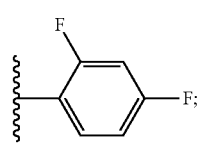

$R_5$ is hydrogen; X and Y are N; and MBG is 1-tetrazolyl.

Another aspect is a compound of the formulae herein, wherein $R_5$ is amino substituted acyl.

Another aspect is a compound of the formulae herein, wherein $R_5$ is —C(O)alkyl optionally substituted with 1 or 2 amino.

Another aspect is a compound of the formulae herein, wherein $R_5$ is phosphato.

In another aspect, disclosed is a compound of formula (I):

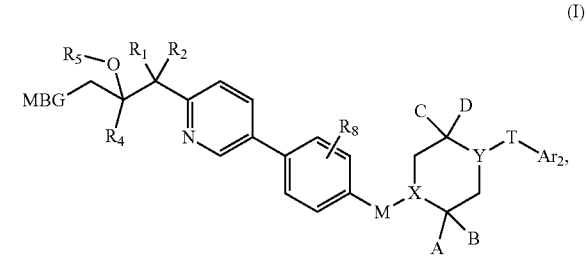

(I)

or salt, solvate, hydrate or prodrug thereof; wherein:

MBG is optionally substituted tetrazolyl, optionally substituted triazolyl, optionally substituted oxazolyl optionally substituted pyrimidinyl, optionally substituted thiazolyl, or optionally substituted pyrazolyl;

$R_1$ is halo or alkyl;

$R_2$ is halo or alkyl;

or $R_1$, $R_2$, and the carbon atom to which they are attached form an optionally substituted cycloalkyl;

$R_4$ is independently aryl, heteroaryl, cycloalkyl, or arylalkyl, each substituted with 0, 1, 2 or 3 independent $R_6$;

$R_5$ is H, alkyl, phosphato, phosphito, alkoxyphosphato, or —C(O)alkyl optionally substituted with 1 or 2 $NH_2$;

each $R_6$ is independently optionally substituted alkyl, cyano, haloalkyl, alkoxy, halo, or haloalkoxy;

$R_8$ is hydrogen or halo;

M is —$(CH_2)_o$— or —(C=O)—;

o is 0, 1, 2, or 3;

T is —$(CH_2)_s$— or —(C=O)—;

s is 0, 1, 2, or 3;

each X and Y is independently $CR_9$ or N;

A and B are each hydrogen; or A, B, and the carbon to which they are attached form a carbonyl;

C and D are each hydrogen; or C, D, and the carbon to which they are attached form a carbonyl;

$Ar_2$ is aryl, heteroaryl, or heterocycloalkyl, each independently substituted with 0, 1, 2, or 3 independent $R_9$, cyano, halo, haloalkyl, $NH_2$, alkoxy, haloalkoxy, optionally substituted arylalkyl,

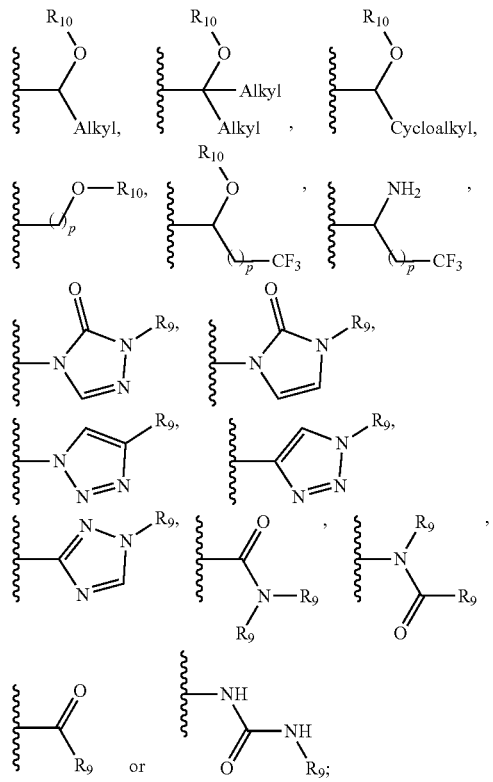

each p is independently 0, 1, 2, or 3;

each $R_9$ is independently optionally substituted alkyl (e.g., alkyl optionally substituted with 1, 2, 3, or 4 independent OH, halo, $NH_2$, NH(alkyl), N(alkyl)$_2$, alkoxy, CN heteroaryl, aryloxy, phosphito, phosphato, carboxy,

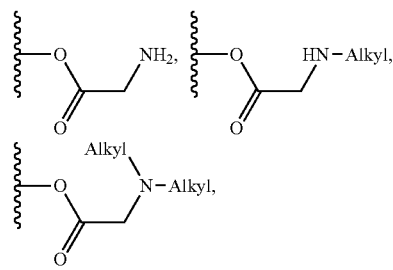

or heteroaryloxy) or hydrogen; and each $R_{10}$ is independently H, alkyl, phosphato, phosphito, alkoxyphosphato, or —C(O)alkyl optionally substituted with 1 or 2 independent $NH_2$.

Another aspect is a compound of formula (II):

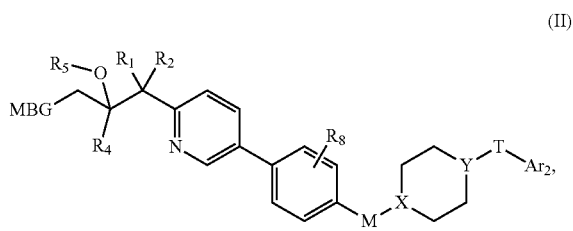

(II)

or salt, solvate, hydrate or prodrug thereof, wherein MBG, $R_1$, $R_2$, $R_4$, $R_5$, $R_8$, M, X, Y, T, and $Ar_2$ are as defined previously.

Another aspect is a compound of formula (III):

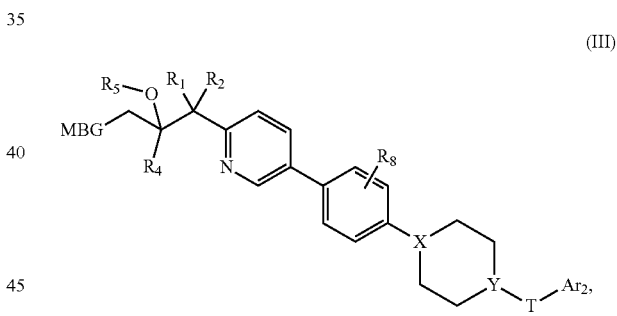

(III)

or salt, solvate, hydrate or prodrug thereof, wherein MBG, $R_1$, $R_2$, $R_4$, $R_5$, $R_8$, X, Y, T, and $Ar_2$ are as defined previously.

Another aspect is a compound of formula (III), or salt, solvate, hydrate or prodrug thereof, wherein $R_1$ is fluoro.

Another aspect is a compound of formula (III), or salt, solvate, hydrate or prodrug thereof, wherein $R_2$ is fluoro.

Another aspect is a compound of formula (III), or salt, solvate, hydrate or prodrug thereof, wherein $R_1$ and $R_2$ are fluoro.

Another aspect is a compound of formula (III), or salt, solvate, hydrate or prodrug thereof, wherein $R_4$ is phenyl optionally substituted with 0, 1, 2 or 3 independent $R_6$.

Another aspect is a compound of formula (III), or salt, solvate, hydrate or prodrug thereof, wherein $R_4$ is phenyl optionally substituted with 0, 1, 2 or 3 independent halo.

Another aspect is a compound of formula (III), or salt, solvate, hydrate or prodrug thereof, wherein $R_4$ is phenyl optionally substituted with 0, 1, 2 or 3 independent fluoro.

Another aspect is a compound of formula (III), or salt, solvate, hydrate or prodrug thereof, wherein $R_4$ is

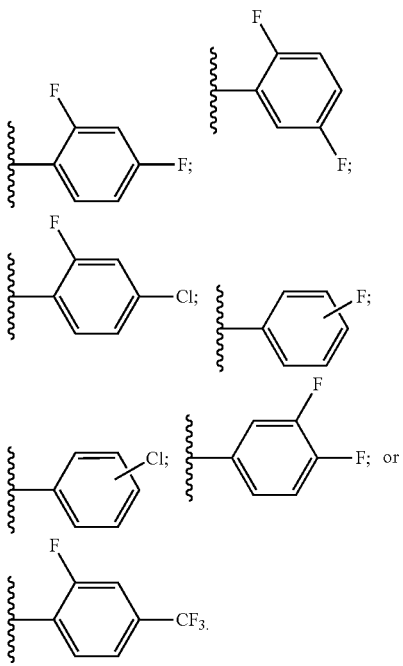

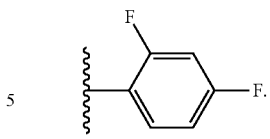

Another aspect is a compound of formula (III), or salt, solvate, hydrate or prodrug thereof, wherein $R_4$ is

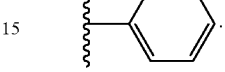

Another aspect is a compound of formula (III), or salt, solvate, hydrate or prodrug thereof, wherein $R_4$ is

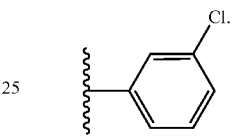

Another aspect is a compound of formula (III), or salt, solvate, hydrate or prodrug thereof, wherein T is —(CH$_2$)$_s$— and s is 0.

Another aspect is a compound of formula (III), or salt, solvate, hydrate or prodrug thereof, wherein X is N and Y is CH.

Another aspect is a compound of formula (III), or salt, solvate, hydrate or prodrug thereof, wherein X is CH and Y is N.

Another aspect is a compound of formula (III), or salt, solvate, hydrate or prodrug thereof, wherein both X and Y are N.

Another aspect is a compound of formula (III), or salt, solvate, hydrate or prodrug thereof, wherein $R_1$ is fluoro; $R_2$ is fluoro; $R_4$ is

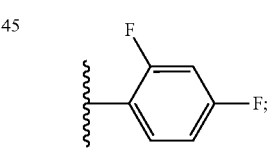

$R_5$ is hydrogen; and MBG is 1-tetrazolyl.

Another aspect is a compound of formula (III), or salt, solvate, hydrate or prodrug thereof, wherein $R_1$ is fluoro; $R_2$ is fluoro; $R_4$ is

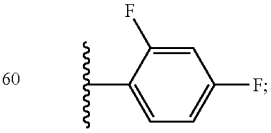

$R_5$ is hydrogen; X and Y are N; and MBG is 1-tetrazolyl.

Another aspect is a compound of formula (III), or salt, solvate, hydrate or prodrug thereof, wherein $R_1$ is fluoro; $R_2$ is fluoro; $R_4$ is Another aspect is a compound of formula (III), or salt, solvate, hydrate or prodrug thereof, wherein $R_4$ is

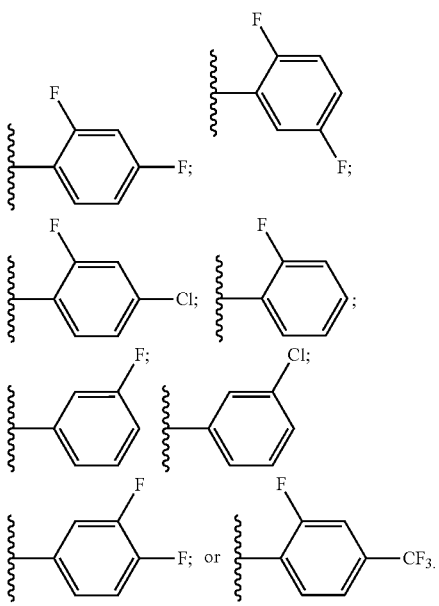

Another aspect is a compound of formula (III), or salt, solvate, hydrate or prodrug thereof, wherein $R_4$ is

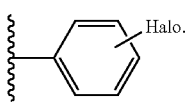

Another aspect is a compound of formula (III), or salt, solvate, hydrate or prodrug thereof, wherein $R_4$ is

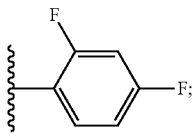 [SMILES: *c1ccc(F)cc1F]

$R_5$ is hydrogen; T is —(CH$_2$)$_s$—; s is 0; and MBG is 1-tetrazolyl.

Another aspect is a compound of formula (III), or salt, solvate, hydrate or prodrug thereof, wherein $R_1$ is fluoro; $R_2$ is fluoro; $R_4$ is

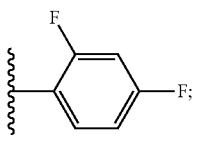 [SMILES: *c1ccc(F)cc1F]

$R_5$ is hydrogen; X and Y are N; T is —(CH$_2$)$_s$—; s is 0; and MBG is 1-tetrazolyl.

Another aspect is a compound of formula (III), or salt, solvate, hydrate or prodrug thereof, wherein $R_1$ is fluoro; $R_2$ is fluoro; $R_4$ is

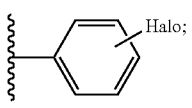

$R_5$ is hydrogen; and MBG is 1-tetrazolyl.

Another aspect is a compound of formula (III), or salt, solvate, hydrate or prodrug thereof, wherein $R_1$ is fluoro; $R_2$ is fluoro; $R_4$ is

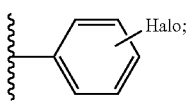

$R_5$ is hydrogen; X and Y are N; and MBG is 1-tetrazolyl.

Another aspect is a compound of formula (III), or salt, solvate, hydrate or prodrug thereof, wherein $R_1$ is fluoro; $R_2$ is fluoro; $R_4$ is

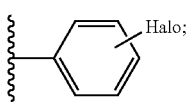

$R_5$ is hydrogen; T is —(CH$_2$)$_s$—; s is 0; and MBG is 1-tetrazolyl.

Another aspect is a compound of formula I), or salt, solvate, hydrate or prodrug thereof, wherein $R_1$ is fluoro; $R_2$ is fluoro; $R_4$ is

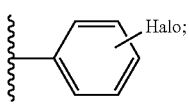

$R_5$ is hydrogen; X and Y are N; T is —(CH$_2$)$_s$—; s is 0; and MBG is 1-tetrazolyl.

Another aspect is a compound of formula (III), or salt, solvate, hydrate or prodrug thereof, wherein $R_1$ is fluoro; $R_2$ is fluoro; $R_4$ is

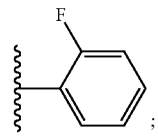 [SMILES: *c1ccccc1F]

$R_5$ is hydrogen; and MBG is 1-tetrazolyl.

Another aspect is a compound of formula (III), or salt, solvate, hydrate or prodrug thereof, wherein $R_1$ is fluoro; $R_2$ is fluoro; $R_4$ is

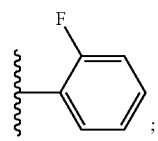 [SMILES: *c1ccccc1F]

$R_5$ is hydrogen; X and Y are N; and MBG is 1-tetrazolyl.

Another aspect is a compound of formula (III), or salt, solvate, hydrate or prodrug thereof, wherein $R_1$ is fluoro; $R_2$ is fluoro; $R_4$ is

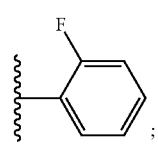 [SMILES: *c1ccccc1F]

$R_5$ is hydrogen; T is —(CH$_2$)$_s$—; s is 0; and MBG is 1-tetrazolyl.

Another aspect is a compound of formula (III), or salt, solvate, hydrate or prodrug thereof, wherein $R_1$ is fluoro; $R_2$ is fluoro; $R_4$ is

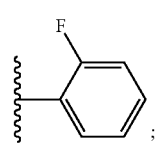 [SMILES: *c1ccccc1F]

$R_5$ is hydrogen; X and Y are N; T is —(CH$_2$)$_s$—; s is 0; and MBG is 1-tetrazolyl.

Another aspect is a compound of formula (I), or salt, solvate, hydrate or prodrug thereof, wherein $R_1$ is fluoro; $R_2$ is fluoro; $R_4$ is

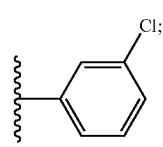

$R_5$ is hydrogen; and MBG is 1-tetrazolyl.

Another aspect is a compound of formula (III), or salt, solvate, hydrate or prodrug thereof, wherein $R_1$ is fluoro; $R_2$ is fluoro; $R_4$ is

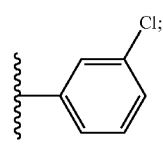

R$_5$ is hydrogen; X and Y are N; and MBG is 1-tetrazolyl.

Another aspect is a compound of formula (III), or salt, solvate, hydrate or prodrug thereof, wherein R$_1$ is fluoro; R$_2$ is fluoro; R$_4$ is

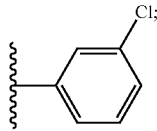 [SMILES: *c1cccc(Cl)c1]

R$_5$ is hydrogen; T is —(CH$_2$)$_s$—; s is 0; and MBG is 1-tetrazolyl.

Another aspect is a compound of formula (III), or salt, solvate, hydrate or prodrug thereof, wherein R$_1$ is fluoro; R$_2$ is fluoro; R$_4$ is

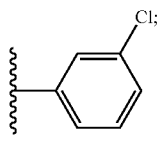 [SMILES: *c1cccc(Cl)c1]

R$_5$ is hydrogen; X and Y are N; T is —(CH$_2$)$_s$—; s is 0; and MBG is 1-tetrazolyl.

Another aspect is a compound of formula (III), or salt, solvate, hydrate or prodrug thereof, wherein R$_5$ is hydrogen.

Another aspect is a compound of formula (III), or salt, solvate, hydrate or prodrug thereof, wherein R$_5$ is amino substituted acyl.

Another aspect is a compound of formula (III), or salt, solvate, hydrate or prodrug thereof, wherein R$_5$ is —C(O) alkyl optionally substituted with 1 or 2 NH$_2$.

Another aspect is a compound of formula (III), or salt, solvate, hydrate or prodrug thereof, wherein R$_5$ is phosphato.

Another aspect is a compound of the formulae herein, wherein Ar$_2$ is monocyclic heteroaryl, bicyclic heteroaryl, monocyclic aryl, or bicyclic aryl.

Another aspect is a compound of the formulae herein, wherein Ar$_2$ is monocyclic heteroaryl, bicyclic heteroaryl, or monocyclic aryl.

Another aspect is a compound of the formulae herein, wherein Ar$_2$ is monocyclic aryl.

Another aspect is a compound of the formulae herein, wherein Ar$_2$ is phenyl or pyridyl.

Another aspect is a compound of the formulae herein, wherein Ar$_2$ is:

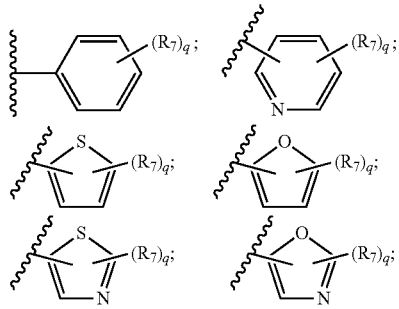

-continued

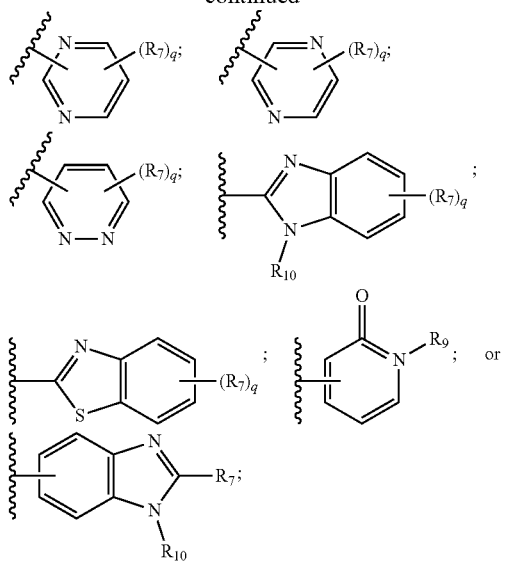

wherein each R$_7$ is independently R$_9$, cyano, halo, haloalkyl, NH$_2$, alkoxy, haloalkoxy, optionally substituted arylalkyl,

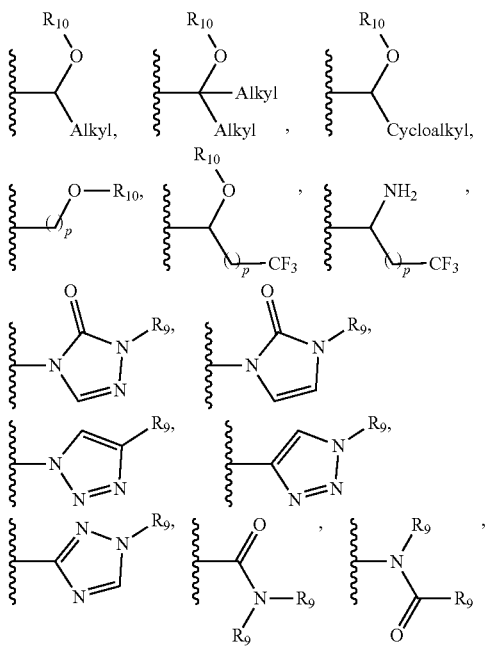

each p is independently 0, 1, 2, or 3;

each q is independently 0, 1, 2, or 3;

each R$_9$ is independently optionally substituted alkyl (e.g., alkyl optionally substituted with 1, 2, 3, or 4 independent OH, halo, NH$_2$, NH(alkyl), N(alkyl)$_2$, alkoxy, CN, aryl, heteroaryl, aryloxy, phosphito, phosphato, carboxy,

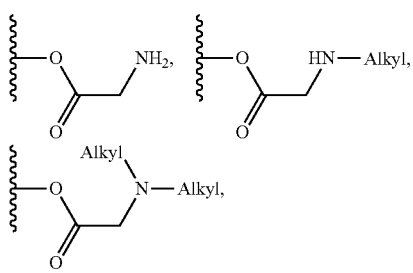

or heteroaryloxy) or hydrogen; and
each $R_{10}$ is independently H, alkyl, phosphato, phosphito, alkoxyphosphato, or —C(O)alkyl optionally substituted with 1 or 2 $NH_2$.

In certain embodiments, each $R_1$ is independently optionally substituted alkyl (e.g., alkyl optionally substituted with 1, 2, 3, or 4 independent OH, halo, $NH_2$, NH(Me), $N(Me)_2$, alkoxy, CN, phosphito, phosphato,

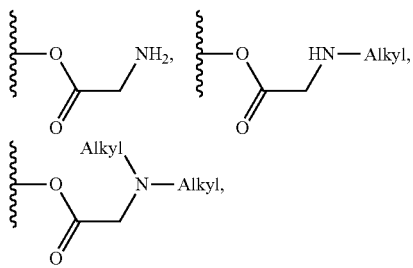

or carboxy) or hydrogen.

In certain embodiments, each $R_1$ is independently optionally substituted $C_{1-6}$ alkyl (e.g., $C_{1-6}$ alkyl optionally substituted with 1, 2, 3, or 4 independent OH, halo, $NH_2$, NH(Me), $N(Me)_2$, alkoxy, CN, phosphito, phosphato,

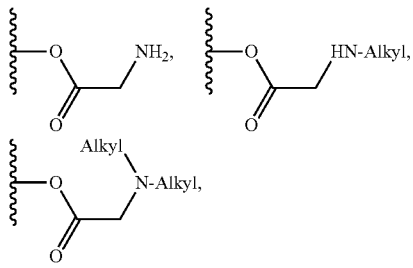

or carboxy) or hydrogen;

Another aspect is a compound of the formulae herein, wherein $Ar_2$ is:

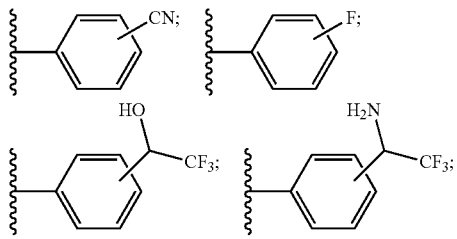

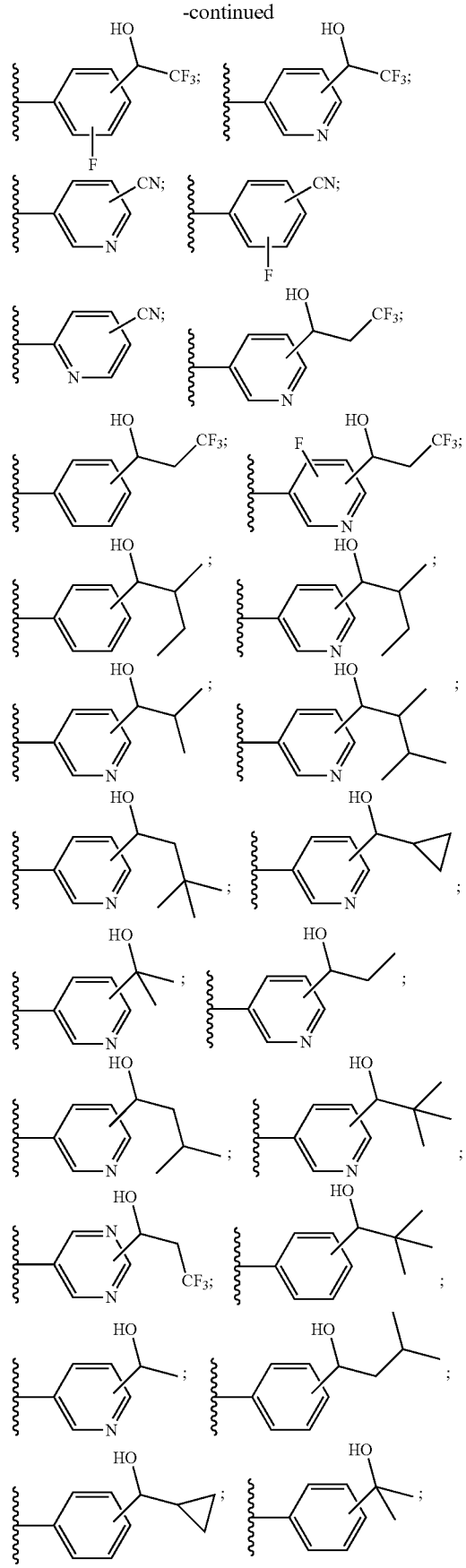

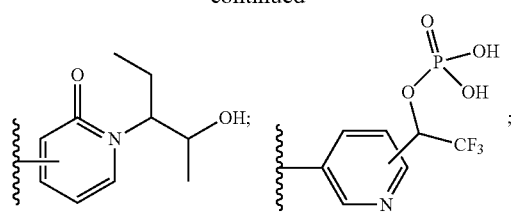
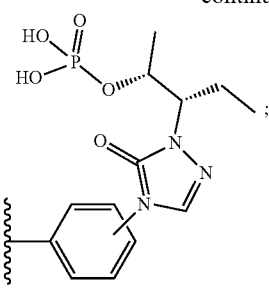
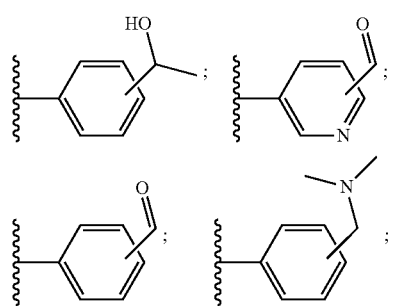
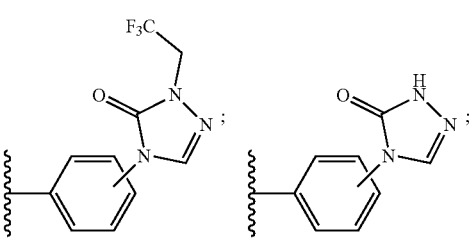
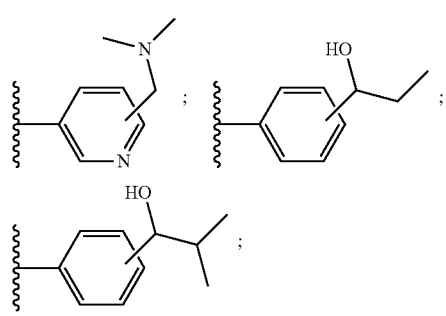
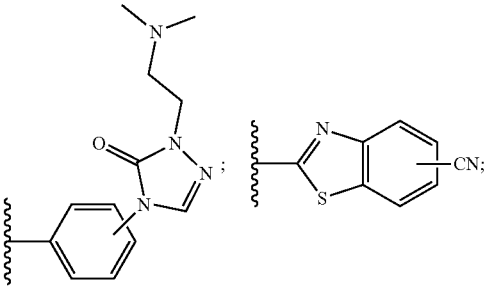
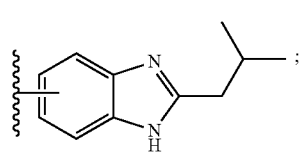
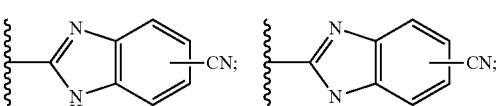
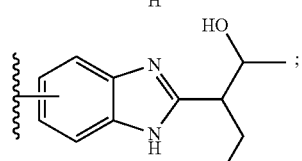
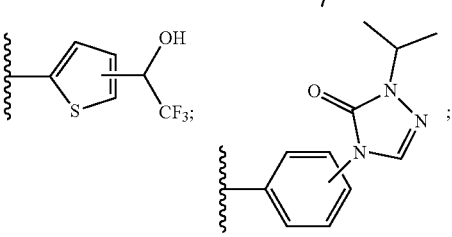
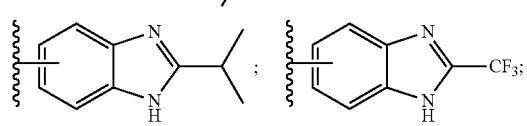
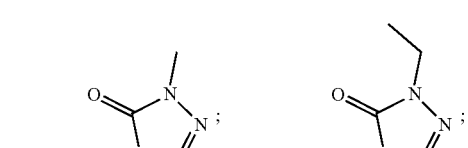
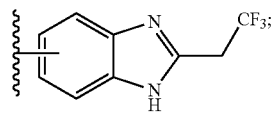
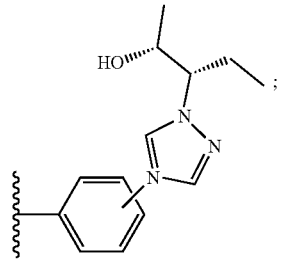
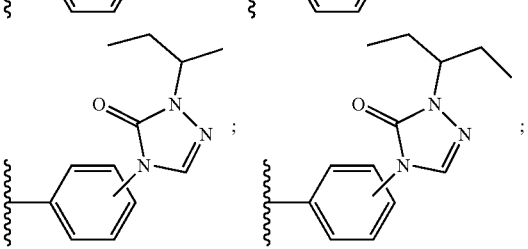

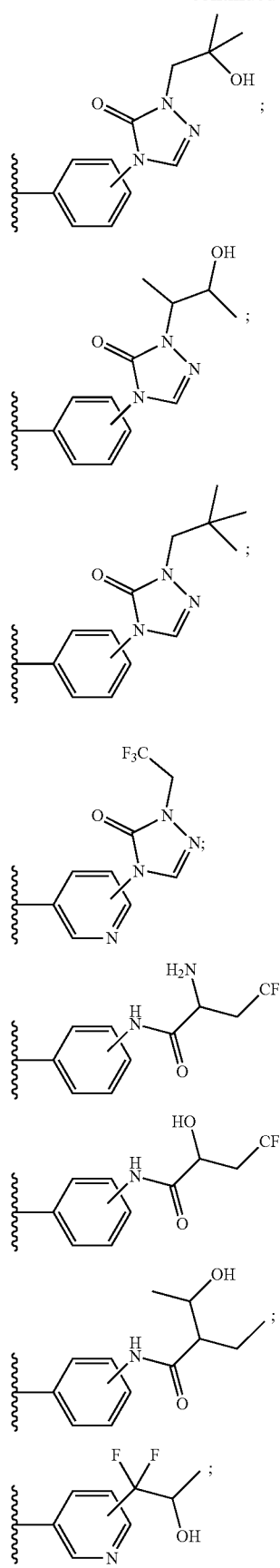
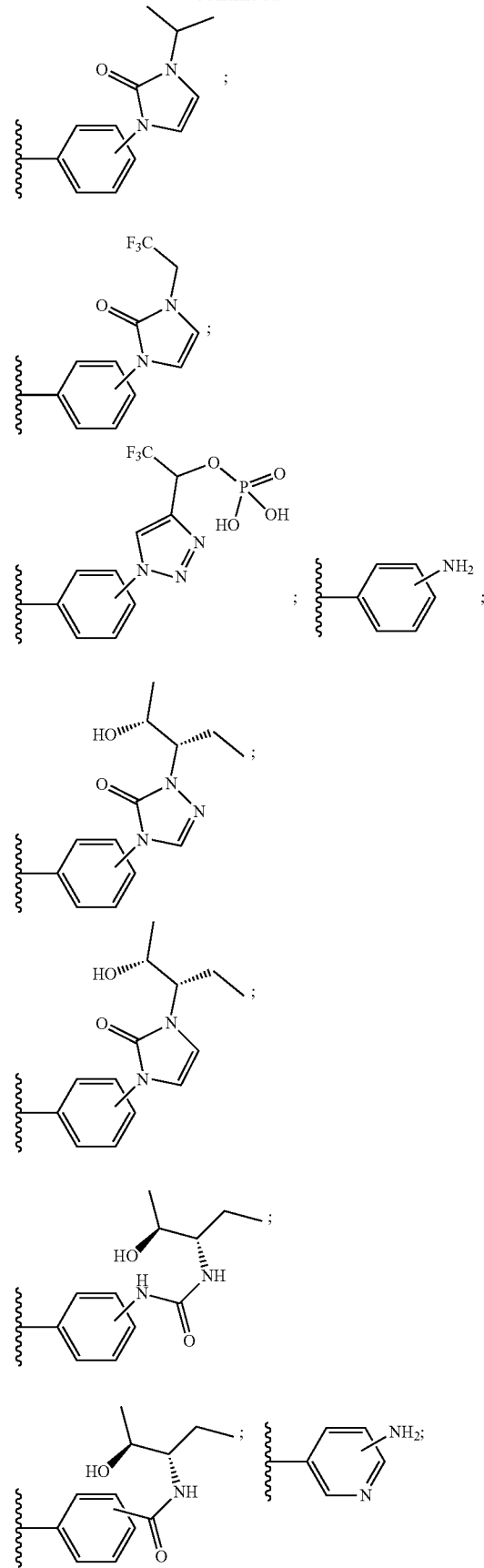

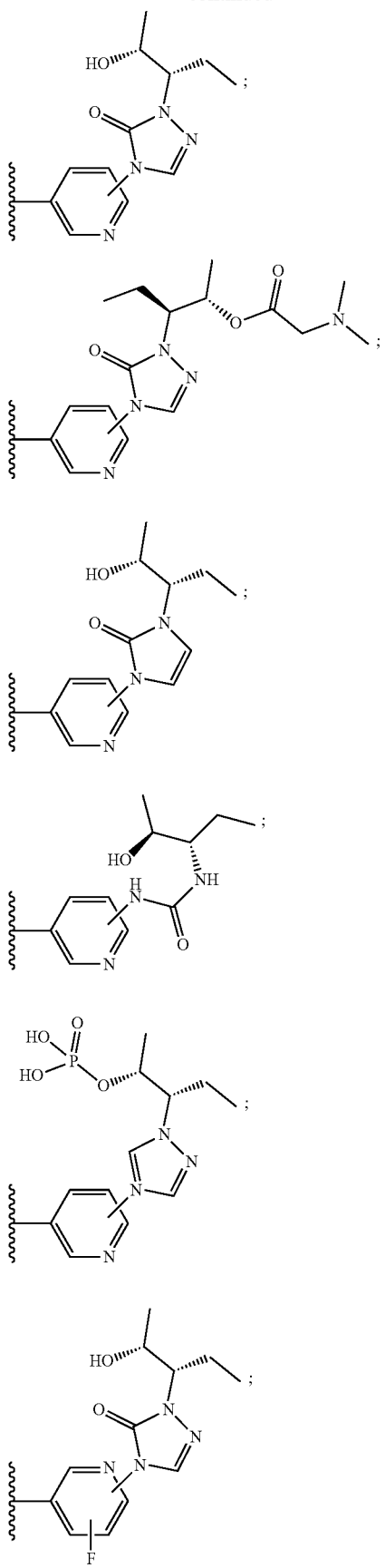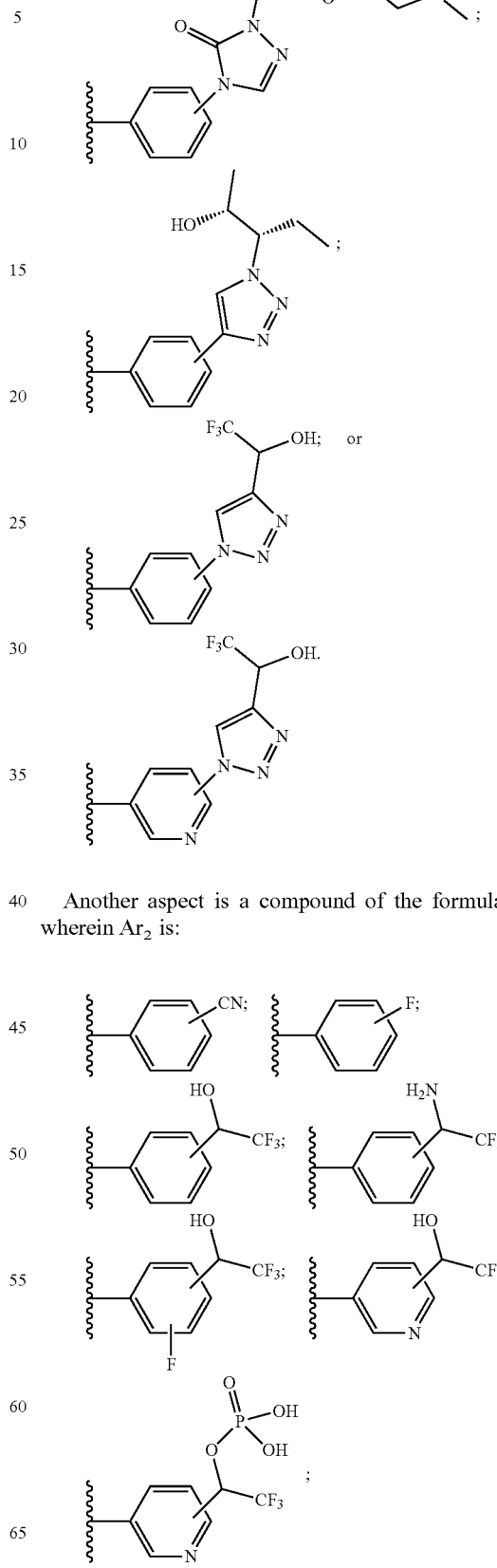
Another aspect is a compound of the formulae herein, wherein Ar₂ is:

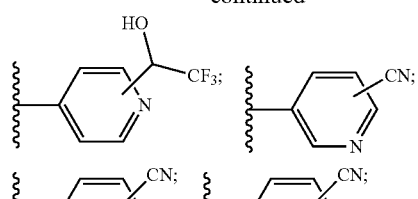
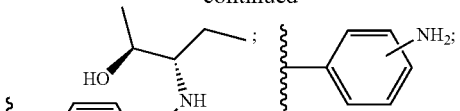
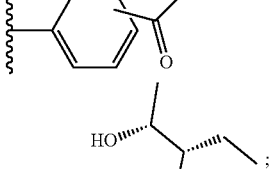
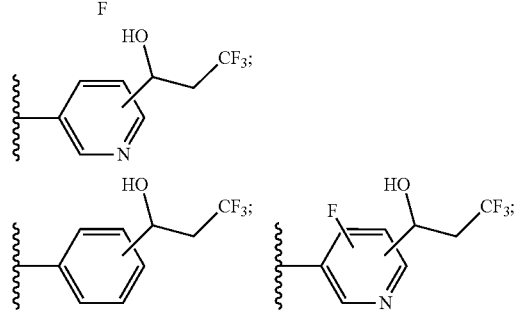
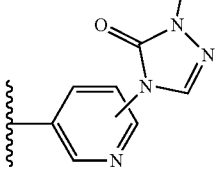
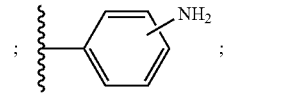
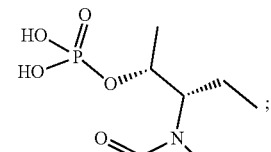
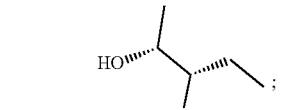
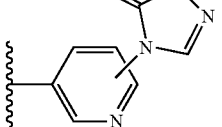

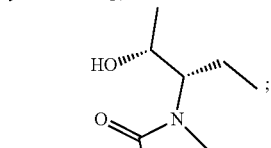
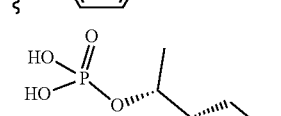
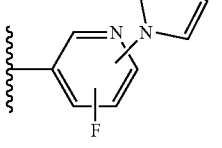
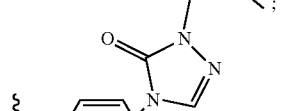
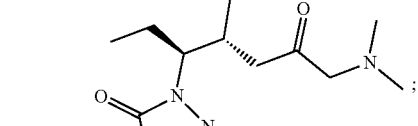
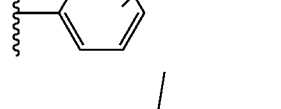
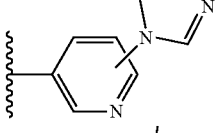
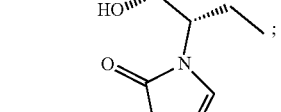
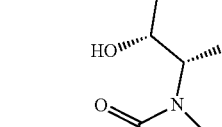
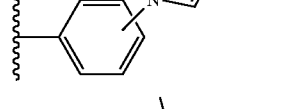
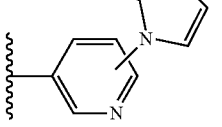
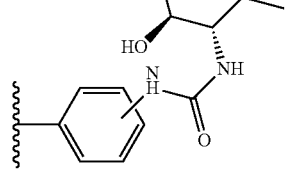
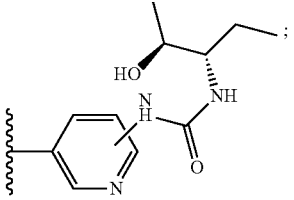

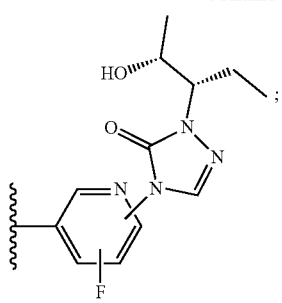
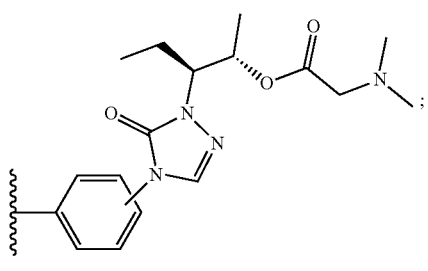
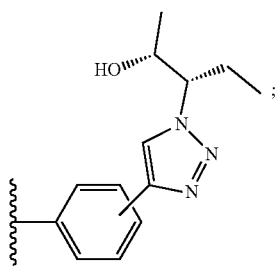
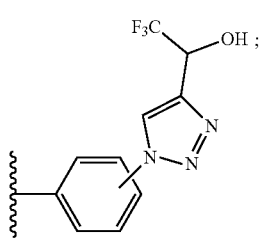
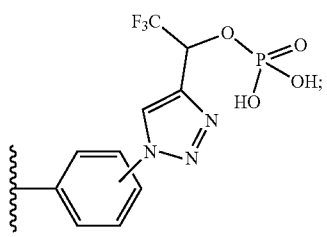
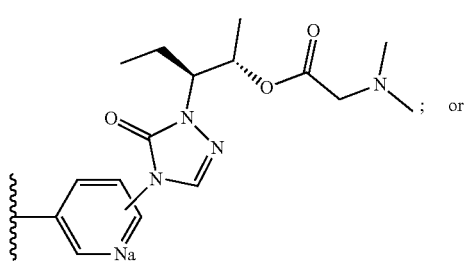
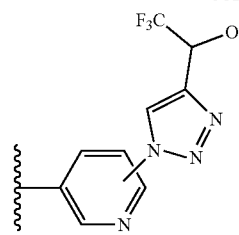
Another aspect is a compound of the formulae herein, wherein Ar$_2$ is:
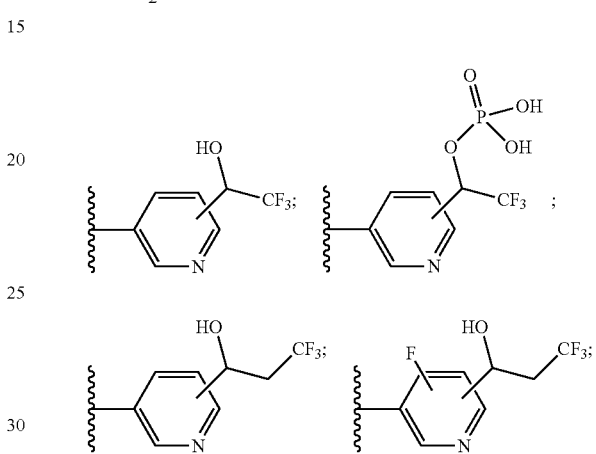
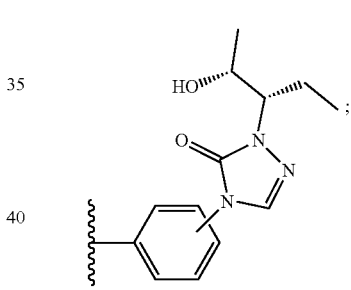
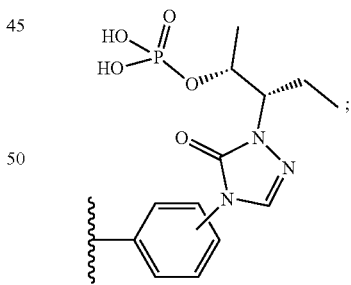
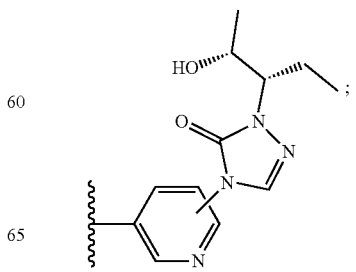

-continued
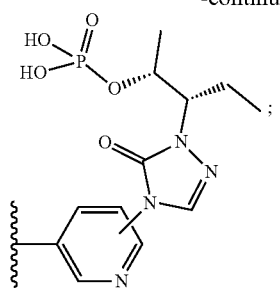
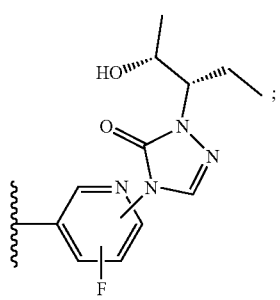
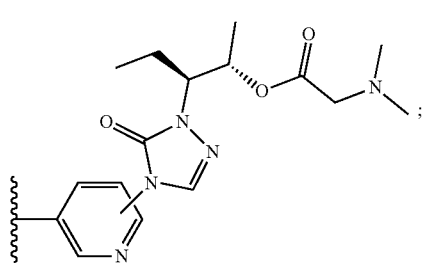
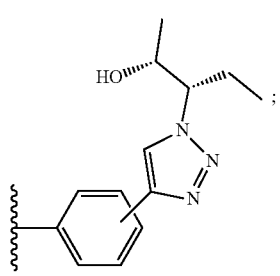
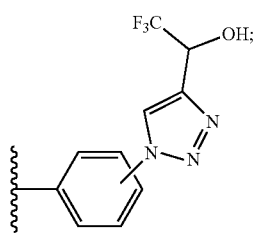
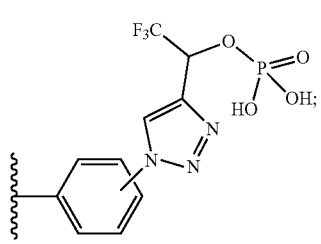
-continued
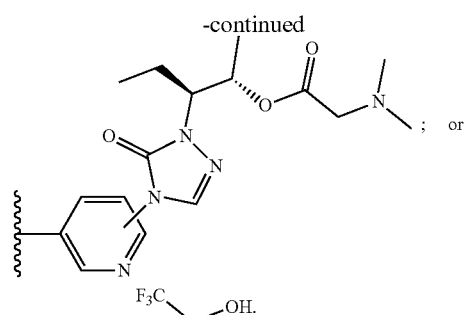
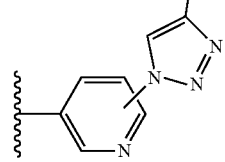
Another aspect is a compound of the formulae herein, wherein Ar$_2$ is:
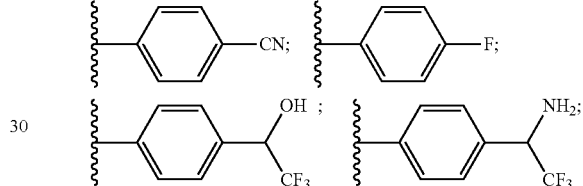
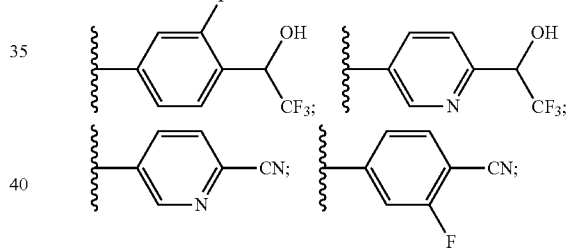
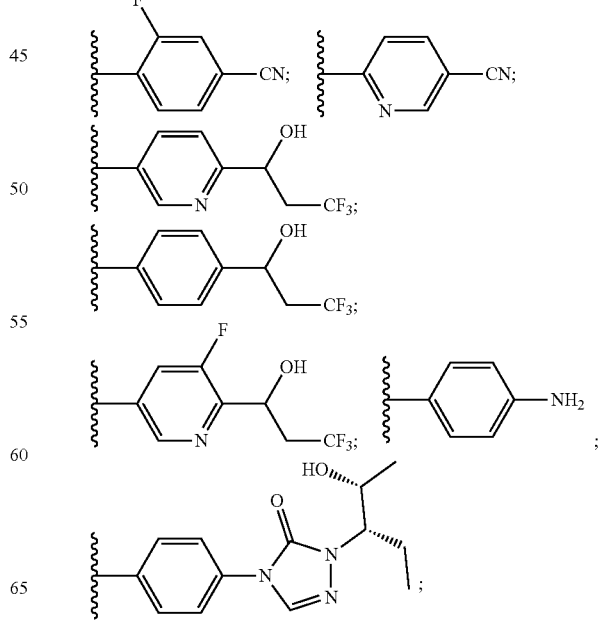

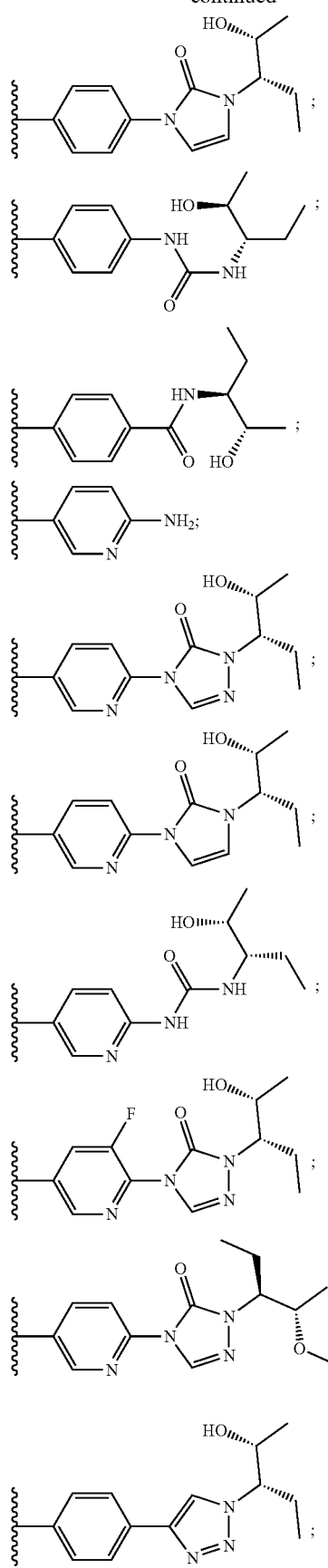
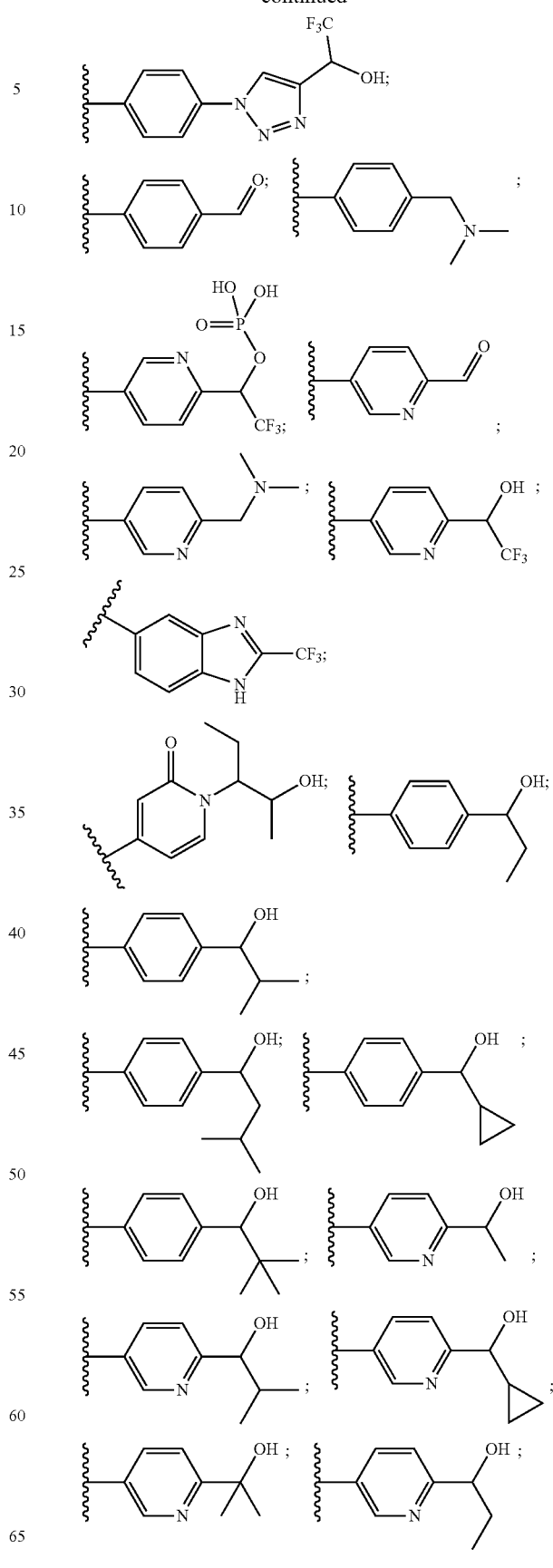

-continued
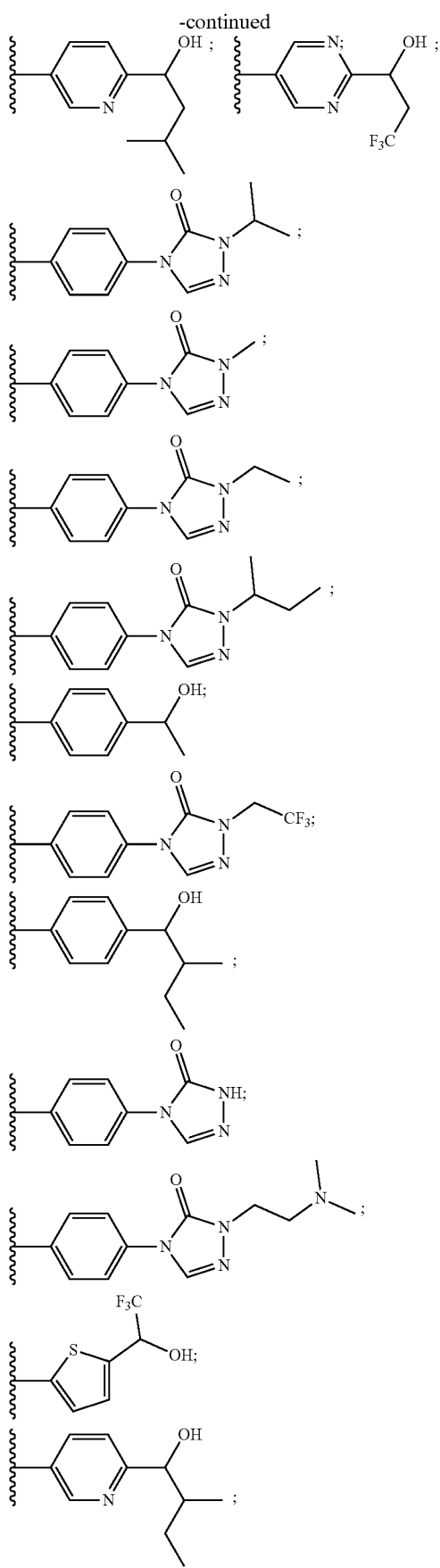
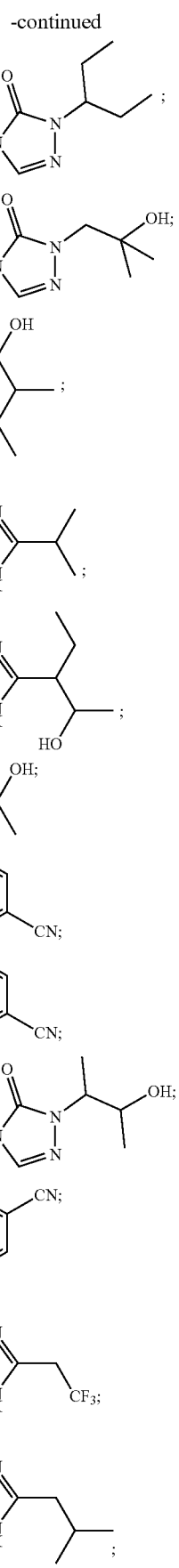

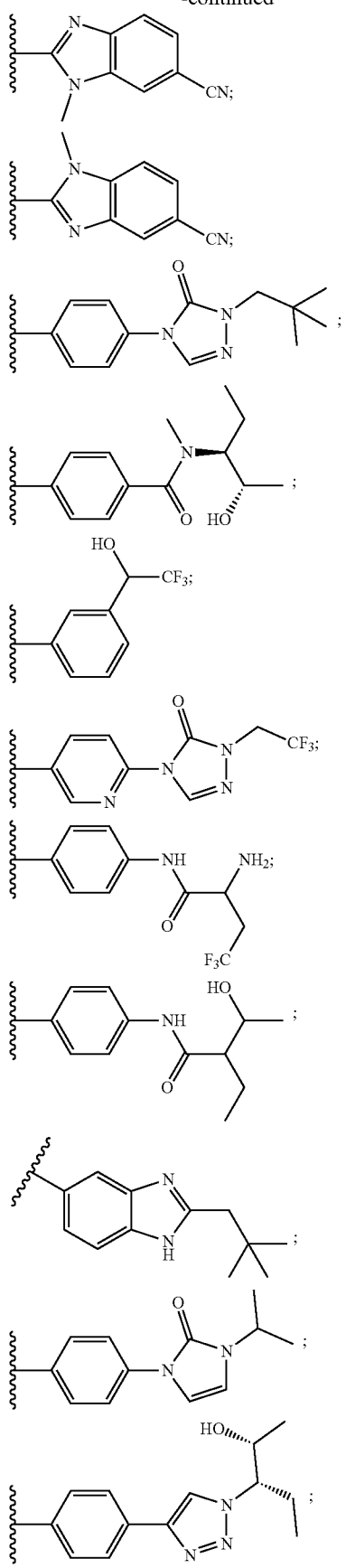
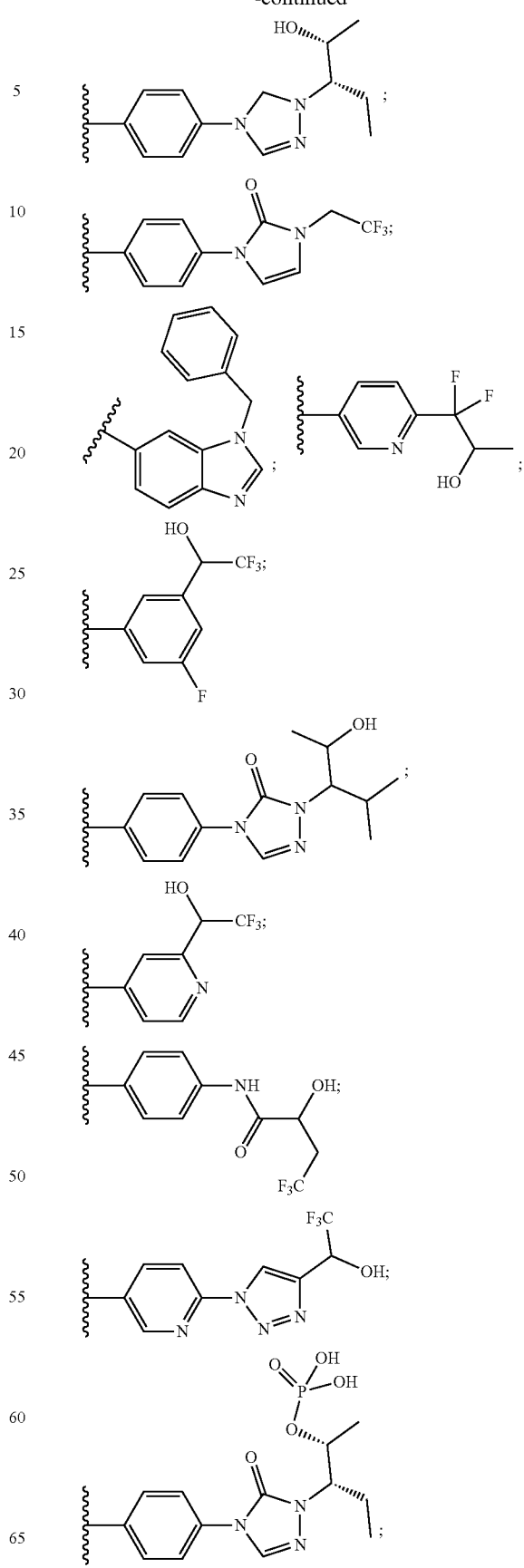

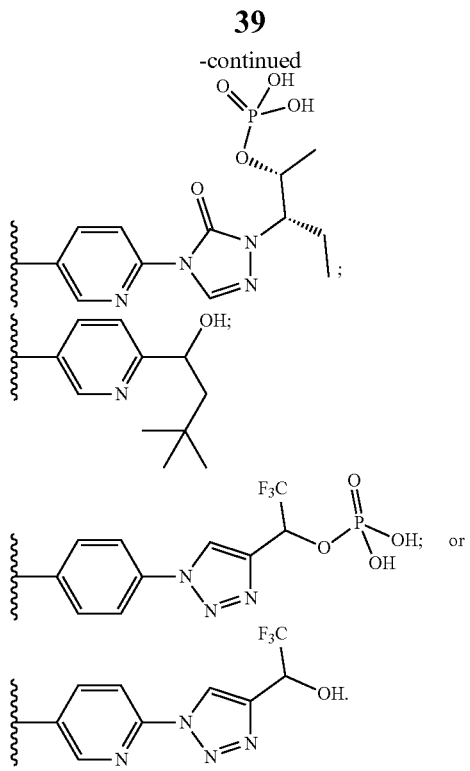
Another aspect is a compound of the formulae herein, wherein Ar₂ is:
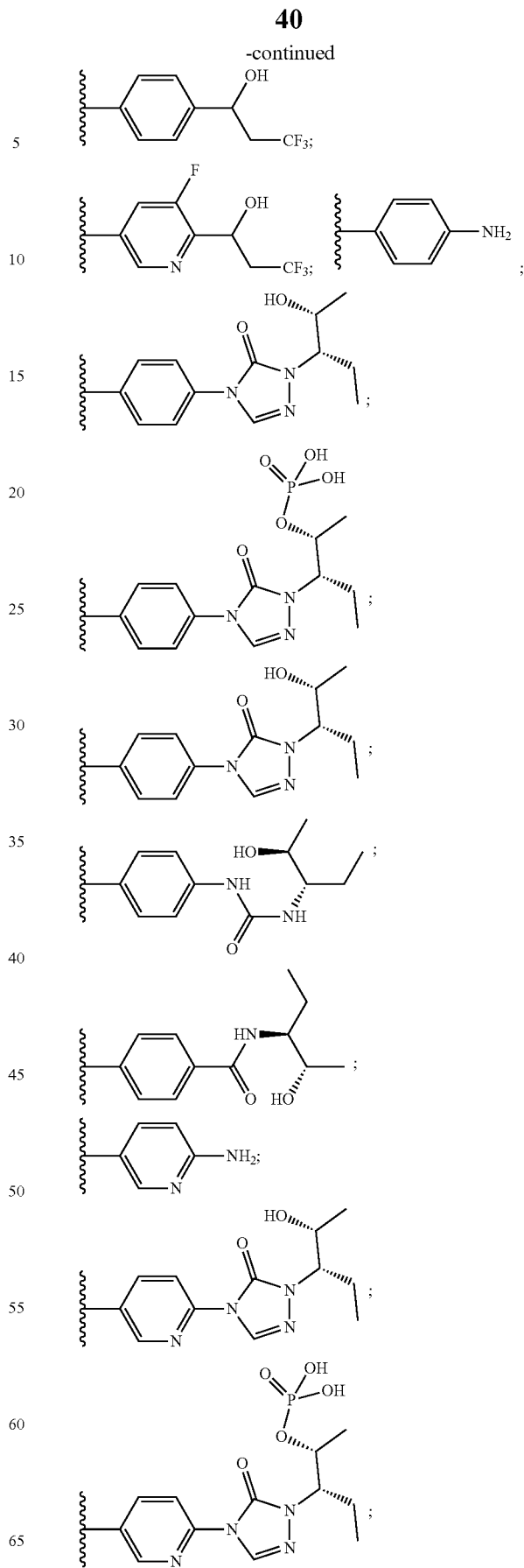

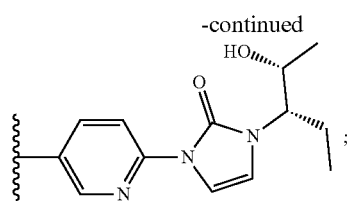
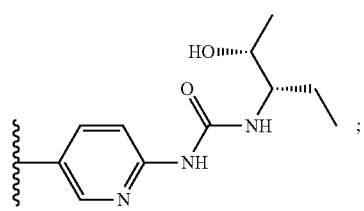
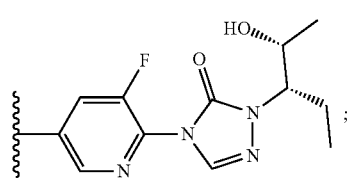
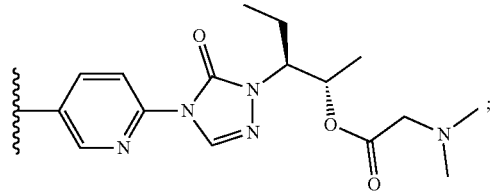
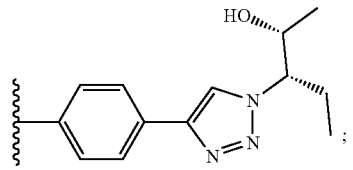
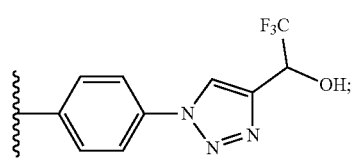
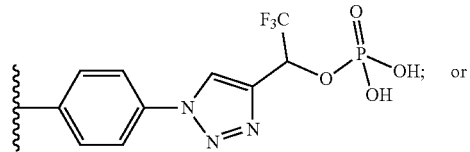
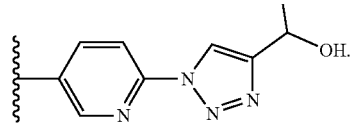
Another aspect is a compound of the formulae herein, wherein Ar$_2$ is:
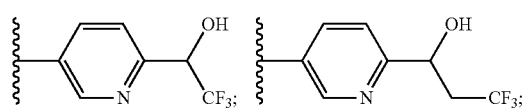
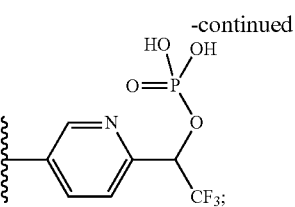
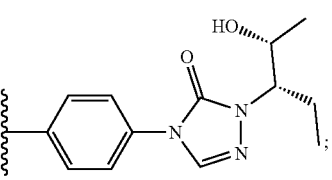
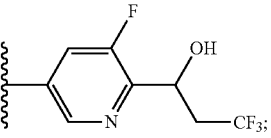
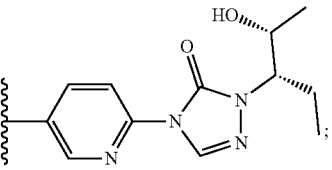
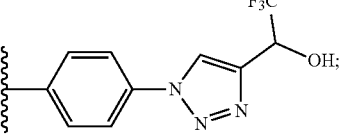
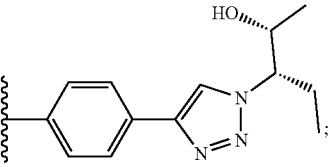
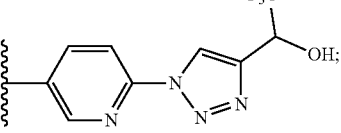
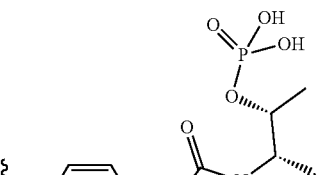
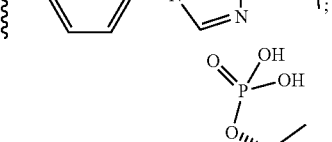
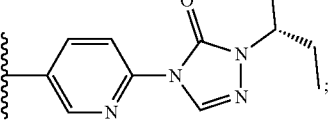

-continued

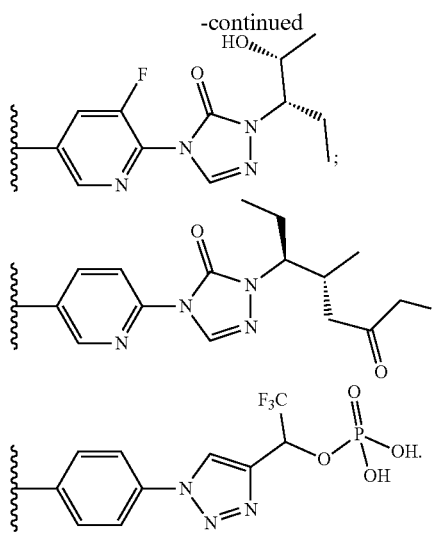

Another aspect is a compound of the formulae herein, wherein R₁ is fluoro.

Another aspect is a compound of the formulae herein, wherein R₂ is fluoro.

Another aspect is a compound of the formulae herein, wherein R₁ and R₂ are fluoro.

Another aspect is a compound of the formulae herein, wherein R₄ is phenyl optionally substituted with 0, 1, 2 or 3 independent R₆.

Another aspect is a compound of the formulae herein, wherein R₄ is phenyl optionally substituted with 0, 1, 2 or 3 independent halo.

Another aspect is a compound of the formulae herein, wherein R₄ is phenyl optionally substituted with 0, 1, 2 or 3 independent fluoro.

Another aspect is a compound of the formulae herein, wherein R₄ is phenyl optionally substituted with 0, 1, 2 or 3 independent chloro.

Another aspect is a compound of the formulae herein, wherein R₄ is

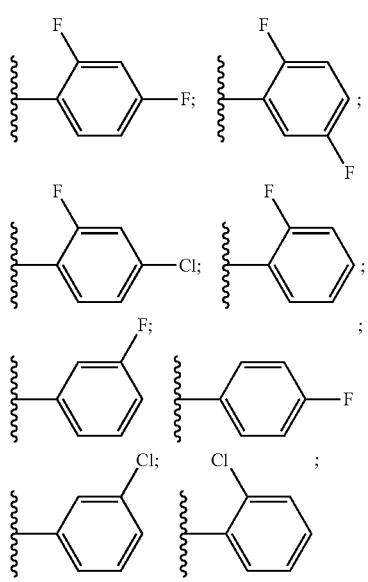

-continued

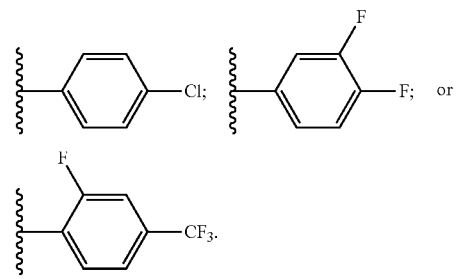

Another aspect is a compound of the formulae herein, wherein R₄ is

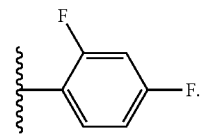 [SMILES: *c1ccc(F)cc1F]

Another aspect is a compound of the formulae herein, wherein R₄ is

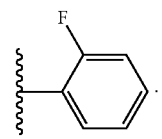 [SMILES: *c1ccccc1F]

Another aspect is a compound of the formulae herein, wherein R₄ is

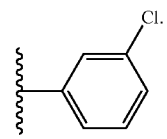

Another aspect is a compound of the formulae herein, wherein X is N and Y is CH.

Another aspect is a compound of the formulae herein, wherein X is CH and Y is N.

Another aspect is a compound of the formulae herein, wherein both X and Y are N.

Another aspect is a compound of the formulae herein, wherein R₁ is fluoro; R₂ is fluoro; R₄ is

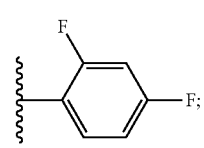 [SMILES: *c1ccc(F)cc1F]

R₅ is hydrogen; and MBG is 1-tetrazolyl.

Another aspect is a compound of the formulae herein, wherein R₁ is fluoro; R₂ is fluoro; R₄ is

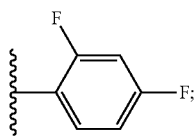 [SMILES: *c1ccc(F)cc1F]

$R_5$ is hydrogen; X and Y are N; and MBG is 1-tetrazolyl.

Another aspect is a compound of the formulae herein, wherein $R_1$ is fluoro; $R_2$ is fluoro; $R_4$ is

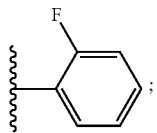 [SMILES: *c1ccccc1F]

$R_5$ is hydrogen; and MBG is 1-tetrazolyl.

Another aspect is a compound of the formulae herein, wherein $R_1$ is fluoro; $R_2$ is fluoro; $R_4$ is

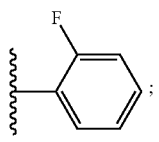 [SMILES: *c1ccccc1F]

$R_5$ is hydrogen; X and Y are N; and MBG is 1-tetrazolyl.

Another aspect is a compound of the formulae herein, wherein $R_1$ is fluoro; $R_2$ is fluoro; $R_4$ is

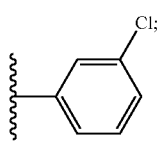 [SMILES: *c1cccc(Cl)c1]

$R_5$ is hydrogen; and MBG is 1-tetrazolyl or 2-tetrazolyl.

Another aspect is a compound of the formulae herein, wherein $R_1$ is fluoro; $R_2$ is fluoro; $R_4$ is

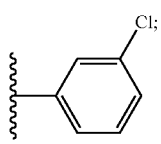 [SMILES: *c1cccc(Cl)c1]

$R_5$ is hydrogen; X and Y are N; and MBG is 1-tetrazolyl or 2-tetrazolyl.

Another aspect is a compound of the formulae herein, wherein $R_5$ is hydrogen.

Another aspect is a compound of the formulae herein, wherein $R_5$ is amino substituted acyl.

Another aspect is a compound of the formulae herein, wherein $R_5$ is —C(O)alkyl optionally substituted with 1 or 2 amino.

Another aspect is a compound of the formulae herein, wherein $R_5$ is phosphato.

Another aspect is a compound of formula (IV):

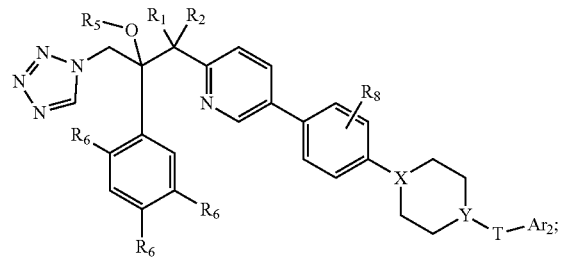

(IV)

or salt, solvate, hydrate or prodrug thereof.

In certain embodiments, each $R_6$ is independently hydrogen, fluoro, or chloro.

Another aspect is a compound of formula (V):

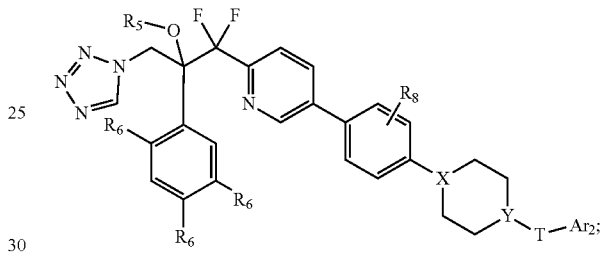

(V)

or salt, solvate, hydrate or prodrug thereof.

In certain embodiments, each $R_6$ is independently hydrogen, fluoro, or chloro.

Another aspect is a compound of formula (VI):

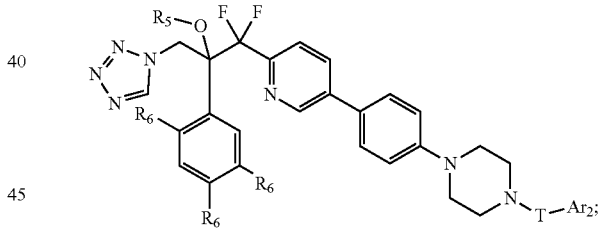

(VI)

or salt, solvate, hydrate or prodrug thereof.

In certain embodiments, each $R_6$ is independently hydrogen, fluoro, or chloro; and $Ar_2$ is phenyl or pyridyl.

Another aspect is a compound of formula (VII):

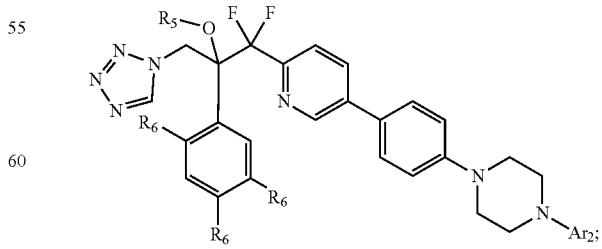

(VII)

or salt, solvate, hydrate or prodrug thereof.

In certain embodiments, each $R_6$ is independently hydrogen, fluoro, or chloro; and $Ar_2$ is phenyl or pyridyl.

Another aspect is a compound of formula (VIII):

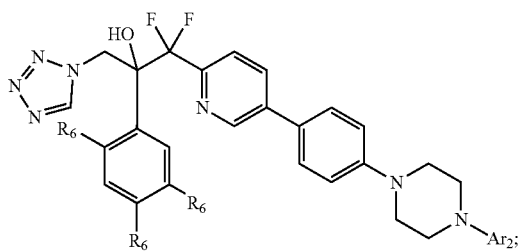

(VIII)

or salt, solvate, hydrate or prodrug thereof.

In certain embodiments, each RP is independently hydrogen, fluoro, or chloro; and $Ar_2$ is phenyl or pyridyl.

Another aspect is a compound of formula (IX):

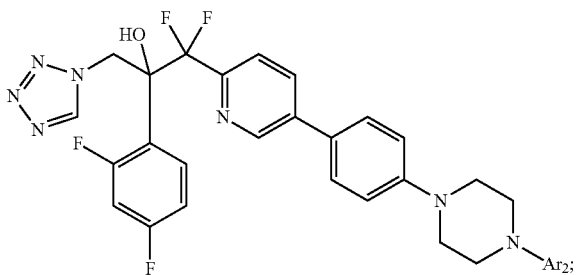

(IX)

or salt, solvate, hydrate or prodrug thereof.

In certain embodiments, $Ar_2$ is phenyl or pyridyl.

Another aspect is a compound of formula (X):

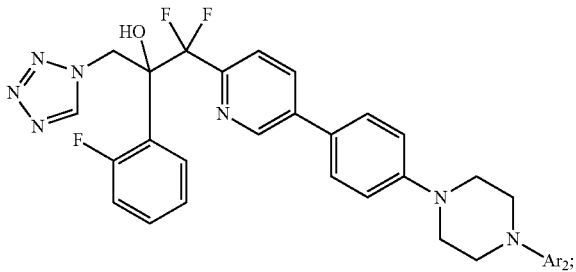

(X)

or salt, solvate, hydrate or prodrug thereof.

In certain embodiments, $Ar_2$ is phenyl or pyridyl.

Another aspect is a compound of formula (XI):

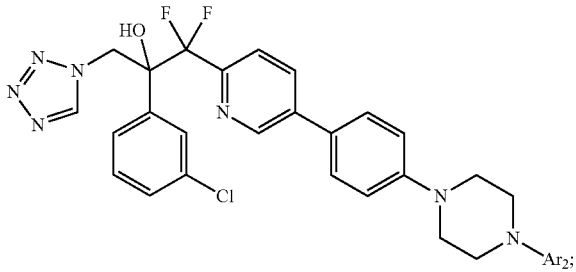

(XI)

or salt, solvate, hydrate or prodrug thereof.

In certain embodiments, $Ar_2$ is phenyl or pyridyl.

In one aspect, the compound of any of the formulae herein (e.g., formulae I-XI) is that wherein the compound inhibits (or is identified to inhibit) lanosterol demethylase (CYP51).

In one aspect, the compound of any of the formulae herein (e.g., formulae I-XI) is that wherein the compound is identified as having an activity range against a target enzyme (e.g., C. albicans MIC <1.0 µg/mL and A. fumigatus MIC ≤64 µg/mL) in vitro and/or in vivo.

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions. The compounds can also attain affinity through weaker interactions with the metal such as van der Waals interactions, pi cation interactions, pi-anion interactions, dipole-dipole interactions, ion-dipole interactions. In one aspect, the compound is identified as having a bonding interaction with the metal via the 1-tetrazolyl moiety; in another aspect, the compound is identified as having a bonding interaction with the metal via the N2 of the 1-tetrazolyl moiety; in another aspect, the compound is identified as having a bonding interaction with the metal via the N3 of the 1-tetrazolyl moiety; in another aspect, the compound is identified as having a bonding interaction with the metal via the N4 of the 1-tetrazolyl moiety. In one aspect, the compound is identified as having a bonding interaction with the metal via the 2-tetrazolyl moiety; in another aspect, the compound is identified as having a bonding interaction with the metal via the N1 of the 2-tetrazolyl moiety; in another aspect, the compound is identified as having a bonding interaction with the metal via the N3 of the 2-tetrazolyl moiety; in another aspect, the compound is identified as having a bonding interaction with the metal via the N4 of the 2-tetrazolyl moiety.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In certain instances, the compounds of the invention are selected from the following of any of the formulae herein (e.g., formulae I-XI) (and pharmaceutically acceptable salts, solvates, or hydrates thereof)

(R)-4-(4-(4-(6-(2-(2,4-difluorophenyl)-1,1-difluoro-2-hydroxy-3-(1H-tetrazol-1-yl)propyl)pyridin-3-yl)phenyl) piperazin-1-yl)benzonitrile (1);

(R)-2-(2,4-difluorophenyl)-1,1-difluoro-1-(5-(4-(4-(4-fluorophenyl)piperazin-1-yl)phenyl)pyridin-2-yl)-3-(1H-tetrazol-1-yl)propan-2-ol (2);

(2R)-2-(2,4-difluorophenyl)-1,1-difluoro-3-(1H-tetrazol-1-yl)-1-(5-(4-(4-(4-(2,2,2-trifluoro-1-hydroxyethyl)phenyl) piperazin-1-yl)phenyl)pyridin-2-yl)propan-2-ol (3);

(2R)-1-(5-(4-(4-(4-(1-amino-2,2,2-trifluoroethyl)phenyl) piperazin-1-yl)phenyl)pyridin-2-yl)-2-(2,4-difluorophenyl)-1,1-difluoro-3-(1H-tetrazol-1-yl)propan-2-ol (4);

(2R)-2-(2,4-difluorophenyl)-1,1-difluoro-1-(5-(4-(4-(3-fluoro-4-(2,2,2-trifluoro-1-hydroxyethyl)phenyl)piperazin-1-yl)phenyl)pyridin-2-yl)-3-(1H-tetrazol-1-yl)propan-2-ol (5);

(2R)-2-(2,4-difluorophenyl)-1,1-difluoro-3-(1H-tetrazol-1-yl)-1-(5-(4-(4-(6-(2,2,2-trifluoro-1-hydroxyethyl)pyridin-3-yl)piperazin-1-yl)phenyl)pyridin-2-yl)propan-2-ol (6);

(R)-5-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)picolinonitrile (7);

(R)-4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-2-fluorobenzonitrile (8);

(R)-4-(4-(4-(6-(2-(2,4-difluorophenyl)-1,1-difluoro-2-hydroxy-3-(1H-tetrazol-1-yl)propyl)pyridin-3-yl)-2-fluorophenyl)piperazin-1-yl)-3-fluorobenzonitrile (9);

(R)-4-(4-(4-(6-(2-(2,4-difluorophenyl)-1,1-difluoro-2-hydroxy-3-(1H-tetrazol-1-yl)propyl)pyridin-3-yl)-2-fluorophenyl)piperazin-1-yl)benzonitrile (10);

(R)-4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-3-fluorobenzonitrile (11);

(R)-6-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)nicotinonitrile (12);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-3,3,3-trifluoropropan-1-ol (13);

(R)-1-(5-(4-(4-(4-aminophenyl)piperazin-1-yl)phenyl)pyridin-2-yl)-2-(2,4-difluorophenyl)-1,1-difluoro-3-(1H-tetrazol-1-yl)propan-2-ol (14);

(−)-2-(2,5-difluorophenyl)-1,1-difluoro-3-(1H-tetrazol-1-yl)-1-(5-(4-(4-(4-(2,2,2-trifluoro-1-hydroxyethyl)phenyl)piperazin-1-yl)phenyl)pyridin-2-yl)propan-2-ol (15(−));

(+)-2-(2,5-difluorophenyl)-1,1-difluoro-3-(1H-tetrazol-1-yl)-1-(5-(4-(4-(4-(2,2,2-trifluoro-1-hydroxyethyl)phenyl)piperazin-1-yl)phenyl)pyridin-2-yl)propan-2-ol (15(+));

(2R)-2-(2,4-difluorophenyl)-1,1-difluoro-3-(4H-1,2,4-triazol-4-yl)-1-(5-(4-(4-(4-(2,2,2-trifluoro-1-hydroxyethyl)phenyl)piperazin-1-yl)phenyl)pyridin-2-yl)propan-2-ol (16);

(R)-4-((4-(4-(6-(2-(2,4-difluorophenyl)-1,1-difluoro-2-hydroxy-3-(1H-tetrazol-1-yl)propyl)pyridin-3-yl)phenyl)piperazin-1-yl)methyl)benzonitrile (17);

(R)-4-(4-(4-(6-(2-(2,4-difluorophenyl)-1,1-difluoro-2-hydroxy-3-(1H-tetrazol-1-yl)propyl)pyridin-3-yl)benzyl)piperazin-1-yl)benzonitrile (18);

(R)-4-(4-(4-(6-(2-(2,4-difluorophenyl)-1,1-difluoro-2-hydroxy-3-(1H-tetrazol-1-yl)propyl)pyridin-3-yl)benzoyl)piperazin-1-yl)benzonitrile (19);

4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (20);

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-3-((2S,3S)-2-hydroxypentan-3-yl)urea (21);

(R)-4-(4-(4-(6-(2-(2,4-difluorophenyl)-1,1-difluoro-2-hydroxy-3-(1H-tetrazol-1-yl)propyl)pyridin-3-yl)phenyl)piperidin-1-yl)benzonitrile (22);

(R)-4-(4-(4-(6-(2-(2,4-difluorophenyl)-1,1-difluoro-2-hydroxy-3-(1H-tetrazol-1-yl)propyl)pyridin-3-yl)phenyl)piperazine-1-carbonyl)benzonitrile (23);

(R)-4-(4-(4-(6-(2-(2,4-difluorophenyl)-1,1-difluoro-2-hydroxy-3-(1H-tetrazol-1-yl)propyl)pyridin-3-yl)phenyl)-3-oxopiperazin-1-yl)benzonitrile (24);

(R)-4-(4-(4-(6-(2-(2,4-difluorophenyl)-1,1-difluoro-2-hydroxy-3-(1H-tetrazol-1-yl)propyl)pyridin-3-yl)phenyl)-2-oxopiperazin-1-yl)benzonitrile (25);

(R)-4-(1-(4-(6-(2-(2,4-difluorophenyl)-1,1-difluoro-2-hydroxy-3-(1H-tetrazol-1-yl)propyl)pyridin-3-yl)phenyl)piperidin-4-yl)benzonitrile (26);

(R)-4-(4-(4-(6-(2-(2,4-difluorophenyl)-1,1-difluoro-2-hydroxy-3-(1H-tetrazol-1-yl)propyl)pyridin-3-yl)benzyl)-3-oxopiperazin-1-yl)benzonitrile (27);

(R)-4-((4-(4-(6-(2-(2,4-difluorophenyl)-1,1-difluoro-2-hydroxy-3-(1H-tetrazol-1-yl)propyl)pyridin-3-yl)phenyl)-2-oxopiperazin-1-yl)methyl)benzonitrile (28);

(R)-4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)benzaldehyde (29);

(R)-2-(2,4-difluorophenyl)-1-(5-(4-(4-(4-((dimethylamino)methyl)phenyl)piperazin-1-yl)phenyl)pyridin-2-yl)-1,1-difluoro-3-(1H-tetrazol-1-yl)propan-2-ol (30);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2,2,2-trifluoroethyl dihydrogen phosphate (31);

(R)-5-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)picolinaldehyde (32);

(R)-2-(2,4-difluorophenyl)-1-(5-(4-(4-(6-((dimethylamino)methyl)pyridin-3-yl)piperazin-1-yl)phenyl)pyridin-2-yl)-1,1-difluoro-3-(1H-tetrazol-1-yl)propan-2-ol (33);

(2R)-2-(2,4-difluorophenyl)-1,1-difluoro-3-(1H-tetrazol-1-yl)-1-(5-(4-(4-(5-(2,2,2-trifluoro-1-hydroxyethyl)pyridin-2-yl)piperazin-1-yl)phenyl)pyridin-2-yl)propan-2-ol (34);

(R)-2-(2,4-difluorophenyl)-1,1-difluoro-3-(1H-tetrazol-1-yl)-1-(5-(4-(4-(2-(trifluoromethyl)-1H-benzo[d]imidazol-5-yl)piperazin-1-yl)phenyl)pyridin-2-yl)propan-2-ol (35);

4-(4-(4-(6-(2-cyclopropyl-1,1-difluoro-2-hydroxy-3-(1H-tetrazol-1-yl)propyl)pyridin-3-yl)phenyl)piperazin-1-yl)benzonitrile (36);

4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-1-(2-hydroxypentan-3-yl)pyridin-2(1H)-one (37);

4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38);

(−)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(−));

(+)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(+));

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)propan-1-ol (39);

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-2-methylpropan-1-ol (40);

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-3-methylbutan-1-ol (41);

(2R)-1-(5-(4-(4-(4-(cyclopropyl(hydroxy)methyl)phenyl)piperazin-1-yl)phenyl)pyridin-2-yl)-2-(2,4-difluorophenyl)-1,1-difluoro-3-(1H-tetrazol-1-yl)propan-2-ol (42);

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-2,2-dimethylpropan-1-ol (43);

(2R)-2-(2,4-difluorophenyl)-1,1-difluoro-1-(5-(4-(4-(6-(1-hydroxyethyl)pyridin-3-yl)piperazin-1-yl)phenyl)pyridin-2-yl)-3-(1H-tetrazol-1-yl)propan-2-ol (44);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2-methylpropan-1-ol (45);

(2R)-1-(5-(4-(4-(6-(cyclopropyl(hydroxy)methyl)pyridin-3-yl)piperazin-1-yl)phenyl)pyridin-2-yl)-2-(2,4-difluorophenyl)-1,1-difluoro-3-(1H-tetrazol-1-yl)propan-2-ol (46);

(R)-2-(2,4-difluorophenyl)-1,1-difluoro-1-(5-(4-(4-(6-(2-hydroxypropan-2-yl)pyridin-3-yl)piperazin-1-yl)phenyl)pyridin-2-yl)-3-(1H-tetrazol-1-yl)propan-2-ol (47);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)propan-1-ol (48);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-3-methylbutan-1-ol (49);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2,2-dimethylpropan-1-ol (50);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyrimidin-2-yl)-3,3,3-trifluoropropan-1-ol (51);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-isopropyl-1H-1,2,4-triazol-5(4H)-one (52);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-methyl-1H-1,2,4-triazol-5(4H)-one (53);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-ethyl-1H-1,2,4-triazol-5(4H)-one (54);

1-(sec-butyl)-4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,4-triazol-5(4H)-one (55);

(2R)-2-(2,4-difluorophenyl)-1,1-difluoro-1-(5-(4-(4-(4-(1-hydroxyethyl)phenyl)piperazin-1-yl)phenyl)pyridin-2-yl)-3-(1H-tetrazol-1-yl)propan-2-ol (56);

4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-N-((2S,3S)-2-hydroxypentan-3-yl)benzamide (57);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-(2,2,2-trifluoroethyl)-1H-1,2,4-triazol-5(4H)-one (58);

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-2-methylbutan-1-ol (59);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,4-triazol-5(4H)-one (60);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-(2-(dimethylamino)ethyl)-1H-1,2,4-triazol-5(4H)-one (61);

(2R)-2-(2,4-difluorophenyl)-1,1-difluoro-3-(1H-tetrazol-1-yl)-1-(5-(4-(4-(5-(2,2,2-trifluoro-1-hydroxyethyl)thiophen-2-yl)piperazin-1-yl)phenyl)pyridin-2-yl)propan-2-ol (62);

(+)-4-(4-(4-(4-(6-(1,1-difluoro-2-(4-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (63(+));

(+)-4-(4-(4-(4-(6-(1,1-difluoro-2-(3-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (64(+));

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2-methylbutan-1-ol (65);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-(pentan-3-yl)-1H-1,2,4-triazol-5(4H)-one (66);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-(2-hydroxy-2-methylpropyl)-1H-1,2,4-triazol-5(4H)-one (67);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2,3-dimethylbutan-1-ol (68);

(R)-2-(2,4-difluorophenyl)-1,1-difluoro-1-(5-(4-(4-(2-isopropyl-1H-benzo[d]imidazol-6-yl)piperazin-1-yl)phenyl)pyridin-2-yl)-3-(1H-tetrazol-1-yl)propan-2-ol (69);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-3-fluoropyridin-2-yl)-3,3,3-trifluoropropan-1-ol (70);

3-(6-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-1H-benzo[d]imidazol-2-yl)pentan-2-ol (71);

(R)-2-(2,4-difluorophenyl)-1,1-difluoro-1-(5-(4-(4-(4-(2-hydroxypropan-2-yl)phenyl)piperazin-1-yl)phenyl)pyridin-2-yl)-3-(1H-tetrazol-1-yl)propan-2-ol (72);

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)benzo[d]thiazole-6-carbonitrile (73);

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-1H-benzo[d]imidazole-6-carbonitrile (74);

4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1-(3-hydroxybutan-2-yl)-1H-1,2,4-triazol-5(4H)-one (75);

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)benzo[d]thiazole-5-carbonitrile (76);

(R)-2-(2,4-difluorophenyl)-1,1-difluoro-3-(1H-tetrazol-1-yl)-1-(5-(4-(4-(2-(2,2,2-trifluoroethyl)-1H-benzo[d]imidazol-6-yl)piperazin-1-yl)phenyl)pyridin-2-yl)propan-2-ol (77);

(R)-2-(2,4-difluorophenyl)-1,1-difluoro-1-(5-(4-(4-(2-isobutyl-1H-benzo[d]imidazol-6-yl)piperazin-1-yl)phenyl)pyridin-2-yl)-3-(1H-tetrazol-1-yl)propan-2-ol (78);

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-1-methyl-1H-benzo[d]imidazole-6-carbonitrile (79);

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-1-methyl-1H-benzo[d]imidazole-5-carbonitrile (80);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-neopentyl-1H-1,2,4-triazol-5(4H)-one (81);

4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (82);

4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-N-((2S,3S)-2-hydroxypentan-3-yl)-N-methylbenzamide (83);

(+)-4-(4-(4-(4-(6-(1,1-difluoro-2-(3-fluorophenyl)-2-hydroxy-3-(3-methyl-1H-1,2,4-triazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (84(+));

(+)-4-(4-(4-(4-(6-(1,1-difluoro-2-(3-fluorophenyl)-2-hydroxy-3-(5-methyl-1H-1,2,4-triazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (85(+));

(2R)-2-(2,4-difluorophenyl)-1,1-difluoro-3-(1H-tetrazol-1-yl)-1-(5-(4-(4-(3-(2,2,2-trifluoro-1-hydroxyethyl)phenyl)piperazin-1-yl)phenyl)pyridin-2-yl)propan-2-ol (86);

(R)-4-(5-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-1-(2,2,2-trifluoroethyl)-1H-1,2,4-triazol-5(4H)-one (87);

2-amino-N-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-4,4,4-trifluorobutanamide (58);

N-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-2-ethyl-3-hydroxybutanamide (89);

(R)-2-(2,4-difluorophenyl)-1,1-difluoro-1-(5-(4-(4-(2-neopentyl-1H-benzo[d]imidazol-6-yl)piperazin-1-yl)phenyl)pyridin-2-yl)-3-(1H-tetrazol-1-yl)propan-2-ol (90);

(R)-1-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-3-isopropyl-1H-imidazol-2(3H)-one (91);

(2S,3S)-3-(3-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,4-triazol-1-yl)pentan-2-ol (92);

4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1-(2-hydroxypentan-3-yl)-1H-1,2,4-triazol-5(4H)-one (93);

(2R)-2-(2,4-difluorophenyl)-1,1-difluoro-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (94);

(2S,3S)-3-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-1-yl)pentan-2-ol (95);

(R)-1-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-3-(2,2,2-trifluoroethyl)-1H-imidazol-2(3H)-one (96);

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-3-(2-hydroxypentan-3-yl)-1H-imidazol-2(3H)-one (97);

(R)-1-(5-(4-(4-(1-benzyl-1H-benzo[d]imidazol-6-yl)piperazin-1-yl)phenyl)pyridin-2-yl)-2-(2,4-difluorophenyl)-1,1-difluoro-3-(1H-tetrazol-1-yl)propan-2-ol (98);

(2R)-1-(5-(4-(4-(6-(1,1-difluoro-2-hydroxypropyl)pyridin-3-yl)piperazin-1-yl)phenyl)pyridin-2-yl)-2-(2,4-difluorophenyl)-1,1-difluoro-3-(1H-tetrazol-1-yl)propan-2-ol (99);

(2R)-2-(2,4-difluorophenyl)-1,1-difluoro-1-(5-(4-(4-(3-fluoro-5-(2,2,2-trifluoro-1-hydroxyethyl)phenyl)piperazin-1-yl)phenyl)pyridin-2-yl)-3-(1H-tetrazol-1-yl)propan-2-ol (100);

4-(4-(4-(6-(2-(2,4-difluorophenyl)-1,1-difluoro-2-hydroxy-3-(1H-pyrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (101);

(−)-4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (102(−));

(+)-4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (102(+));

4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1-(2-hydroxy-4-methylpentan-3-yl)-1H-1,2,4-triazol-5(4H)-one (103);

(2R)-2-(2,4-difluorophenyl)-1,1-difluoro-3-(1H-tetrazol-1-yl)-1-(5-(4-(4-(2-(2,2,2-trifluoro-1-hydroxyethyl)pyridin-4-yl)piperazin-1-yl)phenyl)pyridin-2-yl)propan-2-ol (104);

N-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-4,4,4-trifluoro-2-hydroxybutanamide (105);

(+)-4-(4-(4-(4-(6-(1,1-difluoro-2-(2-fluorophenyl)-2-hydroxy-3-(3-(trifluoromethyl)-1H-1,2,4-triazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (106(+));

4-(4-(4-(4-(6-(2-(2,4-difluorophenyl)-1,1-difluoro-2-hydroxy-3-(2H-1,2,3-triazol-2-yl)propyl)pyridin-3-yl)phenyl)piperazin-1-yl)phenyl)-1-((2S,3S)-2-hydroxypentan-3-yl)-1H-1,2,4-triazol-5(4H)-one (107);

(−)-1,1-difluoro-2-(2-fluorophenyl)-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (108(−));

(+)-1,1-difluoro-2-(2-fluorophenyl)-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (108(+));

(−)-4-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (109(−));

(+)-4-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (109(+));

(−)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (110(−));

(+)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (110(+));

(2R)-2-(2,4-difluorophenyl)-1,1-difluoro-3-(1H-tetrazol-1-yl)-1-(5-(4-(4-(6-(4-(2,2,2-trifluoro-1-hydroxyethyl)-1H-

1,2,3-triazol-1-yl)pyridin-3-yl)piperazin-1-yl)phenyl)
pyridin-2-yl)propan-2-ol (111);

(2S,3S)-3-(4-(4-(4-(4-(6-((R)-2-(2,4-difluorophenyl)-1,1-
difluoro-2-hydroxy-3-(1H-tetrazol-1-yl)propyl)pyridin-
3-yl)phenyl)piperazin-1-yl)phenyl)-5-oxo-4,5-dihydro-
1H-1,2,4-triazol-1-yl)pentan-2-yl dihydrogen phosphate
(112);

(2S,3S)-3-(4-(5-(4-(4-(6-((R)-2-(2,4-difluorophenyl)-1,1-
difluoro-2-hydroxy-3-(1H-tetrazol-1-yl)propyl)pyridin-
3-yl)phenyl)piperazin-1-yl)pyridin-2-yl)-5-oxo-4,5-di-
hydro-1H-1,2,4-triazol-1-yl)pentan-2-yl dihydrogen
phosphate (113);

(+)-(2S,3S)-3-(4-(4-(4-(4-(6-(1,1-difluoro-2-(2-fluorophe-
nyl)-2-hydroxy-3-(1H-tetrazol-1-yl)propyl)pyridin-3-yl)
phenyl)piperazin-1-yl)phenyl)-5-oxo-4,5-dihydro-1H-1,
2,4-triazol-1-yl)pentan-2-yl dihydrogen phosphate (114);

4-(4-(4-(4-(6-(1,1-difluoro-2-(2-fluorophenyl)-2-hydroxy-
3-(1H-tetrazol-5-yl)propyl)pyridin-3-yl)phenyl)piper-
azin-1-yl)phenyl)-1-((2S,3S)-2-hydroxypentan-3-yl)-1H-
1,2,4-triazol-5(4H)-one (115);

4-(4-(4-(4-(6-(1,1-difluoro-2-(2-fluorophenyl)-2-hydroxy-
3-(2H-1,2,3-triazol-2-yl)propyl)pyridin-3-yl)phenyl)pip-
erazin-1-yl)phenyl)-1-((2S,3S)-2-hydroxypentan-3-yl)-
1H-1,2,4-triazol-5(4H)-one (116);

4-(4-(4-(4-(6-(1,1-difluoro-2-(2-fluorophenyl)-2-hydroxy-
3-(1H-pyrazol-1-yl)propyl)pyridin-3-yl)phenyl)piper-
azin-1-yl)phenyl)-1-((2S,3S)-2-hydroxypentan-3-yl)-1H-
1,2,4-triazol-5(4H)-one (117);

1-(5-(4-(4-(6-((R)-2-(2,4-difluorophenyl)-1,1-difluoro-2-
hydroxy-3-(1H-tetrazol-1-yl)propyl)pyridin-3-yl)phenyl)
piperazin-1-yl)pyridin-2-yl)-3,3-dimethylbutan-1-ol
(118);

(−)-1-(5-(4-(4-(6-(1,1-difluoro-2-(3-fluorophenyl)-2-hy-
droxy-3-(1H-tetrazol-1-yl)propyl)pyridin-3-yl)phenyl)
piperazin-1-yl)pyridin-2-yl)-3,3,3-trifluoropropan-1-ol
(119(−));

(+)-1-(5-(4-(4-(6-(1,1-difluoro-2-(3-fluorophenyl)-2-hy-
droxy-3-(1H-tetrazol-1-yl)propyl)pyridin-3-yl)phenyl)
piperazin-1-yl)pyridin-2-yl)-3,3,3-trifluoropropan-1-ol
(119(+));

(−)-1-(5-(4-(4-(6-(2-(2,4-difluorophenyl)-1,1-difluoro-2-
hydroxy-3-(1H-1,2,4-triazol-1-yl)propyl)pyridin-3-yl)
phenyl)piperazin-1-yl)pyridin-2-yl)-3,3,3-trifluoropro-
pan-1-ol (120(−));

(+)-1-(5-(4-(4-(6-(2-(2,4-difluorophenyl)-1,1-difluoro-2-
hydroxy-3-(1H-1,2,4-triazol-1-yl)propyl)pyridin-3-yl)
phenyl)piperazin-1-yl)pyridin-2-yl)-3,3,3-trifluoropro-
pan-1-ol (120(+));

(−)-1-(5-(4-(4-(6-(1,1-difluoro-2-(4-fluorophenyl)-2-hy-
droxy-3-(1H-tetrazol-1-yl)propyl)pyridin-3-yl)phenyl)
piperazin-1-yl)pyridin-2-yl)-3,3,3-trifluoropropan-1-ol
(121(−));

(+)-1-(5-(4-(4-(6-(1,1-difluoro-2-(4-fluorophenyl)-2-hy-
droxy-3-(1H-tetrazol-1-yl)propyl)pyridin-3-yl)phenyl)
piperazin-1-yl)pyridin-2-yl)-3,3,3-trifluoropropan-1-ol
(121(+));

(−)-1-(5-(4-(4-(6-(1,1-difluoro-2-(2-fluorophenyl)-2-hy-
droxy-3-(1H-tetrazol-1-yl)propyl)pyridin-3-yl)phenyl)
piperazin-1-yl)pyridin-2-yl)-3,3,3-trifluoropropan-1-ol
(122(−));

(+)-1-(5-(4-(4-(6-(1,1-difluoro-2-(2-fluorophenyl)-2-hy-
droxy-3-(1H-tetrazol-1-yl)propyl)pyridin-3-yl)phenyl)
piperazin-1-yl)pyridin-2-yl)-3,3,3-trifluoropropan-1-ol
(122(+));

(−)-4-(4-(4-(4-(6-(2-(2,4-difluorophenyl)-1,1-difluoro-2-
hydroxy-3-(1H-1,2,4-triazol-1-yl)propyl)pyridin-3-yl)
phenyl)piperazin-1-yl)phenyl)-1-((2S,3S)-2-hydroxypen-
tan-3-yl)-1H-1,2,4-triazol-5(4H)-one (123(−));

(+)-4-(4-(4-(4-(6-(2-(2,4-difluorophenyl)-1,1-difluoro-2-
hydroxy-3-(1H-1,2,4-triazol-1-yl)propyl)pyridin-3-yl)
phenyl)piperazin-1-yl)phenyl)-1-((2S,3S)-2-hydroxypen-
tan-3-yl)-1H-1,2,4-triazol-5(4H)-one (123(+));

4-(5-(4-(4-(6-((R)-2-(2,4-difluorophenyl)-1,1-difluoro-2-
hydroxy-3-(1H-tetrazol-1-yl)propyl)pyridin-3-yl)phenyl)
piperazin-1-yl)-3-fluoropyridin-2-yl)-1-((2S,3S)-2-hy-
droxypentan-3-yl)-1H-1,2,4-triazol-5(4H)-one (124);

4-(4-(4-(4-(6-(2-(3-chlorophenyl)-1,1-difluoro-2-hydroxy-
3-(2H-1,2,3-triazol-2-yl)propyl)pyridin-3-yl)phenyl)pip-
erazin-1-yl)phenyl)-1-((2S,3S)-2-hydroxypentan-3-yl)-
1H-1,2,4-triazol-5(4H)-one (125);

4-(4-(4-(4-(6-(2-(3-chlorophenyl)-1,1-difluoro-2-hydroxy-
3-(1H-pyrazol-1-yl)propyl)pyridin-3-yl)phenyl)piper-
azin-1-yl)phenyl)-1-((2S,3S)-2-hydroxypentan-3-yl)-1H-
1,2,4-triazol-5(4H)-one (126);

4-(4-(4-(4-(6-(2-(3-chlorophenyl)-1,1-difluoro-2-hydroxy-
3-(1H-tetrazol-1-yl)propyl)pyridin-3-yl)phenyl)piper-
azin-1-yl)phenyl)-1-((2S,3S)-2-hydroxypentan-3-yl)-1H-
1,2,4-triazol-5(4H)-one (127);

(−)-4-(4-(4-(4-(6-(2-(3-chlorophenyl)-1,1-difluoro-2-hy-
droxy-3-(1H-tetrazol-1-yl)propyl)pyridin-3-yl)phenyl)
piperazin-1-yl)phenyl)-1-((2S,3S)-2-hydroxypentan-3-
yl)-1H-1,2,4-triazol-5(4H)-one (127(−));

(+)-4-(4-(4-(4-(6-(2-(3-chlorophenyl)-1,1-difluoro-2-hy-
droxy-3-(1H-tetrazol-1-yl)propyl)pyridin-3-yl)phenyl)
piperazin-1-yl)phenyl)-1-((2S,3S)-2-hydroxypentan-3-
yl)-1H-1,2,4-triazol-5(4H)-one (127(+));

(+)-(2S,3S)-3-(4-(5-(4-(4-(6-(1,1-difluoro-2-(2-fluorophe-
nyl)-2-hydroxy-3-(1H-tetrazol-1-yl)propyl)pyridin-3-yl)
phenyl)piperazin-1-yl)pyridin-2-yl)-5-oxo-4,5-dihydro-
1H-1,2,4-triazol-1-yl)pentan-2-yl dihydrogen phosphate
(128);

1-(1-(4-(4-(4-(6-((R)-2-(2,4-difluorophenyl)-1,1-difluoro-2-
hydroxy-3-(1H-tetrazol-1-yl)propyl)pyridin-3-yl)phenyl)
piperazin-1-yl)phenyl)-1H-1,2,3-triazol-4-yl)-2,2,2-trif-
luoroethyl dihydrogen phosphate (129); or (2S,3S)-3-(4-(5-(4-(4-(6-(1,1-difluoro-2-(2-fluorophenyl)-
2-hydroxy-3-(1H-tetrazol-1-yl)propyl)pyridin-3-yl)phe-
nyl)piperazin-1-yl)pyridin-2-yl)-5-oxo-4,5-dihydro-1H-
1,2,4-triazol-1-yl)pentan-2-yl 2-(dimethylamino)acetate
(130).

In certain instances, the compounds of the invention are selected from the following of any of the formulae herein (e.g., formulae I-XI) (and pharmaceutically acceptable salts, solvates, or hydrates thereof)

(2R)-2-(2,4-difluorophenyl)-1,1-difluoro-3-(1H-tetrazol-1-
yl)-1-(5-(4-(4-(6-(2,2,2-trifluoro-1-hydroxyethyl)pyridin-
3-yl)piperazin-1-yl)phenyl)pyridin-2-yl)propan-2-ol (6);

1-(5-(4-(4-(6-((R)-2-(2,4-difluorophenyl)-1,1-difluoro-2-
hydroxy-3-(1H-tetrazol-1-yl)propyl)pyridin-3-yl)phenyl)
piperazin-1-yl)pyridin-2-yl)-3,3,3-trifluoropropan-1-ol
(13);

1-(5-(4-(4-(6-((R)-2-(2,4-difluorophenyl)-1,1-difluoro-2-
hydroxy-3-(1H-tetrazol-1-yl)propyl)pyridin-3-yl)phenyl)
piperazin-1-yl)pyridin-2-yl)-2,2,2-trifluoroethyl dihydro-
gen phosphate (31);

4-(4-(4-(4-(6-(1,1-difluoro-2-(2-fluorophenyl)-2-hydroxy-
3-(1H-tetrazol-1-yl)propyl)pyridin-3-yl)phenyl)piper-
azin-1-yl)phenyl)-1-((2S,3S)-2-hydroxypentan-3-yl)-1H-
1,2,4-triazol-5(4H)-one (38);

(−)-4-(4-(4-(4-(6-(1,1-difluoro-2-(2-fluorophenyl)-2-hy-
droxy-3-(1H-tetrazol-1-yl)propyl)pyridin-3-yl)phenyl)
piperazin-1-yl)phenyl)-1-((2S,3S)-2-hydroxypentan-3-
yl)-1H-1,2,4-triazol-5(4H)-one (38(−));

(+)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(+));

(+)-4-(4-(4-(4-(6-(1,1-difluoro-2-(4-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (63(+));

(+)-4-(4-(4-(4-(6-(1,1-difluoro-2-(3-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (64(+));

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-3-fluoropyridin-2-yl)-3,3,3-trifluoropropan-1-ol (70);

4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (82);

(2R)-2-(2,4-difluorophenyl)-1,1-difluoro-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (94);

(2S,3S)-3-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-1-yl)pentan-2-ol (95);

(−)-4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (102(−));

(+)-4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (102(+));

(−)-1,1-difluoro-2-(2-fluorophenyl)-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (108(−));

(+)-1,1-difluoro-2-(2-fluorophenyl)-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (108(+));

(−)-4-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (109(−));

(+)-4-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (109(+));

(−)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (110(−));

(+)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (110(+));

(2R)-2-(2,4-difluorophenyl)-1,1-difluoro-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (111);

(2S,3S)-3-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-5-oxo-4,5-dihydro-1H-1,2,4-triazol-1-yl)pentan-2-yl dihydrogen phosphate (112);

(2S,3S)-3-(4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl dihydrogen phosphate (113);

(+)-(2S,3S)-3-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-5-oxo-4,5-dihydro-1H-1,2,4-triazol-1-yl)pentan-2-yl dihydrogen phosphate (114);

(−)-1-(5-(4-(4-(6-(1,1-difluoro-2-(3-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (119(−));

(+)-1-(5-(4-(4-(6-(1,1-difluoro-2-(3-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (119(+));

(−)-1-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (121(−));

(+)-1-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (121(+));

(−)-1-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (122(−));

(+)-1-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (122(+));

4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-3-fluoropyridin-2-yl)-1-((2S,3S)-2-hydroxypentan-3-yl)-1H-1,2,4-triazol-5(4H)-one (124);

(+)-4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127);

(−)-4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127(−));

(+)-4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127(+));

(+)-(2S,3S)-3-(4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl dihydrogen phosphate (128);

1-(1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-4-yl)-2,2,2-trifluoroethyl dihydrogen phosphate (129); or (2S,3S)-3-(4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl 2-(dimethylamino)acetate (130).

In certain instances, the compounds of the invention are selected from the following of any of the formulae herein (e.g., formulae I-XI) (and pharmaceutically acceptable salts, solvates, or hydrates thereof)

(2R)-2-(2,4-difluorophenyl)-1,1-difluoro-3-(1H-tetrazol-1-yl)-1-(5-(4-(4-(6-(2,2,2-trifluoro-1-hydroxyethyl)pyridin-3-yl)piperazin-1-yl)phenyl)pyridin-2-yl)propan-2-ol (6);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-3,3,3-trifluoropropan-1-ol (13);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2,2,2-trifluoroethyl dihydrogen phosphate (31);

4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38);

(+)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(+));

(+)-4-(4-(4-(4-(6-(1,1-difluoro-2-(4-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (63(+));

(+)-4-(4-(4-(4-(6-(1,1-difluoro-2-(3-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (64(+));

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-3-fluoropyridin-2-yl)-3,3,3-trifluoropropan-1-ol (70);

4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (82);

(2R)-2-(2,4-difluorophenyl)-1,1-difluoro-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (94);

(2S,3S)-3-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-1-yl)pentan-2-ol (95);

(+)-4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (102(+));

(+)-1,1-difluoro-2-(2-fluorophenyl)-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (108(+));

(+)-4-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (109(+));

(+)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (110(+));

(2R)-2-(2,4-difluorophenyl)-1,1-difluoro-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (111);

(2S,3S)-3-(4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-5-oxo-4,5-dihydro-1H-1,2,4-triazol-1-yl)pentan-2-yl dihydrogen phosphate (112);

(2S,3S)-3-(4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl dihydrogen phosphate (113);

(+)-(2S,3S)-3-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-5-oxo-4,5-dihydro-1H-1,2,4-triazol-1-yl)pentan-2-yl dihydrogen phosphate (114);

(+)-1-(5-(4-(4-(6-(1,1-difluoro-2-(3-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (119(+));

(+)-1-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (121(+));

(+)-1-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (122(+));

4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-3-fluoropyridin-2-yl)-1-((2S,3S)-2-hydroxypentan-3-yl)-1H-1,2,4-triazol-5(4H)-one (124);

(+)-(2S,3S)-3-(4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl dihydrogen phosphate (128);

1-(1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-4-yl)-2,2,2-trifluoroethyl dihydrogen phosphate (129); or (2S,3S)-3-(4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl 2-(dimethylamino)acetate (130).

In certain instances, the compounds of the invention are selected from the following of any of the formulae herein (e.g., formulae I-XI) (and pharmaceutically acceptable salts, solvates, or hydrates thereof)

4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38);

(−)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(−));

(+)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(+));

4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127);

(−)-4-(4-(4-(4-(6-(2-(3-chlorophenyl)-1,1-difluoro-2-hydroxy-3-(1H-tetrazol-1-yl)propyl)pyridin-3-yl)phenyl)

piperazin-1-yl)phenyl)-1-((2S,3S)-2-hydroxypentan-3-yl)-1H-1,2,4-triazol-5(4H)-one (127(−)); or (+)-4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127(+)).

In another aspect, the invention provides a pharmaceutical composition comprising the compound of any of the formulae herein (e.g., formulae I-XI) and a pharmaceutically acceptable carrier.

In other aspects, the invention provides a method of modulating metalloenzyme activity in a subject, comprising contacting the subject with a compound of any of the formulae herein (e.g., formulae I-XI), in an amount and under conditions sufficient to modulate metalloenzyme activity.

In another aspect, the invention provides a method of treating a subject suffering from or susceptible to a disorder or disease, wherein the subject has been identified as in need of treatment for the disorder or disease, comprising administering to said subject in need thereof, an effective amount of a compound or pharmaceutical composition of any of the formulae herein (e.g., formulae I-XI), such that said subject is treated for said disorder.

In another aspect the subject is an animal other than a human.

The methods herein include those wherein the disorder or disease is associated with one or more of the following pathogenic fungi: *Absidia corymbifera, Ajellornyces dermatitidis, Arthroderma benhamiae, Arthroderma fulvum, Arthroderma gypseum, Arthroderma incurvaturn, Arthroderma otae, Arthroderma vanbreuseghemii, Aspergillus flavus, Aspergillus fumigates, Aspergillus niger, Blastomyces dermatitidis, Candida albicans, Candida glabrata, Candida guilliermondii, Candida krusei, Candida parapsilosis, Candida tropicalis, Candida pelliculosa, Cladophialophora carrionii, Coccidioides immitis, Cryptococcus neoformans, Cunninghamella sp., Epidermophyton floccosum, Exophiala dermatitidis, Filobasidiella neoformans, Fonsecaea pedrosoi, Fusarium solani, Geotrichum candidum, Histoplasma capsulaturn, Hortaea werneckii, Issatschenkia orientalis, Madurella grisae, Malassezia fur fur, Malassezia globosa, Malassezia obtusa, Malassezia pachydermatis, Malassezia restricta, Malassezia slooffiae, Malassezia sympodialis, Microsporum canis, Microsporum fulvum, Microsporum gypseum, Mucor circinelloides, Nectria haematococca, Paecilomyces variotii, Paracoccidioides brasiliensis, Penicillium marneffei, Pichia anomala, Pichia guilliermondii, Pneumocystis carinii, Pseudallescheria boydii, Rhizopus oryzae, Rhodotorula rubra, Scedosporium apiospernium, Schizophyllum commune, Sporothrix schenckii, Trichophyton mentagrophytes, Trichophyton rubrum, Trichophyton verrucosum, Trichophyton violaceum, Trichosporon asahii, Trichosporon cutaneum, Trichosporon inkin, Trichosporon mucoides*.

The methods herein include those wherein the disorder or disease is Aspergillosis, Blastomycosis, Candidiasis, Chromomycosis, Coccidioidomycosis, Cryptococcosis, Dermatophytoses, Histoplasmosis, Keratomycosis, Lobomycosis, *Malassezia* infection, Mucormycosis, Paracoccidioidomycosis, *Penicillium marneffei* infection, Phaeohyphomycosis, Pneumocyctis pneumonia, or Rhinosporidiosis.

The methods herein include those wherein the disorder or disease is Chagas disease (Genus *Trypanosoma*), African trypanosomiasis (Genus *Trypanosoma*), leishmaniasis (Genus *Leishmania*), tuberculosis (Genus *Mycobacterium*), leprosy (Genus *Mycobacterium*), malaria (Genus *Plasmodium*), or tinea (*capitis, corporis, pedis, tonsurans, versicolor*).

The methods herein include those wherein the disorder or disease is associated with aberrant Hedgehog signaling.

In certain embodiments, the disorder or disease associated with aberrant Hedgehog signaling is cancer. In certain embodiments, the cancer is brain cancer, lung cancer, breast cancer, prostate cancer, pancreatic cancer, hematological cancer, or skin cancer. In certain embodiments, the skin cancer is basal cell carcinoma. In certain embodiments, the brain cancer is medullablastoma or glioma. In certain embodiments, the hematological cancer is leukemia (e.g., AML, CML, CLL, or ALL).

In one aspect, the invention provides a method of treating a subject suffering from or susceptible to a metalloenzyme-related disorder or disease, comprising administering to the subject an effective amount of a compound or pharmaceutical composition of any of the formulae herein (e.g., formulae I-XI).

In another aspect, the invention provides a method of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of any of the formulae herein (e.g., formulae I-XI), such that said subject is treated for said disorder.

In another aspect, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any of the formulae herein (e.g., formulae I-XI), such that metalloenzyme activity in said subject is modulated (e.g., down regulated, inhibited).

The methods herein include those wherein the disease or disorder is mediated by any of 4-hydroxyphenyl pyruvate dioxygenase, 5-lipoxygenase, adenosine deaminase, alcohol dehydrogenase, aminopeptidase N, angiotensin converting enzyme, aromatase (CYP19), calcineurin, carbamoyl phosphate synthetase, carbonic anhydrase family, catechol o-methyl transferase, cyclooxygenase family, dihydropyrimidine dehydrogenase-1, DNA polymerase, farnesyl diphosphate synthase, farnesyl transferase, fumarate reductase, GABA aminotransferase, HIF-prolyl hydroxylase, histone deacetylase family, HIV integrase, HIV-1 reverse transcriptase, isoleucine tRNA ligase, lanosterol demethylase (CYP51), matrix metalloprotease family, methionine aminopeptidase, neutral endopeptidase, nitric oxide synthase family, phosphodiesterase III, phosphodiesterase IV, phosphodiesterase V, pyruvate ferredoxin oxidoreductase, renal peptidase, ribonucleoside diphosphate reductase, thromboxane synthase (CYP5a), thyroid peroxidase, tyrosinase, urease, or xanthine oxidase.

The methods herein include those wherein the disease or disorder is mediated by any of 1-deoxy-d-xylulose-5-phosphate reductoisomerase (DXR), 17-alpha hydroxylase (CYP17), aldosterone synthase (CYP11B2), aminopeptidase P, anthrax lethal factor, arginase, beta-lactamase, cytochrome P450 2A6, d-ala d-ala ligase, dopamine beta-hydroxylase, endothelin converting enzyme-1, glutamate carboxypeptidase II, glutaminyl cyclase, glyoxalase, heme oxygenase, HPV/HSV E1 helicase, indoleamine 2,3-dioxygenase, leukotriene A4 hydrolase, methionine aminopeptidase 2, peptide deformylase, phosphodiesterase VII, relaxase, retinoic acid hydroxylase (CYP26), TNF-alpha converting enzyme (TACE), UDP-(3-O—(R-3-hydroxymyristoyl))-N-acetylglucosamine deacetylase (LpxC), vascular adhesion protein-1 (VAP-1), or vitamin D hydroxylase (CYP24).

The methods herein include those wherein the disease or disorder is cancer, cardiovascular disease, inflammatory disease, infectious disease, metabolic disease, ophthalmologic disease, central nervous system (CNS) disease, urologic disease, or gastrointestinal disease.

The methods herein include those wherein the disease or disorder is prostate cancer, breast cancer, inflammatory bowel disease, psoriasis, systemic fungal infection, skin structure fungal infection, mucosal fungal infection, or onychomycosis.

Methods delineated herein include those wherein the subject is identified as in need of a particular stated treatment. Identifying a subject in need of such treatment can be in the judgment of a subject or a health care professional and can be subjective (e.g., opinion) or objective (e.g., measurable by a test or diagnostic method).

Another aspect of the invention is a composition comprising a compound of a formulae herein (e.g., formulae I-XI) and an agriculturally acceptable carrier.

Another aspect of the invention is a method of treating or preventing a metalloenzyme-mediated disease or disorder in or on a plant comprising contacting a compound herein with the plant.

Another aspect of the invention is a method of inhibiting metalloenzyme activity in or on a plant comprising contacting a compound herein with the plant.

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%/a, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore, the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "haloalkyl" refers to an alkyl group that is substituted by one or more halo substituents. Examples of haloalkyl groups include fluoromethyl, difluoromethyl, trifluoromethyl, bromomethyl, chloromethyl, and 2,2,2-trifluoroethyl.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "arylalkenyl" refers to an unsaturated hydrocarbon chain that may be a straight chain or branched chain, containing 2 to 12 carbon atoms and at least one carbon-carbon double bond wherein one or more of the $sp^2$ hybridized carbons of the alkenyl unit attaches to an aryl moiety. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The term "arylalkynyl" refers to an unsaturated hydrocarbon chain that may be a straight chain or branched chain, containing 2 to 12 carbon atoms and at least one carbon-carbon triple bond wherein one or more of the sp hybridized carbons of the alkynyl unit attaches to an aryl moiety. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl substituent.

As used herein, the term "halogen", "hal" or "halo" means —F, —Cl, —Br or —I.

The term "alkylthio" refers to an —S-alkyl substituent.

The term "alkoxyalkyl" refers to an -alkyl-O-alkyl substituent.

The term "haloalkoxy" refers to an —O-alkyl that is substituted by one or more halo substituents. Examples of haloalkoxy groups include trifluoromethoxy, and 2,2,2-trifluoroethoxy.

The term "haloalkoxyalkyl" refers to an -alkyl-O-alkyl' where the alkyl' is substituted by one or more halo substituents.

The term "haloalkylaminocarbonyl" refers to a —C(O)-amino-alkyl where the alkyl is substituted by one or more halo substituents.

The term "haloalkylthio" refers to an —S-alkyl that is substituted by one or more halo substituents. Examples of haloalkylthio groups include trifluoromethylthio, and 2,2,2-trifluoroethylthio.

The term "haloalkylcarbonyl" refers to an —C(O)-alkyl that is substituted by one or more halo substituents. An example of a haloalkylcarbonyl group includes trifluoroacetyl.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation.

Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "cycloalkoxy" refers to an —O-cycloalkyl substituent.

The term "cycloalkoxyalkyl" refers to an -alkyl-O-cycloalkyl substituent.

The term "cycloalkylalkoxy" refers to an —O-alkyl-cycloalkyl substituent.

The term "cycloalkylaminocarbonyl" refers to an —C(O)—NH-cycloalkyl substituent.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "aryloxy" refers to an —O-aryl substituent.

The term "arylalkoxy" refers to an —O-alkyl-aryl substituent.

The term "arylalkylthio" refers to an —S-alkyl-aryl substituent.

The term "arylthioalkyl" refers to an -alkyl-S-aryl substituent.

The term "arylalkylaminocarbonyl" refers to a —C(O)-amino-alkyl-aryl substituent.

The term "arylalkylsulfonyl" refers to an —S(O)$_2$-alkyl-aryl substituent.

The term "arylalkylsulfinyl" refers to an —S(O)-alkyl-aryl substituent.

The term "aryloxyalkyl" refers to an -alkyl-O-aryl substituent.

The term "alkylaryl" refers to an -aryl-alkyl substituent.

The term "arylalkyl" refers to an -alkyl-aryl substituent.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heteroaryloxy" refers to an —O-heteroaryl substituent.

The term "heteroarylalkoxy" refers to an —O-alkyl-heteroaryl substituent.

The term "heteroaryloxyalkyl" refers to an -alkyl-O-heteroaryl substituent.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, pyridine-2 (1H)-one, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(OXOEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carboxamido, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2nd Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artisan by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

As can be appreciated by the skilled artisan, methods of synthesizing the compounds of the formulae herein will be evident to those of ordinary skill in the art, including in the schemes and examples herein. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In one aspect, the invention provides a method of treating a subject suffering from or susceptible to a disorder or disease, comprising administering to the subject an effective amount of a compound or pharmaceutical composition of any of the formulae herein (e.g., formulae I-XI).

In other aspects, the invention provides a method of treating a subject suffering from or susceptible to a disorder or disease, wherein the subject has been identified as in need of treatment for a metalloenzyme-mediated disorder or disease, comprising administering to said subject in need thereof, an effective amount of a compound or pharmaceutical composition of any of the formulae herein (e.g., formulae I-XI), such that said subject is treated for said disorder.

In one aspect, the invention provides a method of modulating the metalloenzyme activity of a cell in a subject, comprising contacting the subject with a compound of any of the formulae herein (e.g., formulae I-XI), in an amount and under conditions sufficient to modulate metalloenzyme activity.

In one embodiment, the modulation is inhibition.

In another aspect, the invention provides a method of treating a subject suffering from or susceptible to a metalloenzyme-mediated disorder or disease, comprising administering to the subject an effective amount of a compound or pharmaceutical composition of any of the formulae herein (e.g., formulae I-XI).

In other aspects, the invention provides a method of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any of the formulae herein (e.g., formulae I-XI), such that said subject is treated for said disorder.

In other aspects, the invention provides a method of treating a subject suffering from or susceptible to a disorder or disease associated with aberrant Hedgehog signaling, wherein the subject has been identified as in need of treatment for a disorder or disease associated with aberrant Hedgehog signaling, comprising administering to said subject in need thereof, an effective amount of a compound or pharmaceutical composition of any of the formulae herein (e.g., formulae I-XI), such that said subject is treated for said disorder.

In certain embodiments, the invention provides a method of treating a disease, disorder or symptom thereof, wherein the disorder is cancer, cardiovascular disease, inflammatory disease or infectious disease. In other embodiments the disease, disorder or symptom thereof is metabolic disease, ophthalmologic disease, central nervous system (CNS) disease, urologic disease, or gastrointestinal disease. In certain embodiments the disease is brain cancer (e.g., medullablastoma, glioma), lung cancer, breast cancer, prostate cancer, pancreatic cancer, hematological cancer (e.g., a leukemia (e.g., acute myeloid leukemia (AML), chronic myeloid leukemia (CML), acute lymphocytic leukemia (ALL), chronic lymphocytic leukemia (CLL))), skin cancer (e.g., basal cell carcinoma), inflammatory bowel disease, psoriasis, systemic fungal infection, skin structure fungal infection, mucosal fungal infection, or onychomycosis.

In certain embodiments, the subject is a mammal, preferably a primate or human.

In another embodiment, the invention provides a method as described above, wherein the effective amount of the compound of any of the formulae herein (e.g., formulae I-XI) is as described above.

In another embodiment, the invention provides a method as described above, wherein the compound of any of the formulae herein (e.g., formulae I-XI) is administered intravenously, intramuscularly, subcutaneously, intracerebroventricularly, orally or topically.

In another embodiment, the invention provides a method as described herein wherein the compound of any of the formulae herein (e.g., formulae I-XI) demonstrates selectivity for an activity range against a target enzyme (e.g., *C. albicans* MIC <1.0 µg/mL and *A. fumigatus* MIC ≤64 µg/mL).

In other embodiments, the invention provides a method as described above, wherein the compound of any of the formulae herein (e.g., formulae I-XI) is administered alone or in combination with one or more other therapeutics. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

Pharmaceutical Compositions

In one aspect, the invention provides a pharmaceutical composition comprising the compound of any of the formulae herein (e.g., formulae I-XI) and a pharmaceutically acceptable carrier.

In another embodiment, the invention provides a pharmaceutical composition further comprising an additional therapeutic agent. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In one aspect, the invention provides a kit comprising an effective amount of a compound of any of the formulae herein (e.g., formulae I-XI), in unit dosage form, together with instructions for administering the compound to a subject suffering from or susceptible to a metalloenzyme-mediated disease or disorder, including cancer, solid tumor, cardiovascular disease, inflammatory disease, infectious disease. In other embodiments the disease, disorder or symptom thereof is metabolic disease, ophthalmologic disease, central nervous system (CNS) disease, urologic disease, or gastrointestinal disease.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered traganeanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Agricultural Applications

The compounds and compositions herein can be used in methods of modulating metalloenzyme activity in a microorganism on a plant comprising contacting a compound herein with the plant (e.g., seed, seedling, grass, weed, grain). The compounds and compositions herein can be used to treat a plant, field or other agricultural area (e.g., as herbicides, pesticides, growth regulators, etc.) by administering the compound or composition (e.g., contacting, applying, spraying, atomizing, dusting, etc.) to the subject plant, field or other agricultural area. The administration can be either pre- or post-emergence. The administration can be either as a treatment or preventative regimen.

One aspect is a method of treating or preventing a fungal disease or disorder in or on a plant comprising contacting a compound of any of the formulae herein with the plant. Another aspect is a method of treating or preventing fungi growth in or on a plant comprising contacting a compound of any of the formulae herein with the plant. Another aspect is a method of inhibiting microorganisms in or on a plant comprising contacting a compound of any of the formulae herein with the plant.

The compositions comprising compounds herein can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Granules, e.g. coated granules, impregnated granules and homogeneous granules, can be prepared by binding the active ingredients (e.g., compounds herein) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The compounds herein can be formulated as ordinary tablets, capsules, solids, liquids, emulsions, slurries, oils, fine granules or powders, which are suitable for administration to plants, fields or other agricultural areas. In preferred embodiments, the preparation includes between 1 and 95% (e.g., 1, 2, 3, 4, 5, 6, 7, 8, 9, 10, 25%, 75%, 80%, 90%, 95%) compound herein in a carrier or diluent. The compositions delineated herein include the compounds of the formulae delineated herein, as well as additional agricultural agents if present, in amounts effective for controlling (e.g., modulating, inhibiting) a metalloenzyme-mediated agricultural disease or disorder.

In one approach, a compound herein is provided in an encapsulated formulation (liquid or powder). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a compound specified herein through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries.

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of active compound herein. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the compound herein is provided in an oil-based delivery system. Oil release substrates include vegetable and/or mineral oils. In one embodiment, the substrate also contains a surface active agent that renders the composition readily dispersable in water; such agents include wetting agents, emulsifying agents, dispersing agents, and the like.

Compounds of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Alternatively, compounds of the invention may also be formulated in a solid tablet and comprise (and preferably consist essentially of) an oil, a protein/carbohydrate material (preferably vegetable based), a sweetener and an active ingredient useful in the prevention or treatment of a metalloenzyme-mediated agricultural disease or disorder. In one embodiment the invention provides a solid tablet and comprises (and preferably consist essentially of) an oil, a protein/carbohydrate material (preferably vegetable based), a sweetener and an active ingredient (e.g., compound herein or combinations or derivatives thereof) useful in the prevention or treatment a metalloenzyme-mediated agricultural disease or disorder. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cotton seed, walnut, palm, castor, earth almond, hazelnut, avocado, sesame, croton tiglium, cacao, linseed, rape-seed, and canola oils and their hydrogenated derivatives; petroleum derived oils (e.g., paraffins and petroleum jelly), and other water immiscible hydrocarbons (e.g., paraffins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodic carboxymethylcellulose, ethyl cellulose, hydroxypropyl methyl cellulose, and mixtures thereof.

The invention provides kits for the treatment or prevention of agricultural or plant disease or disorders. In one embodiment, the kit includes a composition containing an effective amount of a compound herein in a form suitable for delivery to a site plant. In some embodiments, the kit comprises a container which contains a compound any of the formulae herein (e.g formulae I-XI); such containers can be boxes, ampules, bottles, vials, tubes, bags, pouches, blister-packs, or other suitable container forms known in the art. Such containers can be made of plastic, glass, laminated paper, metal foil, or other materials suitable for holding compounds.

If desired the compound(s) of the invention is provided together with instructions for administering it to a plant, field, or other agricultural area. The instructions will generally include information about the use of the composition for the treatment or prevention of a metalloenzyme-mediated agricultural disease or disorder. In other embodiments, the instructions include at least one of the following: description of the compound; dosage schedule and administration for treatment or prevention of a metalloenzyme-mediated agricultural disease or disorder; precautions; warnings; description of research studies; and/or references. The instructions may be printed directly on the container (when present), or as a label applied to the container, or as a separate sheet, pamphlet, card, or folder supplied in or with the container.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of Azoles
Intermediate-1 (Int-1)

(R)-1-(5-bromopyridin-2-yl)-2-(2,4-difluorophenyl)-1,1-difluoro-3-(1H-tetra ol-1-yl)propan-2-ol (Int-1)

Preparation of ethyl 2-(5-bromopyridin-2-yl)-2,2-difluoroacetate (B)

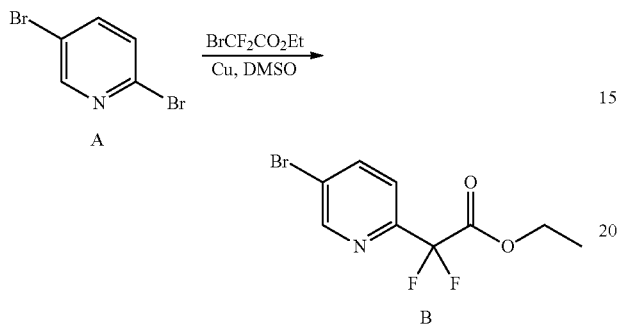

In a clean multi-neck round bottom flask, copper powder (274.7 g, 2.05 eq) was suspended in dimethyl sulfoxide (DMSO; 3.5 L, 7 vol) at 20-35° C. Ethyl bromodifluoroacetate (449 g, 1.05 eq) was slowly added to the reaction mixture at 20-25° C. and stirred for 1-2 h. 2,5-dibromopyridine A (500 g, 1 eq) was then added to the reaction mixture and the temperature was increased to 35-40° C. The reaction mixture was maintained at this temperature for 18-24 h and the reaction progress was monitored by gas chromatography (GC).

After the completion of the reaction, ethyl acetate (EtOAC: 7 L, 14 vol) was added to the reaction mixture and stirring was continued for 60-90 min at 20-35° C. The reaction mixture was filtered through a Celite bed (100 g; 0.2 times w/w Celite and IL; 2 vol ethyl acetate). The reactor was washed with ethyl acetate (6 L, 12 vol) and the washings were filtered through a Celite bed. The Celite bed was finally washed with ethyl acetate (1 L, 2 vol) and all the filtered mother liquors were combined. The pooled ethyl acetate solution was cooled to 8-10° C., washed with a buffer solution (5 L, 10 vol) below 15° C. (Note: The addition of buffer solution was exothermic in nature. Controlled addition of buffer was required to maintain the reaction mixture temperature below 15° C.). The ethyl acetate layer was washed again with the buffer solution until (7.5 L; 3×5 vol) the aqueous layer remained colorless. The organic layer was washed with a 1:1 solution of 10% w/w aqueous sodium chloride and the buffer solution (2.5 L; 5 vol). The organic layer was then transferred into a dry reactor and the ethyl acetate was distilled under reduced pressure to afford the crude material. The crude material was purified by high vacuum fractional distillation and the distilled fractions having purity greater than 93% were pooled together. Additional material was obtained by re-distillation of impure fractions resulting in overall yield of B of ~55-60% as a pale yellow liquid. $^1$H NMR: δ values with respect to TMS (DMSO-$d_6$; 400 MHz): 8.85 (1H, d, 1.6 Hz), 8.34 (1H, dd, J=2.0 Hz, 6.8 Hz), 7.83 (1H, d, J=6.8 Hz), 4.33 (2H, q, J=6.0 Hz), 1.22 (3H, t, J=6.0 Hz). $^{13}$C NMR: 162.22 (t, —C=O), 150.40 (Ar—C), 149.35 (t, Ar—C), 140.52 (Ar—C), 123.01 (Ar—C), 122.07 (Ar—C), 111.80 (t, —CF$_2$), 63.23 (—OCH$_2$—), 13.45 (—CH$_2$CH$_3$).

Preparation of 2-(5-bromopyridin-2-yl)-1-(2,4-difluorophenyl)-2,2-difluoroethanone (C)

A. One-Step Method

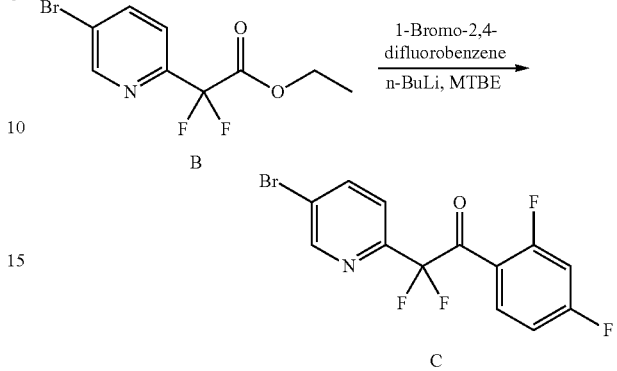

1-Bromo-2,4-difluorobenzene (268.7 g, 1.3 eq) was dissolved in methyl tert butyl ether (MTBE, 3.78 L, 12.6 vol) at 20-35° C., and the reaction mixture was cooled to −70 to −65° C. using acetone/dry ice bath. n-Butyl lithium (689 mL, 1.3 eq; 2.5 M) was then added to the reaction mixture maintaining the reaction temperature below −65° C. (Note: Controlled addition of the n-Butyl Lithium to the reaction mixture was needed to maintain the reaction mixture temperature below −65° C.). After maintaining the reaction mixture at this temperature for 30-45 min, B (300 g, 1 eq) dissolved in MTBE (900 mL, 3 vol) was added to the reaction mixture below −65° C. The reaction mixture was continued to stir at this temperature for 60-90 min and the reaction progress was monitored by GC.

The reaction was quenched by slow addition of a 20% w/w ammonium chloride solution (750 mL, 2.5 vol) below −65° C. The reaction mixture was gradually warmed to 20-35° C., and an additional amount of a 20% w/w ammonium chloride solution (750 mL, 2.5 vol) was added. The aqueous layer was separated and the organic layer was washed with a 10% w/w a sodium bicarbonate solution (600 mL, 2 vol) followed by a 5% sodium chloride wash (600 mL, 2 vol). The organic layer was dried over sodium sulfate (Na$_2$SO$_4$; 60 g; 0.2 times w/w), filtered and the sodium sulfate was washed with MTBE (300 mL, 1 vol). The organic layer along with the washings were distilled below 45° C. under reduced pressure until no more solvent was collected in the receiver. The distillation temperature was increased to 55-60° C., maintained under vacuum for 3-4 h and cooled to 20-35° C. to afford 275 g (73.6% yield, 72.71% purity by HPLC) of C as a pale yellow liquid. $^1$H NMR: δ values with respect to TMS (DMSO-$d_6$; 400 MHz): 8.63 (1H, d, 1.6 Hz, Ar—H), 8.07-8.01 (2H, m, 2×Ar—H), 7.72 (1H, d, J=6.8 Hz, Ar—H), 7.07-6.82 (1H, m, Ar—H), 6.81-6.80 (1H, m, Ar—H). $^{13}$C NMR: 185.60 (t, —C=O), 166.42 (dd, Ar—C—), 162.24 (dd, Ar—C), 150.80 (Ar—C), 150.35 (Ar—C), 140.02 (Ar—C), 133.82 (Ar—C), 123.06 (Ar—C), 1122.33 (Ar—C), 118.44 (Ar—C), 114.07 (—CF$_2$—), 122.07 (Ar—C), 105.09 (Ar—C).

B. Two-Step Method Via D

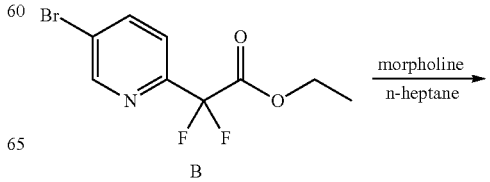

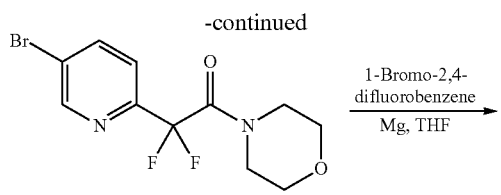

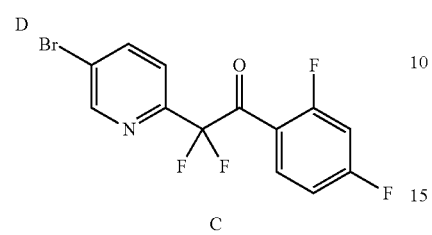

B (147.0 g) was dissolved in n-heptane (1.21 L) and transferred to a 5-L reactor equipped with an overhead stirrer, a thermocouple, a condenser and an addition funnel. Morpholine (202 ml) was added. The solution was heated to 60° C., and stirred overnight. The reaction was complete by HPLC analysis. The reaction was cooled to room temperature and 1.21 L of MTBE was added. The solution was cooled to ~4° C., and quenched by slow addition of 30% citric acid (563 ml) to maintain the internal temperature <15° C. After stirring for one hour, the layers were allowed to settle and were separated (Aq. pH=5). The organic layer was washed with 30% citric acid (322 ml) and 9% NaHCO$_3$ (322 ml, aq. pH 7+ after separation). The organic layer was concentrated on the rotary evaporator to yield 454 g (some precipitation started immediately and increased during concentration). After stirring at room temperature the suspension was filtered and the product cake was washed with n-heptane (200 ml). The solid was dried in a vacuum oven at room temperature to provide 129.2 g (77%) of D as a dense powder. The purity was 96.5% by HPLC analysis.

To a 1-L flask equipped with overhead stirring, thermocouple, condenser and addition funnel was added magnesium turnings (14.65 g), tetrahydrofuran (THF, 580 ml) and 1-bromo-2,4-difluorobenzene (30.2 g, 0.39 equiv). The mixture was stirred until the reaction initiated and self-heating brought the reaction temperature to 44° C. The temperature was controlled with a cooling bath as the remaining 1-bromo-2,4-difluorobenzene (86.1 g, 1.11 equiv) was added over about 30 min. at an internal temperature of 35-40° C. The reaction was stirred for 2 hours while gradually cooling to room temperature. The dark yellow solution was further cooled to 12° C.

During the Grignard formation, a jacketed 2-L flask equipped with overhead stirring, thermocouple, and addition funnel was charged with morpholine amide D (129.0 g) and THF (645 ml). The mixture was stirred at room temperature until the solid dissolved, and then the solution was cooled to −8.7° C. The Grignard solution was added via addition funnel over about 30 min. at a temperature of −5 to 0° C. The reaction was stirred at 0° C. for 1 hour and endpointed by HPLC analysis. The reaction mixture was cooled to −5° C., and quenched by slow addition of 2N HCl over 1 hour at ≤10° C. The mixture was stirred for 0.5 h then the layers were allowed to settle and were separated. The aqueous layer was extracted with MTBE (280 ml). The combined organic layers were washed with 9% NaHCO$_3$ (263 g) and 20% NaCl (258 ml). The organic layer was concentrated on the rotary evaporator with THF rinses to transfer all the solution to the distillation flask. Additional THF (100 ml) and toluene (3×100 ml) were added and distilled to remove residual water from the product. After drying under vacuum, the residue was 159.8 g of C as a dark brown waxy solid (>theory). The purity was approximately 93% by HPLC analysis.

Preparation of 5-bromo-2-((2-(2,4-difluorophenyl)oxiran-2-yl)difluoromethyl)pyridine (E)

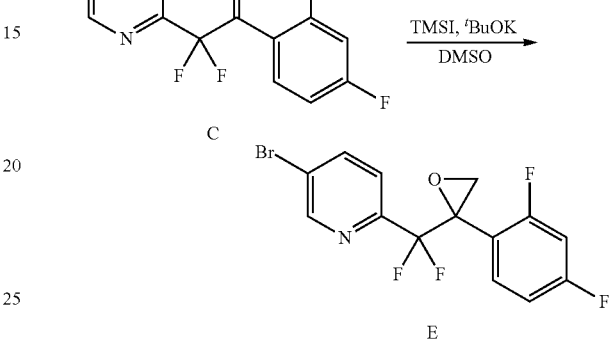

Trimethyl sulfoxonium iodide (TMSI, 37.93 g: 1.2 eq) was added into a mixture of dimethyl sulfoxide (300 mL, 5 vol) and tetrahydrofuran (500 mL, 10 vol) at 20-35° C. (pale yellow suspension was observed). A potassium tert-butoxide solution in THF (172.5 mL, 1.2 eq) was then added into the reaction mixture and stirred for 60-90 min at 20-35° C., resulting in a clear solution. The reaction mixture was then cooled to 0-5° C. and a solution of C (50 g, 1 eq) in tetrahydrofuran (150 mL, 3 vol) was added, maintaining the reaction mixture temperature below 15° C. The reaction progress was monitored by GC. The reaction was quenched by adding 1M hydrochloric acid (500 mL, 10 vol) at 0-15° C. such that the reaction mixture pH was less than 3. The reaction mixture was maintained at this temperature for 10-15 min and then a 10% sodium bicarbonate solution (300 mL, 6 vol) was added to bring the pH of the solution to greater than 7. After maintaining the reaction mixture at 10-15° C. for about 15 min, the reaction mixture was diluted with MTBE (770 mL, 13.5 vol) and brought to 20-30° C. The organic layer was separated, washed twice with water (100 mL, 2 vol) followed by 10% sodium chloride (200 mL, 4 vol). The organic layer was dried over anhydrous sodium sulfate (12.5 g, 0.25 w/w), filtered and the sodium sulfate was washed with MTBE (100 mL, 2 vol). The filtrate and washings were pooled together and the solvent was distilled below 45° C. under reduced pressure to afford 35 g (88% yield, purity >60% by GC) of the crude material.

The crude material was dissolved in MTBE, adsorbed onto silica gel and purified by silica gel chromatography using 5-10% ethyl acetate in heptane as the mobile phase. The obtained solid was further purified by slurrying in a 5% ethyl acetate in heptane solution (4 vol) at room temperature. The solid was filtered and dried under reduced pressure below 40° C. to afford 15 g (37% yield, >95%) of E as a pale brown solid. $^1$H NMR: δ values with respect to TMS (DMSO-d$_6$; 400 MHz): 8.82 (1H, d, J=1.6 Hz, Ar—H), 8.21 (1H, dd, J=6.8 Hz, 1.6 Hz, Ar—H), 7.50 (1H, d, J=6.8 Hz, Ar—H), 7.43-7.38 (1H, m, Ar—H), 7.27-7.23 (1H, m, Ar—H), 7.11-7.07 (1H, m, Ar—H), 3.39 (1H, d, J=3.6 Hz, —OCH$_A$H$_B$—), 3.14 (1H, d, J=2.0 Hz, —OCH$_A$H$_B$—). $^{13}$C NMR: 163.87-159.78 (dd, 2×Ar—C—), 150.19 (Ar—C), 149.45 (t, Ar—C), 140.14 (Ar—C), 132.80 (Ar—C), 123.18 (Ar—C), 122.50 (Ar—C), 117.41 (1. —CF$_2$—), 116.71 (Ar—C), 111.58 (Ar—C), 104.04 (t, Ar—C), 57.03 (—C—O—CH$_2$—), 49.57 (—CH$_2$—O—).

Preparation of 3-amino-1-(5-bromopyridin-2-yl)-2-(2,4-difluorophenyl)-1,1-difluoropropan-2-ol (±F)

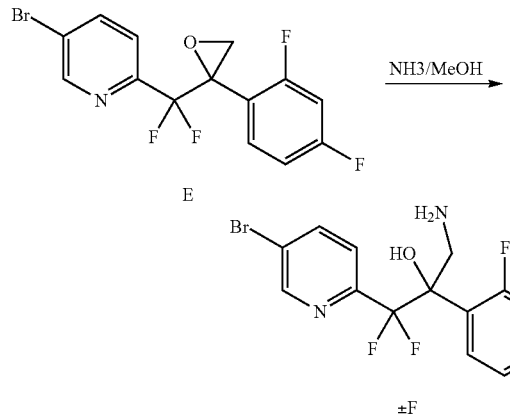

E (200 g, 1 eq) was added into methanolic ammonia (8.0 L; 40 vol; ammonia content: 15-20% w/v) in an autoclave at 10-20° C. The reaction mixture was gradually heated to 60-65° C., and at 3-4 kg/cm$^2$ under sealed conditions for 10-12 h. The reaction progress was monitored by GC. After completion of the reaction, the reaction mixture was cooled to 20-30° C., and released the pressure gradually. The solvent was distilled under reduced pressure below 50° C. and the crude obtained was azeotroped with methanol (2×600 mL, 6 vol) followed by with isopropanol (600 mL, 2 vol) to afford 203 g (96.98% yield, purity by HPLC: 94.04%) of ±F.

Preparation of 3-amino-1-(5-bromopyridin-2-yl)-2-(2,4-difluorophenyl)-1,1-difluoropropan-2-ol (F)

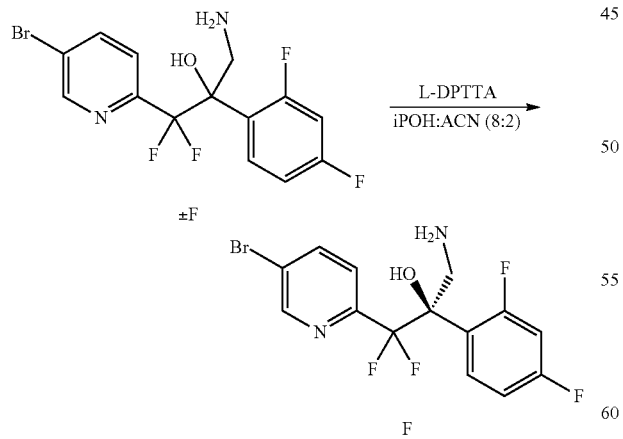

Amino alcohol ±F (150 g, 1 eq) was dissolved in an isopropanol/acetonitrile mixture (1.5 L, 8:2 ratio, 10 vol) and di-p-toluoyl-L-tartaric acid (L-DPTTA) (84.05 g, 0.55 eq) was added into the reactor at 20-30° C. The reaction mixture was heated to 45-50° C. for 1-1.5 h (Note: The reaction mixture becomes clear and then became heterogeneous). The reaction mixture was gradually cooled to 20-30° C. and stirred for 16-18 h. The progress of the resolution was monitored by chiral HPLC analysis.

After the completion of the resolution, the reaction mixture was gradually cooled to 20-35° C. The reaction mixture was filtered and the filtered solid was washed with a mixture of acetonitrile and isopropanol (8:2 mixture, 300 mL, 2 vol) and then dried to afford 75 g of the L-DPTTA salt (95.37% ee). The L-DPTTA salt obtained was chirally enriched by suspending the salt in isopropanol/acetonitrile (8:2 mixture, 750 mL, 5 vol) at 45-50° C. for 24-48 h. The chiral enhancement was monitored by chiral HPLC; the solution was gradually cooled to 20-25° C., filtered and washed with an isopropanol/acetonitrile mixture (8:2 mixture; 1 vol). The purification process was repeated and after filtration, the salt resulted in chiral purity greater than 96% ee. The filtered compound was dried under reduced pressure at 35-40° C. to afford 62 g of the enantio-enriched L-DPPTA salt with 97.12% ee as an off-white solid.

The enantio-enriched L-DPTTA salt (50 g, 1 eq) was dissolved in methanol (150 mL, 3 vol) at 20-30° C., and a potassium carbonate solution (18.05 g K$_2$CO$_3$ in 150 mL water) was slowly added at 20-30° C. under stirring. The reaction mixture was maintained at this temperature for 2-3 h (pH of the solution at was maintained at pH=9). Water (600 mL, 12 vol) was added into the reaction mixture through an additional funnel and the reaction mixture was stirred for 2-3 h at 20-30° C. The solids were filtered, washed with water (150 mL, 3 vol) and dried under vacuum at 40-45° C. to afford 26.5 g of amino alcohol F with 99.54% chemical purity, 99.28% ee as an off-white solid. (Water content of the chiral amino alcohol is below 0.10% w/w). $^1$H NMR: δ values with respect to TMS (DMSO-d$_6$; 400 MHz): 8.68 (1H, d, J=2.0 Hz, Ar—H), 8.16 (1H, dd, J=8.0 Hz, 2.0 Hz, Ar—H), 7.49-7.43 (1H, m, Ar—H), 7.40 (1H, d, J=8 Hz, Ar—H), 7.16-7.11 (1H, m, Ar—H), 7.11-6.99 (1H, m, Ar—H), 3.39-3.36 (1H, m, —OCH$_A$H$_B$—), 3.25-3.22 (1H, m, —OCH$_A$H$_B$—). $^{13}$C NMR: 163.87-158.52 (dd, 2×Ar—C—), 150.88 (Ar—C), 149.16 (Ar—C), 139.21 (Ar—C), 132.39 (Ar—C), 124.49 (Ar—C), 122.17 (Ar—C), 121.87 (d, Ar—C), 119.91 (1, —CF$_2$—), 110.68 (Ar—C), 103.97 (t, Ar—C), 77.41 (t, —C—OH), 44.17 (—CH—NH$_2$).

(R)-1-(5-bromopyridin-2-yl)-2-(2,4-difluorophenyl-1,1-difluoro-3-(1H-tetrazol-1-yl)propan-2-ol (Int-1)

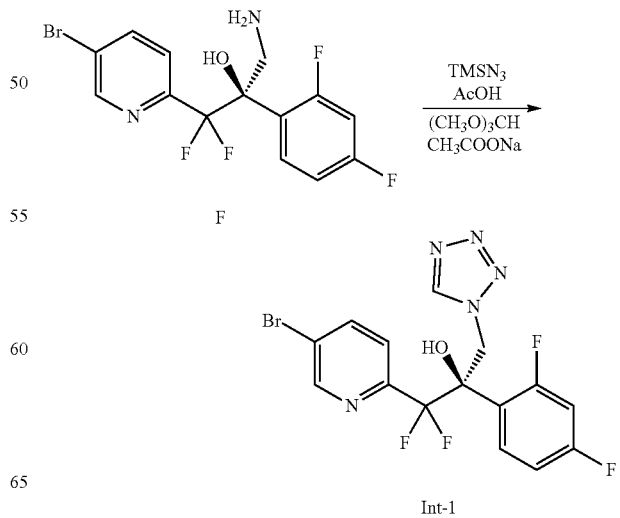

F (20.0 g, 1 eq.) was added to acetic acid (50 mL, 2.5 vol) at 25-35° C. followed by the addition of anhydrous sodium acetate (4.32 g, 1 eq) and trimethyl orthoformate (15.08 g, 2.7 eq). The reaction mixture was stirred for 15-20 min at this temperature and trimethylsilyl azide (12.74 g, 2.1 eq) was added to the reaction mixture (Chilled water was circulated through the condenser to minimize the loss of trimethylsilyl azide from the reaction mixture by evaporation). The reaction mixture was then heated to 70-75° C. and maintained at this temperature for 2-3 h. The reaction progress was monitored by HPLC. Once the reaction was complete, the reaction mixture was cooled to 25-35° C. and water (200 mL, 10 vol) was added. The reaction mixture was extracted with ethyl acetate (400 mL, 20 vol) and the aqueous layer was back extracted with ethyl acetate (100 mL, 5 vol). The combined organic layers were washed with a 10% potassium carbonate solution (3×200 mL; 3×10 vol) followed by a 10% NaCl wash (1×200 mL, 10 vol). The organic layer was distilled under reduced pressure below 45° C. The crude obtained was azeotroped with heptanes (3×200 mL) to afford 21.5 g (94% yield, 99.26 5 purity) of Int-1 as a pale brown solid (low melting solid), $^1$H NMR: δ values with respect to TMS (DMSO-d$_6$; 400 MHz NMR instrument): 9.13 (1H, Ar—H), 8.74 (1H, Ar—H), 8.22-8.20 (1H, m, Ar—H), 7.44 (1H, d, J=7.2 Hz, Ar—H), 7.29 (1H, Ar—H), 7.23-7.17 (1H, m, Ar—H), 6.92-6.88 (1H, Ar—H), 5.61 (1H, d, J=11.2 Hz, —OCH$_A$H$_B$—), 5.08 (1H, d, J=5.6 Hz, —OCH$_A$H$_B$—). $^{13}$C NMR: 163.67-161.59 (dd, Ar—C—), 160.60-158.50 (dd, Ar—C—), 149.65 (Ar—C), 144.99 (Ar—C), 139.75 (Ar—C), 131.65 (Ar—C), 124.26 (Ar—C), 122.32 (d, Ar—C), 119.16 (t, —CF$_2$—), 118.70 (d, Ar—C), 111.05 (d, Ar—C) 104.29 (t, Ar—C), 76.79 (t, —C—OH), 59.72 (Ar—C), 50.23 (—OCH$_2$N—).

Example 1

(R)-4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) benzonitrile (1)

Preparation of 4-(4-(4-bromophenyl)piperazin-1-yl) benzonitrile (1)

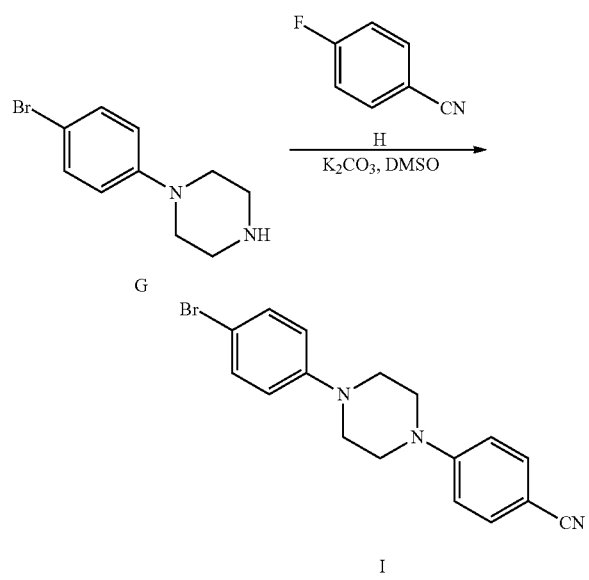

To a stirred solution of 1-(4-bromophenyl) piperazine G (1.09 g, 4.54 mmol) in DMSO (10 mL) under argon atmosphere were added potassium carbonate (1.14 g, 8.26 mmol) and 4-fluorobenzonitrile H (500 mg, 4.13 mmol) at room temperature (RT). The reaction mixture was stirred at 120° C. for 6 h. The reaction was cooled to RT, diluted with water (20 mL), and the product was extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 50% EtOAc/Hexane) to afford Compound I (700 mg, 2.04 mmol, 50%) as an off-white solid. $^1$H NMR (400 MHz, CDCl$_3$): δ 7.57 (d, J=9.2 Hz, 2H), 7.43 (d, J=9.2 Hz, 2H), 6.95 (d, J=9.6 Hz, 2H), 6.87 (d, J=9.2 Hz, 2H), 3.55-3.51 (m, 4H), 3.38-3.33 (m, 4H).

Preparation of 4-(4-(4-(4,4,5,5-tetramethyl-1,3,2-dioxaborolan-2-yl) phenyl) piperazin-1-yl) benzonitrile (J)

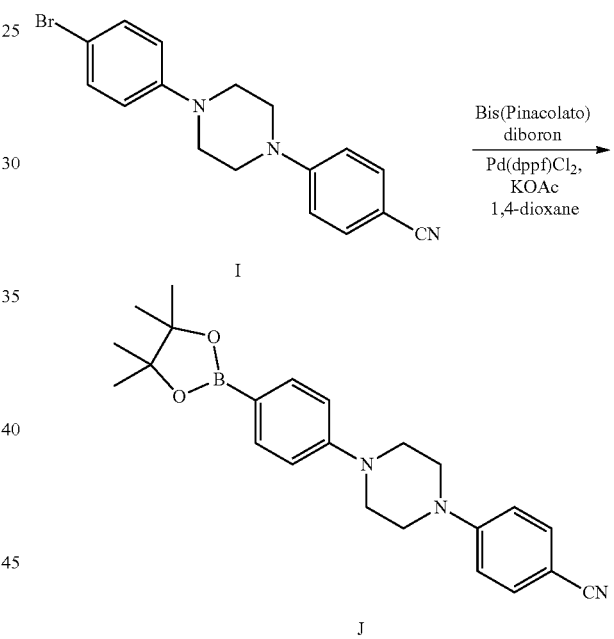

To a stirred solution of Compound I (400 mg, 1.16 mmol) in 1,4-dioxane (30 mL) under argon atmosphere were added bis(pinacolato)diboron (473 mg, 1.87 mmol) and potassium acetate (343 mg, 3.50 mmol) at RT. The reaction mixture was purged with argon for 20 min, then Pd(dppf)Cl$_2$ (85 mg, 0.11 mmol) was added and the reaction mixture was purged with argon for 5 min at RT. The reaction mixture was stirred at 90° C. for 4 h. The reaction mixture was cooled to RT, diluted with water (20 mL), and the product was extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 20% EtOAc/Hexane) to afford Compound J (300 mg, 0.77 mmol, 66%) as an off-white solid. $^1$H NMR (400 MHz, CDCl$_3$): δ 7.74 (d, J=7.6 Hz, 2H), 7.52 (d, J=7.9 Hz, 2H), 6.92-6.88 (m, 4H), 3.52-3.47 (m, 4H), 3.45-3.40 (m, 4H), 1.33 (s, 12H)

Preparation of (R)-4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) benzonitrile (1)

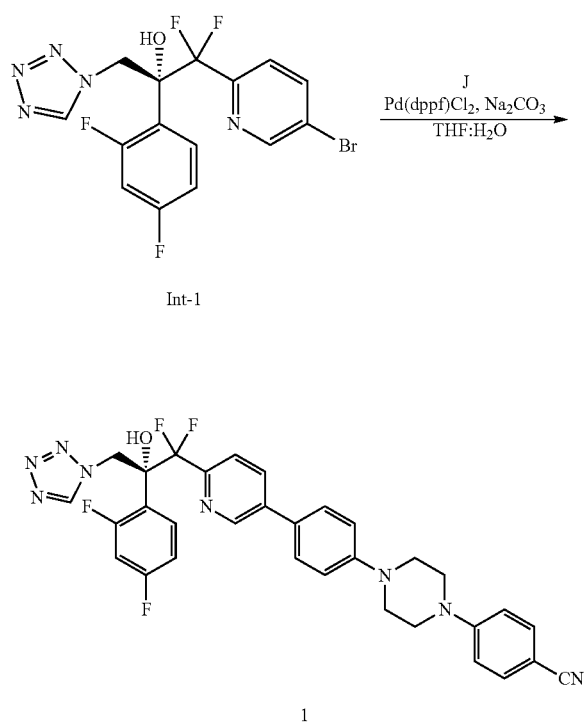 [SMILES: O[C@@](Cn1cnnn1)(c1ccc(F)cc1F)C(F)(F)c1ccc(Br)cn1 ; "THF:H2O" ; N#Cc1ccc(N2CCN(c3ccc(-c4ccc(C(F)(F)[C@](O)(Cn5cnnn5)c5ccc(F)cc5F)nc4)cc3)CC2)cc1]

To a stirred solution of Int-1 (150 mg, 0.34 mmol) in THF:H$_2$O (20 mL) under argon atmosphere were added Compound J (162 mg, 0.41 mmol) and sodium carbonate (110 mg, 1.04 mmol). The reaction mixture was purged with argon for 20 min at RT, then Pd(dppf)Cl$_2$ (25 mg, 0.03 mmol) was added to and the reaction mixture was purged with argon for 10 min at RT. The reaction mixture was stirred at reflux for 2 h. The reaction mixture was diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 50% EtOAc/Hexane) to afford 1 (80 mg, 0.13 mmol, 37%) as an off-white solid. $^1$H NMR (400 MHz, CDCl$_3$): δ 8.76 (s, 1H), 8.72 (s, 1H), 7.94 (dd, J=8.3, 2.2 Hz, 1H), 7.83 (s, 1H), 7.61 (d, J=8.3 Hz, 1H), 7.55-7.51 (m, 4H), 7.43-7.35 (m, 1H), 7.04 (d, J=8.9 Hz, 2H), 6.92 (t, J=6.1 Hz, 2H), 6.80-6.74 (m, 1H), 6.70-6.64 (m, 1H), 5.60 (d, J=14.3 Hz, 1H), 5.12 (d, J=14.3 Hz, 1H), 3.55-3.51 (m, 4H), 3.48-3.43 (m, 4H); MS (ESI): m/z 615.5 [M+H]$^+$; HPLC: 97.19%; Optical rotation $[α]_D^{19}$: +161.6 (c=0.1% in MeOH).

Example 2

(R)-2-(2,4-difluorophenyl)-1,1-difluoro-1-(5-(4-(4-(4-fluorophenyl) piperazin-1-yl) phenyl) pyridin-2-yl)-3-(1H-tetrazol-1-yl) propan-2-ol (2)

Preparation of 1-(4-bromophenyl)-4-(4-fluorophenyl) piperidine (L)

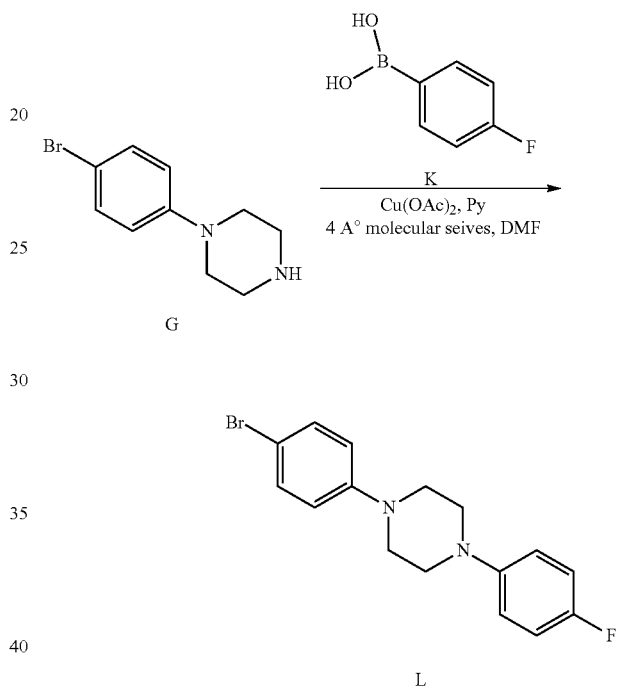

To a stirred solution of copper (II) acetate (900 mg, 4.97 mmol) in dimethylformamide (DMF; 20 mL) under argon atmosphere were added pyridine (1.6 mL, 20.74 mmol) and 4A° molecular sieves (2 g) at RT. The reaction was stirred for 30 min, then Compound G (1 g, 4.14 mmol) and (4-fluorophenyl) boronic acid L (580 mg, 4.14 mmol) were added to the reaction mixture. The reaction mixture was stirred at 70° C. for 16 h. The reaction mixture was cooled to RT and filtered. The filtrate was diluted with water (100 mL), and the product was extracted with EtOAc (2×100 mL). The combined organic layers were dried over anhydrous Na$_2$SO$_4$ and concentrated under reduced pressure. The crude material was purified by silica gel column chromatography (eluent: 5% EtOAc/Hexane) to afford Compound L (200 mg, 0.60 mmol, 15%) as a white solid. $^1$H NMR (400 MHz, CDCl$_3$): δ 7.37 (d, J=9.2 Hz, 2H), 7.02-6.90 (m, 4H), 6.84 (d, J=9.0 Hz, 2H), 3.33-3.28 (m, 4H), 3.27-3.21 (m, 4H).

Preparation of 1-(4-fluorophenyl-4-(4-(4,4,5,5-tetramethyl-1,3,2-dioxaborolan-2-yl) phenyl) piperazine (M)

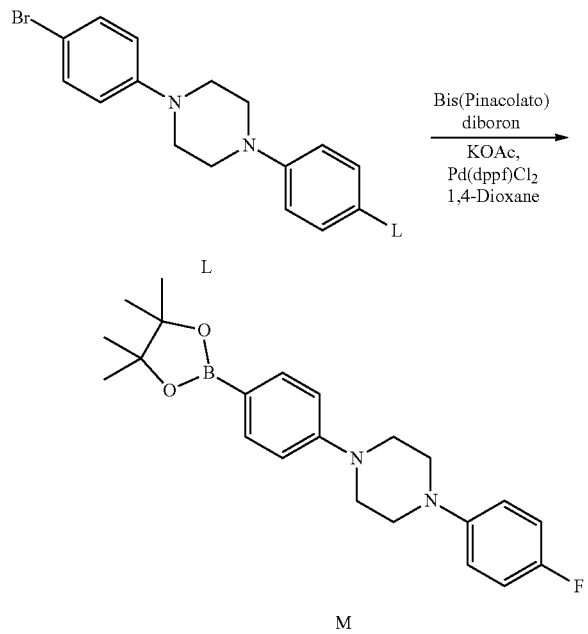

To a stirred solution of Compound L (150 mg, 0.44 mmol) in 1,4-dioxane (10 mL) under argon atmosphere were added bis(pinacolato)diboron (225 mg, 0.90 mmol) and potassium acetate (175 mg, 1.78 mmol). The reaction mixture was purged with argon for 10 min at RT, then Pd(dppf)Cl$_2$ (30 mg, 0.04 mmol) was added and the reaction mixture was purged with argon for 10 min at RT. The reaction was stirred at 90° C. for 2 h. The reaction mixture was cooled to RT, diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 50% EtOAc/Hexane) to afford Compound M (60 mg, 0.16 mmol, 27%) as a white solid. $^1$H NMR (400 MHz, CDCl$_3$): δ 7.73 (d, J=7.5 Hz, 2H), 7.02-6.88 (m, 6H), 3.47-3.35 (m, 4H), 3.29-3.20 (m, 4H), 1.33 (s, 12H).

Preparation of (R)-2-(2,4-difluorophenyl)-1,1-difluoro-1-(5-(4-(4-(4-fluorophenyl) piperazin-1-yl) phenyl) pyridin-2-yl)-3-(1H-tetrazol-1-yl) propan-2-ol (2)

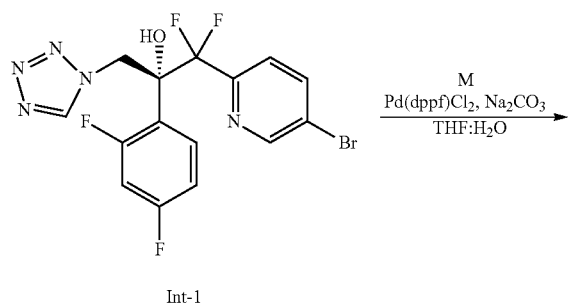

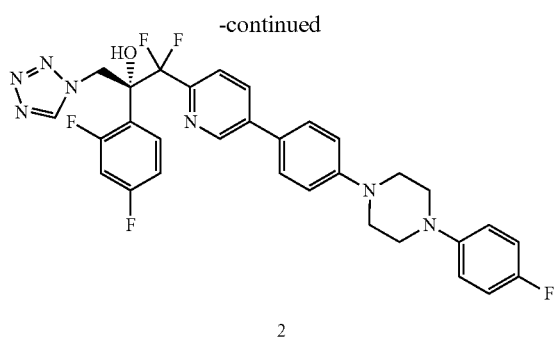

To a stirred solution of Int-1 (100 mg, 0.23 mmol) in THF:H$_2$O (9:1, 10 mL) under argon atmosphere were added Compound M (111 mg, 0.23 mmol) and sodium carbonate (73 mg, 0.70 mmol). The reaction mixture was purged with argon for 10 min at RT, then Pd(dppf)Cl$_2$ (16 mg, 0.02 mmol) was added and the reaction was stirred at 90° C. for 2 h. The reaction mixture was cooled to RT, diluted with water (20 mL), and the product was extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 40% EtOAc/Hexane) to afford 2 (60 mg, 0.01 mmol, 42%) as a yellow solid. $^1$H NMR (400 MHz, CDCl$_3$): δ 8.76 (s, 1H), 8.73 (s, 1H), 7.94 (d, J=10.2 Hz, 1H), 7.85 (s, 1H), 7.60 (d, J=8.4 Hz, 1H), 7.51 (d, J=8.5 Hz, 2H), 7.43-7.34 (m, 1H), 7.06 (d, J=9.8 Hz, 2H), 7.03-6.92 (m, 4H), 6.79-6.74 (m, 1H), 6.69-6.65 (m, 1H), 5.61 (d, J=14.3 Hz, 1H), 5.10 (d, J=14.3 Hz, 1H), 3.47-3.41 (m, 4H), 3.30-3.25 (m, 4H); MS (ESI): m/z 608.5 [M+H]$^+$; HPLC: 99.25%; Optical rotation $[α]_D^{20}$: +56.6 (c=0.1% in MeOH).

Example 3

(2R)-2-(2,4-difluorophenyl)-1,1-difluoro-3-(1H-tetrazol-1-yl)-1-(5-(4-(4-(4-(2,2,2-trifluoro-1-hydroxyethyl) phenyl) piperazin-1-yl) phenyl) pyridin-2-yl) propan-2-ol (3)

Preparation of 4-(4-(4-bromophenyl) piperazin-1-yl) benzaldehyde (N)

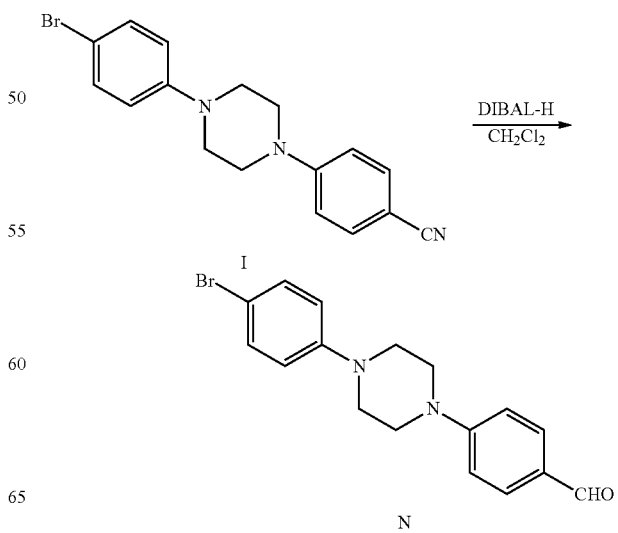

To a stirred solution of Compound I (1.2 g, 3.50 mmol) in CH₂Cl₂ (50 mL) under argon atmosphere was added diisobutylaluminumhydride (DIBAL-H, 7 mL, 7.01 mmol, 1M in toluene) at 0° C. The reaction mixture was warmed to RT and stirred for 3 h. The reaction was quenched with a saturated ammonium chloride solution (100 mL), and the product was extracted with CH₂Cl₂ (2×50 mL). The combined organic extracts were washed with water (50 mL), brine (50 mL), dried over anhydrous Na₂SO₄ and concentrated under reduced pressure. The crude material was purified by silica gel column chromatography (eluent: 50% EtOAc/Hexane) to afford Compound N (1.0 g, 2.89 mmol, 74%) as a yellow solid. $^1$H NMR (400 MHz, DMSO-d₆): δ 9.73 (s, 1H), 7.74 (d, J=8.9 Hz, 2H), 7.37 (d, J=8.9 Hz, 2H), 7.10 (d, J=8.8 Hz, 2H), 6.95 (d, J=9.0 Hz, 2H), 3.63-3.46 (m, 4H), 3.36-3.23 (m, 4H).

Preparation of 1-(4-(4-(4-bromophenyl) piperazin-1-yl) phenyl)-2,2,2-trifluoroethan-1-ol (O)

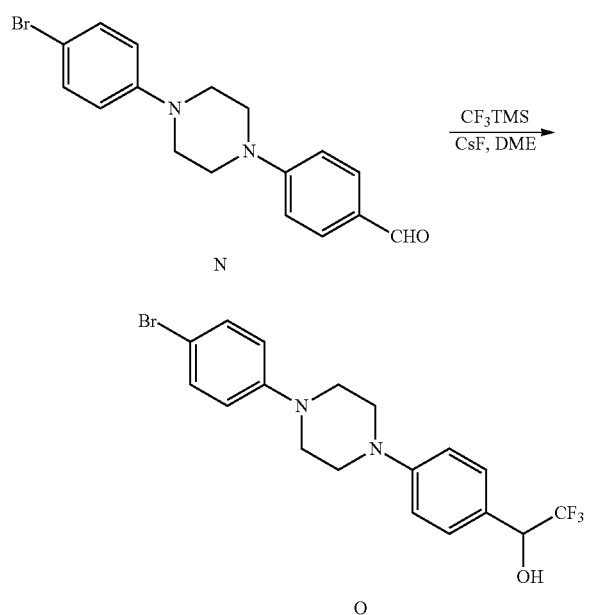

To a stirred solution of Compound N (200 mg, 0.57 mmol) in dimethoxyethane (DME; 10 mL) under argon atmosphere were added cesium fluoride (44 mg, 0.28 mmol) and CF₃TMS (0.09 mL, 0.63 mmol) at 0° C. The reaction mixture was warmed to RT and stirred for 3 h. The reaction was quenched with 1.0 N HCl solution (20 mL), and the product was extracted with EtOAc (2×20 mL). The combined organic layers were washed with water (20 mL), dried over anhydrous Na₂SO₄ and concentrated under reduced pressure. The crude material was purified by silica gel column chromatography (eluent: 40% EtOAc/Hexane) to afford Compound O (200 mg, 0.5 mmol, 83%) as an off-white solid. $^1$H NMR (400 MHz. CDCl₃): δ 7.41-7.36 (m, 4H), 7.01 (d, J=8.7 Hz, 2H), 6.87 (d, J=8.9 Hz, 2H), 4.97-4.92 (m, 1H), 3.43-3.37 (m, 4H), 3.36-3.31 (m, 4H).

Preparation of 2,2,2-trifluoro-1-(4-(4-(4-(4,4,5,5-tetramethyl-1,3,2-dioxaborolan-2-yl) phenyl) piperazin-1-yl) phenyl) ethan-1-ol (P)

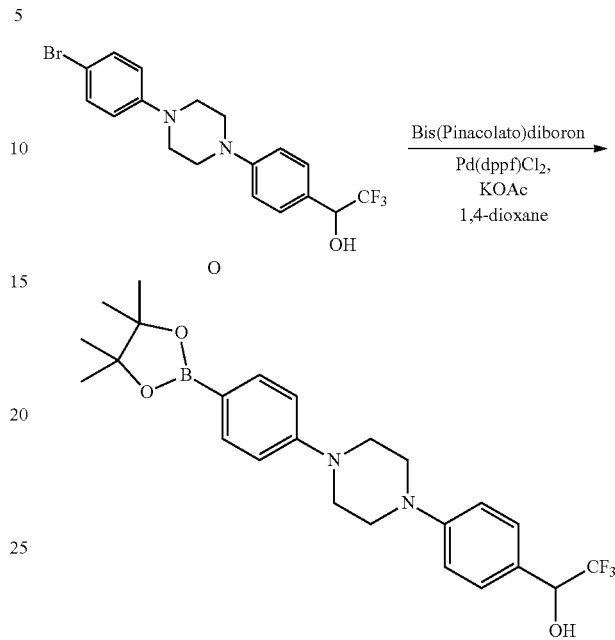

To a stirred solution of Compound O (200 mg, 0.48 mmol) in 1,4-dioxane (30 mL) under argon atmosphere were added bis(pinacolato)diboron (195 mg, 0.77 mmol) and potassium acetate (141 mg, 1.44 mmol) at RT. The reaction mixture was purged with argon for 20 min, then Pd(dppf)Cl₂ (35 mg, 0.05 mmol) was added and the reaction mixture was purged with argon for 10 min at RT. The reaction mixture was stirred at 90° C. for 16 h. The reaction was cooled to RT, diluted with water (10 mL), and the product was extracted with EtOAc (2×10 mL). The combined organic layers were washed with water (10 mL), brine (10 mL), dried over anhydrous Na₂SO₄ and concentrated under reduced pressure. The crude material was purified by silica gel column chromatography (eluent: 20% EtOAc/Hexane) to afford Compound P (100 mg, 0.21 mmol, 45%) as an off-white solid. $^1$H NMR (500 MHz, DMSO-d₆): δ 7.52 (d, J=8.7 Hz, 2H), 7.31 (d, J=8.4 Hz, 2H), 6.98 (d, J=9.0 Hz, 2H), 6.95 (d, J=8.7 Hz, 2H), 6.58 (d, J=5.5 Hz, 1H), 5.02-4.94 (m, 1H), 3.39-3.31 (m, 4H), 3.30-3.26 (m, 4H), 1.25 (s, 12H).

Preparation of (2R)-2-(2,4-difluorophenyl)-1,1-difluoro-3-(1H-tetrazol-1-yl)-1-(5-(4-(4-(2,2,2-trifluoro-1-hydroxyethyl) phenyl) piperazin-1-yl) phenyl) pyridin-2-yl) propan-2-ol (3)

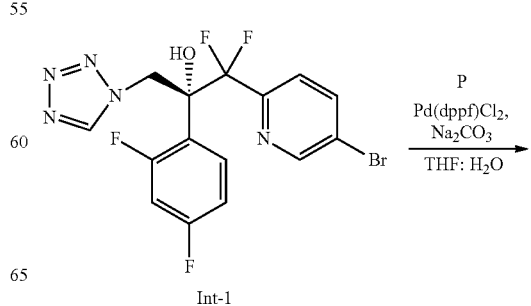

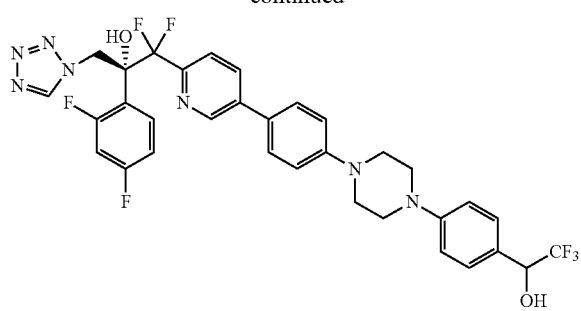

3

To a stirred solution of Int-1 (80 mg, 0.18 mmol) in THF:H$_2$O (4:1, 20 mL) under argon atmosphere were added Compound P (102 mg, 0.22 mmol) and sodium carbonate (58 mg, 0.55 mmol). The reaction mixture was purged with argon for 10 min at RT, then Pd(dppf)Cl$_2$ (13.5 mg, 0.02 mmol) was added and the reaction was stirred at 90° C. for 3 h. The reaction was cooled to RT, diluted with water (20 mL), and the product was extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 50% EtOAc/Hexane) to afford 3 (50 mg, 0.07 mmol, 39%) as a white solid. $^1$H NMR (500 MHz, DMSO-d$_6$): δ 9.13 (s, 1H), 8.89 (s, 1H), 8.15 (dd, J=8.1, 2.0 Hz, 1H), 7.68 (d, J=9.0 Hz, 2H), 7.47 (d, J=8.1 Hz, 1H), 7.33 (d, J=8.7 Hz, 2H), 7.30-7.27 (m, 1H), 7.21-7.15 (m, 1H), 7.12 (d, J=9.0 Hz, 2H), 7.01 (d, J=9.0 Hz, 2H), 6.92-6.87 (m, 1H), 6.59 (d, J=5.5 Hz, 1H), 5.65 (d, J=14.7 Hz, 1H), 5.09 (d, J=14.7 Hz, 1H), 5.03-4.97 (m, 1H), 3.39-3.37 (m, 4H), 3.34-3.31 (m, 4H); MS (ESI): m/z 688.1 [M+H]$^+$; HPLC: 99.61%; Optical rotation [α]$_D^{19}$: +36.8 (c=0.1% in MeOH).

Example 4

(2R)-1-(5-(4-(4-(4-(1-amino-2,2,2-trifluoroethyl) phenyl) piperazin-1-yl) phenyl) pyridin-2-yl)-2-(2,4-difluorophenyl)-1,1-difluoro-3-(1H-tetrazol-1-yl) propan-2-ol (4)

Preparation of 1-(4-(4-(4-bromophenyl) piperazin-1-yl) phenyl)-2,2,2-trifluoroethan-1-one (Q)

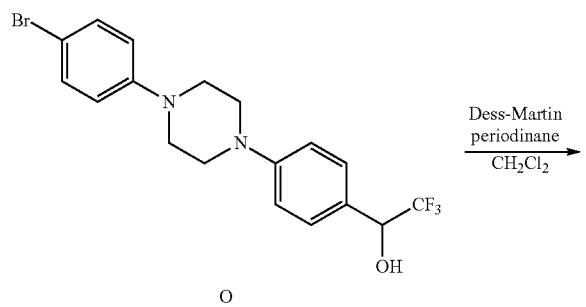

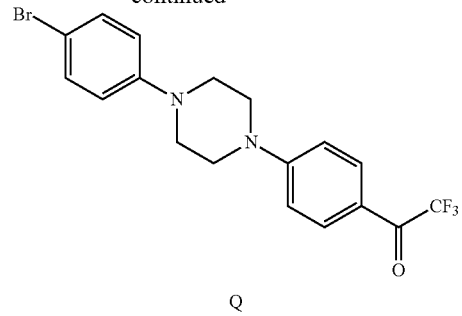

Q

To a stirred solution of Compound O (700 mg, 1.68 mmol) in CH$_2$Cl$_2$ (50 mL) under argon atmosphere was added Dess-Martin periodinane (1.07 g, 2.53 mmol) at 0° C. The reaction mixture was warmed to RT and stirred for 16 h. The reaction mixture was quenched with saturated sodium bicarbonate, a sodium thiosulfate solution (1:1, 100 mL), and the product was extracted with EtOAc (2×100 mL). The combined organic layers were washed with water (100 mL), dried over anhydrous Na$_2$SO$_4$ and concentrated under reduced pressure. The crude material was purified by silica gel column chromatography (eluted with 25% EtOAc/Hexane) to afford Compound Q (380 mg, 0.92 mmol, 54%) as a white solid. $^1$H NMR (500 MHz, DMSO-d$_6$): δ 7.88 (d, J=8.7 Hz, 2H), 7.38 (d, J=8.2 Hz, 2H), 7.13 (d, J=9.3 Hz, 2H), 6.94 (d, J=8.3 Hz, 2H), 3.70-3.64 (m, 4H), 3.37-3.25 (m, 4H).

Preparation of 1-(4-(4-(4-bromophenyl) piperazin-1-yl) phenyl)-2,2,2-trifluoroethan-1-amine (R)

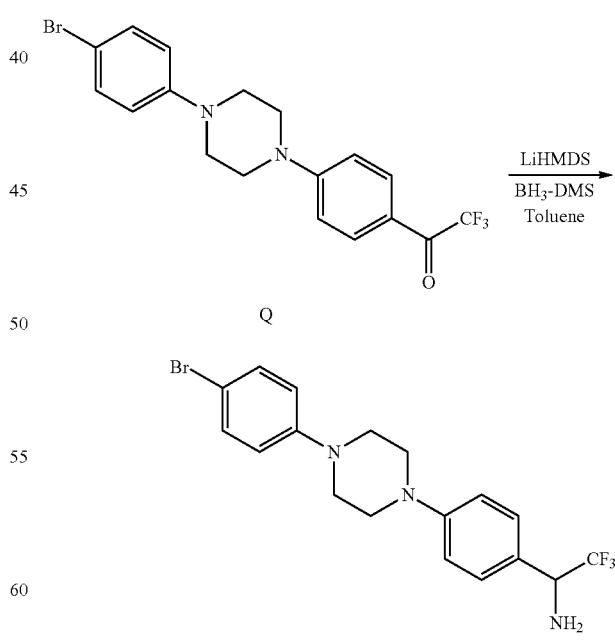

To a stirred solution of Compound Q (800 mg, 1.93 mmol) in toluene (20 mL) under argon atmosphere was added lithium bis(trimethylsilyl)amide (LiHDS, 1M in THF, 4.8 mL, 4.84 mmol) at 0° C. The reaction mixture was warmed to RT and stirred for 1 h. Then borane-dimethylsulfide (BH₃DMS, 1.9 mL, 1.93 mmol, 1M in THF) was added at 0° C. and the reaction was warmed to RT and stirred for 4 h. The reaction mixture was quenched with a 2N NaOH solution (30 mL), and the product was extracted with EtOAc (2×30 mL). The combined organic layers were washed with water (30 mL), brine (30 mL), dried over anhydrous Na₂SO₄ and concentrated under reduced pressure. The crude material was purified by silica gel column chromatography (eluent: 40-50% EtOAc/Hexane) to afford Compound R (350 mg, 0.84 mmol, 43%) as a colorless liquid. ¹H NMR (500 MHz, DMSO-d₆): δ 7.37 (d, J=9.0 Hz, 2H), 7.33 (d, J=8.4 Hz, 2H), 6.99 (d, J=8.7 Hz, 2H), 6.96 (d, J=9.0 Hz, 2H), 4.36 (d, J=7.2 Hz, 1H), 3.31 (s, 8H), 2.36 (brs, 2H).

Preparation of 2,2,2-trifluoro-1-(4-(4-(4-(4,4,5,5-tetramethyl-1,3,2-dioxaborolan-2-yl) phenyl) piperazin-1-yl) phenyl) ethan-1-amine (S)

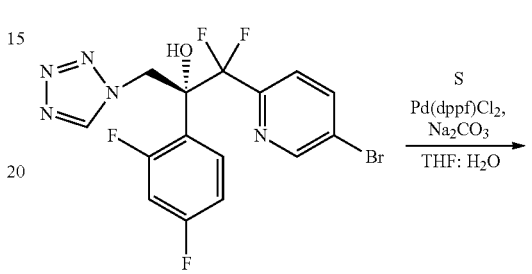

To a stirred solution of Compound R (300 mg, 0.72 mmol) in 1,4-dioxane (30 mL) under argon atmosphere were added bis(pinacolato)diboron (293 mg, 1.15 mmol) and potassium acetate (212 mg, 2.17 mmol). The reaction mixture was purged with argon for 20 min at RT, then Pd(dppf)Cl₂ (53 mg, 0.07 mmol) was added and the reaction mixture was purged with argon for 20 min. The reaction mixture was stirred at 90° C. for 3 h. The reaction was cooled to RT, diluted with water (20 mL), and the product was extracted with EtOAc (2×20 mL). The combined organic extracts were washed with water (20 mL), brine (20 mL), dried over anhydrous Na₂SO₄ and concentrated under reduced pressure. The crude material was purified by silica gel column chromatography (eluent: 50% EtOAc/Hexane) to afford Compound S (171 mg, 0.37 mmol, 51%) as a white solid. ¹H NMR (500 MHz, DMSO-d₆): δ 7.54 (d, J=8.7 Hz, 2H), 7.33 (d, J=8.7 Hz, 2H), 6.99-6.96 (m, 4H), 4.40-4.33 (m, 1H), 3.38-3.35 (m, 4H), 3.29-3.27 (m, 4H), 2.36 (brs, 2H), 1.27 (s, 12H).

(2R)-1-(5-(4-(4-(4-(1-amino-2,2,2-trifluoroethyl) phenyl) piperazin-1-yl) phenyl) pyridin-2-yl)-2-(2, 4-difluorophenyl-1,1-difluoro-3-(1H-tetrazol-1-yl) propan-2-ol (4)

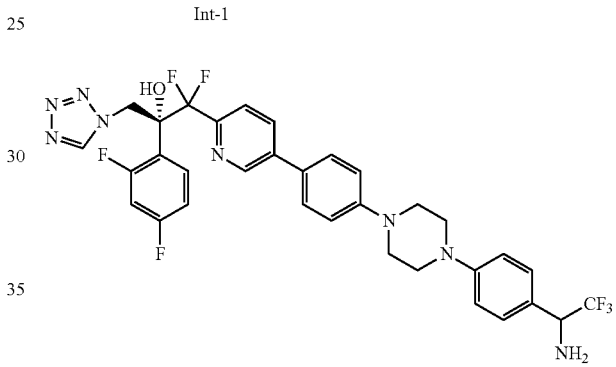

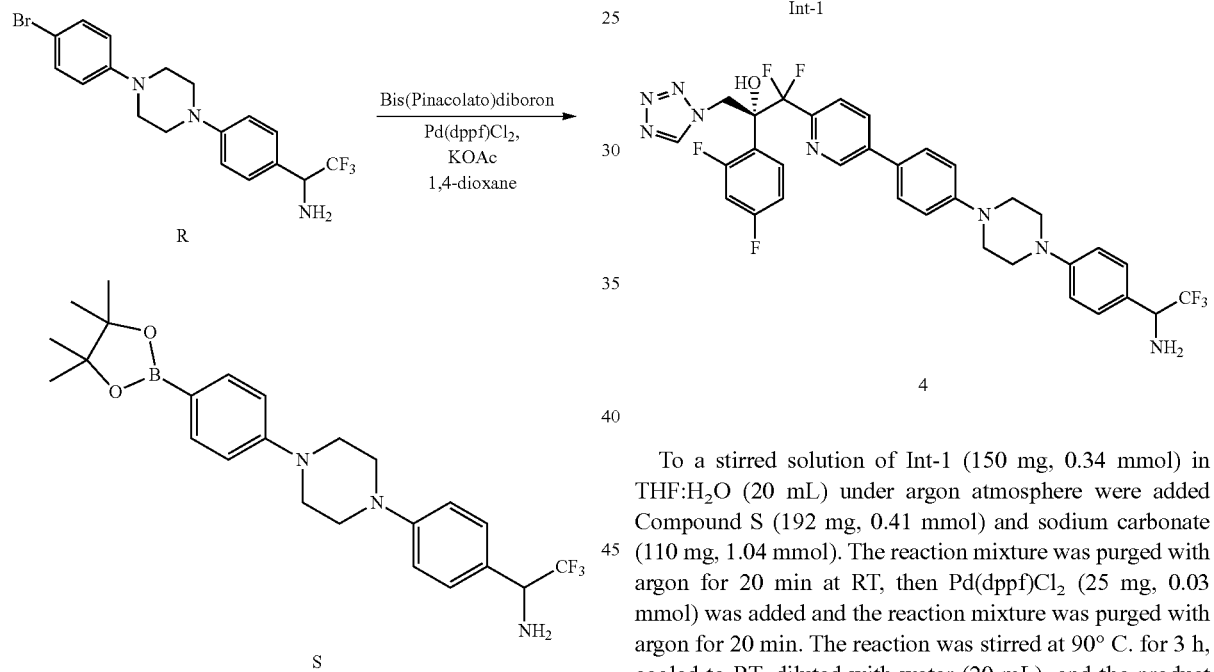

To a stirred solution of Int-1 (150 mg, 0.34 mmol) in THF:H₂O (20 mL) under argon atmosphere were added Compound S (192 mg, 0.41 mmol) and sodium carbonate (110 mg, 1.04 mmol). The reaction mixture was purged with argon for 20 min at RT, then Pd(dppf)Cl₂ (25 mg, 0.03 mmol) was added and the reaction mixture was purged with argon for 20 min. The reaction was stirred at 90° C. for 3 h, cooled to RT, diluted with water (20 mL), and the product was extracted with EtOAc (2×20 mL). The combined organic extracts were washed with water (20 mL), brine (20 mL), dried over anhydrous Na₂SO₄ and concentrated under reduced pressure. The crude material was purified by silica gel column chromatography (eluent: 4% Methanol/CH₂Cl₂) to afford 4 (60 mg, 0.08 mmol, 25%) as an off-white solid. ¹H NMR (500 MHz, DMSO-d₆): δ 9.14 (s, 1H), 8.90 (s, 1H), 8.16 (d, J=8.4 Hz, 1H), 7.69 (d, J=8.7 Hz, 2H), 7.47 (d, J=8.1 Hz, 1H), 7.33 (d, J=8.7 Hz, 2H), 7.30-7.27 (m, 2H), 7.22-7.16 (m, 1H), 7.13 (d, J=8.7 Hz, 2H), 7.00 (d, J=8.7 Hz, 2H), 6.93-6.87 (m, 1H), 5.66 (d, J=14.7 Hz, 1H), 5.10 (d, J=14.7 Hz, 1H), 4.40-4.33 (m, 1H), 3.40-3.37 (m, 4H), 3.34-3.29 (m, 4H), 2.39 (brs, 2H); MS (ESI): m/z 685.3 [M–H]⁻; HPLC: 96.43%; Optical rotation $[\alpha]_D^{20}$: +24.0 (c=0.1% in MeOH).

Example 5

(2R)-2-(2,4-difluorophenyl)-1,1-difluoro-1-(5-(4-(4-(3-fluoro-4-(2,2,2-trifluoro-1-hydroxyethyl) phenyl) piperazin-1-yl) phenyl) pyridin-2-yl)-3-(1H-tetrazol-1-yl) propan-2-ol (5)

Preparation of 4-(4-(4-bromophenyl) piperazin-1-yl)-2-fluorobenzonitrile (U

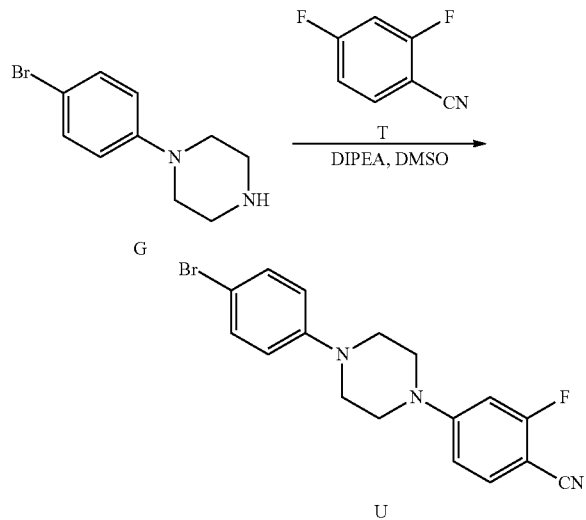

To a stirred solution of Compound G (1 g, 4.14 mmol) in DMSO (10 mL) under argon atmosphere was added diisopropyl ethylamine (1.5 mL, 8.29 mmol) at RT. After 5 minutes, 2,4-difluorobenzonitrile T (576 mg, 4.14 mmol) was added to the reaction mixture at RT. The reaction mixture was stirred at 90° C. for 8 h. The reaction was cooled to RT, diluted with ice cold water (50 mL), and the product was extracted with EtOAc (2×50 mL). The combined organic layers were washed with water (50 mL), brine (50 mL), dried over anhydrous Na$_2$SO$_4$ and concentrated under reduced pressure. The crude material was purified by silica gel column chromatography (eluent: 20-50% EtOAc/Hexane) to afford Compound U (1 g, 2.77 mmol, 67%) as an off-white solid. $^1$H NMR (500 MHz, CDCl$_3$): δ 7.44 (dd, J=8.7, 7.8 Hz, 1H), 7.38 (d, J=9.0 Hz, 2H), 6.81 (d, J=9.0 Hz, 2H), 6.67 (dd, J=8.7, 2.3 Hz, 1H), 6.60 (dd, J=12.7, 2.3 Hz, 1H), 3.54-3.46 (m, 4H), 3.34-3.26 (m, 4H).

Preparation of 4-(4-(4-bromophenyl) piperazin-1-yl)-2-fluorobenzaldehyde (V)

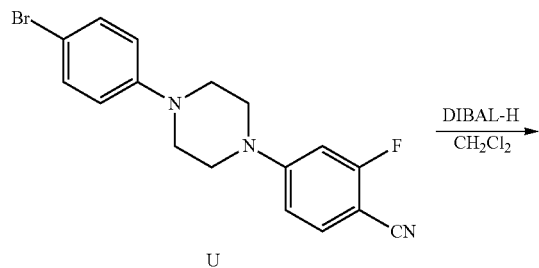

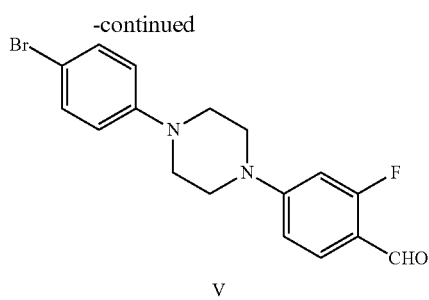

To a stirred solution of Compound U (400 mg, 1.11 mmol) in CH$_2$Cl$_2$ (15 mL) under argon atmosphere was added DIBAL-H (1.0M in toluene, 2.2 mL, 2.22 mmol) at 0° C. The reaction was stirred for 6 h and then quenched with 1.0N HCl solution (20 mL) at 0° C. The product was extracted with CH$_2$Cl$_2$ (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 25% EtOAc/Hexane) to afford Compound V (300 mg, 0.82 mmol, 75%) as a yellow solid. $^1$H NMR (500 MHz, CDCl$_3$): δ 10.13 (s, 1H), 7.78 (t, J=8.5 Hz, 1H), 7.46 (d, J=9.0 Hz, 2H), 7.06 (d, J=8.1 Hz, 2H), 6.72 (dd, J=9.0, 2.3 Hz, 1H), 6.53 (dd, J=13.9, 2.3 Hz, 1H), 3.73-3.68 (m, 4H), 3.44-3.34 (m, 4H).

Preparation of 1-(4-(4-(4-bromophenyl) piperazin-1-yl)-2-fluorophenyl)-2,2,2-trifluoroethan-1-ol (W)

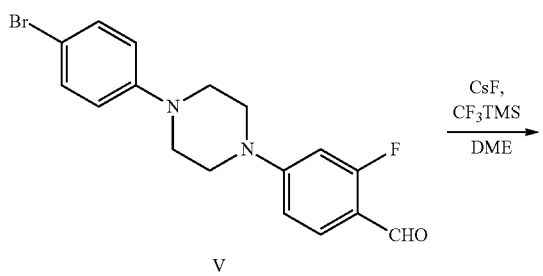

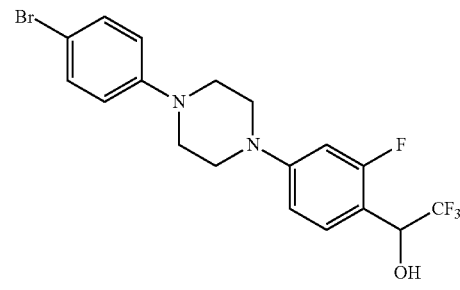

To a stirred solution of Compound V (300 mg, 0.82 mmol) in DME (5 mL) under argon atmosphere were added cesium fluoride (62 mg, 0.41 mmol) and CF$_3$TMS (0.17 mL, 1.23 mmol) at 0° C. The reaction was stirred for 16 h and quenched with 1.0N HCl solution. After stirring at 0° C. for 2 h, the reaction was allowed to warm to RT, diluted with water (20 mL), and the product was extracted with EtOAc (2×20 mL). The combined organic layers were washed with water (20 mL), dried over anhydrous Na$_2$SO$_4$ and concentrated under reduced pressure. The crude material was purified by silica gel column chromatography (eluent: 20% EtOAc/Hexane) to afford Compound W (300 mg, 0.7 mmol, 84%) as a colorless thick syrup. $^1$H NMR (500 MHz, CDCl$_3$): δ 7.54-7.36 (m, 3H), 7.01 (brs, 2H), 6.78 (dd, J=8.7, 2.3 Hz, 1H), 6.64 (dd, J=13.3, 2.3 Hz, 1H), 5.31 (d, J=6.4 Hz, 1H), 3.52-3.47 (m, 4H), 3.38-3.33 (m, 4H), 2.59 (brs, 1H).

Preparation of 2,2,2-trifluoro-1-(2-fluoro-4-(4-(4-(4,4,5,5-tetramethyl-1,3,2-dioxaborolan-2-yl)phenyl) piperazin-1-yl) phenyl) ethan-1-ol (X)

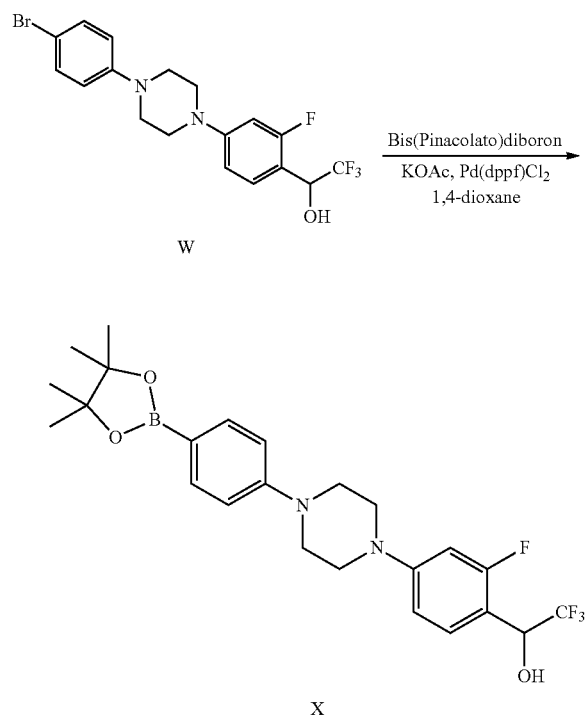

To a stirred solution of Compound W (220 mg, 0.51 mmol) in 1,4-dioxane (10 mL) under argon atmosphere were added bis(pinacolato)diboron (260 mg, 1.02 mmol) and potassium acetate (150 mg, 1.53 mmol) at RT. The reaction mixture was purged with argon for 15 min, then Pd(dppf)Cl$_2$ (37 mg, 0.05 mmol) was added and the reaction mixture was purged with argon for 5 min at RT. The reaction mixture was stirred at 90° C. for 16 h. The reaction mixture was cooled to RT, diluted with water (10 mL), and the product was extracted with EtOAc (2×10 mL). The combined organic layers were washed with water (10 mL), brine (10 mL), dried over anhydrous Na$_2$SO$_4$ and concentrated under reduced pressure. The crude material was purified by silica gel column chromatography (eluent: 30% EtOAc/Hexane) to afford Compound X (150 mg, 0.37 mmol, 72%) as an off-white solid. $^1$H NMR (500 MHz, CDCl$_3$): δ 7.74 (d, J=8.7 Hz, 2H), 7.44 (t, J=8.5 Hz, 1H), 6.93 (d, J=8.4 Hz, 2H), 6.76 (dd, J=8.7, 2.3 Hz, 1H), 6.61 (dd, J=13.6, 2.0 Hz, 1H), 5.30 (t, J=6.2 Hz, 1H), 3.42-3.38 (m, 8H), 2.54 (d, J=5.5 Hz, 1H), 1.33 (s, 12H).

Preparation of (2R)-2-(2,4-difluorophenyl)-1,1-difluoro-1-(5-(4-(4-(3-fluoro-4-(2,2,2-trifluoro-1-hydroxyethyl) phenyl) piperazin-1-yl) phenyl) pyridin-2-yl)-3-(1H-tetrazol-1-yl) propan-2-ol (5)

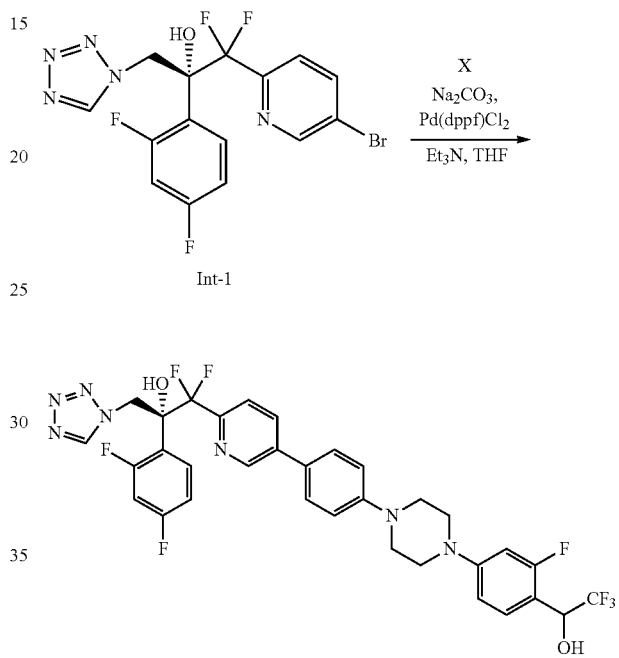

To a stirred solution of Int-1-(150 mg, 0.35 mmol) in THF:Et$_3$N (9:1, 10 mL) under argon atmosphere were added Compound X (141 mg, 0.35 mmol) and sodium carbonate (110 mg, 1.04 mmol). The reaction mixture was purged with argon for 10 min at RT, then Pd(dppf)Cl$_2$ (25 mg, 0.03 mmol) was added and the reaction was stirred at 60° C. for 8 h. The reaction was cooled to RT, diluted with water (20 mL), and the product was extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 40% EtOAc/Hexane) to afford 5 (90 mg, 0.01 mmol, 36%) as a yellow solid. $^1$H NMR (500 MHz, DMSO-d$_6$): δ 9.15 (s, 1H), 8.90 (s, 1H), 8.17 (dd, J=8.1, 1.7 Hz, 1H), 7.70 (d, J=8.7 Hz, 2H), 7.48 (d, J=8.4 Hz, 1H), 7.42 (t, J=8.7 Hz, 1H), 7.32-7.26 (m, 2H), 7.22-7.17 (m, 1H), 7.13 (d, J=8.7 Hz, 2H), 6.91 (dd, J=5.2, 2.9 Hz, 2H), 6.84 (d, J=13.9 Hz, 1H), 6.79 (d, J=5.8 Hz, 1H), 5.67 (d, J=14.7 Hz, 1H), 5.25-5.18 (m, 1H), 5.11 (d, J=14.7 Hz, 1H), 3.39 (s, 8H); MS (ESI): m/z 706.4 [M+H]$^+$; HPLC: 98.65%; Optical rotation $[α]_D^{19}$: +38.8 (c=0.1% in MeOH).

Examples 6, 6-Fr-I and 6-Fr-II (2R)-2-(2,4-difluorophenyl)-1,1-difluoro-3-(1H-tetrazol-1-yl)-1-(5-(4-(4-(6-(2,2,2-trifluoro-1-hydroxyethyl) pyridin-3-yl) piperazin-1-yl) phenyl) pyridin-2-yl) propan-2-ol (6)

Preparation of 5-(4-(4-bromophenyl) piperazin-1-yl) picolinonitrile (Z)

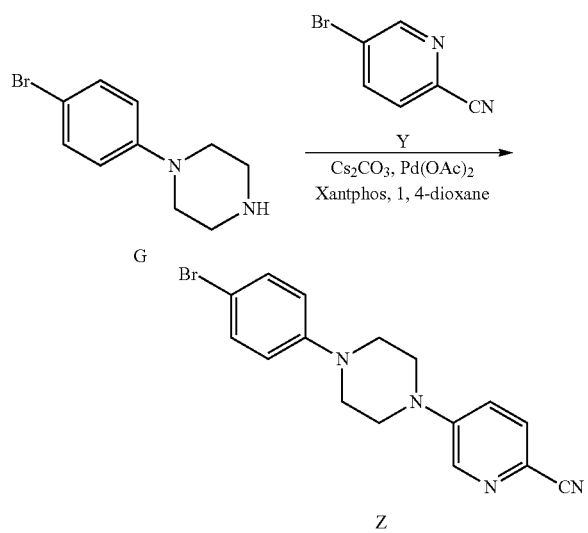

To a stirred solution of 1-(4-bromophenyl)-piperazine G (2 g, 8.29 mmol) in 1,4-dioxane (20 mL) in a sealed tube under argon atmosphere were added cesium carbonate (4.32 g, 13.27 mmol), Xantphos (575 mg, 0.99 mmol), and 5-bromopicolinonitrile (Y, 2.27 g, 12.49 mmol) at RT. The reaction mixture was purged with argon for 20 min, then Pd(OAc)₂ (223 mg, 0.33 mmol) was added and the reaction mixture was stirred at 120° C. for 6 h. The reaction was cooled to RT, diluted with water (100 mL), and the product was extracted with EtOAc (2×100 mL). The combined organic extracts were washed with water (50 mL), brine (50 mL), dried over anhydrous Na₂SO₄ and concentrated under reduced pressure. The crude material was purified by silica gel column chromatography (eluent: 20% EtOAc/Hexane) to afford Compound Z (1.9 g, 5.55 mmol, 67%) as a yellow solid. ¹H NMR (500 MHz, CDCl₃): δ 8.36 (s, 1H), 7.54 (d, J=8.7 Hz, 1H), 7.39 (d, J=9.0 Hz, 2H), 7.14 (dd, J=8.7, 2.9 Hz, 1H), 6.82 (d, J=9.0 Hz, 2H), 3.56-3.51 (m, 4H), 3.36-3.30 (m, 4H).

Preparation of 5-(4-(4-bromophenyl) piperazin-1-yl) picolinaldehyde (AA)

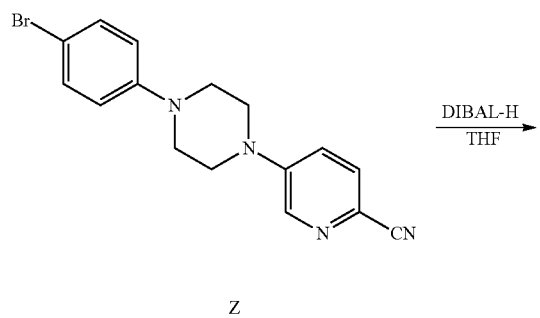

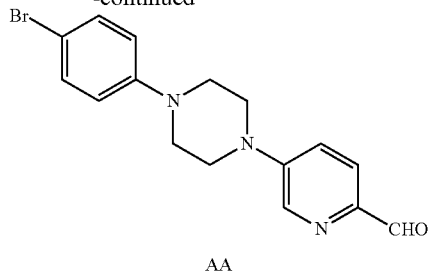

To a stirred solution of Compound Z (1.5 g, 4.38 mmol) in THF (30 mL) under argon atmosphere was added DIBAL-H (8.7 mL, 8.77 mmol, 1M in toluene) at −78° C. The reaction was stirred for 2 h at −78° C. The reaction mixture was quenched with 1N HCl solution (100 mL) and filtered. The filtrate was diluted water (50 mL), and the product was extracted with EtOAc (2×50 mL). The combined organic extracts were dried over anhydrous Na₂SO₄ and concentrated under reduced pressure. The crude material was purified by silica gel column chromatography (eluent: 40% EtOAc/Hexane) to afford Compound AA (320 mg, 0.92 mmol, 21%) as a yellow solid. ¹H NMR (400 MHz, CDCl₃): δ 9.96 (s, 1H), 8.44 (brs, 1H), 7.91 (d, J=8.8 Hz, 1H), 7.40 (d, J=8.9 Hz, 2H), 7.25-7.22 (m, 1H), 6.86 (d, J=8.3 Hz, 2H), 3.66-3.58 (m, 4H), 3.41-3.31 (m, 4H).

Preparation of 1-(5-(4-(4-bromophenyl) piperazin-1-yl) pyridin-2-yl)-2,2,2-trifluoroethan-1-ol (AB)

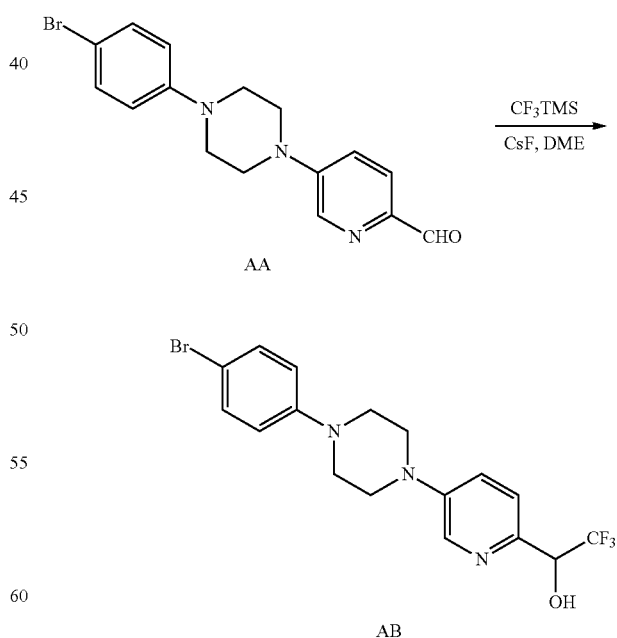

To a stirred solution of Compound AA (320 mg, 0.92 mmol) in DME (10 mL) under argon atmosphere were added cesium fluoride (140 mg, 0.92 mmol) and CF₃TMS (197 mg, 1.39 mmol) at 0° C. The reaction mixture was warmed to RT and stirred for 6 h. The reaction mixture was quenched with a 1.0N HCl solution (20 mL) at 0° C. stirred for 2 h, diluted with water (20 mL), and the product was extracted with EtOAc (2×20 mL). The combined organic layers were washed with water (20 mL), dried over anhydrous $Na_2SO_4$ and concentrated under reduced pressure. The crude material was purified by silica gel column chromatography (eluent: 40% EtOAc/Hexane) to afford Compound AB (180 mg, 0.43 mmol, 47%) as an off-white solid. $^1$H NMR (400 MHz, $CDCl_3$): δ 8.31 (s, 1H), 7.39 (d, J=8.9 Hz, 2H), 7.35 (d, J=8.4 Hz, 1H), 7.34 (d, J=8.4 Hz, 1H), 6.86 (d, J=9.0 Hz, 2H), 5.05-5.00 (m, 1H), 3.48-3.42 (m, 4H), 3.36-3.31 (m, 4H).

Preparation of 2,2,2-trifluoro-1-(5-(4-(4-(4,4,5,5-tetramethyl-1,3,2-dioxaborolan-2-yl phenyl) piperazin-1-yl) pyridin-2-yl) ethan-1-ol (AC)

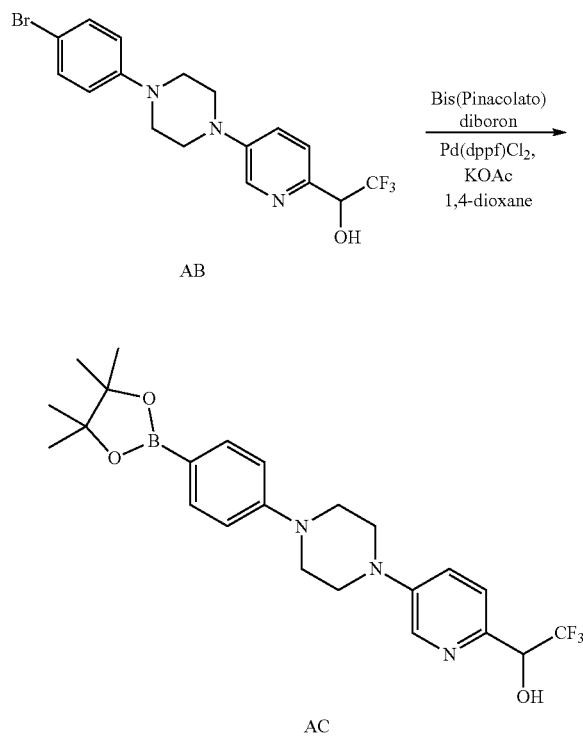

To a stirred solution of Compound AB (180 mg, 0.43 mmol) in 1,4-dioxane (5 mL) under argon atmosphere were added bis(pinacolato)diboron (175 mg, 0.69 mmol) and potassium acetate (127 mg, 1.30 mmol) at RT. The reaction mixture was purged with argon for 10 min, then $Pd(dppf)Cl_2$ (32 mg, 0.04 mmol) was added and the reaction mixture was purged with argon for 10 min at RT. The reaction mixture was stirred at 90° C. for 12 h. The reaction was cooled to RT, diluted with water (10 mL), and the product was extracted with EtOAc (2×10 mL). The combined organic layers were washed with water (10 mL), brine (10 mL), dried over anhydrous $Na_2SO_4$ and concentrated under reduced pressure. The crude material was purified by silica gel column chromatography (eluent: 20% EtOAc/Hexane) to afford Compound AC (120 mg, 0.25 mmol, 60%) as an off-white solid. $^1$H NMR (500 MHz, $CDCl_3$): δ 8.31 (s, 1H), 7.75 (d, J=8.4 Hz, 2M), 7.34 (s, 2H), 6.96 (d, J=8.4 Hz, 2H), 5.04-5.00 (m, 1H), 3.45 (s, 8H), 1.33 (s, 12H).

Preparation of (2R)-2-(2,4-difluorophenyl)-1,1-difluoro-3-(1H-tetrazol-1-yl)-1-(5-(4-(4-(6-(2,2,2-trifluoro-1-hydroxyethyl) pyridin-3-yl) piperazin-1-yl) phenyl) pyridin-2-yl) propan-2-ol (6)

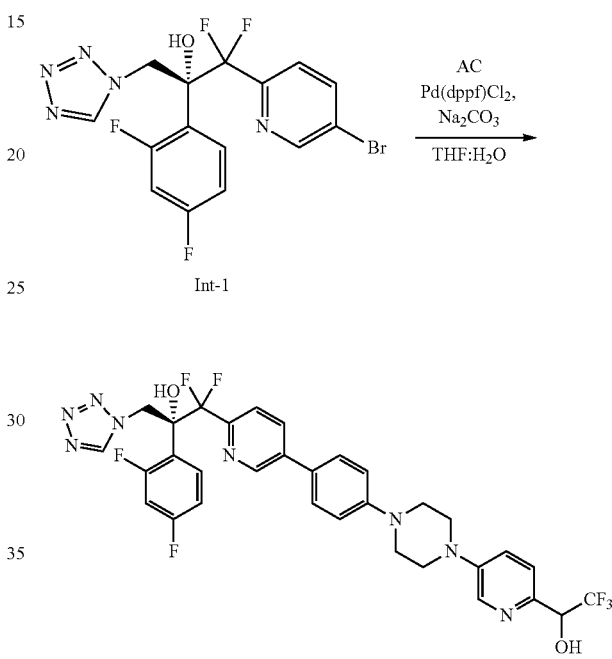

To a stirred solution of Int-1 (100 mg, 0.23 mmol) in $THF:H_2O$ (4:1, 5 mL) under argon atmosphere were added Compound AC (117 mg, 0.25 mmol) and sodium carbonate (74 mg, 0.70 mmol) at RT. The reaction mixture was purged with argon for 10 min, then $Pd(dppf)Cl_2$ (17 mg, 0.02 mmol) was added and the reaction mixture was purged with argon for 5 min at RT. The reaction mixture was stirred at 80° C. for 3 h. The reaction was cooled to RT, diluted with water (10 mL), and the product was extracted with EtOAc (2×10 mL). The combined organic layers were washed with water (10 mL), brine (10 mL), dried over anhydrous $Na_2SO_4$ and concentrated under reduced pressure. The crude material was purified by silica gel column chromatography (eluent: 1% $MeOH/CH_2Cl_2$) to afford 6 (29 mg, 0.06 mmol, 18%) as an off-white solid. $^1$H NMR (500 MHz, DMSO-$d_6$): δ 9.15 (s, 1H), 8.91 (s, 1H), 8.34 (s, 1H), 8.17 (dd, J=8.2, 2.2 Hz, 1H), 7.70 (d, J=9.0 Hz, 2H), 7.51-7.42 (m, 3H), 7.31-7.27 (m, 2H), 7.23-7.17 (m, 1H), 7.15 (d, J=8.7 Hz, 2H), 6.94-6.88 (m, 1H), 6.77 (d, J=6.1 Hz, 1H), 5.67 (d, J=14.7 Hz, 1H), 5.11 (d, J=14.7 Hz, 1H), 5.04-4.98 (m, 1H), 3.41 (s, 8H); MS (ESI): m/z 687.3 [M−H]$^−$; HPLC: 93.83%; Optical rotation $[α]_D^{19}$: +42.1 (c=0.1% in MeOH).

Chiral Preparative HPLC Details for AB-Fr-I & AB-Fr-II:

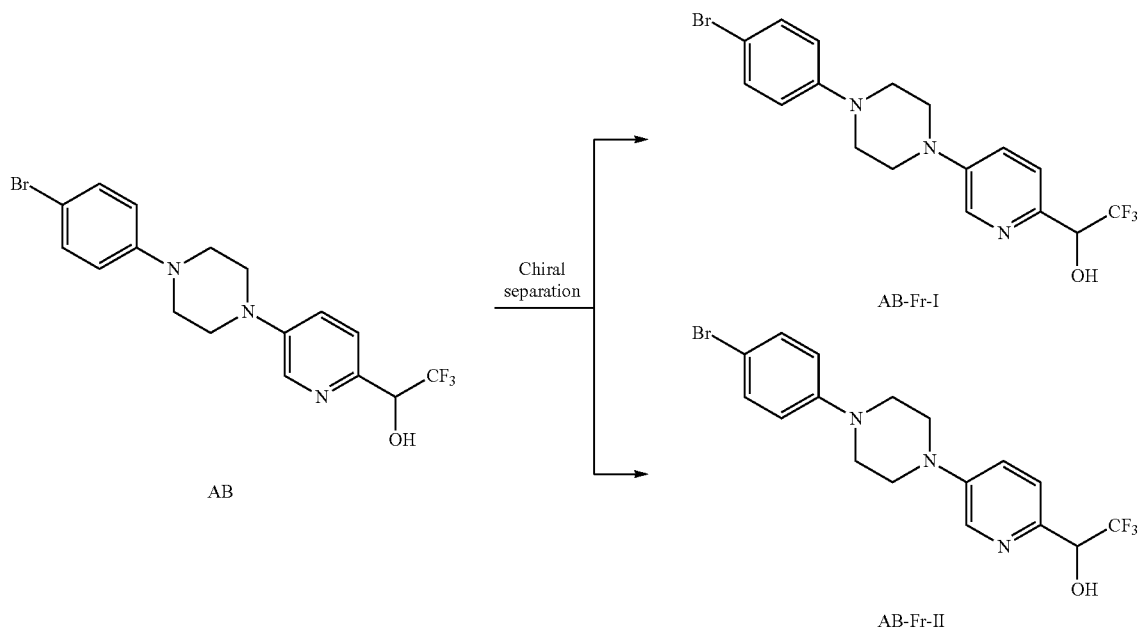 [SMILES: OC(c1ccc(N2CCN(c3ccc(Br)cc3)CC2)cn1)C(F)(F)F ; OC(c1ccc(N2CCN(c3ccc(Br)cc3)CC2)cn1)C(F)(F)F ; OC(c1ccc(N2CCN(c3ccc(Br)cc3)CC2)cn1)C(F)(F)F ; "AB-Fr-II" ; "AB-Fr-I"]

The enantiomers (600 mg of AB, 1.44 mmol) were separated by normal-phase preparative high performance liquid chromatography (CHIRALPAK-IA®, 250×20 mm, 5μ; using 0.1% DEA MeOH:(B) CH$_2$Cl$_2$:MeOH (10:90) (70:30) as a mobile phase; Flow rate: 20 mL/min) to obtain AB-Fr-I (220 mg) and AB-Fr-II (220 mg).

AB-Fr-I:
$^1$H NMR (400 MHz, CDCl$_3$): δ 8.31 (s, 1H), 7.39 (d, J=8.9 Hz, 2H), 7.35 (d, J=8.4 Hz, 1H), 7.34 (d, J=8.4 Hz, 1H), 6.86 (d, J=9.0 Hz, 21H), 5.05-5.00 (m, 1H), 3.48-3.42 (m, 4H), 3.36-3.31 (m, 4H); LC-MS: 415.9 [M+H]$^+$ at 2.56 RT (98.90% purity); HPLC: 99.39%; Chiral HPLC Purity: 100%, R$_t$=7.06 min (CHIRALPAK-IA®, 250×4.6 mm, 5μ; mobile phase (A) 0.1% DEA MeOH:(B) CH$_2$Cl$_2$:MeOH (10:90) (70:30); flow Rate: 1.0 mL/min); Optical rotation [α]$_D^{19}$: −21.4 (C=0.1% in MeOH).

AB-Fr-II:
$^1$H NMR (400 MHz, CDCl$_3$): δ 8.31 (s, 1H), 7.39 (d, J=8.9 Hz, 2H), 7.35 (d, J=8.4 Hz, 1H), 7.34 (d, J=8.4 Hz, 1H), 6.86 (d, J=9.0 Hz, 2H), 5.05-5.00 (m, 1H), 3.48-3.42 (m, 4H), 3.36-3.31 (m, 4H); LC-MS: 415.9 [M+H]$^+$ at 2.56 RT (97.08% purity); HPLC: 95.88%; Chiral HPLC Purity: 99.32%. R$_t$=9.65 min (CHIRALPAK-IA®, 250×4.6 mm, 5μ; mobile phase (A) 0.1% DEA MeOH:(B) CH$_2$Cl$_2$:MeOH (10:90) (70:30); flow Rate: 1.0 mL/min); Optical rotation [α]$_D^{19}$: +23.0 (C=0.1% in MeOH)

2,2,2-trifluoro-1-(5-(4-(4-(4,4,5,5-tetramethyl-1,3,2-dioxaborolan-2-yl) phenyl) piperazin-1-yl) pyridin-2-yl) ethan-1-ol (AC-Fr-I)

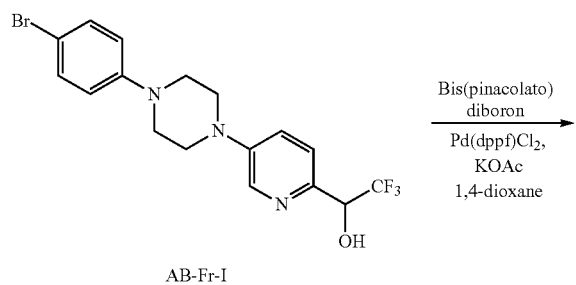

-continued

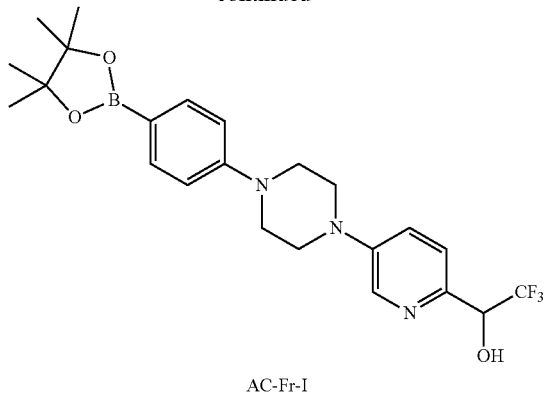

AC-Fr-I

To a stirred solution of AB-Fr-I (220 mg, 0.53 mmol) in 1,4-dioxane (20 mL) under argon atmosphere were added bis(pinacolato)diboron (214 mg, 0.84 mmol) and KOAc (155 mg, 1.59 mmol) at RT. The reaction mixture was purged with argon for 20 min, then Pd(dppf)Cl$_2$ (38 mg, 0.053 mmol) was added and the reaction mixture was purged under argon for 10 min at RT. The reaction mixture was stirred at 100° C. for 5 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 30% EtOAc/Hexane) to afford compound AC-Fr-I (200 mg, 0.43 mmol, 81%) as an off-white solid used in the next step without further purification.

2,2,2-trifluoro-1-(5-(4-(4-(4,4,5,5-tetramethyl-1,3,2-dioxaborolan-2-yl)phenyl)piperazin-1-yl)pyridin-2-yl)ethan-1-ol (AC-Fr-II)

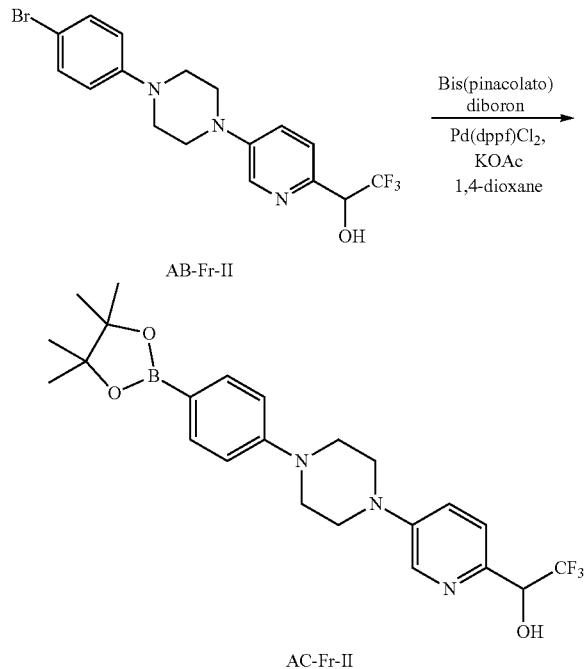

To a stirred solution of AB-Fr-II (220 mg, 0.528 mmol) in 1,4-dioxane (30 mL) under argon atmosphere were added bis(pinacolato)diboron (214 mg, 0.846 mmol) and KOAc (155 g, 1.58 mmol) at RT. The reaction mixture was purged with argon for 20 min, then Pd(dppf)Cl₂ (38 mg, 0.052 mmol) was added and the reaction mixture was purged under argon for 10 min at RT. The reaction mixture was stirred at 90° C. for 5 h. The reaction mixture was quenched with water (20 mL) and extracted with EtOAc (2×20 mL). The combined organic layers were washed with water (20 mL), brine (20 mL), dried over anhydrous Na₂SO₄ and concentrated under reduced pressure. The crude material was purified by silica gel column chromatography (eluent: 50% EtOAc/Hexane) to afford compound AC-Fr-II (200 mg, 0.475 mmol, 81%) as an off-white solid used in the next step without further purification.

2R)-2-(2,4-difluorophenyl)-1,1-difluoro-3-(1H-tetrazol-1-yl)-1-(5-(4-(4-(6-(2,2,2-trifluoro-1-hydroxyethyl) pyridin-3-yl) piperazin-1-yl) phenyl) pyridin-2-yl) propan-2-ol (6-Fr-I)

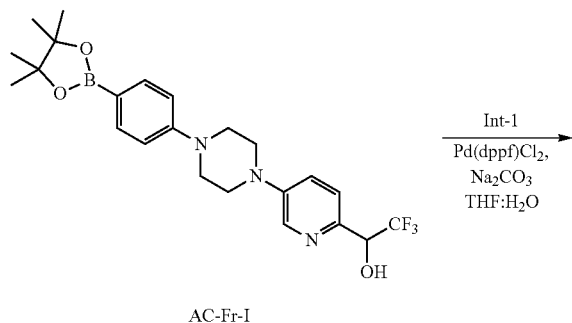

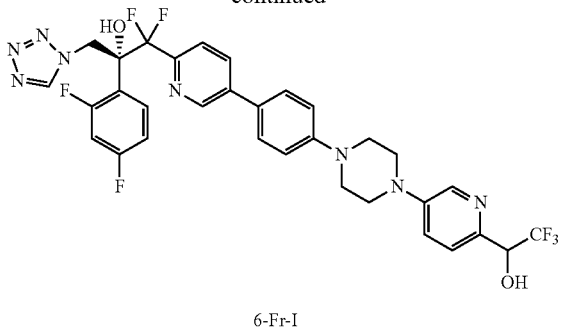

To a stirred solution of Int-1 (120 mg, 0.27 mmol) in THF:H₂O (4:1, 10 mL) under argon atmosphere were added AC-Fr-I (154 mg, 0.33 mmol) and sodium carbonate (88 mg, 0.83 mmol) at RT. The reaction mixture was purged with argon for 20 min, then Pd(dppf)Cl₂ (20 mg, 0.02 mmol) was added and the reaction mixture was purged under argon for 10 min at RT. The reaction mixture was stirred at 80° C. for 3 h. The reaction mixture was quenched with water (20 mL) and extracted with EtOAc (2×20 mL). The combined organic layers were washed with water (20 mL), brine (20 mL), dried over anhydrous Na₂SO₄ and concentrated under reduced pressure. The crude material was purified by silica gel column chromatography (eluent: 40% EtOAc/Hexane) to afford 6-Fr-I (42 mg, 0.06 mmol, 24%) as an off-white solid. ¹H NMR (400 MHz, DMSO-d₆): δ 9.15 (s, 1H), 8.91 (d, J=2.0 Hz, 1H), 8.34 (d, J=2.4 Hz, 1H), 8.17 (dd, J=8.2, 2.2 Hz, 1H), 7.70 (d, J=8.9 Hz, 2H), 7.54-7.38 (m, 3H), 7.32-7.25 (m, 2H), 7.23-7.13 (m, 3H), 6.94-6.88 (m, 1H), 6.77 (d, J=6.1 Hz, 1H), 5.67 (d, J=14.7 Hz, 1H), 5.11 (d, J=14.7 Hz, 1H), 5.06-4.95 (m, 1H), 3.41 (s, 8H); MS (ESI): m/z 687.5 [M−H]⁻; HPLC: 95.61%; Optical rotation [α]$_D^{19}$: +33.80 (c=0.1% in MeOH).

(2R)-2-(2,4-difluorophenyl)-1,1-difluoro-3-(1H-tetrazol-1-yl)-1-(5-(4-(4-(6-(2,2,2-trifluoro-1-hydroxyethyl pyridin-3-yl) piperazin-1-yl) phenyl) pyridin-2-yl) propan-2-ol (6-Fr-II)

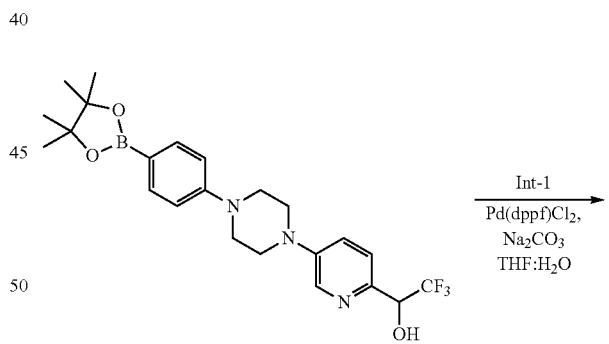

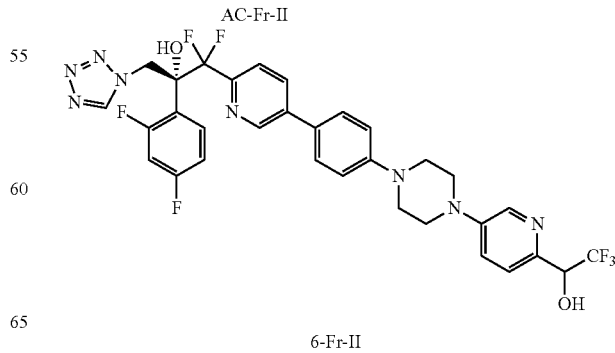

To a stirred solution of Int-1 (120 mg, 0.27 mmol) in THF:H$_2$O (4:1, 20 mL) under argon atmosphere were added AC-Fr-II (154 mg, 0.33 mmol) and sodium carbonate (88 mg, 0.83 mmol) at RT. The reaction mixture was purged with argon for 20 min, then Pd(dppf) Cl$_2$ (20 mg, 0.02 mmol) was added and the reaction mixture was purged under argon for 10 min at RT. The reaction mixture was stirred at 80° C. for 6 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 2% MeOH/CH$_2$Cl$_2$) to afford 6-Fr-II (45 mg, 0.06 mmol, 23%) as an off-white solid. $^1$H NMR (400 MHz, DMSO-d$_6$): δ 9.15 (s, 1H), 8.91 (d, J=2.0 Hz, 1H), 8.34 (d, J=2.4 Hz, 1H), 8.17 (dd, J=8.2, 2.2 Hz, 1H), 7.70 (d, J=8.9 Hz, 2H), 7.54-7.38 (m, 3H), 7.32-7.25 (m, 2H), 7.23-7.13 (m, 3H), 6.94-6.88 (m, 1H), 6.77 (d, J=6.1 Hz, 1H), 5.67 (d, J=14.7 Hz, 1H), 5.11 (d, J=14.7 Hz, 1H), 5.06-4.95 (m, 1H), 3.41 (s, 8H); MS (ESI): m/z 689.7 [M+H]$^+$; HPLC: 95.48%; Optical rotation [α]$_D^{19}$: +55.4 (c=0.1% in MeOH).

Example 7

(R)-5-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) picolinonitrile (7)

Preparation of 5-(4-(4-(4,4,5,5-tetramethyl-1,3,2-dioxaborolan-2-yl) phenyl) piperazin-1-yl) picolinonitrile (AD)

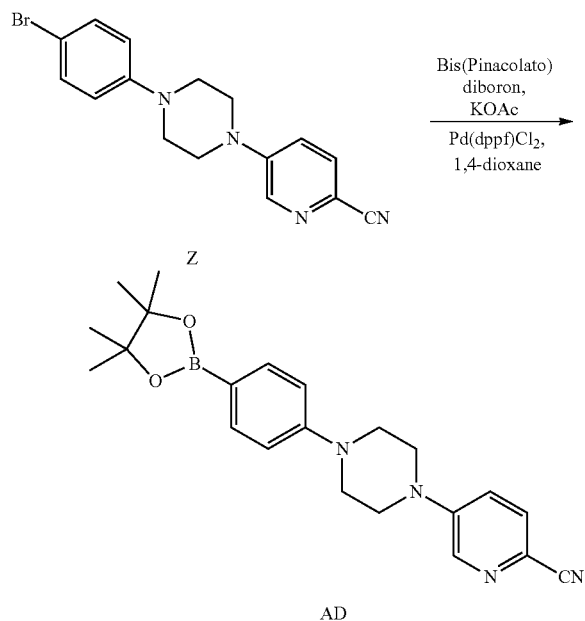

To a stirred solution of Compound Z (400 mg, 1.16 mmol) in 1,4-dioxane (10 mL) in a sealed tube under argon atmosphere were added bis(pinacolato)diboron (473 mg, 1.87 mmol) and potassium acetate (343 mg, 3.50 mmol) at RT. The reaction mixture was purged with argon for 15 min. then Pd(dppf)Cl$_2$ (85 mg, 0.11 mmol) was added and the reaction mixture was stirred at 90° C. for 5 h. The reaction was cooled to RT, diluted with water (30 mL), and the product was extracted with EtOAc (2×30 mL). The combined organic extracts were washed with water (30 mL), brine (30 mL), dried over anhydrous Na$_2$SO$_4$ and concentrated under reduced pressure. The crude material was purified by silica gel column chromatography (eluent: 10% EtOAc/Hexane) to afford Compound AD (220 mg, 0.56 mmol, 48.3%) as a yellow solid. $^1$H NMR (400 MHz, CDCl$_3$): δ 8.35 (d, J=2.7 Hz, 1H), 7.75 (d, J=8.6 Hz, 2H), 7.54 (d, J=8.8 Hz, 1H), 7.12 (t, J=5.4 Hz, 1H), 6.92 (d, J=8.8 Hz, 2H), 3.56-3.52 (m, 4H), 3.47-3.43 (m, 4H), 1.33 (s, 12H).

Preparation of (R)-5-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) picolinonitrile (7)

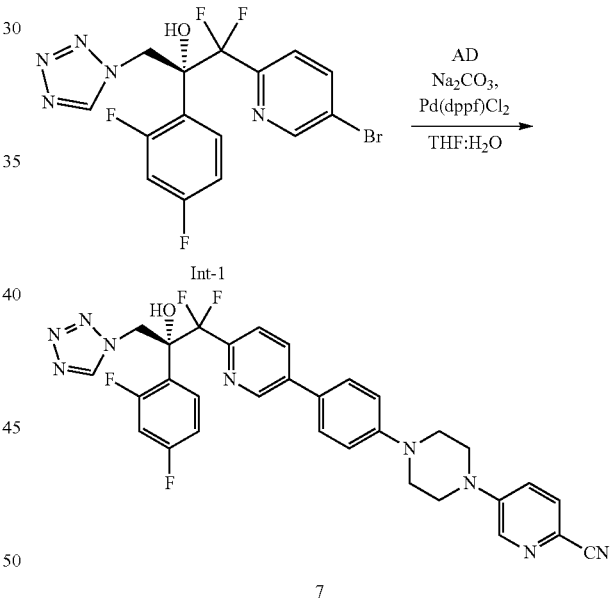

To a stirred solution of Int-1 (150 mg, 0.34 mmol) in THF:H$_2$O (4:1, 5 mL) in a sealed tube under argon atmosphere were added Compound AD (162 mg, 0.41 mmol) and sodium carbonate (110 rug, 1.04 mmol) at RT. The reaction mixture was purged with argon for 10 min, then Pd(dppf)Cl$_2$ (25.3 mg, 0.0.3 mmol) was added and the reaction mixture was stirred at 90° C. for 2 h. The reaction was cooled to RT, diluted with water (10 mL), and the product was extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluent: 60% EtOAc/Hexane) to afford 7 (80 mg, 0.13 mmol, 37.5%) as a yellow solid. ¹H NMR (500 MHz, DMSO-$d_6$): δ 9.13 (s, 1H), 8.89 (s, 1H), 8.47 (d, J=2.9 Hz, 1H), 8.15 (dd, J=8.4, 2.0 Hz, 1H), 7.77 (d, J=9.0 Hz, 1H), 7.69 (d, J=9.0 Hz, 2H), 7.46 (d, J=8.4 Hz, 1H), 7.42 (dd, J=9.0, 2.9 Hz, 1H), 7.31-7.24 (m, 2H), 7.20-7.15 (m, 1H), 7.11 (d, J=9.0 Hz, 2H), 6.92-6.87 (m, 1H), 5.65 (d, J=14.7 Hz, 1H), 5.09 (d, J=14.7 Hz, 1H), 3.61-3.57 (m, 4H), 3.42-3.38 (m, 4H); MS (ESI): m/z 614.2 [M−H]⁻; HPLC: 97.27%; Optical rotation $[α]_D^{20}$: +61.4 (c=0.1% in MeOH).

Example 8

(R)-4-(4-(4-(6-(2,4-difluorophenyl)-1,1-difluoro-2-hydroxy-3-(1H-tetrazol-1-yl) propyl) pyridin-3-yl) phenyl) piperazin-1-yl)-2-fluorobenzonitrile (8)

Preparation of 2-fluoro-4-(4-(4-(4,4,5,5-tetramethyl-1,3,2-dioxaborolan-2-yl) phenyl) piperazin-1-yl) benzonitrile (AE)

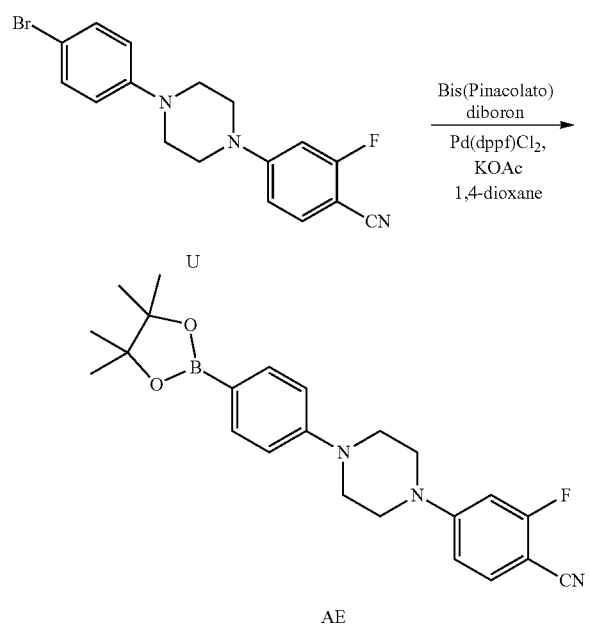

To a stirred solution of Compound U (400 mg, 0.11 mmol) in 1,4-dioxane (10 mL) under argon atmosphere were added bis(pinacolato)diboron (560 mg, 2.22 mmol) and potassium acetate (435 mg, 4.44 mmol) at RT. The reaction mixture was purged with argon for 15 min, then Pd(dppf)Cl₂ (81 mg, 0.11 mmol) was added and the reaction mixture was purged with argon for 5 min at RT. The reaction mixture was stirred at 90° C. for 2 h. The reaction was cooled to RT, diluted with water (20 mL), and the product was extracted with EtOAc (2×20 mL). The combined organic layers were washed with water (20 mL), brine (20 mL), dried over anhydrous Na₂SO₄ and concentrated under reduced pressure. The crude material was purified by silica gel column chromatography (eluent: 30% EtOAc/Hexane) to afford Compound AE (300 mg, 0.73 mmol, 67%) as an off-white solid. ¹H NMR (500 MHz, CDCl₃): δ 7.76 (d, J=8.7 Hz, 2H), 7.45 (t, J=8.1 Hz, 1H), 6.95 (d, J=8.1 Hz, 2H), 6.68 (d, J=8.5 Hz, 1H), 6.60 (dd, J=12.9, 2.2 Hz, 1H), 3.59-3.50 (m, 4H), 3.49-3.40 (m, 4H), 1.35 (s, 12H)

Preparation of (R)-4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl)-2-fluorobenzonitrile (8)

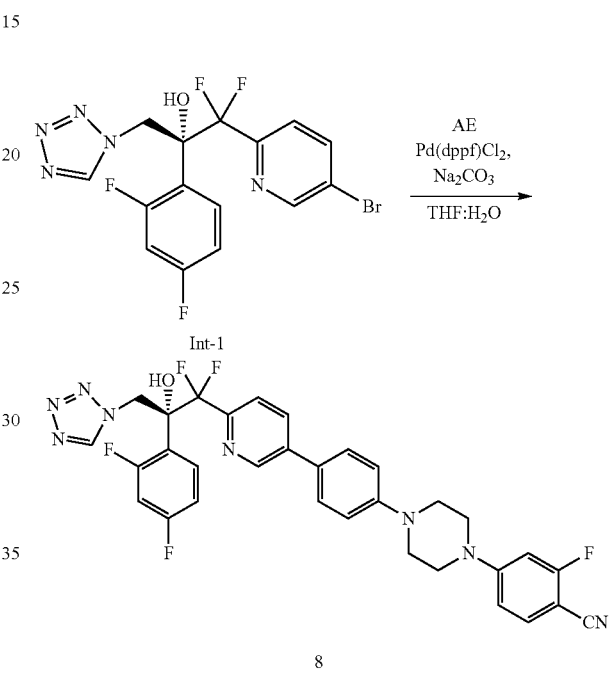

To a stirred solution of Int-1 (150 mg, 0.35 mmol) in THF:H₂O (9:1, 10 mL) under argon atmosphere were added Compound AE (141 ng, 0.35 mmol) and sodium carbonate (110 mg, 1.04 mmol). The reaction was purged with argon for 10 min at RT, then Pd(dppf)Cl₂ (0.025 mg, 0.03 mmol) was added and the reaction mixture was stirred at 90° C. for 2 h. The reaction was cooled to RT, diluted with water (20 mL), and the product was extracted with EtOAc (2×20 mL). The combined organic extracts were washed with water (20 mL), brine (20 mL), dried over anhydrous Na₂SO₄ and concentrated under reduced pressure. The crude material was purified by silica gel column chromatography (eluent: 40% EtOAc % Hexane) to afford 8 (85 mg, 0.13 mmol, 38%) as a yellow solid. ¹H NMR (400 MHz, CDCl₃): δ 8.76 (s, 1H), 8.71 (s, 1H), 7.95 (dd, J=8.3, 2.2 Hz, 1H), 7.84 (s, 1H), 7.62 (d, J=8.4 Hz, 1H), 7.52 (d, J=8.8 Hz, 2H), 7.48-7.35 (m, 2H), 7.03 (d, J=8.8 Hz, 2H), 6.81-6.74 (m, 1H), 6.68 (dd, J=8.9, 2.4 Hz, 2H), 6.66-6.58 (m, 1H), 5.59 (d, J=14.3 Hz, 1H), 5.12 (d, J=14.3 Hz, 1H), 3.58-3.52 (m, 4H), 3.47-3.43 (m, 4H); MS (ESI): m/z 631.3 [M−H]⁻; HPLC: 97.56%; Optical rotation $[α]_D^{19}$: +84.4 (c=0.1% in MeOH).

Example 9

(R)-4-(4-(4-(6-(2-(2,4-difluorophenyl)-1,1-difluoro-2-hydroxy-3-(1H-tetrazol-1-yl)propyl) pyridin-3-yl)-2-fluorophenyl) piperazin-1-yl)-3-fluorobenzonitrile (9)

Preparation of tert-butyl 4-(4-bromo-2-fluorophenyl) piperazine-1-carboxylate (AH)

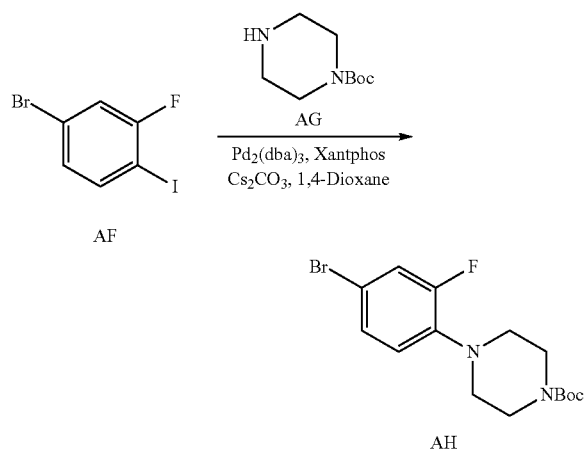

To a stirred solution of 4-bromo-2-fluoro-1-iodobenzene AF (2.5 g, 8.30 mmol) in 1,4-dioxane (50 mL) under argon atmosphere were added tert-butyl piperazine-1-carboxylate (AG, 1.8 g, 9.96 mmol), Xantphos (240 mg, 0.41 mmol) and cesium carbonate (4 g, 12.45 mmol). The reaction was purged with argon for 10 min at RT, then $Pd_2(dba)_3$ (379 mg, 0.41 mmol) was added and the reaction was stirred at 100° C. for 16 h. The reaction was cooled to RT, diluted with water (20 mL), and the product was extracted with EtOAc (2×20 mL). The combined organic extracts were washed with water (20 mL), dried over anhydrous $Na_2SO_4$ and concentrated under reduced pressure. The crude material was purified by silica gel column chromatography (eluent: 3% EtOAc/Hexane) to afford Compound AH (1.3 g, 3.63 mmol, 44%) as a pale yellow solid. $^1$H NMR (500 MHz, DMSO-$d_6$): δ 7.84-7.77 (m, 1H), 7.51-7.36 (m, 1H), 7.00 (t, J=9.0 Hz, 1H), 3.47-3.45 (m, 4H), 3.00-2.88 (m, 4H), 1.42 (s, 9H).

Preparation of 1-(4-bromo-2-fluorophenyl) piperazine hydrochloride (AI)

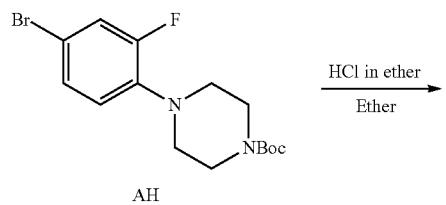

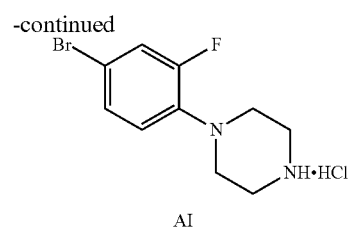

To a stirred solution of Compound AH (1.3 g, 3.62 mmol) in diethyl ether (20 mL) under argon atmosphere was added 1.0 M HCl in $Et_2O$ (7.2 mL, 7.29 mmol) at 0° C. The reaction mixture was warmed to RT and stirred for 4 h. The precipitated solid was filtered, washed with diethyl ether (3×10 mL) and dried under reduced pressure to obtain Compound AI (700 mg, 2.38 mmol, 70%) as an off-white solid. $^1$H NMR (400 MHz, DMSO-$d_6$): δ 9.36 (brs, 1H), 7.49 (dd, J=12.1, 2.3 Hz, 1H), 7.35-7.31 (m, 1H), 7.06 (t, J=9.1 Hz, 1H), 4.65 (brs, 8H).

Preparation of 4-(4-(4-bromo-2-fluorophenyl) piperazin-1-yl)-3-fluorobenzonitrile (AK)

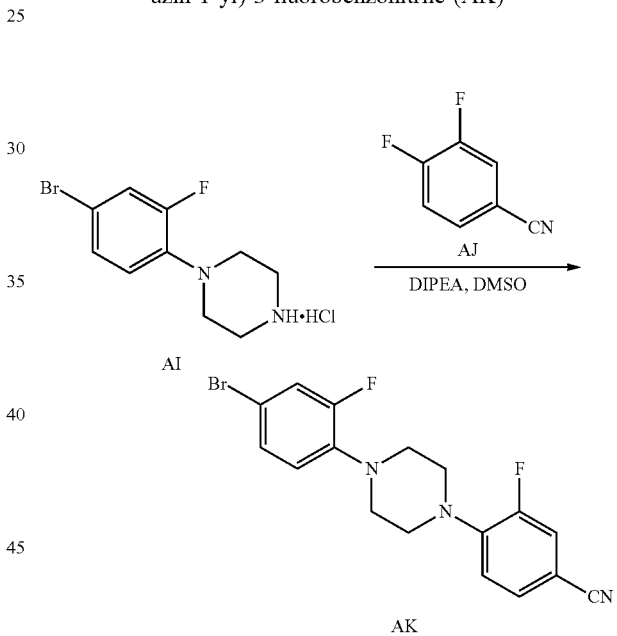

To a stirred solution of 3,4-difluorobenzonitrile AJ (300 mg, 2.15 mmol) in DMSO (10 mL) under argon atmosphere were added Compound AI (612 mg, 2.37 mmol) and diisopropylethylamine (1.1 mL, 6.47 mmol) at RT. The reaction mixture was stirred at 90° C. for 5 h. The reaction was cooled to RT, diluted with water (20 mL), and the product was extracted with EtOAc (2×20 mL). The combined organic extracts were washed with water (20 mL), dried over anhydrous $Na_2SO_4$ and concentrated under reduced pressure. The crude material was purified by silica gel column chromatography (eluent: 10% EtOAc/Hexane) to afford Compound AK (350 mg, 0.92 mmol, 43%) as an off-white solid. $^1$H NMR (500 MHz, DMSO-$d_6$): δ 7.73 (dd, J=13.3, 1.7 Hz, 1H), 7.60 (dd, J=8.5, 1.6 Hz, 1H), 7.47 (dd, J=12.3, 2.2 Hz, 1H), 7.33 (dd, J=8.7, 1.4 Hz, 1H), 7.19 (t, J=8.8 Hz, 1H), 7.05 (t, J=9.1 Hz, 1H), 3.36-3.32 (m, 4H), 3.21-3.12 (m, 4H).

Preparation of 3-fluoro-4-(4-(2-fluoro-4-(4,4,5,5-tetramethyl-1,3,2-dioxaborolan-2-yl) phenyl) piperazin-1-yl) benzonitrile (AL)

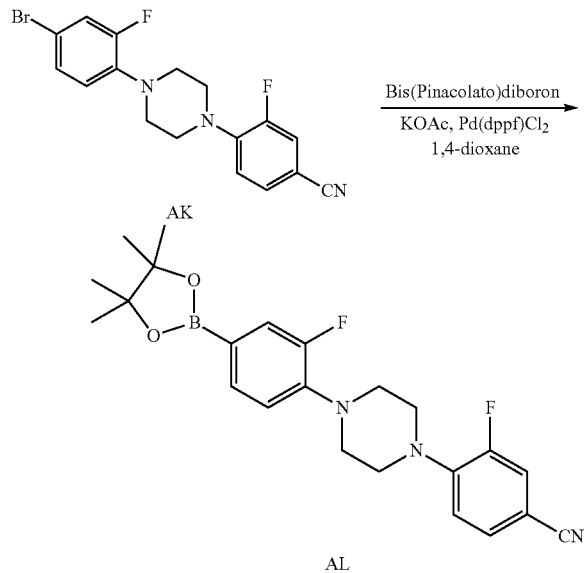

To a stirred solution of Compound AK (300 mg, 0.80 mmol) in 1,4-dioxane (20 mL) under argon atmosphere were added bis(pinacolato)diboron (322 mg, 1.26 mmol) and potassium acetate (233 mg, 2.38 mmol) at RT. The reaction mixture was purged with argon for 10 min, then Pd(dppf)Cl$_2$ (58 mg, 0.08 mmol) was added and the reaction mixture was stirred at 90° C. for 5 h. The reaction was cooled to RT, diluted with water (20 mL), and the product was extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 5% EtOAc-Hexane) to afford Compound AL (250 mg, 0.58 mmol, 63%) as an off-white solid. $^1$H NMR (400 MHz, DMSO-d$_6$): δ 7.73 (dd, J=13.3, 1.9 Hz, 1H), 7.60 (dd, J=8.5, 1.7 Hz, 1H), 7.42 (dd, J=7.9, 1.3 Hz, 1H), 7.29 (dd, J=13.5, 1.2 Hz, 1H), 7.20 (t, J=8.8 Hz, 1H), 7.08 (t, J=8.4 Hz, 1H), 3.37-3.32 (m, 4H), 3.26-3.21 (m, 4H), 1.28 (s, 12H).

Preparation of (R)-4-(4-(4-(6-(2-(2,4-difluorophenyl)-1,1-difluoro-2-hydroxy-3-(1H-tetrazol-1-yl) propyl) pyridin-3-yl)-2-fluorophenyl) piperazin-1-yl)-3-fluorobenzonitrile (9)

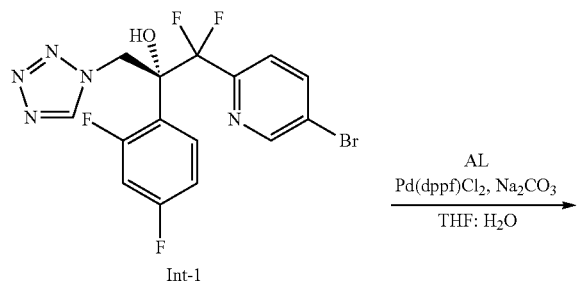

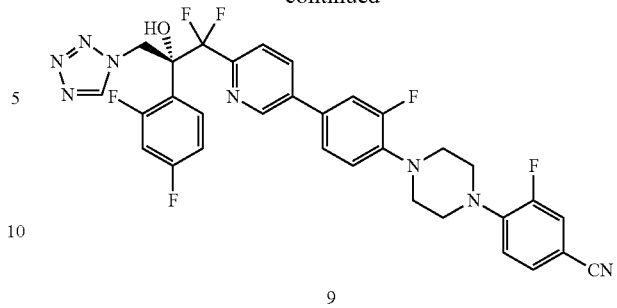

To a stirred solution of Int-1-(150 mg, 0.34 mmol) in THF:H$_2$O (4:1, 25 mL) under argon atmosphere were added Compound AL (177 mg, 0.41 mmol) and sodium carbonate (110 mg, 1.04 mmol) at RT. The reaction mixture was purged with argon for 10 min. then Pd(dppf)Cl$_2$ (25 mg, 0.03 mmol) was added and the reaction mixture was stirred at reflux for 16 h. The reaction was cooled to RT, diluted with water (20 mL), and the product was extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 50% EtOAc/Hexane) to afford 9 (120 mg, 0.18 mmol, 53%) as an off-white solid. $^1$H NMR (400 MHz, DMSO-d$_6$): δ 9.14 (s, 1H), 8.95 (s, 1H), 8.23 (dd, J=8.2, 2.2 Hz, 1H), 7.78-7.68 (m, 2H), 7.61 (d, J=8.5 Hz, 2H), 7.51 (d, J=8.2 Hz, 1H), 7.30 (s, 1H), 7.27-7.17 (m, 3H), 6.93-6.88 (m, 1H), 5.67 (d, J=14.7 Hz, 1H), 5.11 (d, J=14.7 Hz, 1H), 3.40-3.34 (m, 4H), 3.28-3.24 (m, 4H); MS (ESI): m/z 649.2 [M−H]$^−$; HPLC: 96.43%; Optical rotation [α]$_D^{20}$: +136.0 (c=0.1% in MeOH).

Example 10

(R)-4-(4-(4-(6-(2-(2,4-difluorophenyl)-1,1-difluoro-2-hydroxy-3-(1H-tetrazol-1-yl) propyl) pyridin-3-yl)-2-fluorophenyl) piperazin-1-yl) benzonitrile (10)

Preparation of 4-(4-(4-bromo-2-fluorophenyl) piperazin-1-yl) benzonitrile (AM)

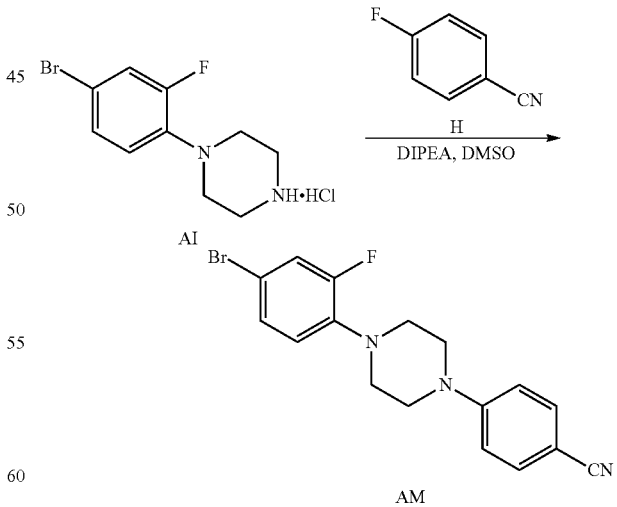

To a stirred solution of Compound AI (700 mg, 2.71 mmol) in DMSO (5 mL) under argon atmosphere were added diisopropyl ethyl amine (1.4 mL, 8.13 mmol) and 4-fluorobenzonitrile H (360 mg, 2.98 mmol) at 0° C. The reaction mixture was warmed to RT and stirred for 16 h. The reaction was diluted with water (20 mL) and the product was extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 40% EtOAc/Hexane) to afford Compound AM (380 mg, 1.05 mmol, 39%) as an off-white solid. $^1$H NMR (400 MHz, DMSO-d$_6$): δ 7.61 (d, J=9.0 Hz, 2H), 7.47 (dd, J=12.2, 2.2 Hz, 1H), 7.33 (d, J=7.9 Hz, 1H), 7.08 (d, J=9.1 Hz, 2H), 7.03 (d, J=9.2 Hz, 1H), 3.53-3.46 (m, 4H), 3.16-3.10 (m, 4H).

Preparation of 4-(4-(2-fluoro-4-(4,4,5,5-tetramethyl-1,3,2-dioxaborolan-2-yl) phenyl) piperazin-1-yl) benzonitrile (AN)

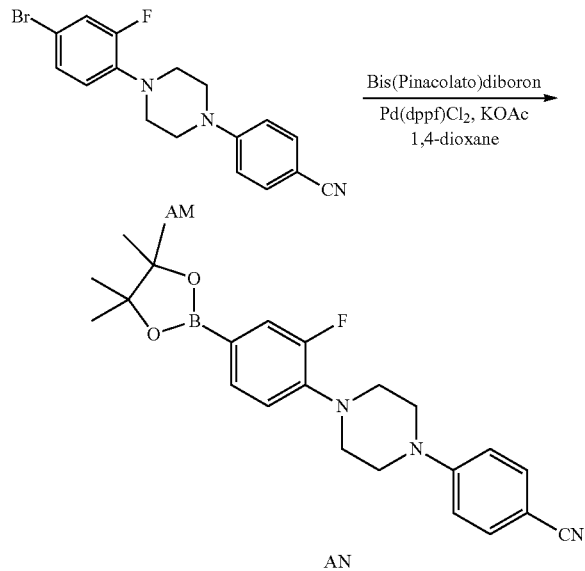

To a stirred solution of Compound AM (380 mg, 1.05 mmol) in 1,4-dioxane (15 mL) under argon atmosphere were added bis(pinacolato)diboron (535 mg, 2.11 mmol) and potassium acetate (415 mg, 4.23 mmol) at RT. The reaction mixture was purged with argon for 15 min, then Pd(dppf)Cl$_2$ (77 mg, 0.10 mmol) was added and the reaction mixture was purged with argon for 5 min at RT. The reaction mixture was stirred at 110° C. for 6 h. The reaction was cooled to RT, diluted with water (20 mL), and the product was extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 30% EtOAc/Hexane) to afford Compound AN (200 mg, 0.50 mmol, 47%) as an off-white solid. $^1$H NMR (500 MHz, DMSO-d$_6$): δ 7.61 (d, J=9.0 Hz, 2H), 7.42 (d, J=7.9 Hz, 1H), 7.29 (d, J=13.6 Hz, 1H), 7.10-7.04 (m, 3H), 3.55-3.45 (m, 4H), 3.26-3.16 (m, 4H), 1.28 (s, 12H).

Preparation of (R)-4-(4-(4-(6-(2-(2,4-difluorophenyl)-1,1-difluoro-2-hydroxy-3-(1H-tetrazol-1-yl) propyl) pyridin-3-yl)-2-fluorophenyl) piperazin-1-yl) benzonitrile (10)

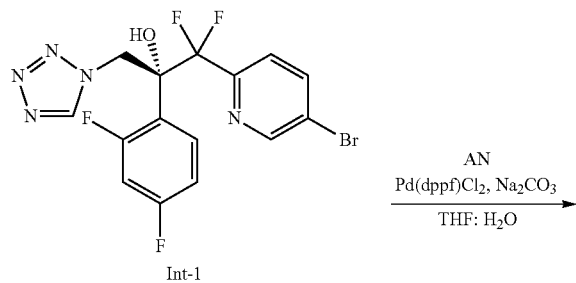

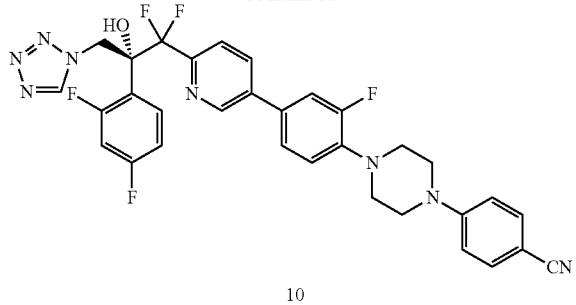

To a stirred solution of Int-1 (150 mg, 0.34 mmol) in THF:H$_2$O (8:2, 20 mL) under argon atmosphere were added Compound AN (169 mg, 0.41 mmol) and sodium carbonate (110 mg, 1.04 mmol) at RT. The reaction mixture was purged with argon for 20 min, then Pd(dppf)Cl$_2$ (25 mg, 0.03 mmol) was added and the reaction mixture was purged with argon for 5 min at RT. The reaction mixture was stirred at 90° C. for 6 h. The reaction was cooled to RT, diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 40% Acetone/Hexane) to afford 10 (100 mg, 0.15 mmol, 47.6%) as an off-white solid. $^1$H NMR (500 MHz, DMSO-d$_6$): δ 9.13 (s, 1H), 8.94 (s, 1H), 8.22 (d, J=10.1 Hz, 1H), 7.70 (d, J=8.4 Hz, 1H), 7.63-7.57 (m, 3H), 7.49 (d, J=8.4 Hz, 1H), 7.29-7.15 (m, 4H), 7.09 (d, J=9.0 Hz, 2H), 6.92-6.86 (m, 1H), 5.65 (d, J=14.7 Hz, 1H), 5.10 (d, J=14.7 Hz, 1H), 3.52-3.50 (m, 4H), 3.23-3.21 (m, 4H); MS (ESI): m/z 633.5 [M+H]$^+$; HPLC: 97.53%; Optical rotation [α]$_D^{19}$: +44.1 (c=0.1% in MeOH).

Example 11

(R)-4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl)-3-fluorobenzonitrile (11)

Preparation of tert-butyl 4-(4-bromophenyl) piperazine-1-carboxylate (AO)

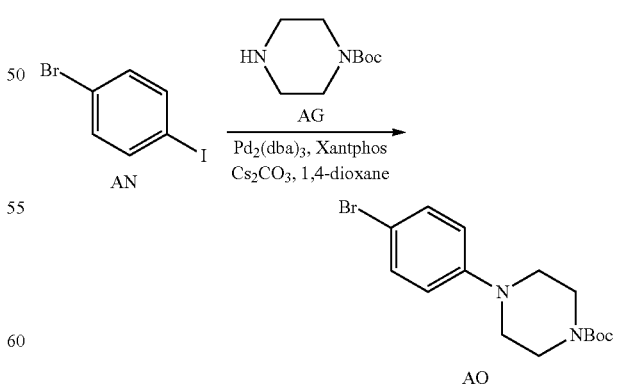

To a stirred solution of 1-bromo-4-iodobenzene AN (1 g, 3.53 mmol) in 1,4-dioxane (15 mL) under argon atmosphere were added tert-butyl piperazine-1-carboxylate AG (750 mg, 4.02 mmol), cesium carbonate (1.65 g, 5.06 mmol) and Xantphos (160 mg, 0.27 mmol) at RT. The reaction mixture was purged with argon for 20 min, then Pd$_2$(dba)$_3$ (87.5 mg, 0.09 mmol) was added and the reaction mixture was stirred at 110° C. for 16 h. The reaction was cooled to RT and filtered. The filtrate was concentrated under reduced pressure. The residue was diluted with water (50 mL) and the product was extracted with EtOAc (2×50 mL). The combined organic extracts were washed with water (50 mL), brine (50 mL), dried over anhydrous Na$_2$SO$_4$ and concentrated under reduced pressure. The crude material was purified by silica gel column chromatography (eluent: 5% EtOAc/Hexane) to afford Compound AO (700 mg, 2.05 mmol, 58%) as a brown solid. $^1$H NMR (500 MHz, CDCl$_3$): δ 7.35 (d, J=10.4 Hz, 2H), 6.79 (d, J=9.0 Hz, 2H), 3.60-3.54 (m, 4H), 3.14-3.06 (m, 4H), 1.48 (s, 9H).

Preparation of 1-(4-(4-bromophenyl)-114-piperazin-1-yl)-2,2,2-trifluoroethan-1-one (AP)

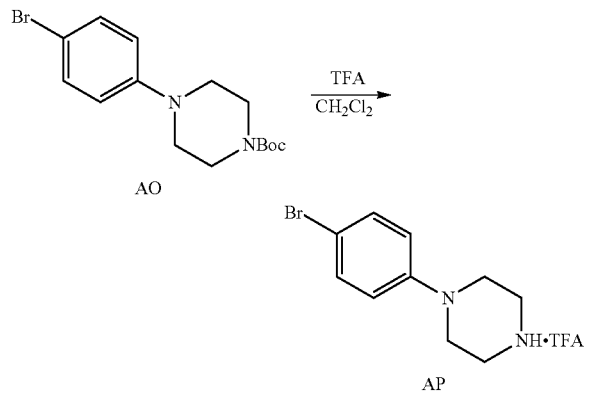

To a stirred solution of Compound AO (700 mg, 2.05 mmol) in CH$_2$Cl$_2$ (20 mL) under argon atmosphere was added trifluoro acetic acid (10 mL) at 0° C. The reaction mixture was warmed to RT and stirred for 3 h. The volatiles were concentrated under reduced pressure. The residue was washed with diethyl ether (2×20 mL) to obtain Compound AP (500 mg, 1.41 mmol) as a brown solid. $^1$H NMR (500 MHz, DMSO-d$_6$): δ 8.76 (brs, 1H), 7.40 (d, J=8.2 Hz, 2H), 6.96 (d, J=8.2 Hz, 2H), 3.38-3.31 (m, 4H), 3.26-3.20 (m, 4H).

Preparation of 4-(4-(4-bromophenyl) piperazin-1-yl)-3-fluorobenzonitrile (AQ)

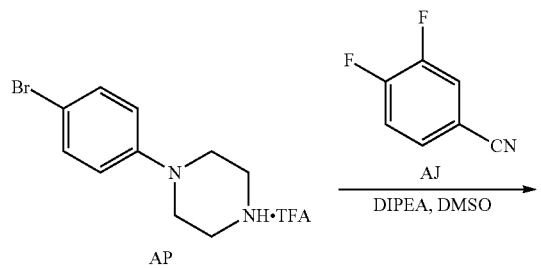

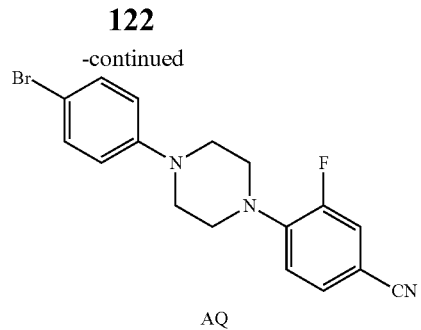

To a stirred solution of Compound AP (100 mg, 0.71 mmol) in DMSO (1 mL) under argon atmosphere was added diisopropyl ethyl amine (0.39 mL) at RT. The reaction mixture was stirred at 90° C. for 6 h. The reaction was cooled to RT, diluted with water (10 mL), and the product was extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluent: 10% EtOAc/Hexane) to afford Compound AQ (200 mg, 0.55 mmol, 77%) as a brown solid. $^1$H NMR (500 MHz, CDCl$_3$): δ 7.49-7.37 (m, 3H), 7.33 (dd, J=12.6, 1.9 Hz, 1H), 7.07-6.95 (m, 3H), 3.52-3.36 (m, 8H).

Preparation of 3-fluoro-4-(4-(4-(4,4,5,5-tetramethyl-1,3,2-dioxaborolan-2-yl) phenyl) piperazin-1-yl) benzonitrile (AR)

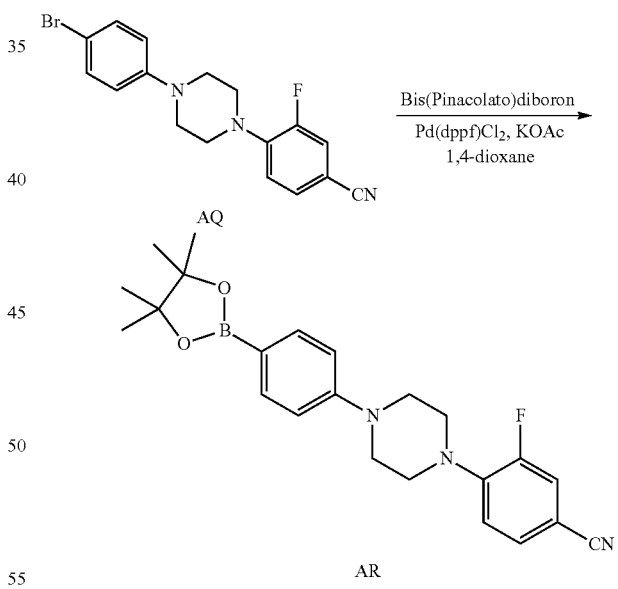

To a stirred solution of Compound AQ (200 mg, 0.55 mmol) in 1,4-dioxane (20 mL) under argon atmosphere were added bis(pinacolato)diboron (225 mg, 0.88 mmol), potassium acetate (163 mg, 1.66 mmol) at RT. The reaction mixture was purged with argon for 20 min, then Pd(dppf)Cl$_2$ (40.5 mg, 0.05 mmol) was added and the reaction mixture was stirred at 90° C. for 14 h. The reaction was cooled to RT and filtered through a Celite pad. The filtrate was diluted with water (50 mL) and the product was extracted with EtOAc (2×50 mL). The combined organic extracts were washed with water (50 mL), brine (50 mL), dried over anhydrous Na₂SO₄ and concentrated under reduced pressure. The crude material was purified by silica gel column chromatography (eluent: 10% EtOAc/Hexane) to afford Compound AR (180 mg, 0.44 mmol, 80%) as a white solid. ¹H NMR (500 MHz, DMSO-d₆): δ 7.73 (dd, J=13.4, 1.9 Hz, 1H), 7.59 (d, J=8.4 Hz, 1H), 7.54 (d, J=8.4 Hz, 2H), 7.18 (t, J=8.7 Hz, 1H), 6.96 (t, J=8.0 Hz, 2H), 3.40-3.36 (m, 4H), 3.35-3.32 (m, 4H), 1.24 (s, 12H).

Preparation of (R)-4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl)-3-fluorobenzonitrile (11)

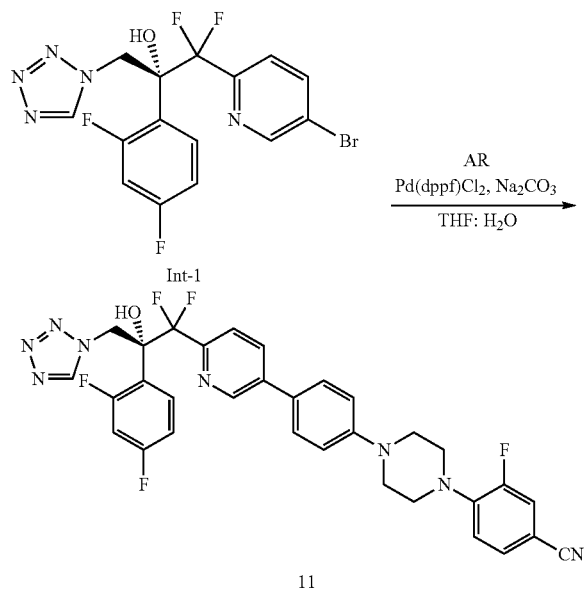

To a stirred solution of Int-1 (150 mg, 0.34 mmol) in THF:H₂O (4:1, 20 mL) under argon atmosphere were added Compound AR (170 mg, 0.41 mmol) and sodium carbonate (110 mg, 1.0 mmol) at RT. The reaction mixture was purged with argon for 20 min, then Pd(dppf)Cl₂ (25.4 mg, 0.03 mmol) was added and the reaction mixture was stirred at 70° C. for 4 h. The reaction was cooled to RT, diluted with water (10 mL), and the product was extracted with EtOAc (2×10 mL). The combined organic extracts were washed with water (10 mL), brine (10 mL), dried over anhydrous Na₂SO₄ and concentrated under reduced pressure. The crude material was purified by silica gel column chromatography (eluent: 40% EtOAc/Hexane) to afford 11 (60 mg, 0.09 mmol, 27%) as an off-white solid. ¹H NMR (400 MHz, DMSO-d₆): δ 9.15 (s, 1H), 8.91 (s, 1H), 8.17 (dd, J=8.3, 2.2 Hz, 1H), 7.74 (dd, J=13.4, 1.9 Hz, 1H), 7.70 (d, J=8.9 Hz, 2H), 7.61 (dd, J=8.4, 1.6 Hz, 1H), 7.48 (d, J=8.4 Hz, 1H), 7.32-7.16 (m, 4H), 7.13 (d, J=9.0 Hz, 2H), 6.93-6.88 (m, 1H), 5.67 (d, J=14.3 Hz, 1H), 5.11 (d, J=14.3 Hz, 1H), 3.41-3.35 (m, 8H); MS (ESI): m/z 633.5 [M+H]⁺; HPLC: 99.31%; Optical rotation [α]$_D^{20}$: +155.4 (c=0.1% in MeOH).

Example 12

(R)-6-(4-(4-(6-(2-(2,4-difluorophenyl-1,1-difluoro-2-hydroxy-3-(1H-tetrazol-1-yl) propyl) pyridin-3-yl) phenyl) piperazin-1-yl) nicotinonitrile (12)

Preparation of 6-(4-(4-bromophenyl) piperazin-1-yl) nicotinonitrile (AT)

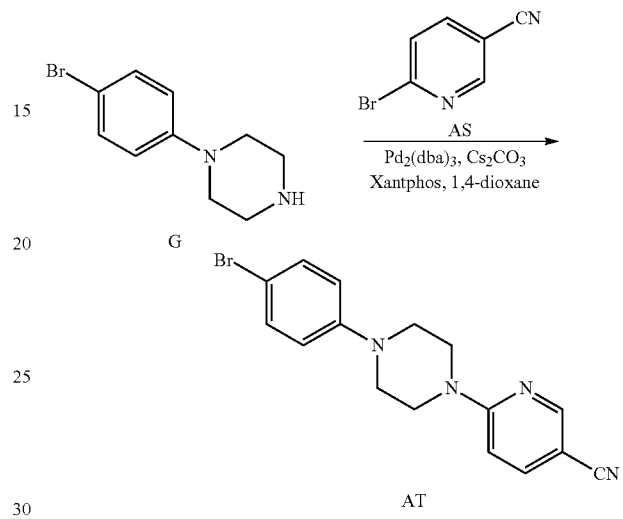

To a stirred solution of Compound G (1.0 g, 4.14 mmol) in 1,4-dioxane (25 mL) under argon atmosphere were added 6-bromonicotinonitrile AS (1.1 g, 6.22 mmol), Xantphos (647 mg, 1.12 mmol) and cesium carbonate (4.0 g, 12.44 mmol) at RT. The reaction mixture was purged with argon for 20 min, then Pd₂(dba)₃ (38 mg, 0.04 mmol) was added and the reaction mixture was purged with argon for 5 min at RT. The reaction mixture was stirred at 90° C. for 16 h. The reaction was cooled to RT and filtered. The filtrate was diluted with water (20 mL) and the product was extracted with EtOAc (2×20 mL). The combined organic layers were washed with water (20 mL), brine (20 mL), dried over anhydrous Na₂SO₄ and concentrated under reduced pressure. The crude material was purified by silica gel column chromatography (eluent: 10% EtOAc/Hexane) to afford Compound AT (700 mg, 2.04 mmol, 38%) as an off-white solid. ¹H NMR (500 MHz, DMSO-d₆): δ 8.51 (s, 1H), 7.88 (dd, J=9.0, 2.0 Hz, 1H), 7.38 (d, J=8.0 Hz, 1H), 7.36 (d, J=8.0 Hz, 1H), 6.99 (d, J=9.3 Hz, 1H), 6.94 (d, J=9.0 Hz, 2H), 3.84-3.77 (m, 4H), 3.28-3.22 (m, 4H).

Preparation of 6-(4-(4-(4,4,5,5-tetramethyl-1,3,2-dioxaborolan-2-yl) phenyl) piperazin-1-yl) nicotinonitrile (AU)

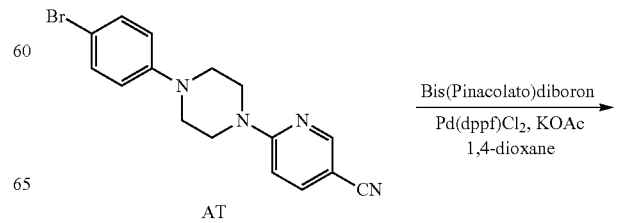

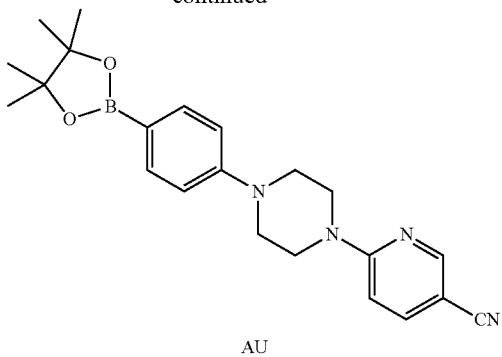

AU

To a stirred solution of Compound AT (700 mg, 2.04 mmol) in 1,4-dioxane (70 mL) under argon atmosphere were added bis(pinacolato)diboron (826 mg, 3.26 mmol) and potassium acetate (600 mg, 6.12 mmol) at RT. The reaction mixture was purged with argon for 20 min, then Pd(dppf)Cl$_2$ (150 mg, 0.20 mmol) was added and the reaction mixture was purged with argon for 5 min at RT. The reaction mixture was stirred at 90° C. for 16 h. The reaction was cooled to RT and filtered. The filtrate was diluted with water (20 mL) and the product was extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 10% EtOAc/Hexane) to afford Compound AU (700 mg, 1.79 mmol, 88%) as an off-white solid. $^1$H NMR (500 MHz, DMSO-d$_6$): δ 8.51 (s, 1H), 7.88 (dd, J=9.0, 2.0 Hz, 1H), 7.53 (d, J=8.1 Hz, 2H), 6.98 (d, J=9.3 Hz, 1H), 6.94 (d, J=8.7 Hz, 2H), 3.84-3.78 (m, 4H), 3.38-3.33 (m, 4H), 1.26 (s, 12H).

Preparation of (R)-6-(4-(4-(6-(2-(2,4-difluorophenyl)-1,1-difluoro-2-hydroxy-3-(1H-tetrazol-1-yl) propyl) pyridin-3-yl) phenyl piperazin-1-yl) nicotinonitrile (12)

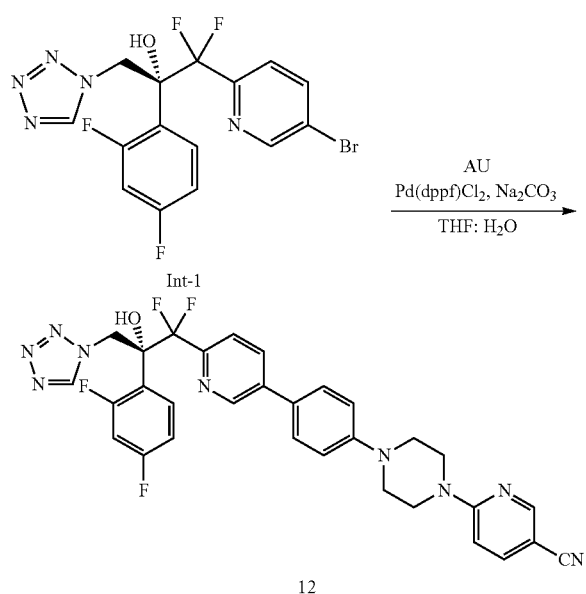

To a stirred solution of Int-1 (150 mg, 0.34 mmol) in THF:H$_2$O (20 mL) under argon atmosphere were added Compound AU (162.5 mg, 0.41 mmol) and sodium carbonate (110 mg, 1.04 mmol) at RT. The reaction mixture was purged with argon for 20 min, then Pd(dppf)Cl$_2$ (25.3 mg, 0.03 mmol) was added and the reaction mixture was purged with argon for 5 min at RT. The reaction mixture was stirred at 70° C. for 6 h. The reaction was cooled to RT, diluted with water (20 mL), and the product was extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 50% EtOAc/Hexane) to afford 12 (80 mg, 0.13 mmol, 37%) as a brown solid. $^1$H NMR (500 MHz, DMSO-d$_6$): δ 9.13 (s, 1H), 8.89 (s, 1H), 8.51 (s, 1H), 8.15 (dd, J=8.4, 2.0 Hz, 1H), 7.87 (dd, J=9.0, 2.3 Hz, 1H), 7.68 (d, J=8.1 Hz, 2H), 7.46 (d, J=8.4 Hz, 1H), 7.30-7.24 (m, 2H), 7.18-7.16 (m, 1H), 7.10 (d, J=9.0 Hz, 2H), 6.99 (d, J=9.0 Hz, 1H), 6.92-6.87 (m, 1H), 5.65 (d, J=14.7 Hz, 1H), 5.09 (d, J=14.7 Hz, 1H), 3.87-3.79 (m, 4H), 3.40-3.32 (m, 4H); MS (ESI): m/z 616.1 [M+H]$^+$; HPLC: 94.61%; Optical rotation [α]$_D^{20}$: +56.0 (c=0.1% in MeOH).

Example 13, 13-Fr-I, and 13-Fr-II 1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-3,3,3-trifluoropropan-1-ol (13)

1-(5-bromopyridin-2-yl)-3,3,3-trifluoropropan-1-ol (AV)

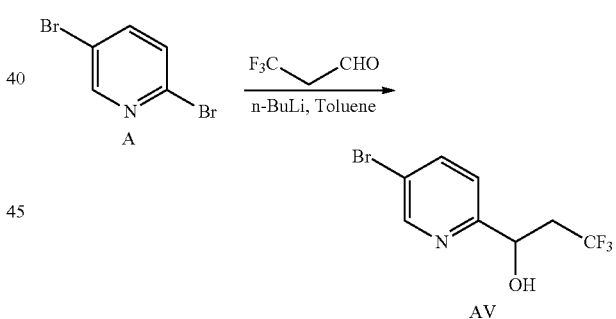

To a stirred solution of A (7.5 g, 3.16 mmol) in toluene (150 mL) under argon atmosphere was added n-BuLi (17.8 mL, 2.84 mmol, 1.6 M in hexane) at −78° C. and stirred for 45 min. Then a solution of 3,3,3-trifluoropropanal (3.27 mL, 3.79 mmol) was added to the reaction mixture at −78° C. and stirred for another 1.5 h. The reaction was quenched with aqueous ammonium chloride solution (I L) and extracted with ethyl acetate (2×1.0 L). The combined organic layers were washed with water (2×1.0 L), brine (2×1.0 L), dried over anhydrous Na$_2$SO$_4$ and concentrated under reduced pressure. The crude compound was purified by column chromatography (SiO$_2$, 100-200 mesh; eluent: 8% EtOAc/Hexane) to afford compound AV (4.6 g, 17.03 mmol, 27%) as a pale yellow syrup. $^1$H NMR (500 MHz, CDCl$_3$): δ 8.64 (s, 1H), 7.87 (dd, J=8.1, 2.3 Hz, 1H), 7.31 (d, J=8.1 Hz, 1H), 5.12-5.05 (m, 1H), 3.58 (d, J=6.4 Hz, 1H), 2.73-2.61 (m, 1H), 2.60-2.47 (m, 1H).

5-bromo-2-(3,3,3-trifluoro-1-(tetrahydro-2H-rain-2-yl) oxy) propyl) pyridine (AW)

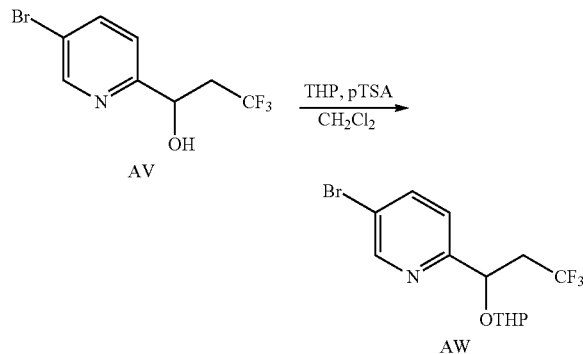

To a stirred solution of compound AV (4.6 g, 17.03 mmol) in CH$_2$Cl$_2$ (100 mL) under argon atmosphere were added p-toluene sulphonic acid (80 mg, 0.42 mmol) and 3,4-Dihydro-2H-pyran (2.5 mL, 20.44 mmol) at 0° C. The reaction mixture was warmed to RT and stirred for 16 h. The reaction was diluted with water (500 mL) and extracted with CH$_2$Cl$_2$ (2×500 mL). The combined organic layers were washed with water (2×500 mL), dried over anhydrous Na$_2$SO$_4$ and concentrated under reduced pressure. The crude compound was purified by column chromatography (SiO$_2$, 100-200 mesh; eluent: 5% EtOAc/Hexane) to afford compound AW (4.6 g, 12.99 mmol, 76%) as colorless syrup. $^1$H NMR (500 MHz, CDCl$_3$): δ 8.68 (s, 0.5H), 8.61 (s, 0.5H), 7.83 (d, J=8.3, 2.2 Hz, 1H), 7.50 (d, J=8.7 Hz, 0.5H), 7.28 (d, J=8.1 Hz, 0.5H), 5.15-5.12 (m, 0.5H), 4.83-4.79 (m, 0.5H), 3.98-3.76 (m, 1H), 3.63-3.42 (m, 2H), 2.83-2.56 (m, 2H), 1.91-1.51 (m, 6H).

1-(4-bromophenyl)-4-(6-(3,3,3-trifluoro-1-((tetrahydro-2H-pyran-2-yl) oxy) propyl) pyridin-3-yl) piperazine (AX)

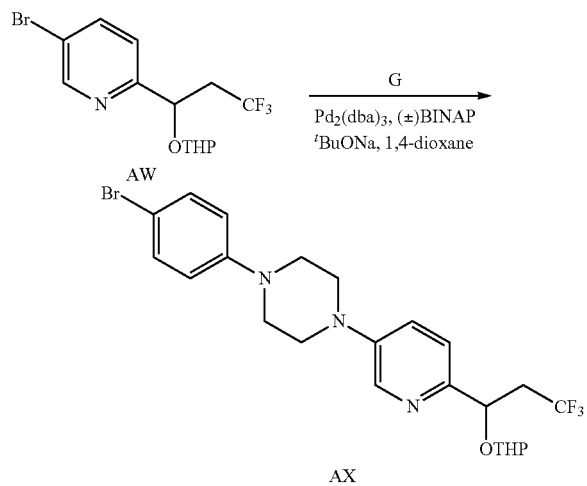

To a stirred solution of compound AW (4.6 g, 12.99 mmol) in 1,4-dioxane (100 mL) under argon atmosphere were added G (3.7 g, 15.59 mmol), (±) BINAP (484 mg, 0.77 mmol), sodium tertiary butoxide (1.8 g, 19.49 mmol) and purged under argon for 10 min at RT. Then Pd$_2$(dba)$_3$ (237 mg, 0.25 mmol) was added and the reaction mixture was purged under argon for 10 min at RT. The reaction mixture was stirred at 80° C. for 16 h. The reaction mixture was diluted with water (500 mL) and extracted with EtOAc (2×500 mL). The combined organic extracts were dried over anhydrous Na$_2$SO$_4$ and concentrated under reduced pressure. The crude material was purified by silica gel column chromatography (eluent: 15% EtOAc/Hexane) to afford compound AX (2.8 g, 5.44 mmol, 42%) as a pale yellow solid. $^1$H NMR (500 MHz, CDCl$_3$): δ 8.37-8.28 (m, 1H), 7.43 (d, J=8.7 Hz, 0.5H), 7.38 (d, J=8.7 Hz, 2H), 7.26-7.19 (m, 1.5H), 6.86-6.82 (m, 2H), 5.10-5.08 (m, 0.5H), 4.98-4.95 (m, 0.5H), 4.83-4.81 (m, 0.5H), 4.46-4.45 (m, 0.5H), 3.95-3.90 (m, 1H), 3.62-3.51 (m, 1H), 3.39-3.26 (m, 8H), 2.86-2.50 (m, 2H), 1.95-1.37 (m, 6H).

1-(5-(4-(4-bromophenyl) piperazin-1-yl) pyridin-2-yl)-3,3,3-trifluoropropan-1-ol (A1)

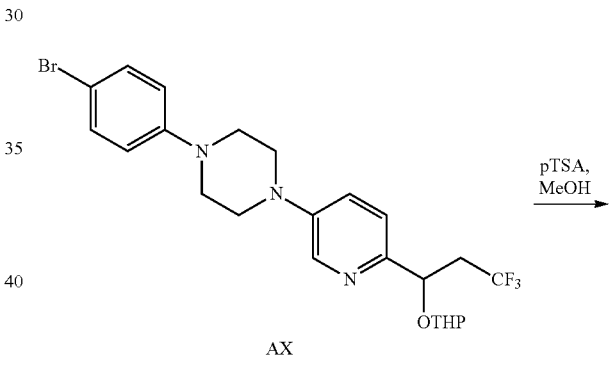

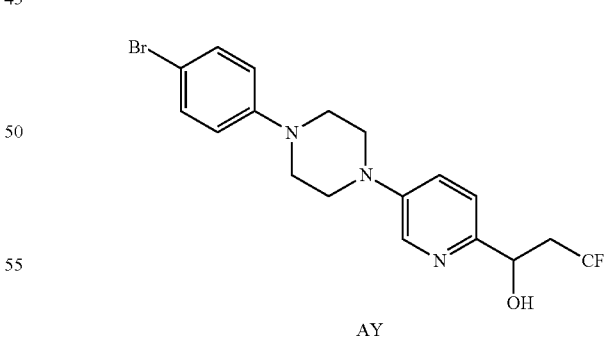

To a stirred solution of compound AX (2.8 g, 5.44 mmol) in MeOH (80 mL) under argon atmosphere was added p-toluene sulphonic acid (2 g, 10.89 mmol) at 0° C. The reaction mixture was warmed to RT and stirred for 48 h. The progress of the reaction was monitored by TLC; the reaction was diluted with 10% sodium bicarbonate solution (500 mL) and extracted with CH$_2$Cl$_2$ (2×500 mL). The combined organic layers were washed with water (2×500 mL), dried over anhydrous Na$_2$SO$_4$ and concentrated under reduced pressure. The crude compound was purified by column chromatography (SiO$_2$, 100-200 mesh; eluent: 30% EtOAc/Hexane) to afford compound AY (1.8 g, 4.18 mmol, 77%) as an off-white solid. $^1$H NMR (500 MHz, CDCl$_3$): δ 8.28 (d, J=2.3 Hz, 1H), 7.38 (d, J=8.7 Hz, 2H), 7.29-7.27 (m, 1H), 7.22 (d, J=8.6 Hz, 1H), 6.85 (d, J=9.3 Hz, 2H), 5.07-4.97 (m, 1H), 3.85-3.83 (m, 1H), 3.42-3.23 (m, 8H), 2.68-2.46 (m, 2H).

Preparation of 3,3,3-trifluoro-1-(5-(4-(4-(4,4,5,5-tetramethyl-1,3,2-dioxaborolan-2-yl) phenyl) piperazin-1-yl) pyridin-2-yl) propan-1-ol (AZ)

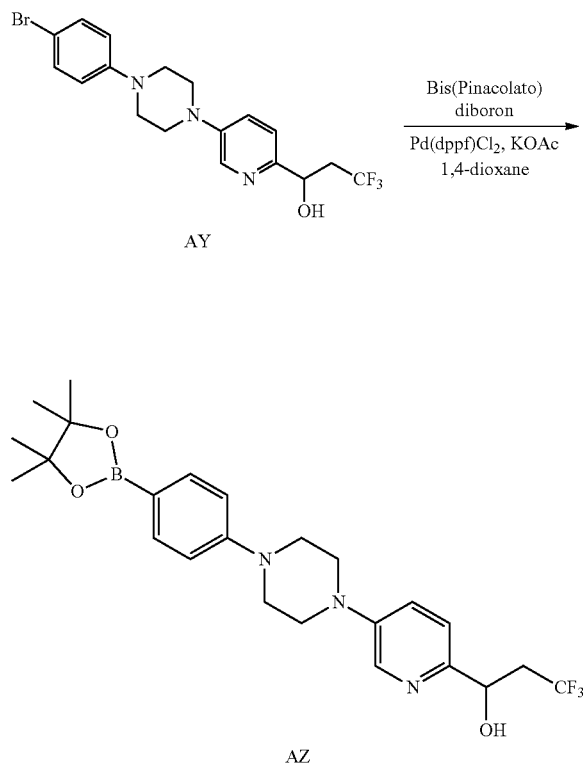

To a stirred solution of Compound AY (100 mg, crude) in 1,4-dioxane (5 mL) under argon atmosphere were added bis(pinacolato)diboron (95 mg, 0.37 mmol) and potassium acetate (68.5 mg, 0.70 mmol) at RT. The reaction mixture was purged with argon for 20 min, then Pd(dppf)Cl$_2$ (17 mg, 0.02 mmol) was added and the reaction mixture was purged with argon for 5 min at RT. The reaction mixture was stirred at 90° C. for 3 h. The reaction was cooled to RT, diluted with water (20 mL), and the product was extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 40% EtOAc/Hexane) to afford Compound AZ (55 mg, 0.11 mmol, 49%) as an off-white solid. LC-MS: 478.2 [M+H]$^+$ at 3.64 RT (80.8% purity).

Preparation of 1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-3,3,3-trifluoropropan-1-ol (13)

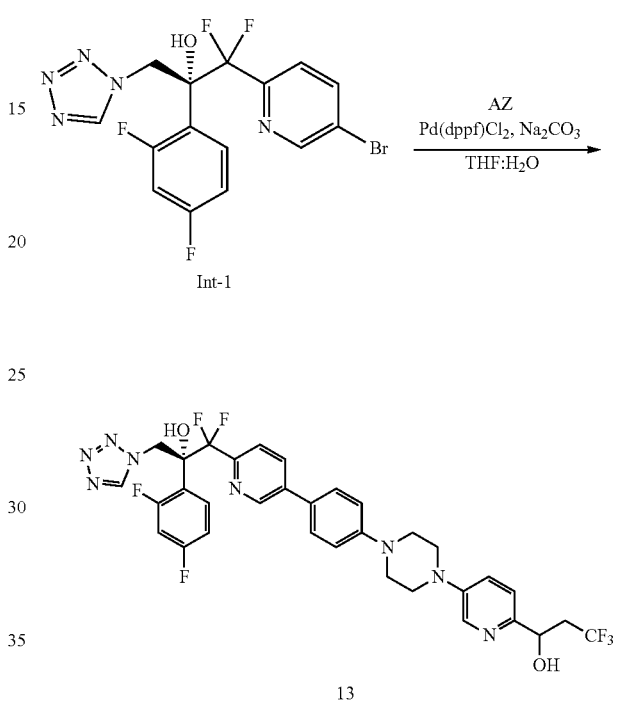

To a stirred solution of Int-1 (55 mg, 0.11 mmol) in THF:H$_2$O (4:1, 10 mL) under argon atmosphere were added Compound AZ (50 mg, 0.11 mmol) and sodium carbonate (36.6 mg, 0.34 mmol) at RT. The reaction mixture was purged with argon for 15 min, then Pd(dppf)Cl$_2$ (8.4 mg, 0.01 mmol) was added and the reaction mixture was purged with argon for 10 min at RT. The reaction mixture was stirred at 75° C. for 6 h. The reaction was cooled to RT, diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) followed by preparative HPLC to afford 13 (20 mg, 0.03 mmol, 24%) as an off-white solid. $^1$H NMR (400 MHz, DMSO-d$_6$): δ 9.15 (s, 1H), 8.91 (s, 1H), 8.30 (s, 1H), 8.17 (dd, J=8.3, 2.1 Hz, 1H), 7.70 (d, J=8.9 Hz, 2H), 7.48 (d, J=8.6 Hz, 1H), 7.46-7.39 (m, 2H), 7.34-7.25 (m, 2H), 7.22-7.16 (m, 1H), 7.14 (d, J=9.0 Hz, 2H), 6.94-6.88 (m, 1H), 5.70 (s, 1H), 5.67 (d, J=15.0 Hz, 1H), 5.11 (d, J=15.0 Hz, 1H), 4.87-4.82 (m, 1H), 3.43-3.40 (m, 4H), 3.37-3.34 (m, 4H), 2.83-2.74 (m, 1H), 2.61-2.53 (m, 1H); MS (ESI): m/z 703.3 [M+H]$^+$; HPLC: 94.22%; Optical rotation [α]$_D^{20}$: +53.9 (c=0.1% in MeOH).

Chiral Preparative HPLC Details for 13-Fr-I and 13-Fr-II

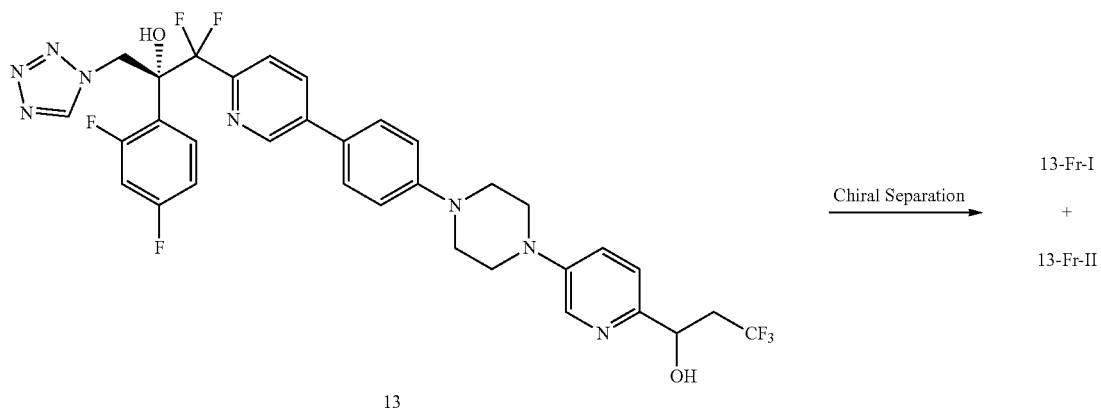 [SMILES: OC(CC(F)(F)F)c1ccc(N2CCN(c3ccc(-c4ccc(C(F)(F)[C@](O)(Cn5cnnn5)c5ccc(F)cc5F)nc4)cc3)CC2)cn1 ; "13"]

13 (300 mg, 0.42 mmol) was separated by normal-phase preparative high performance liquid chromatography (Chiralpak IC®, 250×20 mm, 5μ; using (A) $CH_2Cl_2$:(B) IPA:DEA (50:50:0.1) as a mobile phase; Flow rate: 20 mL/min) to obtain 13-Fr-I (40 mg) and 13-Fr-II (50 mg).

13-Fr-I:
$^1$H NMR (400 MHz, DMSO-$d_6$): δ 9.15 (s, 1H), 8.91 (s, 1H), 8.30 (s, 1H), 8.17 (dd, J=8.3, 2.1 Hz, 1H), 7.70 (d, J=8.9 Hz, 2H), 7.48 (d, J=8.6 Hz, 1H), 7.46-7.39 (m, 2H), 7.34-7.25 (m, 2H), 7.22-7.16 (m, 1H), 7.14 (d, J=9.0 Hz, 2H), 6.94-6.88 (m, 1H), 5.70 (s, 1H), 5.67 (d, J=15.0 Hz, 1H), 5.11 (d, J=15.0 Hz, 1H), 4.87-4.82 (m, 1H), 3.43-3.40 (m, 4H), 3.37-3.34 (m, 4H), 2.83-2.74 (m, 1H), 2.61-2.53 (m, 1H); MS (ESI): m/z 703.6 [M+H]$^+$; HPLC: 99.14%; Chiral HPLC Purity: 100%. $R_t$=11.37 min (CHIRALPAK-IC®, 250×4.6 mm, 5μ; mobile phase (A) $CH_2Cl_2$:(B) IPA:DEA (80:20) (50:50:0.1); flow Rate: 0.8 mL/min); Optical rotation $[α]_D^{19}$: +70.4 (C=0.1% in MeOH).

13-Fr-II:
$^1$H NMR (400 MHz, DMSO-$d_6$): δ 9.15 (s, 1H), 8.91 (s, 1H), 8.30 (s, 1H), 8.17 (dd, J=8.3, 2.1 Hz, 1H), 7.70 (d, J=8.9 Hz, 2H), 7.48 (d, J=8.6 Hz, 1H), 7.46-7.39 (m, 2H), 7.34-7.25 (m, 2H), 7.22-7.16 (m, 1H), 7.14 (d, J=9.0 Hz, 2H), 6.94-6.88 (m, 1H), 5.70 (s, 1H), 5.67 (d, J=15.0 Hz, 1H), 5.11 (d J=15.0 Hz, 1H), 4.87-4.82 (m, 1H), 3.43-3.40 (m, 4H), 3.37-3.34 (m, 4H), 2.83-2.74 (m, 1H), 2.61-2.53 (m, 1H); MS (ESI): m/z 703.6 [M+H]$^+$; HPLC: 99.67%; Chiral HPLC Purity: 99.61%, $R_t$=7.32 min (CHIRALPAK-IC®, 250×4.6 mm, 5μ; mobile phase (A) $CH_2Cl_2$:(B) IPA:DEA (80:20) (50:50:0.1); flow Rate: 0.8 mL/min); Optical rotation $[α]_D^{19}$: +46.4 (C=0.1% in MeOH).

Example 14

(R)-1-(5-(4-(4-(4-aminophenyl) piperazin-1-yl) phenyl) pyridin-2-yl)-2-(2,4-difluorophenyl)-1,1-difluoro-3-(1H-tetrazol-1-yl) propan-2-ol (14)

Preparation of 1-(4-bromophenyl)-4-(4-nitrophenyl) piperazine (BB)

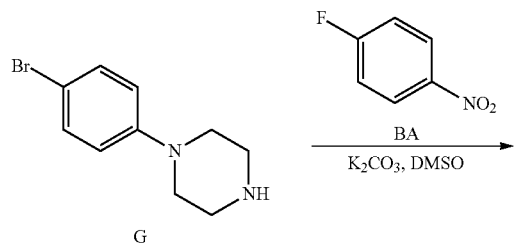

-continued

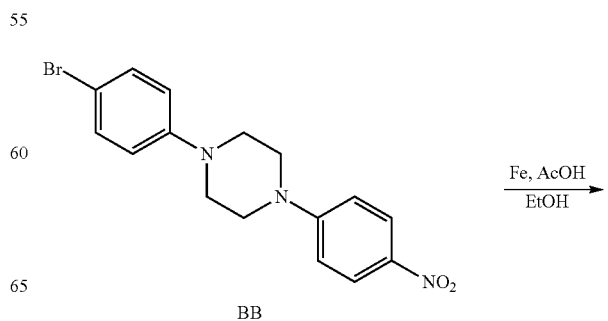

To a stirred solution of 1-(4-bromophenyl) piperazine G (5.0 g, 20.74 mmol) in DMSO (50 mL) under argon atmosphere were added potassium carbonate (5.72 g, 41.48 mmol) and 1-fluoro-4-nitrobenzene BA (2.42 mL, 22.82 mmol) at RT. The reaction mixture was stirred at 120° C. for 6 h. The reaction was cooled to RT, diluted with water (100 mL) to obtain the solid which was filtered, washed with water (50 mL) and dried under reduced pressure. The solid was purified by silica gel column chromatography (eluent: 50% EtOAc/Hexane) to afford Compound BB (4.0 g, 11.05 mmol, 53%) as a brown solid. $^1$H NMR (400 MHz, CDCl$_3$): δ 8.18 (d, J=9.3 Hz, 2H), 7.46 (d, J=8.9 Hz, 2H), 7.02 (d, J=8.4 Hz, 2H), 6.90 (d, J=9.3 Hz, 2H), 3.76-3.65 (m, 4H), 3.45-3.36 (m, 4H).

Preparation of 4-(4-(4-bromophenyl) piperazin-1-yl) aniline (BC)

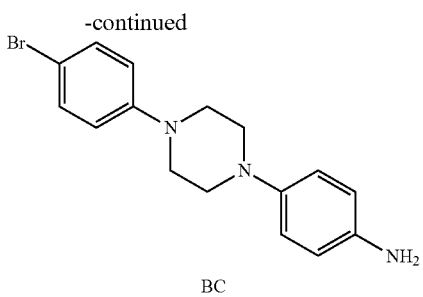

BC

To a stirred solution of Compound BB (4.0 g, 11.05 mmol) in EtOH:AcOH (1:1, 80 mL) under argon atmosphere was added Fe powder (4.4 g, 78.67 mmol) at RT. The reaction mixture was stirred at 80° C. for 4 h. The reaction mixture was filtered, the filtrate was diluted with saturated sodium bicarbonate solution (100 mL), and the product was extracted with EtOAc (2×100 mL). The combined organic extracts were dried over anhydrous $Na_2SO_4$ and concentrated under reduced pressure. The crude material was purified by silica gel column chromatography (eluent: 40% Acetone/Hexane) to afford Compound BC (2.5 g, 7.53 mmol, 69%) as an off-white solid. $^1$H NMR (400 MHz, DMSO-$d_6$): δ 7.36 (d, J=7.7 Hz, 2H), 6.94 (d, J=9.1 Hz, 2H), 6.74 (d, J=7.6 Hz, 2H), 6.51 (d, J=7.6 Hz, 2H), 4.58 (s, 2H), 3.27-3.21 (m, 4H), 3.06-2.99 (m, 4H).

Preparation of 4-(4-(4-(4,4,5,5-tetramethyl-1,3,2-dioxaborolan-2-yl) phenyl) piperazin-1-yl)

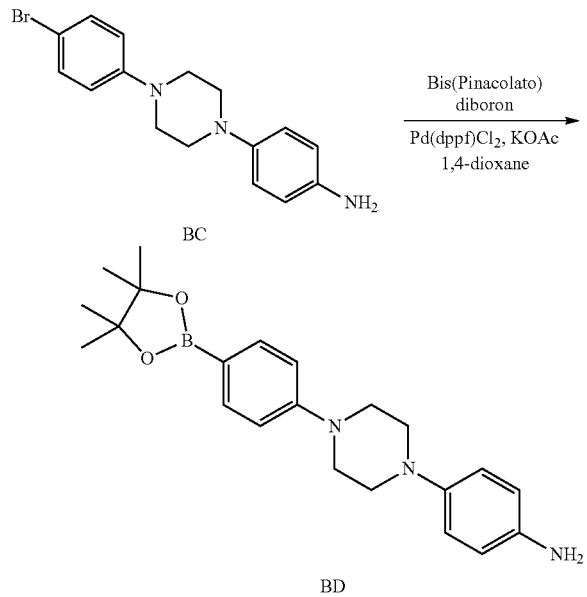

To a stirred solution of Compound BC (300 mg, 0.90 mmol) in 1,4-dioxane (30 mL) under argon atmosphere were added bis(pinacolato)diboron (365 mg, 1.44 mmol) and potassium acetate (265 mg, 2.71 mmol) at RT. The reaction mixture was purged with argon for 20 min, then Pd(dppf)Cl$_2$ (66 mg, 0.09 mmol) was added and the reaction mixture was purged with argon for 5 min at RT. The reaction mixture was stirred at 90° C. for 6 h. The reaction was cooled to RT, diluted with water (20 mL), and the product was extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 20% EtOAc % Hexane) to afford Compound BD (210 mg, 0.55 mmol, 61%) as a brown solid. $^1$H NMR (400 MHz. DMSO-$d_6$): δ 7.53 (d, J=8.5 Hz, 2H), 6.95 (d, J=8.7 Hz, 2H), 6.74 (d, J=8.8 Hz, 2H), 6.51 (d, J=7.4 Hz, 2H), 4.59 (brs, 2H), 3.35-3.30 (m, 4H), 3.18-2.97 (m, 4H), 1.26 (s, 12H).

Preparation of (R)-1-(5-(4-(4-(4-aminophenyl) piperazin-1-yl) phenyl) pyridin-2-yl)-2-(2,4-difluorophenyl)-1,1-difluoro-3-(1H-tetrazol-1-yl) propan-2-ol (14)

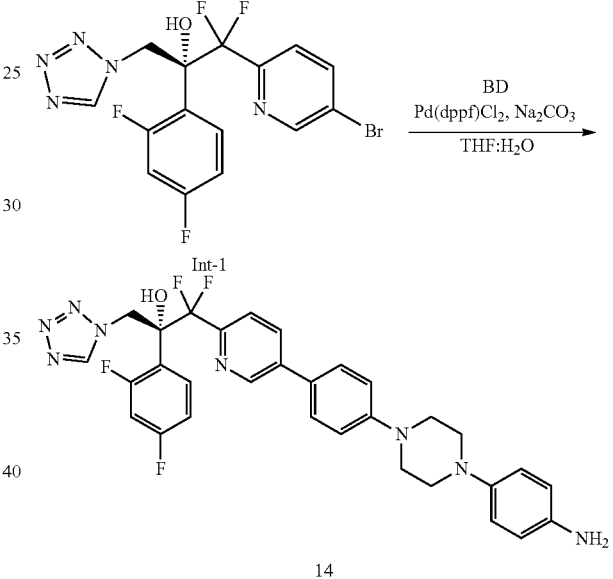

To a stirred solution of Int-1 (150 mg, 0.34 mmol) in THF:H$_2$O (4:1, 20 mL) under argon atmosphere were added Compound BD (158 mg, 0.41 mmol) and sodium carbonate (110 mg, 1.04 mmol) at RT. The reaction mixture was purged with argon for 15 min, then Pd(dppf)Cl$_2$ (25.4 mg, 0.03 mmol) was added and the reaction mixture was purged with argon for 10 min at RT. The reaction mixture was stirred at 70° C. for 6 h. The reaction was cooled to RT, diluted with water (20 mL), and the product was extracted with EtOAc (2×20 mL). The combined organic extracts were dried over anhydrous $Na_2SO_4$ and concentrated under reduced pressure. The crude material was purified by silica gel column chromatography (eluent: 2% MeOH/CH$_2$Cl$_2$) to afford 14 (80 mg, 0.13 mmol, 38%) as an off-white solid. $^1$H NMR (400 MHz, DMSO-$d_6$): δ 9.14 (s, 1H), 8.90 (s, 1H), 8.16 (dd, J=8.3, 2.3 Hz, 1H), 7.69 (d, J=8.9 Hz, 2H), 7.48 (d, J=8.3 Hz, 1H), 7.33-7.25 (m, 2H), 7.22-7.16 (m, 1H), 7.12 (d, J=9.0 Hz, 2H), 6.93-6.88 (m, 1H), 6.76 (d, J=8.8 Hz, 2H), 6.52 (d, J=8.7 Hz, 2H), 5.67 (d, J=14.7 Hz, 1H), 5.11 (d, J=14.9 Hz, 1H), 4.60 (brs, 2H), 3.39-3.33 (m, 4H), 3.09-3.03

(m, 4H); MS (ESI): m/z: 605.1 [M+H]+; HPLC: 94.41%; Optical rotation $[\alpha]_D^{20}$: +55.3 (c=0.1% in MeOH).

Example 15(−) and 15(+)

(+)- and (−)-2-(2,5-difluorophenyl)-1,1-difluoro-3-(1H-tetrazol-1-yl)-1-(5-(4-(4-(4-(2,2,2-trifluoro-1-hydroxyethyl)phenyl)piperazin-1-yl)phenyl)pyridin-2-yl)propan-2-ol (15)

Preparation of 2-(5-bromopyridin-2-yl)-1-(2,5-difluorophenyl)-2,2-difluoroethan-1-one (BF)

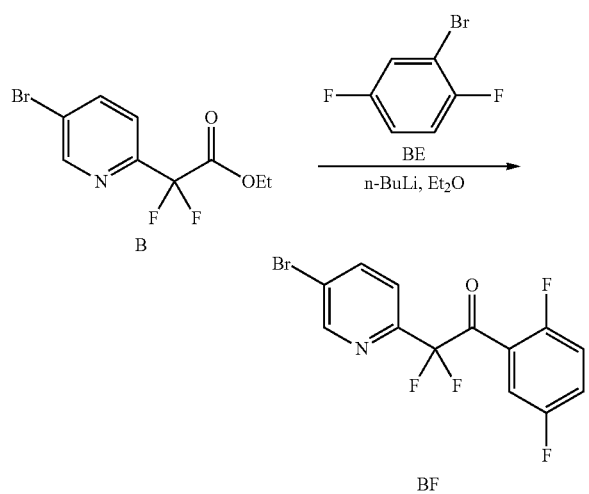

To a stirred solution of 2-bromo-1,4-difluorobenzene BE (15.2 g, 80.35 mmol) in diethyl ether (150 mL) under argon atmosphere was added n-butyllithium (n-BuLi, 50.22 mL, 80.35 mmol, 1.6 M in hexane) at −78° C., and the reaction was stirred for 1 h. Then Compound B (15 g, 53.57 mmol) in diethyl ether was added to the reaction mixture at −78° C., and the reaction was stirred for another 90 min. The reaction was quenched with a saturated ammonium chloride solution (500 mL) and the product was extracted with ethyl acetate (3×500 mL). The combined organic layers were washed with water (300 mL), brine (300 mL), dried over anhydrous Na2SO4 and concentrated under reduced pressure. The crude material was purified by silica gel column chromatography (eluent: 10% EtOAc/Hexane) to afford Compound BF (20 g, crude) as a pale yellow syrup. $^1$H NMR (500 MHz, CDCl$_3$): δ 8.63 (s, 1H), 8.04 (dd, J=8.4, 2.3 Hz, 1H), 7.72 (d, J=8.4 Hz, 1H), 7.71-7.62 (m, 1H), 7.34-7.20 (m, 1H), 7.09-7.04 (m, 1H).

Preparation of 5-bromo-2-((2-(2,5-difluorophenyl) oxiran-2-yl) difluoromethyl) pyridine (BG)

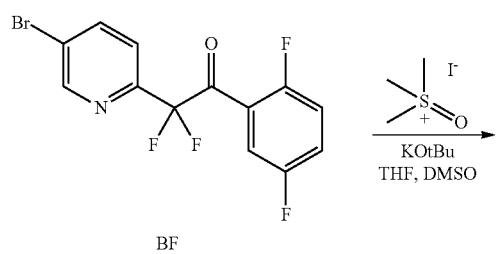

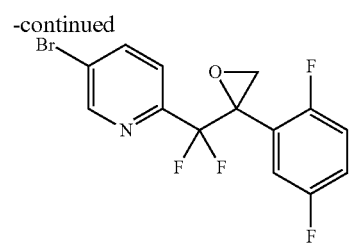

To a stirred solution of potassium tert-butoxide (7.0 g. crude) in THF:DMSO (2:1, 200 mL) under argon atmosphere was added trimethylsulfoxonium iodide (13.9 g, 63.21 mmol) and the reaction was stirred at RT for 1 h. Then Compound BF (20 g, 57.47 mmol) in THF (20 mL) was added to the reaction mixture at 0° C., and the reaction was stirred for 1 h. The reaction was quenched with ice cold water (150 mL) and the product was extracted with EtOAc (2×150 mL). The combined organic layers were washed with a 10% sodium thiosulfate solution (150 mL), a saturated sodium bicarbonate solution (150 mL), water (150 mL), brine (150 mL), dried over anhydrous Na2SO4 and concentrated under reduced pressure. The crude material was purified by silica gel column chromatography (eluent: 10% EtOAc/Hexane) to afford Compound BG (10 g, 27.62 mmol) as a pale yellow syrup. $^1$H NMR (400 MHz, CDCl$_3$): δ 8.73 (s, 1H), 7.90 (dd, J=8.4, 2.2 Hz, 1H), 7.40 (dd, J=8.4, 0.6 Hz, 1H), 7.14-7.10 (m, 1H), 7.06-6.93 (m, 2H), 3.44 (d, J=5.0 Hz, 1H), 3.03-2.96 (m, 1H).

Preparation of 3-amino-1-(5-bromopyridin-2-yl)-2-(2,5-difluorophenyl)-1,1-difluoropropan-2-ol (BH)

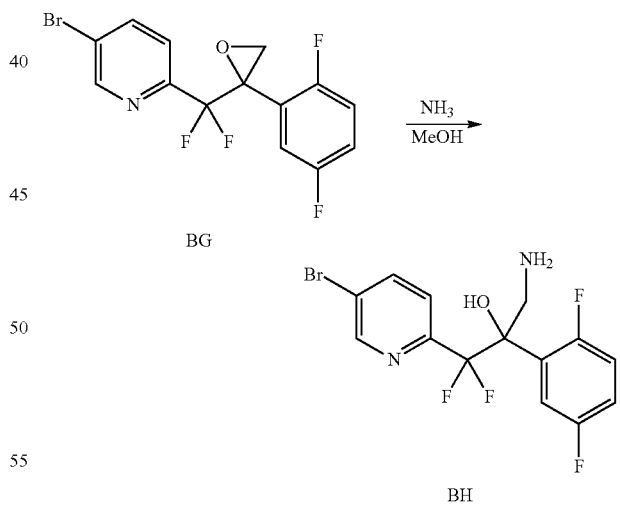

To Compound BG (5.0 g, 138.12 mmol) in MeOH (5 mL) in an autoclave was added methanolic-ammonia (30 mL) at −78° C. The temperature was raised slowly to 50° C., and the reaction was stirred for 12 h. The volatiles were removed under reduced pressure. The crude material was purified by silica gel column chromatography (eluent: 30% EtOAc/Hexane) to afford Compound BH (5.0 g, 13.22 mmol, 47%) as a pale yellow solid. $^1$H NMR (500 MHz, CDCl$_3$): δ 8.63 (s, 1H), 7.87 (dd, J=8.4, 2.3 Hz, 1H), 7.33 (d, J=8.4 Hz, 1H), 7.26-7.21 (m, 1H), 6.98-6.93 (m, 2H), 3.89 (d, J=13.6, 1H), 3.67 (brs, 2H), 3.35 (d, J=13.9 Hz, 1H).

Preparation of 1-(5-bromopyridin-2-yl)-2-(2,5-difluorophenyl)-1,1-difluoro-3-(1H-tetrazol-1-yl propan-2-ol (BI-Fr-I and BI-Fr-II)

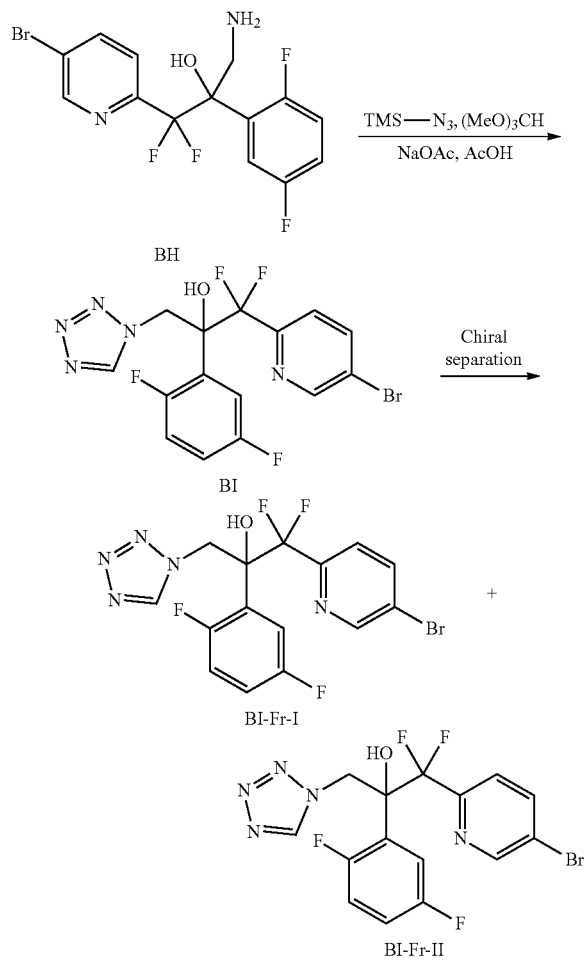

To a stirred solution of Compound BH (4.0 g, 10.58 mmol) in acetic acid (10 mL) under argon atmosphere were added trimethylorthoformate (2.96 g, 28.57 mmol) and sodium acetate (820 m, 10.58 mmol). After stirring at RT for 15 min, trimethylsilylazide (TMS-azide, 2.77 mL, 22.22 mmol) was added to the reaction mixture. The reaction was stirred at 60° C. for 3 h. The reaction was diluted with a 10% sodium bicarbonate solution (200 mL) and the product was extracted with EtOAc (2×200 mL). The separated organic layer was washed with brine (100 mL), dried over anhydrous $Na_2SO_4$ and concentrated under reduced pressure. The crude material was purified by silica gel column chromatography (eluent: 40% EtOAc/Hexane) to afford Compound BI (3 g, 6.94 mmol, 69%) as pale yellow solid. $^1$H NMR (400 MHz, $CDCl_3$): δ 8.74 (s, 1H), 8.64 (s, 1H), 7.97 (dd, J=8.4, 2.1 Hz, 1H), 7.49 (d, J=8.4 Hz, 1H), 7.08-7.01 (m, 1H), 7.00-6.87 (m, 2H), 5.60 (d, J=14.3 Hz, 1H), 5.13 (d, J=14.3 Hz, 1H).

Chiral Preparative HPLC Details for Enantiomers BI-Fr-I & BI-Fr-III

The enantiomers of BI (600 mg, 1.40 mmol) were separated by normal-phase preparative high performance liquid chromatography (Chiralpak IC®, 250×20 mm, 5μ; using (A) 0.1% DEA in n-hexane:(B) $CH_2Cl_2$:MeOH (80:20) (A:B=75:25) as a mobile phase; Flow rate: 20 mL/min) to obtain 200 mg of each BI-Fr-I and BI-Fr-I.

Analytical Data of BI-FR-I:
$^1$H NMR (400 MHz, DMSO-$d_6$): δ 9.15 (s, 1H), 8.76 (s, 1H), 8.23 (dd, J=8.5, 2.3 Hz, 1H), 7.47 (d, J=8.5 Hz, 1H), 7.37 (s, 1H), 7.27-7.17 (m, 2H), 6.98-6.90 (m, 1H), 5.64 (d, J=14.7 Hz, 1H), 5.08 (d, J=14.7 Hz, 1H); MS (ESI): m/z 432.2 [M+H]$^+$; HPLC: 99.59%; Chiral HPLC Purity: 99.59%, $R_t$=11.37 min (CHIRALPAK-IC®, 250×4.6 mm, 5μ; mobile phase (A) 0.1% DEA in n-hexane:(B) $CH_2Cl_2$:MeOH (80:20) (A:B=75:25); flow Rate: 1.00 mL/min); Optical rotation $[α]_D^{19}$: +24.4 (C=0.1% in MeOH).

Analytical Data of BI-FR-II:
$^1$H NMR (400 MHz, DMSO-$d_6$): δ 9.15 (s, 1H), 8.76 (s, 1H), 8.23 (dd, J=8.5, 2.3 Hz, 1H), 7.47 (d, J=8.5 Hz, 1H), 7.37 (s, 1H), 7.27-7.17 (m, 2H), 6.98-6.90 (m, 1H), 5.64 (d, J=14.7 Hz, 1H), 5.08 (d, J=14.7 Hz, 1H); MS (ESI): m/z 432.2 [M+H]$^+$; HPLC: 99.23%; Chiral HPLC Purity: 100%, $R_t$=15.03 min (CHIRALPAK-IC®, 250×4.6 mm, 5μ; mobile phase (A) 0.1% DEA in n-hexane:(B) $CH_2Cl_2$:MeOH (80:20) (A:B=75:25); flow Rate: 1.00 mL/min); Optical rotation $[α]_D^{19}$: −24.0 (C=0.1% in MeOH).

Preparation of 2-(2,5-difluorophenyl)-1,1-difluoro-3-(1H-tetrazol-1-yl)-1-(5-(4-(4-(4-(2,2,2-trifluoro-1-hydroxyethyl) phenyl) piperazin-1-yl) phenyl) pyridin-2-yl) propan-2-ol (15(−))

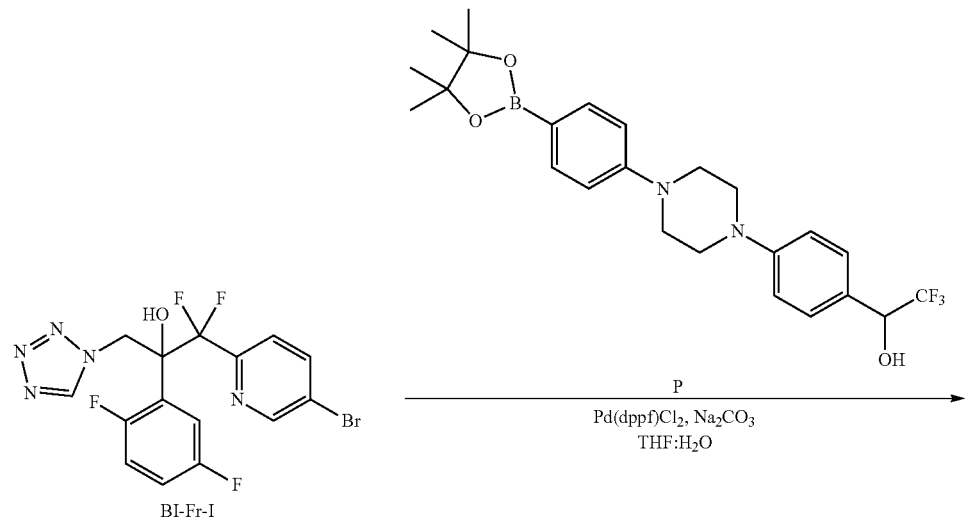

-continued

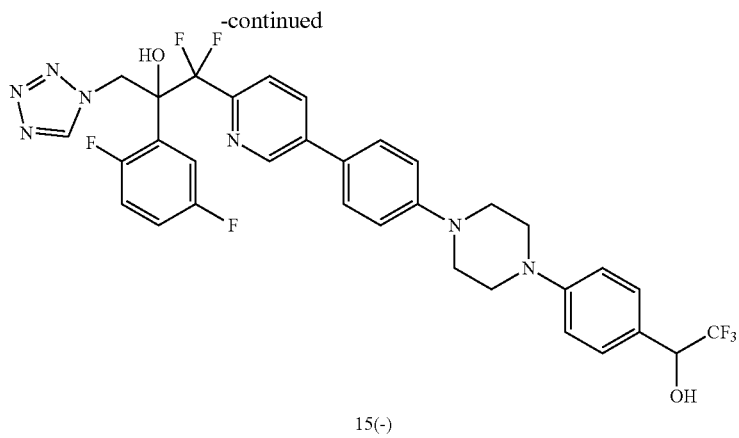

15(−)

To a stirred solution of Compound BI-Fr-I (150 mg, 0.34 mmol) in THF:H₂O (4:1, 20 mL) under argon atmosphere were added Compound P (160 mg, 0.34 mmol) and sodium carbonate (110 mg, 1.04 mmol) at RT. The reaction mixture was purged with argon for 5 min, then Pd(dppf)Cl$_2$ (25.4 mg, 0.03 mmol) was added and the reaction mixture was purged with argon for 10 min at RT. The reaction mixture was stirred at 70° C. for 5 h. The reaction was cooled to RT, diluted with water (30 mL), and the product was extracted with EtOAc (2×30 mL). The combined organic extracts were washed with water (30 mL), dried over anhydrous Na$_2$SO$_4$ and concentrated under reduced pressure. The crude material was purified by silica gel column chromatography (eluent: 2% MeOH/CH$_2$Cl$_2$) to afford 15(−) (80 mg, 0.11 mmol, 33%) as a pale yellow solid. ¹H NMR (400 MHz, DMSO-d$_6$): δ 9.16 (s, 1H), 8.92 (s, 1H), 8.18 (dd, J=8.3, 2.2 Hz, 1H), 7.70 (d, J=8.9 Hz, 2H), 7.52 (d, J=8.3 Hz, 1H), 7.34 (m, 3H), 7.23-7.20 (m, 2H), 7.14 (d, J=8.9 Hz, 2H), 7.03 (d, J=8.7 Hz, 3H), 6.61 (d, J=5.5 Hz, 1H), 5.70 (d, J=14.6 Hz, 1H), 5.12 (d, J=14.6 Hz, 1H), 5.02 (t, J=6.7 Hz, 1H), 3.43-3.37 (m, 4H), 3.34-3.31 (m, 4H); MS (ESI): m/z 686.4 [M−H]⁻; HPLC: 95.76%; Optical rotation [α]$_D^{19}$: −91.4 (c=0.1% in MeOH).

Preparation of 2-(2,5-difluorophenyl-1,1-difluoro-3-(1H-tetrazol-1-yl)-1-(5-(4-(4-(4-(2,2,2-trifluoro-1-hydroxyethyl) phenyl) piperazin-1-yl) phenyl) pyridin-2-yl) propan-2-ol (15(+))

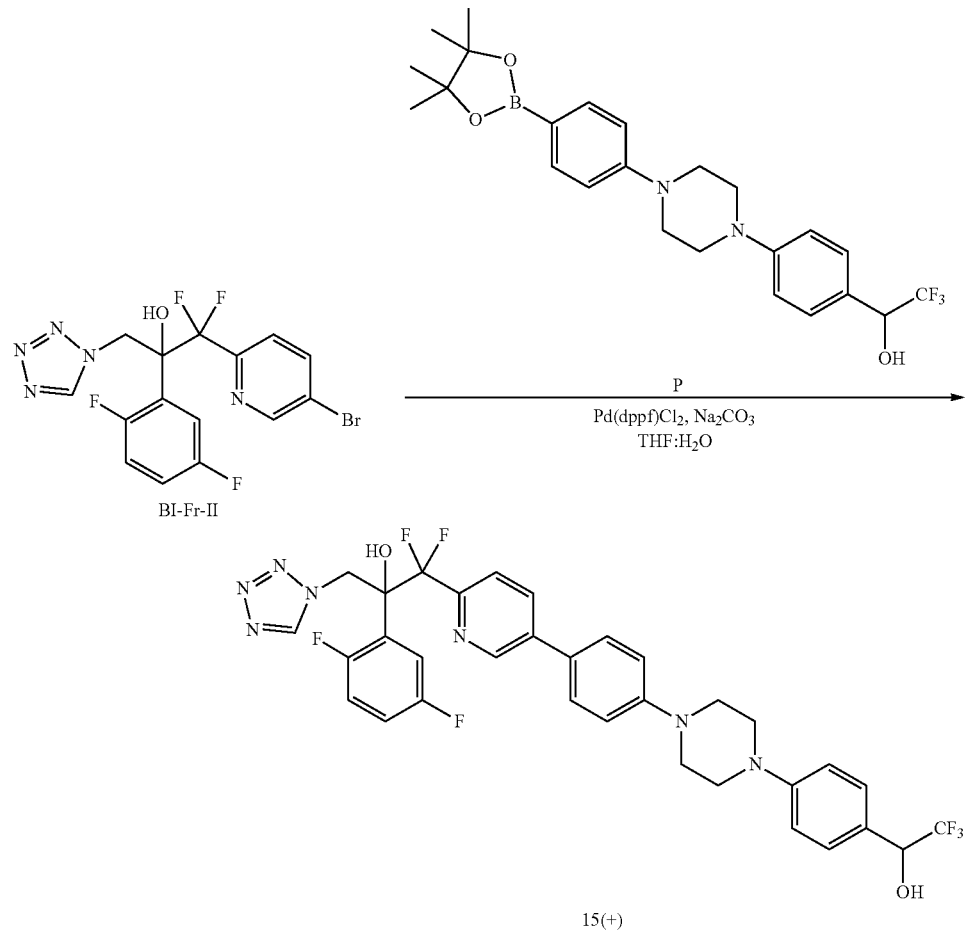

To a stirred solution of Compound BI-Fr-II (150 mg, 0.34 mmol) in THF:H₂O (4:1, 20 mL) under argon atmosphere were added Compound P (160 mg, 0.34 mmol) and sodium carbonate (110 mg, 1.04 mmol) at RT. The reaction mixture was purged with argon for 5 min, then Pd(dppf)Cl₂ (25.4 mg, 0.03 mmol) was added and the reaction mixture was purged with argon for 10 min at RT. The reaction mixture was stirred at 80° C. for 6 h. The reaction was cooled to RT, diluted with water (30 mL), and the product was extracted with EtOAc (2×30 mL). The combined organic extracts were washed with water (30 mL), dried over anhydrous Na₂SO₄ and concentrated under reduced pressure. The crude material was purified by silica gel column chromatography (eluent: 2% MeOH/CH₂Cl₂) to afford 15(+) (80 mg, 0.11 mmol, 33%) as a pale yellow solid. ¹H NMR (400 MHz, DMSO-d₆): δ 9.16 (s, 1H), 8.92 (s, 1H), 8.18 (dd, J=8.3, 2.2 Hz, 1H), 7.70 (d, J=8.9 Hz, 2H), 7.52 (d, J=8.3 Hz, 1H), 7.34 (m, 3H), 7.23-7.20 (m, 2H), 7.14 (d, J=8.9 Hz, 2H), 7.03 (d, J=8.7 Hz, 3H), 6.61 (d, J=5.5 Hz, 1H), 5.70 (d, J=14.6 Hz, 1H), 5.12 (d, J=14.6 Hz, 1H), 5.02 (t, J=6.7 Hz, 1H), 3.43-3.37 (m, 4H), 3.34-3.31 (m, 4H); MS (ESI): m/z 686.5 [M−H]⁻; HPLC: 97.46%; Optical rotation [α]$_D^{19}$: +43.2 (c=0.1% in MeOH).

Example 16

(2R)-2-(2,4-difluorophenyl)-1,1-difluoro-3-(4H-1,2,4-triazol-4-yl)-1-(5-(4-(4-(4-(2,2,2-trifluoro-1-hydroxyethyl) phenyl) piperazin-1-yl) phenyl) pyridin-2-yl) propan-2-ol (16)

Preparation of (R)-1-(5-bromopyridin-2-yl)-2-(2,4-difluorophenyl)-1,1-difluoro-3-(4H-1,2,4-triazol-4-yl) propan-2-ol (BJ)

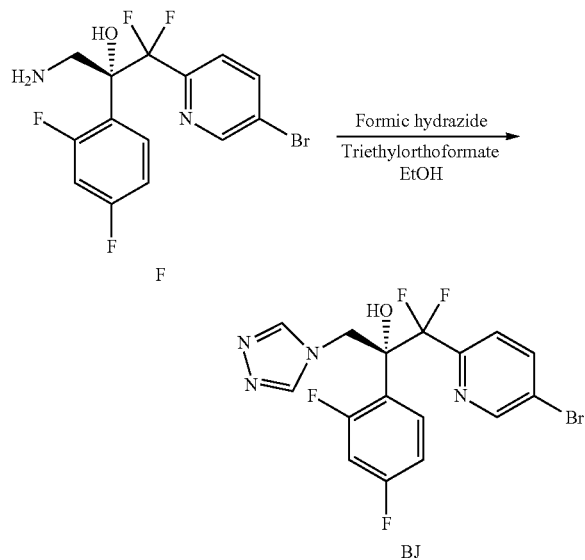

To a stirred solution of formic hydrazide (1.2 g, 21.22 mmol) in EtOH (80 mL) under argon atmosphere was added triethylorthoformate (6.2 g, 42.44 mmol) at RT. The reaction was stirred at reflux for 4 h. Then Compound F (4.0 g, 10.61 mmol) was added to the reaction mixture at 0° C., and the reaction mixture was stirred at reflux for 16 h. The volatiles were concentrated under reduced pressure. The residue was diluted with water (200 mL) and the product was extracted with EtOAc (2×200 mL). The combined organic extracts were washed with water (200 mL), brine (100 mL), dried over anhydrous Na₂SO₄ and concentrated under reduced pressure. The crude material was purified by silica gel column chromatography (eluent: 2% MeOH/CH₂Cl₂) to afford Compound BJ (2.5 g, 5.80 mmol, 55%) as an off-white solid. ¹H NMR (400 MHz, DMSO-d₆): δ 8.73 (s, 1H), 8.23 (s, 2H), 8.20 (dd, J=8.5, 2.4 Hz, 1H), 7.40 (d, J=8.4 Hz, 1H), 7.31-7.25 (m, 1H), 7.23 (s, 1H), 7.21-7.15 (m, 1H), 6.96-6.91 (m, 1H), 5.19 (d, J=15.5 Hz, 1H), 4.62 (d, J=15.5 Hz, 1H).

Preparation of (2R)-2-(2,4-difluorophenyl)-1,1-difluoro-3-(4H-1,2,4-triazol-4-yl)-1-(5-(4-(4-(4-(2,2,2-trifluoro-1-hydroxyethyl) phenyl) piperazin-1-yl) phenyl) pyridin-2-yl) propan-2-ol (16)

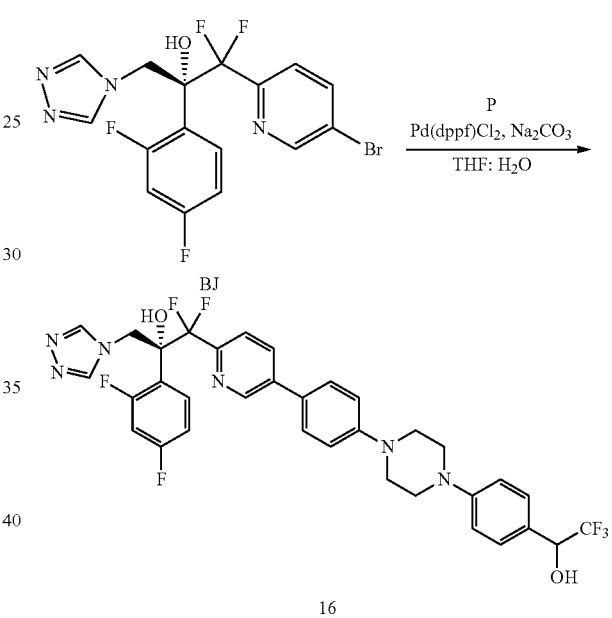

To a stirred solution of Compound BJ (150 mg, 0.34 mmol) in THF:H₂O (4:1, 20 mL) under argon atmosphere were added Compound P (192 mg, 0.41 mmol) and sodium carbonate (110 mg, 1.04 mmol) at RT. The reaction mixture was purged with argon for 20 min, then Pd(dppf)Cl₂ (25 mg, 0.03 mmol) was added and the reaction mixture was stirred at 80° C. for 16 h. The reaction was cooled to RT, diluted with water (10 mL), and the product was extracted with EtOAc (2×10 mL). The combined organic extracts were washed with water (10 mL), brine (10 mL), dried over anhydrous Na₂SO₄ and concentrated under reduced pressure. The crude material was purified by silica gel column chromatography (eluted with 3% MeOH/CH₂Cl₂) to afford 16 (100 mg, 0.14 mmol, 42%) as an off-white solid. ¹H NMR (400 MHz, DMSO-d₆): δ 8.89 (s, 1H), 8.24 (s, 2H), 8.16 (dd, J=8.3, 2.2 Hz, 1H), 7.69 (d, J=7.6 Hz, 2H), 7.45 (d, J=8.3 Hz, 1H), 7.41-7.32 (m, 3H), 7.20 (s, 1H), 7.18-7.11 (m, 3H), 7.03 (d, J=8.9 Hz, 2H), 6.97-6.93 (m, 1H), 6.61 (d, J=5.5 Hz, 1H), 5.24 (d, J=15.4 Hz, 1H), 5.05-4.97 (m, 1H), 4.65 (d, J=15.4 Hz, 1H), 3.42-3.37 (m, 4H), 3.36-3.31 (m, 4H); MS (ESI): m/z 685.4 [M−H]⁻; HPLC: 98.67%; Optical rotation [α]$_D^{19}$: +59.0 (c=0.1% in MeOH).

Example 17

(R)-4-((4-(4-(6-(2-(2,4-difluorophenyl)-1,1-difluoro-2-hydroxy-3-(1H-tetrazol-1-yl) propyl) pyridin-3-yl) phenyl) piperazin-1-yl) methyl) benzonitrile (17)

Preparation of 4-((4-(4-(4-bromophenyl) piperazin-1-yl) methyl) benzonitrile (BL)

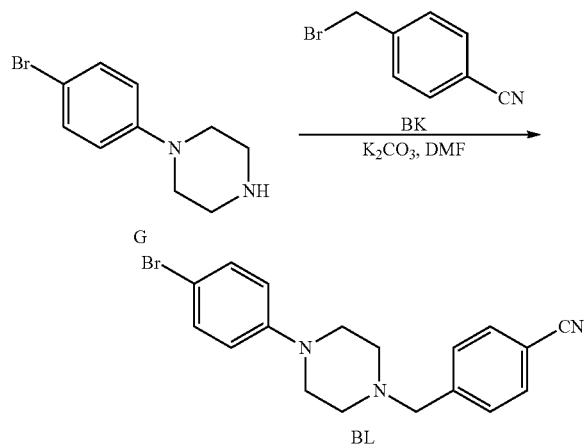

To a stirred solution of 1-(4-bromophenyl) piperazine G (1.0 g, 4.14 mmol) in DMF (10 mL) under argon atmosphere were added potassium carbonate (1.14 g, 8.29 mmol) and 4-(bromomethyl) benzonitrile BK (890 mg, 4.56 mmol) at RT. The reaction was stirred at RT for 12 h. The reaction was diluted with water (50 mL), and the product was extracted with EtOAc (2×50 mL). The combined organic layers were washed with water (50 mL), brine (50 mL), dried over anhydrous $Na_2SO_4$ and concentrated under reduced pressure. The crude material was purified by silica gel column chromatography (eluent: 20% EtOAc/Hexane) to afford Compound BL (1.1 g, 3.09 mmol, 75%) as an off-white solid. $^1$H NMR (500 MHz. $CDCl_3$): δ 7.64 (d, J=8.1 Hz, 2H), 7.57-7.47 (m, 2H), 7.35 (d, J=8.7 Hz, 2H), 6.79 (d, J=9.0 Hz, 2H), 3.64 (brs, 2H), 3.20 (s, 4H), 2.63 (s, 4H).

Preparation of 4-((4-(4-(4,4,5,5-tetramethyl-1,3,2-dioxaborolan-2-yl) phenyl) piperazin-1-yl) methyl) benzonitrile (BM)

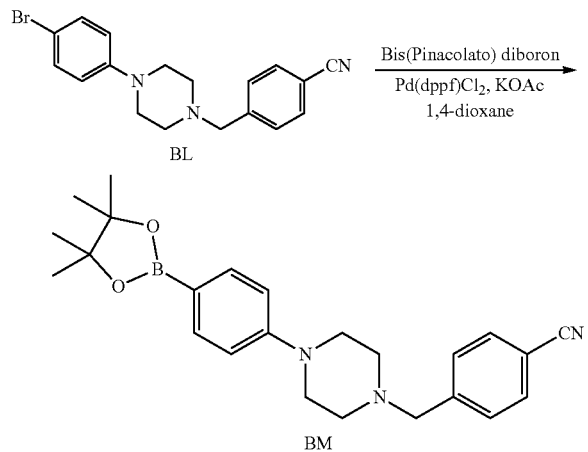

To a stirred solution of Compound BL (500 mg, 1.40 mmol) in 1,4-dioxane (10 mL) under argon atmosphere were added bis(pinacolato)diboron (355 mg, 1.40 mmol) and potassium acetate (412 mg, 4.21 mmol) at RT. The reaction mixture was purged with argon for 20 min, then $Pd(dppf)Cl_2$ (103 mg, 0.14 mmol) was added and the reaction mixture was purged with argon for 5 min at RT. The reaction was stirred at 100° C. for 16 h. The reaction was cooled to RT, diluted with water (20 mL), and the product was extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 20% EtOAc/Hexane) to afford Compound BM (350 mg, 0.86 mmol, 62%) as an off-white solid. $^1$H NMR (400 MHz, $CDCl_3$): δ 7.71 (d, J=8.7 Hz, 2H), 7.65 (d, J=7.9 Hz, 2H), 7.55 (d, J=8.7 Hz, 2H), 6.87 (d, J=7.9 Hz, 2H), 3.70 (s, 2H), 3.38-3.32 (m, 4H), 2.68-2.62 (m, 4H), 1.32 (s, 12H).

Preparation of (R)-4-((4-(4-(6-(2-(2,4-difluorophenyl)-1,1-difluoro-2-hydroxy-3-(1H-tetrazol-1-yl) propyl) pyridin-3-yl) phenyl) piperazin-1-yl) methyl) benzonitrile (17

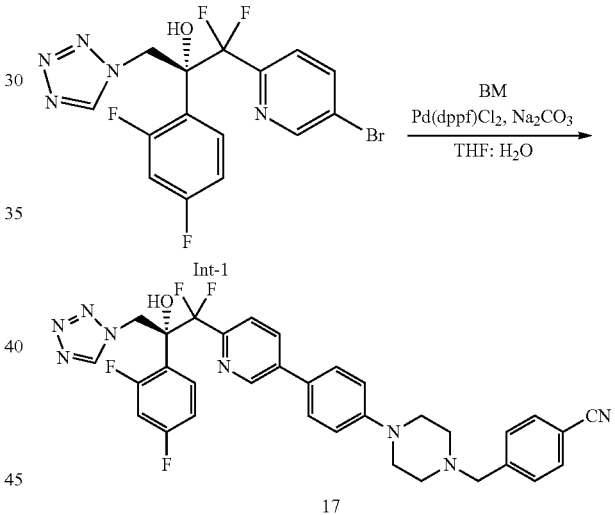

To a stirred solution of Int-1 (150 mg, 0.34 mmol) in $THF:H_2O$ (20 mL) under argon atmosphere were added Compound BM (167 mg, 0.41 mmol) and sodium carbonate (110 mg, 1.04 mmol) at RT. The reaction mixture was purged with argon for 20 min. then $Pd(dppf)Cl_2$ (25 mg, 0.03 mmol) was added and the reaction mixture was purged with argon for 10 min at RT. The reaction was stirred at 80° C. for 6 h. The reaction was cooled to RT, diluted with water (20 mL), and the product was extracted with EtOAc (2×20 mL). The combined organic extracts were dried over anhydrous $Na_2SO_4$ and concentrated under reduced pressure. The crude material was purified by silica gel column chromatography (eluent: 70% EtOAc/Hexane) to afford 17 (70 mg, 0.11 mmol, 24%) as an off-white solid. $^1$H NMR (400 MHz, DMSO-$d_6$): δ 9.14 (s, 1H), 8.89 (s, 1H), 8.14 (dd, J=8.3, 2.2 Hz, 1H), 7.82 (d, J=8.3 Hz, 2H), 7.66 (d, J=8.9 Hz, 2H), 7.56 (d, J=8.3 Hz, 2H), 7.47 (d, J=8.4 Hz, 1H), 7.31-7.15 (m, 3H), 7.05 (d, J=8.9 Hz, 2H), 6.93-6.87 (m, 1H), 5.66 (d, J=14.6 Hz, 1H), 5.10 (d, J=14.6 Hz, 1H), 3.64 (s, 2H), 3.28-3.22 (m, 4H), 2.57-2.51 (m, 4H); MS (ESI): m/z 629.7 [M+H]$^+$; HPLC: 95.87%; Optical rotation $[\alpha]_D^{19}$: +51.2 (c=0.1% in MeOH).

Example 18

(R)-4-(4-(4-(6-(2-(2,4-difluorophenyl)-1,1-difluoro-2-hydroxy-3-(1H-tetrazol-1-yl) propyl) pyridin-3-yl) benzyl) piperazin-1-yl) benzonitrile (18)

Preparation of tert-bur 4-(4-cyanophenyl) piperazine-1-carboxylate (BN)

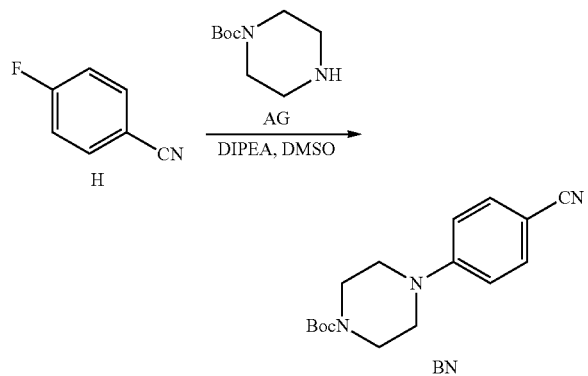

To a stirred solution of 4-fluorobenzonitrile H (3.0 g, 24.79 mmol) in DMSO (50 mL) under argon atmosphere were added diisopropyl ethyl amine (12.8 mL, 74.38 mmol) and tert-butyl piperazine-1-carboxylate AG (5.0 g, 27.27 mmol) at RT. The reaction mixture was stirred at 90° C. for 16 h. The reaction was cooled to RT, diluted with water (100 mL), and the product was extracted with EtOAc (2×100 mL). The combined organic extracts were washed with water (100 mL), dried over anhydrous Na$_2$SO$_4$ and concentrated under reduced pressure. The crude material was purified by silica gel column chromatography (eluent: 10% EtOAc/Hexane) to afford Compound BN (45 mg, 16.60 mmol, 67%) as a white solid. $^1$H NMR (500 MHz, DMSO-d$_6$): δ 7.58 (d, J=8.2 Hz, 2H), 7.00 (d, J=9.0 Hz, 2H), 3.48-3.37 (m, 4H), 3.35-3.30 (m, 4H), 1.40 (s, 9H).

Preparation of 4-(piperazin-1-yl) benzonitrile hydrochloride (BO)

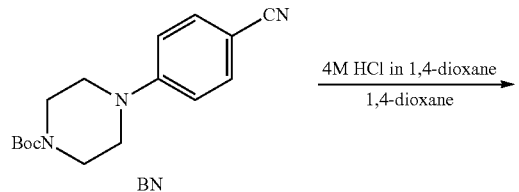

To a stirred solution of Compound BN (2.0 g, 7.38 mmol) in 1,4-dioxane (15 mL) under argon atmosphere was added 4.0 M HCl in 1,4-dioxane (3.7 mL, 14.76 mmol) at 0° C. The reaction was warmed to RT and stirred for 16 h. The volatiles were concentrated under reduced pressure. The residue was washed with diethyl ether (2×20 mL) and dried under reduced pressure to obtain Compound BO (1.2 g, 5.79 mmol, 86%) as a white solid. $^1$H NMR (400 MHz, DMSO-d$_6$): δ 7.64 (d, J=10.6 Hz, 2H), 7.08 (d, J=10.6 Hz, 2H), 3.66-3.53 (m, 4H), 3.20-3.16 (m, 4H), 1.32-1.26 (m, 1H).

Preparation of 4-(4-(4-bromobenzyl) piperazin-1-yl) benzonitrile (BQ)

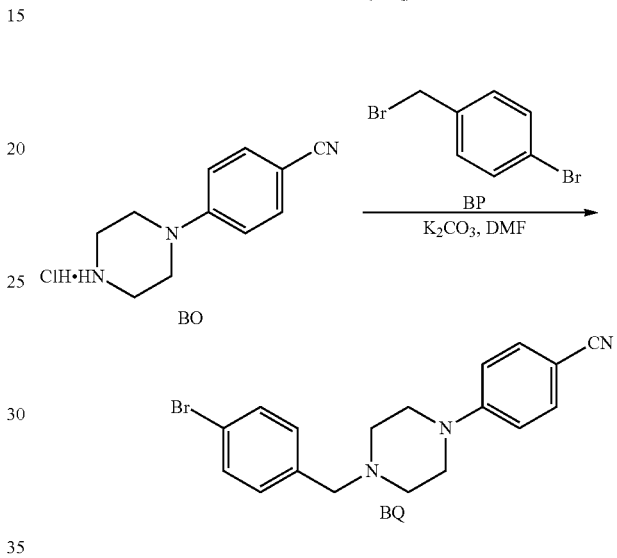

To a stirred solution of Compound BO (500 mg, 2.24 mmol) in DMF (25 mL) under argon atmosphere was added potassium carbonate (928 mg, 6.72 mmol) at RT and the reaction was stirred for 30 min. Then 1-bromo-4-(bromomethyl) benzene BP (616 mg, 2.46 mmol) was added and the reaction was stirred for 16 h. The reaction mixture was diluted with water (20 mL) and the product was extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 15% EtOAc/Hexane) to afford Compound BQ (550 mg, 1.54 mmol, 69%) as a white solid. $^1$H NMR (500 MHz, DMSO-d$_6$): δ 7.56 (d, J=8.2 Hz, 2H), 7.53 (d, J=7.7 Hz, 2H), 7.29 (d, J=8.1 Hz, 2H), 7.00 (d, J=8.3 Hz, 2H), 3.49 (s, 2H), 3.34-3.30 (m, 4H), 2.49-2.46 (m, 4H).

Preparation of 4-(4-(4-(4,4,5,5-tetramethyl-1,3,2-dioxaborolan-2-yl) benzyl) piperazin-1-yl benzonitrile (BR)

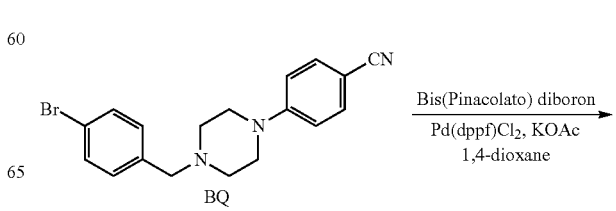

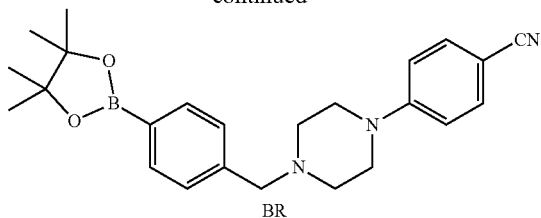

To a stirred solution of Compound BQ (500 mg, 1.40 mmol) in 1,4-dioxane (50 mL) under argon atmosphere were added potassium acetate (412 mg, 4.21 mmol) and bis(pinacolato)diboron (570 mg, 2.24 mmol) at RT. The reaction mixture was purged with argon for 10 min, then Pd(dppf)Cl$_2$ (102 mg, 0.14 mmol) was added to the reaction mixture at RT. The reaction was stirred at 90° C. for 16 h. The reaction was cooled to RT, diluted with water (20 mL), and the product was extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 10% EtOAc/Hexane) to afford Compound BR (375 mg, 0.93 mmol, 60%) as a white solid. $^1$H NMR (500 MHz, DMSO-d$_6$): δ 7.63 (d, J=7.8 Hz, 2H), 7.55 (d, J=8.3 Hz, 2H), 7.33 (d, J=7.8 Hz, 2H), 6.98 (d, J=9.0 Hz, 2H), 3.52 (s, 2H), 3.30 (s, 4H), 2.50-2.43 (m, 4H), 1.27 (s, 12H).

Preparation of (R)-4-(4-(4-(6-(2-(2,4-difluorophenyl)-1,1-difluoro-2-hydroxy-3-(1H-tetrazol-1-yl) propyl) pyridin-3-yl) benzyl) piperazin-1-yl) benzonitrile (18)

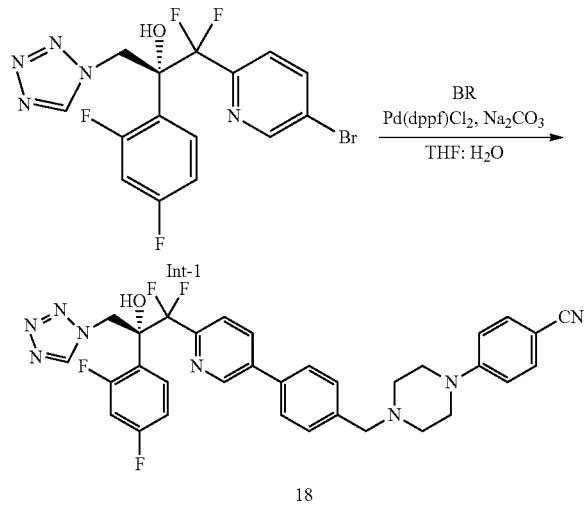

To a stirred solution of Int-1 (150 mg, 0.34 mmol) in THF:H$_2$O (4:1, 25 mL) under argon atmosphere were added Compound BR (168 mg, 0.41 mmol) and sodium carbonate (110 mg, 1.04 mmol) at RT. The reaction mixture was purged with argon for 5 min, then Pd(dppf)Cl$_2$ (25 mg, 0.03 mmol) was added and the reaction was stirred at reflux for 16 h. The reaction was cooled to RT, diluted with water (20 mL), and the product was extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 60% EtOAc/Hexane) to afford 18 (60 mg, 0.09 mmol, 27%) as an off-white solid. $^1$H NMR (400 MHz, CDCl$_3$): δ 8.76 (s, 1H), 8.74 (s, 1H), 7.99 (dd, J=8.2, 2.2 Hz, 1H), 7.72 (s, 1H), 7.66 (d, J=8.3 Hz, 1H), 7.57-7.45 (m, 6H), 7.44-7.38 (m, 1H), 6.85 (d, J=9.0 Hz, 2H), 6.82-6.75 (m, 1H), 6.71-6.65 (m, 1H), 5.57 (d, J=14.3 Hz, 1H), 5.16 (d, J=14.3 Hz, 1H), 3.63 (s, 2H), 3.37-3.32 (m, 4H), 2.65-2.60 (m, 4H); MS (ESI): m/z 627.4 [M−H]$^-$; HPLC: 99.43%; Optical rotation [α]$_D^{19}$: +44.1 (c=0.1% in MeOH).

Example 19

(R)-4-(4-(4-(6-(2-(2,4-difluorophenyl)-1,1-difluoro-2-hydroxy-3-(1H-tetrazol-1-yl) propyl) pyridin-3-yl) benzoyl) piperazin-1-yl) benzonitrile (19)

Preparation of 4-(4-(4-bromobenzoyl piperazin-1-yl) benzonitrile (BT)

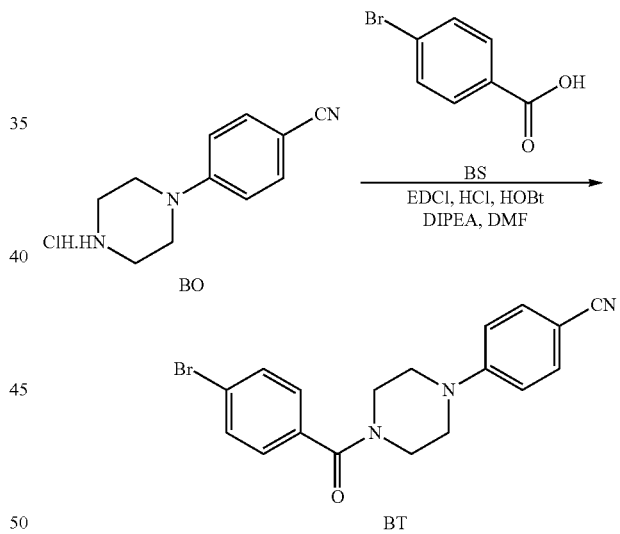

To a stirred solution of Compound BO (122 mg, 0.54 mmol) in DMF (4 mL) under argon atmosphere were added 4-bromobenzoic acid (BS, 100 mg, 0.50 mmol), 1-ethyl-3-(3-dimethylaminopropyl)carbodiimide (EDCI.HCl, 142 mg, 0.74 mmol), hydroxybenzotriazole (HOBt, 114 mg, 0.74 mmol) and diisopropylethylamine (0.27 mL, 1.49 mmol) at 0° C. The reaction was warmed to RT and stirred for 2 h. The reaction was diluted with water (10 mL) to obtain the solid, which was filtered and dried under reduced pressure to obtain Compound BT (120 mg, 0.32 mmol, 65%) as an off-white solid. The Compound BT was used in the next step without further purification. $^1$H NMR (400 MHz, DMSO-d$_6$): δ 7.67 (d, J=8.5 Hz, 2H), 7.61 (d, J=9.0 Hz, 2H), 7.41 (d, J=8.5 Hz, 2H), 7.02 (d, J=9.1 Hz, 2H), 3.81-3.38 (m, 8H).

Preparation of 4-(4-(4-(4,4,5,5-tetramethyl-1,3,2-dioxaborolan-2-yl) benzoyl piperazin-1-yl) benzonitrile (BU)

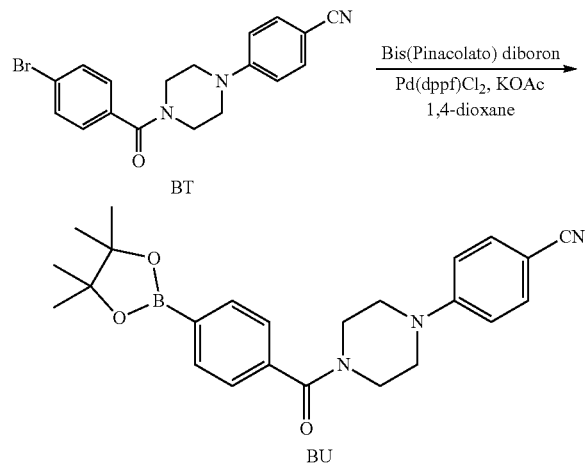

To a stirred solution of Compound BT (120 mg, 0.32 mmol) in 1,4-dioxane (5 mL) under argon atmosphere were added bis(pinacolato)diboron (132 mg, 0.52 mmol) and potassium acetate (95.6 mg, 0.97 mmol) at RT. The reaction mixture was purged with argon for 20 min, then Pd(dppf)Cl$_2$ (23.7 mg, 0.03 mmol) was added and the reaction mixture was purged with argon for 5 min at RT. The reaction was stirred at 90° C. for 4 h. The reaction was cooled to RT, diluted with water (20 mL), and the product was extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 50% EtOAc/Hexane) to afford Compound BU (60 mg, 0.14 mmol, 44%) as an off-white solid. $^1$H NMR (400 MHz, DMSO-d$_6$): δ 7.75 (d, J=7.1 Hz, 2H), 7.61 (d, J=8.7 Hz, 2H), 7.44 (d, J=8.0 Hz, 2H), 7.02 (d, J=6.3 Hz, 2H), 3.79-3.40 (m, 8H), 1.31 (s, 12H).

Preparation of (R)-4-(4-(4-(6-(2-(2,4-difluorophenyl)-1,1-difluoro-2-hydroxy-3-(1H-tetrazol-1-yl) propyl) pyridin-3-yl) benzoyl piperazin-1-yl, benzonitrile (19)

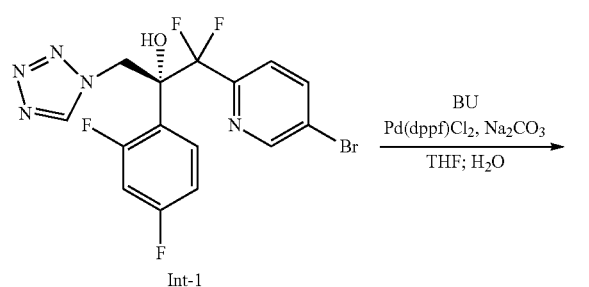

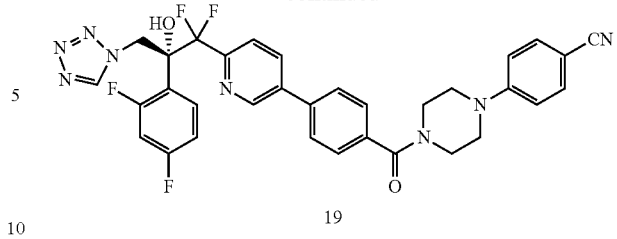

To a stirred solution of Int-1 (120 mg, 0.27 mmol) in THF:H$_2$O (4:1, 20 mL) under argon atmosphere were added Compound BU (139 mg, 0.33 mmol) and sodium carbonate (88.3 mg, 0.83 mmol) at RT. The reaction mixture was purged with argon for 20 min. then Pd(dppf)Cl$_2$ (20 mg, 0.03 mmol) was added and the reaction mixture was purged with argon for 5 min at RT. The reaction was stirred at 80° C. for 4 h. The reaction was cooled to RT, diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 60% Acetone/Hexane) to afford 19 (80 mg, 0.12 mmol, 46%) as an off-white solid. $^1$H NMR (400 MHz, DMSO-d$_6$): δ 9.15 (s, 1H), 8.99 (s, 1H), 8.29 (dd, J=8.3, 2.2 Hz, 1H), 7.88 (d, J=8.4 Hz, 2H), 7.64-7.58 (m, 5H), 7.32 (s, 1H), 7.30-7.17 (m, 2H), 7.04 (d, J=9.0 Hz, 2H), 6.93-6.88 (m, 1H), 5.68 (d, J=14.7 Hz, 1H), 5.13 (d, J=14.7 Hz, 1H), 3.84-3.38 (m, 8H); MS (ESI): m/z 641.2 [M–H]$^-$; HPLC: 93.37%; Optical rotation [α]$_D^{20}$: +51.0 (c=0.1% in MeOH).

Example 20

4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-((2S, 3S)-2-hydroxypentan-3-yl)-2,4-dihydro-3H-1,2,4-triazol-3-one (20)

Preparation of Phenyl (4-(4-(4-bromophenyl) piperazin-1-yl) phenyl) carbamate (BC)

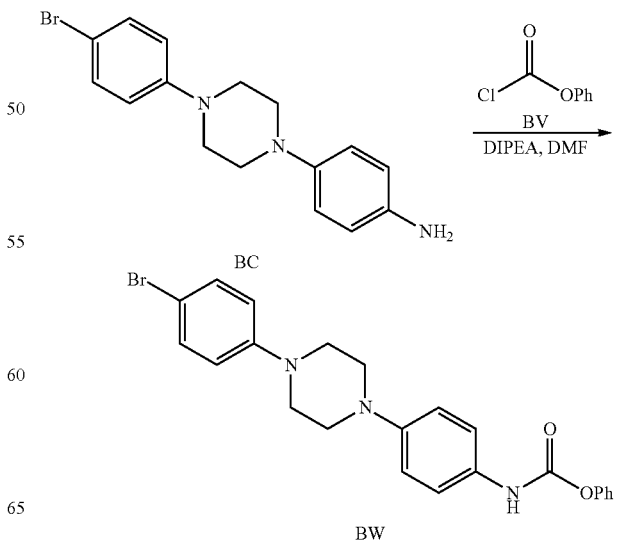

To a stirred solution of Compound BC (100 mg, 0.30 mmol) in DMF (1 mL) under argon atmosphere were added diisopropylethylamine (0.05 mL, 0.30 mmol) and phenyl carbonochloridate (BV, 0.04 mL, 0.36 mmol) at RT. The reaction was stirred at RT for 4 h. The reaction was quenched with ice cold water (20 mL) to obtain the solid. The solid was filtered, washed with water (20 mL), and dried under reduced pressure. Then the solid was dissolved in isopropyl alcohol, heated to 60° C. for 1 h, cooled to RT, filtered, washed with isopropyl alcohol (2×5 mL) and dried under reduced pressure to obtain Compound BW (50 mg, 0.11 mmol, 37%) as an off-white solid. $^1$H NMR (500 MHz, DMSO-$d_6$): δ 9.96 (brs, 1H), 7.45-7.33 (m, 6H), 7.25 (d, J=6.9 Hz, 2H), 7.20 (d, J=7.8 Hz, 1H), 7.02-6.94 (m, 4H), 3.29-3.19 (m, 8H).

Preparation of 2-((2S,3S)-2-(benzyloxy) pentan-3-yl)-4-(4-(4-(4-bromophenyl) piperazin-1-yl) phenyl)-2,4-dihydro-3H-1,2,4-triazol-3-one (BY)

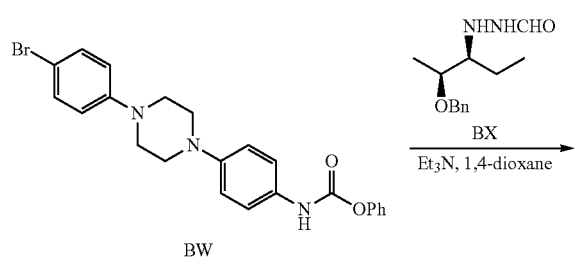

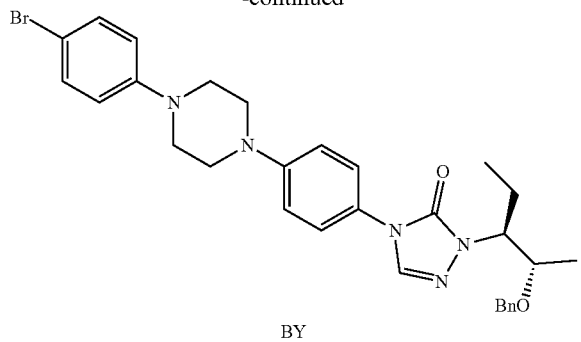

To a stirred solution of N'-((2S,3S)-2-(benzyloxy) pentan-3-yl)formohydrazide BX (198 mg, 0.60 mmol) in 1,4-dioxane (2.5 mL) under argon atmosphere were added triethylamine (0.15 mL, 1.06 mmol) and Compound BW (250 mg, 0.55 mmol) at RT. The reaction was stirred at 90° C. for 16 h. The reaction was cooled to RT, diluted with water (20 mL), and the product was extracted with $CH_2Cl_2$ (2×10 mL). The combined organic extracts were dried over anhydrous $Na_2SO_4$ and concentrated under reduced pressure. The crude material was purified by silica gel column chromatography (eluent: 40% EtOAc/Hexane) to afford Compound BY (210 mg, 0.36 mmol, 66%) as a brown solid. $^1$H NMR (500 MHz, DMSO-$d_6$): δ 8.31 (s, 1H), 7.47 (d, J=7.7 Hz, 2H), 7.38 (d, J=9.0 Hz, 2H), 7.34 (d, J=4.3 Hz, 1H), 7.25-7.19 (m, 2H), 7.17 (d, J=7.8 Hz, 2H), 7.12 (d, J=9.3 Hz, 2H), 6.98 (d, J=9.3 Hz, 2H), 4.53 (d, J=11.9 Hz, 1H), 4.27 (d, J=11.9 Hz, 1H), 4.00-3.96 (m, 1H), 3.76-3.70 (m, 1H), 3.35-3.26 (m, 8H), 1.80-1.69 (m, 2H), 1.22 (d, J=6.1 Hz, 3H), 0.78 (t, J=7.4 Hz, 3H).

Preparation of 2-((2S,3S)-2-(benzyloxy) pentan-3-yl)-4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (BZ)

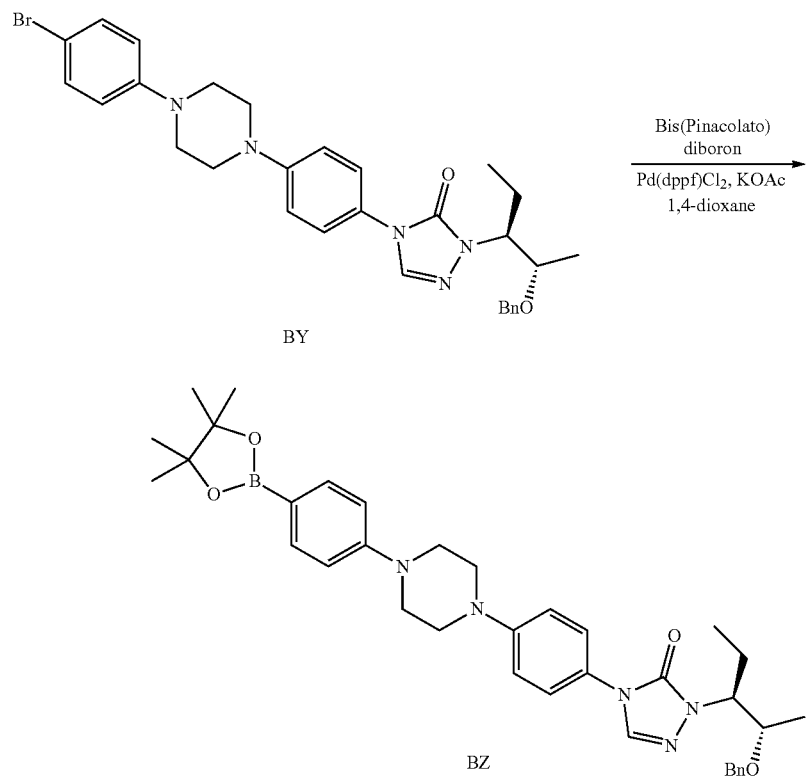

To a stirred solution of Compound BY (210 mg, 0.36 mmol) in 1,4-dioxane (20 mL) under argon atmosphere were added bis(pinacolato)diboron (148 mg, 0.58 mmol) and potassium acetate (107 mg, 1.09 mmol) at RT. The reaction mixture was purged with argon for 15 min, then Pd(dppf)Cl$_2$ (26.6 mg, 0.03 mmol) was added and the reaction mixture was purged with argon for 10 min at RT. The reaction was stirred at 90° C. for 6 h. The reaction was cooled to RT and filtered. The filtrate was diluted with water (20 mL) and the product was extracted with EtOAc (2×20 mL). The combined organic layers were washed with water (20 mL), dried over anhydrous Na$_2$SO$_4$ and concentrated under reduced pressure. The crude material was purified by silica gel column chromatography (eluent: 30% EtOAc/Hexane) to afford Compound BZ (200 mg, 0.32 mmol, 88%) as a brown solid. $^1$H NMR (400 MHz, DMSO-d$_6$): δ 8.31 (s, 1H), 7.55 (d, J=8.6 Hz, 2H), 7.48 (d, J=9.1 Hz, 2H), 7.26-7.15 (m, 5H), 7.11 (d, J=9.1 Hz, 2H), 6.98 (d, J=8.8 Hz, 2H), 4.53 (d, J=11.8 Hz, 1H), 4.27 (d, J=11.9 Hz, 1H), 4.06-3.94 (m, 1H), 3.77-3.69 (m, 1H), 3.41-3.32 (m, 8H), 1.81-1.67 (m, 2H), 1.27 (s, 12H), 1.22 (d, J=6.3 Hz, 3H), 0.78 (t, J=7.3 Hz, 3H).

Preparation of 2-((2S,3S)-2-(benzyloxy) pentan-3-yl)-4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2,4-dihydro-3H-1,2,4-triazol-3-one (CA)

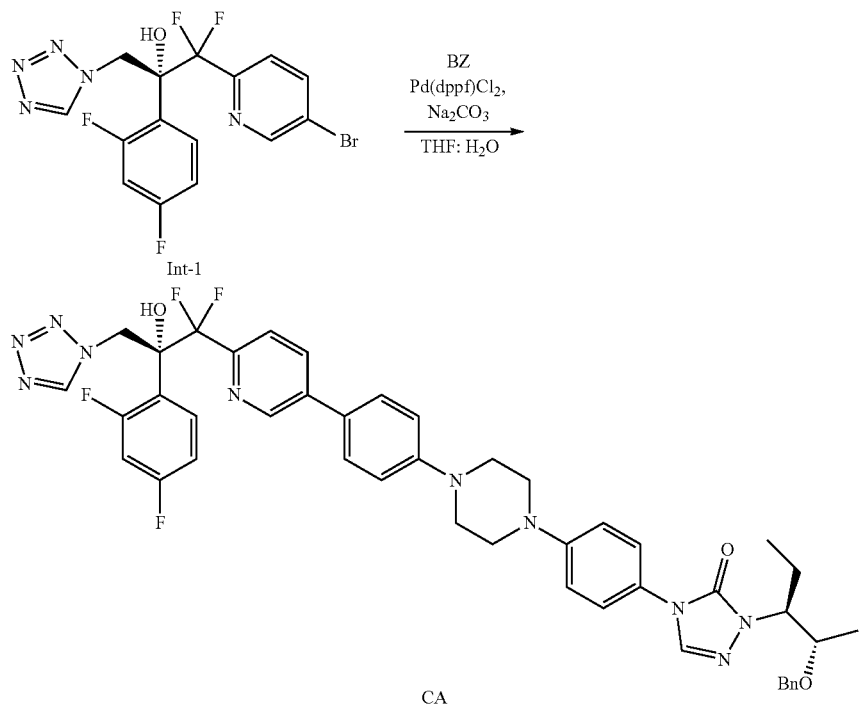

To a stirred solution of Int-1 (130 mg, 0.30 mmol) in THF:H$_2$O (4:1, 20 mL) under argon atmosphere were added Compound BZ (225 mg, 0.36 mmol) and sodium carbonate (96 mg, 0.90 mmol) at RT. The reaction mixture was purged with argon for 20 min, then Pd(dppf)Cl$_2$ (22 mg, 0.03 mmol) was added and the reaction mixture was purged with argon for 10 min at RT. The reaction was stirred at 70° C. for 6 h. The reaction was cooled to RT and filtered. The filtrate was diluted with water (20 mL) and the product was extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford Compound CA (115 mg, 0.13 mmol, 45%) as a brown solid. $^1$H NMR (400 MHz, DMSO-d$_6$): δ 9.15 (s, 1H), 8.91 (s, 1H), 8.31 (s, 1H), 8.17 (dd, J=8.3, 2.2 Hz, 1H), 7.71 (d, J=8.8 Hz, 2H), 7.49 (d, J=8.9 Hz, 2H), 7.44 (d, J=8.9 Hz, 1H), 7.31-7.11 (m, 12H), 6.95-6.87 (m, 1H), 5.67 (d, J=14.5 Hz, 1H), 5.12 (d, J=14.5 Hz, 1H), 4.54 (d, J=11.8 Hz, 1H), 4.27 (d, J=11.8 Hz, 1H), 4.03-3.95 (m, 1H), 3.79-3.69 (m, 1H), 3.43-3.36 (m, 8H), 1.81-1.70 (m, 2H), 1.13 (d, J=6.3 Hz, 3H), 0.79 (t, J=7.3 Hz, 3H).

Preparation of 4-(4-(4-(4-(6-(R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (20)

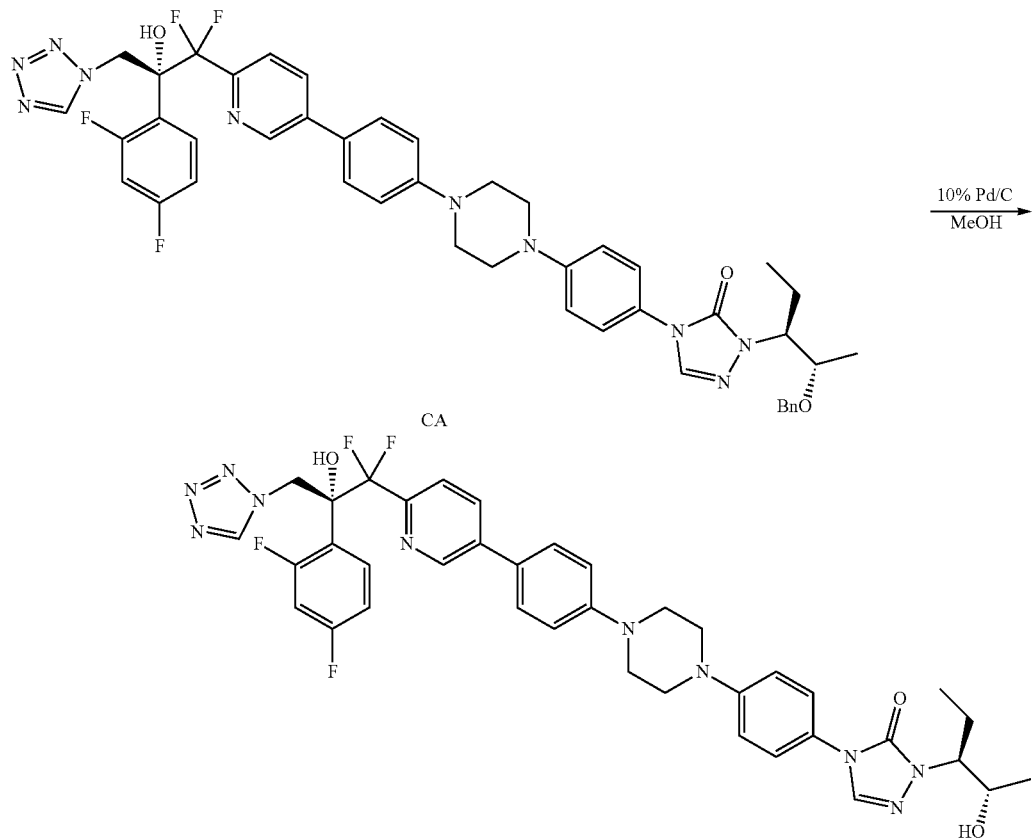

To a stirred solution of Compound CA (115 mg, 0.13 mmol) in MeOH (1.5 mL) under argon atmosphere were added 10% Pd/C (27 mg) and 5.0 N HCl (0.2 mL) at RT. The reaction mixture was stirred at 50° C. for 12 h under hydrogen atmosphere (50 psi). The reaction was cooled to RT and filtered through Celite. The filtrate was concentrated under reduced pressure. The residue was neutralized with saturated sodium bicarbonate solution (20 mL) and the product was extracted with $CH_2Cl_2$ (2×20 mL). The combined organic extracts were dried over anhydrous $Na_2SO_4$ and concentrated under reduced pressure. The crude material was purified by silica gel column chromatography (eluent: 2% MeOH/$CH_2Cl_2$) followed by preparative TLC (eluent: 3% MeOH/$CH_2Cl_2$) to afford 20 (55 mg, 0.07 mmol, 54%) as an off-white solid. $^1$H NMR (400 MHz, DMSO-$d_6$): δ 9.15 (s, 1H), 8.91 (s, 1H), 8.34 (s, 1H), 8.17 (dd, J=8.2, 2.1 Hz, 1H), 7.70 (d, J=8.8 Hz, 2H), 7.53 (d, J=9.0 Hz, 2H), 7.48 (d, J=8.4 Hz, 1H), 7.34-7.24 (m, 2H), 7.22-7.11 (m, 5H), 6.93-6.89 (m, 1H), 5.67 (d, J=14.6 Hz, 1H), 5.11 (d, J=14.6 Hz, 1H), 4.67 (d, J=4.9 Hz, 1H), 3.85-3.76 (m, 2H), 3.44-3.33 (m, 8H), 1.74-1.67 (m, 2H), 1.12 (d, J=5.9 Hz, 3H), 0.74 (t, J=7.3 Hz, 3H); MS (ESI): m/z 759.3 [M+H]$^+$; HPLC: 96.66%; Optical rotation [α]$_D^{19}$: +42.5 (c=0.1% in MeOH).

Example 21

1-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-3-((2S,3S)-2-hydroxypentan-3-yl) urea (21)

Preparation of 1-(4-(4-(4-bromophenyl) piperazin-1-yl) phenyl)-3-((2S,3S)-2-hydroxypentan-3-yl) urea (CC)

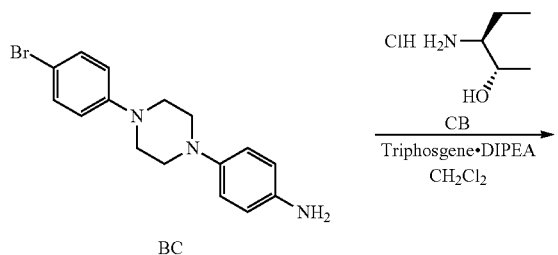

-continued

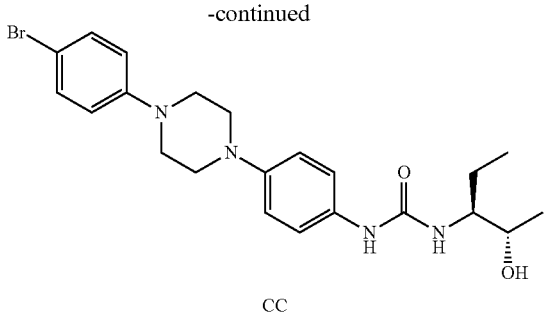

CC

To a stirred solution of triphosgene (156 mg, 0.52 mmol) in CH$_2$Cl$_2$ (25 mL) under argon atmosphere were added Compound BC (500 mg, 1.50 mmol) in CH$_2$Cl$_2$ (25 mL) and diisopropylethylamine (0.83 mL, 4.51 mmol) slowly over 5 min. Then (2S,3S)-3-aminopentan-2-ol hydrochloride (CB, 523 mg, 3.76 mmol) was added and the reaction was stirred for 1 h. The reaction was quenched with a citric acid solution (20 mL), and the product was extracted with CH$_2$Cl$_2$ (20 mL). The combined organic extracts were dried over anhydrous Na$_2$SO$_4$ and concentrated under reduced pressure. The crude material was purified by silica gel column chromatography (eluent: 5% MeOH/CH$_2$Cl$_2$) to afford Compound CC (320 mg, 0.70 mmol, 46%) as an off-white solid. $^1$H NMR (500 MHz, DMSO-d$_6$): δ 8.31 (s, 1H), 7.36 (d, J=9.0 Hz, 2H), 7.25 (d, J=9.0 Hz, 2H), 6.95 (d, J=9.0 Hz, 2H), 6.88 (d, J=9.0 Hz, 2H), 5.74 (d, J=9.0 Hz, 1H), 4.70 (d, J=4.3 Hz, 1H), 3.73-3.70 (m, 1H), 3.43-3.36 (m, 1H), 3.30-3.23 (m, 4H), 3.19-3.12 (m, 4H), 1.57-1.48 (m, 1H), 1.40-1.32 (m, 1H), 1.01 (d, J=6.4 Hz, 3H), 0.86 (t, J=7.4 Hz, 3H).

Preparation of 1-((2S,3S)-2-hydroxypentan-3-yl)-3-(4-(4-(4,4,5,5-tetramethyl-1,3,2-dioxaborolan-2-yl) phenyl) piperazin-1-yl) phenyl) urea (CD)

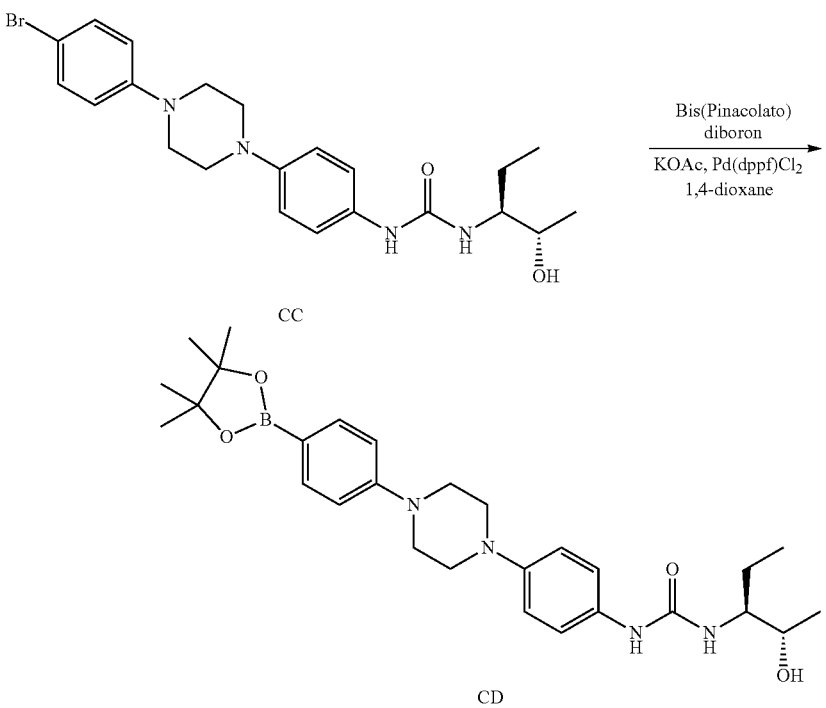

To a stirred solution of Compound CC (320 mg, 0.69 mmol) in 1,4-dioxane (30 mL) under argon atmosphere were added bis(Pinacolato)diboron (282 mg, 1.11 mmol) and potassium acetate (204 mg, 2.08 mmol) at RT. The reaction mixture was purged with argon for 15 min, then Pd(dppf)Cl$_2$ (50.7 mg, 0.70 mmol) was added and the reaction mixture was purged with argon for 10 min. The reaction mixture was stirred at 90° C. for 6 h. The reaction was cooled to RT and filtered. The filtrate was diluted with water (20 mL) and the product was extracted with EtOAc (2×20 mL). The combined organic layers were washed with water (20 mL), dried over anhydrous Na$_2$SO$_4$ and concentrated under reduced pressure. The crude material was purified by silica gel column chromatography (eluent: 3% MeOH/CH$_2$Cl$_2$) to afford Compound CD (220 mg, 0.43 mmol, 62%) as a brown solid. $^1$H NMR (500 MHz, DMSO-d$_6$): δ 8.29 (s, 1H), 7.52 (d, J=6.5 Hz, 2H), 7.23 (d, J=7.8 Hz, 2H), 6.95 (d, J=7.7 Hz, 2H), 6.87 (d, J=6.4 Hz, 2H), 5.73 (d, J=9.3 Hz, 1H), 4.68 (d, J=4.0 Hz, 1H), 3.74-3.66 (m, 1H), 3.40-3.31 (m, 5H), 3.16-3.10 (m, 4H), 1.55-1.44 (m, 1H), 1.38-1.31 (m, 1H), 1.25 (s, 12H), 1.00 (d, J=6.4 Hz, 3H), 0.84 (t, J=7.4 Hz, 3H).

Preparation of 1-(4-(4-(4-(6-((R)-2-(2,4-difluoro-phenyl)-1,1-difluoro-2-hydroxy-3-(1H-tetrazol-1-yl) propyl) pyridin-3-yl) phenyl) piperazin-1-yl) phenyl)-3-((2S,3S)-2-hydroxypentan-3-yl) urea (21)

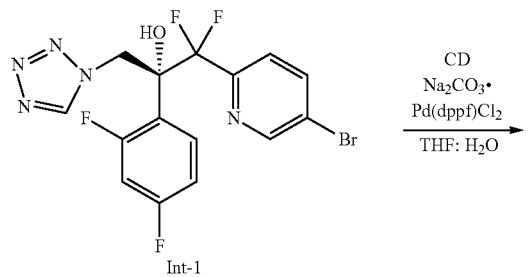

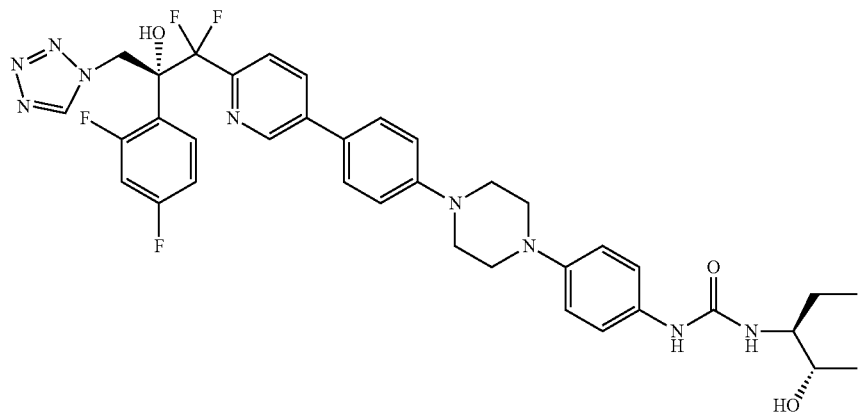

To a stirred solution of Int-1 (150 mg, 0.34 mmol) in THF:H$_2$O (4:1, 20 mL) under argon atmosphere were added Compound CD (212 mg, 0.41 mmol) and sodium carbonate (110 mg, 1.04 mmol) at RT. The reaction mixture was purged with argon for 20 min, then Pd(dppf)Cl$_2$ (25.3 mg, 0.03 mmol) was added and the reaction mixture was purged with argon for 10 min. The reaction was stirred at 70° C. for 6 h. The reaction was cooled to RT and filtered. The filtrate was diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) followed by preparative HPLC to afford 21 (90 mg, 0.12 mmol, 35%) as an off-white solid. $^1$H NMR (400 MHz, DMSO-d$_6$): δ 9.15 (s, 1H), 8.91 (s, 1H), 8.32 (s, 1H), 8.17 (dd, J=8.4, 2.1 Hz, 1H), 7.70 (d, J=8.9 Hz, 2H), 7.48 (d, J=8.2 Hz, 1H), 7.33-7.24 (m, 4H), 7.21-7.19 (m, 1H), 7.13 (d, J=8.9 Hz, 1H), 6.93-6.89 (m, 3H), 5.76 (d, J=9.2 Hz, 1H), 5.67 (d, J=14.6 Hz, 1H), 5.11 (d, J=14.9 Hz, 1H), 4.72 (d, J=4.0 Hz, 1H), 3.75-3.68 (m, 1H), 3.39-3.37 (m, 4H), 3.19-3.17 (m, 4H), 1.57-1.46 (m, 1H), 1.42-1.30 (m, 1H), 1.01 (d, J=6.3 Hz, 3H), 0.86 (t, J=7.4 Hz, 3H); MS (ESI): m/z 734.2 [M+H]$^+$; HPLC: 95.25%; Optical rotation [α]$_D^{20}$: +33.7 (c=0.1% in MeOH).

Example 22

(R)-4-(4-(4-(6-(2-(2,4-difluorophenyl)-1,1-difluoro-2-hydroxy-3-(1H-tetrazol-1-yl) propyl) pyridin-3-yl) phenyl) piperidin-1-yl) benzonitrile (22)

Preparation of 4-(4-(4-bromophenyl) piperidin-1-yl) benzonitrile (CF)

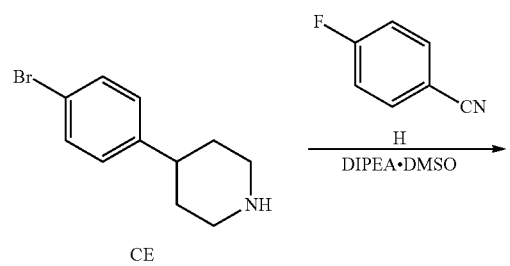

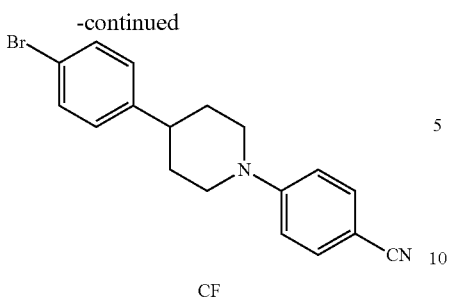

CF

To a stirred solution of 4-(4-bromophenyl) piperidine CE (500 mg, 2.08 mmol) in DMSO (5 mL) under argon atmosphere were added diisopropylethylamine (1.1 mL, 6.24 mmol) and 4-fluorobenzonitrile H (302 mg, 2.50 mmol) at RT. The reaction was stirred at 50° C. for 16 h. The reaction was cooled to RT, diluted with ice cold water (20 mL), and the product was extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 20% EtOAc/Hexane) to afford Compound CF (400 mg, 1.17 mmol, 43%) as an off-white solid. $^1$H NMR (400 MHz, DMSO-$d_6$): δ 7.57 (d, J=7.9 Hz, 2H), 7.48 (d, J=7.5 Hz, 2H), 7.23 (d, J=8.4 Hz, 2H), 7.05 (d, J=9.1 Hz, 2H), 4.08-4.04 (m, 2H), 2.98-2.91 (m, 2H), 2.84-2.75 (m, 1H), 1.86-1.82 (m, 2H), 1.68-1.58 (m, 2H).

Preparation of 4-(4-(4-(4,4,5,5-tetramethyl-1,3,2-dioxaborolan-2-yl) phenyl) piperidin-1-yl) benzonitrile (CG)

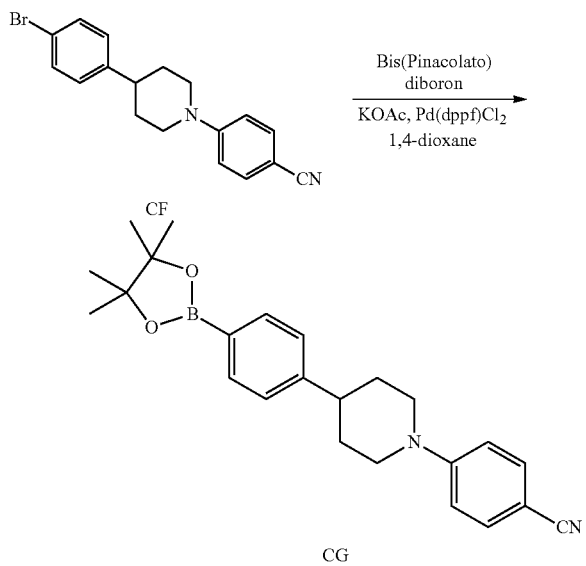

To a stirred solution of Compound CF (400 mg, 1.17 mmol) in 1,4-dioxane (10 mL) under argon atmosphere were added bis(pinacolato)diboron (595 mg, 2.35 mmol), potassium acetate (460 mg, 4.70 mmol), and Pd(dppf)Cl$_2$ (85 mg, 0.11 mmol) at RT. The reaction was purged with argon for 10 min and stirred at 90° C. for 2 h. The reaction was cooled to RT, diluted with water (30 mL), and the product was extracted with EtOAc (2×30 mL). The combined organic layers were washed with water (30 mL), dried over anhydrous $Na_2SO_4$ and concentrated under reduced pressure. The crude material was purified by silica gel column chromatography (eluent: 40% EtOAc/Hexane) to afford Compound CG (380 mg, 0.97 mmol, 84%) as an off-white solid. $^1$H NMR (400 MHz, DMSO-$d_6$): δ 7.61 (d, J=8.0 Hz, 2H), 7.57 (d, J=9.1 Hz, 2H), 7.26 (d, J=8.0 Hz, 2H), 7.05 (d, J=9.1 Hz, 2H), 4.08-4.05 (m, 2H), 3.00-2.94 (m, 2H), 2.85-2.79 (m, 1H), 1.85-1.82 (m, 2H), 1.72-1.58 (m, 2H), 1.28 (s, 12H).

Preparation of (R)-4-(4-(4-(6-(2-(2,4-difluorophenyl)-1,1-difluoro-2-hydroxy-3-(1H-tetrazol-1-yl) propyl) pyridin-3-yl) phenyl) piperidin-1-yl) benzonitrile (22)

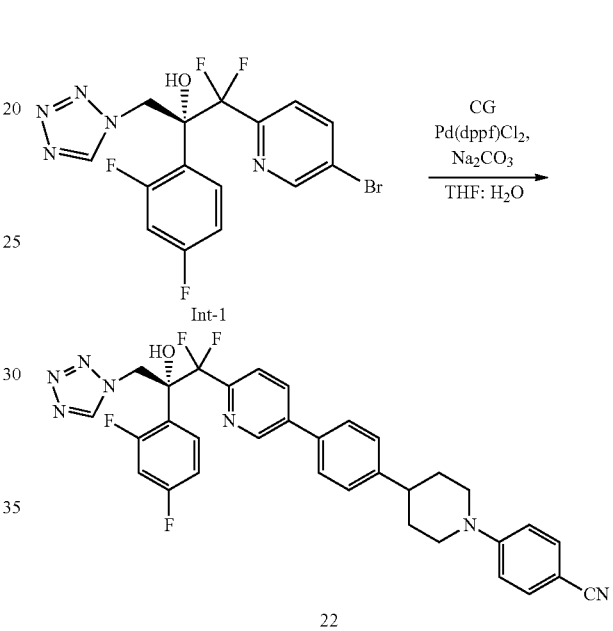

To a stirred solution of Int-1 (150 mg, 0.34 mmol) in THF:H$_2$O (3:1, 20 mL) under argon atmosphere were added Compound CG (161 mg, 0.41 mmol) and sodium carbonate (110 mg, 1.04 mmol) at RT. The reaction mixture was purged with argon for 20 min, then Pd(dppf)Cl$_2$ (25 mg, 0.03 mmol) was added and the reaction mixture was purged with argon for 10 min. The reaction was stirred at 70° C. for 5 h. The reaction was cooled to RT, diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 50% EtOAc/Hexane) to afford 22 (100 mg, 0.16 mmol, 47%) as an off-white solid. $^1$H NMR (500 MHz, CDCl$_3$): δ 8.76 (s, 1H), 8.72 (s, 1H), 7.98 (dd, J=8.1, 2.0 Hz, 1H), 7.72 (s, 1H), 7.65 (d, J=8.4 Hz, 1H), 7.52 (t, J=8.2 Hz, 4H), 7.43-7.39 (m, 1H), 7.37 (d, J=8.1 Hz, 2H), 6.92 (d, J=8.8 Hz, 2H), 6.81-6.75 (m, 1H), 6.69-6.65 (m, 1H), 5.58 (d, J=14.2 Hz, 1H), 5.15 (d, J=14.2 Hz, 1H), 4.03-4.00 (m, 2H), 3.04-2.99 (m, 2H), 2.86-2.80 (m, 1H), 2.01-1.99 (m, 2H), 1.89-1.81 (m, 2H); MS (ESI): m/z 614.1 [M+H]$^+$; HPLC: 98.61%; Optical rotation $[α]_D^{20}$: +45.9 (c=0.1% in MeOH).

Example 23

(R)-4-(4-(4-(6-(2-(2,4-difluorophenyl-1,1-difluoro-2-hydroxy-3-(1H-tetrazol-1-yl) propyl) pyridin-3-yl) phenyl) piperazine-1-carbonyl) benzonitrile (23)

Preparation of 4-(4-(4-bromophenyl) piperazine-1-carbonyl) benzonitrile (CI)

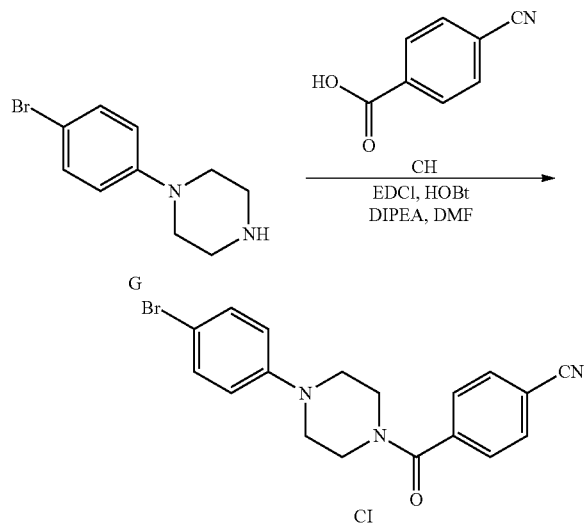

To a stirred solution of 4-cyanobenzoic acid CH (300 mg, 2.04 mmol) in DMF (10 mL) under argon atmosphere were added 1-(4-bromophenyl) piperazine G (541 mg, 2.24 mmol), EDCI.HCl (584 mg, 3.06 mmol), HOBt (468 mg, 3.06 mmol) and diisopropylethylamine (1.12 mL, 6.12 mmol) at 0° C. The reaction was warmed to RT and stirred for 12 h. The reaction was diluted with water (20 m L) and the product was extracted with EtOAc (2×20 mL). The combined organic layers were washed with water (20 mL), dried over anhydrous Na₂SO₄ and concentrated under reduced pressure. The crude material was purified by silica gel column chromatography (eluent: 20% EtOAc/Hexane) to afford Compound CI (400 mg, 1.08 mmol, 53%) as an off-white solid. ¹H NMR (400 MHz, CDCl₃): δ 7.74 (d, J=8.6 Hz, 2H), 7.54 (d, J=8.8 Hz, 2H), 7.37 (d, J=9.1 Hz, 2H), 6.79 (d, J=9.0 Hz, 2H), 4.00-3.85 (m, 2H), 3.58-3.48 (m, 2H), 3.33-3.04 (m, 4H).

Preparation of 4-(4-(4-(4,4,5,5-tetramethyl-1,3,2-dioxaborolan-2-yl) phenyl) piperazine-1-carbonyl) benzonitrile (CJ)

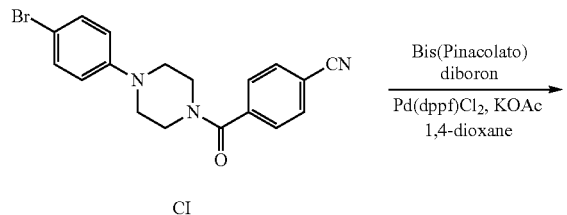

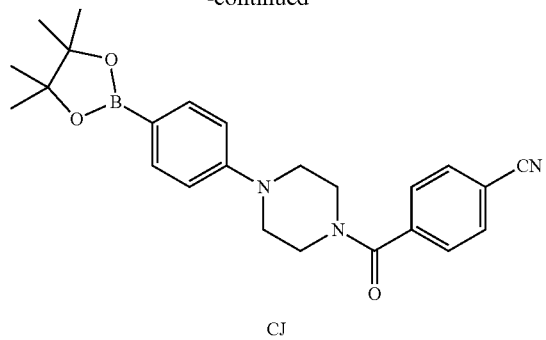

To a stirred solution of Compound CI (400 mg, 1.08 mmol) in 1,4-dioxane (10 mL) under argon atmosphere were added bis(pinacolato)diboron (273 mg, 1.08 mmol) and potassium acetate (317 mg, 3.24 mmol) at RT. The reaction mixture was purged with argon for 15 min, then Pd(dppf)Cl₂ (79 mg, 0.10 mmol) was added and the reaction mixture was purged with argon for 10 min. The reaction was stirred at 100° C. for 12 h. The reaction was cooled to RT, diluted with water (20 mL), and the product was extracted with EtOAc (2×20 mL). The combined organic layers were washed with water (20 mL), brine (20 mL), dried over anhydrous Na₂SO₄ and concentrated under reduced pressure. The crude material was purified by silica gel column chromatography (eluent: 40% EtOAc/Hexane) to afford Compound CJ (320 mg, 0.76 mmol, 71%) as an off-white solid. ¹H NMR (400 MHz, CDCl₃): δ 7.76-7.72 (m, 4H), 7.53 (d, J=8.6 Hz, 2H), 6.89 (d, J=8.8 Hz, 2H), 3.99-3.90 (m, 2H), 3.57-3.49 (m, 2H), 3.35-3.22 (m, 4H), 1.33 (s, 12H).

Preparation of (R)-4-(4-(4-(6-(2-(2,4-difluorophenyl)-1,1-difluoro-2-hydroxy-3-(1H-tetrazol-1-yl) propyl) pyridin-3-yl) phenyl) piperazine-1-carbonyl) benzonitrile (23)

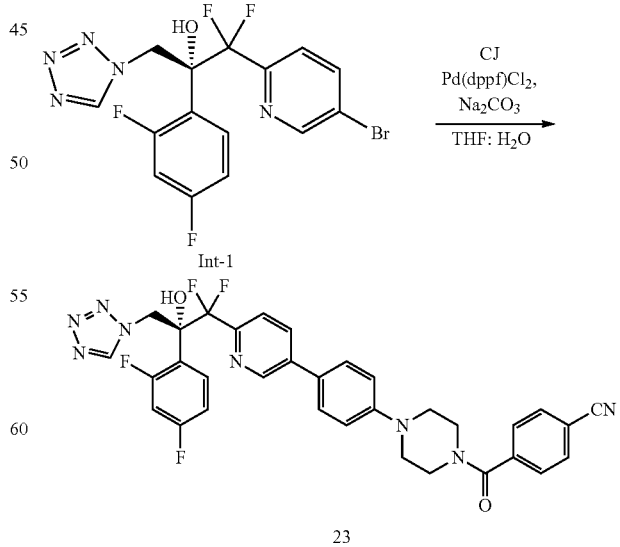

To a stirred solution of Int-1 (200 mg, 0.46 mmol) in THF:H₂O (4:1, 20 mL) under argon atmosphere were added Compound CJ (231 mg, 0.55 mmol) and sodium carbonate (147 mg, 1.38 mmol) at RT. The reaction mixture was purged with argon for 20 min, then Pd(dppf)Cl$_2$ (34 mg, 0.04 mmol) was added and the reaction mixture was purged with argon for 10 min. The reaction was stirred at 80° C. for 6 h. The reaction was cooled to RT, diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 70% EtOAc/Hexane) to afford 23 (100 mg, 0.15 mmol, 34%) as an off-white solid $^1$H NMR (400 MHz, DMSO-d$_6$): δ 9.14 (s, 1H), 8.90 (s, 1H), 8.16 (dd, J=8.3, 2.2 Hz, 1H), 7.96 (d, J=8.4 Hz, 2H), 7.69 (d, J=8.9 Hz, 2H), 7.65 (d, J=8.5 Hz, 2H), 7.48 (d, J=8.4 Hz, 1H), 7.31-7.24 (m, 2H), 7.21-7.16 (m, 1H), 7.08 (d, J=9.0 Hz, 2H), 6.93-6.88 (m, 1H), 5.66 (d, J=14.7 Hz, 1H), 5.11 (d, J=14.7 Hz, 1H), 3.83-3.77 (m, 2H), 3.50-3.34 (m, 4H), 3.27-3.22 (m, 2H); MS (ESI): m/z 641.4 [M−H]$^-$; HPLC: 94.92%; Optical rotation [α]$_D^{20}$: +48.0 (c=0.1% in MeOH).

Example 24

(R)-4-(4-(4-(6-(2-(2,4-difluorophenyl)-1,1-difluoro-2-hydroxy-3-(1H-tetrazol-1-yl) propyl) pyridin-3-yl) phenyl)-3-oxopiperazin-1-yl) benzonitrile (24)

Preparation of 4-(3-oxopiperazin-1-yl) benzonitrile (CL)

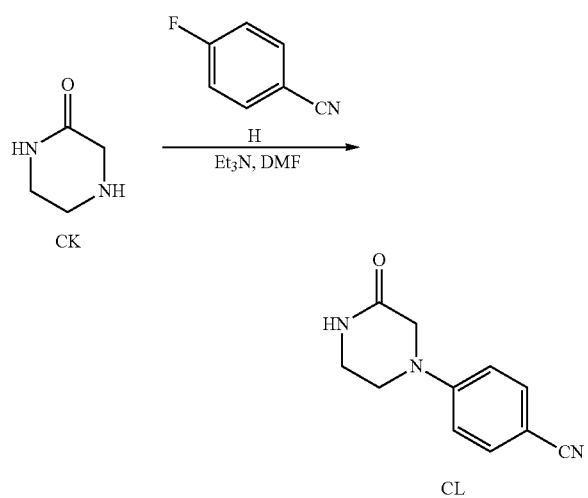

To a stirred solution of piperazin-2-one CK (3.0 g, 30 mmol) in DMF (15 mL) under argon atmosphere were added triethylamine (15 mL) and 4-fluorobenzonitrile H (3.63 g, 30 mmol) at RT. The reaction was stirred at 120° C. for 16 h. The reaction was cooled to RT, diluted with ice cold water (100 mL), and the product was extracted with EtOAc (2×100 mL). The combined organic layers were washed with water (100 mL), dried over anhydrous Na$_2$SO$_4$ and concentrated under reduced pressure. The crude material was purified by silica gel column chromatography (eluent: 40% EtOAc/Hexane) to afford Compound CL (1.0 g, 4.97 mmol, 16%) as an off-white solid. $^1$H NMR (400 MHz, DMSO-d$_6$): δ 8.18 (brs, 1H), 7.60 (d, J=9.0 Hz, 2H), 6.97 (d, J=9.0 Hz, 2H), 3.87 (s, 2H), 3.56-3.53 (m, 2H), 3.35-3.29 (m, 2H).

Preparation of 4-(4-(4-bromophenyl)-3-oxopiperazin-1-yl) benzonitrile (CM)

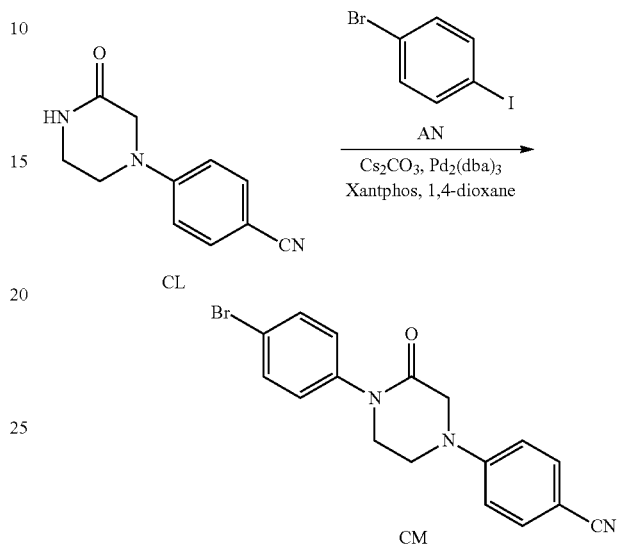

To a stirred solution of Compound CL (1.4 g, 4.94 mmol) in 1,4-dioxane (20 mL) under argon atmosphere were added 1-bromo-4-iodobenzene AN (990 mg, 4.94 mmol), cesium carbonate (3.21 g, 9.89 mmol) and Xantphos (200 ng, 0.34 mmol) at RT. The reaction mixture was purged with argon for 20 min, then Pd$_2$(dba)$_3$ (226 mg, 0.29 mmol) was added and the reaction mixture was purged with argon for 10 min at RT. The reaction was stirred at 110° C. for 1 h. The reaction was cooled to RT, diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 40% EtOAc/Hexane) to afford Compound CM (450 mg, 1.26 mmol, 25%) as an off-white solid. $^1$H NMR (400 MHz, DMSO-d$_6$): δ 7.64-7.60 (m, 4H), 7.37 (d, J=8.8 Hz, 2H), 7.02 (d, J=9.0 Hz, 2H), 4.15 (s, 2H), 3.92-3.85 (m, 2H), 3.79-3.73 (m, 2H).

Preparation of 4-(3-oxo-4-(4-(4,4,5,5-tetramethyl-1,3,2-dioxaborolan-2-yl) phenyl) piperazin-1-yl) benzonitrile (CN)

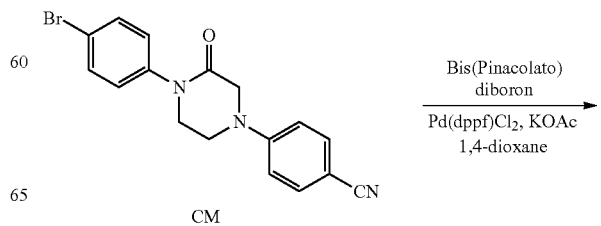

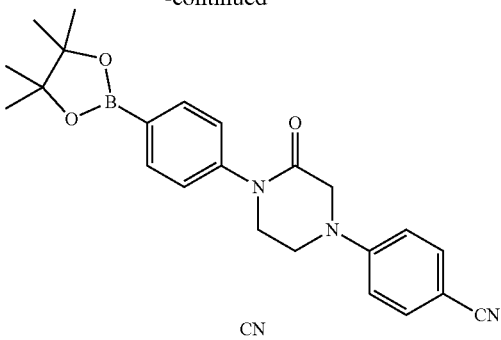

To a stirred solution of Compound CM (450 mg, 1.26 mmol) in 1,4-dioxane (10 mL) under argon atmosphere were added bis(pinacolato)diboron (513 mg, 2.02 mmol) and potassium acetate (370 mg, 3.78 mmol) at RT. The reaction mixture was purged with argon for 15 min, then Pd(dppf)Cl$_2$ (92 mg, 0.12 mmol) was added and the reaction mixture was purged with argon for 10 min at RT. The reaction was stirred at 100° C. for 8 h. The reaction was cooled to RT, diluted with ice cold water (30 mL), and the product was extracted with EtOAc (2×30 mL). The combined organic extracts were dried over anhydrous Na$_2$SO$_4$ and concentrated under reduced pressure. The crude material was purified by silica gel column chromatography (eluent: 30% EtOAc/Hexane) to afford Compound CN (250 mg, 0.62 mmol, 49%) as a pale brown solid. $^1$H NMR (500 MHz, DMSO-d$_6$): δ 7.71 (d, J=8.4 Hz, 2H), 7.63 (d, J=9.0 Hz, 2H), 7.43 (d, J=8.4 Hz, 2H), 7.01 (d, J=7.3 Hz, 2H), 4.16 (s, 2H), 3.93-3.87 (m, 2H), 3.79-3.75 (m, 2H), 1.30 (s, 12H).

Preparation of (R)-4-(4-(4-(6-(2-(2,4-difluorophenyl)-1,1-difluoro-2-hydroxy-3-(1H-tetrazol-1-yl)propyl) pyridin-3-yl) phenyl)-3-oxopiperazin-1-yl) benzonitrile (24)

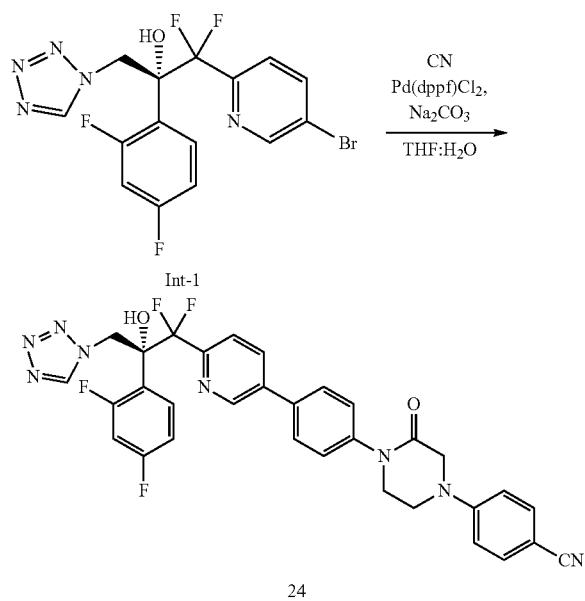

To a stirred solution of Int-1 (150 mg, 0.34 mmol) in THF:H$_2$O (4:1, 25 mL) under argon atmosphere were added Compound CN (140 mg, 0.34 mmol) and sodium carbonate (110 mg, 1.04 mmol) at RT. The reaction mixture was purged with argon for 10 min, then Pd(dppf)Cl$_2$ (25 mg, 0.03 mmol) was added and the reaction mixture was purged with argon for 10 min at RT. The reaction was stirred at 70° C. for 6 h. The reaction was cooled to RT, diluted with ice cold water (10 mL), and the product was extracted with EtOAc (2×10 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 24 (40 mg, 0.06 mmol, 18%) as a pale yellow solid. $^1$H NMR (400 MHz, DMSO-d$_6$): δ 9.15 (s, 1H), 8.97 (s, 1H), 8.26 (dd, J=8.2, 2.3 Hz, 1H), 7.85 (d, J=8.7 Hz, 2H), 7.65 (d, J=8.9 Hz, 2H), 7.59-7.55 (m, 3H), 7.31 (s, 1H), 7.29-7.17 (m, 2H), 7.04 (d, J=9.0 Hz, 2H), 6.94-6.88 (m, 1H), 5.68 (d, J=14.7 Hz, 1H), 5.13 (d, J=14.7 Hz, 1H), 4.19 (s, 2H), 3.98-3.93 (m, 2H), 3.83-3.78 (m, 2H); MS (ESI): m/z 629 [M+H]$^+$; HPLC: 99.38%; Optical rotation $[\alpha]_D^{20}$: +32.3 (c=0.1% in MeOH).

Example 25

(R)-4-(4-(4-(6-(2-(2,4-difluorophenyl)-1,1-difluoro-2-hydroxy-3-(1H-tetrazol-1-yl) propyl) pyridin-3-yl) phenyl)-2-oxopiperazin-1-yl) benzonitrile (25)

Preparation of tert-butyl 3-oxopiperazine-1-carboxylate (CO)

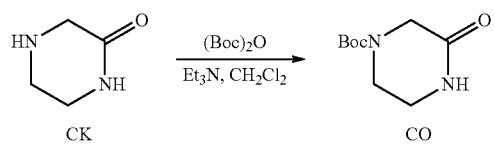

To a stirred solution of piperazin-2-one CK (3 g, 30 mmol) in CH$_2$Cl$_2$ (50 mL) under argon atmosphere were added triethylamine (8.65 mL, 60 mmol) and di-t-butyl dicarbonate (Boc anhydride, 8.2 mL, 36 mmol) at 0° C. The reaction was warmed to RT and stirred for 16 h. The reaction was diluted with water (100 mL) and the product was extracted with CH$_2$Cl$_2$ (2×100 mL). The combined organic layers were dried over anhydrous Na$_2$SO$_4$ and concentrated under reduced pressure to obtain Compound CO (4 g, 20 mmol, 66%) as a white solid, which was used in the next step without further purification. $^1$H NMR (400 MHz, CDCl$_3$): δ 6.90 (br s, 1H), 4.08 (s, 2H), 3.63-3.59 (m, 2H), 3.35-3.31 (m, 2H), 1.44 (s, 9H).

Preparation of tert-butyl 4-(4-cyanophenyl)-3-oxopiperazine-1-carboxylate (CQ)

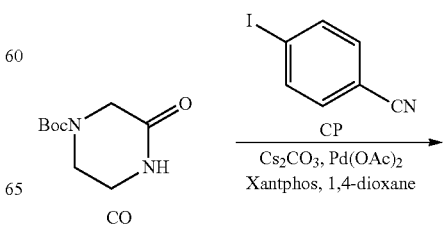

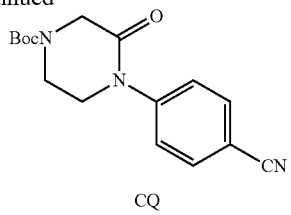

To a stirred solution of Compound CO (500 mg, 2.50 mmol) in 1,4-dioxane (15 mL) under argon atmosphere were added 4-iodobenzonitrile CP (744 mg, 3.25 mmol), cesium carbonate (1.3 g, 4 mmol), and Xantphos (173 mg, 0.30 mmol) at RT. The reaction mixture was purged with argon for 20 min, then Pd(OAc)$_2$ (67 mg, 0.10 mmol) was added and the reaction mixture was purged with argon for 10 min at RT. The reaction was stirred at 90° C. for 16 h. The reaction was cooled to RT, diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 40% EtOAc/Hexane) to afford Compound CQ (680 mg, 2.25 mmol, 90%) as a brown syrup. $^1$H NMR (500 MHz, DMSO-d$_6$): δ 7.87 (d, J=7.9 Hz, 2H), 7.60 (d, J=7.7 Hz, 2H), 4.11 (brs, 2H), 3.80 (t, J=5.2 Hz, 2H), 3.68 (d, J=4.9 Hz, 2H), 1.44 (s, 9H).

Preparation of 4-(2-oxopiperazin-1-yl) benzonitrile (CR)

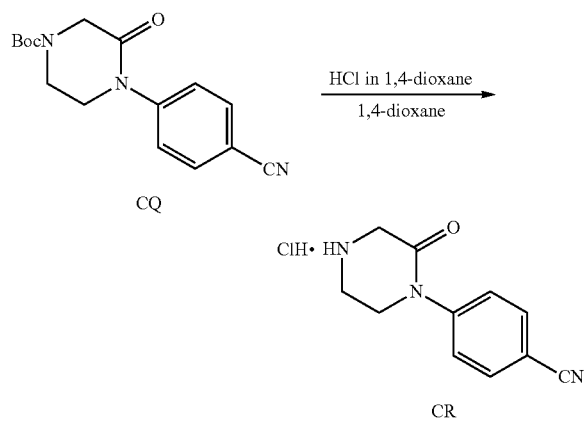

To a stirred solution of Compound CQ (680 mg, 2.65 mmol) in 1,4-dioxane (5 mL) under argon atmosphere was added HCl in 1,4-dioxane (6.6 mL, 26.57 mmol) at 0° C. The reaction was warmed to RT and stirred for 4 h. The volatiles were evaporated under reduced pressure. The residue was diluted with ice cold water (20 mL) and the product was extracted with EtOAc (2×20 mL). The combined organic layers were washed with water (20 mL), dried over anhydrous Na$_2$SO$_4$ and concentrated under reduced pressure. The crude material was purified by silica gel column chromatography (eluent: 50% EtOAc/Hexane) to afford Compound CR (450 mg) as an off-white solid. $^1$H NMR (500 MHz, DMSO-d$_6$): δ 9.76 (brs, 2H), 7.92 (d, J=8.0 Hz, 2H), 7.59 (d, J=7.9 Hz, 2H), 3.95 (t, J=5.2 Hz, 2H), 3.90 (s, 2H), 3.53 (t, J=5.5 Hz, 2H).

Preparation of 4-(4-(4-bromophenyl)-2-oxopiperazin-1-yl) benzonitrile (CS)

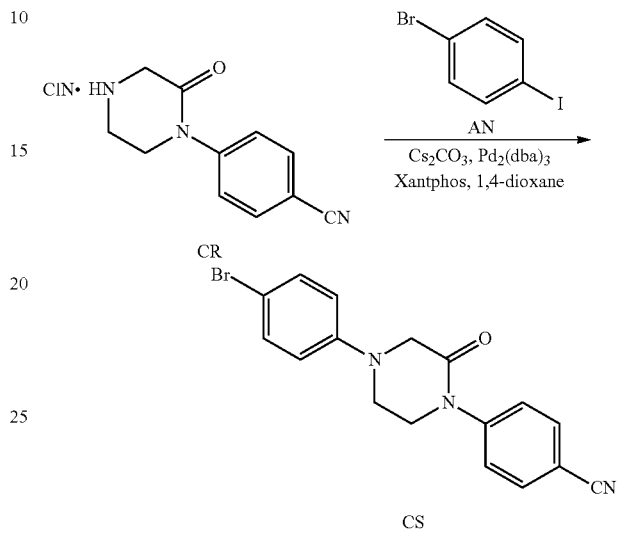

To a stirred solution of Compound CR (450 mg, 2.33 mmol) in 1,4-dioxane (25 mL) under argon atmosphere were added 1-bromo-4-iodobenzene (635 mg, 4.47 mmol), cesium carbonate (2.1 g, 6.71 mmol), and Xantphos (129 mg, 0.22 mmol) at RT. The reaction mixture was purged with argon for 20 min, then Pd$_2$(dba)$_3$ (200 mg, 0.22 mmol) was added and the reaction mixture was purged with argon for 10 min at RT. The reaction mixture was stirred at 90° C. for 16 h. The reaction mixture was diluted with water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 30% EtOAc/Hexane) to afford Compound CS (200 mg, 0.56 mmol, 25%) as a brown syrup. $^1$H NMR (400 MHz, DMSO-d$_6$): δ 7.88 (d, J=8.0 Hz, 2H), 7.63 (d, J=7.5 Hz, 2H), 7.39 (d, J=8.0 Hz, 2H), 6.91 (d, J=7.5 Hz, 2H), 4.01 (s, 2H), 3.93-3.90 (m, 2H), 3.63-3.60 (m, 2H).

Preparation of 4-(2-oxo-4-(4-(4,4,5,5-tetramethyl-1,3,2-dioxaborolan-2-yl) phenyl) piperazin-1-yl) benzonitrile (CT)

-continued

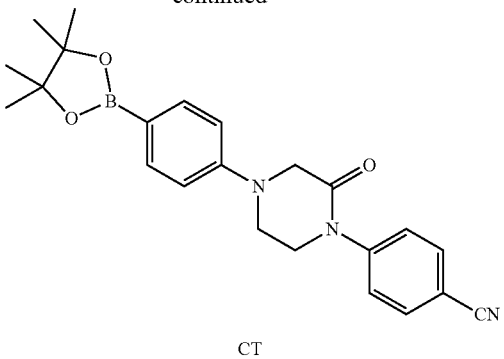

CT

To a stirred solution of Compound CS (200 mg, 0.56 mmol) in 1,4-dioxane (10 mL) under argon atmosphere were added bis(pinacolato)diboron (284 mg, 1.12 mmol) and potassium acetate (220 mg, 2.24 mmol) at RT. The reaction mixture was purged with argon for 20 min, then Pd(dppf)Cl$_2$ (41 mg, 0.05 mmol) was added and the reaction mixture was purged with argon for 10 min at RT. The reaction was stirred at 100° C. for 8 h. The reaction was cooled to RT, diluted with ice cold water (30 mL), and the product was extracted with EtOAc (2×30 mL). The combined organic extracts were dried over anhydrous Na$_2$SO$_4$ and concentrated under reduced pressure. The crude material was purified by silica gel column chromatography (eluent: 20-30% EtOAc/Hexane) to afford Compound CT (110 mg, 0.27 mmol, 48%) as an off-white solid. $^1$H NMR (400 MHz, DMSO-d$_6$): δ 7.89 (d, J=8.0 Hz, 2H), 7.65 (d, J=8.0 Hz, 2H), 7.55 (d, J=8.0 Hz, 2H), 6.91 (d, J=7.5 Hz, 2H), 4.08 (s, 2H), 3.94-3.89 (m, 2H), 3.70-3.67 (m, 2H), 1.23 (s, 12H).

Preparation of (R)-4-(4-(4-(6-(2-(2,4-difluorophenyl)-1,1-difluoro-2-hydroxy-3-(1H-tetrazol-1-yl) propyl) pyridin-3-yl) phenyl)-2-oxopiperazin-1-yl) benzonitrile (25)

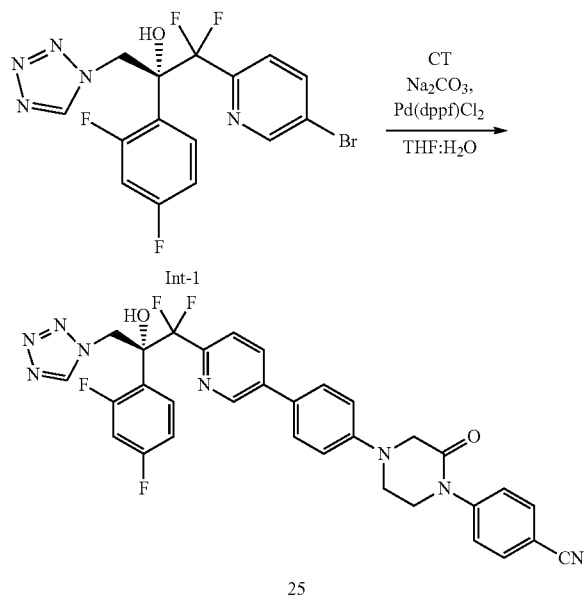

To a stirred solution of Int-1 (150 mg, 0.34 mmol) in THF:H$_2$O (4:1, 25 mL) under argon atmosphere were added Compound CT (140 mg, 0.34 mmol) and sodium carbonate (110 mg, 1.04 mmol) at RT. The reaction mixture was purged with argon for 10 min, then Pd(dppf)Cl$_2$ (38 mg, 0.05 mmol) was added and the reaction mixture was purged with argon for 10 min at RT. The reaction was stirred at 70° C. for 6 h. The reaction was cooled to RT, diluted with ice cold water (10 mL), and the product was extracted with EtOAc (2×10 mL). The combined organic extracts were dried over anhydrous Na$_2$SO$_4$ and concentrated under reduced pressure. The crude material was purified by silica gel column chromatography (eluent: 30% EtOAc/Hexane) followed by washings with diethyl ether:pentane (2×5 mL) to afford 25 (40 mg, 0.06 mmol, 18%) as a pale yellow solid. $^1$H NMR (400 MHz, CDCl$_3$): δ 8.76 (s, 1H), 8.72 (s, 1H), 7.95 (d, J=7.2 Hz, 1H), 7.80 (s, 1H), 7.72 (d, J=8.0 Hz, 2H), 7.01 (d, J=7.5 Hz, 1H), 7.58-7.50 (m, 4H), 7.41-7.38 (m, 1H), 6.99 (d, J=7.5 Hz, 2H), 6.80-6.75 (m, 1H), 6.70-3.64 (m, 1H), 5.58 (d, J=14.5 Hz, 1H), 5.13 (d, J=14.5 Hz, 1H), 4.19 (s, 2H), 4.00-3.97 (m, 2H), 3.76-3.71 (m, 2H); MS (ESI): m/z 629.3 [M+H]$^+$; HPLC: 92.32%; Optical rotation [α]$_D^{20}$: +59.0 (c=0.1% in MeOH).

Example 26

(R)-4-(1-(4-(6-(2-(2,4-difluorophenyl)-1,1-difluoro-2-hydroxy-3-(1H-tetrazol-1-yl) propyl) pyridin-3-yl) phenyl) piperidin-4-yl) benzonitrile (26)

Preparation of 4-(1-(4-bromophenyl) piperidin-4-yl) benzonitrile (CW)

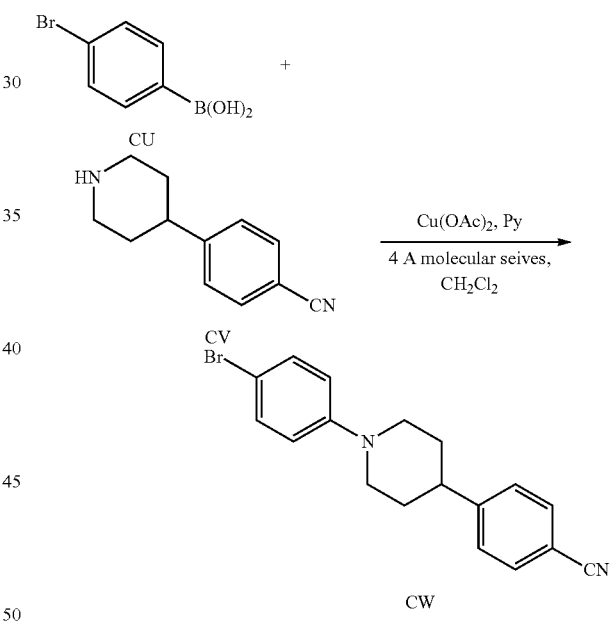

To a stirred solution of 4-(piperidin-4-yl)benzonitrile CV (1 g, 5.37 mmol) in CH$_2$Cl$_2$ (20 mL) were added (4-bromophenyl)boronic acid CU (2.1 g, 10.75 mmol), copper (II) acetate (1.16 g, 6.45 mmol), 4 A molecular sieves (2 g) and pyridine (2.1 mL, 26.88 mmol) under an oxygen atmosphere at RT. The reaction was stirred at 40° C. for 24 h. The reaction was cooled to RT, diluted with water (50 mL), and the product was extracted with EtOAc (2×50 mL). The combined organic layers were washed with water (50 mL), brine (50 mL), dried over anhydrous Na$_2$SO$_4$ and concentrated under reduced pressure. The crude material was purified by silica gel column chromatography (eluent: 20% EtOAc/Hexane) to afford Compound CW (400 mg, 1.17 mmol, 21%) as a pale yellow solid. $^1$H NMR (500 MHz, DMSO-d$_6$): δ 7.75 (d, J=8.5 Hz, 2H), 7.50 (d, J=8.5 Hz, 2H), 7.32 (d, J=9.0 Hz, 2H), 6.93 (d, J=8.0 Hz, 2H), 3.83-3.78 (m, 21H) 2.81-2.73 (m, 3H), 1.87-1.80 (m, 2H), 1.79-1.70 (m, 21).

Preparation of 4-(1-(4-(4,4,5,5-tetramethyl-1,3,2-dioxaborolan-2-yl) phenyl) piperidin-4-yl) benzonitrile (CX)

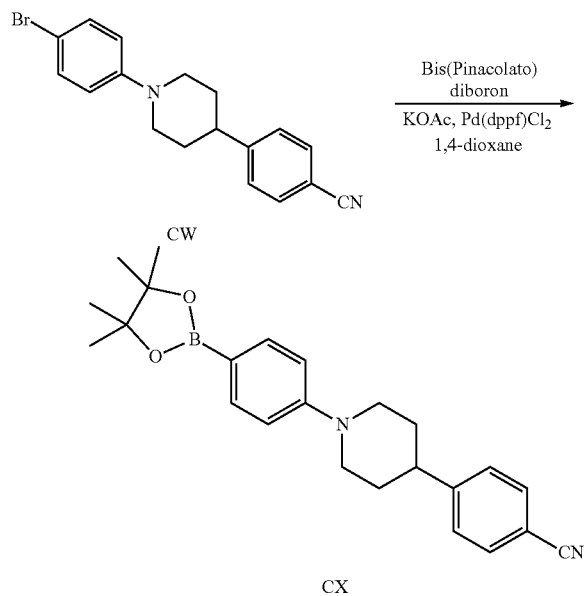

To a stirred solution of Compound CW (300 mg, 0.88 mmol) in 1,4-dioxane (15 mL) under argon atmosphere were added bis(pinacolato)diboron (356 mg, 1.41 mmol) and potassium acetate (259.3 mg, 2.64 mmol) at RT. The reaction mixture was purged with argon for 20 min, then Pd(dppf)Cl$_2$ (64.4 mg, 0.08 mmol) was added and the reaction mixture was purged with argon for 10 min at RT. The reaction was stirred at 90° C. for 6 h. The reaction was cooled to RT, diluted with ice cold water (20 mL), and the product was extracted with EtOAc (2×20 mL). The combined organic extracts were dried over anhydrous Na$_2$SO$_4$ and concentrated under reduced pressure. The crude material was purified by silica gel column chromatography (eluent: 30% EtOAc/Hexane) to afford Compound CX (170 ng, 0.44 mmol, 50%) as a pale yellow solid. $^1$H NMR (500 MHz, DMSO-d$_6$): δ 7.77 (d, J=7.2 Hz, 2H), 7.50-7.42 (m, 4H), 6.94 (d, J=7.5 Hz, 2H), 3.98-3.90 (m, 2H), 2.87-2.80 (m, 3H), 1.88-1.83 (m, 2H), 1.78-1.69 (m, 2H), 1.22 (s, 12H).

Preparation of (R)-4-(1-(4-(6-(2-(2,4-difluorophenyl)-1,1-difluoro-2-hydroxy-3-(1H-tetrazol-1-yl) propyl) pyridin-3-yl) phenyl) piperidin-4-yl) benzonitrile (26)

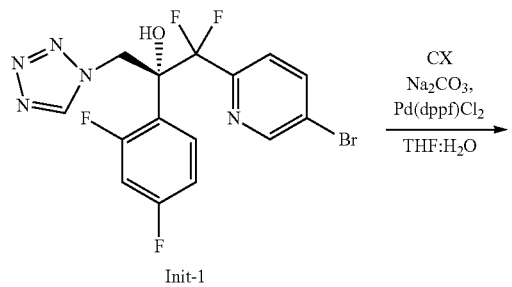

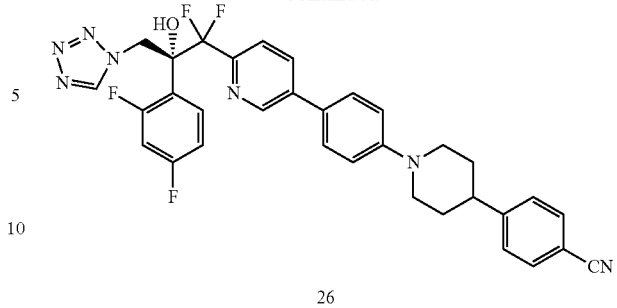

To a stirred solution of Int-1 (150 mg, 0.38 mmol) in THF:H$_2$O (4:1, 25 mL) under argon atmosphere were added Compound CX (166 mg, 0.38 mmol) and sodium carbonate (122 mg, 1.15 mmol) at RT. The reaction mixture was purged with argon for 10 min, then Pd(dppf)Cl$_2$ (28 mg, 0.04 mmol) was added and the reaction mixture was purged with argon for 10 min at RT. The reaction was stirred at 70° C. for 6 h. The reaction was cooled to RT, diluted with ice cold water (10 mL), and the product was extracted with EtOAc (2×10 mL). The combined organic extracts were dried over anhydrous Na$_2$SO$_4$ and concentrated under reduced pressure. The crude material was purified by silica gel column chromatography (eluent: 1% MeOH/CH$_2$Cl$_2$) to afford 26 (90 mg, 0.14 mmol, 38%) as a pale yellow solid. $^1$H NMR (400 MHz, DMSO-d$_6$): δ 9.13 (s, 1H), 8.89 (s, 1H), 8.12 (dd, J=8.5, 2.0 Hz, 1H), 7.75 (d, J=8.0 Hz, 2H), 7.65 (d, J=8.0 Hz, 2H), 7.50-7.40 (m, 3H), 7.30-7.23 (m, 2H), 7.21-7.14 (m, 1H), 7.10 (d, J=7.5 Hz, 2H), 6.91-6.88 (m, 1H), 5.65 (d, J=14.0 Hz, 1H), 5.10 (d, J=14.0 Hz, 1H), 4.00-3.94 (m, 2H), 3.90-2.80 (m, 3H), 1.91-1.85 (m, 2H), 1.80-1.70 (m, 2H); MS (ESI): m/z 614 [M+H]$^+$; HPLC: 95.07%; Optical rotation [α]$_D^{20}$: +143.60 (c=0.1% in MeOH).

Example 27

(R)-4-(4-(4-(6-(2-(2,4-difluorophenyl)-1,1-difluoro-2-hydroxy-3-(1H-tetrazol-1-yl) propyl) pyridin-3-yl) benzyl)-3-oxopiperazin-1-yl) benzonitrile (27)

4-(3-oxopiperazin-1-yl) benzonitrile (CY)

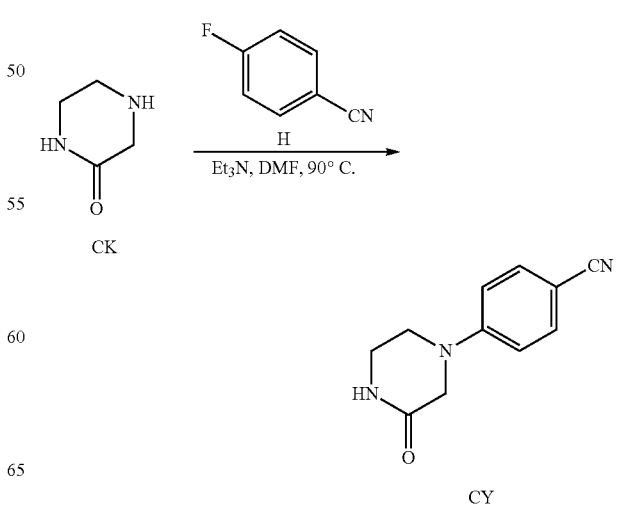

To a stirred solution of piperazin-2-one CK (4.0 g, 40 mmol) in DMF (50 mL) under argon atmosphere were added triethylamine (17.31 mL, 120 mmol) and H (4.84 g, 40 mmol) at RT. The reaction mixture was stirred at 100° C. for 16 h. The reaction mixture was diluted with water (100 mL) and extracted with EtOAc (2×100 mL). The combined organic layers were dried over anhydrous Na$_2$SO$_4$ and concentrated under reduced pressure to obtain compound CY (700 mg, crude) as an off-white solid. $^1$H NMR (500 MHz, DMSO-d$_6$): δ 8.16 (brs, 1H), 7.58 (d, J=9.0 Hz, 2H), 6.95 (d, J=9.0 Hz, 2H), 3.85 (s, 2H), 3.55-3.47 (m, 2H), 3.33-3.25 (m, 2H).

4-(4-(4-bromobenzyl)-3-oxopiperazin-1-yl) benzonitrile-4-(4-(4-bromobenzyl)-3-oxopiperazin-1-yl) benzonitrile (CZ)

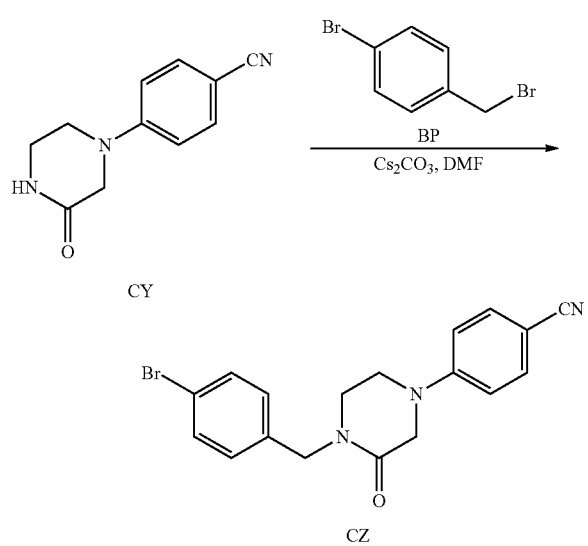

To a stirred solution of compound CY (300 mg, 1.50 mmol) in DMF (10 mL) under argon atmosphere were added cesium carbonate (967 mg, 3 mmol) and BP (410 mg, 1.64 mmol) at 0° C. The reaction mixture was warmed to RT and stirred for 16 h. The reaction mixture was diluted with water (20 mL) and extracted with EtOAc (2×20 mL). The combined organic layers were dried over anhydrous Na$_2$SO$_4$ and concentrated under reduced pressure. The crude material was purified by silica gel column chromatography (eluent: 30% EtOAc/Hexane) to afford compound CZ (180 mg, 0.48 mmol, 33%) as an off-white solid. $^1$H NMR (500 MHz, DMSO-d$_6$): δ 7.58 (d, J=8.7 Hz, 2H), 7.52 (d, J=8.4 Hz, 2H), 7.22 (d, J=8.4 Hz, 2H), 6.97 (d, J=9.0 Hz, 2H), 4.55 (s, 2H), 4.03 (s, 2H), 3.62-3.59 (nm 2H), 3.40-3.34 (m, 2H).

4-(3-oxo-4-(4-(4,4,5,5-tetramethyl-1,3,2-dioxaborolan-2-yl) benzyl) piperazin-1-yl) benzonitrile (DA)

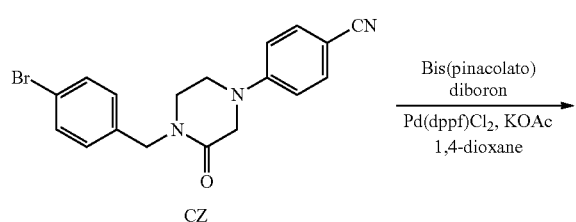

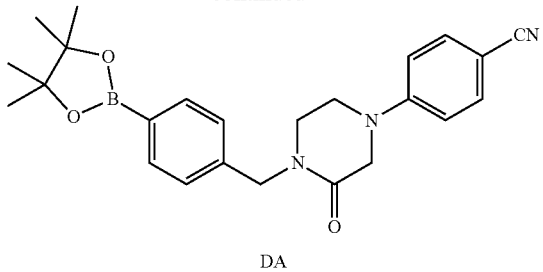

To a stirred solution of compound CZ (200 mg, 0.54 mmol) in 1,4-dioxane (10 mL) under argon atmosphere were added bis(pinacolato)diboron (218 mg, 0.86 mmol) and KOAc (158 mg, 1.62 mmol) at RT. The reaction mixture was purged with argon for 20 min, then Pd(dppf)Cl$_2$ (40 mg, 0.05 mmol) was added and the reaction mixture was purged under argon for 10 min at RT. The reaction mixture was stirred at 100° C. for 6 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 30% EtOAc/Hexane) to afford compound DA (120 mg, 0.28 mmol, 53%) as an off-white solid. $^1$H NMR (500 MHz, DMSO-d$_6$): δ 7.63 (d, J=7.8 Hz, 2H), 7.59 (d, J=8.7 Hz, 2H), 7.27 (d, J=7.5 Hz, 2H), 6.97 (d, J=8.7 Hz, 2H), 4.61 (s, 2H), 4.04 (s, 2H), 3.61-3.59 (m, 2H), 3.35-3.33 (m, 2H), 1.27 (s, 12H).

(R)-4-(4-(4-(6-(2-(2,4-difluorophenyl)-1,1-difluoro-2-hydroxy-3-(1H-tetrazol-1-yl) propyl) pyridin-3-yl) benzyl)-3-oxopiperazin-1-yl) benzonitrile (27)

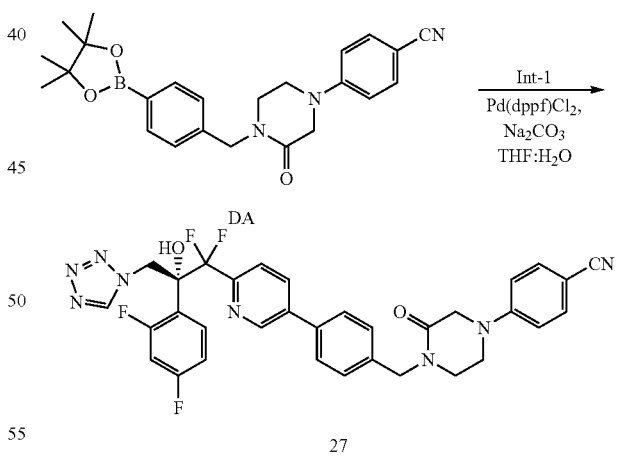

To a stirred solution of Int-1 (100 mg, 0.23 mmol) in THF:H2O (4:1, 10 mL) under argon atmosphere were added compound DA (106 mg, 0.25 mmol) and sodium carbonate (74 mg, 0.70 mmol) at RT. The reaction mixture was purged with argon for 20 min. then Pd(dppf)Cl$_2$ (17 mg, 0.02 mmol) was added and the reaction mixture was purged under argon for 10 min at RT. The reaction mixture was stirred at 80° C. for 3 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 50% EtOAc/Hexane) to afford 27 (53 mg, 0.08 mmol, 36%) as an off-white solid. $^1$H NMR (500 MHz, DMSO-$d_6$): δ 9.14 (s, 1H), 8.93 (s, 1H), 8.22 (dd, J=8.2, 1.9 Hz, 1H), 7.77 (d, J=8.1 Hz, 2H), 7.61 (d, J=8.7 Hz, 2H), 7.54 (d, J=8.4 Hz, 1H), 7.43 (d, J=8.1 Hz, 2H), 7.29 (s, 1H), 7.27-7.16 (m, 2H), 7.00 (d, J=8.7 Hz, 2H), 6.93-6.88 (m, 1H), 5.67 (d, J=14.7 Hz, 1H), 5.12 (d, J=14.7 Hz, 1H), 4.67 (s, 2H), 4.08 (s, 2H), 3.65 (t, J=5.2 Hz, 2H), 3.43 (t, J=5.2 Hz, 2H); MS (ESI): m/z 643.6 [M+H]$^+$; HPLC: 96.73%; Optical rotation $[α]_D^{20}$: +30.40 (=0.1% in MeOH).

Example 28

(R)-4-((4-(4-(6-(2-(2,4-difluorophenyl)-1,1-difluoro-2-hydroxy-3-(1H-tetrazol-1-yl)propyl)pyridin-3-yl)phenyl)-2-oxopiperazin-1-yl)methyl)benzonitrile (28)

tert-butyl 4-(4-cyanobenzyl)-3-oxopiperazine-1-carboxylate (DB)

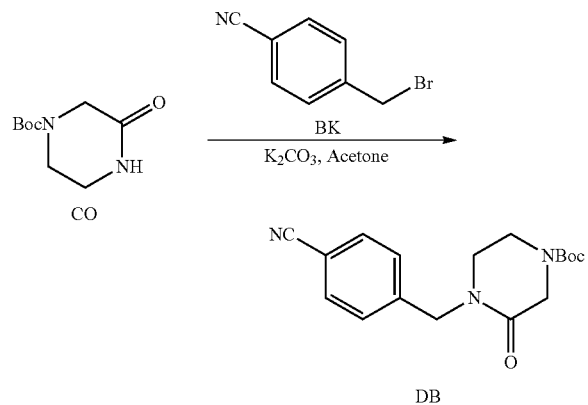

To a stirred solution of compound CO (2.0 g, 10 mmol) in acetone (30 mL) under argon atmosphere were added potassium carbonate (2.76 g, 20 mmol) and BK (2.94 g, 15 mmol) at RT. The reaction mixture was stirred at 70° C. for 12 h. The progress of the reaction was monitored by TLC. The reaction mixture was diluted with water (100 mL) and extracted with EtOAc (2×100 mL). The combined organic layers were dried over anhydrous Na$_2$SO$_4$ and concentrated under reduced pressure. The crude material was purified by silica gel column chromatography (eluent: 30% EtOAc/Hexane) to afford compound DB (2.0 g, 6.34 mmol, 63%) as a white solid. $^1$H NMR (500 MHz, CDCl$_3$): δ 7.65 (d, J=8.1 Hz, 2H), 7.39 (d, J=7.7 Hz, 2H), 4.67 (s, 2H), 4.18 (s, 2H), 3.64 (t, J=5.4 Hz, 2H), 3.29 (t, J=4.9 Hz, 2H), 1.48 (s, 9H).

4-((2-oxopiperazin-1-yl) methyl) benzonitrile hydrochloride (DC)

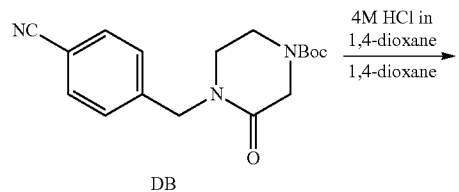

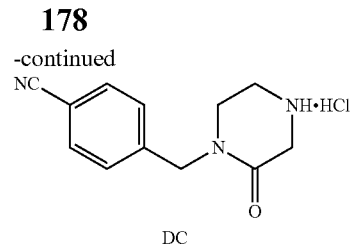

To a stirred solution of compound DB (2.0 g, 6.34 mmol) in 1,4-dioxane (20 mL) under argon atmosphere was added 4M HCl in 1,4-dioxane (7.93 mL, 31.74 mmol) at RT and stirred for 12 h. The progress of the reaction was monitored by TLC. The volatiles were evaporated under reduced pressure. The crude washed with ether (2×20 mL) and pentane (2×20 mL) to obtain compound DC (1.5 g, crude) as a white solid used in the next step without further purification. $^1$H NMR (500 MHz, DMSO-$d_6$): δ 10.12 (brs, 2H), 7.81 (d, J=8.1 Hz, 2H), 7.52 (d, J=8.1 Hz, 2H), 4.67 (s, 2H), 3.78 (s, 2H), 3.52 (t, J=5.2 Hz, 2H), 3.40 (t, J=5.6 Hz, 2H).

4-((4-(4-bromophenyl-2-oxopiperazin-1-yl) methyl) benzonitrile (DD)

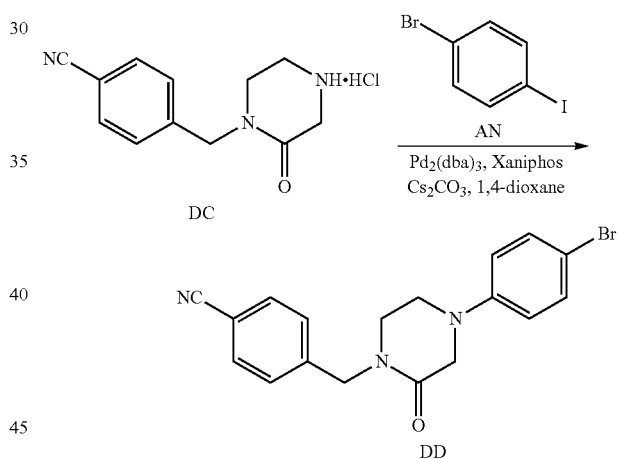

To a stirred solution of compound DC (1.0 g, 2.84 mmol) in 1,4-dioxane (50 mL) under argon atmosphere were added AN (886 mg, 3.13 mmol), cesium carbonate (1.3 g, 3.98 mmol), Xantphos (115 mg, 0.20 mmol) and purged under argon for 20 min at RT. Then Pd$_2$(dba)$_3$ (52 mg, 0.05 mmol) was added to the reaction mixture at RT and stirred at 100° C. for 16 h. The reaction mixture was diluted with water (50 mL) and extracted with EtOAc (2×50 mL). The combined organic extracts were washed with water (50 mL), brine (50 mL), dried over anhydrous Na$_2$SO$_4$ and concentrated under reduced pressure. The crude material was purified by silica gel column chromatography (eluent: 50% EtOAc/Hexane) to afford compound DD (500 mg, 1.35 mmol 47%) as an off-white solid. $^1$H NMR (400 MHz, CDCl$_3$): δ 7.81 (d, J=8.1 Hz, 2H), 7.41 (d, J=8.9 Hz, 2H), 7.39 (d, J=7.7 Hz, 2H), 6.90 (d, J=8.7 Hz, 2H), 4.67 (s, 2H), 3.90 (s, 2H), 3.51-3.48 (m, 2H), 3.40 3.37 (m, 2H).

4-((2-oxo-4-(4-(4,4,5,5-tetramethyl-1,3,2-dioxaborolan-2-yl) phenyl) piperazin-1-yl) methyl) benzonitrile (DE)

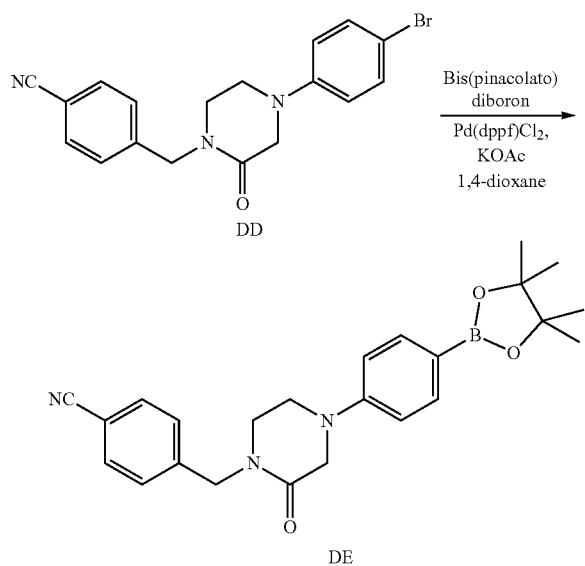

To a stirred solution of compound DD (300 mg, 0.81 mmol) in 1,4-dioxane (30 mL) under argon atmosphere were added bis(pinacolato)diboron (328 mg, 1.30 mmol) and KOAc (238 mg, 2.43 mmol) at RT. The reaction mixture was purged with argon for 20 min, then Pd(dppf)Cl$_2$ (59 mg, 0.08 mmol) was added and the reaction mixture was purged under argon for 10 min at RT. The reaction mixture was stirred at 90° C. for 4 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 50% EtOAc/Hexane) to afford compound DE (250 mg, 0.60 mmol, 73%) as an off-white solid. $^1$H NMR (500 MHz, DMSO-d$_6$): δ 7.80 (d, J=6.4 Hz, 2H), 7.54 (d, J=8.4 Hz, 2H), 7.45 (d, J=8.1 Hz, 2H), 6.90 (d, J=8.7 Hz, 2H), 4.67 (s, 2H), 3.96 (s, 2H), 3.57 (t, J=5.2 Hz, 2H), 3.39 (t, J=5.4 Hz, 2H), 1.26 (s, 12H).

(R)-4-((4-(4-(6-(2-(2,4-difluorophenyl)-1,1-difluoro-2-hydroxy-3-(1H-tetrazol-1-yl)propyl)pyridin-3-yl) phenyl)-2-oxopiperazin-1-yl)methyl)benzonitrile (28)

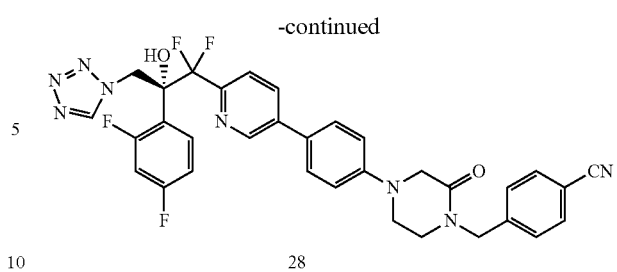

To a stirred solution of Int-1 (120 mg, 0.27 mmol) in THF:H2O (4:1, 20 mL) under argon atmosphere were added compound DE (139 mg, 0.33 mmol) and sodium carbonate (88 mg, 0.83 mmol) at RT. The reaction mixture was purged with argon for 20 min, then Pd(dppf)Cl$_2$ (20 mg, 0.02 mmol) was added and the reaction mixture was purged under argon for 10 min at RT. The reaction mixture was stirred at 90° C. for 2 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 2% MeOH/CH$_2$Cl$_2$) to afford 28 (80 mg, 0.12 mmol, 44%) as an off-white solid. $^1$H NMR (400 MHz, DMSO-d$_6$): δ 9.15 (s, 1H), 8.91 (s, 1H), 8.16 (dd, J=8.2, 2.2 Hz, 1H), 7.82 (d, J=8.3 Hz, 2H), 7.70 (d, J=8.9 Hz, 2H), 7.49-7.46 (m, 3H), 7.34-7.24 (m, 2H), 7.22-7.17 (m, 1H), 7.08 (d, J=9.0 Hz, 2H), 6.93-6.86 (m, 1H), 5.67 (d, J=14.7 Hz, 1H), 5.11 (d, J=14.7 Hz, 1H), 4.69 (s, 2H), 4.01 (s, 2H), 3.61 (t, J=5.3 Hz, 2H), 3.42 (t, J=5.3 Hz, 2H); MS (ESI): m/z 641.4 [M−H]$^−$; HPLC: 93.54%; Optical rotation [α]$_D^{19}$: +29.76 (c=0.1% in MeOH).

Example 29

(R)-4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) benzaldehyde (29)

4-(4-(4-(4,4,5,5-tetramethyl-1,3,2-dioxaborolan-2-yl) phenyl) piperazin-1-yl) benzaldehyde

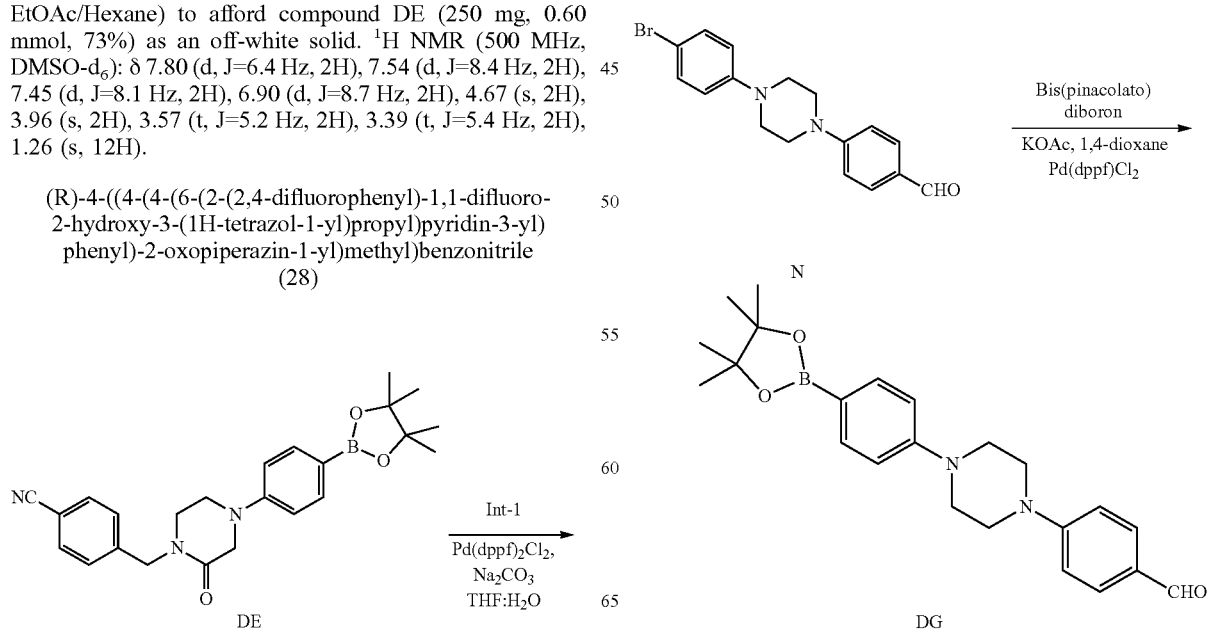

To a stirred solution of compound N (500 mg, 1.45 mmol) in 1,4-dioxane (30 mL) under argon atmosphere were added KOAc (426 mg, 4.34 mmol) and Bis(pinacolato)diboron (588 mg, 2.31 mmol) and purged under argon for 10 min at RT. Then Pd(dppf)Cl$_2$ (105 mg, 0.14 mmol) was added to the reaction mixture at RT. The reaction mixture was stirred at 100° C. for 6 h. The reaction mixture was quenched with water (30 mL) and extracted with EtOAc (2×30 mL). The combined organic extracts were washed with water (20 mL), dried over anhydrous Na$_2$SO$_4$ and concentrated under reduced pressure. The crude material was purified by silica gel column chromatography (eluent: 10% EtOAc/Hexane) to afford compound DG (500 mg, 1.27 mmol, 88%) as a pale yellow solid which was used in the next step without further purification.

(R)-4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) benzaldehyde (29)

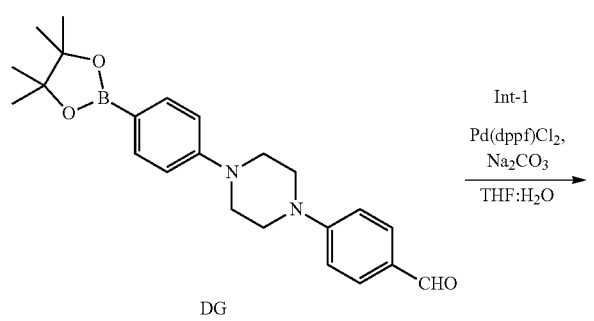

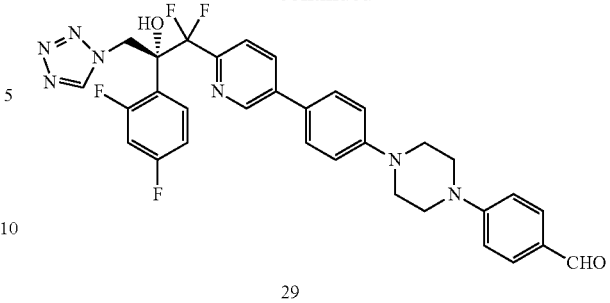

29

To a stirred solution of Int-1 (200 mg, 0.46 mmol) in THF:H2O (4:1, 25 mL) under argon atmosphere were added compound DG (217 mg, 0.55 mmol), sodium carbonate (147 mg, 1.38 mmol) and purged under argon for 5 min at RT. Then Pd(dppf)$_2$Cl$_2$ (33.8 mg, 0.04 mmol) was added to the reaction mixture at RT and stirred at 75° C. for 6 h. The reaction mixture was diluted with water (20 mL) and extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 50% EtOAc/Hexane) to afford 29 (180 mg, 0.32 mmol, 63%) as a pale yellow solid. $^1$H NMR (400 MHz, CDCl$_3$): δ 9.82 (s, 1H), 8.77 (s, 1H), 8.72 (d, J=1.9 Hz, 1H), 7.95 (dd, J=8.2, =2.3 Hz, 1H), 7.84 (s, 1H), 7.80 (d, J=8.8 Hz, 2H), 7.61 (d, J=8.3 Hz, 1H), 7.52 (d, J=8.8 Hz, 2H), 7.42-7.36 (m, 1H), 7.04 (d, J=8.8 Hz, 2H), 6.97 (d, J=8.9 Hz, 2H), 6.80-6.74 (m, 1H), 6.69-6.63 (m, 1H), 5.60 (d, J=14.2 Hz, 1H), 5.12 (d, J=14.2 Hz, 1H), 3.64-3.34 (m, 8H); MS (ESI): m/z 618.1 [M+H]$^+$; HPLC: 99.68%; Optical rotation $[α]_D^{20}$: +158.04 (c=0.1% in CH$_2$Cl$_2$).

Example 30

(R)-2-(2,4-difluorophenyl)-1-(5-(4-(4-((dimethylamino) methyl) phenyl) piperazin-1-yl) phenyl) pyridin-2-yl)-1,1-difluoro-3-(1H-tetrazol-1-yl) propan-2-ol (30)

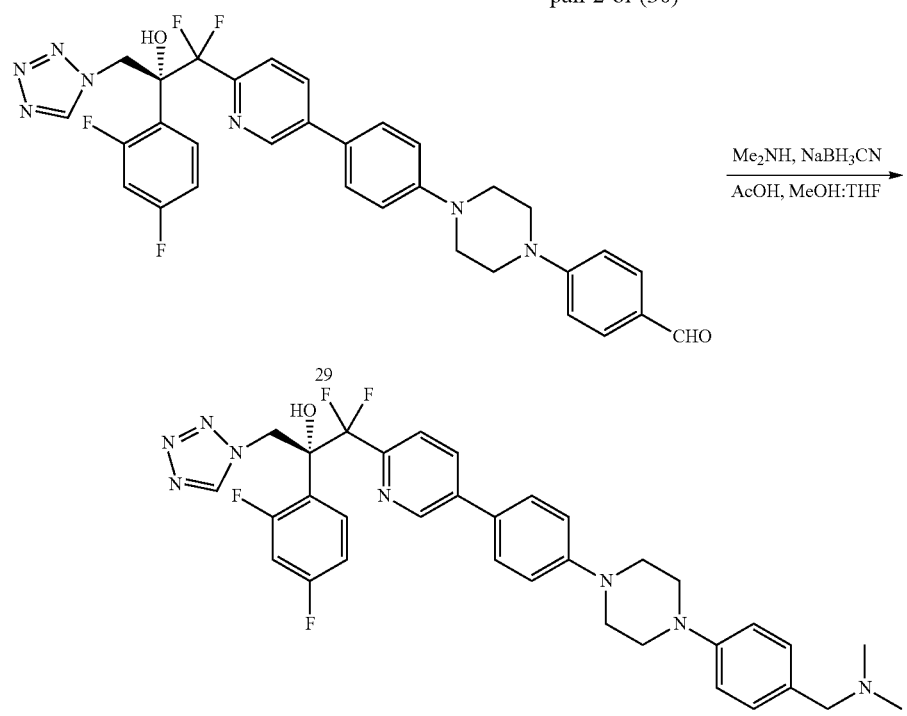

30

To a stirred solution of 29 (100 mg, 0.16 mmol) in MeOH:THF (4:1, 20 mL) under argon atmosphere were added acetic acid (catalytic amount), dimethyl amine solution (0.4 mL, 0.81 mmol, 2.0 M in THF) at 0° C. The reaction mixture was stirred at 50° C. for 2 h. Then sodium cyanoborohydride (50 mg, 0.81 mmol) was added to the reaction mixture at RT and stirred for 16 h. The volatiles were concentrated under reduced pressure. The residue was diluted with water (20 mL) and extracted with $CH_2Cl_2$ (2×20 mL). The combined organic extracts were washed with water (20 mL), dried over anhydrous $Na_2SO_4$ and concentrated under reduced pressure. The crude material was purified by silica gel column chromatography (eluent: 5% MeOH/$CH_2Cl_2$) to afford 30 (60 mg, 0.09 mmol, 58%) as an off-white solid. $^1$H NMR (400 MHz, $CD_3OD$): δ 9.04 (s, 1H), 8.80 (d, J=2.0 Hz, 1H), 8.08 (dd, J=8.3, 2.1 Hz, 1H), 7.63 (d, J=8.8 Hz, 2H), 7.54 (d, J=8.4 Hz, 1H), 7.40-7.27 (m, 3H), 7.15 (d, J=8.8 Hz, 2H), 7.08 (d, J=8.7 Hz, 2H), 6.95-6.89 (m, 1H), 6.81-6.71 (m, 1H), 5.77 (d, J=14.6 Hz, 1H), 5.19 (d, J=14.6 Hz, 1H), 3.91 (s, 2H), 3.44-3.40 (m, 8H), 2.61 (s, 6H); MS (ESI): m/z 647.7 [M+H]$^+$; HPLC: 96.86%; Optical rotation $[α]_D^{19}$: +38.4 (c=0.1% in MeOH).

Example 31

1-(5-(4-(4-(6-(R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2,2,2-trifluoroethyl dihydrogen phosphate (31)

1-(5-(4-(4-bromophenyl) piperazin-1-yl) pyridin-1-yl)-2,2,2-trifluoroethyl diethyl phosphate (DH)

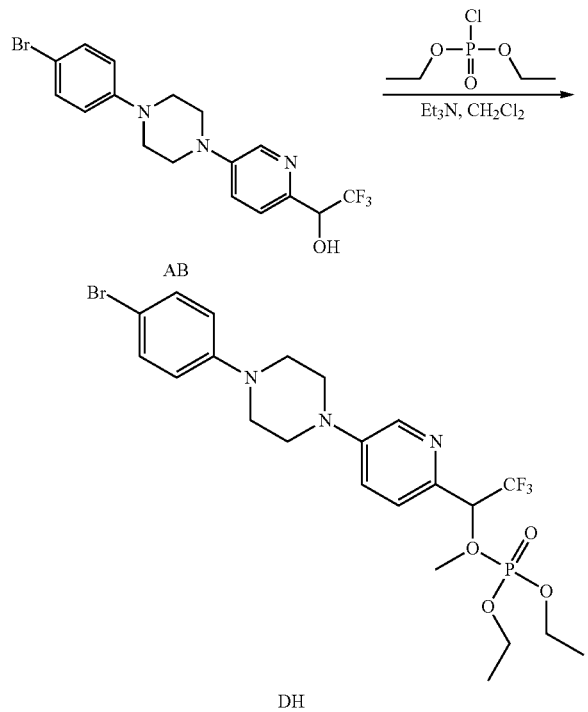

To a stirred solution of compound AB (600 mg, 1.43 mmol) in $CH_2Cl_2$ (15 mL) under argon atmosphere were added triethyl amine (1.03 mL, 7.19 mmol) at 0° C. The reaction mixture was stirred at 0° C. for 30 min. Then diethyl chlorophosphate (1.3 mL, 7.19 mmol) was added to the reaction mixture at RT. The reaction mixture was stirred at RT for 16 h. The progress of the reaction was monitored by TLC. The reaction mixture was diluted with water (100 mL) and extracted with $CH_2Cl_2$ (2×100 mL). The combined organic layers were dried over anhydrous $Na_2SO_4$ and concentrated under reduced pressure. The crude material was purified by silica gel column chromatography (eluent: 0-2% MeOH/$CH_2Cl_2$) to afford compound DH (700 mg, 1.27 mmol, 87%) as an off-white solid. $^1$H NMR (500 MHz, $CDCl_3$): δ 8.33 (d, J=2.6 Hz, 1H), 7.47 (d, J=8.7 Hz, 1H), 7.38 (d, J=8.97 Hz, 2H), 7.27-7.23 (m, 1H), 6.84 (d, J=9.0 Hz, 2H), 5.86-5.60 (m, 1H), 4.20-3.92 (m, 4H), 3.34-3.28 (m, 8H), 1.26-1.20 (m, 6H).

Diethyl (2,2,2-trifluoro-1-(5-(4-(4-(4,4,5,5-tetramethyl-1,3,2-dioxaborolan-2-yl) phenyl) piperazin-1-yl) pyridin-2-yl) ethyl) phosphate (DI)

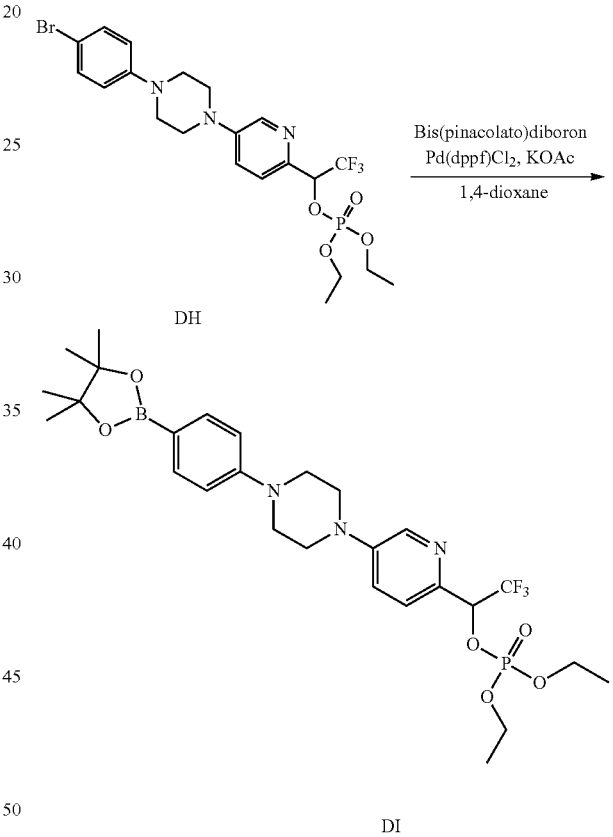

To a stirred solution of compound DH (700 mg, 1.25 mmol) in 1,4-dioxane (30 mL) under argon atmosphere were added bis(pinacolato)diboron (510 mg, 2.01 mmol) and potassium acetate (407 mg, 3.77 mmol) at RT. The reaction mixture was purged with argon for 20 min, then Pd(dppf)Cl$_2$ (92 mg, 0.12 mmol) was added and the reaction mixture was purged under argon for 5 min at RT. The reaction mixture was stirred at 90° C. for 16 h. The volatiles were concentrated under reduced pressure. The crude material was purified by silica gel column chromatography (eluent: 2% MeOH/$CH_2Cl_2$) to afford compound DI (400 mg, 0.66 mmol, 53%) as an off-white solid. $^1$H NMR (400 MHz, $CDCl_3$): δ 8.34 (d, J=2.6 Hz, 1H), 7.74 (d, J=8.7 Hz, 2H), 7.47 (d, J=8.8 Hz, 1H), 7.29-7.21 (m, 1H), 6.94 (d, J=8.8 Hz, 2H), 5.73-5.63 (m, 1H), 4.14-4.11 (in 4H), 3.44-3.42 (m, 8H), 1.34-1.32 (m, 6H), 1.24 (s, 12H).

1-(5-(4-(4-(4-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2,2,2-trifluoroethyl diethyl phosphate (DJ)

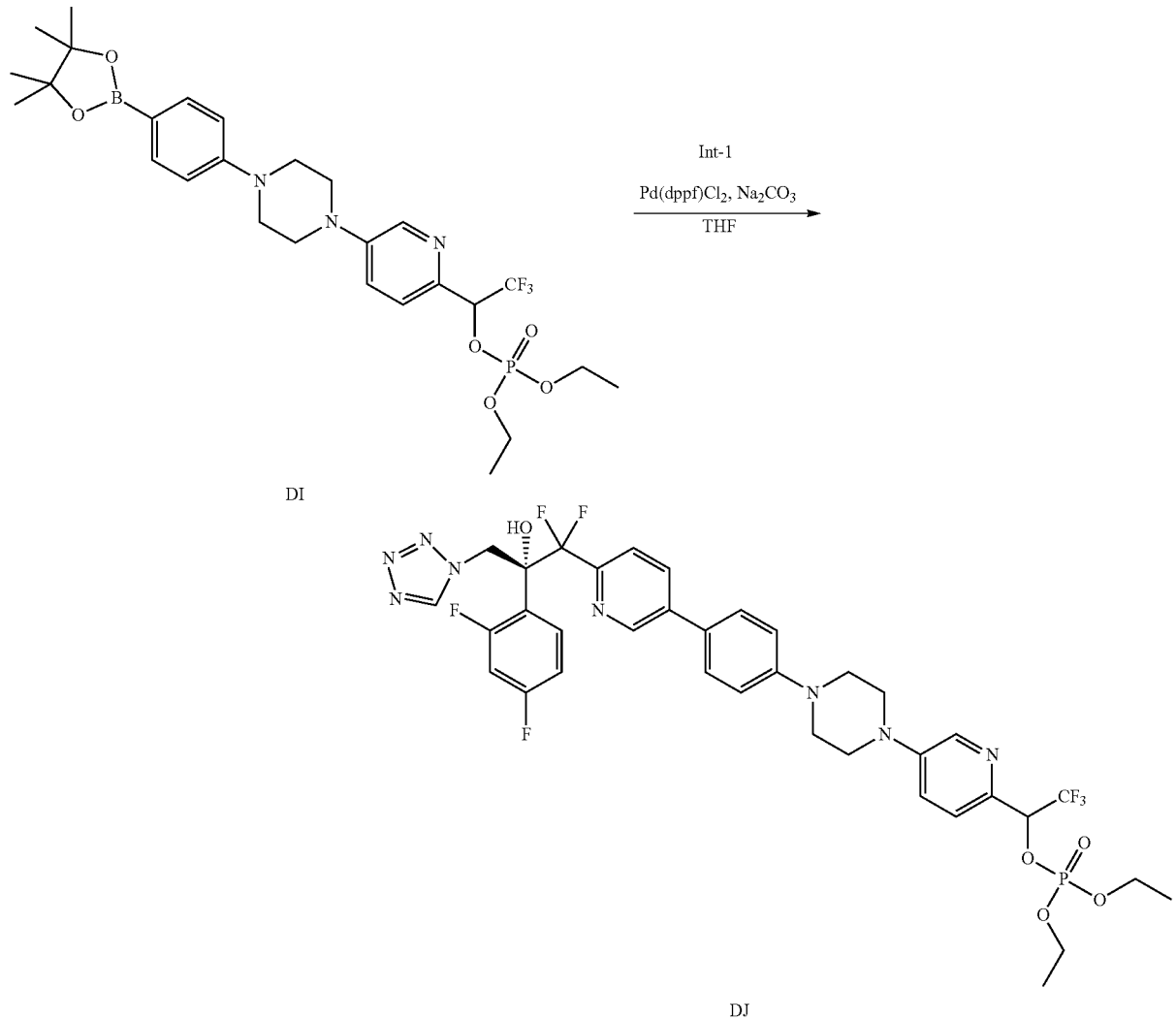

To a stirred solution of Int-1 (400 mg, 0.66 mmol) in THF (20 mL) under argon atmosphere were added compound DI (288 mg, 0.66 mmol), sodium carbonate (196 mg, 2.00 mmol) and purged under argon for 15 min at RT. Then Pd(dppf)Cl$_2$ (49 mg, 0.06 mmol) was added and the reaction mixture was purged under argon for 10 min at RT. The reaction mixture was stirred at 70° C. for 16 h. The reaction mixture was filtered and the filtrate was concentrated under reduced pressure. The crude material was purified by silica gel column chromatography (eluent: 5% MeOH/CH$_2$Cl$_2$) to afford compound DJ (200 mg, 0.33 mmol, 36%) as an off-white solid. $^1$H NMR (400 MHz, CD$_3$OD): δ 9.05 (s, 1H), 8.81 (s, 1H), 8.35 (s, 1H), 8.09 (dd, J=8.3, 2.3 Hz, 1H), 7.61-7.58 (m, 3H), 7.53-7.50 (m, 2H), 7.33-7.28 (m, 1H), 7.14 (d, J=7.6 Hz, 2H), 6.95-6.89 (m, 1H), 6.79-6.74 (m, 1H), 5.78 (d, J=14.6 Hz, 1H), 5.66-5.61 (m, 1H), 5.20 (d, J=14.6 Hz, 1H), 4.20-4.00 (m, 4H), 3.52-3.47 (m, 8H), 1.34-1.30 (m, 3H), 1.25-020 (m, 3H); LC-MS: 825.3 [M+H]r at 3.61 RT (73.3% purity).

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2,2,2-trifluoroethyl dihydrogen phosphate (31)

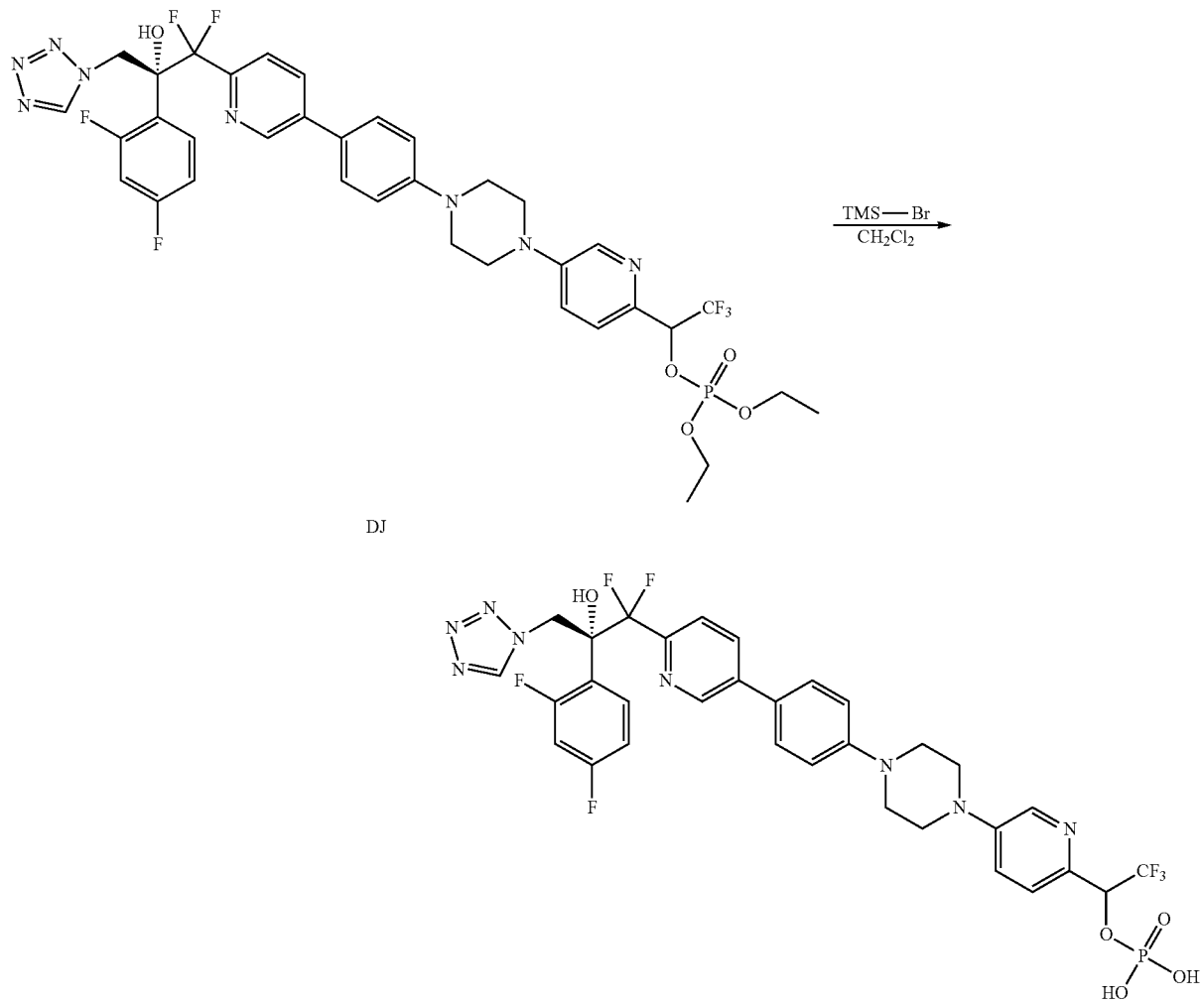

To a stirred solution of compound DJ (50 mg, 0.06 mmol) in CH$_2$Cl$_2$ (5 mL) under argon atmosphere was added TMS-Br (48 mg, 0.30 mmol) at 0° C. The reaction mixture was stirred at 0° C. for 22 h. The progress of the reaction was monitored by TLC. The volatiles were concentrated under reduced pressure. The crude material was purified by preparative HPLC to afford 31 (8 mg, 0.01 mmol, 17%) as an off-white solid. $^1$H NMR (400 MHz, CD$_3$OD): δ 9.04 (s, 1H), 8.81 (d, J=2.1 Hz, 1H), 8.25 (d, J=2.8 Hz, 1H), 8.09 (dd, J=8.3, 2.3 Hz, 1H), 7.67-7.62 (m, 3H), 7.54 (d, J=8.3 Hz, 1H), 7.50 (dd, J=8.8, 2.8 Hz, 1H), 7.36-7.33 (m, 1H), 7.16 (d, J=8.9 Hz, 2H), 6.95-6.89 (m, 1H), 6.79-6.74 (m, 1H), 5.78 (d, J=14.6 Hz, 1H), 5.56-5.51 (m, 1H), 5.18 (d, J=14.6 Hz, 1H), 3.45 (s, 8H); $^{31}$P NMR (400 MHz, CD$_3$OD): δ −0.40 (s); MS (ESI): m/z 769.6 [M+H]$^+$; HPLC: 99.56%; Optical rotation [α]$_D^{20}$: +50.20 (c=0.1% in MeOH).

Example 32

(R)-5-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) picolinaldehyde (32)

5-(4-(4-(4,4,5,5-tetramethyl-1,3,2-dioxaborolan-2-yl) phenyl) piperazin-1-yl) picolinaldehyde (DX)

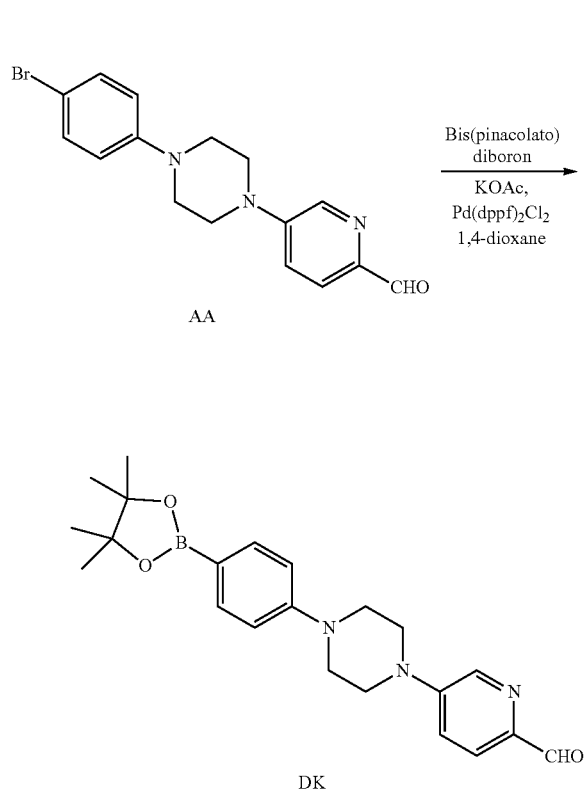

To a stirred solution of compound AA (400 mg, 1.15 mmol) in 1,4-dioxane (20 mL) under argon atmosphere were added KOAc (341 mg, 3.47 mmol), Bis(pinacolato)diboron (469 mg, 1.85 mmol) and purged under argon for 20 min at RT. Then Pd(dppf)$_2$Cl$_2$ (85 mg, 0.11 mmol) was added to the reaction mixture at RT and stirred at 110° C. for 16 h. The reaction mixture was diluted with water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 50% EtOAc/Hexane) to afford compound DK (305 mg, 0.77 mmol, 67%) as an off-white solid. $^1$H NMR (500 MHz, DMSO-d$_6$): δ 9.78 (s, 1H), 8.51 (d, J=2.6 Hz, 1H), 7.79 (d, J=9.0 Hz, 1H), 7.54 (d, J=8.7 Hz, 2H), 7.44 (dd, J=9.0, 2.6 Hz, 1H), 6.95 (d, J=8.7 Hz, 2H), 3.68-3.58 (m, 4H), 3.47-3.38 (m, 4H), 1.26 (s, 12H).

(R)-5-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) picolinaldehyde (32)

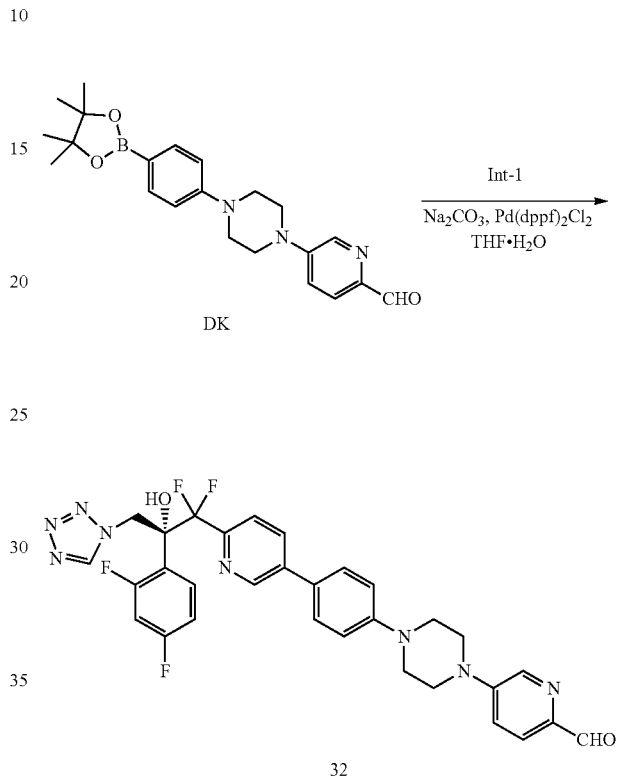

To a stirred solution of Int-1 (200 mg, 0.46 mmol) in THF:H2O (4:1, 15 mL) under argon atmosphere were added sodium carbonate (153 mg, 1.40 mmol), compound DK (200 ng, 0.51 mmol) and purged under argon for 20 min at RT. Then Pd(dppf)$_2$Cl$_2$ (34 mg, 0.04 mmol) was added to the reaction mixture at RT and stirred at 70° C. for 4 h. The reaction mixture was diluted with water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 80-70% EtOAc/Hexane) to afford 32 (150 mg, 0.22 mmol, 52%) as an off-white solid. $^1$H NMR (500 MHz, DMSO-d$_6$): δ 9.79 (s, 1H), 9.14 (s, 1H), 8.90 (s, 1H), 8.54 (d, J=2.3 Hz, 1H), 8.17 (dd, J=8.1, 1.4 Hz, 1H), 7.80 (d, J=9.0 Hz, 1H), 7.71 (d, J=8.7 Hz, 2H), 7.55-7.40 (m, 2H), 7.32-7.26 (m, 2H), 7.23-7.16 (m, 1H), 7.13 (d, J=8.7 Hz, 2H), 6.93-6.87 (m, 1H), 5.67 (d, J=14.5 Hz, 1H), 5.11 (d, J=14.5 Hz, 1H), 3.70-3.64 (m, 4H), 3.46-3.42 (m, 4H); MS (ESI): m/z 619.1 [M+H]$^+$; HPLC: 97.09%; Optical rotation [α]$_D^{19}$: +122.2 (c=0.1% in CH$_2$Cl$_2$).

Example 33

(R)-2-(2,4-difluorophenyl)-1-(5-(4-(4-(6-((dimethyl-amino) methyl) pyridin-3-yl) piperazin-1-yl) phenyl) pyridin-2-yl)-1,1-difluoro-3-(1H-tetrazol-1-yl) propan-2-ol (33)

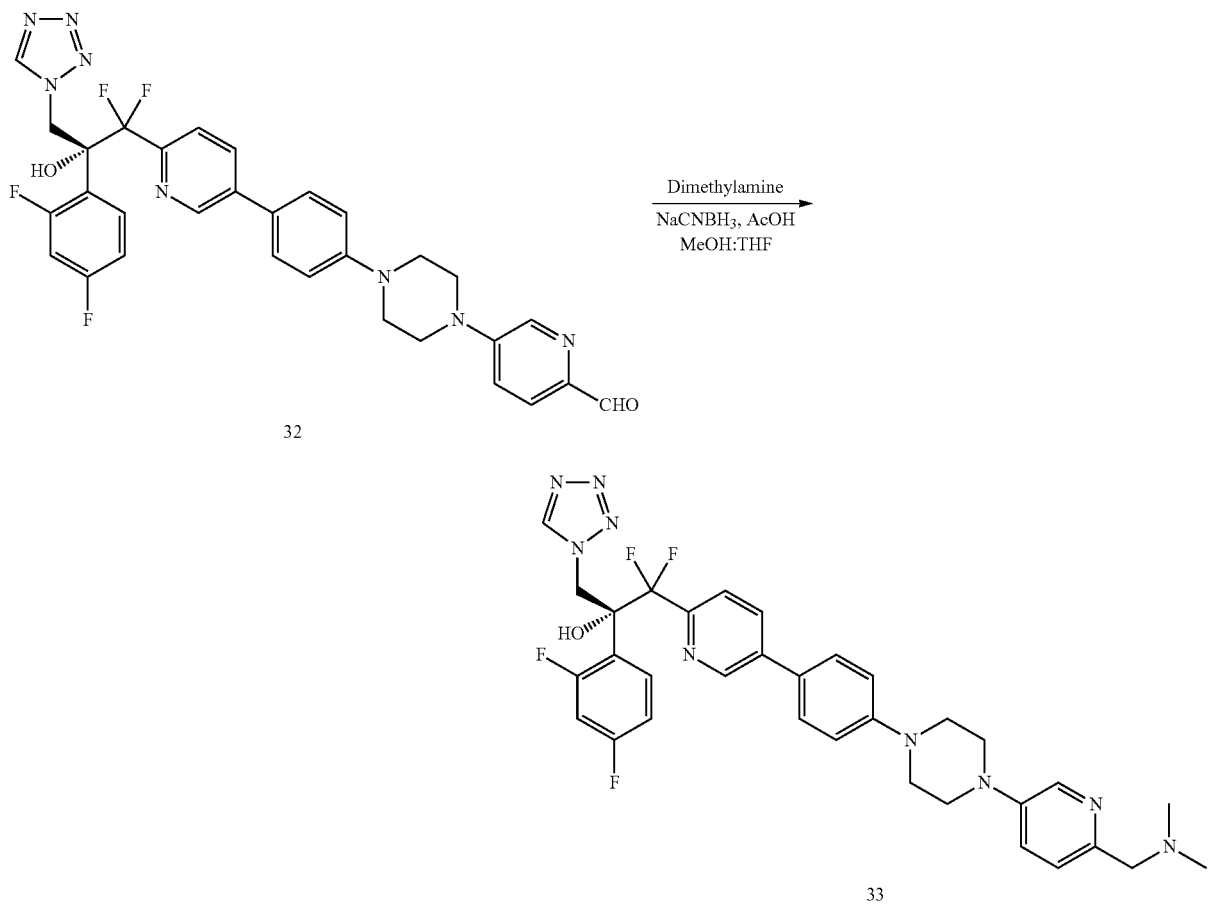

To a stirred solution of compound 32 (75 mg, 0.11 mmol) in MeOH:THF (1:1, 7 mL) under argon atmosphere were added dimethyl amine solution (0.2 mL, 0.46 mmol) and acetic acid (catalytic amount) at RT. The reaction mixture stirred at 40° C. for 2 h. Then the reaction mixture was cooled to RT, sodium cyanoborohydride (16 mg, 0.23 mmol) was added and stirred at 40° C. for 24 h. The reaction mixture was diluted with ice cold water (20 mL) and extracted with EtOAc (2×20 mL). The combined organic extracts were washed with water (20 mL), brine (20 mL), dried over anhydrous $Na_2SO_4$ and concentrated under reduced pressure. The crude material was purified by silica gel column chromatography (eluent: 5% MeOH/$CH_2Cl_2$) to afford 33 (45 mg, 0.07 mmol, 57%) as colorless thick syrup. $^1$H NMR (400 MHz, $CD_3OD$): δ 9.03 (s, 1H), 8.80 (d, J=2.0 Hz, 1H), 8.41 (d, J=2.6 Hz, 1H), 8.08 (dd, J=8.3, 2.3 Hz, 1H), 7.65-7.61 (m, 2H), 7.54 (dd, J=8.3, 0.6, Hz, 1H), 7.48 (d, J=7.4 Hz, 1H), 7.42-7.28 (m, 2H), 7.16 (d, J=9.0 Hz, 2H), 6.94-6.88 (m, 1H), 6.80-6.73 (m, 1H), 5.77 (d, J=14.6 Hz, 1H), 5.19 (d, J=14.6 Hz, 1H), 4.18 (s, 2H), 3.51-3.42 (m, 8H), 2.78 (s, 6H); MS (ESI): m/z 648.3 [M+H]$^+$; HPLC: 90.15%; Optical rotation $[\alpha]_D^{19}$: +39.0 (c=0.1% in MeOH).

Example 34

(2R)-2-(2,4-difluorophenyl)-1,1-difluoro-3-(1H-tetrazol-1-yl)-1-(5-(4-(4-(5-(2,2,2-trifluoro-1-hydroxyethyl) pyridin-2-yl) piperazin-1-yl) phenyl) pyridin-2-yl) propan-2-ol (34)

6-bromonicotinaldehyde (DL)

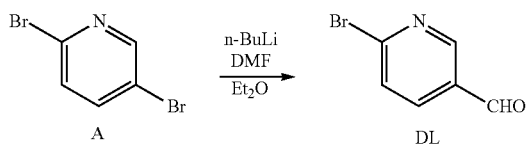

To a stirred solution of 2,5-dibromopyridine A (99 mL, 105.53 mmol) in diethyl ether (250 mL) under argon atmosphere was added n-BuLi (99 mL, 158.30 mol, 1.6 M in hexanes) at −78° C., and stirred for 40 min. Then DMF (16 mL, 211.06 mol) was added to the reaction mixture at −78°

C., and stirred for another 2 h. The progress of the reaction was monitored by TLC. The reaction was quenched with aqueous ammonium chloride solution (20 mL) and extracted with EtOAc (2×20 mL). The combined organic layers were washed with water (2×20 mL), dried over anhydrous Na$_2$SO$_4$ and concentrated under reduced pressure. The crude material was purified by silica gel column chromatography (eluent: 20% EtOAc/Hexane) to afford compound DL (11 g, 59.13 mmol, 56%) as a pale yellow solid. $^1$H NMR (500 MHz, CDCl$_3$): δ 10.07 (s, 1H), 8.80 (s, 1H), 8.00 (dd, J=8.1, 2.3 Hz, 1H), 7.66 (d, J=8.1 Hz, 1H).

6-(4-(4-bromophenyl) piperazin-1-yl) nicotinaldehyde (DM)

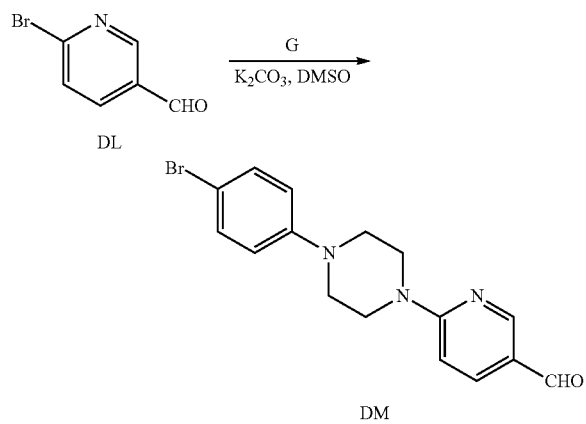

To a stirred solution of compound DL (200 mg, 0.82 mmol) in DMSO (5 mL) under argon atmosphere were added potassium carbonate (228 mg, 1.65 mmol) and 1-(4-bromophenyl) piperazine G (185 mg, 0.99 mmol) at RT. The reaction mixture was stirred at 120° C. for 12 h. The progress of the reaction was monitored by TLC. The reaction mixture was diluted with water (20 mL) and extracted with EtOAc (2×200 mL). The combined organic layers were dried over anhydrous Na$_2$SO$_4$ and concentrated under reduced pressure. The crude material was purified by silica gel column chromatography (eluent: 40% EtOAc/Hexane) to afford compound DM (200 mg, 0.57 mmol, 70%) as a white solid. $^1$H NMR (500 MHz, CDCl$_3$): δ 9.81 (s, 1H), 8.59 (s, 1H), 7.96 (dd, J=9.0, 2.3 Hz, 1H), 7.38 (d, J=9.0 Hz, 2H), 6.82 (d, J=9.0 Hz, 2H), 6.71 (d, J=9.0 Hz, 1H), 3.95-3.86 (m, 4H), 3.31-3.24 (m, 4H).

1-(6-(4-(4-bromophenyl) piperazin-1-yl) pyridin-3-yl)-2,2,2-trifluoroethan-1-ol (DN)

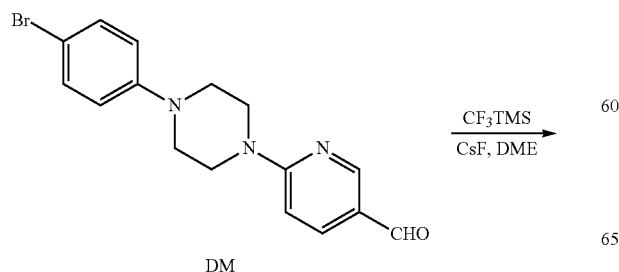

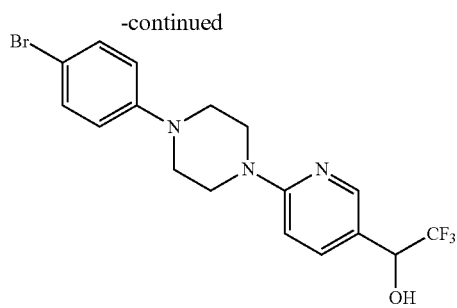

To a stirred solution of compound DM (200 mg, 0.57 mmol) in 1,2-DME (20 mL) under argon atmosphere were added cesium fluoride (44 mg, 0.29 mmol) and CF$_3$TMS (0.09 mL, 0.63 mmol) at 0° C. The reaction mixture was warmed to RT and stirred for 2 h. The progress of the reaction was monitored by TLC. The reaction mixture was quenched with 2 N HCl solution (20 mL), stirred for 2 h and then extracted with EtOAc (2×20 mL). The combined organic layers were washed with water (20 mL), dried over anhydrous Na$_2$SO$_4$ and concentrated under reduced pressure. The crude material was purified by silica gel column chromatography (eluent: 50% EtOAc/Hexane) to afford compound DN (180 mg, 0.43 mmol, 75%) as an off-white solid. $^1$H NMR (400 MHz, CDCl$_3$): δ 8.20 (d, J=2.4 Hz, 1H), 7.65 (dd, J=8.8, 2.2 Hz, 1H), 7.37 (d, J=9.0 Hz, 2H), 6.83 (d, J=9.0 Hz, 2H), 6.72 (d, J=8.9 Hz, 1H), 4.96-4.91 (m, 1H), 3.75-3.71 (m, 4H), 3.28-3.22 (m, 4H).

2,2,2-trifluoro-1-(6-(4-(4-(4,4,5,5-tetramethyl-1,3,2-dioxaborolan-2-yl) phenyl) piperazin-1-yl) pyridin-3-yl) ethan-1-ol (DO)

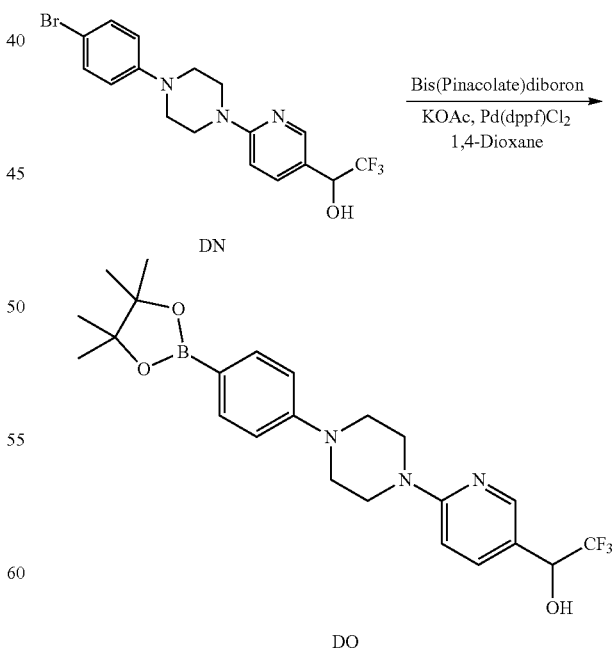

To a stirred solution of compound DN (180 mg, 0.43 mmol) in 1,4-dioxane (20 mL) under argon atmosphere were added bis(pinacolato)diboron (175 mg, 0.70 mmol) and KOAc (127 mg, 1.30 mmol) at RT. The reaction mixture was purged with argon for 20 min, then Pd(dppf)Cl$_2$ (31 mg, 0.04 mmol) was added and the reaction mixture was purged under argon for 10 min at RT. The reaction mixture was stirred at 100° C. for 6 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure to obtain compound DO (100 mg, crude) as an off-white solid and as such taken for next step without further purification.

(2R)-2-(2,4-difluorophenyl)-1,1-difluoro-3-(1H-tetrazol-1-yl)-1-(5-(4-(4-(5-(2,2,2-trifluoro-1-hydroxyethyl) pyridin-2-yl) piperazin-1-yl) phenyl) pyridin-2-yl) propan-2-ol (34)

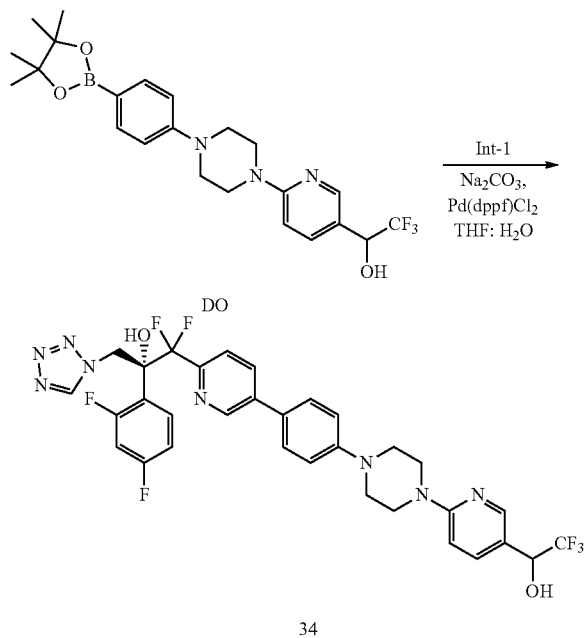

To a stirred solution of Int-1 (150 mg, 0.34 mmol) in THF:H2O (4:1, 20 mL) under argon atmosphere were added compound DO (192 mg, 0.41 mmol), sodium carbonate (110 mg, 1.04 mmol) and purged under argon for 20 min at RT. Then Pd(dppf)Cl$_2$ (25 mg, 0.03 mmol) was added and the reaction mixture was purged under argon for 10 min at RT. The reaction mixture was stirred at reflux for 2 h. The progress of the reaction was monitored by TLC. The reaction mixture was diluted with water (30 mL) and extracted with EtOAc (2×30 mL). The combined organic extracts were dried over anhydrous Na$_2$SO$_4$ and concentrated under reduced pressure. The crude material was purified by silica gel column chromatography (eluent: 60% EtOAc/Hexane) to afford 34 (80 mg, 0.11 mmol, 33% (overall yield from two steps) as an off-white solid. $^1$H NMR (400 MHz, DMSO-d$_6$): δ 9.15 (s, 1H), 8.91 (s, 1H), 8.20 (d, J=2.1 Hz, 1H), 8.16 (dd, J=8.3, 2.2 Hz, 1H), 7.70 (d, J=8.8 Hz, 2H), 7.64 (dd, J=8.8, 1.9 Hz, 1H), 7.48 (d, J=8.3 Hz, 1H), 7.34-7.24 (m, 2H), 7.23-7.15 (m, 1H), 7.13 (d, J=8.9 Hz, 2H), 6.94 (d, J=8.8 Hz, 1H), 6.91-6.87 (m, 1H), 6.72 (d, J=5.6 Hz, 1H), 5.67 (d, J=14.8 Hz, 1H), 5.11 (d, J=14.8 Hz, 1H), 5.08-5.01 (m, 1H), 3.73-3.67 (m, 4H), 3.40-3.33 (m, 4H); MS (ESI): m/z 689.1 [M+H]$^+$; HPLC: 99.59%; Optical rotation [α]$_D^{20}$: +50.32 (c=0.1% in MeOH).

Example 35

(R)-2-(2,4-difluorophenyl)-1,1-difluoro-3-(1H-tetrazol-1-yl)-1-(5-(4-(4-(2-(trifluoromethyl)-1H-benzo[d] imidazol-5-yl) piperazin-1-yl) phenyl) pyridin-2-yl) propan-2-ol (35)

5-(4-(4-bromophenyl) piperazin-1-yl)-2-nitroaniline (DQ)

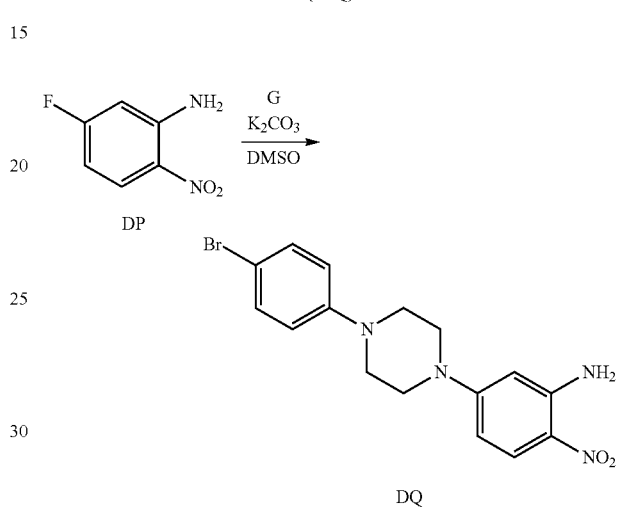

To a stirred solution of 5-fluoro-2-nitroaniline DP (4.0 g, 25.6 mmol) in DMSO (50 mL) under argon atmosphere were added potassium carbonate (7.0 g, 51.2 mmol) and 1-(4-bromophenyl) piperazine G (6.1 g, 23.6 mmol) at RT and stirred for 20 min. The reaction mixture was stirred at 120° C. for 16 h. The reaction mixture was quenched with ice water (100 mL) and extracted with EtOAc (2×100 mL). The combined organic layers were washed with water (50 mL), brine (50 mL), dried over anhydrous Na$_2$SO$_4$ and concentrated under reduced pressure. The crude material was purified by silica gel column chromatography (eluted with 50% EtOAc/Hexane) to afford compound DQ (3.0 g, 7.95 mmol, 31%) as a brown solid. $^1$H NMR (400 MHz, DMSO-d$_6$): δ 7.84 (d, J=9.8 Hz, 1H), 7.37 (d, J=8.6 Hz, 2H), 7.28 (s, 2H), 6.94 (d, J=9.6 Hz, 2H), 6.46-6.41 (m, 1H), 6.26 (d, J=2.6 Hz, 1H), 3.51-3.46 (m, 4H), 3.34-3.24 (m, 4H).

N-(5-(4-(4-bromophenyl) piperazin-1-yl)-2-nitrophenyl)-2,2,2-trifluoroacetamide (DR)

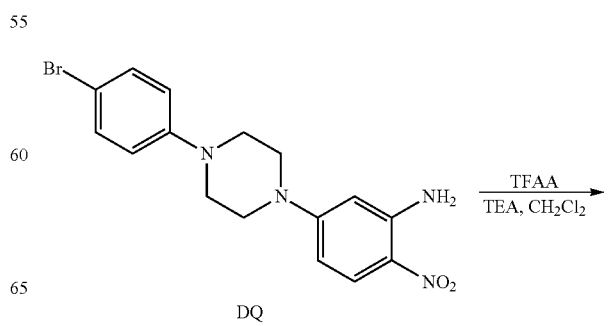

-continued

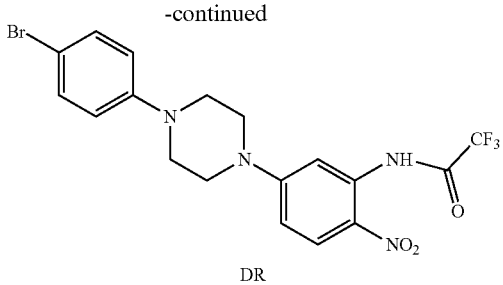

DR

To a stirred solution of compound DQ (2.0 g, 5.3 mmol) in CH$_2$Cl$_2$ (40 mL) under argon atmosphere were added triethylamine (0.91 mL, 6.36 mmol), trifluoroacetic anhydride (2.2 g, 10.6 mmol) at 0° C. The reaction mixture warmed to RT and stirred for 4 h. The progress of the reaction was monitored by TLC. The reaction mixture was diluted with ice cold water (50 mL) and extracted with CH$_2$Cl$_2$ (2×30 mL). The combined organic layers were washed with ice cold water (30 mL), brine (30 mL), dried over anhydrous Na$_2$SO$_4$ and concentrated under reduced pressure to obtain compound DR (2.0 g, crude) as a brown solid: the material was as such taken for next step without further purification. $^1$H NMR (400 MHz, CDCl$_3$): δ 12.09 (brs, 1H), 8.23 (d, J=7.0 Hz, 2H), 7.39 (d, J=9.0 Hz, 2H), 6.81 (d, J=9.0 Hz, 2H), 6.68 (dd, J=9.7, 2.8 Hz, 1H), 3.71-3.67 (m, 4H), 3.36-3.32 (m, 4H).

5-(4-(4-bromophenyl) piperazin-1-yl)-2-(trifluoromethyl)-1H-benzo [d] imidazole (1S)

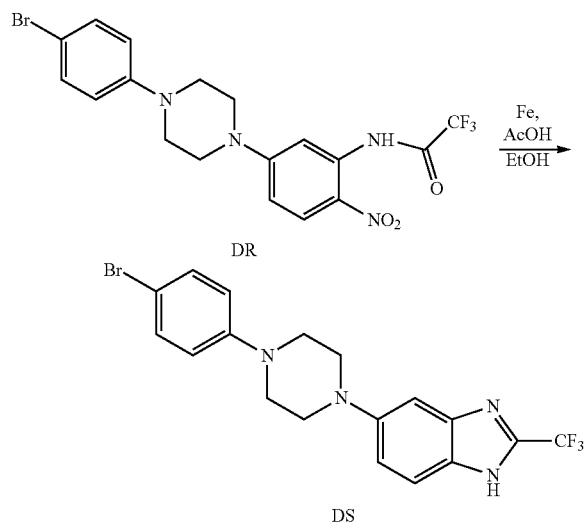

To a stirred solution of compound DR (3.0 g, 6.30 mmol) in EtOH (30 mL) under argon atmosphere were added acetic acid (30 mL) and Fe powder (1.4 g, 25.30 mmol) at RT. The reaction mixture was stirred at reflux for 4 h. The progress of the reaction was monitored by TLC. The reaction mixture was quenched with saturated sodium bicarbonate solution (50 mL) and extracted with EtOAc (2×50 mL). The combined organic layers were washed with water (30 mL), brine (30 mL), dried over anhydrous Na$_2$SO$_4$ and concentrated under reduced pressure. The crude material was purified by silica gel column chromatography (eluted with 40% EtOAc/Hexane) to afford compound DS (1.1 g, 2.60 mmol, 41%) as a brown solid, which was taken for next step without further purification. LC-MS: 426.9 [M+2H]$^+$ at 2.69 RT (90.0% purity).

5-(4-(4-(4,4,5,5-tetramethyl-1,3,2-dioxaborolan-2-yl) phenyl) piperazin-1-yl)-2-(trifluoromethyl)-1H-benzo[d]imidazole (DT)

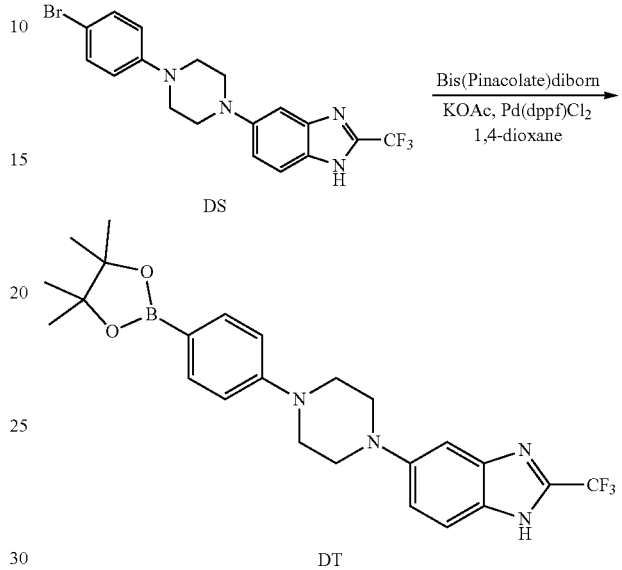

To a stirred solution of compound DS (600 mg, 1.41 mmol) in 1,4-dioxane (50 mL) under argon atmosphere were added bis(pinacolato)diboron (574 mg, 2.26 mmol) and potassium acetate (416 mg, 4.25 mmol) at RT. The reaction mixture was purged with argon for 20 min, then Pd(dppf)Cl$_2$ (103.6 mg, 0.14 mmol) was added and the reaction mixture was purged under argon for 5 min at RT. The reaction mixture was stirred at 110° C. for 16 h. The reaction mixture was quenched with ice cold water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluted with 30% EtOAc/Hexane) to afford compound DT (800 mg, 1.69 mmol, 59%) as a brown solid, which was as such taken for next step without further purification. LC-MS: 473.2 [M+H]$^+$ at 3.78 RT (75.3% purity).

(R)-2-(2,4-difluorophenyl)-1,1-difluoro-3-(1 H-tetrazol-1-yl)-1-(5-(4-(4-(2-(trifluoromethyl-1H-benzo [d] imidazol-5-yl) piperazin-1-yl) phenyl) pyridin-2-yl) propan-2-ol (35)

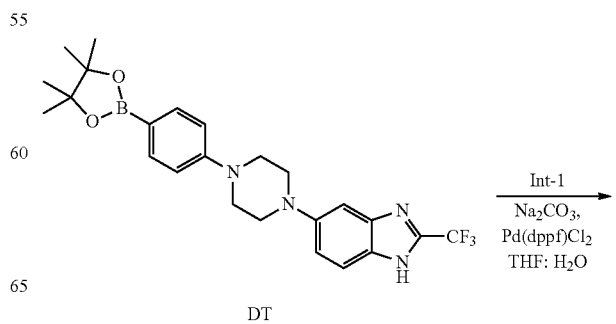

-continued

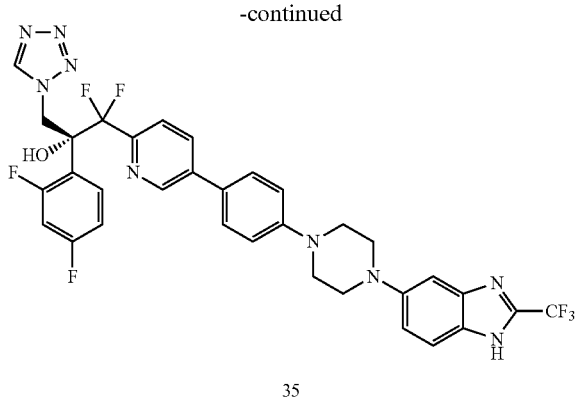

35

To a stirred solution of Int-1 (200 mg, 0.46 mmol) in THF:H2O (4:1, 30 mL) under argon atmosphere were added compound DT (273 mg, 0.46 mmol), sodium carbonate (147 mg, 1.39 mmol) and purged under argon for 20 min at RT. Then Pd(dppf)Cl$_2$ (33.9 mg, 0.04 mmol) was added and the reaction mixture was purged under argon for 10 min at RT. The reaction mixture was stirred at 90° C. for 16 h. The reaction mixture was diluted with ice cold water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 35 (60 mg, 0.08 mmol, 18%) as a brown solid. $^1$H NMR (400 MHz, CDCl$_3$): δ 9.70-9.63 (m, 1H), 8.77 (s, 1H), 8.73 (s, 1H), 7.95 (dd, J=8.2, 2.2 Hz, 1H), 7.88-7.84 (m, 1H), 7.78 (d, J=9.0 Hz, 1H), 7.61 (d, J=8.2 Hz, 1H), 7.52 (d, J=8.7 Hz, 2H), 7.47 (d, J=8.9 Hz, 1H), 7.43-7.34 (m, 1H), 7.25-7.20 (m, 1H), 7.16 (dd, J=9.0, 2.3 Hz, 1H), 7.08 (d, J=8.8 Hz, 2H), 6.99 (d, J=2.0 Hz, 1H), 6.80-6.69 (m, 1H), 6.70-6.62 (m, 1H), 5.66-5.57 (m, 1H), 5.16-5.07 (m, 1H), 3.59-3.45 (m, 4H), 3.43-3.33 (m, 4H) MS (ESI): m/z 698.3 [M+H]$^+$; HPLC: 98.75%; Optical rotation [α]$_D^{20}$: +47.64 (c=0.1% in MeOH).

Example 36

4-(4-(4-(6-(2-cyclopropyl-1,1-difluoro-2-hydroxy-3-(1H-tetrazol-1-yl) propyl) pyridin-3-yl) phenyl) piperazin-1-yl) benzonitrile (36)

2-(5-bromopyridin-2-yl)-1-cyclopropyl-2,2-difluoroethan-1-one (DU)

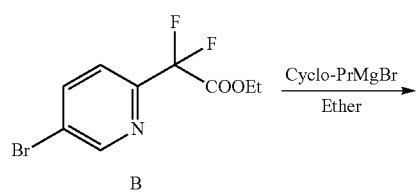

To a stirred solution of ethyl 2-(5-bromopyridin-2-yl)-2,2-difluoroacetate (B; 10 g, 35.7 mmol) in diethylether (250 mL) was added cyclopropyl magnesium bromide (140 mL, 71.42 mmol, 0.5 M in THF) at −78° C., and stirred for 5 h. The reaction mixture was quenched with 1N HCl solution (100 mL) and extracted with EtOAc (2×100 mL). The combined organic extracts were washed with water (100 mL), dried over anhydrous Na$_2$SO$_4$ and concentrated under reduced pressure to obtain the crude. The crude material was purified by silica gel column chromatography (eluent: 5% EtOAc/Hexane) to afford compound DU (8.6 g, 30.82 mmol, 87.7%) as yellow oil. $^1$H NMR (500 MHz, CDCl$_3$): δ 8.72 (s, 1H), 8.00 (dd, J=8.0, 1.9 Hz, 1H), 7.63 (d, J=9.0 Hz, 1H), 2.50-2.43 (m, 1H), 0.27-0.22 (m, 2H), 0.18-0.10 (m, 2H).

5-bromo-2-((2-cyclopropyloxiran-2-yl) difluoromethyl) pyridine (DV)

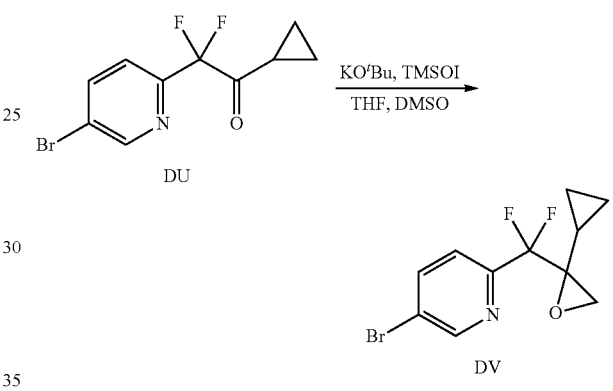

To a stirred solution of TMSOI (7.5 g, 34.20 mmol) and potassium tert-butoxide (3.6 g, 32.71 mmol) in THF:DMSO (3:1, 100 mL) was stirred at RT for 1 h. Then compound DU (8.6 g, 31.15 mmol) in THF (20 mL) was added to the reaction mixture at 0° C. The reaction mixture was stirred at −10° C. for 4 h. The reaction mixture was quenched with 1 N HCl solution (100 mL) and extracted with EtOAc (2×100 mL). The combined organic extracts were washed with brine (100 mL), dried over anhydrous Na$_2$SO$_4$ and concentrated under reduced pressure to obtain the crude. The crude material was purified by silica gel column chromatography (eluent: 10% EtOAc/Hexane) to afford compound DV (5.5 g, 18.96 mmol, 61.1%) as colorless oil. $^1$H NMR (400 MHz, CDCl$_3$): δ 8.72 (s, 1H), 7.93 (dd, J=8.0, 1.9 Hz, 1H), 7.58 (d, J=9.0 Hz, 1H), 3.20-3.17 (m, 1H), 2.63-2.61 (m, 1H), 1.30-1.23 (m, 1H), 0.43-0.40 (m, 1H), 0.39-0.31 (m, 1H), 0.30-0.21 (m, 1H), 0.20-0.12 (m, 1H).

1-(5-bromopyridin-2-yl)-2-cyclopropyl-1,1-difluoro-3-(1H-tetrazol-1-yl) propan-2-ol (DW)

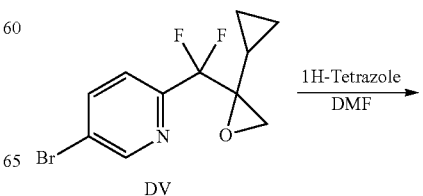

-continued

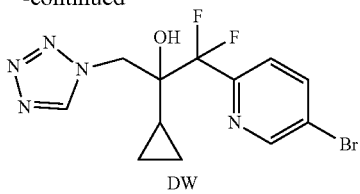

To a stirred solution of compound DV (2.5 g, 0.39 mmol) in DMF (15 mL) were added potassium carbonate (1.19 g, 8.62 mmol) and 1H-tetrazole (905 mg, 12.9 mmol) at RT and stirred at 60° C. for 2 h. The progress of the reaction was monitored by TLC and the reaction mixture was diluted with water (100 mL) and extracted with EtOAc (2×100 mL). The combined organic extracts were washed with water (100 mL), dried over anhydrous Na$_2$SO$_4$ and concentrated under reduced pressure to obtain the crude. The crude material was purified by silica gel column chromatography (eluent: 40% EtOAc/Hexane) to afford compound DW (2.1 g, 5.83 mmol, 67.74%) as a pale yellow solid. $^1$H NMR (500 MHz, DMSO-d$_6$): δ 9.25 (s, 1H), 8.86 (s, 1H), 8.26 (d, J=8.0 Hz, 1H), 7.63 (d, J=9.0 Hz, 1H), 6.00 (s, 1H), 4.99 (d, J=14.5 Hz, 1H), 4.79 (d, J=14.5 Hz, 1H), 0.84-0.81 (m, 1H), 0.03-0.01 (m, 1H), 0.07-0.09 (m, 1H), 0.13-0.16 (m, 1H), 0.59-0.62 (m, 1H).

4-(4-(4-(6-(2-cyclopropyl-1,1-difluoro-2-hydroxy-3-(1H-tetrazol-1-yl) propyl) pyridin-3-yl) phenyl) piperazin-1-yl) benzonitrile (36)

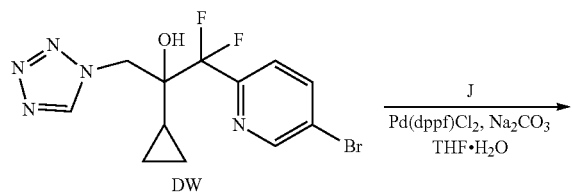

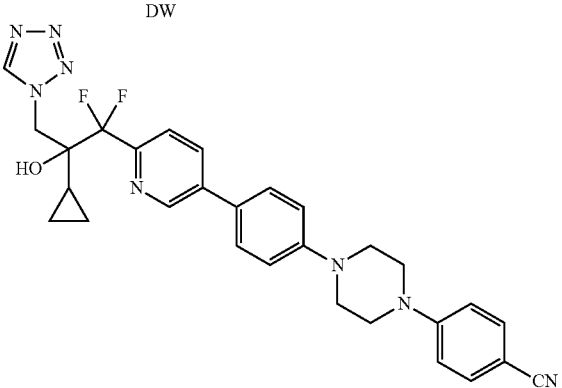

36

To a stirred solution of compound DX (500 mg, 1.16 mmol) in THF:H$_2$O (4:1, 10 mL) under argon atmosphere were added compound J (676 mg, 1.74 mmol) and sodium carbonate (368 mg, 3.48 mmol) at RT. The reaction mixture was purged with argon for 20 min, then Pd(dppf)Cl$_2$ (85 mg, 0.11 mmol) was added and the reaction mixture was purged under argon for 10 min at RT. The reaction mixture was stirred at 80° C. for 16 h. The reaction mixture was quenched with water (20 mL) and extracted with EtOAc (2×20 mL).

The combined organic layers were dried over anhydrous Na$_2$SO$_4$ and concentrated under reduced pressure. The crude material was purified by silica gel column chromatography (eluent: 2% MeOH/CH$_2$Cl$_2$) to afford 36 (250 mg, 0.46 mmol, 39%) as yellow solid. $^1$H NMR (500 MHz, DMSO-d$_6$): δ 9.23 (s, 1H), 8.97 (s, 1H), 8.20 (dd, J=8.2, 1.9 Hz, 1H), 7.77 (d, J=8.1 Hz, 2H), 7.70 (s, 1H), 7.60 (d, J=8.7 Hz, 2H), 7.20-7.11 (m, 4H), 5.97 (s, 1H), 5.02 (d, J=14.7 Hz, 1H), 4.82 (d, J=14.7 Hz, 1H), 3.51-3.49 (m, 4H), 3.41-3.39 (m, 4H), 0.73-0.70 (m, 2H), 0.10-0.02 (m, 1H), 0.90-0.82 (m, 1H), 0.50-0.42 (m, 1H); MS (ESI): m/z 543.7 [M+H]$^+$; HPLC: 99.60%.

Example 37

4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl)-1-(2-hydroxypentan-3-yl) pyridin-2(1H)-one (37)

3-bromopentan-2-one (DZ)

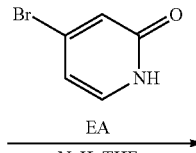

The mixture of pentan-2-one (DY; 1.0 g, 11.6 mmol) in [BIMM]Br$_3$ (2.2 g) under argon atmosphere was stirred at 0° C. for 20 min. The reaction mixture was warmed to RT and stirred for 1 h. The reaction mixture was quenched with ice cold water (50 mL) and extracted with ether (2×50 mL). The combined organic layers were washed with water (50 mL), brine (50 mL), dried over anhydrous Na$_2$SO$_4$ and concentrated under reduced pressure to obtain compound DZ (2.0 g, crude) as yellow syrup which was used in the next step without further purification. $^1$H NMR (500 MHz, CDCl$_3$): δ 4.20-4.18 (m, 1H), 2.37 (s, 3H), 2.11-2.00 (m, 1H), 2.00-1.91 (m, 1H), 1.05 (t, J=7.4 Hz, 3H).

4-bromo-1-(2-oxopentan-3-yl) pyridin-2(1H)-one (EB)

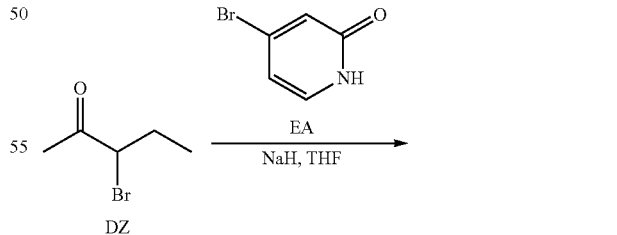

To a stirred solution of compound EA (1.5 g, 9.14 mmol) in THF (20 mL) under argon atmosphere was added sodium hydride (437.7 mg, 18.28 mmol) at RT and stirred for 30 min. Then compound DZ (1.5 g, 9.14 mmol) was added to the reaction mixture and stirred for 16 h. The reaction mixture was diluted with saturated ammonium chloride solution (50 mL) and extracted with EtOAc (2×50 mL). The combined organic layers were washed with water (50 mL), dried over anhydrous Na$_2$SO$_4$ and concentrated under reduced pressure. The crude material was purified by silica gel column chromatography (eluent: 2% MeOH/CH$_2$Cl$_2$) to afford compound EB (1.0 g, 3.89 mmol, 42%) as a brown solid. $^1$H NMR (400 MHz, CDCl$_3$): δ 7.03 (d, J=7.4 Hz, 1H), 6.86 (d, J=2.3 Hz, 1H), 6.40 (dd, J=7.4, 2.1 Hz, 1H), 5.49-5.45 (m, 1H), 2.24 (s, 3H), 2.23-2.15 (m, 1H), 1.84-1.73 (m, 1H), 0.92 (t, J=7.3 Hz, 3H).

4-bromo-1-(2-hydroxypentan-3-yl) pyridin-2(1H)-one (EC)

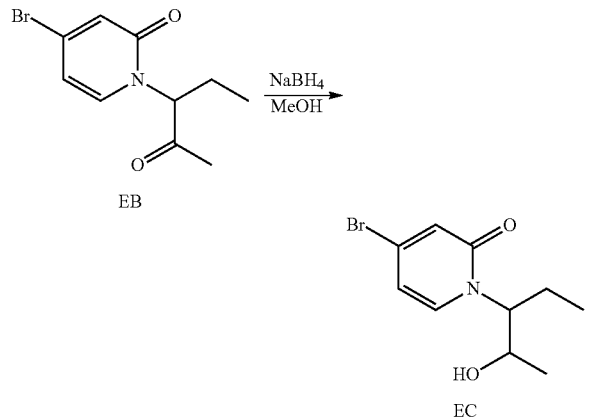

To a stirred solution of compound EB (1.1 g, 4.28 mmol) in MeOH (20 mL) under argon atmosphere was added sodium borohydride (487 mg, 12.84 mmol) at 0° C., and stirred at RT for 3 h. The progress of the reaction was monitored by TLC. The reaction mixture was quenched with ice cold water (30 mL) and extracted with CH$_2$Cl$_2$ (2×30 mL). The combined organic layers were washed with water (30 mL), dried over anhydrous Na$_2$SO$_4$ and concentrated under reduced pressure. The crude material was purified by silica gel column chromatography (eluent: 5% MeOH CH$_2$Cl$_2$) to afford compound EC (500 mg, 1.93 mmol 45%) as a pale yellow syrup and as such taken for next step. LC-MS: 259.9 [M+H]$^+$ at 1.78 RT (97.6% purity).

4-(4-(4-bromophenyl) piperazin-1-yl)-1-(2-hydroxypentan-1-yl) pyridin-2(1H)-one (ED)

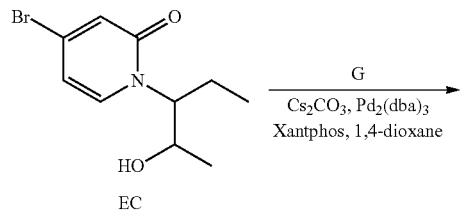

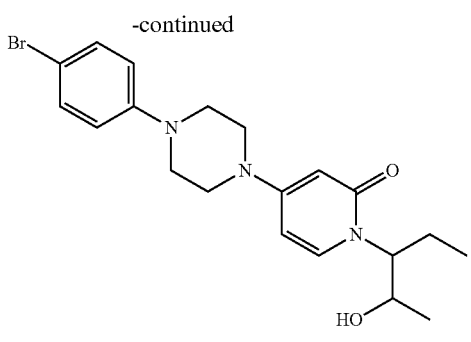

To a stirred solution of compound EC (450 mg, 1.73 mmol) in 1,4-dioxane (20 mL) under argon atmosphere were added G (418 mg, 1.73 mmol), cesium carbonate (1.13 g, 3.47 mmol) and purged under argon for 20 min at RT. Then Pd$_2$(dba)$_3$ (79.1 mg, 0.08 mmol) was added and the reaction mixture was purged under argon for 15 min at RT. The reaction mixture was stirred at 110° C. for 16 h. The reaction mixture was diluted with ice cold water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 5% MeOH/CH$_2$Cl$_2$) to afford compound ED (300 mg, 0.71 mmol, 41%) as a pale yellow solid. $^1$H NMR (400 MHz, CDCl$_3$): δ 7.37 (d, J=9.0 Hz, 2H), 7.12 (brs, 1H), 6.80 (d, J=9.0 Hz, 2H), 5.97 (dd, J=7.8, 2.8 Hz, 1H), 5.79 (d, J=2.9 Hz, 1H), 4.01 (dd, J=11.6, 6.6 Hz, 1H), 3.51-3.44 (m, 4H), 3.31-3.22 (m, 4H), 1.96-1.91 (m, 1H), 1.20-1.17 (m, 2H), 1.15 (d, J=6.4 Hz, 3H), 0.89 (t, J=7.4 Hz, 3H).

1-(2-hydroxypentan-3-yl)-4-(4-(4-(4,4,5,5-tetramethyl-1,3,2-dioxaborolan-2-yl) phenyl) piperazin-1-yl) pyridin-2(1H)-one (EE)

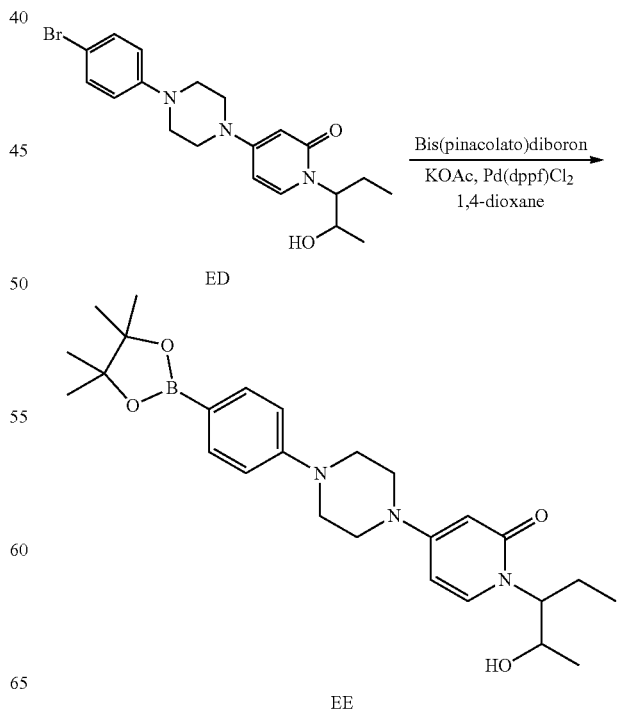

To a stirred solution of compound ED (300 mg, 0.71 mmol) in 1,4-dioxane (10 mL) under argon atmosphere were added bis(pinacolato)diboron (290 mg, 1.14 mmol) and potassium acetate (209 mg, 2.14 mmol) at RT. The reaction mixture was purged with argon for 20 min, then Pd(dppf)Cl$_2$ (52.1 mg, 0.07 mmol) was added and the reaction mixture was purged under argon for 5 min at RT. The reaction mixture was stirred at 110° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 2% MeOH/CH$_2$Cl$_2$) to afford compound EE (180 mg, 0.38 mmol, 53%) as a brown solid. LC-MS: 468.3 [M+H]$^+$ at 3.22 RT (68.9% purity).

4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl)-1-(2-hydroxypentan-3-yl) pyridin-2(1H-one (37)

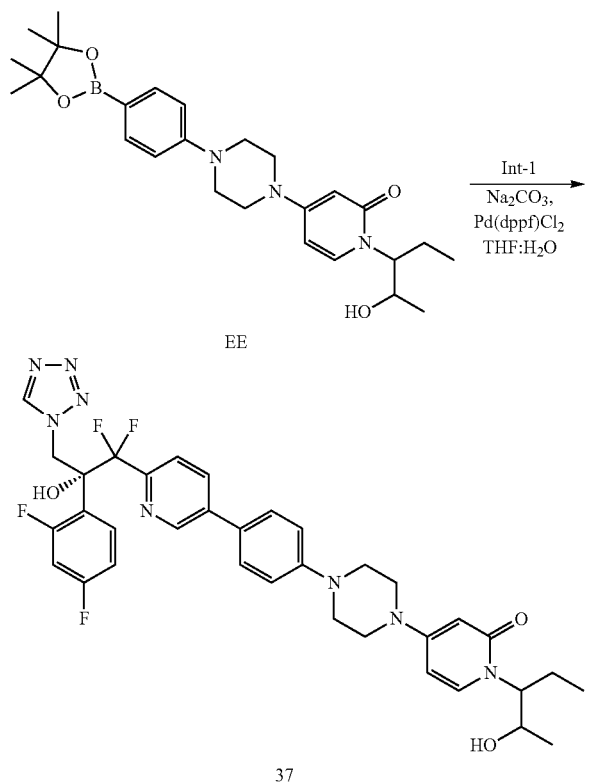

To a stirred solution of Int-1 (180 mg, 0.38 mmol) in THF:H2O (4:1, 30 mL) under argon atmosphere were added compound EE (165 mg, 0.38 mmol), sodium carbonate (122 mg, 1.15 mmol) and purged under argon for 20 min at RT. Then Pd(dppf)Cl$_2$ (28 mg, 0.04 mmol) was added and the reaction mixture was purged argon for 10 min at RT. The reaction mixture was stirred at 90° C. for 12 h. The progress of the reaction was monitored by TLC. The reaction mixture was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) to afford 37 (30 mg, 0.04 mmol, 11%) as a pale yellow solid. $^1$H NMR (400 MHz, CD$_3$OD): δ 9.04 (s, 1H), 8.80 (s, 1H), 8.08 (dd, J=8.3, 2.1 Hz, 1H), 7.63 (d, J=8.9 Hz, 3H), 7.54 (d, J=7.9 Hz, 1H), 7.38-7.31 (m, 1H), 7.12 (d, J=8.8 Hz, 2H), 6.91-6.88 (m, 1H), 6.79-6.73 (m, 1H), 6.40 (d, J=7.3 Hz, 1H), 5.86 (s, 1H), 5.77 (d, J=14.4 Hz, 1H), 5.19 (d, J=14.4 Hz, 1H), 4.05 (brs, 1H), 3.65-3.58 (m, 4H), 3.45-3.40 (m, 4H), 3.37-3.35 (m, 1H), 1.88 (brs, 2H), 1.08 (d, J=6.4 Hz, 3H), 0.85 (t, J=7.3 Hz, 3H); MS (ESI): m/z 693.8 [M+H]$^+$; HPLC: 93.40%; Optical rotation [α]$_D^{19}$: +41.96 (c=0.1% in MeOH).

Examples 38, 38(−), and 38(+)

4-(4-(4-(4-(6-(1,1-difluoro-2-(2-fluorophenyl)-2-hydroxy-3-1H-tetrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (38)

2-(5-bromopyridin-2-yl)-2,2-difluoro-1-(2-fluorophenyl) ethan-1-one (EG)

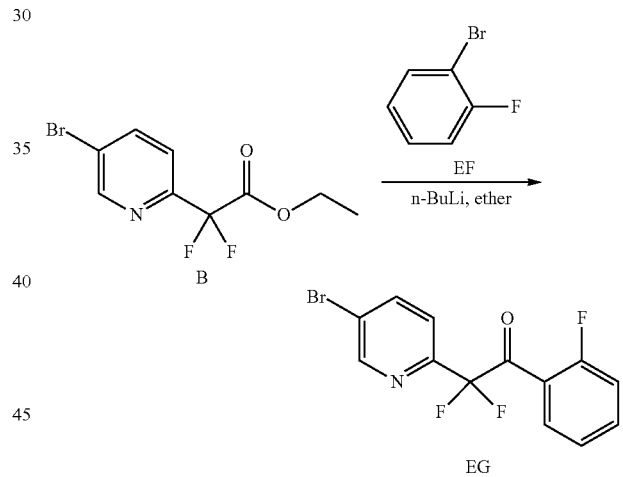

To a stirred solution of 1-bromo-2-fluorobenzene EF (3.43 g, 19.64 mmol) in diethyl ether (25 mL) was added n-BuLi (12.2 mL, 19.64 mmol, 1.6 Min Hexanes) at −78° C. under argon atmosphere and stirred for 1 h. Then compound B (5 g, 17.85 mmol) in diethyl ether (25 mL) was added to reaction mixture at −78° C., and stirred for 1 h. The progress of the reaction was monitored by TLC. The reaction was quenched with saturated ammonium chloride solution (200 mL) and extracted with ethyl acetate (3×200 mL). The combined organic layers were dried over anhydrous Na$_2$SO$_4$ and concentrated under reduced pressure. The crude material was purified by silica gel column chromatography (eluent: 2% EtOAc/Hexane) to afford compound EG (2.9 g, 8.84 mmol, 50%) as pale yellow liquid which was as such taken for next step. LC-MS: m/z 329.8 [M+H]r at 2.29 RT (30.19% purity).

5-bromo-2-(difluoro(2-(2-fluorophenyl) oxiran-2-yl) methyl) pyridine (EH)

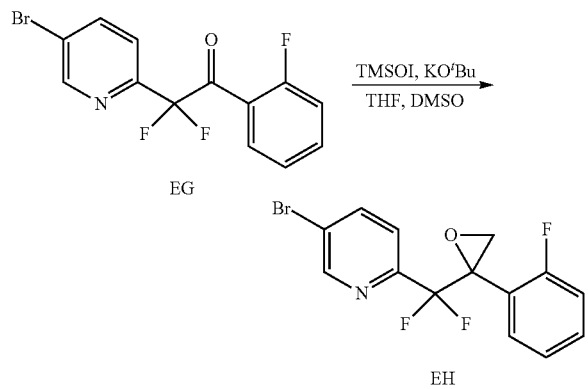

To a stirred solution of TMSOI (2.1 g, 9.69 mmol) and potassium tert-butoxide (1.1 g, 9.69 mmol) in THF:DMSO (3:1, 40 mL) was stirred at RT for 1 h. Then compound EG (2.9 g, 8.81 mmol) was added to the reaction mixture at 0° C. The reaction mixture was warmed to RT and stirred for 3 h. The reaction mixture was quenched with water (100 mL) and extracted with EtOAc (2×100 mL). The combined organic extracts were dried over anhydrous $Na_2SO_4$ and concentrated under reduced pressure. The crude material was purified by silica gel column chromatography (eluent: 2% EtOAc/Hexane) to afford compound EH (1.4 g, 4.09 mmol, 46%) as colorless oil. $^1$H NMR (500 MHz, $CDCl_3$): δ 8.72 (s, 1H), 7.87 (dd, J=8.4, 2.0 Hz, 1H), 7.40-7.30 (m, 3H), 7.10 (t, J=7.5 Hz, 1H), 6.99 (t, J=9.1 Hz, 1H), 3.46 (d, J=4.9 Hz, 1H), 3.00 (d, J=2.6 Hz, 1H).

1-(5-bromopyridin-2-yl)-1,1-difluoro-2-(2-fluorophenyl)-3-(1H-tetrazol-1-yl) propan-2-ol (E)

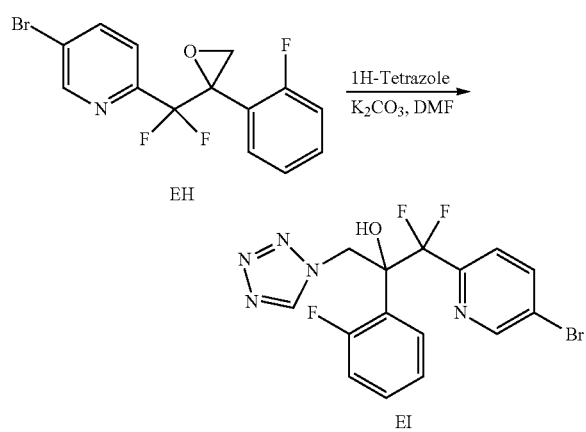

To a stirred solution of compound EH (1.4 g, 4.06 mmol) in DMF (15 mL) were added potassium carbonate (842 mg, 6.10 mmol) and 1H-Tetrazole (570 mg, 8.13 mmol) at RT. The reaction mixture was stirred at 60° C. for 16 h. The reaction mixture was diluted with water (50 mL) and extracted with EtOAc (2×50 mL). The combined organic extracts were washed with water (50 mL), dried over anhydrous $Na_2SO_4$ and concentrated under reduced pressure to obtain the crude. The crude material was purified by silica gel column chromatography (eluent: 30% EtOAc/Hexane) to afford compound EI (600 mg, 1.44 mmol, 36%) as a white solid. $^1$H NMR (400 MHz, $CDCl_3$): δ 8.74 (s, 1H), 8.63 (s, 1H), 7.91 (dd, J=8.3, 2.1 Hz, 1H), 7.42 (d, J=8.4 Hz, 1H), 7.32-7.16 (m, 2H), 7.05-6.90 (m, 2H), 6.72 (s, 1H), 5.65 (d, J=14.3 Hz, 1H), 5.17 (d, J=14.4 Hz, 1H).

2-((2S,3S)-2-(benzyloxy) pentan-3-yl)-4-(4-(4-(6-(1,1-difluoro-2-(2-fluorophenyl)-2-hydroxy-3-(1H-tetrazol-1-yl) propyl) pyridin-3-yl) phenyl) piperazin-1-yl) phenyl)-2,4-dihydro-3H-1,2,4-triazol-3-one (EJ)

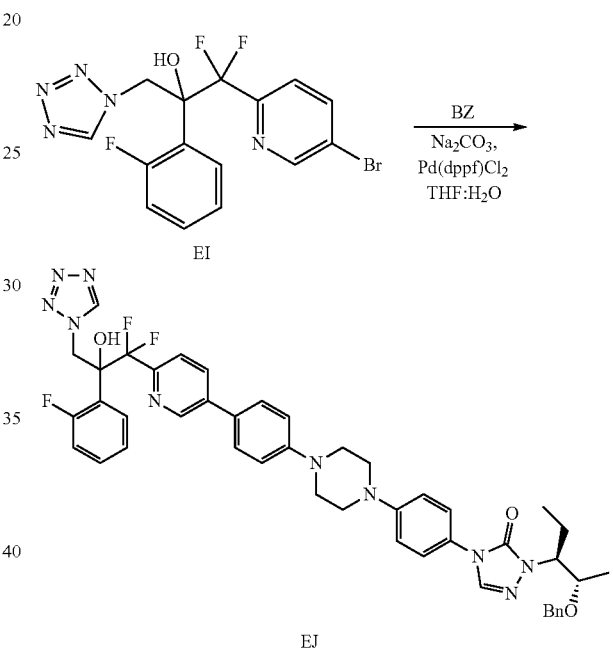

To a stirred solution of compound EI (400 mg, 0.96 mmol) in THF:H2O (4:1, 10 mL) under argon atmosphere were added compound BZ (722 mg, 1.15 mmol), sodium carbonate (307 mg, 2.89 mmol) and purged under argon for 20 min at RT. Then $Pd(dppf)Cl_2$ (70.6 mg, 0.09 mmol) was added and the reaction mixture was purged under argon for 10 min at RT. The reaction mixture was stirred at reflux for 16 h. The reaction mixture was diluted with water (30 mL) and extracted with EtOAc (2×30 mL. The combined organic extracts were dried over anhydrous $Na_2SO_4$ and concentrated under reduced pressure. The crude material was purified by silica gel column chromatography (eluent: 2% MeOH/$CH_2Cl_2$) to afford compound EJ (500 mg, 0.60 mmol, 62%) as a pale brown solid. $^1$H NMR (400 MHz, DMSO-$d_6$): δ 9.13 (s, 1H), 8.92 (d, J=2.1 Hz, 1H), 8.32 (s, 1H), 8.15 (dd, J=8.3, 2.3 Hz, 1H); 7.70 (d, J=8.9 Hz, 2H), 750-7.43 (m, 3H), 7.37-7.28 (m, 2H), 7.25-7.11 (t, 10H), 7.05-6.98 (m, 1H), 5.75 (s, 1H), 5.71 (d, J=14.6 Hz, 1H), 5.11 (d, =14.6 Hz, 1H), 4.54 (d, J=11.8 Hz, 1H), 4.27 (d, J=11.8 Hz, 1H), 4.01-3.97 (m, 1H), 3.78-3.70 (m, 1H), 3.42-3.36 (m, 8H), 1.83-1.66 (m, 2), 1.23 (d, J=6.1 Hz, 3H), 0.79 (t, J=7.3 Hz, 3H).

4-(4-(4-(4-(6-(1,1-difluoro-2-(2-fluorophenyl)-2-hydroxy-3-(1H-tetrazol-1-yl) propyl) pyridin-3-yl) phenyl) piperazin-1-yl) phenyl)-2-((2S,3S)-2-hydroxyphenyl-3-yl)-2,4-dihydro-3H-1,2,4-triazol-3-one (38)

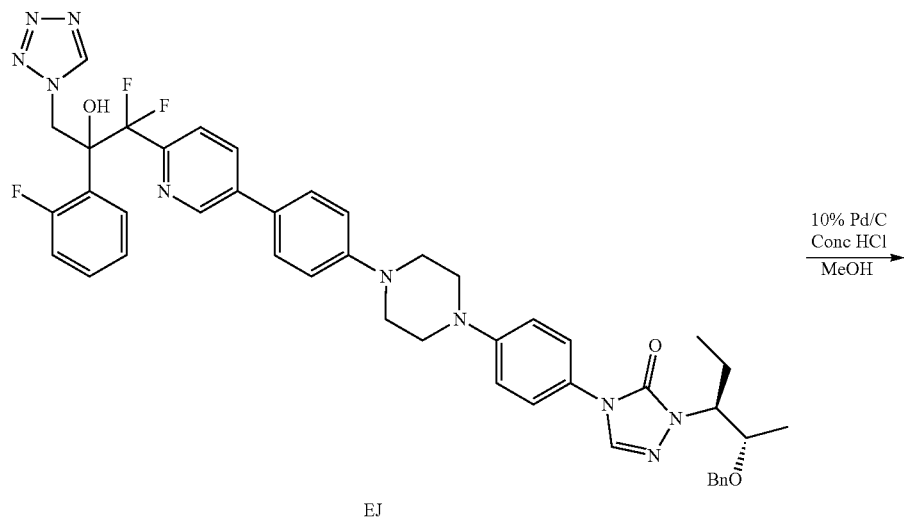

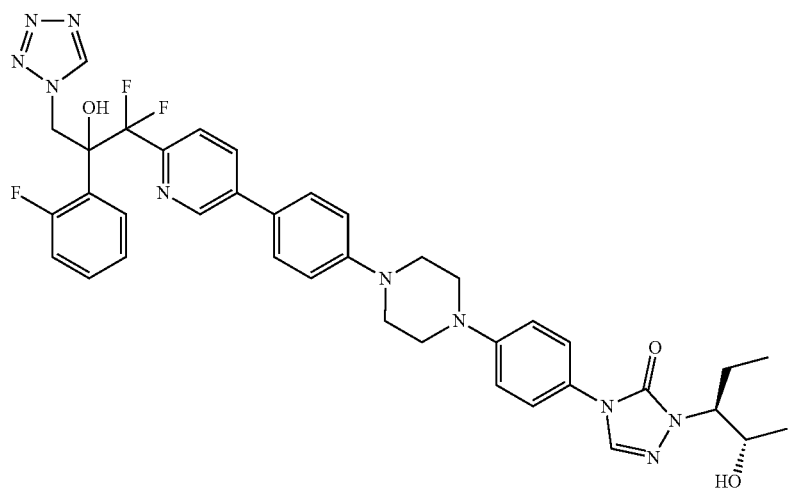

To a stirred solution of compound EJ (2.05 g, 2.46 mmol) in MeOH (35 mL) under argon atmosphere were added 10% Pd/C (495 mg) and 5N HCl (2.5 mL) at RT. The reaction mixture was stirred at RT for 16 h under hydrogen atmosphere (50 psi). The progress of the reaction was monitored by TLC, the reaction mixture was filtered and the filtrate was diluted with 10% sodium carbonate solution (20 mL) and extracted with 10% MeOH/CH$_2$Cl$_2$ (2×20 mL). The combined organic layers were dried over anhydrous Na$_2$SO$_4$ and concentrated under reduced pressure. The crude material was purified by silica gel column chromatography (eluent: 3% MeOH/CH$_2$Cl$_2$) to afford 38 (1.45 g, 0.19 mmol, 46%) as an off-white solid. $^1$H NMR (400 MHz, DMSO-d$_6$): δ 9.12 (s, 1H), 8.91 (d, J=2.0 Hz, 1H), 8.33 (s, 1H), 8.15 (dd, J=8.2, 2.2 Hz, 1H), 7.70 (d, J=8.8 Hz, 2H), 7.53 (d, J=9.0 Hz, 2H), 7.45 (d, J=8.3 Hz, 1H), 7.37-7.28 (m, 2H), 7.19 (s, 1H), 7.17-7.09 (m, 5H), 7.04-6.98 (m, 1H), 5.71 (d, J=14.6 Hz, 1H), 5.11 (d, J=14.6 Hz, 1H), 4.66 (d, J=4.9 Hz, 1H), 3.82-3.79 (m, 2H), 3.49-3.33 (m, 8H), 1.74-1.61 (m, 2H), 1.12 (d, J=5.9 Hz, 3H), 0.74 (t, J=7.3 Hz, 3H); MS (ESI): m/z 741.7 [M+H]$^+$; HPLC: 97.33%.

Chiral Preparative HPLC Details

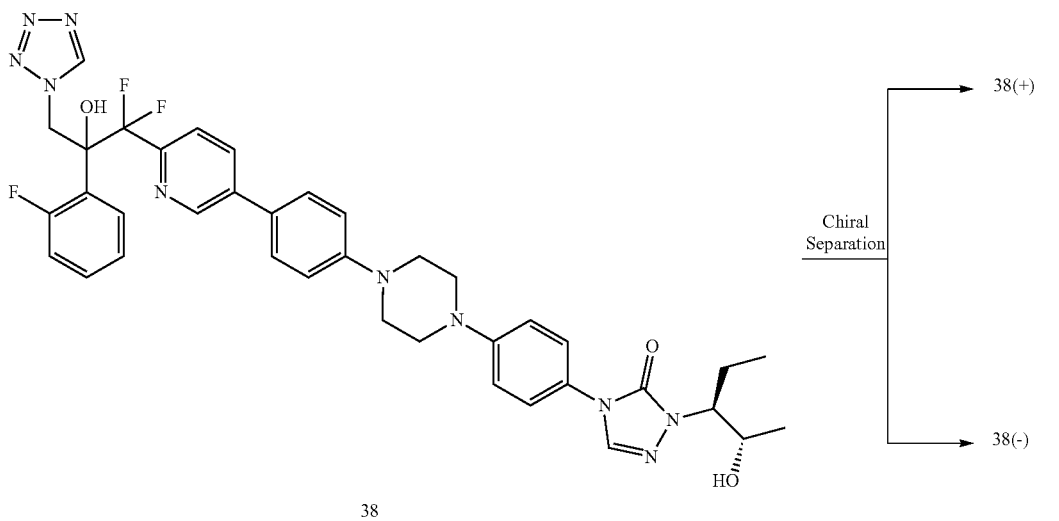 [SMILES: CC[C@@H]([C@H](C)O)n1ncn(-c2ccc(N3CCN(c4ccc(-c5ccc(C(F)(F)C(O)(Cn6cnnn6)c6ccccc6F)nc5)cc4)CC3)cc2)c1=O]

38

38 (700 mg of, 0.94 mmol) was separated by normal-phase preparative high performance liquid chromatography (Chiralpak IA®, 250×20 mm, 5μ; using 0.1% DEA in n-Hexane:(B) CH$_2$Cl$_2$:MeOH (50:50) (35:65); Flow rate: 20 mL/min) to obtain 38(−) (220 mg) and 38(+) (220 mg).

Analytical Data for 38(−):

$^1$H NMR (500 MHz, DMSO-d$_6$): δ 9.11 (s, 1H), 8.91 (s, 1H), 8.32 (s, 1H), 8.14 (dd, J=8.2, 1.6 Hz, 1H), 7.69 (d, J=8.7 Hz, 2H), 7.52 (d, J=9.0 Hz, 2H), 7.44 (d, J=8.4 Hz, 1H), 7.36-7.27 (m, 2H), 7.18 (s, 1H), 7.16-7.07 (m, 5H), 7.01 (t, J=7.5 Hz, 1H), 5.70 (d, J=14.7 Hz, 1H), 5.10 (d, J=14.7 Hz, 1H), 4.65 (d, J=4.6 Hz, 1H), 3.86-3.73 (m, 2H), 3.42-3.31 (m, 8H), 1.72-1.68 (m, 2H), 1.11 (d, J=5.8 Hz, 3H), 0.73 (t, J=7.2 Hz, 3H); MS (ESI): m/z 741.4 [M+H]$^+$; HPLC: 99.06%; Chiral HPLC Purity: 98.89%, R$_t$=11.04 min (CHIRALPAK-IA®, 250×4.6 mm, 5μ; mobile phase (A) 0.1% DEA in n-Hexane:(B) CH$_2$Cl$_2$:MeOH (50:50) (35:65); flow Rate: 1.0 mL/min); Optical rotation [α]$_D^{20}$: −50.1 (c=0.1% in MeOH).

Analytical Data for 38(+):

$^1$H NMR (400 MHz, DMSO-d$_6$): δ 9.12 (s, 1H), 8.91 (d, J=2.0 Hz, 1H), 8.33 (s, 1H), 8.15 (dd, J=8.2, 2.2 Hz, 1H), 7.70 (d, J=8.8 Hz, 2H), 7.53 (d, J=9.0 Hz, 2H), 7.45 (d, J=8.3 Hz, 1H), 7.37-7.28 (m, 2H), 7.19 (s, 1H), 7.17-7.09 (m, 5H), 7.04-6.98 (m, 1H), 5.71 (d, J=14.6 Hz, 1H), 5.11 (d, J=14.6 Hz, 1H), 4.66 (d, J=4.9 Hz, 1H), 3.82-3.79 (m, 2H), 3.49-3.33 (m, 8H), 1.74-1.61 (m, 2H), 1.12 (d, J=5.9 Hz, 3H), 0.74 (t, J=7.3 Hz, 3H); MS (ESI): m/z 739.5 [M−H]$^−$; HPLC: 99.54%; Chiral HPLC Purity: 99.59%, R$_t$=15.92 min (CHIRALPAK-IA®, 250×4.6 mm, 5μ; mobile phase (A) 0.1% DEA in n-Hexane:(B) CH$_2$Cl$_2$:MeOH (50:50) (35:65); flow Rate: 1.0 mL/min); Optical rotation [α]$_D^{20}$: +50.01 (c=0.1% in MeOH)

Example 39

1-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl) propan-1-ol (39)

1-(4-(4-(4-bromophenyl) piperazin-1-yl) phenyl) propan-1-ol (EK)

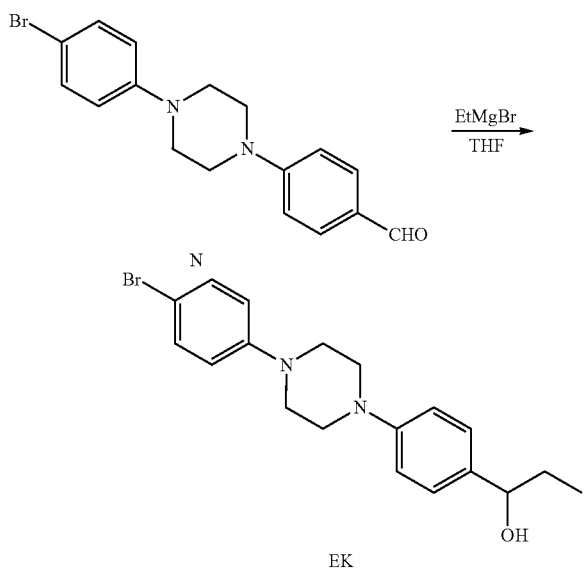

EK

To a stirred solution of compound N (300 mg, 0.86 mmol) in THF (20 mL) under argon atmosphere was added ethyl magnesium bromide (1.3 mL, 1.30 mmol, 1.0 M in THF) at 0° C. The reaction mixture was warmed to RT and stirred for 1 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous $Na_2SO_4$ and concentrated under reduced pressure. The crude material was purified by silica gel column chromatography (eluent: 10-20% EtOAc/Hexane) to afford compound EK (230 mg, 0.61 mmol, 70.5%) as a yellow solid. $^1$H NMR (500 MHz, $CDCl_3$): δ 7.37 (d, J=9.0 Hz, 2H), 7.28 (s, 2H), 6.96 (d, J=8.7 Hz, 2H), 6.84 (d, J=9.0 Hz, 2H), 4.57-4.52 (m, 1H), 3.32 (d, J=4.6 Hz, 8H), 1.87-1.74 (m, 1H), 1.71 (d, J=3.5 Hz, 1H), 0.91 (t, J=7.4 Hz, 3H).

1-(4-(4-(4-(4,4,5,5-tetramethyl-1,3,2-dioxaborolan-2-yl) phenyl) piperazin-1-yl) phenyl) propan-1-ol (EL)

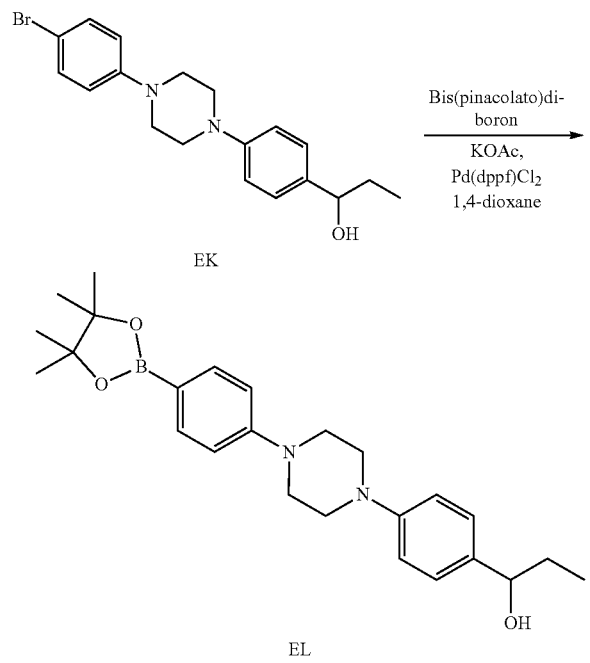

To a stirred solution of compound EK (230 mg, 0.61 mmol) in 1,4-dioxane (20 mL) under argon atmosphere were added bis(pinacolato)diboron (249 mg, 0.98 mmol) and potassium acetate (174 mg, 1.83 mmol) at RT. The reaction mixture was purged with argon for 20 min, then $Pd(dppf)Cl_2$ (44 mg, 0.06 mmol) was added and the reaction mixture was purged under argon for 5 min at RT. The reaction mixture was stirred at 100° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 10-40% EtOAc/Hexane) to afford compound EL (120 mg, 0.28 mmol, 35%) as an off-white solid. $^1$H NMR (500 MHz, $CDCl_3$): δ 7.73 (d, J=8.7 Hz, 2H), 7.28 (s, 2H) 6.95 (dd, J=8.5, 6.5 Hz, 4H), 4.55-4.52 (m, 1H), 3.44-3.30 (m, 8H), 1.89-1.72 (m, 1H), 1.71 (d, J=3.5 Hz, 2H), 1.33 (s, 12H), 0.91 (t, J=7.5 Hz, 3H).

1-((4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl) propan-1-ol (39)

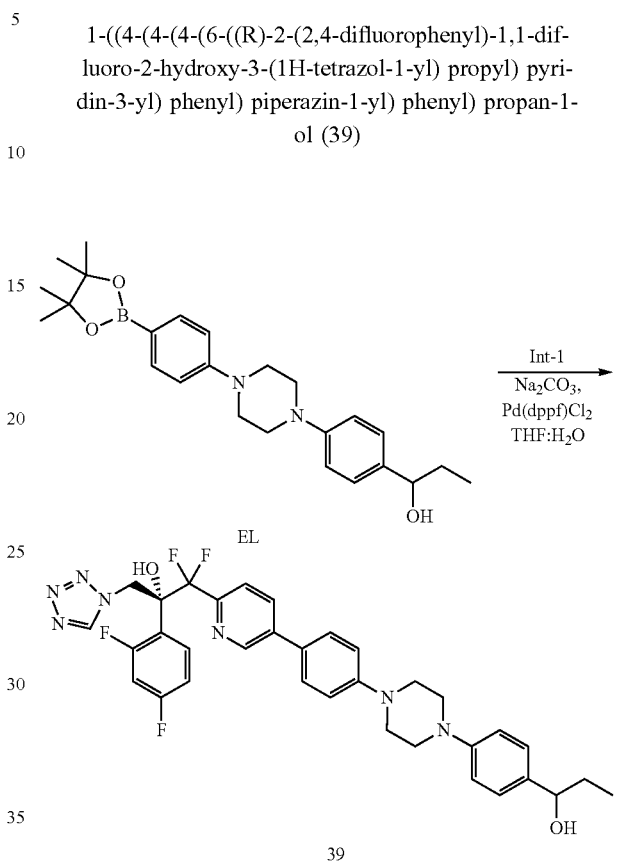

To a stirred solution of Int-1 (120 mg, 0.27 mmol) in THF:H2O (4:1, 25 mL) under argon atmosphere were added compound EL (120 mg, 0.30 mmol), sodium carbonate (88 mg, 0.83 mmol) and purged under argon for 15 min at RT. Then $Pd(dppf)Cl_2$ (20 mg, 0.02 mmol) was added and the reaction mixture was purged under argon for 10 min at RT. The reaction mixture was stirred at 70° C. for 8 h. The progress of the reaction was monitored by TLC. The reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 0-2% $MeOH/CH_2Cl_2$) followed by preparative HPLC to afford 39 (55 mg, 0.08 mmol, 30%) as an off-white solid. $^1$H NMR (400 MHz, $CDCl_3$): δ 8.79 (s, 1H), 8.76 (d, J=2.0 Hz, 1H), 7.97 (dd, J=8.2, 2.2 Hz, 1H), 7.89 (s, 1H), 7.63 (d, J=8.3 Hz, 1H), 7.54 (d, J=8.9 Hz, 2H), 7.44-7.38 (m, 1H), 7.31 (d, J=8.5 Hz, 2H), 7.09 (d, J=8.9 Hz, 2H), 7.00 (d, J=8.8 Hz, 2H), 6.83-6.76 (m, 1H), 6.72-6.66 (m, 1H), 5.65 (d, J=14.2 Hz, 1H), 5.13 (d, J=14.2 Hz, 1H), 4.60-4.54 (m, 1H), 3.50-3.44 (m, 4H), 3.41-3.35 (m, 4H), 1.90-1.72 (m, 3H), 0.94 (t, J=7.4 Hz, 3H); MS (ESI): m/z 646.5 [M–H]$^-$; HPLC: 98.65%; Optical rotation $[α]_D^{20}$: 149.0 (c=0.1% in MeOH).

Example 40

1-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-methylpropan-1-ol (40)

1-(4-(4-(4-bromophenyl) piperazin-1-yl) phenyl)-2-methylpropan-1-ol (EM)

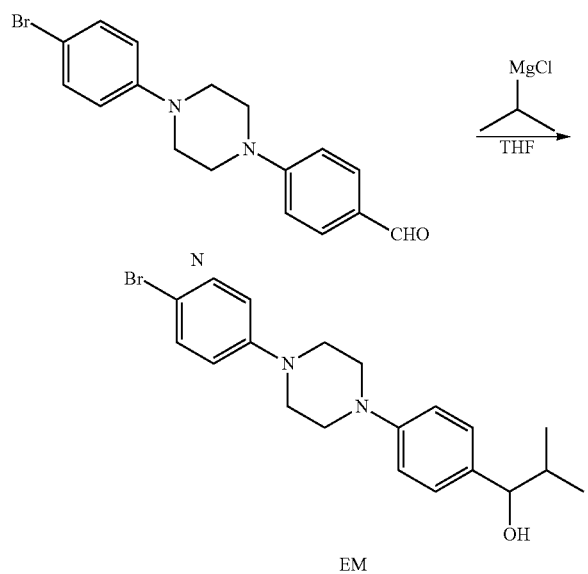

To a stirred solution of compound N (300 mg, 0.86 mmol) in THF (20 mL) under argon atmosphere was added isopropyl magnesium chloride (0.65 mL, 1.30 mmol, 2.0 M in THF) at 0° C. The reaction mixture was stirred at RT for 1 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous $Na_2SO_4$ and concentrated under reduced pressure. The crude material was purified by silica gel column chromatography (eluent: 30% EtOAc/Hexane) to afford compound EM (270 mg, 0.69 mmol, 80%) as a white solid. $^1$H NMR (500 MHz, $CDCl_3$): δ 7.37 (d, J=9.0 Hz, 2H), 7.24 (d, J=8.4 Hz, 2H), 6.94 (d, J=8.7 Hz, 2H), 6.84 (d, J=9.0 Hz, 2H), 4.29 (d, J=6.9 Hz, 1H), 3.32 (d, J=4.3 Hz, 8H), 1.98-1.94 (ml, 1H), 1.72 (brs, 1H), 1.01 (d, J=6.7 Hz, 3H), 0.78 (d, J=6.7 Hz, 3H).

2-methyl-1-(4-(4-(4-(4,4,5,5-tetramethyl-1,3,2-dioxaborolan-2-yl) phenyl) piperazin-1-yl) phenyl) propan-1-ol (EN)

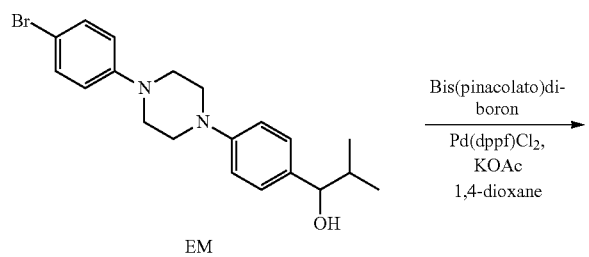

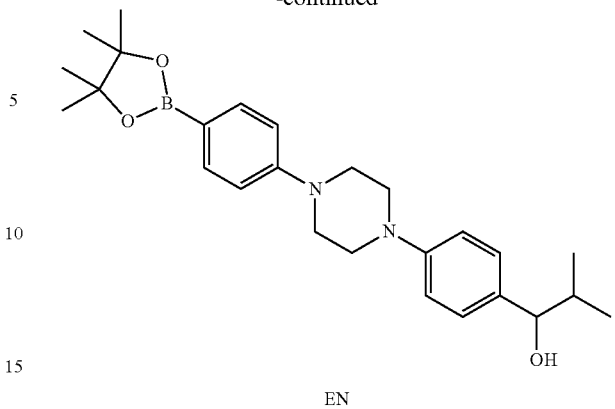

To a stirred solution of compound EM (270 mg, 0.69 mmol) in 1,4-dioxane (30 mL) under argon atmosphere were added bis(pinacolato)diboron (281 mg, 1.11 mmol) and potassium acetate (204 mg, 2.08 mmol) at RT. The reaction mixture was purged with argon for 20 min, then $Pd(dppf)Cl_2$ (50 mg, 0.07 mmol) was added and the reaction mixture was purged under argon for 5 min at RT. The reaction mixture was stirred at 110° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 30% EtOAc/Hexane) to afford compound EN (150 mg, 0.34 mmol, 50%) as an off-white solid which was as such taken for next step. LC-MS: 437.3 $[M+H]^+$ at 2.97 RT (76.6% purity).

1-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-methylpropan-1-ol (40)

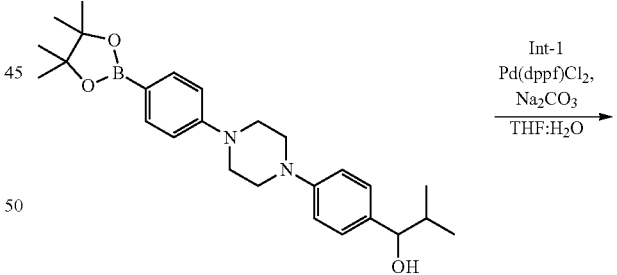

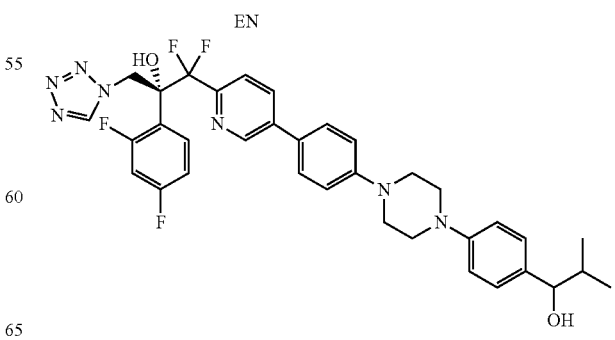

To a stirred solution of Int-1 (120 mg, 0.27 mmol) in THF:H2O (4:1, 20 mL) under argon atmosphere were added compound EN (145 mg, 0.33 mmol), sodium carbonate (88 mg, 0.83 mmol) and purged under argon for 15 min at RT. Then Pd(dppf)Cl$_2$ (20 mg, 0.03 mmol) was added and the reaction mixture was purged under argon for 10 min at RT. The reaction mixture was stirred at 80° C. for 4 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 70% EtOAc/Hexane) to afford 40 (60 mg, 0.09 mmol, 32%) as an off-white solid. $^1$H NMR (400 MHz, DMSO-d$_6$): δ 9.15 (s, 1H), 8.91 (s, 1H), 8.17 (dd, J=8.3, 2.3 Hz, 1H), 7.70 (d, J=8.8 Hz, 2H), 7.48 (d, J=8.2 Hz, 1H), 7.32-7.25 (m, 2H), 7.23-7.10 (m, 5H), 6.98-6.84 (m, 3H), 5.67 (d, J=14.7 Hz, 1H), 5.11 (d, J=14.7 Hz, 1H), 4.88 (d, J=4.4 Hz, 1H), 4.14 (dd, J=6.1, 4.1 Hz, 1H), 3.44-3.33 (m, 4H), 3.31-3.21 (m, 4H), 1.83-1.66 (m, 1H), 0.86 (d, J=6.7 Hz, 3H), 0.72 (d, J=6.8 Hz, 3H); MS (ESI): m/z, 662.3 [M+H]$^+$; HPLC: 98.32%; Optical rotation [α]$_D^{20}$: +52.0 (c=0.1% in MeOH).

Example 41

1-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-3-methylbutan-1-ol (41)

1-(4-(4-(4-bromophenyl) piperazin-1-yl) phenyl)-3-methylbutan-1-ol (EO)

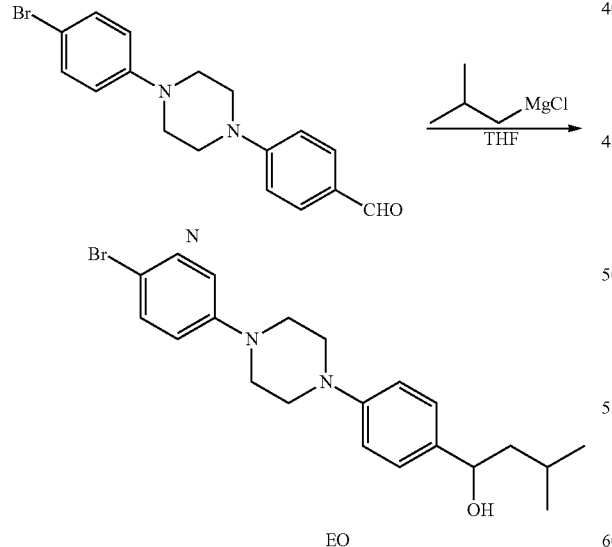

To a stirred solution of compound N (300 mg, 0.86 mmol) in THF (0 mL) under argon atmosphere was added isobutyl magnesium chloride (0.65 mL, 1.30 mmol, 2.0 M in diethyl ether) at 0° C. The reaction mixture was stirred at RT for 1 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous Na$_2$SO$_4$ and concentrated under reduced pressure. The crude material was purified by silica gel column chromatography (eluent: 30% EtOAc/Hexane) to afford compound EO (250 mg, 0.62 mmol, 71%) as yellow solid. $^1$H NMR (400 MHz, CDCl$_3$): δ 7.37 (d, J=9.0 Hz, 2H), 7.28 (d, J=8.5 Hz, 2H), 6.95 (d, J=8.8 Hz, 2H), 6.84 (d, J=9.0 Hz, 2H), 4.70-4.68 (m, 1H), 3.37-3.23 (m, 8H), 1.79-1.62 (m, 3H), 1.54-1.49 (m, 1H), 0.94 (dd, J=6.5, 3.8 Hz, 6H).

3-methyl-1-(4-(4-(4-(4,4,5,5-tetramethyl-1,3,2-dioxaborolan-2-yl) phenyl) piperazin-1-yl) phenyl) butan-1-ol (EP)

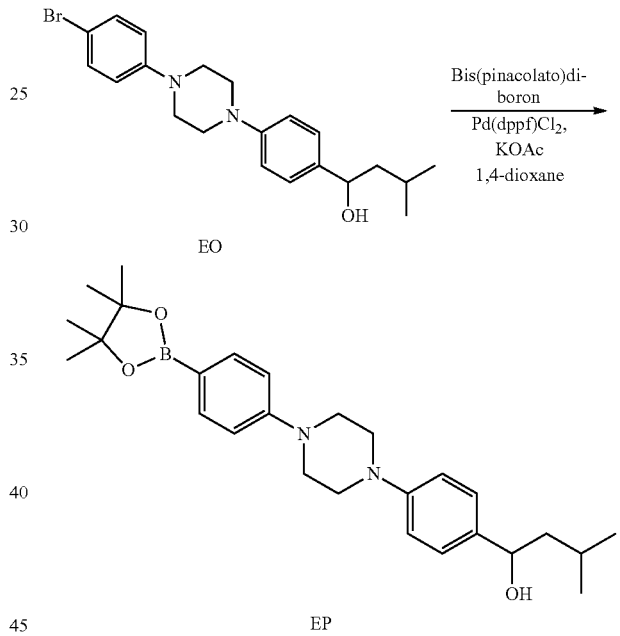

To a stirred solution of compound EO (250 mg, 0.62 mmol) in 1,4-dioxane (30 mL) under argon atmosphere were added bis(pinacolato)diboron (260 mg, 1.03 mmol) and potassium acetate (189 mg, 1.93 mmol) at RT. The reaction mixture was purged with argon for 20 min, then Pd(dppf)Cl$_2$ (47 mg, 0.06 mmol) was added and the reaction mixture was purged under argon for 5 min at RT. The reaction mixture was stirred at 110° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 30% EtOAc/Hexane) to afford compound EP (180 mg, 0.40 mmol, 62%) as an off-white solid which was as such taken for next step. LC-MS: 451.3 [M+H]$^+$ at 4.21 RT (94.6% purity).

1-(4-(4-(4-(6-((R)-2-(2,4-difluorophenyl-1,1-difluoro-2-hydroxy-3-(1H-tetrazol-1-yl) propyl) pyridin-3-yl) phenyl) piperazin-1-yl) phenyl)-3-methylbutan-1-ol (41)

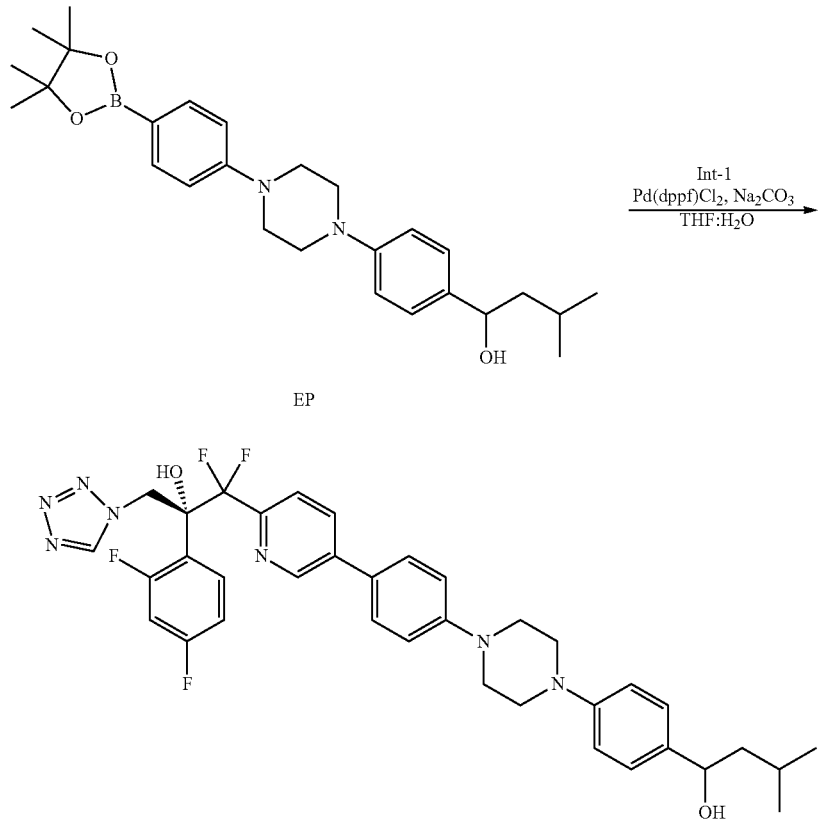

To a stirred solution of Int-1 (120 mg, 0.27 mmol) in THF:H2O (4:1, 20 mL) under argon atmosphere were added compound EP (150 mg, 0.33 mmol), sodium carbonate (88 mg, 0.83 mmol) and purged under argon for 15 min at RT. Then Pd(dppf)Cl$_2$ (20 mg, 0.03 mmol) was added and the reaction mixture was purged under argon for 10 min at RT. The reaction mixture was stirred at 80° C. for 4 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 70% EtOAc/Hexane) to afford 41 (80 mg, 0.11 mmol, 48%) as an off-white solid. $^1$H NMR (400 MHz, DMSO-d$_6$): δ 9.15 (s, 1H), 8.91 (s, 1H), 8.17 (dd, J=8.3, 2.2 Hz, 1H), 7.70 (d, J=8.8 Hz, 2H), 7.48 (d, J=8.4 Hz, 1H), 7.32-7.25 (m, 2H), 7.23-7.11 (m, 5H), 6.98-6.86 (m, 3H), 5.67 (d, J=14.7 Hz, 1H), 5.11 (d, J=14.7 Hz, 1H), 4.86 (d, J=4.5 Hz, 1H), 4.52-4.40 (m, 1H), 3.41-3.34 (m, 4H), 3.29-3.20 (m, 4H), 1.65-1.50 (m, 2H), 1.37-1.22 (m, 1H), 0.88 (dd, J=6.5, 1.9 Hz, 6H); MS (ESI): m/z 674.4 [M−H]$^-$; HPLC: 94.11%; Optical rotation [α]$_D^{20}$: +72.76 (c=0.1% in MeOH).

Example 42

(2R)-1-(5-(4-(4-(4-(cyclopropyl (hydroxy) methyl) phenyl) piperazin-1-yl) phenyl) pyridin-2-yl)-2-(2, 4-difluorophenyl)-1,1-difluoro-3-(1H-tetrazol-1-yl) propan-2-ol (42)

Cyclopropyl (4-(4-(4-(4,4,5,5-tetramethyl-1,3,2-dioxaborolan-2-yl) phenyl) piperazin-1-yl) phenyl) methanol (EQ)

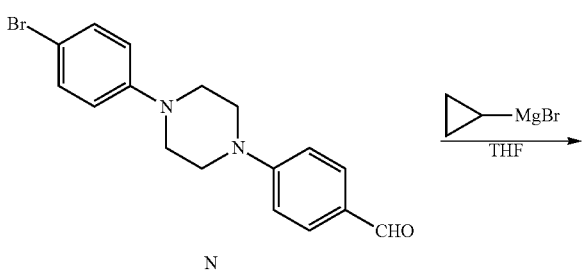

221

-continued

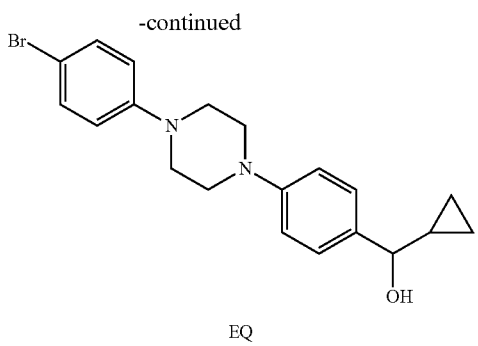

EQ

To a stirred solution of compound N (300 mg, 0.82 mmol) in THF (15 mL) under argon atmosphere was added cyclo propyl magnesium bromide (2.46 mL, 1.23 mmol, 0.5 Min THF) at 0° C., and stirred for 1 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous Na$_2$SO$_4$ and concentrated under reduced pressure to obtain compound EQ (175 mg, 0.45 mmol, 55%) as an off-white solid which was as such taken for next step without further purification. LC-MS: m/z 409.2 [M+H]$^+$ at 3.55 RT (84.00% purity).

cyclopropyl(4-(4-(4-(4,4,5,5-tetramethyl-1,3,2-dioxaborolan-2-yl) phenyl) piperazin-1-yl) phenyl) methanol (ER)

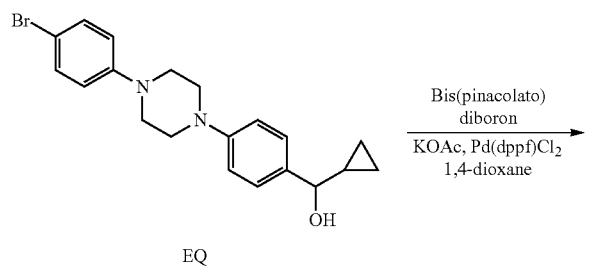

222

-continued

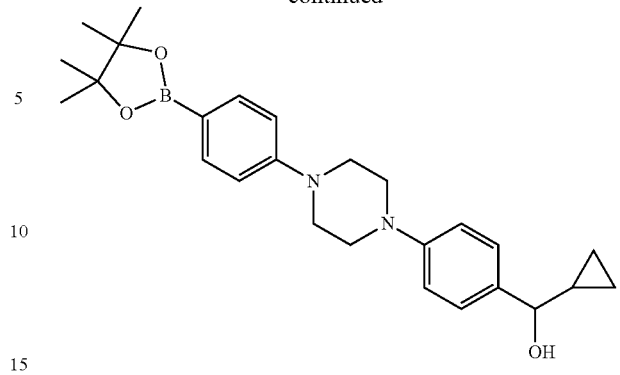

ER

To a stirred solution of compound EQ (170 mg, 0.42 mmol) in 1,4-dioxane (20 mL) under argon atmosphere were added bis(pinacolato)diboron (178 mg, 0.70 mmol), KOAc (129 mg, 1.31 mmol) at RT and purged under argon for 15 min. Then Pd(dppf)Cl$_2$ (32 mg, 0.04 mmol) was added to the reaction mixture at RT and stirred at 110° C. for 6 h in a sealed tube. The progress of the reaction was monitored by TLC, the reaction mixture was diluted with water (30 mL) and extracted with EtOAc (2×30 mL). The combined organic extracts were washed with water (30 mL), brine (30 mL), dried over anhydrous Na$_2$SO$_4$ and concentrated under reduced pressure. The crude material was purified by silica gel column chromatography (eluent: 40% EtOAc/Hexane) to afford compound ER (150 mg, 0.39 mmol, 78%) as an off-white solid which was as such taken for next step without further purification.

(2R)-1-(5-(4-(4-(4-(cyclopropyl (hydroxy) methyl) phenyl) piperazin-1-yl) phenyl) pyridin-2-yl)-2-(2, 4-difluorophenyl)-1,1-difluoro-3-(1H-tetrazol-1-yl) propan-2-ol (42)

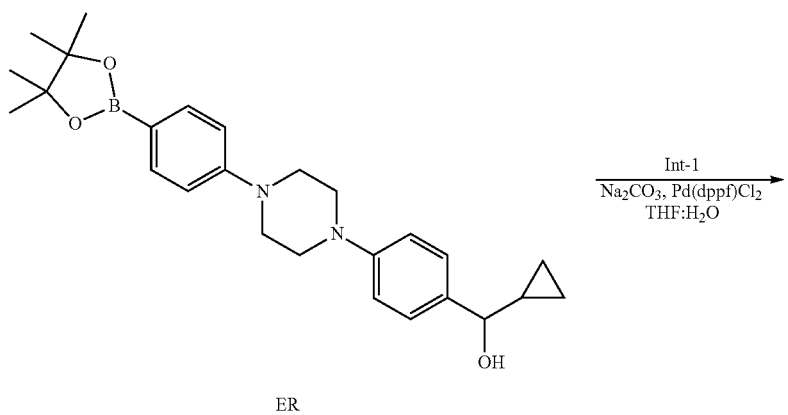

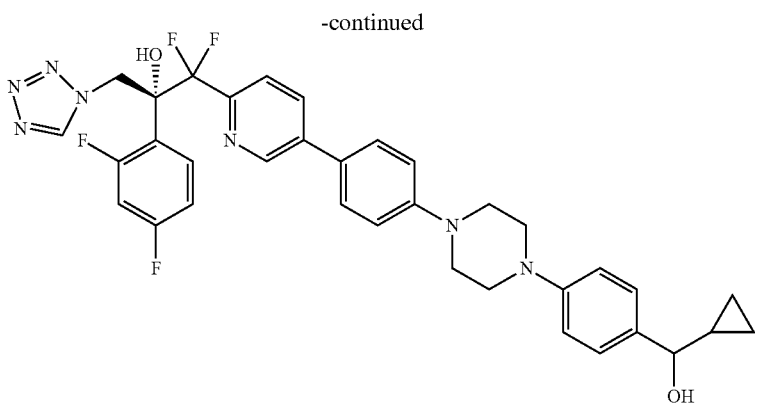

42

To a stirred solution of Int-1 (120 mg, 0.27 mmol) in THF:H2O (4:2, 10 mL) under argon atmosphere were added compound ER (129 mg, 0.33 mmol), sodium carbonate (88 mg, 0.83 mmol) at RT and purged under argon for 10 min. Then Pd(dppf)Cl$_2$ (20 mg, 0.02 mmol) was added to the reaction mixture at RT and stirred at 80° C. for 5 h in a sealed tube. The progress of the reaction was monitored by TLC, the reaction mixture was diluted with water (10 mL) and extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluent: 60% EtOAc/Hexane) which was further purified by preparative HPLC to afford 42 (35 mg, 0.05 mmol, 19%) as an off-white solid. $^1$H NMR (400 MHz, DMSO-d$_6$): δ 9.15 (s, 1H), 8.91 (s, 1H), 8.17 (d, J=8.0 Hz, 1H), 7.70 (d, J=8.5 Hz, 2H), 7.48 (d, J=8.2 Hz, 1H), 7.35-7.10 (m, 7H), 7.04-6.84 (m, 3H), 5.67 (d, J=14.7 Hz, 1H), 5.11 (d, J=14.7 Hz, 1H), 4.96 (d, J=4.4 Hz, 1H), 3.89 (dd, J=6.8, 4.6 Hz, 1H), 3.50-3.20 (m, 8H), 1.07-0.94 (m, 1H), 0.46-0.20 (m, 4H); MS (ESI): m/z 658.3 [M−H]$^-$; HPLC: 91.58%; Optical rotation [α]$_D^{19}$: +52.84 (c=0.1% in MeOH).

Example 43

1-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2,2-dimethylpropan-1-ol (43)

1-(4-(4-(4-bromophenyl) piperazin-1-yl) phenyl)-2,2-dimethylpropan-1-ol (ES)

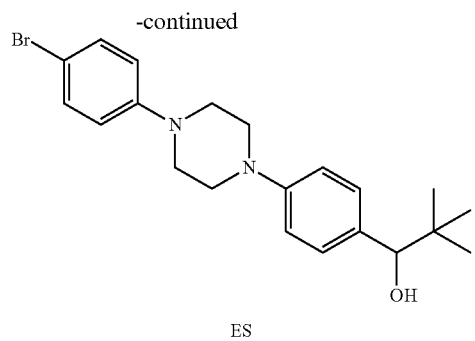

ES

To a stirred solution of compound N (300 mg, 0.87 mmol) in THF (10 mL) under argon atmosphere was added tert-butyl magnesium chloride (0.65 mL, 1.30 mmol, 2.0 M in THF) at 0° C. The reaction mixture was stirred at 0° C.-RT for 5 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous Na$_2$SO$_4$ and concentrated under reduced pressure. The crude material was purified by silica gel column chromatography (eluent: 30% EtOAc/Hexane) to afford compound ES (170 mg, 0.42 mmol, 48%) as an off-white solid. $^1$H NMR (400 MHz, CDCl$_3$): δ 7.37 (d, J=9.0 Hz, 2H), 7.23 (d, J=8.5 Hz, 2H), 6.92 (d, J=8.7 Hz, 2H), 6.84 (d, J=9.2 Hz, 2H), 4.35 (d, J=2.5 Hz, 1H), 3.35-3.27 (m, 8H), 1.75 (d, J=2.8 Hz, 1H), 0.92 (s, 9H).

2,2-dimethyl-1-(4-(4-(4-(4,4,5,5-tetramethyl-1,3,2-dioxaborolan-2-yl) phenyl) piperazin-1-yl) phenyl) propan-1-ol (ET)

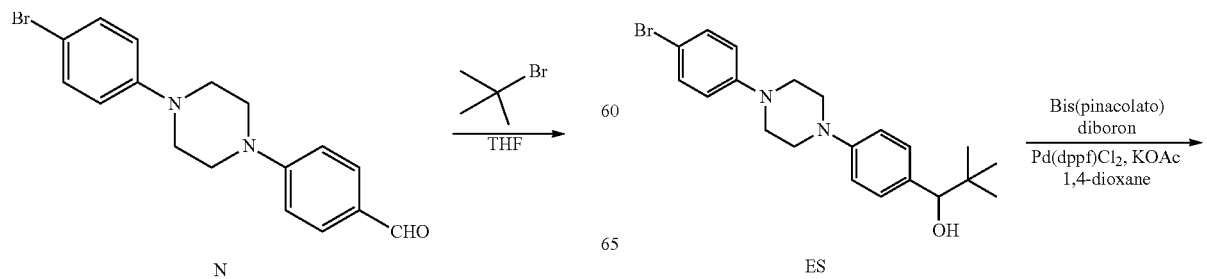

N      ES

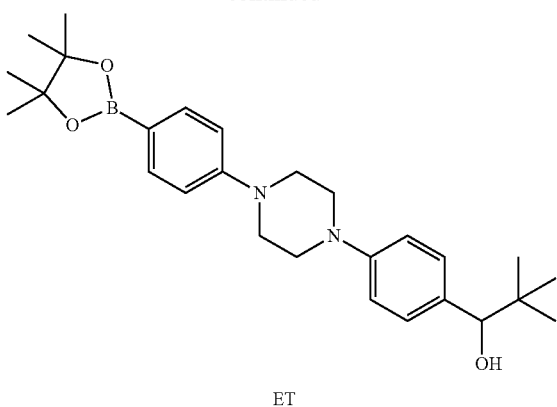

ET

To a stirred solution of compound ES (170 mg, 0.42 mmol) in 1,4-dioxane (20 mL) under argon atmosphere were added bis(pinacolato)diboron (171 mg, 0.67 mmol), KOAc (124 mg, 1.26 mmol) at RT and purged under argon for 15 min. Then Pd(dppf)Cl$_2$ (31 mg, 0.04 mmol) was added to the reaction mixture at RT and stirred at 110° C. for 6 h in a sealed tube. The progress of the reaction was monitored by TLC, the reaction mixture was diluted with water (30 mL) and extracted with EtOAc (2×30 mL). The combined organic extracts were washed with water (30 mL), brine (30 mL), dried over anhydrous Na$_2$SO$_4$ and concentrated under reduced pressure. The crude material was purified by silica gel column chromatography (eluent: 40% EtOAc/Hexane) to afford compound ET (130 mg, 0.28 mmol, 68%) as an off-white solid. $^1$H NMR (500 MHz, CDCl$_3$): δ 7.73 (d, J=8.7 Hz, 2H), 7.23 (d, J=8.4 Hz, 2H), 6.93 (dd, J=8.7, 11.6 Hz, 4H), 4.35 (s, 1H), 3.44-3.30 (m, 8H), 1.33 (s, 12H), 0.92 (s, 9H).

1-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2,2-dimethylpropan-1-ol (43)

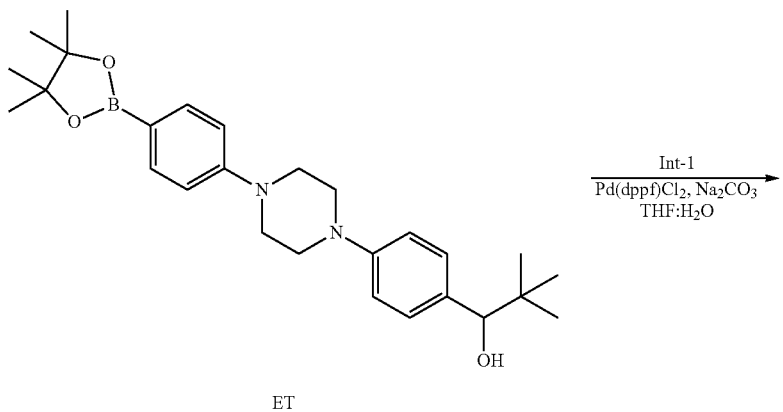

ET

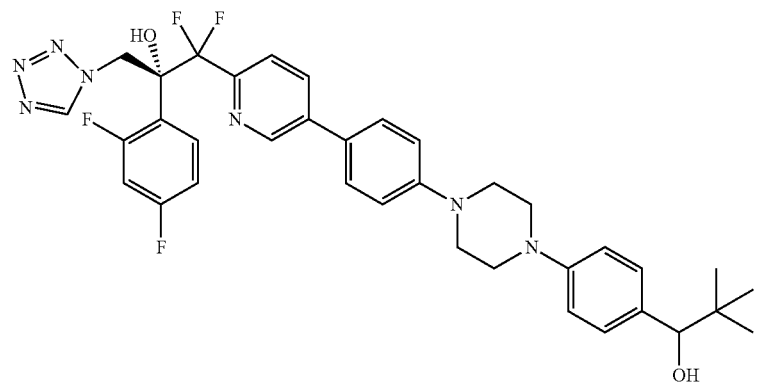

To a stirred solution of Int-1 (100 mg, 0.23 mmol) in THF:H2O (4:1, 10 mL) under argon atmosphere were added compound ET (111 mg, 0.27 mmol), sodium carbonate (74 mg, 0.70 mmol) at RT and purged under argon for 10 min. Then Pd(dppf)Cl₂ (17 mg, 0.02 mmol) was added to the reaction mixture at RT and stirred at 80° C. for 5 h in a sealed tube. The progress of the reaction was monitored by TLC, the reaction mixture was diluted with water (10 mL) and extracted with EtOAc (2×10 mL). The combined organic extracts were washed with water (10 mL), brine (10 mL), dried over anhydrous Na₂SO₄ and concentrated under reduced pressure. The crude material was purified by silica gel column chromatography (eluent: 50% EtOAc/Hexane) to afford 43 (40 mg, 0.06 mmol, 25.6%) as an off-white solid. ¹H NMR (400 MHz, CDCl₃): δ 8.77 (s, 1H), 8.73 (d, J=1.8 Hz, 1H), 7.95 (dd, J=8.3, 2.1 Hz, 1H), 7.87 (s, 1H), 7.61 (d, J=8.2 Hz, 1H), 7.51 (d, J=8.8 Hz, 2H), 7.42-7.33 (m, 1H), 7.24 (s, 2H), 7.07 (d, J=8.8 Hz, 2H), 6.94 (d, J=8.3 Hz, 2H), 6.80-6.74 (m, 1H), 6.70-6.63 (m, 1H), 5.62 (d, J=14.2 Hz, 1H), 5.10 (d, J=14.2 Hz, 1H), 4.36 (s, 1H), 3.49-3.33 (m, 9H), 0.92 (s, 9H); MS (ESI): m/z 674.4 [M–H]⁻; HPLC: 96.02%; Optical rotation [α]$_D^{19}$: +55.64 (c=0.1% in MeOH).

Example 44

(2R)-2-(2,4-difluorophenyl)-1,1-difluoro-1-(5-(4-(4-(6-(1-hydroxyethyl) pyridin-3-yl) piperazin-1-yl) phenyl) pyridin-2-yl)-3-(1H-tetrazol-1-yl) propan-2-ol (44)

1-(5-(4-(4-bromophenyl) piperazin-1-yl) pyridin-2-yl) ethan-1-ol (EU)

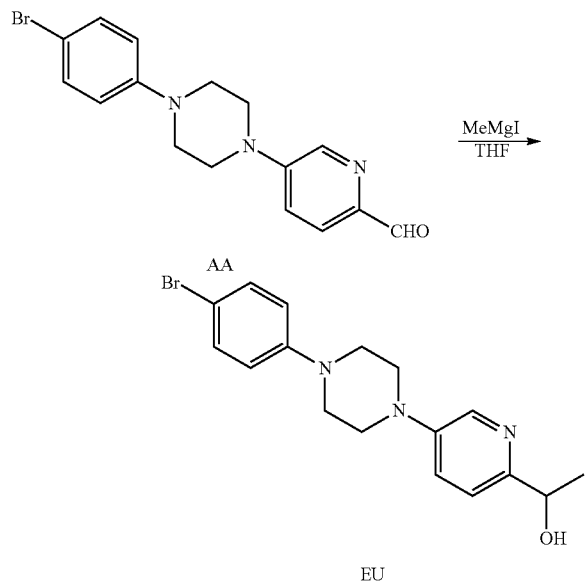

To a stirred solution of compound AA (300 mg, 0.87 mmol) in THF (10 mL) under argon atmosphere was added methyl magnesium iodide (0.87 mL, 2.61 mmol, 3.0 M in diethyl ether) at 0° C. The reaction mixture was warmed to RT and stirred for 2 h. The progress of the reaction was monitored by TLC. The reaction mixture was quenched with ice-cold water (20 mL) and extracted with EtOAc (2×20 mL). The combined organic extracts were washed with water (20 mL), brine (10 mL), dried over anhydrous Na₂SO₄ and concentrated under reduced pressure. The crude material was purified by silica gel column chromatography (eluent: 30% EtOAc/Hexane) to afford compound EU (240 mg, 0.66 mmol, 76%) as pale yellow solid. ¹H NMR (400 MHz, CDCl₃): δ 8.26 (d, J=2.6 Hz, 1H), 7.38 (d, J=9.2 Hz, 2H), 7.28-7.26 (m, 2H), 7.20-7.17 (m, 1H), 6.84 (d, J=9.0 Hz, 2H), 4.87-4.82 (m, 1H), 3.40-3.27 (m, 8H), 1.49 (d, J=6.4 Hz, 3H).

1-(5-(4-(4-(4,4,5,5-tetramethyl-1,3,2-dioxaborolan-2-yl) phenyl) piperazin-1-yl) pyridin-2-yl) ethan-1-ol (EV)

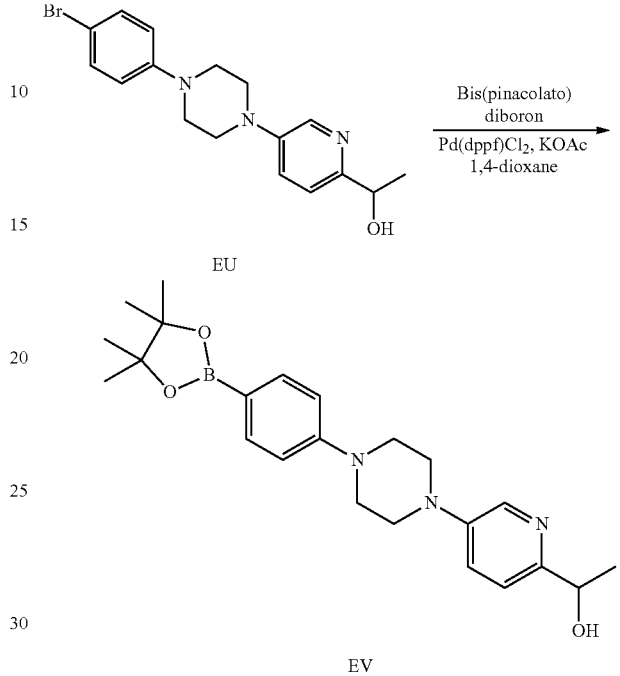

To a stirred solution of compound EU (240 rag, 0.66 mmol) in 1,4-dioxane (20 mL) under argon atmosphere were added bis(pinacolato)diboron (254 mg, 1.06 mmol) and potassium acetate (195 mg, 1.99 mmol) at RT. The reaction mixture was purged with argon for 20 min, then Pd(dppf)Cl₂ (48.5 ng, 0.06 mmol) was added and the reaction mixture was purged under argon for 10 min at RT. The reaction mixture was stirred at 110° C. for 12 h. The progress of the reaction was monitored by TLC. The reaction mixture was quenched with ice cold water (20 mL) and extracted with CH₂Cl₂ (2×20 mL). The combined organic extracts were dried over anhydrous Na₂SO₄ and concentrated under reduced pressure. The crude material was purified by silica gel column chromatography (eluent: 3% MeOH/CH₂Cl₂) to afford compound EV (200 mg, 0.48 mmol, 73%) as a pale yellow solid. ¹H NMR (400 MHz, CDCl₃): δ 8.26 (d, J=2.6 Hz, 1H), 7.74 (d, J=8.7 Hz, 2H), 7.31-7.27 (m, 2H), 7.21-7.18 (m, 1H), 6.94 (d, J=8.7 Hz, 2H), 4.87-4.82 (m, 1H), 3.47-3.41 (m, 4H), 3.37-3.32 (m, 4H), 1.49 (d, J=6.5 Hz, 3H), 1.33 (s, 12H).

(2R)-2-(2,4-difluorophenyl)-1,1-difluoro-1-(5-(4-(4-(6-(1-hydroxyethyl) pyridin-3-yl) piperazin-1-yl) phenyl) pyridin-2-yl)-3-(1H-tetrazol-1-yl) propan-2-ol (44)

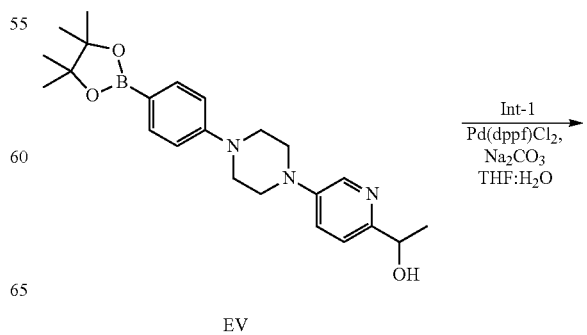

229

-continued

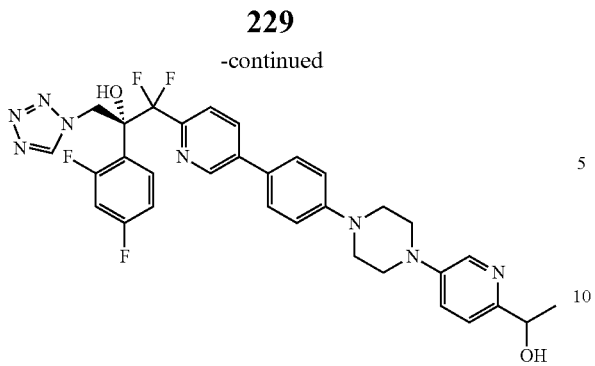

44

To a stirred solution of Int-1 (150 mg, 0.35 mmol) in THF:H2O (4:1, 20 mL) under argon atmosphere were added compound EV (142 mg, 0.35 mmol) and sodium carbonate (110 mg, 1.04 mmol) at RT and purged under argon for 10 min. Then Pd(dppf)Cl$_2$ (25.4 mg, 0.03 mmol) was added and the reaction mixture was purged under argon for 10 min at RT. The reaction mixture was stirred at 90° C. for 8 h. The progress of the reaction was monitored by TLC. The reaction mixture was quenched with ice cold water (10 mL) and extracted with EtOAc (2×10 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) to afford 44 (40 mg, 0.06 mmol, 18%) as a pale yellow solid. $^1$H NMR (400 MHz, CDCl$_3$): δ 8.76 (s, 1H), 8.73 (s, 1H), 8.28 (d, J=2.6 Hz, 1H), 7.95 (dd, J=8.3, 2.3 Hz, 1H), 7.85 (s, 1H), 7.61 (d, J=8.3 Hz, 1H), 7.52 (d, J=8.9 Hz, 2H), 7.42-7.36 (m, 1H), 7.31-7.27 (m, 1H), 7.22-7.18 (m, 1H), 7.07 (d, J=8.8 Hz, 2H), 6.80-6.74 (m, 1H), 6.69-6.65 (m, 1H), 5.61 (d, J=14.2 Hz, 1H), 5.11 (d, J=14.2 Hz, 1H), 4.85 (d, J=4.5 Hz, 1H), 3.94 (brs, 1H), 3.50-3.43 (m, 4H), 3.42-3.34 (m, 4H), 1.49 (d, J=6.4 Hz, 3H); MS (ESI): m/z 635.6 [M+H]$^+$; HPLC: 97.79% Optical rotation [α]$_D^{20}$: +38.32 (c=0.1% in MeOH).

Example 45

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-methylpropan-1-ol (45)

1-(5-(4-(4-bromophenyl) piperazin-1-yl) pyridin-2-yl)-2-methylpropan-1-ol (EW)

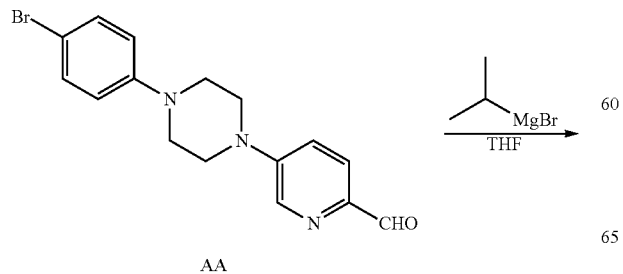

AA

230

-continued

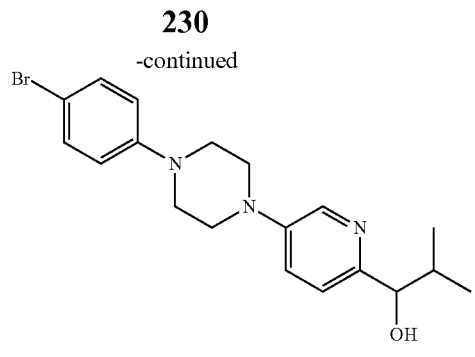

EW

To a stirred solution of compound AA (300 mg, 0.86 mmol) in THF (20 mL) under argon atmosphere was added isopropyl magnesium bromide (0.52 mL, 1.04 mmol, 2.0 M in THF) at 0° C., and stirred for 5 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous Na$_2$SO$_4$ and concentrated under reduced pressure. The crude material was purified by silica gel column chromatography (eluent: 30% EtOAc/Hexane) to afford compound EW (220 mg, 0.56 mmol, 66%) as an off-white solid. $^1$H NMR (400 MHz. DMSO-d$_6$): δ 8.24 (d, J=2.6 Hz, 1H), 7.42-7.35 (m, 3H), 7.27 (d, J=8.7 Hz, 1H), 6.97 (d, J=9.0 Hz, 2H), 5.01 (d, J=5.0 Hz, 1H), 4.26 (t, J=5.3 Hz, 1H), 3.41-3.25 (m, 8H), 2.03-1.81 (m, 1H), 0.81-0.77 (m, 6H).

2-methyl-1-(5-(4-(4-(4,4,5,5-tetramethyl-1,3,2-dioxaborolan-2-yl) phenyl) piperazin-1-yl) pyridin-2-yl) propan-1-ol (EX)

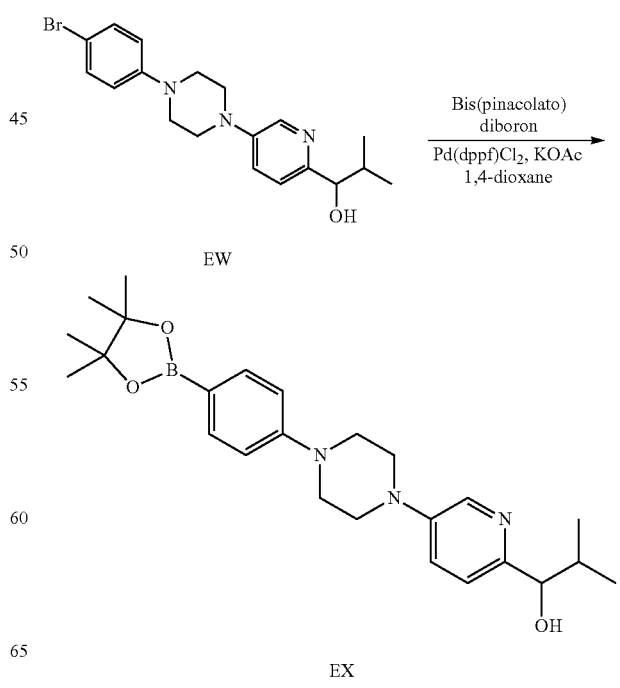

To a stirred solution of compound EW (220 mg, 0.56 mmol) in 1,4-dioxane (20 mL) under argon atmosphere were added bis(pinacolato)diboron (286 mg, 1.13 mmol) and potassium acetate (22.1 mg, 2.26 mmol) at RT. The reaction mixture was purged with argon for 20 min, then Pd(dppf)Cl$_2$ (62 mg, 0.08 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 40% EtOAc/Hexane) to afford compound EX (180 mg, 0.41 mmol, 73%) as a brown solid. $^1$H NMR (400 MHz, DMSO-d$_6$): δ 8.23 (d, J=2.6 Hz, 1H), 7.57-7.47 (m, 2H), 7.43-7.39 (m, 1H), 7.36-7.29 (m, 1H), 6.98 (d, J=8.7 Hz, 2H), 5.09 (d, J=4.8 Hz, 1H), 4.06-4.03 (m, 1H), 3.40-3.37 (m, 4H), 3.32-3.30 (m, 4H), 1.27 (s, 12H), 1.12-1.08 (m, 1H), 0.39-0.29 (m, 6H)

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-methylpropan-1-ol (45)

To a stirred solution of Int-1 (180 mg, 0.41 mmol) in THF:H2O (4:1, 20 mL) under argon atmosphere were added compound EX (178 mg, 0.41 mmol), sodium carbonate (131 mg, 1.23 mmol) and purged under argon for 15 min at RT. Then Pd(dppf)Cl$_2$ (45 mg, 0.06 mmol) was added and the reaction mixture was purged under argon for 10 min at RT. The reaction mixture was stirred at 80° C. for 6 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/EtOAc) to afford 45 (40 mg, 0.06 mmol, 15%) as an off-white solid. $^1$H NMR (400 MHz, CDCl$_3$): δ 8.76 (s, 1H), 8.73 (d, J=2.0 Hz, 1H), 8.28 (d, J=2.6 Hz, 1H), 7.97-7.91 (m, 1H), 7.85 (s, 1H), 7.61 (d, J=8.4 Hz, 1H), 7.57-7.48 (m, 2H), 7.42-7.36 (m, 1H), 7.31-7.25 (m, 1H), 7.14 (d, J=8.5 Hz, 1H), 7.07 (d, J=8.8 Hz, 2H), 6.80-6.74 (m, 1H), 6.72-6.60 (m, 1H), 5.61 (d, J=14.2 Hz, 1H), 5.11 (d, J=14.2 Hz, 1H), 4.49 (d, J=4.6 Hz, 1H), 3.95-3.88 (m, 1H), 3.50-3.44 (m, 4H), 3.42-3.35 (m, 4H), 2.04-1.96 (m, 1H), 0.98 (d, J=6.8 Hz, 3H), 0.82 (d, J=6.8 Hz, 3H); MS (ESI): m/z 663.6 [M+H]$^+$; HPLC: 97.81%; Optical rotation [α]$_D^{20}$: +50.7 (c=0.1% in MeOH).

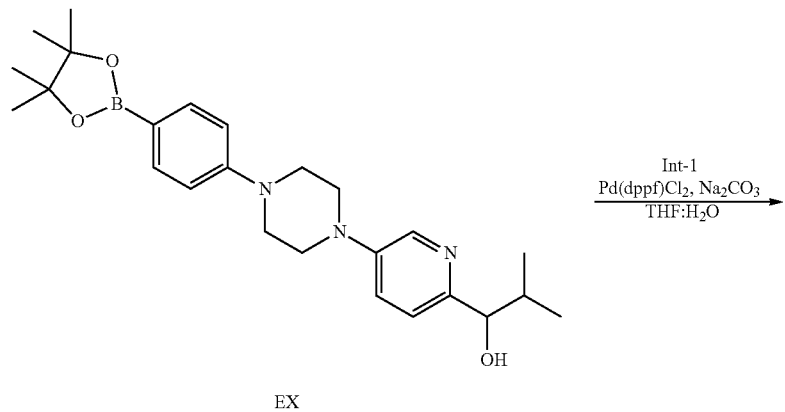

EX

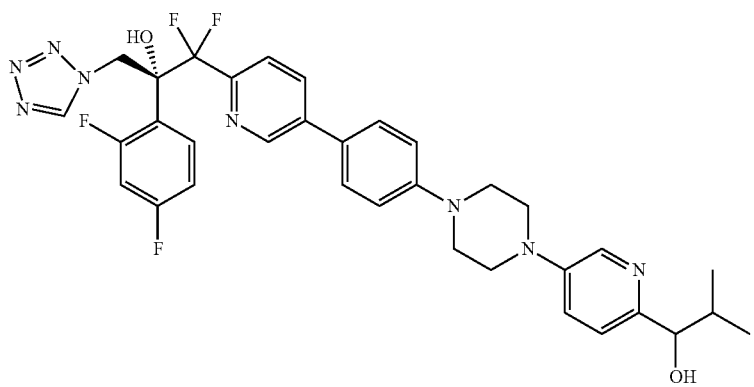

45

Example 46

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-methylpropan-1-ol (46)

1-(5-(4-(4-bromophenyl) piperazin-1-yl) pyridin-2-yl)-2-methylpropan-1-ol (EY)

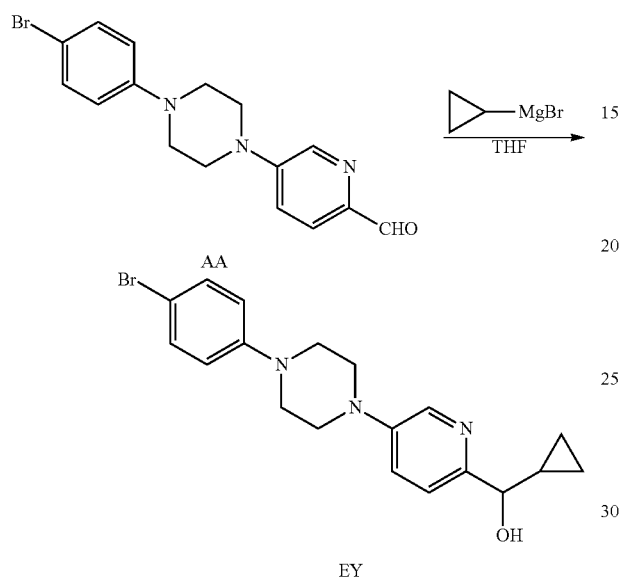

To a stirred solution of compound AA (300 mg, 0.87 mmol) in THF (20 mL) under argon atmosphere was added cyclopropyl magnesium bromide (5.2 mL, 2.62 mmol, 2.0 M in THF) at 0° C., and stirred for 5-6 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous $Na_2SO_4$ and concentrated under reduced pressure. The crude material was purified by silica gel column chromatography (eluent: 40% EtOAc/Hexane) to afford compound EY (200 mg, 0.51 mmol, 60%) as a brown solid. $^1$H NMR (400 MHz, DMSO-$d_6$): δ 8.23 (d, J=2.6 Hz, 1H), 7.44 (dd, J=8.7, 2.7 Hz, 1H), 7.41-7.31 (m, 3H), 6.97 (d, J=9.0 Hz, 2H), 5.14 (br s, 1H), 4.06 (br d, J=6.8 Hz, 1H), 3.32-3.30 (m, 8H), 1.15-1.02 (m, 1H), 0.43-0.25 (m, 4H).

2-methyl-1-(5-(4-(4-(4,4,5,5-tetramethyl-1,3,2-dioxaborolan-2-yl) phenyl) piperazin-1-yl) pyridin-2-yl) propan-1-ol (EZ)

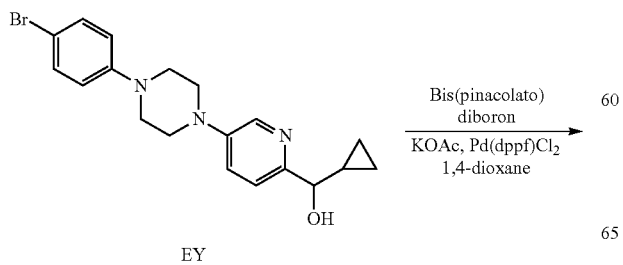

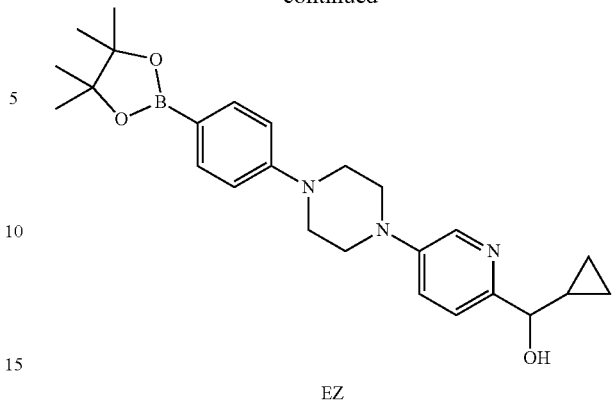

To a stirred solution of compound EY (200 mg, 0.51 mmol) in 1,4-dioxane (20 mL) under argon atmosphere were added bis(pinacolato)diboron (261 mg, 1.03 mmol) and potassium acetate (202 mg, 2.06 mmol) at RT. The reaction mixture was purged with argon for 20 min, then Pd(dppf)Cl$_2$ (56 mg, 0.07 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 50% EtOAc/Hexane) to afford compound EZ (150 mg, 0.34 mmol, 67%) as a brown solid. $^1$H NMR (400 MHz, DMSO-$d_6$): δ 8.23 (d, J=2.6 Hz 1H), 7.55-7.53 (m, 2H), 7.43-7.38 (m, 1H), 7.35-7.29 (m, 1H), 6.98 (d, J=8.7 Hz, 2H), 5.09 (d, J=4.8 Hz, 1H), 4.06-4.03 (m, 1H), 3.44-3.24 (m, 8H), 1.27 (s, 12H), 1.13-1.08 (m, 1H), 0.49-0.21 (m, 4H).

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-methylpropan-1-ol (46)

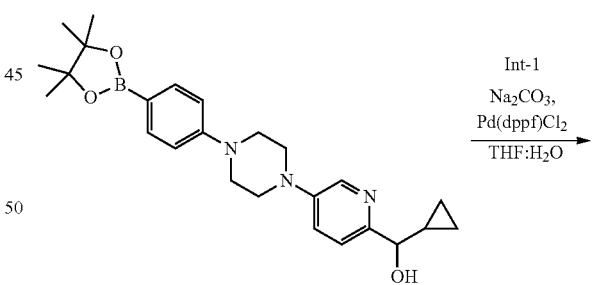

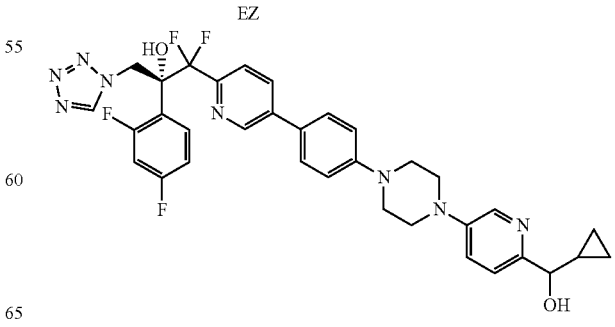

To a stirred solution of Int-1 (130 mg, 0.30 mmol) in THF:H2O (4:1, 20 mL) under argon atmosphere were added compound EZ (143 mg, 0.33 mmol), sodium carbonate (95 mg, 0.90 mmol) and purged under argon for 15 min at RT. Then Pd(dppf)Cl$_2$ (32 mg, 0.04 mmol) was added and the reaction mixture was purged under argon for 10 min at RT. The reaction mixture was stirred at 80° C. for 16 h. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 46 (38 mg, 0.06 mmol, 19%) as an off-white solid. $^1$H NMR (400 MHz, CDCl$_3$): δ 8.76 (s, 1H), 8.73 (d, J=2.0 Hz, 1H), 8.28 (d, J=2.0 Hz, 1H), 7.95 (dd, J=8.2, 2.2 Hz, 1H), 7.85 (s, 1H), 7.61 (d, J=8.3 Hz, 1H), 7.52 (d, J=8.8 Hz, 2H), 7.43-7.26 (m, 3H), 7.07 (d, J=8.9 Hz, 2H), 6.80-6.74 (m, 1H), 6.71-6.64 (m, 1H), 5.61 (d J=14.3 Hz, 1H), 5.11 (d, J=14.32 Hz, 1H), 4.07 (d, J=8.0 Hz, 2H), 3.51-3.32 (m, 8H), 1.16-1.05 (m, 1H), 0.65-0.45 (m, 4H); MS (ESI): m/z 661.6 [M+H]$^+$; HPLC: 98.17%; Optical rotation [α]$_D^{19}$: +42.8 (c=0.1% in MeOH).

Example 47

(R)-2-(2,4-difluorophenyl)-1,1-difluoro-1-(5-(4-(4-(6-(2-hydroxypropan-2-yl) pyridin-3-yl) piperazin-1-yl) phenyl) pyridin-2-yl)-3-(1H-tetrazol-1-yl) propan-2-ol (47)

2-(5-(4-(4-bromophenyl) piperazin-1-yl) pyridin-2-yl) propan-2-ol (FA)

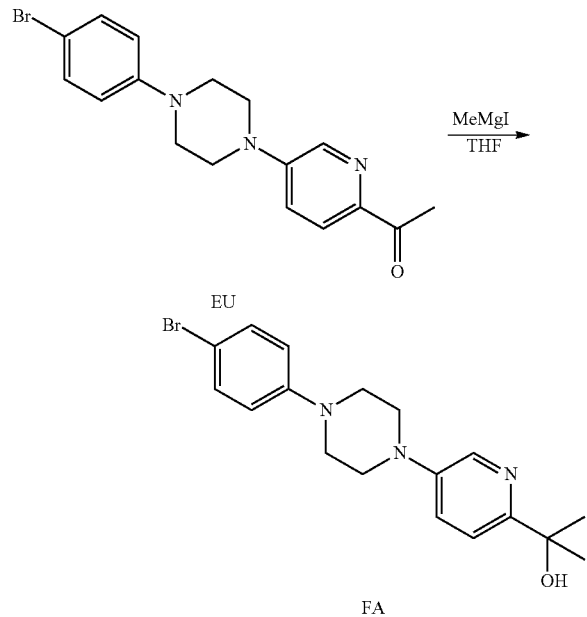

To a stirred solution of compound EU (300 mg, 0.83 mmol) in THF (10 mL) under argon atmosphere was added methyl magnesium iodide (0.83 mL, 2.50 mmol, 3.0 M in diethyl ether) at 0° C. The reaction mixture was warmed to RT and stirred for 6 h. The progress of the reaction was monitored by TLC. The reaction mixture was quenched with ice cold water (50 mL) and extracted with EtOAc (2×50 mL). The combined organic extracts were dried over anhydrous Na$_2$SO$_4$ and concentrated under reduced pressure. The crude material was purified by silica gel column chromatography (eluent: 5% MeOH/CH$_2$Cl$_2$) to afford compound FA (110 mg, 0.29 mmol, 35%) as a brown syrup. $^1$H NMR (400 MHz, CDCl$_3$): δ 8.23 (dd, J=1.1, 2.4 Hz, 1H), 7.38 (d, J=9.0 Hz, 2H), 7.28 (s, 2H), 6.85 (d, J=9.2 Hz, 2H), 3.56-3.51 (m, 1H), 3.37-3.30 (m, 8H), 1.52 (s, 6H).

2-(5-(4-(4-(4,4,5,5-tetramethyl-1,3,2-dioxaborolan-2-yl) phenyl) piperazin-1-yl) pyridin-2-yl) propan-2-ol (FB)

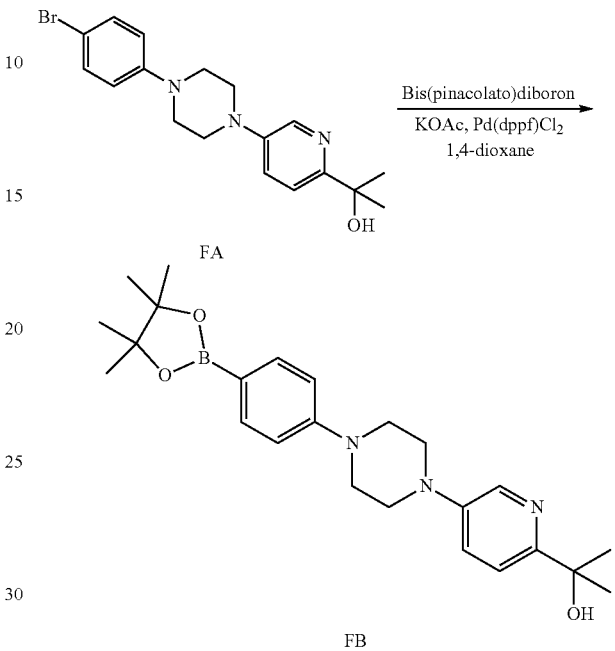

To a stirred solution of compound FA (300 mg, 0.80 mmol) in 1,4-dioxane (20 mL) under argon atmosphere were added bis(pinacolato)diboron (325 mg, 1.28 mmol) and potassium acetate (235 mg, 2.40 mmol) at RT. The reaction mixture was purged with argon for 20 min, then Pd(dppf)Cl$_2$ (58.4 mg, 0.08 mmol) was added and the reaction mixture was purged under argon for 5 min at RT. The reaction mixture was stirred at 110° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure to obtain compound FB (200 mg, 0.47 mmol, 58%) as an off-white solid. $^1$H NMR (400 MHz, CDCl$_3$): δ 8.23 (s, 1H), 7.74 (d, J=8.6 Hz, 2H), 7.28-7.27 (m, 2H), 6.94 (d, J=8.8 Hz, 2l), 3.47-3.40 (m, 4H), 3.38-3.29 (m, 4H), 1.52 (s, 6H), 1.33 (s, 12H).

(R)-2-(2,4-difluorophenyl)-1,1-difluoro-1-(5-(4-(4-(6-(2-hydroxypropan-2-yl) pyridin-3-yl) piperazin-1-yl) phenyl) pyridin-2-yl)-3-(1H-tetrazol-1-yl) propan-2-ol (47)

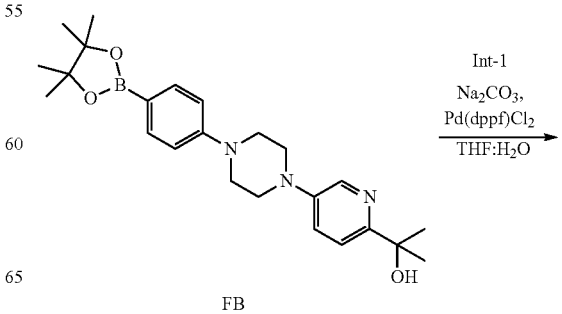

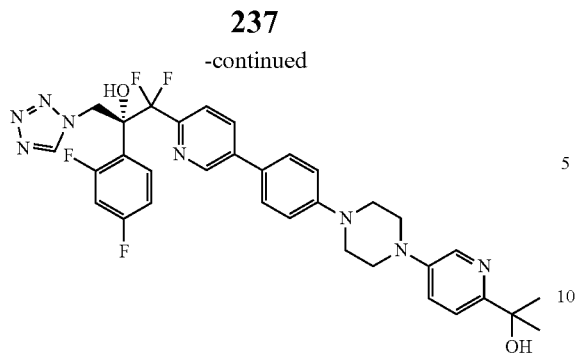

47

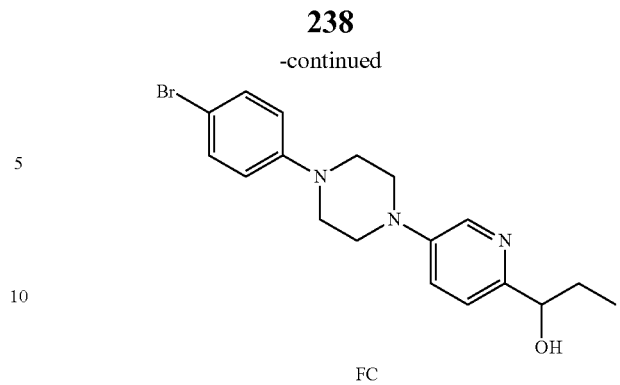

FC

To a stirred solution of Int-1 (150 mg, 0.34 mmol) in THF:H2O (4:1, 20 mL) under argon atmosphere were added compound FB (200 mg, 0.34 mmol), sodium carbonate (110 mg, 1.04 mmol) and purged under argon for 20 min at RT. Then Pd(dppf)Cl$_2$ (25 mg, 0.03 mmol) was added and the reaction mixture was purged under argon for 10 min at RT. The reaction mixture was stirred at 90° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) to afford 47 (25 mg, 0.03 mmol, 11%) as a pale yellow solid. $^1$H NMR (400 MHz, CDCl$_3$): δ 8.76 (s, 1H), 8.73 (s, 1H), 8.24 (s, 1H), 7.95 (dd, J=8.3, 2.1 Hz, 1H), 7.85 (s, 1H), 7.61 (d, J=8.2 Hz, 1H), 7.52 (d, J=8.8 Hz, 2H), 7.42-7.35 (m, 1H), 7.30-7.28 (m, 2H), 7.07 (d, J=8.8 Hz, 2H), 6.80-6.78 (m, 1H), 6.70-6.64 (m, 1H), 5.61 (d, J=14.3 Hz, 1H), 5.11 (d, J=14.6 Hz, 1H), 4.80 (s, 1H), 3.49-3.34 (m, 8H), 1.53 (s, 6H); MS (ESI): m/z 649.6 [M+H]$^+$; HPLC: 95.17%; Optical rotation [α]$_D^{19}$: +54.36 (c=0.1% in MeOH).

To a stirred solution of compound AA (300 mg, 0.87 mmol) in THF (20 mL) under argon atmosphere was added cyclopropyl magnesium bromide (2.6 mL, 2.62 mmol, 1.0 M in THF) at 0° C., and stirred for 6 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous Na$_2$SO$_4$ and concentrated under reduced pressure. The crude material was purified by silica gel column chromatography (eluent: 40% EtOAc/Hexane) to afford compound FC (180 mg, 0.50 mmol, 55%) as an off-white solid. $^1$H NMR (400 MHz. DMSO-d$_6$): δ 8.26-8.19 (m, 1H), 7.44-7.36 (m, 2H), 7.04-6.83 (m, 4H), 5.21-5.07 (m, 1H), 4.49-4.32 (m, 1H), 3.40-3.38 (m, 8H), 1.63-1.56 (m, 2H), 0.82 (t, J=7.4 Hz, 3H).

1-(5-(4-(4-(4,4,5,5-tetramethyl-1,3,2-dioxaborolan-2-yl) phen, piperazin-1-yl) pyridin-2-yl) propan-1-ol (FD)

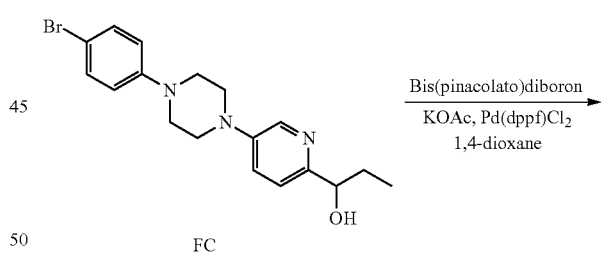

FC

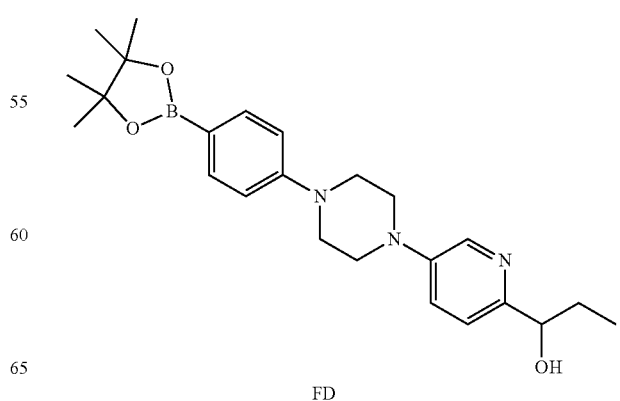

FD

Example 48

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)propan-1-ol (48)

1-(5-(4-(4-bromophenyl) piperazin-1-yl) pyridin-2-yl) propan-1-ol (FC)

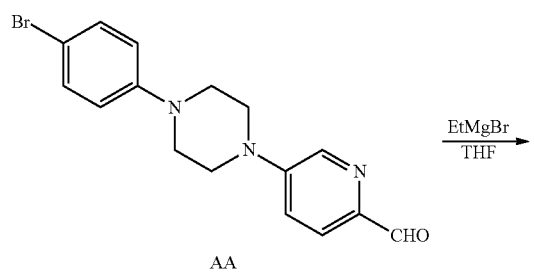

AA

To a stirred solution of FC (180 mg, 0.47 mmol) in 1,4-dioxane (20 mL) under argon atmosphere were added bis(pinacolato)diboron (242 mg, 0.95 mmol) and potassium acetate (187 mg, 1.91 mmol) at RT. The reaction mixture was purged with argon for 20 min. then Pd(dppf)Cl$_2$ (52 mg, 0.07 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 5% MeOH/CH$_2$Cl$_2$) to afford compound FD (120 mg, 0.28 mmol, 59%) as a brown solid. $^1$H NMR (400 MHz, DMSO-d$_6$): δ 8.23 (d, J=2.8 Hz, 1H), 7.54 (d, J=8.5 Hz, 2H), 7.39 (dd, J=8.6, 2.9 Hz, 1H), 7.33-7.26 (m, 1H), 6.97 (d, J=8.7 Hz, 2H), 5.08 (d, J=4.9 Hz, 1H), 4.45-4.40 (m, 1H), 3.41-3.33 (m, 8H), 1.76-1.53 (m, 2H), 1.27 (s, 12H), 0.82 (t, J=7.4 Hz, 3H).

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)propan-1-ol (48)

reaction mixture was purged under argon for 10 min at RT. The reaction mixture was stirred at 80° C. for 16 h. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/EtOAc) to afford 48 (40 mg, 0.06 mmol, 22%) as a white solid. $^1$H NMR (400 MHz, CDCl$_3$): δ 8.78 (s, 1H), 8.74 (d, J=1.6 Hz, 1H), 8.30 (d, J=2.5 Hz, 1H), 7.96 (dd, J=8.2, 2.1 Hz, 1H), 7.86 (s, 1H), 7.63 (d, J=8.3 Hz, 1H), 7.54 (d, J=8.7 Hz, 2H), 7.44-7.36 (m, 1H), 7.33-7.29 (m, 1H), 7.19 (d, J=8.7 Hz, 1H), 7.08 (d, J=8.8 Hz, 2H), 6.82-6.76 (m, 1H), 6.73-6.64 (m, 1H), 5.62 (d, J=14.2 Hz, 1H), 5.13 (d, J=14.2 Hz, 1H), 4.66 (t, J=5.6 Hz, 1H), 3.88 (br s, 1H), 3.54-3.44 (m, 4H), 3.43-3.39 (m, 4H), 1.96-1.83 (m, 1H), 1.79-1.67 (m, 1H), 0.96 (t, J=7.3 Hz, 3H); MS (ESI): m/z 649.3 [M+H]$^+$; HPLC Purity: 98.95%; Optical rotation [α]$_D^{20}$: +50.64 (c=0.1% in MeOH).

Example 49

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-3-methylbutan-1-ol (49)

1-(5-(4-(4-bromophenyl) piperazin-1-yl) pyridin-2-yl)-3-methylbutan-1-ol (FE)

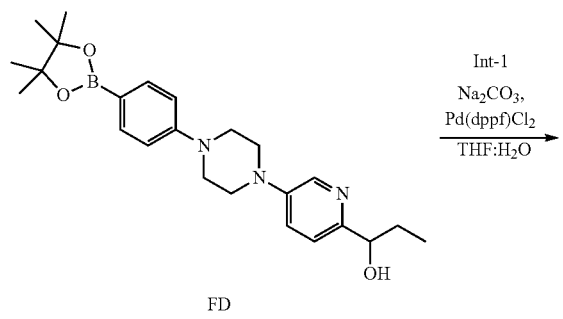

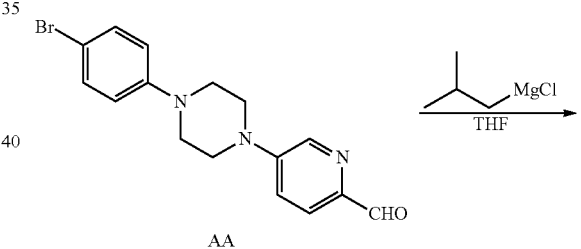

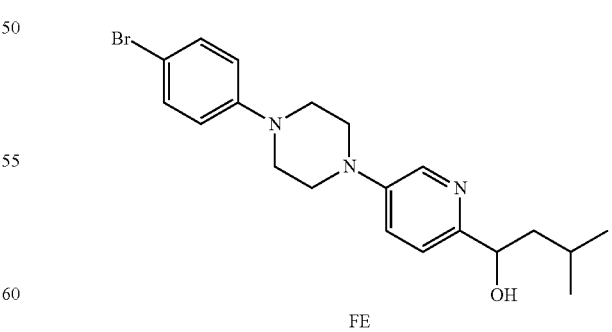

To a stirred solution of Int-1 (120 mg, 0.27 mmol) in THF:H2O (4:1, 20 mL) under argon atmosphere were added compound FD (128 mg, 0.30 mmol), sodium carbonate (90 mg, 0.83 mmol) and purged under argon for 15 min at RT. Then Pd(dppf)Cl$_2$ (30 mg, 0.04 mmol) was added and the To a stirred solution of compound AA (500 mg, 1.46 mmol) in THF (30 mL) under argon atmosphere were added isobutyl magnesium chloride (2.1 mL, 4.33 mmol, 2.0 M in Diethyl ether) at 0° C. The reaction mixture was stirred at RT for 3 h. The progress of the reaction was monitored by TLC. The reaction mixture was diluted with saturated ammonium chloride solution (20 mL) and extracted with EtOAc (2×20 mL). The combined organic layers were washed with water (20 mL), dried over anhydrous $Na_2SO_4$ and concentrated under reduced pressure. The crude material was purified by silica gel column chromatography (eluent: 3% MeOH/$CH_2Cl_2$) to afford compound FE (140 mg, 0.34 mmol, 24%) as yellow solid. $^1$H NMR (500 MHz, DMSO-$d_6$): δ 8.22 (d, J=2.6 Hz, 1H), 7.41-7.28 (m, 4H), 6.97 (d, J=9.0 Hz, 2H), 5.04 (d, J=5.2 Hz, 1H), 4.60-4.49 (m, 1H), 3.32-3.27 (m, 8H), 1.77-1.65 (m, 1H), 1.51-1.44 (m, 2H), 0.95-0.78 (m, 6H).

3-methyl-1-(5-(4-(4-(4,4,5,5-tetramethyl-1,3,2-dioxaborolan-2-yl) phenyl) piperazin-1-yl) pyridin-2-yl) butan-1-ol (FF)

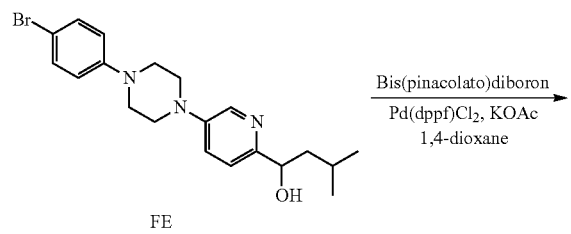

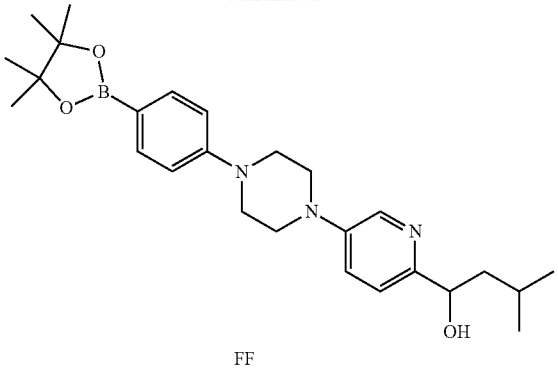

FF

To a stirred solution of compound FE (140 mg, 0.34 mmol) in 1,4-dioxane (15 mL) under argon atmosphere were added bis (pinacolato) diboron (140 mg, 0.55 mmol), KOAc (101 mg, 1.03 mmol) and purged under argon for 5 min at RT. Then Pd(dppf)Cl$_2$ (25 mg, 0.03 mmol) was added to the reaction mixture at RT and stirred at 110° C. for 5 h. The reaction mixture was diluted with water (20 mL) and extracted with EtOAc (2×20 mL). The combined organic extracts were washed with water (20 mL), dried over anhydrous $Na_2SO_4$ and concentrated under reduced pressure. The crude material was purified by silica gel column chromatography (eluent: 30% EtOAc/Hexane) to afford compound FF (250 mg, crude) as a brown thick syrup and the crude material as such taken for next step without further purification.

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-3-methylbutan-1-ol (49)

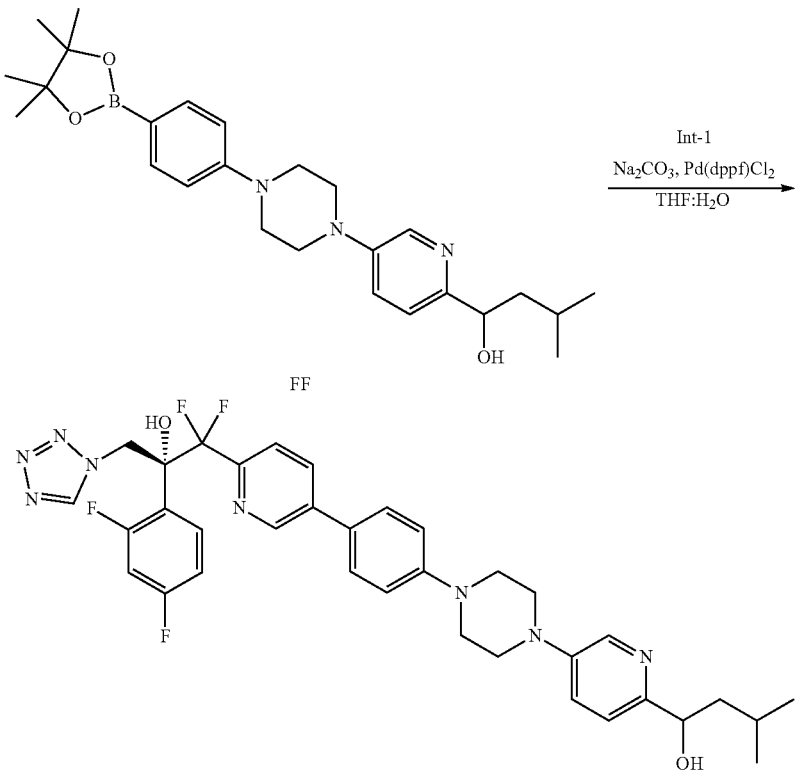

To a stirred solution of Int-1 (100 mg, 0.23 mmol) in THF:H2O (4:1, 15 mL) under argon atmosphere were added compound FF (114 mg, 0.25 mmol), sodium carbonate (73 mg, 0.69 mmol) and purged under argon for 5 min at RT. Then Pd(dppf)Cl$_2$ (16.9 mg, 0.02 mmol) was added and the reaction mixture was purged under argon for 10 min at RT, stirred at 75° C. for 6 h. The reaction mixture was diluted with water (20 mL) and extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 40% EtOAc/Hexane) to afford 49 (45 mg, 0.06 mmol, 29%) as an off-white solid. $^1$H NMR (400 MHz, CDCl$_3$): δ 8.76 (s, 1H), 8.73 (s, 1H), 8.28 (d, J=2.5 Hz, 1H), 7.95 (dd, J=8.2, 2.2 Hz, 1H), 7.85 (s, 1H), 7.61 (d, J=8.2 Hz, 1H), 7.52 (d, J=8.8 Hz, 2H), 7.44-7.34 (m, 1H), 7.31-7.27 (m, 1H), 7.18 (d, J=8.5 Hz, 1H), 7.07 (d, J=8.9 Hz, 2H), 6.80-6.75 (m, 1H), 6.71-6.62 (m, 1H), 5.61 (d, J=14.2 Hz, 1H), 5.11 (d, J=14.2 Hz, 1H), 4.74 (brs, 1H), 3.65 (brs, 1H), 3.48-3.43 (m, 4H), 3.40-3.36 (m, 4H), 1.99-1.73 (m, 1H), 1.69-1.48 (m, 2H), 1.00 (d, J=6.7 Hz, 3H), 0.96 (d, J=6.7 Hz, 3H); MS (ESI): m/z 677.7 [M+H]$^+$; HPLC: 99.03%; Optical rotation [α]$_D^{20}$: +53.96 (c=0.1% in MeOH).

Example 50

1-(5-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2,2-dimethylpropan-1-ol (50)

1-(5-(4-(4-bromophenyl) piperazin-1-yl) pyridin-2-yl)-2,2-dimethylpropan-1-ol (FG)

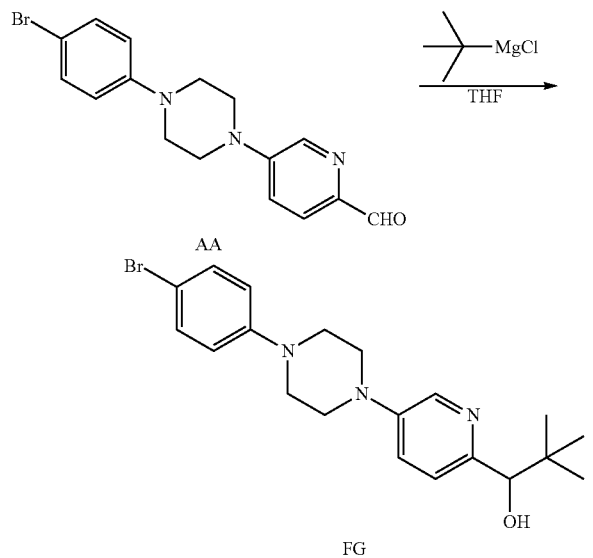

To a stirred solution of compound AA (500 mg, 1.44 mmol) in THF (10 mL) under argon atmosphere was added tert-butyl magnesium chloride (1.08 mL, 2.16 mmol, 2.0 M in THF) at 0° C. The reaction mixture was stirred at 0° C.-RT for 5 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous Na$_2$SO$_4$ and concentrated under reduced pressure. The crude material was purified by silica gel column chromatography (eluent: 5% MeOH/CH$_2$Cl$_2$) to afford compound FG (250 mg, 0.62 mmol, 42.8%) as an off-white solid. $^1$H NMR (500 MHz, CDCl$_3$): δ 8.30 (d, J=2.6 Hz, 1H), 7.40 (d, J=9.0 Hz, 2H), 7.23 (dd, J=8.7, 2.9 Hz, 1H), 7.11 (d, J=8.4 Hz, 1H), 6.86 (d, J=9.0 Hz, 2H), 4.32 (s, 1H), 4.10 (brs, 1H), 3.40-3.33 (m, 8H), 0.93 (s, 9H).

2,2-dimethyl-1-(5-(4-(4-(4,4,5,5-tetramethyl-1,3,2-dioxaborolan-2-yl) phenyl) piperazin-1-yl) pyridin-2-yl) propan-1-ol (FH)

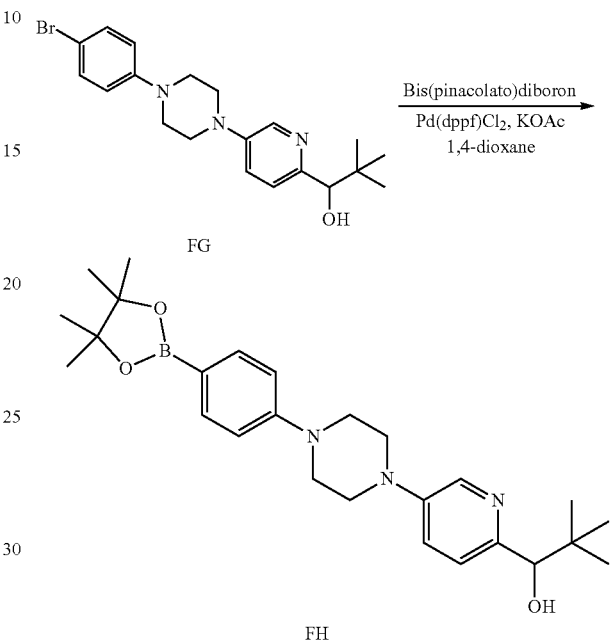

To a stirred solution of compound FG (250 mg, 0.30 mmol) in 1,4-dioxane (20 mL) under argon atmosphere were added bis(pinacolato)diboron (125 mg, 0.50 mmol), KOAc (182 mg, 1.85 mmol) at RT and purged under argon for 15 min. Then Pd(dppf)Cl$_2$ (45 mg, 0.06 mmol) was added to the reaction mixture at RT and stirred at 110° C. for 6 h in a sealed tube. The progress of the reaction was monitored by TLC, the reaction mixture was diluted with water (30 mL) and extracted with EtOAc (2×30 mL). The combined organic extracts were washed with water (30 mL), brine (30 mL), dried over anhydrous Na$_2$SO$_4$ and concentrated under reduced pressure to obtain compound FH (160 mg, crude) as an off-white solid. $^1$H NMR (500 MHz, CDCl$_3$): δ 8.29 (d, J=2.6 Hz, 1H), 7.76 (d, J=8.7 Hz, 2H), 7.22 (dd, J=8.5, 2.7 Hz, 1H), 7.11 (d, J=8.4 Hz, 1H), 6.96 (d, J=8.4 Hz, 2H), 4.32 (s, 1H), 3.48-3.34 (m, 9H), 1.35 (s, 12H), 0.92 (s, 9H).

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2,2-dimethylpropan-1-ol (50)

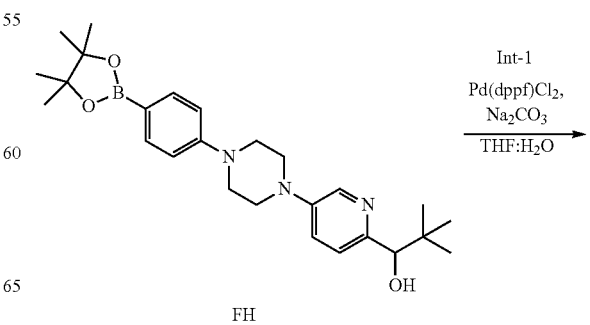

-continued

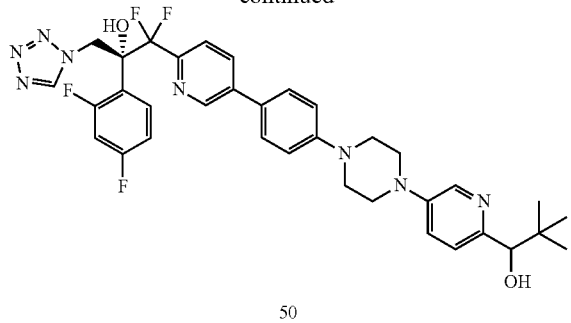

50

To a stirred solution of Int-1 (120 mg, 0.27 mmol) in THF:H2O (4:2, 10 mL) under argon atmosphere were added compound FH (134 mg, crude), sodium carbonate (88 mg, 0.83 mmol) at RT and purged under argon for 10 min. Then Pd(dppf)Cl$_2$ (20 mg, 0.02 mmol) was added to the reaction mixture at RT and stirred at 80° C. for 5 h in a sealed tube. The progress of the reaction was monitored by TLC, the reaction mixture was diluted with water (10 mL) and extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluent: 40% EtOAc/Hexane) to afford 50 (70 mg, 0.10 mmol, 37.4%) as an off-white solid. $^1$H NMR (400 MHz, DMSO-d$_6$): δ 9.15 (s, 1H), 8.91 (s, 1H), 8.25 (d, J=2.4 Hz, 1H), 8.17 (d, J=8.2 Hz, 1H), 7.70 (d, J=8.7 Hz, 2H), 7.48 (d, J=8.2 Hz, 1H), 7.40 (dd, J=8.7, 2.6 Hz, 1H), 7.33-7.10 (m, 6H), 6.91 (t, J=8.3 Hz, 1H), 5.67 (d, J=14.6 Hz, 1H), 5.11 (d, J=14.7 Hz, 1H), 5.03 (d, J=4.9 Hz, 1H), 4.22 (d, J=4.9 Hz, 1H), 3.46-3.32 (m, 8H), 0.84 (s, 9H); MS (ESI): m/z 677.7 [M+H]$^+$; HPLC: 96.47%; Optical rotation $[α]_D^{20}$: +55.76 (c=0.1% in MeOH).

Example 51

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyrimidin-2-yl)-3,3,3-trifluoropropan-1-ol (51)

tert-butyl 4-(4-(4,4,5,5-tetramethyl-1,3,2-dioxaborolan-2-yl)phenyl)piperazine-1-carboxylate (FJ)

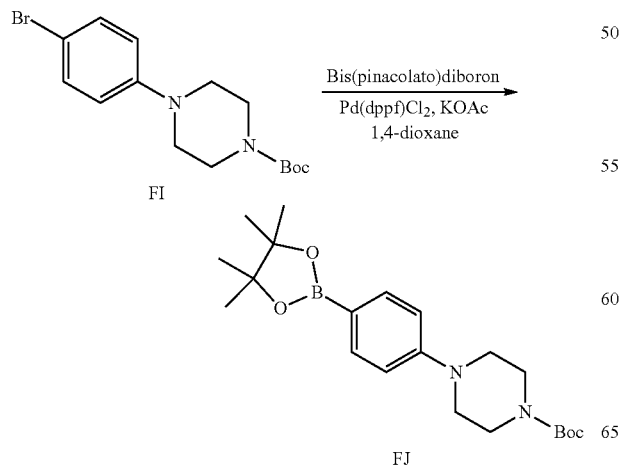

To a stirred solution of compound FI (2.0 g, 5.86 mmol) in 1,4-dioxane (40 mL) under argon atmosphere were added bis(pinacolato)diboron (2.3 g, 9.37 mmol), KOAc (1.7 g, 17.59 mmol) at RT and purged under argon for 15 min. Then Pd(dppf)Cl$_2$ (428 mg, 0.58 mmol) was added to the reaction mixture at RT and stirred at 110° C. for 6 h in a sealed tube. The progress of the reaction was monitored by TLC, the reaction mixture was diluted with water (50 mL) and extracted with EtOAc (2×50 mL). The combined organic extracts were washed with water (50 mL), brine (50 mL), dried over anhydrous Na$_2$SO$_4$ and concentrated under reduced pressure to obtain compound FJ (2.0 g, 5.15 mmol, 87%) as a white solid. $^1$H NMR (500 MHz, CDCl$_3$): δ 7.7 (d, J=2.6 Hz, 1H), 6.90 (d, J=8.7 Hz, 2H), 3.6 (m, 4H), 3.2-3.3 (m, 4H), 1.35 (s, 12H).

tert-butyl (R)-4-(4-(6-(2-(2,4-difluorophenyl)-1,1-difluoro-2-hydroxy-3-(1H-tetrazol-1-yl) propyl) pyridin-3-yl) phenyl) piperazine-1-carboxylate (FL)

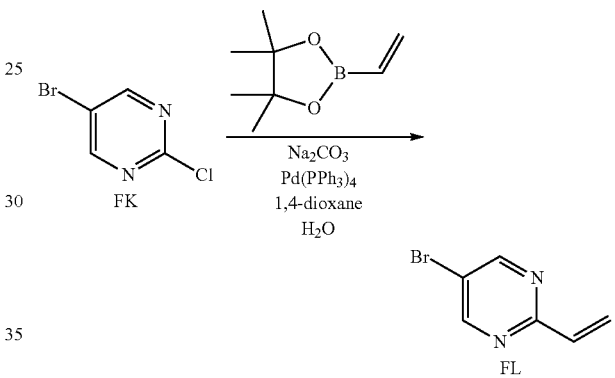

To a stirred solution of compound FK (1.0 g, 5.18 mmol) in 1,4-dioxane:H$_2$O (4:1, 25 mL) under argon atmosphere were added 4,4,5,5-tetramethyl-2-vinyl-1,3,2-dioxaborolane (877 mg, 5.69 mmol), sodium carbonate (1.6 g, 15.54 mmol) and purged under argon for 5 min at RT. Then Pd (PPh$_3$)$_4$ (149 mg, 0.12 mmol) was added to the reaction mixture at RT and stirred at 80° C. for 16 h. The reaction mixture was diluted with water (50 mL) and extracted with EtOAc (2×50 mL). The combined organic extracts were washed with water (20 mL), dried over anhydrous Na$_2$SO$_4$ and concentrated under reduced pressure. The crude material was purified by silica gel column chromatography (eluent: 3% EtOAc/Hexane) to afford compound FL (700 mg, 3.78 mmol, 73%) as a brown thick syrup. $^1$H NMR (500 MHz, CDCl$_3$): δ 8.65 (s, 2H), 6.68-6.62 (m, 1H), 5.94 (d, J=17.6 Hz, 1H), 5.56 (d, J=11.3 Hz, 1H).

(R)-2-(2,4-difluorophenyl)-1,1-difluoro-(1-(5-(4-(piperazin-1-yl) phenyl) pyridin-2-yl)-3-(1H-tetrazol-1-yl) propan-2-ol (FM)

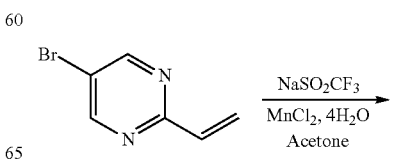

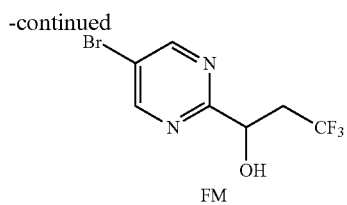

To a stirred solution of compound FL (350 mg, 1.89 mmol) in acetone (30 mL) under argon atmosphere were added sodium triflinate (1.1 g, 7.56 mmol) and MnCl$_2$.4H$_2$O (149 mg, 0.75 mmol) at RT. The reaction mixture stirred at RT for 16 h. The reaction mixture was diluted with water (50 mL) and extracted with EtOAc (2×50 mL). The combined organic extracts were washed with water (20 mL), dried over anhydrous Na$_2$SO$_4$ and concentrated under reduced pressure. The crude material was purified by silica gel column chromatography (eluent: 15% EtOAc/Hexane) to afford compound FM (150 mg, 0.55 mmol, 15%) as an off-white solid. $^1$H NMR (500 MHz, CDCl$_3$): δ 8.69 (s, 2H), 5.31-5.18 (m, 1H), 2.79-2.61 (m, 1H), 2.58-2.45 (m, 2H).

tert-butyl (R)-4-(4-(6-(2-(2,4-difluorophenyl)-1,1-difluoro-2-hydroxy-3-(1H-tetrazol-1-yl) propyl) pyridin-3-yl) phenyl) piperazine-1-carboxylate (FN)

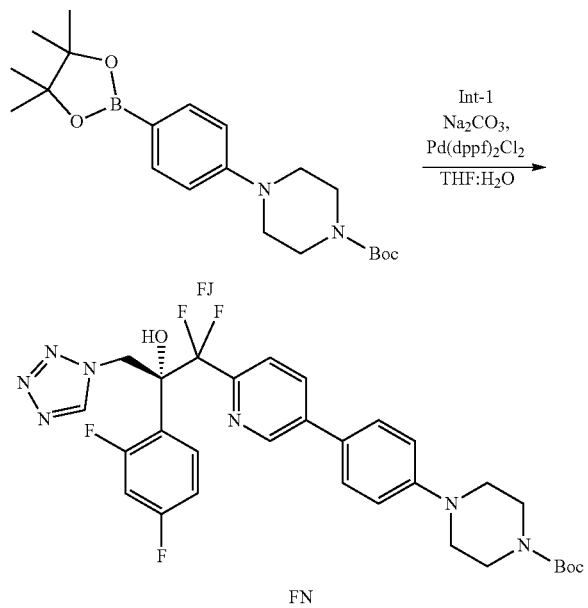

To a stirred solution of Int-1 (2.0 g, 4.62 mmol) in THF:H2O (4:1, 50 mL) under argon atmosphere were added compound FJ (1.97 g, 5.09 mmol), sodium carbonate (1.47 mL, 13.88 mmol) and purged under argon for 5 min at RT. Then Pd(dppf)Cl$_2$ (338 mg, 0.46 mmol) was added to the reaction mixture at RT and stirred at 80° C. for 16 h. The reaction mixture was diluted with water (50 mL) and extracted with EtOAc (2×50 mL). The combined organic extracts were washed with water (20 mL), dried over anhydrous Na$_2$SO$_4$ and concentrated under reduced pressure. The crude material was purified by silica gel column chromatography (eluent: 40% EtOAc/Hexane) to afford compound FN (2.0 g, 3.26 mmol, 7%) as an off-white solid. $^1$H NMR (500 MHz, DMSO-d$_6$): δ 9.14 (s, 1H), 8.89 (s, 1H), 8.15 (dd, J=8.1, 2.0 Hz, 1H), 7.68 (d, J=8.7 Hz, 2H), 7.48 (d, J=8.1 Hz, 1H), 7.31-7.25 (m, 2H), 7.23-7.15 (m, 1H), 7.08 (d, J=8.7 Hz, 2H), 6.96-6.81 (m, 1H), 5.67 (d, J=14.7 Hz, 1H), 5.11 (d, J=14.7 Hz, 1H), 3.49-3.46 (m, 4H), 3.24-3.17 (m, 4H), 1.43 (s, 9H).

(R)-2-(2,4-difluorophenyl-1,1-difluoro-1-(5-(4-piperazin-1-yl) phenyl)pyridin-2-yl)-3-(1H-tetrazol-1-yl) propan-2-ol (FO)

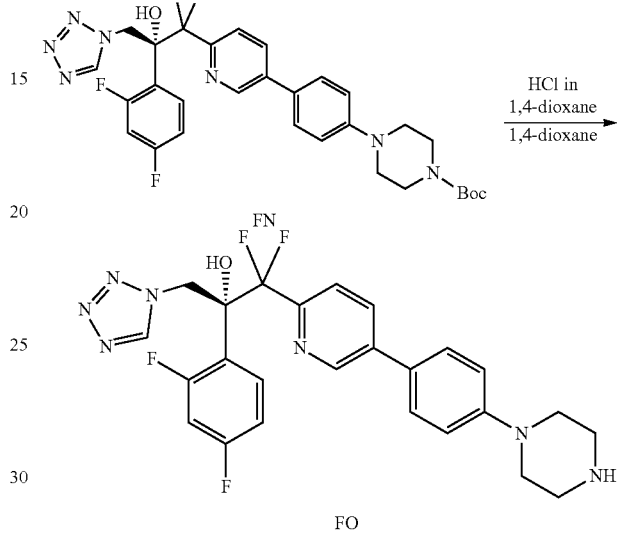

To a stirred solution of compound FN (1.2 g, 1.95 mmol) in 1,4-dioxane (20 mL) under argon atmosphere was added 4M HCl in 1,4-dioxane (1.2 mL, 4.89 mmol) at 0° C. The reaction mixture was warmed to RT and stirred for 4 h. The reaction mixture was quenched with saturated sodium bicarbonate solution (50 mL) and extracted with 5% MeOH:CH$_2$Cl$_2$ (2×50 mL). The combined organic extracts were washed with water (20 mL), dried over anhydrous Na$_2$SO$_4$ and concentrated under reduced pressure. The crude material was washed with n-pentane (2×10 mL) to afford compound FO (600 mg, 1.16 mmol, 60%) as an off-white solid. $^1$H NMR (500 MHz, DMSO-d$_6$): δ 9.14 (s, 1H), 8.88 (s, 1H), 8.14 (dd, J=8.4, 2.0 Hz, 1H), 7.65 (d, J=9.0 Hz, 2H), 7.47 (d, J=8.4 Hz, 1H), 7.34-7.25 (m, 2H), 7.22-7.16 (m, 1H), 7.04 (d, J=9.0 Hz, 2H), 6.94-6.88 (m, 1H), 5.66 (d, J=14.5 Hz, 1H), 5.11 (d, J=14.5 Hz, 1H), 3.16-3.12 (m, 4H), 2.88-2.81 (m, 4H).

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyrimidin-2-yl)-3,3,3-trifluoropropan-1-ol (51)

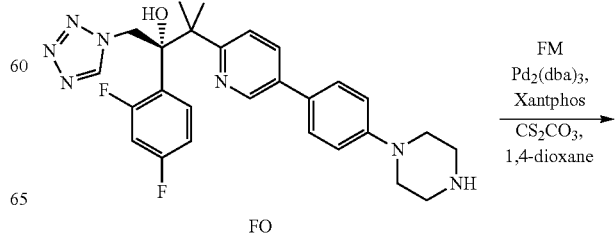

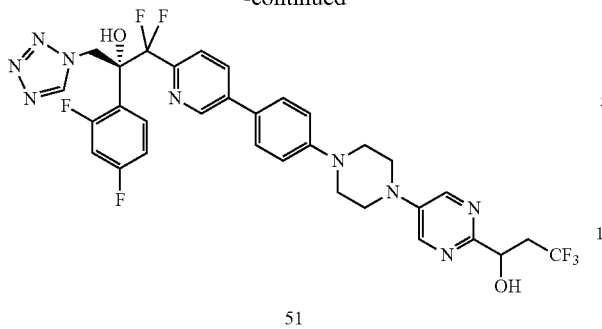

51

To a stirred solution of compound FM (200 mg, 0.38 mmol) in 1,4-dioxane (20 mL) under argon atmosphere were added compound FO (113 mg, 0.42 mmol), Xantphos (27 mg, 0.04 mmol), $Cs_2CO_3$ (380 mg, 1.16 mmol) and purged under argon for 10 min at RT. Then $Pd_2(dba)_3$ (8.9 mg, 0.09 mmol) was added to the reaction mixture at RT and stirred at 80° C. for 16 h. The reaction mixture was diluted with water (20 mL) and extracted with EtOAc (2×20 mL). The combined organic extracts were washed with water (20 mL), dried over anhydrous $Na_2SO_4$ and concentrated under reduced pressure. The crude material was purified by silica gel column chromatography (eluent: 50% EtOAc/Hexane) to afford 51 (15 mg, 0.02 mmol, 5%) as an off-white solid. $^1$H NMR (400 MHz, $CDCl_3$): δ 8.76 (s, 1H), 8.72 (s, 1H), 8.37 (s, 2H), 7.94 (dd, J=8.2, 2.3 Hz, 1H), 7.60 (d, J=8.3 Hz, 1H), 7.51 (d, J=8.9 Hz, 2H), 7.42-7.31 (m, 1H), 7.05 (d, J=8.9 Hz, 2H), 6.77-6.74 (m, 1H), 6.70-6.59 (m, 1H), 5.62 (d, J=14.2 Hz, 1H), 5.10 (d, J=14.2 Hz, 1H), 5.01-4.98 (m, 1H), 4.06-3.99 (m, 4H), 3.41-3.19 (m, 4H), 2.79-2.60 (m, 1H), 2.50-2.42 (m, 1H); MS (ESI): m/z 704.6 $[M+H]^+$; HPLC: 97.86%; Optical rotation $[α]_D^{20}$: +53.36 (c=0.1% in MeOH).

Example 52

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-isopropyl-2,4-dihydro-3H-1,2,4-triazol-3-one (52)

N-(4-(4-(4-bromophenyl) piperazin-1-yl) phenyl) hydrazine carboxamide (FP)

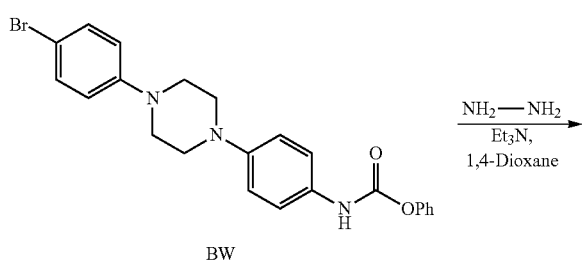

To a stirred solution of compound BW (4.0 g, 8.84 mmol) in 1,4-dioxane (80 mL) under argon atmosphere was added hydrazine hydrate (2.32 mL, 47.78 mmol) at RT. The reaction mixture was stirred at 110° C. for 4 h. The progress of the reaction was monitored by TLC. The reaction mixture was diluted with water (50 mL) to obtain the solid. The solid was filtered, washed with water (50 mL), isopropanol (50 mL) and dried under reduced pressure to obtain compound FP (2.5 g. crude) as an off-white solid which was used in the next step without further purification. $^1$H NMR (400 MHz, DMSO-$d_6$): δ 8.39 (s, 1H), 7.38-7.35 (m, 4H), 7.23 (brs, 1H), 6.96 (d, J=9.2 Hz, 2H), 6.90 (d, J=9.0 Hz, 2H), 4.29 (brs, 2H), 3.29-3.23 (m, 4H), 3.18-3.14 (m, 4H).

4-(4-(4-(4-bromophenyl)piperazin-1-yl) phenyl)-2,4-dihydro-3H-1,2,4-triazol-3-one (FQ)

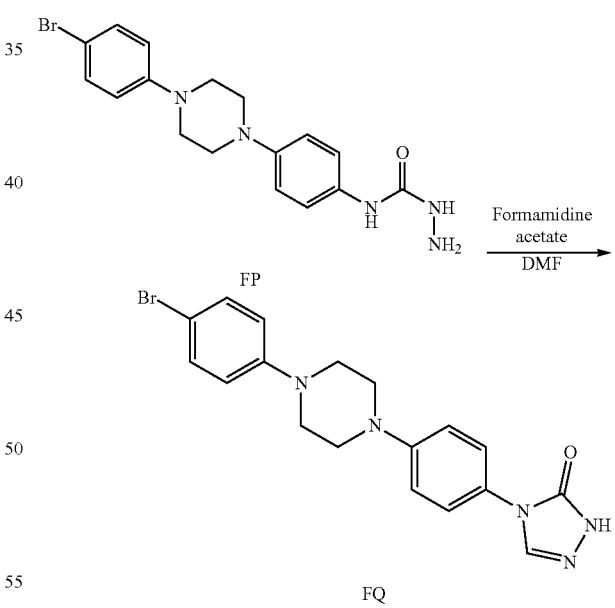

To a stirred solution of compound FP (2.5 g, 6.41 mmol) in DMF (30 mL) under argon atmosphere was added formamidine acetate (2.93 g, 28.20 mmol) at RT. The reaction mixture was stirred at 120° C. for 4 h. The progress of the reaction was monitored by TLC. The reaction mixture was diluted with water (50 mL) to obtain the solid. The solid was filtered and dried under reduced pressure. The crude material was purified by silica gel column chromatography (eluent: 2% MeOH/$CH_2Cl_2$) to afford compound FQ (1 g, 2.50 mmol, 40%) as a pale yellow solid. $^1$H NMR (400 MI-Hz, DMSO-$d_6$): δ 11.85 (brs, 1H), 8.24 (s, 1H), 7.48 (d, J=9.0 Hz, 2H), 7.37 (d, J=9.0 Hz, 2H), 7.09 (d, J=9.2 Hz, 2H), 6.97 (d, J=9.0 Hz, 2H), 3.34-3.26 (m, 8H).

4-(4-(4-(4-bromophenyl) piperazin-1-yl) phenyl)-2-isopropyl-2,4-dihydro-3H-1,2,4-triazol-3-one (FR)

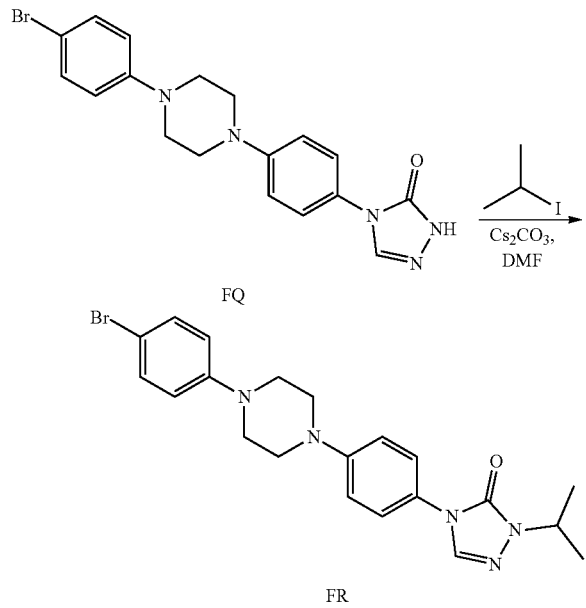

To a stirred solution of compound FQ (300 mg, 0.75 mmol) in DMF (10 mL) under argon atmosphere were added cesium carbonate (611 mg 0.87 mmol) and 2-iodo propane (382 mg, 2.25 mmol) at 0° C. The reaction mixture was warmed to RT and stirred for 16 h. The reaction mixture was quenched with ice cold water (20 mL) and extracted with EtOAc (2×20 mL). The combined organic extracts were washed with water (20 mL), brine (10 mL), dried over anhydrous $Na_2SO_4$ and concentrated under reduced pressure. The crude material was purified by silica gel column chromatography (eluent: 1-5% MeOH/$CH_2Cl_2$) to afford compound FR (220 mg, 0.49 mmol, 66.6%) as yellow solid. $^1$H NMR (400 MHz, CDCl$_3$): δ 7.60 (s, 1H), 7.44-7.36 (m, 4H), 7.02 (d, J=9.0 Hz, 2H), 6.84 (d, J=9.0 Hz, 2H), 4.59-4.52 (m, 1H), 3.38-3.28 (m, 8H), 1.42 (d, J=6.7 Hz, 6H).

2-isopropyl-4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (FS)

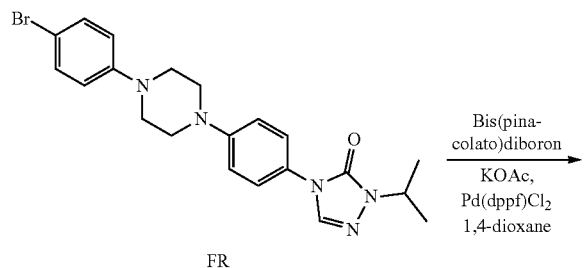

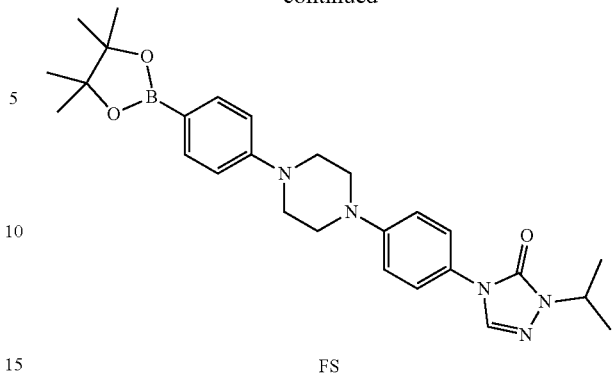

To a stirred solution of compound FR (220 mg, 0.49 mmol) in 1,4-dioxane (30 mL) under argon atmosphere were added bis(pinacolato)diboron (202 mg, 0.79 mmol) and potassium acetate (141 mg, 1.49 mmol) at RT. The reaction mixture was purged with argon for 20 min, then Pd(dppf)Cl$_2$ (36 mg, 0.05 mmol) was added and the reaction mixture was purged under argon for 5 min at RT. The reaction mixture was stirred at 110° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 40% EtOAc/Hexane) to afford compound FS (150 mg, 0.30 mmol, 62%) as an off-white solid. $^1$H NMR (500 MHz, CDCl$_3$): δ 7.74 (d, J=8.4 Hz, 2H), 7.60 (s, 1H), 7.41 (d, J=9.0 Hz, 2H), 7.02 (d, J=9.0 Hz, 2H), 6.94 (d, J=8.4 Hz, 2H), 4.58-4.53 (m, 1H), 3.45-3.33 (m, 8H), 1.41 (d, J=6.9 Hz, 6H), 1.33 (s, 12H).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-isopropyl-2,4-dihydro-3H-1,2,4-triazol-3-one (52)

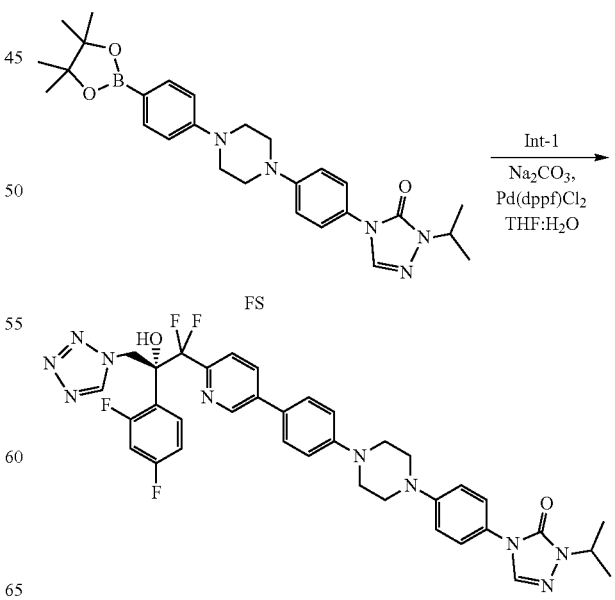

To a stirred solution of Int-1 (130 mg, 0.30 mmol) in THF:H$_2$O (4:1, 25 mL) under argon atmosphere were added compound FS (147 mg, 0.30 mmol), sodium carbonate (95 mg, 0.90 mmol) and purged under argon for 15 min at RT. Then Pd(dppf)Cl$_2$ (21 mg, 0.03 mmol) was added and the reaction mixture was purged under argon for 10 min at RT. The reaction mixture was stirred at reflux for 16 h. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 10-80% EtOAc % Hexane) to afford 52 (53 mg, 0.07 mmol, 25%) as an off-white solid. $^1$H NMR (400 MHz, DMSO-d$_6$): δ 9.15 (s, 1H), 8.91 (d, J=1.9 Hz, 1H), 8.32 (s, 1H), 8.17 (dd, J=8.3, 2.2 Hz, 1H), 7.70 (d, J=8.9 Hz, 2H), 7.56-7.45 (m, 3H), 7.33-7.08 (m, 7H), 6.95-6.84 (m, 1H), 5.67 (d, J=14.7 Hz, 1H), 5.11 (d, J=14.7 Hz, 1H), 4.40-4.33 (m, 1H), 3.45-3.34 (m, 8H), 1.30 (d, J=6.8 Hz, 6H); MS (ESI): m/z: 715.7 [M+H]$^+$; HPLC: 98.26%; Optical rotation [α]$_D^{19}$: +137.84 (c=0.1% in CH$_2$Cl$_2$).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-methyl-2,4-dihydro-3H-1,2,4-triazol-3-one (53)

4-(4-(4-(4-bromophenyl) piperazin-1-yl) phenyl)-2-methyl-2,4-dihydro-3H-1,2,4-triazol-3-one (FT)

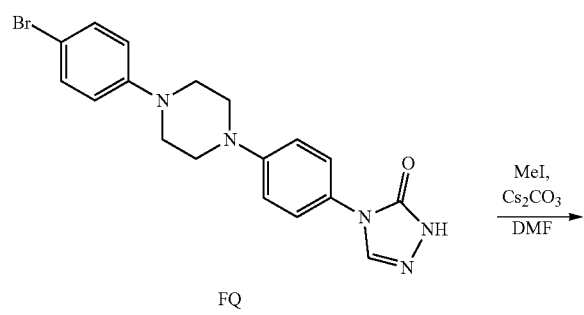

FQ

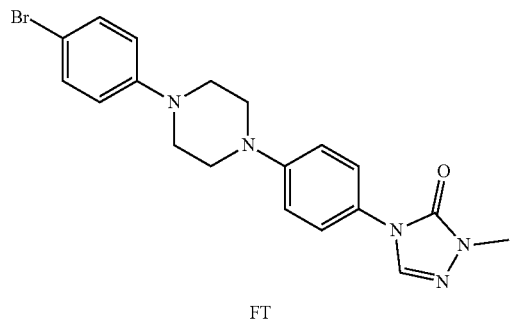

FT

To a stirred solution of compound FQ (250 mg, 0.62 mmol) in DMF (20 mL) under argon atmosphere were added cesium carbonate (509 mg, 1.56 mmol) and methyl iodide (0.11 mL, 1.87 mmol) at 0° C. The reaction mixture was stirred at RT for 5 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford compound FT (250 mg, 0.60 mmol, 80%) as an off-white solid. $^1$H NMR (400 MHz, DMSO-d$_6$): δ 8.32 (s, 1H), 7.48 (d, J=9.0 Hz, 2H), 7.37 (d, J=9.0 Hz, 2H), 7.10 (d, J=9.2 Hz, 2H), 6.97 (d, J=9.2 Hz, 2H), 3.37 (s, 3H), 3.31 (s, 8H).

2-methyl-4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (FU)

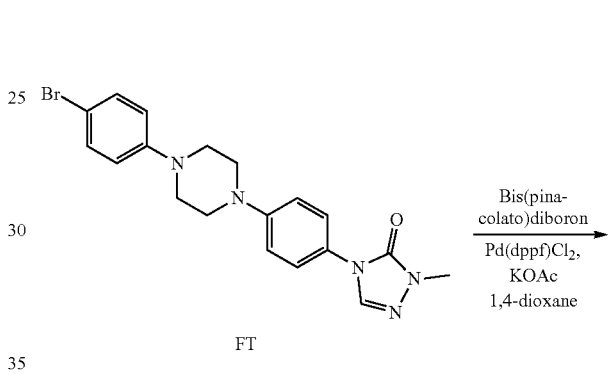

FT

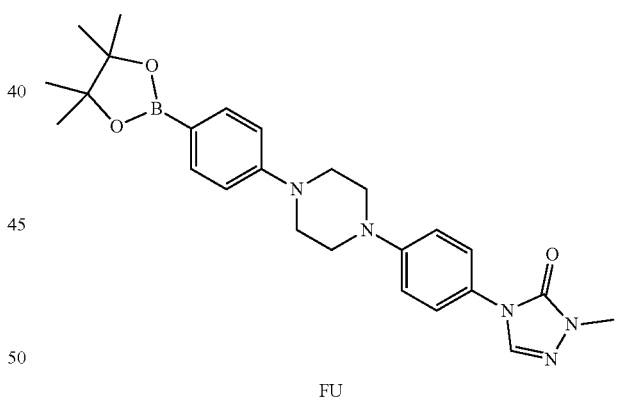

FU

To a stirred solution of compound FT (250 mg, 0.60 mmol) in 1,4-dioxane (30 mL) under argon atmosphere were added bis(pinacolato)diboron (244 mg, 0.96 mmol) and potassium acetate (177 mg, 1.80 mmol) at RT. The reaction mixture was purged with argon for 20 min, then Pd(dppf)Cl$_2$ (44 mg, 0.06 mmol) was added and the reaction mixture was purged under argon for 5 min at RT. The reaction mixture was stirred at 110° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 3% MeOH/Hexane) to afford compound FU (200 mg, 0.43 mmol, 71%) as an off-white solid. $^1$H NMR (400 MHz, DMSO-$d_6$): δ 8.32 (s, 1H), 7.54 (d, J=8.7 Hz, 2H), 7.48 (d, J=9.2 Hz, 2H), 7.10 (d, J=9.2 Hz, 2H), 6.97 (d, J=8.8 Hz, 2H), 3.37 (s, 8H), 3.31 (s, 3H), 1.27 (s, 12H).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-methyl-2,4-dihydro-3H-1,2,4-triazol-3-one (53)

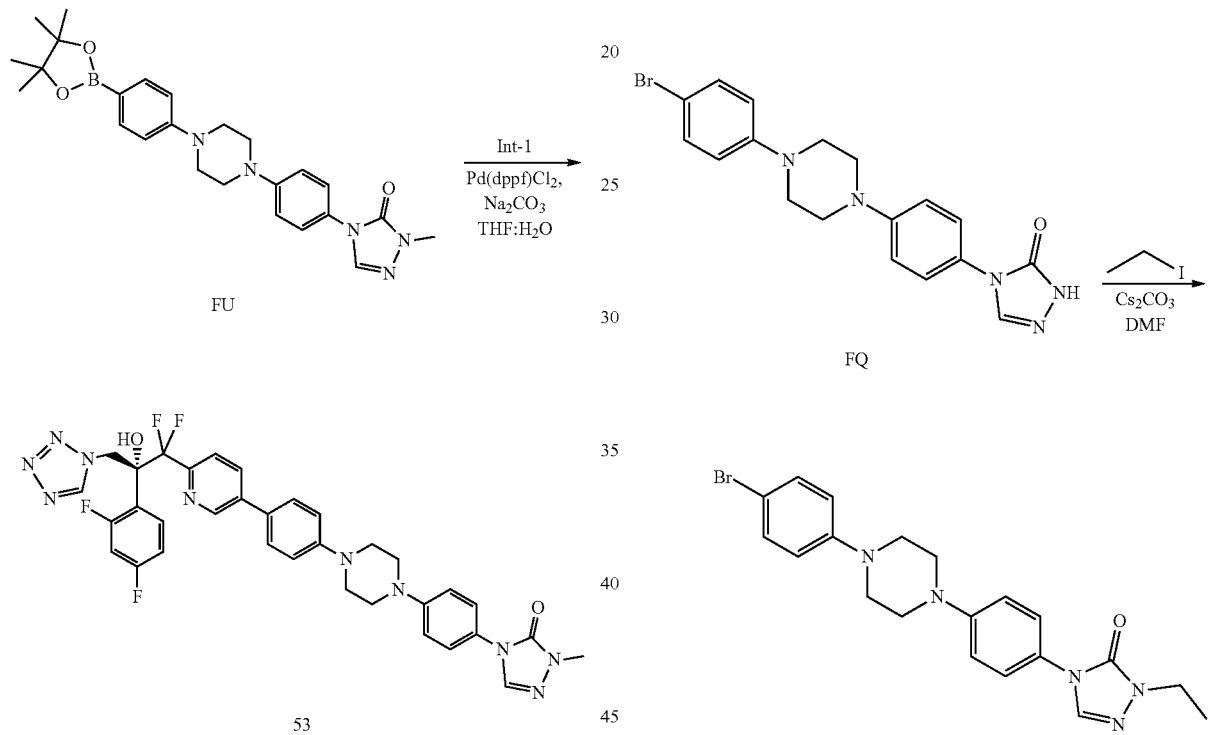

To a stirred solution of Int-1 (150 mg, 0.34 mmol) in THF:H2O (30 mL) under argon atmosphere were added compound FU (176 mg, 0.40 mmol), sodium carbonate (110 mg, 1.04 mmol) and purged under argon for 20 min at RT. Then Pd(dppf)Cl$_2$ (25 mg, 0.03 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 53 (60 mg, 0.09 mmol, 25%) as an off-white solid. $^1$H NMR (400 MHz, DMSO-$d_6$): δ 9.15 (s, 1H), 8.91 (s, 1H), 8.32 (s, 1H), 8.17 (dd, J=8.3, 2.1 Hz, 1H), 7.70 (d, J=8.8 Hz, 2H), 7.51-7.46 (m, 3H), 7.32-7.24 (m, 2H), 7.23-7.16 (m, 1H), 7.16-7.11 (m, 4H), 6.93-6.89 (m, 1H), 5.67 (d, J=14.7 Hz, 1H), 5.11 (d, J=14.7 Hz, 1H), 3.44-3.32 (m, 11H); MS (ESI): m/z 687.7 [M+H]$^+$; HPLC: 96.86%; Optical rotation $[α]_D^{20}$: +127.7 (c=0.1% in CH$_2$Cl$_{12}$).

Example 54

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-ethyl-2,4-dihydro-3H-1,2,4-triazol-3-one (54)

4-(4-(4-(4-bromophenyl) piperazin-1-yl) phenyl)-2-ethyl-2,4-dihydro-3H-1,2,4-triazol-3-one (FV)

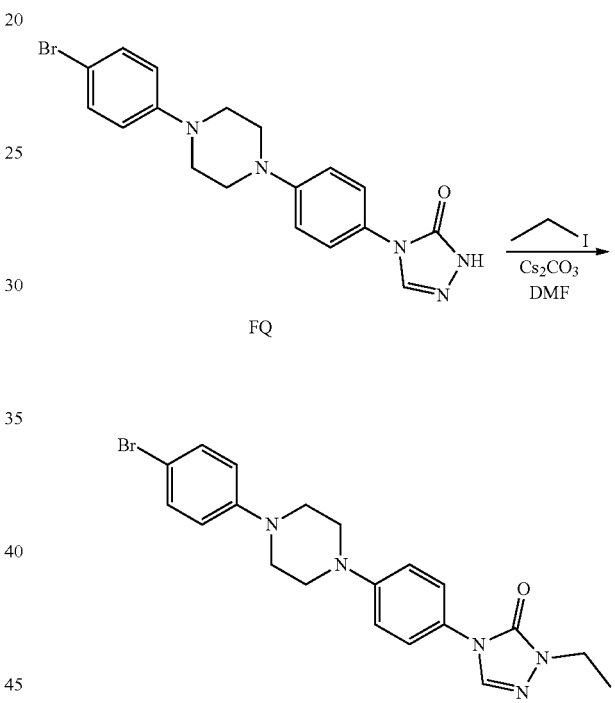

To a stirred solution of compound FQ (200 mg, 0.50 mmol) in DMF (15 mL) under argon atmosphere were added cesium carbonate (407 mg, 1.27 mmol) and ethyl iodide (0.12 mL, 1.5 mmol) at RT and stirred for 5 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 2% MeOH/CH$_2$Cl$_2$) to afford compound FV (200 mg, 0.46 mmol, 75%) as a pale yellow solid. $^1$H NMR (400 MHz, DMSO-$d_6$): δ 8.32 (s, 1H), 7.49 (d, J=9.0 Hz, 2H), 7.38 (d, J=9.0 Hz, 2H), 7.10 (d, J=9.0 Hz, 2H), 6.97 (d, J=9.0 Hz, 2H), 3.78-3.75 (m, 2H), 3.35-3.25 (m, 8H), 1.25 (t, J=7.2 Hz, 3H).

2-ethyl-4-(4-(4-(4-(4,4,5,5-tetramethyl-1,3,2-dioxaborolan-2-yl) phenyl) piperazin-1-yl) phenyl-2,4-dihydro-3H-1,2,4-triazol-3-one (FW)

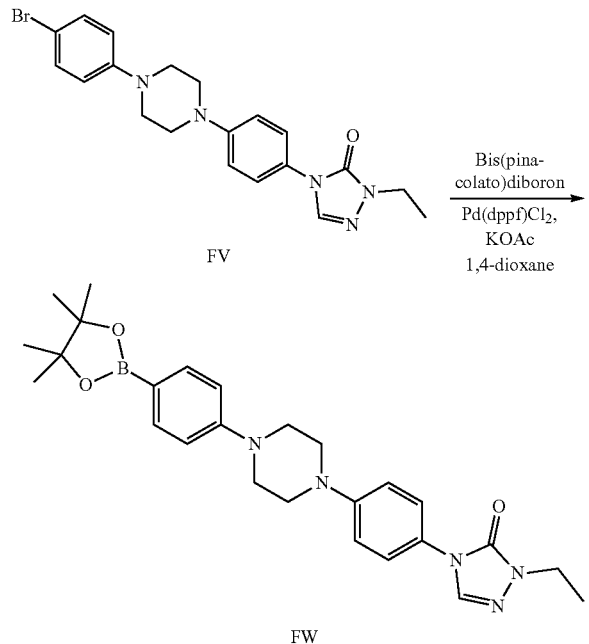

To a stirred solution of compound FV (200 mg, 0.46 mmol) in 1,4-dioxane (200 mL) under argon atmosphere were added bis(pinacolato)diboron (189 mg, 0.80 mmol) and potassium acetate (137 mg, 1.40 mmol) at RT. The reaction mixture was purged with argon for 20 min, then Pd(dppf)Cl$_2$ (34 mg, 0.04 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 20% EtOAc/Hexane) to afford compound FW (180 mg, 0.37 mmol, 81%) as a pale yellow solid. $^1$H NMR (500 MHz, DMSO-d$_6$): δ 8.46 (s, 1H), 7.54 (d, J=8.1 Hz, 2H), 7.49 (d, J=8.7 Hz, 2H), 7.12 (d, J=8.7 Hz, 2H), 6.98 (d, J=8.1 Hz, 2H), 3.91 (s, 2H), 3.41-3.31 (m, 8H), 1.29-1.26 (m, 3H), 1.17 (s, 12H).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-ethyl-2,4-dihydro-3H-1,2,4-triazol-3-one (54)

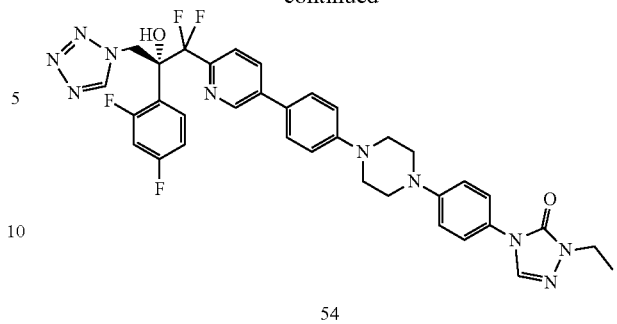

To a stirred solution of Int-1 (150 mg, 0.34 mmol) in THF:H2O (4:1, 20 mL) under argon atmosphere were added compound FW (181 mg, 0.35 mmol), sodium carbonate (110 mg, 1.04 mmol) and purged under argon for 20 min at RT. Then Pd(dppf)Cl$_2$ (25 mg, 0.03 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 50% EtOAc/Hexane) to afford 54 (70 mg, 0.1 mmol, 25%) as an off-white solid. $^1$H NMR (400 MHz, DMSO-d$_6$): δ 9.15 (s, 1H), 8.91 (s, 1H), 8.33 (s, 1H), 8.17 (dd, J=8.3, 2.3 Hz, 1H), 7.70 (d, J=8.8 Hz, 2H), 7.58-7.47 (m, 3H), 7.36-7.02 (m, 7H), 6.93-6.89 (m, 1H), 5.67 (d, J=14.7 Hz, 1H), 5.11 (d, J=14.7 Hz, 1H), 3.79-3.73 (m, 2H), 3.44-3.29 (m 8H), 1.25 (t, J=7.2 Hz, 3H); MS (ESI): m/z 701.8 [M+H]$^+$; HPLC: 94.32%; Optical rotation $[α]_D^{20}$: +110.48 (c=0.1% in CH$_2$Cl$_2$).

Example 55

2-(sec-butyl)-4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2,4-dihydro-3H-1,2,4-triazol-3-one (55)

4-(4-(4-(4-bromophenyl) piperazin-1-yl) phenyl)-2-(sec-butyl)-2,4-dihydro-3H-1,2,4-triazol-3-one (FX)

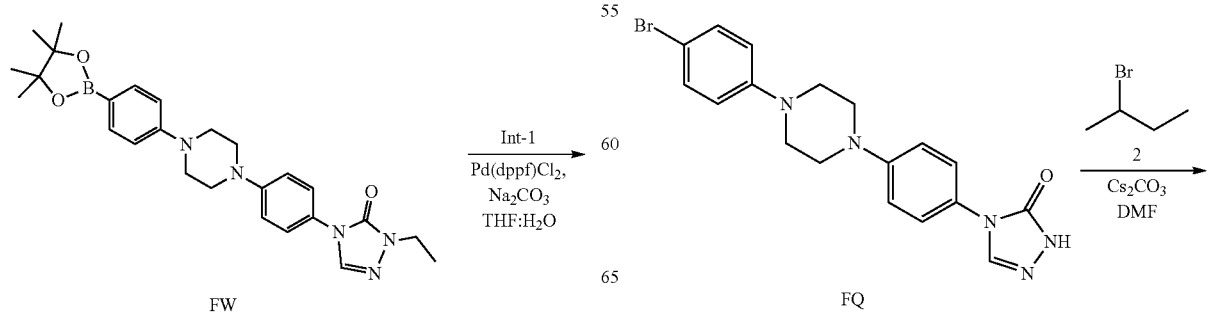

-continued

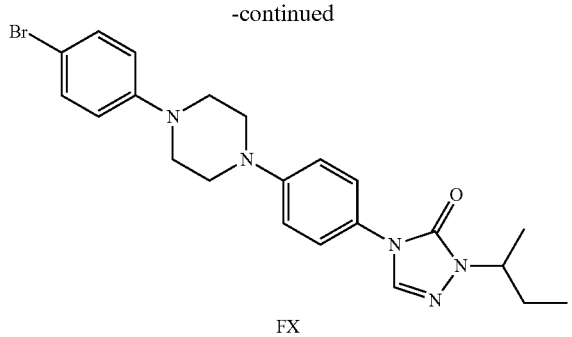

FX

-continued

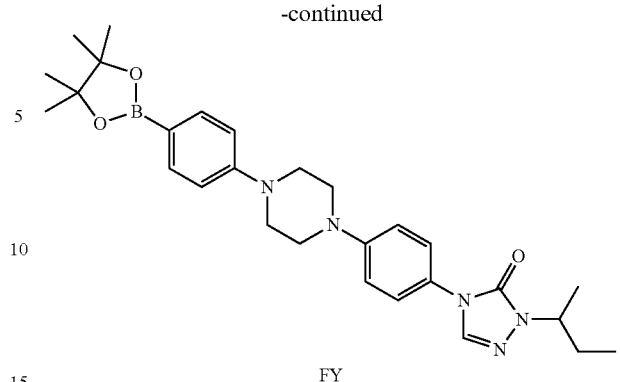

FY

To a stirred solution of compound FQ (300 mg, 0.75 mmol) in DMF (20 mL) under argon atmosphere were added cesium carbonate (611 mg, 1.87 mmol) and 2-bromobutane 2 (308 mg, 2.25 mmol) at 0° C. The reaction mixture was warmed to RT and stirred for 6 h. The progress of the reaction was monitored by TLC. The reaction mixture was diluted with water (50 mL) and extracted with EtOAc (2×50 mL). The combined organic extracts were washed with water (20 mL), brine (20 mL), dried over anhydrous $Na_2SO_4$ and concentrated under reduced pressure. The crude material was purified by silica gel column chromatography (eluent: 30% EtOAc/Hexane) to afford compound FX (220 mg, 0.48 mmol, 64.5%) as an off-white solid. $^1$H NMR (400 MHz, DMSO-$d_6$): δ 8.32 (s, 1H), 7.50 (d, J=9.2 Hz, 2H), 7.38 (d, J=9.0 Hz, 2H), 7.10 (d, J=9.0 Hz, 2H), 6.97 (d, J=9.2 Hz, 2H), 4.16-4.06 (m, 1H), 3.37-3.27 (m, 8H), 1.87-1.53 (m, 2H), 1.28 (d, J=6.8 Hz, 3H), 0.79 (t, J=7.4 Hz, 3H).

2-(sec-butyl)-4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (FY)

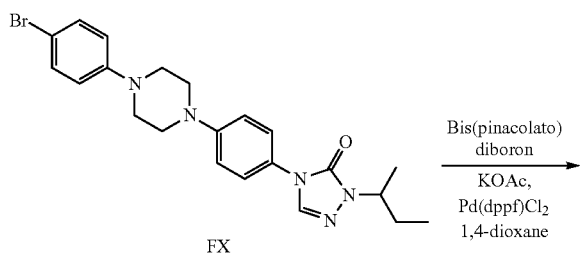

To a stirred solution of compound FX (220 mg, 0.48 mmol) in 1,4-dioxane (20 mL) under argon atmosphere were added bis(pinacolato)diboron (195 mg, 0.77 mmol), KOAc (142 mg, 1.48 mmol) at RT and purged under argon for 15 min. Then Pd(dppf)Cl$_2$ (35 mg, 0.04 mmol) was added to the reaction mixture at RT and again purged under argon for 5 min at RT, stirred at reflux for 16 h in a sealed tube. The progress of the reaction was monitored by TLC, the reaction mixture was diluted with water (30 mL) and extracted with EtOAc (2×30 mL). The combined organic extracts were washed with water (30 mL), brine (30 mL), dried over anhydrous $Na_2SO_4$ and concentrated under reduced pressure. The crude material was purified by silica gel column chromatography (eluent: 30% EtOAc/Hexane) to afford compound FY (140 mg, 0.27 mmol, 57.6%) as an off-white solid. $^1$H NMR (400 MHz, DMSO-$d_6$): δ 8.32 (s, 1H), 7.54 (d, J=8.7 Hz, 2H), 7.50 (d, J=9.2 Hz, 2H), 7.10 (d, J=9.2 Hz, 2H), 6.98 (d, J=8.8 Hz, 2H), 4.17-4.06 (m, 1H), 3.43-3.33 (m, 8H), 1.78-1.56 (m, 2H), 1.27 (s, 12H), 1.07 (s, 3H), 0.79 (t, J=7.4 Hz, 3H).

2-(sec-butyl)-4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2,4-dihydro-3H-1,2,4-triazol-3-one (55)

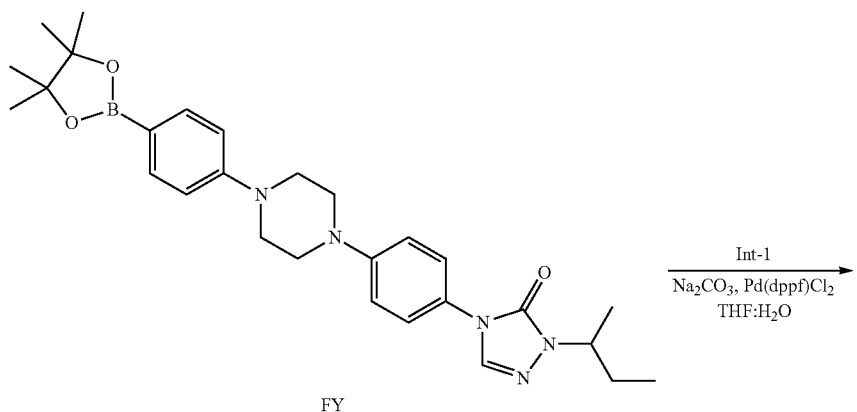

-continued

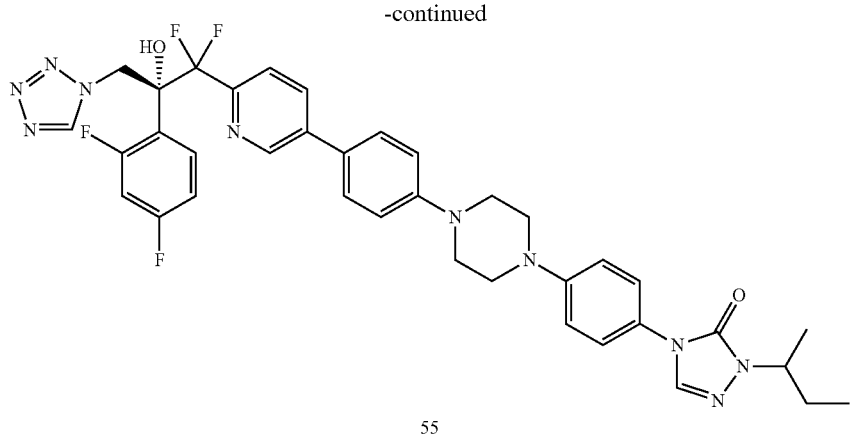

55

To a stirred solution of Int-1 (100 mg, 0.23 mmol) in THF:H2O (4:1, 10 mL) under argon atmosphere were added compound FY (139 mg, 0.27 mmol), sodium carbonate (74 mg, 0.70 mmol) at RT and purged under argon for 10 min. Then Pd(dppf)Cl$_2$ (17 mg, 0.02 mmol) was added to the reaction mixture at RT and stirred at 80° C. for 12 h in a sealed tube. The progress of the reaction was monitored by TLC, the reaction mixture was diluted with water (10 mL) and extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluent: 80% EtOAc/Hexane) to afford 55 (35 mg, 0.05 mmol, 23.4%) as yellow solid. $^1$H NMR (400 MHz, DMSO-d$_6$): δ 9.15 (s, 1H), 8.91 (s, 1H), 8.33 (s, 1H), 8.17 (dd, J=8.3, 2.0 Hz, 1H), 7.70 (d, J=8.8 Hz, 2H), 7.58-7.43 (m, 3H), 7.32-7.24 (m, 2H), 7.23-7.08 (m, 5H), 6.97-6.88 (m, 1H), 5.67 (d, J=14.7 Hz, 1H), 5.11 (d, J=14.7 Hz, 1H), 4.17-4.07 (m, 1H), 3.51-3.32 (m, 8H), 1.80-1.58 (m, 2H), 1.29 (d, J=6.8 Hz, 3H), 0.80 (t, J=7.3 Hz, 3H); MS (ESI): m/z 729.6 [M+H]$^+$; HPLC: 98.49% b; Optical rotation $[\alpha]_D^{19}$: +76.16 (c=0.1% in MeOH).

Example 56

(2R)-2-(2,4-difluorophenyl)-1,1-difluoro-1-(5-(4-(4-(1-hydroxyethyl) phenyl) piperazin-1-yl) phenyl) pyridin-2-yl)-3-(1H-tetrazol-1-yl) propan-2-ol (56)

1-(4-(4-(4-bromophenyl) piperazin-1-yl) phenyl) ethan-1-ol (FZ)

The same procedure used for compound EK was used to synthesize FZ (350 mg, 0.96 mmol, 69.7%) as an off-white solid. $^1$H NMR (400 MHz, DMSO-d$_6$): δ 7.37 (d, J=9.2 Hz, 2H), 7.20 (d, J=8.4 Hz, 2H), 6.97-6.93 (m, 4H), 4.93 (d, J=4.1 Hz, 1H), 4.67-4.59 (m, 1H), 3.30-3.20 (m, 8H), 1.29 (d, J=6.4 Hz, 3H).

1-(4-(4-(4-(4,4,5,5-tetramethyl-1,3,2-dioxaborolan-2-yl) phenyl piperazin-1-yl) phenyl) ethan-1-ol (GA)

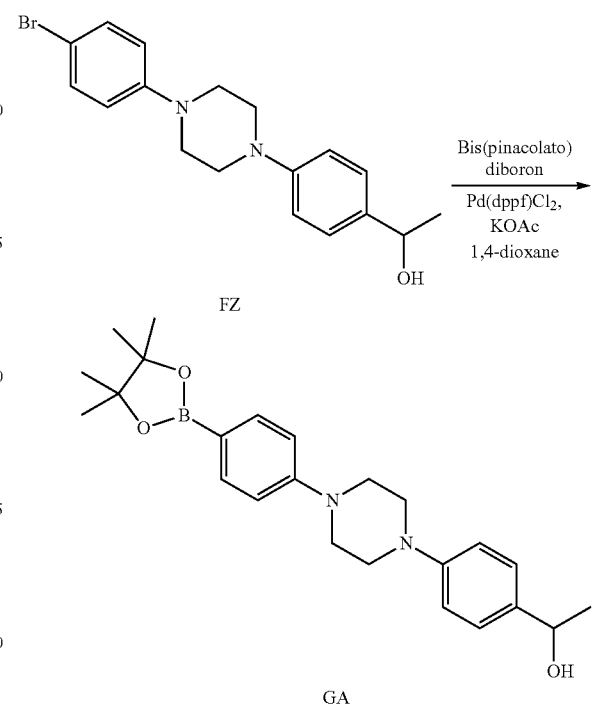

To a stirred solution of compound FZ (350 rug, 0.96 mmol) in 1,4-dioxane (20 mL) under argon atmosphere were added bis(pinacolato)diboron (392 mg, 1.55 mmol), KOAc (285 mg, 2.90 mmol) at RT and purged under argon for 15 min. Then Pd(dppf)Cl$_2$ (70 mg, 0.09 mmol) was added to the reaction mixture at RT and stirred at 110° C. for 12 h in a sealed tube. The progress of the reaction was monitored by TLC, the reaction mixture was diluted with water (30 mL) and extracted with EtOAc (2×30 mL). The combined organic extracts were washed with water (30 mL), brine (30 mL), dried over anhydrous Na$_2$SO$_4$ and concentrated under reduced pressure. The crude material was purified by silica gel column chromatography (eluent: 30% EtOAc/Hexane) to afford compound GA (170 mg, 0.41 mmol, 43%) as an off-white solid. LC-MS: m/z 409.2 [M+H]+ at 3.55 RT (84% purity).

(2R)-2-(2,4-difluorophenyl)-1,1-difluoro-1-(5-(4-(4-(4-(1-hydroxyethyl) phenyl) piperazin-1-yl) phenyl) pyridin-2-yl)-3-(1H-tetrazol-1-yl) propan-2-ol (56)

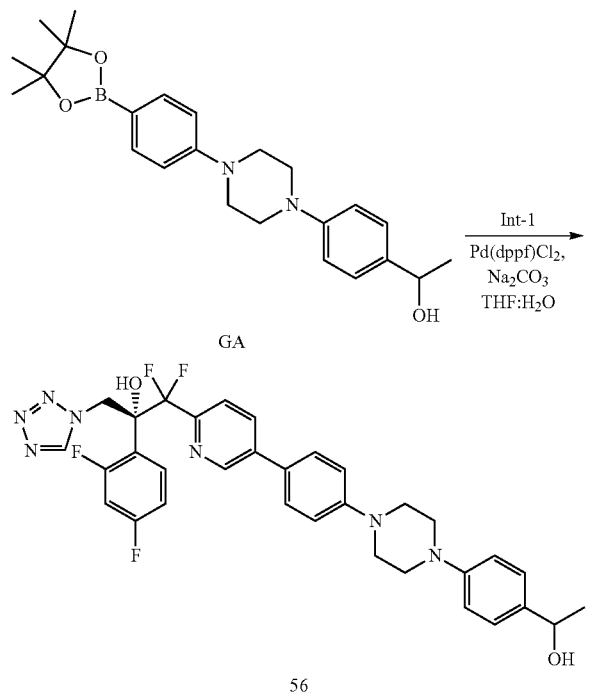

To a stirred solution of Int-1 (130 mg, 0.30 mmol) in THF:H2O (4:2, 10 mL) under argon atmosphere were added compound GA (151 mg, 0.36 mmol), sodium carbonate (96 mg, 0.90 mmol) at RT and purged under argon for 10 min. Then Pd(dppf)Cl₂ (22 mg, 0.03 mmol) was added to the reaction mixture at RT and again purged under argon for 5 min at RT, stirred at 80° C. for 5 h in a sealed tube. The progress of the reaction was monitored by TLC, the reaction mixture was diluted with water (10 mL) and extracted with EtOAc (2×10 mL). The combined organic extracts were washed with water (10 mL), brine (10 mL), dried over anhydrous Na₂SO₄ and concentrated under reduced pressure. The crude material was purified by silica gel column chromatography (eluent: 50% EtOAc/Hexane) to afford 56 (70 rug, 0.11 mmol, 33.6%) as an off-white solid. ¹H NMR (400 MHz, DMSO-d₆): δ 9.15 (s, 1H), 8.91 (d, J=1.9 Hz, 1H), 8.16 (dd, J=8.3, 2.1 Hz, 1H), 7.70 (d, J=8.8 Hz, 2H), 7.48 (d, J=8.3 Hz, 1H), 7.33-7.25 (m, 3H), 7.22 (d, J=8.4 Hz, 2H), 7.13 (d, J=8.8 Hz, 2H), 6.96 (d, J=8.7 Hz, 2H), 6.93-6.88 (m, 1H), 5.67 (d, J=14.7 Hz, 1H), 5.11 (d, J=14.7 Hz, 1H), 4.94 (d, J=4.3 Hz, 1H), 4.68-4.59 (m, 1H), 3.40-3.37 (m, 4H), 3.28-3.25 (m, 4H), 1.29 (d, J=6.4 Hz, 3H); MS (ESI): m/z 632.3 [M–H]⁻; HPLC: 95.67%; Optical rotation [α]$_D^{20}$: +46.68 (c=0.1% in MeOH).

Example 57

4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl)-N-((2S,3S)-2-hydroxypentan-3-yl) benzamide (57)

Ethyl 4-(4-(4-bromophenyl) piperazin-1-yl) benzoate (GC)

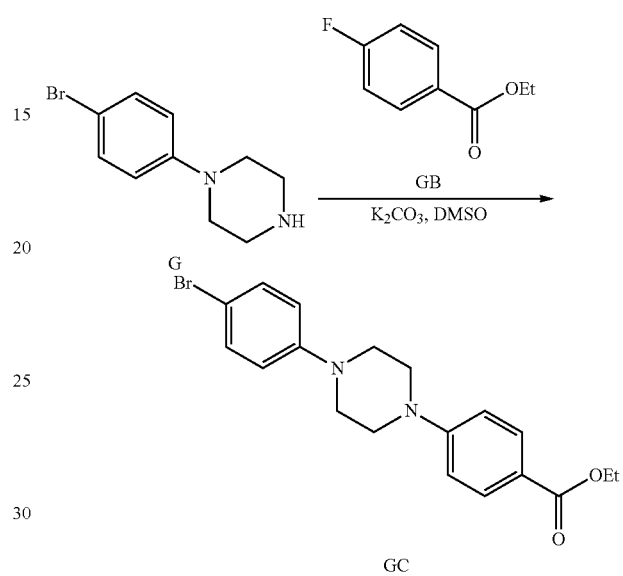

To a stirred solution of compound G (1 g, 4.14 mmol) in DMSO (10 mL) under argon atmosphere was added potassium carbonate (1.1 g, 8.29 mmol) at RT and stirred for 5 min. Then compound GB (0.8 mL, 4.97 mmol) was added to the reaction mixture at RT. The reaction mixture was stirred at 120° C. for 12 h. The progress of the reaction was monitored by TLC. The reaction mixture was quenched with ice cold water (50 mL) and extracted with EtOAc (2×50 mL). The combined organic layers were washed with water (50 mL), brine (50 mL), dried over anhydrous Na₂SO₄ and concentrated under reduced pressure. The crude material was purified by silica gel column chromatography (eluent: 20-40% EtOAc/Hexane) to afford compound GC (400 mg, 1.02 mmol, 25%) as colorless semi-solid. ¹H NMR (400 MHz, CDCl₃): δ 7.96 (d, J=9.0 Hz, 2H), 7.38 (d, J=9.0 Hz, 2H), 6.91 (d, J=9.0 Hz, 21H), 6.83 (d, J=9.0 Hz, 2H), 4.37-4.31 (m, 2H), 3.52-3.44 (m, 4H), 3.34-3.28 (m, 4H), 1.38 (t, J=7.2 Hz, 3H).

4-(4-(4-bromophenyl)piperazin-1-yl)benzoic acid (GD)

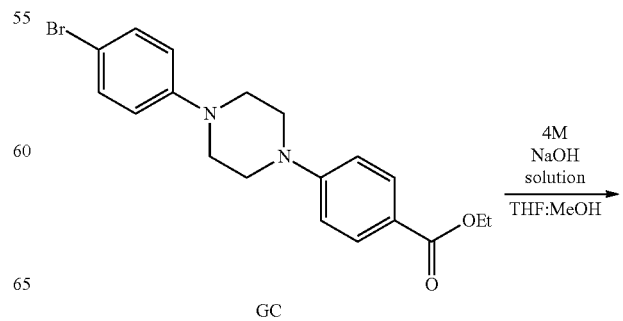

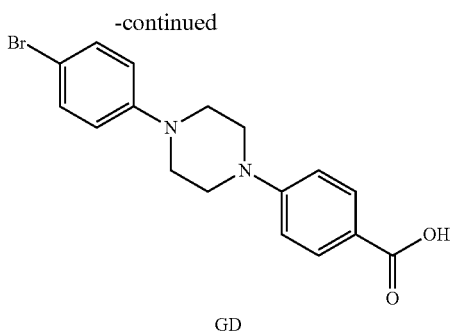

To a stirred solution of compound GC (1.0 g, 2.57 mmol) in THF:MeOH (5 mL) under argon atmosphere was added 4M NaOH solution (10 mL) at 0° C., and stirred at reflux for 18 h. The progress of the reaction was monitored by TLC. The reaction mixture was concentrated to remove excess solvent and the residue acidified using 1.0 N HCl solution (20 mL) and extracted with EtOAc (2×100 mL). The combined organic layers were dried over anhydrous Na$_2$SO$_4$ and concentrated under reduced pressure. The crude material was with n-pentane to afford GD (500 mg, 1.38 mmol, 53%) as an off-white solid. $^1$H NMR (400 MHz, DMSO-d$_6$): δ 7.72 (d, J=8.8 Hz, 2H), 7.37 (d, J=9.0 Hz, 2H), 6.96 (d, J=9.0 Hz, 2H), 6.86 (br d, J=8.8 Hz, 2H), 3.31-3.21 (m, 8H).

4-(4-(4-bromophenyl)piperazin-1-yl)-N-((2S,3S)-2-hydroxypentan-3-yl)benzamide (GE)

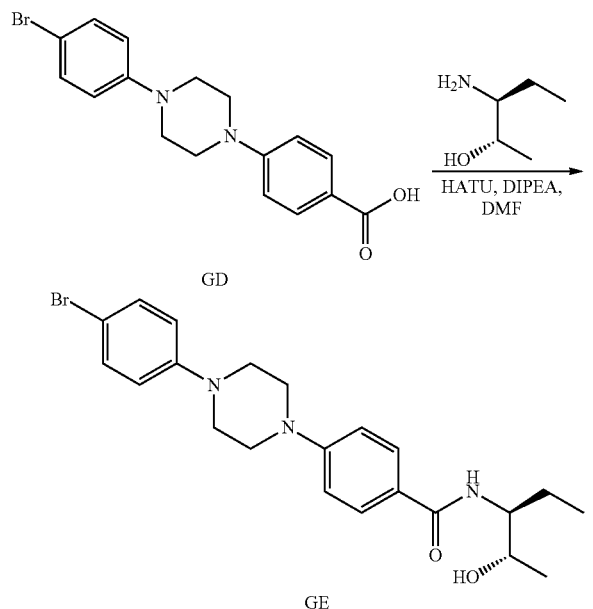

To a stirred solution of compound GD (500 mg, 1.38 mmol) in DMF (20 mL) were added (2S,3S)-3-aminopentan-2-ol (143 mg, 1.38 mmol), HATU (633 mg, 1.66 mmol) and ethyldiisopropylamine (0.48 mL, 2.77 mmol) at 0° C. under inert atmosphere. The reaction mixture was stirred at RT for 16 h. The reaction mixture was quenched with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 40% EtOAc/Hexane) to afford compound GE (300 mg, 0.68 mmol, 49%) as an off-white solid. $^1$H NMR (500 MHz, CDCl$_3$): δ 7.75 (d, J=8.8 Hz, 2H), 7.38 (d, J=9.0 Hz, 2H), 6.96 (d, J=9.0 Hz, 2H), 6.88 (d, J=8.8 Hz, 2H), 4.56 (d, J=6.4 Hz, 1H), 3.77-3.58 (m, 2H), 3.52-3.47 (m, 4H), 3.38-3.33 (m, 4H), 1.58-1.43 (m, 2H), 1.00 (d, J=6.3 Hz, 3H), 0.88 (t, J=7.4 Hz, 3H).

N-((2S,3S)-2-hydroxypentan-3-yl)-4-(4-(4,4,5,5-tetramethyl-1,3,2-dioxaborolan-2-yl) phenyl) piperazin-1-yl) benzamide (GF)

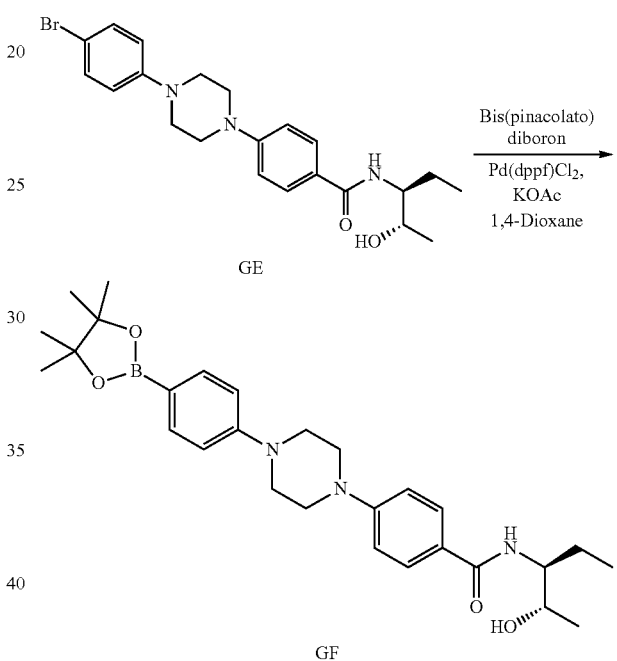

To a stirred solution of compound GE (300 mg, 0.68 mmol) in 1,4-dioxane (10 mL) under argon atmosphere were added bis(pinacolato)diboron (285 mg, 1.08 mmol) and potassium acetate (200 mg, 2.04 mmol) at RT and purged under argon for 15 min. Then Pd(dppf)Cl$_2$ (49 mg, 0.068 mmol) was added and the reaction mixture was purged under argon for 5 min at RT. The reaction mixture was stirred at 110° C. for 12 h. The progress of the reaction was monitored by TLC. The reaction mixture was quenched with water (10 mL) and extracted with EtOAc (2×50 mL). The combined organic layers were washed with water (25 mL), brine (20 mL), dried over anhydrous Na$_2$SO$_4$ and concentrated under reduced pressure. The crude material was purified by silica gel column chromatography (eluent: 60% EtOAc/Hexane) to afford compound GF (300 mg, 77% LC-MS purity) as colorless semi-solid. $^1$H NMR (500 MHz, CDCl$_3$): δ 7.79 (d, J=8.8 Hz, 2H), 7.56 (d, J=9.0 Hz, 2H), 7.01 (d, J=9.0 Hz, 2H), 6.96 (d, J=8.8 Hz, 2H), 4.56 (d, J=6.4 Hz, 1H), 3.77-3.58 (m, 2H), 3.52-3.47 (m, 4H), 3.38-3.33 (m, 4H), 1.58-1.43 (m, 2H), 1.33 (s, 12H), 1.00 (d, J=6.3 Hz, 3H), 0.88 (t, J=7.4 Hz, 3H).

4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl)-N-((2S,3S)-2-hydroxypentan-3-yl) benzamide (57)

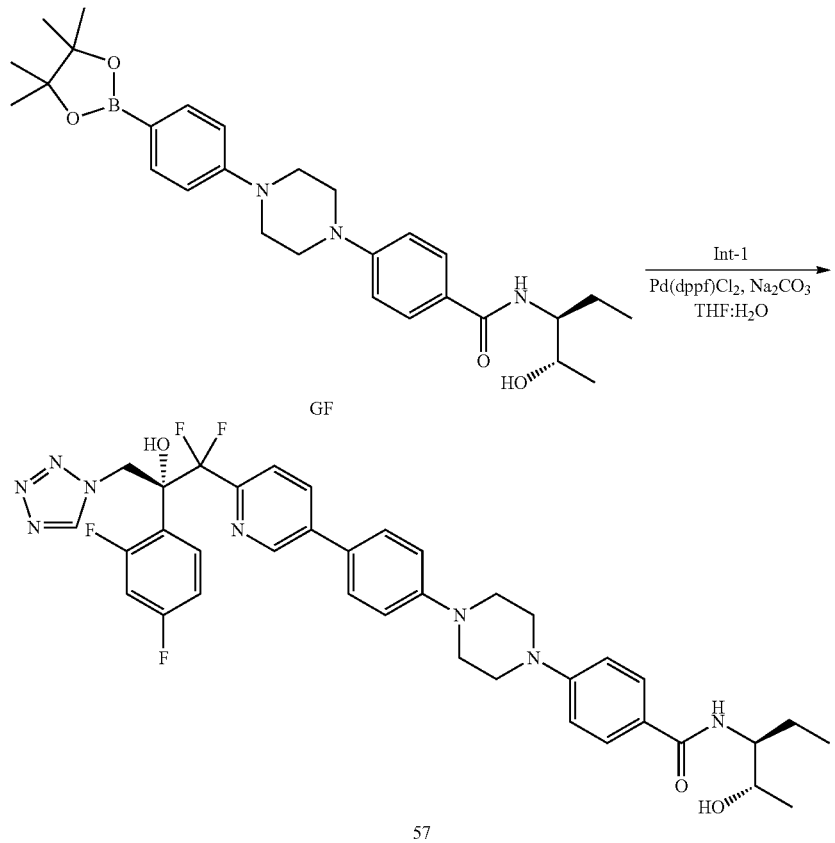

To a stirred solution of Int-1 (150 mg, 0.35 mmol) in THF:H2O (4:1, 10 mL) under argon atmosphere were added compound GF (201 mg, 0.408 mmol), sodium carbonate (140 mg, 1.02 mmol) and purged under argon for 10 min at RT. Then Pd(dppf)Cl$_2$ (12.5 mg, 0.017 mmol) was added to the reaction mixture at RT and stirred at 60° C. for 8 h. The progress of the reaction was monitored by TLC. The reaction mixture was diluted with water (20 mL) and extracted with EtOAc (2×50 mL). The combined organic extracts were washed with water (20 mL), brine (20 mL), dried over anhydrous Na$_2$SO$_4$ and concentrated under reduced pressure. The crude material was purified by silica gel column chromatography (eluent: 3% MeOH/DCM) to afford 57 (44 mg, 0.061 mmol, 17.5%) as an off-white solid. $^1$H NMR (400 MHz, CDCl$_3$): δ 8.76 (s, 1H), 8.73 (d, J=1.9 Hz, 1H), 7.95 (dd, J=8.2, 2.2 Hz, 1H), 7.85 (s, 1H), 7.76 (d, J=8.9 Hz, 2H), 7.61 (d, J=8.2 Hz, 1H), 7.52 (d, J=8.8 Hz, 2H), 7.42-7.36 (m 1H), 7.06 (d, J=8.8 Hz, 2H), 6.96 (d, J=8.9 Hz, 2H), 6.81-6.75 (m, 1H), 6.71-6.63 (m, 1H), 6.20 (d, J=8.9 Hz, 1H), 5.61 (d, J=14.2 Hz, 1H), 5.11 (d, J=14.2 Hz, 1H), 4.02-3.88 (m, 2H), 3.48-3.46 (m, 8H), 2.08 (br s, 1H), 1.76-1.59 (m, 2H), 1.24 (d, J=6.3 Hz, 3H), 1.00 (t, J=7.4 Hz, 3H); MS (ESI): m/z 719.7 [M+H]$^+$; HPLC: 96.83%; Optical rotation [α]$_D^{19}$: +44.16 (c=0.1% in MeOH).

Example 58

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-(2,2,2-trifluoroethyl)-2,4-dihydro-3H-1,2,4-triazol-3-one (58)

4-(4-(4-(4-bromophenyl) piperazin-1-yl) phenyl)-2-(2,2,2-trifluoroethyl)-2,4-dihydro-3H-1,2,4-triazol-3-one (GG)

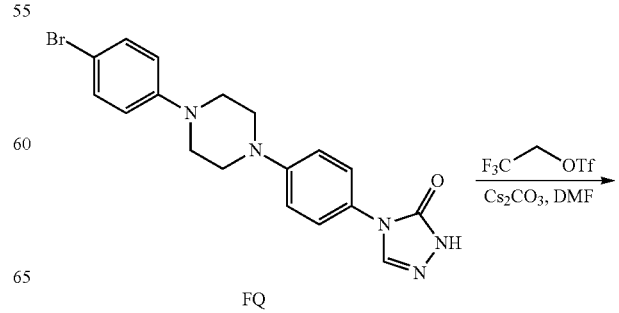

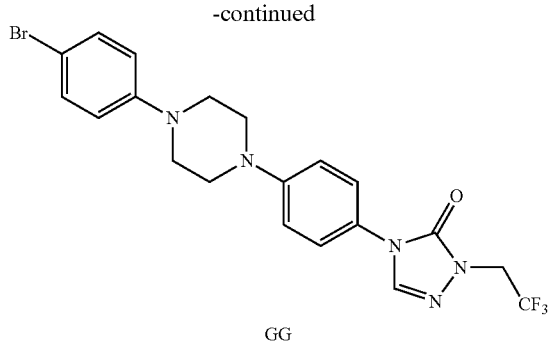

GG

To a stirred solution of compound FQ (200 mg, 0.50 mmol) in DMF (15 mL) under argon atmosphere were added cesium carbonate (489 mg, 1.5 mmol) and 2,2,2-trifluoroethyl trifluoromethanesulfonate (0.18 mL, 1.25 mmol) at RT and stirred for 5 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 2% MeOH/$CH_2Cl_2$) to afford compound GG (220 mg, 0.45 mmol, 73%) as a pale yellow solid. $^1$H NMR (400 MHz, DMSO-$d_6$): δ 8.46 (s, 1H), 7.49 (d, J=9.2 Hz, 2H), 7.40-7.36 (m, 2H), 7.12 (d, J=9.2 Hz, 2H), 7.00-6.93 (m, 2H), 4.71-4.64 (m, 2H), 3.37-3.27 (m, 8H).

4-(4-(4-(4-(4,4,5,5-tetramethyl-1,3,2-dioxaborolan-2-yl) phenyl) piperazin-1-yl) phenyl)-2-(2,2,2-trifluoroethyl)-2,4-dihydro-3H-1,2,4-triazol-3-one (GH)

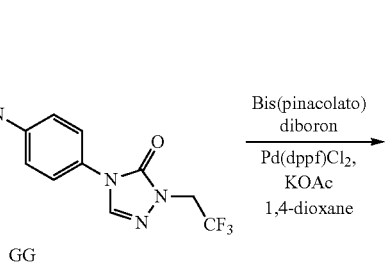

GG

Bis(pinacolato)diboron
Pd(dppf)Cl$_2$, KOAc
1,4-dioxane
→

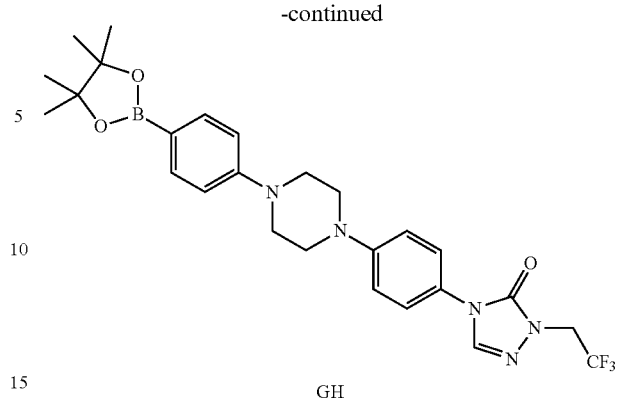

GH

To a stirred solution of compound CG (220 mg, 0.45 mmol) in 1,4-dioxane (20 mL) under argon atmosphere were added bis(pinacolato)diboron (185 mg, 0.73 mmol) and potassium acetate (134 mg, 1.36 mmol) at RT. The reaction mixture was purged with argon for 20 min, then Pd(dppf)Cl$_2$ (33 mg, 0.04 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 2% MeOH/$CH_2Cl_2$) to afford compound GH (200 mg, 0.37 mmol, 83%) as an off-white solid. $^1$H NMR (500 MHz, DMSO-$d_6$): δ 8.46 (s, 1H), 7.54 (d, J=8.1 Hz, 2H), 7.49 (d, J=8.7 Hz, 2H), 7.12 (d, J=8.7 Hz, 2H), 6.98 (d, J=8.1 Hz, 2H), 4.70-4.64 (m, 2H), 3.43-3.32 (m, 8H), 1.17 (s, 12H).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-(2,2,2-trifluoroethyl)-2,4-dihydro-3H-1,2,4-triazol-3-one (58)

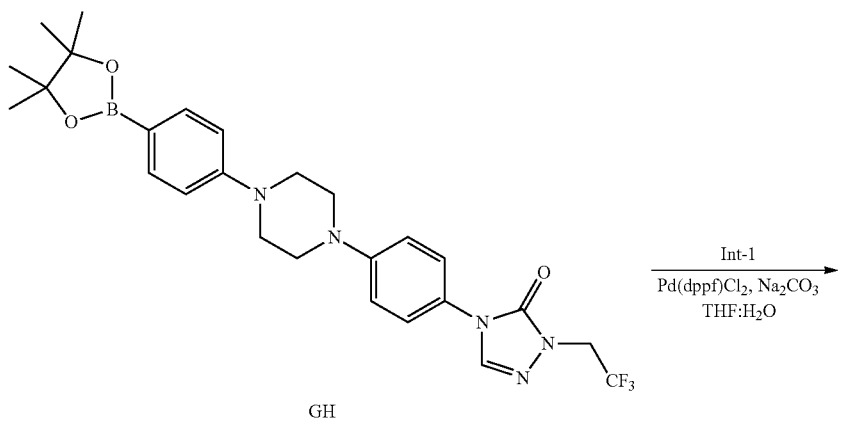

GH

Int-1
Pd(dppf)Cl$_2$, Na$_2$CO$_3$
THF:H$_2$O
→

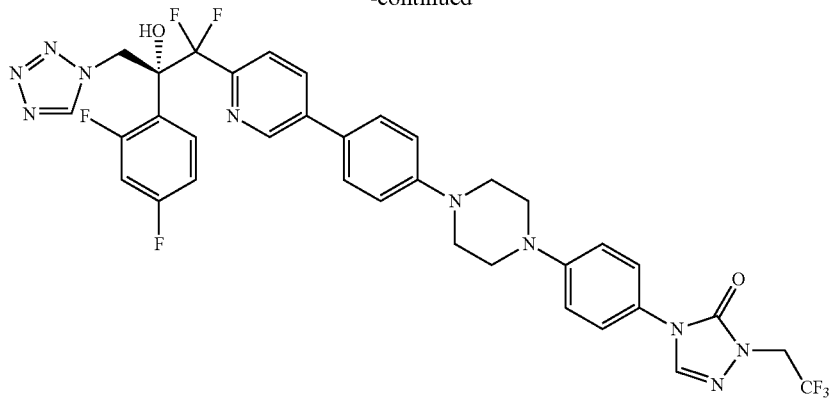

58

To a stirred solution of Int-1 (150 mg, 0.34 mmol) in THF:H2O (4:1.20 mL) under argon atmosphere were added compound GH (200 mg, 0.38 mmol), sodium carbonate (110 mg, 1.04 mmol) and purged under argon for 20 min at RT. Then Pd(dppf)Cl$_2$ (25 mg, 0.03 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The 1343 combined organic extracts were dried over anhydrous Na$_2$SO$_4$ and concentrated under reduced pressure. The crude material was purified by silica gel column chromatography (eluent: 60% EtOAc/Hexane) to afford 58 (55 mg, 0.07 mmol, 21%) as a pale yellow solid. $^1$H NMR (400 MHz, DMSO-d$_6$): δ 9.15 (s, 1H), 8.91 (s, 1H), 8.47 (s, 1H), 8.17 (dd, J=8.3, 2.1 Hz, 1H), 7.70 (d, J=8.8 Hz, 2H), 7.56-7.42 (m, 3H), 7.35-7.25 (m, 2H), 7.22-7.09 (m, 8H), 6.93-6.89 (m, 1H), 5.67 (d, J=14.8 Hz, 1H), 5.11 (d, J=14.8 Hz, 1H), 4.71-4.64 (m, 2H), 3.44-3.33 (m, 8H); MS (ESI): m/z 755.7 [M+H]$^+$; HPLC: 93.35%; Optical rotation [α]$_D^{20}$: +126 (c=0.1% in CH$_2$Cl$_2$).

Example 59

1-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-methylbutan-1-ol (59)

1-(4-(4-(4-bromophenyl) piperazin-1-yl) phenyl)-2-methylbutan-1-ol (GI)

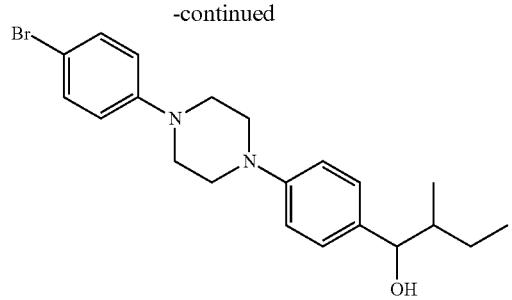

To a stirred solution of compound N (500 mg, 1.14 mmol) in THF (50 mL) under argon atmosphere was added sec-butyl magnesium chloride (2.1 mL, 4.34 mmol 2.0 M in ether) at 0° C. The reaction mixture was warmed to RT and stirred for 16 h. The reaction mixture was quenched with ammonium chloride solution (20 mL) and extracted with EtOAc (2×20 mL). The combined organic layers were washed with water (10 mL), brine (10 mL), dried over anhydrous Na$_2$SO$_4$ and concentrated under reduced pressure. The crude material was purified by silica gel column chromatography (eluent: 20% EtOAc/Hexane) to afford compound GI (400 mg, 0.99 mmol, 68%) as an off-white solid. $^1$H NMR (400 MHz, DMSO-d$_6$): δ 7.37 (d, J=9.2 Hz, 2H), 7.14 (dd, J=8.8, 2.4 Hz, 2H), 6.98-6.88 (m, 4H), 4.87-4.83 (m, 1H), 4.30-4.27 (m, 0.5H), 4.21-4.19 (m, 0.5H), 3.30-3.19 (m, 8H), 1.63-1.47 (m, 2H), 1.40-1.22 (m, 1H), 0.87-0.76 (m, 4.5H), 0.65 (d, J=6.7 Hz, 1.5H).

2-methyl-1-(4-(4-(4-(4,4,5,5-tetramethyl-1,3,2-dioxaborolan-2-yl) phenyl piperazin-1-yl) phenyl) butan-1-ol (GJ)

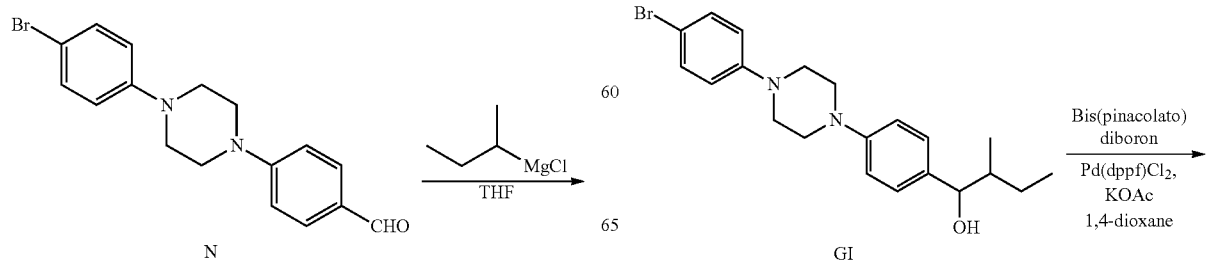

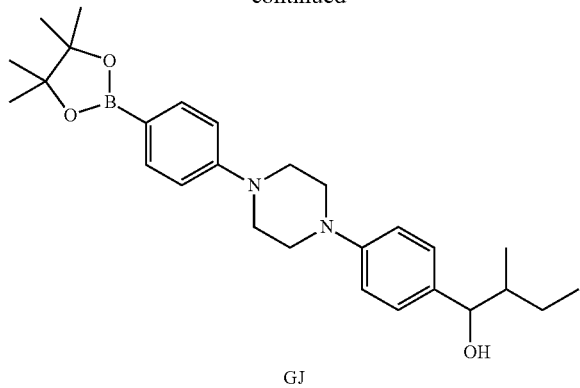

GJ

To a stirred solution of compound GI (400 mg, 0.99 mmol) in 1,4-dioxane (25 mL) under argon atmosphere were added bis(pinacolato)diboron (403 mg, 1.58 mmol) and potassium acetate (291 mg, 2.97 mmol) at RT. The reaction mixture was purged with argon for 20 min, then Pd(dppf)Cl$_2$ (72 mg, 0.09 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 20% EtOAc/Hexane) to afford compound GJ (250 mg, 0.55 mmol, 56%) as a pale yellow solid. $^1$H NMR (500 MHz, DMSO-d$_6$): δ 7.54 (d, J=8.4 Hz, 2H), 7.17-7.08 (m, 2H), 6.97 (d, J=8.4 Hz, 2H), 6.93 (d, J=8.4 Hz, 2H), 4.87-4.83 (m, 1H), 4.30-4.28 (m, 0.5H), 4.21-4.19 (m, 0.5H), 3.37-3.35 (m, 4H), 3.24-3.22 (m, 4H), 1.61-1.46 (m, 2H), 1.27 (s, 12H), 1.22-1.10 (m, 1H), 0.88-0.73 (m, 4.5H), 0.65 (d, J=6.7 Hz, 1.5H).

1-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-methylbutan-1-ol (59

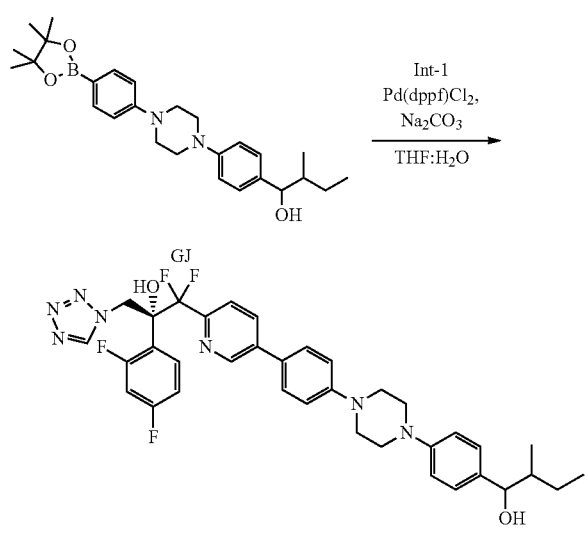

59

To a stirred solution of Int-1 (150 mg, 0.34 mmol) in THF:H2O (4:1, 25 mL) under argon atmosphere were added compound GJ (187 mg, 0.41 mmol), sodium carbonate (110 mg, 1.04 mmol) and purged under argon for 20 min at RT. Then Pd(dppf)Cl$_2$ (25 mg, 0.03 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 60% EtOAc/Hexane) to afford 59 (60 mg, 0.08 mmol, 25%) as an off-white solid. $^1$H NMR (400 MHz, DMSO-d$_6$): δ 9.15 (s, 1H), 8.91 (s, 1H), 8.17 (dd, J=8.3, 2.3 Hz, 1H), 7.70 (d, J=8.9 Hz, 2H), 7.48 (d, J=8.4 Hz, 1H), 7.32-7.07 (m, 7H), 6.99-6.83 (m, 3H), 5.67 (d, J=14.7 Hz, 1H), 5.11 (d, J=14.7 Hz, 1H), 4.87-4.83 (m, 1H), 4.31-4.28 (m, 0.5H), 4.22-4.20 (m, 0.5H), 3.44-3.30 (m, 4H), 3.29-3.26 (m, 4H), 1.69-1.46 (m, 2H), 1.40-1.19 (m, 1H), 0.88-0.80 (m, 4.5H), 0.66 (d, J=6.8 Hz, 1.5H); MS (ESI): m/z 674.4 [M–H]$^-$; HPLC: 96.56%; Optical rotation $[α]_D^{20}$: +56 (c=0.1% in MeOH).

Example 60

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2,4-dihydro-3H-1,2,4-triazol-3-one (60)

4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (GK)

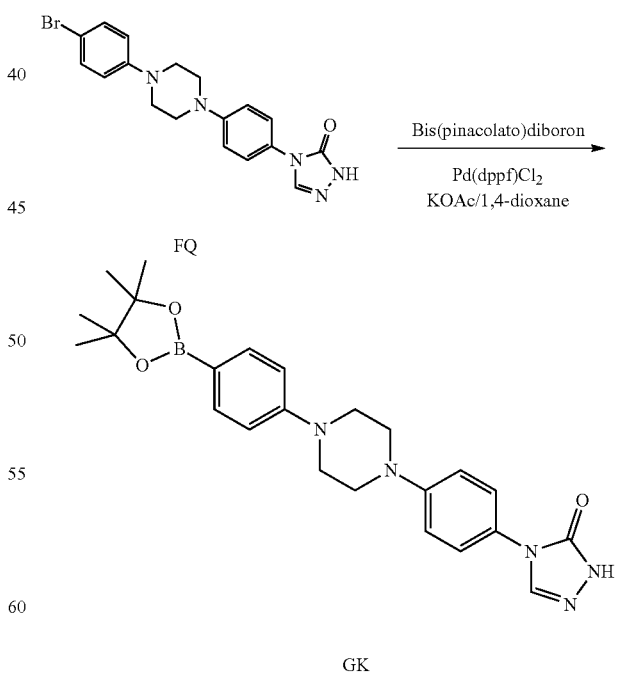

GK

To a stirred solution of compound FQ (400 mg, 1.00 mmol) in 1,4-dioxane (30 mL) under argon atmosphere were added bis(pinacolato)diboron (404 mg, 1.60 mmol) and potassium acetate (294 mg, 3.00 mmol) at RT. The reaction mixture was purged with argon for 20 min, then Pd(dppf)Cl$_2$ (73.1 mg, 0.10 mmol) was added and the reaction mixture was purged under argon for 5 min at RT. The reaction mixture was stirred at 110° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 4% MeOH/Hexane) to afford compound GK (200 mg, 0.44 mmol, 44%) as an off-white solid. $^1$H NMR (500 MHz, DMSO-d$_6$): δ 11.86 (brs, 1H), 8.24 (s, 1H), 7.54 (d, J=8.1 Hz, 2H), 7.48 (d, J=9.0 Hz, 2H), 7.09 (d, J=9.0 Hz, 2H), 6.97 (d, J=8.4 Hz, 2H), 3.39-3.37 (m, 4H), 3.31 (s, 4H), 1.27 (s, 12H).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2,4-dihydro-3H-1,2,4-triazol-3-one (60)

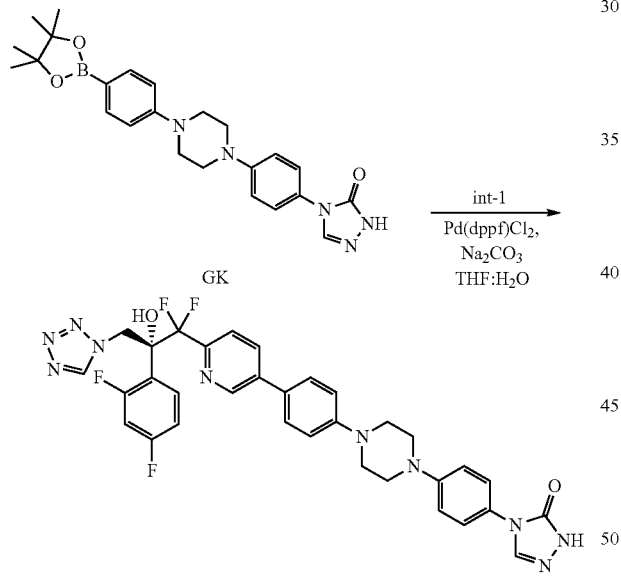

To a stirred solution of Int-1 (150 mg, 0.34 mmol) in THF:H2O (30 mL) under argon atmosphere were added compound GK (170 mg, 0.38 mmol), sodium carbonate (110 mg, 1.04 mmol) and purged under argon for 20 min at RT. Then Pd(dppf)Cl$_2$ (25 mg, 0.03 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) to afford 60 (70 mg, 0.10 mmol, 30/%) as an off-white solid. $^1$H NMR (400 MHz, DMSO-d$_6$): δ 11.86 (br s, 1H), 9.15 (s, 1H), 8.91 (s, 1H), 8.24 (s, 1H), 8.17 (dd, J=8.3, 2.2 Hz, 1H), 7.70 (d, J=8.9 Hz, 2H), 7.51-7.45 (m, 3H), 7.33-7.23 (m, 2H), 7.24-7.09 (m, 5H), 6.93-6.89 (m, 1H), 5.67 (d, J=14.7 Hz, 1H), 5.11 (d, J=14.7 Hz, 1H), 3.45-3.39 (m, 4H), 3.37-3.32 (m, 4H); MS (ESI): m/z 673.7 [M+H]$^+$; HPLC: 96.58%, Optical rotation [α]$_D^{20}$: +137.9 (c=0.1% in CH$_2$Cl$_2$).

Example 61

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-(2-(dimethylamino) ethyl)-2,4-dihydro-3H-1,2,4-triazol-3-one (61)

4-(4-(4-(4-bromophenyl) piperazin-1-yl) phenyl)-2-(2-(dimethyl amino) ethyl)-2,4-dihydro-3H-1,2,4-triazol-3-one (GL)

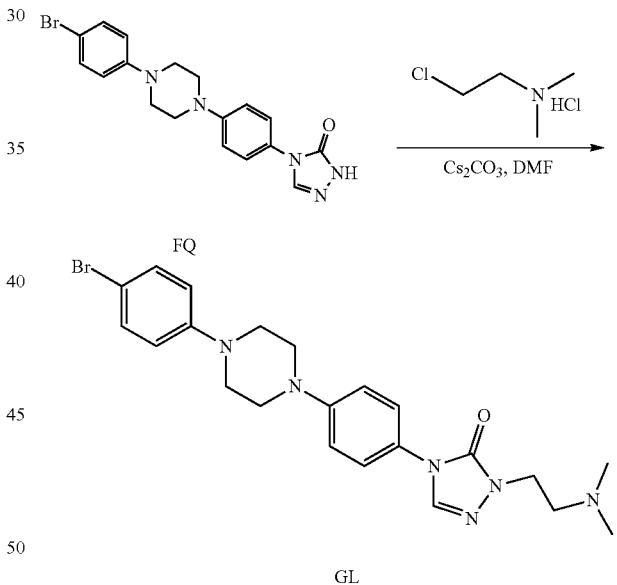

To a stirred solution of compound FQ (400 mg, 1.0 mmol) in DMF (20 mL) under argon atmosphere were added cesium carbonate (1.3 g, 4 mmol) and 2-chloro-N, N-dimethylethan-1-amine hydrochloride (432 mg, 3.0 mmol) at 0° C. The reaction mixture was warmed to RT and stirred for 16 h. The reaction mixture was diluted with water (30 mL), the obtained solid was filtered and dried under reduced pressure to obtain compound GL (300 mg, 0.63 mmol, 63.6%) as an off-white solid. $^1$H NMR (500 MHz, DMSO-d$_6$): δ 8.33 (s, 1H), 7.50 (d, J=9.0 Hz, 2H), 7.38 (d J=8.7 Hz, 2H), 7.10 (d, J=9.3 Hz, 2H), 6.97 (d, J=9.0 Hz, 2H), 3.80 (t, J=6.5 Hz, 2H), 3.34-3.23 (m, 8H), 2.56 (t, J=6.5 Hz, 2H), 2.17 (s, 6H).

2-(2-(dimethylamino) ethyl)-4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (GM)

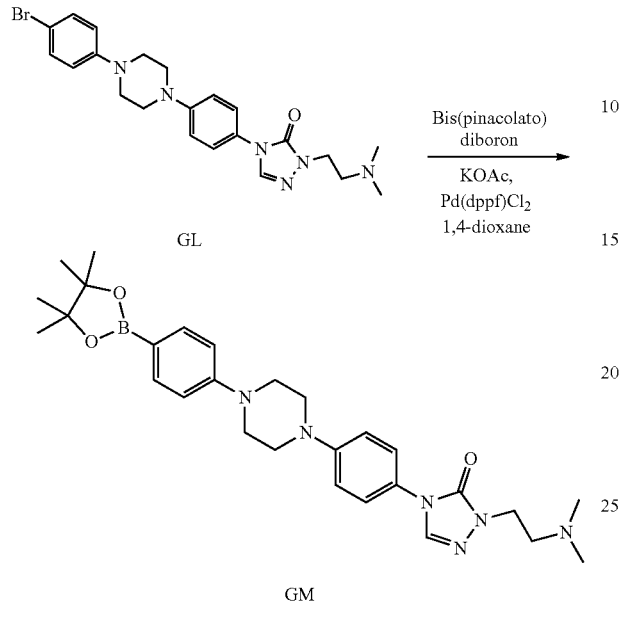

To a stirred solution of compound GL (300 mg, 0.63 mmol) in 1,4-dioxane (20 mL) under argon atmosphere were added bis(pinacolato)diboron (258 mg, 1.01 mmol), KOAc (187 mg, 1.91 mmol) at RT and purged under argon for 15 min. Then Pd(dppf)Cl$_2$ (46 mg, 0.06 mmol) was added to the reaction mixture at RT and again purged under argon for 10 min at RT, stirred at 110° C. for 16 h in a sealed tube. The progress of the reaction was monitored by TLC, the reaction mixture was diluted with water (30 mL) and extracted with EtOAc (2×30 mL). The combined organic extracts were washed with water (30 mL), brine (30 mL), dried over anhydrous Na$_2$SO$_4$ and concentrated under reduced pressure. The crude material was purified by silica gel column chromatography (eluent: 7% MeOH/CH$_2$Cl$_2$) to afford compound GM (220 mg, 0.42 mmol, 66.8%) as an off-white solid. $^1$H NMR (400 MHz, DMSO-d$_6$): δ 8.33 (s, 1H), 7.54 (d, J=8.7 Hz, 2H), 7.50 (d, J=9.2 Hz, 2H), 7.10 (d, J=9.2 Hz, 2H), 6.98 (d, J=8.8 Hz, 2H), 3.81 (t, J=6.5 Hz, 2H), 3.42-3.34 (m, 8H), 2.56-2.55 (m, 2H), 2.18 (brs, 6H), 1.27 (s, 12H).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-(2-(dimethylamino) ethyl)-2,4-dihydro-3H-1,2,4-triazol-3-one (61)

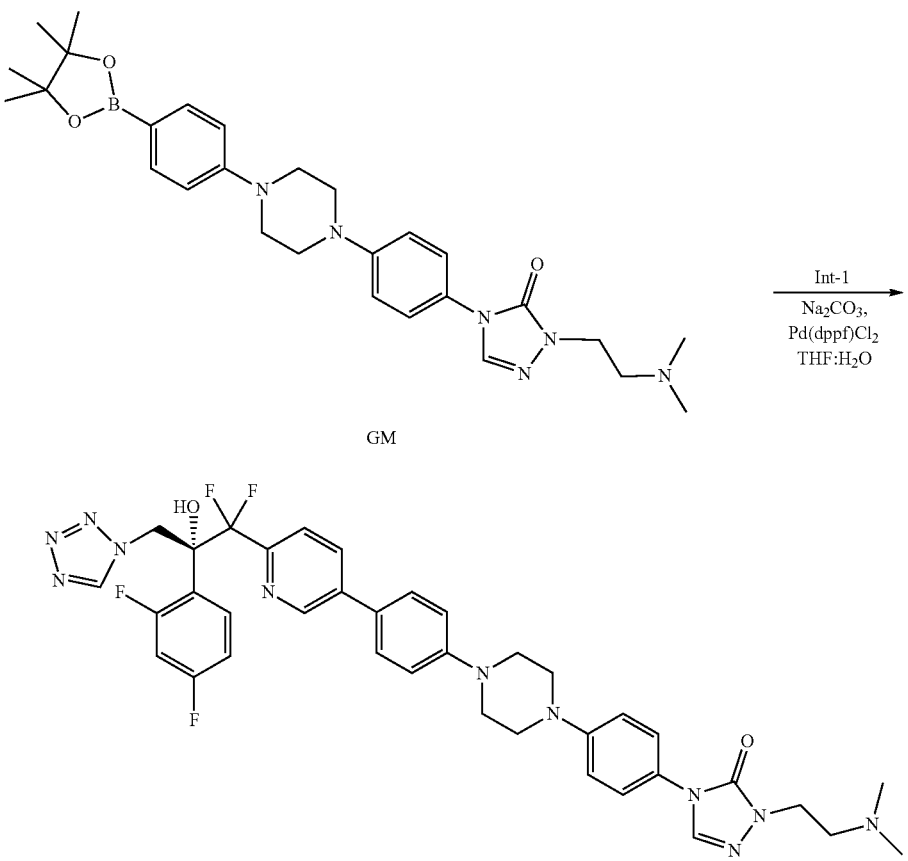

To a stirred solution of Int-1 (130 mg, 0.30 mmol) in THF:H2O (4:2, 10 mL) under argon atmosphere were added compound GM (187 mg, 0.36 mmol), sodium carbonate (96 mg, 0.90 mmol) at RT and purged under argon for 10 min. Then Pd(dppf)Cl$_2$ (22 mg, 0.03 mmol) was added to the reaction mixture at RT and stirred at 80° C. for 16 h in a sealed tube. The progress of the reaction was monitored by TLC, the reaction mixture was diluted with water (10 mL) and extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluent: 8% MeOH/CH$_2$Cl$_2$) to afford 61 (50 mg, 0.06 mmol, 22.4%) as yellow solid. $^1$H NMR (400 MHz, DMSO-d$_6$): δ 9.15 (s, 1H), 8.91 (s, 1H), 8.34 (s, 1H), 8.17 (dd, J=8.3, 2.0 Hz, 1H), 7.70 (d, J=8.8 Hz, 2H), 7.54-7.45 (m, 3H), 7.34-7.22 (m, 2H), 7.21-7.08 (m, 5H), 6.95-6.86 (m, 1H), 5.67 (d, J=14.7 Hz, 1H), 5.11 (d, J=14.7 Hz, 1H), 3.83 (t, J=6.4 Hz, 2H), 3.41-3.35 (m, 8H), 2.68-2.57 (m, 2H), 2.21 (s, 6H); MS (ESI): m/z 742.4 [M−H]$^−$; HPLC: 97.28%; Optical rotation [α]$_D^{20}$: +51.28 (c=0.1% in MeOH).

Example 62

(2R)-2-(2,4-difluorophenyl)-1,1-difluoro-3-(1H-tetrazol-1-yl)-1-(5-(4-(4-(5-(2,2,2-trifluoro-1-hydroxyethyl) thiophen-2-yl) piperazin-1-yl) phenyl) pyridin-2-yl) propan-2-ol (62)

5-(4-(4-bromophenyl) piperazin-1-yl) thiophene-2-carbaldehyde (GO)

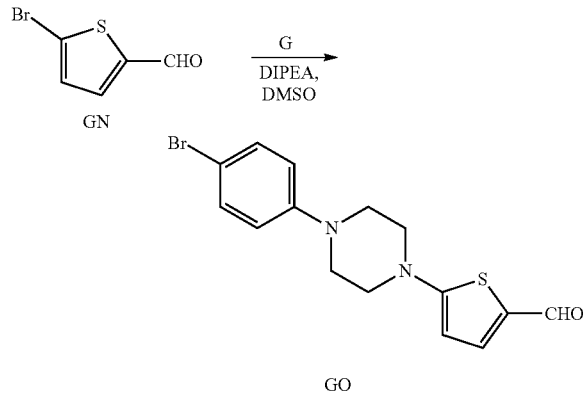

To a stirred solution of 1-(4-bromophenyl) piperazine G (2 g, 8.29 mmol) in DMSO (20 mL) under argon atmosphere were added diisopropyl ethyl amine (3 mL, 16.59 mmol) and 5-bromothiophene-2-carbaldehyde GN (1.7 g, 9.12 mmol) at RT. The reaction mixture was stirred at 130° C. for 6 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure to afford compound GO (700 mg, crude) as yellow solid which was used in the next step without further purification. $^1$H NMR (400 MHz, CDCl$_3$): δ 9.58 (s, 1H), 7.51 (d, J=8.3 Hz, 1H), 7.39 (d, J=9.2 Hz, 2H), 6.81 (d, J=9.2 Hz, 2H), 6.17 (d, J=3.9 Hz, 1H), 3.51-3.48 (m, 4H), 3.31-3.28 (m, 4H).

1-(5-(4-(4-bromophenyl) piperazin-1-yl) thiophen-2-yl)-2,2,2-trifluoroethan-1-ol (GP)

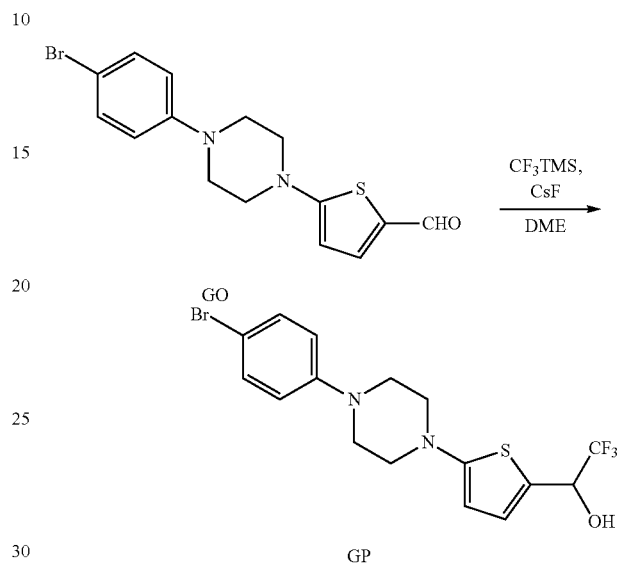

To a stirred solution of compound GO (1.5 g, 4.27 mmol) in 1,2-DME (50 mL) under argon atmosphere were added cesium fluoride (1.0 g, 6.41 mmol) and CF$_3$TMS (1.8 mL, 12.82 mmol) at 0° C. The reaction mixture was warmed to RT and stirred for 32 h. The progress of the reaction was monitored by TLC. The reaction mixture was quenched with 1 N HCl (20 mL), stirred for 2 h and then extracted with EtOAc (2×20 mL). The combined organic layers were washed with water (20 mL), dried over anhydrous Na$_2$SO$_4$ and concentrated under reduced pressure. The crude material was purified by silica gel column chromatography (eluent: 10-30% EtOAc % Hexane) to afford compound GP (600 mg, 1.42 mmol, 33%) as an off-white solid.

$^1$H NMR (400 MHz, CDCl$_3$): δ 7.37 (d, J=9.2 Hz, 2H), 6.90 (d, J=3.8 Hz, 1H), 6.83 (d, J=9.2 Hz, 2H), 6.07 (d, J=3.9 Hz, 1H), 5.15-5.06 (m, 1H), 3.35-3.13 (m, 8H), 2.48 (d, 5.14 Hz, 1H).

2,2,2-trifluoro-1-(5-(4-(4-(4,4,5,5-tetramethyl-1,3,2-dioxaborolan-2-yl) phenyl) piperazin-1-yl) thiophen-2-yl) ethan-1-ol (GQ)

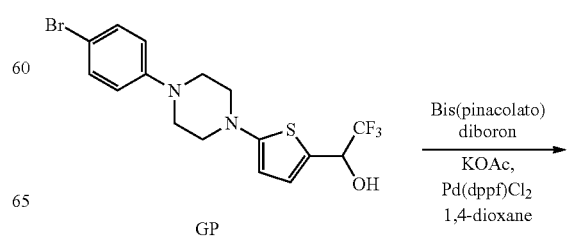

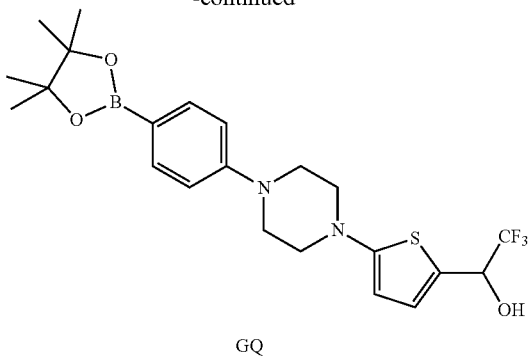

GQ

To a stirred solution of compound GP (300 mg, 0.71 mmol) in 1,4-dioxane (10 mL) under argon atmosphere were added bis(pinacolato)diboron (358 mg, 1.42 mmol) and potassium acetate (280 mg, 2.85 mmol) at RT. The reaction mixture was purged with argon for 20 min, then Pd(dppf)Cl$_2$ (80 mg, 0.10 mmol) was added and the reaction mixture was purged under argon for 10 min at RT. The reaction mixture was stirred at 110° C. for 16 h. The reaction mixture was quenched with water (20 mL) and extracted with EtOAc (2×20 mL). The combined organic layers were washed with water (10 mL), brine (10 mL), dried over anhydrous Na$_2$SO$_4$ and concentrated under reduced pressure. The crude material was purified by silica gel column chromatography (eluent: 30% EtOAc/Hexane) to afford compound GQ (200 mg, 0.42 mmol, 60%) as an off-white solid. $^1$H NMR (400 MHz, CDCl$_3$): δ 7.71 (d, J=9.2 Hz, 2H), 6.93-6.90 (m, 3H), 6.05 (d, J=3.9 Hz, 1H), 5.13-5.10 (m, 1H), 3.41-3.39 (m, 4H), 3.31-3.28 (m, 4H), 2.42 (d, J=5.14 Hz, 1H), 1.30 (s, 12H).

(2R)-2-(2,4-difluorophenyl)-1,1-difluoro-3-(1H-tetrazol-1-yl)-1-(5-(4-(4-(5-(2,2,2-trifluoro-1-hydroxyethyl) thiophen-2-yl) piperazin-1-yl) phenyl) pyridin-2-yl) propan-2-ol (62)

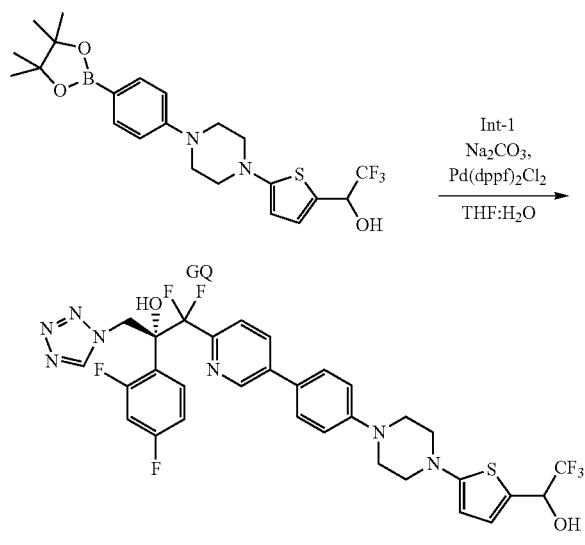

To a stirred solution of Int-1 (150 mg, 0.34 mmol) in THF:H2O (9:1, 20 mL) under argon atmosphere were added compound GQ (178 mg, 0.38 mmol), sodium carbonate (110 mg, 1.04 mmol) and purged under argon for 15 min at RT. Then Pd(dppf)Cl$_2$ (38 mg, 0.05 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 40% EtOAc/Hexane) to afford 62 (75 mg, 0.10 mmol, 31%) as an off-white solid. $^1$H NMR (400 MHz, DMSO-d$_6$): δ 9.15 (s, 1H), 8.91 (d, J=2.0 Hz, 1H), 8.17 (dd, J=8.3, 2.1 Hz, 1H), 7.70 (d, J=8.9 Hz, 2H), 7.48 (d, J=8.3 Hz, 1H), 7.34-7.09 (m, 5H), 6.95-6.87 (m, 3H), 6.15 (d, J=3.9 Hz, 1H), 5.67 (d, J=14.7 Hz, 1H), 5.31-5.23 (m, 1H), 5.11 (d, J=14.7 Hz, 1H), 3.42-3.37 (m, 4H), 3.26-3.19 (m, 4H); MS (ESI): m/z 692.5 [M−H]$^−$; HPLC: 95%; Optical rotation [α]$_D^{20}$: +61.5 (c=0.1% in MeOH).

Example 63(+)

(+)-4-(4-(4-(6-(1,1-difluoro-2-(4-fluorophenyl)-2-hydroxy-3-(1H-tetrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (63(+))

2-(5-bromopyridin-2-yl)-2,2-difluoro-1-(4-fluorophenyl) ethan-1-one (GR)

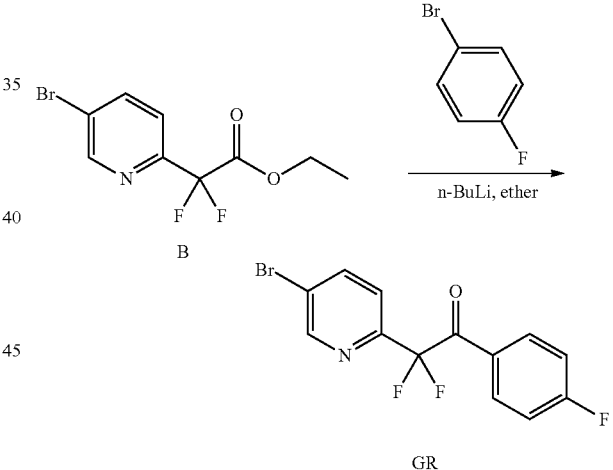

To a stirred solution of 1-bromo-4-fluorobenzene (6.24 g, 35.7 mmol) in diethyl ether (25 mL) was added n-BuLi (30 mL, 44.62 mmol, 1.6 M in Hexanes) at −78° C. under argon atmosphere and stirred for 1 h. Then compound B (5 g, 17.85 mmol) in diethyl ether (25 mL) was added to reaction mixture at −78° C., and stirred for 2 h. The reaction mixture stirred at RT for 1 h. The progress of the reaction was monitored by TLC. The reaction was quenched with a saturated ammonium chloride solution (200 mL) and extracted with ethyl acetate (2×200 mL). The combined organic layers were washed with brine (100 mL), dried over anhydrous Na$_2$SO$_4$ and concentrated under reduced pressure. The crude material was purified by silica gel column chromatography (eluent: 4% EtOAc/Hexane) to afford compound GR (2.8 g, 8.51 mmol, 48%) as a brown liquid. $^1$H NMR (400 MHz, CDCl$_3$): δ 8.67 (d, J=1.9 Hz, 1H), 8.14-8.10 (m, 2H), 8.03 (dd, J=8.4, 2.3 Hz, 1H), 7.72 (dd, J=8.4, 0.6 Hz, 1H), 7.16-7.11 (m, 2H).

5-bromo-2-(difluoro(2-(4-fluorophenyl) oxiran-2-yl) methyl) pyridine (GS)

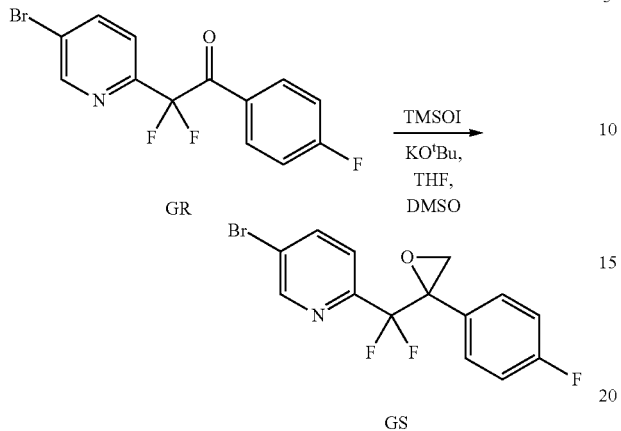

To a stirred solution of potassium tert-butoxide (1 g, 8.93 mmol) in THF:DMSO (2:1, 22 mL) under argon atmosphere was added trimethylsulfoxonium iodide (2.05 g, 9.36 mmol) and stirred at RT for 1 h. Then compound GR (2.8 g, 8.51 mmol) in THF (10 mL) was added to the reaction mixture at 0° C., and stirred for another 1 h. The progress of the reaction was monitored by TLC. The reaction was quenched with a saturated ammonium chloride solution (200 mL) and extracted with EtOAc (2×200 mL). The combined organic layers were dried over anhydrous $Na_2SO_4$ and concentrated under reduced pressure. The crude material was purified by silica gel column chromatography (eluent: 4% EtOAc/Hexanes) to afford compound GS (1.6 g, 4.67 mmol, 49%) as an off-white solid $^1H$ NMR (500 MHz, $CDCl_3$): δ 8.70 (s, 1H), 7.87 (dd, J=8.3, 2.1 Hz, 1H), 7.30-7.37 (m, 3H), 6.97-6.92 (m, 2H), 3.42-3.40 (m, 1H), 2.90-2.87 (m, 1H).

1-(5-bromopyridin-2-yl)-1,1-difluoro-2-(4-fluorophenyl)-3-(1H-tetrazol-1-yl) propan-2-ol (GT)

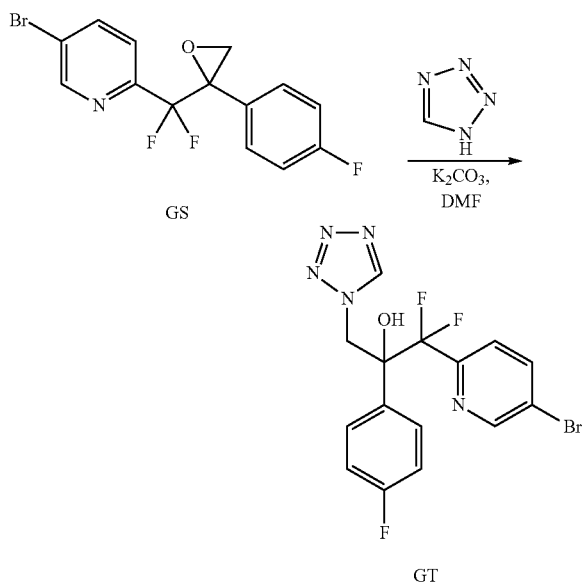

To a stirred solution of compound GS (1.6 mg, 4.66 mmol) in DMF (20 mL) under argon atmosphere were added potassium carbonate (960 mg, 6.99 mmol) and 1H-tetrazole (650 mg, 9.32 mmol) at RT. The reaction mixture was stirred at 80° C. for 16 h. The reaction mixture was diluted with water (50 mL) and extracted with EtOAc (2×50 mL). The combined organic layers were dried over anhydrous $Na_2SO_4$ and concentrated under reduced pressure. The crude material was purified by silica gel column chromatography (eluent: 40% EtOAc/Hexane) to afford compound GT (600 mg, 0.57 mmol, 31%) as a white solid. LC-MS: 415.9 $[M+2H]^+$ at 2.38 RT (96.22% purity).

2-((2S,3S)-2-(benzyloxy) pentan-3-yl)-4-(4-(4-(4-(6-(1,1-difluoro-2-(4-fluorophenyl)-2-hydroxy-3-(1H-tetrazol-1-yl) propyl) pyridin-3-yl) phenyl) piperazin-1-yl) phenyl)-2,4-dihydro-3H-1,2,4-triazol-3-one (GU)

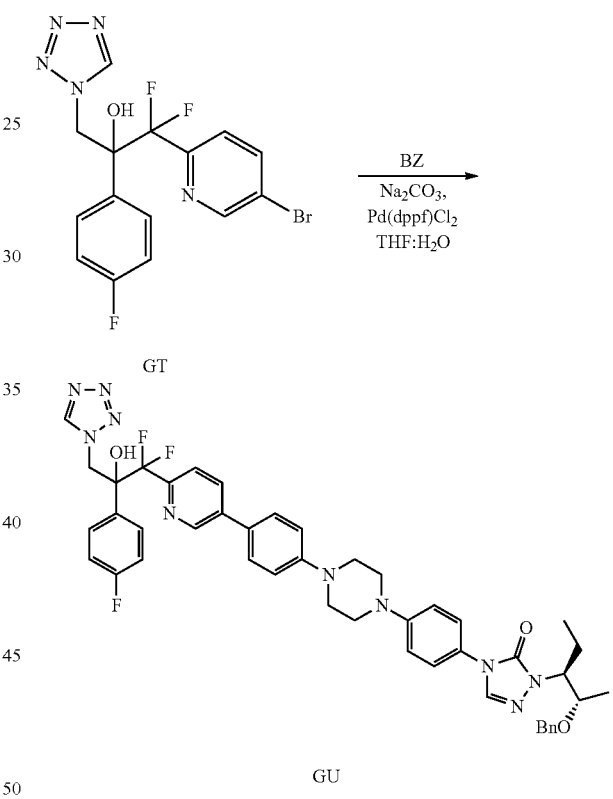

To a stirred solution of compound GT (300 mg, 0.22 mmol) in THF:H2O (4:1, 10 mL) under argon atmosphere were added compound BZ (540 mg, 0.86 mmol), sodium carbonate (229 mg, 2.16 mmol) and purged under argon for 10 min at RT. Then $Pd(dppf)Cl_2$ (53 mg, 0.07 mmol) was added to the reaction mixture at RT and stirred at reflux for 4 h. The progress of the reaction was monitored by TLC. The reaction mixture was diluted with water (20 mL) and extracted with EtOAc (2×50 mL). The combined organic extracts were washed with water (20 mL), brine (20 mL), dried over anhydrous $Na_2SO_4$ and concentrated under reduced pressure. The crude material was purified by silica gel column chromatography (eluent: 2% MeOH/DCM) to afford compound GU (500 mg, 0.60 mmol, 83%) as an off-white solid. $^1H$ NMR (500 MHz, DMSO-$d_6$): δ 9.01 (s, 1H), 8.92 (d, J=1.7 Hz, 1H), 8.32 (s, 1H), 8.14 (dd, J=8.4, 2.0 Hz, 1H), 7.70 (d, J=8.7 Hz, 2H), 7.49 (d, J=8.7 Hz, 2H), 7.44-7.41 (m, 3H), 7.27-7.21 (m, 3H), 7.18-7.12 (m, 6H), 7.10-7.03 (m, 3H), 5.61 (d, J=14.5 Hz, 1H), 5.17 (d, J=14.5 Hz, 1H), 4.53 (d, J=11.9 Hz, 1H), 4.27 (d, J=11.9 Hz, 1H), 4.01-3.96 (m, 1H), 3.79-3.71 (m, 1H), 3.44-3.34 (m, 8H), 1.80-1.69 (m, 2H), 1.23 (d, J=6.4 Hz, 3H), 0.79 (t, J=7.4 Hz, 3H).

(+)-4-(4-(4-(4-(6-(1,1-difluoro-2-(4-fluorophenyl)-2-hydroxy-3-(1H-tetrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (63(+))

dried over anhydrous $Na_2SO_4$ and concentrated under reduced pressure. The crude material was purified by silica gel column chromatography (eluent: 2% MeOH/DCM) to afford 63 (250 mg, 0.30 mmol, 62%) as an off-white solid.

Chiral Preparative HPLC Details 63 (250 mg, 0.33 mmol) was separated by normal-phase preparative high performance liquid chromatography (Chiralpak IA®, 250×20 mm, 5μ; using 0.1% DEA in n-Hexane:(B) $CH_2Cl_2$:MeOH (50:50) (35:65) as a mobile phase; Flow rate: 20 mL/min) to obtain 63(+) (76 mg). Chiral HPLC Purity: 100%, $R_t$=16.32 min (CHIRALPAK-IA®, 250×4.6 mm, 5μ; mobile phase (A) 0.1% DEA in n-Hexane:(B) $CH_2Cl_2$:MeOH (50:50) (35:65); flow Rate: 1.0 mL/min); $^1$H

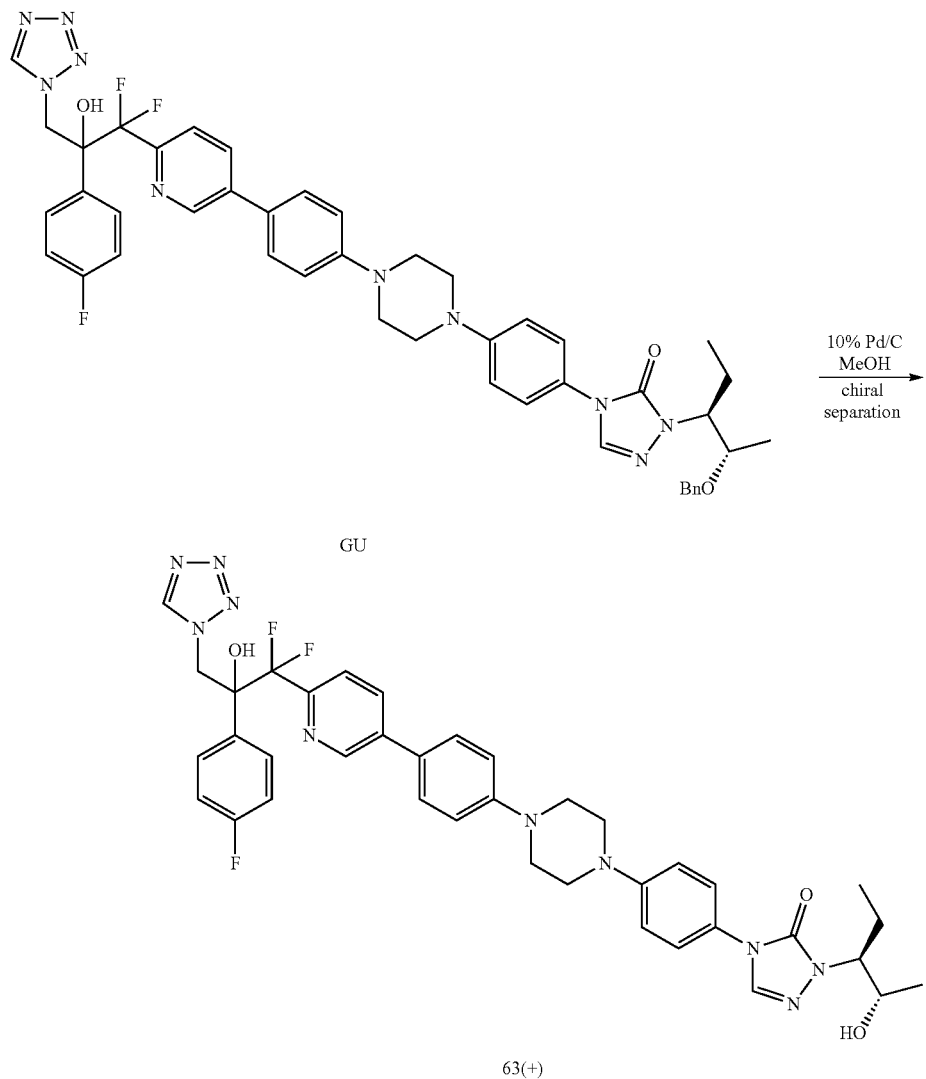

To a stirred solution of compound GU (450 mg, 0.54 mmol) in MeOH (10 mL) under argon atmosphere were added 10% Pd/C (200 mg) and Concentrated HCl (0.1 mL) at RT. The reaction mixture was stirred at RT for 3 h under hydrogen atmosphere (50 psi). The progress of the reaction was monitored by TLC. The reaction mixture was basified with saturated sodium carbonate solution (20 mL) and extracted with EtOAc (2×50 mL). The combined organic extracts were washed with water (20 mL), brine (20 mL), NMR (400 MHz, DMSO-de): δ 9.01 (s, 1H), 8.92 (d, J=1.9 Hz, 1H), 8.33 (s, 1H), 8.14 (dd, J=8.3, 2.1 Hz, 1H), 7.70 (d, J=8.8 Hz, 2H), 7.53 (d, J=9.0 Hz, 2H), 7.44-7.41 (m, 3H), 7.15-7.02 (m, 7H), 5.61 (d, J=14.6 Hz, 1H), 5.17 (d, J=14.6 Hz, 1H), 4.66 (d, J=4.9 Hz, 1H), 3.83-3.78 (m, 2H), 3.47-3.34 (m, 8H), 1.77-1.65 (m, 2H), 1.12 (d, J=5.9 Hz, 3H), 0.74 (t, J=7.3 Hz, 3H); MS (ESI): m/z 741.8 [M+H]$^+$; HPLC: 93.84% Optical rotation $[α]_D^{19}$: +101.0 (c=0.1% in $CH_2Cl_2$).

Example 64(+)

(+)-4-(4-(4-(4-(6-(1,1-difluoro-2-(3-fluorophenyl)-2-hydroxy-3-(1H-tetrazol-1 yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (64(+))

2-(5-bromopyridin-2-yl)-2,2-difluoro-1-(3-fluorophenyl) ethan-1-one (GV)

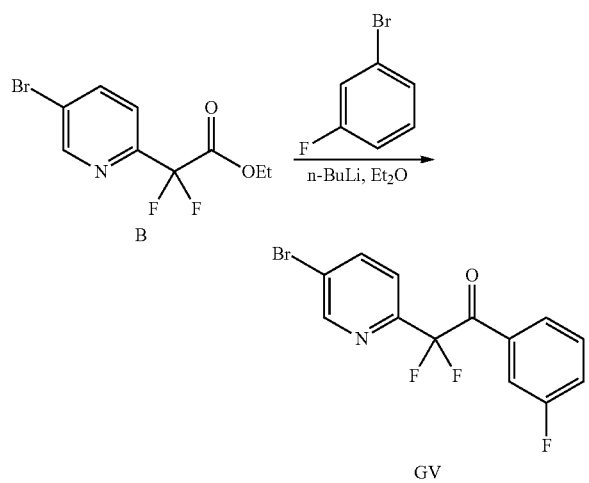

To a stirred solution of 1-bromo-3-fluorobenzene (6.9 g, 39.27 mmol) in diethyl ether (50 mL) was added n-BuLi (25 mL, 39.27 mmol, 1.6 M in Hexanes) at −78° C. under argon atmosphere and stirred for 1 h. Then compound B (10 g, 35.71 mmol) in diethyl ether (50 mL) was added to reaction mixture at −78° C., and stirred for 1 h. The progress of the reaction was monitored by TLC. The reaction was quenched with a saturated ammonium chloride solution (200 mL) and extracted with ethyl acetate (3×200 mL). The combined organic layers were dried over anhydrous Na₂SO₄ and concentrated under reduced pressure. The crude material was purified by silica gel column chromatography (eluent: 4% EtOAc/Hexane) to afford compound GV (6.9 g, 20.90 mmol, 59%) as an off-white solid. ¹H NMR (400 MHz, CDCl₃): δ 8.67 (d, J=1.8 Hz, 1H), 8.04 (dd, J=8.4, 2.3 Hz, 1H), 7.87-7.82 (m, 1H), 7.78-7.71 (m, 2H), 7.47-7.42 (m, 1H), 7.33-7.28 (m, 1H).

5-bromo-2-(difluoro (2-(3-fluorophenyl) oxiran-2-yl) methyl) pyridine (GX)

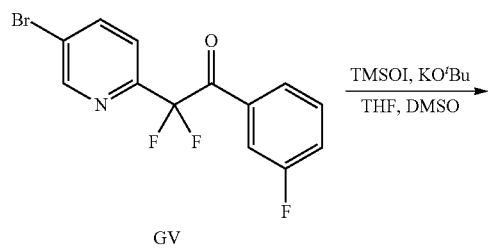

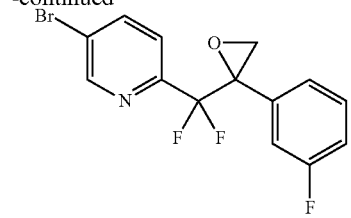

To a stirred solution of TMSOI (5.05 g, 22.99 mmol) and potassium tert-butoxide (2.56 g, 22.99 mmol) in THF:DMSO (3:1, 60 mL) was stirred at RT for 1 h. Then compound GV (6.9 g, 20.90 mmol) was added to the reaction mixture at 0° C. The reaction mixture was warmed to RT and stirred for 3 h. The progress of the reaction was monitored by TLC. The reaction mixture was quenched with ammonium chloride solution (200 mL) and extracted with EtOAc (2×200 mL). The combined organic extracts were dried over anhydrous Na₂SO₄ and concentrated under reduced pressure. The crude material was purified by silica gel column chromatography (eluent: 4% EtOAc/Hexane) to afford compound GX (2.7 g, 7.84 mmol, 38%) as an off-white solid. ¹H NMR (400 MHz, CDCl₃): δ 8.71 (d, J=1.9 Hz, 1H), 7.88 (dd, J=8.4, 2.3 Hz, 1H), 7.43-7.38 (m, 1H), 7.30-7.21 (m, 1H), 7.19-7.09 (m, 2H), 7.03-6.98 (m, 1H), 3.45 (d, J=5.3 Hz, 1H), 2.92-2.90 (m, 1H).

1-(5-bromopyridin-2-yl)-1,1-difluoro-2-(3-fluorophenyl)-3-(1H-tetrazol-1-yl) propan-2-ol (GY)

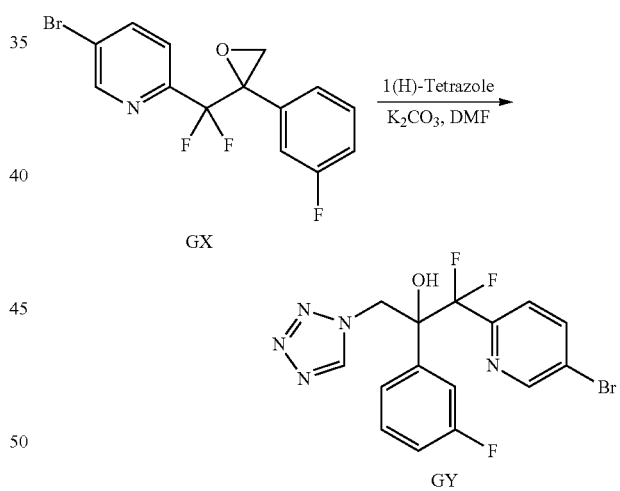

To a stirred solution of compound GX (2.7 g, 7.84 mmol) in DMF (27 mL) under argon atmosphere were added potassium carbonate (2.16 g, 15.69 mmol) and 1H-Tetrazole (824 mg, 11.77 mmol) at RT. The reaction mixture was stirred at 80° C. for 16 h. The reaction mixture was diluted with water (50 mL) and extracted with EtOAc (2×50 mL). The combined organic layers were dried over anhydrous Na₂SO₄ and concentrated under reduced pressure. The crude material was purified by silica gel column chromatography (eluent: 50% EtOAc/Hexane) to afford compound GY (1.6 g, 3.86 mmol, 49%) as yellow solid. ¹H NMR (400 MHz, CDCl₃): δ 8.75 (s, 1H), 8.58 (s, 1H), 7.90 (d, J=8.7 Hz, 1H), 7.41 (dd, J=8.7, 2.9 Hz, 1H), 7.20-7.12 (m, 2H), 7.10-7.08 (m, 1H), 6.90-6.85 (m, 1H), 6.80 (s, 1H), 5.15 (s, 2H).

2-((2S,3S)-2-(benzyloxy) pentan-3-yl)-4-(4-(4-(4-(6-(1,1-difluoro-2-(3-fluorophenyl)-2-hydroxy-3-(1H-tetrazol-1-yl) propyl) pyridin-3-yl) phenyl) piperazin-1-yl) phenyl)-2,4-dihydro-3H-1,2,4-triazol-3-one (GZ)

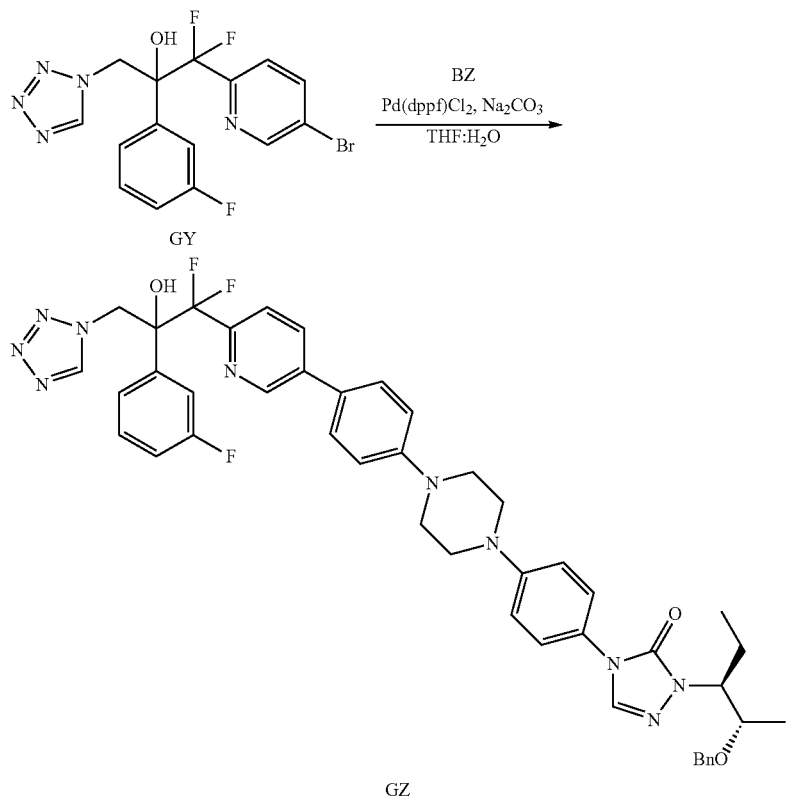 [SMILES: OC(Cn1cnnn1)(c1cccc(F)c1)C(F)(F)c1ccc(Br)cn1 ; "THF:H2O" ; CC[C@@H]([C@H](C)OCc1ccccc1)n1ncn(-c2ccc(N3CCN(c4ccc(-c5ccc(C(F)(F)C(O)(Cn6cnnn6)c6cccc(F)c6)nc5)cc4)CC3)cc2)c1=O]

To a stirred solution of compound GY (500 mg, 1.20 mmol) in THF:H2O (4:1, 10 mL) under argon atmosphere were added compound BZ (902 mg, 1.44 mmol), sodium carbonate (384 mg, 3.62 mmol) and purged under argon for 20 min at RT. Then Pd(dppf)Cl$_2$ (88 mg, 0.12 mmol) was added and the reaction mixture was purged under argon for 10 min at RT. The reaction mixture was stirred at reflux for 16 h. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford compound GZ (750 mg, 0.90 mmol, 75%) as a pale yellow solid. $^1$H NMR (400 MHz, CDCl$_3$): δ 8.78 (s, 1H), 8.68 (d, J=2.0 Hz, 1H), 7.90 (dd, J=8.3, 2.1 Hz, 1H), 7.64 (s, 1H), 7.58 (s, 1H), 7.56 (s, 1H), 7.49 (d, J=8.9 Hz, 2H), 7.42 (d, J=9.0 Hz, 2H), 7.25-7.15 (m, 7H), 7.07-7.01 (m, 4H), 6.90-6.85 (m, 1H), 5.26-5.12 (m, 2H), 4.63 (d, J=11.9 Hz, 1H), 4.40 (d, J=11.9 Hz, 1H), 4.21-4.16 (m, 1H), 3.84-3.77 (m, 1H), 3.49-3.36 (m, 8H), 1.27 (d, J=6.3 Hz, 3H), 1.24 (s, 2H), 0.88 (t, J=7.3 Hz, 3H).

(+)-4-(4-(4-(4-(6-(1,1-difluoro-2-(3-fluorophenyl)-2-hydroxy-3-(1H-tetrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (64(+))

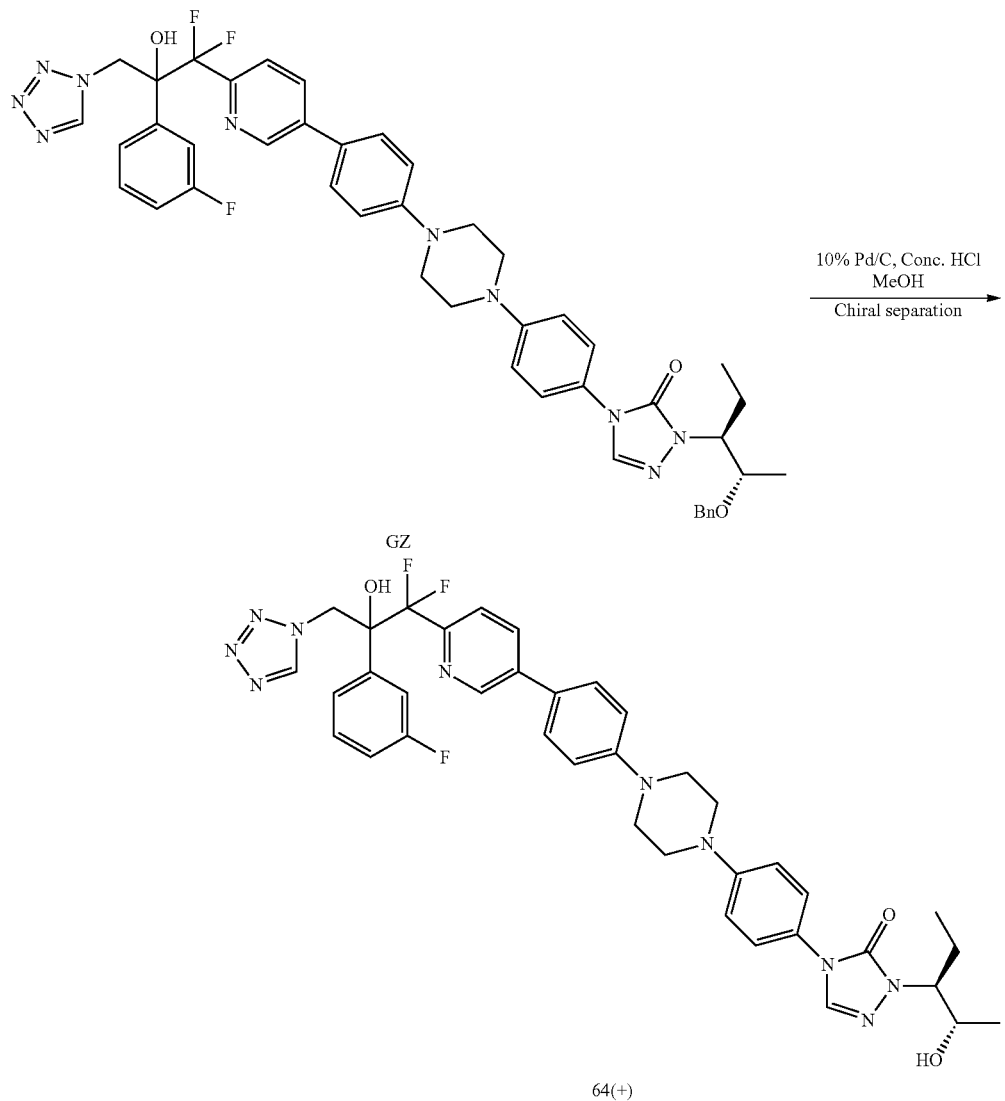

To a stirred solution of compound GZ (600 mg, 0.72 mmol) in MeOH (12 mL) under argon atmosphere were added 10% Pd/C (200 mg) and concentrated hydrochloric acid (0.1 mL) at RT. The reaction mixture was stirred at RT for 6 h under hydrogen atmosphere. The progress of the reaction was monitored by TLC, the reaction mixture was filtered and the filtrate was concentrated under reduced pressure. The residue was diluted with saturated sodium carbonate solution (20 mL) and extracted with EtOAc (20 mL). The combined organic layers were dried over anhydrous $Na_2SO_4$ and concentrated under reduced pressure. The crude material was triturated with n-pentane (2×20 mL) to afford 64 (400 mg, 0.54 mmol, 75%) as an off-white solid.

Chiral Preparative HPLC Details 64 (400 mg, 0.54 mmol) was separated by normal-phase preparative high performance liquid chromatography (Chiralpak IB®, 250×20 mm, 5µ; using 0.1% DEA in n-Hexane:(B) $CH_2Cl_2$:MeOH (80:20) (50:50); Flow rate: 20 mL/min) to obtain 64(+) (110 mg). Chiral HPLC Purity: 100%, R 6.19 min (CHIRALPAK-IB®, 250×4.6 mm, 5µ; mobile phase (A) 0.1% DEA in n-Hexane:(B) $CH_2Cl_2$:MeOH (80:20) (50:50); flow Rate: 1.0 mL/min); $^1H$ NMR (500 MHz, DMSO-$d_6$): δ 9.02 (s, 1H), 8.92 (s, 1H), 8.33 (s, 1H), 8.15 (dd, J=8.2, 1.9 Hz, 1H), 7.70 (d, J=8.7 Hz, 2H), 7.53 (d, J=9.0 Hz, 2H), 7.47 (d, J=8.1 Hz, 1H), 7.35-7.27 (m, 1H), 7.26-7.17 (m, 2H), 7.16-7.07 (m, 6H), 5.62 (d, J=14.5 Hz, 1H), 5.18 (d, J=14.5 Hz, 1H), 4.66 (d, J=4.9 Hz, 1H), 3.87-3.78 (m, 2H), 3.47-3.34 (m, 8H), 1.71 (t, J=6.9 Hz, 2H), 1.12 (d, J=5.8 Hz, 3H), 0.74 (t, J=7.2 Hz, 3H); MS (ESI): m/z 741.7 [M+H]$^+$; HPLC: 95.94%; Optical rotation $[α]_D^{20}$: +38.6 (c=0.1% in MeOH)

Example 65

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-methylbutan-1-ol (65)

1-(5-(4-(4-bromophenyl) piperazin-1-yl) pyridin-2-yl)-2-methylbutan-1-ol (HA)

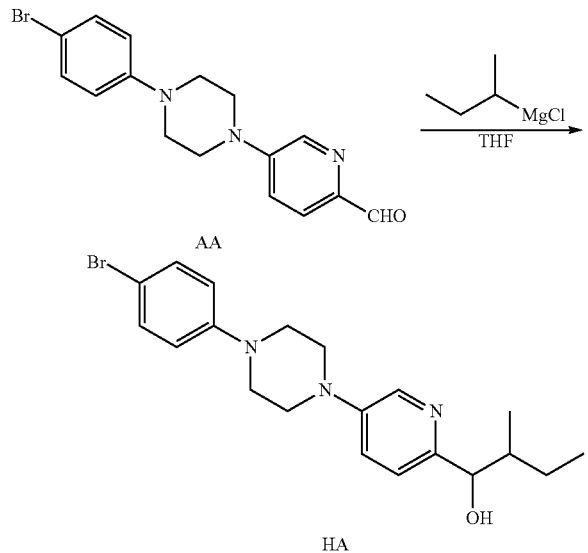

To a stirred solution of compound AA (300 mg, 0.86 mmol) in THF (10 mL) under argon atmosphere was added sec-butyl magnesium iodide (2.6 mL, 5.20 mmol, 2.0 M in THF) at 0° C., and stirred for 1 h. The reaction mixture was warmed to RT and stirred for 3 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous $Na_2SO_4$ and concentrated under reduced pressure. The crude material was purified by silica gel column chromatography (eluent: 20-30% EtOAc/Hexane) to afford compound HA (200 mg, 0.49 mmol, 57%) as yellow solid. $^1$H NMR (400 MHz, DMSO-$d_6$): δ 8.24 (s, 1H), 7.36-7.36 (m, 3H), 7.32-7.24 (m, 1H), 6.97 (d, J=9.0 Hz, 2H), 5.01-4.99 (m, 1H), 4.45-4.27 (m, 1H), 3.30-3.28 (m, 8H), 1.79-1.69 (m, 1H), 1.48-1.33 (m, 1H), 1.20-1.01 (m, 1H), 0.87 (br t, J=7.4 Hz, 3H), 0.73 (d, J=6.9 Hz, 3H).

2-methyl-1-(5-(4-(4-(4,4,5,5-tetramethyl-1,3,2-dioxaborolan-2-yl) phenyl) piperazin-1-yl) pyridin-2-yl) butan-1-ol (HB)

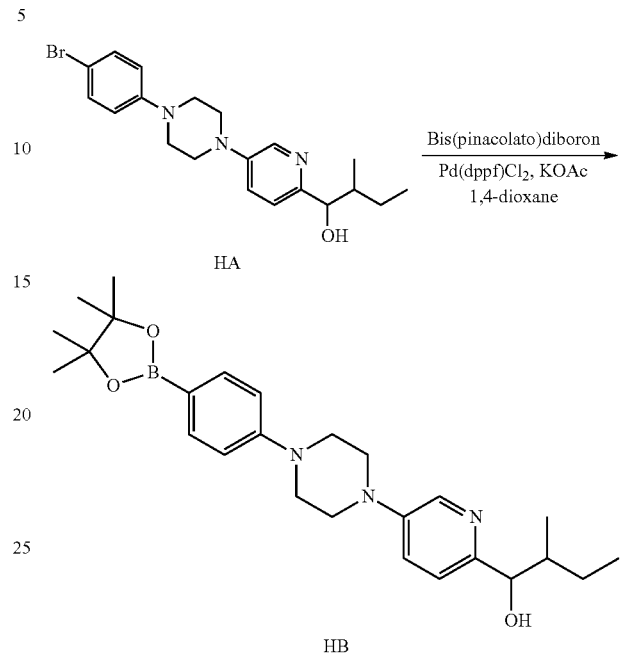

To a stirred solution of compound HA (200 mg, 0.50) in 1,4-dioxane (10 mL) under argon atmosphere were added bis(pinacolato)diboron (201 mg, 0.80 mmol) and potassium acetate (145 mg, 1.50 mmol) at RT. The reaction mixture was purged with argon for 20 min, then Pd(dppf)Cl$_2$ (36 rig, 0.05 mmol) was added and the reaction mixture was purged under argon for 5 min at RT. The reaction mixture was stirred at 90° C. for 12 h. The progress of the reaction was monitored by TLC. The reaction mixture was filtered, the filtrate was quenched with water (20 mL) and extracted with EtOAc (2×20 mL). The combined organic layers were washed with water (20 mL), brine (20 mL), dried over anhydrous $Na_2SO_4$ and concentrated under reduced pressure. The crude material was purified by silica gel column chromatography (eluent: 40% EtOAc/Hexane) to afford compound HB (165 mg, 0.36 mmol, 74%) as a brown solid and the impure material was as such taken for next step without further purification. LC-MS: 452.3 [M+H]$^+$ at 3.79, 3.82 RT (28.53%, 49.15% purity).

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-methylbutan-1-ol (65)

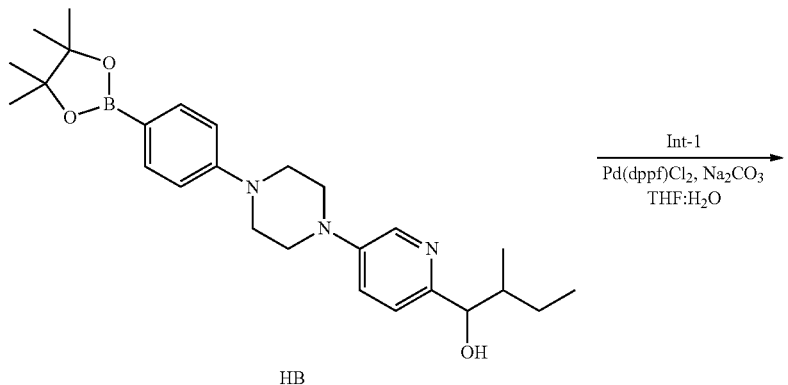

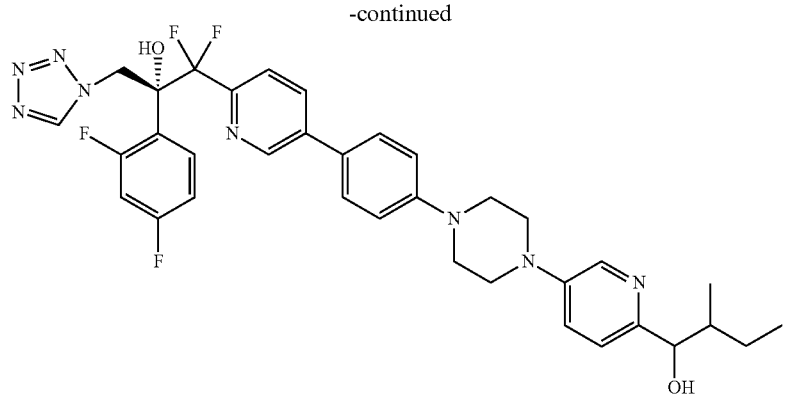

65

To a stirred solution of Int-1 (130 mg, 0.30 mmol) in THF:H2O (4:1, 15 mL) under argon atmosphere were added compound HB (162 mg, 0.36 mmol), sodium carbonate (95.4 mg, 0.90 mmol) and purged under argon for 15 min at RT. Then Pd(dppf)Cl$_2$ (65.8 mg, 0.09 mmol) was added and the reaction mixture was purged under argon for 10 min at RT. The reaction mixture was stirred at 70° C. for 12 h. The progress of the reaction was monitored by TLC. The reaction mixture was filtered, the filtrate was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) followed by preparative HPLC to afford 65 (20 mg, 0.03 mmol, 10%) as an off-white solid. $^1$H NMR (400 MHz, DMSO-d$_6$): δ 9.15 (s, 1H), 8.91 (d, J=2.0 Hz, 1H), 8.26 (d, J=2.3 Hz, 1H), 8.17 (dd, J=8.3, 2.3 Hz, 1H), 7.70 (d, J=8.8 Hz, 2H), 7.48 (d, J=8.3 Hz, 1H), 7.43-7.39 (m, 1H), 7.33-7.25 (m, 3H), 7.23-7.16 (m, 1H), 7.15 (d, J=8.9 Hz, 2H), 6.93-6.88 (m, 1H), 5.67 (d, J=14.7 Hz, 1H), 5.11 (d, J=14.7 Hz, 1H), 5.01-4.98 (m, 1H), 4.47-4.30 (m, 1H), 3.46-3.32 (m, 8H), 1.84-1.69 (m, 1H), 1.49-1.24 (m, 1H), 1.18-1.01 (m, 1H), 0.87 (t, J=7.4 Hz, 3H), 0.73 (d, J=6.9 Hz, 3H); MS (ESI): m/z 677.3 [M+H]$^+$; HPLC: 99.13%; Optical rotation [α]$_D^{19}$: +53.56 (c=0.1% in MeOH).

Example 66

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-(pentan-3-yl)-2,4-dihydro-3H-1,2,4-triazol-3-one (66)

4-(4-(4-(4-bromophenyl) piperazin-1-yl) phenyl)-2-(pentan-3-yl)-2,4-dihydro-3H-1,2,4-triazol-3-one (HB)

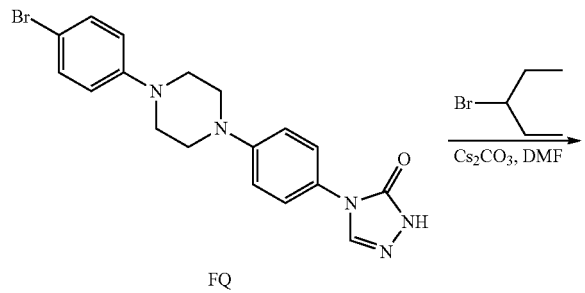

FQ

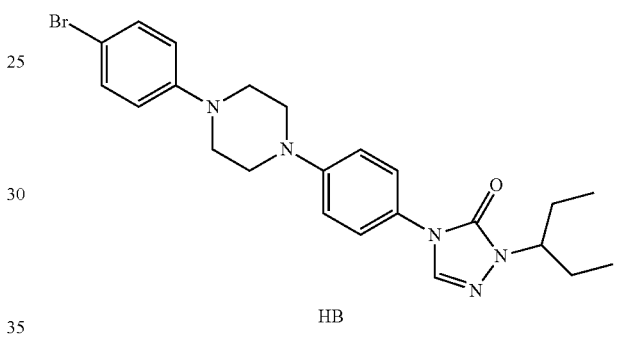

HB

To a stirred solution of compound FQ (300 mg, 0.75 mmol) in DMF (10 mL) under argon atmosphere were added cesium carbonate (733 mg, 2.25 mmol) and 3-bromopentane (340 mg, 2.25 mmol) at 0° C. The reaction mixture was warmed to RT and stirred for 16 h. The reaction mixture was diluted with water (10 mL) and extracted with EtOAc (2×10 mL). The combined organic extracts were washed with water (10 mL), brine (30 mL), dried over anhydrous Na$_2$SO$_4$ and concentrated under reduced pressure. The crude material was purified by silica gel column chromatography (eluent: 30% EtOAc/Hexane) to afford compound HB (220 mg, 0.46 mmol, 62.6%) as an off-white solid. $^1$H NMR (500 MHz, DMSO-de): δ 8.33 (s, 1H), 7.50 (d, J=9.0 Hz, 2H), 7.36 (d, J=9.0 Hz, 2H), 7.09 (d, J=9.0 Hz, 2H), 6.96 (d, J=9.0 Hz, 2H), 3.89-3.86 (m, 1H), 3.91-3.76 (m, 4H), 3.34-3.24 (m, 4H), 1.73-1.58 (m, 4H), 0.76 (t, J=7.4 Hz, 6H).

2-(pentan-3-yl)-4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (HC)

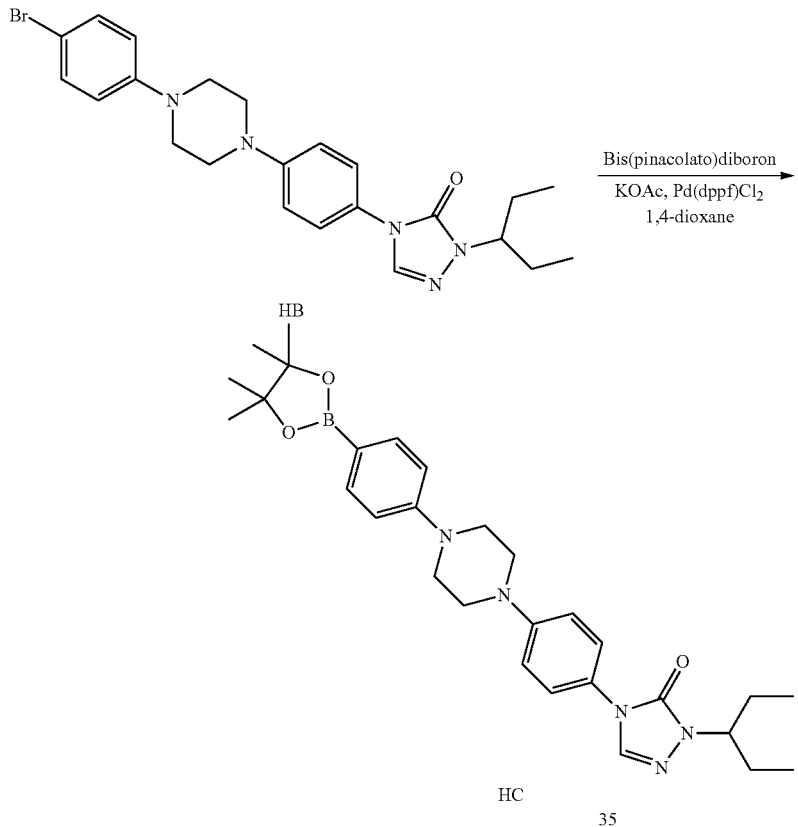

To a stirred solution of compound HB (220 mg, 0.46 mmol) in 1,4-dioxane (15 mL) under argon atmosphere were added bis(pinacolato)diboron (190 mg, 0.75 mmol), KOAc (137 mg, 1.40 mmol) at RT and purged under argon for 15 min. Then Pd(dppf)Cl$_2$ (34 mg, 0.04 mmol) was added to the reaction mixture at RT and stirred at 110° C. for 16 h in a sealed tube. The progress of the reaction was monitored by TLC, the reaction mixture was diluted with water (30 mL) and extracted with EtOAc (2×30 mL). The combined organic extracts were washed with water (30 mL), brine (30 mL), dried over anhydrous Na$_2$SO$_4$ and concentrated under reduced pressure. The crude material was purified by silica gel column chromatography (eluent: 30% EtOAc/Hexane) to afford compound HC (170 mg, 0.32 mmol, 70.2%) as an off-white solid. $^1$H NMR (400 MHz, DMSO-d$_6$): δ 8.35 (s, 1H), 7.55-7.50 (m, 4H), 7.10 (d, J=9.0 Hz, 2H), 6.98 (d, J=8.7 Hz, 2H), 3.93-3.83 (m, 1H), 3.41-3.36 (m, 8H), 1.76-1.60 (m, 4H), 1.27 (s, 12H), 0.78 (t, J=7.4 Hz, 6H).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-(pentan-3-yl)-2,4-dihydro-3H-1,2,4-triazol-3-one (66)

-continued

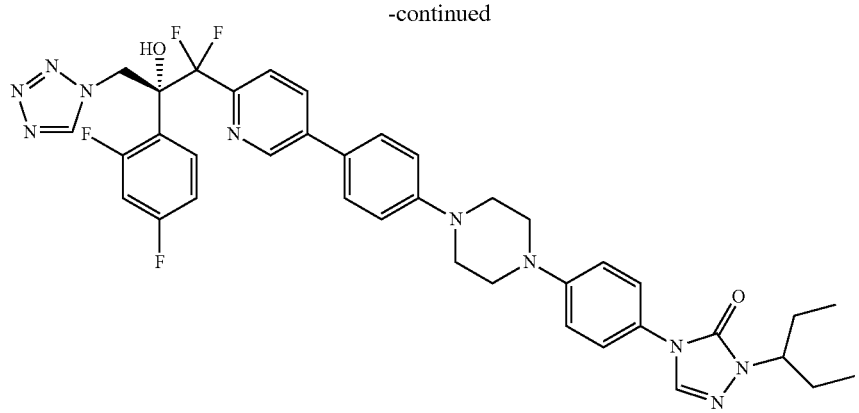

66

To a stirred solution of Int-1 (120 mg, 0.27 mmol) in THF:H2O (4:2, 10 mL) under argon atmosphere were added compound HC (172 mg, 0.33 mmol), sodium carbonate (88 mg, 0.83 mmol) at RT and purged under argon for 10 min. Then Pd(dppf)Cl$_2$ (20 mg, 0.02 mmol) was added to the reaction mixture at RT and again purged under argon for 10 min at RT, stirred at 80° C. for 16 h in a sealed tube. The progress of the reaction was monitored by TLC, the reaction mixture was diluted with water (10 mL) and extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluent: 70% EtOAc/Hexane) to afford 66 (45 mg, 0.06 mmol, 22%) as an off-white solid. $^1$H NMR (400 MHz, DMSO-d$_6$): δ 9.15 (s, 1H), 8.91 (d, J=2.0 Hz, 1H), 8.35 (s, 1H), 8.17 (dd, J=8.2, 2.2 Hz, 1H), 7.70 (d, J=8.8 Hz, 2H), 7.53 (d, J=9.0 Hz, 2H), 7.48 (d, J=8.3 Hz, 1H), 7.34-7.25 (m, 2H), 7.23-7.18 (m, 1H), 7.17-7.10 (m, 4H), 6.93-6.89 (m, 1H), 5.71-5.61 (m, 1H), 5.11 (d, J=14.8 Hz, 1H), 3.96-3.73 (m, 1H), 3.47-3.33 (m, 8H), 1.74-1.66 (m, 4H), 0.78 (t, J=7.3 Hz, 6H); MS (ESI): m/z 743.8 [h+H]$^+$; HPLC: 96.16%; Optical rotation [α]$_D^{26}$: +13.8 (c=0.1% in MeOH).

Example 67

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-(2-hydroxy-2-methylpropyl)-2,4-dihydro-3H-1,2,4-triazol-3-one (67)

4-(4-(4-(4-bromophenyl) piperazin-1-yl) phenyl)-2-(2-hydroxy-2-methylpropyl)-2,4-dihydro-3H-1,2,4-triazol-3-one (HD)

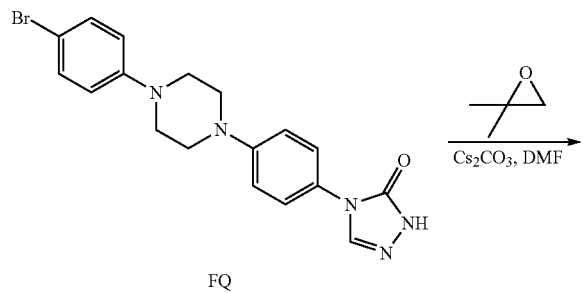

-continued

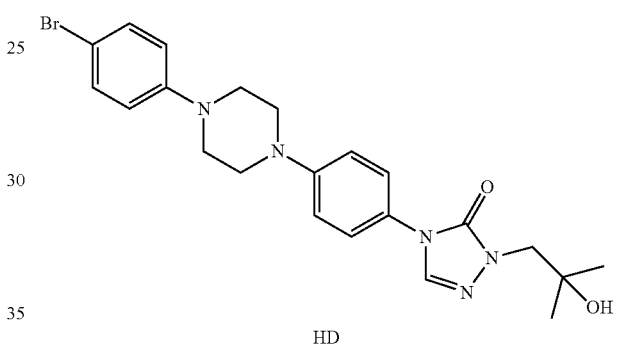

HD

To a stirred solution of compound FQ (200 mg, 0.50 mmol) in DMF (5 mL) under argon atmosphere were added 2,2-dimethyloxirane (324 mg, 4.50 mmol) and cesium carbonate (244 mg, 0.75 mmol) at 0° C. The reaction mixture was heated to 60° C. for 48 h in a sealed tube. The progress of the reaction was monitored by TLC. The reaction mixture was diluted with ice cold water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford compound HID (90 mg, 0.20 mmol, 38%) as a brown solid. $^1$H NMR (400 MHz. CDCl$_3$): δ 7.77 (s, 1H), 7.45-7.38 (m, 4H), 7.03 (d, J=8.8 Hz, 2H), 6.83 (d, J=9.0 Hz, 2H), 3.92 (s, 2H), 3.52 (s, 1H), 3.38-3.30 (m, 8H), 1.30 (s, 6H).

2-(2-hydroxy-2-methylpropyl)-4-(4-(4-(4-(4,4,5,5-tetramethyl-1,3,2-dioxaborolan-2-yl) phenyl) piperazin-1-yl) phenyl)-2,4-dihydro-3H-1,2,4-triol-3-one (HE)

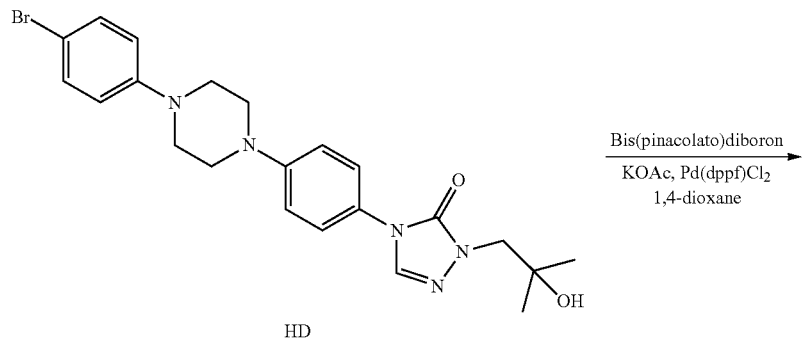

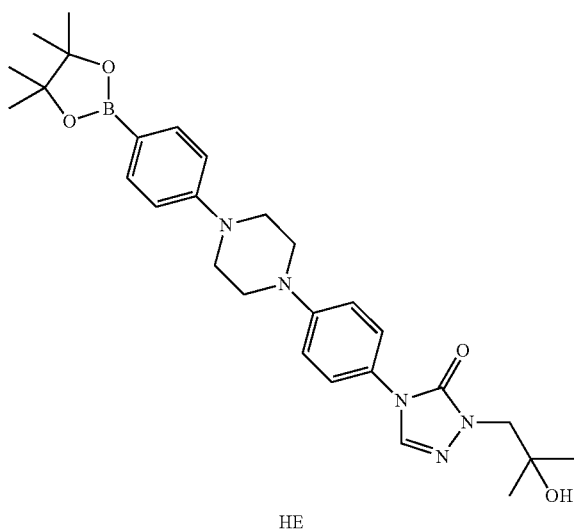

To a stirred solution of compound HD (300 mg, 0.63 mmol) in 1,4-dioxane (20 mL) under argon atmosphere were added bis(pinacolato)diboron (257 mg, 1.01 mmol), KOAc (186 mg, 1.90 mmol) and purged under argon for 20 min at RT. Then Pd(dppf)Cl₂ (46.4 mg, 0.06 mmol) was added to the reaction mixture at RT and stirred at 110° C. for 12 h. The reaction mixture was filtered, the filtrate was diluted with water (50 mL) and extracted with $CH_2Cl_2$ (2×50 mL). The combined organic extracts were dried over anhydrous $Na_2SO_4$ and concentrated under reduced pressure. The crude material was purified by silica gel column chromatography (eluted with 2% MeOH/$CH_2Cl_2$) to afford compound HE (150 mg, 0.28 mmol, 45%) as a brown solid. ¹H NMR (400 MHz, DMSO-d₆): δ 8.32 (s, 1H), 7.55-7.50 (m, 4H), 7.09 (d, J=8.8 Hz, 2H), 6.98 (d, J=9.0 Hz, 2H), 3.90 (s, 2H), 3.63 (s, 1H), 3.40-3.37 (m, 8H), 1.27 (s, 12H), 1.12 (s, 6H).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-(2-hydroxy-2-methylpropyl)-2,4-dihydro-3H-1,2,4-triazol-3-one (67)

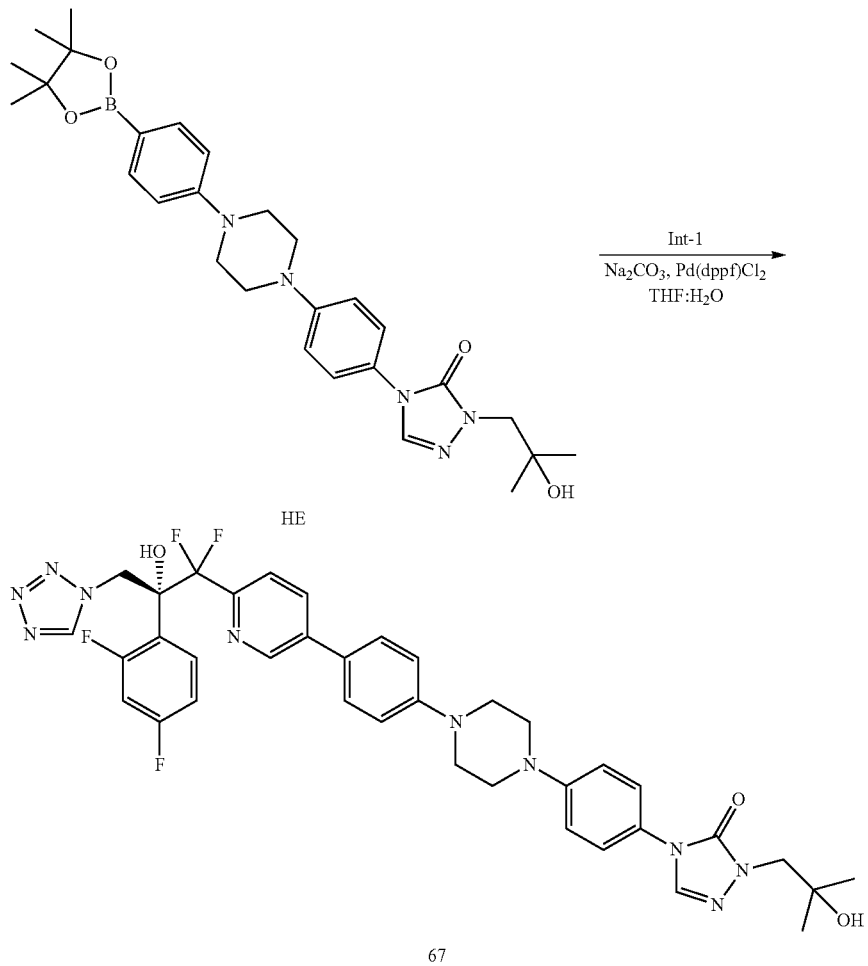

To a stirred solution of Int-1 (130 mg, 0.25 mmol) in THF:H2O (4:1, 20 mL) under argon atmosphere were added compound HE (107 mg, 0.25 mmol), sodium carbonate (79.5 mg, 0.75 mmol) and purged under argon for 15 min at RT. Then Pd(dppf)Cl$_2$ (18.2 mg, 0.02 mmol) was added and the reaction mixture was purged under argon for 10 min at RT. The reaction mixture was stirred at 90° C. for 12 h. The progress of the reaction was monitored by TLC. The reaction mixture was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 67 (50 mg, 0.07 mmol, 26%) as a pale yellow solid. $^1$H NMR (400 MHz, DMSO-d$_6$): δ 9.14 (s, 1H), 8.91 (d, J=2.0 Hz, 1H), 8.30 (s, 1H), 8.17 (dd, J=8.3, 2.2 Hz, 1H), 7.70 (d, J=8.8 Hz, 2H), 7.51-7.48 (m, 3H), 7.30-7.20 (m, 3H), 7.18-7.10 (m, 4H), 6.93-6.88 (m, 1H), 5.67 (d, J=14.8 Hz, 1H), 5.11 (d, J=14.8 Hz, 1H) 4.60 (s, 1H), 3.63 (s, 2H), 3.41-3.30 (m, 8H), 1.14 (s, 6H); MS (ESI): m/z 745.8 [M+H]$^+$; HPLC: 93.42%; Optical rotation [α]$_D^{20}$: +50.3 (c=0.1% in MeOH).

Example 68

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2,3-dimethylbutan-1-ol (68)

1-(5-(4-(4-(4-bromophenyl) piperazin-1-yl) pyridin-2-yl)-3-methylbutan-1-one (HF)

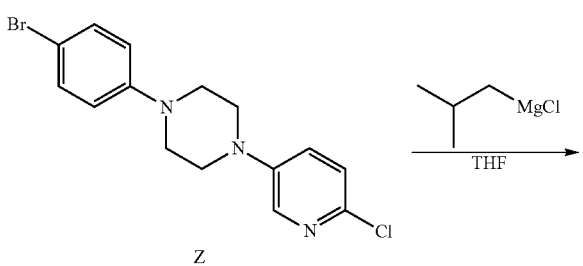

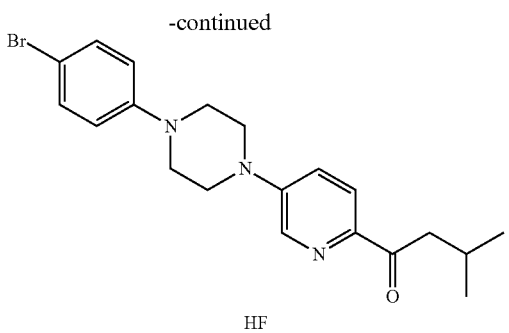

HF

To a stirred solution of compound Z (2.0 g, 5.83 mmol) in THF (20 mL) under argon atmosphere was added isobutyl magnesium chloride (8.74 mL, 17.49 mmol, 2.0 M in Diethyl ether) at 0° C. The reaction mixture was warmed to RT and stirred for 3 h. The progress of the reaction was monitored by TLC. The reaction mixture was quenched with saturated ammonium chloride solution (100 mL) and extracted with EtOAc (2×100 mL). The combined organic extracts were washed with water (50 mL), brine (50 mL), dried over anhydrous $Na_2SO_4$ and concentrated under reduced pressure. The crude material was purified by silica gel column chromatography (eluent: 20% EtOAc/Hexane) to afford compound HF (1.3 g, 3.24 mmol, 56%) as yellow solid. $^1$H NMR (500 MHz, $CDCl_3$): δ 8.33 (d, J=2.9 Hz, 1H), 8.00 (d, J=8.7 Hz, 1H), 7.40 (d, J=9.0 Hz, 2H), 7.23 (dd, J=8.7, 2.9 Hz, 1H), 6.85 (d, J=8.7 Hz, 2H), 3.57-3.52 (m, 4H), 3.37-3.33 (m, 4H), 3.04 (d, J=6.9 Hz, 2H), 2.35-2.28 (m, 1H), 1.00 (d, J=6.9 Hz, 6H).

1-(5-(4-(4-bromophenyl) piperazin-1-yl) pyridin-2-yl)-2,3-dimethylbutan-1-one (HG)

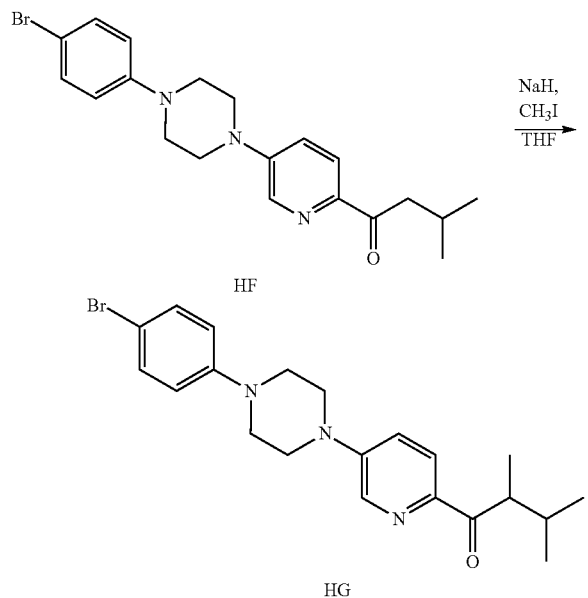

To a stirred solution of compound HF (800 mg, 1.99 mmol) in THF (25 mL) under argon atmosphere was added sodium hydride (71 mg, 2.99 mmol) at 0° C., and stirred for 30 min. Then methyl iodide (0.191 mL, 2.99 mmol) was added to the reaction mixture at 0° C. The reaction mixture was warmed to RT and stirred for 36 h. The progress of the reaction was monitored by TLC. The reaction mixture was diluted with ice cold water (50 mL) and extracted with EtOAc (2×50 mL). The combined organic layers were washed with water (50 mL), brine (30 mL), dried over anhydrous $Na_2SO_4$ and concentrated under reduced pressure. The crude material was purified by silica gel column chromatography (eluent: 10-20% EtOAc/Hexane) to afford compound HG (550 mg, 1.32 mmol, 66%) as yellow solid. $^1$H NMR (400 MHz, $CDCl_3$): δ 8.35 (d, J=2.8 Hz, 1H), 8.01 (d, J=9.2 Hz, 1H), 7.40 (d, J=9.0 Hz, 2H), 7.24 (dd, J=8.9, 3.0 Hz, 1H), 6.85 (d, J=9.2 Hz, 2H), 3.94-3.89 (m, 1H), 3.57-3.51 (m, 4H), 3.41-3.28 (m, 4H), 2.16-2.05 (m, 1H), 1.12 (d, J=7.0 Hz, 3H), 0.93 (d, J=6.8 Hz, 6H).

1-(5-(4-(4-bromophenyl) piperazin-1-yl) pyridin-2-yl)-2,3-dimethylbutan-1-ol (HH)

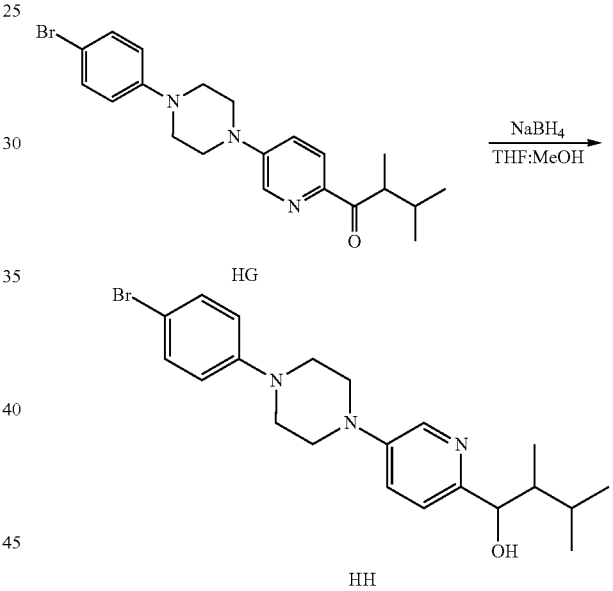

To a stirred solution of compound HG (500 mg, 1.20 mmol) in THF:EtOH (1:1, 55 mL) under argon atmosphere was added sodium borohydride (136 mg, 3.60 mmol) at 0° C. and stirred at RT for 2 h. The progress of the reaction was monitored by TLC. The reaction mixture was quenched with ice cold water (30 mL) and extracted with EtOAc (2×30 mL). The combined organic layers were washed with water (30 mL), dried over anhydrous $Na_2SO_4$ and concentrated under reduced pressure. The crude material was purified by silica gel column chromatography (eluent: 40% EtOAc/Hexane) to afford compound HH (300 mg, 0.71 mmol, 54%) as an off-white solid.

$^1$H NMR (500 MHz, $CDCl_3$): δ 8.31 (d, J=2.6 Hz, 1H), 7.40 (d, J=9.0 Hz, 2H), 7.25 (dd, J=8.5, 2.7 Hz, 1H), 7.13 (d, J=8.7 Hz, 1H), 6.86 (d, J=9.0 Hz, 2H), 3.40-3.29 (m, 8H), 2.20-2.09 (m, 1H), 1.74-1.72 (m, 1H), 0.96 (d, J=6.9 Hz, 3H), 0.90 (d, J=6.7 Hz, 3H), 0.65 (d, J=7.2 Hz, 3H)

2,3-dimethyl-1-(5-(4-(4-(4,4,5,5-tetramethyl-1,3,2-dioxaborolan-2-yl) phenyl) piperazin-1-yl) pyridin-2-yl) butan-1-ol (HI)

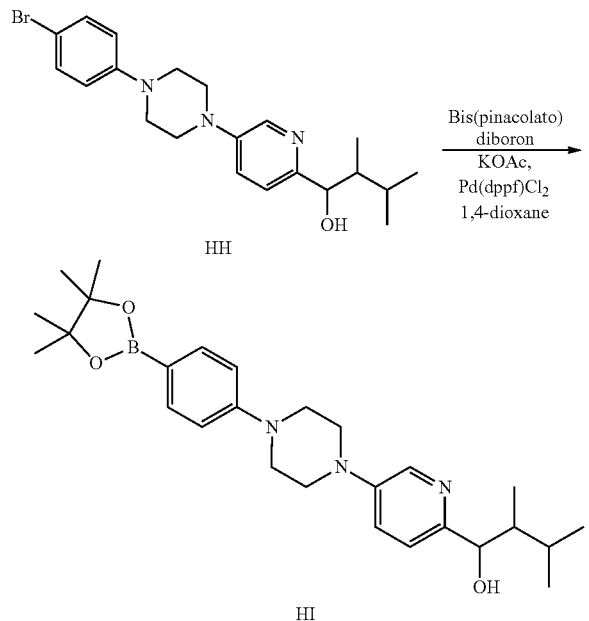

To a stirred solution of compound HH (300 mg, 0.71 mmol) in 1,4-dioxane (30 mL) under argon atmosphere were added bis(pinacolato)diboron (291 mg, 1.14 mmol) and potassium acetate (204 mg, 2.15 mmol) at RT. The reaction mixture was purged with argon for 20 min, then Pd(dppf)Cl$_2$ (52 mg, 0.07 mmol) was added and the reaction mixture was purged under argon for 5 min at RT. The reaction mixture was stirred at 110° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 0-3% MeOH/CH$_2$Cl$_2$) to afford compound HI (200 mg, 0.43 mmol, 60%) as a brown solid. $^1$H NMR (400 MHz, CDCl$_3$): δ 8.29 (d, J=2.8 Hz, 1H), 7.74 (d, J=8.7 Hz, 2H), 7.23 (dd, J=8.5, 2.9 Hz, 1H), 7.11 (d, J=8.5 Hz, 1H), 6.94 (d, J=8.7 Hz, 2H), 4.44 (t, J=7.2 Hz, 1H), 3.46-3.30 (m, 9H), 2.17-2.08 (m, 1H), 1.76-1.68 (m, 1H), 1.33 (s, 12H), 0.94 (d, J=6.9 Hz, 3H), 0.89 (d, J=6.8 Hz, 3H), 0.63 (d, J=7.0 Hz, 3H).

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2,3-dimethylbutan-1-ol (68)

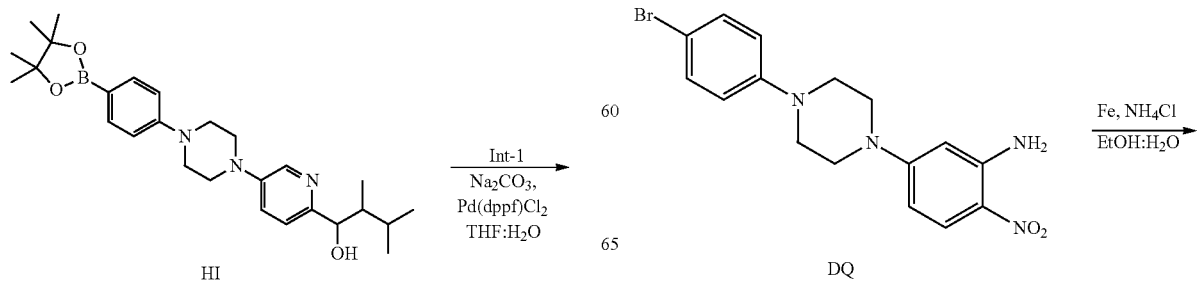

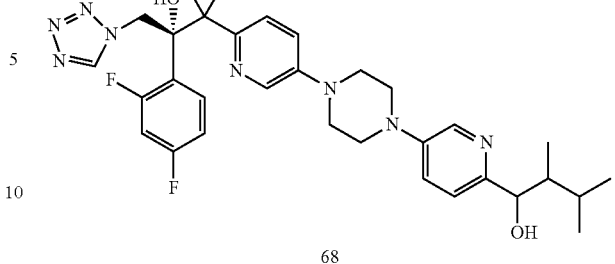

To a stirred solution of Int-1 (110 mg, 0.40 mmol) in THF:H2O (4:1, 35 mL) under argon atmosphere were added compound HI (200 mg, 0.43 mmol), sodium carbonate (117 mg, 1.11 mmol) and purged under argon for 15 min at RT. Then Pd(dppf)Cl$_2$ (27 mg, 0.04 mmol) was added and the reaction mixture was purged under argon for 10 min at RT. The reaction mixture was stirred at 70° C. for 12 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 50-90% MeOH/CH$_2$Cl$_2$) to afford 68 (74 mg, 0.10 mmol, 27%) as an off-white solid. $^1$H NMR (400 MHz, DMSO-d$_6$): δ 9.15 (s, 1H), 8.91 (d, J=2.0 Hz, 1H), 8.25 (d, J=2.8 Hz, 1H), 8.17 (dd, J=8.3, 2.2 Hz, 1H), 7.70 (d, J=8.8 Hz, 2H), 7.48 (d, J=8.3 Hz, 1H), 7.41 (dd, J=8.7, 2.8 Hz, 1H), 7.32-7.23 (m, 3H), 7.22-7.11 (m, 3H), 6.93-6.88 (m, 1H), 5.67 (d, J=14.8 Hz, 1H), 5.11 (d, J=14.8 Hz, 1H), 4.98 (d, J=5.3 Hz, 1H), 4.30 (dd, J=8.3, 5.3 Hz, 1H), 3.48-3.33 (m, 8H), 2.13-2.05 (m, 1H), 1.77-1.62 (m, 1H), 0.90 (d, J=6.9 Hz, 3H), 0.80 (d, J=6.8 Hz, 3H), 0.48 (d, J=6.9 Hz, 3H); MS (ESI): m/z 691.7 [M+H]$^+$; HPLC: 98.39%; Optical rotation [α]$_D^{20}$: +47.08 (c=0.1% in MeOH).

Example 69

(R)-2-(2,4-difluorophenyl)-1,1-difluoro-1-(4-(4-(2-isopropyl-1H-benzo [d] imidazol-5-yl) piperazin-1-yl) phenyl) pyridin-2-yl)-3-(1H-tetrazol-1-yl) propan-2-ol (69)

4-(4-(4-bromophenyl) piperazin-1-yl) benzene-1,2-diamine (HJ)

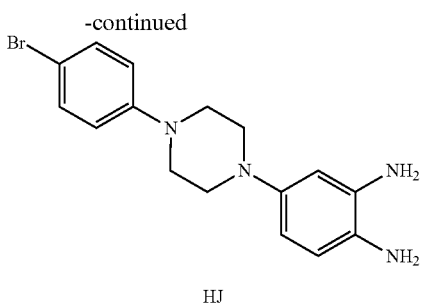

To a stirred solution of compound DQ (5 g, 13.26 mmol) in EtOH:water (4:2, 150 mL) under argon atmosphere were added iron powder (3.7 g, 66.31 mmol) and ammonium chloride (7.09 g, 132.62 mmol) at RT. The reaction mixture was stirred at 80° C. for 4 h. The progress of the reaction was monitored by TLC. The volatiles were evaporated under reduced pressure. The residue diluted with water (100 mL), basified with aqueous ammonium solution (50 mL) and extracted with 10% MeOH:CH$_2$Cl$_2$ (2×100 mL). The combined organic layers were washed with water (50 mL), brine (50 mL), dried over anhydrous Na$_2$SO$_4$ and concentrated under reduced pressure. The crude material was purified by silica gel column chromatography (eluent: 0-3% MeOH/CH$_2$Cl$_2$) to afford compound HJ (3 g, 8.64 mmol, 65%) as a pale brown solid. $^1$H NMR (500 MHz, DMSO-d$_6$): δ 7.35 (d, J=9.8 Hz, 2H), 6.92 (d, J=8.6 Hz, 2H), 6.42 (d, J=9.6 Hz, 1H), 6.28 (s, 1H), 6.09-6.06 (m, 1H), 4.35 (s, 2H), 4.00 (s, 2H), 3.23-3.20 (m, 4H), 3.01-2.98 (m, 4H).

5-(4-(4-bromophenyl) piperazin-1-yl)-2-isopropyl-1H-benzo [d] imidazole (HK)

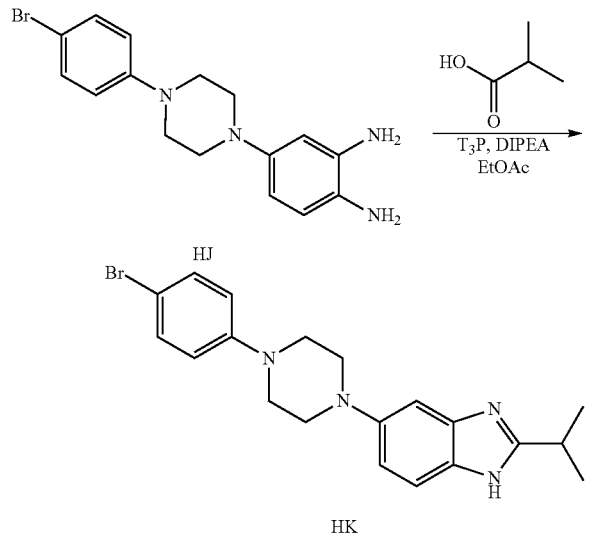

To a stirred solution of compound HJ (300 mg, 0.86 mmol) in EtOAc (5 mL) under argon atmosphere were added isobutyric acid (0.1 mL, 1.29 mmol), T$_3$P (0.5 mL, 1.72 mmol, 50% in EtOAc) and DIPEA (0.2 mL, 1.29 mmol) in sealed tube at RT. The reaction mixture was stirred at 100° C. for 2 h. The progress of the reaction was monitored by TLC. The reaction mixture was quenched with ammonium chloride solution (20 mL) and extracted with EtOAc (2×20 mL). The combined organic layers were washed with water (10 mL), brine (10 mL), dried over anhydrous Na$_2$SO$_4$ and concentrated under reduced pressure to obtain compound HK (120 mg, 0.30 mmol, 35%) as a pale brown solid. $^1$H NMR (500 MHz, CD$_3$OD): δ 7.43 (d, J=8.7 Hz, 1H), 7.37 (d, J=9.0 Hz, 2H), 7.13 (s, 1H), 7.05 (dd, J=8.7, 2.3 Hz, 1H), 6.96 (d, J=9.0 Hz, 2H), 3.41-3.25 (m, 4H), 3.24-3.15 (m, 4H), 3.23-3.12 (m, 1H), 1.42 (d, J=6.9 Hz, 6H).

2-isopropyl-5-(4-(4-(4,4,5,5-tetramethyl-1,3,2-dioxaborolan-2-yl) phenyl) piperazin-1-yl)-1H-benzo [d] imidazole (HL)

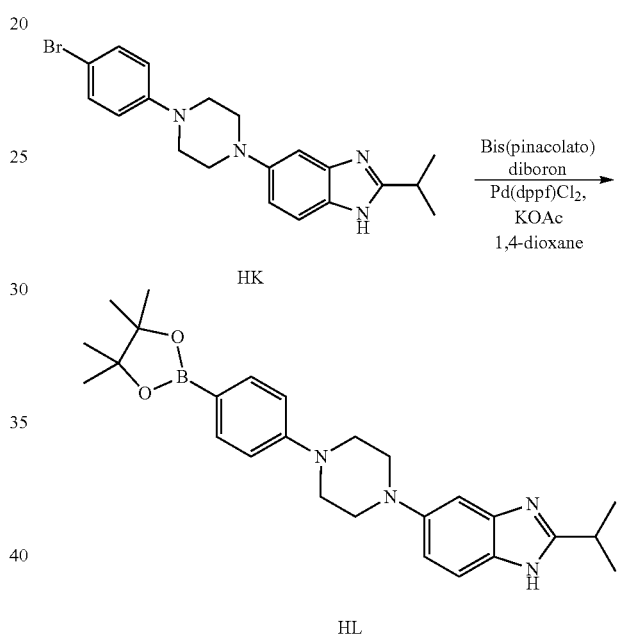

To a stirred solution of compound HK (120 mg, 0.30 mmol) in 1,4-dioxane (15 mL) under argon atmosphere were added bis(pinacolato)diboron (122 mg, 0.48 mmol) and potassium acetate (88.6 mg, 0.90 mmol) at RT. The reaction mixture was purged with argon for 20 min, then Pd(dppf)Cl$_2$ (22 mg, 0.03 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 2% MeOH/CH$_2$Cl$_2$) to afford compound HL (120 mg, 0.26 mmol, 60%) as a pale brown solid. $^1$H NMR (500 MHz, DMSO-d$_6$): δ 11.95 (brs, 1H), 7.54 (d, J=8.7 Hz, 2H), 7.50-7.47 (m, 1H), 7.35 (d, J=8.7 Hz, 1H), 6.97 (d, J=8.4 Hz, 2H), 6.92 (dd, J=8.7, 2.0 Hz, 1H), 3.42-3.38 (m, 4H), 3.24-3.15 (m, 4H), 3.12-3.07 (m, 1H), 1.32 (d, J=6.9 Hz, 6H), 1.27 (s, 12H).

311

(R)-2-(2,4-difluorophenyl)-1,1-difluoro-1-(5-(4-(4-(2-isopropyl-1H-benzo [d] imidazol-5-yl) piperazin-1-yl) phenyl) pyridin-2-yl)-3-(1H-tetrazol-1-yl) propan-2-ol (69)

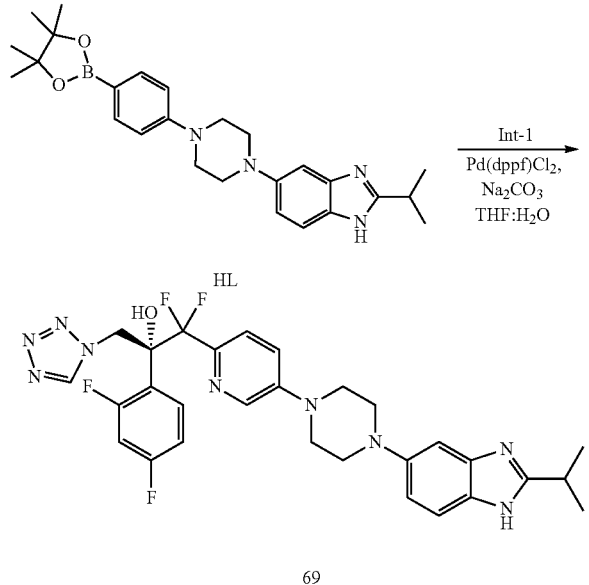

To a stirred solution of Int-1 (100 mg, 0.23 mmol) in THF:H2O (4:1, 25 mL) under argon atmosphere were added compound HL (123 mg, 0.27 mmol), sodium carbonate (73.6 mg, 0.69 mmol) and purged under argon for 20 min at RT. Then Pd(dppf)Cl$_2$ (17 mg, 0.02 mmol) was added and the reaction mixture was purged under argon for 5 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2-3% MeOH/CH$_2$Cl$_2$) to afford 69 (35 mg, 0.05 mmol, 27%) as an off-white solid. $^1$H NMR (400 MHz, DMSO-d$_6$): δ 14.14 (brs, 1H), 9.15 (s, 1H), 8.90 (s, 1H), 8.17 (dd, J=8.3, 2.3 Hz, 1H), 7.71 (d, J=8.9 Hz, 2H), 7.61 (d, J=9.0 Hz, 1H), 7.48 (d, J=8.2 Hz, 1H), 7.33-7.09 (m, 7H), 6.93-6.88 (m, 1H), 5.67 (d, J=14.7 Hz, 1H), 5.12 (d, J=14.7 Hz, 1H), 3.49-3.40 (m, 9H), 1.43 (d, J=7.0 Hz, 6H); MS (ESI): m/z 672.6 [M+H]$^+$; HPLC: 98.73%; Optical rotation [α]$_D^{20}$: +46.32 (c=0.1% in MeOH).

Example 70

1-(5-(4-(4-(6-((R)-2-(2,4-difluorophenyl-1,1-difluoro-2-hydroxy-3-(1H-tetrazol-1-yl) propyl) pyridin-3-yl) phenyl) piperazin-1-yl)-3-fluoropyridin-2-yl)-3,3,3-trifluoropropan-1-ol (70)

(5-bromo-3-fluoro-2-vinylpyridine (HN)

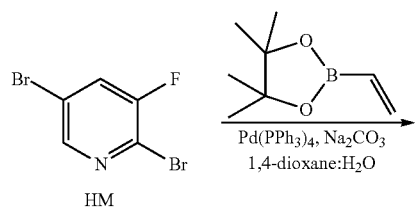

312

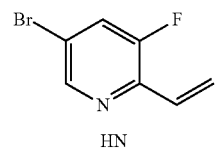

To a stirred solution of 2,5-dibromo-3-fluoropyridine (HM: 2.0 g, 7.87 mmol) in 1,4-dioxane:H$_2$O (4:1, 50 mL) under argon atmosphere were added 4,4,5,5-tetramethyl-2-vinyl-1,3,2-dioxaborolane (1.2 g, 7.87 mmol), sodium carbonate (2.5 g, 23.62 mmol) and purged under argon for 20 min at RT. Then Pd (PPh$_3$)$_4$(227 mg, 0.19 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% EtOAc/Hexane) to afford compound HN (1.0 g, 4.97 mmol, 63%) as colorless syrup. $^1$H NMR (400 MHz, CDCl$_3$): δ 8.45 (s, 1H), 7.56 (dd, J=9.4, 2.0 Hz, 1H), 6.98-6.90 (m, 1H), 6.43 (dd, J=17.4, 1.6 Hz, 1H), 5.62 (dd, J=10.9, 1.6 Hz, 1H).

1-(5-bromo-3-fluoropyridin-2-yl)-3,3,3-trifluoropropan-1-ol (HO)

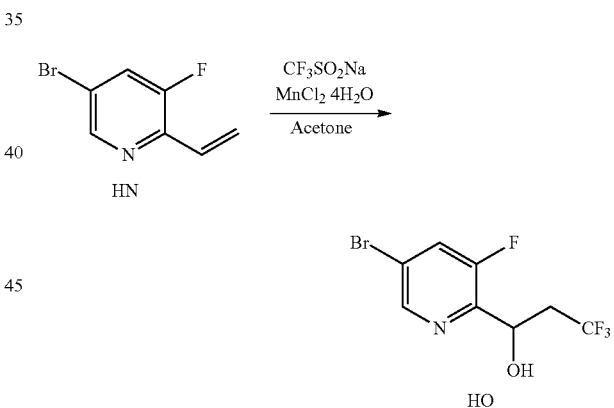

To a stirred solution of compound HN (1.0 g, 4.97 mmol) in acetone (25 mL) under argon atmosphere were added sodium trifluoromethanesulfinate (3.1 g, 19.90 mmol), MnCl$_2$.4H$_2$O (392 mg, 1.99 mmol) at RT and stirred for 16 h. The volatiles were evaporated under reduced pressure. The residue was diluted with water (50 mL) and extracted with EtOAc (2×50 mL). The combined organic extracts were dried over anhydrous Na$_2$SO$_4$ and concentrated under reduced pressure. The crude material was purified by silica gel column chromatography (eluent: 10% EtOAc/Hexane) to afford compound HO (500 mg, 1.73 mmol, 35%) as a pale brown solid. $^1$H NMR (400 MHz, CDCl$_3$): δ 8.51 (s, 1H), 7.66 (dd, J=8.7, 1.8 Hz, 1H), 5.32-5.27 (m, 1H), 3.95 (d, J=7.5 Hz, 1H), 2.70-2.49 (m, 2H).

313

1-(5-(4-(4-bromophenyl) piperazin-1-yl)-3-fluoro-pyridin-2-yl)-3,3,3-trifluoropropan-1-ol (HP)

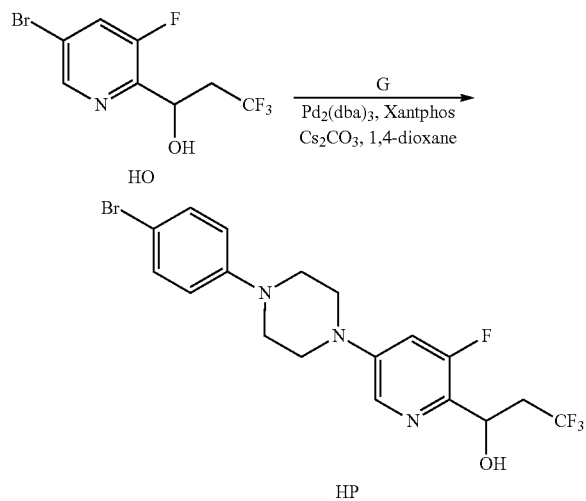

To a stirred solution of compound HO (300 mg, 1.24 mmol) in 1,4-dioxane (15 mL) under argon atmosphere were added G (394 mg, 1.36 mmol), Xantphos (87 mg, 0.14 mmol), Cs$_2$CO$_3$ (1.2 g, 3.73 mmol) and purged under argon for 10 min at RT. Then Pd$_2$(dba)$_3$ (57 mg, 0.06 mmol) was added to the reaction mixture at RT and stirred at 80° C. for 16 h. The reaction mixture was diluted with water (20 mL) and extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 25% EtOAc/Hexane) to afford compound HP (250 mg, 055 mmol, 49%) as a pale yellow solid. $^1$H NMR (500 MHz, DMSO-d$_6$): δ 8.20 (s, 1H), 7.38 (d, J=9.0 Hz, 2H), 7.31 (dd, J=13.6, 2.0 Hz, 1H), 6.97 (d, J=9.0 Hz, 2H), 5.62 (d, J=6.1 Hz, 1H), 5.08-5.05 (m, 1H), 3.44-3.36 (m, 4H), 3.29-3.24 (m, 4H), 2.91-2.75 (m, 2H).

3,3,3-trifluoro-1-(3-fluoro-5-(4-(4-(4,4,5,5-tetramethyl-1,3,2-dioxaborolan-2-yl) phenyl) piperazin-1-yl) pyridin-2-yl) propan-1-ol (HQ)

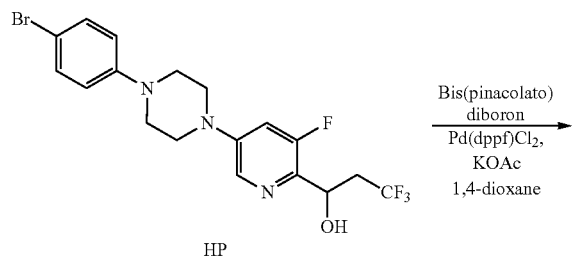

314

-continued

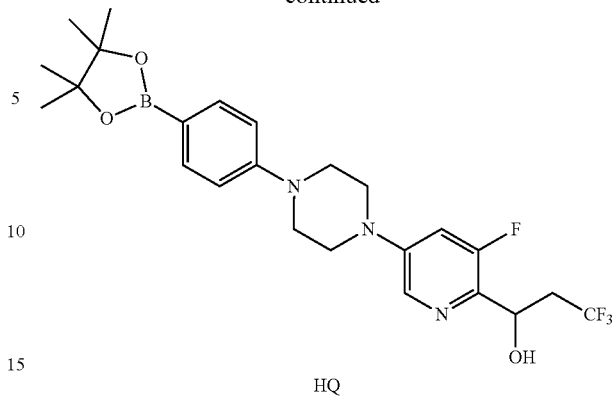

To a stirred solution of compound HP (250 mg, 0.55 mmol) in 1,4-dioxane (15 mL) under argon atmosphere were added bis(pinacolato)diboron (226 mg, 0.89 mmol) and potassium acetate (164 mg, 1.67 mmol) at RT. The reaction mixture was purged with argon for 20 min, then Pd(dppf)Cl$_2$ (168 mg, 0.22 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 20% EtOAc/Hexane) to afford compound HQ (150 mg, 0.30 mmol, 54%) as a pale yellow solid. $^1$H NMR (400 MHz, CDCl$_3$): δ 8.10 (s, 1H), 7.75 (d, J=8.7 Hz, 2H), 6.98-6.87 (m, 3H), 5.27-5.20 (m, 1H), 4.51 (brs, 1H), 3.44-3.40 (m, 8H), 2.69-2.45 (m, 2H), 1.24 (s, 12H).

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl)-3-fluoropyridin-2-yl)-3,3,3-trifluoropropan-1-ol (70)

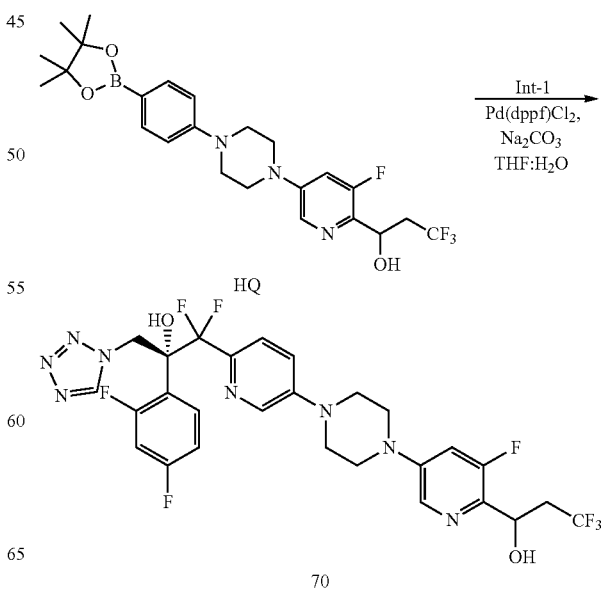

To a stirred solution of Int-1 (100 mg, 0.23 mmol) in THF:H2O (4:1, 20 mL) under argon atmosphere were added compound HQ (137 mg, 0.27 mmol), sodium carbonate (73.6 mg, 0.69 mmol) and purged under argon for 20 min at RT. Then Pd(dppf)Cl$_2$ (17 mg, 0.02 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 70% EtOAc/Hexane) to afford 70 (40 mg, 0.05 mmol, 24%) as an off-white solid. $^1$H NMR (400 MHz, DMSO-d$_6$): δ 9.15 (s, 1H), 8.90 (s, 1H), 8.22 (s, 1H), 8.17 (d, J=8.3 Hz, 1H), 7.70 (d, J=8.7 Hz, 2H), 7.48 (d, J=8.2 Hz, 1H), 7.37-7.17 (m, 4H), 7.15 (d, J=8.8 Hz, 2H), 6.95-6.82 (m, 1H), 5.67 (d, J=14.8 Hz, 1H), 5.63 (d, J=6.1 Hz, 1H), 5.15-5.02 (m, 2H), 3.43-3.41 (m, 8H), 2.87-2.72 (m, 2H). MS (ESI): m/z 721.4 [M+H]$^+$; HPLC: 99.46% Optical rotation [α]$_D^{25}$: +11.60 (c=0.1% in MeOH).

Example 71

3-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl)-1H-benzo [d] imidazol-2-yl)pentan-2-ol (71)

N-(5-(4-(4-bromophenyl)piperazin-1-yl)-2-nitrophenyl)-2-ethyl-3-oxobutanamide (HR)

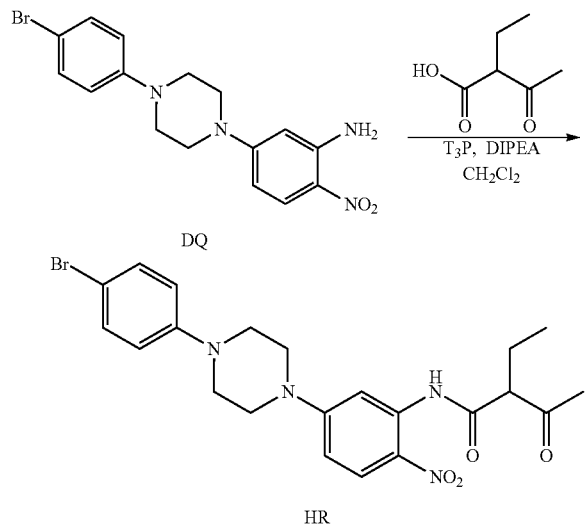

To a stirred solution of compound DQ (1 g, 2.65 mmol) in CH$_2$Cl$_2$ (30 mL) under argon atmosphere were added 2-ethyl-3-oxobutanoic acid (1.02 g, 7.93 mmol), T$_3$P (2.5 mL, 7.95 mmol, 50% in EtOAc) and diisopropyl ethyl amine (1.4 mL, 7.95 mmol) at 0° C. The reaction mixture was warmed to RT and stirred for 4 h. The progress of the reaction was monitored by TLC. The reaction mixture was quenched with water (50 mL) and extracted with CH$_2$Cl$_2$ (2×50 mL). The combined organic layers were washed with water (50 mL), dried over anhydrous Na$_2$SO$_4$ and concentrated under reduced pressure. The crude material was purified by silica gel column chromatography (eluent: 30% EtOAc/Hexane) to afford impure HR (500 mg) as yellow solid. The material was used as such in the next step.

3-(5-(4-(4-bromophenyl) piperazin-1-yl)-1H-benzo d imidazol-2-yl) pentan-2-one (HS)

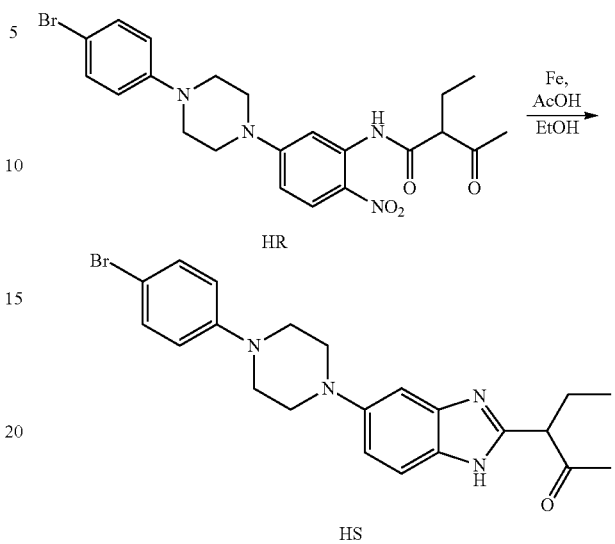

To a stirred solution of compound HR (700 mg, 1.43 mmol) in AcOH:EtOH (1:1, 20 mL) under argon atmosphere was added Fe powder (572 mg, 10.04 mmol) at RT. The reaction mixture was stirred at 80° C. for 2 h. The progress of the reaction was monitored by TLC. The reaction mixture was diluted with ammonium chloride solution (50 mL) and extracted with CH$_2$Cl$_2$ (2×50 mL). The combined organic layers were dried over anhydrous Na$_2$SO$_4$ and concentrated under reduced pressure. The crude material was purified by silica gel column chromatography (eluted with 50% EtOAc/Hexane) to afford compound HS (500 mg, 1.13 mmol, 79%) as a pale yellow solid. $^1$H NMR (400 MHz, DMSO-d$_6$): δ 7.84 (d, J=9.8 Hz, 1H), 7.37 (d, J=8.6 Hz, 2H), 7.28 (s, 2H), 6.94 (d, J=9.6 Hz, 2H), 6.46-6.41 (m, 1H), 6.26 (d, J=2.6 Hz, 1H), 3.51-3.46 (m, 4H), 3.34-3.24 (m, 4H).

3-(5-(4-(4-bromophenyl) piperazin-1-yl)-1H-benzo [d] imidazol-2-yl) pentan-2-ol (HT)

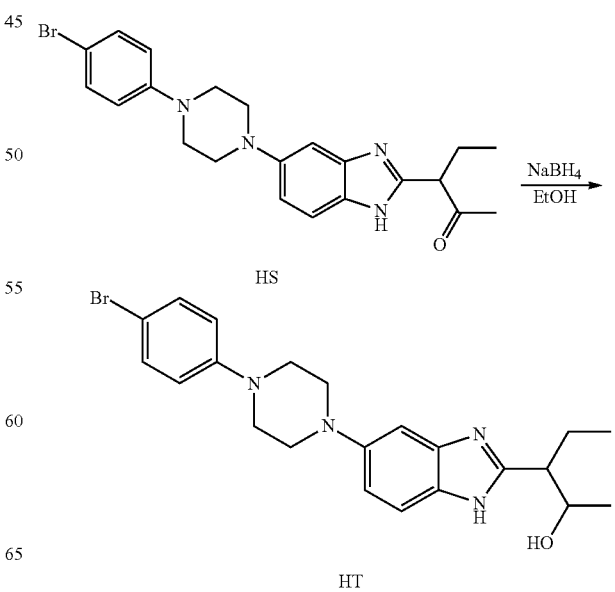

To a stirred solution of compound HS (500 mg, 1.13 mmol) in MeOH (30 mL) under argon atmosphere was added sodium borohydride (215 mg, 5.68 mmol) at 0° C. The reaction mixture was warmed to RT and stirred for 72 h. The progress of the reaction was monitored by TLC. The reaction mixture was quenched with water (30 mL) and extracted with $CH_2Cl_2$ (2×30 mL). The combined organic layers were washed with water (20 mL), dried over anhydrous $Na_2SO_4$ and concentrated under reduced pressure. The crude material was purified by silica gel column chromatography (eluent: 50% EtOAc/Hexane) to afford compound HT (450 mg, 1.01 mmol, 89%) as an off-white solid. $^1$H NMR (400 MHz, DMSO-$d_6$): δ 9.30 (s, 1H), 7.37 (d, J=8.9 Hz, 2H), 6.92 (d, J=7.5 Hz, 2H), 6.79 (d, J=7.5 Hz, 1H), 6.63-6.60 (m, 1H), 6.50 (s, 1H), 4.93-4.91 (m, 1H), 3.74-3.70 (m, 1H), 3.25-3.20 (m, 4H), 3.10-3.05 (m, 4H), 2.43-2.40 (m, 1H), 1.69-1.60 (m, 1H), 1.20-1.10 (m, 1H), 1.01 (d, J=5.4 Hz, 3H), 0.75 (t, J=6.8 Hz, 3H).

3-(5-(4-(4-(4,4,5,5-tetramethyl-1,3,2-dioxaborolan-2-yl) phenyl) piperazin-1-yl)-1H-benzo

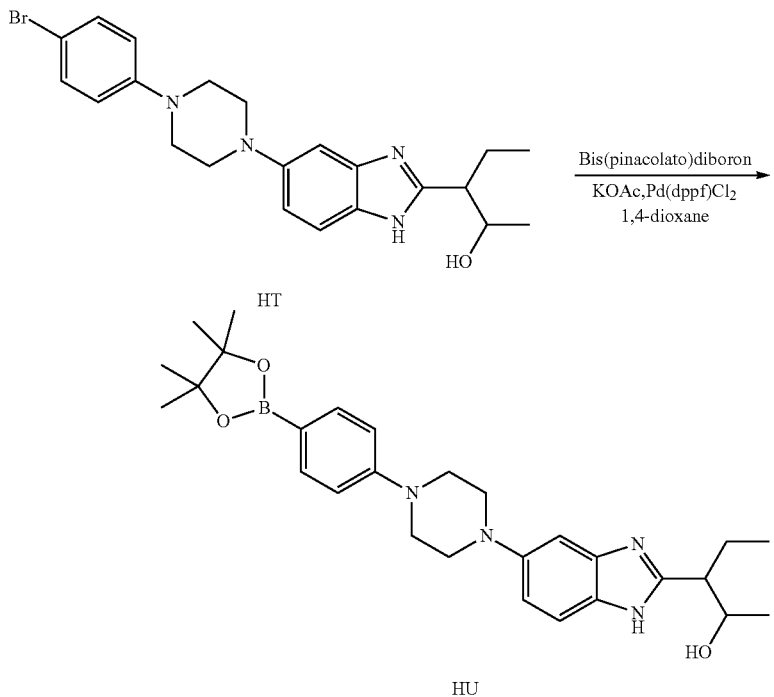

To a stirred solution of compound HT (500 mg, 1.12 mmol) in 1,4-dioxane (50 mL) under argon atmosphere were added bis(pinacolato)diboron (571 mg, 2.25 mmol) and potassium acetate (442 mg, 4.51 mmol) at RT. The reaction mixture was purged with argon for 20 min, then Pd(dppf)Cl$_2$ (123 mg, 0.16 mmol) was added and the reaction mixture was purged under argon for 10 min at RT. The reaction mixture was stirred at 110° C. for 16 h. The reaction mixture was quenched with water (20 mL) and extracted with EtOAc (2×20 mL). The combined organic layers were washed with water (10 mL), brine (10 mL), dried over anhydrous $Na_2SO_4$ and concentrated under reduced pressure. The crude material was purified by silica gel column chromatography (eluent: 60% EtOAc/Hexane) to afford compound HU (280 mg, 0.57 mmol, 51%) as an off-white solid. $^1$H NMR (400 MHz, DMSO-$d_6$): δ 9.30 (s, 1H), 7.56 (d, J=8.9 Hz, 2H), 6.92 (d, J=7.5 Hz, 2H), 6.79 (d, J=7.5 Hz, 1H), 6.63-6.60 (m, 1H), 6.50 (s, 1H), 4.93-4.91 (m, 1H), 3.74-3.70 (m, 1H), 3.35-3.30 (m, 4H), 3.13-3.05 (m, 4H), 2.43-2.40 (m, 1H), 1.69-1.60 (m, 1H), 1.30 (s, 12H), 1.20-1.10 (m, 1H), 1.01 (d, J=5.4 Hz, 3H), 0.75 (t, J=6.8 Hz, 3H).

3-(5-(4-(4-(4-(6-R)-2-(2,4-difluorophenyl-1,1-difluoro-2-hydroxy-3-(1H-tetrazol-1-yl) propyl) pyridin-3-yl) phenyl) piperazin-1-yl)-1H-benzo [d] imidazol-2-yl)pentan-2-ol (71)

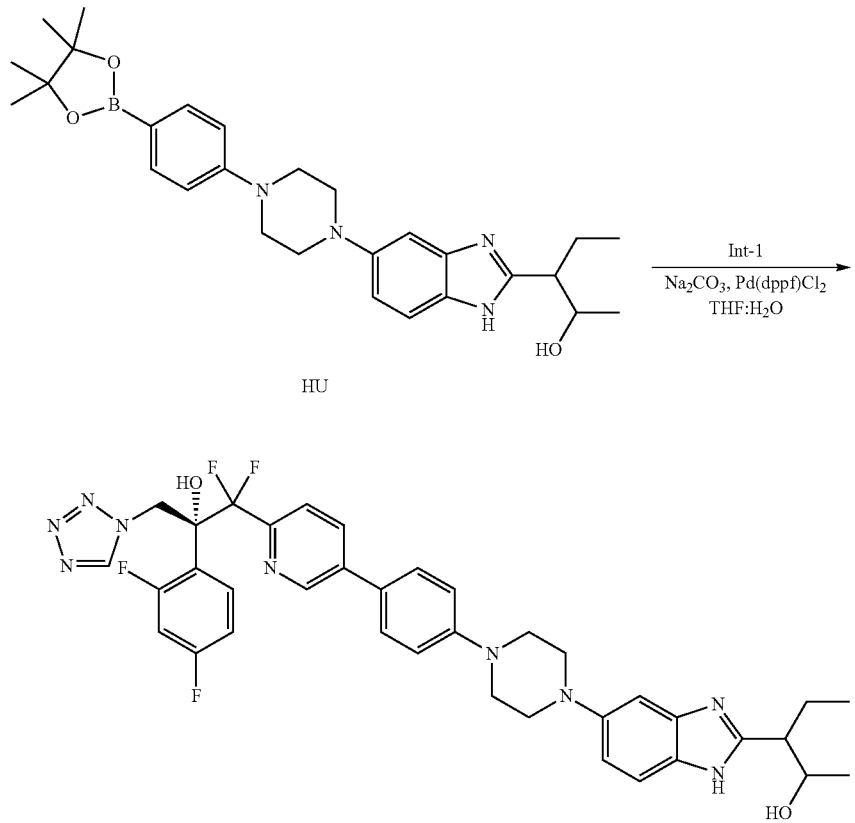

To a stirred solution of Int-1 (150 mg, 0.34 mmol) in THF:H2O (9:1, 30 mL) under argon atmosphere were added compound HU (186 mg, 0.38 mmol), sodium carbonate (110 mg, 1.04 mmol) and purged under argon for 15 min at RT. Then Pd(dppf)Cl$_2$ (38 mg, 0.05 mmol) was added and the reaction mixture was purged under argon for 10 min at RT. The reaction mixture was stirred at 80° C. for 16 h. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 5% MeOH/CH$_2$Cl$_2$) to afford 71 (75 mg, 0.10 mmol, 31%) as an off-white solid. $^1$H NMR (400 MHz, DMSO-d$_6$): δ 9.35 (s, 1H), 9.15 (s, 1H), 8.91 (s, 1H), 8.17 (dd, J=8.3, 2.1 Hz, 1H), 7.70 (d, J=8.9 Hz, 2H), 7.48 (d, J=8.6 Hz, 1H), 7.30-7.10 (m, 5H), 6.94-6.88 (m, 1H), 6.79 (d, J=7.5 Hz, 1H), 6.63-6.60 (m, 1H), 6.55 (s, 1H), 5.67 (d, J=15.0 Hz, 1H), 5.11 (d, J=15.0 Hz, 1H), 4.93-4.91 (m, 1H), 3.74-3.70 (m, 1H), 3.35-3.30 (m, 4H), 3.13-3.05 (m, 4H), 2.43-2.40 (m, 1H), 1.69-1.60 (m, 1H), 1.20-1.10 (m, 1H), 1.01 (d, J=5.4 Hz, 3H), 0.75 (t, J=6.8 Hz, 3H); MS (ESI): m/z 716.6 [M+H]$^+$; HPLC: 95.48%; Optical rotation [α]$_D^{25}$: +19.2 (c=0.1% in MeOH).

Example 72

(R)-2-(2,4-difluorophenyl)-1,1-difluoro-1-(5-(4-(4-(4-(2-hydroxypropan-2-yl) phenyl) piperazin-1-yl) phenyl) pyridin-2-yl)-3-(1H-tetrazol-1-yl) propan-2-ol (72)

2-(4-(4-(4-bromophenyl) piperazin-1-yl) phenyl) propan-2-ol (HV)

The same general procedure used for compound EK was used to synthesize compound HV (280 mg, 0.75 mmol, 89%) as yellow solid. $^1$H NMR (500 MHz, CDCl$_3$): δ 7.41 (d, J=8.7 Hz, 2H), 7.36 (d, J=9.0 Hz, 2H), 6.94 (d, J=8.7 Hz, 2H), 6.84 (d, J=9.0 Hz, 2H), 3.52-3.49 (m, 1H), 3.35-3.20 (m, 8H), 1.54 (s, 6H).

321

2-(4-(4-(4-(4,4,5,5-tetramethyl-1,3,2-dioxaborolan-2-yl) phenyl) piperazin-1-yl) phenyl) propan-2-ol (HW)

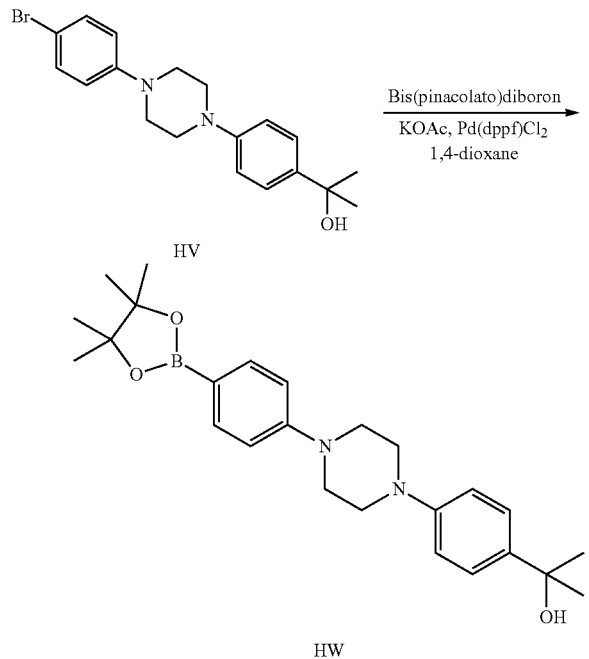

To a stirred solution of compound HV (280 mg, 0.74 mmol) in 1,4-dioxane (15 mL) under argon atmosphere were added bis(pinacolato)diboron (303 mg, 1.19 mmol), KOAc (219 mg, 2.23 mmol) at RT and purged under argon for 15 min. Then Pd(dppf)Cl$_2$ (54.5 mg, 0.07 mmol) was added to the reaction mixture at RT and again purged under argon for 5 min at RT, stirred at 90° C. for 16 h in a sealed tube. The progress of the reaction was monitored by TLC, the reaction mixture was diluted with water (30 mL) and extracted with EtOAc (2×30 mL). The combined organic extracts were washed with water (30 mL), brine (30 mL), dried over anhydrous Na$_2$SO$_4$ and concentrated under reduced pressure. The crude material was purified by silica gel column chromatography (eluent: 40% EtOAc/Hexane) to afford compound HW (280 mg, 0.66 mmol, 88%) as an off-white solid. $^1$H NMR (400 MHz, CDCl$_3$): δ 7.73 (d, J=8.8 Hz, 2H), 7.41 (d, J=8.9 Hz, 2H), 6.94 (dd, J=8.8, 2.4 Hz, 4H), 3.45-3.39 (m, 4H), 3.36-3.28 (m, 4H), 1.57 (s, 6H), 1.33 (s, 12H).

(R)-2-(2,4-difluorophenyl)-1,1-difluoro-1-(5-(4-(4-(4-(2-hydroxypropan-2-yl) phenyl) piperazin-1-yl) phenyl) pyridin-2-yl)-3-(1H-tetrazol-1-yl) propan-2-ol (72)

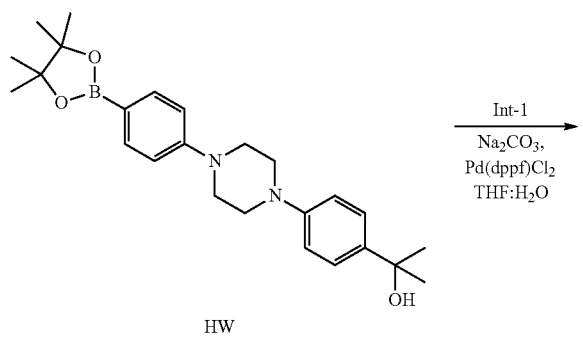

322

-continued

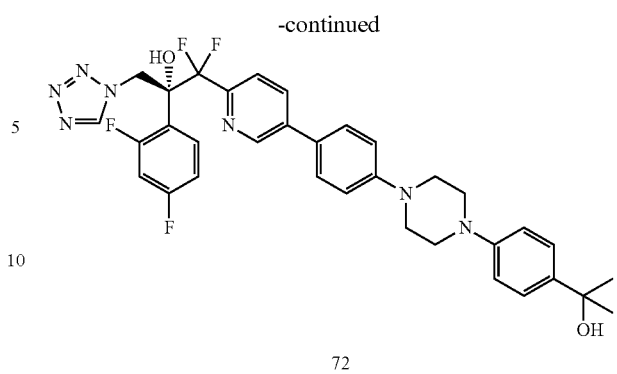

72

To a stirred solution of Int-1 (130 mg, 0.30 mmol) in THF:H2O (4:2, 10 mL) under argon atmosphere were added compound HW (152 mg, 0.36 mmol), sodium carbonate (95 mg, 0.90 mmol) at RT and purged under argon for 10 min. Then Pd(dppf)Cl$_2$ (22 mg, 0.03 mmol) was added to the reaction mixture at RT and stirred at 80° C. for 4 h in a sealed tube. The progress of the reaction was monitored by TLC, the reaction mixture was diluted with water (10 mL) and extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluent: 20% EtOAc/Hexane) which was further purified by preparative HPLC to afford 72 (14 mg, 0.12 mmol, 34%) as an off-white solid. $^1$H NMR (400 MHz, CDCl$_3$): δ 8.76 (s, 1H), 8.73 (d, J=2.1 Hz, 1H), 7.94 (dd, J=2.3, 8.3 Hz, 1H), 7.87 (s, 1H), 7.60 (d, J=8.3 Hz, 1H), 7.51 (d, J=8.9 Hz, 2H), 7.43 (d, J=8.9 Hz, 1H), 7.40-7.31 (m, 2H), 7.06 (d, J=8.9 Hz, 2H), 6.96 (d, J=8.9 Hz, 2H), 6.81-6.73 (m, 1H), 6.70-6.61 (m, 1H), 5.62 (d, J=14.2 Hz, 1H), 5.10 (d, J=14.2 Hz, 1H), 3.48-3.41 (m, 4H), 3.39-3.34 (m, 4H), 1.58 (s, 3H), 1.55 (s, 3H). MS (ESI): m/z 648.5 [M+H]$^+$; HPLC: 91.43%; Optical rotation [α]$_D^{20}$: +133.6 (c=0.1% in CH$_2$Cl$_2$).

Example 73

(R)-2-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) benzo [d] thiazole-6-carbonitrile (73)

2-mercaptobenzo [d] thiazole-6-carbonitrile (HY)

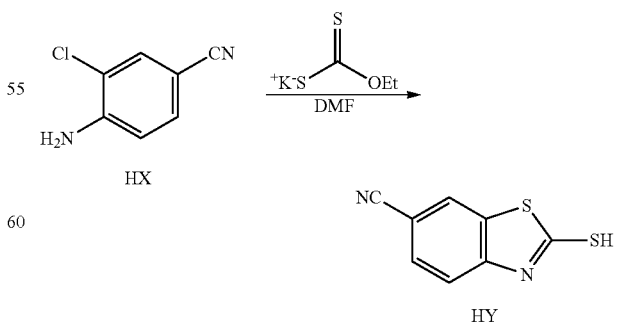

To a stirred solution of 4-amino-3-chlorobenzonitrile (HX, 1.0 g, 6.55 mmol) in DMF (20 mL) under argon atmosphere was added potassium O-ethylcarbonodithioate (2.62 g, 16.38 mmol)) at RT. The reaction mixture was stirred at 110° C. for 16 h. The reaction mixture was diluted water (30 mL) and acidified using IV HCl to pH=2, to obtain the solid. The solid was filtered, washed with Hexane (2×20 mL) and dried under reduced pressure to obtain compound HY (700 mg, 3.64 mmol, 56%) as yellow solid. $^1$H NMR (500 MHz, DMSO-d$_6$): δ 14.13 (br s, 1H), 8.24 (s, 1H), 7.83 (dd, J=8.1, 1.2 Hz, 1H), 7.41 (d, J=8.1 Hz, 1H).

2-chlorobenzo [d] thiazole-6-carbonitrile (HZ)

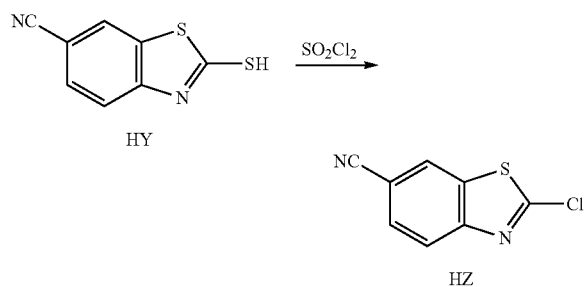

The mixture of compound HY (2.1 g, 10.93 mmol) in SO$_2$Cl$_2$ (20 mL) under argon atmosphere was stirred at RT for 1 h. The reaction mixture was stirred at 60° C. for 1 h. The progress of the reaction was monitored by TLC. The reaction mixture was diluted with ice cold water (50 mL), to obtain the solid. The solid was filtered. The crude material was purified by silica gel column chromatography (eluent: 10-20% EtOAc/Hexane) to afford compound HZ (600 mg, 3.08 mmol, 28%) as an off-white solid. $^1$H NMR (500 MHz, DMSO-d$_6$): δ 8.70 (s, 1H), 7.15 (d, J=8.5 Hz, 1H), 7.98 (dd, J=8.5, 1.7 Hz, 1H).

2-(4-(4-bromophenyl) piperazin-1-yl) benzo [d] thiazole-6-carbonitrile (IA)

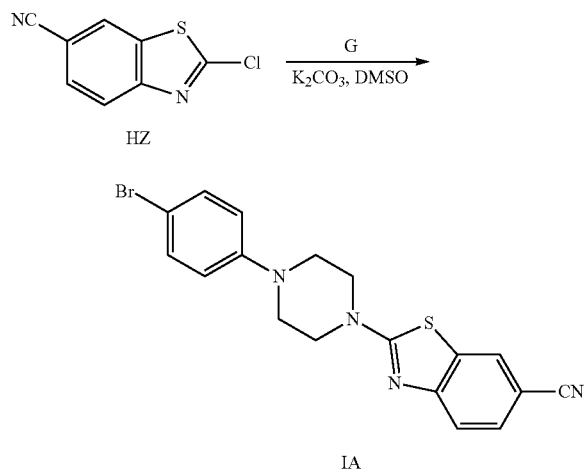

To a stirred solution of compound HZ (600 mg, 3.08 mmol) in DMSO (15 mL) under argon atmosphere were added potassium carbonate (1.28 g, 9.25 mmol) and G (743 mg, 3.08 mmol) at RT. The reaction mixture was stirred at 120° C. for 16 h. The reaction mixture was quenched with ice cold water (30 mL), to obtain the solid. The solid was filtered. The crude material was purified by silica gel column chromatography (eluent: 10-40% EtOAc/Hexane) to afford compound IA (800 mg, 2.0 mmol, 65%) as an off-white solid. $^1$H NMR (400 MHz, DMSO-d$_6$): δ 8.33 (s, 1H), 7.69 (dd, J=8.4, 1.8 Hz, 1H), 7.55 (d, J=8.4 Hz, 1H), 7.39 (d, J=9.0 Hz, 2H), 6.96 (d, J=9.2 Hz, 2H), 3.81-3.74 (m, 4H), 3.31-3.34 (m, 4H).

2-(4-(4-(4,4,5,5-tetramethyl-1,3,2-dioxaborolan-2-yl) phe yl) piperazin-1-yl) benzo [d]thiazole-6-carbonitrile (IB)

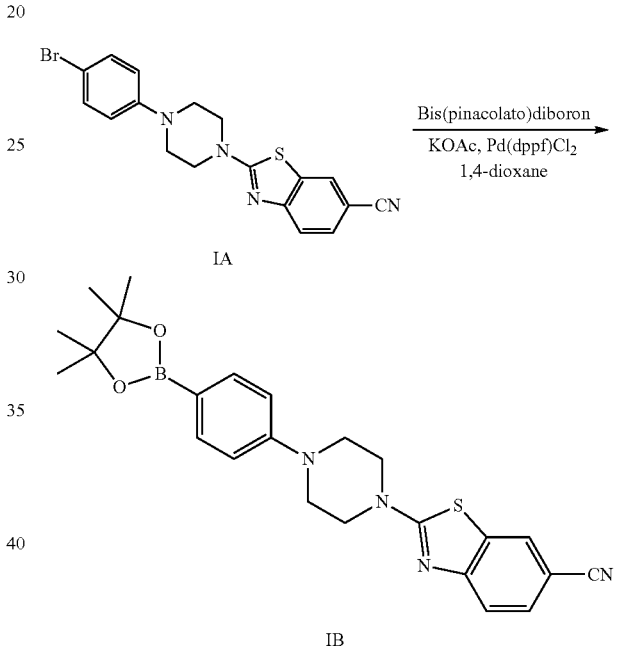

To a stirred solution of compound IA (400 mg, 1.02 mmol) in 1,4-dioxane (40 mL) under argon atmosphere were added bis(pinacolato)diboron (407 mg, 1.60 mmol) and potassium acetate (285 mg, 3.00 mmol) at RT. The reaction mixture was purged with argon for 20 min, then Pd(dppf)Cl$_2$ (75 mg, 0.10 mmol) was added and the reaction mixture was purged under argon for 5 min at RT. The reaction mixture was stirred at 110° C. for 12 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 10-20% EtOAc/Hexane) to afford compound IB (350 mg, 0.78 mmol, 79%) as an off-white solid. $^1$H NMR (400 MHz, DMSO-d$_6$): δ 8.34 (s, 1H), 7.69 (dd, J=8.4, 1.6 Hz, 1H), 7.55 (dd, J=8.5, 1.5 Hz, 3H), 6.97 (d, J=8.8 Hz, 2H), 3.81-3.75 (m, 4H), 3.48-3.36 (m, 4H), 1.27 (s, 12H).

(R)-2-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) benzo [d] thiazole-6-carbonitrile (73)

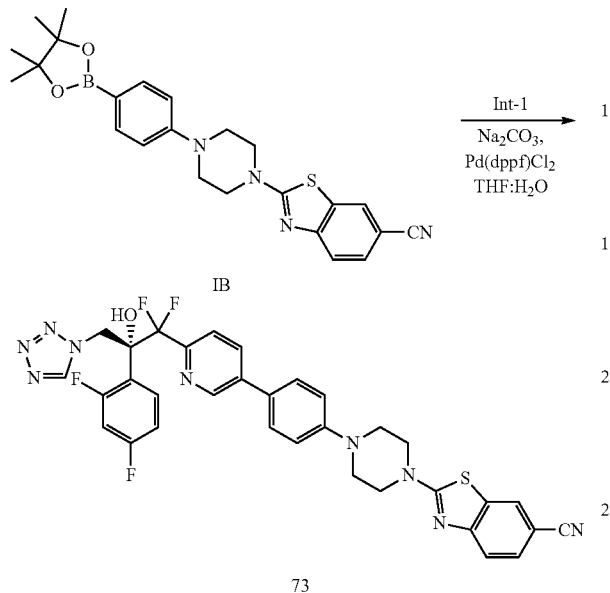

To a stirred solution of Int-1 (150 mg, 0.36 mmol) in THF:H2O (4:1, 28:7 mL) under argon atmosphere were added compound IB (170 mg, 0.38 mmol), sodium carbonate (110 mg, 1.04 mmol) and purged under argon for 15 min at RT. Then Pd(dppf)Cl$_2$ (25 mg, 0.03 mmol) was added and the reaction mixture was purged under argon for 10 min at RT. The reaction mixture was stirred at 70° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 50% EtOAc/Hexane) to afford 73 (70 mg, 0.10 mmol, 30%) as an off-white solid. $^1$H NMR (500 MHz, DMSO-d$_6$): δ 9.13 (s, 1H), 8.90 (d, J=2.0 Hz, 1H), 8.33 (d, J=1.7 Hz, 1H), 8.16 (dd, J=8.2, 2.2 Hz, 1H), 7.73-7.64 (m, 3H), 7.55 (d, J=8.4 Hz, 1H), 7.47 (d, J=8.4 Hz, 1H), 7.31-7.23 (m, 2H), 7.18-1.76 (m, 1H), 7.12 (d, J=8.7 Hz, 2H), 6.91-6.87 (m, 1H), 5.65 (d, J=14.7 Hz, 1H), 5.10 (d, J=14.7 Hz, 1H), 3.84-3.76 (m, 4H), 3.47-3.41 (m, 4H); MS (ESI): m/z 670.4 [M–H]$^-$; HPLC: 96.96%; Optical rotation $[α]_D^{26}$: +42.5 (c=0.1% in CH$_2$Cl$_2$).

Example 74

(R)-2-(4-(4-(6-(2-(2,4-difluorophenyl)-1,1-difluoro-2-hydroxy-3-(1H-tetrazol-1-yl) propyl) pyridin-3-yl) phenyl) piperazin-1-yl)-1H-benzo [d] imidazole-6-carbonitrile (74)

2-oxo-2,3-dihydro-1H-benzo [d] imidazole-5-carbonitrile (ID)

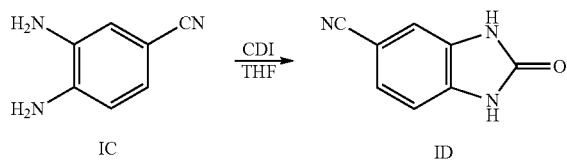

To a stirred solution of 3,4-diaminobenzonitrile (IC; 200 mg, 1.5 mmol) in THF (10 mL) under argon atmosphere was added carbonyl diimidazole (243 mg, 1.5 mmol) at RT and stirred for 16 h. The volatiles were concentrated under reduced pressure. The crude material was purified by silica gel column chromatography (eluent: 40% Acetone/Hexane) to afford compound ID (60 mg, 0.37 mmol, 24%) as an off-white solid. $^1$H NMR (400 MHz, DMSO-d$_6$): δ 11.16 (br s, 1H), 11.04 (br s, 1H), 7.39 (dd, J=8.1, 1.6 Hz, 1H), 7.30 (s, 1H), 7.06 (d, J=8.2 Hz, 1H).

2-chloro-1H-benzo [d] imidazole-6-carbonitrile (IE)

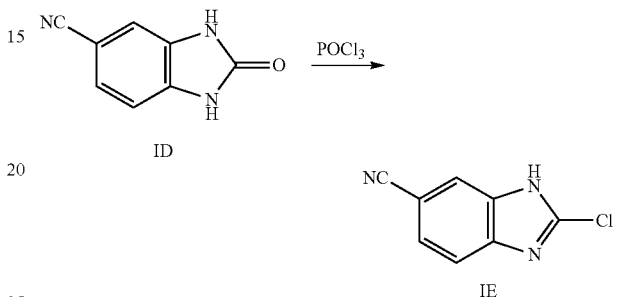

To a stirred solution of compound ID (500 mg, 3.14 mmol) in POCl$_3$ (2 mL) under argon atmosphere was stirred at 120° C. for 2 h. The reaction mixture was diluted with ice cold water (50 mL), saturated sodium bicarbonate solution (30 mL) up to pH=7 and extracted with EtOAc (2×10 mL). The combined organic extracts were dried over anhydrous Na$_2$SO$_4$ and concentrated under reduced pressure. The crude material was purified by silica gel column chromatography (eluent: 40% acetone/Hexane) to afford compound IE (160 mg, 0.90 mmol, 28%) as an off-white solid. $^1$H NMR (400 MHz, DMSO-d$_6$): δ 13.88 (br s, 1H), 8.10 (s, 1H), 7.70-7.67 (m, 1H), 7.65-7.61 (m, 1H).

2-(4-(4-bromophenyl) piperazin-1-yl)-1H-benzo [d] imidazole-6-carbonitrile (IF)

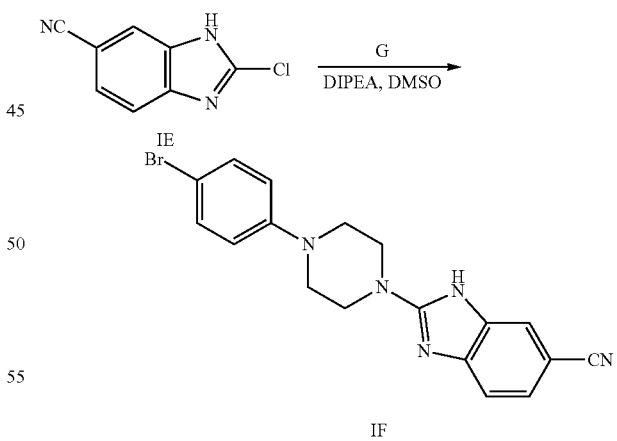

To a stirred solution of compound IE (160 mg, 0.90 mmol) in DMSO (5 mL) under argon atmosphere was added diisopropyl ethylamine (0.6 mL, 3.50 mmol) and G (323 mg, 1.34 mmol) at RT. The reaction mixture was stirred at 80° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure to obtain compound IF (160 mg, crude) as a brown solid. $^1$H NMR (400 MHz, DMSO-d$_6$): δ 12.08-

11.82 (m, 1H), 7.69-7.52 (m, 1H), 7.41-7.30 (m, 4H), 6.98 (d, J=9.2 Hz, 2H), 3.72-3.67 (m, 4H), 3.30-3.27 (m, 4H).

2-(4-(4-(4,4,5,5-tetramethyl-1,3,2-dioxaborolan-2-yl) phenyl) piperazin-1-yl)-1H-benzo [d] imidazole-6-carbonitrile (IG)

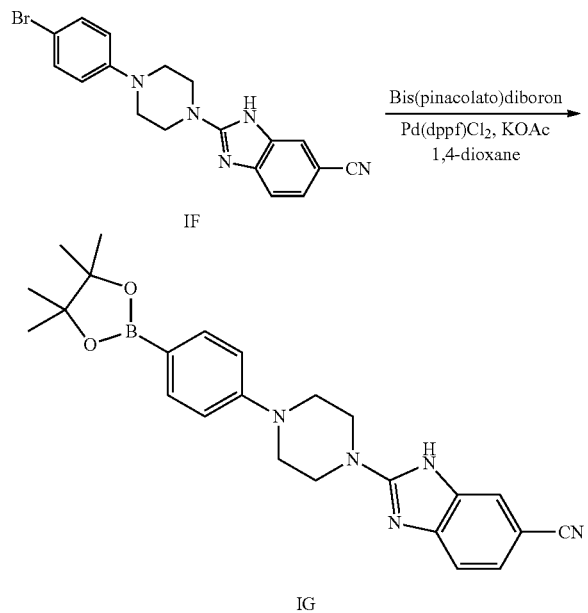

To a stirred solution of compound IF (300 mg, 0.78 mmol) in 1,4-dioxane (20 mL) under argon atmosphere were added bis(pinacolato)diboron (317 mg, 1.25 mmol) and potassium acetate (230 mg, 2.34 mmol) at RT and purged under argon for 15 min. Then Pd(dppf)Cl$_2$ (57 mg, 0.08 mmol) was added and the reaction mixture was purged under argon for 5 min at RT. The reaction mixture was stirred at 110° C. for 16 h. The reaction mixture was quenched with water (10 mL) and extracted with EtOAc (2×10 mL). The combined organic layers were washed with water (10 mL), brine (10 mL), dried over anhydrous Na$_2$SO$_4$ and concentrated under reduced pressure to obtain compound IG (200 mg, crude) as an off-white solid. $^1$H NMR (500 MHz, CDCl$_3$) δ 8.51 (br s, 2H), 7.74 (d, J=8.7 Hz, 2H), 7.51-7.38 (m, 2H), 6.93 (d, J=8.7 Hz, 2H), 3.76 (br s, 4H), 3.45-3.41 (m, 4H), 1.33 (s, 12H).

(R)-2-(4-(4-(6-(2-(2,4-difluorophenyl)-1,1-difluoro-2-hydroxy-3-(1H-tetrazol-1-yl) propyl) pyridin-3-yl) phenyl) piperazin-1-yl)-1H-benzo [d] imidazole-6-carbonitrile (74)

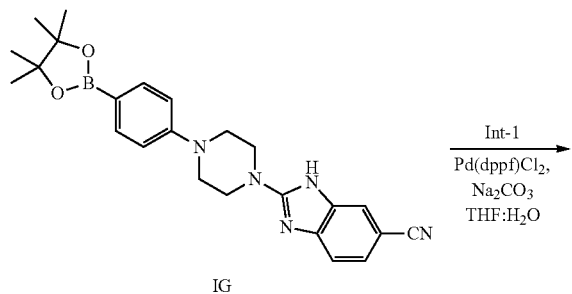

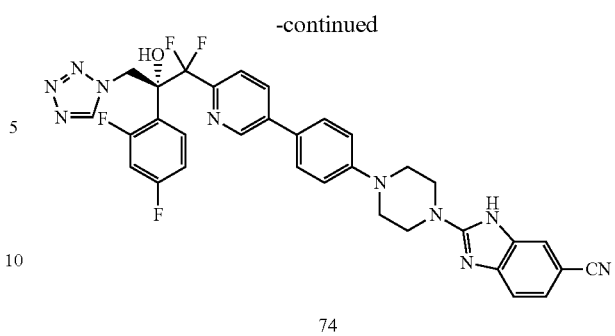

To a stirred solution of Int-1 (200 mg, 0.46 mmol) in THF:H2O (4:1, 20 mL) under argon atmosphere were added compound IG (201 ng, 0.46 mmol), sodium carbonate (148 mg, 1.4 mmol) and purged under argon for 10 min at RT. Then Pd(dppf)Cl$_2$ (34 mg, 0.05 mmol) was added to the reaction mixture at RT and stirred at 90° C. for 6 h. The progress of the reaction was monitored by TLC. The reaction mixture was diluted with water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 50% acetone/Hexane) to afford 74 (90 mg, 0.13 mmol, 28%) as an off-white solid. $^1$H NMR (500 MHz, DMSO-d$_6$): δ 12.08-11.86 (m, 1H), 9.13 (s, 1H), 8.90 (s, 1H), 8.16 (dd, J=8.2, 1.9 Hz, 1H), 7.69 (d, J=8.7 Hz, 2H), 7.63-7.55 (m, 1H), 7.47 (d, J=8.4 Hz, 1H), 7.39-7.24 (m, 4H), 7.21-7.11 (m, 3H), 6.93-6.87 (m, 1H), 5.65 (d, J=14.7 Hz, 1H), 5.10 (d, J=14.7 Hz, 1H), 3.78-3.64 (m, 4H), 3.46-3.35 (m, 4H); MS (ESI): m/z 655.6 [M+H]$^+$; HPLC: 98.37%; Optical rotation $[\alpha]_D^{25}$: +18.3 (c=0.1% in MeOH).

Example 75

4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-(3-hydroxybutan-2-yl)-2,4-dihydro-3H-1,2,4-triazol-3-one (75)

3-bromobutan-2-one (II)

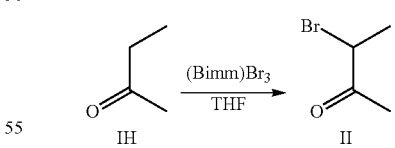

The mixture of butan-2-one (IH; 600 mg, 8.33 mmol) and [BIMM] Br$_3$ (1.57 g, 4.16 mmol) in THF (10 mL) under argon atmosphere was stirred at 0° C., and for 30 min. The progress of the reaction was monitored by TLC. The reaction mixture was quenched with water (20 mL) and extracted with ether (2×20 mL). The combined organic extracts were washed with water (20 mL), brine (10 mL), dried over anhydrous Na$_2$SO$_4$ and concentrated under reduced pressure to obtain compound II (500 mg, crude) as colorless syrup used in the next step without further purification.

4-(4-(4-(4-bromophenyl) piperazin-1-yl) phenyl)-2-(3-oxobutan-2-yl)-2,4-dihydro-3H-1,2,4-triazol-3-one (IJ)

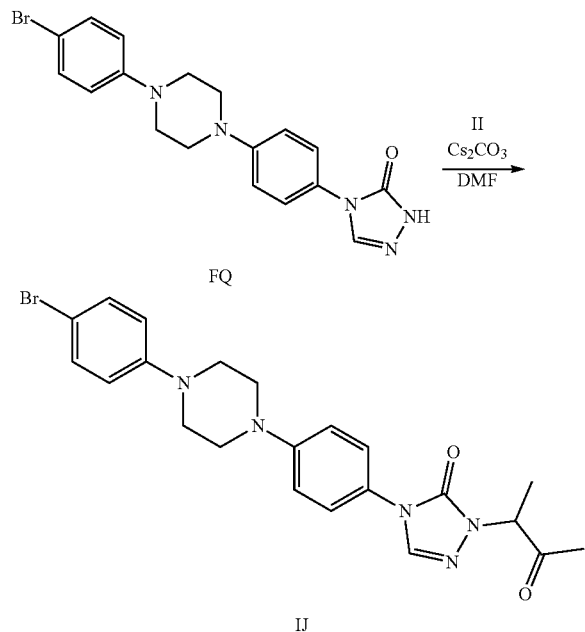

To a stirred solution of compound FQ (300 mg, 0.75 mmol) in DMF (5 mL) under argon atmosphere were added compound II (500 mg, crude) and cesium carbonate (734 mg, 2.25 mmol) at 0° C. The reaction mixture was warmed to RT and stirred for 3 h. The progress of the reaction was monitored by TLC. The reaction mixture was diluted with ice cold water (20 mL) and extracted with EtOAc (2×20 mL). The combined organic extracts were dried over anhydrous $Na_2SO_4$ and concentrated under reduced pressure. The crude material was purified by silica gel column chromatography (eluent: 1-2% $MeOH/CH_2Cl_2$) to afford compound IJ (300 mg, 0.63 mmol, 85%) as an off-white solid. $^1H$ NMR (500 MHz, DMSO-$d_6$): δ 8.42 (s, 1H), 7.52 (d, J=9.0 Hz, 2H), 7.38 (d, J=9.0 Hz, 2H), 7.12 (d, J=9.3 Hz, 2H), 6.97 (d, J=9.0 Hz, 2H), 4.92-4.88 (m, 1H), 3.37-3.26 (m, 8H), 2.10 (s, 3H), 1.47 (d, J=7.2 Hz, 3H).

4-(4-(4-(4-bromophenyl) piperazin-1-yl) phenyl)-2-(3-hydroxybutan-2-yl)-2,4-dihydro-3H-1,2,4-triazol-3-one (IK)

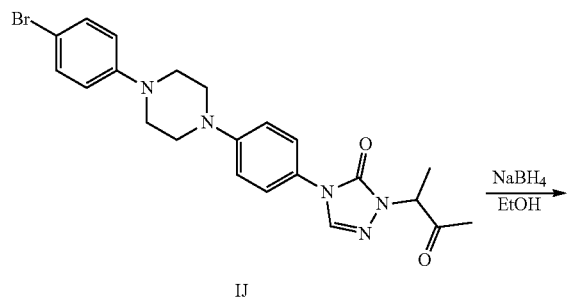

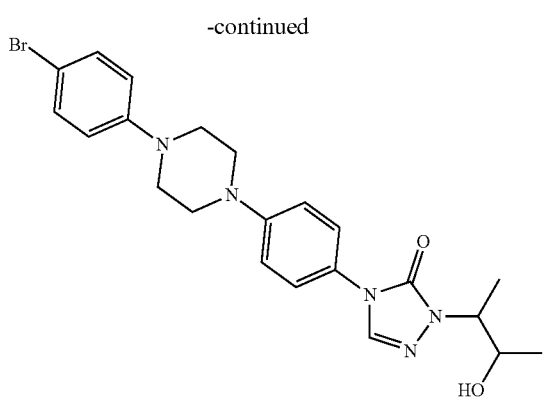

To a stirred solution of compound IJ (250 mg, 0.53 mmol) in EtOH (10 mL) under argon atmosphere was added sodium borohydride (40 mg, 1.06 mmol) at 0° C. The reaction mixture was warmed to RT and stirred for 4 h. The progress of the reaction was monitored by TLC. The volatiles were evaporated and the residue was diluted with water (20 mL) and extracted with EtOAc (2×20 mL). The combined organic extracts were washed with water (20 mL), brine (20 mL), dried over anhydrous $Na_2SO_4$ and concentrated under reduced pressure to afford compound IK (250 mg, 0.53 mmol, 99%) as an off-white solid which was used in the next step without further purification.

2-(3-hydroxybutan-2-yl)-4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (IL)

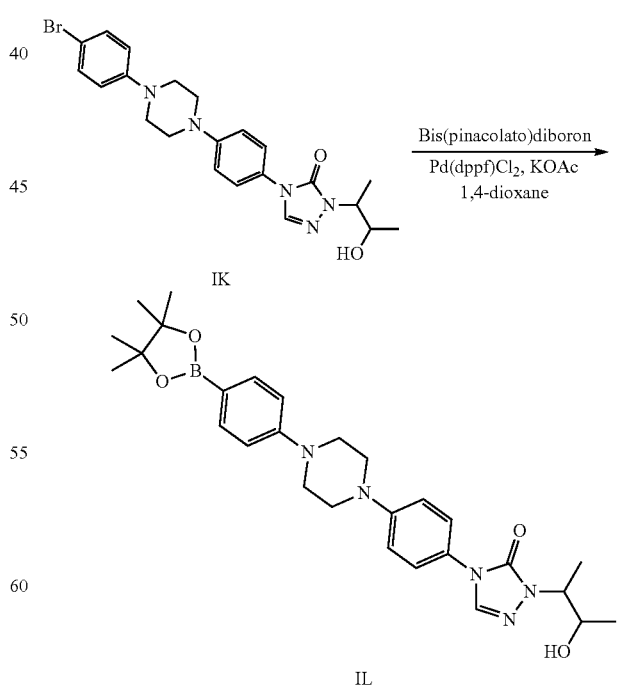

To a stirred solution of compound IK (250 mg, 0.42 mmol) in 1,4-dioxane (10 mL) under argon atmosphere were added bis(pinacolato)diboron (172 mg, 0.67 mmol) and potassium acetate (124 mg, 1.26 mmol) at RT. The reaction mixture was purged with argon for 20 min, then Pd(dppf)Cl$_2$ (31 mg, 0.04 mmol) was added and the reaction mixture was purged under argon for 5 min at RT. The reaction mixture was stirred at 90° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 1-2% MeOH/CH$_2$Cl$_2$) to afford compound IL (220 mg, 0.42 mmol, 80%) as a brown solid. $^1$H NMR (400 MHz, DMSO-d$_6$): δ 8.31 (d, J=8.8 Hz, 1H), 7.54 (d, J=8.7 Hz, 2H), 7.50 (dd, J=9.1, 2.9 Hz, 2H), 7.10 (d, J=9.2 Hz, 2H), 6.98 (d, J=8.8 Hz, 2H), 4.90-4.70 (m, 1H), 4.05-4.00 (m, 1H), 3.84-3.76 (m, 1H), 3.46-3.31 (m, 8H), 1.27 (s, 12H), 1.18-1.15 (m, 6H).

4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl-2-(3-hydroxybutan-2-yl)-2,4-dihydro-3H-1,2,4-triazol-3-one (75)

To a stirred solution of Int-1 (150 mg, 0.35 mmol) in THF:H2O (4:1, 15 mL) under argon atmosphere were added compound IL (216 mg, 0.41 mmol), sodium carbonate (110 mg, 1.04 mmol) and purged under argon for 15 min at RT. Then Pd(dppf)Cl$_2$ (25.3 mg, 0.03 mmol) was added and the reaction mixture was purged under argon for 10 min at RT. The reaction mixture was stirred at 70° C. for 16 h. The reaction mixture was filtered, the filtrate was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 1-2% MeOH/CH$_2$Cl$_2$) followed by preparative HPLC to afford 75 (57.3 mg, 0.07 mmol, 22%) as an off-white solid. $^1$H NMR (400 MHz, DMSO-d$_6$): δ 9.15 (s, 1H), 8.91 (d, J=2.1 Hz, 1H), 8.32 (d, J=8.8 Hz, 1H), 8.17 (dd, J=8.4, 2.3 Hz, 1H), 7.70 (d, J=9.0 Hz, 2H), 7.55-7.39 (m, 3H), 7.33-7.25 (m, 3H), 7.23-7.14 (m, 4H), 6.93-6.88 (m, 1H), 5.67 (d, J=14.6 Hz, 1H), 5.11 (d, J=14.6 Hz, 1H), 4.88 (d, J=5.9 Hz, 0.44H), 4.70 (d, J=5.9 Hz, 0.62H), 4.07-3.90 (m, 1H), 3.85-3.74 (m, 1H), 3.44-3.34 (m, 8H), 1.34 (d, J=6.8 Hz, 2H), 1.26-1.22 (m, 1H), 1.11 (d, J=6.3 Hz, 2H), 0.97 (d, J=6.3 Hz, 1H); MS (ESI): m/z 745.2 [M+H]$^+$; HPLC: 99.39%; Optical rotation [α]$_D^{26}$: +13.6 (c=0.1% in MeOH).

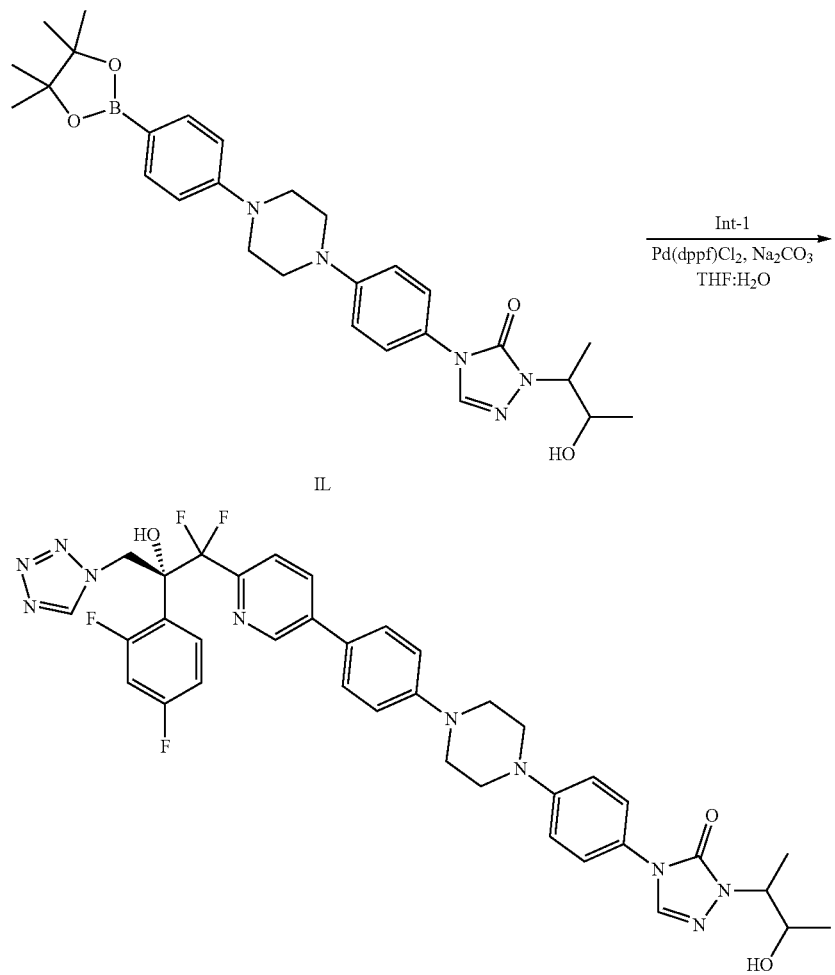

Example 76

(R)-2-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) benzo [d] thiazole-5-carbonitrile (76)

2-mercaptobenzo [d] thiazole-5-carbonitrile (IN)

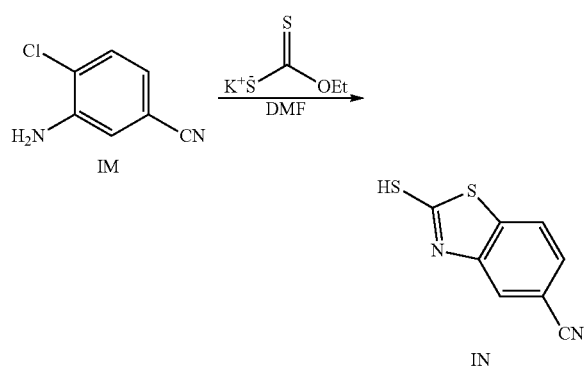

To a stirred solution of compound IM (1.0 g, 6.57 mmol) in DMF (20 mL) under argon atmosphere was added potassium ethyl xanthate (2.6 g, 16.44 mmol) at RT. The reaction mixture was heated to 110° C. for 12 h. The progress of the reaction was monitored by TLC. The reaction mixture was acidified with 1N HCl solution (50 mL) to pH-2 to get the solid. The solid was filtered, washed with n-hexane (2×20 mL) and dried under reduced pressure to obtain compound IN (1.0 g, 5.20 mmol, 80%) as a brown solid. $^1$H NMR (400 MHz, CDCl$_3$): δ 10.03 (brs, 1H), 7.55 (s, 2H), 7.48 (s, 1H).

2-chlorobenzo [d] thiazole-5-carbonitrile (IO)

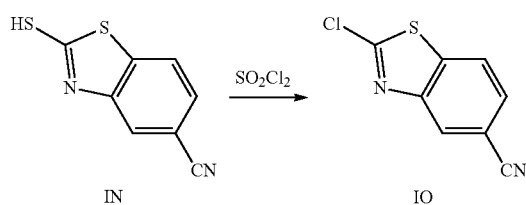

To a stirred solution of compound IN (800 mg, 0.52 mmol) in SO$_2$Cl$_2$ (3 mL) under argon atmosphere was stirred at RT for 1 h. Then the reaction mixture was heated to 60° C. for 1 h. The progress of the reaction was monitored by TLC. The reaction mixture was quenched with ice cold water (20 mL) to obtain the solid. The solid was filtered, washed with n-hexane (2×20 mL) and dried under reduced pressure to obtain compound IO (800 mg, 4.12 mmol, 79%) as a brown solid.

2-(4-(4-bromophenyl) piperazin-1-yl) benzo [d] thiazole-5-carbonitrile (IP)

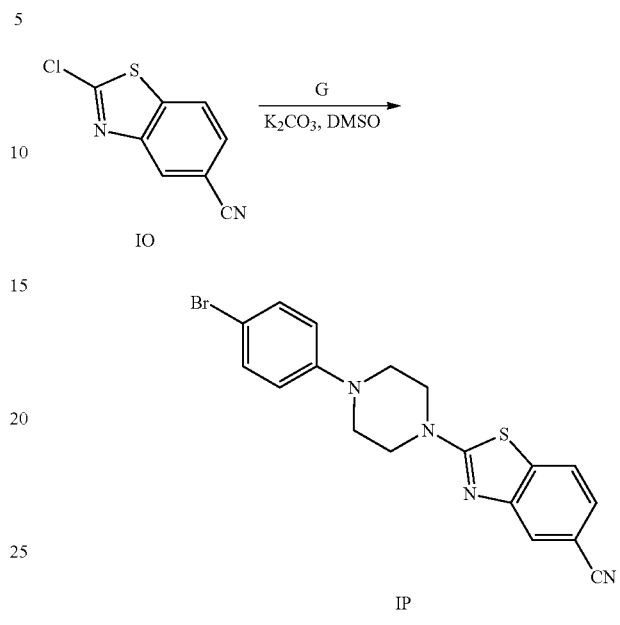

To a stirred solution of G (800 mg, 4.12 mmol) in DMSO (20 mL) under argon atmosphere were added potassium carbonate (1.7 g, 12.37 mmol) and compound IO (993 mg, 4.12 mmol) at RT. The reaction mixture was stirred at 110° C. for 12 h. The progress of the reaction was monitored by TLC. The reaction mixture was quenched with ice cold water (20 mL) and extracted with CH$_2$Cl$_2$ (2×20 mL). The combined organic layers were dried over anhydrous Na$_2$SO$_4$ and concentrated under reduced pressure. The crude material was purified by silica gel column chromatography (eluent: 2% MeOH/CH$_2$Cl$_2$) to afford compound IP (450 mg, 1.13 mmol, 46%) as a brown solid. $^1$H NMR (400 MHz, DMSO-d$_6$): δ 8.02 (d, J=8.2 Hz, 1H), 7.88 (s, 1H), 7.47 (dd, J=8.1, 1.6 Hz, 1H), 7.39 (d, J=9.03 Hz, 2H), 6.96 (d, J=9.0 Hz, 2H), 3.78-3.71 (m, 4H), 3.33-3.31 (m, 4H).

2-(4-(4-(4,4,5,5-tetramethyl-1,3,2-dioxaborolan-2-yl) phenyl) piperazin-1-yl) benzo [d]thiazole-5-carbonitrile (IQ)

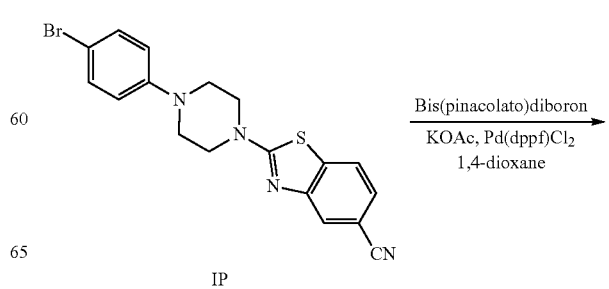

-continued

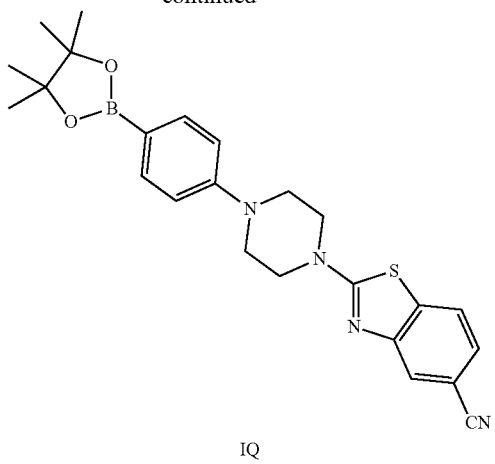

IQ

To a stirred solution of compound IP (500 mg, 1.25 mmol) in 1,4-dioxane (30 mL) under argon atmosphere were added bis(pinacolato)diboron (1.01 g, 4.01 mmol) and potassium acetate (736 mg, 7.51 mmol) at RT. The reaction mixture was purged with argon for 20 min, then Pd(dppf)Cl$_2$ (91.5 mg, 0.12 mmol) was added and the reaction mixture was purged under argon for 5 min at RT. The reaction mixture was stirred at 110° C. for 12 h. The progress of the reaction was monitored by TLC. The reaction mixture was quenched with water (25 mL) and extracted with CH$_2$Cl$_2$ (2×25 mL). The combined organic layers were dried over anhydrous Na$_2$SO$_4$ and concentrated under reduced pressure. The crude material was purified by silica gel column chromatography (eluent: 2% MeOH/CH$_2$Cl$_2$) to afford compound IQ (300 mg, crude) as a brown solid and the obtained material was as such taken for next step without further purification.

(R)-2-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) benzo [d] thiazole-5-carbonitrile (76)

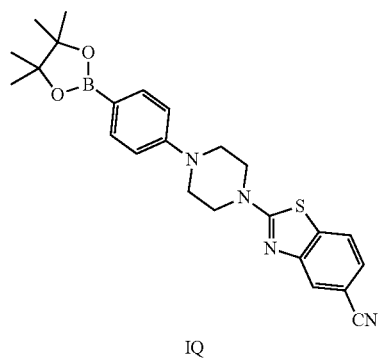

-continued

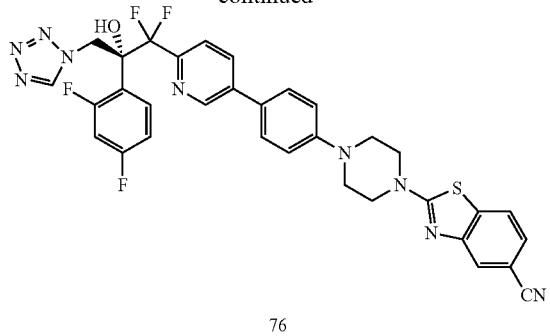

76

To a stirred solution of Int-1 (180 mg, 0.41 mmol) in THF:H2O (4:1, 15 mL) under argon atmosphere were added compound IQ (186 mg, 0.41 mmol), sodium carbonate (132 mg, 1.25 mmol) and purged under argon for 15 min at RT. Then Pd(dppf)Cl$_2$ (30.4 mg, 0.04 mmol) was added and the reaction mixture was purged under argon for 10 min at RT. The reaction mixture was stirred at 90° C. for 12 h. The progress of the reaction was monitored by TLC. The reaction mixture was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 40% EtOAc/Hexane) to afford 76 (55 mg, 0.07 mmol, 20%) as an off-white solid. $^1$H NMR (400 MHz, DMSO-d$_6$): δ 9.15 (s, 1H), 8.91 (d, J=2.1 Hz, 1H), 8.17 (dd, J=8.3, 2.3 Hz, 1H), 8.03 (d, J=8.2 Hz, 1H), 7.89 (d, J=1.3 Hz, 1H), 7.71 (d, J=8.9 Hz, 2H), 7.48 (dd, J=8.2, 1.5 Hz, 2H), 7.35-7.11 (m, 5H), 6.93-6.88 (m, 1H), 5.67 (d, J=14.7 Hz, 1H), 5.11 (d, J=14.7 Hz, 1H), 3.82-3.74 (m, 4H), 3.49-3.38 (m, 4H); MS (ESI): m/z 672.1 [M+H]$^+$; HPLC: 96.54%; Optical rotation [α]$_D^{26}$: +63.1 (c=0.1% in CH$_2$Cl$_2$).

Example 77

(R)-2-(2,4-difluorophenyl)-1,1-difluoro-3-(1H-tetrazol-1-yl)-1-(5-(4-(4-(2-(2,2,2-trifluoroethyl)-1H-benzo [d] imidazol-6-yl) piperazin-1-yl) phenyl) pyridin-2-yl) propan-2-ol (77)

6-(4-(4-bromophenyl) piperazin-1-yl)-2-(2,2,2-trifluoroethyl)-1H-benzo [d] imidazole (IR)

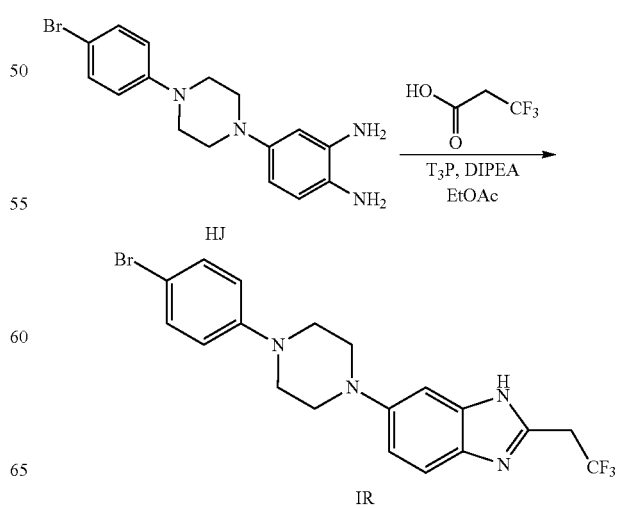

To a stirred solution of compound HJ (500 ng, 1.44 mmol) in EtOAc (10 mL) under argon atmosphere were added 3,3,3-trifluoropropanoic acid (553 mg, 4.32 mmol), $T_3P$ (1.37 mL, 4.32 mmol, in 50% EtOAc) and diisopropyl ethyl amine (0.8 mL, 4.32 mmol) at RT. The reaction mixture was stirred at 120° C. for 2-3 h. The progress of the reaction was monitored by TLC. The reaction mixture was quenched with ice water (20 mL) and extracted with EtOAc (2×20 mL). The combined organic layers were washed with water (20 mL), dried over anhydrous $Na_2SO_4$ and concentrated under reduced pressure to obtain compound IR (350 mg, crude) as yellow solid and the obtained material was as such taken for next step without purification.

6-(4-(4-(4,4,5,5-tetramethyl-1,3,2-dioxaborolan-2-yl) phenyl) piperazin-1-yl)-2-(2,2,2-trifluoroethyl)-1H-benzo [d] indazole (IS)

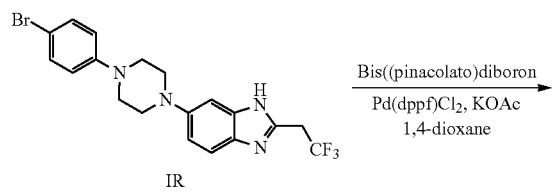

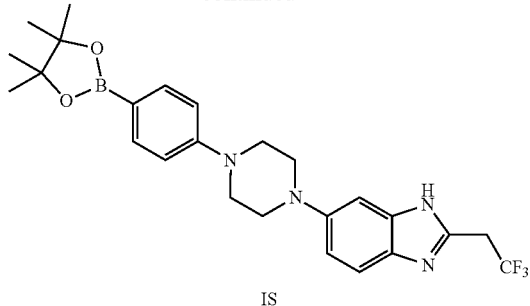

To a stirred solution of compound IR (300 mg, 0.67 mmol) in 1,4-dioxane (20 mL) under argon atmosphere were added bis(pinacolato)diboron (342 mg, 1.35 mmol) and potassium acetate (265 mg, 2.70 mmol) at RT. The reaction mixture was purged with argon for 20 min, then $Pd(dppf)Cl_2$ (74 mg, 0.10 mmol) was added and the reaction mixture was purged under argon for 5 min at RT. The reaction mixture was stirred at 110° C. for 16 h. The reaction mixture was quenched with ice water (20 mL) and extracted with EtOAc (2×20 mL). The combined organic layers were washed with water (20 mL), dried over anhydrous $Na_2SO_4$ and concentrated under reduced pressure to obtain compound IS (120 mg, crude) as red solid. The crude material was used as such in the next step.

(R)-2-(2,4-difluorophenyl)-1,1-difluoro-3-(1H-tetrazol-1-yl)-1-(5-(4-(4-(2-(2,2,2-trifluoroethyl)-1H-benzo [d] imidazol-6-yl) piperazin-1-yl) phenyl) pyridin-2-yl) propan-2-ol (77)

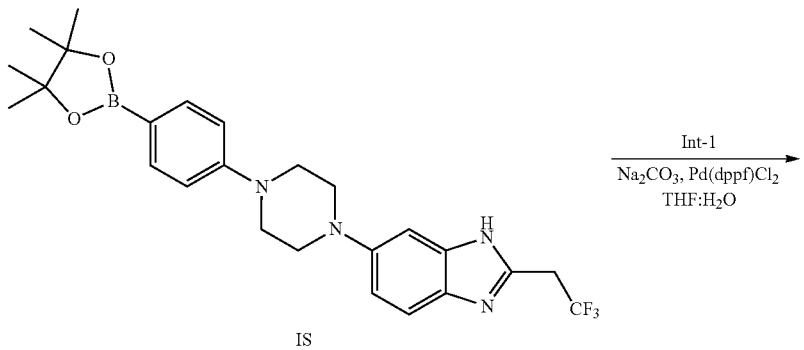

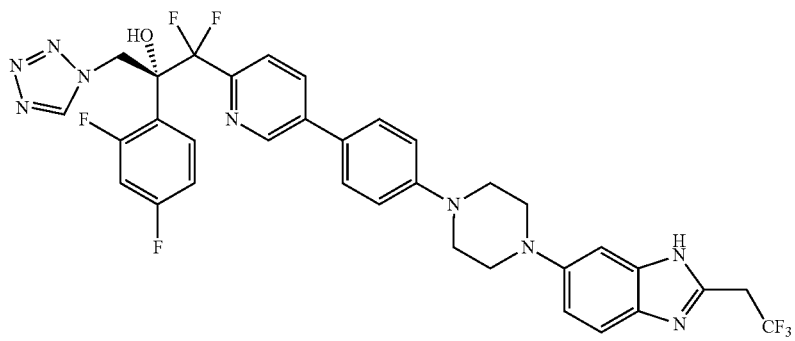

To a stirred solution of Int-1 (130 mg, 0.30 mmol) in THF:H2O (9:1, 20 mL) under argon atmosphere were added compound IS (146 mg, 0.30 mmol), sodium carbonate (95 mg, 0.90 mmol) and purged under argon for 15 min at RT. Then Pd(dppf)Cl$_2$ (32 mg, 0.04 mmol) was added and the reaction mixture was purged under argon for 10 min at RT. The reaction mixture was stirred at 80° C. for 16 h. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) to afford 77 (40 mg, 0.05 mmol, 19%) as yellow solid. $^1$H NMR (400 MHz, CDCl$_3$): δ 8.77 (s, 1H), 8.73 (d, J=2.0 Hz, 1H), 7.95 (dd, J=8.2, 2.2 Hz, 1H), 7.88 (s, 1H), 7.60 (d, J=8.3 Hz, 1H), 7.54-7.51 (m, 3H), 7.40-7.35 (m, 1H), 7.15 (brs, 1H), 7.10-7.07 (m, 3H), 6.80-6.74 (m, 1H), 6.72-6.61 (m, 1H), 5.62 (d, J=14.2 Hz, 1H), 5.11 (d, J=14.2 Hz, 1H), 3.84-3.76 (m, 2H), 3.50-3.44 (m, 4H), 3.38-3.28 (m, 4H); MS (ESI): m/z 712.7 [M+H]$^+$; HPLC: 95.84%; Optical rotation [α]$_D^{26}$: +15.0 (c=0.1% in MeOH).

Example 78

(R)-2-(2,4-difluorophenyl)-1,1-difluoro-1-(5-(4-(4-(2-isobutyl-1H-benzo [d] imidazol-6-yl) piperazin-1-yl) phenyl) pyridin-2-yl)-3-(1H-tetrazol-1-yl) propan-2-ol (78)

6-(4-(4-bromophenyl) piperazin-1-yl)-2-isobutyl-1H-benzo [d] imidazole (IT)

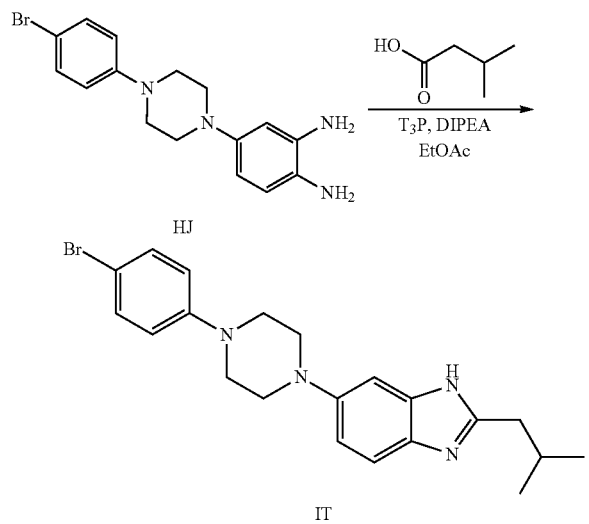

To a stirred solution of compound HJ (500 mg, 1.44 mmol) in EtOAc (10 mL) in a sealed tube under argon atmosphere were added isovaleric acid (0.32 mL, 2.88 mmol), T$_3$P (1.4 mL, 4.32 mmol, 50% in EtOAc) and DIPEA (0.8 mL, 4.32 mmol) at RT. The reaction mixture was stirred at 100° C. for 2 h. The progress of the reaction was monitored by TLC. The reaction mixture was quenched with ammonium chloride solution (20 mL) and extracted with EtOAc (2×20 mL). The combined organic layers were washed with water (10 mL), brine (10 mL), dried over anhydrous Na$_2$SO$_4$ and concentrated under reduced pressure to obtain compound IT (280 mg, crude) as a pale brown solid. $^1$H NMR (400 MHz, DMSO-d$_6$): δ 11.87 (br s, 1H), 7.39-7.35 (m, 2H), 7.18 (br d, J=2.5 Hz, 1H), 6.99-6.88 (m, 3H), 6.85 (dd, J=8.6, 2.6 Hz, 1H), 3.31-3.11 (m, 8H), 2.65 (d, J=7.4 Hz, 2H), 2.34-2.21 (m, 1H), 0.95 (d, J=6.7 Hz, 6H).

2-isobutyl-6-(4-(4-(4,4,5,5-tetramethyl-1,3,2-dioxaborolan-2-yl) phenyl) piperazin-1-yl)-1H-benzo [d] imidazole (IU)

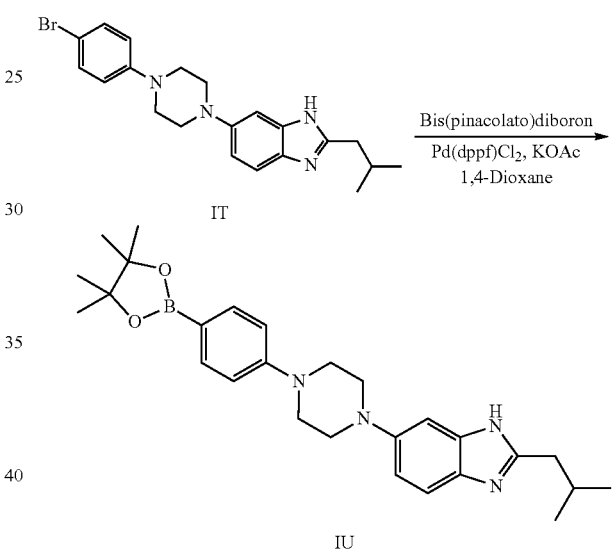

To a stirred solution of compound IT (280 mg, 0.679 mmol) in 1,4-dioxane (10 mL) under argon atmosphere were added bis(pinacolato)diboron (276 mg, 1.08 mmol) and potassium acetate (200 mg, 2.03 mmol) at RT. The reaction mixture was purged with argon for 20 min, then Pd(dppf)Cl$_2$ (5 mg, 0.006 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 3% MeOH/CH$_2$Cl$_2$) to afford compound impure IU (140 mg) as a light brown semi-solid. $^1$H NMR (400 MHz, DMSO-d$_6$): δ 11.91-11.79 (m, 1H), 7.57-7.50 (m, 3H), 7.40-7.34 (m, 1H), 7.31-7.20 (m, 1H), 6.92 (br d, J=7.8 Hz, 2H), 3.24-3.13 (m, 8H), 2.62 (d, J=7.2 Hz, 2H), 2.20-1.92 (m, 1H), 0.95 (d, J=6.7 Hz, 6H), 0.96-0.89 (m, 12H).

(R)-2-(2,4-difluorophenyl)-1,1-difluoro-1-(5-(4-(4-(2-isobutyl-1H-benzo[d]imidazol-6-yl)piperazin-1-yl)phenyl)pyridin-2-yl)-3-(1H-tetrazol-1-yl)propan-2-ol (78)

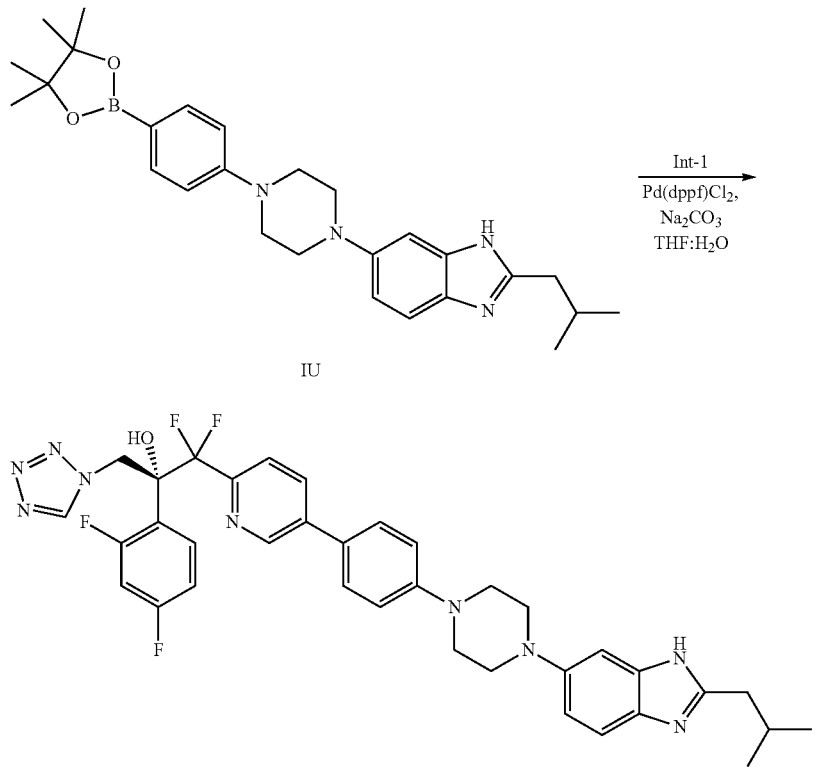

To a stirred solution of Int-1 (120 mg, 0.27 mmol) in THF:H2O (4:1, 20 mL) under argon atmosphere were added compound IU (153 mg, 0.33 mmol), sodium carbonate (88 mg, 0.83 mmol) and purged under argon for 20 min at RT. Then Pd(dppf)Cl$_2$ (20 mg, 0.02 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2-3% MeOH/CH$_2$Cl$_2$) followed by HPLC purification to afford 78 (30 mg, 0.043 mmol, 15% overall yield) as an off-white solid. $^1$H NMR (400 MHz, CD$_3$OD): δ 9.04 (s, 1H), 8.80 (d, J=2.1 Hz, 1H), 8.09 (dd, J=8.3, 2.3 Hz, 1H), 7.64 (d, J=8.9 Hz, 2H), 7.61 (d, J=9.3 Hz, 1H), 7.54 (dd, J=8.3, 0.6 Hz, 1H), 7.39 (dd, J=9.2, 2.3 Hz, 1H), 7.36-7.31 (m, 1H), 7.19-7.15 (m, 3H), 6.95-6.89 (m, 1H), 6.79-6.73 (m, 1H), 5.77 (d, J=14.6 Hz, 1H), 5.19 (d, J=14.6 Hz, 1H), 3.54-3.37 (m, 8H), 2.99 (d, J=7.4 Hz, 2H), 2.34-2.21 (m, 1H), 1.06 (d, J=6.7 Hz, 6H); MS (ESI): m/z 686.8 [M+H]$^+$; HPLC: 98.93%; Optical rotation [α]$_D^{20}$: +13.6 (c=0.1% in MeOH).

Example 79

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-1-methyl-1H-benzo[d]imidazole-6-carbonitrile (79)

2-(4-(4-bromophenyl)piperazin-1-yl)-1-methyl-1H-benzo[d]imidazole-6-carbonitrile (IV)

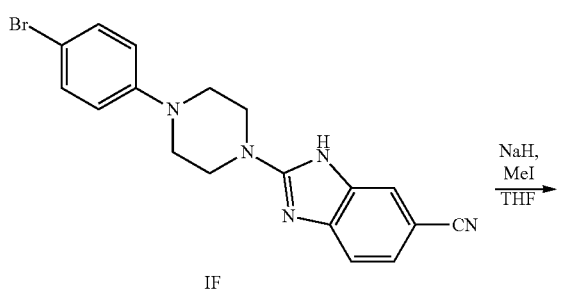

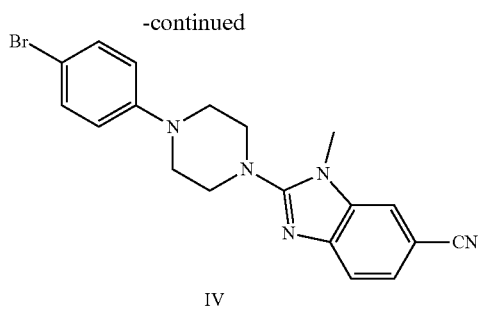

To a stirred solution of compound IF (880 mg, 2.30 mmol) in THF (40 mL) under argon atmosphere was added 60% sodium hydride (110.5 mg, 2.76 mmol) at RT and stirred for 5 min. Then methyl iodide (0.17 mL, 2.76 mmol) was added to the reaction mixture and stirred for 2 h. The progress of the reaction was monitored by TLC. The reaction mixture was diluted with water (20 mL) and extracted with EtOAc (2×20 mL). The combined organic layers were washed with water (20 mL), dried over anhydrous Na$_2$SO$_4$ and concentrated under reduced pressure. The crude material was purified by preparative HPLC to afford compound IV (900 mg, 2.20 mmol, 95%) as an off-white solid. $^1$H NMR (400 MHz, DMSO-d$_6$): δ 7.94 (s, 1H), 7.57-7.44 (m, 2H), 7.39 (d, J=9.2 Hz, 2H), 6.98 (d, J=9.2 Hz, 2H), 3.70 (s, 3H), 3.52-3.41 (m, 4H), 3.36-3.31 (m, 4H).

1-methyl-2-(4-(4-(4,4,5,5-tetramethyl-1,3,2-dioxaborolan-2-yl) phenyl) piperazin-1-yl)-1H-benzo [d] imidazole-6-carbonitrile (IW)

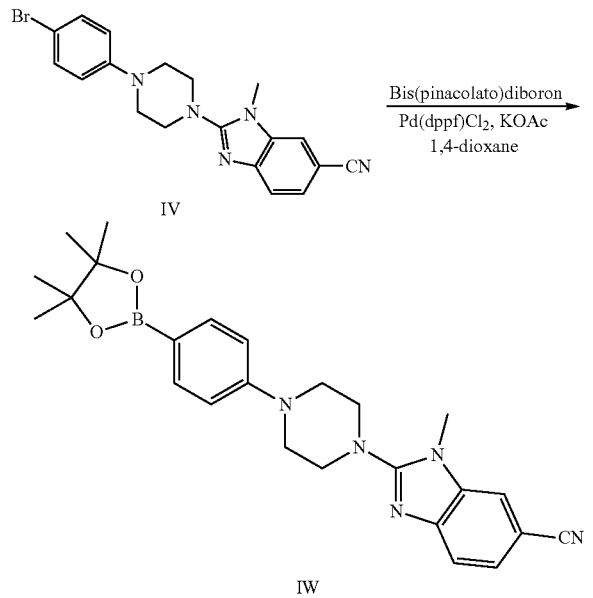

To a stirred solution of compound IV (240 mg, 0.60 mmol) in 1,4-dioxane (20 mL) under argon atmosphere were added bis(pinacolato)diboron (246 mg, 0.97 mmol) and potassium acetate (178 mg, 1.80 mmol) at RT and purged under argon for 15 min. Then Pd(dppf)Cl$_2$ (44.3 mg, 0.06 mmol) was added and the reaction mixture was purged under argon for 5 min at RT. The reaction mixture was stirred at 110° C. for 16 h. The reaction mixture was quenched with water (10 mL) and extracted with EtOAc (2×10 mL). The combined organic layers were washed with water (10 mL), brine (10 mL), dried over anhydrous Na$_2$SO$_4$ and concentrated under reduced pressure to obtain compound IW (240 mg, 89.9% with LC-MS purity) as an off-white solid. $^1$H NMR (400 MHz, CDCl$_3$): δ 7.88 (s, 1H), 7.75 (d, J=8.7 Hz, 2H), 7.46 (dd, J=8.2, 1.4 Hz, 1H), 7.24 (s, 1H), 6.96 (d, J=8.7 Hz, 2H), 3.69 (s, 3H), 3.54-3.51 (m, 4H), 3.50-3.41 (m, 4H), 1.34 (s, 12H).

(R)-2-(4-(4-(6-(2-(2,4-difluorophenyl)-1,1-difluoro-2-hydro-3-(1H-tetrazol-1-yl) propyl) pyridin-3-yl) phenyl) piperazin-1-yl)-1-methyl-1H-benzo [d] imidazole-6-carbonitrile (79)

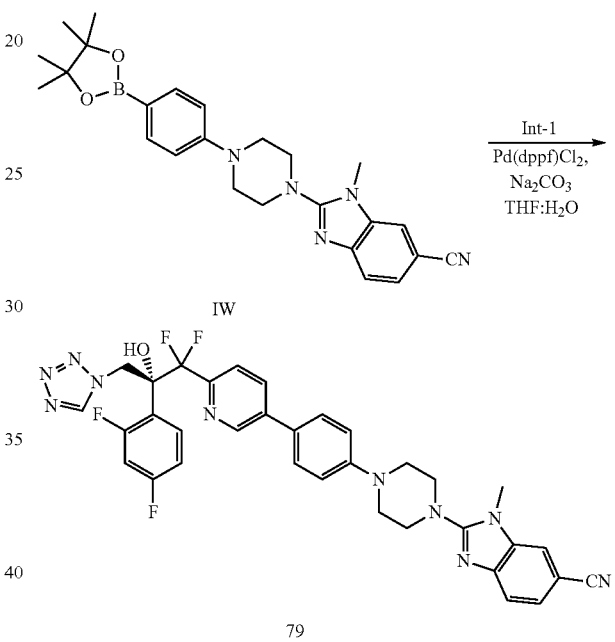

To a stirred solution of compound IW (250 mg, 0.56 mmol) in THF:H2O (4:1, 20 mL) under argon atmosphere were added Int-1 (242 mg, 0.56 mmol), sodium carbonate (179 mg, 1.70 mmol) and purged under argon for 10 min at RT. Then Pd(dppf)Cl$_2$ (41.2 mg, 0.05 mmol) was added to the reaction mixture at RT and stirred at 90° C. for 6 h. The progress of the reaction was monitored by TLC. The reaction mixture was diluted with water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 50% acetone/Hexane) to afford 79 (200 mg, 0.3 mmol, 53%) as an off-white solid. $^1$H NMR (500 MHz, DMSO-d$_6$): δ 9.15 (s, 1H), 8.91 (s, 1H), 8.18 (dd, J=8.4, 2.0 Hz, 1H), 7.95 (s, 1H), 7.72 (d, J=8.7 Hz, 2H), 7.56-7.46 (m, 3H), 7.32-7.25 (m, 2H), 7.23-7.17 (m, 2H), 7.15 (d, J=8.7 Hz, 1H), 6.93-6.89 (m, 1H), 5.67 (d, J=14.5 Hz, 1H), 5.11 (d, J=14.5 Hz, 1H), 3.72 (s, 3H), 3.56-3.51 (m, 4H), 3.47-3.43 (m, 4H); MS (ESI): m/z 669.8 [M+H]$^+$; HPLC: 96.24%; Optical rotation $[n]_D^{20}$: +109.3 (c=0.1% in CH$_2$Cl$_2$).

Example 80

(R)-2-(4-(4-(6-(2-(2,4-difluorophenyl)-1,1-difluoro-2-hydroxy-3-(1H-tetrazol-1-yl) propyl) pyridin-3-yl) phenyl) piperazin-1-yl)-1-methyl-1H-benzo [d] imidazole-5-carbonitrile (80)

2-(4-(4-bromophenyl) piperazin-1-yl)-1-methyl-1H-benzo [d] imidazole-5-carbonitrile (IX)

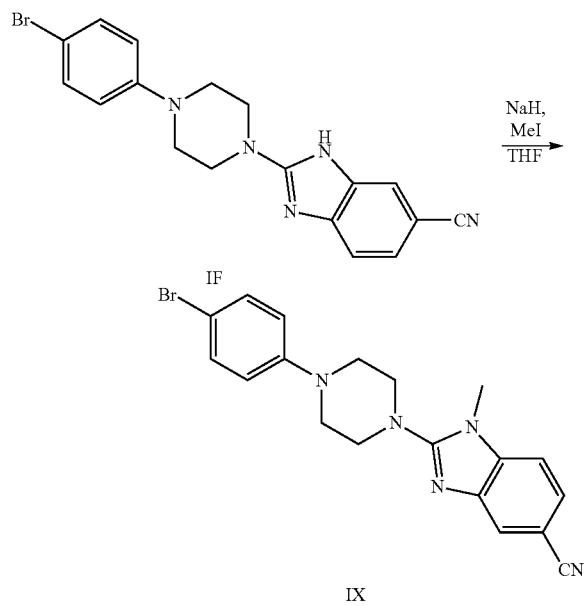

To a stirred solution of compound IF (880 mg, 2.30 mmol) in THF (40 mL) under argon atmosphere was added 60% sodium hydride (110.5 ng, 2.76 mmol) at RT and stirred for 5 min. Then methyl iodide (0.17 mL, 2.76 mmol) was added to the reaction mixture and stirred for 2 h. The progress of the reaction was monitored by TLC. The reaction mixture was diluted with water (20 mL) and extracted with EtOAc (2×20 mL). The combined organic layers were washed with water (20 mL), dried over anhydrous $Na_2SO_4$ and concentrated under reduced pressure. The crude material was purified by preparative HPLC to afford compound IX (900 mg, 2.20 mmol, 95%) as an off-white solid. $^1$H NMR (400 MHz, DMSO-$d_6$): δ 7.94 (s, 1H), 7.57-7.44 (m, 2H), 7.39 (d, J=9.2 Hz, 2H), 6.98 (d, J=9.2 Hz, 2H), 3.70 (s, 3H), 3.52-3.41 (m, 4H), 3.36-3.31 (m, 4H).

1-methyl-2-(4-(4-(4,4,5,5-tetramethyl-1,3,2-dioxaborolan-2-yl) phenyl) piperazin-1-yl)-1H-benzo [d] imidazole-5-carbonitrile (IY)

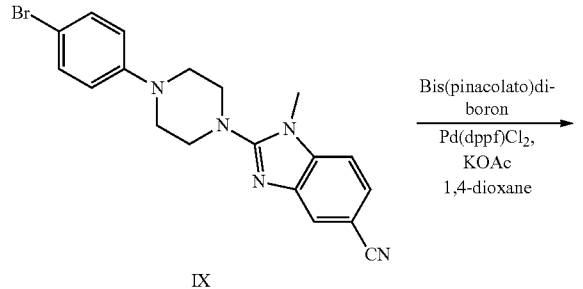

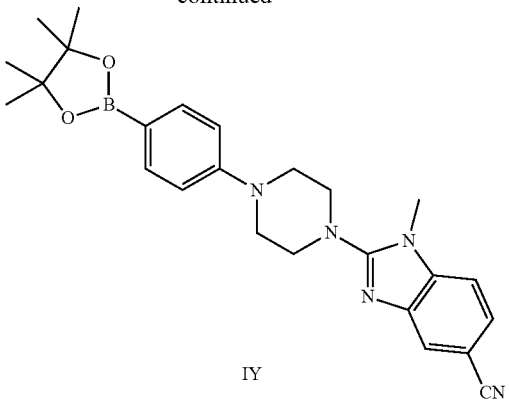

To a stirred solution of compound IX (285 mg, 0.70 mmol) in 1,4-dioxane (20 mL) under argon atmosphere were added bis(pinacolato)diboron (292 mg, 1.15 mmol) and potassium acetate (211.6 mg, 2.16 mmol) at RT and purged under argon for 15 min. Then $Pd(dppf)Cl_2$ (52.6 mg, 0.07 mmol) was added and the reaction mixture was purged under argon for 5 min at RT. The reaction mixture was stirred at 110° C. for 16 h. The reaction mixture was quenched with water (10 mL) and extracted with EtOAc (2×10 mL). The combined organic layers were washed with water (10 mL), brine (10 mL), dried over anhydrous $Na_2SO_4$ and concentrated under reduced pressure. The crude material was purified by silica gel column chromatography (eluent: 30% acetone/Hexane) to afford compound IY (300 mg, 0.67 mmol, 96%) as an off-white solid. $^1$H NMR (400 MHz, CDCl$_3$): δ 7.88 (s, 1H), 7.75 (d, J=8.7 Hz, 2H), 7.46 (dd, J=8.2, 1.4 Hz, 1H), 7.24 (s, 1H), 6.96 (d, J=8.7 Hz, 2H), 3.69 (s, 3H), 3.56-3.50 (m, 4H), 3.48-3.43 (m, 4H), 1.34 (s, 12H).

(R)-2-(4-(4-(6-(2-(2,4-difluorophenyl)-1,1-difluoro-2-hydroxy-3-(1H-tetrazol-1-yl) propyl) pyridin-3-yl) phenyl) piperazin-1-yl)-1-methyl-1H-benzo [d] imidazole-S-carbonitrile (80)

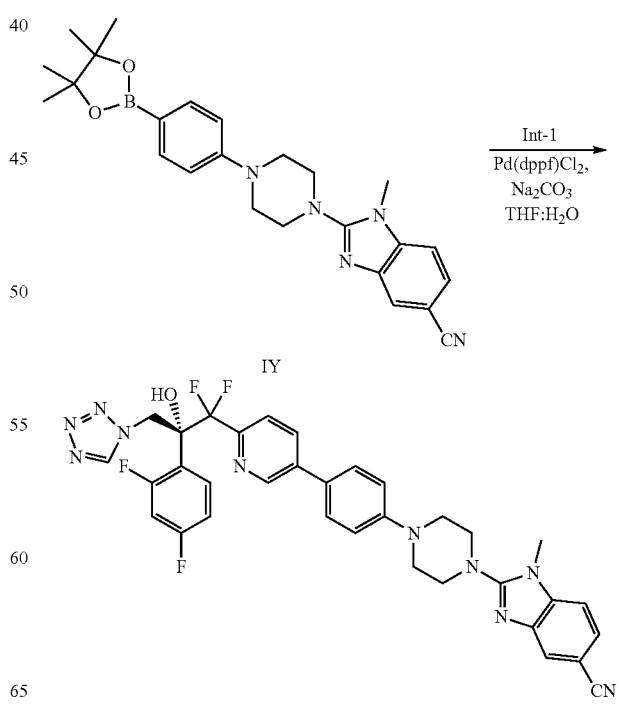

To a stirred solution of compound IY (300 mg, 0.67 mmol) in THF:H2O (4:1, 20 mL) under argon atmosphere were added Int-1 (291 mg, 0.67 mmol), sodium carbonate (215 mg, 2.03 mmol) and purged under argon for 10 min at RT. Then Pd(dppf)Cl$_2$ (49.5 mg, 0.07 mmol) was added to the reaction mixture at RT and stirred at 90° C. for 16 h. the reaction mixture was diluted with water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 50% acetone/Hexane) to afford 80 (100 mg, 0.15 mmol, 22%) as an off-white solid. $^1$H NMR (400 MHz, DMSO-d$_6$): δ 9.15 (s, 1H), 8.92 (s, 1H), 8.18 (dd, J=8.3, 2.3 Hz, 1H), 7.90 (s, 1H), 7.72 (d, J=8.8 Hz, 2H), 7.61-7.46 (m, 3H), 7.33-7.25 (m, 2H), 7.23-7.19 (m, 2H), 7.16 (d, J=9.03 Hz, 1H), 6.96-6.75 (m, 1H), 5.67 (d, J=14.8 Hz, 1H), 5.11 (d, J=14.8 Hz, 1H), 3.72 (s, 3H), 3.52-3.43 (m, 8H); MS (ESI): m/z 669.7 [M+H]$^+$; HPLC: 98.08%; Optical rotation [α]$_D^{20}$: +125.4 (c=0.1% in CH$_2$Cl$_2$).

Example 81

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-neopentyl-2,4-dihydro-3H-1,2,4-triazol-3-one (81)

4-(4-(4-(4-bromophenyl) piperazin-1-yl) phenyl)-2-neopentyl-2,4-dihydro-3H-1,2,4-triazol-3-one (IZ)

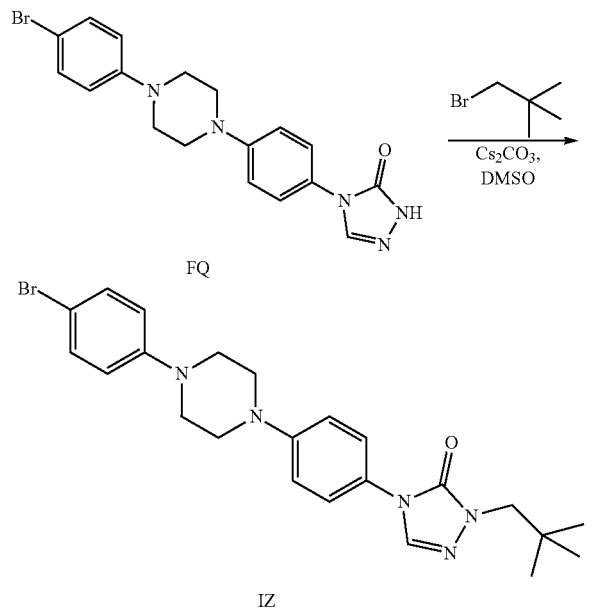

To a stirred solution of compound FQ (500 mg, 1.25 mmol) in DMSO (5 mL) under argon atmosphere were added cesium carbonate (1.22 g, 3.75 mmol) and 1-bromo-2,2-dimethylpropane (0.5 mL, 3.75 mmol) at RT. The reaction mixture was stirred at 110° C. for 24 h in a sealed tube. The progress of the reaction was monitored by TLC. The reaction mixture was quenched with water (30 mL) and extracted with EtOAc (2×30 mL). The combined organic layers were washed with water (30 mL), dried over anhydrous Na$_2$SO$_4$ and concentrated under reduced pressure. The crude material was purified by silica gel column chromatography (eluent: 30% EtOAc/Hexane) to afford compound IZ (250 mg, 0.53 mmol, 42%) as an off-white solid. $^1$H NMR (400 MHz, CDCl$_3$): δ 7.60 (s, 1H), 7.43 (d, J=9.0 Hz, 2H), 7.37 (d, J=8.7 Hz, 2H), 7.00 (d, J=9.0 Hz, 2H), 6.82 (d, J=8.6 Hz, 2H), 3.62 (s, 2H), 3.35-3.25 (m, 8H), 1.01 (s, 9H); LC-MS: 472.1 [M+2H] at 3.67 RT (71.65% purity).

2-neopentyl-4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (JA)

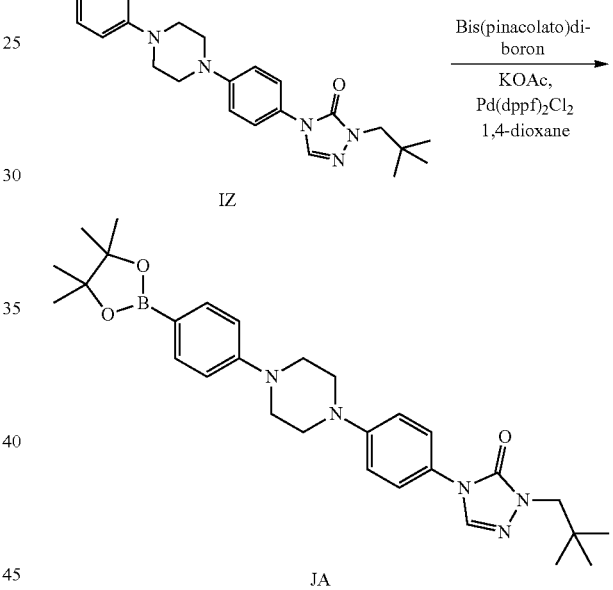

To a stirred solution of compound IZ (300 mg, 0.63 mmol) in 1,4-dioxane (30 mL) under argon atmosphere were added bis(pinacolato)diboron (322 mg, 1.27 mmol) and potassium acetate (250 mg, 2.55 mmol) at RT. The reaction mixture was purged with argon for 20 min, then Pd(dppf)Cl$_2$ (70 mg 0.09 mmol) was added and the reaction mixture was purged under argon for 10 min at RT. The reaction mixture was stirred at 110° C. for 16 h. The reaction mixture was quenched with water (20 mL) and extracted with EtOAc (2×20 mL). The combined organic layers were washed with water (10 mL), brine (10 mL), dried over anhydrous Na$_2$SO$_4$ and concentrated under reduced pressure. The crude material was purified by silica gel column chromatography (eluent: 30-40% EtOAc/Hexane) to afford compound JA (180 mg, 0.34 mmol, 54%) as a white solid. $^1$H NMR (400 MHz, CDCl$_3$): δ 7.74 (d, J=8.7 Hz, 2H), 7.61 (s, 1H) 7.43 (d, J=9.0 Hz, 2H), 7.02 (d, J=9.0 Hz, 2H), 6.94 (d, J=8.6 Hz, 2H), 3.65 (s, 2H), 3.46-3.38 (m, 4H), 3.37-3.31 (m, 4H), 1.33 (s, 12H), 1.03 (s, 9H).

(R)-4-(4-(4-(4-(6-(2-(2,4-difluorophenyl)-1,1-difluoro-2-hydroxy-3-(1H-tetrazol-1-yl) propyl) pyridin-3-yl)phenyl)piperazin-1-yl) phenyl)-2-neopentyl-2,4-dihydro-3H-1,2,4-triazol-3-one (81)

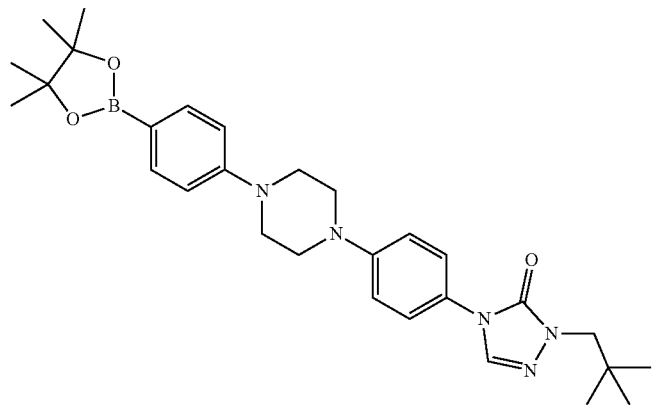

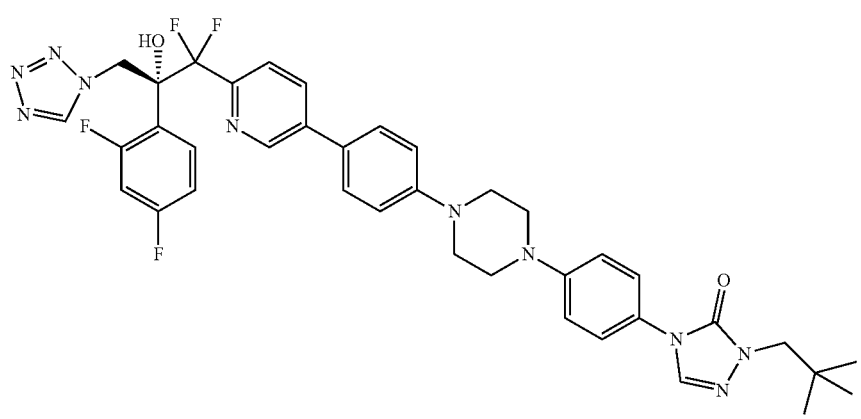

To a stirred solution of Int-1 (150 mg, 0.34 mmol) in THF:H2O (9:1, 20 mL) under argon atmosphere were added compound JA (196 mg, 0.38 mmol), sodium carbonate (110 tug, 1.04 mmol) and purged under argon for 15 min at RT. Then Pd(dppf)Cl$_2$ (38 mg, 0.05 mmol) was added and the reaction mixture was purged under argon for 10 min at RT. The reaction mixture was stirred at 80° C. for 16 h. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 70% EtOAc/Hexane) to afford 81 (70 mg, 0.10 mmol, 27%) as an off-white solid. $^1$H NMR (400 MHz, DMSO-d$_6$): δ 9.15 (s, 1H), 8.89 (s, 1H), 8.30 (s, 1H), 8.17 (dd, J=8.3, 2.1 Hz, 1H), 7.70 (d, J=8.9 Hz, 2H), 7.52-7.48 (m, 3H), 7.34-7.25 (m, 21H), 7.22-7.16 (m, 5H), 6.94-6.88 (m, 1H), 5.67 (d, J=14.2 Hz, 1H), 5.11 (d, J=14.2 Hz, 1H), 3.51 (s, 2H), 3.42-3.37 (m, 4H), 3.36-3.30 (m, 4H), 0.98 (s, 9H). MS (ESI): m/z 743.8 [M+H]$^+$; HPLC: 98.43%; Optical rotation [α]$_D^{19}$: +124.7 (c=0.1% in CH$_2$Cl$_2$).

Example 82

4-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-((2S,3S)-2-hydroxypentan-3-yl)-2,4-dihydro-3H-1,2,4-triazol-3-one (82)

Phenyl (5-iodopyridin-2-yl) carbamate (JO)

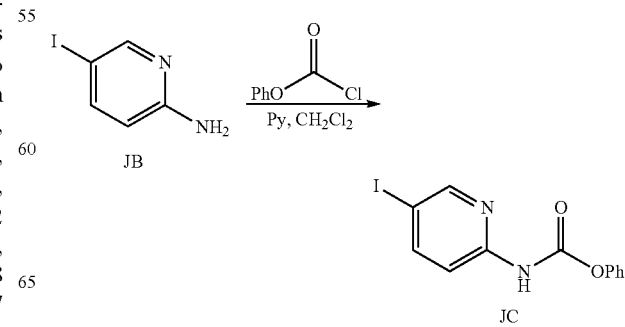

To a stirred solution of 5-iodopyridin-2-amine (JB; 3.0 g, 13.63 mmol) in CH$_2$Cl$_2$ (100 mL) under argon atmosphere were added phenyl carbonochloridate (2.1 mL, 16.36 mmol) and pyridine (1.3 mL, 16.36 mmol) at 0° C. The reaction mixture was warmed to RT and stirred for 3 h. The progress of the reaction was monitored by TLC. The reaction mixture was diluted with water (50 mL) and extracted with CH$_2$Cl$_2$ (2×50 mL). The combined organic extracts were dried over anhydrous Na$_2$SO$_4$ and concentrated under reduced pressure. The crude material was purified by silica gel column chromatography (eluent: 20% EtOAc/Hexanes) to afford compound JC (3.0 g, 8.82 mmol, 65%) as a white solid and the material was as such taken for next step without further purification. LC-MS: 340.8 [M+H]$^+$ at 3.24 RT (99.69% purity).

2-((2S,3S)-2-(benzyloxy) pentan-3-yl)-4-(5-iodopyridin-2-yl)-2,4-dihydro-3H-1,2,4-triazol-3-one (JD)

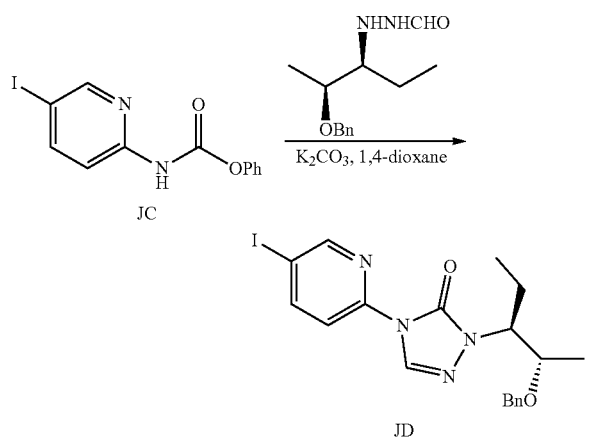

To a stirred solution of compound JC (1.5 g, 4.41 mmol) in 1,4-dioxane (50 mL) under argon atmosphere were added N'-((2S,3S)-2-(benzyloxy) pentan-3-yl) formohydrazide (1.1 g, 4.85 mmol) and potassium carbonate (1.2 g, 8.82 mmol) at 0° C. The reaction mixture was stirred at 90° C. for 16 h. The reaction mixture was diluted with water (50 mL) and extracted with CH$_2$Cl$_2$(2×50 mL). The combined organic extracts were dried over anhydrous Na$_2$SO$_4$ and concentrated under reduced pressure. The crude material was purified by silica gel column chromatography (eluent: 10% EtOAc/Hexane) to afford compound JD (1.8 g, 3.87 mmol, 45%) as a white solid. $^1$H NMR (400 MHz, DMSO-d$_6$): δ 8.73 (dd, J=2.3, 0.6 Hz, 1H), 8.58 (s, 1H), 8.38 (dd, J=8.7, 2.3 Hz, 1H), 8.06 (dd, J=8.7, 0.8 Hz, 1H), 7.24-7.11 (m, 5H), 4.08-3.82 (m, 1H), 3.77-3.68 (m, 1H), 3.57 (s, 2H), 1.79-1.71 (m, 2H), 1.22 (d, J=6.3 Hz, 3H), 0.78 (t, J=7.3 Hz, 3H).

2-((2S,3S)-2-(benzyloxy) pentan-3-yl)-4-(5-(4-(4-bromophenyl) piperazin-1-yl) pyridin-2-yl)-2,4-dihydro-3H-1,2,4-triazol-3-one (JE)

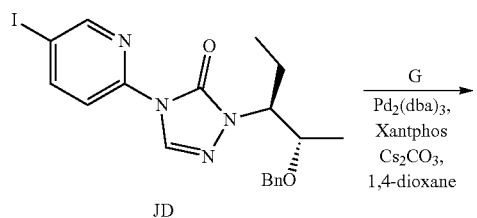

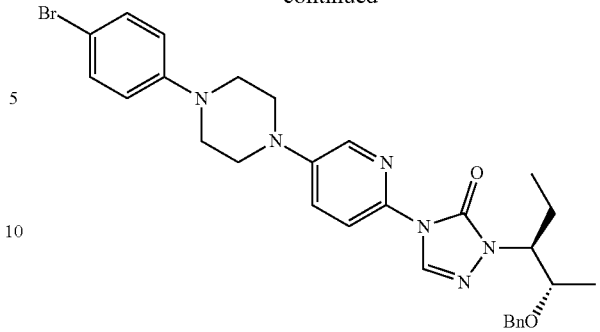

To a stirred solution of compound JD (500 mg, 2.07 mmol) in 1,4-dioxane (40 mL) under argon atmosphere were added G (1 g, 2.28 mmol), Xantphos (143 mg, 0.24 mmol), Cs$_2$CO$_3$ (2 g, 6.22 mmol) and purged under argon for 10 min at RT. Then Pd$_2$(dba)$_3$ (95 mg, 0.10 mmol) was added and the reaction mixture was purged under argon for 5 min at RT. The reaction mixture was stirred at 80° C. for 16 h. The reaction mixture was diluted with water (20 mL) and extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 15% EtOAc/Hexane) to afford compound JE (350 mg, 0.60 mmol, 29%) as a pale yellow solid. $^1$H NMR (400 MHz, DMSO-d$_6$): δ 8.49 (s, 1H), 8.24 (d, J=2.9 Hz, 1H), 7.97 (d, J=8.9 Hz, 1H), 7.66 (dd, J=9.1, 3.1 Hz, 1H), 7.42-7.34 (m, 2H), 7.20-7.10 (m, 5H), 6.98 (d, J=9.2 Hz, 2H), 4.52 (d, J=11.9 Hz, 1H), 4.26 (d, J=11.9 Hz, 1H), 4.09-3.95 (m, 1H), 3.74-3.71 (m, 1H), 3.43-3.34 (m, 8H), 1.83-1.70 (m, 2H), 1.28-1.19 (m, 3H), 0.78 (t, J=7.1 Hz, 3H).

2-((2S,3S)-2-(benzyloxy) pentan-3-yl)-4-(5-(4-(4-(4,4,5,5-tetramethyl-1,3,2-dioxaborolan-2-yl) phenyl) piperazin-1-yl) pyridin-2-yl)-2,4-dihydro-3H-1,2,4-triazol-3-one (JF)

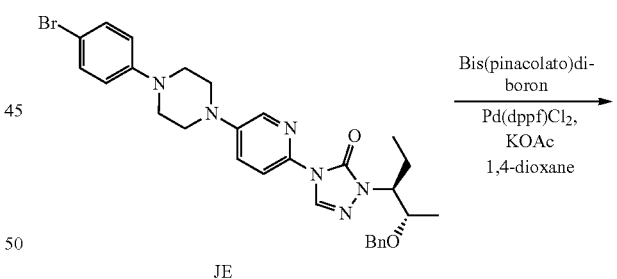

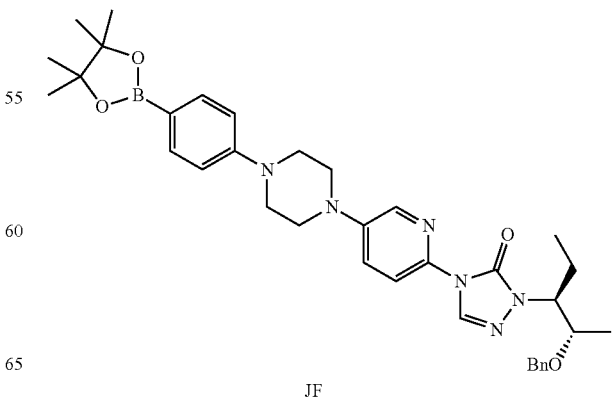

To a stirred solution of compound JE (350 mg, 0.60 mmol) in 1,4-dioxane (25 mL) under argon atmosphere were added bis(pinacolato)diboron (246 mg, 0.97 mmol) and potassium acetate (178 mg, 1.81 mmol) at RT. The reaction mixture was purged with argon for 20 min, then Pd(dppf)Cl$_2$ (44 tug, 0.06 mmol) was added and the reaction mixture was purged under argon for 5 min at RT. The reaction mixture was stirred at 110° C. for 36 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 20% EtOAc/Hexane) to afford compound JF (250 mg, 0.40 mmol, 66%) as an off-white solid. $^1$H NMR (400 MHz, DMSO-d$_6$): δ 8.49 (s, 1H), 8.23 (d, J=2.9 Hz, 1H), 7.97 (d, J=9.0 Hz, 1H), 7.65 (dd, J=9.0, 3.0 Hz, 1H), 7.55 (d, J=8.7 Hz, 1H), 7.42-7.33 (m, 1H), 7.20-7.11 (m, 5H), 7.03-6.94 (m, 2H), 4.52 (d, J=11.9 Hz, 1H), 4.26 (d, J=11.9 Hz, 1H), 4.07-3.94 (m, 1H), 3.77-3.65 (m, 1H), 3.42-3.38 (m, 8H), 1.83-1.64 (m, 2H), 1.16 (d J=3.3 Hz, 3H), 1.07 (s, 12H), 0.81-0.74 (m, 3H)

2-((2S,3S)-2-(benzyloxy) pentan-3-yl)-4-(5-(4-(4-(6-((R)-2-(2,4-difluorophenyl)-1,1-difluoro-2-hydroxy-3-(1H-tetrazol-1-yl) propyl)pyridin-3-yl) phenyl) piperazin-1-yl) pyridin-2-yl)-2,4-dihydro-3H-1,2,4-triazol-3-one (JG)

To a stirred solution of Int-1 (150 mg, 0.34 mmol) in THF:H2O (4:1, 25 mL) under argon atmosphere were added compound JF (239 mg, 0.38 mmol), sodium carbonate (110 mg, 1.04 mmol) and purged under argon for 20 min at RT. Then Pd(dppf)Cl$_2$ (25 mg, 0.03 mmol) was added and the reaction mixture was purged under argon for 10 min at RT. The reaction mixture was stirred at 80° C. for 8 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 60% EtOAc/Hexane) to afford compound JG (120 mg, 0.14 mmol, 40%) as an off-white solid. $^1$H NMR (500 MHz, DMSO-d$_6$): δ 9.15 (s, 1H), 8.92 (s, 1H), 8.50 (s, 1H), 8.26 (d, J=2.9 Hz, 1H), 8.17 (dd, J=8.1, 1.7 Hz, 1H), 7.99 (d, J=9.3 Hz, 1H), 7.71 (d, J=9.3 Hz, 2H), 7.68 (dd, J=9.3, 2.9 Hz, 1H), 7.49 (d, J=8.1 Hz, 1H), 7.32-7.28 (m, 2H), 7.23-7.12 (m, 8H), 6.93-6.90 (m, 1H), 5.68 (d, J=14.5 Hz, 1H), 5.12 (d, J=14.5 Hz, 1H), 4.53 (d, J=11.6 Hz, 1H), 4.27 (d, J=11.6 Hz, 1H), 4.05-3.97 (m, 1H), 3.79-3.69 (m, 1H), 3.44-3.41 (m, 8H), 1.81-1.72 (m, 2H), 1.18 (t, J=7.2 Hz, 3H), 0.79 (t, J=7.0 Hz, 3H).

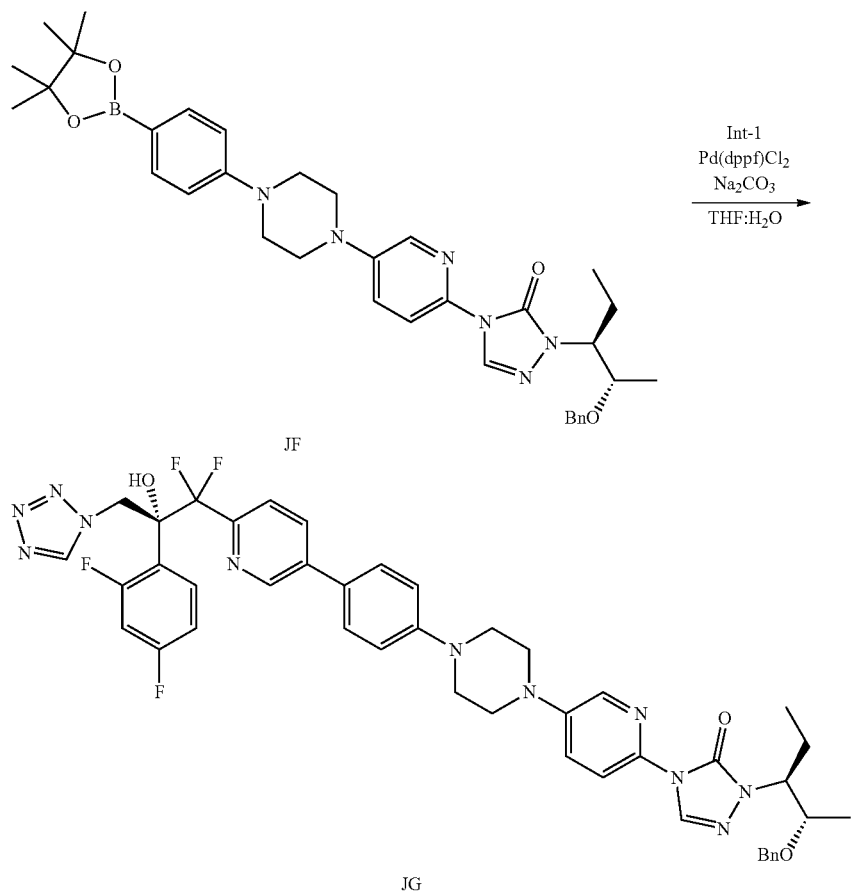

4-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-((2S,3S)-2-hydroxypentan-3-yl)-2,4-dihydro-3H-1,2,4-triazol-3-one (82)

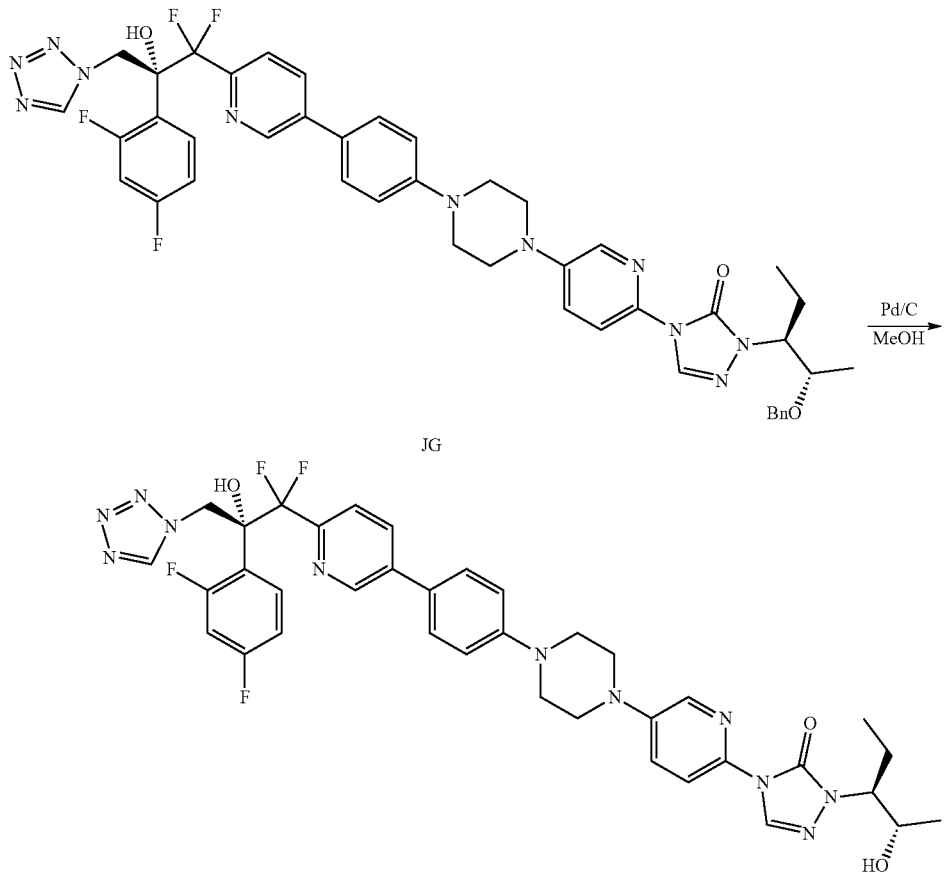

To a stirred solution of compound JG (100 mg, 0.11 mmol) in MeOH (30 ml) under argon atmosphere were added 10% Pd/C (50 mg) and 5.0 N HCl (0.2 mL) at RT. The reaction mixture was stirred at RT for 3 h under hydrogen atmosphere (50 psi). The progress of the reaction was monitored by TLC. The reaction mixture was filtered through celite, the filtrate was concentrated under reduced pressure. The residue was diluted with 8% sodium bicarbonate solution (20 ml) and extracted with $CH_2Cl_2$ (2×20 ml). The combined organic extracts were dried over anhydrous $Na_2SO_4$ and concentrated under reduced pressure. The crude material was washed with n-pentane (2×10 ml) to afford 82 (45 mg, 0.05 mmol, 42%) as an off-white solid. $^1$H NMR (400 MHz, $CDCl_3$): δ 8.76 (s, 1H), 8.73 (s, 1H), 8.39 (s, 1H), 8.22 (d, J=9.0 Hz, 1H), 8.12 (d, J=2.8 Hz, 1H), 7.95 (dd, J=8.2, 2.2 Hz, 1H), 7.84 (s, 1H), 7.62 (d, J=8.3 Hz, 1H), 7.53 (d, J=8.8 Hz, 2H), 7.43-7.35 (m, 2H), 7.07 (d, J=8.9 Hz, 2H), 6.80-6.74 (m, 1H), 6.71-6.64 (m, 1H), 5.61 (d, J=14.2 Hz, 1H), 5.12 (d, J=14.2 Hz, 1H), 4.14-3.96 (m, 2H), 3.50-3.38 (m, 8H), 2.91 (d, J=8.8 Hz, 1H), 2.07-1.96 (m, 1H), 1.95-1.84 (m, 1H), 1.22 (d, J=6.3 Hz, 3H), 0.94 (t, J=7.4 Hz, 3H); MS (ESI): m/z: 760.8 [M+H]$^+$; HPLC: 92.43%; Optical rotation $[α]_D^{19}$: +21.4 (c=0.1% in MeOH).

Example 83

4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl)-N-((2S,3S)-2-hydroxypentan-3-yl)-N-methylbenzamide (83)

4-(4-(4-bromophenyl) piperazin-1-yl)-N-((2S,3S)-2-((tert-butyldimethylsilyl) oxy) pentan-3-yl)-N-methylbenzamide (JH)

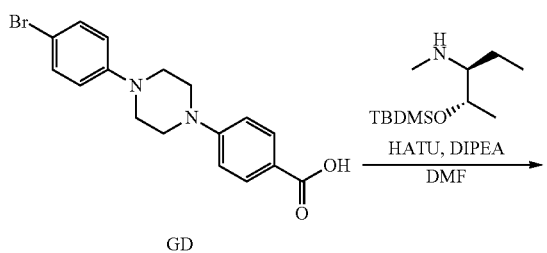

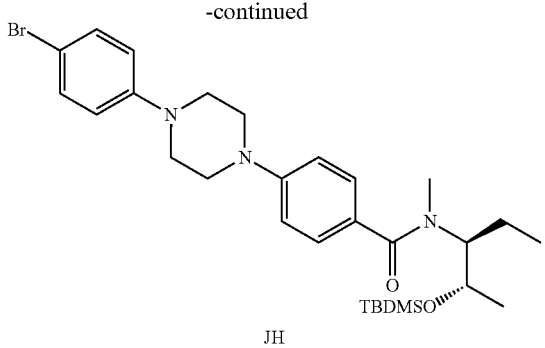

JH

To a stirred solution of compound (2S,3S)-2-((tert-butyldimethylsilyl) oxy)-N-methylpentan-3-amine (500 mg, 1.40 mmol) in DMF (20 mL) were added compound GD (320 mg, 1.40 mmol), HATU (633 mg 1.66 mmol) and ethyldiisopropylamine (0.48 mL, 2.77 mmol) at 0° C. under argon atmosphere. The reaction mixture was stirred at RT for 16 h. The reaction mixture was quenched with water (20 mL) and extracted with EtOAc (2×20 mL). The combined organic extracts were dried over anhydrous Na₂SO₄ and concentrated under reduced pressure. The crude material was purified by silica gel column chromatography (eluent: 40% EtOAc/Hexane) to afford compound JH (350 mg, 0.61 mmol, 44%) as an off-white solid ¹H NMR (500 MHz, DMSO-d₆): δ 7.39-7.32 (m, 4H), 7.09-6.95 (m, 4H), 4.12 (m, 0.5H), 4.37 (m, 0.5H), 3.85 (m, 0.5H), 3.57 (m, 0.5H), 3.35-3.27 (m, 8H), 2.82 (s, 3H), 1.58-1.41 (m, 2H), 1.08 (d, J=6.3 Hz, 3H), 0.95 (s, 9H), 0.77 (t, J=7.4 Hz, 3H, 0.02 (m, 6H).

4-(4-(4-bromophenyl) piperazin-1-yl)-N-((2S,3S)-2-hydroxypentan-3-yl)-N-methylbenzamide (JI)

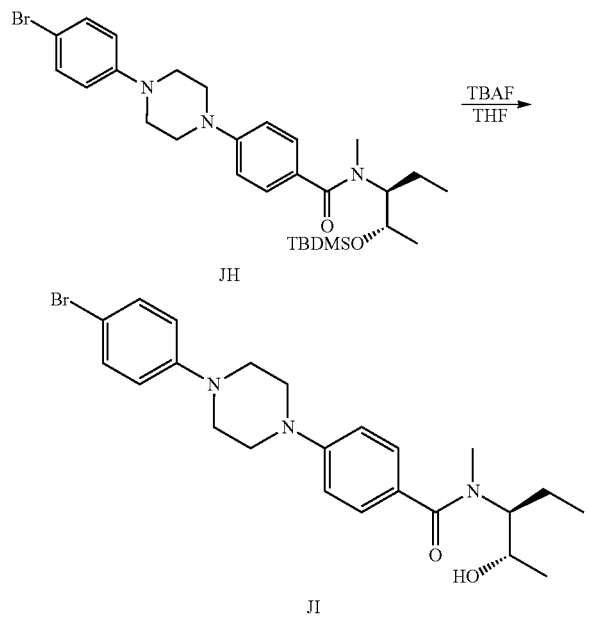

To a stirred solution of compound JH (250 mg, 0.43 mmol) in THF (10 mL) under argon atmosphere was added TBAF (1.3 mL, 1.30 mmol, 1.0 M in THF) at 0° C. The reaction mixture was warmed to RT and stirred for 6 h. The progress of the reaction was monitored by TLC. The reaction mixture was diluted with water (50 mL) and extracted with EtOAc (2×50 mL). The combined organic extracts were washed with water (50 mL), brine (50 mL), dried over anhydrous Na₂SO₄ and concentrated under reduced pressure to obtain the crude. The crude material was purified by silica gel column chromatography (eluent: 5% MeOH/CH₂Cl₂) to afford compound JI (250 mg, 0.54 mmol, 89%) as an off-white solid, ¹H NMR (500 MHz, DMSO-d₆): δ 7.38-7.29 (m, 4H), 7.05-6.98 (m, 4H), 4.88 (d, J=6.3 Hz, 1H), 4.65 (m, 0.5H), 4.27 (m, 0.5H), 3.81-3.62 (m, 1H), 3.39-3.23 (m, 8H), 2.84 (s, 3H), 1.64-1.54 (m, 1H), 1.47-1.35 (m, 1H), 1.00 (d J=6.3 Hz, 3H), 0.76 (t, J=7.4 Hz, 3H); LC-MS: 462.1 [M+H]⁺; at 3.29 RT (96.66% purity).

N-((2S,3S)-2-hydroxypentan-3-yl)-N-methyl-4-(4-(4-(4,4,5,5-tetramethyl-1,3,2-dioxaborolan-2-yl) phenyl) piperazin-1-yl) benzamide (J)

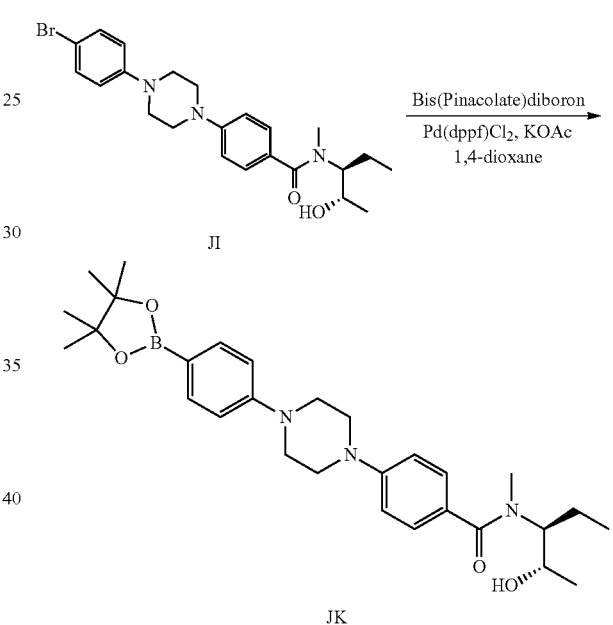

To a stirred solution of compound JI (250 mg, 0.54 mmol) in 1,4-dioxane (20 mL) under argon atmosphere were added bis(pinacolato)diboron (220 mg, 0.86 mmol) and KOAc (160 mg, 1.62 mmol) at RT. The reaction mixture was purged with argon for 20 min, then Pd(dppf)Cl₂ (39 mg, 0.05 mmol) was added and the reaction mixture was purged under argon for 10 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na₂SO₄ and concentrated under reduced pressure. The crude material was purified by silica gel column chromatography (eluent: 4% MeOH/CH₂Cl₂) to afford compound JK as a rotameric mixture (180 mg, 0.35 mmol, 65%) as an off-white solid. ¹H NMR (500 MHz, DMSO-d₆): δ 7.58 (d, J=8.7 Hz, 2H), 7.37 (d, J=9.0 Hz, 2H), 7.00-6.96 (m, 4H), 4.87 (d, J=6.3 Hz, 1H), 4.62 (m, 0.5H), 4.25 (m, 0.5H), 3.80-3.61 (m, 1H), 3.39-3.28 (m, 8H), 2.81 (s, 3H), 1.60-1.49 (m, 1H), 1.45-1.31 (m, 1H), 1.21 (s, 12H), 1.01 (d, J=6.3 Hz, 3H), 0.77 (t, J=7.4 Hz, 3H); LC-MS: 508.3 [M+H]⁺ at 2.708 RT (79.76% purity).

4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl)-N-((2S,3S)-2-hydroxypentan-3-yl)-N-methylbenzamide (83)

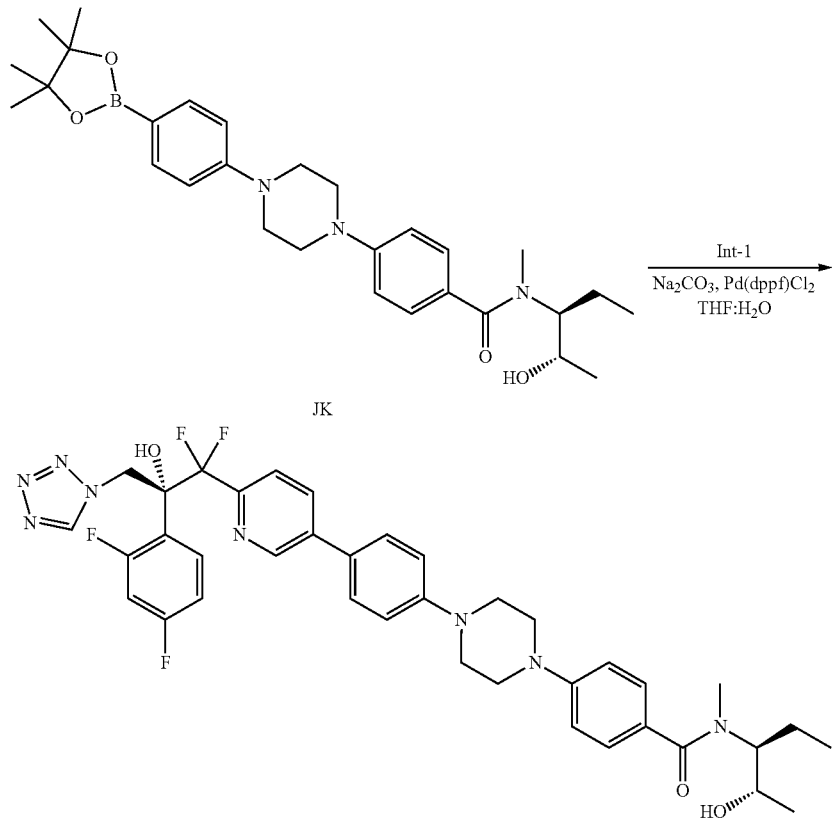

To a stirred solution of Int-1 (130 mg, 0.30 mmol) in THF:H2O (4:1, 20 mL) under argon atmosphere were added compound JK (183 mg, 0.36 mmol), sodium carbonate (95 mg, 0.90 mmol) and purged under argon for 20 min at RT. Then Pd(dppf)Cl$_2$ (11 mg, 0.01 mmol) was added and the reaction mixture was purged under argon for 10 min at RT. The reaction mixture was stirred at reflux for 16 h. The reaction mixture was diluted with water (30 mL) and extracted with EtOAc (2×30 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) to afford 83 as a rotameric mixture (90 mg, 0.10 mmol, 41%) as an off-white solid. $^1$H NMR (400 MHz, DMSO-d$_6$): δ 9.15 (s, 1H), 8.91 (s, 1H), 8.17 (dd, J=8.2, 2.2 Hz, 1H), 7.70 (d, J=8.8 Hz, 2H), 7.49 (d, J=8.4 Hz, 1H), 7.36-7.26 (m, 4H), 7.23-7.11 (m, 3H), 7.06-6.98 (m, 2H), 6.93-6.88 (m, 1H), 5.67 (d, J=14.7 Hz, 1H), 5.11 (d, J=14.7 Hz, 1H), 4.89 (brs, 1H), 3.79-3.63 (m, 1H), 3.40-3.38 (m, 8H), 2.84-2.76 (m, 3H), 1.65-1.35 (m, 2H), 1.15-0.98 (m, 3H), 0.91-0.64 (m, 3H); MS (ESI): m/z 733.8 [M+H]$^+$; HPLC: 95.43%; Optical rotation [α]$_D^{20}$: +20.5 (c=0.1% in MeOH).

Example 84(+)

(+)-4-(4-(4-(4-(6-(1,1-difluoro-2-(3-fluorophenyl)-2-hydroxy-3-(5-methyl-1H-1,2,4-triazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (84(+))

1-(5-bromopyridin-2-yl)-1,1-difluoro-2-(3-fluoro-phenyl)-3-(3-methyl-1H-1,2,4-triazol-1-yl) propan-2-ol (JL) & 1-(5-bromopyridin-2-yl)-1,1-difluoro-2-(3-fluorophenyl)-3-(3-methyl-2H-1,2,4-triazol-1-yl) propan-2-ol (JM)

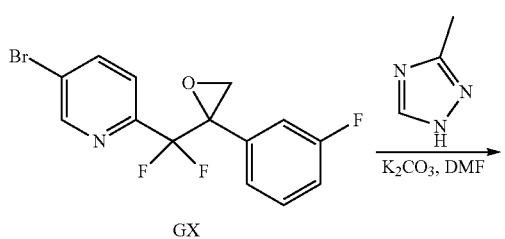

GX

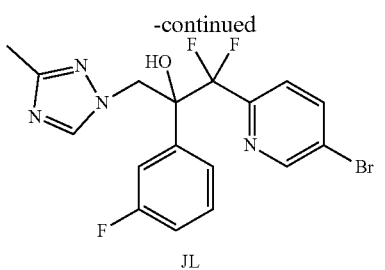

JL

JM

To a stirred solution of compound GX (1 g, 2.91 mmol) in DMF (10 mL) under argon atmosphere were added potassium carbonate (602 mg, 4.36 mmol) and 3-methyl-1H-1,2,4-triazole (483 mg, 5.82 mmol) at RT. The reaction mixture was stirred at 80° C. for 16 h. The reaction mixture was diluted with water (50 mL) and extracted with EtOAc (2×50 mL). The combined organic layers were dried over anhydrous Na₂SO₄ and concentrated under reduced pressure. The crude material was purified by silica gel column chromatography (eluent: 50% EtOAc/Hexane) which was further purified by preparative HPLC to afford compound JL (550 mg, 1.29 mmol, 44%) & compound JM (550 mg, 1.29 mmol, 44%) as an off-white solids. JL data: ¹H NMR (500 MHz, DMSO-d₆): δ 8.71 (s, 1H), 8.15 (dd, J=8.7, 2.3 Hz, 1H), 8.01 (s, 1H), 7.37 (d, J=8.1 Hz, 1H), 7.31-7.24 (m, 1H), 7.24-7.18 (m, 1H), 7.17-7.14 (m, 1H), 7.09-7.05 (m, 1H), 6.79 (s, 1H), 5.15 (d, J=14.5 Hz, 1H), 4.75 (d, J=15.1 Hz, 1H), 2.04 (s, 3H); JM data: ¹H NMR (500 MHz, DMSO-d₆): δ 8.71 (s, 1H), 8.17 (dd, J=8.1, 2.3 Hz, 1H), 7.56 (s, 1H), 7.44 (d, J=8.1 Hz, 1H), 7.33-7.27 (m, 1H), 7.26-7.22 (m, 1H), 7.19-7.16 (m, 1H), 7.10-7.06 (m, 1H), 6.66 (s, 1H), 4.98 (d, J=14.49 Hz, 1H), 4.86 (d, J=13.91 Hz, 1H), 2.22 (s, 3H).

2-((2S,3S)-2-(benzyloxy) pentan-3-yl)-4-(4-(4-(4-(6-(1,1-difluoro-2-(3-fluorophenyl)-2-hydroxy-3-(5-methyl-1H-1,2,4-triazol-1-yl) propyl) pyridin-3-yl) phenyl) piperazin-1-yl) phenyl)-2,4-dihydro-3H-1,2,4-triazol-3-one (JN)

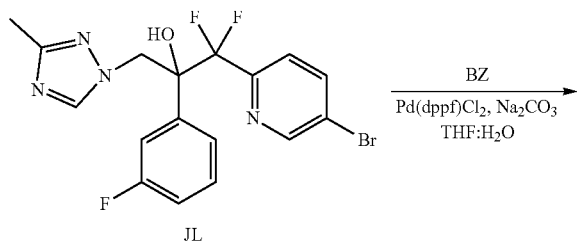

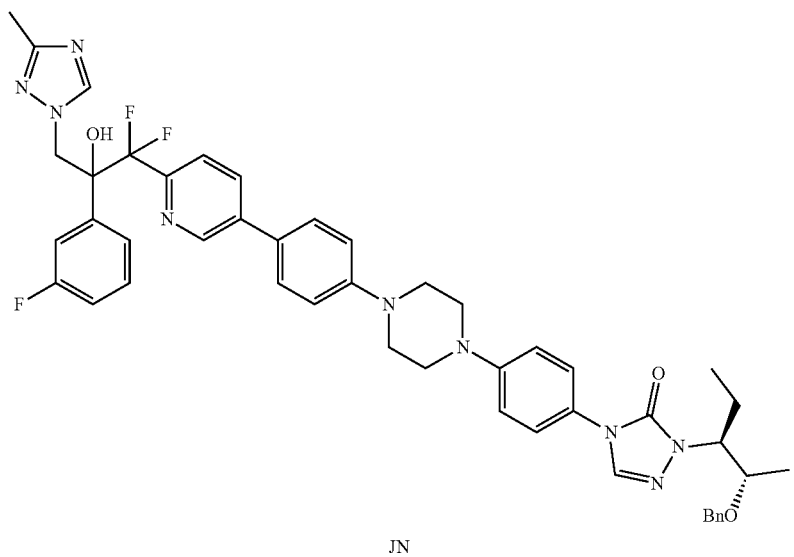

JN

To a stirred solution of compound JL (300 mg, 0.70 mmol) in THF:H2O (4:1, 10 mL) under argon atmosphere were added compound BZ (524 mg, 0.84 mmol), sodium carbonate (222 mg, 2.10 mmol) and purged under argon for 20 min at RT. Then Pd(dppf)Cl₂ (51 mg, 0.07 mmol) was added and the reaction mixture was purged under argon for 10 min at RT. The reaction mixture was stirred at reflux for 4 h. The progress of the reaction was monitored by TLC. The reaction mixture was diluted with water (20 mL) and extracted with EtOAc (2×20 mL). The combined organic extracts were dried over anhydrous Na₂SO₄ and concentrated under reduced pressure. The crude material was purified by silica gel column chromatography (eluent: 2% MeOH/CH₂Cl₂) to afford compound JN (400 mg, 0.47 mmol, 67%) as an off-white solid. ¹H NMR (500 MHz, CDCl₃): δ 8.65 (s, 1H), 7.95 (s, 1H), 7.89 (dd, J=8.4, 2.0 Hz, 1H), 7.58 (d, J=8.7 Hz, 1H), 7.56 (s, 1H), 7.50 (d, J=8.7 Hz, 2H), 7.42 (d, J=8.7 Hz, 2H), 7.33-7.21 (m, 8H), 7.17 (s, 1H), 7.06-7.02 (m, 3H), 6.95-6.91 (m, 1H), 4.95 (d, J=14.5 Hz, 1H), 4.75 (d, J=14.5 Hz, 1H), 4.63 (d, J=11.6 Hz, 1H), 4.41 (d, J=11.6 Hz, 1H), 4.21-4.16 (m, 1H), 3.83-3.78 (m, 1H), 3.49-3.28 (m, 8H), 2.18 (s, 3H), 1.99-1.92 (m, 1H), 1.85-1.76 (m, 1H), 1.28 (d, J=6.4 Hz, 3H), 0.89 (t, J=7.2 Hz, 3H).

(+)-4-(4-(4-(4-(6-(1,1-difluoro-2-(3-fluorophenyl)-2-hydroxy-3-(5-methyl-1H-1,2,4-triazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (84(+))

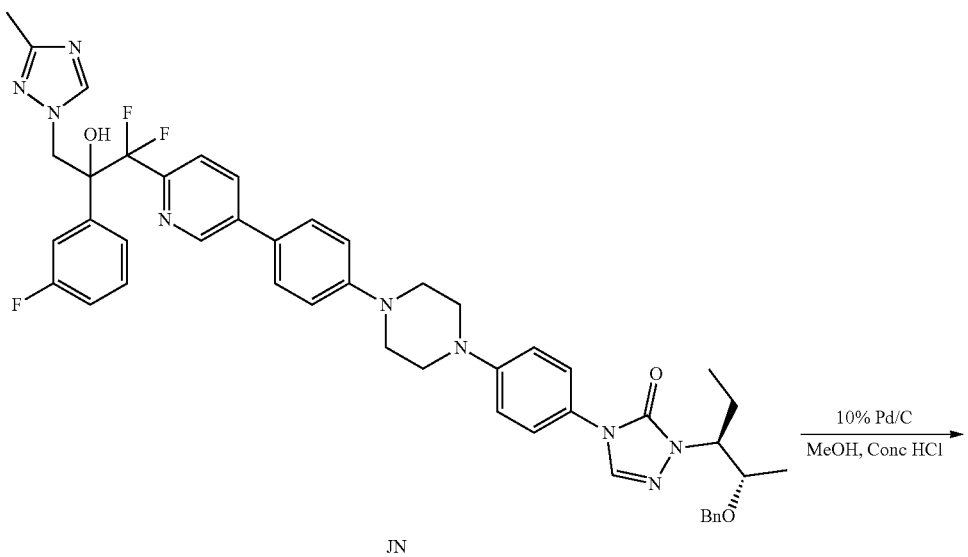

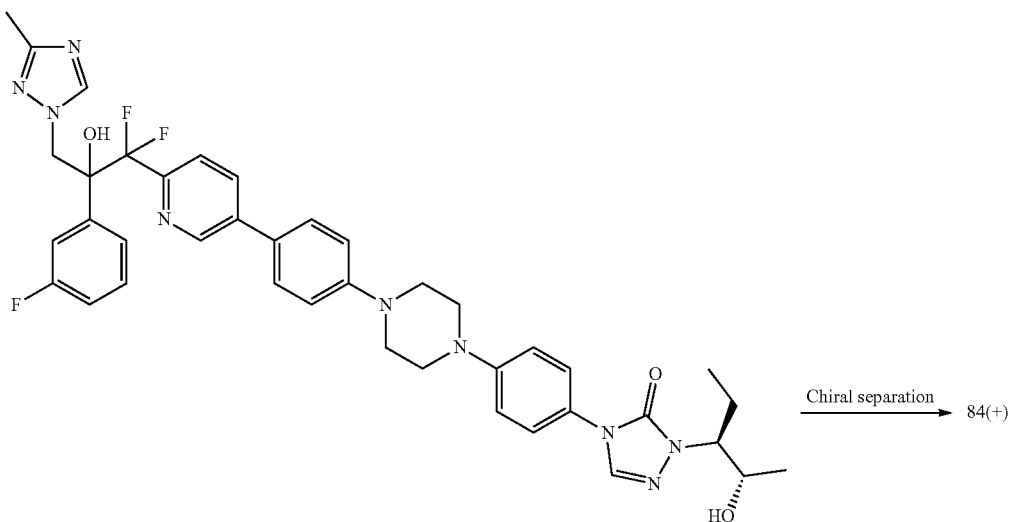

To a stirred solution of compound JN (400 mg, 0.47 mmol) in MeOH (10 mL) under argon atmosphere were added 10% Pd/C (200 mg) and concentrated hydrochloric acid (0.1 mL) at RT. The reaction mixture was stirred at RT for 3 h under hydrogen atmosphere. The progress of the reaction was monitored by TLC. The reaction mixture was filtered through celite, the filtrate was concentrated under reduced pressure. The residue was diluted with saturated sodium bicarbonate solution (20 mL) and extracted with EtOAc (2×20 mL). The combined organic extracts were dried over anhydrous $Na_2SO_4$ and concentrated under reduced pressure to afford 84 (280 mg, 0.37 mmol, 78%) as an off-white solid.

Chiral Preparative HPLC Details for 84(+)

84 (280 mg, 0.37 mmol) was separated by normal-phase preparative high performance liquid chromatography (CHIRALPAK-IA®, 250×20 mm, 5μ; using 0.1% DEA in n-Hexane:(B) $CH_2Cl_2$:MeOH (50:50) (35:65); Flow rate: 20 mL/min) to obtain 84(+) (80 mg). Chiral HPLC Purity: 99.68%. $R_t$=16.68 min (CHIRALPAK-IA®, 250×4.6 mm, 5μ; mobile phase (A) 0.1% DEA in n-Hexane:(B) $CH_2Cl_2$: MeOH (50:50) (35:65); flow Rate: 1.0 mL/min); $^1$H NMR (400 MHz, DMSO-$d_6$): δ 8.88 (d, J=2.0 Hz, 1H), 8.33 (s, 1H), 8.12 (dd, J=8.3, 2.2 Hz, 1H), 8.04 (s, 1H), 7.69 (d, J=8.9 Hz, 2H), 7.53 (d, J=9.0 Hz, 2H), 7.45 (d, J=8.4 Hz, 1H), 7.33-7.24 (m, 2H), 7.21-7.18 (m, 1H), 7.16-7.04 (m, 5H), 6.84 (s, 1H), 5.18 (d, J=14.5 Hz, 1H), 4.82 (d, J=14.6 Hz, 1H), 4.65 (d, J=4.9 Hz, 1H), 3.90-3.74 (m, 2H), 3.45-3.35 (m, 8H), 2.04 (s, 3H), 1.79-1.65 (m, 2H), 1.12 (d, J=6.0 Hz, 3H), 0.75 (t, J=7.3 Hz, 3H); MS (ESI): m/z 754.8 $[M+H]^+$; HPLC: 99.24%; Optical rotation $[α]_D^{20}$: +53.7 (c=0.1% in MeOH).

Example 85(+)

(+)-4-(4-(4-(4-(6-(1,1-difluoro-2-(3-fluorophenyl)-2-hydroxy-3-(5-methyl-1H-1,2,4-triazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (85(+))

2-((2S,3S)-2-(benzyloxy) pentan-3-yl)-4-(4-(4-(4-(6-(1,1-difluoro-2-(3-fluorophenyl)-2-hydroxy-3-(5-methyl-1H-1,2,4-triazol-1-yl) propyl) pyridin-3-yl) phenyl) piperazin-1-yl) phenyl)-2,4-dihydro-3H-1,2,4-triazol-3-one (OR)

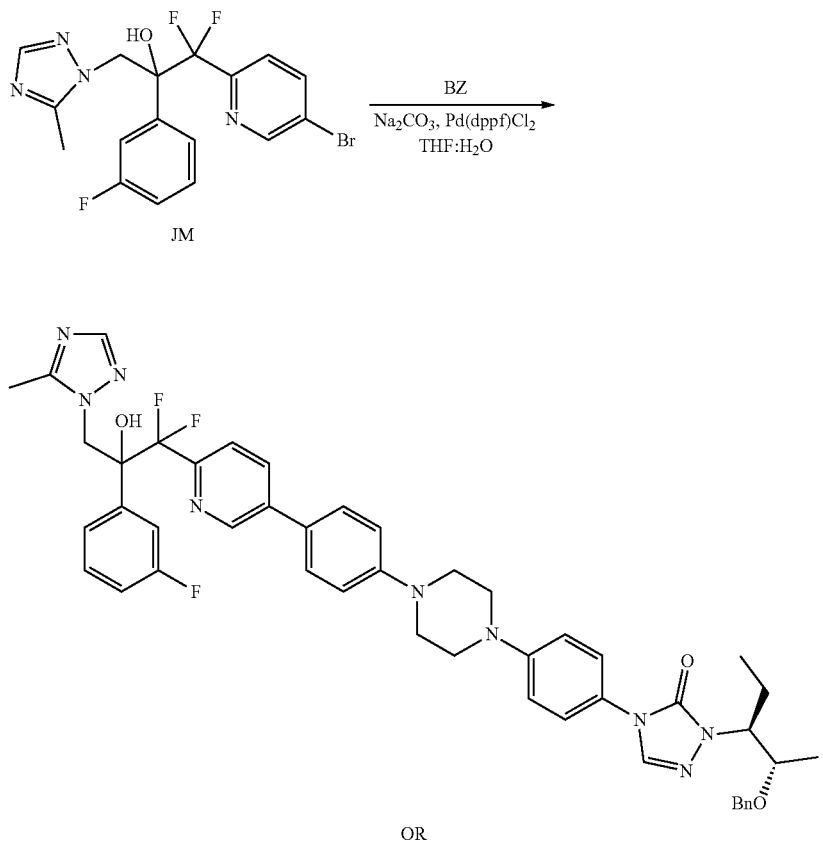 [SMILES: Cc1ncnn1CC(O)(c1cccc(F)c1)C(F)(F)c1ccc(Br)cn1 ; CC[C@@H]([C@H](C)OCc1ccccc1)n1ncn(-c2ccc(N3CCN(c4ccc(-c5ccc(C(F)(F)C(O)(Cn6ncnc6C)c6cccc(F)c6)nc5)cc4)CC3)cc2)c1=O]

To a stirred solution of compound JM (150 mg, 0.40 mmol) in THF:H2O (4:1, 10 mL) under argon atmosphere were added compound BZ (263 mg, 0.42 mmol), sodium carbonate (112 mg, 1.05 mmol) and purged under argon for 20 min at RT. Then Pd(dppf)Cl₂ (26 mg, 0.03 mmol) was added and the reaction mixture was purged under argon for 10 min at RT. The reaction mixture was stirred at reflux for 3 h. The progress of the reaction was monitored by TLC. The reaction mixture was diluted with water (20 mL) and extracted with EtOAc (2×20 mL). The combined organic extracts were dried over anhydrous Na₂SO₄ and concentrated under reduced pressure. The crude material was purified by silica gel column chromatography (eluent: 2% MeOH/CH₂Cl₂) to afford compound OR (210 mg, 0.25 mmol, 71%) as an off-white solid. ¹H NMR (500 MHz, CDCl₃): δ 8.65 (s, 1H), 7.88 (dd, J=8.1, 2.3 Hz, 1H), 7.59 (d, J=8.1 Hz, 2H), 7.56 (d, J=4.6 Hz, 2H), 7.50 (d, J=8.7 Hz, 2H), 7.42 (d, J=8.7 Hz, 8H), 7.33-7.28 (m, 1H), 7.25-7.21 (m, 4H), 6.95-6.91 (m, 1H), 6.89 (s, 1H), 4.93 (d, J=14.5 Hz, 1H), 4.76 (d, J=14.5 Hz, 1H), 4.63 (d, J=12.2 Hz, 1H), 4.41 (d, J=12.2 Hz, 1H), 4.21-4.17 (m, 1H), 3.83-3.78 (m, 1H), 3.50-3.31 (m, 8H), 2.45 (s, 3H), 1.98-1.90 (m, 1H), 1.83-1.78 (m, 1H), 1.28 (d, J=5.8 Hz, 3H), 0.89 (t, J=7.2 Hz, 3H).

(+)-4-(4-(4-(4-(6-(1,1-difluoro-2-(3-fluorophenyl)-2-hydroxy-3-(5-methyl-1H-1,2,4-triazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (85(+))

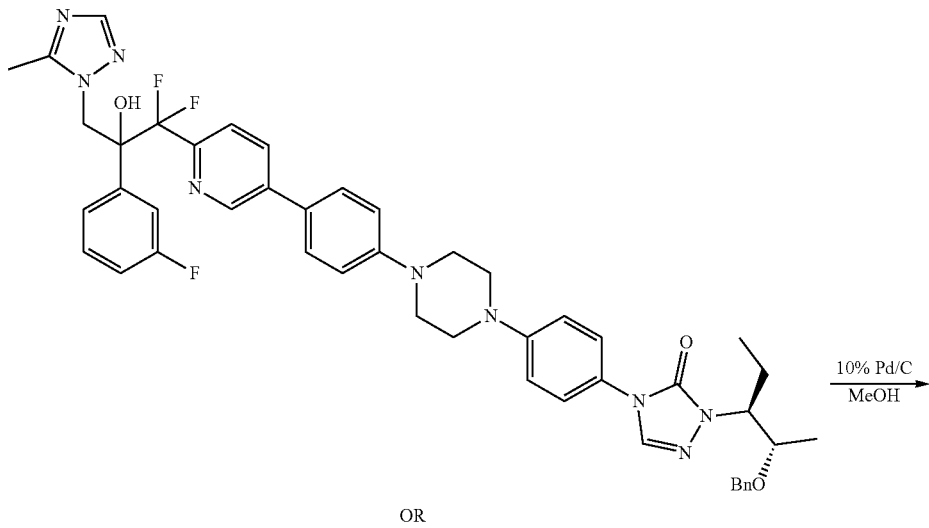

OR

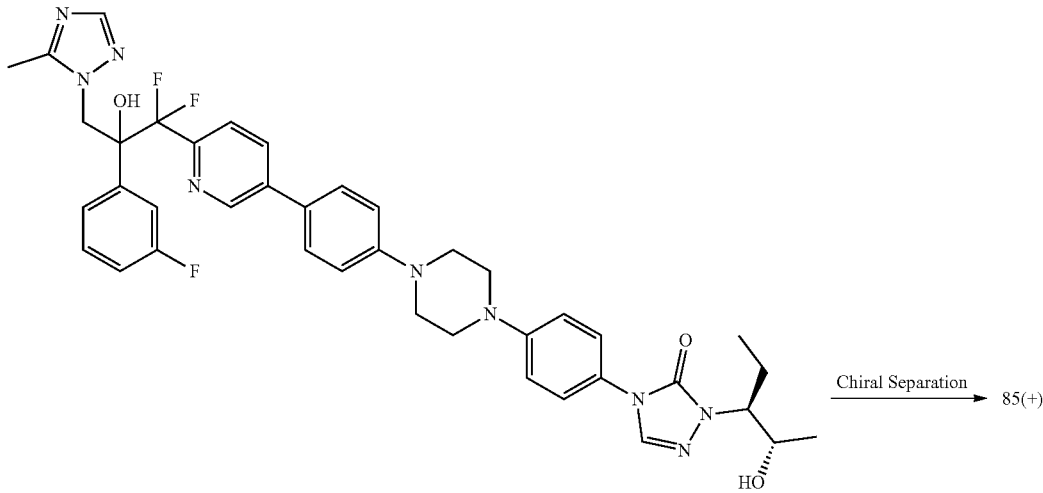

To a stirred solution of compound OR (210 mg, 0.25 mmol) in MeOH (5 mL) under argon atmosphere were added 10% Pd/C (100 mg) and concentrated hydrochloric acid (0.1 mL) at RT. The reaction mixture was stirred at RT for 3 h under hydrogen atmosphere. The progress of the reaction was monitored by TLC. The reaction mixture was filtered through celite, the filtrate was concentrated under reduced pressure. The residue was diluted with saturated sodium bicarbonate solution (20 mL) and extracted with EtOAc (2×20 mL). The combined organic extracts were dried over anhydrous $Na_2SO_4$ and concentrated under reduced pressure to afford 85 (150 mg, 0.19 mmol, 13%) as an off-white solid.

Chiral Preparative HPLC Details for 85(+) 85 (150 mg, 0.19 mmol) was separated by normal-phase preparative high performance liquid chromatography (CHIRALPAK-IA®, 250×20 mm, 5µ; using 0.1% DEA in n-Hexane:(B) $CH_2Cl_2$: MeOH (50:50) (35:65); Flow rate: 20 mL/min) to obtain 85(+) (25 mg). Chiral HPLC Purity: 100%, $R_t$=9.63 min (CHIRALPAK-IA®, 250×4.6 mm, 5µ; mobile phase (A) 0.1% DEA in n-Hexane:(B) $CH_2Cl_2$:MeOH (50:50) (35:65); flow Rate: 1.0 mL/min); $^1$H NMR (500 MHz, DMSO-$d_6$): δ 8.89 (d, J=1.7 Hz, 1H), 8.33 (s, 1H), 8.14 (dd, J=8.4, 2.0 Hz, 1H), 7.69 (d, J=8.7 Hz, 2H), 7.56 (s, 1H), 7.54-7.52 (m, 3H), 7.34-7.28 (m, 2H), 7.23-7.21 (m, 1H), 7.16-7.06 (m, 5H), 6.75 (s, 1H), 5.10-4.89 (m, 2H), 4.66 (d, J=5.2 Hz, 1H), 3.96-3.75 (m, 2H), 3.43-3.34 (m, 8H), 2.25 (s, 3H), 1.77-1.64 (m, 2H), 1.12 (d, J=5.8 Hz, 3H), 0.74 (t, J=7.5 Hz, 3H); MS (ESI): m/z 754.3 [M+H]$^+$; HPLC: 99.70%; Optical rotation $[\alpha]_D^{20}$: +38.8 (c=0.1% in MeOH).

Example 86

(2R)-2-(2,4-difluorophenyl)-1,1-difluoro-3-(1H-tetrazol-1-yl)-1-(5-(4-(4-(3-(2,2,2-trifluoro-1-hydroxyethyl) phenyl) piperazin-1-yl) phenyl)pyridin-2-yl) propan-2-ol (86)

1-(3-bromophenyl)-2,2,2-trifluoroethan-1-ol (JP)

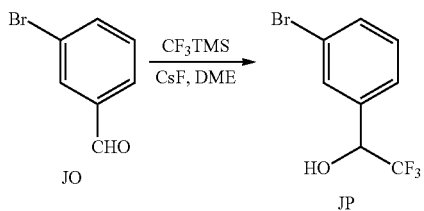 [SMILES: O=Cc1cccc(Br)c1 ; OC(c1cccc(Br)c1)C(F)(F)F ; "CF3TMS"]

To a stirred solution of 3-bromobenzaldehyde (JO; 1 g, 5.40 mmol) in THF (20 mL) under argon atmosphere were added cesium fluoride (0.41 g, 2.70 mmol) and $CF_3TMS$ (1.15 g, 8.1 mmol) at 0° C. The reaction mixture was warmed to RT and stirred for 30 min. The progress of the reaction was monitored by TLC. The reaction mixture was quenched with 1.0N HCl solution (20 mL) at 0° C., stirred for 2 h, diluted with water (50 mL) and extracted with EtOAc (2×50 mL). The combined organic layers were dried over anhydrous $Na_2SO_4$ and concentrated under reduced pressure to obtain compound JP (1.5 g, crude) as colorless liquid which was used in the next step without further purification. $^1$H NMR (400 MHz, CDCl$_3$): δ 7.65 (s, 1H), 7.57-7.51 (m, 1H), 7.41 (dd, J=7.8, 0.6 Hz, 1H), 7.32-7.26 (m, 1H), 5.03-4.98 (m, 1H), 2.67 (brs, 1H).

1-(3-(4-(4-bromophenyl) piperazin-1-yl) phenyl)-2,2,2-trifluoroethan-1-ol (JQ)

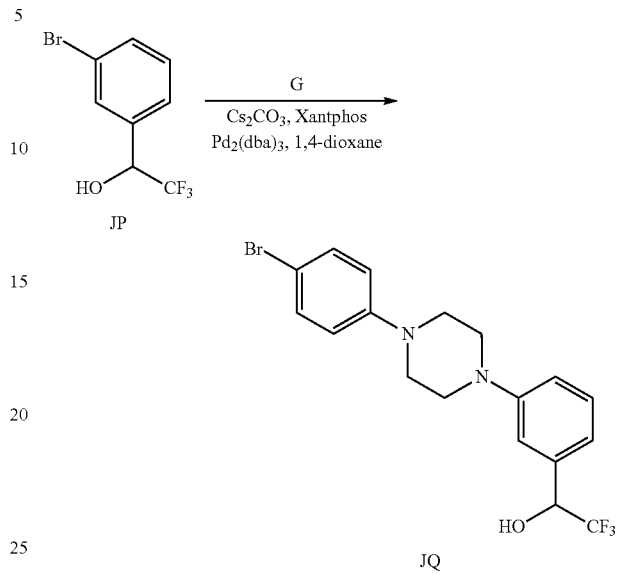

To a stirred solution of compound JP (1.4 g, 5.5 mmol) in 14-dioxane (20 mL) under argon atmosphere were added G (1.32 g, 5.5 mmol), cesium carbonate (5.4 g, 16.5 mmol), Xantphos (220 mg, 0.38 mmol) and purged under argon for 20 min at RT. Then Pd$_2$ (dba)$_3$ (250 mg, 0.27 mmol) was added to the reaction mixture at RT and stirred at 110° C. for 16 h in a sealed tube. The progress of the reaction was monitored by TLC, the reaction mixture was diluted with water (50 mL) and extracted with $CH_2Cl_2$ (2×50 mL). The combined organic extracts were washed with water (50 mL), brine (50 mL), dried over anhydrous $Na_2SO_4$ and concentrated under reduced pressure. The crude material was purified by silica gel column chromatography (eluent: 30% EtOAc/Hexane) to afford compound JQ (300 mg, 0.72 mmol, 13%) as yellow solid. $^1$H NMR (400 MHz, DMSO-$d_6$): δ 7.38 (d, J=9.0 Hz, 2H), 7.26 (t, J=7.9 Hz, 1H), 7.11 (s, 1H), 7.03-6.99 (m, 1H), 6.97 (d, J=9.2 Hz, 2H), 6.93 (d, J=7.6 Hz, 1H), 6.72 (d, J=5.6 Hz, 1H), 5.17-4.90 (m, 1H), 3.28 (s, 8H).

2,2,2-trifluoro-1-(3-(4-(4-(4,4,5,5-tetramethyl-1,3,2-dioxaborolan-2-yl) phenyl) piperazin-1-yl) phenyl) ethan-1-ol (JR)

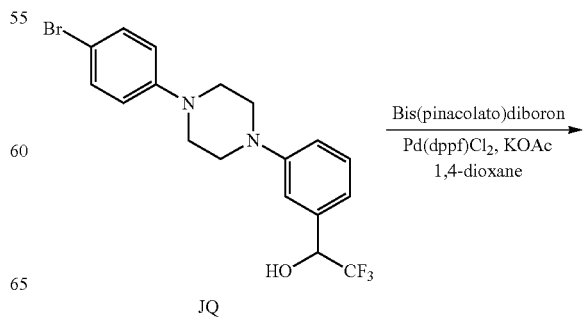

-continued

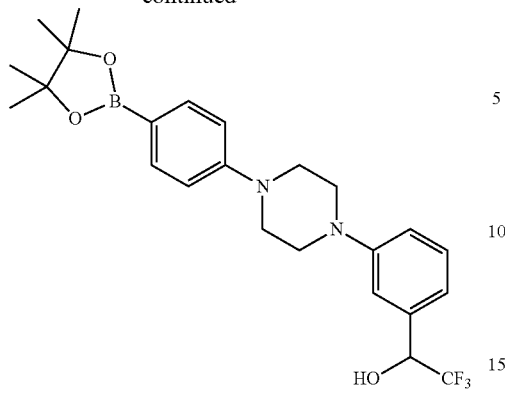

JR

To a stirred solution of compound JQ (300 mg, 0.72 mmol) in 1,4-dioxane (10 mL) under argon atmosphere were added bis(pinacolato)diboron (294 mg, 1.16 mmol) and potassium acetate (213 mg, 2.17 mmol) at RT and purged under argon for 15 min. Then Pd(dppf)Cl$_2$ (53 mg, 0.07 mmol) was added and the reaction mixture was purged under argon for 5 min at RT. The reaction mixture was stirred at 110° C. for 16 h. The reaction mixture was quenched with water (10 mL) and extracted with CH$_2$Cl$_2$ (2×10 mL). The combined organic layers were washed with water (10 mL), brine (10 mL), dried over anhydrous Na$_2$SO$_4$ and concentrated under reduced pressure. The crude material was purified by silica gel column chromatography (eluent: 30% EtOAc/Hexane) to afford compound JR (300 mg, crude) as yellow solid. $^1$H NMR (500 MHz, DMSO-d$_6$): δ 7.53 (d, J=8.7 Hz, 2H), 7.29-7.21 (m, 1H), 7.10 (s, 1H), 6.99 (d, J=8.7 Hz, 1H), 6.96 (d, J=8.7 Hz, 1H), 6.91 (d, J=7.5 Hz, 1H), 6.71 (d, J=5.2 Hz, 1H), 5.10-5.02 (m, 1H), 3.92-3.88 (m, 1H), 3.38-3.34 (m, 4H), 3.28-3.24 (m, 4H), 1.25 (s, 12H).

(2R)-2-(2,4-difluorophenyl)-1,1-difluoro-3-(1H-tetrazol-1-yl)-1-(5-(4-(4-(3-(2,2,2-trifluoro-1-hydroxyethyl) phenyl) piperazin-1-yl) phenyl)pyridin-2-yl) propan-2-ol (86)

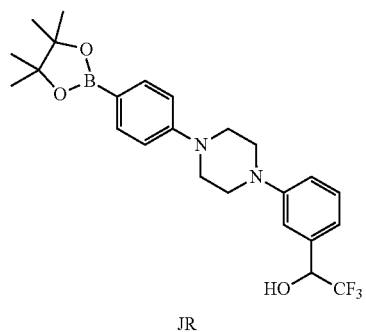

-continued

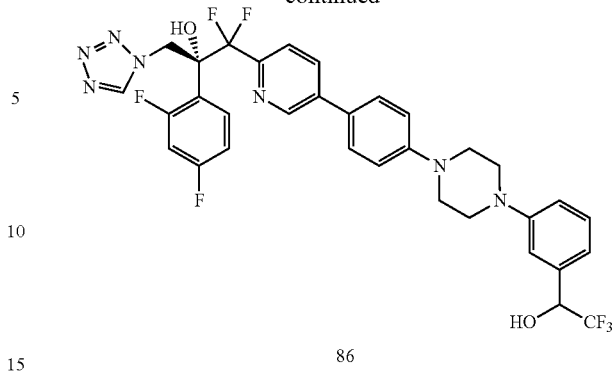

86

To a stirred solution of compound JR (300 mg, 0.65 mmol) in THF:H2O (4:1, 20 mL) under argon atmosphere were added Int-1 (280 mg, 0.65 mmol), sodium carbonate (207 mg, 1.95 mmol) and purged under argon for 10 min at RT. Then Pd(dppf)Cl$_2$ (47.5 mg, 0.06 mmol) was added to the reaction mixture at RT and stirred at 90° C. for 16 h. The reaction mixture was diluted with water (20 mL) and extracted with CH$_2$Cl$_2$ (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 50% acetone/Hexane) to afford 86 (100 mg, 0.14 mmol, 21.5%) as an off-white solid. $^1$H NMR (400 MHz, DMSO-d$_6$): δ 9.14 (s, 1H), 8.91 (d, J=2.0 Hz, 1H), 8.17 (dd, J=8.3, 2.2 Hz, 1H), 7.70 (d, J=8.9 Hz, 2H), 7.48 (d, J=8.2 Hz, 1H), 7.34-7.25 (m, 3H), 7.24-7.09 (m, 4H), 7.06-6.84 (m, 3H), 6.73 (d, J=5.6 Hz, 1H), 5.67 (d, J=14.6 Hz, 1H), 5.11 (d, J=14.6 Hz, 1H), 5.08-5.04 (m, 1H), 3.44-3.36 (m, 4H), 3.34-3.27 (m, 4H); MS (ESI): m/z 688.2 [M+H]$^+$; HPLC: 96.01%; Optical rotation [α]$_D^{19}$: +36.1 (c=0.1% in MeOH).

Example 87

(R)-4-(5-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-(2,2,2-trifluoroethyl)-2,4-dihydro-3H-1,2,4-triazol-3-one (87)

N-(5-iodopyridin-2-yl) hydrazinecarboxamide (JS)

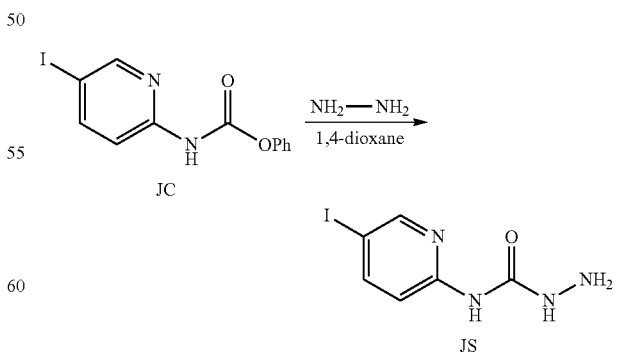

To a stirred solution of compound JC (200 mg, 0.58 mmol) in 1,4-dioxane (10 mL) under argon atmosphere was added hydrazine hydrate (0.15 mL, 3.17 mmol) at RT. The reaction mixture was stirred at 110° C. for 3 h. The progress of the reaction was monitored by TLC. The reaction mixture was diluted with water (20 mL) and extracted with EtOAc (2×20 mL). The combined organic layers were dried over anhydrous $Na_2SO_4$ and concentrated under reduced pressure to obtain compound JS (150 g, 0.54 mmol, 93%) as an off-white solid. $^1$H NMR (500 MHz, DMSO-$d_6$): δ 9.16 (brs, 1H), 8.39 (s, 1H), 8.00 (d, J=7.5 Hz, 2H), 7.46 (br s, 1H), 4.64 (brs, 1H), 4.20 (brs, 1H).

4-(5-iodopyridin-2-yl)-2,4-dihydro-3H-1,2,4-triazol-3-one (JT)

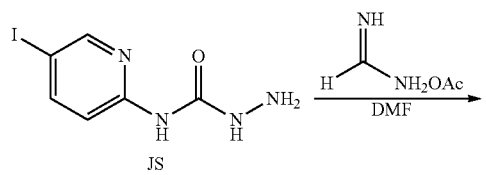

To a stirred solution of compound JS (5.0 g, 18 mmol) in DMF (50 mL) under argon atmosphere was added formamidine acetate (7.5 g, 72 mmol) at RT. The reaction mixture was stirred at 110° C. for 3 h. The reaction mixture was diluted with water (100 mL), filtered, washed with water (2×100 mL), dried under reduced pressure. The crude material was purified by silica gel column chromatography (eluent: 40% EtOAc/Hexane) to afford compound JT (2.0 g, 7 mmol, 38%) as an off-white solid. $^1$H NMR (400 MHz, DMSO-$d_6$): δ 12.15 (brs, 1H), 8.71 (dd, J=2.3, 0.6 Hz, 1H), 8.52 (s, 1H), 8.35 (dd, J=8.7, 2.3 Hz, 1H), 8.06 (dd, J=8.7, 0.6 Hz, 1H).

4-(5-iodopyridin-2-yl)-2-(2,2,2-trifluoroethyl)-2,4-dihydro-3H-1,2,4-triazol-3-one (J)

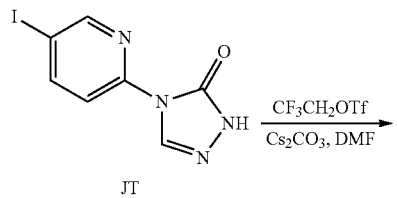

To a stirred solution of compound JT (100 mg, 0.34 mmol) in DMF (3 mL) under argon atmosphere were added $CF_3CH_2OTf$ (241 mg, 1.04 mmol), cesium carbonate (340 mg, 1.04 mmol) at RT and stirred for 2 h. The progress of the reaction was monitored by TLC. The reaction mixture was diluted with water (20 mL) and extracted with EtOAc (2×20 mL). The combined organic layers were dried over anhydrous $Na_2SO_4$ and concentrated under reduced pressure to obtain compound JU (120 mg, crude) as an off-white solid used in the next step without further purification. $^1$H NMR (500 MHz, DMSO-$d_6$): δ 8.76 (s, 1H), 8.74 (d, J=1.7 Hz, 1H), 8.40 (dd, J=8.4, 2.0 Hz, 1H), 8.00 (d, J=8.7 Hz, 1H), 4.75-4.70 (m, 2H).

4-(5-(4-(4-bromophenyl) piperazin-1-yl) pyridin-2-yl)-2-(2,2,2-trifluoroethyl)-2,4-dihydro-3H-1,2,4-triazol-3-one (JV)

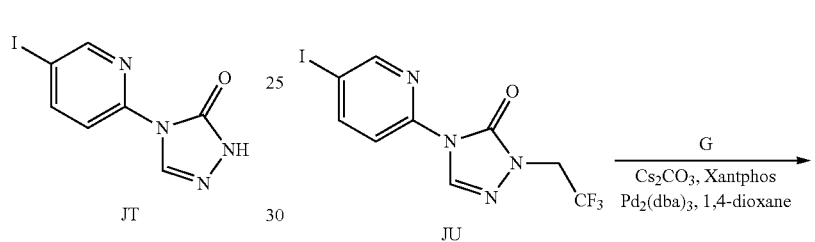

To a stirred solution of compound JU (1.0 g, 2.7 mmol) in 1,4-dioxane (20 mL) under argon atmosphere were added G (650 mg, 2.70 mmol), cesium carbonate (2.6 g, 8.1 mmol), Xantphos (110 mg, 0.19 mmol) and purged under argon for 20 min at RT. Then $Pd_2$(dba)$_3$ (120 mg, 0.13 mmol) was added to the reaction mixture at RT and stirred at 90° C. for 16 h in a sealed tube. The progress of the reaction was monitored by TLC, the reaction mixture was diluted with water (50 mL) and extracted with $CH_2Cl_2$ (2×50 mL). The combined organic layers were dried over anhydrous $Na_2SO_4$ and concentrated under reduced pressure. The crude material was purified by silica gel column chromatography (eluent: 40% EtOAc/Hexane) to afford compound JV (380 mg, 0.78 mmol, 78%) as yellow solid. $^1$H NMR (400 MHz, DMSO-$d_6$): δ 8.66 (s, 1H), 8.25 (d, J=2.9 Hz, 1H), 7.91 (d, J=9.2 Hz, 1H), 7.66 (dd, J=9.0, 3.1 Hz, 1H), 7.38 (d, J=9.0 Hz, 2H), 6.98 (d, J=9.2 Hz, 2H), 4.74-4.69 (m, 2H), 3.41-3.35 (m, 4H), 3.35-3.30 (m, 4H).

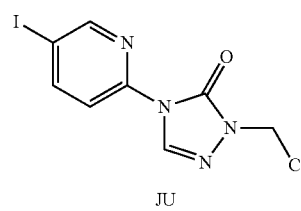

4-(5-(4-(4-(4,4,5,5-tetramethyl-1,3,2-dioxaborolan-2-yl) phenyl) piperazin-1-yl) pyridin-2-yl)-2-(2,2,2-trifluoroethyl)-2,4-dihydro-3H-1,2,4-triazol-3-one (JW)

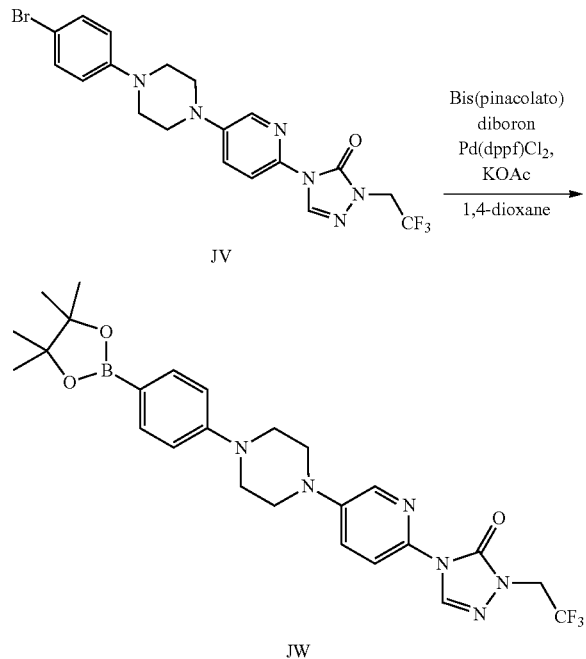

To a stirred solution of compound JV (380 mg, 0.78 mmol) in 1,4-dioxane (20 mL) under argon atmosphere were added bis(pinacolato)diboron (320 mg, 1.26 mmol) and potassium acetate (231.7 ng, 2.36 mmol) at RT and purged under argon for 15 min. Then Pd(dppf)Cl$_2$ (57.6 mg, 0.07 mmol) was added and the reaction mixture was purged under argon for 5 min at RT. The reaction mixture was stirred at 110° C. for 16 h. The reaction mixture was quenched with water (20 mL) and extracted with CH$_2$Cl$_2$ (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 40% EtOAc/Hexane) to afford compound JW (280 mg, 0.53 mmol, 68%) as an off-white solid. $^1$H NMR (500 MHz, DMSO-d$_6$): δ 8.66 (s, 1H), 8.24 (d, J=2.9 Hz, 1H), 7.91 (d, J=8.7 Hz, 1H), 7.66 (dd, J=9.0, 3.2 Hz, 1H), 7.54 (d, J=8.7 Hz, 2H), 6.99 (d, J=8.7 Hz, 2H), 4.73-4.68 (m, 2H), 3.39 (s, 8H), 1.27 (s, 12H).

(R)-4-(5-(4-(4-(((6-(2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-(2,2,2-trifluoroethyl)-2,4-dihydro-3H-1,2,4-triazol-3-one (87)

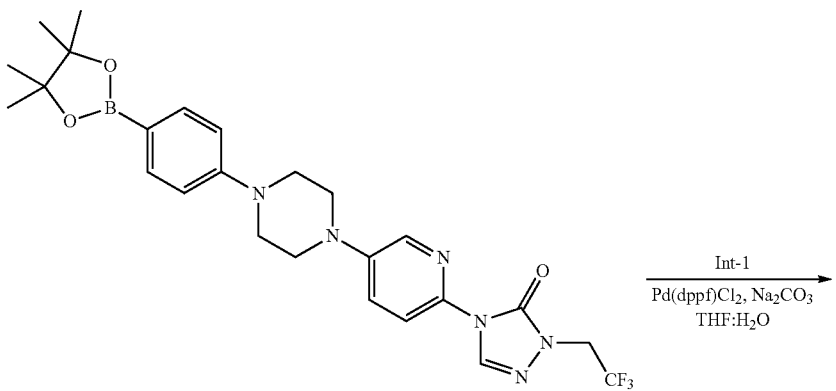

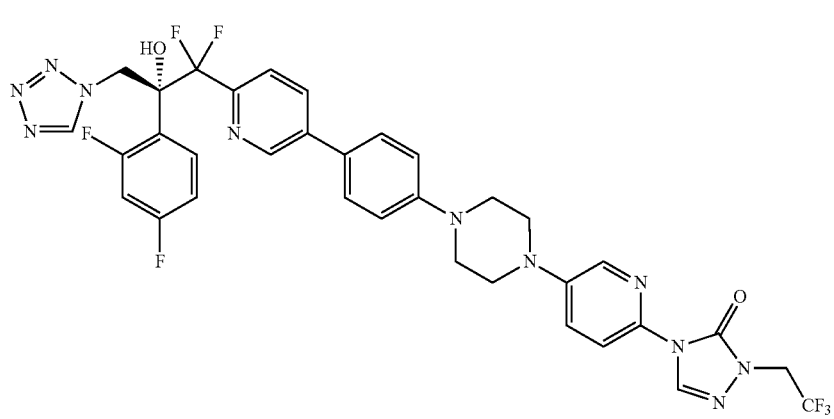

To a stirred solution of compound JW (280 mg, 0.53 mmol) in THF:H2O (4:1, 20 mL) under argon atmosphere were added Int-1 (227 mg, 0.53 mmol), sodium carbonate (168 mg, 1.58 mmol) and purged under argon for 10 min at RT. Then Pd(dppf)Cl$_2$ (38.7 mg, 0.05 mmol) was added to the reaction mixture at RT and stirred at 90° C. for 16 h. The reaction mixture was diluted with water (20 mL) and extracted with CH$_2$Cl$_2$ (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 50% acetone/Hexane) to afford 87 (100 mg, 0.13 mmol, 24%) as an off-white solid. $^1$H NMR (400 MHz, DMSO-d$_6$): δ 9.15 (s, 1H), 8.91 (d, J=2.1 Hz, 1H), 8.66 (s, 1H), 8.27 (d, J=2.9 Hz, 1H), 8.17 (dd, J=8.2, 2.1 Hz, 1H), 7.92 (d, J=9.0 Hz, 1H), 7.77-7.63 (m, 3H), 7.49 (d, J=8.2 Hz, 1H), 7.33-7.25 (m, 2H), 7.24-7.12 (m, 3H), 6.93-6.88 (m, 1H), 5.67 (d, J=14.6 Hz, 1H), 5.11 (d, J=14.6 Hz, 1H), 4.74-4.67 (m, 2H), 3.43 (s, 8H); MS (ESI): m/z 756.7 [M+H]$^+$; HPLC: 96.13%; Optical rotation [α]$_D^{20}$: +89.3 (c=0.1% in CH$_2$Cl$_2$).

Example 88

2-amino-N-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-4,4,4-trifluorobutanamide (88)

2-((tert-butoxycarbonyl) amino)-4,4,4-trifluorobutanoic acid (JI)

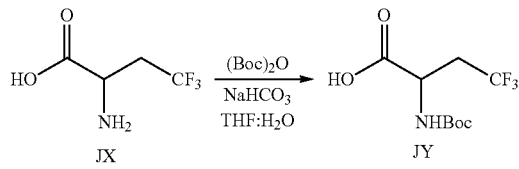 [SMILES: "(Boc)2O" ; NC(CC(F)(F)F)C(=O)O ; CC(C)(C)OC(=O)NC(CC(F)(F)F)C(=O)O]

To a stirred solution of 2-amino-4,4,4-trifluorobutanoic acid (JX; 500 mg, 3.18 mmol) in THF:H2O (1:1, 10 mL) under argon atmosphere were added sodium bicarbonate (547 mg, 6.36 mmol) and boc anhydride (694 mg, 3.18 mmol) at 0° C. The reaction mixture was stirred at 80° C. for 16 h. The reaction mixture was acidified (pH=1) with citric acid solution (10 mL) and extracted with EtOAc (2×10 mL). The combined organic extracts were washed with water (10 mL), brine (30 mL), dried over anhydrous Na$_2$SO$_4$ and concentrated under reduced pressure to obtain compound JY (700 mg, crude) as an off-white solid. $^1$H NMR (400 MHz, DMSO-d$_6$): δ 12.95 (br s, 1H), 7.33 (d, J=8.5 Hz, 1H), 4.25-4.16 (m, 1H), 2.78-2.69 (m, 1H), 2.67-2.56 (m, 1H), 1.38 (s, 9H).

Tert-butyl (1-((4-(4-(4-bromophenyl) piperazin-1-yl) phenyl) amino)-4,4,4-trifluoro-1-oxobutan-2-yl) carbamate (JZ)

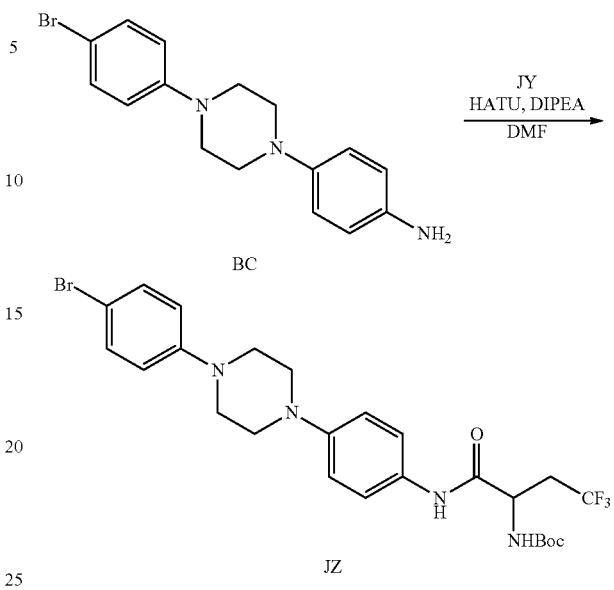

To a stirred solution of compound JY (930 mg, 2.20 mmol) in DMF (15 mL) under argon atmosphere were added HATU (1.77 g, 4.66 mmol), diisopropyl ethyl amine (930 mg, 2.20 mmol) and compound BC (600 mg, 2.33 mmol) at 0° C. The reaction mixture was stirred at RT for 16 h. The reaction mixture was diluted with water (20 mL) and extracted with EtOAc (2×20 mL). The combined organic extracts were washed with water (10 mL), brine (30 mL), dried over anhydrous Na$_2$SO$_4$ and concentrated under reduced pressure. The crude material was purified by silica gel column chromatography (eluent: 30% EtOAc/Hexane) to afford compound JZ (1.2 g, 2.10 mmol, 77%) as an off-white solid. $^1$H NMR (400 MHz, DMSO-d$_6$): δ 9.89 (s, 1H), 7.46 (d, J=9.2 Hz, 2H), 7.37 (d, J=9.0 Hz, 2H), 7.27 (d, J=8.4 Hz, 1H), 6.96 (d, J=9.0 Hz, 4H), 4.43 (d, J=4.4 Hz, 1H), 3.28-3.20 (m, 8H), 2.81-2.55 (m, 2H), 1.39 (s, 9H)

tert-butyl (4,4,4-trifluoro-1-oxo-1-((4-(4-(4-(4,4,5,5-tetramethyl-1,3,2-dioxaborolan-2-yl) phenyl) piperazin-1-yl) phenyl) amino) butan-2-yl) carbamate (14)

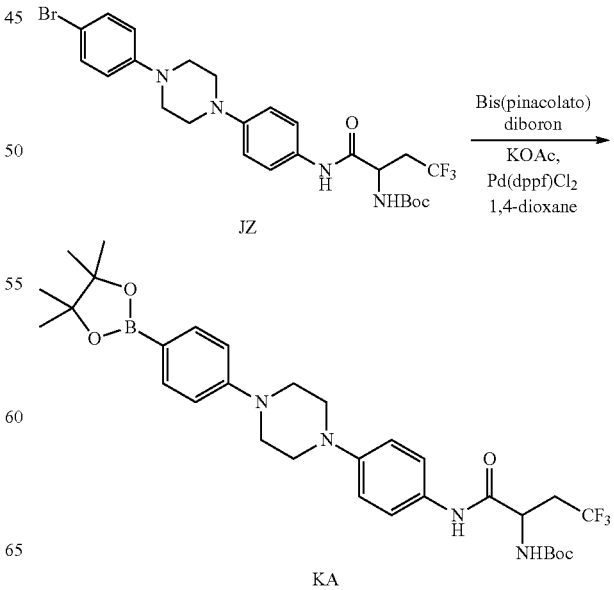

To a stirred solution of compound JZ (350 mg, 0.61 mmol) in 1,4-dioxane (15 mL) under argon atmosphere were added bis(pinacolato)diboron (248 mg, 0.98 mmol), KOAc (180 mg, 1.83 mmol) at RT and purged under argon for 15 min. Then Pd(dppf)Cl$_2$ (45 mg, 0.06 mmol) was added to the reaction mixture at RT and again purged under argon for 5 min at RT, stirred at 110° C. for 16 h in a sealed tube. The progress of the reaction was monitored by TLC. The reaction mixture was diluted with water (30 mL) and extracted with EtOAc (2×30 mL). The combined organic extracts were washed with water (30 mL), brine (30 mL), dried over anhydrous Na$_2$SO$_4$ and concentrated under reduced pressure. The crude material was purified by silica gel column chromatography (eluent: 40% EtOAc/Hexane) to afford compound KA (260 mg, crude) as an off-white solid. $^1$H NMR (400 MHz, DMSO-d$_6$): δ 9.92 (s, 1H), 7.54 (d, J=8.7 Hz, 2H), 7.47 (d, J=9.0 Hz, 2H), 7.30 (d, J=8.4 Hz, 1H), 6.96 (dd, J=8.9, 2.1 Hz, 4H), 4.42 (brs, 1H), 3.39-3.35 (m, 4H), 3.22-3.20 (m, 4H), 2.78-2.56 (m, 2H), 1.39 (s, 9H), 1.07 (s, 12H).

tert-butyl (1-((4-(4-(4-(6-((R)-2-(2,4-difluorophenyl)-1,1-difluoro-2-hydroxy-3-(1H-tetrazol-1-yl)propyl) pyridin-3-yl) phenyl) piperazin-1-yl) phenyl) amino)-4,4,4-trifluoro-1-oxobutan-2-yl) carbamate (KB)

To a stirred solution of Int-1 (150 mg, 0.34 mmol) in THF:H2O (4:2, 10 mL) under argon atmosphere were added compound KA (257 mg, 0.41 mmol), sodium carbonate (110 mg, 1.04 mmol) at RT and purged under argon for 10 min. Then Pd(dppf)Cl$_2$ (25 mg, 0.03 mmol) was added to the reaction mixture at RT and stirred at 80° C. for 5 h in a sealed tube. The progress of the reaction was monitored by TLC. The reaction mixture was diluted with water (10 mL) and extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluent: 60% EtOAc/Hexane) to afford compound KB (100 mg, 0.12 mmol, 34%) as an off-white solid. $^1$H NMR (400 MHz, DMSO-d$_6$): δ 9.93 (s, 1H), 9.15 (s, 1H), 8.91 (s, 1H), 8.17 (d, J=8.0 Hz, 1H), 7.70 (d, J=8.7 Hz, 2H), 7.48 (d, J=8.9 Hz, 3H), 7.33-7.26 (m, 3H), 7.23-7.16 (m, 1H), 7.14 (d, J=8.7 Hz, 2H), 6.98 (d, J=8.9 Hz, 2H), 6.91 (t, J=8.5 Hz, 1H), 5.67 (d, J=14.6 Hz, 1H), 5.11 (d, J=14.6 Hz, 1H), 4.44 (brs, 1H), 3.40-3.38 (m, 4H), 3.26-3.24 (m, 4H), 2.79-2.55 (m, 2H), 1.39 (s, 9H).

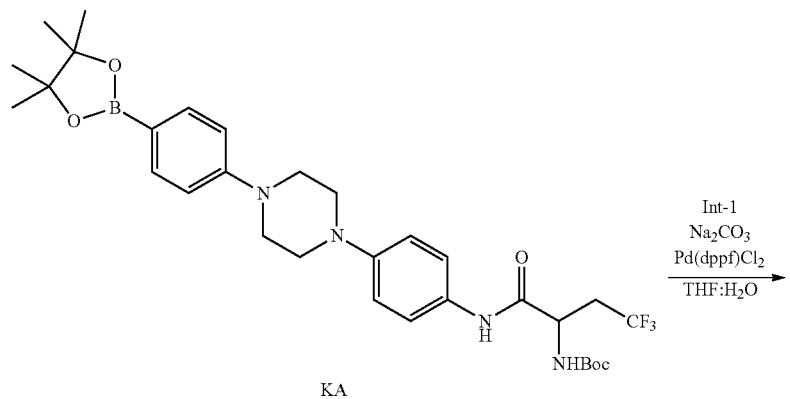

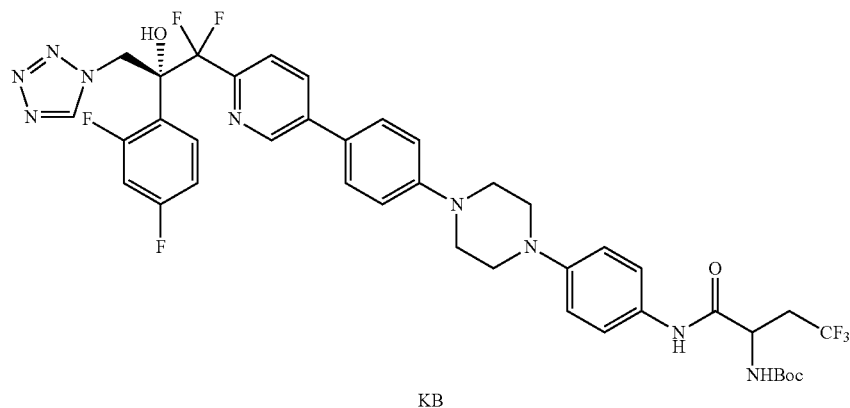

2-amino-N-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-4,4,4-trifluorobutanamide (88)

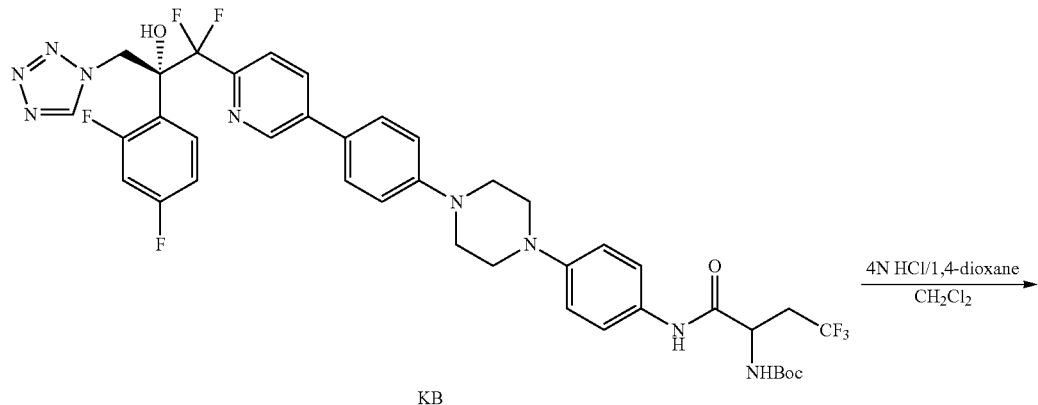

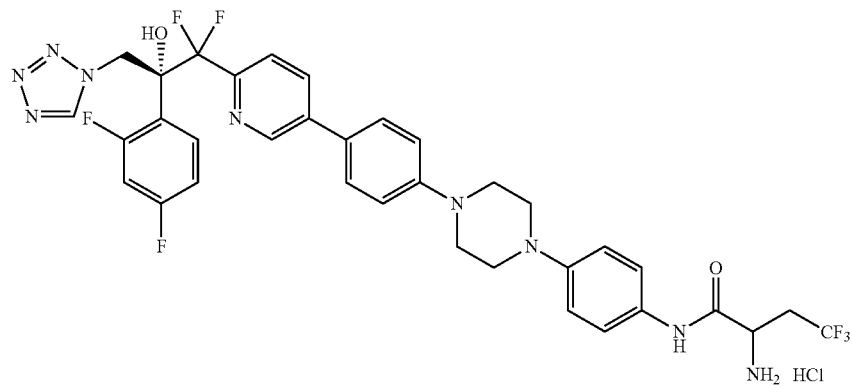

To a stirred solution of compound KB (100 mg, 0.11 mmol) in CH$_2$Cl$_2$ (5 mL) under argon atmosphere was added 4.0 M HCl in 1,4-dioxane (1 mL) at 0° C. The reaction mixture was warmed to RT and stirred for 2 h. The progress of the reaction was monitored by TLC. The volatiles were evaporated under reduced pressure. The residue was washed with diethyl ether (2×10 mL) dried under reduced pressure to obtain 88 as HCl salt (60 mg, 0.07 mmol, 65%) as yellow solid. $^1$H NMR (400 MHz, DMSO-d$_6$): δ 10.80 (brs, 1H), 9.18 (s, 1H), 8.90 (s, 1H), 8.74 (brs, 3H), 8.21-8.11 (m, 1H), 7.71 (d, J=8.8 Hz, 2H), 7.54 (d, J=8.8 Hz, 2H), 7.49 (d, J=8.3 Hz, 1H), 7.33-7.21 (m, 2H), 7.18-7.16 (m, 5H), 6.94-6.86 (m, 1H), 5.67 (d, J=14.7 Hz, 1H), 5.13 (d, J=14.7 Hz, 1H), 4.18 (brs, 1H), 3.46 (brs, 4H), 3.35 (brs, 4H), 3.08-2.80 (m, 2H)

MS (ESI): m/z 744.8 [(M-HCl)+H]$^+$; HPLC: 96.51%; Optical rotation [α]$_D^{19}$: +23.7 (c=0.1% in MeOH).

Example 89

N-(4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-ethyl-3-hydroxybutanamide (89)

N-(4-(4-(4-bromophenyl) piperazin-1-yl) phenyl)-2-ethyl-3-oxobutanamide (KC)

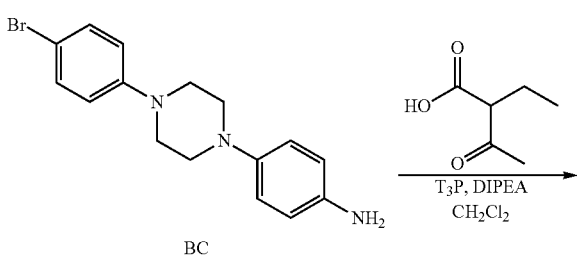

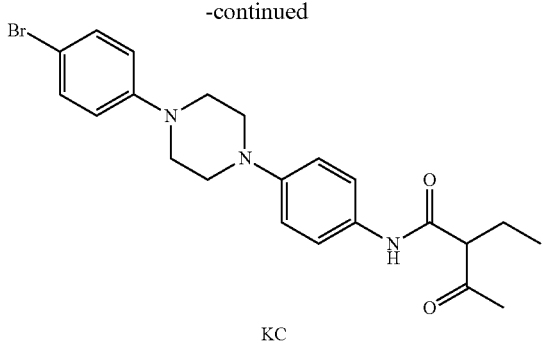

KC

To a stirred solution of 2-ethyl-3-oxobutanoic acid (1 g, 3.01 mmol) in CH$_2$Cl$_2$ (5 mL) under argon atmosphere were added compound BC (1.17 g, 9.03 mmol), T$_3$P (2.87 mL, 9.03 mmol, 50% in EtOAc) and diisopropyl ethyl amine (1.16 mL, 9.03 mmol) at 0° C. The reaction mixture was stirred at 0° C. for 3-4 h. The progress of the reaction was monitored by TLC. The reaction mixture was quenched with ice water (50 mL) and extracted with EtOAc (2×50 mL). The combined organic layers were washed with water (50 mL), dried over anhydrous Na$_2$SO$_4$ and concentrated under reduced pressure. The crude material was purified by silica gel column chromatography (eluent: 3% MeOH/CH$_2$Cl$_2$) to afford compound KC (600 mg, 1.35 mmol, 46%) as yellow solid. $^1$H NMR (400 MHz, DMSO-d$_6$): δ 10.03 (s, 1H), 7.47 (d, J=9.0 Hz, 2H), 7.37 (d, J=10.4 Hz, 2H), 6.96 (d, J=9.2 Hz, 4H), 3.43 (t, J=7.2 Hz, 1H), 3.29-3.19 (i, 8H), 2.15 (s, 3H), 1.80-1.68 (m, 2H), 0.85 (t, J=7.4 Hz, 3H).

N-(4-(4-(4-bromophenyl) piperazin-1-yl) phenyl)-2-ethyl-3-hydroxybutanamide (KD)

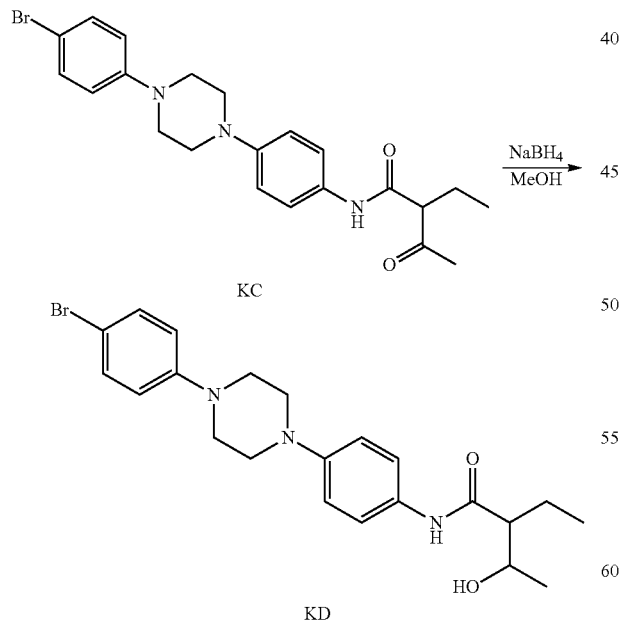

To a stirred solution of compound KC (400 mg, 0.90 mmol) in MeOH (20 mL) under argon atmosphere was added sodium borohydride (102 mg, 2.70 mmol) at 0° C., and stirred for 16 h. The reaction mixture was quenched with ice cold water (30 mL) and extracted with CH$_2$Cl$_2$ (2×30 mL). The combined organic layers were washed with water (30 mL), dried over anhydrous Na$_2$SO$_4$ and concentrated under reduced pressure. The crude material was purified by silica gel column chromatography (eluent: 100% EtOAc/Hexane) to afford compound KD (300 mg, 0.67 mmol, 75%) as an off-white solid. $^1$H NMR (400 MHz, DMSO-d$_6$) (Diastereomeric mixture): δ 9.65-9.55 (m, 1H), 7.51-7.46 (m, 2H), 7.37 (d, J=9.0 Hz, 2H), 6.99-6.92 (m, 4H), 4.66-4.61 (m, 1H), 3.88-3.46 (m, 1H), 3.29-3.17 (m, 8H), 2.23-2.10 (m, 1H), 1.54-1.52 (m, 0.6H), 1.51-1.48 (m, 1.44H), 1.06 (d, J=6.1 Hz, 3H), 0.83 (t, J=7.3 Hz, 3H).

2-ethyl-3-hydroxy-N-(4-(4-(4-(4,4,5,5-tetramethyl-1,3,2-dioxaborolan-2-yl) phenyl) piperazin-1-yl) % phenyl) butanamide (KE)

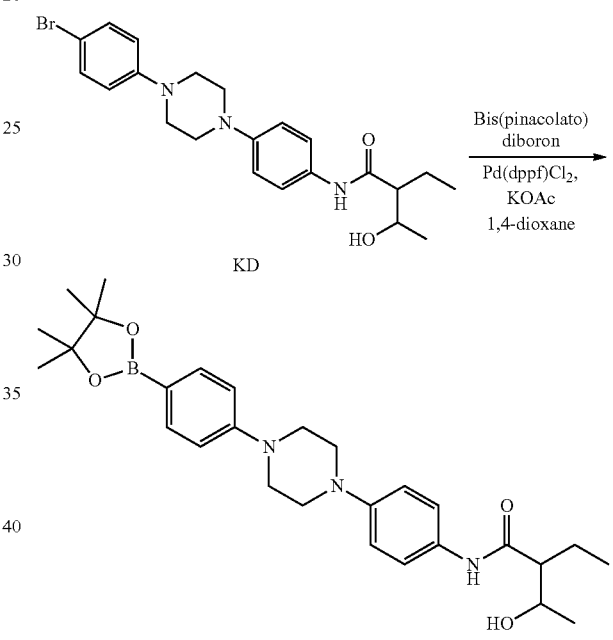

To a stirred solution of compound KD (300 mg, 0.61 mmol) in 1,4-dioxane (20 mL) under argon atmosphere were added bis(pinacolato)diboron (309 mg, 1.22 mmol) and potassium acetate (239 mg, 2.44 mmol) at RT. The reaction mixture was purged with argon for 20 min, then Pd(dppf)Cl$_2$ (67 mg, 0.09 mmol) was added and the reaction mixture was purged under argon for 5 min at RT. The reaction mixture was stirred at 110° C. for 16 h. The reaction mixture was quenched with ice water (20 mL) and extracted with EtOAc (2×20 mL). The combined organic layers were washed with water (20 mL), dried over anhydrous Na$_2$SO$_4$ and concentrated under reduced pressure. The crude material was purified by silica gel column chromatography (eluent: 40% EtOAc/Hexane) to afford compound KE (250 mg, 0.50 mmol, 75%) as an off-white solid. $^1$H NMR (400 MHz, DMSO-d$_6$) (diastereomeric mixture): δ 9.68-9.40 (m, 1H), 7.61-7.42 (m, 4H), 6.97-6.92 (m, 4H), 4.65-4.61 (m, 1H), 3.79-3.57 (m, 1H), 3.39-3.33 (m, 4H), 3.22-3.13 (m, 4H), 2.25-2.05 (m, 1H), 1.81-1.37 (m, 2H), 1.27 (s, 12H), 1.10 (d, J=6.3 Hz, 3H), 0.83 (t, J=7.4 Hz, 3H).

N-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-ethyl-3-hydroxybutanamide (89)

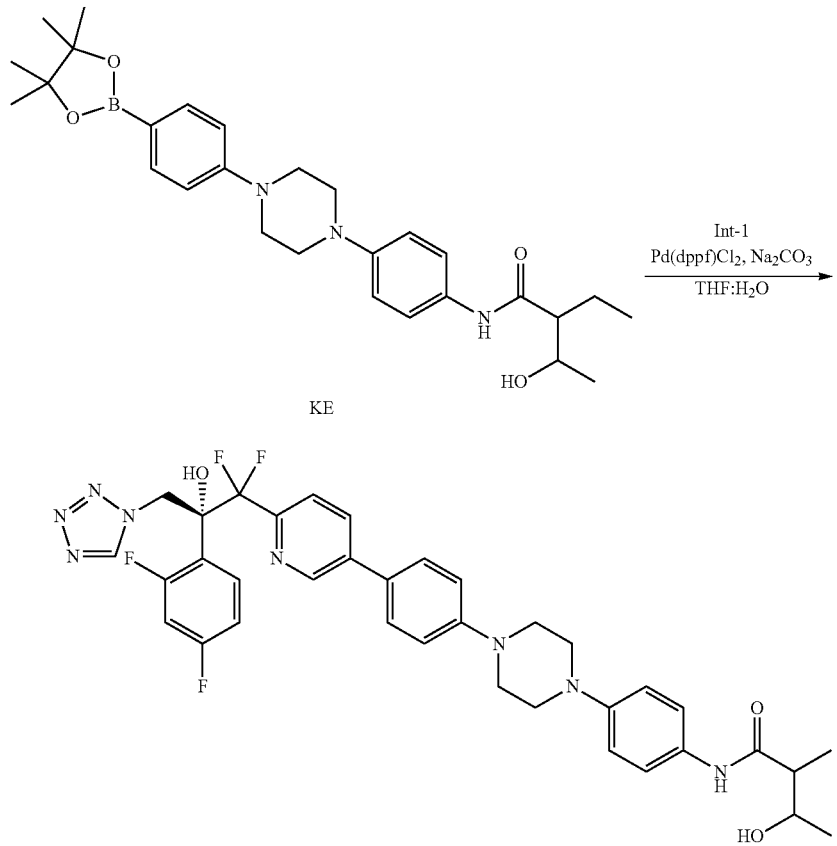

To a stirred solution of Int-1 (150 mg, 0.34 mmol) in THF:H2O (9:1, 20 mL) under argon atmosphere were added compound KE (188 mg, 0.38 mmol), sodium carbonate (110 mg, 1.04 mmol) and purged under argon for 15 min at RT. Then Pd(dppf)Cl$_2$ (38 mg, 0.05 mmol) was added and the reaction mixture was purged under argon for 10 min at RT. The reaction mixture was stirred at 80° C. for 16 h. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 70% EtOAc/Hexane) to afford 89 (75 mg, 0.10 mmol, 30%) as yellow solid. $^1$H NMR (400 MHz, DMSO-d$_6$) (diastereomeric mixture): δ 9.71-9.45 (m, 1H), 9.14 (s, 1H), 8.90 (d, J=2.0 Hz, 1H), 8.16 (dd, J=8.2, 2.1 Hz, 1H), 7.69 (d, J=8.9 Hz, 2H), 7.56-7.44 (m, 3H), 7.33-7.24 (m, 2H), 7.22-7.16 (m, 1H), 7.13 (d, J=9.0 Hz, 2H), 6.95 (d, J=9.0 Hz, 2H), 6.94-6.88 (m, 1H), 5.67 (d, J=14.6 Hz, 1H), 5.11 (d, J=14.6 Hz, 1H), 4.67-4.62 (m, 1H), 3.88-3.62 (m, 1H), 3.40-3.37 (m, 4H), 3.24-3.21 (m, 4H), 2.24-2.09 (m, 1H), 1.78-1.70 (m, 0.50H), 1.59-1.44 (m, 1.38H), 1.11-1.05 (m, 3H), 0.83 (t, J=7.4 Hz, 3H); MS (ESI): m/z 719.8 [M+H]$^+$; HPLC: 51.53% & 46.0%; Optical rotation [α]$_D^{19}$: +23.0 (c=0.1% in MeOH).

Example 90

(R)-2-(2,4-difluorophenyl)-1,1-difluoro-1-(5-(4-(4-(2-neopentyl-1H-benzo [d] imidazol-6-yl) piperazin-1-yl) phenyl) pyridin-2-yl)-3-(1H-tetrazol-1-yl) propan-2-ol (90)

N-(2-amino-5-((4-(4-bromophenyl) piperazin-1-yl) phenyl)-3,3-dimethylbutanamide (KF)

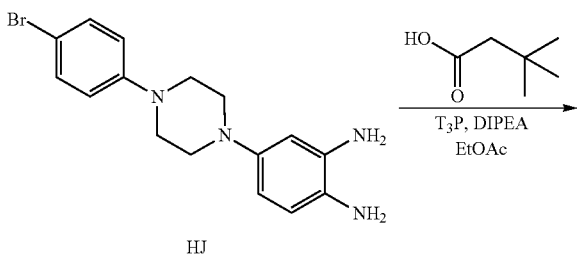

387
-continued

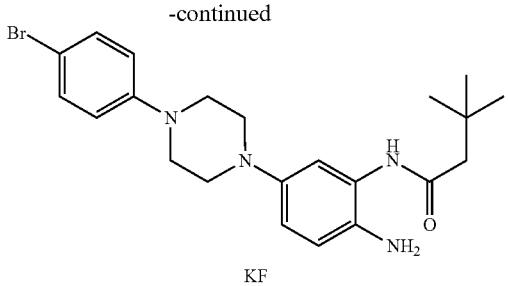

KF

To a stirred solution of compound HJ (500 mg, 1.44 mmol) in EtOAc (10 mL) under argon atmosphere were added 3,3-dimethylbutanoic acid 2 (185.6 mL, 1.44 mmol), T$_3$P (1.83 mL, 2.88 mmol, 50% in EtOAc) and diisopropyl ethyl amine (398 mL, 2.16 mmol) at RT and stirred for 1 h. The progress of the reaction was monitored by TLC. The reaction mixture was diluted with saturated sodium bicarbonate solution (20 mL) and extracted with EtOAc (2×20 mL). The combined organic extracts were dried over anhydrous Na$_2$SO$_4$ and concentrated under reduced pressure to obtain compound KF (450 mg, crude) as an off-white solid which was used in the next step without further purification. LC-MS: 445 [M+H]$^+$ at 2.43 RT (60.47% purity).

6-(4-(4-bromophenyl) piperazin-1-yl)-2-neopentyl-1H-benzo [d] imidazole (KG)

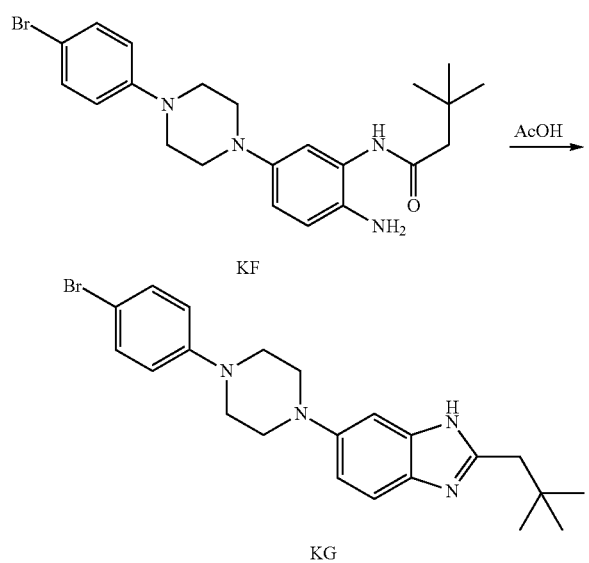

To a stirred solution of compound KF (450 mg, 1.01 mmol) in AcOH (10 mL) under argon atmosphere was heated at 100° C. for 5 h. The progress of the reaction was monitored by TLC. The reaction mixture was diluted with saturated sodium bicarbonate solution (30 mL) and extracted with CH$_2$Cl$_2$ (2×30 mL). The combined organic extracts were dried over anhydrous Na$_2$SO$_4$ and concentrated under reduced pressure to obtain compound KG (180 mg, crude) as an off-white solid and the material was as such taken for next step without further purification. $^1$H NMR (500 MHz, DMSO-d$_6$): δ 11.89-11.72 (m, 1H), 7.38-7.36 (m, 3H), 6.98-6.96 (m, 4H), 3.31 (s, 2H), 3.20-3.18 (m, 8H), 0.98 (s, 9H).

388

2-neopentyl-6-(4-(4-(4,4,5,5-tetramethyl-1,3,2-dioxaborolan-2-yl) phenyl) piperazin-1-yl)-1H-benzo[d] imidazole (KH)

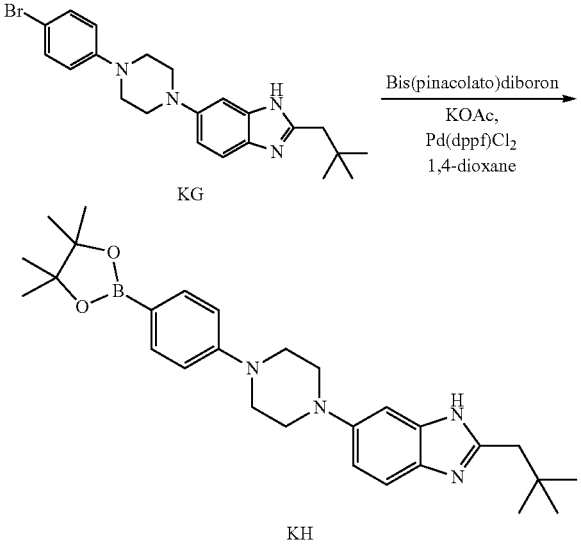

To a stirred solution of compound KG (180 mg, 0.42 mmol) in 1,4-dioxane (10 mL) under argon atmosphere were added bis(pinacolato)diboron (171 mg, 0.67 mmol) and potassium acetate (123 mg, 1.26 mmol) at RT. The reaction mixture was purged with argon for 20 min, then Pd(dppf)Cl$_2$ (30.7 mg, 0.04 mmol) was added and the reaction mixture was purged under argon for 5 min at RT. The reaction mixture was stirred at 100° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 2% MeOH/CH$_2$Cl$_2$) to afford compound KH (170 mg, 0.35 mmol, 85%) as a brown solid. $^1$H NMR (400 MHz, DMSO-d$_6$): δ 11.83 (br s, 1H), 7.54 (d, J=8.8 Hz, 2H), 6.92 (d, J=7.78 Hz, 1H), 6.98 (d, J=8.8 Hz, 4H), 3.43-3.37 (m, 4H), 3.22-3.20 (m, 4H), 2.62 (s, 2H), 1.27 (s, 12H), 0.98 (s, 9H).

(R)-2-(2,4-difluorophenyl)-1,1-difluoro-1-(5-(4-(4-(2-neopentyl-1H-benzo [d] imidazol-6-yl) piperazin-1-yl) phenyl) pyridin-2-yl)-3-(1H-tetrazol-1-yl) propan-2-ol (90)

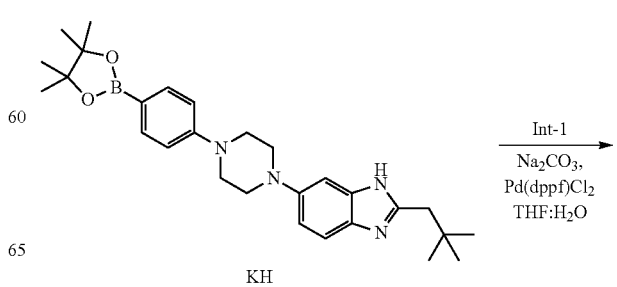

389
-continued

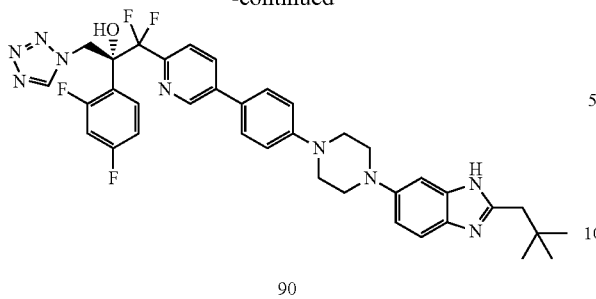

90

To a stirred solution of Int-1 (130 mg, 0.30 mmol) in THF:H2O (4:1, 15 mL) under argon atmosphere were added compound KH (170 mg, 0.36 mmol), sodium carbonate (95.5 mg, 0.90 mmol) and purged under argon for 20 min at RT. Then Pd(dppf)Cl$_2$ (22 mg, 0.03 mmol) was added and the reaction mixture was purged under argon for 10 min at RT. The reaction mixture was stirred at 70° C. for 16 h. The reaction mixture was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 5% MeOH/CH$_2$Cl$_2$) to afford 90 (60 mg, 0.08 mmol, 28%) as an off-white solid. $^1$H NMR (400 MHz, DMSO-d$_6$): δ 11.90 (brs, 1H), 9.15 (s, 1H), 8.91 (d, J=1.9 Hz, 1H), 8.17 (dd, J=8.2, 2.1 Hz, 1H), 7.70 (d, J=8.8 Hz, 2H), 7.48 (d, J=8.3 Hz, 1H), 7.41-7.24 (m, 3H), 7.23-7.11 (m, 3H), 6.97-6.85 (m, 3H), 5.67 (d, J=14.7 Hz, 1H), 5.11 (d, J=14.7 Hz, 1H), 3.45-3.36 (m, 4H), 3.26-3.24 (m, 4H), 2.63 (s, 2H), 0.98 (s, 9H); MS (ESI): m/z 700.7 [M+H]$^+$; HPLC: 94.35%; Optical rotation [α]$_D^{20}$: +101.96 (c=0.1% in CH$_2$Cl$_2$).

Example 91

1-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-3-isopropyl-1,3-dihydro-2H-imidazol-2-one (91)

N-(2,2-dimethoxyethyl) propan-2-amine (KJ)

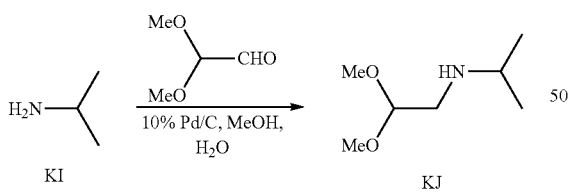

To a stirred solution of 2,2-dimethoxyacetaldehyde (3.48 mL, 33.89 mmol) in MeOH (20 mL) under argon atmosphere was added propan-2-amine (KI; 2 g, 33.89 mmol) at RT. The reaction mixture was stirred at RT for 20 h. Then Pd/C (500 mg) in water (5 mL) was added to the reaction mixture at RT. The reaction mixture was stirred at RT for 6 h under hydrogen atmosphere. The progress of the reaction was monitored by TLC, the reaction mixture was filtered, washed with MeOH (3×20 mL), the filtrate was concentrated under reduced pressure to obtain compound KJ (1 g, crude) as a brown syrup. $^1$H NMR (400 MHz, CDCl$_3$): 4.51-4.45 (m, 1H), 3.39 (s, 6H), 2.84-2.78 (m, 1H), 2.73 (d, J=5.65 Hz, 2H), 1.07 (d, J=6.3 Hz, 6H)

390

3-(4-(4-(4-bromophenyl)piperazin-1-yl) phenyl)-1-(2,2-dimethoxyethyl)-1-isopropylurea (KK)

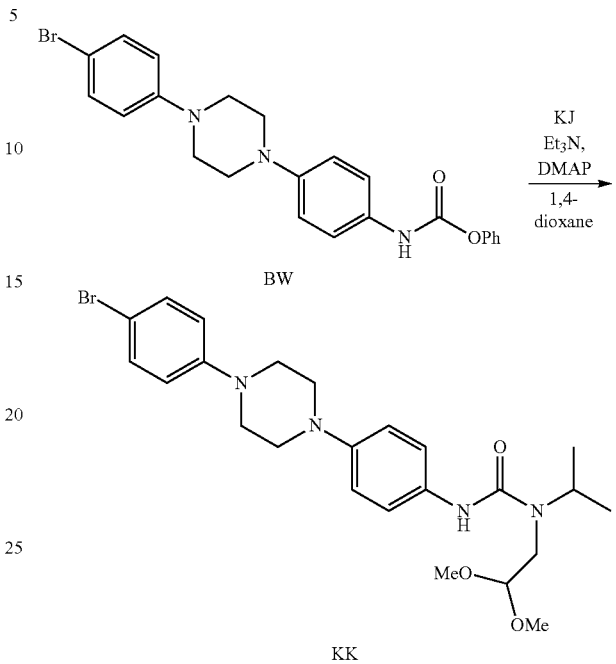

To a stirred solution of compound BW (300 mg, 0.66 mmol) in 1,4-dioxane (20 mL) under argon atmosphere were added compound KJ (117 ng, 0.80 mmol), triethyl amine (0.095 mL, 0.66 mmol) and dimethyl amino pyridine (80 mg, 0.66 mmol) at RT. The reaction mixture was stirred at reflux for 5 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure to obtain the crude. The crude material was purified by silica gel column chromatography (eluent: 30-40% EtOAc/Hexane) to afford compound KK (250 mg, 0.50 mmol, 79%) as an off-white solid. $^1$H NMR (400 MHz, DMSO-d$_6$): δ 8.16 (s, 1H), 7.37 (d, J=9.0 Hz, 2H), 7.24 (d, J=9.0 Hz, 2H), 6.98-6.94 (m, 2H), 6.90 (d, J=9.2 Hz, 2H), 4.45 (t, J=5.0 Hz, 1H), 4.32-4.17 (m, 1H), 3.39 (s, 6H), 3.29-3.24 (m, 6H), 3.20-3.15 (m, 4H), 1.11 (d, J=6.7 Hz, 6H).

1-(4-(4-(4-bromophenyl)piperazin-1-yl)phenyl)-3-isopropyl-1,3-dihydro-2H-imidazol-2-one (KE)

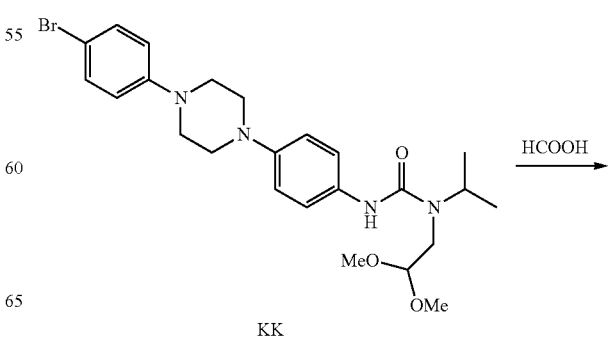

-continued

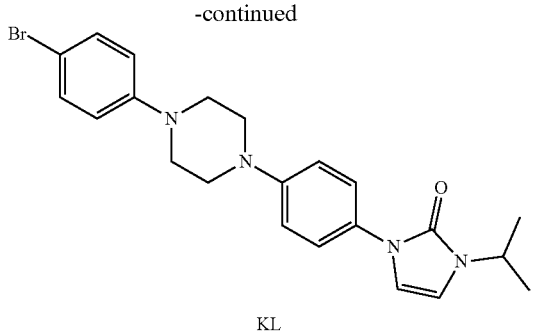

KL

To a stirred solution of compound KK (450 mg, 0.90 mmol) in formic acid (6 mL) under argon atmosphere was stirred at reflux for 4 h. The progress of the reaction was monitored by TLC. The reaction mixture was diluted with water (20 mL), neutralized with saturated sodium bicarbonate solution (20 mL) and extracted with EtOAc (2×20 mL). The combined organic extracts were dried over anhydrous $Na_2SO_4$ and concentrated under reduced pressure. The crude material was washed with n-hexane (2×10 mL) and n-pentane (2×10 mL) and dried under reduced pressure to afford compound KL (350 mg, 0.79 mmol, 89%) as a pale brown solid. $^1H$ NMR (400 MHz, DMSO-$d_6$): δ 7.52 (d, J=9.0 Hz, 2H), 7.37 (d, J=9.0 Hz, 2H), 7.05 (d, J=9.2 Hz, 2H), 6.97 (d, J=9.2 Hz, 2H), 6.91 (d, J=3.2 Hz, 1H), 6.78 (d, J=3.2 Hz, 1H), 4.30-4.18 (m, 1H), 3.28 (s, 8H), 1.26 (d, J=6.7 Hz, 6H).

1-isopropyl-3-(4-(4-(4-(4,4,5,5-tetramethyl-1,3,2-dioxaborolan-2-yl) phenyl) piperazin-1-yl) phenyl)-1,3-dihydro-2H-imidazol-2-one (KM)

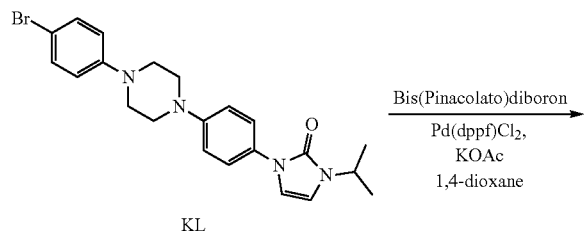

KL

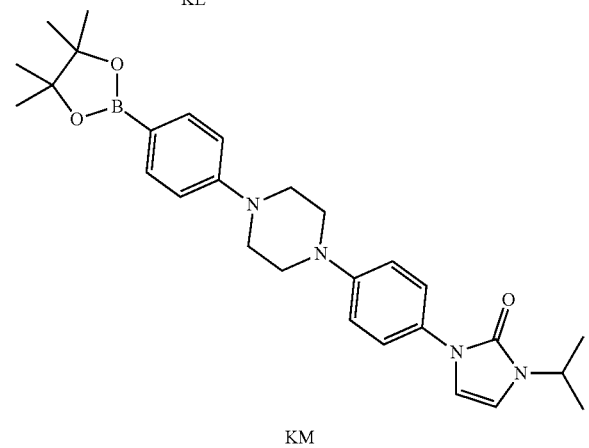

KM

To a stirred solution of compound KL (350 mg, 0.80 mmol) in 1,4-dioxane (30 mL) under argon atmosphere were added bis(pinacolato)diboron (322 mg, 1.26 mmol) and KOAc (226 mg, 2.38 mmol) at RT. The reaction mixture was purged with argon for 20 min, then Pd(dppf)Cl$_2$ (58 mg, 0.08 mmol) was added and the reaction mixture was purged under argon for 10 min at RT. The reaction mixture was stirred at 110° C. for 8 h. The progress of the reaction was monitored by TLC. The reaction mixture was quenched with water (20 mL) and extracted with EtOAc (2×20 mL). The combined organic extracts were washed with water (20 mL), brine (20 mL), dried over anhydrous $Na_2SO_4$ and concentrated under reduced pressure. The crude material was purified by silica gel column chromatography (eluent: 0-3% MeOH/CH$_2$Cl$_2$) to afford compound KM (220 mg, 0.45 mmol, 57%) as an off-white solid $^1H$ NMR (400 MHz, DMSO-$d_6$): δ 7.57-7.49 (m, 4H), 7.04 (d, J=9.3 Hz, 2H), 6.97 (d, J=8.9 Hz, 2H), 6.90 (d, J=3.2 Hz, 1H), 6.78 (d, J=3.2 Hz, 1H), 4.29-4.16 (m, 1H), 3.40-3.35 (m, 4H), 3.29-3.26 (m, 4H), 1.27 (s, 18H).

1-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-3-isopropyl-1,3-dihydro-2H-imidazol-2-one (91)

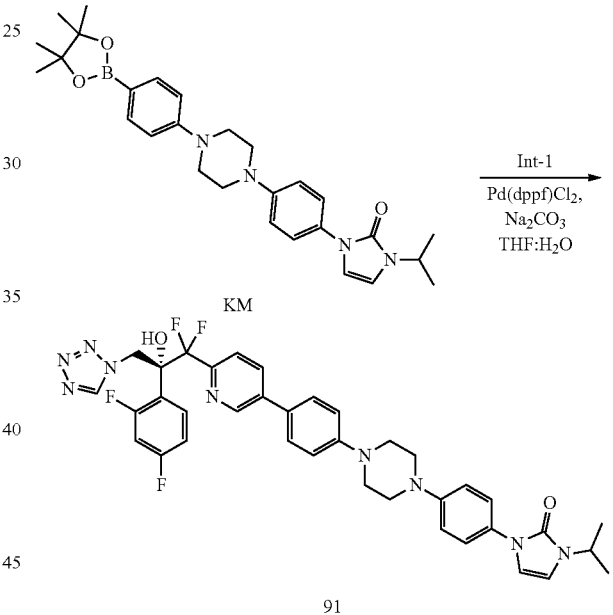

91

To a stirred solution of Int-1 (150 mg, 0.34 mmol) in THF:H2O (4:1, 10 mL) under argon atmosphere were added compound KM (203 mg, 0.41 mmol) and sodium carbonate (110 mg, 1.04 mmol) at RT. The reaction mixture was purged with argon for 20 min, then Pd(dppf)Cl$_2$ (25 mg, 0.03 mmol) was added and the reaction mixture was purged under argon for 10 min at RT. The reaction mixture was stirred at 80° C. for 8 h. The progress of the reaction was monitored by TLC. The reaction mixture was quenched with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 2-5% MeOH/CH$_2$Cl$_2$) to afford 91 (77 mg, 0.10 mmol, 31%) as an off-white solid. $^1H$ NMR (400 MHz, DMSO-$d_6$): δ 9.15 (s, 1H), 8.91 (d, J=2.0 Hz, 1H), 8.17 (dd, J=8.3, 2.2 Hz, 1H), 7.70 (d, J=8.9 Hz, 2H), 7.54 (d, J=9.2 Hz, 2H), 7.48 (d, J=8.2 Hz, 1H), 7.33-7.25 (m, 2H), 7.23-7.17 (m, 2H), 7.14 (d, J=9.0 Hz, 1H), 7.07 (d, J=9.2 Hz, 2H), 6.94-6.88 (m, 2H), 6.79 (d, J=3.1 Hz, 1H), 5.67 (d, J=14.8 Hz, 1H), 5.11 (d, J=14.8 Hz, 1H), 4.36-4.19 (m, 1H), 3.45-3.38 (m, 4H), 3.32-3.30 (s, 4H), 1.27 (d, J=6.9 Hz, 6H). MS (ESI): m/z 714.8 [M+H]$^+$; HPLC: 99%; Optical rotation [r]$_D^{20}$: +29.1 (c=0.1% in MeOH).

Example 92

(2S,3S)-3-(3-(4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-1H-1,2,4-triazol-1-yl) pentan-2-ol (92)

Methyl 4-bromobenzimidate hydrochloride (KO)

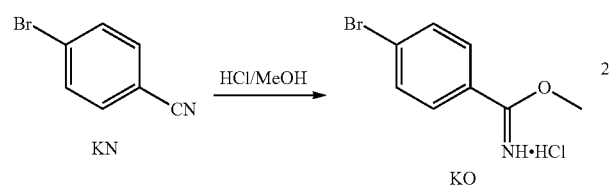

To a stirred solution of 4-bromobenzonitrile (KN; 500 mg, 2.70 mmol) in MeOH (50 mL) under argon atmosphere was bubbled with HCl gas for 1 h at 0° C. The progress of the reaction was monitored by TLC. The volatiles were evaporated under reduced pressure. The crude material was washed with diethyl ether (2×10 mL) to obtain compound KO (500 mg, crude) as an off-white solid and the obtained material was as such taken for next step without further purification. $^1$H NMR (400 MHz, DMSO-d$_6$): δ 12.00 (brs, 1H), 7.82 (d, J=8.7 Hz, 2H), 7.65 (d, J=8.7 Hz, 2H), 3.05 (s, 3H)

N'-((2S,3S)-2-(benzyloxy) pentan-3-yl)-4-bromobenzimidohydrazide hydrochloride (KP)

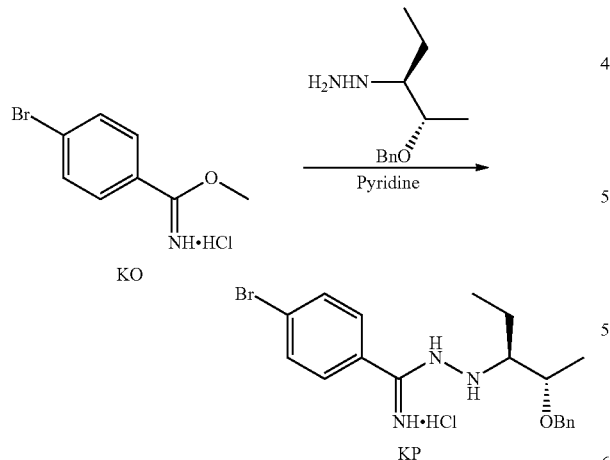

To a stirred solution of compound KO (4.0 g, 18.69 mmol) in pyridine (40 mL) under argon atmosphere was added ((2S,3S)-2-(benzyloxy) pentan-3-yl) hydrazine (3.8 g, 18.69 mmol) at RT. The reaction mixture was stirred at 60-65° C. for 16 h. The volatiles were evaporated under reduced pressure. The crude material was washed with diethyl ether (2×10 mL) to obtain compound KP (4 g, crude) as an off-white solid. The crude compound was used as such in the next step.

1-((2S,3S)-2-(benzyloxy) pentan-3-yl)-3-(4-bromophenyl)-1H-1,2,4-triazole (KQ)

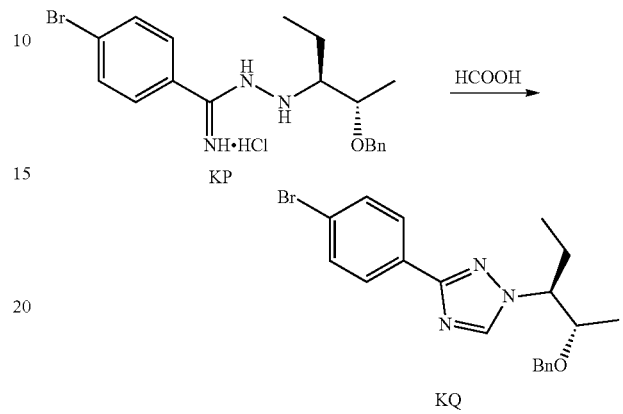

To a stirred solution of compound KP (4.0 g, 10.25 mmol) in formic acid (40 mL) under argon atmosphere was stirred at reflux for 24 h. The progress of the reaction was monitored by TLC. The volatiles were evaporated under reduced pressure. The residue was diluted with saturated sodium bicarbonate solution (100 mL) and extracted with EtOAc (2×100 mL). The combined organic extracts were dried over anhydrous Na$_2$SO$_4$ and concentrated under reduced pressure. The crude material was purified by silica gel column chromatography (eluent: 20% EtOAc/Hexane) to afford compound KQ (650 mg, 1.62 mmol, 15%) as an off-white solid. LC-MS: 400 [M+H]$^+$ at 3.16 RT (96.32% purity)

1-(4-(1-((2S,3S)-2-(benzyloxy) pentan-3-yl)-1H-1,2,4-triazol-3-yl) phenyl))-4-(4-bromophenyl) piperazine (KR)

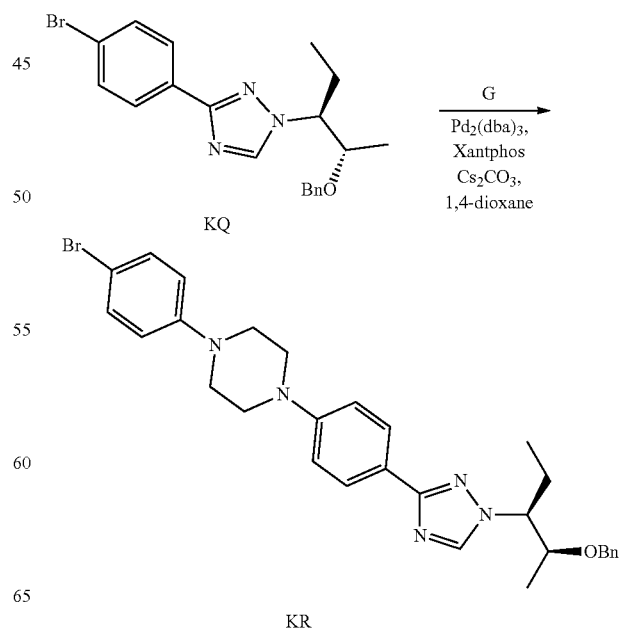

To a stirred solution of compound KQ (600 mg, 1.50 mmol) in 1,4-dioxane (25 mL) under argon atmosphere were added G (433 mg, 1.80 mmol), Xantphos (104 mg, 0.18 mmol), $Cs_2CO_3$ (1.4 g, 4.50 mmol) and purged under argon for 10 min at RT. Then $Pd_2$ (dba)$_3$ (68 mg, 0.07 mmol) was added to the reaction mixture at RT and stirred at 110° C. for 24 h. The progress of the reaction was monitored by TLC. The reaction mixture was diluted with water (20 mL) and extracted with EtOAc (2×20 mL). The combined organic extracts were washed with water (20 mL), brine (20 mL), dried over anhydrous $Na_2SO_4$ and concentrated under reduced pressure. The crude material was purified by silica gel column chromatography (eluent: 1% MeOH/$CH_2Cl_2$) to afford compound KR (350 mg, 0.62 mmol, 41%) as a pale yellow solid. LC-MS: 560.1 [M+H]$^+$ at 4.41 RT (48.08% purity).

1-(4-(1-(2S,3S)-2-(benzyloxy) pentan-3-yl)-1H-1,2,4-triazol-3-yl) phenyl)-4-(4-(4,4,5,5-tetramethyl-1,3,2-dioxaborolan-2-yl) phenyl) piperazine (S)

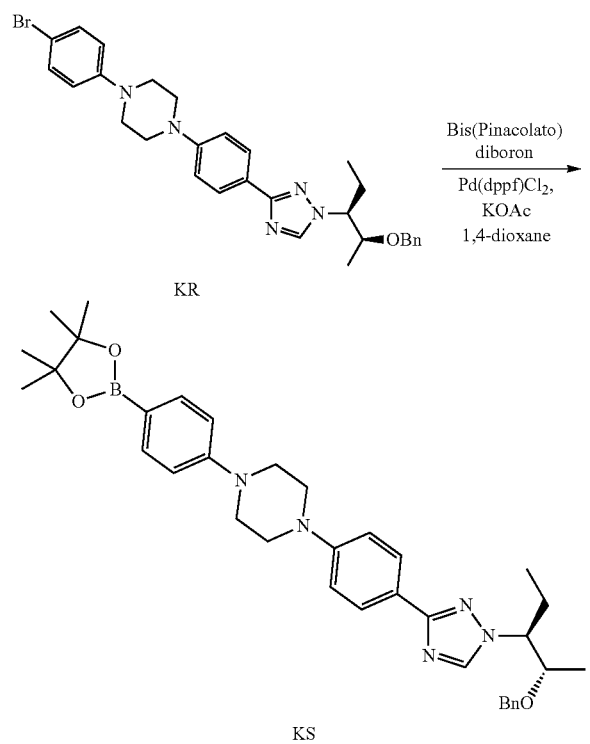

To a stirred solution of compound KR (350 mg, 0.62 mmol) in 1,4-dioxane (25 mL) under argon atmosphere were added bis(pinacolato)diboron (254 mg, 1 mmol), KOAc (183 mg, 1.87 mmol) and purged under argon for 10 min at RT. Then Pd(dppf)Cl$_2$ (45 mg, 0.06 mmol) was added to the reaction mixture at RT and stirred at 110° C. for 16 h. The reaction mixture was diluted with water (20 mL) and extracted with EtOAc (2×20 mL). The combined organic extracts were washed with water (20 mL), dried over anhydrous $Na_2SO_4$ and concentrated under reduced pressure to obtain compound KS (250 mg, crude) as a brown thick syrup. LC-MS: 608.2 [M+H]$^+$ at 4.54 RT (53.53% purity).

1-(5-(4-(4-(4-(1-(2S,3S)-2-(benzyloxy) pentan-3-yl)-1H-1,2,4-triazol-3-yl) phenyl) piperazin-1-yl) phenyl) pyridin-2-yl)-2-(2,4-difluorophenyl)-1,1-difluoro-3-(1H-tetrazol-1-yl) propan-2-ol (KT)

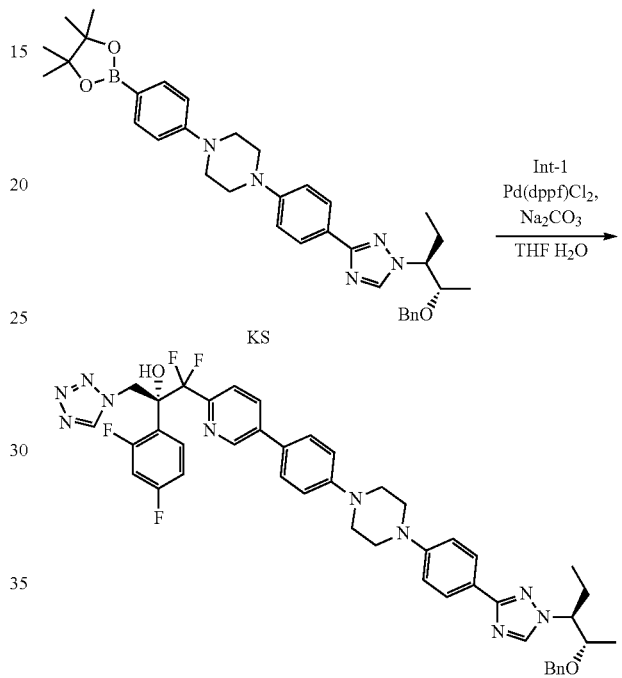

To a stirred solution of Int-1 (100 mg, 0.23 mmol) in THF:H2O (4:1, 15 mL) under argon atmosphere were added compound KS (140 mg, 0.23 mmol), sodium carbonate (73 mg, 0.70 mmol) and purged under argon for 10 min at RT. Then Pd(dppf)Cl$_2$ (17 mg, 0.02 mmol) was added to the reaction mixture at RT and stirred at 80° C. for 16 h. The reaction mixture was diluted with water (20 mL) and extracted with EtOAc (2×20 mL). The combined organic extracts were washed with water (20 mL), dried over anhydrous $Na_2SO_4$ and concentrated under reduced pressure. The crude material was purified by silica gel column chromatography (eluent: 70% b EtOAc/Hexane) to afford compound KT (70 mg, 0.08 mmol, 33%) as an off-white solid. $^1$H NMR (400 MHz, DMSO-d$_6$): δ 9.14 (s, 1H), 8.91 (s, 1H), 8.47 (s, 1H), 8.17 (dd, J=8.3, 2.2 Hz, 1H), 7.88 (d, J=8.9 Hz, 2H), 7.70 (d, J=8.9 Hz, 2H), 7.48 (d, J=8.4 Hz, 1H), 7.33-7.04 (m, 12H), 6.94-6.83 (m, 1H), 5.67 (d, J=14.6 Hz, 1H), 5.11 (d, J=14.6 Hz, 1H), 4.48 (d, J=11.9 Hz, 1H), 4.23 (d, J=11.9 Hz, 1H), 4.25-4.22 (m, 1H), 3.87-3.84 (m, 1H), 3.42-3.39 (m, 8H), 1.96-1.81 (m, 2H), 1.19 (d, J=6.3 Hz, 3H), 0.73 (t, J=7.2 Hz, 3H).

(2S,3S)-3-(3-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-1H-1, 2,4-triazol-1-yl) pentan-2-ol (92)

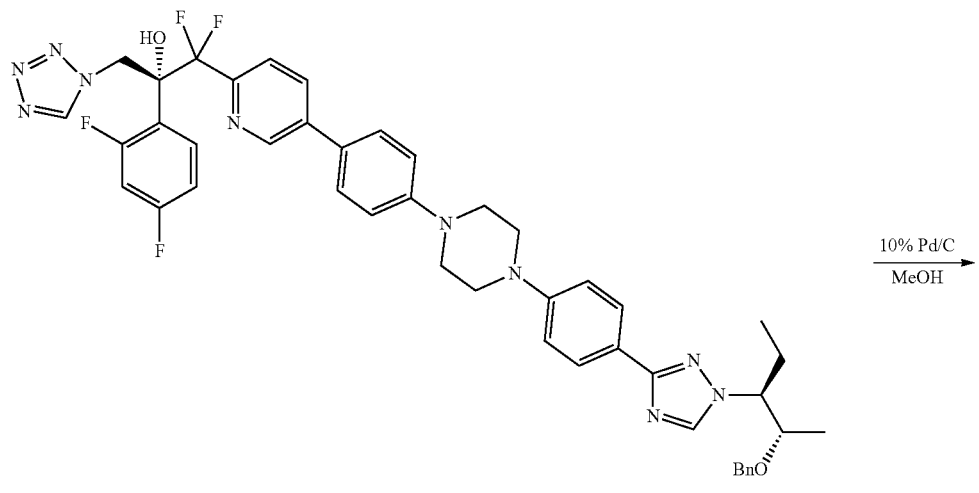

KT

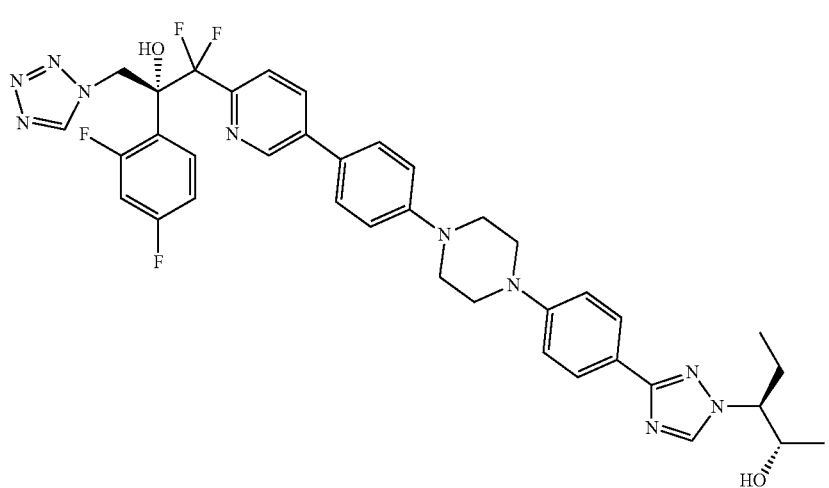

92

To a stirred solution of compound KT (70 mg, 0.08 mmol) in MeOH (20 mL) under argon atmosphere were added 10% Pd/C (35 mg) and 5.0 N HCl (catalytic amount) at RT. The reaction mixture was stirred at RT for 2 h under hydrogen atmosphere (50 psi). The progress of the reaction was monitored by TLC. The reaction mixture was filtered through celite, washed with MeOH (2×20 mL), the filtrate was concentrated under reduced pressure. The residue was washed with n-pentane (2×5 mL) to afford 92 (35 mg, 0.05 mmol, 56%) as an off-white solid. $^1$H NMR (400 MHz, CDCl$_3$): δ 8.76 (s, 1H), 8.74 (s, 1H), 8.08 (s, 1H), 8.03 (d, J=8.9 Hz, 2H), 7.95 (dd, J=8.2, 2.3 Hz, 1H), 7.86 (brs, 1H), 7.61 (d, J=8.1 Hz, 1H), 7.52 (d, J=8.9 Hz, 2H), 7.42-7.34 (m, 1H), 7.08-7.02 (m, 4H), 6.80-6.74 (m, 1H), 6.70-6.62 (m, 1H), 5.62 (d, J=14.2 Hz, 1H), 5.10 (d, J=14.2 Hz, 1H), 4.16 (brs, 1H), 3.97-3.92 (m, 1H), 3.46 (s, 8H), 3.08 (brs, 1H), 2.20-2.07 (m, 11H), 2.03-1.91 (m, 1H), 1.13 (d, J=6.4 Hz, 2H), 0.88 (t, J=7.4 Hz, 3H); MS (ESI): m/z 743.8 [M+H]$^+$; HPLC: 90.1%; Optical rotation [α]$_D^{20.01}$: +95.2 (c=0.1% in CH$_2$C).

Example 93

4-(4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-(2-hydroxypentan-3-yl)-2,4-dihydro-3H-1,2,4-triazol-3-one (93)

4-(4-(4-(4-bromophenyl) piperazin-1-yl) phenyl)-2-(2-oxopentan-3-yl)-2,4-dihydro-3H-1,2,4-triazol-3-one (KU)

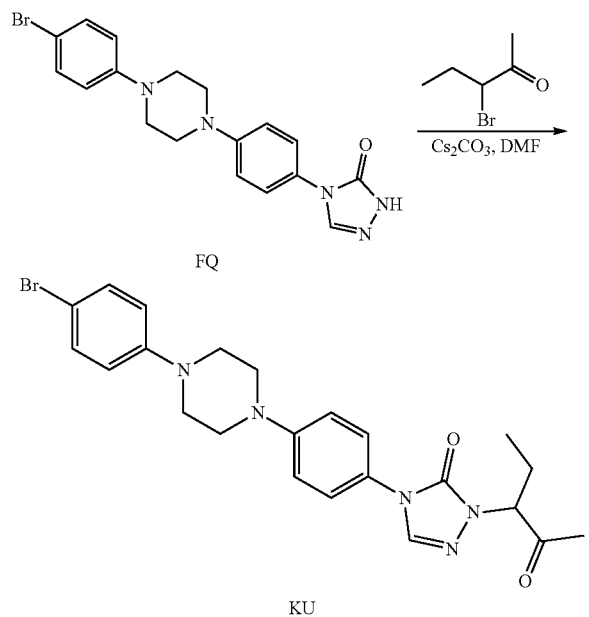

To a stirred solution of compound FQ (300 mg, 0.75 mmol) in DMF (10 mL) under argon atmosphere was added cesium carbonate (730 mg, 2.25 mmol) at RT and stirred for 30 min. Then 3-bromopentan-2-one (185 mg, 1.12 mmol) was added to the reaction mixture and stirred at RT for 16 h. The reaction mixture was diluted with water (20 mL) to obtain the solid. The solid was filtered, washed with water (20 mL) and concentrated under reduced pressure to obtain compound KU (300 mg, crude) as colorless thick syrup and the obtained material was as such taken for next step without further purification. $^1$H NMR (400 MHz, DMSO-$d_6$): δ 8.43 (s, 1H), 7.52 (d, J=9.0 Hz, 2H), 7.37 (d, J=9.0 Hz, 2H), 7.12 (d, J=9.0 Hz, 2H), 6.97 (d, J=9.2 Hz, 2H), 4.71 (s, 1H), 3.36-3.26 (m, 8H), 2.10 (s, 3H), 1.96-1.82 (m, 1H), 1.60-1.49 (m, 1H), 0.85 (t, J=7.6 Hz, 3H); LC-MS: 484.1 [M+H]$^+$ at 2.80 RT (89.08% purity).

(4-(4-(4-(4-bromophenyl) piperazin-1-yl) phenyl)-2-(2-hydroxypentan-3-yl)-2,4-dihydro-3H-1,2,4-triazol-3-one (KV)

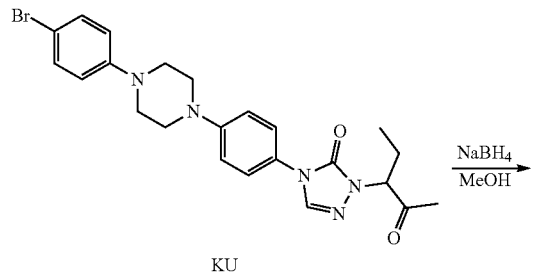

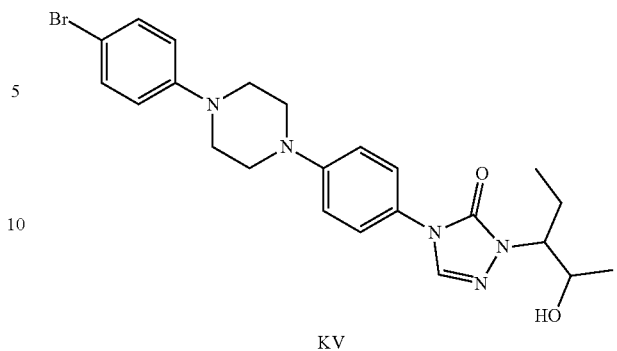

To a stirred solution of compound KU (300 mg, 0.61 mmol) in MeOH (10 mL) under argon atmosphere was added sodium borohydride (47 mg, 1.23 mmol) at 0° C. The reaction mixture was warmed to RT and stirred for 2 h. The progress of the reaction was monitored by TLC. The volatiles were evaporated and the residue was diluted with water (10 mL) and extracted with EtOAc (2×10 mL). The combined organic extracts were dried over anhydrous Na$_2$SO$_4$ and concentrated under reduced pressure to obtain compound KV (250 mg, crude) as yellow syrup and the obtained material was as such taken for next step without further purification. LC-MS: (diastereomeric mixture) 486.1 [M+H]r at 3.23, 3.33 RT (70.67, 21.31% purity)

2-(2-hydroxypentan-3-yl)-4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (KW)

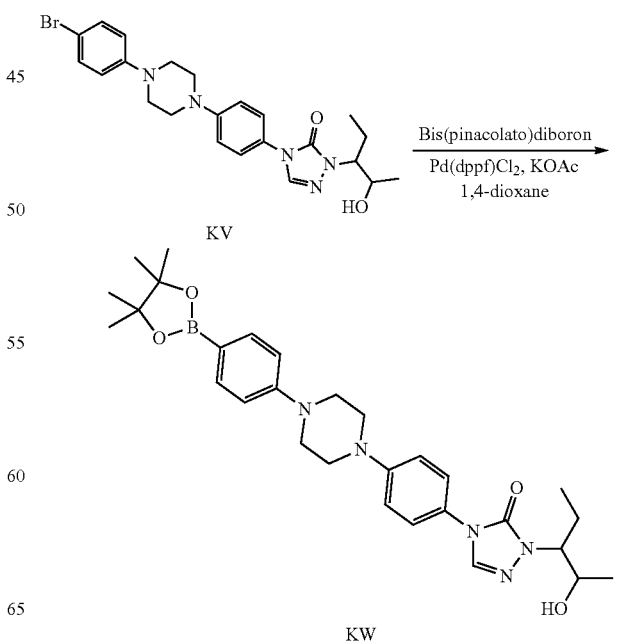

To a stirred solution of compound KV (250 mg, 0.51 mmol) in 1,4-dioxane (10 mL) under argon atmosphere were added bis(pinacolato)diboron (209 mg, 0.82 mmol) and potassium acetate (151 mg, 1.54 mmol) at RT. The reaction mixture was purged with argon for 20 min, then Pd(dppf)Cl$_2$ (38 mg, 0.05 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 3% MeOH/CH$_2$Cl$_2$) to afford compound KW (220 mg, 0.41 mmol, 80%) as an off-white solid. LC-MS: (diastereomeric mixture) 534.3 [M+H]$^+$ at 3.43, 3.51 RT (65.92, 22.98% purity).

4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl-2-(2-hydroxypentan-3-yl)-2,4-dihydro-3H-1,2,4-triazol-3-one (93)

To a stirred solution of Int-1 (140 mg, 0.32 mmol) in THF:H2O (4:1, 10 mL) under argon atmosphere were added compound KW (207 mg, 0.11 mmol), sodium carbonate (103 mg, 0.97 mmol) and purged under argon for 15 min at RT. Then Pd(dppf)Cl$_2$ (24 mg, 0.03 mmol) was added and the reaction mixture was purged under argon for 10 min at RT. The reaction mixture was stirred at 70° C. for 6 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 3% EtOAc/Hexane) to afford 93 (120 mg, 0.15 mmol, 51%) as an off-white solid. $^1$H NMR (400 MHz, DMSO-d$_6$): (diastereomeric mixture) δ 9.14 (s, 1H), 8.91 (d, J=2.0 Hz, 1H), 8.35-8.30 (m, 1H), 8.17 (dd, J=8.2, 2.3 Hz, 1H), 7.70 (d, J=8.9 Hz, 2H), 7.56-7.45 (m, 3H), 7.33-7.24 (m, 3H), 7.22-7.09 (m, 4H), 6.95-6.81 (m, 1H), 5.67 (d, J=14.6 Hz, 1H), 5.11 (d, J=14.6 Hz, 1H), 4.88 (d, J=5.8 Hz, 0.27H), 4.76 (d, J=5.6 Hz, 0.26H), 4.65 (d, J=5.0 Hz, 0.62H), 3.86-3.76 (m, 2H), 3.44-3.34 (m, 8H), 1.74-1.68 (m, 1H), 1.37-1.20 (m, 1H), 1.12 (d, J=6.0 Hz, 2H), 0.96 (d, J=6.0 Hz, 1H), 0.89-0.84 (m, 1H), 0.80-0.59 (m, 2H); MS (ESI): m/z 759.8 [M+H]$^+$; HPLC: 94.2%; Optical rotation [α]$_D^{20}$: +36.9 (c=0.1% in MeOH).

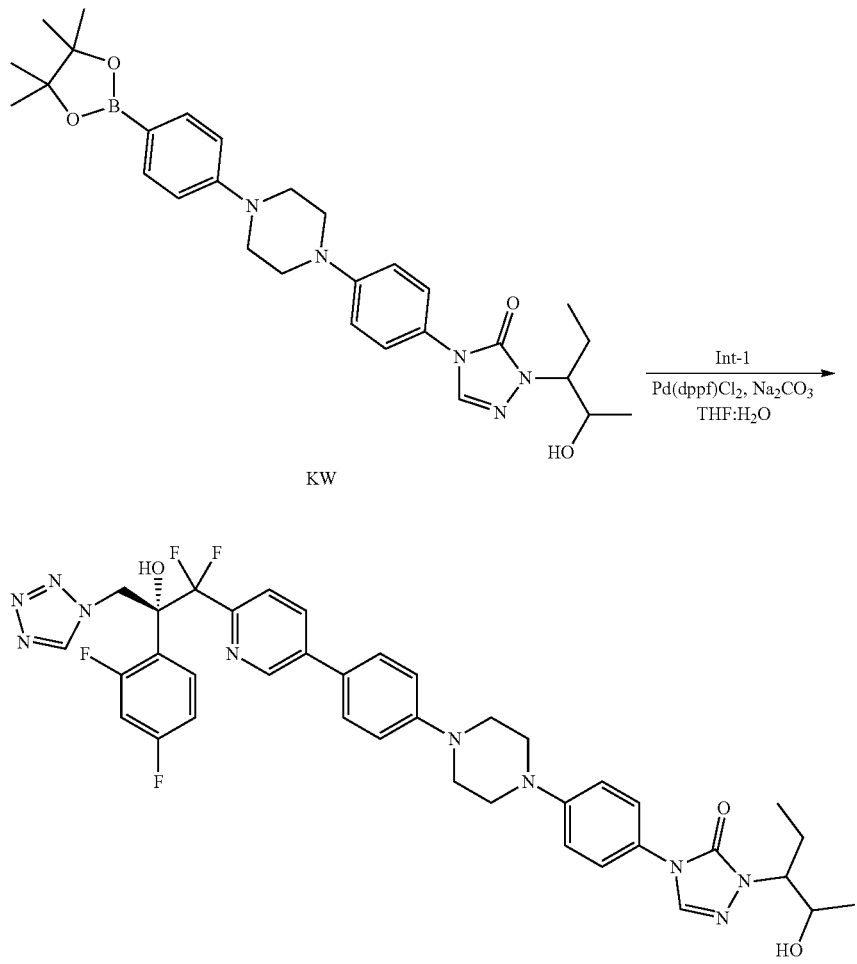

Examples 94, 94-Fr-I, and 94-Fr-II (2R)-2-(2,4-difluorophenyl)-1,1-difluoro-3-(1H-tetrazol-1-yl)-1-(5-(4-(4-(4-(2,2,2-trifluoro-1-hydroxyethyl)-1H-1,2,3-triazol-1-yl) phenyl) piperazin-1-yl) phenyl) pyridin-2-yl) propan-2-ol (94)

1-azido-4-bromobenzene (KY)

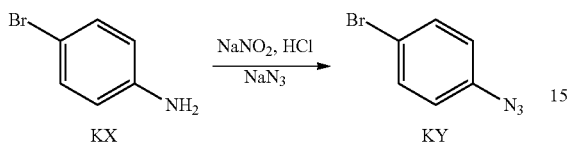

To a stirred solution of 4-bromoaniline (KX; 1.72 g, 10 mmol) in 6.0 N HCl solution (10 mL) under argon atmosphere was added sodium nitrate (1.03 g, 15 mmol) at 0° C., and stirred for 45 min. Then sodium azide (2.6 g, 40 mmol) was added to the reaction mixture at 0° C., and stirred for 2 h. The progress of the reaction was monitored by TLC. The reaction mixture was quenched with ice cold water (50 mL) and extracted with EtOAc (2×50 mL). The combined organic extracts were dried over anhydrous $Na_2SO_4$ and concentrated under reduced pressure to obtain compound KY (1.5 g, crude) as yellow syrup and the obtained material was as such taken for next step without further purification.

(1-(4-bromophenyl)-1H-1,2,3-triazol-4-yl) methanol (KZ)

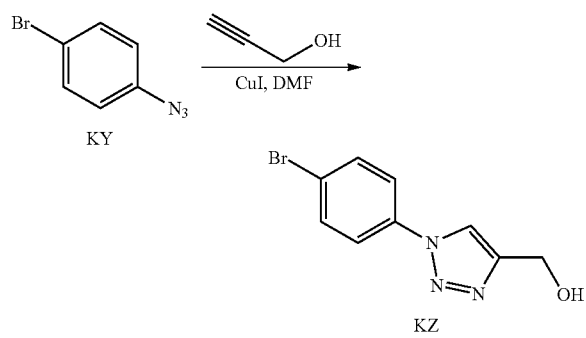

To a stirred solution of compound KY (100 mg, crude) in DMF (5 mL) under argon atmosphere were added copper iodide (10 mg, 0.05 mmol) and propargyl alcohol (33.6 mg, 0.60 mmol) at RT and stirred for 12 h. Then sodium azide (2.6 g, 40 mmol) was added to the reaction mixture at 0 SC and stirred for 2 h. The progress of the reaction was monitored by TLC. The reaction mixture was quenched with ice cold water (20 mL) and extracted with EtOAc (2×20 mL). The combined organic extracts were dried over anhydrous $Na_2SO_4$ and concentrated under reduced pressure. The crude material was purified by silica gel column chromatography (eluent: 5% MeOH/$CH_2Cl_2$) to afford compound KZ [90 mg, 0.35 mmol, 71% (over all yield from two steps)] as a pale yellow solid. $^1$H NMR (400 MHz, DMSO-$d_6$): δ 8.71 (s, 1H), 7.90-7.87 (m, 2H), 7.81-7.77 (m, 2H), 5.33 (t, J=5.6 Hz, 1H), 4.61 (d, J=5.6 Hz, 2H).

1-(4-bromophenyl-1H-1,2,3-triazole-4-carbaldehyde (LA)

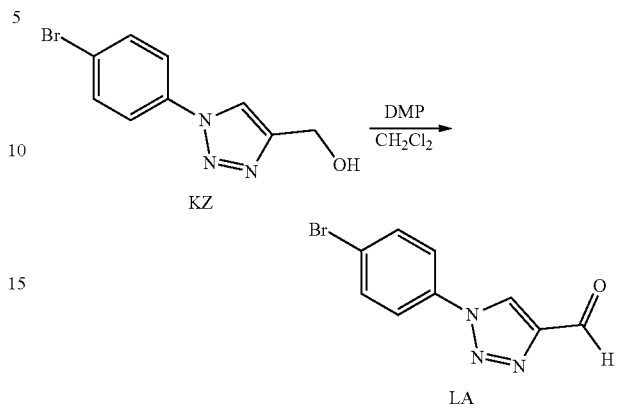

To a stirred solution of compound KZ (1.3 g, 5.15 mmol) in $CH_2Cl_2$ (30 mL) under argon atmosphere was added Dess-Martin periodinane (2.6 g, 6.19 mmol) at 0° C. The reaction mixture was warmed to RT and stirred for 16 h. The reaction mixture was quenched with ice cold water (100 mL) and extracted with $CH_2Cl_2$ (2×100 mL). The combined organic layers were washed with water (100 mL), dried over anhydrous $Na_2SO_4$ and concentrated under reduced pressure. The crude material was purified by silica gel column chromatography (eluted with 30% EtOAc/Hexane) to afford compound LA (1 g, 4 mmol, 77%) as a white solid. $^1$H NMR (400 MHz, DMSO-$d_6$): δ 10.11 (s, 1H), 9.59 (s, 1H), 7.96 (d, J=9.2 Hz, 2H), 7.85 (d, J=8.9 Hz, 2H).

1-(1-(4-bromophenyl)-1H-1,2,3-triazol-4-yl)-2,2,2-trifluoroethan-1-ol (LB)

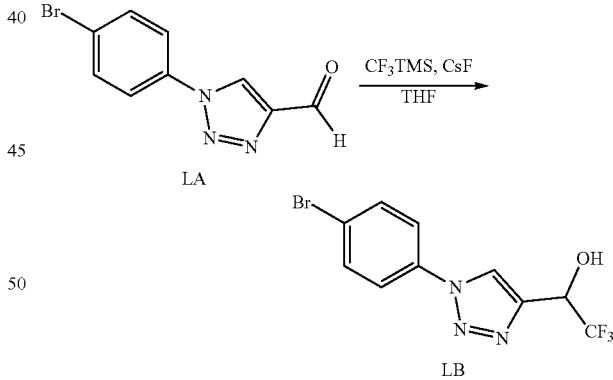

To a stirred solution of compound LA (800 mg, 3.2 mmol) in THF (20 mL) under argon atmosphere were added cesium fluoride (243 mg, 1.6 mmol) and $CF_3TMS$ (908.8 mg, 6.4 mmol) at 0° C. The reaction mixture was warmed to RT and stirred for 6 h. The progress of the reaction was monitored by TLC. The reaction mixture was quenched with 2.0 N HCl solution (10 mL), stirred at 0° C. for 6 h. diluted with water (20 mL) and extracted with EtOAc (2×20 mL). The combined organic extracts were washed with water (20 mL), dried over anhydrous $Na_2SO_4$ and concentrated under reduced pressure. The crude material was purified by silica gel column chromatography (eluent: 30% EtOAc/Hexane) to afford compound LB (600 mg, 1.86 mmol, 58%) as a brown solid. $^1$H NMR (400 MHz, DMSO-$d_6$): δ 8.98 (s, 1H), 7.94 (d, J=8.9 Hz, 2H), 7.81 (d, J=9.0 Hz, 2H), 7.12 (d, J=6.1 Hz, 1H), 5.44-5.37 (m, 1H).

1-(1-(4-(4-(4-(4-bromophenyl) piperazin-1-yl) phenyl)-1H-1,2,3-triazol-4-yl)-2,2,2-trifluoroethan-1-ol (LC)

2,2,2-trifluoro-1-(1-(4-(4-(4-(4,4,5,5-tetramethyl-1,3,2-dioxaborolan-2-yl) phenyl) piperazin-1-yl) phenyl)-1H-1,2,3-triazol-4-yl) ethan-1-ol (LD)

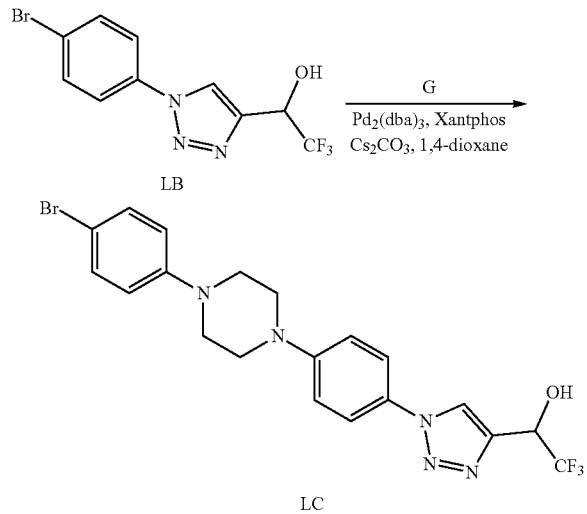

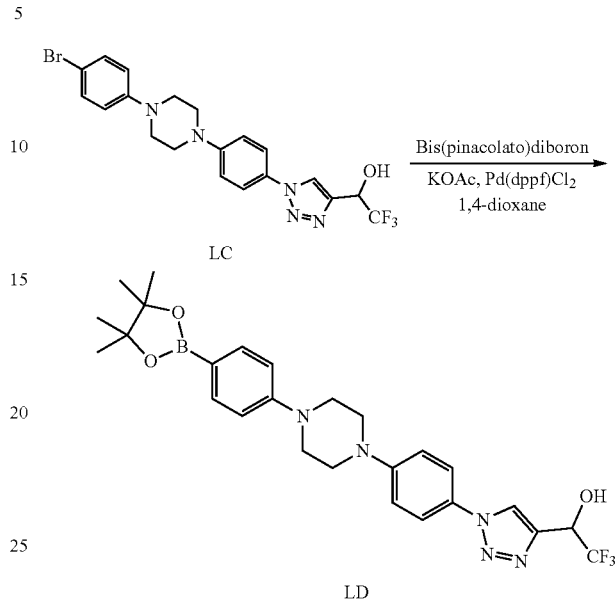

To a stirred solution of compound LB (800 mg, 2.50 mmol) in 1,4-dioxane (20 mL) in a sealed tube under argon atmosphere were added cesium carbonate (2.4 g, 7.47 mmol), Xantphos (100 mg, 0.17 mmol), G (600 mg, 2.49 mmol) at RT and purged under argon for 15 min. Then Pd$_2$(dba)$_3$ (113 mg, 0.12 mmol) was added to the reaction mixture at RT and stirred at 110° C. for 12 h. The progress of the reaction was monitored by TLC. The reaction mixture was diluted with water (30 mL) and extracted with EtOAc (2×30 mL). The combined organic extracts were washed with water (30 mL), brine (30 mL), dried over anhydrous Na$_2$SO$_4$ and concentrated under reduced pressure. The crude material was purified by silica gel column chromatography (eluent: 30% EtOAc/Hexane) to afford compound impure LC (220 mg) as a pale yellow solid. $^1$H NMR (400 MHz, DMSO-$d_6$): δ 8.79 (s, 1H), 7.77 (d, J=9.2 Hz, 2H), 7.38 (d, J=9.0 Hz, 2H), 7.17 (d, J=9.2 Hz, 2H), 7.05 (d, J=6.3 Hz, 1H), 6.98 (d, J=9.2 Hz, 2H), 5.38-5.35 (m, 1H), 3.42-3.35 (m, 4H), 3.33-3.22 (m, 4H).

To a stirred solution of compound LC (220 mg, 0.46 mmol) in 1,4-dioxane (20 mL) under argon atmosphere were added bis(pinacolato)diboron (184 mg, 0.73 mmol) and potassium acetate (134 mg, 1.37 mmol) at RT and purged under argon for 10 min. Then Pd(dppf)Cl$_2$ (33 mg, 0.04 mmol) was added and the reaction mixture was purged under argon for 10 min at RT. The reaction mixture was stirred at 110° C. for 12 h. The progress of the reaction was monitored by TLC. The reaction mixture was quenched with water (10 mL) and extracted with CH$_2$Cl$_2$ (2×10 mL). The combined organic layers were washed with water (10 mL), brine (10 mL), dried over anhydrous Na$_2$SO$_4$ and concentrated under reduced pressure to obtain compound LD (200 mg, crude) as a brown syrup and the obtained material was as such taken for next step without further purification.

(2R)-2-(2,4-difluorophenyl)-1,1-difluoro-3-(1H-tetrazol-1-yl)-1-(5-(4-(4-(4-(2,2,2-trifluoro-1-hydroxyethyl)-1H-1,2,3-triazol-1-yl) phenyl) piperazin-1-yl) phenyl) pyridin-2-yl) propan-2-ol (94)

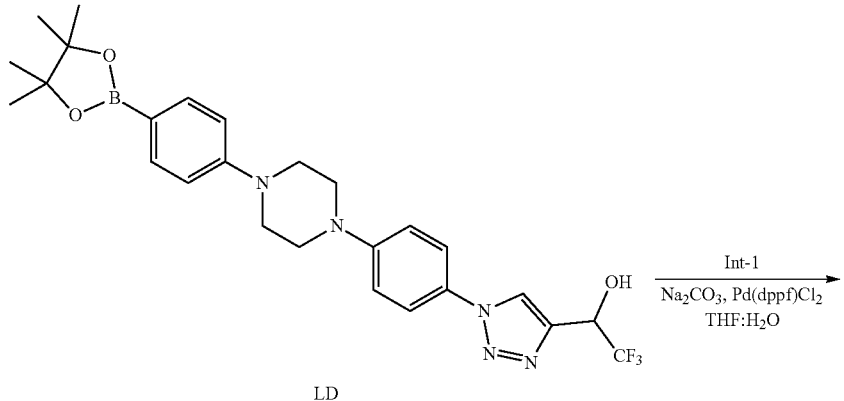

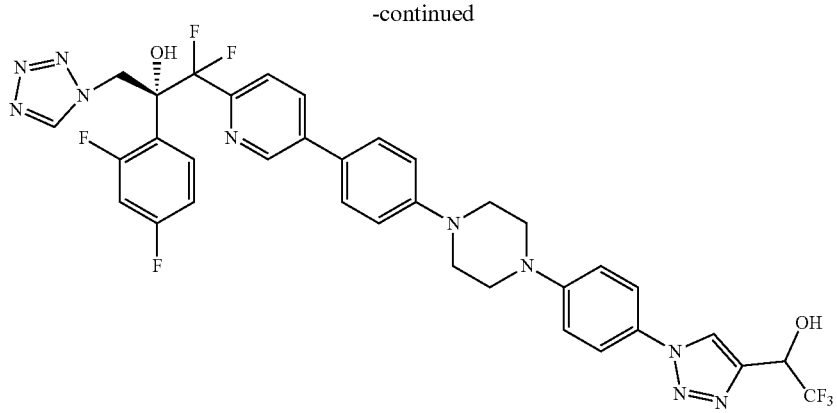

94

To a stirred solution of Int-1 (163 mg, 0.40 mmol) in THF:H2O (4:1, 15 mL) under argon atmosphere were added compound LD (201 mg, 0.40 mmol), sodium carbonate (121 mg, 1.14 mmol) and purged under argon for 20 min at RT. Then Pd(dppf)Cl$_2$ (28 mg, 0.04 mmol) was added and the reaction mixture was purged under argon for 10 min at RT. The reaction mixture was stirred at 90° C. for 12 h. The progress of the reaction was monitored by TLC. The reaction mixture was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 94 (35 mg, 0.05 mmol, 12%) as an off-white solid. $^1$H NMR (400 MHz, DMSO-d$_6$): δ 9.15 (s, 1H), 8.91 (s, 1H), 8.79 (s, 1H), 8.17 (dd, J=8.2, 2.1 Hz, 1H), 7.78 (d, J=9.2 Hz, 2H), 7.71 (d, J=8.9 Hz, 2H), 7.49 (d, J=8.2 Hz, 1H), 7.33-7.24 (m, 2H), 7.23-7.12 (m, 5H), 7.05 (d, J=6.1 Hz, 1H), 6.93-6.89 (m, 1H), 5.67 (d, J=14.6 Hz, 1H), 5.40-5.33 (m, 1H), 5.11 (d, J=14.8 Hz, 1H), 3.43 (s, 8H); MS (ESI): m/z 755.3 [M+H]$^+$; HPLC: 95.01%; Optical rotation [α]$_D^{20}$: +108.4 (c=0.1% in CH$_2$Cl$_2$).

Examples 94-Fr-I and 94-Fr-II (2R)-2-(2,4-difluorophenyl)-1,1-difluoro-3-(1H-tetrazol-1-yl)-1-(5-(4-(4-(4-(4-(2,2,2-trifluoro-1-hydroxyethyl)-1H-1,2,3-triazol-1-yl) phenyl) piperazin-1-yl) phenyl) pyridin-2-yl) propan-2-ol (94-Fr-I)

(2R)-2-(2,4-difluorophenyl)-1,1-difluoro-3-(1H-tetrazol-1-yl)-1-(5-(4-(4-(4-(4-(2,2,2-trifluoro-1-hydroxyethyl)-1H-1,2,3-triazol-1-yl) phenyl) piperazin-1-yl) phenyl) pyridin-2-yl) propan-2-ol (94-Fr-II)

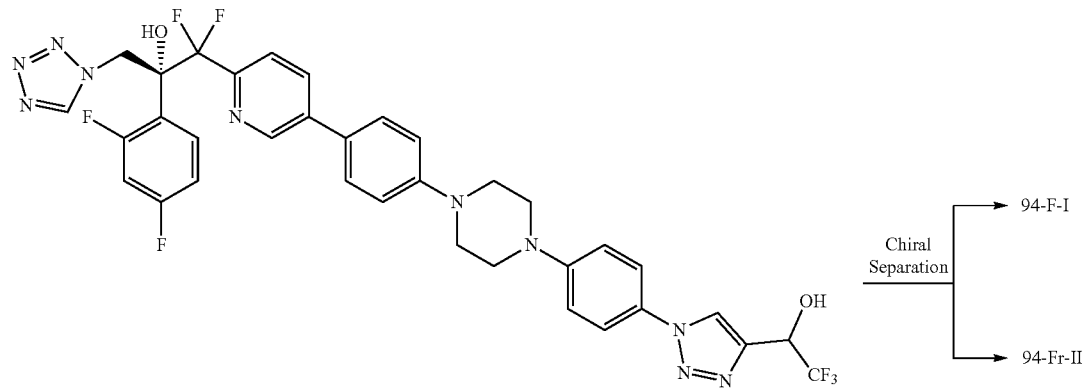 [SMILES: OC(c1cn(-c2ccc(N3CCN(c4ccc(-c5ccc(C(F)(F)[C@](O)(Cn6cnnn6)c6ccc(F)cc6F)nc5)cc4)CC3)cc2)nn1)C(F)(F)F]

94 (250 mg, 0.26 mmol) was separated by normal-phase preparative high performance liquid chromatography (CHIRALPAK-IC®, 250×20 mm, 5µ; using (A) 0.1% DEA in n-hexane:(B) CH$_2$Cl$_2$:MeOH (80:20) (A:B=40:60) as a mobile phase; Flow rate: 20 mL/min) to obtain 94-Fr-I (50 mg) and 94-Fr-II (50 mg).

94-Fr-I:

$^1$H NMR (400 MHz, DMSO-d$_6$): δ 9.15 (s, 1H), 8.91 (s, 1H), 8.79 (s, 1H), 8.17 (dd, J=8.3, 2.1 Hz, 1H), 7.79 (d, J=9.2 Hz, 2H), 7.71 (d, J=8.9 Hz, 2H), 7.49 (d, J=8.2 Hz, 1H), 7.33-7.24 (m, 2H), 7.23-7.12 (m, 5H), 7.06 (d, J=6.1 Hz, 1H), 6.93-6.89 (m, 1H), 5.67 (d J=14.6 Hz, 1H), 5.43-5.30 (m, 1H), 5.11 (d, J=14.6 Hz, 1H), 3.43 (s, 8H); MS (ESI): m/z 753.7 [M−H]$^−$; HPLC: 97.18%; Chiral HPLC Purity: 100%, R$_f$=11.20 min (CHIRALPAK-IC®, 250×4.6 mm, 5µ; mobile phase (A) 0.1% DEA in n-hexane:(B) CH$_2$Cl$_2$:MeOH (80:20) (A:B=40:60); flow Rate: 1.00 mL/min); Optical rotation [α]$_D^{19.98}$: +101.84° (c=0.1% in CH$_2$Cl$_2$).

94-Fr-II:

$^1$H NMR (400 MHz, DMSO-d$_6$): δ 9.15 (s, 1H), 8.91 (s, 1H), 8.79 (s, 1H), 8.17 (dd, J=8.3, 2.1 Hz, 1H), 7.79 (d, J=9.2 Hz, 2H), 7.71 (d, J=8.9 Hz, 2H), 7.49 (d, J=8.2 Hz, 1H), 7.33-7.24 (m, 2H), 7.23-7.12 (m, 5H), 7.06 (d, J=6.1 Hz, 1H), 6.93-6.89 (m, 1H), 5.67 (d, J=14.6 Hz, 1H), 5.43-5.30 (m, 1H), 5.11 (d, J=14.6 Hz, 1H), 3.43 (s, 8H); MS (ESI): m/z 753.6 [M−H]$^−$; HPLC: 95.68%; Chiral HPLC Purity: 100%, R$_f$=13.26 min (CHIRALPAK-IC®, 250×4.6 mm, 5µ; mobile phase (A) 0.1% DEA in n-hexane:(B) CH$_2$Cl$_2$:MeOH (80:20) (A:B=40:60); flow Rate: 1.00 mL/min); Optical rotation [α]$_D^{20}$: +121.92 (c=0.1% in CH$_2$Cl$_2$).

Example 95

(2S,3S)-3-(4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-1H-1,2,3-triazol-1-yl) pentan-2-ol (95)

(2S,3S)-3-azidopentan-2-ol (LF)

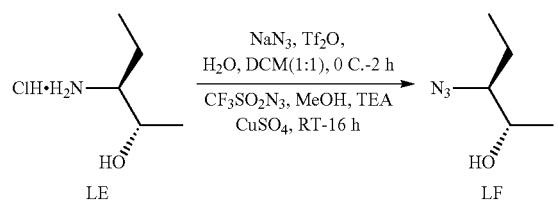

To a stirred solution of sodium azide (400 mg, 1.11 mmol) in H$_2$O:CH$_2$Cl$_2$(1:1) (15 mL) under argon atmosphere was added triflic anhydride (1.8 mL, 2.22 mmol) at 0° C. and stirred for 2 h. Then the reaction mixture was diluted with saturated aq. NaHCO$_3$ solution (10 mL) at 0° C., and the aqueous layer was extracted with CH$_2$Cl$_2$ (20 mL) to afford the triflic azide solution. The obtained triflic azide solution was added to a stirred solution of compound LE in MeOH (25 mL) followed by water (2 mL), copper sulfate solution (90 mg, 0.359 mmol) in MeOH (3 mL) and triethylamine (1.6 mL, 10.79 mmol) at 0° C. The reaction mixture stirred at RT for 16 h. The reaction mixture was quenched saturated aq. NaHCO$_3$ solution (10 mL) at 0° C., and then the excess solvent was evaporated and the residue was extracted with EtOAc (2×50 mL). The combined organic extracts were washed with water (20 mL), brine (20 mL), dried over anhydrous Na$_2$SO$_4$ and concentrated under reduced pressure. The crude LF was as such used in the next without further purification. $^1$H NMR (400 MHz, CDCl$_3$): δ 3.84-3.66 (m, 1H), 3.17-2.98 (m, 2H), 1.81-1.54 (m, 2H), 1.24 (d, J=6.3 Hz, 3H), 1.04 (t, J=7.5 Hz, 3H).

1-(4-bromophenyl)-4-(4-(4-ethynylphenyl) piperazine (LG)

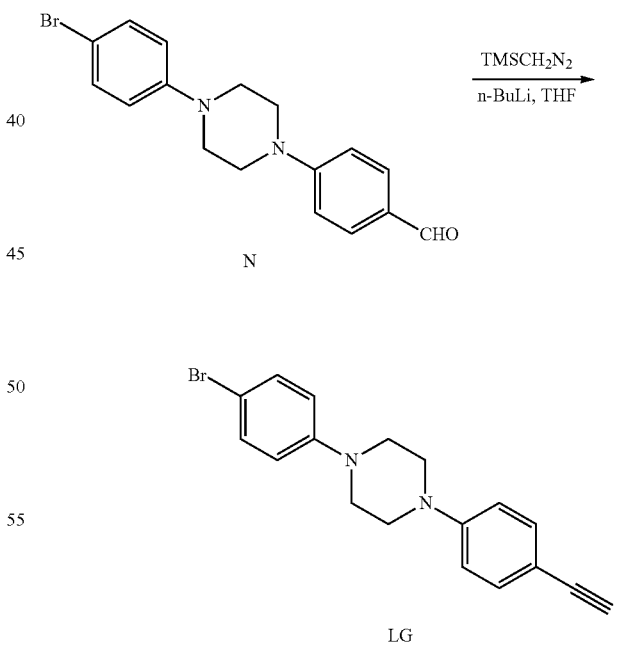

To a stirred solution of TMS-diazomethane (0.62 mL, 5.81 mmol) in THF (30 mL) under argon atmosphere was added n-BuLi (3.6 mL, 5.81 mmol, 1.6 M in hexanes) at −78° C. and stirred for 1 h. Then added compound N (2.0 g, 5.81 mmol) in THF (20 mL) at −78° C. and stirred for another 2 h. The progress of the reaction was monitored by TLC. The reaction mixture was extracted with EtOAc (2×100 mL). The combined organic extracts were washed with water (20 mL), brine (20 mL), dried over anhydrous Na₂SO₄ and concentrated under reduced pressure. The crude material was purified by silica gel column chromatography (eluent: 25% EtOAc/Hexane) to afford compound LG (450 mg, 1.31 mmol, 22%) as an off-white solid. ¹H NMR (400 MHz, CDCl₃): δ 7.41 (d, J=8.9 Hz, 2H), 7.37 (d, J=9.0 Hz, 2H), 6.87 (d, J=9.0 Hz, 2H), 6.83 (d, J=9.0 Hz, 2H), 3.40-3.36 (m, 4H), 3.31-3.24 (m, 4H), 3.00 (s, 1H).

(2S,3S)-3-(4-(4-(4-(4-bromophenyl) piperazin-1-yl) phenyl)-1H-1,2,3-triazol-1-yl) pentan-2-ol (LH)

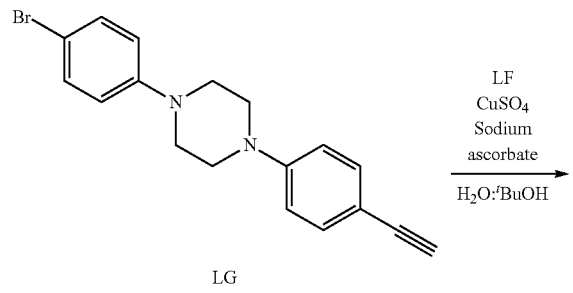

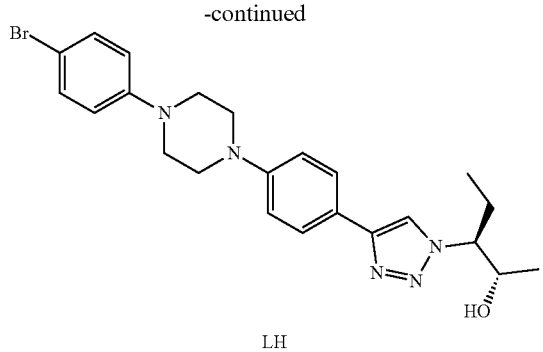

To a stirred solution of compound LG (300 mg, 0.87 mmol) in BuOH:H₂O (1:1) under argon atmosphere were added sodium ascorbate (5 mg, 0.026 mmol), compound LF (340 mg, 2.63 mmol) (20 mL) and copper sulfate penta hydrate (6.5 mg, 0.26 mmol) at RT. The reaction mixture was stirred at reflux for 8 h. The progress of the reaction was monitored by TLC. The reaction mixture was diluted with water (20 mL) and the obtained white precipitate was filtered and washed thoroughly with water and n-pentane. The solid was dried under vacuum for longer hours to afford compound LH (300 mg, 0.63 mmol, 72%) as an off-white solid. ¹H NMR (400 MHz, DMSO-d₆): δ 8.31 (s, 1H), 7.74 (d, J=8.7 Hz, 2H), 7.38 (d, J=9.0 Hz, 2H), 7.06 (d, J=8.9 Hz, 2H), 6.97 (d, J=9.0 Hz, 2H), 5.01 (d, J=4.9 Hz, 1H), 4.33-4.28 (m, 1H), 4.02-3.84 (m, 1H), 3.33-3.30 (m, 8H), 1.99-1.87 (m, 2H), 0.99 (d, J=6.3 Hz, 3H), 0.72 (t, J=7.3 Hz, 3H).

(2S,3S)-3-(4-(4-(4-(4-(4,4,5,5-tetramethyl-1,3,2-dioxaborolan-2-yl) phenyl) piperazin-1-yl) phenyl)-1H-1,2,3-triazol-1-yl) pentan-2-ol (LI)

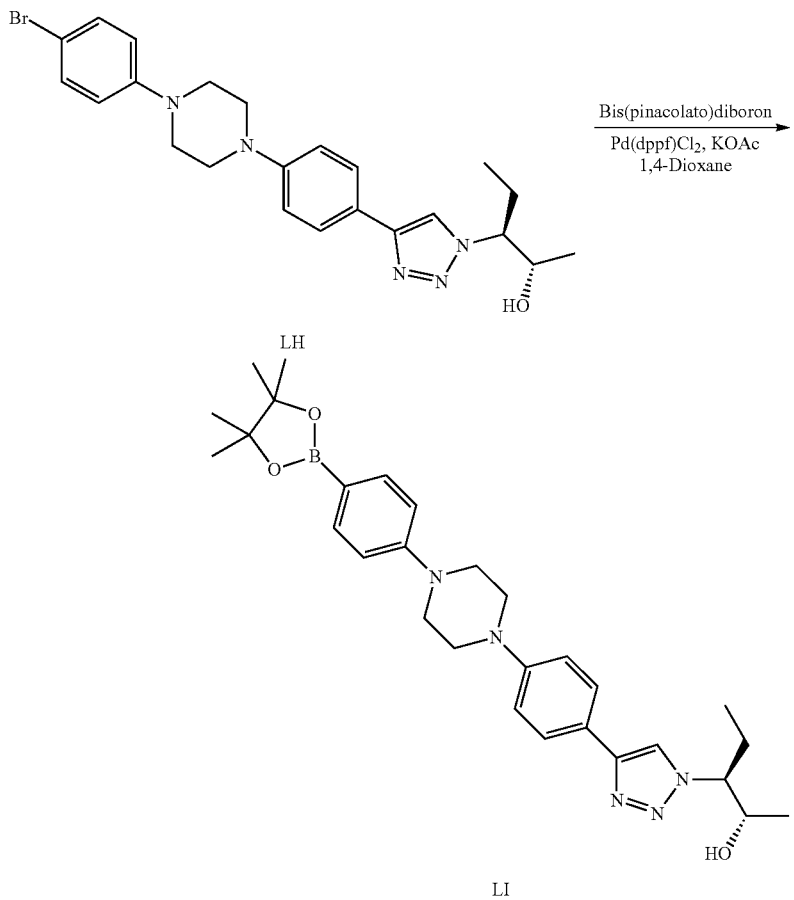

To a stirred solution of compound LH (300 mg, 0.63 mmol) in 1,4-dioxane (20 mL) under argon atmosphere were added bis(pinacolato)diboron (260 mg, 1.02 mmol) and potassium acetate (188 mg, 1.91 mmol) at RT and purged under argon atmosphere for 15 min. Then Pd(dppf)Cl₂ (47 mg, 0.063 mmol) was added and the reaction mixture was purged under argon atmosphere for 5 min at RT. The reaction mixture was stirred at 110° C. for 16 h. The reaction mixture was quenched with water (20 mL) and extracted with EtOAc (2×50 mL). The combined organic layers were washed with water (20 mL), brine (20 mL), dried over anhydrous Na₂SO₄ and concentrated under reduced pressure. The crude material was purified by silica gel column chromatography (eluent: 2% MeOH/DCM) to afford compound LI (280 mg, crude) as colorless semi-solid and the obtained material was as such taken for next step without further purification. LC-MS: 518.3 [M+H]⁺ at 3.606 RT (29.74% purity).

(2S,3S)-3-(4-(4-(4-(4-(6-((R)-2-(2,4-difluorophenyl)-1,1-difluoro-2-hydroxy-3-(1H-tetrazol-1-yl) propyl) pyridin-3-yl) phenyl piperazin-1-yl) phenyl)-1H-1,2,3-triazol-1-yl) pentan-2-ol (95)

To a stirred solution of Int-1 (150 mg, 0.347 mmol) in THF:H2O (4:1, 20 mL) under argon atmosphere were added compound LI (530 mg, 1.04 mmol), sodium carbonate (110 mg, 1.04 mmol) and purged under argon for 10 min at RT. Then Pd(dppf)Cl₂ (13 mg, 0.017 mmol) was added to the reaction mixture at RT and stirred at reflux for 16 h. The reaction mixture was diluted with water (20 mL) and extracted with EtOAc (2×50 mL). The combined organic extracts were washed with water (20 mL), brine (20 mL), dried over anhydrous Na₂SO₄ and concentrated under reduced pressure. The crude material was purified by silica gel column chromatography (eluent: 2% MeOH/DCM) to afford 95 (90 mg, 0.01 mmol, 36%) as an off-white solid. ¹H NMR (400 MHz, DMSO-d₆): δ 9.15 (s, 1H), 8.91 (d, J=2.0 Hz, 1H), 8.32 (s, 1H), 8.17 (dd, J=8.2, 2.1 Hz, 1H), 7.75 (d, J=8.9 Hz, 2H), 7.71 (d, J=8.9 Hz, 2H), 7.49 (d, J=8.4 Hz, 1H), 7.34-7.18 (m, 3H), 7.15 (d, J=8.9 Hz, 2H), 7.08 (d, J=8.9 Hz, 2H), 6.93-6.89 (m, 1H), 5.67 (d, J=14.8 Hz, 1H), 5.11 (d, J=14.8 Hz, 1H), 5.01 (d, J=5.0 Hz, 1H), 4.35-4.28 (m, 1H), 4.04-3.92 (m, 1H), 3.42-3.36 (m, 8H), 2.00-1.84

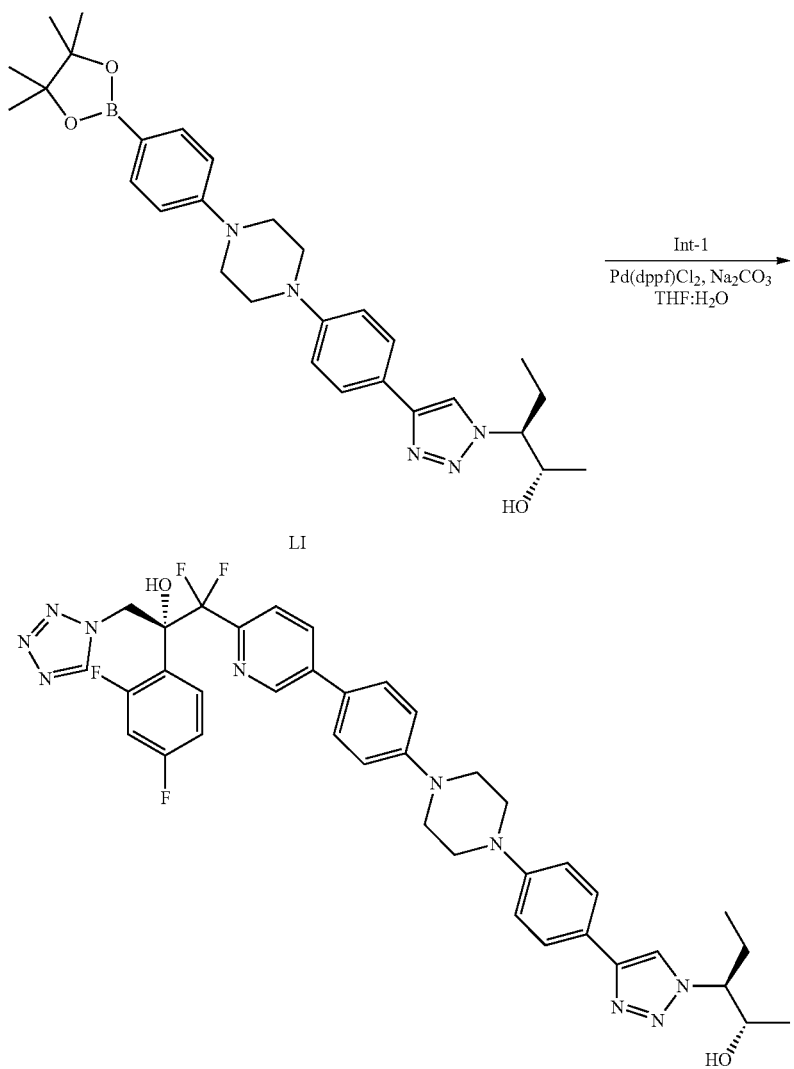

(m, 2H), 0.99 (d, J=6.3 Hz, 3H), 0.73 (t, J=7.3 Hz, 3H); MS (ESI): m/z 743.8 [M+H]+; HPLC: 95.29%; Optical rotation [α]$_D^{19}$: +77.8 (c=0.1% in DCM.

Example 96

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-methyl-2,4-dihydro-3H-1,2,4-triazol-3-one (96)

N-(2,2-dimethoxyethyl)-2,2,2-trifluoroethan-1-amine (LK)

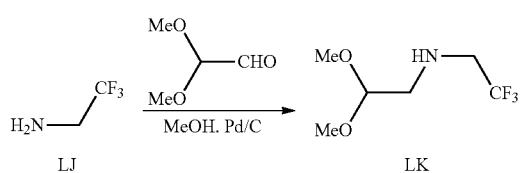 [SMILES: NCC(F)(F)F ; COC(C=O)OC ; COC(CNCC(F)(F)F)OC]

To a stirred solution of compound LJ (2 g, 19.23 mmol) in methanol (30 mL) under argon atmosphere was added 2,2-dimethoxyacetaldehyde (1.9 g, 19.23 mmol) and stirred at RT for 16 h. Then added 10% Pd/C (240 mg in 5 mL of H$_2$O) at RT. The reaction mixture was stirred at RT under hydrogen atmosphere for 4 h. The progress of the reaction was monitored by TLC. The reaction mixture was filtered through celite, the filtrate was concentrated under reduced pressure to obtain compound LK (2.5 g, crude). The obtained crude compound was used in the next step without further purification. $^1$H NMR (400 MHz, CDCl$_3$): δ 4.41 (t, J=5.5 Hz, 1H), 3.38 (s, 6H), 3.22-3.18 (m, 2H), 2.84 (d, J=5.2 Hz, 2H).

3-(4-(4-(4-bromophenyl) piperazin-1-yl) phenyl)-1-(2,2-dimethoxyethyl)-1-(2,2,2-trifluoroethyl) urea (LL)

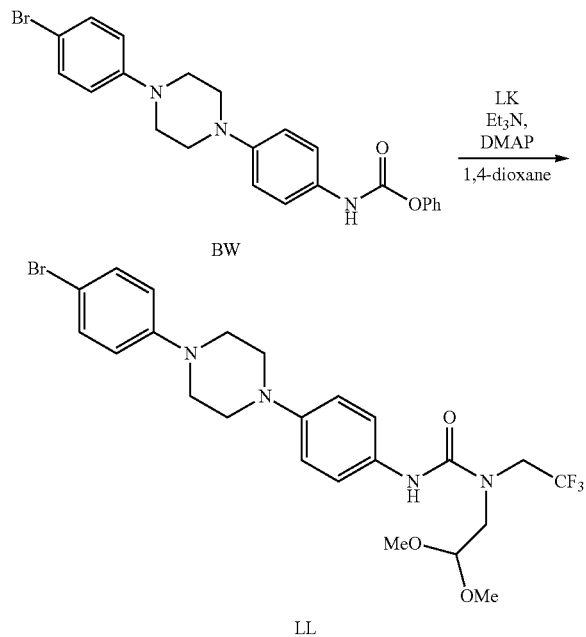

To a stirred solution of compound LK (800 mg, 1.77 mmol) in 1,4-Dioxane (30 mL) under argon atmosphere were added triethylamine (0.25 mL, 1.77 mmol) and DMAP (216 mg, 1.77 mmol) followed by compound BW (397 mg, 2.12 mmol) at RT. The reaction mixture was stirred at 110° C. for 5 h. The progress of the reaction was monitored by TLC. The reaction mixture was diluted with water (50 mL) and extracted with EtOAc (2×50 mL). The combined organic extracts were dried over anhydrous Na$_2$SO$_4$ and concentrated under reduced pressure. The crude material was purified by silica gel column chromatography (eluent: 40% EtOAc/hexane) to afford compound LL (500 mg, 0.919 mmol, 52%) as a light brown solid. $^1$H NMR (500 MHz, DMSO-d$_6$): δ 8.46 (s, 1H), 7.35 (d, J=8.7 Hz, 2H), 7.26 (d, J=8.7 Hz, 2H), 6.95-6.91 (m, 4H), 4.52-4.50 (m, 1H), 4.25-4.23 (m, 2H), 3.55-3.53 (m, 2H), 3.34 (s, 6H), 3.28-3.17 (m, 8H).

4-(4-(4-(4-bromophenyl) piperazin-1-yl) phenyl)-2-methyl-2,4-dihydro-3H-1,2,4-triazol-3-one (LM)

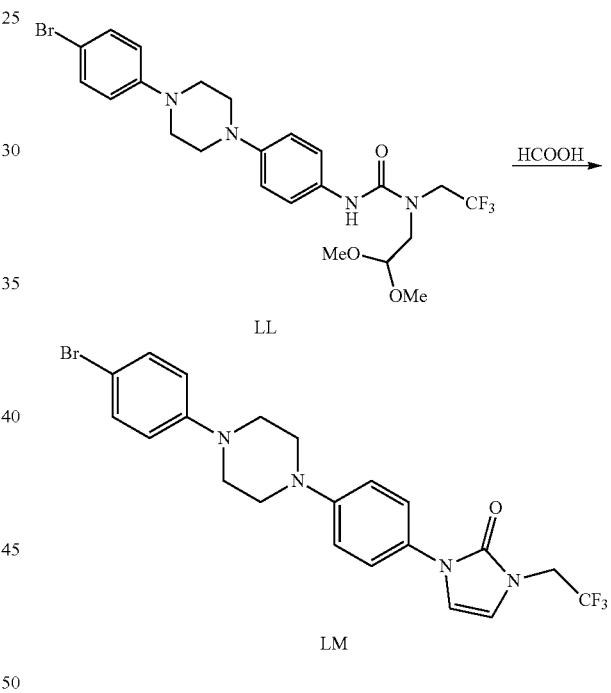

To a stirred solution of compound LL (500 mg, 0.919 mmol) in formic acid (2 mL) under argon atmosphere. The reaction mixture was stirred at reflux for 3 h. The progress of the reaction was monitored by TLC. The reaction mixture was concentrated under reduced pressure and the residue was neutralized with saturated aq. NaHCO$_3$ solution (10 mL) and extracted with EtOAc (2×50 mL). The combined organic extracts were washed with water (50 mL) and dried over anhydrous Na$_2$SO$_4$ and concentrated under reduced pressure. The crude material was purified by silica gel column chromatography (eluent: 50% EtOAc/hexane) to afford compound LM (400 mg, 0.83 mmol, 90%) as a light brown solid. $^1$H NMR (400 MHz, DMSO-d$_6$): δ 7.51 (d, J=9.2 Hz, 2H), 7.37 (d, J=9.0 Hz, 2H), 7.07 (d, J=9.2 Hz, 2H), 7.02 (d, J=3.2 Hz, 1H), 6.99-6.94 (m, 3H), 6.77 (d, J=3.1 Hz, 1H), 4.53-4.46 (m, 1H), 3.30-3.28 (m, 8H).

417

2-methyl-4-(4-(4-(4-(4-(4,4,5,5-tetramethyl-1,3,2-dioxaborolan-2-yl) phenyl) piperazin-1-yl) phenyl)-2,4-dihydro-3H-1,2,4-triazol-3-one (LN)

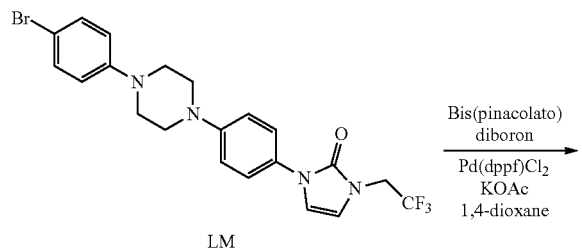

418

To a stirred solution of compound LM (400 mg, 0.831 mmol) in 1,4-dioxane (30 mL) under argon atmosphere were added bis(pinacolato)diboron (336 ng, 1.33 mmol) and potassium acetate (244 mg, 2.49 mmol) at RT. The reaction mixture was purged with argon for 20 min, then Pd(dppf)Cl$_2$ (60 mg, 0.08 mmol) was added and the reaction mixture was purged under argon for 5 min at RT. The reaction mixture was stirred at 110° C. for 12 h. The progress of the reaction was monitored by TLC. The reaction mixture was diluted with water (20 mL) and extracted with EtOAc (2×50 mL). The combined organic layers were washed with water (20 mL), brine (20 mL), dried over anhydrous Na$_2$SO$_4$ and concentrated under reduced pressure. The crude material was purified by silica gel column chromatography (eluent: 60% EtOAC/Hexane) to afford compound LN (300 mg, 0.56 mmol, 68%) as an off-white solid. $^1$H NMR (400 MHz, DMSO-d$_6$): δ 7.61-7.44 (m, 4H), 7.06 (d, J=9.2 Hz, 2H), 7.00 (d, J=3.1 Hz, 1H), 6.96 (d, J=8.9 Hz, 2H), 6.75 (d, J=3.2 Hz, 1H), 3.90 (s, 2H), 3.41-3.23 (m, 8H), 1.26 (s, 12H).

(R)-4-(4-(4-(4-(6-(2-(2,4-difluorophenyl)-1,1-difluoro-2-hydroxy-3-(1H-tetrazol-1-yl) propyl) pyridin-3-yl) phenyl) piperazin-1-yl) phenyl)-2-methyl-2,4-dihydro-3H-1,2,4-triazol-3-one (96)

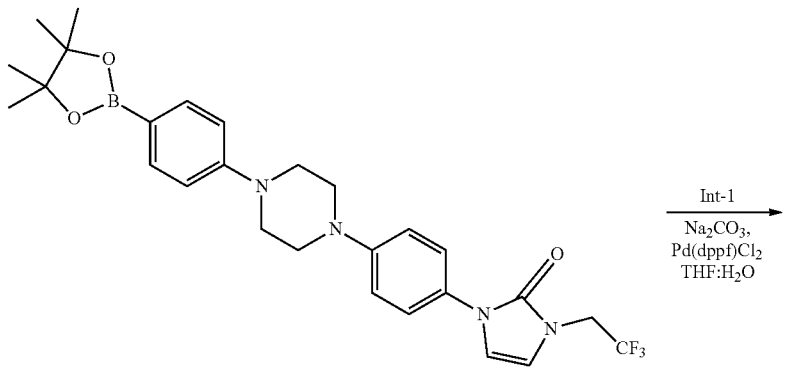

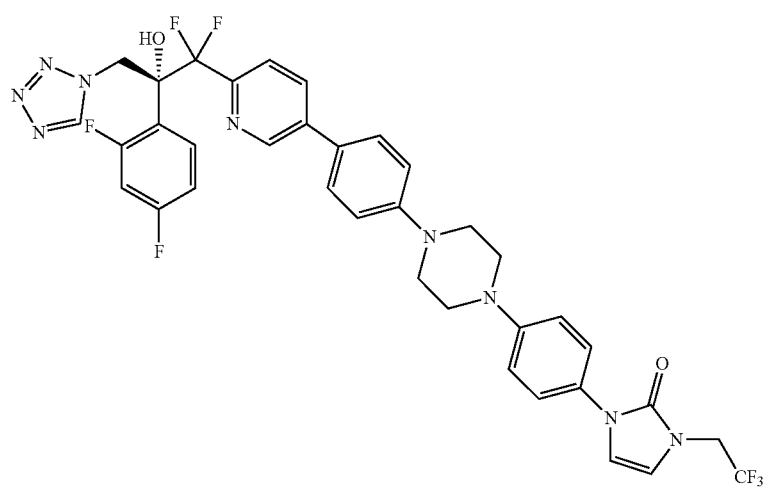

To a stirred solution of Int-1 (150 mg, 0.34 mmol) in THF:H2O (4:1, 20 mL) under argon atmosphere were added compound LN (220 mg, 0.41 mmol), sodium carbonate (110 mg, 1.04 mmol) and purged under argon for 20 min at RT. Then Pd(dppf)Cl$_2$ (13 mg, 0.017 mmol) was added and the reaction mixture was purged under argon for 10 min at RT. The reaction mixture was stirred at 80° C. for 5 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) to afford 96 (80 mg, 0.106 mmol, 31%) as an off-white solid. $^1$H NMR (400 MHz, CDCl$_3$): δ 8.77 (s, 1H), 8.73 (d, J=1.4 Hz, 1H), 7.95 (dd, J=8.2, 2.1 Hz, 1H), 7.86 (s, 1H), 7.60 (d, J=8.2 Hz, 1H), 7.53-7.46 (m, 4H), 7.43-7.32 (m, 1H), 7.07 (d, J=8.8 Hz, 2H), 7.02 (d, J=9.0 Hz, 2H), 6.80-6.74 (m, 1H), 6.71-6.63 (m, 1H), 6.58 (d, J=3.1 Hz, 1H), 6.44 (d, J=2.7 Hz, 1H), 5.62 (d, J=14.2 Hz, 1H), 5.10 (d, J=14.2 Hz, 1H), 4.30-4.26 (m, 2H), 3.48-3.32 (m, 8H); MS (ESI): m/z 754.7 [M+H]$^+$; HPLC: 97.29%; Optical rotation [α]$_D^{20}$: +114.1 (c=0.1% in CH$_2$Cl$_2$).

Example 97

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-3-(2-hydroxypentan-3-yl)-1,3-dihydro-2H-imidazol-2-one (97)

3-bromopentan-2-one (LP)

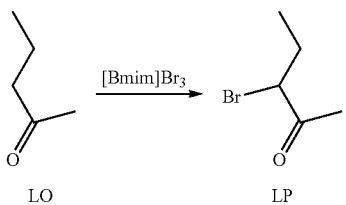

A mixture of pentan-2-one (LO; 500 mg, 5.81 mmol) and [BIMM] Br$_3$ (1.1 g 2.90 mmol) under argon atmosphere was stirred at 0 (C for 20 min. The reaction mixture was warmed to RT and stirred for 1 h. The progress of the reaction was monitored by TLC. The reaction mixture was quenched with ice cold water (30 mL) and extracted with ether (2×30 mL). The combined organic layers were washed with water (50 mL), brine (50 mL), dried over anhydrous Na$_2$SO$_4$ and concentrated under reduced pressure to obtain compound LP (500 mg, crude) as yellow syrup. The crude material as such used in the next step without further purification. $^1$H NMR (500 MHz, CDCl$_3$): δ 4.20-4.18 (m, 1H), 2.37 (s, 3H), 2.11-2.00 (m, 1H), 2.00-1.91 (m, 1H), 1.05 (t, J=7.4 Hz, 3H).

1-(4-(4-(4-bromophenyl) piperazin-1-yl) phenyl)-3-(2,2-dimethoxyethyl) urea (LQ)

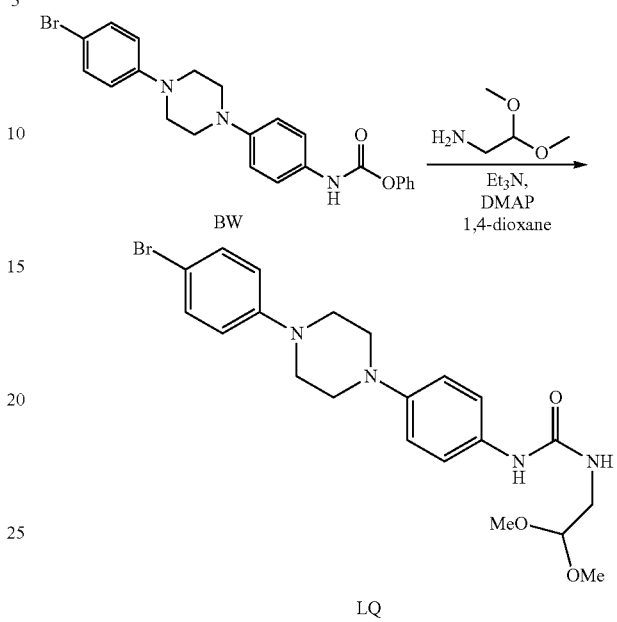

To a stirred solution of compound BW (1.0 g, 2.21 mmol) in 1,4-Dioxane (30 mL) under argon atmosphere were added triethylamine (0.31 mL, 2.21 mmol) and DMAP (270 mg, 2.21 mmol) followed by 2,2-dimethoxyethanamine (0.36 ml, 3.31 mmol) at RT. The reaction mixture was stirred at 110° C. for 4 h. The progress of the reaction was monitored by TLC. The reaction mixture was diluted with water (50 mL) and extracted with EtOAc (2×50 mL). The combined organic extracts were dried over anhydrous Na$_2$SO$_4$ and concentrated under reduced pressure. The crude material was purified by silica gel column chromatography (eluent: 40% EtOAc/hexane) to afford compound LQ (900 mg, 1.94 mmol, 88%) as an off-white solid. $^1$H NMR (500 MHz, DMSO-d$_6$): δ 8.30 (s, 1H), 7.37 (d, J=9.3 Hz, 2H), 7.25 (d, J=8.7 Hz, 2H), 6.95 (br d, J=9.3 Hz, 2H), 6.89 (d, J=8.7 Hz, 2H), 6.00 (t, J=5.8 Hz, 1H), 4.36 (t, J=5.2 Hz, 1H), 3.31 (s, 6H), 3.28-3.24 (m, 4H), 3.20-3.13 (m, 6H).

1-(4-(4-(4-bromophenyl) piperazin-1-yl) phenyl)-1,3-dihydro-2H-imidazol-2-one (LR)

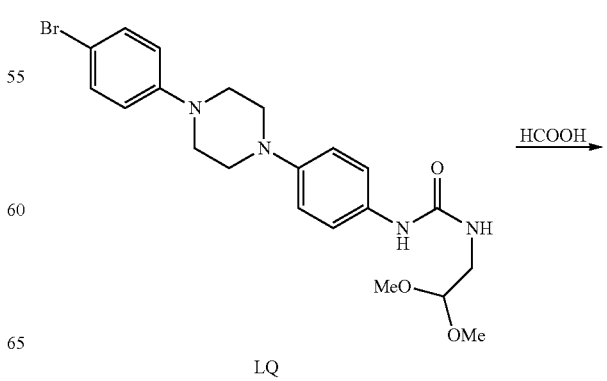

-continued

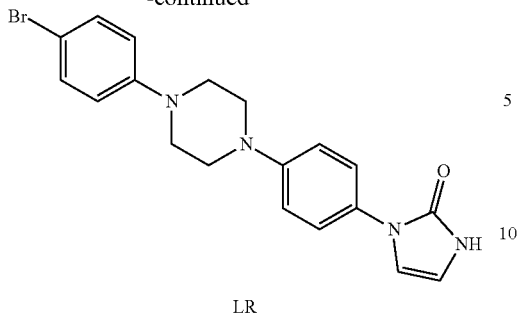

LR

To a stirred solution of compound LQ (700 mg, 1.51 mmol) in formic acid (5 mL) under argon atmosphere was stirred at reflux for 3 h. The progress of the reaction was monitored by TLC. The reaction mixture was concentrated under reduced pressure and the residue neutralized with saturated aq. NaHCO₃ solution (20 mL) and extracted with EtOAc (2×100 mL). The combined organic extracts were washed with water (100 mL) and dried over anhydrous Na₂SO₄ and concentrated under reduced pressure. The crude material was purified by silica gel column chromatography (eluent: 50% EtOAc/hexane) to afford compound LR (500 mg, 76% pure) as an off-white solid. The material as such used in the next step without further purification.

1-(4-(4-(4-bromophenyl) piperazin-1-yl) phenyl)-3-(2-oxopentan-3-yl)-1,3-dihydro-2H-imidazol-2-one (LS)

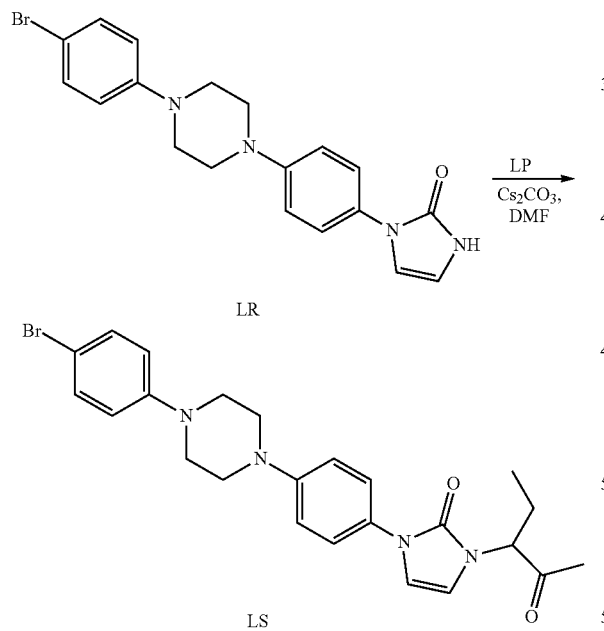

To a stirred solution of compound LR (650 mg, 1.63 mmol) in DMF (20 mL) under argon atmosphere were added cesium carbonate (1.6 g, 4.88 mmol) and compound LP (403 mg, 2.44 mmol) at 0° C. The reaction mixture was stirred at RT for 12 h. The progress of the reaction was monitored by TLC. The reaction mixture was diluted with water (50 mL) and extracted with EtOAc (2×50 mL). The combined organic extracts were dried over anhydrous Na₂SO₄ and concentrated under reduced pressure. The crude material was purified by silica gel column chromatography (eluent: 40% EtOAC/Hexane) to afford compound LS (400 mg, 76 pure %) as an off-white solid. The material as such used in the next step without further purification. $^1$H NMR (400 MHz, DMSO-d₆): δ 7.54 (d, J=9.2 Hz, 2H), 7.37 (d, J=9.0 Hz, 2H), 7.07 (d, J=9.1 Hz, 2H), 7.01-6.91 (m, 3H), 6.73 (d, J=3.1 Hz, 1H), 4.66 (dd, J=10.7, 4.5 Hz, 1H), 3.30-3.27 (m, 8H), 2.13 (s, 3H), 2.09-2.04 (m, 1H), 1.84-1.76 (m, 1H), 0.91-0.79 (m, 3H).

1-(4-(4-(4-bromophenyl) piperazin-1-yl)phenyl)-3-(2-hydroxypentan-3-yl)-1,3-dihydro-2H-imidazol-2-one (LT)

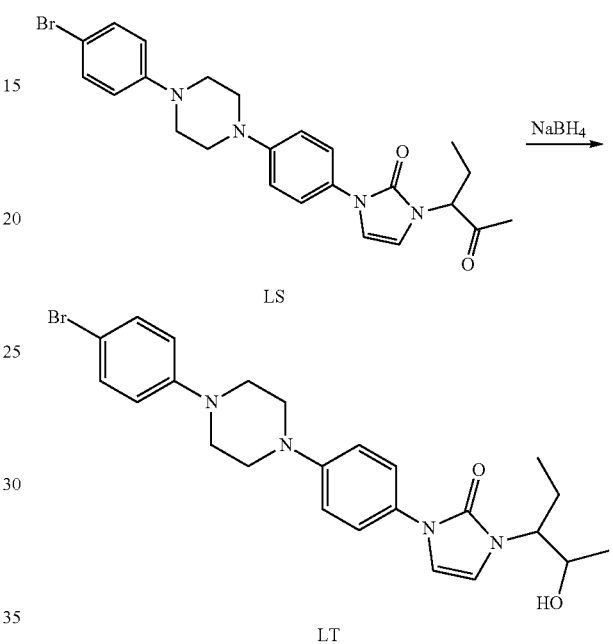

To a stirred solution of compound LS (400 mg, 0.828 mmol) in MeOH (20 mL) under argon atmosphere was added sodium borohydride (47 mg, 1.24 mmol) at 0° C., and stirred at RT for 2 h. The progress of the reaction was monitored by TLC. The reaction mixture was quenched with ice cold water (30 mL) and extracted with EtOAc (2×50 mL). The combined organic layers were washed with water (30 mL), dried over anhydrous Na₂SO₄ and concentrated under reduced pressure to obtain compound LT (350 mg crude) as an off-white solid. The crude material (diastereomeric mixture) as such used in the next step without further purification. LC-MS: (diastereomeric mixture): m/z 485 [M+H]⁺ at 3.30 RT (46.48% purity).

1-(2-hydroxypentan-3-yl)-3-(4-(4-(4-(4,4,5,5-tetramethyl-1,3,2-dioxaborolan-2-yl) phenyl) piperazin-1-yl) phenyl)-1,3-dihydro-2H-imidazol-2-one (LU)

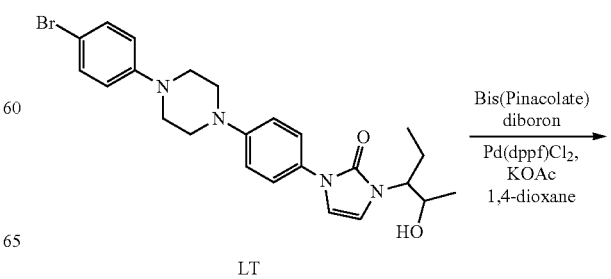

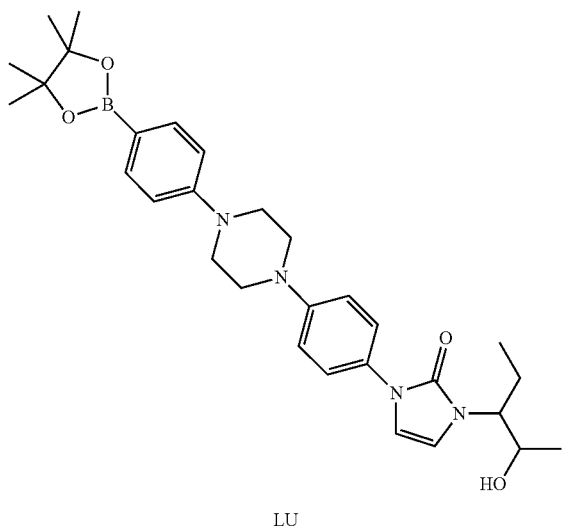

LU

To a stirred solution of compound LT (350 mg, 0.72 mmol) in 1,4-dioxane (30 mL) under argon atmosphere were added bis(pinacolato)diboron (291 mg, 1.15 mmol) and potassium acetate (212 mg, 2.16 mmol) at RT. The reaction mixture was purged with argon for 20 min, then Pd(dppf)Cl$_2$ (52 mg, 0.07 mmol) was added and the reaction mixture was purged under argon for 5 min at RT. The reaction mixture was stirred at 110° C. for 12 h. The progress of the reaction was monitored by TLC. The reaction mixture was diluted with water (20 mL) and extracted with EtOAc (2×50 mL). The combined organic layers were washed with water (20 mL), brine (20 mL), dried over anhydrous Na$_2$SO$_4$ and concentrated under reduced pressure. The crude material was purified by silica gel column chromatography (eluent: 2% MeOH/DCM) to afford compound LU (250 mg, 70%) as an off-white solid. LC-MS: (diastereomeric mixture): m/z 533.3 [M+H]$^+$ at 3.57 RT (12.05% purity).

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-3-(2-hydroxypentan-3-yl)-1,3-dihydro-2H-imidazol-2-one (97)

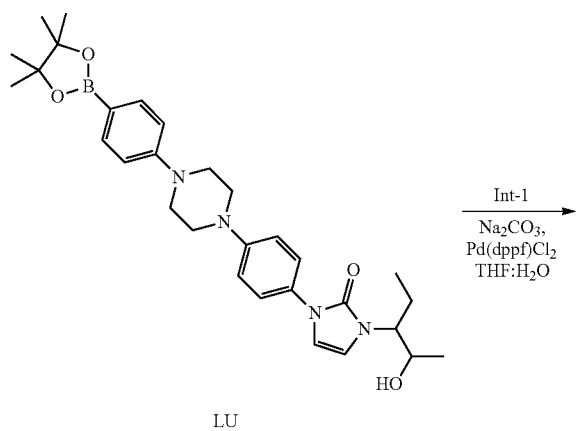

LU

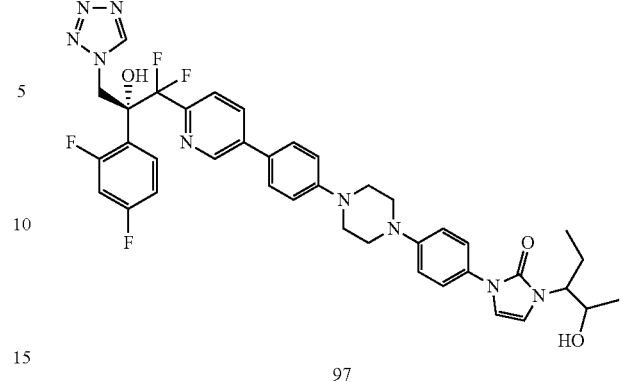

97

To a stirred solution of Int-1 (150 mg, 0.34 mmol) in THF:H2O (20 mL) under argon atmosphere were added compound LU (221 mg, 0.41 mmol), sodium carbonate (110 mg, 1.04 mmol) and purged under argon for 20 min at RT. Then Pd(dppf)Cl$_2$ (13 mg, 0.017 mmol) was added and the reaction mixture was purged under argon for 10 min at RT. The reaction mixture was stirred at 80° C. for 5 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 4% MeOH/CH$_2$Cl$_2$) to afford 97 (50 mg, diastereomeric mixture, 89%) as an off-white solid. $^1$H NMR (400 MHz, DMSO-d$_6$): 9.15 (s, 1H), 8.91 (s, 1H), 8.17 (dd, J=8.2, 2.1 Hz, 1H), 7.70 (d, J=8.9 Hz, 2H), 7.59-7.53 (m, 2H), 7.48 (d, J=8.2 Hz, 1H), 7.35-7.25 (m, 2H), 7.23-7.16 (m, 1H), 7.14 (d, J=9.0 Hz, 2H), 7.07 (d, J=9.0 Hz, 2H), 6.95-6.87 (m, 2H), 6.70-6.64 (m, 1H), 5.67 (d, J=14.8 Hz, 1H), 5.11 (d, J=14.8 Hz, 1H), 4.93-4.75 (m, 1H), 3.95-3.62 (m, 2H), 3.49-3.29 (m, 8H), 1.73-1.69 (m, 1H), 1.32-1.20 (m, 1H), 0.99 (d, J=6.3 Hz, 3H), 0.80-0.75 (m, 3H); MS (ESI): m/z 757.3 [M+H]$^+$; HPLC: 89.5%; Optical rotation [α]$_D^{20}$: +28.7 (c=0.1% in MeOH).

Example 98

(R)-1-(5-(4-(4-(1-benzyl-1H-benzo[d]imidazol-6-yl)piperazin-1-yl)phenyl)pyridin-2-yl)-2-(2,4-difluorophenyl)-1,1-difluoro-3-(1H-tetrazol-1-yl)propan-2-ol (98)

N-benzyl-5-fluoro-2-nitroaniline (LW)

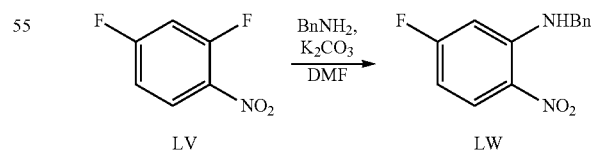

To a stirred solution of benzyl amine (1.38 mL, 12.87 mmol) in Toluene (20 mL) under argon atmosphere was added potassium carbonate (868 mg, 6.28 mmol) at RT. The reaction mixture was stirred at 50° C. for 15 min. Then 2,4-difluoro-1-nitrobenzene (LV; 2 g, 12.57 mmol) was added to the reaction mixture at 50° C. stirred for 3 h. The progress of the reaction was monitored by TLC. The reaction mixture was diluted with ice cold water (100 mL) to obtain the solid. The solid was filtered, dissolved in CH$_2$Cl$_2$ (50 mL), dried over anhydrous Na$_2$SO$_4$ and concentrated under reduced pressure. The crude material was purified by silica gel column chromatography (eluent: 2% EtOAc/Hexane) to afford compound LW (2.6 g, 10.56 mmol, 85%) as a brown solid. $^1$H NMR (400 MHz, CDCl$_3$): δ 8.57 (brs, 1H), 8.27 (dd, J=9.5, 6.1 Hz, 1H), 7.49-7.31 (m, 5H), 6.49 (dd, J=11.4, 2.6 Hz, 1H), 6.51-6.41 (m, 1H), 4.53 (d, J=5.6 Hz, 2H).

N-benzyl-5-(4-(4-bromophenyl) piperazin-1-yl)-2-nitroaniline (LX)

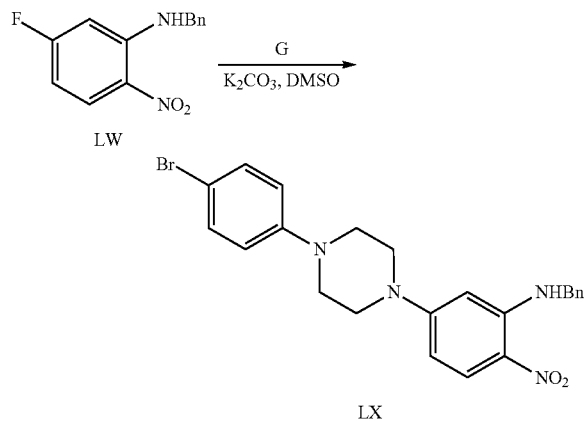

To a stirred solution of compound LW (4 g, 16.59 mmol) in DMSO (80 mL) under argon atmosphere were added potassium carbonate (4.58 g, 33.19 mmol) and G (4.08 g, 16.59 mmol) at RT. The reaction mixture was stirred at 120° C. for 16 h. The reaction mixture was diluted with ice cold water (100 mL) to obtain the solid. The solid was filtered, dissolved in CH$_2$Cl$_2$ (50 mL), dried over anhydrous Na$_2$SO$_4$ and concentrated under reduced pressure. The crude material was purified by silica gel column chromatography (eluent: 20% EtOAc/Hexane) to afford compound LX (5.5 g, 11.80 mmol, 71%) as a brown solid. $^1$H NMR (400 MHz, DMSO-d$_6$): δ 8.82 (t, J=5.8 Hz, 1H), 7.93 (d, J=9.8 Hz, 1H), 7.46-7.36 (m, 6H), 7.30-7.25 (m, 1H), 6.90 (d, J=9.2 Hz, 2H), 6.45 (dd, J=9.8, 2.6 Hz, 1H), 6.02 (d, J=2.4 Hz, 1H), 4.60 (d, J=5.8 Hz, 2H), 3.53-3.47 (m, 4H), 3.24-3.17 (m, 4H).

N1-benzyl-5-(4-(4-bromophenyl) piperazin-1-yl) benzene-1,2-diamine (L)

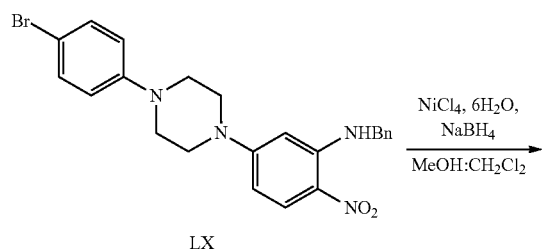

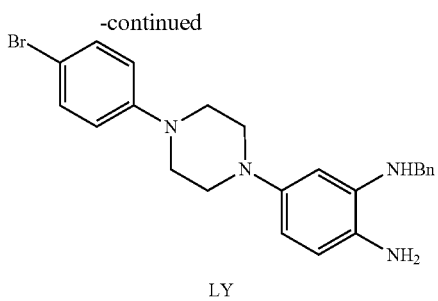

To a stirred solution of compound LX (5.5 g, 11.80 mmol) in MeOH:CH$_2$Cl$_2$ (1:1, 55 mL) under argon atmosphere were added NiCl$_4$.6H$_2$O (280 mg, 1.18 mmol) and sodium borohydride (1.31 g, 35.40 mmol) portion wise at 0° C. The reaction mixture was stirred at 0° C. for 2 h. The progress of the reaction was monitored by TLC. The reaction mixture was diluted with water (20 mL) and extracted with CH$_2$Cl$_2$ (2×20 mL). The combined organic layers were washed with brine (20 mL), dried over anhydrous Na$_2$SO$_4$ and concentrated under reduced pressure. The crude material was purified by silica gel column chromatography (eluent: 20-80% EtOAc/Hexane) to afford compound LY (3.6 g, 8.25 mmol, 70%) as a pale brown solid. $^1$H NMR (500 MHz, DMSO-d$_6$): δ 7.43-7.32 (m, 6H), 7.29-7.18 (m, 1H), 6.91 (d, J=8.7 Hz, 2H), 6.47 (d, J=8.1 Hz, 1H), 6.11 (d, J=2.3 Hz, 1H), 6.07 (dd, J=2.3, 8.1 Hz, 1H), 5.06 (t, J=5.8 Hz, 1H), 4.30 (d, J=5.8 Hz, 2H), 4.15 (s, 2H), 3.21-3.15 (m, 4H), 2.96-2.88 (m, 4H).

1-benzyl-6-(4-(4-bromophenyl) piperazin-1-yl)-1H-benzo[d]imidazole (Z)

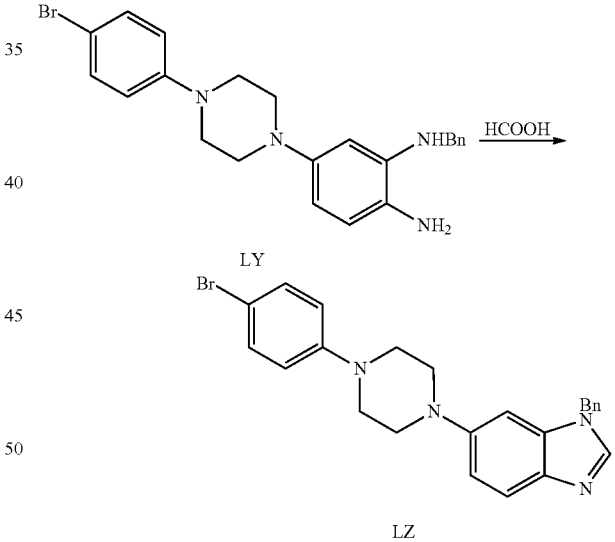

To a stirred solution of compound LY (3.6 g, 8.25 mmol) in formic acid (30 mL) under argon atmosphere was stirred at 100° C. for 12 h. The progress of the reaction was monitored by TLC. The reaction mixture was diluted with water (50 mL), neutralized with ammonium solution (50 mL) and extracted with CH$_2$Cl$_2$ (2×50 mL). The combined organic extracts were dried over anhydrous Na$_2$SO$_4$ and concentrated under reduced pressure. The crude material was purified by silica gel column chromatography (eluent: 0-3% MeOH/CH$_2$Cl$_2$) to afford compound LZ (3 g, 6.72 mmol, 81%) as a brown solid. $^1$H NMR (500 MHz, DMSO-d$_6$): δ 8.20 (s, 1H), 7.51 (d, J=8.7 Hz, 1H), 7.40-7.25 (m, 7H), 7.06 (d, J=2.3 Hz, 1H), 7.01-6.92 (m, 3H), 5.45 (s, 2H), 3.31-3.22 (m, 8H).

1-benzyl-6-(4-(4-(4,4,5,5-tetramethyl-1,3,2-dioxaborolan-2-yl) phenyl) piperazin-1-yl)-1H-benzo [d] imidazole (MA)

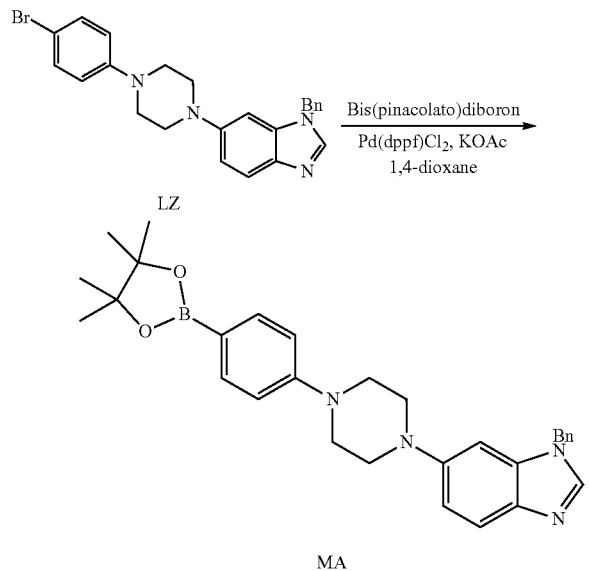

To a stirred solution of compound LZ (300 mg, 0.67 mmol) in 1,4-dioxane (30 mL) under argon atmosphere were added bis(pinacolato) diboron (273 mg, 1.07 mmol) and KOAc (191 mg, 2.01 mmol) at RT. The reaction mixture was purged with argon for 20 min, then Pd(dppf)Cl$_2$ (49 rig, 0.07 mmol) was added and the reaction mixture was purged under argon for 10 min at RT. The reaction mixture was stirred at 110° C. for 8 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 0-2% MeOH/CH$_2$Cl$_2$) to afford compound MA (220 mg, 0.44 mmol, 66%) as an off-white solid. $^1$H NMR (500 MHz, DMSO-d$_6$): δ 8.18 (s, 1H), 7.56-7.42 (m, 3H), 7.36-7.23 (m, 5H), 7.04 (s, 1H), 7.00-6.87 (m, 3H), 5.43 (s, 2H), 3.37-3.35 (m, 4H), 3.22-3.20 (m, 4H), 1.25 (s, 12H).

(R)-1-(5-(4-(4-(1-benzyl-1H-benzo [d] imidazol-6-yl) piperazin-1-yl) phenyl) pyridin-2-yl)-2-(2,4-difluorophenyl)-1,1-difluoro-3-(1H-tetrazol-1-yl) propan-2-ol (98)

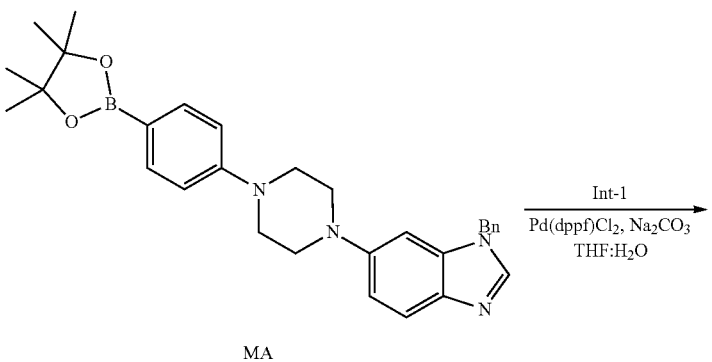

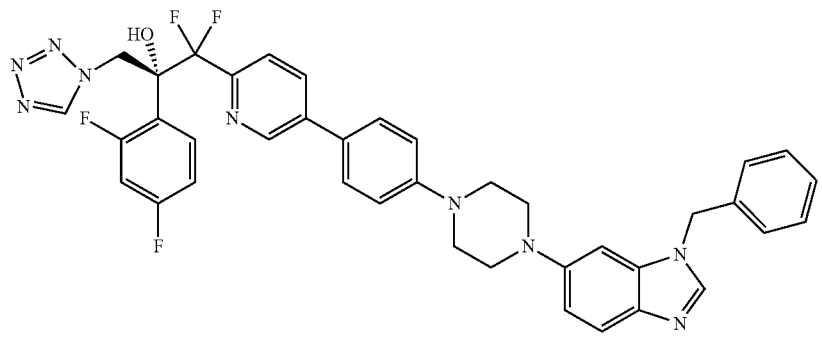

To a stirred solution of Int-1 (150 mg, 0.34 mmol) in THF:H2O (4:1, 10 mL) under argon atmosphere were added compound MA (188 mg, 0.38 mmol) and sodium carbonate (110 mg, 1.04 mmol) at RT. The reaction mixture was purged with argon for 20 min, then Pd(dppf)Cl₂ (25 mg, 0.03 mmol) was added and the reaction mixture was purged under argon for 10 min at RT. The reaction mixture was stirred at 80° C. for 8 h. The progress of the reaction was monitored by TLC. The reaction mixture was quenched with water (20 mL) and extracted with EtOAc (2×20 mL). The combined organic layers were dried over anhydrous Na₂SO₄ and concentrated under reduced pressure. The crude material was purified by silica gel column chromatography (eluent: 0-3% MeOH/CH₂Cl₂) to afford 98 (76 mg, 0.10 mmol, 30%) as an off-white solid. $^1$H NMR (400 MHz, DMSO-d₆): δ 9.15 (s, 1H), 8.91 (d, J=2.0 Hz, 1H), 8.20 (s, 1H), 8.16 (dd, J=8.2, 2.1 Hz, 1H), 7.70 (d, J=8.9 Hz, 2H), 7.50 (dd, J=15.0, 8.5 Hz, 2H), 7.39-7.26 (m, 7H), 7.23-7.16 (m, 1H), 7.14 (d, J=8.9 Hz, 2H), 7.08 (d, J=1.7 Hz, 1H), 7.00 (dd, J=8.9, 2.1 Hz, 1H), 6.93-6.89 (m, 1H), 5.67 (d, J=14.6 Hz, 1H), 5.46 (s, 2H), 5.11 (d, J=14.6 Hz, 1H), 3.42-3.40 (m, 4H), 3.27-3.25 (m, 4H); MS (ESI): m/z 720.7 [M+H]⁺; HPLC: 98.54%; Optical rotation [α]$_D^{19}$: +31.4 (c=0.1% in MeOH).

Example 99

(2R)-1-(5-(4-(4-(6-(1,1-difluoro-2-hydroxypropyl) pyridin-3-yl) piperazin-1-yl) phenyl) pyridin-2-yl)-2-(2,4-difluorophenyl)-1,1-difluoro-3-(1H-tetrazol-1-yl) propan-2-ol (99)

2-(5-bromopyridin-2-yl)-2,2-difluoro-N-methoxy-N-methylacetamide (MB)

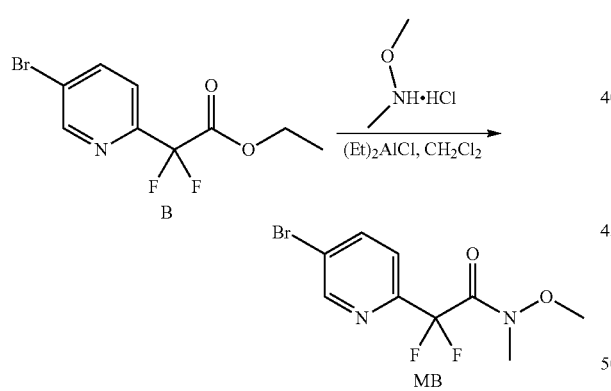

To a stirred solution of compound B (10 g, 35.71 mmol) in CH₂Cl₂ (100 mL) under argon atmosphere were added diethyl aluminum chloride (36 mL, 35.71 mmol, 1.0 M in Hexanes) and N, O-dimethyl hydroxylamine hydrochloride (3.5 g, 35.71 mmol) at 0° C. The reaction mixture warmed to RT and stirred for 3 h. The progress of the reaction was monitored by TLC. The reaction mixture was diluted with ice cold water (100 mL) and extracted with EtOAc (2×100 mL). The combined organic layers were washed with water (20 mL), dried over anhydrous Na₂SO₄ and concentrated under reduced pressure. The crude material was triturated with n-pentane (2×100 mL) to obtain compound MB (8 g, 27.21 mmol, 760%) as an off-white solid. $^1$H NMR (400 MHz, CDCl₃): δ 8.69-8.63 (m, 1H), 7.98 (dd, J=8.4, 2.3 Hz, 1H), 7.58 (dd, J=8.4, 0.6 Hz, 1H), 3.50 (s, 3H), 3.37 (s, 3H).

1-5S-bromopyridin-2-yl)-1,1-difluoropropan-2-one (MC)

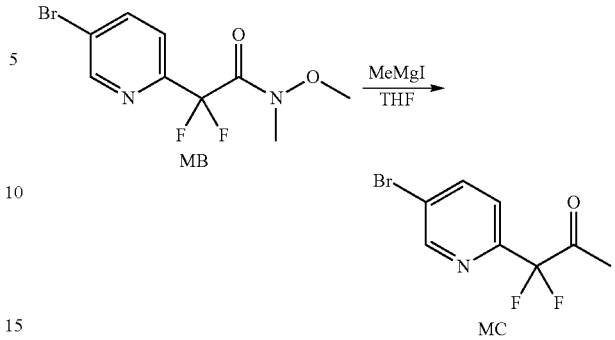

To a stirred solution of compound MB (5.0 g, 17 mmol) in THF (50 mL) under argon atmosphere was added methyl magnesium iodide (14.1 mL, 42.51 mmol, 3.0 Min THF) at 0° C., and stirred for 1 h. The progress of the reaction was monitored by TLC. The reaction mixture was quenched with saturated ammonium chloride solution (100 mL) and extracted with EtOAc (2×100 mL). The combined organic extracts were dried over anhydrous Na₂SO₄ and concentrated under reduced pressure. The crude material was purified by silica gel column chromatography (eluent: 15% EtOAc/hexanes) to afford compound MC (3.0 g, 12.04 mmol, 71%) as colorless liquid. $^1$H NMR (500 MHz, CDCl₃): δ 8.71 (d, J=1.7 Hz, 1H), 8.01 (dd, J=8.4, 2.0 Hz, 1H), 7.63 (d, J=8.4 Hz, 1H), 2.49 (s, 3H).

1-(5-(4-(4-bromophenyl) piperazin-1-yl) pyridin-2-yl)-1,1-difluoropropan-2-one (MD)

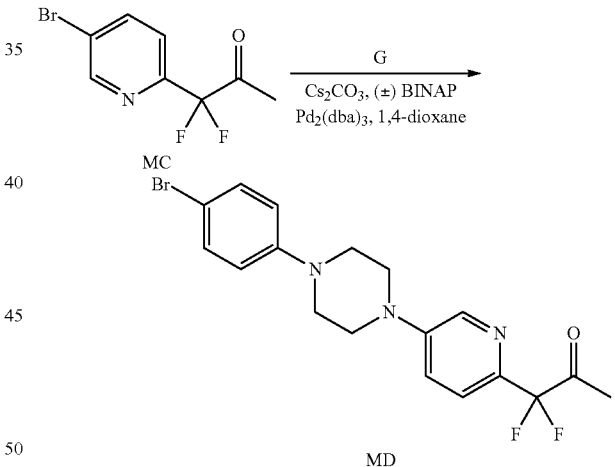

To a stirred solution of compound MC (100 mg, 0.40 mmol) in 1,4-dioxane (5 mL) under argon atmosphere were added 1-(4-bromophenyl) piperazine 5 (96.4 mg, 0.40 mmol), cesium carbonate (391.2 mg, 1.2 mmol), (+) BINAP (17.4 mg, 0.03 mmol) and purged under argon for 20 min at RT. Then Pd₂ (dba)₃ (18.3 mg, 0.02 mmol) was added to the reaction mixture at RT and stirred at 110° C. for 16 h in a sealed tube. The progress of the reaction was monitored by TLC, the reaction mixture was diluted with water (20 mL) and extracted with CH₂Cl₂ (2×20 mL). The combined organic extracts were washed with water (20 mL), brine (20 mL), dried over anhydrous Na₂SO₄ and concentrated under reduced pressure. The crude material was purified by silica gel column chromatography (eluent: 30% EtOAc/Hexane) to afford compound MD (30 mg, 0.07 mmol, 18%) as a brown solid. $^1$H NMR (500 MHz, CDCl₃): δ 8.31 (d, J=2.3 Hz, 1H), 7.59 (d, J=8.7 Hz, 1H), 7.38 (d, J=8.7 Hz, 2H), 7.29-7.27 (m, 1H), 6.83 (d, J=8.7 Hz, 2H), 3.47-3.42 (m, 4H), 3.34-3.28 (m, 4H), 2.46 (s, 3H).

1-(5-(4-(4-bromophenyl) piperazin-1-yl) pyridin-2-yl)-1,1-difluoropropan-2-ol (ME)

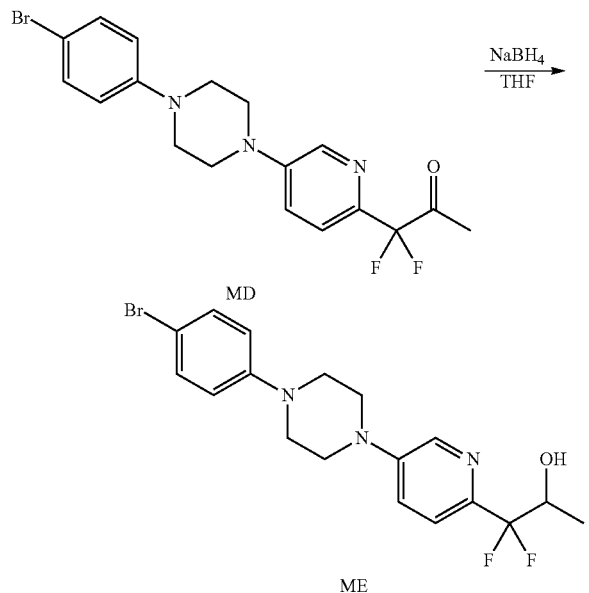

To a stirred solution of compound MD (380 mg, 0.93 mmol) in THF (10 mL) under argon atmosphere was added sodium borohydride (35.3 g, 0.93 mmol) at 0° C., and stirred for 30 min. The progress of the reaction was monitored by TLC, the reaction mixture was quenched with ice water (20 mL) and extracted with CH$_2$Cl$_2$ (2×20 mL). The combined organic layers were washed with water (20 mL), dried over anhydrous Na$_2$SO$_4$ and concentrated under reduced pressure. The crude material was purified by silica gel column chromatography (eluted with 30% EtOAc/CH$_2$Cl$_2$) to afford compound ME (200 mg, 0.48 mmol, 51%) as an off-white solid. $^1$H NMR (500 MHz, CDCl$_3$): δ 8.27 (d, J=2.9 Hz, 1H), 7.59 (d, J=8.7 Hz, 1H), 7.39 (d, J=9.3 Hz, 2H), 7.31 (dd, J=9.0, 2.6 Hz, 1H), 6.84 (d, J=9.3 Hz, 2H), 4.57-4.40 (m, 1H), 4.24 (d, J=5.2 Hz, 1H), 3.48-3.41 (m, 4H), 3.34-3.32 (m, 4H), 1.34 (d J=6.4 Hz, 3H).

1,1-difluoro-1-(5-(4-(4-(4,4,5-tetramethyl-1,3,2-dioxaborolan-2-yl) phenyl) piperazin-1-yl) pyridin-2-1) propan-2-ol (MF)

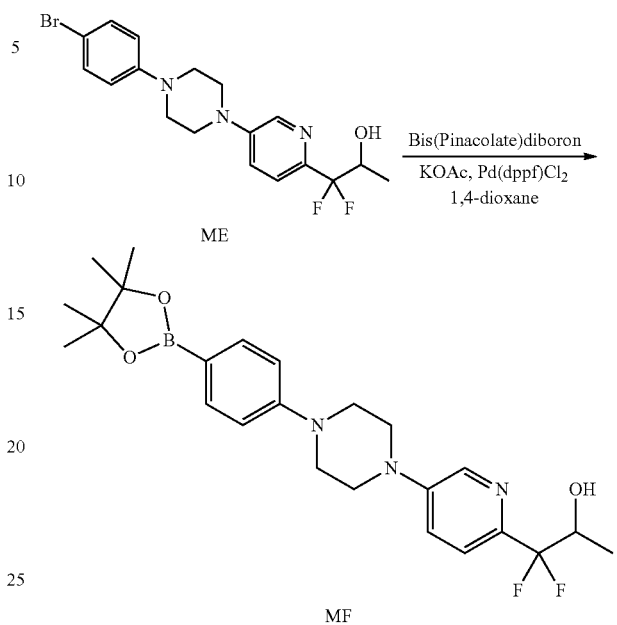

To a stirred solution of compound ME (200 mg, 0.48 mmol) in 1,4-dioxane (10 mL) under argon atmosphere were added bis(pinacolato)diboron (197 mg, 0.77 mmol) and potassium acetate (143 mg, 1.46 mmol) at RT and purged under argon for 15 min. Then Pd(dppf)Cl$_2$ (35.5 mg, 0.05 mmol) was added and the reaction mixture was purged under argon for 5 min at RT. The reaction mixture was stirred at 110° C. for 16 h. The reaction mixture was quenched with water (10 mL) and extracted with CH$_2$Cl$_2$ (2×10 mL). The combined organic layers were washed with water (10 mL), brine (10 mL), dried over anhydrous Na$_2$SO$_4$ and concentrated under reduced pressure to obtain compound MF (120 mg, crude) as a pale brown thick syrup. $^1$H NMR (500 MHz, CDCl$_3$): δ 8.27 (d, J=2.9 Hz, 1H), 7.59 (d, J=8.7 Hz, 1H), 7.39 (d, J=9.3 Hz, 2H), 7.31 (dd, J=9.0, 2.6 Hz, 1H), 6.84 (d, J=9.3 Hz, 2H), 4.52-4.40 (m, 1H), 4.24 (d, J=5.2 Hz, 1H), 3.48-3.40 (m, 4H), 3.34-3.32 (m, 4H), 1.34 (d, J=6.4 Hz, 3H) 1.20 (s, 12H).

(2R)-1-(5-(4-(4-(6-(1,1-difluoro-2-hydroxypropyl) pyridin-3-yl) piperazin-1-yl) phenyl) pyridin-2-yl)-2-(2,4-difluorophenyl)-1,1-difluoro-3-1H-tetrazol-1-yl) propan-2-ol (99)

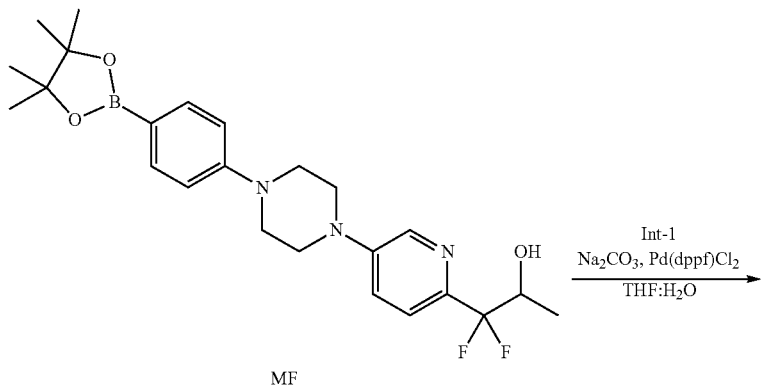

-continued

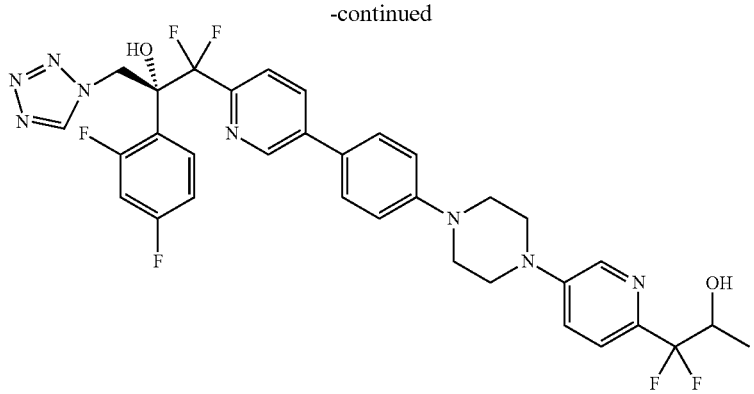

99

To a stirred solution of compound MF (120 mg, 0.26 mmol) in THF:H2O (4:1, 10 mL) under argon atmosphere were added Int-1 (112 mg, 0.26 mmol), sodium carbonate (83 mg, 0.78 mmol) and purged under argon for 10 min at RT. Then Pd(dppf)Cl$_2$ (19.1 mg, 0.03 mmol) was added to the reaction mixture at RT and stirred at 90° C. for 16 h. The reaction mixture was diluted with water (20 mL) and extracted with CH$_2$Cl$_2$ (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 50% acetone/Hexane) to afford 99 (45 mg, 0.06 mmol, 23%) as an off-white solid. $^1$H NMR (400 MHz, CDCl$_3$): δ 8.76 (s, 1H), 8.72 (d, J=1.8 Hz, 1H), 8.29 (d, J=2.9 Hz, 1H), 7.95 (dd, J=8.2, 2.3 Hz, 1H), 7.83 (s, 1H), 7.61 (dd, J=8.5, 5.7 Hz, 2H), 7.53 (d, J=8.9 Hz, 2H), 7.43-7.37 (m, 1H), 7.32 (dd, J=8.7, 2.9 Hz, 1H), 7.06 (d, J=8.9 Hz, 2H), 6.80-6.75 (m, 1H), 6.71-6.64 (m, 1H), 5.60 (d, J=14.3 Hz, 1H), 5.12 (d, J=14.3 Hz, 1H), 4.53-4.40 (m, 1H), 4.21 (d, J=4.7 Hz, 1H), 3.48 (s, 8H), 1.35 (d, J=6.4 Hz, 3H); MS (ESI): m/z 685.7 [M+H]$^+$; HPLC: 99.11%; Optical rotation [α]$_D^{20}$: +33.8 (c=0.1% in MeOH).

Example 100

(2R)-2-(2,4-difluorophenyl)-1,1-difluoro-1-(5-(4-(4-(3-fluoro-5-(2,2,2-trifluoro-1-hydroxyethyl) phenyl) piperazin-1-yl) phenyl) pyridin-2-yl)-3-(1H-tetrazol-1-yl) propan-2-ol (100)

1-(3-bromo-5-fluorophenyl)-2,2,2-trifluoroethan-1-ol (MH)

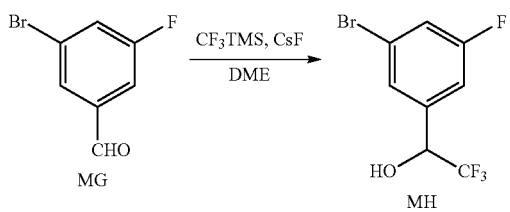

To a stirred solution of 3-bromo-5-fluorobenzaldehyde (MG: 1.0 g, 4.92 mmol) in dimethoxy ethane (10 mL) under argon atmosphere were added cesium fluoride (374 mg, 2.46 mmol) and CF$_3$TMS (1.0 g, 7.38 mmol) at 0° C. The reaction mixture was warmed to RT and stirred for 24 h. The progress of the reaction was monitored by TLC. The reaction mixture was quenched with 6.0N HCl solution (10 mL), stirred at 0° C. for 12 h. diluted with water (50 mL) and extracted with EtOAc (2×50 mL). The combined organic layers were washed with water (20 mL), dried over anhydrous Na$_2$SO$_4$ and concentrated under reduced pressure to obtain compound MH (600 mg, crude) as a brown solid and the obtained crude compound was used in the next step without further purification. LC-MS: m/z 433 [M+H]$^+$ at 3.87 RT (54.44% purity).

1-(3-(4-(4-bromophenyl) piperazin-1-yl)-5-fluorophenyl)-2,2,2-trifluoroethan-1-ol (MI)

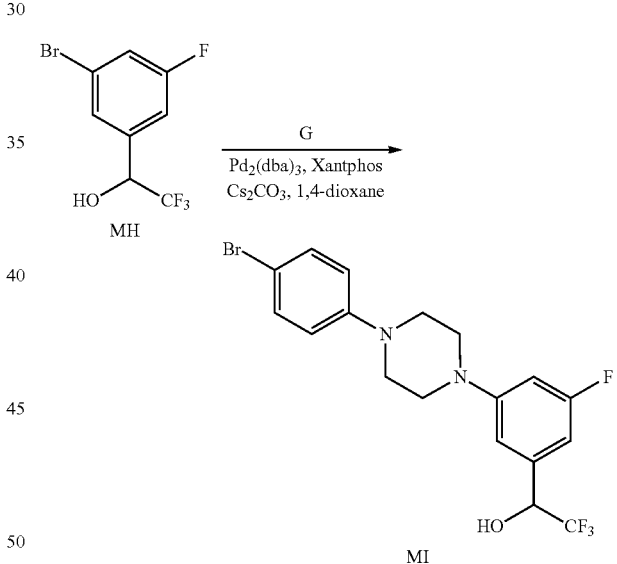

To a stirred solution of compound f (600 mg, crude) in 1,4-dioxane (20 mL) in a sealed tube under argon atmosphere were added cesium carbonate (2 g, 6.54 mmol), Xantphos (88 mg, 0.15 mmol), G (527 mg, 2.18 mmol) at RT and purged under argon for 15 min. Then Pd$_2$ (dba)$_3$ (100 mg, 0.10 mmol) was added to the reaction mixture at RT and stirred at 110° C. for 12 h. The progress of the reaction was monitored by TLC. The reaction mixture was diluted with water (30 mL) and extracted with CH$_2$Cl$_2$ (2×30 mL). The combined organic extracts were dried over anhydrous Na$_2$SO$_4$ and concentrated under reduced pressure to obtain compound MI (650 mg, crude) as a brown solid and the obtained crude compound was used in the next step without further purification. LC-MS: m/z 433 [M+H]$^+$ at 3.87 RT (54.44% purity).

2,2,2-trifluoro-1-(3-fluoro-5-(4-(4-(4,4,5,5-tetramethyl-1,3,2-dioxaborolan-2-yl) phenyl) piperazin-1-yl) phenyl) ethan-1-ol (MJ)

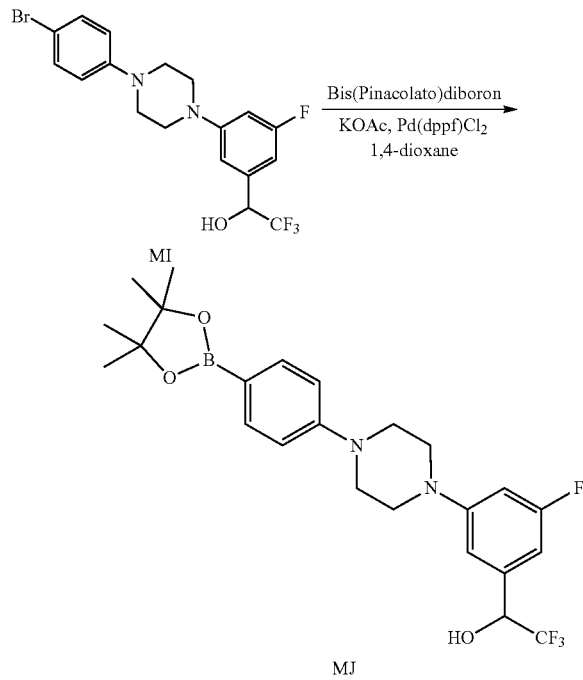

To a stirred solution of compound MI (800 mg, 1.85 mmol) in 1,4-dioxane (25 mL) under argon atmosphere were added bis(pinacolato)diboron (749 mg, 2.96 mmol) and potassium acetate (543 mg, 5.55 mmol) at RT and purged under argon for 10 min. Then Pd(dppf)Cl$_2$ (135 mg, 0.18 mmol) was added and the reaction mixture was purged under argon for 10 min at RT. The reaction mixture was stirred at 110° C. for 12 h. The progress of the reaction was monitored by TLC. The reaction mixture was quenched with water (10 mL) and extracted with CH$_2$Cl$_2$ (2×10 mL). The combined organic layers were washed with water (10 mL), brine (10 mL), dried over anhydrous Na$_2$SO$_4$ and concentrated under reduced pressure. The crude material was purified by silica gel column chromatography (eluent: 3% MeOH/CH$_2$Cl$_2$) to afford compound MJ (400 mg, 0.83 mmol, 45%) as a brown solid and the obtained crude compound was used in the next step without further purification.

(2R)-2-(2,4-difluorophenyl)-1,1-difluoro-5-(5-(4-(3-fluoro-5-(2,2,2-trifluoro-1-hydroxyethyl) phenyl piperazin-1-yl) phenyl) pyridin-2-yl)-3-(1H-tetrazol-1-yl) propan-2-ol (100)

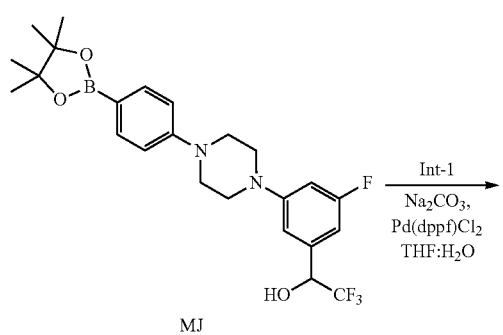

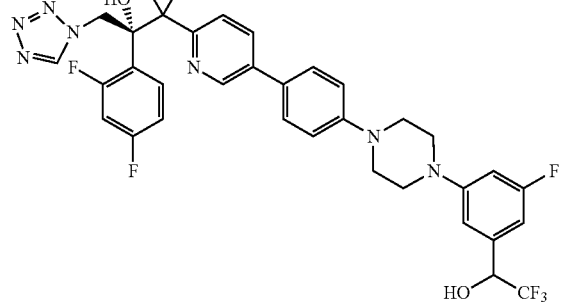

To a stirred solution of Int-1 (180 mg, 0.41 mmol) in THF:H2O (4:1, 15 mL) under argon atmosphere were added compound MJ (200 mg, 0.41 mmol), sodium carbonate (130 mg, 1.23 mmol) and purged under argon for 20 min at RT. Then Pd(dppf)Cl$_2$ (30 mg, 0.04 mmol) was added and the reaction mixture was purged under argon for 10 min at RT. The reaction mixture was stirred at 90° C. for 12 h. The progress of the reaction was monitored by TLC. The reaction mixture was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 1% MeOH/CH$_2$Cl$_2$) to afford 100 (30 mg, 0.04 mmol, 10%) as an off-white solid.
$^1$H NMR (400 MHz, CDCl$_3$): δ 8.76 (s, 1H), 8.74-8.70 (d, 1H), 7.93 (d, J=8.6 Hz, 1H), 7.83 (s, 1H), 7.60 (d, J=7.5 Hz, 1H), 7.54-7.51 (m, 2H), 7.39-7.33 (m, 1H), 7.04 (d, J=8.6 Hz, 2H), 6.85 (s, 1H), 6.78-6.71 (m, 1H), 6.68-6.59 (m, 3H), 5.64 (d, J=14.2 Hz, 1H), 5.11 (d, J=14.2 Hz, 1H), 5.02-4.94 (m, 1H), 3.48-3.37 (m, 8H), 2.67-2.63 (m, 1H); MS (ESI): m/z 706.6 [M+H]$^+$; HPLC: 95.14%; Optical rotation [α]$_D^{20}$: +113.68 (c=0.1% in CH$_2$Cl$_2$).

Example 101

4-(4-(4-(4-(6-(2-(2,4-difluorophenyl)-1,1-difluoro-2-hydroxy-3-(1H-pyrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (101)

1-(S-bromopyridin-2-yl)-2-(2,4-difluorophenyl)-1,1-difluoro-3-(1H-pyrazol-1-yl) propan-2-ol (MK)

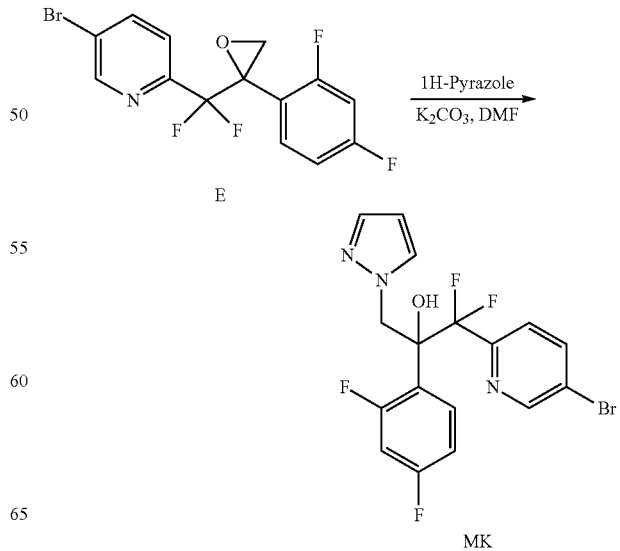

To a stirred solution of compound E (200 mg, 0.27 mmol) in DMF (5 mL) were added potassium carbonate (76 mg, 0.55 mmol) and 1H-pyrazole (28 mg, 0.41 mmol) at RT. The reaction mixture was stirred at 80° C. for 16 h. The reaction mixture was diluted with water (20 mL) and extracted with EtOAc (2×20 mL). The combined organic extracts were dried over anhydrous Na$_2$SO$_4$ and concentrated under reduced pressure to obtain the crude. The crude material was purified by silica gel column chromatography (eluent: 20% EtOAc/Hexane) to afford compound MK (170 mg, 0.40 mmol, 72%) as colorless syrup. $^1$H NMR (400 MHz, CDCl$_3$): δ 8.61 (s, 1H), 7.88 (dd, J=8.5, 2.2 Hz, 1H), 7.44 (dd, J=8.4, 0.6 Hz, 2H), 7.41-7.38 (m, 1H), 7.31 (s, 1H), 6.75-6.58 (m, 2H), 6.49 (s, 1H), 6.07 (t, J=2.1 Hz, 1H), 5.30 (d, J=14.0 Hz, 1H), 4.75 (d, J=14.0 Hz, 1H).

To a stirred solution of compound MK (170 mg, 0.40 mmol) in THF:H2O (4:1, 5 mL) under argon atmosphere were added compound BZ (296 mg, 0.47 mmol) and sodium carbonate (126 mg, 1.18 mmol) at RT. The reaction mixture was purged with argon for 20 min, then Pd(dppf)Cl$_2$ (29 mg, 0.04 mmol) was added and the reaction mixture was purged under argon for 10 min at RT. The reaction mixture was stirred at reflux for 5 h. The progress of the reaction was monitored by TLC. The reaction mixture was quenched with water (20 mL) and extracted with EtOAc (2×20 mL). The combined organic layers were dried over anhydrous Na$_2$SO$_4$ and concentrated under reduced pressure to obtain compound ML (230 mg, 0.21 mol, 69%) as a pale brown solid. $^1$H NMR (500 MHz, DMSO-d$_6$): δ 8.87 (s, 1H), 8.32 (s, 1H), 8.14 (dd, J=8.4, 2.0 Hz, 1H), 7.69 (d, J=8.7 Hz, 2H), 7.64 (s, 1H), 7.52-7.44 (m, 3H), 7.38-7.29 (m, 1H), 7.27-7.04 (m, 10H), 6.89 (s, 1H), 6.87-6.81 (m, 1H), 6.68 (d, J=8.7 Hz, 18H), 6.08-6.06 (m, 1H), 5.37 (d, J=15.1 Hz, 1H), 4.71 (d, J=15.1 Hz, 1H), 4.53 (d, J=11.6 Hz, 1H), 4.27 (d, J=11.6 Hz, 1H), 4.01-3.96 (m, 1H), 3.78-3.69 (m, 1H), 3.45-3.35 (m, 8H), 1.80-1.67 (m, 2H), 1.23 (d, J=6.4 Hz, 3H), 0.79 (t, J=7.2 Hz, 3H).

2-((2S,3S)-2-(benzyloxy) pentan-3-yl)-4-(4-(4-(4-(6-(2-(2,4-difluorophenyl)-1,1-difluoro-2-hydroxy-3-(1H-pyrazol-1-yl) propyl) pyridin-3-yl) phenyl) piperazin-1-yl) phenyl)-2,4-dihydro-3H-1,2,4-triazol-3-one (ML)

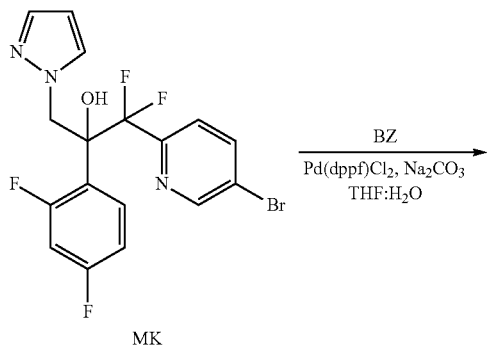

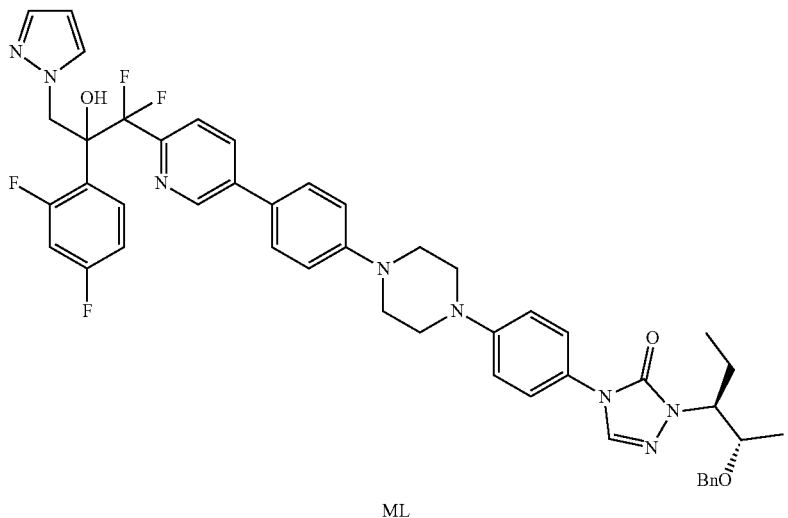

4-(4-(4-(4-(6-(2-(2,4-difluorophenyl-1,1-difluoro-2-hydroxy-3-(1H-pyrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (101)

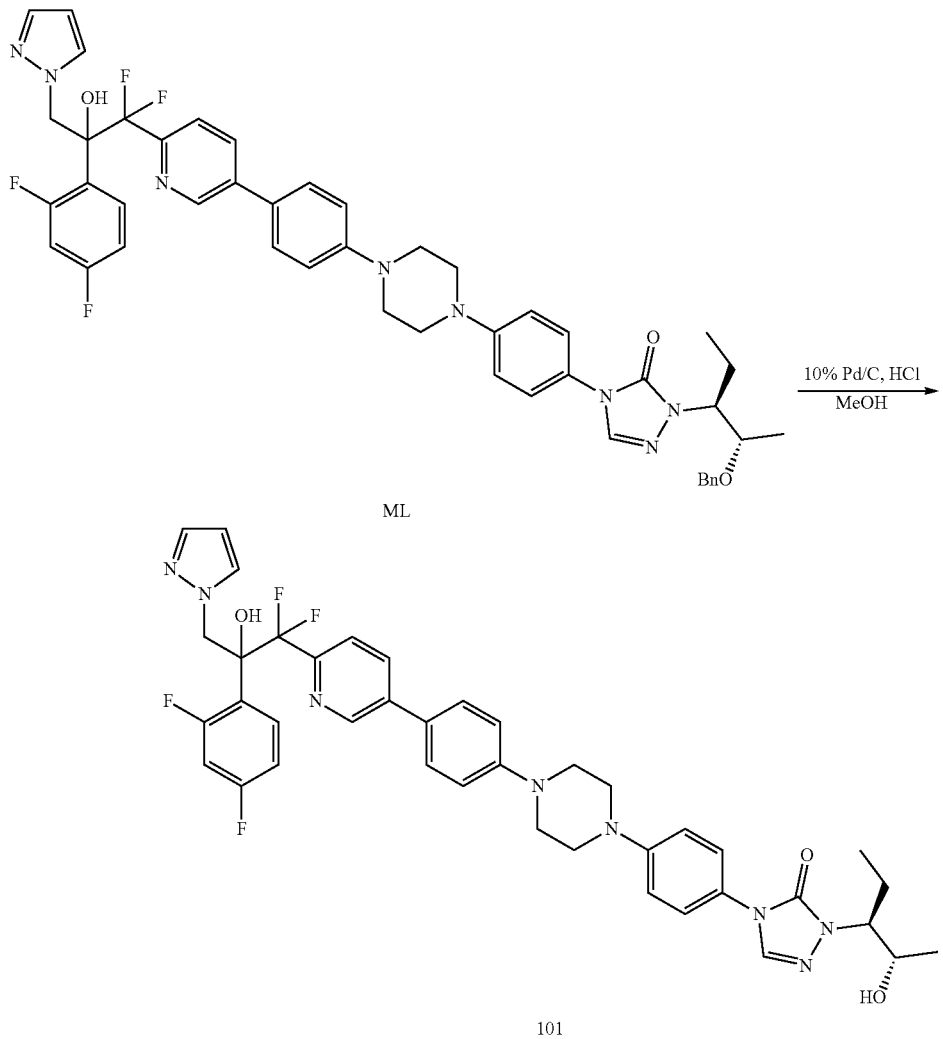

To a stirred solution of compound ML (230 mg, 0.27 mmol) in MeOH (5 mL) under argon atmosphere were added 10% Pd/C (100 mg) and Conc. HCl (0.1 mL) at RT. The reaction mixture was stirred at RT for 3 h under hydrogen atmosphere. The progress of the reaction was monitored by TLC, the reaction mixture was filtered, the filtrate was diluted with water (10 mL), neutralized with sodium bicarbonate solution (10 mL). The combined organic layers were dried over anhydrous $Na_2SO_4$ and concentrated under reduced pressure. The crude material was purified by preparative HPLC to afford 101 (50 mg, 0.24 mmol, 6%) as an off-white solid. $^1$H NMR (500 MHz, DMSO-$d_6$): δ 8.87 (s, 1H), 8.33 (s, 1H), 8.14 (dd, J=8.4, 2.0 Hz, 1H), 7.69 (d, J=8.7 Hz, 2H), 7.64 (s, 1H), 7.53 (d, J=9.3 Hz, 2H), 7.47 (d, J=8.7 Hz, 1H), 7.36-7.25 (m, 1H), 7.21 (s, 1H), 7.15-7.12 (m, 5H), 6.89 (s, 1H), 6.87-6.83 (m, 1H), 6.06 (t, J=2.0 Hz, 1H), 5.37 (d, J=14.5 Hz, 1H), 4.71 (d, J=14.5 Hz, 1H), 4.66 (d, J=4.6 Hz, 1H), 3.86-3.74 (m, 2H), 3.43-3.33 (m, 8H), 1.74-1.68 (m, 2H), 1.12 (d, J=5.8 Hz, 3H), 0.75 (t, J=7.2 Hz, 3H); MS (ESI): m/z 757.7 [M+H]$^+$; HPLC: 99.2%; Optical rotation $[α]_D^{20}$: 12.1 (c=0.1% in MeOH).

Examples 102(+) and 102(−)

(+) and (−)-4-(5-(4-(4-(6-((R)-1,1-difluoro-2-(2-fluorophenyl)-2-hydroxy-3-(1H-tetrazol-1-yl) propyl) pyridin-3-yl) phenyl) piperazin-1-yl) pyridin-2-yl)-2-((2S,3S)-2-hydroxypentan-3-yl)-2,4-dihydro-3H-1,2,4-triazol-3-one (102(−) and 102(+))

Chiral Preparative HPLC Details for EI-Fr-I & EI-Fr-II:

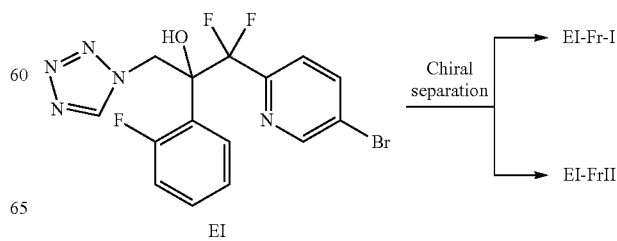

EI (3.5 g, 8.47 mmol) was separated by normal-phase preparative high performance liquid chromatography (Chiralpak IA®, 250×20 mm, 5μ; using 0.1% DEA MeOH:(B) CH$_2$Cl$_2$:MeOH (10:90) (70:30) as a mobile phase; Flow rate: 20 mL/min) to obtain EI-Fr-I (1.2 g) and EI-Fr-II (1.2 g)

EI-Fr-I:
$^1$H NMR (400 MHz, CDCl$_3$): δ 8.74 (s, 1H), 8.63 (s, 1H), 7.91 (dd, J=8.3, 2.1 Hz, 1H), 7.42 (d, J=8.4 Hz, 1H), 7.32-7.16 (m, 2H), 7.05-6.90 (m, 2H), 6.72 (s, 1H), 5.65 (d, J=14.3 Hz, 1H), 5.17 (d, J=14.4 Hz, 1H); LC-MS: 413.9 [M+H]$^+$ at 2.82 RT (98.10% purity); HPLC: 99.72%; Chiral HPLC Purity: 100%. R$_t$=6.52 min (CHIRALPAK-IC®, 250×4.6 mm, 5μ; mobile phase (A) 0.1% DEA in n-Hexane: (B) CH$_2$Cl$_2$:MeOH (80:20) (70:30); flow Rate: 1.0 mL/min); Optical rotation [α]$_D^{20}$: −94.7 (C=0.1% in CH$_2$Cl$_2$).

EI-Fr-II:
$^1$H NMR (400 MHz, CDCl$_3$): δ 8.74 (s, 1H), 8.63 (s, 1H), 7.91 (dd, J=8.3, 2.1 Hz, 1H), 7.42 (d, J=8.4 Hz, 1H), 7.32-7.16 (m, 2H), 7.05-6.90 (m, 2H), 6.72 (s, 1H), 5.65 (d, J=14.3 Hz, 1H), 5.17 (d, J=14.4 Hz, 1H); LC-MS: 411.9 [M−H]$^-$ at 2.81 RT (98.58% purity); HPLC: 98.36%; Chiral HPLC Purity: 99.86%, R$_t$=7.54 min (CHIRALPAK-IC®, 250×4.6 mm, 5μ; mobile phase (A) 0.1% DEA in n-Hexane: (B) CH$_2$Cl$_2$:MeOH (80:20) (70:30); flow Rate: 1.0 mL/min); Optical rotation [α]$_D^{20}$: +93.5 (C=0.1% in CH$_2$Cl$_2$).

2-((2S,3S)-2-(benzyloxy) pentan-3-yl)-4-(5-(4-(4-(6-((R)-1,1-difluoro-2-(2-fluorophenyl)-2-hydroxy-3-(1H-tetrazol-1-yl) propyl) pyridin-3-yl) phenyl) piperazin-1-yl) pyridin-2-yl)-2,4-dihydro-3H-1,2,4-triazol-3-one (MM-Fr-I)

To a stirred solution of compound EI-Fr-I (125 mg, 0.30 mmol) in THF:H2O (4:1, 25 mL) under argon atmosphere were added compound JF (188 mg, 0.30 mmol) and sodium carbonate (96 mg, 0.9 mmol) at RT. The reaction mixture was purged with argon for 20 min, then Pd(dppf)Cl$_2$ (22 mg, 0.03 mmol) was added and the reaction mixture was purged under argon for 10 min at RT. The reaction mixture was stirred at 80° C. for 8 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 1% MeOH/CH$_2$Cl$_2$) to afford compound MM-Fr-I (120 mg, 0.14 mmol, 48%) as an off-white solid. $^1$H NMR (400 MHz, DMSO-d$_6$): δ 9.12 (s, 1H), 8.92 (d, J=2.1 Hz, 1H), 8.50 (s, 1H), 8.26 (d, J=2.9 Hz, 1H), 8.16 (dd, J=2.2, 8.3 Hz, 1H), 7.98 (d, J=9.0 Hz, 1H), 7.74-7.65 (m, 3H), 7.46 (d, J=8.4 Hz, 1H), 7.37-7.26 (m, 2H), 7.22-7.08 (m, 9H), 7.05-6.97 (m, 1H), 5.71 (d, J=14.5 Hz, 1H), 5.11 (d, J=14.5 Hz, 1H), 4.53 (d, J=11.9 Hz, 1H), 4.26 (d, J=11.9 Hz, 1H), 4.05-3.97 (m, 1H), 3.79-3.62 (m, 1H), 3.43 (br s, 8H), 1.79-1.68 (m, 2H), 1.27-1.20 (m, 3H), 0.78 (t, J=7.3 Hz, 3H).

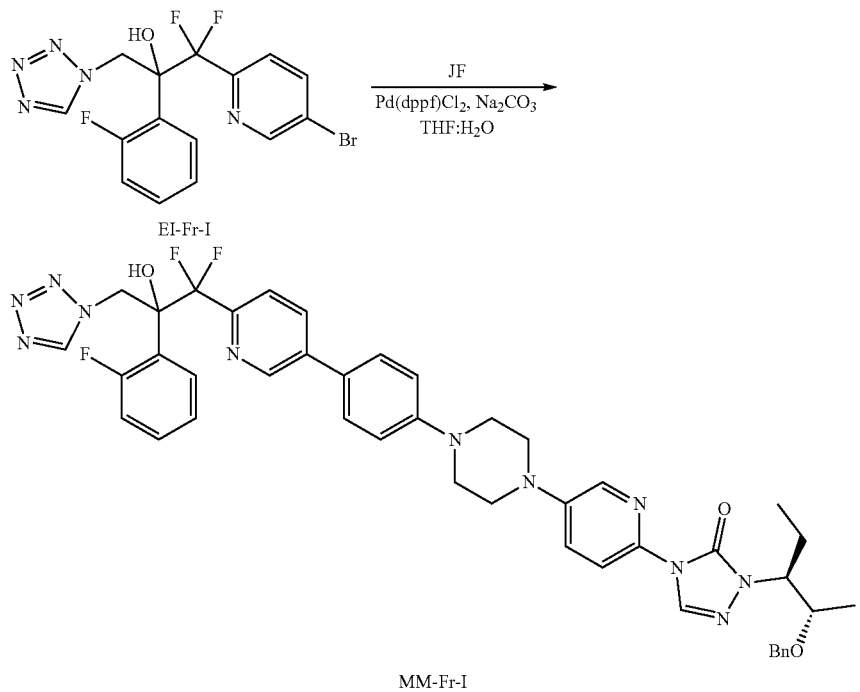

MM-Fr-I 4-(5-(4-(4-(6-((R)-1,1-difluoro-2-(2-fluorophenyl)-2-hydroxy-3-(1H-tetrazol-1-yl) propyl) pyridin-3-yl) phenyl) piperazin-1-yl) pyridin-2-yl)-2-((2S,3S)-2-hydroxypentan-3-yl)-2,4-dihydro-3H-1,2,4-triazol-3-one (102(−))

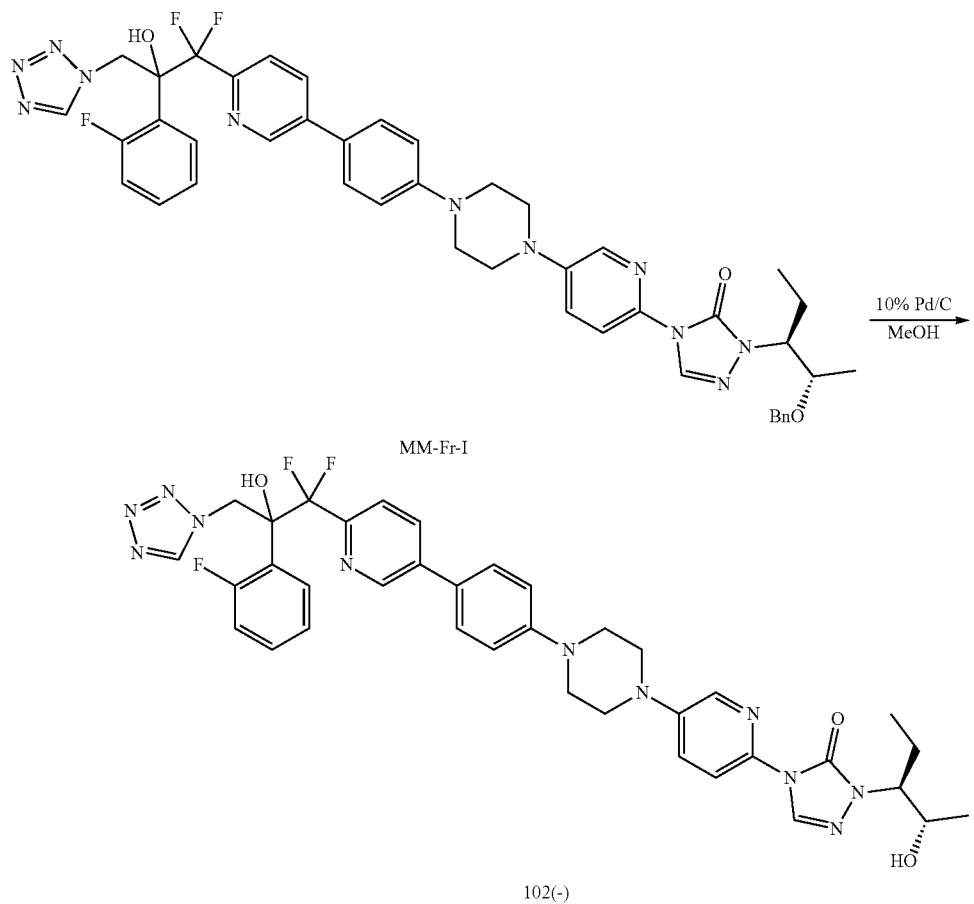

To a stirred solution of compound MM-Fr-I (120 mg, 0.14 mmol) in MeOH (25 mL) under argon atmosphere were added 10% Pd/C (60 mg) and HCl (catalytic amount) at RT and stirred for 3-4 h under hydrogen atmosphere (50 psi). The progress of the reaction was monitored by TLC. The reaction mixture was filtered through celite, the filtrate was washed with 5% sodium carbonate solution (20 mL), dried over anhydrous $Na_2SO_4$ and concentrated under reduced pressure. The crude material was purified by preparative TLC to afford 102(−) (45 mg, 0.06 mmol, 42%) as an off-white solid. $^1$H NMR (400 MHz, DMSO-$d_6$): δ 9.12 (s, 1H), 8.92 (d, J=2.0 Hz, 1H), 8.52 (s, 1H), 8.25 (d, J=2.7 Hz, 1H), 8.15 (dd, J=8.3, 2.1 Hz, 1H), 8.02 (d, J=9.0 Hz, 1H), 7.70 (d, J=8.9 Hz, 2H), 7.67 (dd, J=9.2, 3.0 Hz, 1H), 7.46 (d, J=8.2 Hz, 1H), 7.37-7.27 (m, 2H), 7.21-7.08 (m, 4H), 7.06-6.97 (m, 1H), 5.71 (d, J=14.5 Hz, 1H), 5.11 (d, J=14.5 Hz, 1H), 4.69 (d, J=4.7 Hz, 1H), 3.83-3.78 (m, 2H), 3.43-3.41 (m, 8H), 1.78-1.67 (m, 2H), 1.13 (d J=5.6 Hz, 3H), 0.75 (t, J=7.3 Hz, 3H); MS (ESI): m/z 742.6 [M+H]$^+$; HPLC: 98.80%; Optical rotation $[α]_D^{20}$: −118.6 (c=0.1% in $CH_2Cl_2$).

2-((2S,3S)-2-(benzyloxy) pentan-3-yl)-4-(5-(4-(4-(6-((R)-1,1-difluoro-2-(2-fluorophenyl)-2-hydroxy-3-(1H-tetrazol-1-yl) propyl) pyridin-3-yl) phenyl) piperazin-1-yl) pyridin-2-yl)-2,4-dihydro-3H-1,2,4-triazol-3-one (MM-Fr-II)

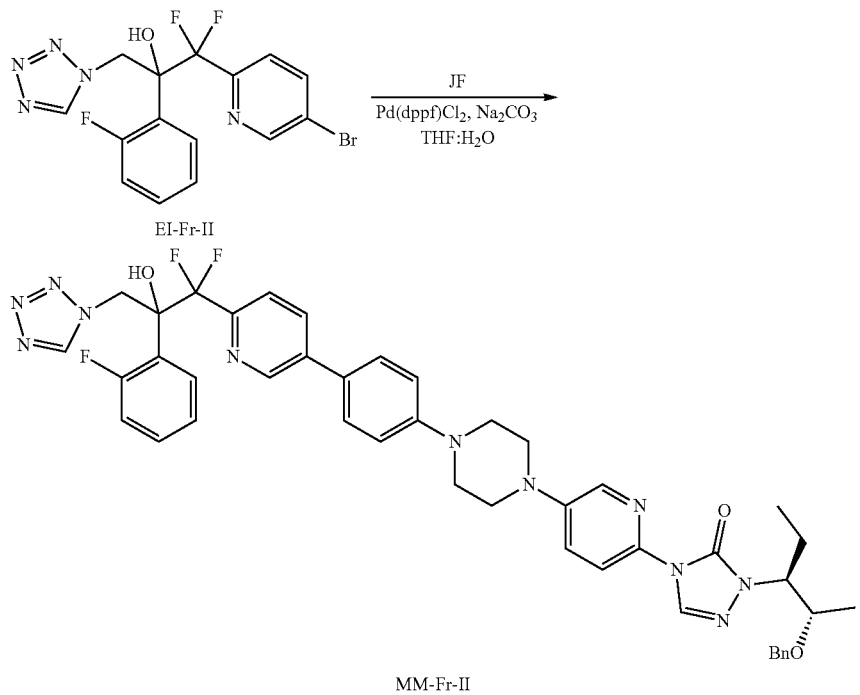

To a stirred solution of compound EI-Fr-II (125 mg, 0.30 mmol) in THF:H2O (4:1, 25 mL) under argon atmosphere were added compound JF (188 mg, 0.30 mmol) and sodium carbonate (96 mg, 0.9 mmol) at RT. The reaction mixture was purged with argon for 20 min, then Pd(dppf)Cl$_2$ (22 mg, 0.03 mmol) was added and the reaction mixture was purged under argon for 10 min at RT. The reaction mixture was stirred at 75° C. for 8 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 1% MeOH/CH$_2$Cl$_2$) to afford compound MM-Fr-II (100 mg, 0.12 mmol, 40%) as an off-white solid. $^1$H NMR (400 MHz, DMSO-d$_6$): δ 9.12 (s, 1H), 8.92 (d, J=2.0 Hz, 1H), 8.50 (s, 1H), 8.26 (d, J=2.9 Hz, 1H), 8.15 (dd, J=8.3, 2.2 Hz, 1H), 7.98 (d, J=9.0 Hz, 1H), 7.74-7.65 (m, 3H), 7.46 (d, J=8.2 Hz, 1H), 7.37-7.26 (m, 2H), 7.23-7.10 (m, 9H), 7.05-6.98 (m, 1H), 5.71 (d, J=14.5 Hz, 1H), 5.11 (d, J=14.5 Hz, 1H), 4.53 (d, J=11.9 Hz, 1H), 4.26 (d, J=11.9 Hz, 1H), 4.08-3.95 (m, 1H), 3.77-3.65 (m, 1H), 3.43 (br s, 8H), 1.81-1.72 (m, 2H), 1.26-1.21 (m, 3H), 0.78 (t, J=7.3 Hz, 3H).

4-(5-(4-(4-(6-((R)-1,1-difluoro-2-(2-fluorophenyl)-2-hydroxy-3-(1H-tetrazol-1-yl) propyl) pyridin-3-yl) phenyl) piperazin-1-yl) pyridin-2-yl)-2-((2S,3S)-2-hydroxypentan-3-yl)-2,4-dihydro-3H-1,2,4-triazol-3-one (102(+))

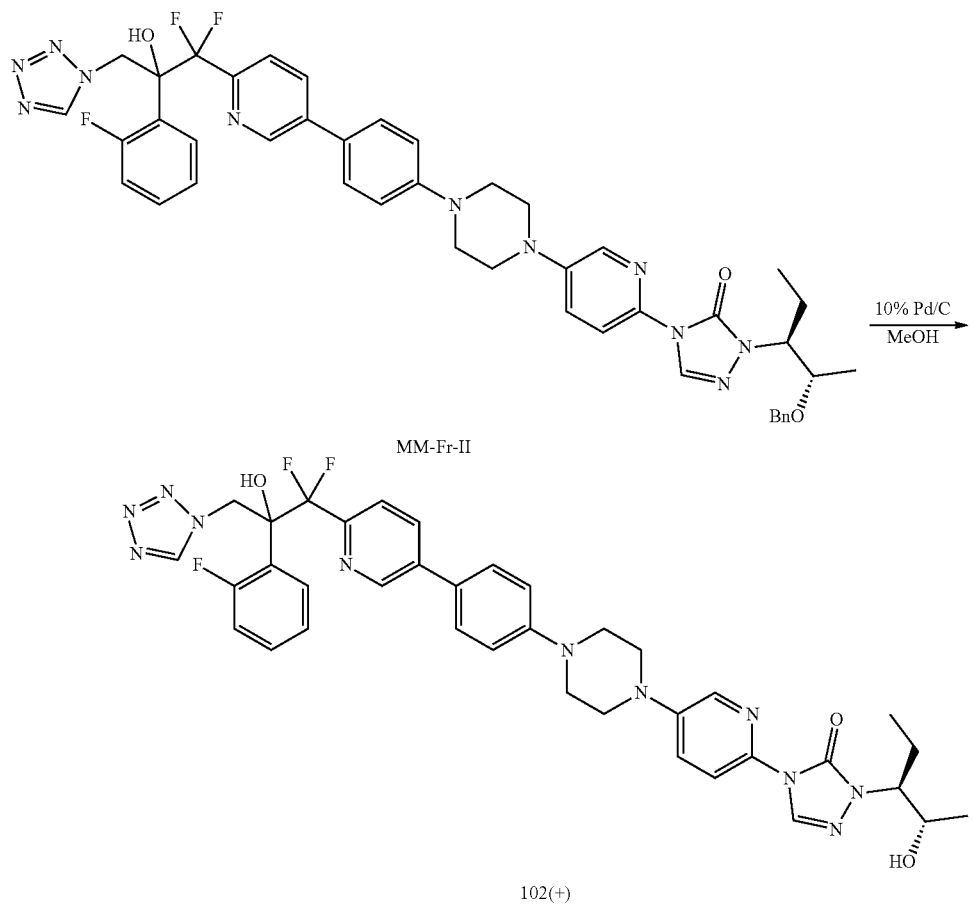

To a stirred solution of compound MM-Fr-II (100 mg, 0.12 mmol) in MeOH (25 mL) under argon atmosphere were added 10% Pd/C (50 mg) and HCl (catalytic amount) at RT and stirred for 3-4 h under hydrogen atmosphere (50 psi). The progress of the reaction was monitored by TLC. The reaction mixture was filtered through celite, the filtrate was concentrated under reduced pressure. The residue was diluted with 8% sodium bicarbonate solution (20 ml) and extracted with $CH_2Cl_2$ (2×20 ml). The combined organic extracts were dried over anhydrous $Na_2SO_4$ and concentrated under reduced pressure. The crude material was purified by preparative TLC to afford 102(+) (45 mg, 0.06 mmol, 42%) as an off-white solid. $^1H$ NMR (400 MHz, DMSO-$d_6$): δ 9.12 (s, 1H), 8.92 (d, J=2.0 Hz, 1H), 8.52 (s, 1H), 8.25 (d, J=2.9 Hz, 1H), 8.15 (dd, J=8.2, 2.3 Hz, 1H), 8.02 (d, J=9.0 Hz, 1H), 7.70 (d, J=8.9 Hz, 2H), 7.67 (dd, J=9.2, 3.1 Hz, 1H), 7.46 (d, J=8.2 Hz, 1H), 7.37-7.26 (m, 2H), 7.21-7.08 (m, 4H), 7.06-6.97 (m, 1H), 5.71 (d, J=14.5 Hz, 1H), 5.11 (d, J=14.5 Hz, 1H), 4.69 (d, J=4.9 Hz, 1H), 3.83-3.78 (m, 2H), 3.43-3.41 (m, 8H), 1.78-1.67 (m, 2H), 1.13 (d, J=5.8 Hz, 3H), 0.75 (t, J=7.3 Hz, 3H); MS (ESI): m/z 742.6 [M+H]$^+$; HPLC: 99.69%; Optical rotation $[α]_D^{20}$: +125.3 (c=0.1% in $CH_2Cl_2$).

Example 103

4-(4-(4-(4-(6-((R)-2-(2,4-difluorophenyl)-1,1-difluoro-2-hydroxy-3-(1H-tetrazol-1-yl) pyridin-3-yl) phenyl) piperazin-1-yl) phenyl)-2-(2-hydroxy-4-methylpentan-3-yl)-2,4-dihydro-3H-1,2,4-triazol-3-one (103)

3-bromopentan-2-one (MO)

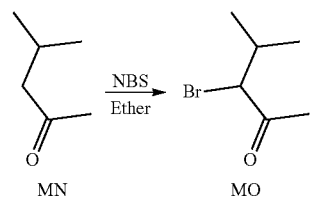

To a stirred solution of 3-bromo-4-methylpentan-2-one (MN: 150 mg, 0.34 mmol) in ether (20 mL) under argon atmosphere was added N-bromo succinimide (1.06 g, 6 mmol) at 200 W lamp and stirred for 30 min. The progress of the reaction was monitored by TLC. The reaction mixture was diluted with water (20 mL) and extracted with ether (2×50 mL). The combined organic layers were washed with

449 water (50 mL), brine (50 mL), dried over anhydrous $Na_2SO_4$ and concentrated under reduced pressure to obtain compound MO (500 mg, crude) as yellow syrup which was used in the next step without further purification.

4-(4-(4-(4-bromophenyl) piperazin-1-yl) phenyl)-2-(2-methyl-4-oxopentan-3-yl)-2,4-dihydro-3H-1,2,4-triazol-3-one (MP)

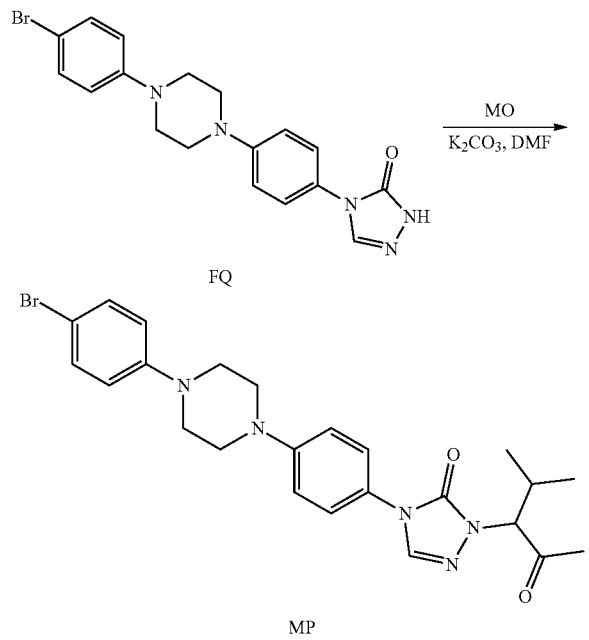

To a stirred solution of compound FQ (500 mg, 1.25 mmol) in DMF (10 mL) under argon atmosphere was added potassium carbonate (517 mg, 3.75 mmol) and compound MO (517 mg, 3.75 mmol) at 0° C. The reaction mixture was warmed to RT and stirred for 16 h. The reaction mixture was diluted with saturated ammonium chloride solution (20 mL) and extracted with EtOAc (2×20 mL). The combined organic layers were washed with water (20 mL), dried over anhydrous $Na_2SO_4$ and concentrated under reduced pressure. The crude material was purified by silica gel column chromatography (eluent: 20% EtOAc/Hexane) to afford compound MP (250 mg, 0.50 mmol, 40%) as a brown solid and the obtained crude compound was used in the next step without further purification. LC-MS: m/z 498.1 [M+H]$^+$ at 3.76 RT (94.60% purity).

4-(4-(4-(4-bromophenyl) piperazin-1-yl) phenyl)-2-(2-hydroxy-4-met ylpentan-3-yl)-2,4-dihydro-3H-1,2,4-triazol-3-one (MQ)

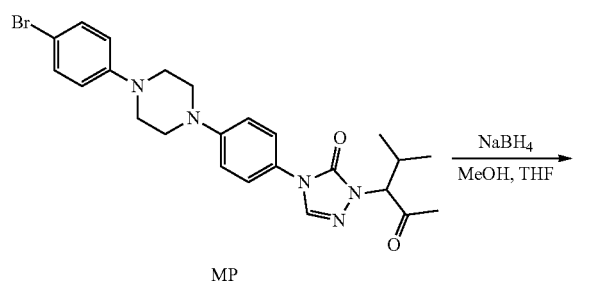

450

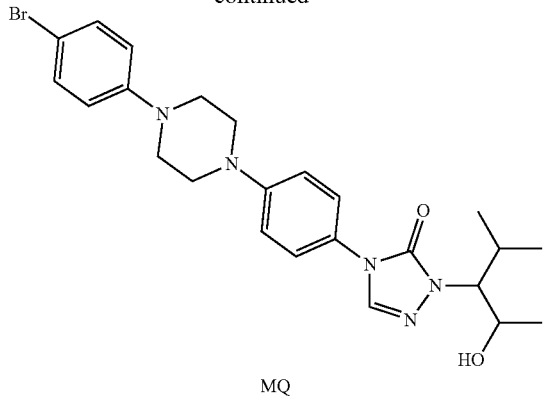

To a stirred solution of compound MP (250 mg, 0.50 mmol) in MeOH:THF (4:1, 10 mL) under argon atmosphere was added sodium borohydride (38 mg, 1.00 mmol) at 0° C. and stirred at RT for 2 h. The progress of the reaction was monitored by TLC. The reaction mixture was quenched with ice cold water (30 mL) and extracted with EtOAc (2×30 mL). The combined organic layers were washed with water (30 mL), dried over anhydrous $Na_2SO_4$ and concentrated under reduced pressure. The crude material was purified by silica gel column chromatography (eluent: 40% EtOAc/Hexane) to afford compound MQ (200 mg, 0.40 mmol, 80%) as an off-white solid. $^1$H NMR (400 MHz, DMSO-$d_6$): δ 8.33 (s, 1H), 7.52 (d, J=9.2 Hz, 2H), 7.38 (d, J=9.0 Hz, 2H), 7.11 (d, J=9.0 Hz, 2H), 6.97 (d, J=9.2 Hz, 2H), 4.42 (d, J=6.1 Hz, 1H), 4.09-4.02 (m, 1H), 3.67 (t, J=6.7 Hz, 1H), 3.31 (s, 8H), 2.26-2.18 (m, 1H), 1.09 (d, J=6.3 Hz, 3H), 0.93 (d, J=6.7 Hz, 3H), 0.83 (d, J=6.7 Hz, 3H).

2-(2-hydroxy-4-methylpentan-3-yl)-4-(4-(4-(4-(4,4,5,5-tetramethyl-1,3,2-dioxaborolan-2-yl phenyl) piperazin-1-yl) phenyl)-2,4-dihydro-3H-1,2,4-triazol-3-one (MR)

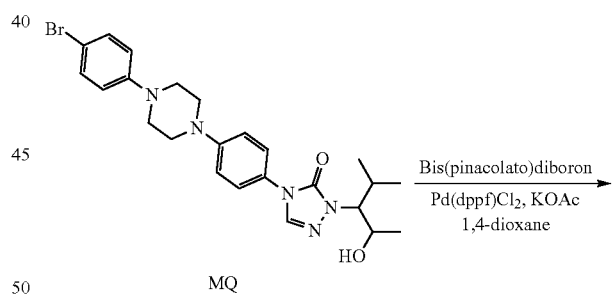

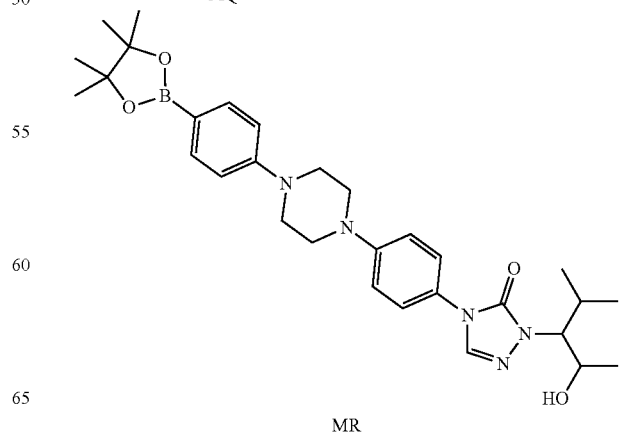

To a stirred solution of compound MQ (200 mg, 0.40 mmol) in 1,4-dioxane (20 mL) under argon atmosphere were added bis(pinacolato)diboron (162 mg, 0.64 mmol) and KOAc (117 mg, 1.20 mmol) at RT. The reaction mixture was purged with argon for 20 min, then Pd(dppf)Cl$_2$ (29 mg, 0.04 mmol) was added and the reaction mixture was purged under argon for 10 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure to obtain compound MR (200 mg, 0.36 mmol, 91%) as an off-white solid. $^1$H NMR (500 MHz, DMSO-d$_6$): 8.33 (s, 1H), 7.55-7.51 (m, 4H), 7.11 (d, J=9.3 Hz, 2H), 6.98 (d, J=8.7 Hz, 2H), 4.42 (d, J=6.4 Hz, 1H), 4.11-4.01 (m, 1H), 3.67 (t, J=6.7 Hz, 1H), 3.39-3.33 (m, 8H), 2.25-2.18 (m, 1H), 1.07 (s, 12H), 0.95-0.80 (m, 9H).

To a stirred solution of Int-1 (150 mg, 0.34 mmol) in THF:H2O (4:1.20 mL) under argon atmosphere were added compound MR (189 mg, 0.34 mmol), sodium carbonate (110 mg, 1.04 mmol) and purged under argon for 20 min at RT. Then Pd(dppf)Cl$_2$ (25 mg, 0.03 mmol) was added and the reaction mixture was purged under argon for 10 min at RT. The reaction mixture was stirred at 80° C. for 6 h. The progress of the reaction was monitored by TLC. The reaction mixture was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 103 (70 mg, 0.09 mmol, 26%) as an off-white solid. $^1$H NMR (400 MHz, DMSO-d$_6$): δ 9.15 (s, 1H), 8.91 (s, 1H), 8.34 (s, 1H), 8.17 (d, J=8.1 Hz, 1H), 7.70 (d, J=8.4 Hz, 2H), 7.56-7.46 (m, 3H), 7.33-7.25 (m, 2H), 7.23-7.10 (m, 5H), 6.91 (t, J=7.4 Hz, 1H), 5.67 (d, J=14.8 Hz, 1H), 5.11 (d, J=14.8 Hz, 1H), 4.43 (d, J=6.0 Hz, 1H), 4.13-4.01 (m, 1H), 3.67 (t, J=6.6 Hz, 1H), 3.47-3.33 (m, 8H), 2.28-2.18 (m, 1H), 1.09 (d, J=6.1 Hz, 3H), 0.93 (d, J=6.7 Hz, 3H), 0.83 (d, J=6.7 Hz, 3H); MS (ESI): m/z 773.3 [M+H]$^+$; HPLC: 86.48%; Optical rotation [α]$_D^{20}$: +34.88 (c=0.1% in MeOH).

4-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-2-(2-hydroxy-4-methylpentan-3-yl)-2,4-dihydro-3H-1,2,4-triazol-3-one (103)

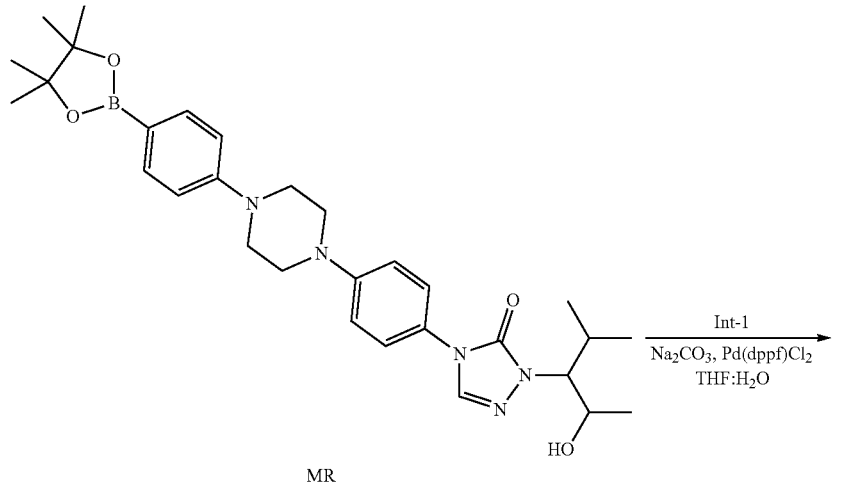

MR

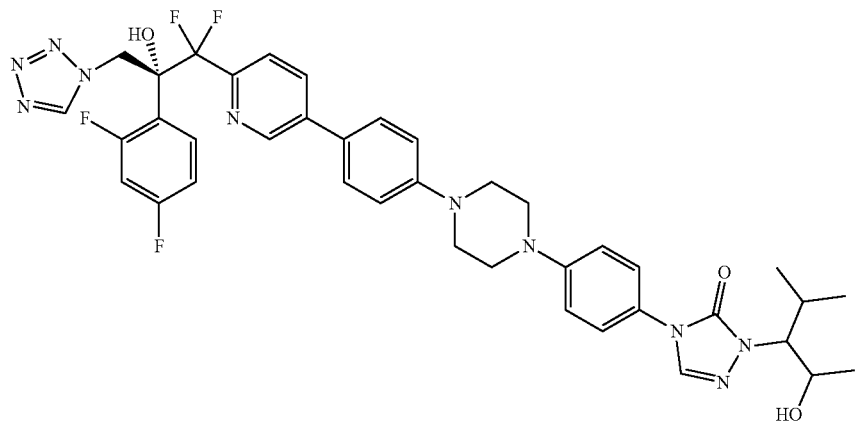

103

Example 104

(2R)-2-(2,4-difluorophenyl)-1,1-difluoro-3-(1H-tetrazol-1-yl)-1-(5-(4-(4-(2-(2,2,2-trifluoro-1-hydroxyethyl) pyridin-4-yl) piperazin-1-yl) phenyl) pyridin-2-yl)propan-2-ol (104)

1-(4-bromopyridin-2-yl)-2,2,2-trifluoroethan-1-ol (MT)

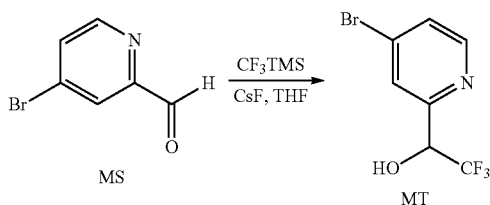

To a stirred solution of compound MS (200 mg, 1.07 mmol) in THF (10 mL) under argon atmosphere were added cesium fluoride (82 mg, 0.53 mmol) and CF$_3$TMS (318 g, 2.15 mmol) at 0° C. The reaction mixture was warmed to RT and stirred for 1 h. The progress of the reaction was monitored by TLC. The reaction mixture was quenched 2.0N HCl solution (20 mL) at 0° C., and stirred at RT for 3 h. The reaction mixture was diluted with water (20 mL) and extracted with EtOAc (2×20 mL). The combined organic extracts were dried over anhydrous Na$_2$SO$_4$ and concentrated under reduced pressure to obtain compound MT (160 mg, crude) as an off-white solid which was used in the next step without further purification.

1-(4-(4-(4-bromophenyl) piperazin-1-yl) pyridin-2-yl)-2,2,2-trifluoroethan-1-ol (MU)

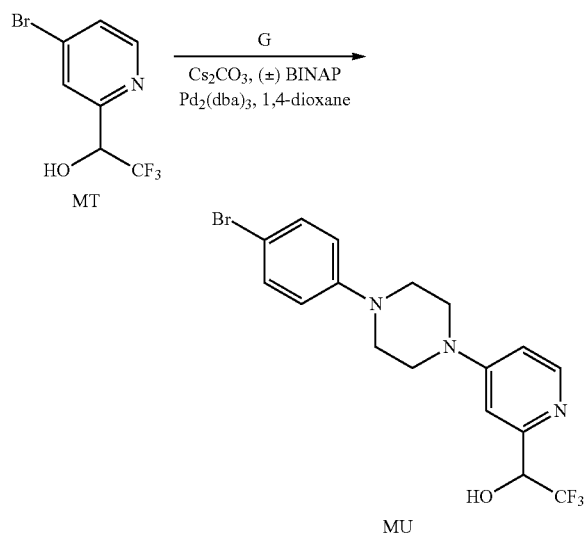

To a stirred solution of compound MT (200 mg, 0.78 mmol) in 1,4-dioxane (10 mL) under argon atmosphere were added G (189 mg, 0.78 mmol), cesium carbonate (767 mg, 2.35 mmol), (+) BINAP (34 mg, 0.05 mmol) and purged under argon for 20 min at RT. Then Pd$_2$(dba)$_3$ (36 mg, 0.04 mmol) was added to the reaction mixture at RT and stirred at 110° C. for 16 h in a sealed tube. The progress of the reaction was monitored by TLC, the volatiles were concentrated under reduced pressure to obtain compound MU (100 mg, crude) as a brown solid and the obtained crude compound was used in the next step without further purification. $^1$H NMR (400 MHz, DMSO-d$_6$): δ 8.18 (d, J=6.0 Hz, 1H), 7.38 (d, J=9.2 Hz, 2H), 7.05 (d, J=2.3 Hz, 1H), 6.95 (d, J=9.2 Hz, 2H), 6.75 (d, J=6.6 Hz, 1H), 5.03-4.91 (m, 1H), 3.53-3.43 (m, 4H), 3.32-3.23 (m, 4H).

1-(4-(4-(4-bromophenyl) piperazin-1-yl) pyridin-2-yl)-2,2,2-trifluoroethan-1-ol (MV)

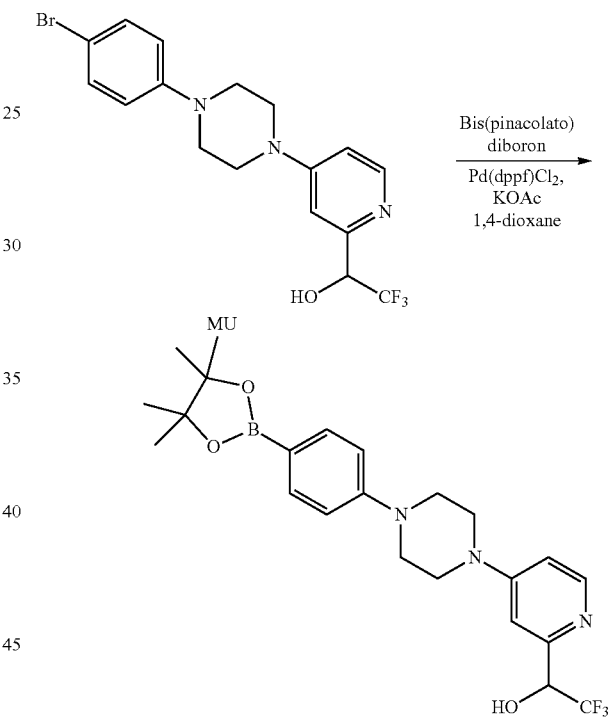

To a stirred solution of compound MU (670 mg, 1.61 mmol) in 1,4-dioxane (20 mL) under argon atmosphere were added bis(pinacolato)diboron (656 mg, 2.60 mmol) and potassium acetate (474 mg, 4.84 mmol) at RT and purged under argon for 15 min. Then Pd(dppf)Cl$_2$ (118 mg, 0.16 mmol) was added and the reaction mixture was purged under argon for 5 min at RT. The reaction mixture was stirred at 110° C. for 16 h. The reaction mixture was quenched with water (20 mL) and extracted with CH$_2$Cl$_2$ (2×20 mL). The combined organic layers were washed with water (20 mL), brine (20 mL), dried over anhydrous Na$_2$SO$_4$ and concentrated under reduced pressure to obtain compound MV (600 mg, crude) as a brown solid and the obtained crude compound was used in the next step without further purification. LC-MS: 464.1 [M+2H]$^+$ at 3.49 RT (54.5% purity).

455

(2R)-2-(2,4-difluorophenyl)-1,1-difluoro-3-(1H-tetrazol-1-yl)-1-(5-(4-(4-(2-(2,2,2-trifluoro-1-hydroxyethyl) pyridin-4-yl) piperazin-1-yl) phenyl) pyridin-2-yl)propan-2-propan-ol (104)

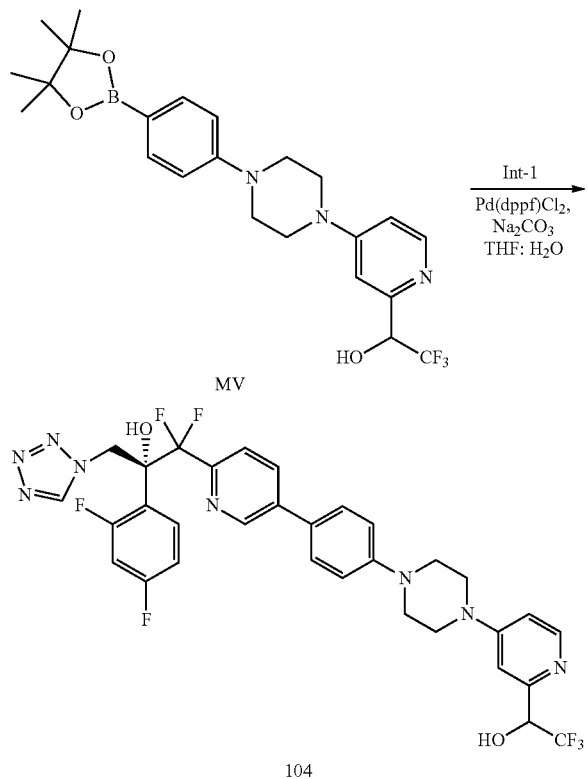

104

To a stirred solution of compound MV (300 mg, 0.64 mmol) in THF:H2O (4:1, 25 mL) under argon atmosphere were added Int-1 (278 mg, 0.64 mmol), sodium carbonate (206 mg, 1.94 mmol) and purged under argon for 10 min at RT. Then Pd(dppf)Cl$_2$ (47 mg, 0.06 mmol) was added to the reaction mixture at RT and stirred at 90° C. for 16 h. The reaction mixture was diluted with water (20 mL) and extracted with CH$_2$Cl$_2$ (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 50% acetone/Hexane) to afford 104 (30 mg, 0.04 mmol, 6%) as an off-white solid. $^1$H NMR (400 MHz, CDCl$_3$): δ 8.76 (s, 1H), 8.72 (d, J=2.0 Hz, 1H), 8.30 (d, J=6.9 Hz, 1H), 7.95 (dd, J=8.2, 2.2 Hz, 1H), 7.83 (s, 1H), 7.62 (d, J=8.2 Hz, 1H), 7.52 (d, J=8.8 Hz, 2H), 7.44-7.36 (m, 1H), 7.04 (d, J=8.8 Hz, 2H), 6.81-6.73 (m, 3H), 6.71-6.64 (m, 1H), 5.60 (d, J=14.2 Hz, 2H), 5.17-5.09 (m, 1H), 4.94-4.84 (m, 1H), 3.61-3.55 (m, 4H), 3.50-3.43 (m, 4H); MS (ESI): m/z 689.6 [M+H]$^+$; HPLC: 99.69%; Optical rotation [α]$_D^{20}$: +43.52 (c=0.1% in MeOH).

456

Example 105

N-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-4,4,4-trifluoro-2-hydroxybutanamide (105)

4,4,4-trifluoro-2-hydroxybutanoic Acid (MX)

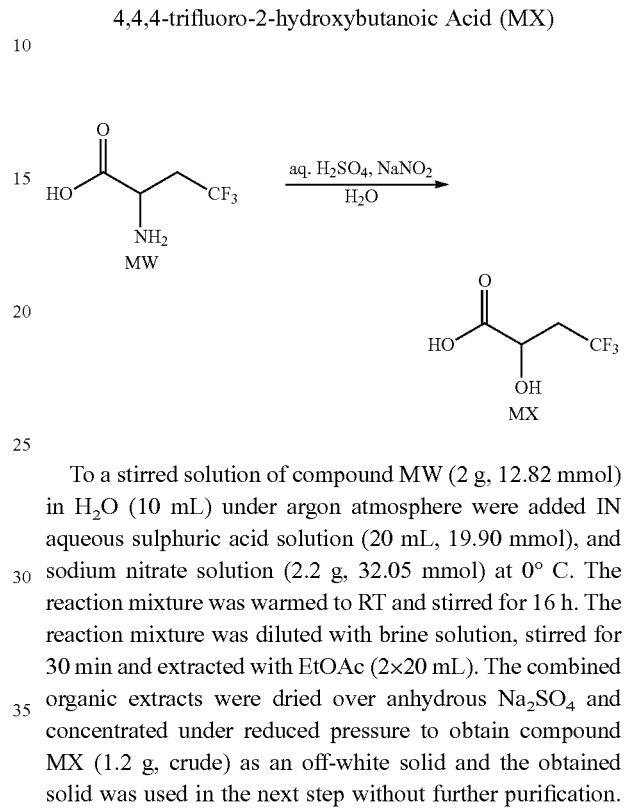

To a stirred solution of compound MW (2 g, 12.82 mmol) in H$_2$O (10 mL) under argon atmosphere were added 1N aqueous sulphuric acid solution (20 mL, 19.90 mmol), and sodium nitrate solution (2.2 g, 32.05 mmol) at 0° C. The reaction mixture was warmed to RT and stirred for 16 h. The reaction mixture was diluted with brine solution, stirred for 30 min and extracted with EtOAc (2×20 mL). The combined organic extracts were dried over anhydrous Na$_2$SO$_4$ and concentrated under reduced pressure to obtain compound MX (1.2 g, crude) as an off-white solid and the obtained solid was used in the next step without further purification.

N-(4-(4-(4-bromophenyl) piperazin-1-yl) phenyl)-4,4,4-trifluoro-2-hydroxybutanamide (MY)

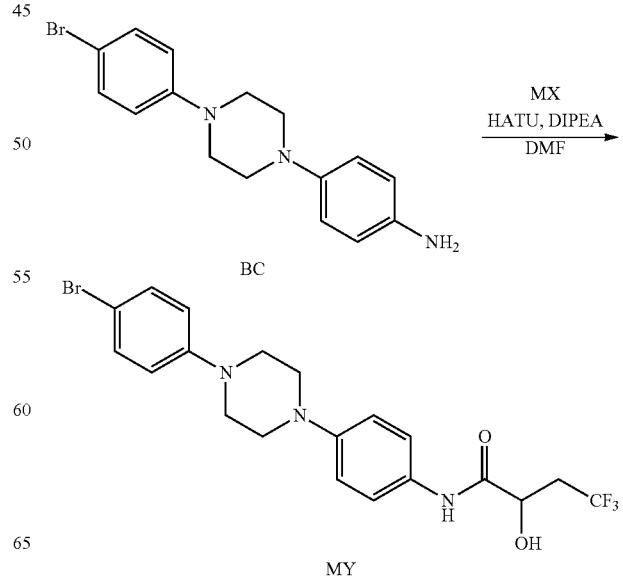

To a stirred solution of compound BC (300 mg, 0.90 mmol) in DMF (15 mL) under argon atmosphere was added HATU (515 mg, 1.35 mmol) and stirred for 5 min. Then compound MX (142 mg, 0.90 mmol) and diisopropyl ethyl amine (0.5 mL, 2.70 mmol) at RT and stirred for 16 h. The reaction mixture was diluted with water (20 mL) and extracted with EtOAc (2×20 mL). The combined organic extracts were dried over anhydrous Na$_2$SO$_4$ and concentrated under reduced pressure to obtain compound MY (200 mg, 0.42 mmol, 47%) as an off-white solid. $^1$H NMR (500 MHz, DMSO-d$_6$): δ 9.69 (s, 1H), 7.56 (d, J=8.7 Hz, 2H), 7.37 (d, J=8.7 Hz, 2H), 6.96 (dd, J=9.3, 2.9 Hz, 4H), 6.22 (d, J=6.4 Hz, 1H), 4.37-4.26 (m, 1H), 3.28-3.19 (m, 8H), 2.82-2.67 (m, 2H).

4,4,4-trifluoro-2-hydroxy-N-(4-(4-(4-(4-(4,4,5,5-tetramethyl-1,3,2-dioxaborolan-2-yl) phenyl) piperazin-1-yl) phenyl) butanamide (MZ)

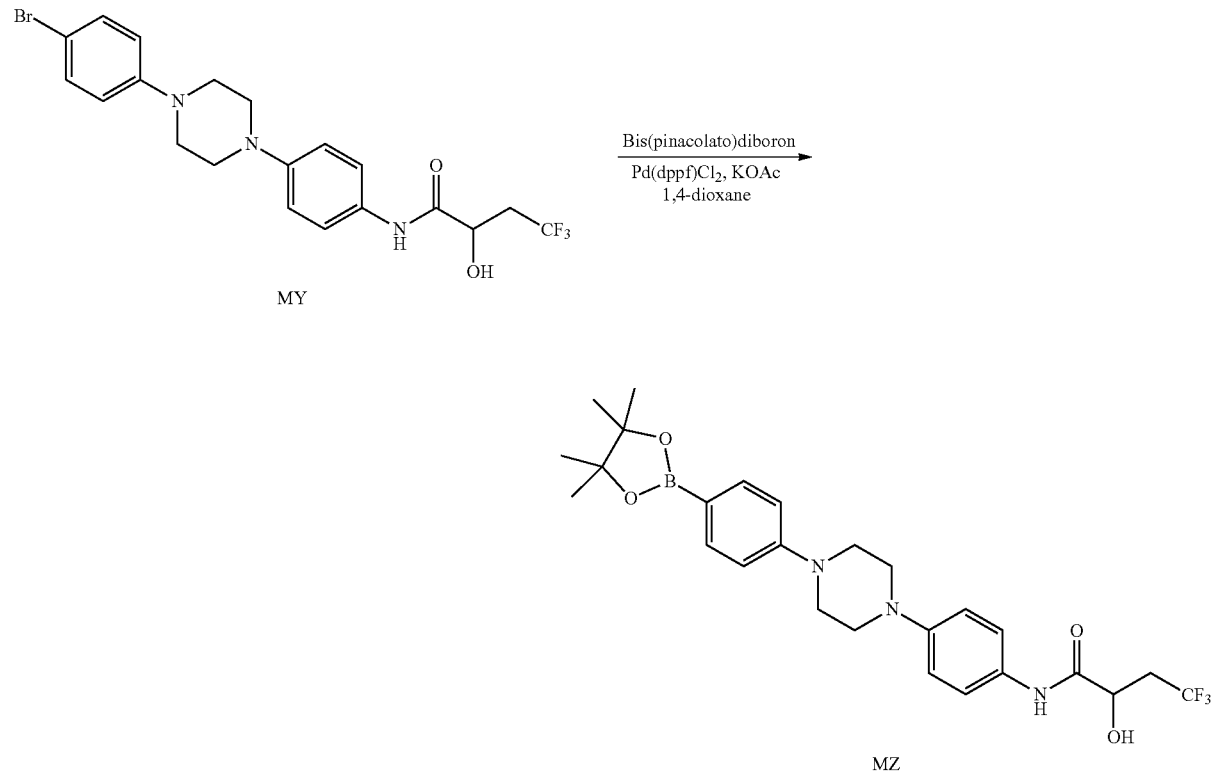

To a stirred solution of compound MY (200 mg, 0.42 mmol) in 1,4-dioxane (5 mL) under argon atmosphere were added bis(pinacolato)diboron (172.3 mg, 0.67 mmol) and potassium acetate (124.4 mg, 1.26 mmol) at RT. The reaction mixture was purged with argon for 20 min, then Pd(dppf)Cl$_2$ (31 mg, 0.04 mmol) was added and the reaction mixture was purged under argon for 5 min at RT. The reaction mixture was stirred at 100° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 20% EtOAc/Hexane) to afford compound MZ (180 mg, 0.34 mmol, 81%) as a brown solid. $^1$H NMR (500 MHz, DMSO-d$_6$): δ 9.69 (s, 1H), 7.60-7.50 (m, 4H), 6.99-6.96 (m, 3H), 6.22 (d, J=6.4 Hz, 1H), 4.33-4.30 (m, 1H), 3.38-3.32 (m, 4H), 3.23-3.20 (m, 4H), 1.27 (s, 12H).

N-(4-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) phenyl)-4,4,4-trifluoro-2-hydroxybutanamide (105)

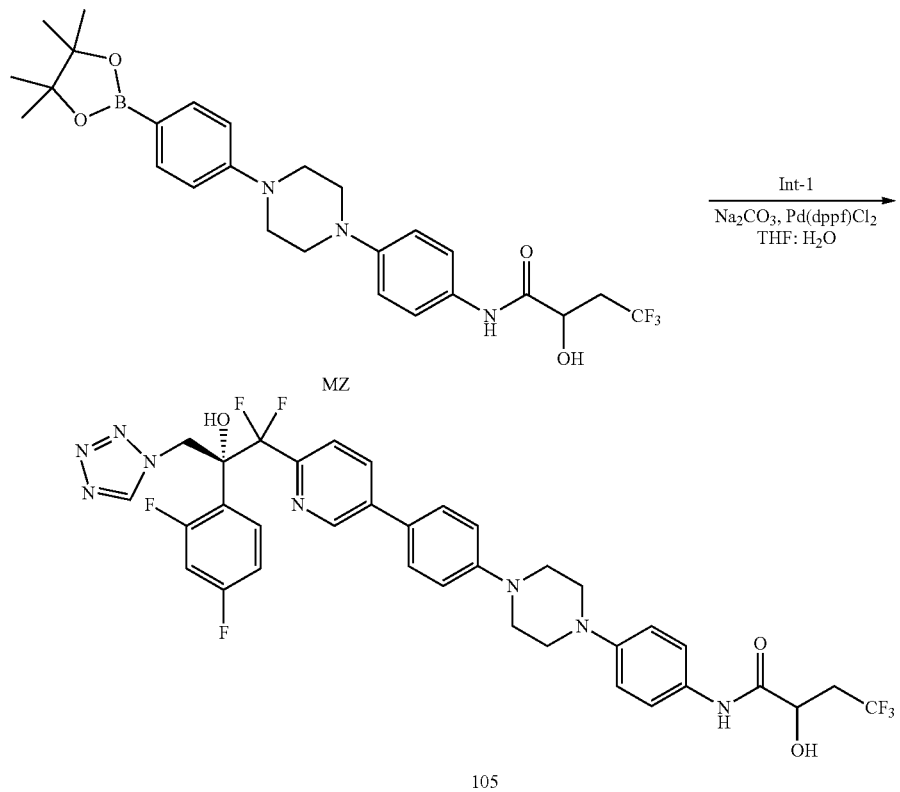

To a stirred solution of Int-1 (125 mg, 0.28 mmol) in THF:H2O (4:1, 15 mL) under argon atmosphere were added compound MZ (180 mg, 0.35 mmol), sodium carbonate (92 mg, 0.86 mmol) and purged under argon for 20 min at RT. Then Pd(dppf)Cl$_2$ (21 mg, 0.03 mmol) was added and the reaction mixture was purged under argon for 10 min at RT. The reaction mixture was stirred at 80° C. for 16 h. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 50% EtOAc/Hexane) to afford 105 (50 mg, 0.06 mmol, 23%) as an off-white solid. $^1$H NMR (400 MHz, DMSO-d$_6$): δ 9.70 (s, 1H), 9.15 (s, 1H), 8.90 (d, J=2.0 Hz, 1H), 8.16 (dd, J=8.3, 2.3 Hz, 1H), 7.70 (d, J=8.9 Hz, 2H), 7.57 (d, J=9.2 Hz, 2H), 7.48 (d, J=8.2 Hz, 1H), 7.34-7.25 (m, 2H), 7.22-7.16 (m, 1H), 7.14 (d, J=9.0 Hz, 2H), 6.98 (d, J=9.0 Hz, 2H), 6.93-6.88 (m, 1H), 6.22 (d, J=6.5 Hz, 1H), 5.67 (d, J=14.7 Hz, 1H), 5.11 (br d, J=14.7 Hz, 1H), 4.38-4.24 (m, 1H), 3.42-3.37 (m, 4H), 3.29-3.23 (m, 4H), 2.82-2.70 (m, 1H), 2.68-2.52 (m, 1H); MS (ESI): m/z 745.7 [M+H]$^+$; HPLC: 92.49%; Optical rotation [α]$_D^{20}$: +23.0 (c=0.1% in DMF).

Example 106(+)

(+)-(4-(4-(4-(6-(1,1-difluoro-2-(2-fluorophenyl)-2-hydroxy-1-(3-(trifluoromethyl)-1H-1,2,4-triazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (106(+))

3-(trifluoromethyl)-1H-1,2,4-triazole (NB)

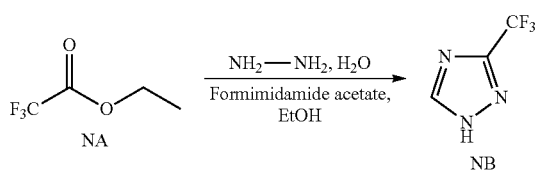

To a stirred solution of hydrazine hydrate (3.52 g, 70.42 mmol) in EtOH (15 mL) under argon atmosphere ethyl 2,2,2-trifluoroacetate (NA; 5 g, 35.21 mmol) in EtOH (10 mL) drop wise for 15 min at 0° C. The reaction mixture was stirred at 0° C. for 2 h. The volatiles were concentrated under reduced pressure. Then the residue was dissolved in EtOH (25 mL) under argon atmosphere was added formimidamide acetate (3.66 g, 35.21 mmol) at 0° C. The reaction mixture was stirred at 0° C. for 4 h. The progress of the reaction was monitored by TLC. The volatiles were concentrated under reduced pressure. The residue was diluted with water (50 mL), basified with saturated sodium bicarbonate solution (50 mL) and extracted with EtOAc (2×50 mL). The combined organic extracts were dried over anhydrous Na$_2$SO$_4$ and concentrated under reduced pressure. The crude material was purified by silica gel column chromatography (eluent: 30% EtOAc/Hexane) to afford compound NB (1 g, 7.29 mmol, 20%) as an off-white solid. $^1$H NMR (400 MHz, CDCl$_3$): δ 12.60 (br s, 1H), 8.45 (s, 1H).

1-(5-bromopyridin-2-yl)-1,1-difluoro-2-(2-fluorophenyl-3-(3-(trifluoromethyl)-1H-1,2,4-triazol-1-yl) propan-2-ol (NC)

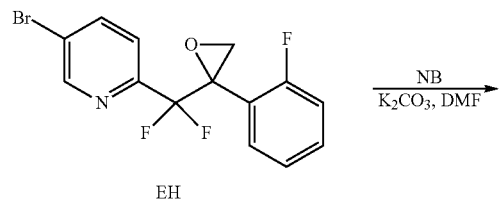

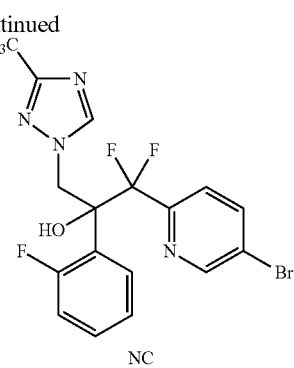

To a stirred solution of compound EH (1 g, 2.91 mmol) in DMF (10 mL) under argon atmosphere was added potassium carbonate (602 mg, 4.36 mmol) at RT and stirred for 15 min. Then compound NB (800 mg, 5.82 mmol) was added to the reaction mixture at RT. The reaction mixture was stirred at 70° C. for 16 h. The reaction mixture was diluted with water (50 mL) and extracted with EtOAc (2×50 mL). The combined organic extracts were dried over anhydrous Na$_2$SO$_4$ and concentrated under reduced pressure. The crude material was purified by silica gel column chromatography (eluent: 20% EtOAc/Hexane) to afford compound NC (700 mg, 1.45 mmol, 50%) as an off-white solid. $^1$H NMR (500 MHz, CDCl$_3$): δ 8.74 (s, 1H), 8.57 (s, 1H), 7.90 (dd, J=8.4, 2.0 Hz, 1H), 7.41 (d, J=8.1 Hz, 1H), 7.36-7.34 (m, 2H), 6.88 (t, J=8.4 Hz, 2H), 6.77 (s, 1H), 5.24-5.12 (m, 2H).

2-((2S,3S)-2-(benzyloxy) pentan-3-yl)-4-(4-(4-(4-(6-(1,1-difluoro-2-(2-fluorophenyl)-2-hydroxy-3-(3-(trifluoromethyl-1H-1,2,4-triazol-1-yl) propyl) pyridin-3-yl) phenyl) piperazin-1-yl) phenyl)-2,4-dihydro-3H-1,2,4-triazol-3-one (ND)

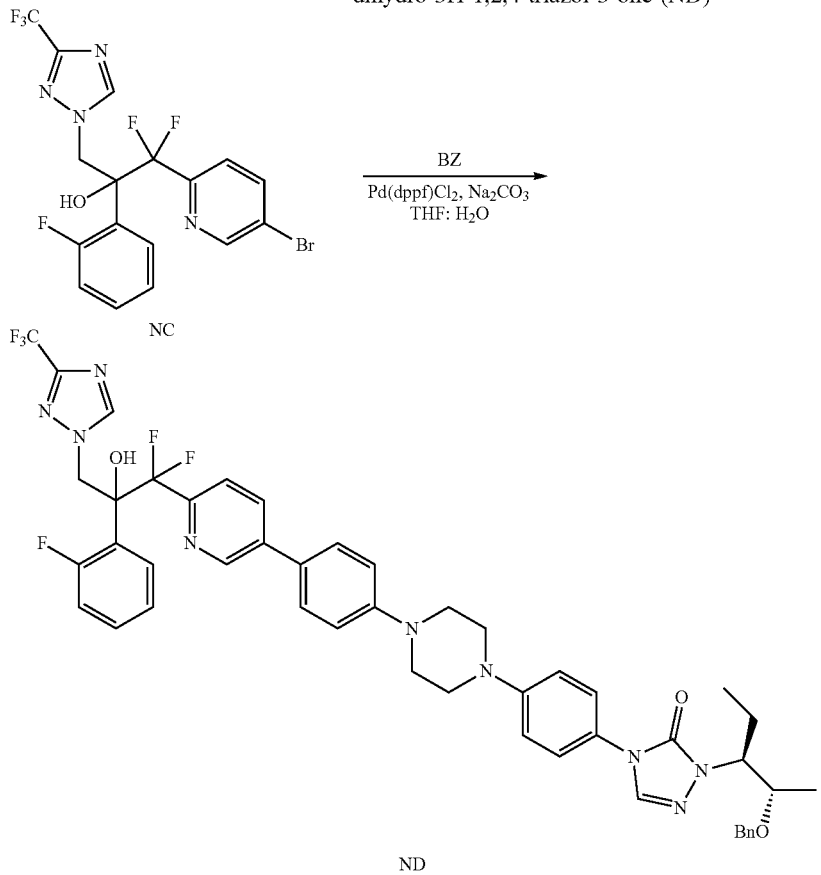

To a stirred solution of compound NC (200 mg, 0.41 mmol) in THF:H2O (4:1, 10 mL) under argon atmosphere were added compound BZ (285 mg, 0.45 mmol) and sodium carbonate (132 mg, 1.24 mmol) at RT. The reaction mixture was purged with argon for 20 min, then Pd(dppf)Cl$_2$ (31 mg, 0.04 mmol) was added and the reaction mixture was purged under argon for 10 min at RT. The reaction mixture was stirred at 70° C. for 5 h. The reaction mixture was quenched with water (20 mL) and extracted with EtOAc (2×20 mL). The combined organic layers were dried over anhydrous Na$_2$SO$_4$ and concentrated under reduced pressure. The crude material was purified by silica gel column chromatography (eluent: 50% EtOAc/Hexane) to afford compound ND (250 mg, 0.27 mmol, 63%) as an off-white solid. $^1$H NMR (400 MHz, DMSO-d$_6$): δ 8.90 (d, J=2.0 Hz, 1H), 8.59 (s, 1H), 8.32 (s, 1H), 8.15 (dd, J=8.3, 2.2 Hz, 1H), 7.70 (d, J=8.9 Hz, 2H), 7.49 (d, J=9.0 Hz, 2H), 7.46 (d, J=8.3 Hz, 1H), 7.36-7.29 (m, 2H), 7.27-7.20 (m, 3H), 7.19-7.07 (m, 8H), 7.04-6.99 (nm 1H), 5.45 (d, J=14.6 Hz, 1H), 5.01 (d, J=14.6 Hz, 1H), 4.53 (d, J=11.9 Hz, 1H), 4.27 (d, J=11.9 Hz, 1H), 4.08-3.85 (m, 1H), 3.78-3.67 (m, 1H), 3.42-3.36 (m, 8H), 1.82-1.66 (m, 2H), 1.23 (d, J=6.1 Hz, 3H), 0.79 (t, J=7.3 Hz, 31H)

4-(4-(4-(4-(6-(1,1-difluoro-2-(2-fluorophenyl)-2-hydroxy-3-(3-(trifluoromethyl)-1H-1,2,4-triazol-1-yl) propyl) pyridin-3-yl) phenyl) piperazin-1-yl) phenyl)-2-(2S,3S)-2-hydroxypentan-3-yl)-2,4-dihydro-3H-1,2,4-triazol-3-one (106(+))

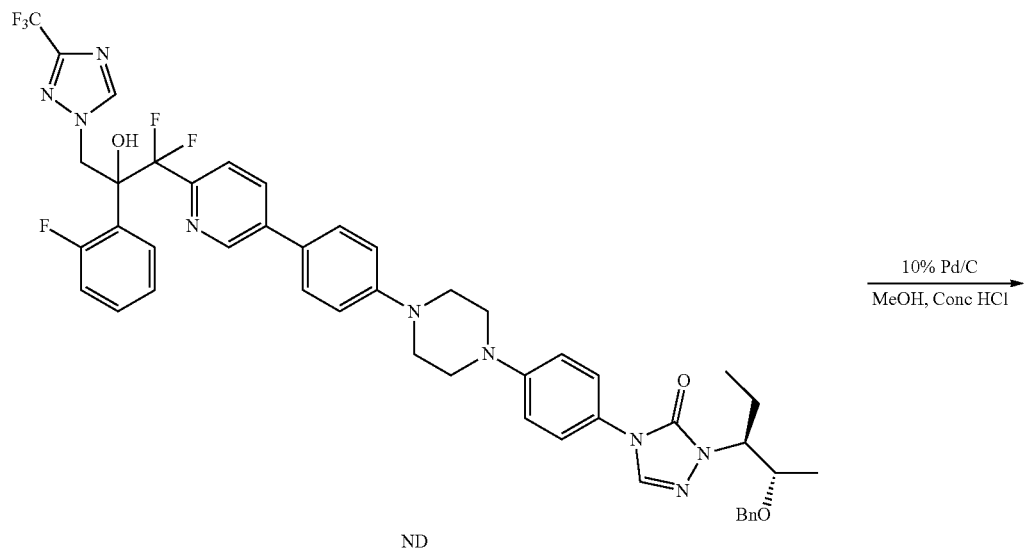

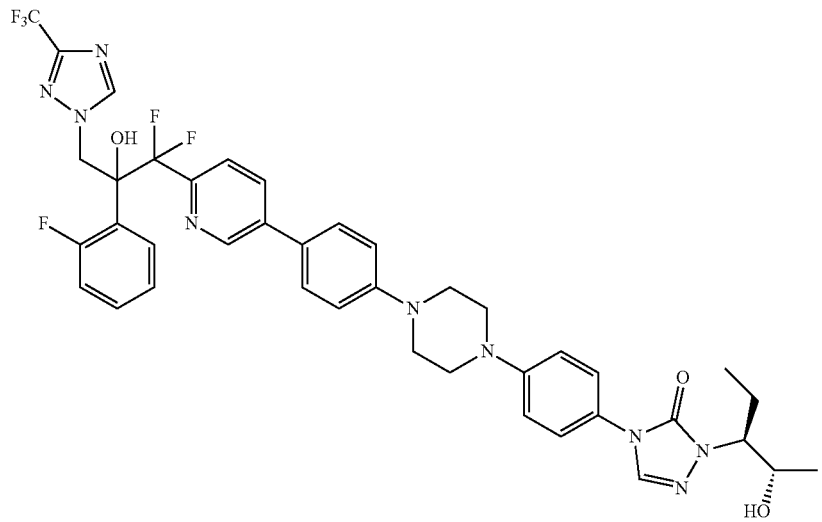

To a stirred solution of compound ND (250 mg, 0.27 mmol) in MeOH (10 mL) under argon atmosphere were added 10% Pd/C (125 mg) and conc. HCl (0.1 mL) at RT. The reaction mixture was stirred at RT for 8 h under hydrogen atmosphere. The progress of the reaction was monitored by TLC, the reaction mixture was filtered, and the filtrate was concentrated under reduced pressure. The residue was neutralized with 10% sodium carbonate solution (20 mL) and extracted with 10% MeOH/CH$_2$Cl$_2$ (2×20 mL). The combined organic layers were dried over anhydrous Na$_2$SO$_4$ and concentrated under reduced pressure. The crude material was purified by silica gel column chromatography (eluent: 2% MeOH/CH$_2$Cl$_2$) to afford 106 (160 mg) as an off-white solid.

Chiral Preparative HPLC Details of 106

106 (160 mg) was separated by normal-phase preparative high performance liquid chromatography (Chiralpak IA®, 250×20 mm, 5µ; using (A) 0.1% DEA in n-hexane:(B) CH$_2$Cl$_2$:MeOH (50:50) (A:B=35:65) as a mobile phase; Flow rate: 20 mL/min) to obtain 106(+) (40 mg) and 106(−) (40 mg), 106(+): $^1$H NMR (400 MHz, DMSO-d$_6$): δ 8.90 (d, J=1.7 Hz, 1H), 8.59 (s, 1H), 8.33 (s, 1H), 8.14 (dd, J=8.5, 1.8 Hz, 1H), 7.70 (d, J=8.7 Hz, 2H), 7.53 (d, J=9.0 Hz, 2H), 7.46 (d, J=8.2 Hz, 1H), 7.34-7.30 (m, 2H), 7.20-7.00 (m, 7H), 5.45 (d, J=14.3 Hz, 1H), 5.01 (br d, J=14.3 Hz, 1H), 4.66 (d, J=4.7 Hz, 1H), 3.85-3.75 (m, 2H), 3.45-3.34 (m, 8H), 1.79-1.64 (m, 2H), 1.12 (d, J=5.6 Hz, 3H), 0.75 (t, J=7.2 Hz, 3H); MS (ESI): m/z 808.8 [M+H]$^+$; HPLC: 99.28%; Chiral HPLC Purity: 99.98%, R$_t$=14.16 min (CHIRALPAK-IA®, 250×4.6 mm, 5µ; mobile phase (A) 0.1% DEA in n-Hexane: (B) CH$_2$Cl$_2$:MeOH (50:50) (35:65); flow Rate: 1.0 mL/min); Optical rotation [α]$_D^{20}$: +45.6 (c=0.1% in MeOH).

Example 107

4-(4-(4-(4-(6-(2-(2,4-difluorophenyl)-1,1-difluoro-2-hydroxy-3-(2H-1,2,3-triazol-2-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (107)

1-(5-bromopyridin-2-yl)-2-(2,4-difluorophenyl)-1,1-difluoro-3-(2H-1,2,3-triazol-2-yl) propan-2-ol (NE)

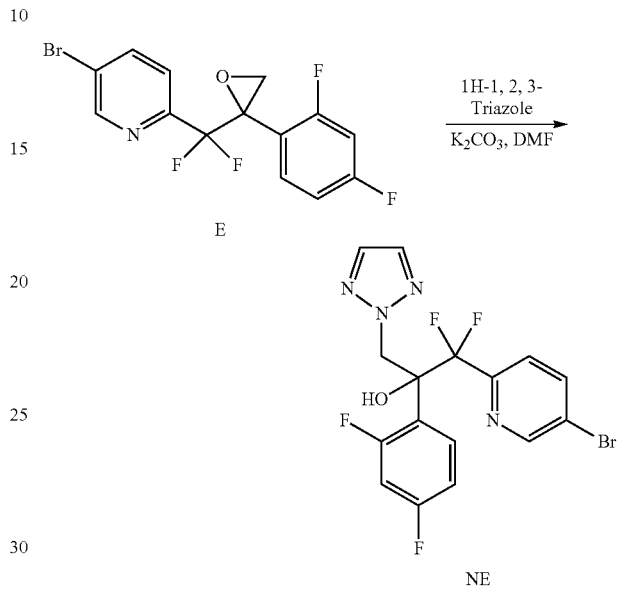

To a stirred solution of compound E (600 mg, 1.65 mmol) in DMF (10 mL) were added potassium carbonate (457 mg, 3.31 mmol) and 1H-1,2,3-Triazole (171 mg, 2.48 mmol) at RT. The reaction mixture was stirred at 80° C. for 16 h. The reaction mixture was diluted with water (20 mL) and extracted with EtOAc (2×20 mL). The combined organic extracts were dried over anhydrous Na$_2$SO$_4$ and concentrated under reduced pressure to obtain the crude. The crude material was purified by silica gel column chromatography (eluent: 20% EtOAc/Hexane) to afford compound NE (200 mg, 0.46 mmol, 28%) as yellow syrup. $^1$H NMR (400 MHz, CDCl$_3$): δ 8.64 (d, J=1.9 Hz, 1H), 7.91 (dd, J=8.4, 2.3 Hz, 1H), 7.46-7.38 (m, 4H), 6.83-6.67 (m, 2H), 5.91 (s, 1H), 5.75 (d, J=14.2 Hz, 1H), 5.13 (d, J=14.2 Hz, 1H)

2-((2S,3S)-2-(benzyloxy) pentan-3-yl)-4-(4-(4-(4-(6-(2-(2,4-difluorophenyl)-1,1-difluoro-2-hydroxy-3-(2H-1,2,3-triazol-2-yl) propyl) pyridin-3-yl) phenyl) piperazin-1-yl) phenyl)-2,4-dihydro-3H-1,2,4-triazol-3-one (NF)

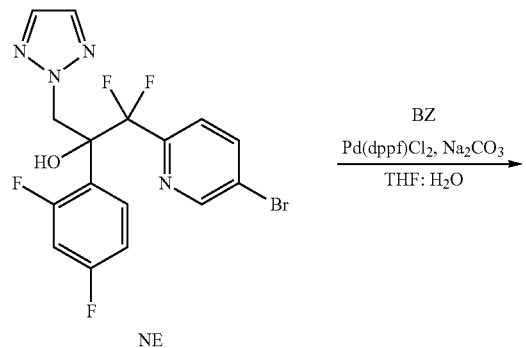

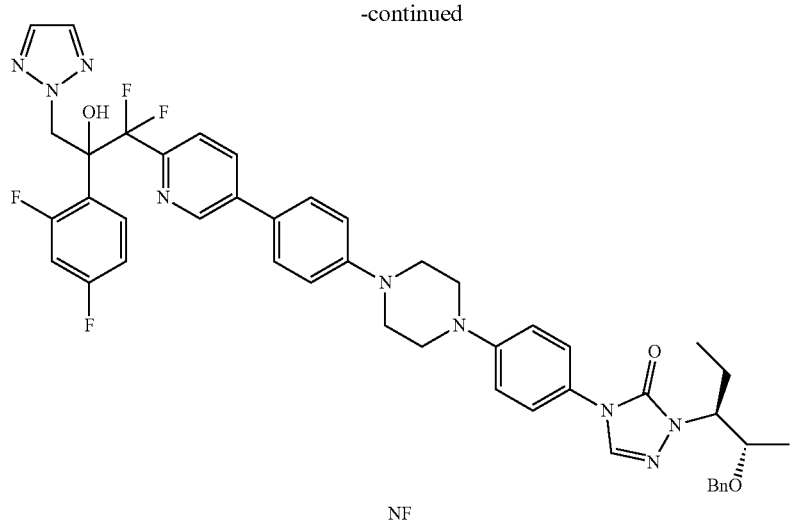

NF

To a stirred solution of compound NE (150 mg, 0.34 mmol) in THF:H2O (4:1, 5 mL) under argon atmosphere were added compound BZ (217 mg, 0.34 mmol) and sodium carbonate (111 mg, 1.04 mmol) at RT. The reaction mixture was purged with argon for 20 min, then Pd(dppf)Cl$_2$ (26 mg, 0.03 mmol) was added and the reaction mixture was purged under argon for 10 min at RT. The reaction mixture was stirred at reflux for 5 h. The reaction mixture was quenched with water (20 mL) and extracted with EtOAc (2×20 mL). The combined organic layers were dried over anhydrous Na$_2$SO$_4$ and concentrated under reduced pressure. The crude material was purified by silica gel column chromatography (eluent: 50% EtOAc/Hexane) to afford compound NF (150 mg, 0.17 mmol, 51%) as an off-white solid. $^1$H NMR (500 MHz, CDCl$_3$): δ 8.78 (d, J=1.7 Hz, 1H), 7.93 (dd, J=8.1, 1.7 Hz, 1H), 7.64-7.50 (m, 5H), 7.47-7.40 (m, 4H), 7.25-7.23 (m, 5H), 7.09 (d, J=9.3 Hz, 2H), 7.05 (d, J=8.7 Hz, 2H), 6.83-6.76 (m, 1H), 6.74-6.69 (m, 1H), 6.54 (s, 1H), 5.72 (d, J=14.5 Hz, 1H), 5.17 (d, J=14.5 Hz, 1H), 4.65 (d, J=11.6 Hz, 1H), 4.43 (d, J=11.6 Hz, 1H), 4.23-4.18 (m, 1H), 3.85-3.80 (m, 1H), 3.52-3.42 (m, 8H), 2.02-1.90 (m, 1H), 1.85-1.78 (m, 1H), 1.29 (d, J=6.4 Hz, 3H), 0.90 (t, J=7.2 Hz, 3H).

4-(4-(4-(4-(6-(2-(2,4-difluorophenyl)-1,1-difluoro-2-hydroxy-3-(2H-1,2,3-triazol-2-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (107)

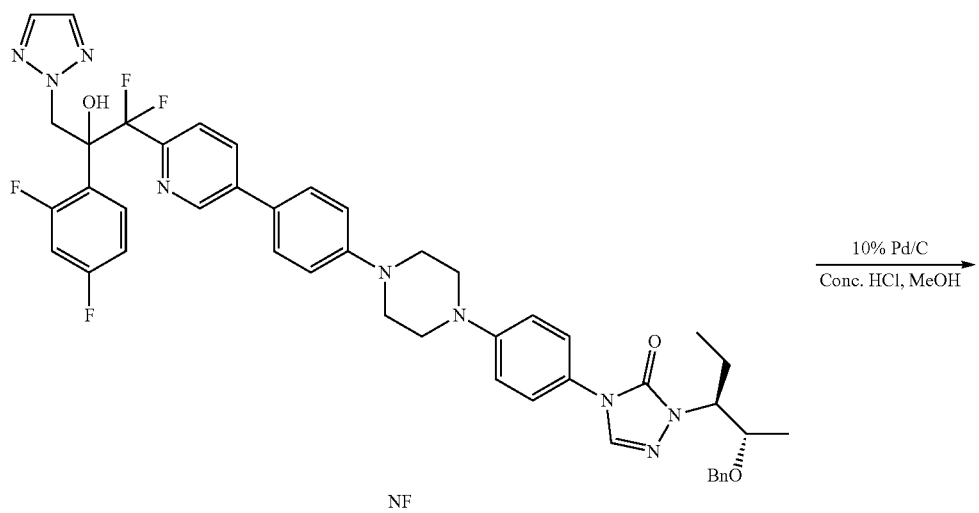

NF

10% Pd/C
―――――――→
Conc. HCl, MeOH

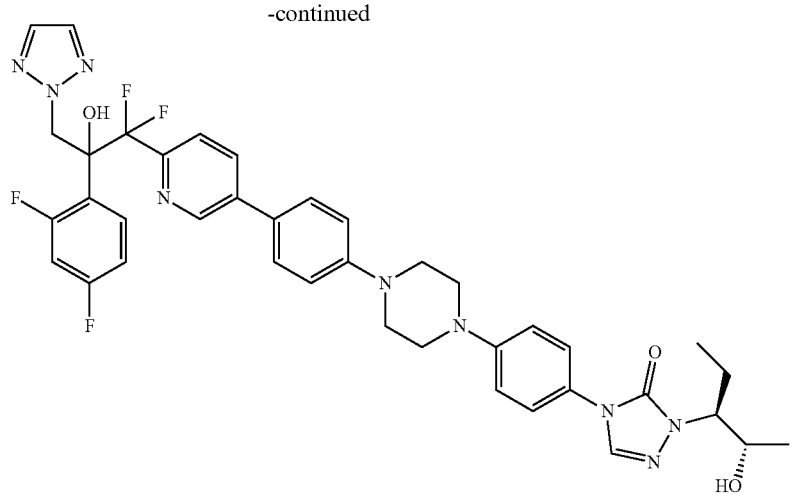

107

To a stirred solution of compound NF (150 mg, 0.17 mmol) in MeOH (5 mL) under argon atmosphere were added 10% Pd/C (80 ng) and conc. HCl (0.1 mL) at RT. The reaction mixture was stirred at RT for 3 h under hydrogen atmosphere. The progress of the reaction was monitored by TLC. The reaction mixture was filtered and the filtrate was concentrated under reduced pressure. The residue was neutralized with sodium carbonate solution (10 mL) and extracted with $CH_2Cl_2$ (2×10 mL). The combined organic layers were dried over anhydrous $Na_2SO_4$ and concentrated under reduced pressure. The crude material was purified by silica gel column chromatography (eluent: 2% MeOH/$CH_2Cl_2$) to afford 107 (55 mg, 0.07 mmol, 41%) as an off-white solid. $^1$H NMR (500 MHz, DMSO-$d_6$): δ 8.84 (s, 1H), 8.32 (s, 1H), 8.13 d, J=8.1 Hz, 1H), 7.68 (d, J=8.7 Hz, 2H), 7.58 (s, 2H), 7.53-7.46 (m, 3H), 7.30-7.21 (m, 1H), 7.15-7.07 (m, 5H), 6.92 (s, 1H), 6.87-6.81 (m, 1H), 5.62 (d, J=13.9 Hz, 1H), 5.07 (d, J=13.9 Hz, 1H), 4.64 (d, J=4.6 Hz, 1H), 3.82-3.73 (m, 2H), 3.40-3.33 (m, 8H), 1.75-1.64 (m, 2H), 1.11 (d, J=5.8 Hz, 3H), 0.73 (t, J=7.5 Hz, 3H); MS (ESI): m/z 758.7 [M+H]$^+$; HPLC: 99.10%; Optical rotation $[α]_D^{20}$: −6.24 (c=0.1% in MeOH).

Example 108(−)

(−)-1,1-difluoro-2-(2-fluorophenyl)-3-(1H-tetrazol-1-yl)-1-(5-(4-(4-(4-(2,2,2-trifluoro-1-hydroxyethyl)-1H-1,2,3-triazol-1-yl) phenyl) piperazin-1-yl) phenyl) pyridin-2-yl) propan-2-ol (108(−))

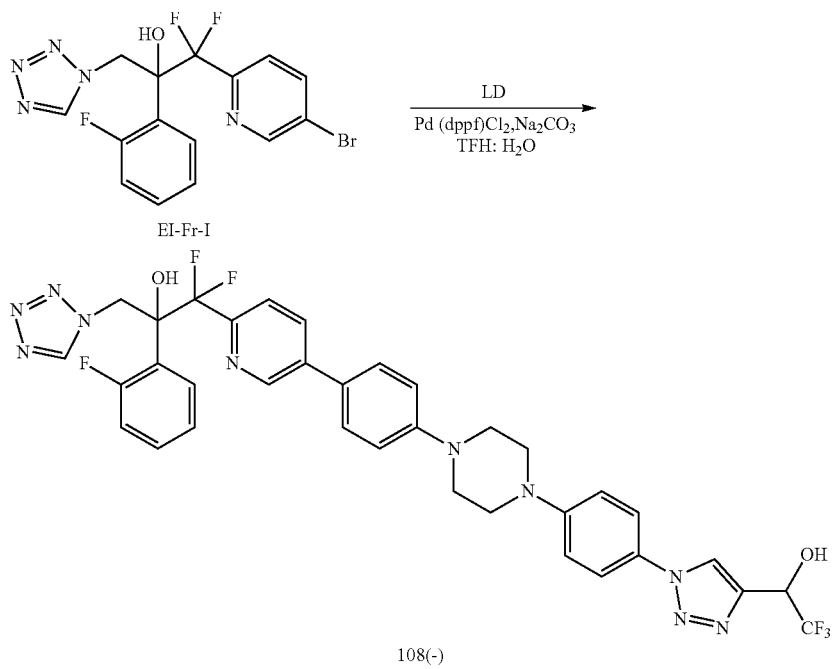

To a stirred solution of EI-Fr-I (150 mg, 0.36 mmol) in THF:H2O (4:1, 20 mL) under argon atmosphere were added compound LD (191 mg, 0.36 mmol), sodium carbonate (115 mg, 1.08 mmol) and purged under argon for 10 min at RT. Then Pd(dppf)Cl$_2$ (26.5 mg, 0.04 mmol) was added to the reaction mixture at RT and stirred at 90° C. for 16 h. The reaction mixture was diluted with water (20 mL) and extracted with CH$_2$Cl$_2$ (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 40% EtOAc/Hexane) to afford 108(−) (40 mg, 0.05 mmol, 15%) as an off-white solid. $^1$H NMR (400 MHz, DMSO-d$_6$): δ 9.13 (s, 1H), 8.92 (d, J=2.0 Hz, 1H), 8.80 (s, 1H), 8.16 (dd, J=8.2, 2.1 Hz, 1H), 7.79 (d, J=9.0 Hz, 2H), 7.71 (d, J=8.9 Hz, 2H), 7.45 (d, J=8.1 Hz, 1H), 7.37-7.24 (m, 2H), 7.20 (s, 2H), 7.18-7.10 (m, 4H), 7.06 (d, J=6.3 Hz, 1H), 7.04-7.00 (m, 1H), 5.71 (d, J=14.6 Hz, 1H), 5.40-5.33 (m, 1H), 5.11 (d, J=14.6 Hz, 1H), 3.43 (s, 8H); MS (ESI): m/z 737.6 [M+H]$^+$; HPLC: 96.49%°; Optical rotation [α]$_D^{20}$: −29.04 (c=0.1% in MeOH).

Example 108(+)

(+)-1,1-difluoro-2-(2-fluorophenyl)-3-(1H-tetrazol-1-yl)-1-(5-(4-(4-(4-(4-(2,2,2-trifluoro-1-hydroxy-ethyl)-1H-1,2,3-triazol-1-yl) phenyl) piperazin-1-yl) phenyl) pyridin-2-yl) propan-2-ol (108(+))

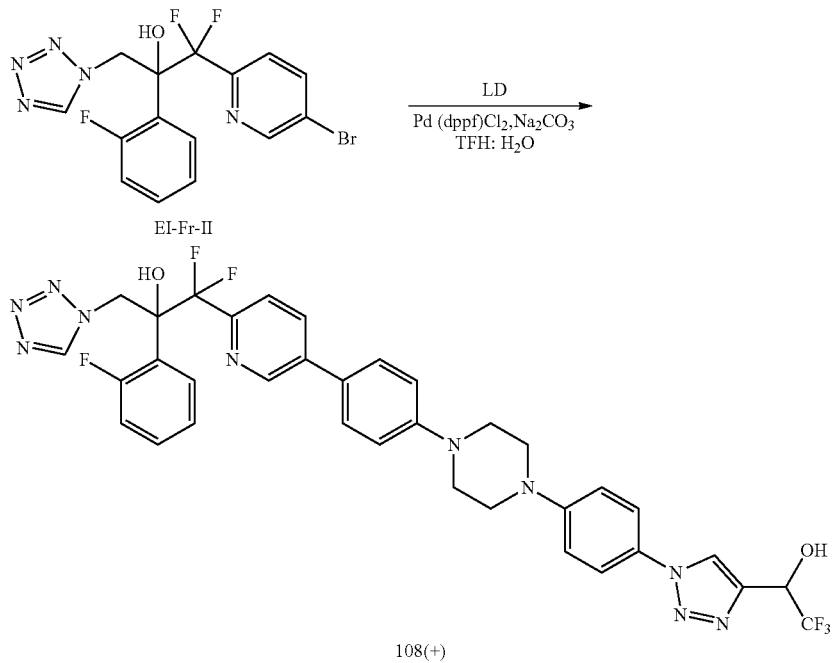

To a stirred solution of EI-Fr-II (150 mg, 0.36 mmol) in THF:H2O (4:1, 20 mL) under argon atmosphere were added compound LD (191 mg, 0.36 mmol), sodium carbonate (115 mg, 1.08 mmol) and purged under argon for 10 min at RT. Then Pd(dppf)Cl$_2$ (26.5 mg, 0.04 mmol) was added to the reaction mixture at RT and stirred at 90° C. for 16 h. The reaction mixture was diluted with water (20 mL) and extracted with CH$_2$Cl$_2$ (2×20 mL). The combined organic extracts were washed with water (20 mL), brine (20 mL), dried over anhydrous Na$_2$SO$_4$ and concentrated under reduced pressure. The crude material was purified by silica gel column chromatography (eluent: 40% EtOAc/Hexane) to afford 108(+) (40 mg, 0.05 mmol, 15%) as an off-white solid. $^1$H NMR (400 MHz, DMSO-d$_6$): δ 9.13 (s, 1H), 8.92 (d, J=2.0 Hz, 1H), 8.80 (s, 1H), 8.16 (dd, J=8.2, 2.1 Hz, 1H), 7.79 (d, J=9.0 Hz, 2H), 7.71 (d, J=8.9 Hz, 2H), 7.45 (d, J=8.1 Hz, 1H), 7.37-7.24 (m, 2H), 7.20 (s, 2H), 7.18-7.10 (m, 4H), 7.06 (d, J=6.3 Hz, 1H), 7.04-7.00 (m, 1H), 5.71 (d, J=14.6 Hz, 1H), 5.40-5.33 (m, 1H), 5.11 (d, J=14.6 Hz, 1H), 3.43 (s, 8H); MS (ESI): m/z 737.6 [M+H]$^+$; HPLC: 93.24%; Optical rotation [α]$_D^{20}$: +28.12 (c=0.1% in MeOH).

Examples 109(−) and 109(+)

(+) and (−)-4-(5-(4-(4-(6-((R)-1,1-difluoro-2-(4-fluorophenyl)-2-hydroxy-3-(1H-tetrazol-1-yl) propyl) pyridin-3-yl) phenyl) piperazin-1-yl) pyridin-2-yl)-2-((2S,3S)-2-hydroxypentan-3-yl)-2,4-dihydro-3H-1,2,4-triazol-3-one (109(−) and 109(+))

Chiral Preparative HPLC for GT-Fr-I and GT-Fr-II

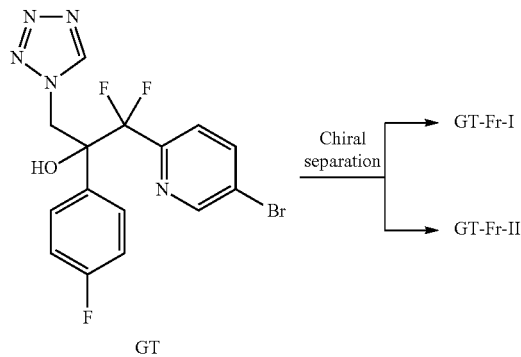 [SMILES: OC(Cn1cnnn1)(c1ccc(F)cc1)C(F)(F)c1ccc(Br)cn1]

GT

GT (1.5 g, 3.63 mmol) was separated by normal-phase preparative high performance liquid chromatography (CHIRALPAK-IC®, 250×20 mm, 5µ; using (A) 0.1% DEA in n-hexane:(B) CH$_2$Cl$_2$:MeOH (80:20) (A:B=70:30) as a mobile phase; Flow rate: 20 mL/min) to obtain GT-Fr-I (500 mg) and GT-Fr-II (500 mg).

GT-Fr-I:
$^1$H NMR (500 MHz, CDCl$_3$): δ 8.74 (s, 1H), 8.57 (s, 1H), 7.90 (dd, J=8.4, 2.0 Hz, 1H), 7.41 (d, J=8.1 Hz, 1H), 7.36-7.34 (m, 2H), 6.88 (t, J=8.4 Hz, 2H), 6.77 (s, 1H), 5.24-5.12 (m, 2H); LC-MS: 414 [M+H]$^+$ at 2.82 RT (99.7% purity); HPLC: 99.59%; Chiral HPLC Purity: 100%, R$_t$=10.53 min (CHIRALPAK-IC®, 250×4.6 mm, 5µ; mobile phase (A) 0.1% DEA in n-hexane:(B) CH$_2$Cl$_2$:MeOH (80:20) (A:B=70:30); flow Rate: 1.00 mL/min); Optical rotation [α]$_D^{20}$: −46.2 (c=0.1% in CH$_2$Cl$_2$).

GT-Fr-II:
$^1$H NMR (500 MHz, CDCl$_3$): δ 8.74 (s, 1H), 8.57 (s, 1H), 7.90 (dd, J=8.4, 2.0 Hz, 1H), 7.41 (d, J=8.1 Hz, 1H), 7.36-7.34 (m, 2H), 6.88 (t, J=8.4 Hz, 2H), 6.77 (s, 1H), 5.24-5.12 (m, 2H); LC-MS: 413.9 [M+H]$^+$ at 2.82 RT (99.23% purity); HPLC: 99.91%; Chiral HPLC Purity: 100%, R$_t$=14.13 min (CHIRALPAK-IC®, 250×4.6 mm, 5µ; mobile phase (A) 0.1% DEA in n-hexane:(B) CH$_2$Cl$_2$:MeOH (80:20) (A:B=70:30); flow Rate: 1.00 mL/min); Optical rotation [α]$_D^{20}$: +49.2 (c=0.1% in CH$_2$Cl$_2$).

2-((2S,3S)-2-(benzyloxy) pentan-3-yl)-4-(5-(4-(4-(6-((R)-1,1-difluoro-2-(4-fluorophenyl-2-hydroxy-3-(1H-tetrazol-1-yl) propyl) pyridin-3-yl) phenyl) piperazin-1-yl) pyridin-2-yl)-2,4-dihydro-3H-1,2,4-triazol-3-one (NG-Fr-I)

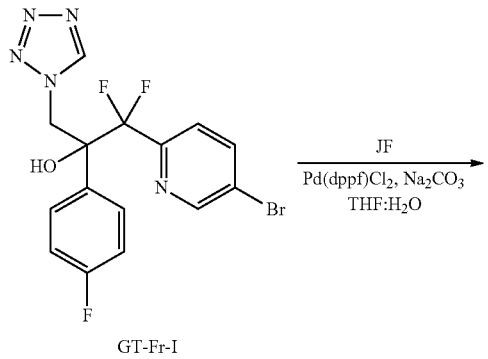

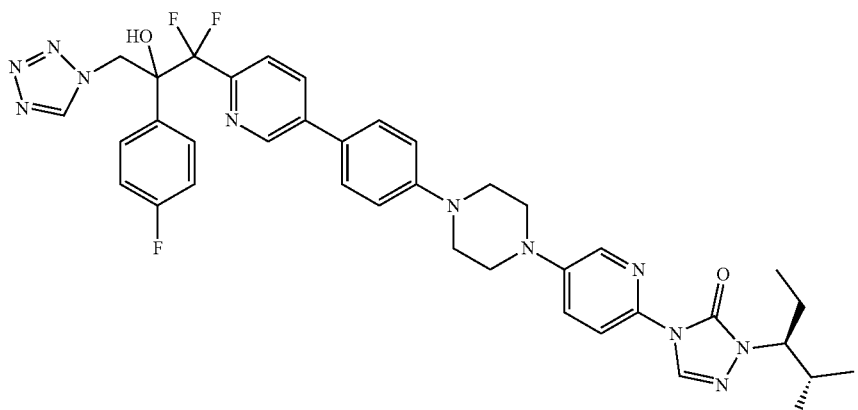

NG-Fr-I

To a stirred solution of compound GT-Fr-I (125 mg, 0.30 mmol) in THF:H2O (4:1, 25 mL) under argon atmosphere were added compound JF (188 mg, 0.30 mmol) and sodium carbonate (96 mg, 0.9 mmol) at RT. The reaction mixture was purged with argon for 20 min. then Pd(dppf)Cl$_2$ (22 mg, 0.03 mmol) was added and the reaction mixture was purged under argon for 10 min at RT. The reaction mixture was stirred at 80° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 60% EtOAc/Hexane) to afford compound NG-Fr-I (125 mg, 0.15 mmol, 50%) as an off-white solid. $^1$H NMR (500 MHz, DMSO-d$_6$): δ 9.01 (s, 1H), 8.92 (d, J=1.7 Hz, 1H), 8.50 (s, 1H), 8.26 (d, J=2.9 Hz, 1H), 8.14 (dd, J=8.4, 2.0 Hz, 1H), 7.98 (d, J=8.7 Hz, 1H), 7.70 (d, J=8.7 Hz, 2H), 7.67 (dd, J=9.3, 2.9 Hz, 1H), 7.46-7.41 (m, 3H), 7.20-7.12 (m, 6H), 7.08 (t, J=9.0 Hz, 2H), 7.05 (s, 1H), 5.61 (d, J=14.5 Hz, 1H), 5.17 (d, J=14.5 Hz, 1H), 4.53 (d, J=12.2 Hz, 1H), 4.26 (d, J=12.2 Hz, 1H), 4.06-3.96 (m, 2H), 3.79-3.67 (m, 1H), 3.43 (s, 8H), 1.81-1.72 (m, 2H), 1.25-1.21 (m, 3H), 0.88-0.76 (m, 3H).

(−)-4-(5-(4-(4-(6-((R)-1,1-difluoro-2-(4-fluorophenyl)-2-hydroxy-3-(1H-tetrazol-1-yl) propyl) pyridin-3-yl) phenyl) piperazin-1-yl) pyridin-2-yl)-2-((2S,3S)-2-hydroxypentan-3-yl)-2,4-dihydro-3H-1,2,4-triazol-3-one (109(−))

To a stirred solution of compound NG-Fr-I (125 mg, 0.15 mmol) in MeOH (20 mL) under argon atmosphere were added 10% Pd/C (75 mg) and concentrated HCl (catalytic amount) at RT and stirred for 2 h under hydrogen atmosphere (50 psi). The progress of the reaction was monitored by TLC. The reaction mixture was filtered through celite, the filtrate was concentrated under reduced pressure. The crude material was washed with n-pentane (2×5 mL) to afford 109(−) (60 mg, 0.08 mmol, 54%) as an off-white solid. $^1$H NMR (400 MHz. CDCl$_3$): δ 8.77 (s, 1H), 8.67 (d, J=2.0 Hz, 1H), 8.38 (s, 1H), 8.20 (d, J=8.9 Hz, 1H), 8.11 (d, J=2.8 Hz, 1H), 7.89 (dd, J=8.3, 2.3 Hz, 1H), 7.58 (s, 1H), 7.54 (d, J=8.2 Hz, 1H), 7.48 (d, J=8.9 Hz, 2H), 7.43-7.38 (m, 3H), 7.04 (d, J=8.9 Hz, 2H), 6.88 (t, J=8.7 Hz, 2H), 5.29-5.11 (m, 2H), 4.12-3.90 (m, 2H), 3.47-3.34 (m, 8H), 2.91 (d, J=8.8 Hz, 1H), 2.05-1.94 (m, 1H), 1.93-1.83 (m, 1H), 1.21 (d, J=6.1 Hz, 3H), 0.93 (t, J=7.4 Hz, 3H); MS (ESI): m/z 742.8 [M+H]$^+$; HPLC: 99.09%; Optical rotation [α]$_D^{20}$: −100.6 (c=0.1% in CH$_2$Cl$_2$).

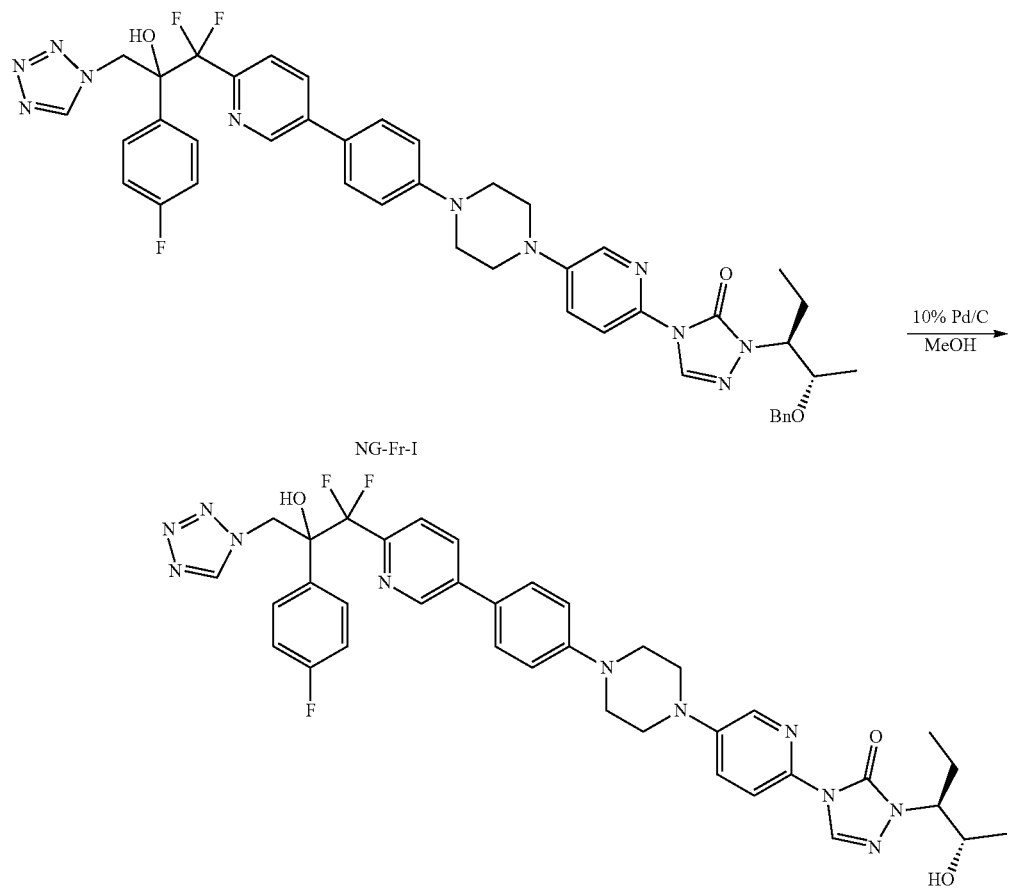

2-((2S,3S)-2-(benzyloxy) pentan-3-yl)-4-(5-(4-(4-(6-((R)-1,1-difluoro-2-(4-fluorophenyl)-2-hydroxy-3-(1H-tetrazol-1-yl) propyl) pyridin-3-yl) phenyl) piperazin-1-yl) pyridin-2-yl)-2,4-dihydro-3H-1,2,4-triazol-3-one (NG-Fr-II)

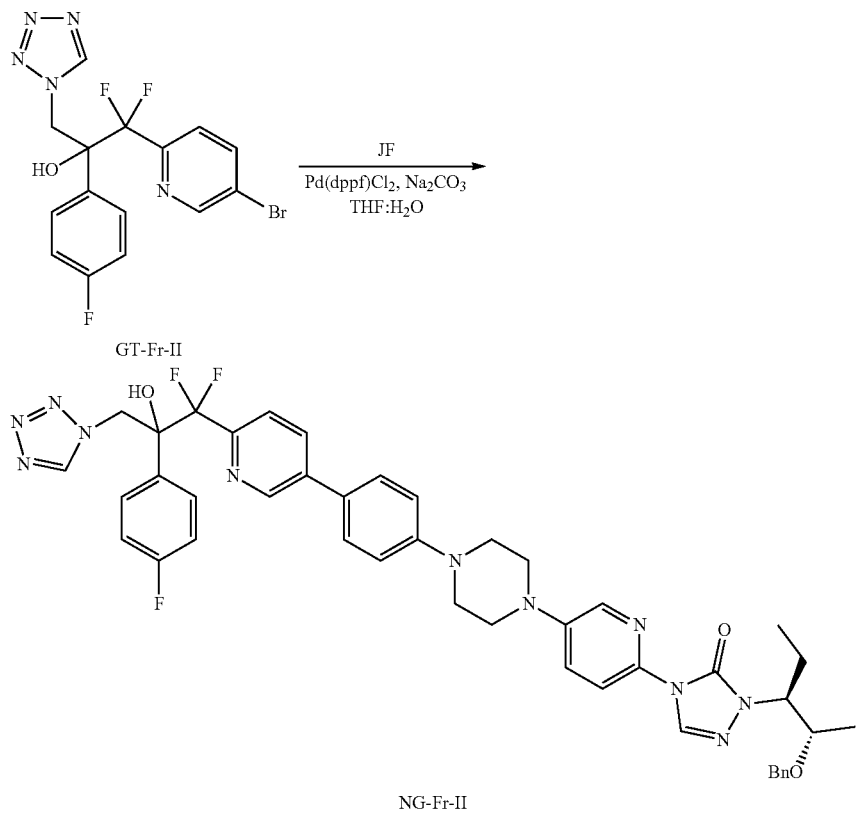

To a stirred solution of compound GT-Fr-II (125 mg, 0.30 mmol) in THF:H2O (4:1, 25 mL) under argon atmosphere were added compound JF (188 mg, 0.30 mmol) and sodium carbonate (96 mg, 0.9 mmol) at RT. The reaction mixture was purged with argon for 20 min. then Pd(dppf)Cl$_2$ (22 mg, 0.03 mmol) was added and the reaction mixture was purged under argon for 10 min at RT. The reaction mixture was stirred at 80° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 60% EtOAc/Hexane) to afford compound NG-Fr-II (125 mg, 0.15 mmol, 50%) as an off-white solid. $^1$H NMR (500 MHz, DMSO-d$_6$): δ 9.01 (s, 1H), 8.92 (s, 1H), 8.50 (s, 1H), 8.26 (d, J=2.9 Hz, 1H), 8.14 (dd, J=8.1, 2.3, Hz, 1H), 7.98 (d, J=8.7 Hz, 1H), 7.70 (d, J=8.7 Hz, 2H), 7.68 (dd, J=9.3, 2.9 Hz, 1H), 7.46-7.36 (m, 3H), 7.20-7.12 (m, 7H), 7.08 (t, J=9.0 Hz, 2H), 7.05 (s, 11H), 5.61 (d, J=14.5 Hz, 1H), 5.17 (d, J=14.5 Hz, 1H), 4.53 (d J=12.2 Hz, 1H), 4.26 (d, J=12.2 Hz, 1H), 4.06-3.98 (m, 1H), 3.75-3.71 (m, 1H), 3.44-3.41 (m, 8H), 1.86-1.63 (m, 2H), 1.28-1.17 (m, 3H), 0.90-0.57 (m, 3H).

(+)-4-(5-(4-(4-(6-((R)-1,1-difluoro-2-(4-fluorophenyl)-2-hydroxy-3-(1H-tetrazol-1-yl) propyl) pyridin-3-yl) phenyl) piperazin-1-yl) pyridin-2-yl)-2-((2S, 3S)-2-hydroxypentan-3-yl)-2,4-dihydro-3H-1,2,4-triazol-3-one (109(+))

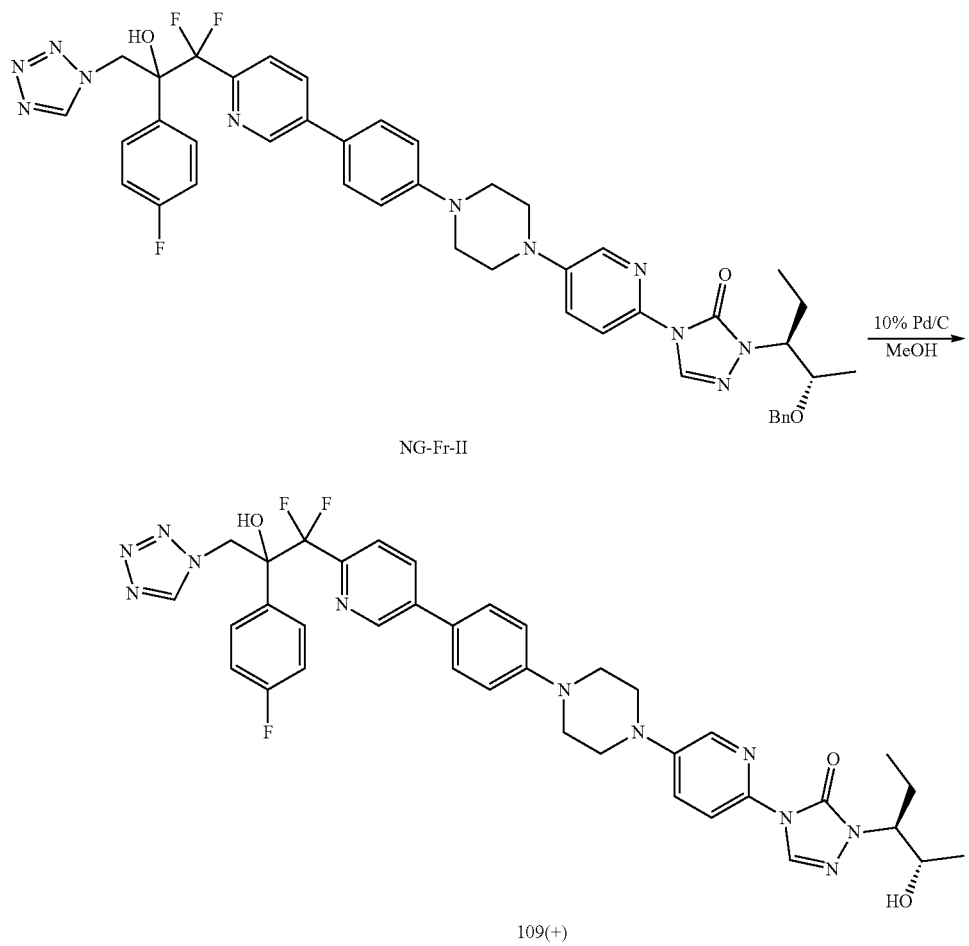

NG-Fr-II

109(+)

To a stirred solution of compound NG-Fr-IH (125 mg, 0.15 mmol) in MeOH (20 mL) under argon atmosphere were added 10% Pd/C (75 mg) and concentrated HCl (catalytic amount) at RT and stirred for 2 h under hydrogen atmosphere (50 psi). The progress of the reaction was monitored by TLC. The reaction mixture was filtered through celite, the filtrate was concentrated under reduced pressure. The crude material was washed with n-pentane (2×5 mL) to afford 109(+) (55 mg, 0.07 mmol, 50%) as an off-white solid. $^1$H NMR (400 MHz, CDCl$_3$): δ 8.77 (s, 1H), 8.68 (d, J=2.0 Hz, 1H), 8.39 (s, 1H), 8.21 (d, J=8.9 Hz, 1H), 8.11 (d, J=2.8 Hz, 1H), 7.90 (dd, J=8.3, 2.3 Hz, 1H), 7.59 (s, 1H), 7.55 (d, J=8.0 Hz, 1H), 7.49 (d, J=8.8 Hz, 2H), 7.44-7.38 (m, 3H), 7.05 (d, J=8.9 Hz, 2H), 6.88 (t, J=8.7 Hz, 2H), 5.30-5.10 (m, 2H), 4.15-3.85 (m, 2H), 3.49-3.44 (m, 4H), 3.43-3.37 (m, 4H), 2.92 (d, J=8.8 Hz, 1H), 2.06-1.95 (m, 1H), 1.94-1.79 (m, 1H), 1.21 (d, J=6.1 Hz, 3H), 0.93 (t, J=7.4 Hz, 3H); MS (ESI): m/z 742.8 [M+H]$^+$; HPLC: 97.53%; Optical rotation [α]$_D^{19}$: +94.7 (c=0.1% in CH$_2$Cl$_2$).

Examples 110(−) and 110(+)

(+) and (−)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl) pyridin-3-yl) piperazin-1-yl) phenyl) pyridin-2-yl) propan-2-ol (110(−) and 110(+))

2-azido-5-bromopyridine (NH)

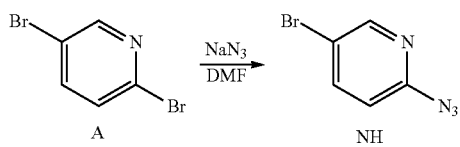

To a stirred solution of 2,5-dibromopyridine (A; 25 g, 105.48 mmol) in DMF (150 mL) under argon atmosphere was added sodium azide (102.8 g, 1528.2 mmol) at RT. The reaction mixture was stirred at 90° C. to RT for 48 h. The progress of the reaction was monitored by TLC. The reaction mixture was diluted with cold water (100 mL), to obtain the solid. The solid was filtered, washed with water (2×100 mL), dried over anhydrous Na$_2$SO$_4$ and concentrated under reduced pressure to obtain compound NH (6.5 g. crude) as a brown solid. The material was used as such in the next step.

(1-(5-bromopyridin-2-yl)-1H-1,2,3-triazol-4-yl) methanol (NI)

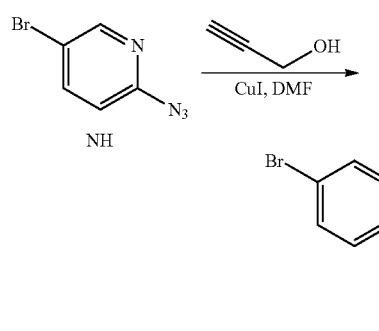

To a stirred solution of compound NH (6.5 g, 32.66 mmol) in DMF (100 mL) under argon atmosphere were added copper iodide (623 mg, 3.26 mmol) and propargyl alcohol (2.26 mL, 39.19 mmol) at 0° C. The reaction mixture was warmed to RT and stirred for 16 h. The reaction mixture was diluted with water (100 mL) and extracted with EtOAc (2×100 mL). The combined organic extracts were dried over anhydrous Na$_2$SO$_4$ and concentrated under reduced pressure. The crude material was purified by silica gel column chromatography (eluent: 30% EtOAc/Hexane) to afford compound NI (3.5 g, 13.8 mmol, 43%) as an off-white solid. $^1$H NMR (500 MHz, DMSO-d$_6$): δ 8.75 (d, J=2.3 Hz, 1H), 8.64 (s, 1H), 8.35 (dd, J=8.7, 2.3 Hz, 1H), 8.08 (d, J=8.7 Hz, 1H), 5.33 (t, J=5.5 Hz, 1H), 4.62 (d, J=5.8 Hz, 2H)

1-(5-bromopyridin-2-yl)-1H-1,2,3-triazole-4-carbaldehyde (NJ)

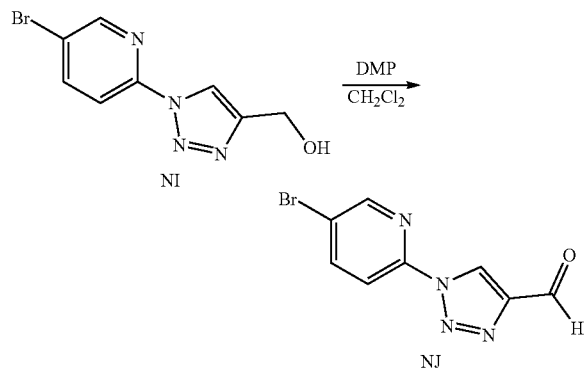

To a stirred solution of compound NI (3.5 g, 13.83 mmol) in CH$_2$Cl$_2$ (100 mL) under argon atmosphere was added Dess-Martin periodinane (7.0 g, 16.6 mmol) at 0° C. The reaction mixture was warmed to RT and stirred for 2 h. The progress of the reaction was monitored by TLC. The reaction mixture was diluted with saturated sodium bicarbonate solution (50 mL) and extracted with CH$_2$Cl$_2$ (2×50 mL). The combined organic extracts were dried over anhydrous Na$_2$SO$_4$ and concentrated under reduced pressure. The crude material was purified by silica gel column chromatography (eluent: 20% EtOAc/Hexane) to afford compound NJ (2.5 g, 9.96 mmol, 72%) as an off-white solid. $^1$H NMR (500 MHz, DMSO-d$_6$): δ 10.13 (s, 1H), 9.51 (s, 1H), 8.83 (d, J=1.7 Hz, 1H), 8.43 (dd, J=8.7, 2.3 Hz, 1H), 8.16 (d, J=8.7 Hz, 1H).

1-(1-(5-bromopyridin-2-yl)-1H-1,2,3-triazol-4-1)-2,2,2-trifluoroethan-1-ol (NK)

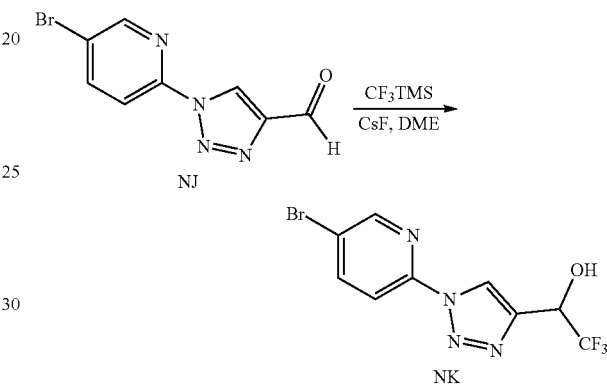

To a stirred solution of compound NJ (3.7 g, 14.74 mmol) in 1, 2-DME (70 mL) under argon atmosphere were added cesium fluoride (1.12 g, 7.37 mmol) and CF$_3$TMS (3.27 mL, 22.11 mmol) at 0° C. The reaction mixture was warmed to RT and stirred for 32 h. The progress of the reaction was monitored by TLC. The reaction mixture was quenched with 1.0N HCl solution (50 mL) and stirred for 1 h, diluted with water (50 mL) and extracted with EtOAc (2×50 mL). The combined organic layers were dried over anhydrous Na$_2$SO$_4$ and concentrated under reduced pressure. The crude material was purified by silica gel column chromatography (eluent: 30% EtOAc/Hexane) to afford compound NK (3.25 g, 10.12 mmol, 69%) as yellow solid. $^1$H NMR (400 MHz, DMSO-d$_6$): δ 8.82 (s, 1H), 8.78 (d, J=1.8 Hz, 1H), 8.38 (dd, J=8.7, 2.4 Hz, 1H), 8.11 (d, J=8.7 Hz, 1H), 7.11 (d, J=6.6 Hz, 1H), 5.46 (t, J=7.1 Hz, 1H).

1-(1-(5-(4-(4-bromophenyl) piperazin-1-yl) pyridin-2-yl)-1H-1,2,3-triazol-4-yl)-2,2,2-trifluoroethan-1-ol (NL)

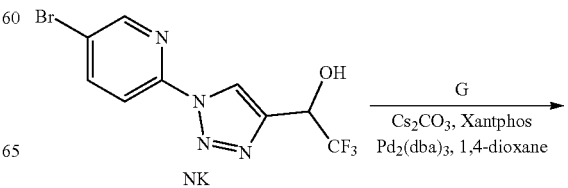

483
-continued

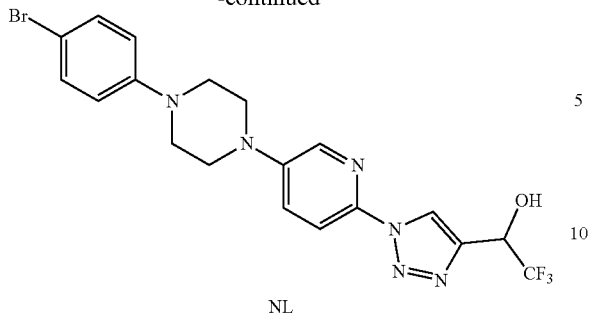

NL

To a stirred solution of compound NK (3.15 g, 10 mmol) in 1,4-dioxane (60 mL) under argon atmosphere were added G (2.36 g, 9.81 mmol), Cs$_2$CO$_3$ (9.6 g, 29.36 mmol), Xantphos (396.5 mg, 0.68 mmol) and purged under argon for 20 min at RT. Then Pd$_2$(dba)$_3$ (448 mg, 0.50 mmol) was added to the reaction mixture at RT and stirred at 110° C. for 16 h. The reaction mixture was filtered, washed with EtOAc (2×50 mL). The combined organic extracts were washed with water (50 mL), dried over anhydrous Na$_2$SO$_4$ and concentrated under reduced pressure. The crude material was purified by silica gel column chromatography (eluted with 30% EtOAc/Hexane) to afford compound NL (1.25 g, 2.59 mmol, 26%) as a brown solid. $^1$H NMR (500 MHz, DMSO-d$_6$): δ 8.67 (s, 1H), 8.31 (d, J=2.9 Hz, 1H), 7.93 (d, J=9.3 Hz, 1H), 7.69 (dd, J=9.3, 2.9 Hz, 1H), 7.37 (d, J=9.3 Hz, 2H), 7.03 (d, J=6.4 Hz, 1H), 6.97 (d, J=8.7 Hz, 2H), 5.40 (t, J=7.2 Hz, 1H), 3.47-3.43 (m, 4H), 3.32-3.30 (m, 4H).

2,2,2-trifluoro-1-(1-(5-(4-(4-(4,4,5,5-tetramethyl-1,3,2-dioxaborolan-2-yl) phenyl) piperazin-1-yl) pyridin-2-yl)-1H-1,2,3-triazol-4-yl) ethan-1-ol (NM)

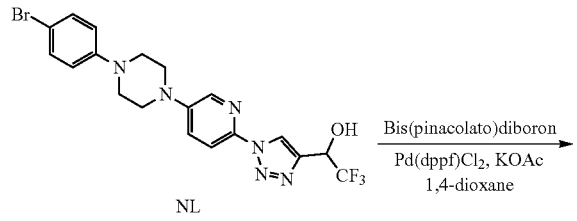

484
-continued

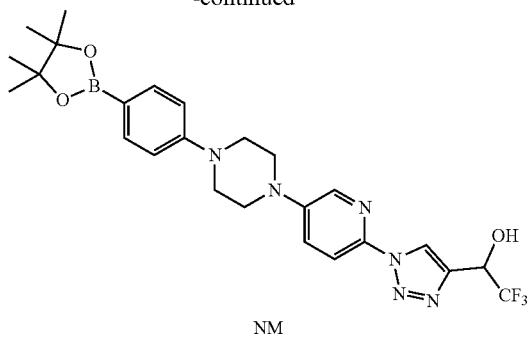

NM

To a stirred solution of compound NL (1.25 g, 2.59 mmol) in 1,4-dioxane (50 mL) under argon atmosphere were added bis (pinacolato) diboron (1.05 mg, 4.15 mmol), KOAc (761 mg, 7.77 mmol) and purged under argon for 20 min at RT. Then Pd(dppf)$_2$Cl$_2$ (189 mg, 0.26 mmol) was added to the reaction mixture at RT and stirred at 90° C. for 16 h. The reaction mixture was filtered, and the filtrate was diluted with water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluted with 20% EtOAc/Hexane) to afford compound NM (800 mg, 1.50 mmol, 58%) as a brown solid. $^1$H NMR (400 MHz, DMSO-d$_6$): δ 8.69 (s, 1H), 8.32 (d, J=2.9 Hz, 1H), 7.95 (d, J=9.0 Hz, 1H), 7.70 (dd, J=9.2, 2.9 Hz, 1H), 7.55 (d, J=8.7 Hz, 2H), 7.05 (d, J=6.7 Hz, 1H), 6.99 (d, J=8.7 Hz, 2H), 5.48-5.26 (m, 1H), 3.47-3.41 (m, 8H), 1.27 (s, 12H).

(−)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl) pyridin-3-1) piperazin-1-yl) phenyl) pyridin-2-yl) propan-2-ol (110(−))

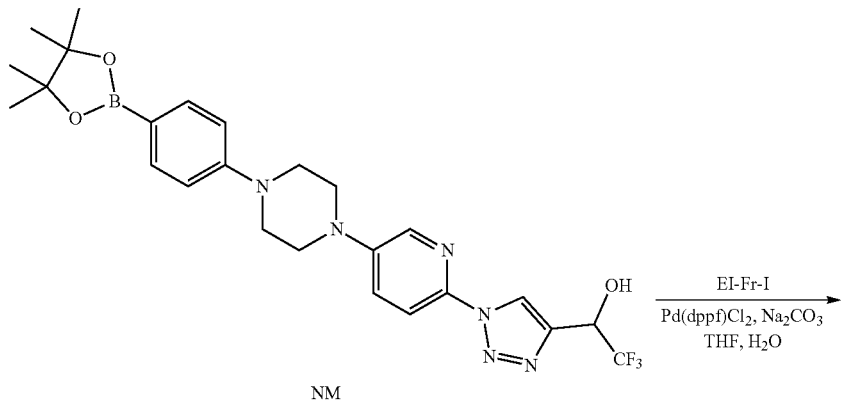

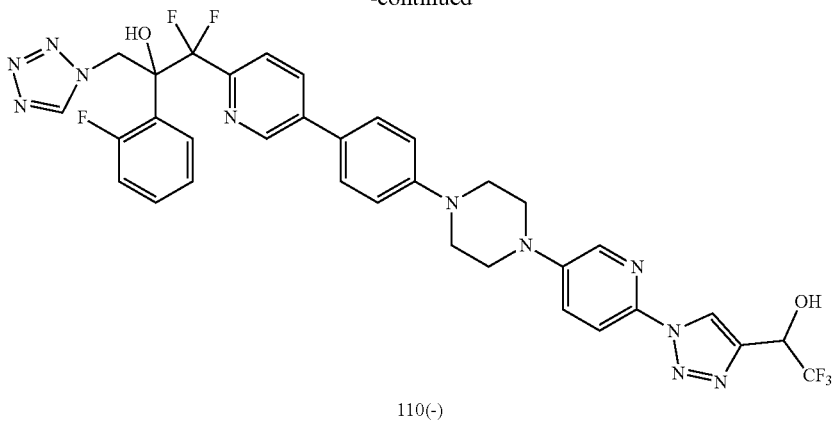

110(−)

To a stirred solution of EI-Fr-I (150 g, 0.36 mmol) in THF:H2O (6:1, 15 mL) under argon atmosphere were added compound NM (230 mg, 0.43 mmol), sodium carbonate (115 mg, 1.08 mmol) and purged under argon for 20 min at RT. Then Pd dppf) Cl$_2$ (26.5 mg, 0.36 mmol) was added to the reaction mixture at RT and stirred at 70° C. for 16 h. The reaction mixture was diluted with water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluted with 70% EtOAc/Hexane) to afford 110(−) (75 mg, 0.10 mmol, 28%) as an off-white solid. $^1$H NMR (400 MHz, DMSO-d$_6$): δ 9.12 (s, 1H), 8.92 (d, J=2.0 Hz, 1H), 8.69 (s, 1H), 8.34 (d, J=2.9 Hz, 1H), 8.16 (dd, J=8.2, 2.2 Hz, 1H), 7.96 (d, J=8.9 Hz, 1H), 7.74-7.70 (m, 3H), 7.46 (d, J=8.7 Hz, 1H), 7.37-7.26 (m, 2H), 7.19 (s, 1H), 7.16 (d, J=9.0 Hz, 2H), 7.13-7.09 (m, 1H), 7.05 (d, J=6.7 Hz, 1H), 7.04-6.99 (m, 1H), 5.71 (d, J=14.7 Hz, 1H), 5.45-5.39 (m, 1H), 5.11 (d, J=14.7 Hz, 1H), 3.50-3.44 (m, 8H); MS (ESI): m/z 738.4 [M+H]$^+$; HPLC: 97.6%; Optical rotation [α]$_D^{20}$: −39.9 (c=0.1% in MeOH).

(+)-1,1-difluoro-2-(2-fluorophenyl)-3-(1H-tetrazol-1-yl)-1-(5-(4-(4-(6-(4-(2,2,2-trifluoro-1-hydroxy-ethyl)-1H-1,2,3-triazol-1-yl) pyridin-3-yl) piperazin-1-yl) phenyl) pyridin-2-yl) propan-2-ol (110(+))

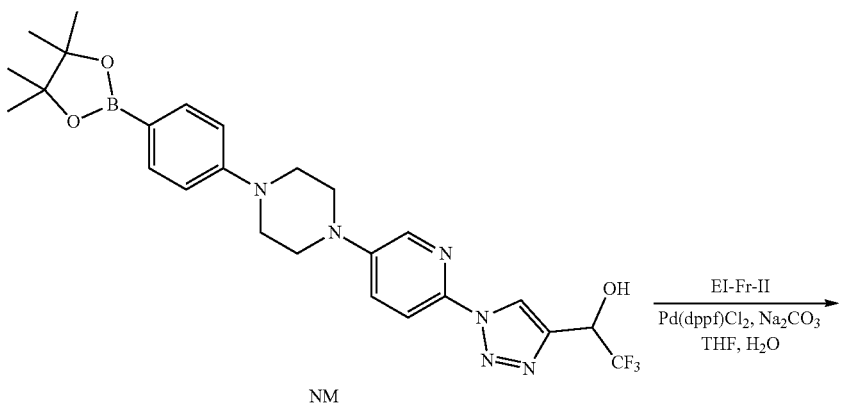

NM

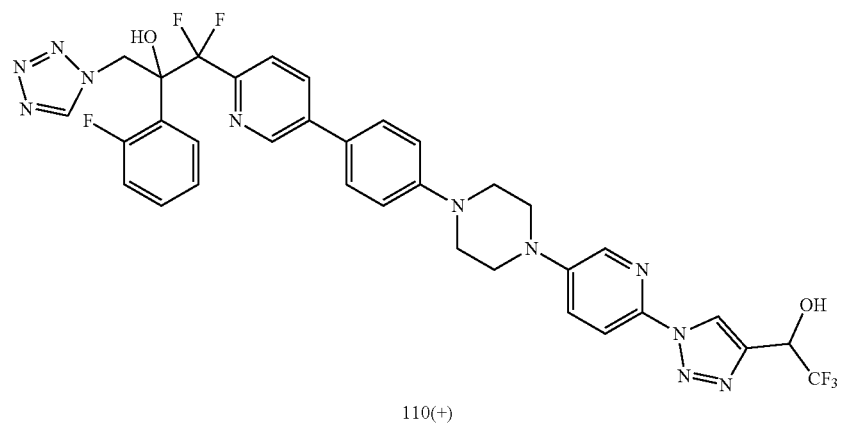

110(+)

To a stirred solution of EI-Fr-II (150 g, 0.36 mmol) in THF:H2O (6:1, 15 mL) under argon atmosphere were added compound NM (230 mg, 0.43 mmol), sodium carbonate (115 mg, 1.08 mmol) and purged under argon for 20 min at RT. Then Pd(dppf)Cl$_2$ (26.5 mg, 0.36 mmol) was added to the reaction mixture at RT and stirred at 70° C. for 16 h. The reaction mixture was diluted with water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was purified by silica gel column chromatography (eluted with 70% EtOAc/Hexane) to afford 110(+) (75 mg, 0.10 mmol, 28%) as an off-white solid. $^1$H NMR (400 MHz, DMSO-d$_6$): δ 9.12 (s, 1H), 8.92 (d, J=2.0 Hz, 1H), 8.69 (s, 1H), 8.34 (d, J=2.9 Hz, 1H), 8.16 (dd, J=8.2, 2.2 Hz, 1H), 7.96 (d, J=8.9 Hz, 1H), 7.74-7.70 (m, 3H), 7.46 (d, J=8.7 Hz, 1H), 7.37-7.26 (m, 2H), 7.19 (s, 1H), 7.16 (d, J=9.0 Hz, 2H), 7.13-7.09 (m, 1H), 7.05 (d, J=6.7 Hz, 1H), 7.04-6.99 (m, 1H), 5.71 (d, J=14.7 Hz, 1H), 5.45-5.39 (m, 1H), 5.11 (d, J=14.7 Hz, 1H), 3.50-3.44 (m, 8H); MS (ESI): m/z 738.7 [M+H]$^+$; HPLC: 96.03%; Optical rotation [α]$_D^{20}$: +48.24 (c=0.1% in MeOH).

Example 111

(2R)-2-(2,4-difluorophenyl)-1,1-difluoro-3-(1H-tetrazol-1-yl)-1-(5-(4-(4-(6-(4-(2,2,2-trifluoro-1-hydroxyethyl)-1H-1,2,3-triazol-1-yl) pyridin-3-yl) piperazin-1-yl) phenyl) pyridin-2-yl) propan-2-ol (111)

To a stirred solution of Int-1 (150 mg, 0.34 mmol) in THF:H2O (4:1, 15 mL) under argon atmosphere were added compound NM (220 mg, 0.41 mmol), sodium carbonate (110 mg, 1.04 mmol) and purged under argon for 20 min at RT. Then Pd(dppf)Cl$_2$ (25.4 mg, 0.03 mmol) was added to the reaction mixture at RT and stirred at 70° C. for 16 h. The reaction mixture was diluted with water (10 mL) and extracted with EtOAc (2×10 mL). The combined organic extracts were washed with water (10 mL), brine (10 mL), dried over anhydrous Na$_2$SO$_4$ and concentrated under reduced pressure. The crude material was purified by silica gel column chromatography (eluted with 70% EtOAc/Hexane) to afford 111 (75 mg, 0.09 mmol, 29%) as an off-white solid. $^1$H NMR (400 MHz, DMSO-d$_6$): δ 9.15 (s, 1H), 8.90 (s, 1H), 8.69 (s, 1H), 8.32 (d, J=2.9 Hz, 1H), 8.18 (d, J=8.7 Hz, 1H), 7.95 (d, J=9.0 Hz, 1H), 7.75-7.70 (m, 3H), 7.49 (d, J=8.7 Hz, 1H), 7.30-7.15 (m, 5H), 7.05 (d, J=6.7 Hz, 1H), 6.92-6.87 (m, 1H), 5.69 (d, J=14.6 Hz, 1H), 5.45-5.40 (m, 1H), 5.13 (d, J=14.6 Hz, 1H), 3.51-3.41 (m, 8H); MS (ESI): m/z 756.6 [M+H]$^+$; HPLC: 96%; Optical rotation [α]$_D^{19.98}$: +46.6 (c=0.1% in MeOH).

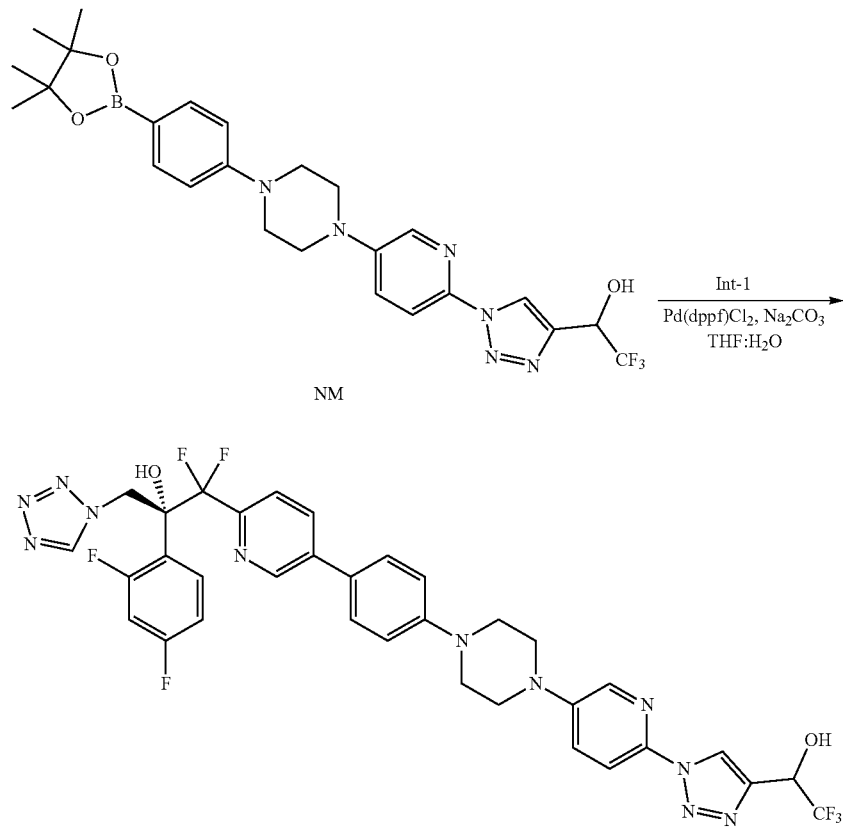

Example 112

(2S,3S)-3(4-(4-(4-(4-(6-(2-(2,4-difluorophenyl)-1,1-difluoro-2-hydroxy-3-(1H-tetrazol-1-yl) propyl) pyridin-3-yl)phenyl)piperazin-1-yl)phenyl)-5-oxo-4,5-dihydro-1H-1,2,4-triazol-1-yl)pentan-2-yl dihydrogen phosphate (112)

dibenzyl (2S,3S)-3-(4-(4-(4-(4-(6-(2-(2,4-difluorophenyl)-1,1-difluoro-2-hydroxy-3-(1H-tetrazol-1-yl) propyl) pyridin-3-yl) phenyl)piperazin-1-yl) phenyl)-5-oxo-4,5-dihydro-1H-1,2,4-triazol-1-yl) pentan-2-yl) phosphate (NO)

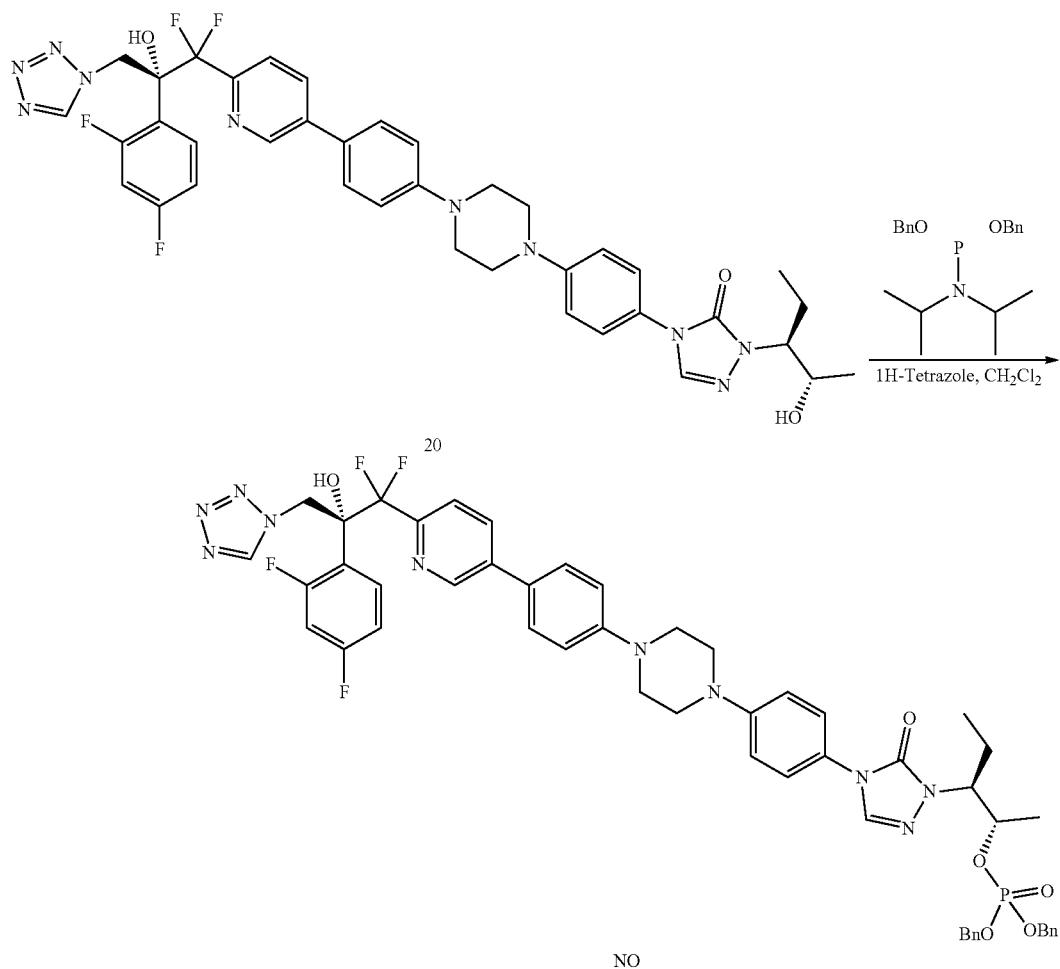

To a stirred solution of 20 (700 mg, 0.92 mmol) in CH$_2$Cl$_2$ (30 mL) under argon atmosphere was added 1H-tetrazole (323 mg, 4.61 mmol) at 0° C. The reaction mixture was warmed to RT and stirred for 1 h. Then dibenzyl diisopropylphosphoramidite (1.2 mL, 3.68 mmol) was added to the reaction mixture at −5° C.-0° C. The reaction mixture warmed to RT and stirred for 4 h. The progress of the reaction was monitored by TLC. The reaction mixture was quenched with TBHP solution (1.0 mL) at −5° C.-0° C., stirred at RT for 1 h, diluted with saturated sodium bicarbonate solution (20 mL) and extracted with CH$_2$Cl$_2$ (2×20 mL). The combined organic layers were dried over anhydrous Na$_2$SO$_4$ and concentrated under reduced pressure to obtain crude compound. The crude compound was purified by column chromatography followed by HPLC to afford compound NO (250 mg, 0.245 mmol, 26%) as a colorless semi-solid. $^1$H NMR (400 MHz, CD$_3$OD): δ 9.02 (s, 1H), 8.81 (d, J=2.1 Hz, 1H), 8.07 (dd, J=8.3, 2.3 Hz, 1H), 7.91 (s, 1H), 7.64 (d, J=8.9 Hz, 2H), 7.54 (d, J=8.2 Hz, 1H), 7.39-7.20 (m, 12H), 7.16 (d, J=8.9 Hz, 2H), 7.07 (d, J=9.2 Hz, 2H), 6.95-6.88 (m, 1H), 6.80-6.73 (m, 1H), 5.78 (d, J=14.6 Hz, 1H), 5.19 (d, J=14.6 Hz, 1H), 5.04-4.87 (m, 5H), 4.79-4.68 (m, 1H), 4.22-4.02 (m, 1H), 3.48-3.36 (m, 8H), 1.97-1.75 (m, 2H), 1.44 (d, J=6.4 Hz, 3H), 1.22 (d, J=6.87 Hz, 1H), 0.87 (t, J=7.3 Hz, 3H).

(2S,3S)-3-(4-(4-(4-(4-(6-(2-(2,4-difluorophenyl)-1,1-difluoro-2-hydroxy-3-(1H-tetrazol-1-yl) propyl) pyridin-3-yl)phenyl)piperazin-1-yl)phenyl-5-oxo-4, 5-dihydro-1H-1,2,4-triazol-1-yl)pentan-2-yl dihydrogen phosphate (112)

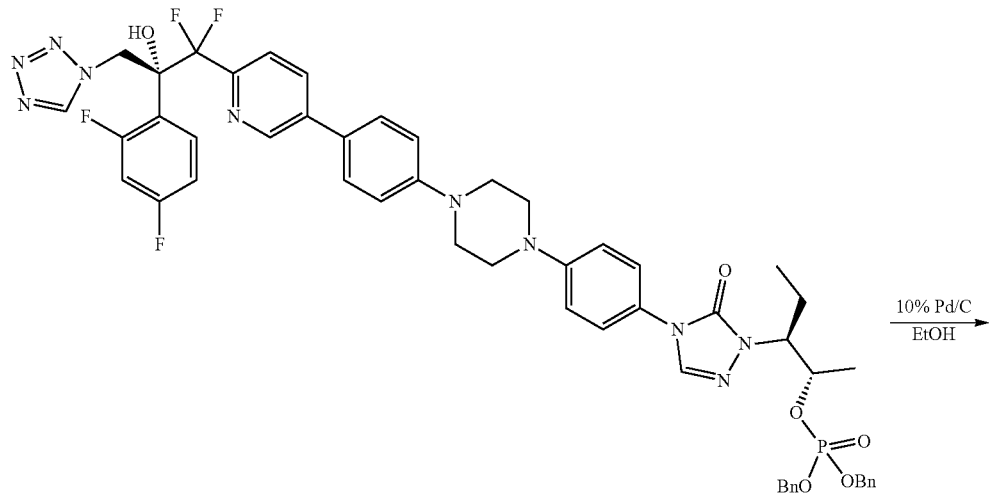

NO

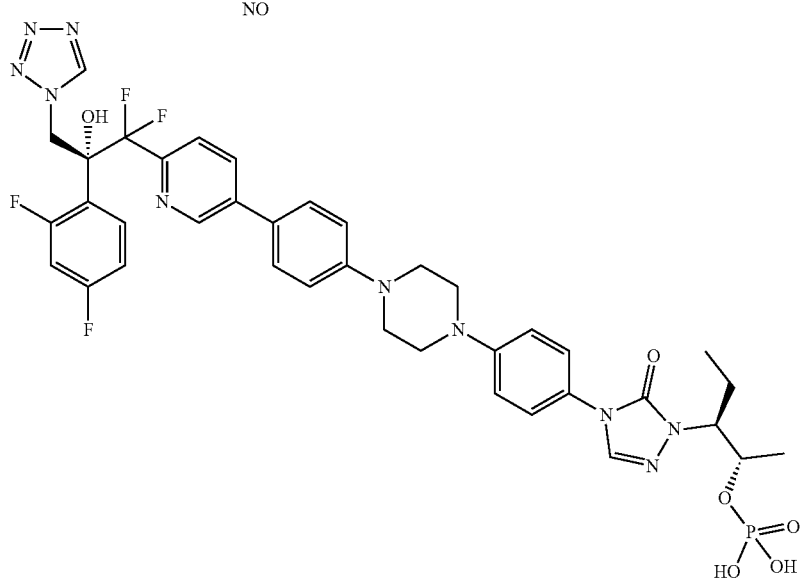

112

To a stirred solution of compound NO (250 mg, 0.245 mmol) in EtOH (50 mL) under argon atmosphere was added 10% Pd/C (150 mg) at RT and stirred for 4 h under hydrogen atmosphere (balloon pressure). The progress of the reaction was monitored by TLC. The reaction mixture was filtered through celite, the filtrate was concentrated under reduced pressure. The residue was washed with n-pentane to afford 112 (140 mg, 0.167 mmol, 68%) as an off-white solid. $^1$H NMR (400 MHz, DMSO-$d_6$): δ 10.88 (brs, 1H), 9.15 (s, 1H), 8.91 (d, J=1.8 Hz, 1H), 8.31 (s, 1H), 8.17 (dd, J=8.3, 2.1 Hz, 1H), 7.70 (d, J=8.8 Hz, 2H), 7.54-7.45 (m, 3H), 7.34-7.09 (m, 7H), 6.93-6.88 (m, 1H), 5.75 (s, 1H), 5.67 (d, J=14.7 Hz, 1H), 5.11 (d, J=14.7 Hz, 1H), 4.52-4.37 (m, 1H), 4.05-4.00 (m, 1H), 3.46-3.29 (m, 8H), 1.89-1.71 (m, 2H), 1.25 (d, J=6.4 Hz, 3H), 0.77 (t, J=7.3 Hz, 3H); $^{31}$P NMR (400 MHz, DMSO-$d_6$): δ −1.79 (s); MS (ESI): m/z 839.8 [M+H]$^+$; HPLC: 97.09%; Optical rotation $[α]_D^{19}$: +12.32 (c=0.1% in MeOH).

Example 113

(2S,3S)-3-(4-(5-(4-(4-(6-(1,1-difluoro-2-(2-fluoro-phenyl)-2-hydroxy-3-(1H-tetrazol-1-yl) propyl) pyridin-3-yl) phenyl) piperazin-1-yl) pyridin-2-yl)-5-oxo-4,5-dihydro-1H-1,2,4-triazol-1-yl) pentan-2-yl dihydrogen phosphate (113)

dibenzyl ((2S,3S)-3-(4-(5-(4-(4-(6-(1,1-difluoro-2-(2-fluorophenyl)-2-hydroxy-3-(1H-tetrazol-1-yl) propyl) pyridin-3-yl) phenyl) piperazin-1-yl) pyridin-2-yl)-5-oxo-4,5-dihydro-1H-1,2,4-triazol-1-yl) pentan-2-yl) phosphate (NP)

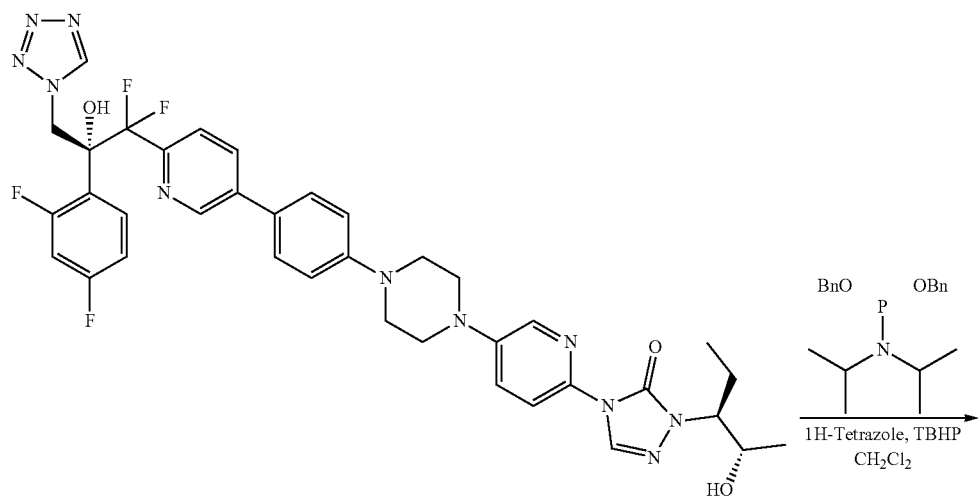

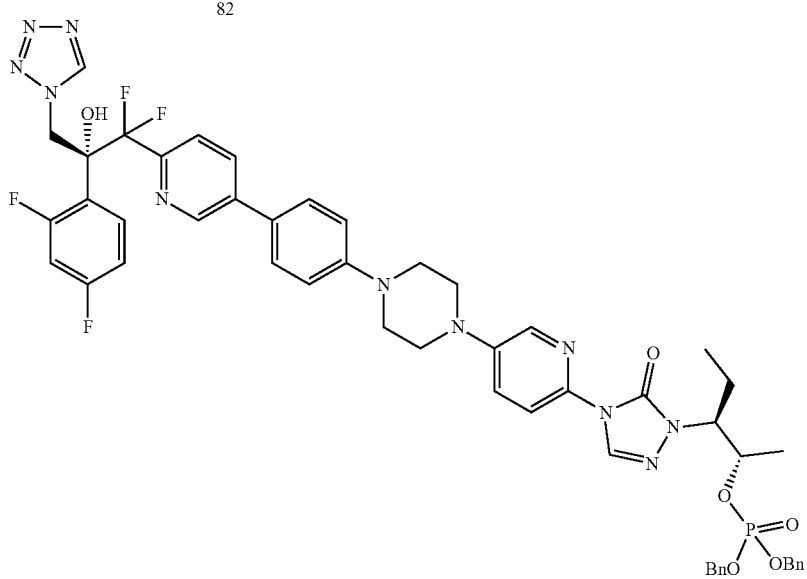

To a stirred solution of compound 82 (350 mg, 0.46 mmol) in CH$_2$Cl$_2$ (30 mL) under argon atmosphere was added 1H-tetrazole (161 mg, 2.30 mmol) at 0° C. The reaction mixture warmed to RT and stirred for 1 h. Then dibenzyl diisopropylphosphoramidite (0.6 mL, 1.84 mmol) was added to the reaction mixture at 0° C. The reaction mixture warmed to RT and stirred for 3 h. The progress of the reaction was monitored by TLC. The reaction mixture was quenched with TBHP solution (10 mL) at 0° C., stirred at RT for 1 h, diluted with saturated sodium bicarbonate solution (20 mL) and extracted with CH$_2$Cl$_2$ (2×20 mL). The combined organic layers were dried over anhydrous Na$_2$SO$_4$ and concentrated under reduced pressure. The crude material was purified by preparative HPLC to afford compound NP (330 ng, 0.32 mmol, 72%) as yellow solid. $^1$H NMR (400 MHz, DMSO-d$_6$): δ 9.15 (s, 1H), 8.91 (d, J=1.9 Hz, 1H), 8.52 (s, 1H), 8.21 (d, J=2.9 Hz, 1H), 8.17 (dd, J=8.3, 2.2 Hz, 1H), 7.94 (d J=8.9 Hz, 1H), 7.71 (d, J=8.8 Hz, 2H), 7.62 (dd, J=9.2, 3.0 Hz, 1H), 7.50 (s, 1H), 7.38-7.12 (m, 15H), 6.93-6.89 (m, 1H), 5.67 (d, J=14.7 Hz, 1H), 5.11 (d, J=14.7

Hz, 1H), 4.98-4.78 (m, 4H), 4.69-4.60 (m, 1H), 4.16-4.07 (m, 1H), 3.43-3.40 (m, 8H), 1.86-1.68 (m, 2H), 1.35 (d, J=6.3 Hz, 3H), 0.77 (t, J=7.3 Hz, 3H).

(2S,3S)-3-(4-(5-(4-(4-(6-(1,1-difluoro-2-(2-fluoro-phenyl)-2-hydroxy-3-(1H-tetrazol-1-yl) propyl) pyridin-3-yl) phenyl) piperazin-1-yl) pyridin-2-yl)-5-oxo-4,5-dihydro-1H-1,2,4-triazol-1-yl) pentan-2-yl) dihydrogen phosphate (113)

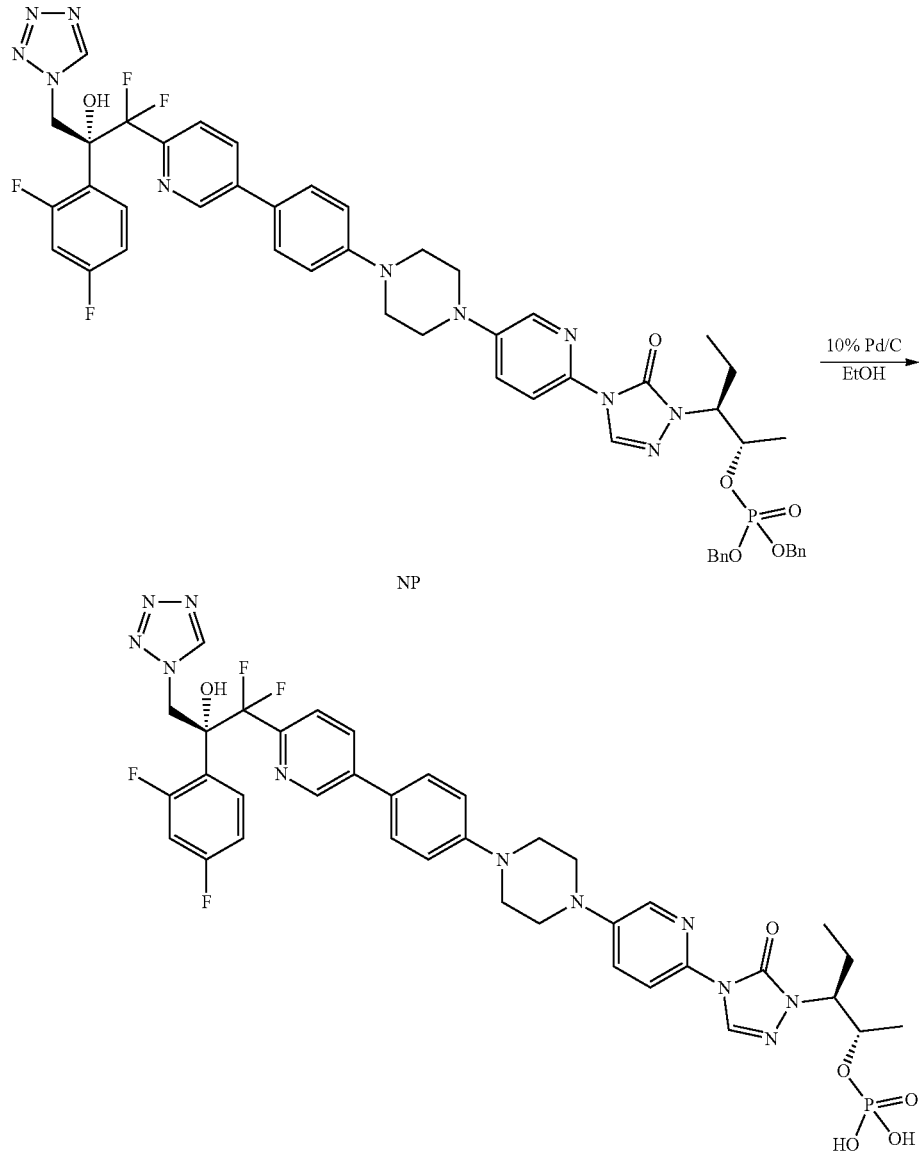

To a stirred solution of compound NP (330 mg, 0.32 mmol) in EtOH (30 mL) under argon atmosphere was added 10% Pd/C (170 mg) at RT and stirred for 5 h under hydrogen atmosphere (balloon pressure). The progress of the reaction was monitored by TLC. The reaction mixture was filtered through celite, the filtrate was concentrated under reduced pressure. The residue was washed with n-pentane to afford 113 (200 mg, 0.23 mmol, 73%) as an off-white solid. $^1$H NMR (400 MHz, DMSO-d$_6$): δ 10.88 (br s, 1H), 9.15 (s, 1H), 8.91 (s. 1H), 8.51 (s, 1H), 8.24 (d, J=3.0 Hz, 1H), 8.17 (dd, J=8.3, 2.3 Hz, 1H), 8.02 (d, J=9.0 Hz, 1H), 7.70 (d, J=8.9 Hz, 2H), 7.67 (dd, J=9.3, 3.0 Hz, 1H), 7.49 (d, J=8.2 Hz, 1H), 7.33-7.25 (m, 2H), 7.23-7.18 (m, 1H), 7.15 (d, J=8.8 Hz, 2H), 6.93-6.88 (m, 1H), 5.67 (d, J=14.7 Hz, 1H), 5.11 (d, J=14.7 Hz, 1H), 4.48-4.43 (m, 1H), 4.11-3.98 (n 1H), 3.53-3.21 (m, 8H), 1.89-1.67 (m, 2H), 1.26 (d, J=6.4 Hz, 3H), 0.76 (t, J=7.3 Hz, 3H); $^{31}$P NMR (400 MHz, DMSO-d$_6$): δ −1.81 (s); MS (ESI): m/z 840.9 [M+H]$^+$; HPLC: 95.26%; Optical rotation [α]$_D^{20}$: +14.64 (c=0.1% in MeOH).

Example 114

(+)-(2S,3S)-3-(4-(4-(4-(4-(6-(1,1-difluoro-2-(2-fluorophenyl)-2-hydroxy-3-(1H-tetrazol-1-yl) propyl) pyridin-3-yl) phenyl) piperazin-1-yl) phenyl)-5-oxo-4, S-dihydro-1H-1,2,4-triazol-1-yl) pentan-2-yl dihydrogen phosphate (114)

dibenzyl ((2S,3S)-3-(4-(4-(4-(4-(6-(1,1-difluoro-2-(2-fluorophenyl)-2-hydroxy-3-(1H-tetrazol-1-yl) propyl) pyridin-3-yl) phenyl) piperazin-1-yl) phenyl)-5-oxo-4,5-dihydro-1H-1,2,4-triazol-1-yl) pentan-2-yl) phosphate (NQ)

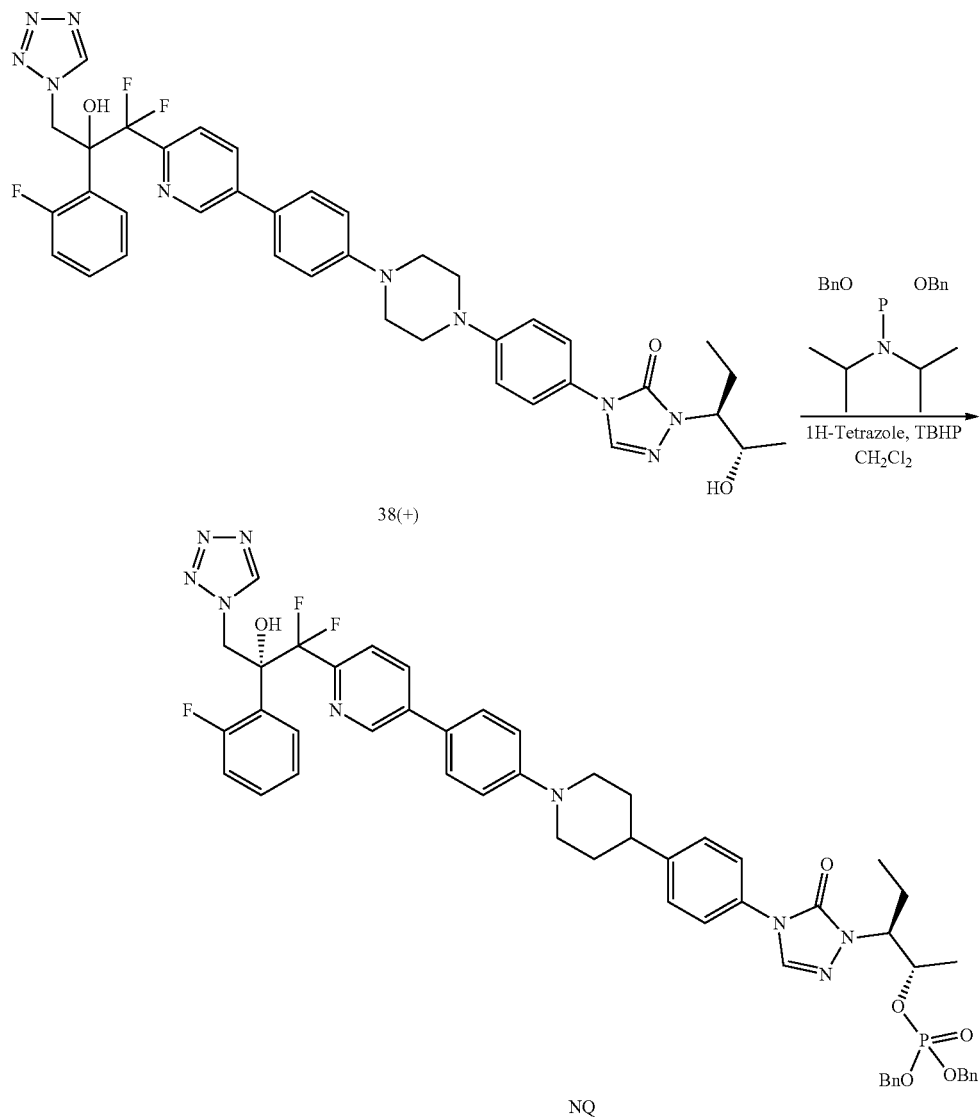

To a stirred solution of compound 38(+) (650 mg, 0.87 mmol) in CH$_2$Cl$_2$ (30 mL) under argon atmosphere was added 1H-tetrazole (472 mg, 6.75 mmol) at 0° C. The reaction mixture warmed to RT and stirred for 1 h. Then dibenzyl diisopropylphosphoramidite (1.2 mL, 3.48 mmol) was added to the reaction mixture at 0° C. The reaction mixture warmed to RT and stirred for 4 h. The progress of the reaction was monitored by TLC. The reaction mixture was quenched with TBHP solution (1.0 mL) at 0° C. stirred at RT for 1 h. diluted with saturated sodium bicarbonate solution (20 mL) and extracted with CH$_2$Cl$_2$ (2×20 mL). The combined organic layers were dried over anhydrous Na$_2$SO$_4$ and concentrated under reduced pressure to obtain crude compound. The crude compound (450 mg with 49%; HPLC purity) was purified by column chromatography followed by HPLC to afford NQ (215 mg, 0.21 mmol, 24%) as a pale green solid. $^1$H NMR (400 MHz, DMSO-d$_6$): δ 9.13 (s, 1H), 8.92 (s, 1H), 8.35 (s, 1H), 8.16 (dd, J=8.3, 2.2 Hz, 1H), 7.71 (d, J=8.9 Hz, 2H), 7.50-7.39 (m, 3H), 7.38-7.27 (m, 10H), 7.27-6.98 (m, 9H), 5.71 (d, J=14.5 Hz, 1H), 5.11 (d, J=14.5 Hz, 1H), 4.98-4.84 (m, 4H), 4.72-4.56 (m, 1H), 4.15-4.03 (m, 1H), 3.50-3.26 (m, 8H), 1.88-1.68 (m, 2H), 1.34 (d, J=6.3 Hz, 3H), 0.76 (t, J=7.2 Hz, 3H).

(+)-(2S,3S)-3-(4-(4-(4-(4-(6-(1,1-difluoro-2-(2-fluorophenyl)-2-hydroxy-3-(1H-tetrazol-1 yl) propyl) pyridin-3-yl) phenyl) piperazin-1-yl) phenyl)-5-oxo-4,5-dihydro-1H-1,2,4-triazol-1-yl) pentan-2-yl dihydrogen phosphate (114)

To a stirred solution of compound NQ (215 mg, 0.21 mmol) in EtOH (20 mL) under argon atmosphere was added 10% Pd/C (50 mg) at RT and stirred for 4 h under hydrogen atmosphere (balloon pressure). The progress of the reaction was monitored by TLC. The reaction mixture was filtered through celite, the filtrate was concentrated under reduced pressure. The residue was washed with n-pentane to afford 114 (150 mg, 0.18 mmol, 87%) as an off-white solid. $^1$H NMR (400 MHz, CD$_3$OD): δ 9.02 (s, 1H), 8.80 (d, J=2.0 Hz, 1H), 8.08-8.02 (m, 2H), 7.62 (d, J=8.9 Hz, 2H), 7.51-7.48 (m, 1H), 7.46 (d, J=9.0 Hz, 1H), 7.38-7.26 (m, 2H), 7.17-7.12 (m, 3H), 7.08-6.95 (m, 2H), 5.80 (d, J=14.6 Hz, 1H), 5.21 (d, J=14.6 Hz, 1H), 4.64-4.59 (m, 1H), 4.15-4.09 (m, 1H), 3.63-3.58 (m, 1H), 3.45-3.40 (m, 8H), 2.06-1.89 (m, 1H), 1.87-1.76 (m, 1H), 1.41 (d, J=6.4 Hz, 3H), 1.32 (d, J=6.5 Hz, 2H), 1.18 (t, J=7.0 Hz, 2H), 0.88 (t, J=7.3 Hz, 3H); $^{31}$P NMR (400 MHz, DMSO-d$_6$): δ −0.83 (s); MS (ESI): m/z 821.8 [M+H]$^+$; HPLC: 97.7%; Optical rotation [α]$_D^{19}$: +16.40 (c=0.1% in MeOH).

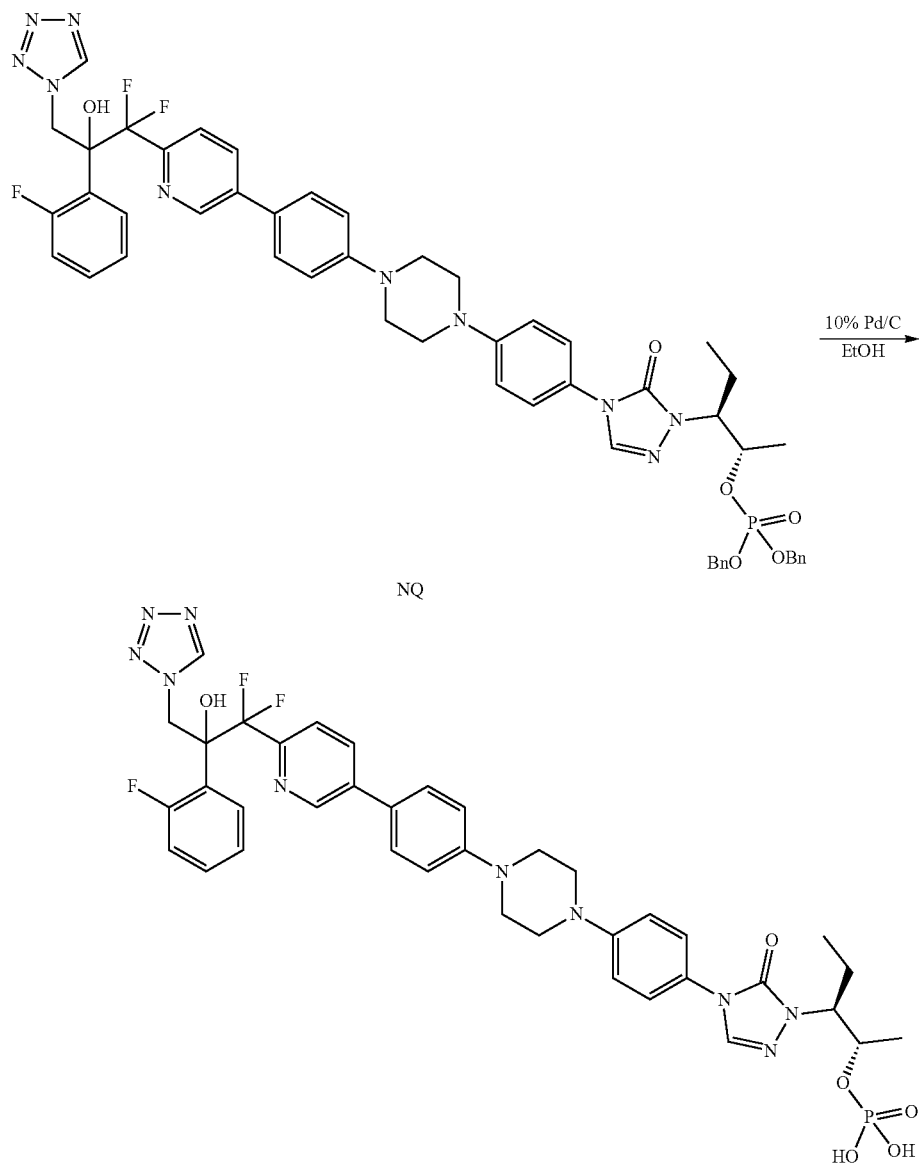

Example 115

4-(4-(4-(4-(6-(1,1-difluoro-2-(2-fluorophenyl)-2-hydroxy-3-(1H-tetrazol-5-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (115)

4-(f-bromopyridin-2-yl)-4,4-difluoro-3-(2-fluorophenyl)-3-hydroxybutanenitrile (NR)

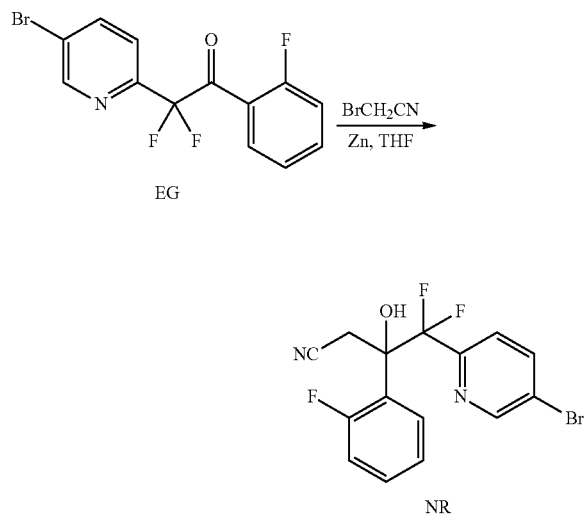

To a stirred solution of activated zinc (1.37 g, 21.21 mmol) in THF (35 mL) under argon atmosphere were added compound EG (3.5 g, 10.60 mmol) and 2-bromoacetonitrile (1.52 g, 12.72 mmol) at 70° C. The reaction mixture was stirred at reflux for 6 h. The progress of the reaction was monitored by TLC. The reaction mixture was quenched with water (100 mL) and extracted with EtOAc (2×100 mL). The combined organic layers were dried over anhydrous $Na_2SO_4$ and concentrated under reduced pressure to afford compound NR (600 mg, crude) as pale brown liquid and the obtained crude compound was used in the next step without further purification.

1-(5-bromopyridin-2-yl)-1,1-difluoro-2-(2-fluorophenyl-3-(1H-tetrazol-5-yl) propan-2-ol (NS)

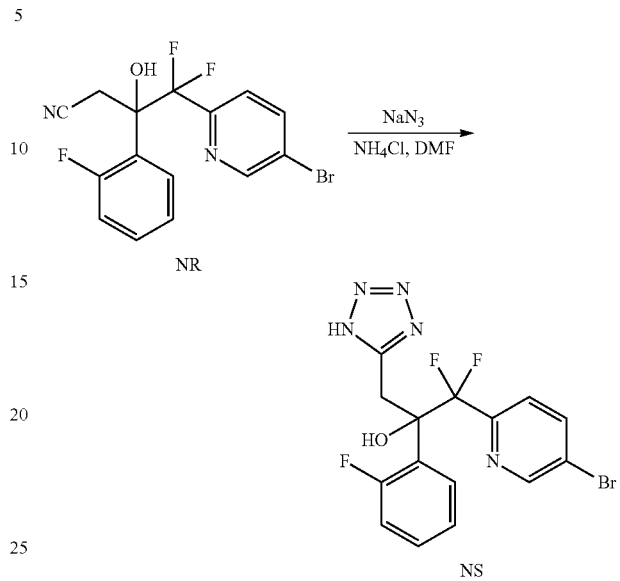

To a stirred solution of compound NR (670 mg, 1.80 mmol) in DMF (5 mL) under argon atmosphere were added sodium azide (352 mg, 5.41 mmol) and ammonium chloride (287 mg, 5.41 mmol) at RT. The reaction mixture was stirred at 130° C. for 2 h in microwave. The progress of the reaction was monitored by TLC. The reaction mixture was quenched with 6.0 N HCl solution (5 mL) and extracted with EtOAc (2×10 mL). The combined organic layers were washed with 2.0 N HCl solution (5×20 mL), dried over anhydrous $Na_2SO_4$ and concentrated under reduced pressure. The crude material was purified by silica gel column chromatography (eluent: 50% EtOAc/Hexane) to afford compound NS (200 mg, 0.48 mmol, 27%) as pale brown solid. $^1$H NMR (500 MHz, DMSO-$d_6$): δ 15.72 (brs, 1H), 8.73 (d, J=2.3 Hz, 1H), 8.19 (dd, J=8.4, 2.0 Hz, 1H), 7.43 (d, J=8.1 Hz, 1H), 7.35 (t, J=7.5 Hz, 1H), 7.31-7.21 (m, 1H), 7.09-6.96 (m, 2H), 6.88 (brs, 1H), 4.23 (d, J=15.1 Hz, 1H), 3.55 (d, J=15.1 Hz, 1H).

2-((2S,3S)-2-(benzyloxy) pentan-3-yl)-4-(4-(4-(6-(1,1-difluoro-2-(2-fluorophenyl)-2-hydroxy-3-(1H-tetrazol-5-yl) propyl) pyridin-3-yl) phenyl) piperazin-1-yl) phenyl)-2,4-dihydro-3H-1,2,4-triazol-3-one (NI)

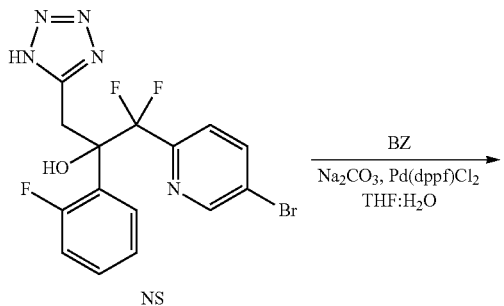

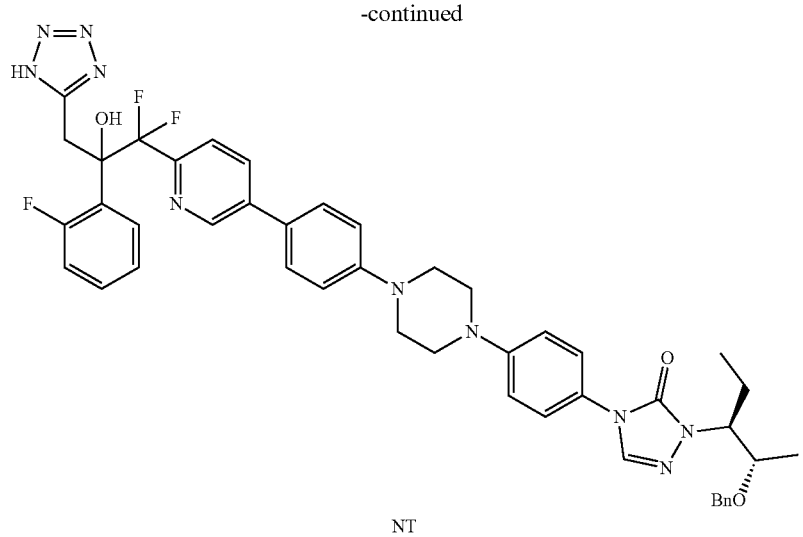

NT

To a stirred solution of compound NS (290 mg, 0.70 mmol) in THF:H2O (4:1, 10 mL) under argon atmosphere were added compound BZ (480 mg, 0.77 mmol) and sodium carbonate (223 mg, 2.10 mmol) at RT. The reaction mixture was purged with argon for 20 min, then Pd(dppf)Cl$_2$ (51.2 mg, 0.07 mmol) was added and the reaction mixture was purged under argon for 10 min at RT. The reaction mixture was stirred at reflux for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure to obtain compound NT (200 mg, crude) as an off-white solid. The obtained crude compound was used in the next step without further purification. $^1$H NMR (400 MHz, DMSO-d$_6$): δ 15.75 (br s, 1H), 8.91 (d, J=1.9 Hz, 1H), 8.32 (s, 1H), 8.15 (dd, J=8.3, 2.1 Hz, 1H), 7.70 (d, J=8.8 Hz, 2H), 7.54-7.40 (m, 4H), 7.31-7.12 (m, 8H), 7.10-6.90 (m, 3H), 4.54 (d, J=11.8 Hz, 1H), 4.34-4.21 (m, 2H), 4.02-3.94 (m, 1H), 3.75-3.72 (m, 1H), 3.61-3.53 (m, 1H), 3.42=3.36 (m, 8H), 2.63-2.54 (m, 1H), 2.26-2.16 (m, 1H), 1.82-1.67 (m, 2H), 1.23 (br d, J=6.3 Hz, 3H), 0.84-0.73 (m, 3H).

4-(4-(4-(4-(6-(1,1-difluoro-2-(2-fluorophenyl-2-hydroxy-3-(1H-tetrazol-5-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (115)

-continued

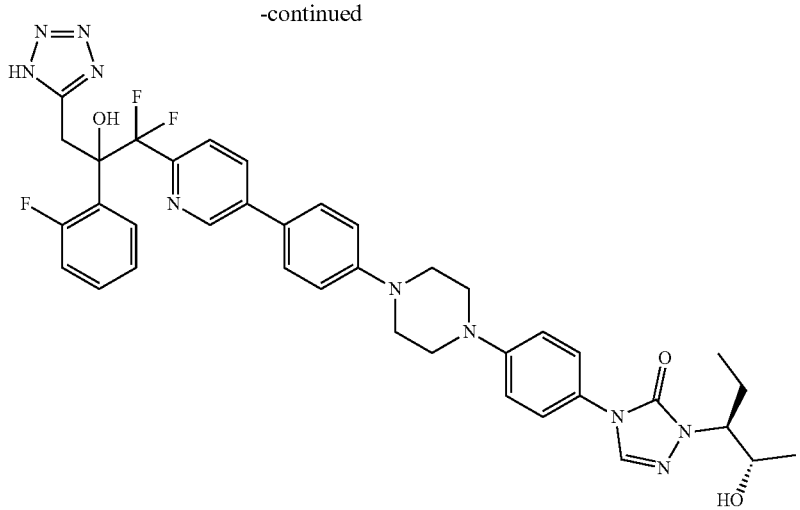

115

To a stirred solution of compound NT (290 mg, 0.35 mmol) in MeOH (5 mL) under argon atmosphere were added 10% Pd/C (150 mg) and conc. HCl (0.1 mL) at RT. The reaction mixture was stirred at RT for 3 h under hydrogen atmosphere. The progress of the reaction was monitored by TLC, the reaction mixture was filtered, the filtrate was diluted with water (10 mL), neutralized with sodium bicarbonate solution (10 mL). The combined organic layers were dried over anhydrous $Na_2SO_4$ and concentrated under reduced pressure. The crude material was purified by preparative HPLC to afford 115 (35 mg, 0.05 mmol, 14%) as a white solid. $^1$H NMR (400 MHz, DMSO-$d_6$): δ 15.75 (brs, 1H), 8.91 (d, J=1.9 Hz, 1H), 8.33 (s, 1H), 8.15 (dd, J=8.3, 2.2 Hz, 1H), 7.70 (d, J=8.9 Hz, 2H), 7.59-7.37 (m, 4H), 7.36-7.26 (m, 1H), 7.17-7.11 (m, 4H), 7.08-7.02 (m, 2H), 6.93 (s, 1H), 4.66 (d, J=4.6 Hz, 1H), 4.28 (d, J=15.4 Hz, 1H), 3.85-3.76 (m, 2H), 3.57 (d, J=15.4 Hz, 1H), 3.43-3.32 (m, 8H), 1.79-1.63 (m, 2H), 1.12 (d, J=5.9 Hz, 3H), 0.74 (t, J=7.3 Hz, 3H); MS (ESI): m/z 739.8 [M−H]$^-$; HPLC: 97.02%; Optical rotation $[α]_D^{20}$: −18.8 (c=0.1% in MeOH).

Example 116

4-(4-(4-(4-(6-(1,1-difluoro-2-(2-fluorophenyl)-2-hydroxy-3-(2H-1,2,3-triazol-2-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (116)

1-(5-bromopyridin-2-yl)-1,1-difluoro-2-(2-fluoro-phenyl)-3-(2H-1,2,3-triazol-2-yl) propan-2-ol (NU)

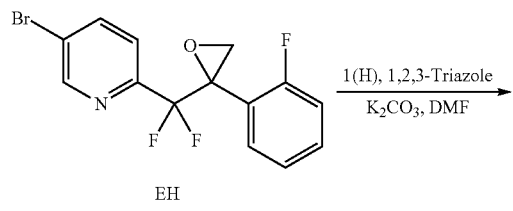

-continued

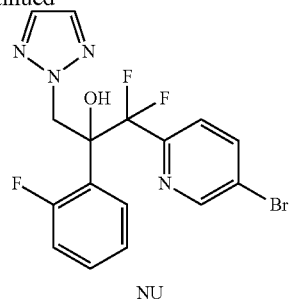

NU

To a stirred solution of EH (300 mg, 0.87 mmol) in DMF (10 mL) under argon atmosphere were added potassium carbonate (240 mg, 1.74 mmol) and 1H-1,2,3-Triazole (90 mg, 1.30 mmol) at RT. The reaction mixture was stirred at 100° C. for 16 h. The reaction mixture was diluted with water (20 mL) and extracted with EtOAc (2×20 mL). The combined organic extracts were washed with water (20 mL), brine (20 mL), dried over anhydrous $Na_2SO_4$ and concentrated under reduced pressure to obtain the crude. The crude material was purified by silica gel column chromatography (eluent: 10-15% EtOAc/Hexane) to afford compound NU (100 mg, 0.24 mmol, 27%) and 1H-tetrazole (100 mg, 0.24 mmol, 27%) as a white solid. $^1$H NMR (500 MHz, CDCl$_3$): δ 8.61 (d, J=1.7 Hz, 1H), 7.85 (dd, J=8.4, 2.0 Hz, 1H), 7.44 (s, 2H), 7.42-7.34 (m, 2H), 7.25-7.20 (m, 1H), 7.01-6.92 (m, 2H), 5.86 (s, 1H), 5.76 (d, J=14.5 Hz, 1H), 5.16 (d, J=14.5 Hz, 1H)

2-((2S,3S)-2-(benzyloxy) pentan-3-yl)-4-(4-(4-(4-(6-(1,1-difluoro-2-(2-fluorophenyl)-2-hydroxy-3-(2H-1,2,3-triazol-2-yl) propyl) pyridin-3-yl) phenyl) piperazin-1-yl) phenyl)-2,4-dihydro-3H-1,2,4-triazol-3-one (NV)

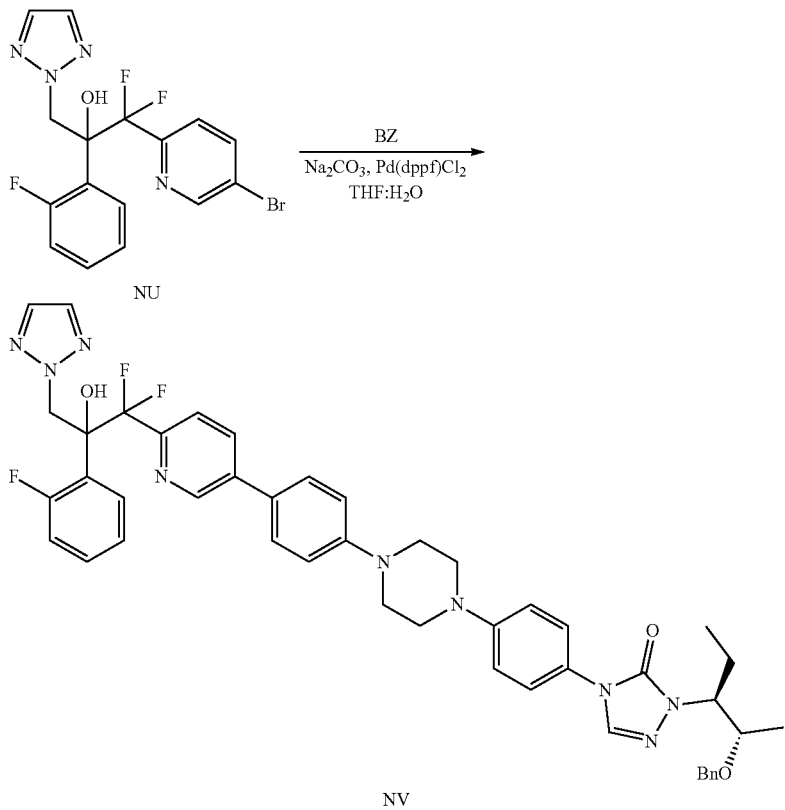

To a stirred solution of compound NU (100 mg, 0.24 mmol) in THF:H2O (4:1, 10 mL) under argon atmosphere were added compound BZ (166 mg, 0.26 mmol), sodium carbonate (76 mg, 0.72 mmol) and purged under argon for 20 min at RT. Then Pd(dppf)Cl$_2$ (17 mg, 0.02 mmol) was added and the reaction mixture was purged under argon for 10 min at RT. The reaction mixture was stirred at reflux for 5 h. The progress of the reaction was monitored by TLC. The reaction mixture was diluted with water (20 mL) and extracted with EtOAc (2×20 mL). The combined organic extracts were washed with brine (20 mL), dried over anhydrous Na$_2$SO$_4$ and concentrated under reduced pressure. The crude material was purified by silica gel column chromatography (eluent: 0-2% MeOH/CH$_2$Cl$_2$) to afford compound NV (120 mg, 0.14 mmol, 60%) as a white solid. $^1$H NMR (400 MHz, CDCl$_3$): δ 8.76 (d, J=2.0 Hz, 1H), 7.88 (dd, J=8.3, 2.3 Hz, 1H), 7.58-7.50 (m, 5H), 7.44-7.39 (m, 4H), 7.26-7.20 (m, 5H), 7.09-7.02 (m, 4H), 7.01-6.94 (m, 2H), 6.44 (s, 1H), 5.75 (d, J=14.2 Hz, 1H), 5.20 (d, J=14.2 Hz, 1H), 4.63 (d, J=11.9 Hz, 11), 4.40 (d, J=11.9 Hz, 1H), 4.21-4.16 (m, 1H), 3.84-3.78 (m, 1H), 3.47-3.37 (m, 8H), 2.01-1.87 (m, 1H), 1.84-1.69 (m, 1H), 1.28 (d, J=6.3 Hz, 3H), 0.89 (t, J=7.3 Hz, 3H).

4-(4-(4-(4-(6-(1,1-difluoro-2-(2-fluorophenyl)-2-hydroxy-3-(2H-1,2,3-triazol-2-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (116)

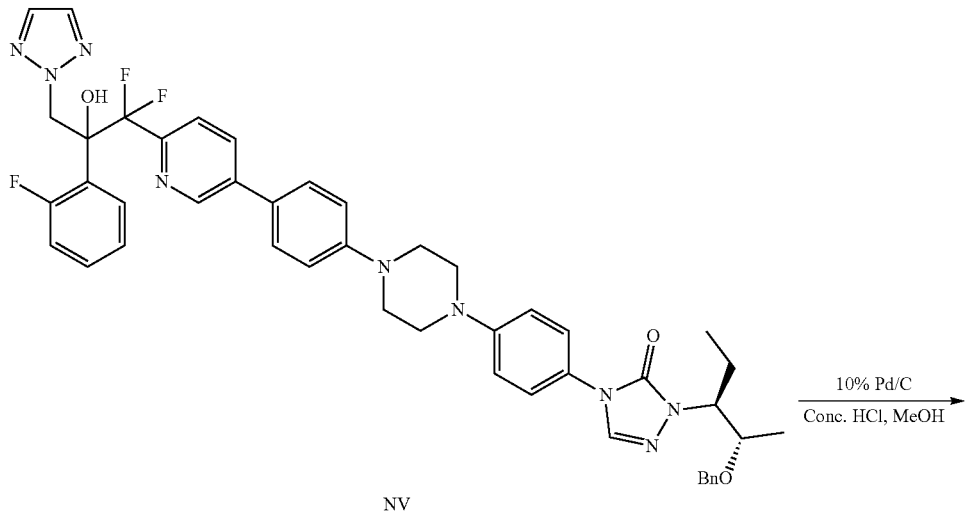

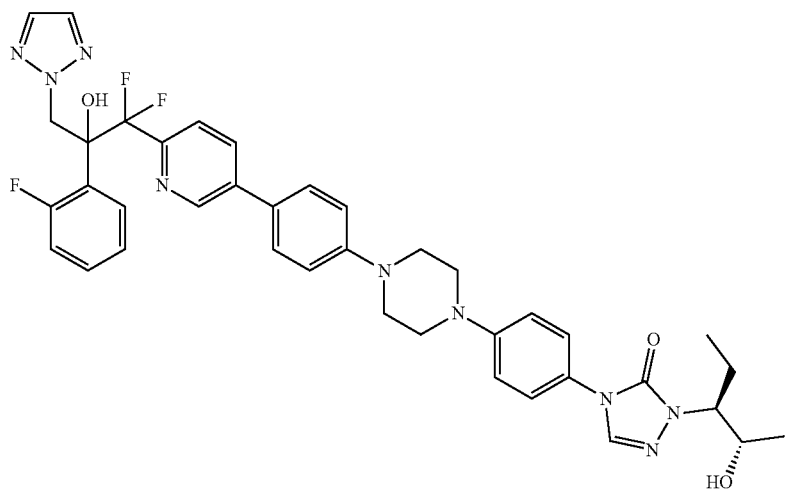

To a stirred solution of compound NV (120 mg, 0.14 mmol) in MeOH (10 mL) under argon atmosphere were added 10% Pd/C (60 mg) and concentrated hydrochloric acid (0.1 mL) at RT. The reaction mixture was stirred at RT for 4 h under hydrogen atmosphere. The progress of the reaction was monitored by TLC, the reaction mixture was filtered and the filtrate was concentrated under reduced pressure. The residue was diluted with saturated sodium carbonate solution (20 mL) and extracted with $CH_2Cl_2$ (2×20 mL). The combined organic layers were dried over anhydrous $Na_2SO_4$ and concentrated under reduced pressure. The crude material was purified by silica gel column chromatography (eluent: 0-2% $MeOH/CH_2Cl_2$) to afford 116 (65 mg, 0.08 mmol, 61%) as an off-white solid. $^1$H NMR (400 MHz, DMSO-$d_6$): δ 8.86 (d, J=2.1 Hz, 1H), 8.33 (s, 1H), 8.13 (dd, J=8.3, 2.2 Hz, 1H), 7.69 (d, J=8.9 Hz, 2H), 7.57 (s, 2H), 7.53 (d, J=8.9 Hz, 2H), 7.49 (d, J=8.2 Hz, 1H), 7.33-7.26 (m, 2H), 7.17-7.04 (m, 5H), 7.00-6.95 (m, 1H), 6.79 (s, 1H), 5.67 (d, J=14.3 Hz, 1H), 5.08 (d, J=14.3 Hz, 1H), 4.66 (d, J=5.0 Hz, 1H), 3.89-3.73 (m, 2H), 3.46-3.33 (m, 8H), 1.76-1.54 (m, 2H), 1.12 (d, J=5.9 Hz, 3H), 0.74 (t, J=7.3 Hz, 3H); MS (ESI): m/z 740.8 [M+H]$^+$; HPLC: 94.46%; Optical rotation $[α]_D^{19}$: +3.76 (c=0.1% V in $CH_2Cl_2$).

Example 117

4-(4-(4-(4-(6-(1,1-difluoro-2-(2-fluorophenyl)-2-hydroxy-3-(1H-pyrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (117)

1-(5-bromopyridin-2-yl)-1,1-difluoro-2-(2-fluorophenyl)-3-(1H-pyrazol-1-yl) propan-2-ol

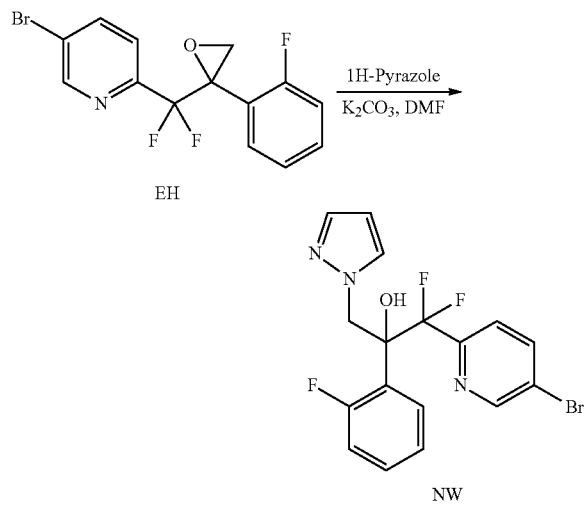

To a stirred solution of EH (200 mg, 0.58 mmol) in DMF (10 mL) under argon atmosphere were added potassium carbonate (120 mg, 0.87 mmol) and 1H-pyrazole (79 mg, 1.16 mmol) at RT. The reaction mixture was stirred at 100° C. for 16 h. The reaction mixture was diluted with water (20 mL) and extracted with EtOAc (2×20 mL). The combined organic extracts were washed with water (20 mL), dried over anhydrous Na₂SO₄ and concentrated under reduced pressure to obtain the crude. The crude material was purified by silica gel column chromatography (eluent: 20% EtOAc/Hexane) to afford compound NW (170 mg, 0.41 mmol, 71%) as colorless syrup. ¹H NMR (400 MHz, CDCl₃): δ 8.61 (d, J=2.1 Hz, 1H), 7.86 (dd, J=8.4, 2.3 Hz, 1H), 7.45-7.38 (m, 3H), 7.31 (d, J=1.9 Hz, 1H), 7.25-7.18 (m, 1H), 6.97 (d, J=7.7 Hz, 1H), 6.95-6.93 (m, 1H), 6.41 (s, 1H), 6.05 (t, J=2.1 Hz, 1H), 5.35 (d, J=14.3 Hz, 1H), 4.79 (d, J=14.3 Hz, 1H).

2-((2S,3S)-2-(benzyloxy) pentan-3-yl)-4-(4-(4-(4-(6-(1,1-difluoro-2-(2-fluorophenyl)-2-hydroxy-3-(1H-pyrazol-1-yl) propyl) pyridin-3-yl) phenyl)) piperazin-1-yl) phenyl)-2,4-dihydro-3H-1,2,4-triazol-3-one (NX)

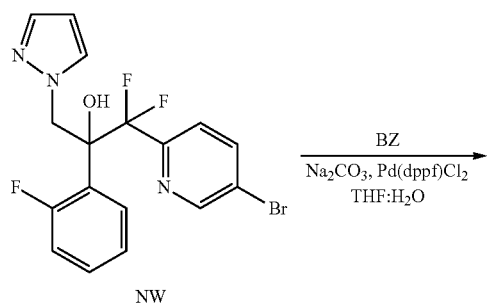

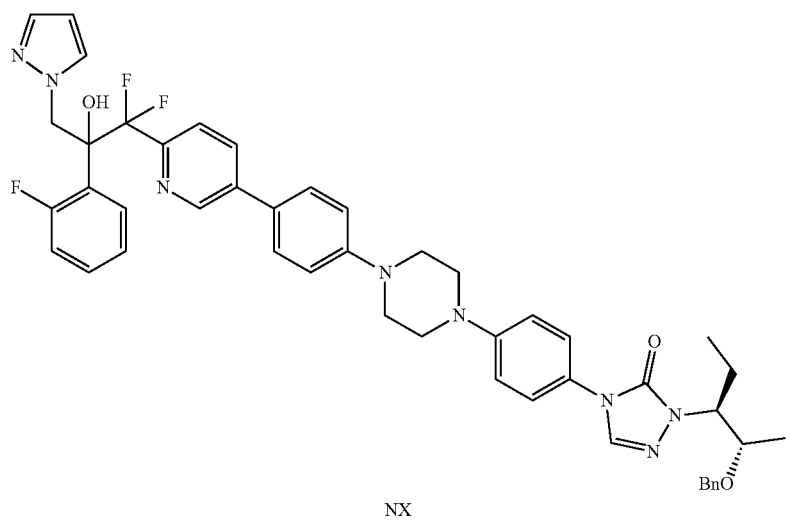

To a stirred solution of compound NW (170 mg, 0.41 mmol) in THF:H2O (4:1, 16 mL) under argon atmosphere were added compound BZ (283 mg, 0.45 mmol), sodium carbonate (131 mg, 1.23 mmol) and purged under argon for 20 min at RT. Then Pd(dppf)Cl$_2$ (30 mg, 0.04 mmol) was added and the reaction mixture was purged under argon for 10 min at RT. The reaction mixture was stirred at reflux for 5 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 50-60% EtOAc/Hexane) to afford compound NX (200 mg, 0.24 mmol, 58%) as an off-white solid. $^1$H NMR (400 MHz, CDCl$_3$): δ 8.77 (d, J=2.0 Hz, 1H), 7.88 (dd, J=8.2, 2.2 Hz, 1H), 7.58-7.51 (m, 5H), 7.45-7.38 (m, 3H), 7.30-7.19 (m, 6H), 7.10-7.02 (m, 4H), 7.01-6.88 (m, 2H), 6.59 (s, 1H), 6.04 (t, J=2.1 Hz, 1H), 5.39 (d, J=14.3 Hz, 1H), 4.84 (d, J=14.3 Hz, 1H), 4.63 (d, J=12.0 Hz, 1H), 4.40 (d, J=12.0 Hz, 1H), 4.21-4.16 (m, 1H), 3.84-3.77 (m, 1H), 3.49-3.32 (m, 8H), 2.00-1.72 (m, 2H), 1.28 (d, J=6.3 Hz, 3H), 0.89 (t, J=7.3 Hz, 3H).

4-(4-(4-(4-(4-(6-(1,1-difluoro-2-(2-fluorophenyl)-2-hydroxy-3-(1H-pyrazol-1-yl) propyl) pyridin-3-yl) phenyl) piperazin-1-yl) phenyl-2-((2S,3S)-2-hydroxypentan-3-yl)-2,4-dihydro-3H-1,2,4-triazol-3-one (117)

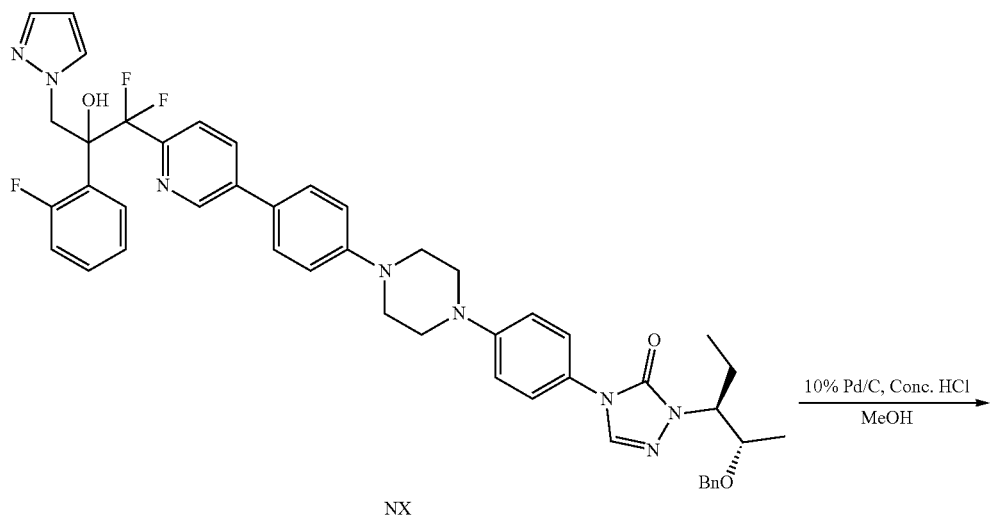

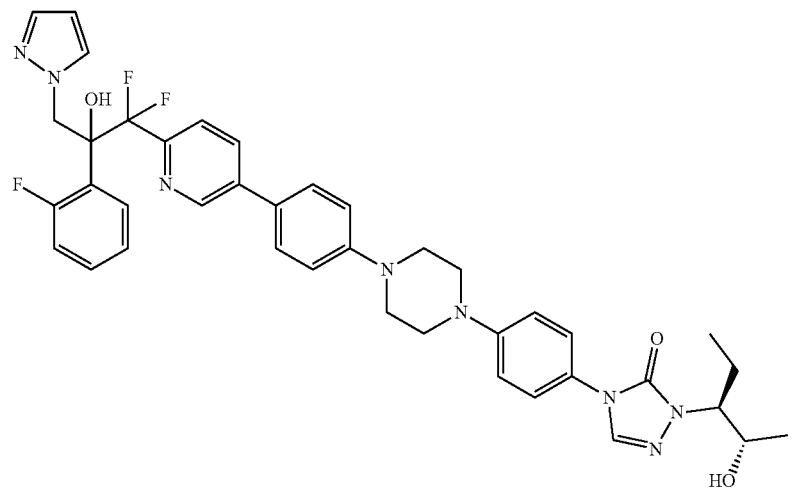

117

To a stirred solution of compound NX (200 mg, 0.24 mmol) in MeOH (10 mL) under argon atmosphere were added 10% Pd/C (100 mg) and concentrated hydrochloric acid (0.1 mL) at RT. The reaction mixture was stirred at RT for 4 h under hydrogen atmosphere. The progress of the reaction was monitored by TLC, the reaction mixture was filtered and the filtrate was concentrated under reduced pressure. The residue was diluted with saturated sodium carbonate solution (20 mL) and extracted with $CH_2Cl_2$ (2×20 mL). The combined organic layers were dried over anhydrous $Na_2SO_4$ and concentrated under reduced pressure. The crude material was purified by silica gel column chromatography (eluent: 0-2% MeOH/$CH_2Cl_2$) to afford 117 (90 mg, 0.12 mmol, 50%) as an off-white solid. $^1$H NMR (400 MHz, DMSO-$d_6$): δ 8.87 (d, J=2.0 Hz, 1H), 8.33 (s, 1H), 8.12 (dd, J=8.3, 2.1 Hz, 1H), 7.69 (d, J=8.8 Hz, 2H), 7.62 (d, J=2.0 Hz, 1H), 7.53 (d, J=9.0 Hz, 2H), 7.45 (d, J=8.3 Hz, 1H), 7.36 (t, J=7.1 Hz, 1H), 7.28-7.26 (m, 1H), 7.21 (d, J=1.5 Hz, 1H), 7.15-7.12 (m, 4H), 7.07-6.94 (m, 2H), 6.80 (s. 1H), 6.05 (t, J=2.0 Hz, 1H), 5.40 (d, J=14.4 Hz, 1H), 4.71 (d, J=14.4 Hz, 1H), 4.66 (d, J=4.9 Hz, 1H), 3.87-3.76 (m, 2H), 3.44-3.35 (m, 8H), 2.51-2.49 (m, 2H), 1.12 (d, J=5.9 Hz, 3H), 0.74 (t, J=7.3 Hz, 3H); MS (ESI): m/z 739.8 [M+H]$^+$; HPLC: 99.83%. Optical rotation $[α]_D^{19}$: +4.08 (c=0.1% in $CH_2Cl_2$).

Example 118

1-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-3,3-dimethylbutan-1-ol (118)

1-(5-(4-(4-bromophenyl) piperazin-1-yl) pyridin-2-yl)-3,3-dimethylbutan-1-ol (NY)

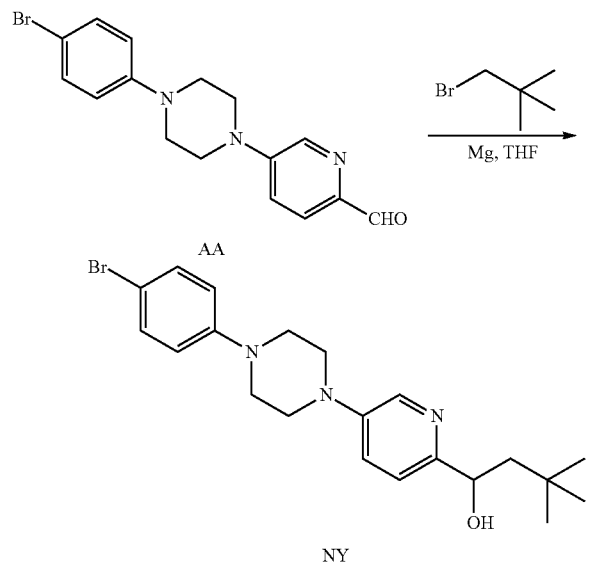

To a stirred solution of magnesium (20 mg, 0.85 mmol) in THF (10 mL) under argon atmosphere was added 1-bromo-2,2-dimethylpropane (0.13 mL, 0.85 mmol) at RT. The reaction mixture was stirred at 50° C. for 30 min. Then compound AA (150 mg, 0.42 mmol) in THF (5 mL) was added to the reaction mixture at 0° C. The reaction mixture was warmed to RT and stirred for 2 h. The progress of the reaction was monitored by TLC. The reaction mixture was quenched with saturated ammonium chloride solution (20 mL) and extracted with EtOAc (2×20 mL). The combined organic extracts were washed with water (20 mL), brine (10 mL), dried over anhydrous $Na_2SO_4$ and concentrated under reduced pressure. The crude material was purified by silica gel column chromatography (eluent: 20% EtOAc/Hexane) to afford compound NY (125 mg, 0.30 mmol, 70%) as yellow solid. $^1$H NMR (400 MHz, CDCl$_3$): δ 8.25 (d, J=2.6 Hz, 1H), 7.38 (d, J=9.2 Hz, 2H), 7.29-7.23 (m, 1H), 7.15 (d, J=8.7 Hz, 1H), 6.84 (d, J=9.0 Hz, 2H), 4.83-4.78 (m, 1H), 3.63 (d, J=5.8 Hz, 1H), 3.42-3.12 (m, 8H), 1.63-1.60 (m, 2H), 1.04 (s, 9H); LC-MS: 426.9 [M+2H]$^+$ at 2.69 RT (90.0% purity).

3,3-dimethyl-1-(5-(4-(4-(4,4,5,5-tetramethyl-1,3,2-dioxaborolan-2-yl) phenyl) piperazin-1-yl) pyridin-2-yl) butan-1-ol (NZ)

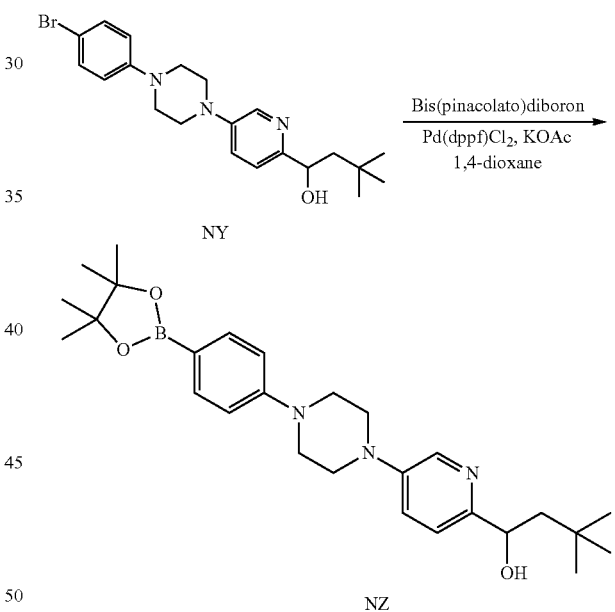

To a stirred solution of compound NY (160 mg, 0.38 mmol) in 1,4-dioxane (15 mL) under argon atmosphere were added bis(pinacolato)diboron (142 mg, 0.57 mmol) and potassium acetate (113 mg, 1.15 mmol) at RT. The reaction mixture was purged with argon for 20 min, then Pd(dppf)Cl$_2$ (28 mg, 0.04 mmol) was added and the reaction mixture was purged under argon for 5 min at RT. The reaction mixture was stirred at 110° C. for 16 h. The reaction mixture was quenched with water (20 mL) and extracted with EtOAc (2×20 mL). The combined organic layers were washed with water (20 mL), brine (20 mL), dried over anhydrous $Na_2SO_4$ and concentrated under reduced pressure to obtain compound NZ (140 mg, crude) as an off-white solid. LC-MS: 466.2 [M+H]$^+$ at 2.36 RT (69.9% purity).

1-(5-(4-(4-(6-((R)-2-(2,4-difluorophenyl)-1,1-difluoro-2-hydroxy-3-(1H-tetrazol-1-yl) propyl pyridin-3-yl) phenyl) piperazin-1-yl) pyridin-2-yl)-3,3-dimethylbutan-1-ol (118)

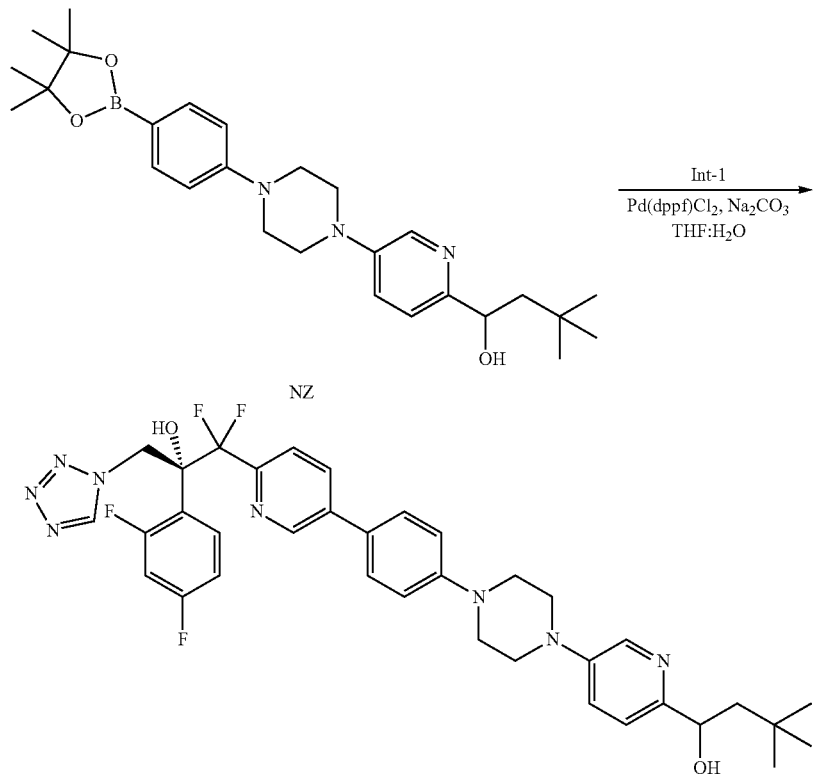

To a stirred solution of Int-1 (140 mg, 0.30 mmol) in THF:H2O (4:1, 10 mL) under argon atmosphere were added compound NZ (130 mg, 0.30 mmol), sodium carbonate (88 mg, 0.90 mmol) and purged under argon for 15 min at RT. Then Pd(dppf)Cl$_2$ (22 mg, 0.03 mmol) was added and the reaction mixture was purged under argon for 10 min at RT. The reaction mixture was stirred at 70° C. for 4 h. The progress of the reaction was monitored by TLC. The reaction mixture was diluted with water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 0-2% MeOH/CH$_2$Cl$_2$) followed by preparative HPLC to afford 118 (50 mg, 0.07 mmol, 24%) as an off-white solid. $^1$H NMR (400 MHz, CDCl$_3$): δ 8.76 (s, 1H), 8.73 (d, J=1.9 Hz, 1H), 8.27 (d, J=2.6 Hz, 1H), 7.95 (dd, J=8.2, 2.2 Hz, 1H), 7.85 (s, 1H), 7.61 (d, J=8.3 Hz, 1H), 7.52 (d, J=8.8 Hz, 2H), 7.43-7.37 (m, 1H), 7.30-7.27 (m, 1H), 7.17 (d, J=8.5 Hz, 1H), 7.07 (d, J=8.9 Hz, 2H), 6.80-6.75 (m, 1H), 6.70-6.64 (m, 1H), 5.61 (d, J=14.3 Hz, 1H), 5.11 (d, J=14.3 Hz, 1H), 4.88-4.72 (m, 1H), 3.62 (d, J=2.3 Hz, 1H), 3.54-3.28 (m, 8H), 1.65-1.59 (m, 2H), 1.05 (s, 9H); MS (ESI): m/z 691.8 [M+H]$^+$; HPLC: 96.87%; Optical rotation $[\alpha]_D^{20}$: +30.28 (c=0.1% in MeOH).

Examples 119(−) and 119(+)

(+) and (−)-1-(5-(4-(4-(6-((R)-1,1-difluoro-2-(3-fluorophenyl)-2-hydroxy-3-(1H-tetrazol-1-yl) propyl) pyridin-3-yl) phenyl) piperazin-1-yl) pyridin-2-yl)-3,3,3-trifluoropropan-1-ol (119(−) and 119(+))

Chiral Preparative HPLC Details for GY-Fr-I and GY-Fr-II:

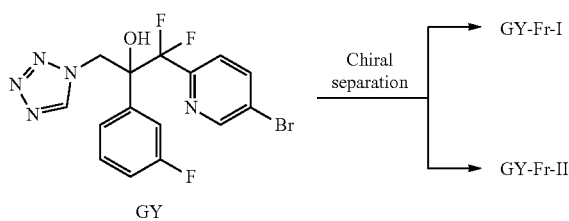 [SMILES: OC(Cn1cnnn1)(c1cccc(F)c1)C(F)(F)c1ccc(Br)cn1]

GY (1.6 g, 3.87 mmol) was separated by normal-phase preparative high performance liquid chromatography (CHIRALPAK-IC®, 250×4.6 mm, 5µ; mobile phase (A) 0.1% DEA in n-Hexane:(B) CH$_2$Cl$_2$:MeOH (80:20) (70:30) as a mobile phase; Flow rate: 20 mL/min) to obtain GY-Fr-I (75 mg) and GY-Fr-II (125 mg).

GY-Fr-I:

$^1$H NMR (400 MHz, CDCl$_3$): δ 8.75 (s, 1H), 8.58 (s, 1H), 7.90 (d, J=8.7 Hz, 1H), 7.41 (dd, J=8.7, 2.9 Hz, 1H), 7.20-7.12 (m, 2H), 7.10-7.08 (m, 1H), 6.90-6.85 (m, 1H), 6.80 (s, 1H), 5.15 (s, 2H); LC-MS: 412 [M−H]$^-$ at 2.83 RT (99.84% purity); HPLC: 95.37%; Chiral HPLC Purity: 99.82%, R$_t$=10.71 min (CHIRALPAK-IC®, 250×4.6 mm, 5µ; mobile phase (A) 0.1% DEA in n-Hexane:(B) CH$_2$Cl$_2$: MeOH (80:20) (70:30); flow Rate: 1.0 mL/min); Optical rotation $[α]_D^{19}$: −16.88 (C=0.1% in MeOH).

GY-Fr-IH:

$^1$H NMR (400 MHz, CDCl$_3$): δ 8.75 (s, 1H), 8.58 (s, 1H), 7.90 (d, J=8.7 Hz, 1H), 7.41 (dd, J=8.7, 2.9 Hz, 1H), 7.20-7.12 (m, 2H), 7.10-7.08 (m, 1H), 6.90-6.85 (m, 1H), 6.80 (s, 1H), 5.15 (s, 2H); LC-MS: 412 [M−H]$^-$ at 2.83 RT (99.85% purity); HPLC: 94.33%; Chiral HPLC Purity: 99.94%, R$_t$=14.98 min (CHIRALPAK-IC®, 250×4.6 mm, 5µ; mobile phase (A) 0.1% DEA in n-Hexane:(B) CH$_2$Cl$_2$: MeOH (80:20) (70:30); flow Rate: 1.0 mL/min); Optical rotation $[α]_D^{19}$: +16.80 (C=0.1% in MeOH).

(−)-1-(5-(4-(4-(6-((R)-1,1-difluoro-2-(3-fluorophenyl)-2-hydroxy-3-(1H-tetrazol-1-yl) propyl) pyridin-3-yl) phenyl) piperazin-1-yl) pyridin-2-yl)-3,3,3-trifluoropropan-1-ol (119(−))

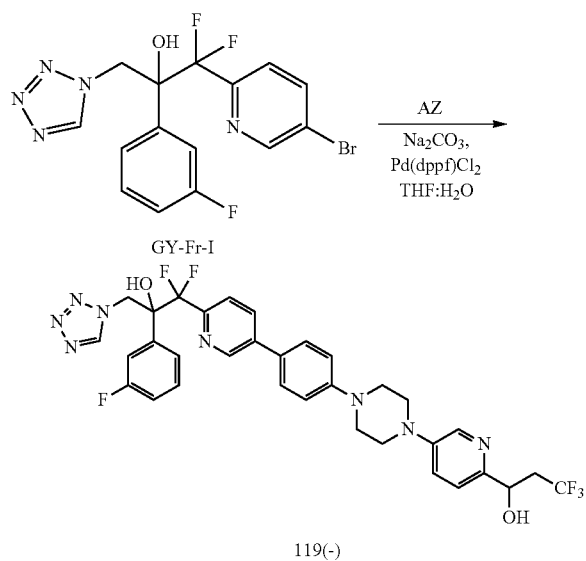

To a stirred solution of compound GY-Fr-I (70 mg, 0.16 mmol) in THF:H2O (4:1, 10 mL) under argon atmosphere were added compound AZ (80 mg, 0.16 mmol) and sodium carbonate (49 mg, 0.50 mmol) at RT. The reaction mixture was purged with argon for 20 min, then Pd(dppf)Cl$_2$ (12 mg, 0.01 mmol) was added and the reaction mixture was purged under argon for 10 min at RT. The reaction mixture was stirred at 80° C. for 8 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 2-5% MeOH/CH$_2$Cl$_2$) to afford 119(−) (35 mg, 0.05 mmol, 30%) as a pale yellow solid. $^1$H NMR (400 MHz, DMSO-d$_6$): δ 9.02 (s, 1H), 8.92 (d, J=2.0 Hz, 1H), 8.30 (d, J=2.4 Hz, 1H), 8.14 (dd, J=8.3, 2.2 Hz, 1H), 7.70 (d, J=8.8 Hz, 2H), 7.49-7.40 (m, 3H), 7.33-7.08 (m, 7H), 5.69 (d, J=5.9 Hz, 1H), 5.62 (d, J=14.6 Hz, 1H), 5.18 (d, J=14.6 Hz, 1H), 4.87-4.82 (m, 1H), 3.45-3.34 (m, 8H), 2.83-2.73 (m, 1H), 2.61-2.53 (m, 1H); MS (ESI): m/z 685.8 [M+H]$^+$; HPLC: 94.69%; Optical rotation $[α]_D^{20}$: −95.8 (c=0.1% in CH$_2$Cl$_2$).

(+)-1-(4-(4-(4-(6-((R)-1,1-difluoro-2-(3-fluorophenyl)-2-hydroxy-3-(1H-tetrazol-1-yl) propyl) pyridin-3-yl) phenyl) piperazin-1-yl) pyridin-2-yl)-3,3,3-trifluoropropan-1-ol (119(+))

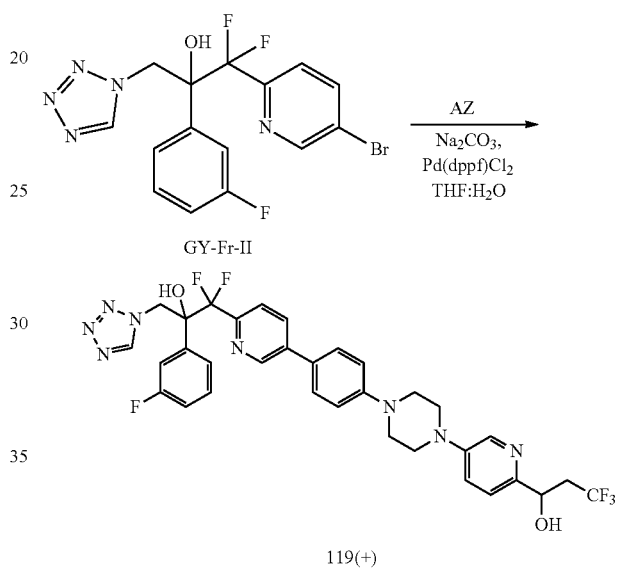

To a stirred solution of compound GY-Fr-II (125 mg, 0.30 mmol) in THF:H2O (4:1, 15 mL) under argon atmosphere were added compound AZ (172 mg, 0.36 mmol) and sodium carbonate (96 mg, 0.90 mmol) at RT. The reaction mixture was purged with argon for 20 min, then Pd(dppf)Cl$_2$ (22 mg, 0.03 mmol) was added and the reaction mixture was purged under argon for 10 min at RT. The reaction mixture was stirred at 70° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 50% EtOAc/Hexane) to afford 119(+) (60 mg, 0.08 mmol, 27%) as a pale yellow solid. $^1$H NMR (400 MHz, DMSO-d$_6$): δ 9.02 (s, 1H), 8.92 (d, J=2.0 Hz, 1H), 8.30 (d, J=2.4 Hz, 1H), 8.14 (dd, J=8.3, 2.2 Hz, 1H), 7.70 (d, J=8.8 Hz, 2H), 7.49-7.40 (m, 3H), 7.33-7.08 (m, 7H), 5.69 (d, J=5.9 Hz, 1H), 5.62 (d, J=14.6 Hz, 1H), 5.18 (d, J=14.6 Hz, 1H), 4.87-4.82 (m, 1H), 3.45-3.34 (m, 8H), 2.83-2.73 (m, 1H), 2.61-2.53 (m, 1H); MS (ESI): m/z 685.7 [M+H]$^+$; HPLC: 96.06%, Optical rotation $[α]_D^{20}$: +81.8 (C=0.1% in CH$_2$Cl$_2$).

Example 120(−) and 120(+)

(+) and (−)-1-(5-(4-(4-(6-((R)-2-(2,4-difluorophenyl)-1,1-difluoro-2-hydroxy-3-(1H-1,2,4-triazol-1-yl) propyl) pyridin-3-yl) phenyl) piperazin-1-yl) pyridin-2-yl)-3,3,3-trifluoropropan-1-ol (120(−) and 120(+))

1-(5-bromopyridin-2-yl)-2-(2,4-difluorophenyl)-1,1-difluoro-3-(1H-1,2,4-triazol-1-yl) propan-2-ol (OA)

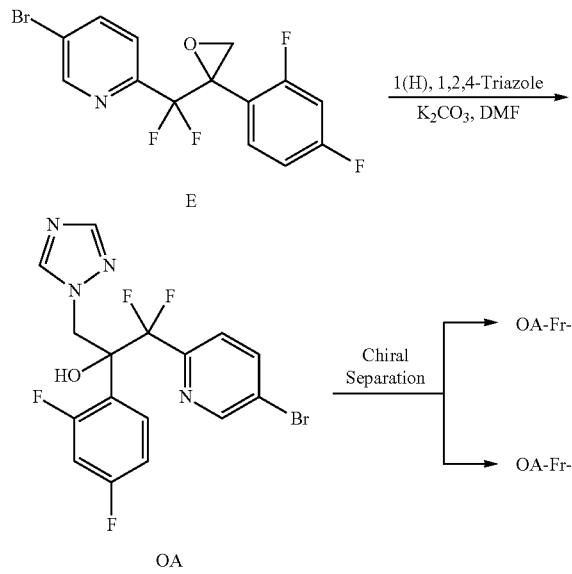

To a stirred solution of compound E (2 g, 5.5 mmol) in DMF (25 mL) under argon atmosphere were added potassium carbonate (2.2 g, 16.62 mmol) and 1H-1,2,4-Triazole (648 mg, 8.31 mmol) at RT. The reaction mixture was stirred at 70° C. for 16 h. The reaction mixture was diluted with water (100 mL) and extracted with EtOAc (2×100 mL). The combined organic layers were dried over anhydrous Na$_2$SO$_4$ and concentrated under reduced pressure. The crude material was purified by silica gel column chromatography (eluent: 20-30% EtOAc/Hexane) to afford compound OA (2 g, 4.65 mmol, 87%) as a white solid. $^1$H NMR (400 MHz, DMSO-d$_6$): δ 8.71 (d, J=2.1 Hz, 1H), 8.34 (s, 1H), 8.19 (dd, J=8.4, 2.3 Hz, 1H), 7.70 (s, 1H), 7.45-7.37 (m, 1H), 7.25-7.09 (m, 2H), 7.03 (s, 1H), 6.87-6.83 (m, 1H), 5.33 (d, J=14.6 Hz, 1H), 4.82 (d, J=14.6 Hz, 1H).

Chiral Preparative HPLC Details

OA (1.2 g) was separated by normal-phase preparative high performance liquid chromatography (CHIRALPAK-IC®, 250×20 mm, 5µ; using (A) 0.1% TFA in n-Hexane:(B) CH$_2$Cl$_2$:MeOH (50:50) (90:10) as a mobile phase; Flow rate: 20 mL/min) to obtain OA-Fr-I (500 mg) and OA-Fr-II (500 mg).

OA-Fr-I:

$^1$H NMR (400 MHz, DMSO-d$_6$): δ 8.71 (d, J=2.1 Hz, 1H), 8.34 (s, 1H), 8.19 (dd, J=8.4, 2.3 Hz, 1H), 7.70 (s, 1H), 7.45-7.37 (m, 1H), 7.25-7.09 (m, 2H), 7.03 (s, 1H), 6.87-6.83 (m, 1H), 5.33 (d, J=14.6 Hz, 1H), 4.82 (d, J=14.6 Hz, 1H); LC-MS: m/z 430.9 [M+H]$^+$ at 2.77 RT (99.89% purity); HPLC: 99.33%; Chiral HPLC Purity: 98.62%, R$_t$=12.78 min (CHIRALPAK-IC®, 250×4.6 mm, 5µ; mobile phase (A) 0.1% TFA in n-Hexane:(B) CH$_2$Cl$_2$:MeOH (50: 50) (90:10); flow Rate: 1.0 mL/min); Optical rotation [α]$_D^{19}$: −22.1 (C=0.1% in MeOH).

OA-Fr-II:

$^1$H NMR (400 MHz, DMSO-d$_6$): δ 8.71 (d, J=2.1 Hz, 1H), 8.34 (s, 1H), 8.19 (dd, J=8.4, 2.3 Hz, 1H), 7.70 (s, 1H), 7.45-7.37 (m, 1H), 7.25-7.09 (m, 2H), 7.03 (s, 1H), 6.87-6.83 (m, 1H), 5.33 (d, J=14.6 Hz, 1H), 4.82 (d, J=14.6 Hz, 1H); LC-MS: m/z 431 [M+H]$^+$ at 2.77 RT (99.71% purity); HPLC: 99.92%; Chiral HPLC Purity: 99.71%, R$_t$=14.27 min (CHIRALPAK-IC®, 250×4.6 mm, 5µ; mobile phase (A) 0.1% TFA in n-Hexane:(B) CH$_2$Cl$_2$:MeOH (50:50) (90:10); flow Rate: 1.0 mL/min); Optical rotation [α]$_D^{20}$: +13.4 (C=0.1% in MeOH).

(−)-1-(5-(4-(4-(6-((R)-2-(2,4-difluorophenyl)-1,1-difluoro-2-hydroxy-3-(1H-1,2,4-triazol-1-yl) propyl) pyridin-3-yl) phenyl) piperazin-1-yl) pyridin-2-yl)-3,3,3-trifluoropropan-1-ol (120(−))

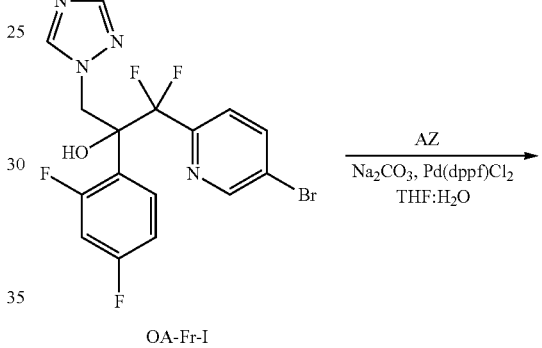

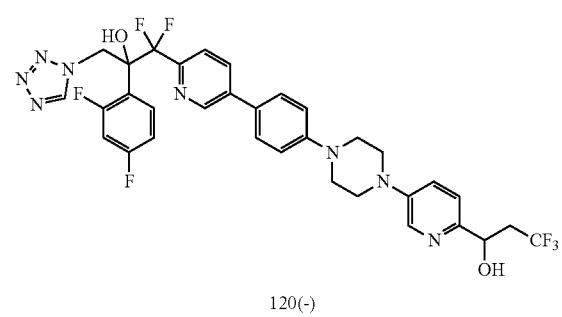

To a stirred solution of compound OA-Fr-I (125 mg, 0.29 mmol) in THF:H2O (4:1, 15 mL) under argon atmosphere were added compound AZ (166 mg, 0.34 mmol) and sodium carbonate (92.2 mg, 0.87 mmol) at RT. The reaction mixture was purged with argon for 20 min, then Pd(dppf)Cl$_2$ (21.2 mg, 0.03 mmol) was added and the reaction mixture was purged under argon for 10 min at RT. The reaction mixture was stirred at 70° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 70% EtOAc/Hexane) to afford 120(−) (40 mg, 0.06 mmol, 20%) as a pale yellow solid. ¹H NMR (400 MHz, DMSO-d₆): δ 8.88 (d, J=2.0 Hz, 1H), 8.35 (s, 1H), 8.30 (d, J=2.4 Hz, 1H), 8.15 (dd, J=8.2, 2.3 Hz, 1H), 7.75-7.64 (m, 3H), 7.51-7.39 (m, 3H), 7.34-7.23 (m, 1H), 7.19-7.07 (m, 3H), 7.01 (s, 1H), 6.89-6.84 (m, 1H), 5.69 (d, J=5.8 Hz, 1H), 5.38 (d, J=14.7 Hz, 1H), 4.85 (d, J=14.7 Hz, 2H), 3.44-3.35 (m, 8H), 2.83-2.74 (m, 1H), 2.62-2.53 (m, 1H); MS (ESI): m/z 702.7 [M+H]⁺; HPLC: 99.74%; Optical rotation [α]$_D^{19}$: −63.4 (c=0.1% in CH₂Cl₂).

(+)-1-(5-(4-(4-(6-((R)-2-(2,4-difluorophenyl)-1,1-difluoro-2-hydroxy-3-(1H-1,2,4-triazol-1-yl) propyl) pyridin-3-yl) phenyl) piperazin-1-yl) pyridin-2-yl)-3,3,3-trifluoropropan-1-ol (120(+))

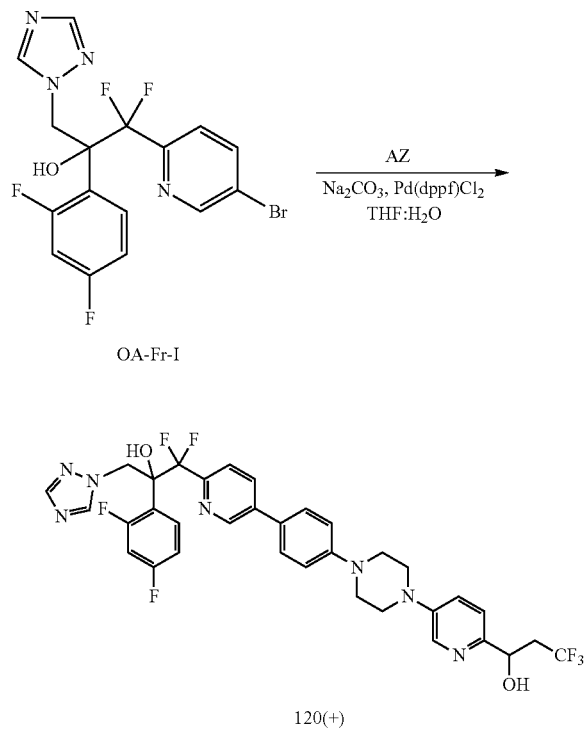

120(+)

To a stirred solution of compound OA-Fr-II (125 mg, 2.90 mmol) in THF:H2O (4:1, 20 mL) under argon atmosphere were added compound AZ (152 mg, 3.19 mmol) and sodium carbonate (93 mg, 0.87 mmol) at RT. The reaction mixture was purged with argon for 20 min, then Pd(dppf)Cl₂ (21 mg, 0.03 mmol) was added and the reaction mixture was purged under argon for 10 min at RT. The reaction mixture was stirred at 80° C. for 16 h. The reaction mixture was quenched with water (20 mL) and extracted with EtOAc (2×20 mL). The combined organic layers were washed with water (20 mL), brine (20 mL), dried over anhydrous Na₂SO₄ and concentrated under reduced pressure. The crude material was purified by silica gel column chromatography (eluent: 2-5% MeOH/CH₂Cl₂) to afford 120(+) (40 mg, 0.06 mmol, 19%) as a pale yellow solid. ¹H NMR (400 MHz, CDCl₃): δ 8.74 (d, J=1.9 Hz, 1H), 8.30 (d, J=2.6 Hz, 1H), 8.17 (s, 1H), 7.93 (dd, J=8.3, 2.3 Hz, 1H), 7.69 (s, 1H), 7.59 (d, J=8.2 Hz, 1H), 7.55-7.46 (m, 3H), 7.31-7.19 (m, 2H), 7.07 (d, J=8.9 Hz, 2H), 6.92 (s, 1H), 6.81-6.67 (m, 2H), 5.37 (d, J=14.6 Hz, 1H), 5.07-4.98 (m, 1H), 4.89 (d, J=14.6 Hz, 1H), 3.85 (d, J=5.9 Hz, 1H), 3.55-3.34 (m, 8H), 2.71-2.33 (m, 2H); MS (ESI): m/z 702.8 [M+H]⁺; HPLC: 95.48%; Optical rotation [α]$_D^{20}$: +84.3 (c=0.1% in CH₂Cl₂).

Example 121(−)

(−)-1-(5-(4-(4-(6-((R)-1,1-difluoro-2-(4-fluorophenyl)-2-hydroxy-3-(1H-tetrazol-1-yl) propyl) pyridin-3-yl) phenyl) piperazin-1-yl) pyridin-2-yl)-3,3,3-trifluoropropan-1-ol (121(−))

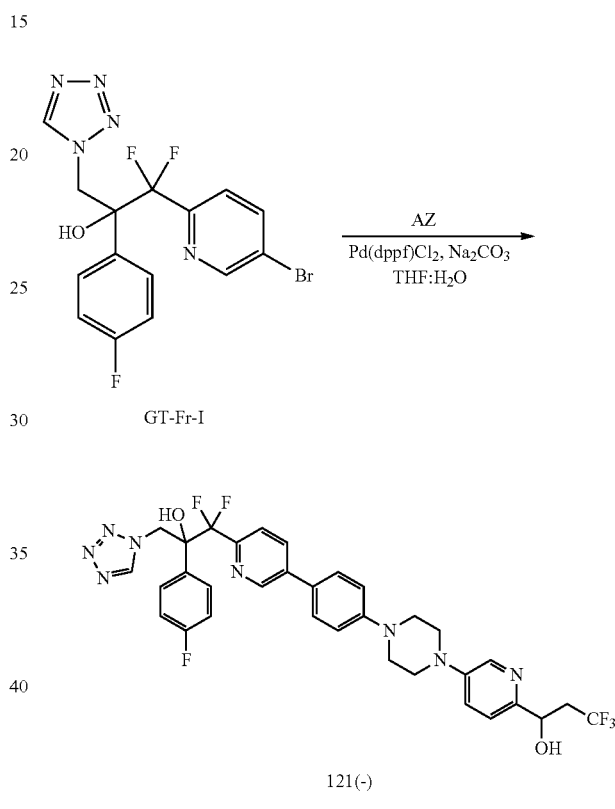

121(−)

To a stirred solution of compound GT-Fr-I (125 mg, 0.30 mmol) in THF:H2O (4:1, 25 mL) under argon atmosphere were added compound AZ (158 mg, 0.33 mmol) and sodium carbonate (96 mg, 0.9 mmol) at RT. The reaction mixture was purged with argon for 20 min, then Pd(dppf)Cl₂ (22 mg, 0.03 mmol) was added and the reaction mixture was purged under argon for 10 min at RT. The reaction mixture was stirred at 80° C. for 8 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na₂SO₄ and concentrated under reduced pressure. The crude material was purified by silica gel column chromatography (eluent: 70% EtOAc/Hexane) to afford 121(−) (45 mg, 0.06 mmol, 22%) as a pale yellow solid. ¹H NMR (400 MHz, CDCl₃): δ 8.77 (s, 1H), 8.68 (d, J=2.0 Hz, 1H), 8.30 (d, J=2.4 Hz, 1H), 7.90 (dd, J=8.2, 2.2 Hz, 1H), 7.59 (s, 1H), 7.55 (d, J=8.2 Hz, 1H), 7.49 (d, J=8.8 Hz, 2H), 7.42 (dd, J=7.4, 5.1 Hz, 2H), 7.31-7.27 (m, 1H), 7.25-7.21 (m, 1H), 7.05 (d, J=8.9 Hz, 2H), 6.88 (t, J=8.7 Hz, 2H), 5.27-5.10 (m, 2H), 5.07-4.97 (m, 1H), 3.82 (br s, 1H), 3.51-3.28 (m, 8H), 2.74-2.42 (m, 2H); MS (ESI): m/z 685.7 [M+H]⁺; HPLC: 99.64%; Optical rotation [α]$_D^{20}$: −95.2 (c=0.1% in CH$_2$Cl$_2$).

Example 121(+)

(+)-1-(5-(4-(4-(6-((R)-1,1-difluoro-2-(4-fluorophenyl)-2-hydroxy-3-(1H-tetrazol-1-yl) propyl) pyridin-3-yl) phenyl) piperazin-1-yl) pyridin-2-yl)-3,3,3-trifluoropropan-1-ol (121(+))

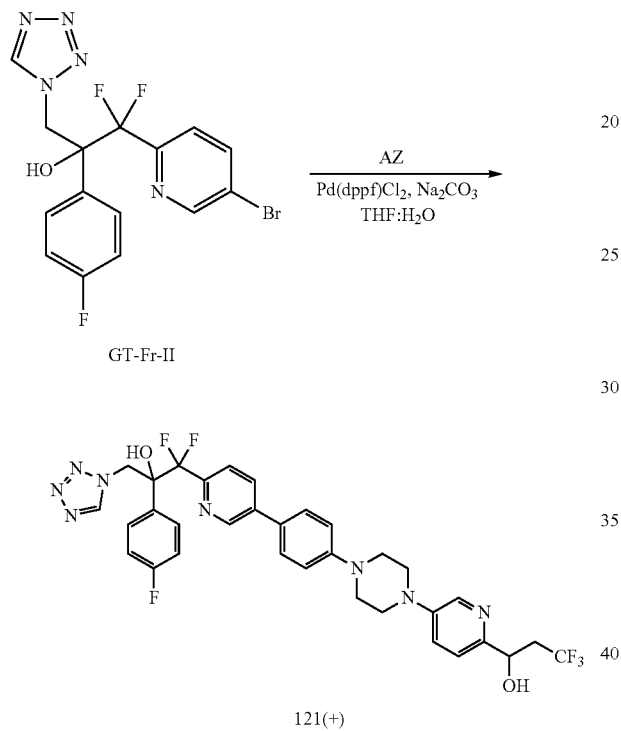

121(+)

To a stirred solution of compound GT-Fr-II (125 mg, 0.30 mmol) in THF:H2O (4:1, 25 mL) under argon atmosphere were added compound AZ (158 mg, 0.33 mmol) and sodium carbonate (96 mg, 0.9 mmol) at RT. The reaction mixture was purged with argon for 20 min. then Pd(dppf)Cl$_2$ (22 mg, 0.03 mmol) was added and the reaction mixture was purged under argon for 10 min at RT. The reaction mixture was stirred at 80° C. for 8 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 5% MeOH/CH$_2$Cl$_2$) to afford 121(+) (40 mg, 0.06 mmol, 19%) as a pale yellow solid. ¹H NMR (400 MHz, CDCl$_3$): δ 8.77 (s, 1H), 8.68 (d, J=2.0 Hz, 1H), 8.30 (d, J=2.5 Hz, 1H), 7.90 (dd, J=8.3, 2.0 Hz, 1H), 7.59 (s, 1H), 7.55 (d, J=8.0 Hz, 1H), 7.49 (d, J=8.8 Hz, 2H), 7.42 (dd, J=7.4, 5.1 Hz, 2H), 7.31-7.27 (m, 1H), 7.25-7.22 (m, 1H), 7.05 (d, J=8.8 Hz, 2H), 6.88 (t, J=8.7 Hz, 2H), 5.28-5.10 (m, 2H), 5.04-5.01 (m, 1H), 3.83 (br s, 1H), 3.45-3.40 (m, 8H), 2.69-2.47 (m, 2H); MS (ESI): m/z 685.8 [M+H]⁺; HPLC: 95.12%; Optical rotation [α]$_D^{20}$: +91.6 (c=0.1% in CH$_2$Cl$_2$).

Example 122(−)

(−)-1-(5-(4-(4-(6-((R)-1,1-difluoro-2-(2-fluorophenyl)-2-hydroxy-3-(1H-tetrazol-1-yl) propyl) pyridin-3-yl) phenyl) piperazin-1-yl) pyridin-2-yl)-3,3,3-trifluoropropan-1-ol (122(−))

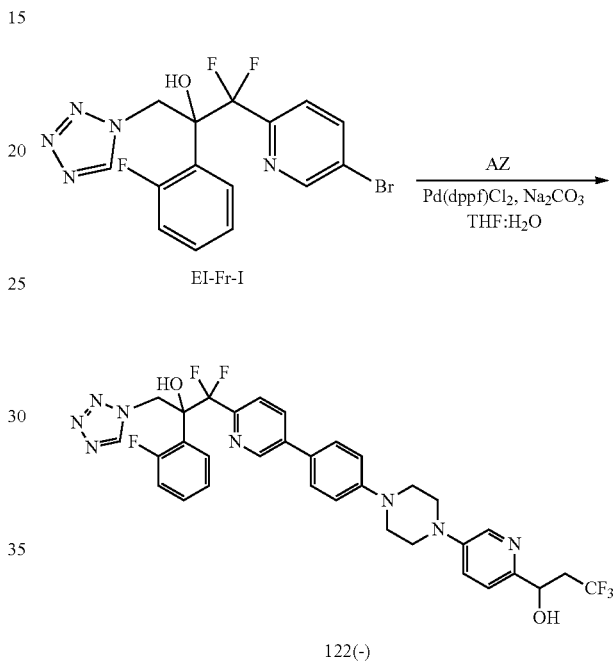

122(−)

To a stirred solution of compound EI-Fr-I (90 mg, 0.18 mmol) in THF:H2O (4:1, 14 mL) under argon atmosphere were added compound AZ (78 mg, 0.18 mmol) and sodium carbonate (60 mg, 0.56 mmol) at RT. The reaction mixture was purged with argon for 20 min, then Pd(dppf)Cl$_2$ (13.7 mg, 0.02 mmol) was added and the reaction mixture was purged under argon for 10 min at RT. The reaction mixture was stirred at 80° C. for 16 h. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 5% MeOH/CH$_2$Cl$_2$) to afford 122(−) (33 mg, 0.05 mmol, 27%) as an off-white solid. ¹H NMR (400 MHz, DMSO-d$_6$): δ 9.12 (s, 1H), 8.91 (d, J=1.8 Hz, 1H), 8.30 (d, J=2.5 Hz, 1H), 8.15 (dd, J=8.3, 2.1 Hz, 1H), 7.70 (d, J=8.9 Hz, 2H), 7.49-7.37 (m, 3H), 7.37-7.27 (m, 2H), 7.19 (s, 1H), 7.17-7.08 (m, 3H), 7.05-6.99 (m, 1H), 5.73-5.70 (m, 1H), 5.69 (s, 1H), 5.11 (d, J=14.8 Hz, 1H), 4.88-4.81 (m, 1H), 3.41-3.36 (m, 8H), 2.87-2.74 (m, 1H), 2.69-2.54 (m, 1H); MS (ESI): m/z 685.8 [M+H]⁺; HPLC: 96.05%; Optical rotation [α]$_D^{20}$: −77.6 (c=0.1% in CH$_2$Cl$_2$)

Example 122(+)

(+)-1-(5-(4-(4-(6-((R)-1,1-difluoro-2-(2-fluorophenyl)-2-hydroxy-3-(1H-tetrazol-1-yl) propyl) pyridin-3-yl) phenyl) piperazin-1-yl) pyridin-2-yl)-3,3,3-trifluoropropan-1-ol (122(+))

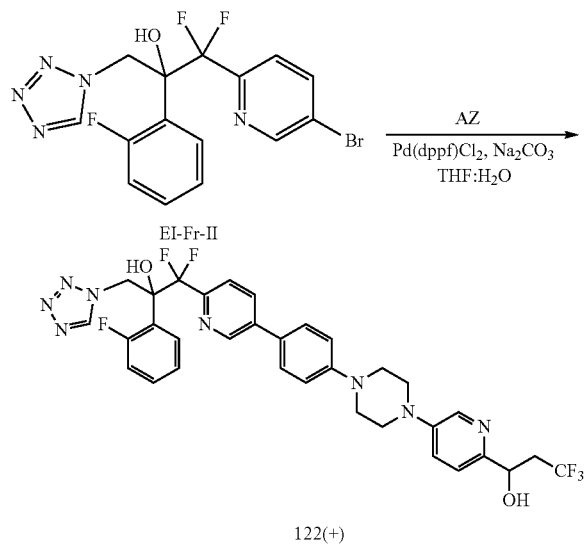

To a stirred solution of compound EI-Fr-II (125 mg, 0.30 mmol) in THF:H2O (4:1, 25 mL) under argon atmosphere were added compound AZ (158 mg, 0.33 mmol) and sodium carbonate (96 mg, 0.9 mmol) at RT. The reaction mixture was purged with argon for 20 min, then Pd(dppf)Cl$_2$ (22 mg, 0.03 mmol) was added and the reaction mixture was purged under argon for 10 min at RT. The reaction mixture was stirred at 80° C. for 8 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 50% EtOAc/Hexane) which was further purified by Preparative TLC to afford 122(+) (40 mg, 0.06 mmol, 19%) as a pale yellow solid. $^1$H NMR (400 MHz, DMSO-d$_6$): δ 9.12 (s, 1H), 8.91 (d, J=1.8 Hz, 1H), 8.30 (d, J=2.5 Hz, 1H), 8.15 (dd, J=8.3, 2.1 Hz, 1H), 7.70 (d, J=8.9 Hz, 2H), 7.49-7.37 (m, 3H), 7.37-7.27 (m, 2H), 7.19 (s, 1H), 7.17-7.08 (m, 3H), 7.05-6.99 (m, 1H), 5.73-5.70 (m, 1H), 5.69 (s, 1H), 5.11 (d, J=14.8 Hz, 1H), 4.88-4.81 (m, 1H), 3.41-3.36 (m, 8H), 2.87-2.74 (m, 1H), 2.69-2.54 (m, 1H); MS (ESI): m/z 685.7 [M+H]$^+$; HPLC: 99.53%; Optical rotation [α]$_D^{20}$: +123.2 (c=0.1% in CH$_2$Cl$_2$).

Example 123(−)

(−)-4-(4-(4-(4-(6-(2-(2,4-difluorophenyl)-1,1-difluoro-2-hydroxy-3-(1H-1,2,4-triazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (123(−))

2-((2S,3S)-2-(benzyloxy) pentan-3-yl)-4-(4-(4-(4-(6-(2-(2,4-difluorophenyl)-1,1-difluoro-2-hydroxy-3-(1H-1,2,4-triazol-1-yl) propyl) pyridin-3-yl) phenyl) piperazin-1-yl) phenyl)-2,4-dihydro-3H-1,2,4-triazol-3-one (OB-Fr-I)

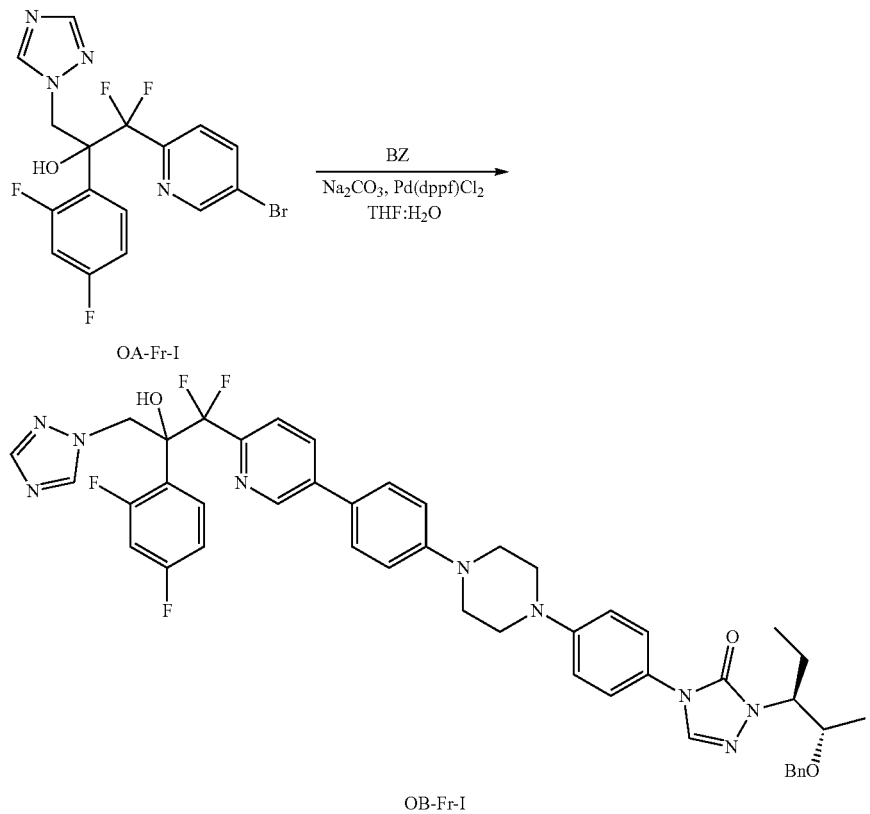

To a stirred solution of compound OA-Fr-I (150 mg, 0.34 mmol) in THF:H2O (9:1, 20 mL) under argon atmosphere were added compound BZ (240 mg, 0.38 mmol) and sodium carbonate (110 mg, 1.04 mmol) at RT. The reaction mixture was purged with argon for 20 min, then Pd(dppf)Cl$_2$ (38 mg, 0.05 mmol) was added and the reaction mixture was purged under argon for 5 min at RT. The reaction mixture was stirred at 70° C. for 16 h. The reaction mixture was quenched with ice water (20 mL) and extracted with EtOAc (2×20 mL). The combined organic layers were washed with water (20 mL), dried over anhydrous Na$_2$SO$_4$ and concentrated under reduced pressure. The crude material was purified by silica gel column chromatography (eluent: 50% EtOAc/Hexane) to afford compound OB-Fr-I (120 mg, 0.14 mmol, 41%) as an off-white solid. $^1$H NMR (400 MHz, CDCl$_3$): δ 8.74 (d, J=1.8 Hz, 1H), 8.17 (s, 1H), 7.93 (dd, J=8.2, 2.2 Hz, 1H), 7.69 (s, 1H), 7.61-7.47 (m, 5H), 7.42 (d, J=8.9 Hz, 2H), 7.25-7.20 (m, 4H), 7.09-7.03 (m, 4H), 6.94 (s, 1H), 6.79-6.65 (m, 2H), 5.37 (d, J=14.6 Hz, 1H), 4.89 (d, J=14.6 Hz, 1H), 4.63 (d, J=11.9 Hz, 1H), 4.41 (d, J=11.9 Hz, 1H), 4.21-4.16 (m, 1H), 3.84-3.78 (m, 1H), 3.49-3.37 (m, 8H), 2.02-1.88 (m, 1H), 1.83-1.77 (m, 1H), 1.28 (d, J=6.3 Hz, 3H), 0.89 (t, J=7.3 Hz, 3H)

(−)-4-(4-(4-(4-(6-(2-(2,4-difluorophenyl)-1,1-difluoro-2-hydroxy-3-(1H-1,2,4-triazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (123(−))

To a stirred solution of compound OB-Fr-I (120 mg, 0.14 mmol) in MeOH (1 mL) under argon atmosphere were added 10% Pd/C (60 mg) and concentrated hydrochloric acid (0.1 mL) at RT. The reaction mixture was stirred at RT for 8 h under hydrogen atmosphere. The progress of the reaction was monitored by TLC, the reaction mixture was filtered and the filtrate was concentrated under reduced pressure. The residue was diluted with saturated sodium carbonate solution (20 mL) and extracted with CH$_2$Cl$_2$ (2×20 mL). The combined organic layers were dried over anhydrous Na$_2$SO$_4$ and concentrated under reduced pressure. The crude material was purified by silica gel column chromatography (eluent: 3% MeOH/CH$_2$Cl$_2$) to afford 123 (−) (66 mg, 0.08 mmol, 61%) as an off-white solid. $^1$H NMR (400 MHz, CDCl$_3$): δ 8.74 (s, 1H), 8.18 (s, 1H), 7.93 (dd, J=8.2, 2.2 Hz, 1H), 7.68 (d, J=6.5 Hz, 2H), 7.59 (d, J=8.3 Hz, 1H), 7.53 (d, J=8.8 Hz, 2H), 7.52-7.47 (m, 1H), 7.45 (d, J=8.9 Hz, 2H), 7.08-7.04 (m, 4H), 6.94 (s, 1H), 6.80-6.68 (m, 2H), 5.37 (d, J=14.6 Hz, 1H), 4.89 (d, J=14.6 Hz, 1H), 4.13-3.96 (m, 2H), 3.51-3.37 (m, 8H), 3.06 (d, J=9.0 Hz, 1H), 2.08-1.96 (m, 1H), 1.96-1.84 (m, 1H), 1.22 (d, J=6.3 Hz, 3H), 0.95 (t, J=7.4 Hz, 3H); MS (ESI): m/z 758.9 [M+H]$^+$; HPLC: 96.11%; Optical rotation [α]$_D^{20}$: −73.6 (c=0.1% in CH$_2$Cl$_2$).

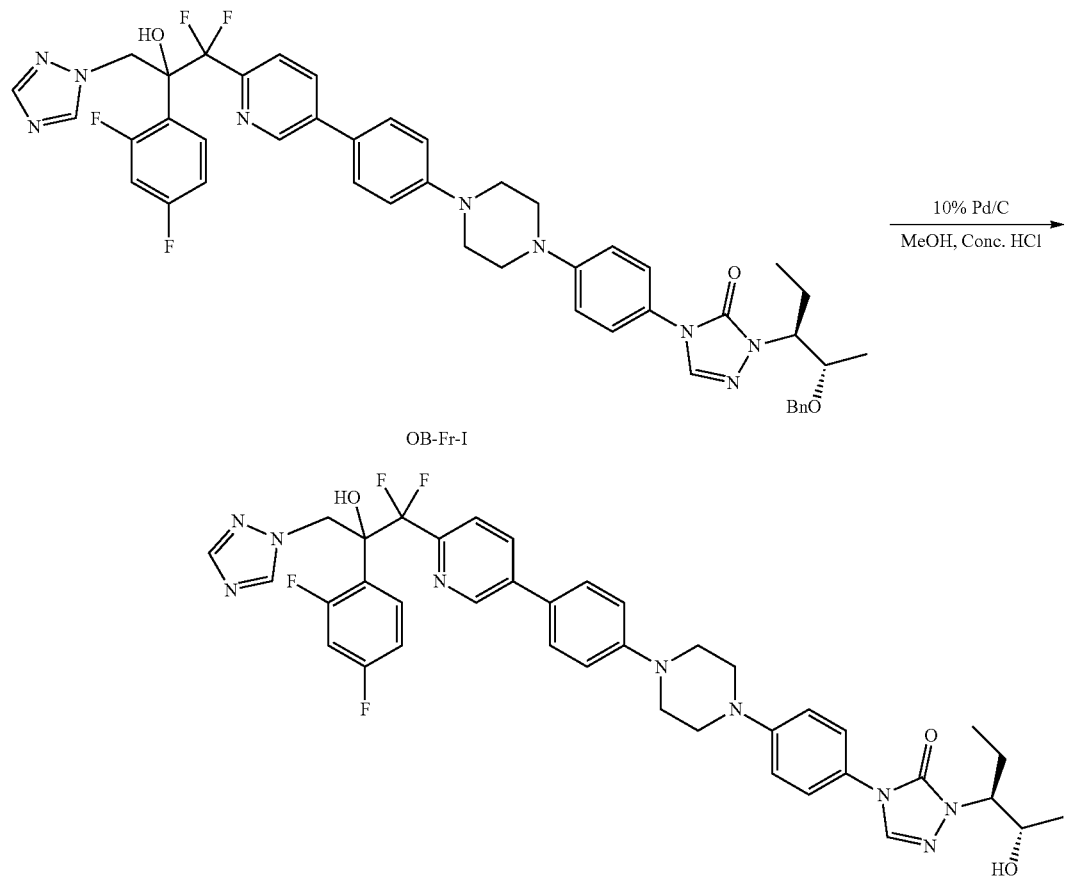

Example 123(+)

(+)-4-(4-(4-(4-(6-(2-(2,4-difluorophenyl)-1,1-difluoro-2-hydroxy-3-(1H-1,2,4-triazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (123(+))

2-((2S,3S)-2-(benzyloxy) pentan-3-yl)-4-(4-(4-(4-(6-(2-(2,4-difluorophenyl)-1,1-difluoro-2-hydroxy-3-(1H-1,2,4-triazol-1-yl) propyl) pyridin-3-yl) phenyl) piperazin-1-yl) phenyl)-2,4-dihydro-3H-1,2,4-triazol-3-one (OB-Fr-II)

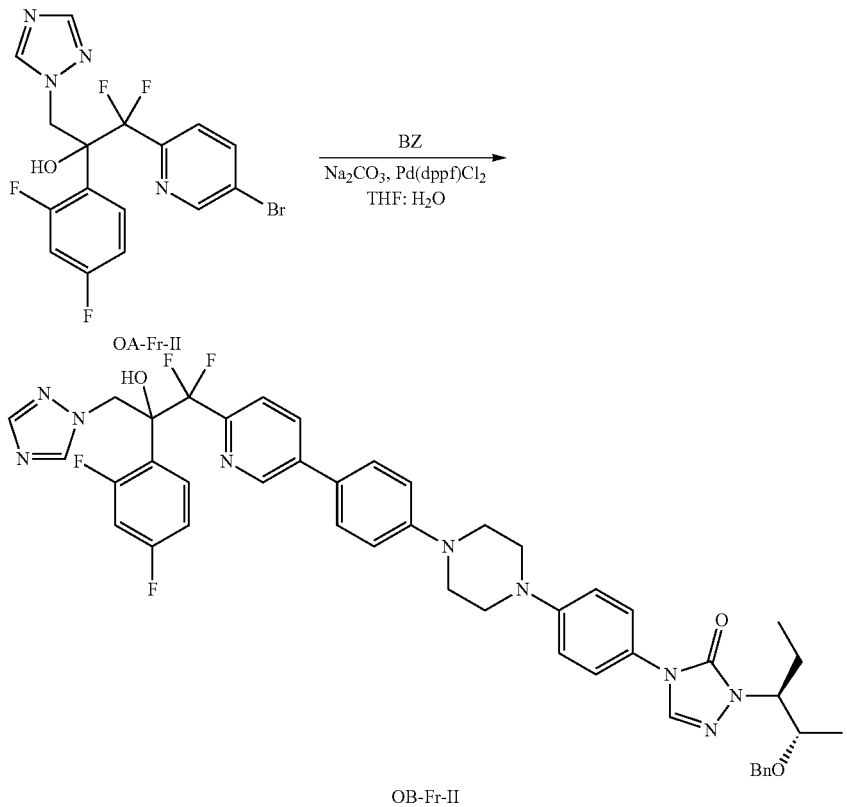

To a stirred solution of compound OA-Fr-II (150 mg, 0.34 mmol) in THF:H2O (9:1, 20 mL) under argon atmosphere were added compound BZ (240 mg, 0.38 mmol) and sodium carbonate (110 mg, 1.04 mmol) at RT. The reaction mixture was purged with argon for 20 min, then Pd(dppf)Cl$_2$ (38 mg, 0.05 mmol) was added and the reaction mixture was purged under argon for 5 min at RT. The reaction mixture was stirred at 70° C. for 16 h. The reaction mixture was quenched with ice water (20 mL) and extracted with EtOAc (2×20 mL). The combined organic layers were washed with water (20 mL), dried over anhydrous Na$_2$SO$_4$ and concentrated under reduced pressure. The crude material was purified by silica gel column chromatography (eluent: 50% EtOAc/Hexane) to afford compound OB-Fr-II (155 mg, 0.18 mmol, 50%) as an off-white solid. $^1$H NMR (400 MHz, CDCl$_3$): δ 8.74 (d, J=1.8 Hz, 1H), 8.17 (s, 1H), 7.93 (dd, J=8.2, 2.2 Hz, 1H), 7.69 (s, 1H), 7.61-7.47 (m, 5H), 7.42 (d, J=8.9 Hz, 2H), 7.25-7.20 (m, 4H), 7.09-7.03 (m, 4H), 6.94 (s, 1H), 6.79-6.65 (m, 2H), 5.37 (d, J=14.6 Hz, 1H), 4.89 (d, J=14.6 Hz, 1H), 4.63 (d, J=11.9 Hz, 1H), 4.41 (d, J=11.9 Hz, 1H), 4.21-4.16 (m, 11H), 3.84-3.78 (m, 1H), 3.49-3.37 (m, 8H), 2.02-1.88 (m, 1H), 1.83-1.77 (m, 1H), 1.28 (d, J=6.3 Hz, 3H), 0.89 (t, J=7.3 Hz, 3H).

(+)-4-(4-(4-(4-(6-(2-(2,4-difluorophenyl)-1,1-difluoro-2-hydroxy-3-(1H-1,2,4-triazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (123(+))

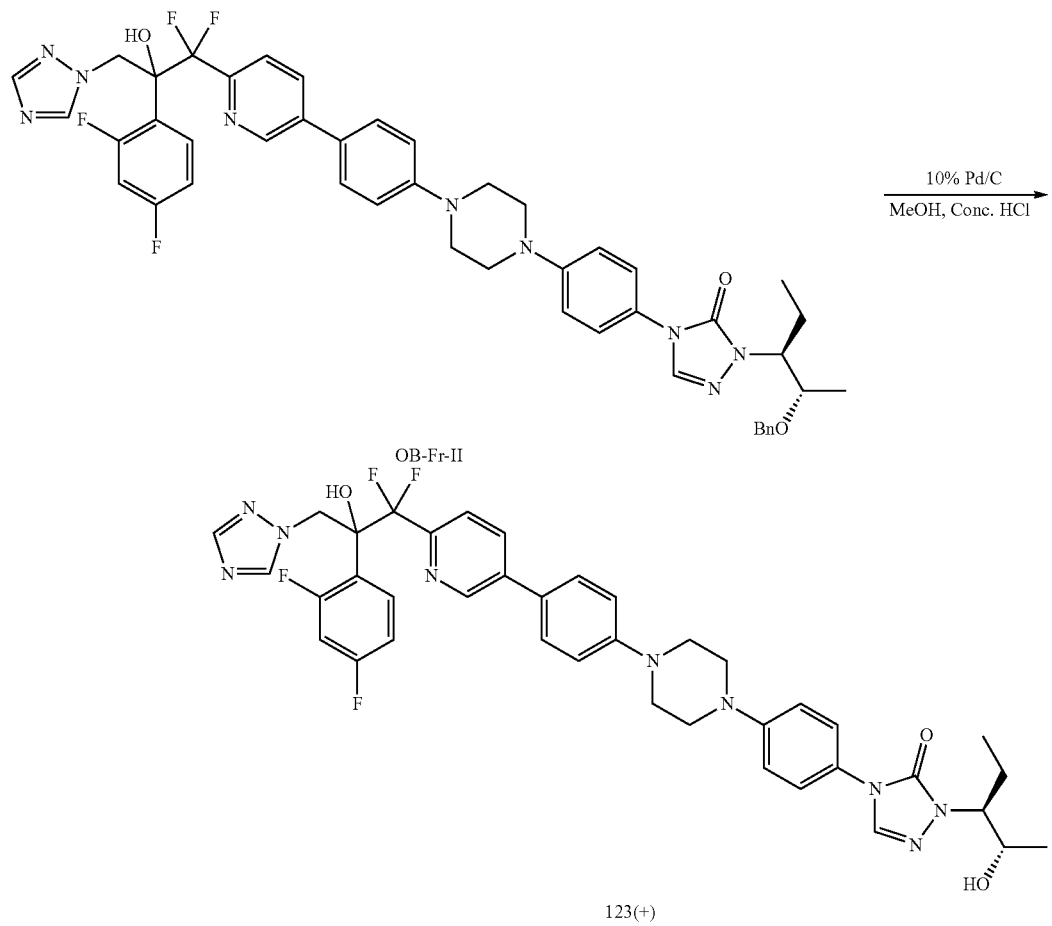

To a stirred solution of compound OB-Fr-II (155 mg, 0.18 mmol) in MeOH (10 mL) under argon atmosphere were added 10% Pd/C (70 mg) and concentrated hydrochloric acid (0.1 mL) at RT. The reaction mixture was stirred at RT for 8 h under hydrogen atmosphere. The progress of the reaction was monitored by TLC, the reaction mixture was filtered and the filtrate was concentrated under reduced pressure. The residue was diluted with saturated sodium carbonate solution (20 mL) and extracted with $CH_2Cl_2$ (2×20 mL). The combined organic layers were dried over anhydrous $Na_2SO_4$ and concentrated under reduced pressure. The crude material was purified by silica gel column chromatography (eluent: 3% MeOH/$CH_2Cl_2$) to afford 123 (+) (55 mg, 0.07 mmol, 39%) as an off-white solid. $^1$H NMR (400 MHz, $CDCl_3$): δ 8.74 (d, J=1.9 Hz, 1H), 8.18 (br s, 1H), 7.93 (dd, J=2.2, 8.2 Hz, 1H), 7.69 (s, 1H), 7.67 (s, 1H), 7.59 (d, J=8.2 Hz, 1H), 7.53 (d, J=8.8 Hz, 2H), 7.52-7.47 (m, 1H), 7.45 (d, J=8.9 Hz, 2H), 7.08-7.04 (m, 4H), 6.94 (br s, 1H), 6.79-6.69 (m, 2H), 5.37 (br d, J=14.3 Hz, 1H), 4.89 (br d, J=14.3 Hz, 1H), 4.07-4.01 (m, 2H), 3.50-3.30 (m, 8H), 3.07-3.00 (m, 1H), 2.06-1.86 (m, 2H), 1.22 (d, J=6.3 Hz, 3H), 0.95 (t, J=7.4 Hz, 3H); MS (ESI): m/z 756.7 [M-H]$^-$; HPLC: 96.56/%; Optical rotation $[\alpha]_D^{20}$: +84.2 (c=0.1% in $CH_2Cl_2$).

Example 124

4-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-((2S,3S)-2-hydroxypentan-3-yl)-2,4-dihydro-3H-1,2,4-triazol-3-one (124)

Phenyl (5-bromo-3-fluoropyridin-2-yl) carbamate (OD)

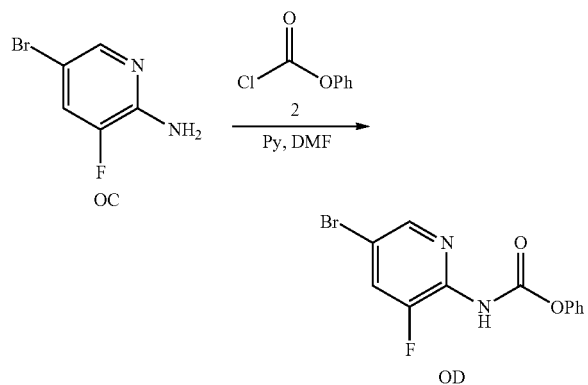

To a stirred solution of 5-bromo-3-fluoropyridin-2-amine (OC; 2.0 g, 10.47 mmol) in CH$_2$Cl$_2$ (50 mL) under argon atmosphere were added pyridine (0.88 mL, 10.47 mmol) and phenyl carbonochloridate 2 (1.3 mL, 10.47 mmol) at 0° C. The reaction mixture was warmed to RT and stirred for 4 h. The progress of the reaction was monitored by TLC. The reaction mixture was diluted with water (100 mL) and extracted with EtOAc (2×100 mL). The combined organic layers were washed with water (100 mL), dried over anhydrous Na$_2$SO$_4$ and concentrated under reduced pressure. The crude material was washed with n-pentane (2×20 mL) to afford compound OD (2.5 g, 8.03 mmol, 78%) as a white solid. The obtained crude compound was used in the next step without further purification. LC-MS: m/z 311.8 [M+H]$^+$ at 2.75 RT (79.44% purity).

2-((2S,3S)-2-(benzyloxy) pentan-3-yl)-4-(5-bromo-3-fluoropyridin-2-yl)-2,4-dihydro-3H-1,2,4-triazol-3-one (OE)

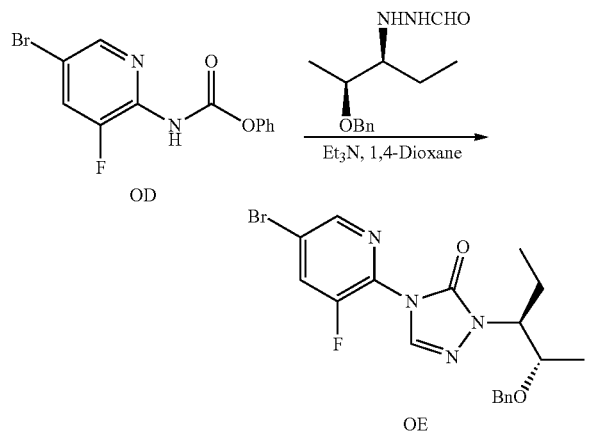

To a stirred solution of compound OD (2.5 g, 8.03 mmol) in 1,4-dioxane (50 mL) under argon atmosphere were added potassium carbonate (2.2 g, 16.07 mmol) and N'-((2S,3S)-2-(benzyloxy) pentan-3-yl) formohydrazide (1.5 g, 6.43 mmol) at RT. The reaction mixture was stirred at 80° C. for 16 h in a sealed tube. The progress of the reaction was monitored by TLC. The reaction mixture was diluted with water (100 mL) and extracted with EtOAc (2×100 mL). The combined organic layers were dried over anhydrous Na$_2$SO$_4$ and concentrated under reduced pressure. The crude material was purified by silica gel column chromatography (eluent: 10% EtOAc/Hexane) to afford compound OE (600 mg, 1.37 mmol, 17%) as a pale yellow solid. $^1$H NMR (400 MHz, DMSO-d$_6$): δ 8.66 (d, J=1.9 Hz, 1H), 8.54 (dd, J=9.2, 2.0 Hz, 1H), 8.29 (s, 1H), 7.29-7.07 (m, 5H), 4.53 (d, J=11.9 Hz, 1H), 4.28 (d, J=11.9 Hz, 1H), 3.98-3.93 (m, 1H), 3.81-3.67 (m, 1H), 1.78-1.71 (m, 2H), 1.22 (d J=6.3 Hz, 3H), 0.78 (t, J=7.3 Hz, 3H).

2-((2S,3S)-2-(benzyloxy) pentan-3-yl)-4-(5-(4-(4-bromophenyl) piperazin-1-yl)-3-fluoropyridin-2-yl)-2,4-dihydro-3H-1,2,4-triazol-3-one (OF)

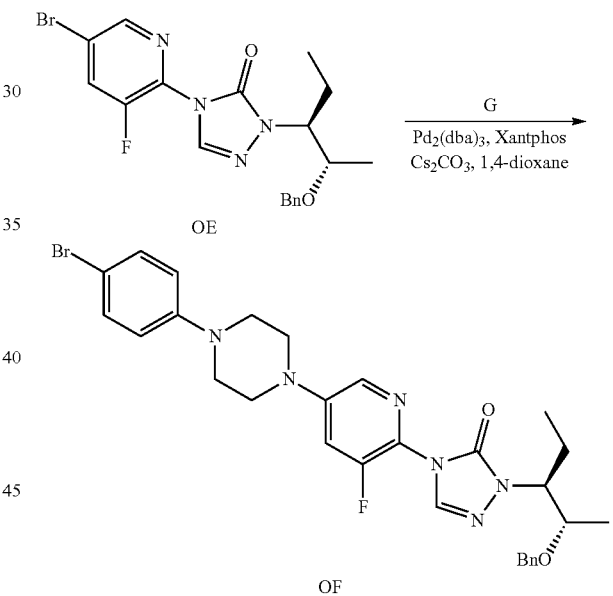

To a stirred solution of compound OE (500 mg, 1.14 mmol) in 1,4-dioxane (30 mL) under argon atmosphere were added G (332 mg, 1.37 mmol), cesium carbonate (1.1 g, 3.44 mmol), Xantphos (80 mg, 0.13 mmol) and purged under argon for 20 min at RT. Then Pd$_2$(dba)$_3$ (52 mg, 0.05 mmol) was added to the reaction mixture at RT and stirred at 90° C. for 16 h. The reaction mixture was diluted with water (50 mL) and extracted with EtOAc (2×50 mL). The combined organic extracts were washed with water (50 mL), brine (50 mL), dried over anhydrous Na$_2$SO$_4$ and concentrated under reduced pressure. The crude material was purified by silica gel column chromatography (eluent: 40% EtOAc/Hexane) to afford compound OF (350 mg, 0.58 mmol, 51%) as a pale yellow solid. LC-MS: m/z 595.1 [M+H]$^+$ at 4.06 RT (85.19% purity).

2-((2S,3S)-2-(benzyloxy) pentan-3-yl)-4-(3-fluoro-5-(4-(4-(4,4,5,5-tetramethyl-1,3,2-dioxaborolan-2-yl) phenyl) piperazin-1-yl) pyridin-2-yl)-2,4-dihydro-3H-1,2,4-triazol-3-one (OG)

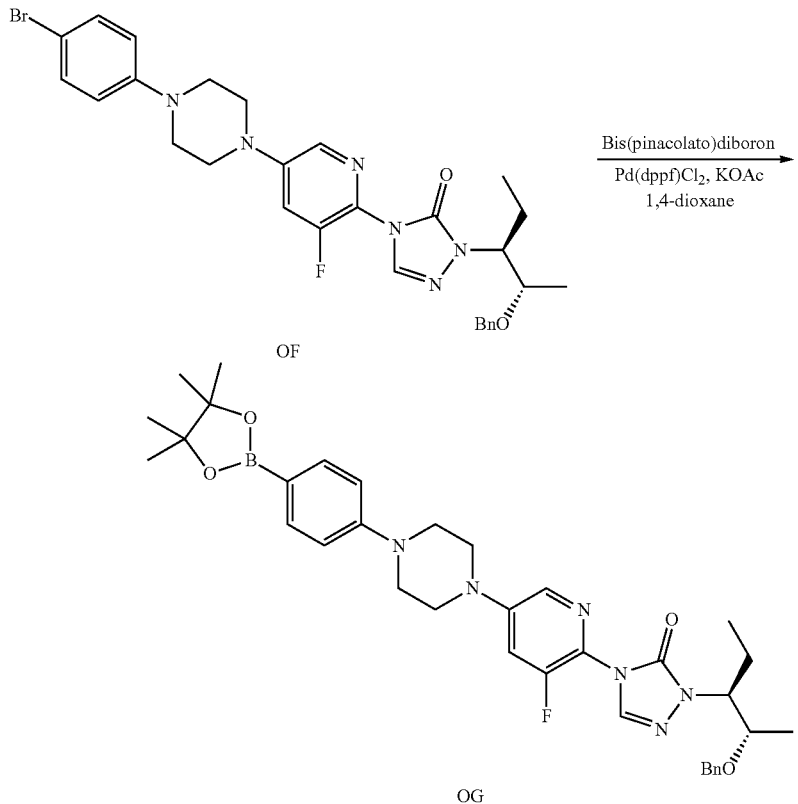

To a stirred solution of compound OF (400 mg, 0.67 mmol) in 1,4-dioxane (25 mL) under argon atmosphere were added bis(pinacolato) diboron (273 mg, 1.07 mmol) and KOAc (197 mg, 2.01 mmol) at RT. The reaction mixture was purged with argon for 20 min, then Pd(dppf)Cl$_2$ (49 mg, 0.06 mmol) was added and the reaction mixture was purged under argon for 10 min at RT. The reaction mixture was stirred at 110° C. for 16 b. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 30% EtOAc/Hexane) to afford compound OG (300 mg, 0.46 mmol, 70%) as a pale yellow solid. LC-MS: m/z 643.1 [M+H]$^+$ at 4.22 RT (77.45% purity).

2-((2S,3S)-2-(benzyloxy) pentan-3-yl)-4-(5-(4-(4-(6-(R)-2-(2,4-difluorophenyl)-1,1-difluoro-2-hydroxy-3-(1H-tetrazol-1-yl) propyl) pyridin-3-yl) phenyl) piperazin-1-yl)-3-fluoropyridin-2-yl)-2,4-dihydro-3H-1,2,4-triazol-3-one (OH)

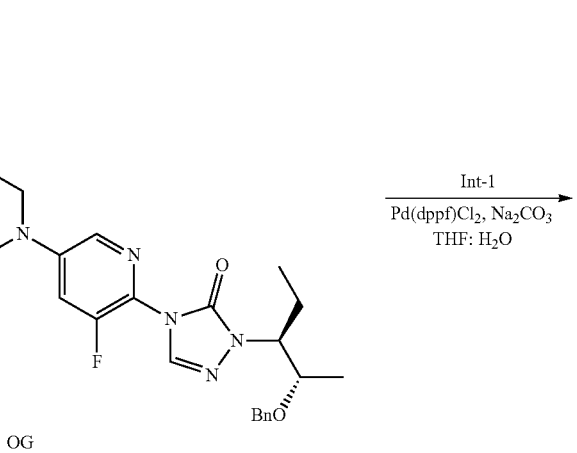

-continued

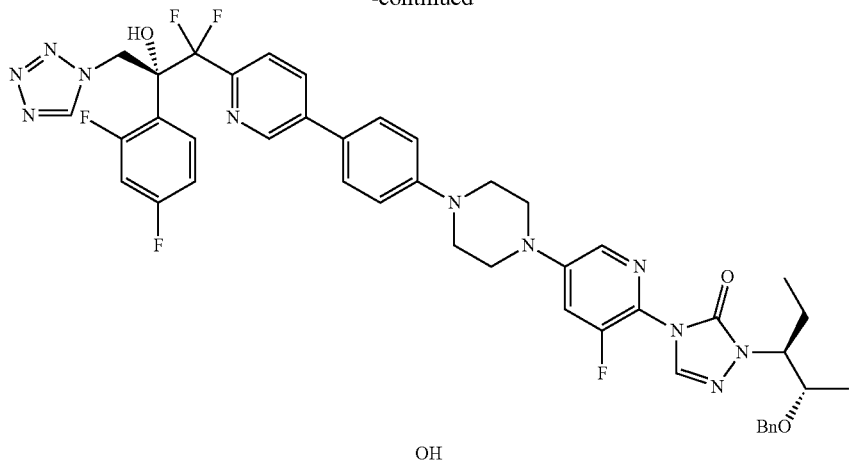

To a stirred solution of Int-1 (200 mg, 0.46 mmol) in THF:H2O (4:1, 25 mL) under argon atmosphere were added compound OG (297 mg, 0.46 mmol) and sodium carbonate (147 mg, 1.38 mmol) at RT. The reaction mixture was purged with argon for 20 min, then Pd(dppf)Cl$_2$ (33.8 mg, 0.04 mmol) was added and the reaction mixture was purged under argon for 10 min at RT. The reaction mixture was stirred at 80° C. for 8 h. The progress of the reaction was monitored by TLC. The reaction mixture was quenched with water (20 mL) and extracted with EtOAc (2×20 mL). The combined organic layers were washed with water (20 mL), brine (20 mL), dried over anhydrous Na$_2$SO$_4$ and concentrated under reduced pressure. The crude material was purified by silica gel column chromatography (eluent: 70% EtOAc/Hexane) to afford compound OH (100 mg, 0.12 mmol, 25%) as a pale yellow solid. $^1$H NMR (400 MHz, DMSO-d$_6$): δ 9.15 (s, 1H), 8.91 (d, J=1.9 Hz, 1H), 8.22-8.15 (m, 3H), 7.71 (d, J=8.9 Hz, 2H), 7.62 (dd, J=12.9, 2.2 Hz, 1H), 7.49 (d, J=8.2 Hz, 1H), 7.32-7.13 (m, 10H), 6.93-6.89 (m, 1H), 5.67 (d, J=14.7 Hz, 1H), 5.11 (d, J=14.7 Hz, 1H), 4.53 (d, J=11.8 Hz, 1H), 4.30 (d, J=11.8 Hz, 1H), 3.98-3.92 (m, 1H), 3.77-3.74 (m, 1H), 3.55-3.53 (m, 4H), 3.44-3.42 (m, 4H), 1.75 (t, J=7.6 Hz, 2H), 1.22 (d, J=6.3 Hz, 3H), 0.78 (t, J=7.28 Hz, 3H)

4-(5-(4-(4-(6-((R)-2-(2,4-difluorophenyl)-1,1-difluoro-2-hydroxy-3-(1H-tetrazol-1-yl) propyl) pyridin-3-yl) phenyl) piperazin-1-yl) pyridin-2-yl)-2-((2S,3S)-2-hydroxypentan-3-yl)-2,4-dihydro-3H-1,2,4-triazol-3-one (124)

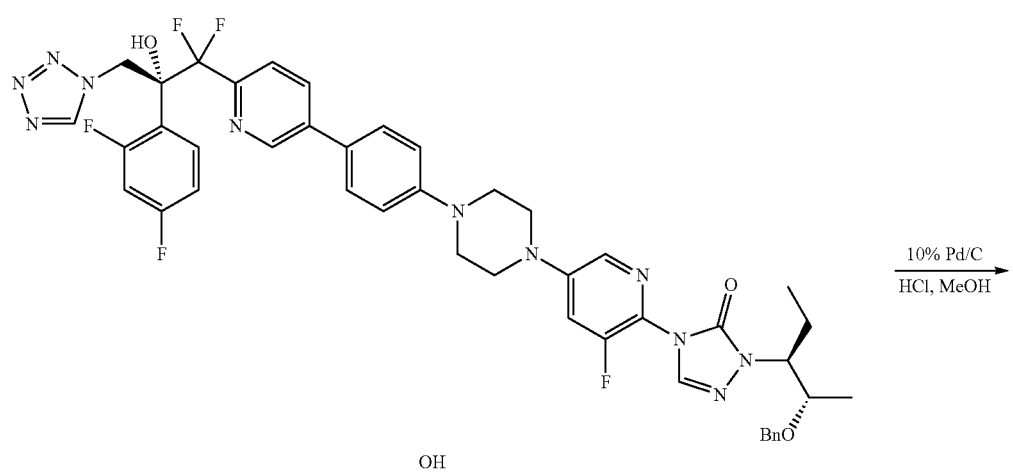

-continued

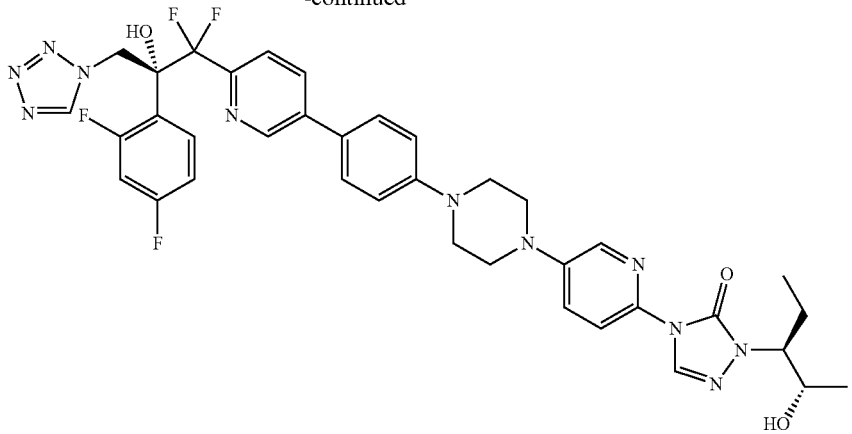

124

To a stirred solution of compound OH (100 g, 0.11 mmol) in MeOH (25 mL) under argon atmosphere were added 10% Pd/C (50 mg) and concentrated HCl (cat) at RT and stirred for 3 h under hydrogen atmosphere (50 psi). The progress of the reaction was monitored by TLC. The reaction mixture was filtered through celite, the filtrate was dried over anhydrous $Na_2SO_4$ and concentrated under reduced pressure. The crude material was washed with n-pentane (2×5 mL) to afford 124 (55 rag, 0.07 mmol, 63%) as an off-white solid. $^1$H NMR (400 MHz. $CDCl_3$): δ 8.76 (s, 1H), 8.72 (d, J=1.8 Hz, 1H), 8.06 (d, J=2.4 Hz, 1H), 7.95 (dd, J=8.3, 2.3 Hz, 1H), 7.82 (br s, 1H), 7.71 (s, 1H), 7.62 (d, J=8.3 Hz, 1H), 7.53 (d, J=8.8 Hz, 2H), 7.44-7.35 (m, 1H), 7.10 (dd, J=11.9, 2.6 Hz, 1H), 7.06 (d, J=8.9 Hz, 2H), 6.80-6.75 (m, 1H), 6.71-6.63 (m, 1H), 5.60 (d, J=14.2 Hz, 1H), 5.12 (d, J=14.2 Hz, 1H), 4.06-4.00 (m, 2H), 3.48 (brs, 8H), 303-2.94 (m, 1H), 2.09-1.97 (m, 1H), 1.94-1.84 (m, 1H), 1.23 (d, J=6.3 Hz, 3H), 0.96 (t, J=7.4 Hz, 3H); MS (ESI): m/z 778.9 [M+H]$^+$; HPLC: 93.80%; Optical rotation $[α]_D^{20}$: +99.6 (c=0.1% in $CH_2Cl_2$).

Example 125

4-(4-(4-(4-(6-(4-(2-(3-chlorophenyl)-1,1-difluoro-2-hydroxy-3-(2H-1,2,3-triazol-2-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (125)

2-(5-bromopyridin-2-yl)-1-(3-chlorophenyl)-2,2-difluoroethan-1-one (OK)

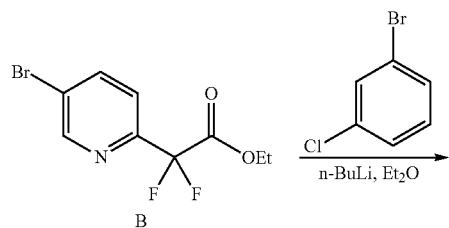

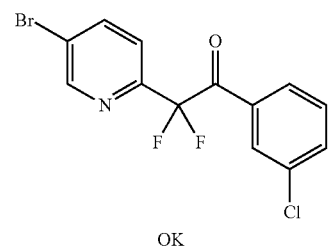

To a stirred solution of 1-bromo-3-chlorobenzene (7.3 mL, 26.17 mmol) in diethyl ether (25 mL) was added n-BuLi (16.3 mL, 26.17 mmol, 1.6 Min Hexanes) at −78° C. under argon atmosphere and stirred for 45 min. Then compound B (5 g, 26.17 mmol) in diethyl ether (25 mL) was added to reaction mixture at −78° C., and stirred for 2 h. The progress of the reaction was monitored by TLC. The reaction was quenched with a saturated ammonium chloride solution (200 mL) and extracted with ethyl acetate (3×200 mL). The combined organic layers were dried over anhydrous $Na_2SO_4$ and concentrated under reduced pressure. The crude material was purified by silica gel column chromatography (eluent: 1% EtOAc/Hexane) to afford compound OK (3.5 g, 10.14 mmol, 39%) as pale yellow liquid. $^1$H NMR (400 MHz. $CDCl_3$): 8.66 (s, 1H), 8.07-8.02 (m, 2H), 8.00 (dd, J=8.4, 2.3 Hz, 1H), 7.94-7.90 (m, 1H), 7.59-7.56 (m, 1H), 7.43-7.38 (m, 1H)

543

5-bromo-2-((2-(3-chlorophenyl) oxiran-2-yl) difluoromethyl) pyridine (OL)

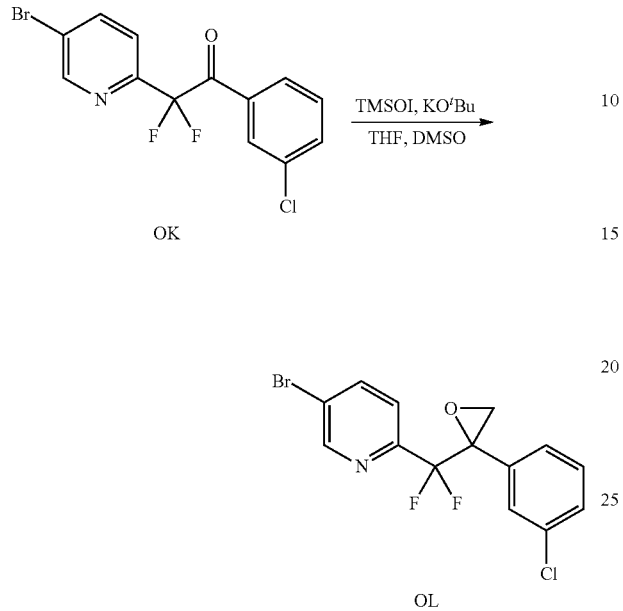

To a stirred solution of TMSOI (2.4 g, 11.15 mmol) and potassium tert-butoxide (1.19 g, 10.65 mmol) in THF: DMSO (3:1, 55 mL) was stirred at RT for 1 h. Then compound OK (3.5 g, 10.14 mmol) was added to the reaction mixture at −10° C., and stirred for 1 h. The reaction mixture was stirred at 0° C. for 1 h. The progress of the reaction was monitored by TLC. The reaction mixture was quenched with 1N HC solution (50 mL) and extracted with EtOAc (2×100 mL). The combined organic extracts were dried over anhydrous Na$_2$SO$_4$ and concentrated under reduced pressure. The crude material was purified by silica gel column chromatography (eluent: 2% EtOAc/Hexane) to afford compound OL (2 g, 5.57 mmol, 55%) as colorless oil. $^1$H NMR (400 MHz, CDCl$_3$): δ 8.72 (d, J=1.9 Hz, 1H), 7.89 (dd, J=8.4, 2.3 Hz, 1H), 7.44-7.41 (m, 2H), 7.31-7.27 (m, 2H), 7.23 (d, J=7.5 Hz, 1H), 3.44 (d, J=5.3 Hz, 1H), 2.91-2.89 (m, 1H)

544

1-(5-bromopyridin-2-yl)-2-(3-chlorophenyl)-1,1-difluoro-3-(2H-1,2,3-triazol-2-yl) propan-2-ol (OM)

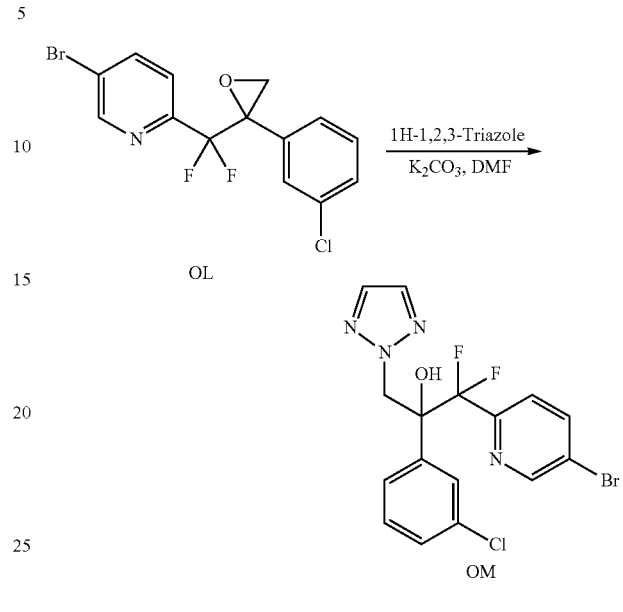

To a stirred solution of compound OL (500 mg, 1.39 mmol) in DMF (10 mL) were added potassium carbonate (384 mg, 2.78 mmol) and 1H-1,2,3-Triazole (144 mg, 2.08 mmol) at RT. The reaction mixture was stirred at 100° C. for 16 h. The reaction mixture was diluted with water (30 mL) and extracted with EtOAc (2×30 mL). The combined organic extracts were washed with brine (30 mL), dried over anhydrous Na$_2$SO$_4$ and concentrated under reduced pressure to obtain the crude. The crude material was purified by silica gel column chromatography (eluent: 30% EtOAc/Hexane) to afford compound OM (200 mg, 0.46 mmol 330) as a white solid. $^1$H NMR (400 MHz, CDCl$_3$): δ 8.59 (d, J=2.0 Hz, 1H), 7.86 (dd, J=8.4, 2.3 Hz, 1H), 7.46-7.44 (m, 3H), 7.39-7.34 (m, 2H), 7.22-7.14 (m, 2H), 5.91 (s, 1H), 5.38-5.31 (m, 1H), 5.21-5.15 (m, 1H).

4-(4-(4-(4-(6-(2-(3-chlorophenyl)-1,1-difluoro-2-hydroxy-3-(2H-1,2,3-triazol-2-yl) propyl) pyridin-3-yl) phenyl) piperazin-1-yl) phenyl-2-((2S,3S)-2-hydroxypentan-3-yl)-2,4-dihydro-3H-1,2,4-triazol-3-one (125)

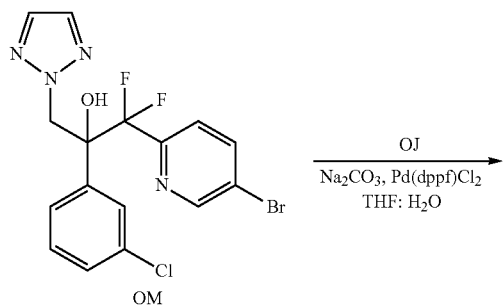

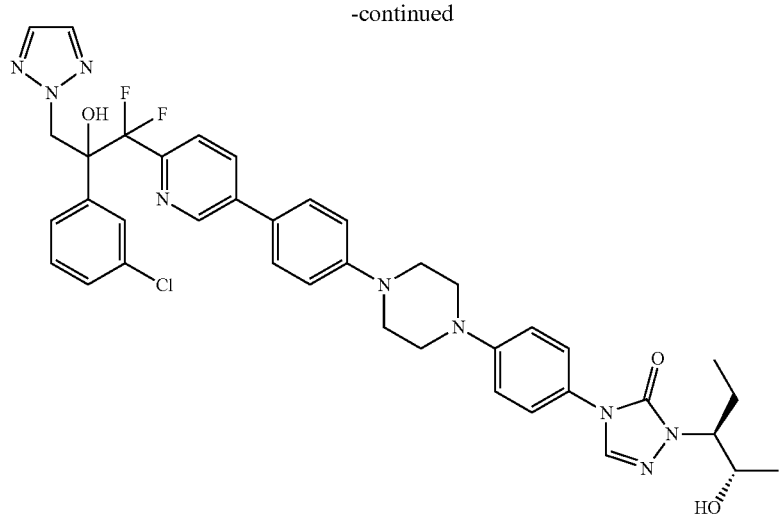

125

To a stirred solution of compound OM (80 mg, 0.18 mmol) in THF:H2O (4:1, 15 mL) under argon atmosphere were added compound OJ (109 mg, 0.20 mmol), sodium carbonate (59 mg, 0.55 mmol) and purged under argon for 20 min at RT. Then Pd(dppf)Cl$_2$ (13 mg, 0.02 mmol) was added and the reaction mixture was purged under argon for 10 min at RT. The reaction mixture was stirred at reflux for 16 h. The reaction mixture was diluted with water (10 mL) and extracted with EtOAc (2×10 mL). The combined organic extracts were washed with brine (10 mL), dried over anhydrous Na$_2$SO$_4$ and concentrated under reduced pressure. The crude material was purified by silica gel column chromatography (eluent: 0-2% MeOH/CH$_2$Cl$_2$) to afford 125 (80 mg, 0.10 mmol, 57%) as an off-white solid. $^1$H NMR (400 MHz, CDCl$_3$): δ 8.72 (d, J=2.1 Hz, 1H), 7.88 (dd, J=8.3, 2.3 Hz, 1H), 7.67 (s, 1H), 7.58-7.48 (m, 4H), 7.46-7.41 (m, 5H), 7.20-7.17 (m, 2H), 7.08-7.03 (m, 4H), 6.53 (s, 1H), 5.33 (d, J=15.2 Hz, 1H), 5.23 (d, J=15.2 Hz, 1H), 4.15-3.94 (m, 2H), 3.53-3.29 (m, 8H), 3.06 (d, J=8.9 Hz, 1H), 2.17-1.84 (m, 2H), 1.22 (d, J=6.3 Hz, 3H), 0.95 (t, J=7.4 Hz, 3H); MS (ESI): m/z 754.3 [M−H]$^−$; HPLC: 98.86%; Optical rotation [α]$_D^{20}$: −18.1 (c=0.1% in MeOH).

Example 126

4-(4-(4-(4-(6-(2-(3-chlorophenyl)-1,1-difluoro-2-hydroxy-3-(1H-pyrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (126)

1-(5-bromopyridin-2-yl)-2-(3-chlorophenyl)-1,1-difluoro-3-(1H-pyrazol-1-yl) propan-2-ol (ON)

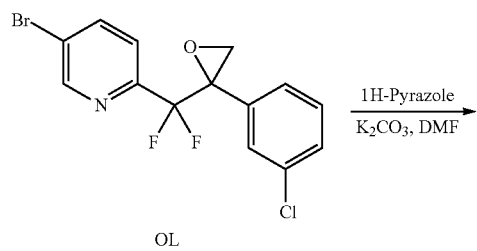

OL

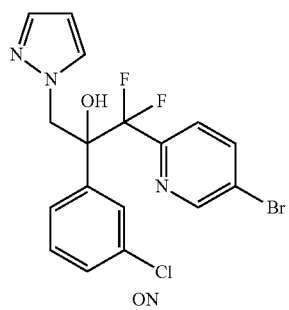

ON

To a stirred solution of OL (500 mg, 1.39 mmol) in DMF (10 mL) under argon atmosphere were added potassium carbonate (288 mg, 2.08 mmol) and 1H-pyrazole (194 mg, 2.78 mmol) at RT. The reaction mixture was stirred at 100° C. for 16 h. The reaction mixture was diluted with water (20 mL) and extracted with EtOAc (2×20 mL). The combined organic extracts were washed with water (20 mL), brine (20 mL), dried over anhydrous Na$_2$SO$_4$ and concentrated under reduced pressure to obtain the crude. The crude material was purified by silica gel column chromatography (eluent: 20% EtOAc/Hexane) to afford compound ON (350 mg, 0.81 mmol, 59%) as colorless syrup. $^1$H NMR (400 MHz, CDCl$_3$): δ 8.56 (d, J=2.0 Hz, 1H), 7.86 (dd, J=8.4, 2.3 Hz, 1H), 7.46 (s, 1H), 7.42 (d, J=8.4 Hz, 1H), 7.37-7.32 (m, 2H), 7.27 (s, 1H), 7.23-7.15 (m, 2H), 6.48 (s, 1H), 6.08 (t, J=2.1 Hz, 1H), 4.93 (d, J=14.8 z, 1H), 4.79 (d, J=14.8 Hz, 1H).

4-(4-(4-(4-(6-(2-(3-chlorophenyl)-1,1-difluoro-2-hydroxy-3-(1H-pyrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (126)

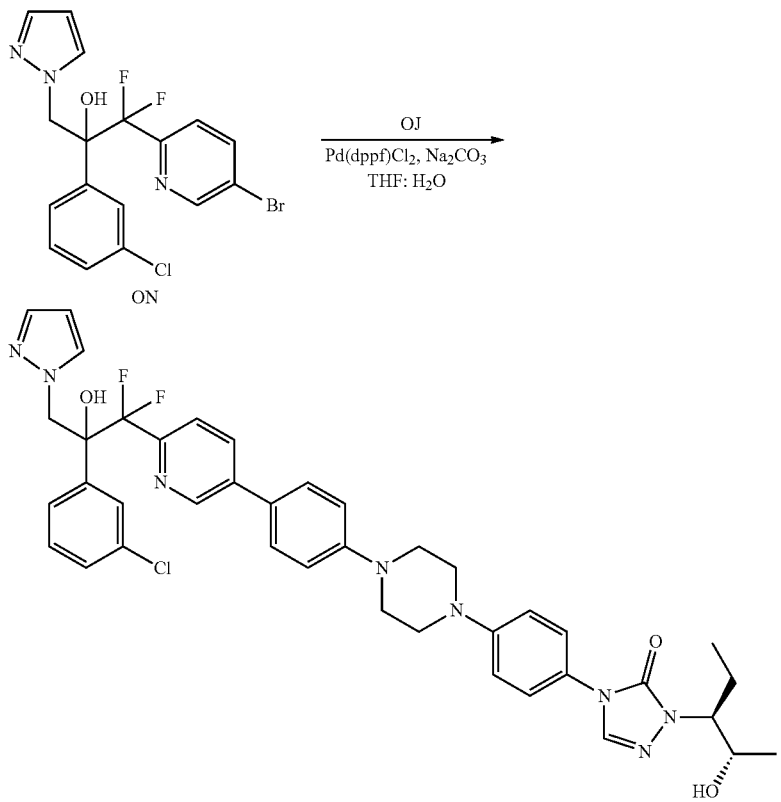

To a stirred solution of compound ON (80 mg, 0.18 mmol) in THF:H2O (4:1, 25 mL) under argon atmosphere were added compound OJ (109 mg, 0.20 mmol), sodium carbonate (59 mg, 0.55 mmol) and purged under argon for 20 min at RT. Then Pd(dppf)Cl$_2$ (13.6 mg, 0.02 mmol) was added and the reaction mixture was purged under argon for 10 min at RT. The reaction mixture was stirred at reflux for 16 h. The reaction mixture was diluted with water (20 mL) and extracted with EtOAc (2×20 mL). The combined organic extracts were washed with brine (20 mL), dried over anhydrous Na$_2$SO$_4$ and concentrated under reduced pressure. The crude material was purified by silica gel column chromatography (eluent: 0-2% MeOH/CH$_2$Cl$_2$) to afford 126 (70 mg, 0.09 mmol, 50%) as an off-white solid. $^1$H NMR (400 MHz, CDCl$_3$): δ 8.69 (d, J=2.1 Hz, 1H), 7.88 (dd, J=8.3, 2.3 Hz, 1H), 7.67 (s, 1H), 7.57 (dd, J=8.3, 0.6 Hz, 1H), 7.53-7.48 (m, 3H), 7.46-7.40 (m, 3H), 7.31 (dd, J=12.5, 1.9 Hz, 2H), 7.21-7.17 (m, 2H), 7.08-7.00 (m, 4H), 6.90-6.84 (m, 1H), 6.07 (t, J=2.1 Hz, 1H), 4.97 (d, J=14.6 Hz, 1H), 4.84 (d, J=14.6 Hz, 1H), 4.17-3.84 (m, 21H), 3.52-3.29 (m, 8H), 3.06 (d, J=8.7 Hz, 1H), 2.06-1.77 (m, 2H), 1.22 (d, J=6.3 Hz, 3H), 0.95 (t, J=7.4 Hz, 3H); MS (ESI): m/z 756.1 [M+2H]1; HPLC: 99.0%; Optical rotation $[\alpha]_D^{20}$: +10.3 (c=0.1% in MeOH).

Examples 127, 127(−), and 127(+)

4-(4-(4-(4-(6-(2-(3-chlorophenyl)-1,1-difluoro-2-hydroxy-3-(1H-tetrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (127)

(+) and (−)-4-(4-(4-(4-(6-(2-(2-(3-chlorophenyl)-1,1-difluoro-2-hydroxy-3-(1H-tetrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (127(−) and 127(+))

5-bromo-2-((2-(3-chlorophenyl) oxiran-2-yl) difluoromethyl) pyridine (OO)

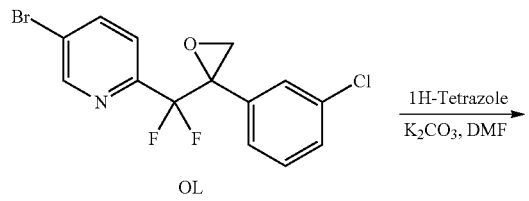

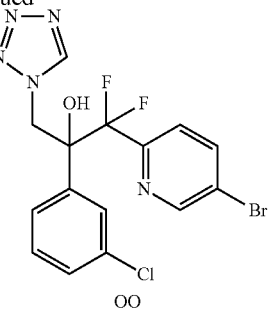

To a stirred solution of compound OL (500 mg, 1.39 mol) in DMF (10 mL) under argon atmosphere were added potassium carbonate (288 mg, 2.08 mol) and 1H-tetrazole (194 mg, 2.78 mmol) at RT. The reaction mixture was stirred at 70° C. for 16 h. The reaction mixture was diluted with water (20 mL) and extracted with EtOAc (2×20 mL). The combined organic extracts were washed with water (20 mL), brine (20 mL), dried over anhydrous $Na_2SO_4$ and concentrated under reduced pressure to obtain the crude. The crude material was purified by silica gel column chromatography (eluent: 0-15% EtOAc/Hexane) to afford compound OO (280 mg, 0.64 mmol, 46%) and 2-tetrazole (100 mg, 0.23 mmol, 16%) as a white solid. $^1H$ NMR (500 MHz, $CDCl_3$): δ 8.75 (s, 1H), 8.57 (d, J=1.7 Hz, 1H), 7.92 (dd, J=8.7, 2.3 Hz, 1H), 7.44 (d, J=8.7 Hz, 1H), 7.39 (d, J=1.2 Hz, 1H), 7.28 (d, J=1.2 Hz, 1H), 7.21-7.12 (m, 2H), 6.82 (s, 1H), 5.17 (s, 2H).

4-(4-(4-(4-(6-(2-(3-chlorophenyl)-1,1-difluoro-2-hydroxy-3-(1H-tetrazol-1-yl) propyl) pyridin-3-yl) phenyl) piperazin-1-yl) phenyl)-2-((2S,3S)-2-hydroxypentan-3-yl)-2,4-dihydro-3H-1,2,4-triazol-3-one (127)

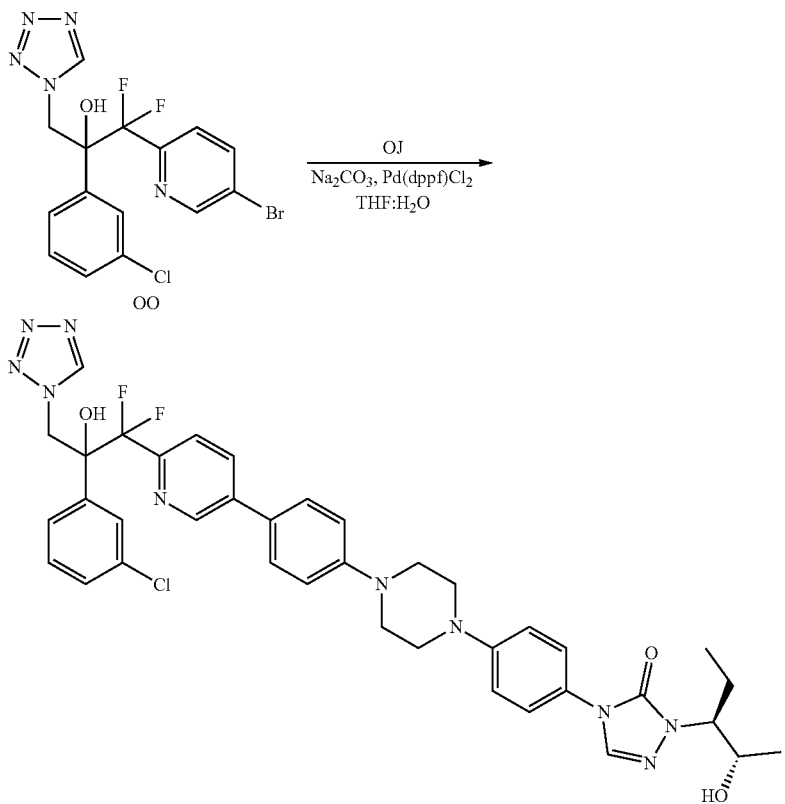

To a stirred solution of compound OO (80 mg, 0.18 mmol) in THF:H2O (4:1, 10 mL) under argon atmosphere were added compound OJ (108 mg, 0.20 mmol), sodium carbonate (59 mg, 0.55 mmol) and purged under argon for 20 min at RT. Then Pd(dppf)Cl$_2$ (13 mg, 0.02 mmol) was added and the reaction mixture was purged under argon for 10 min at RT. The reaction mixture was stirred at reflux for 16 h. The reaction mixture was diluted with water (20 mL) and extracted with EtOAc (2×20 mL). The combined organic extracts were washed with brine (20 mL), dried over anhydrous Na$_2$SO$_4$ and concentrated under reduced pressure. The crude material was purified by silica gel column chromatography (eluent: 0-2% MeOH/CH$_2$Cl$_2$) to afford 127 (61 mg, 0.08 mmol, 43%) as an off-white solid. $^1$H NMR (400 MHz, DMSO-d$_6$): δ 9.04 (s, 1H), 8.93 (d, J=2.0 Hz, 1H), 8.34 (s, 1H), 8.16 (dd, J=8.2, 2.3 Hz, 1H), 7.70 (d, J=8.9 Hz, 2H), 7.53 (d, J=8.9 Hz, 2H), 7.47 (d, J=8.4 Hz, 1H), 7.41-7.22 (m, 4H), 7.16-7.11 (m, 5H), 5.64 (d, J=14.6 Hz, 1H), 5.18 (d, J=14.6 Hz, 1H), 4.66 (d, J=5.0 Hz, 1H), 3.86-3.72 (m, 2H), 3.44-3.32 (m, 8H), 1.74-1.67 (m, 2H), 1.12 (d, J=5.9 Hz, 3H), 0.74 (t, J=7.3 Hz, 3H); MS (ESI): m/z 757.8 [M+H]$^+$; HPLC: 99.18%; Optical rotation [α]$_D^{20}$: −12.68 (c=0.1% in MeOH).

Chiral Preparative HPLC Details for 127(−) and 127(+)

127 (100 mg, 0.13 mmol) was separated by normal-phase preparative high performance liquid chromatography (Chiralpak IA®, 250×20 mm, 5µ; using 0.1% DEA in n-Hexane:(B) CH$_2$Cl$_2$:MeOH (50:50) (40:60); Flow rate: 20 mL/min) to obtain 127(−) (30 mg) and of 127(+) (30 mg)

127(−):
$^1$H NMR (400 MHz, DMSO-d$_6$): δ 9.05 (s, 1H), 8.92 (d, J=1.7 Hz, 1H), 8.33 (s, 1H), 8.15 (dd, J=8.3, 2.1 Hz, 1H), 7.70 (d, J=8.8 Hz, 2H), 7.53 (d, J=9.0 Hz, 2H), 7.47 (d, J=8.3 Hz, 1H), 7.42-7.27 (m, 4H), 7.18-7.10 (m, 5H), 5.64 (d, J=14.6 Hz, 1H), 5.18 (d, J=14.6 Hz, 1H), 4.67-4.65 (m, 1H), 3.86-3.75 (m, 2H), 3.46-3.31 (m, 8H), 1.77-1.59 (m, 2H), 1.12 (d, J=6.0 Hz, 3H), 0.74 (t, J=7.3 Hz, 3H); MS (ESI): m/z 758.1 [M+H]$^+$; HPLC: 98.86%; Chiral HPLC Purity: 100%. R$_t$=13.56 min (CHIRALPAK-IA®, 250×4.6 mm, 5µ; mobile phase (A) 0.1% DEA in n-Hexane:(B) CH$_2$Cl$_2$:MeOH (50:50) (40:60); flow Rate: 1.0 mL/min); Optical rotation [α]$_D^{20}$: −78.56 (c=0.1% in CH$_2$Cl$_2$).

127(−):
$^1$H NMR (400 MHz, DMSO-d$_6$): δ 9.05 (s, 1H), 8.92 (d, J=1.7 Hz, 1H), 8.33 (s, 1H), 8.15 (dd, J=8.3, 2.1 Hz, 1H), 7.70 (d, J=8.8 Hz, 2H), 7.53 (d, J=9.0 Hz, 2H), 7.47 (d, J=8.3 Hz, 1H), 7.42-7.27 (m, 4H), 7.18-7.10 (m, 5H), 5.64 (d, J=14.6 Hz, 1H), 5.18 (d, J=14.6 Hz, 1H), 4.67-4.65 (m, 1H), 3.86-3.75 (m, 2H), 3.46-3.31 (m, 8H), 1.77-1.59 (m, 2H), 1.12 (d, J=6.0 Hz, 3H), 0.74 (t, J=7.3 Hz, 3H); MS (ESI): m/z 758.1 [M+H]$^+$ HPLC: 99.45% Chiral HPLC Purity: 96.68%, R$_t$=15.45 min (CHIRALPAK-IA®, 250×4.6 mm, 5µ; mobile phase (A) 0.1% DEA in n-Hexane:(B) CH$_2$Cl$_2$:MeOH (50:50) (40:60); flow Rate: 1.0 mL/min); Optical rotation [α]$_D^{20}$: +80.92 (c=0.1% in CH$_2$Cl$_2$).

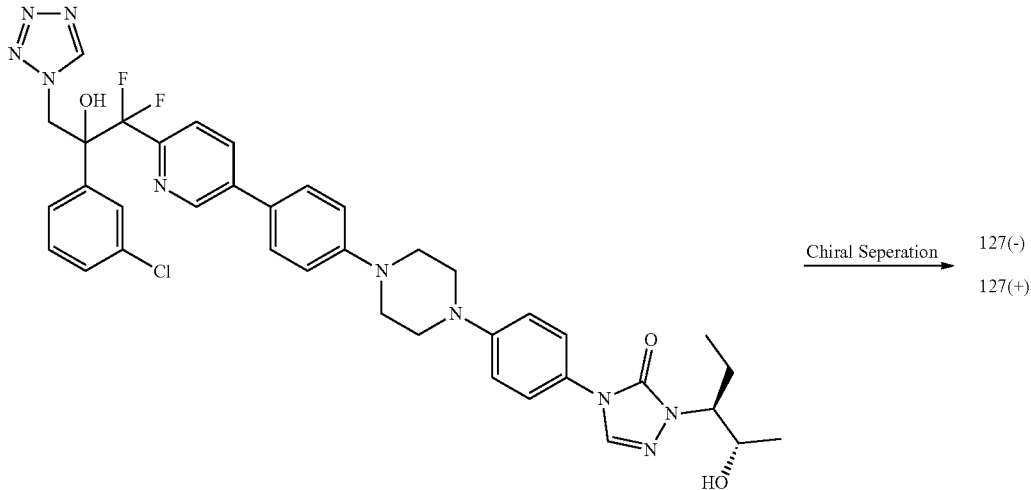

127

Example 128

(+)-(2S,3S)-3-(4-(4-(4-(4-(6-(1,1-difluoro-2-(2-fluorophenyl)-2-hydroxy-3-(1H-tetrazol-1-yl) propyl) pyridin-3-yl) phenyl) piperazin-1-yl) phenyl)-5-oxo-4,5-dihydro-1H-1,2,4-triazol-1-yl) pentan-2-yl dihydrogen phosphate (128)

dibenzyl ((2S,3S)-3-(4-(4-(4-(4-(6-(1,1-difluoro-2-(2-fluorophenyl)-2-hydroxy-3-(1H-tetrazol-1-yl) propyl) pyridin-3-yl) phenyl) piperazin-1-yl) phenyl)-5-oxo-4,5-dihydro-1H-1,2,4-triazol-1-yl) pentan-2-yl) phosphate (OP)

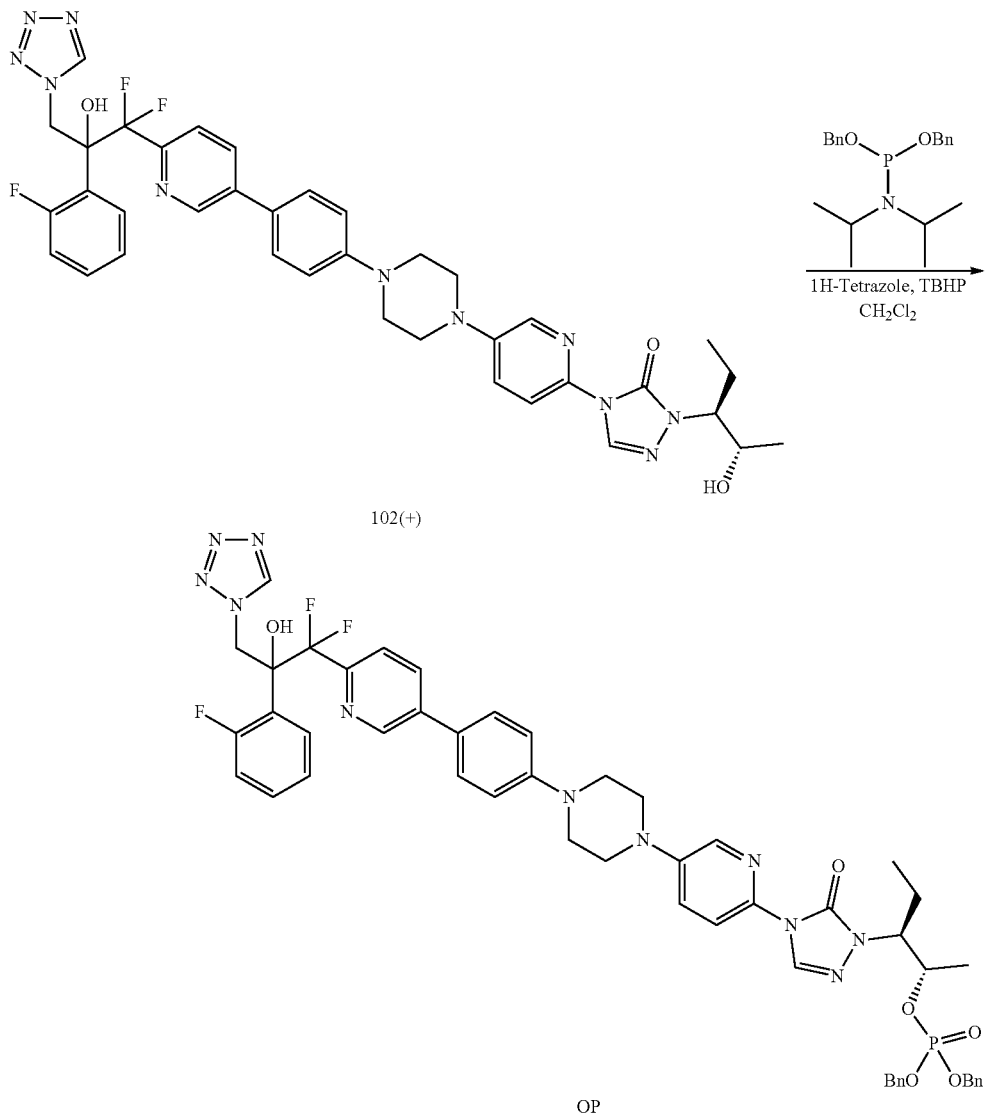

To a stirred solution of compound 102(+) (1.5 g, 2.02 mmol) in CH$_2$Cl$_2$ (30 mL) under argon atmosphere was added 1H-tetrazole (708 mg, 10.12 mmol) at 0° C. The reaction mixture warmed to RT and stirred for 1 h. Then dibenzyl diisopropylphosphoramidite (2.68 mL, 8.096 mmol) was added to the reaction mixture at 0° C. The reaction mixture warmed to RT and stirred for 2 h. The progress of the reaction was monitored by TLC. The reaction mixture was quenched with TBHP solution (1.3 mL) at 0° C., stirred at RT for 1 h, diluted with saturated sodium bicarbonate solution (20 mL) and extracted with CH$_2$Cl$_2$ (2×50 mL). The combined organic layers were dried over anhydrous Na$_2$SO$_4$ and concentrated under reduced pressure to obtain compound OP. The crude compound (1.1 g with 75% HPLC purity) was purified by column chromatography followed by HPLC to afford 2 (380 mg, 0.379, 19%) as a pale yellow solid. $^1$H NMR (400 MHz, DMSO-d$_6$): δ 9.12 (s, 1H), 8.92 (s, 1H), 8.52 (s, 1H), 8.21 (d, J=2.5 Hz, 1H), 8.15 (dd, J=8.5, 1.4 Hz, 1H), 7.94 (d, J=9.0 Hz, 1H), 7.71 (d, J=8.7 Hz, 2H), 7.62 (dd, J=9.1, 2.7 Hz, 1H), 7.46 (d, J=8.2 Hz, 1H), 7.39-7.23 (m, 10H), 7.22-7.08 (m, 6H), 7.02 (t, J=7.6 Hz, 1H), 5.71 (d, J=14.6 Hz, 1H), 5.11 (br d, J=14.6 Hz, 1H), 4.97-4.87 (m, 2H), 4.87-4.78 (m, 2H), 4.70-4.62 (m, 1H), 4.17-4.07 (m, 1H), 3.45-3.43 (m, 8H), 1.86-1.71 (m, 2H), 1.35 (d, J=6.3 Hz, 3H), 0.77 (t, J=7.2 Hz, 3H).

(+)-(2S,3S)-3-(4-(4-(4-(4-(6-(1,1-difluoro-2-(2-fluorophenyl)-2-hydroxy-3-(1H-tetrazol-1-yl) propyl) pyridin-3-yl) phenyl) piperazin-1-yl) phenyl)-5-oxo-4,5-dihydro-1H-1,2,4-triazol-1-yl) pentan-2-yl dihydrogen phosphate (128)

To a stirred solution of compound OP (380 mg, 0.379 mmol) in EtOH (30 mL) under argon atmosphere was added 10% Pd/C (190 mg) at RT and stirred for 4 h under hydrogen atmosphere (balloon pressure). The progress of the reaction was monitored by TLC. The reaction mixture was filtered through celite, the filtrate was concentrated under reduced pressure. The residue was washed with n-pentane to afford 128 (250 mg, 0.304 mmol, 80%) as yellow solid. $^1$H NMR (400 MHz, CD$_3$OD): δ 9.02 (s, 1H), 8.80 (d, J=2.0 Hz, 1H), 8.43 (s, 1H), 8.22 (d, J=2.9 Hz, 1H), 8.06 (dd, J=8.3, 2.3 Hz, 1H), 8.01 (d, J=9.0 Hz, 1H), 7.63 (d, J=8.8 Hz, 2H), 7.60 (d, J=3.0 Hz, 1H), 7.50 (dd, J=8.3, 0.6 Hz, 1H), 7.37-7.26 (m, 2H), 7.17 (d, J=8.9 Hz, 2H), 7.08-6.93 (m, 2H), 5.80 (d, J=14.6 Hz, 1H), 5.23 (d, J=14.6 Hz, 1H), 4.67-4.57 (m, 1H), 4.16-4.11 (m, 1H), 3.49-3.40 (m, 8H), 2.04-1.90 (m, 1H), 1.88-1.81 (m, 1H), 1.42 (d, J=6.4 Hz, 3H), 0.87 (t, J=7.3 Hz, 3H); $^{31}$P NMR (400 MHz, CD$_3$OD): −δ 0.56 (s); MS (ESI): m/z 822.8 [M+H]$^+$; HPLC: 95.09%; Optical rotation $[α]_D^{19}$: +14.68 (c=0.1% in MeOH).

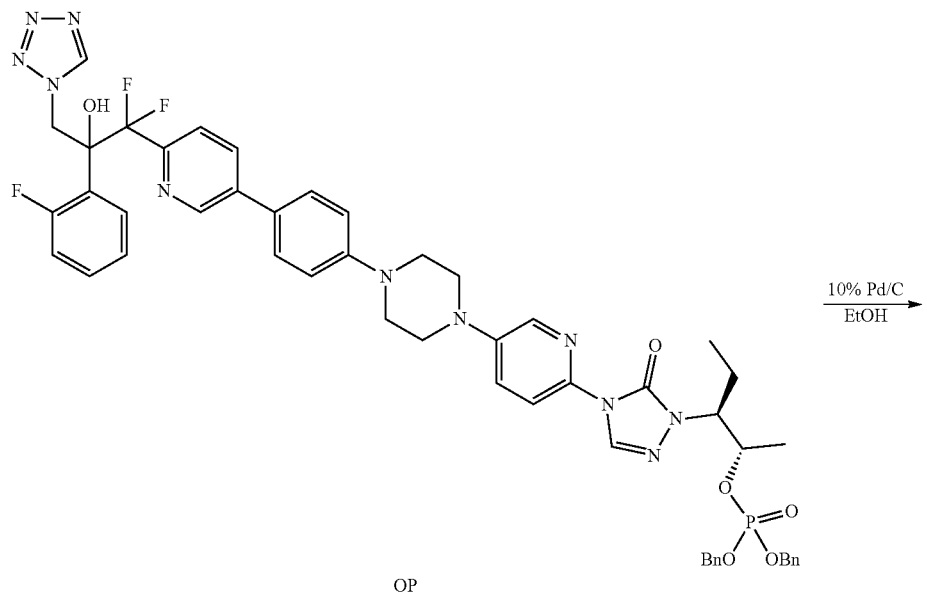

OP

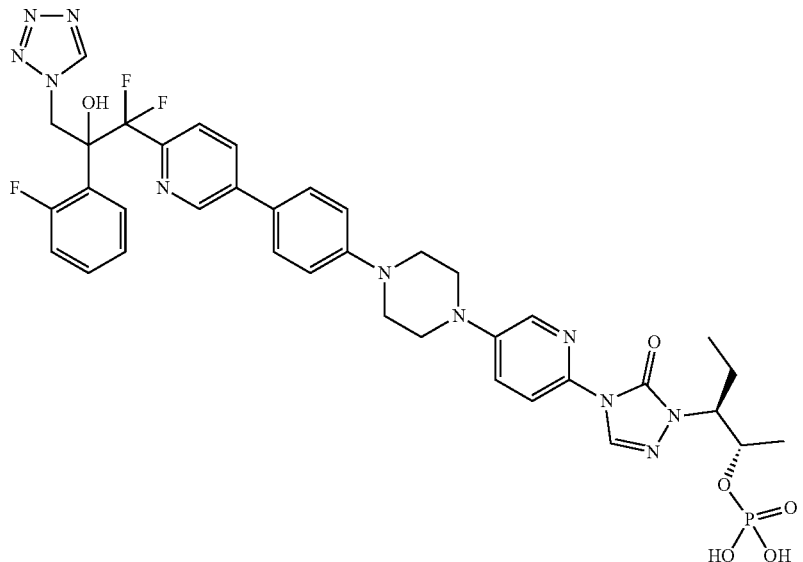

128

Example 129

1-(1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-4-yl)-2,2,2-trifluoroethyl dihydrogen phosphate (129)

dibenzyl (1-(1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-4-yl)-2,2,2-trifluoroethyl) phosphate (OQ)

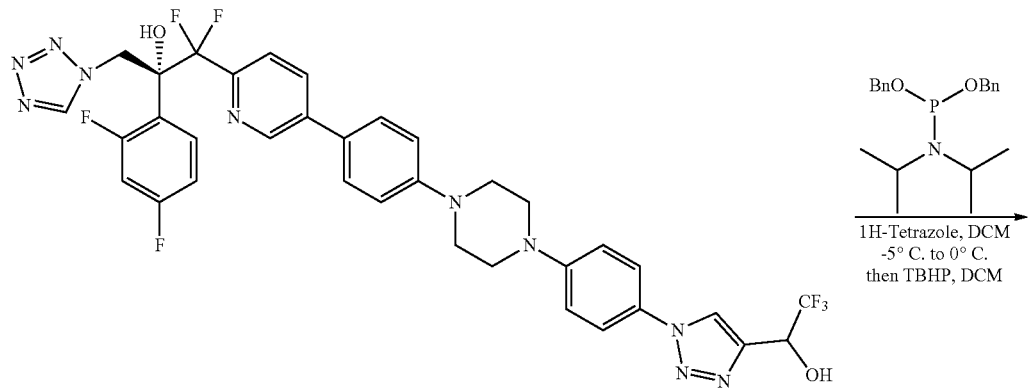

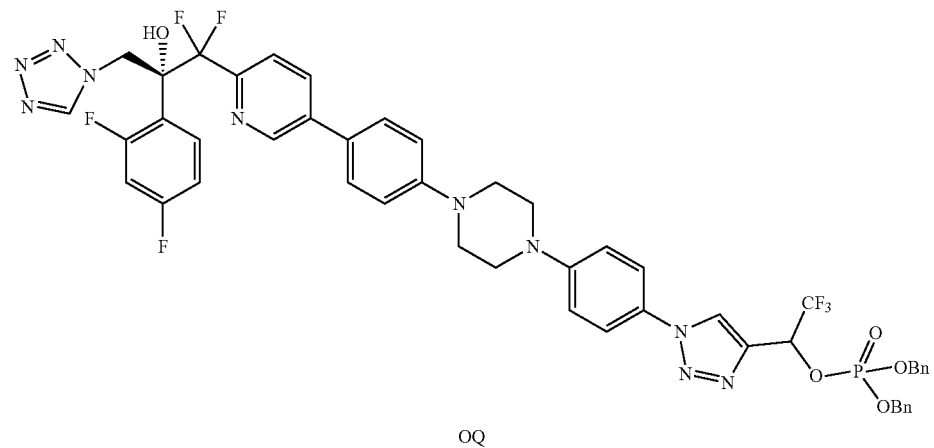

To a stirred solution of 94 (200 mg, 0.26 mmol) in CH$_2$Cl$_2$ (30 mL) under argon atmosphere was added 1H-tetrazole (91 mg, 1.32 mmol) at 0° C. The reaction mixture warmed to RT and stirred for 1 h. Then dibenzyl diisopropylphosphoramidite (0.34 mL, 1.06 mmol) was added to the reaction mixture at −5° C.-0° C. The reaction mixture slowly warmed to RT and stirred for 4 h. The progress of the reaction was monitored by TLC; then the reaction mixture was quenched with TBHP solution (1 mL) at −5° C.-0° C., stirred at RT for 1 h, diluted with saturated sodium bicarbonate solution (20 mL) and extracted with CH$_2$Cl$_2$ (2×20 mL). The combined organic layers were dried over anhydrous Na$_2$SO$_4$ and concentrated under reduced pressure to obtain crude. The crude compound was purified by column chromatography followed by HPLC to afford OQ (50 mg, 0.049, 18% overall yield) as colorless semi-solid. $^1$H NMR (400 MHz, DMSO-d$_6$): δ 9.15 (s, 1H), 8.91 (s, 1H), 8.79 (s, 1H), 8.17 (dd, J=8.2, 2.1 Hz, 1H), 7.78-7.71 (m, 4H), 7.49 (d, J=8.2 Hz, 1H), 7.38-7.23 (m, 10H), 7.24-7.12 (m, 8H), 6.93-6.89 (m, 1H), 6.30-6.37 (m, 1H), 5.67 (d, J=14.6 Hz, 1H), 5.17-5.09 (m, 3H), 5.01 (d, J=14.8 Hz, 1H), 3.43 (s, 8H); $^{31}$P NMR (400 MHz, DMSO-d$_6$): 3-1.93 (s).

1-(1-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-4-yl)-2,2,2-trifluoroethyl dihydrogen phosphate (129)

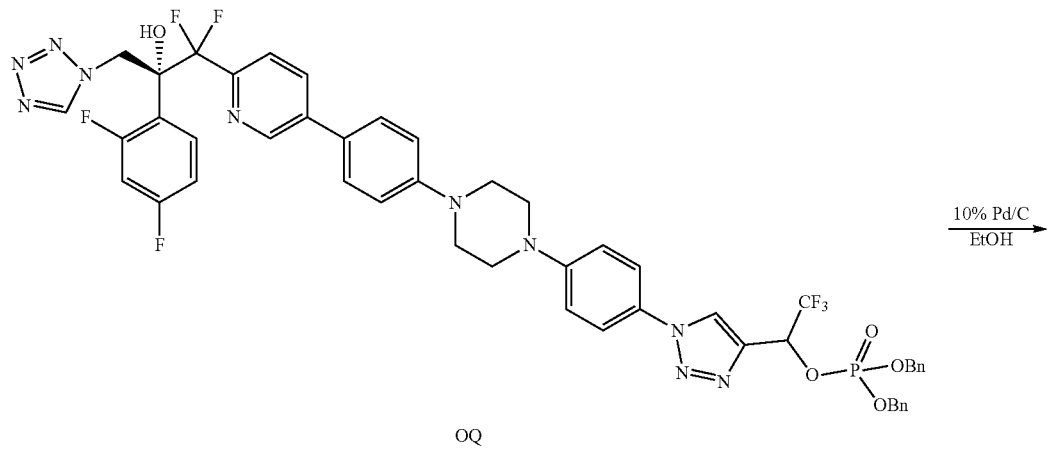

OQ

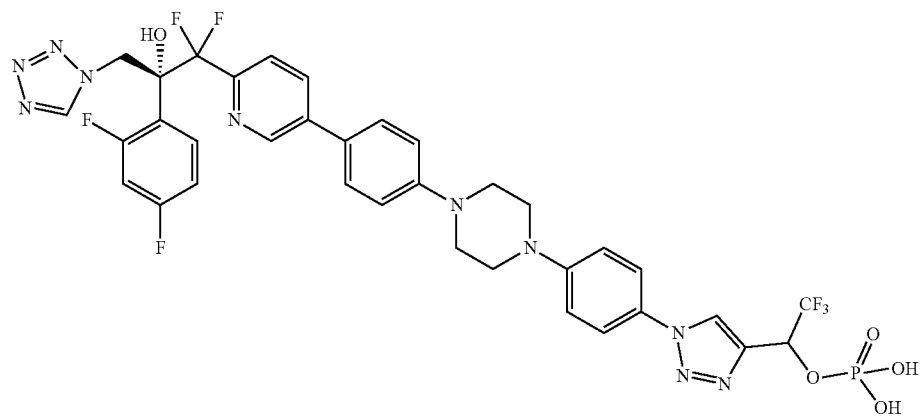

129

To a stirred solution of compound OQ (50 mg, 0.049 mmol) in EtOH (10 mL) under argon atmosphere was added 10% Pd/C (30 mg) at RT and stirred for 4 h under hydrogen atmosphere (50 psi). The progress of the reaction was monitored by TLC/LC-MS; the reaction mixture was filtered through celite, the filtrate was concentrated under reduced pressure. The residue was washed with n-pentane to afford 129 (10 mg, 0.011 mmol, 22%) as an off-white solid. $^1$H NMR (400 MHz, DMSO-$d_6$): δ 9.02 (s, 1H), 8.80 (s, 1H), 8.66 (s, 1H), 8.17 (dd, J=8.3, 2.3 Hz, 1H), 7.77 (d, J=8.9 Hz, 2H), 7.67 (dd, J=9.3, 3.0 Hz, 2H), 7.52 (d, J=8.2 Hz, 1H), 7.33-7.25 (m, 1H), 7.23-7.18 (m, 4H), 6.93-6.88 (m, 1H), 6.79-6.74 (m, 1H), 5.96-5.87 (m, 1H), 5.67 (d, J=14.6 Hz, 1H), 5.19 (d, J=14.6 Hz, 1H), 3.43 (s, 8H); MS (ESI): m/z 835.3 [M+H]$^+$; HPLC: 90.63%; Optical rotation $[α]_D^{20}$: +15.04 (c=0.1% in MeOH).

Example 130

(+)-(2S,3S)-3-(4-(5-(4-(4-(6-((R)-1,1-difluoro-2-(2-fluorophenyl)-2-hydroxy-3-(1H-tetrazol-1-yl) propyl) pyridin-3-yl) phenyl) piperazin-1-yl) pyridin-2-yl)-5-oxo-4,5-dihydro-1H-1,2,4-triazol-1-yl) pentan-2-yl) dimethylglycinate (130)

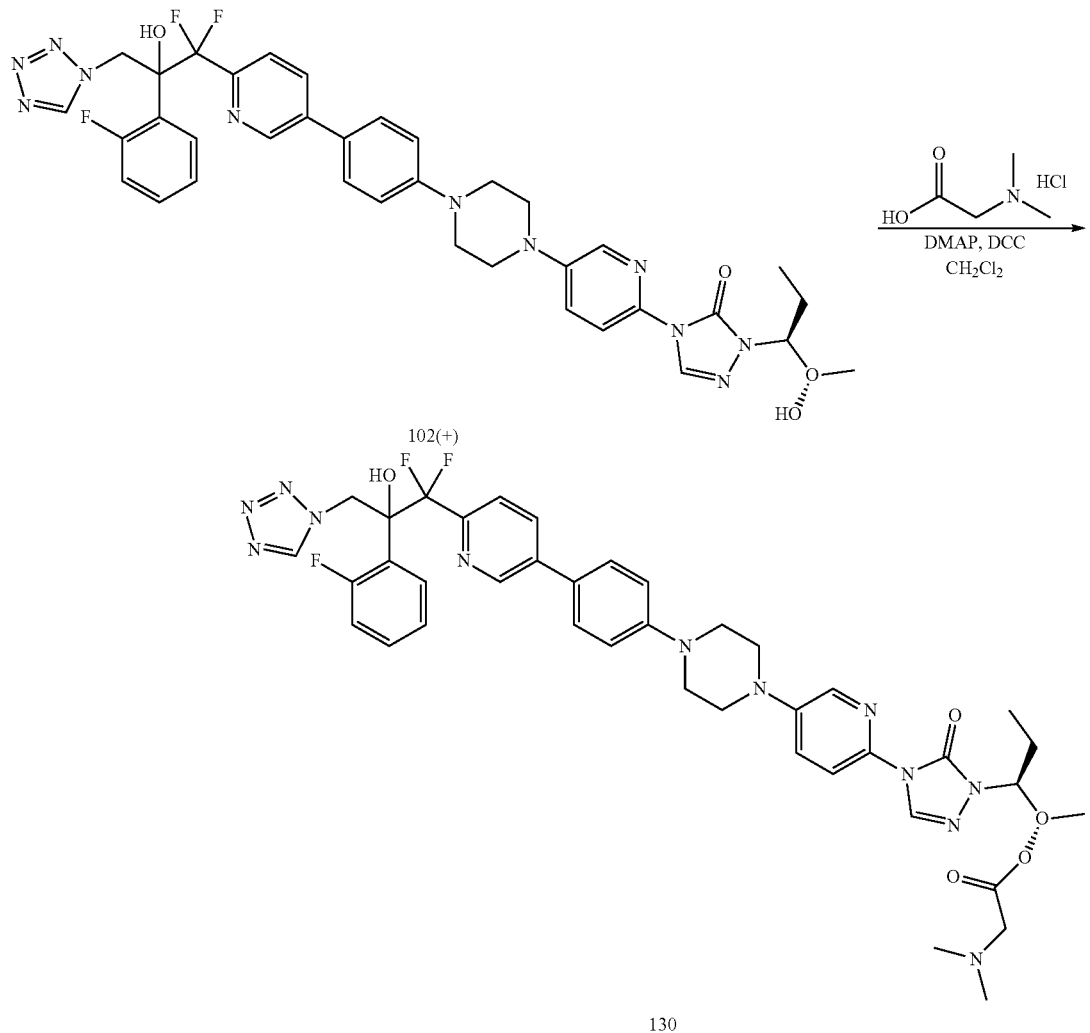

To a stirred solution of 102(+) (50 mg, 0.06 mmol) in CH$_2$Cl$_2$ (10 mL) under argon atmosphere were added dimethylglycine hydrochloride (10 mg, 0.07 mmol), dimethyl amino pyridine (12.4 mg 0.10 mmol) and DCC (21 mg, 0.10 mmol) at 0° C. The reaction mixture was warmed to RT and stirred for 48 h. The progress of the reaction was monitored by TLC; the reaction was diluted with water (50 mL) and extracted with CH$_2$Cl$_2$(2×50 mL). The combined organic layers were washed with water (2×50 mL), dried over anhydrous Na$_2$SO$_4$ and concentrated under reduced pressure. The crude compound was purified by preparative HPLC to afford 130 (15 mg, 0.02 mmol, 27%) as a pale yellow solid. $^1$H NMR (400 MHz, CDCl$_3$): δ 8.77 (s, 1H), 8.75 (d, J=2.0 Hz, 1H), 8.33 (s, 1H), 8.12 (d, J=8.0 Hz, 2H), 7.93 (dd, J=8.2, 2.2 Hz, 1H), 7.56 (s, 1H), 7.53 (d, J=8.9 Hz, 2H), 7.41 (dd, J=9.1, 2.8 Hz, 1H), 7.38-7.35 (m, 1H), 7.25-7.19 (m, 1H), 7.08 (d, J=8.8 Hz, 2H), 7.05-6.99 (m, 1H), 6.96-6.91 (m, 1H), 5.67 (d, J=14.2 Hz, 1H), 5.39-5.32 (m, 1H), 5.18 (d, J=14.2 Hz, 1H), 4.24-4.19 (m, 1H), 3.93-3.77 (m, 2H), 3.53-3.36 (m, 8H), 2.90 (s, 6H), 2.03-1.90 (m, 1H), 1.83-1.75 (m, 1H), 1.38 (d, J=6.5 Hz, 3H), 0.90 (t, J=7.3 Hz, 3H); LC-MS: 827.4 [M+H]$^+$ at 3.36 RT (92.2% purity); HPLC: 93.66%.

Example 131: Metalloenzyme Activity

A. Minimum Inhibitory Concentration (MIC)

The antifungal potency of the test compounds was measured using the in vitro broth microdilution assay under assay conditions described by the Clinical and Laboratory Standards Institute (CLSI M27-A2). The test compounds were dissolved in 100% DMSO, suspended completely by sonication or vortexing, diluted by 2-fold serial titrations in the same vehicle, for a total of 11 test concentrations. A 4 μL aliquot of each dilution was added to 196 μL of RPMI-1640+MOPS medium seeded with the *C. albicans* (ATCC 90028) suspension in wells of a 96 well plate (fungal cell count: $1 \times 10^3$ to $1 \times 10^4$ colony forming units per mL). The final volume was 200 μL in each well and the final DMSO concentration was 2 percent. The inoculated plates were incubated for 2 days at 36° C. Following incubation, the test plates were visually examined and wells were scored for growth to define the minimum inhibitory concentration. The test compound concentration ranges was 8-0.0078 μg/mL and the MIC was reported as the concentration at which growth was significantly reduced (about 50% reduction). Each test substance was evaluated in duplicate. Vehicle-control and an active reference agent (e.g., posaconazole) were used as blank and positive controls, respectively.

*A. fumigatus* MICs were determined at 100% growth inhibition following CLSI guidelines at a concentration range of 8-0.0078 μg/mL (CLSI M38-A2).

Results: Antifungal Activity

| Example Number | *Candida albicans* MIC (μg/mL) | *Aspergillus fumigatus* MIC (μg/mL) |
|---|---|---|
| 1 | ≤0.0078-0.010 | 0.25-1.0 |
| 2 | ≤0.0078-0.010 | 0.25-1.0 |
| 3 | ≤0.0078-0.010 | 0.25-1.0 |
| 4 | 0.010-0.10 | 0.25-1.0 |
| 5 | ≤0.0078-0.010 | 0.25-1.0 |
| 6 | ≤0.0078-0.010 | 0.25-1.0 |
| 6-Fr-I | 0.010-0.10 | 0.25-1.0 |
| 6-Fr-II | ≤0.0078-0.010 | 0.25-1.0 |
| 7 | ≤0.0078-0.010 | 0.25-1.0 |
| 8 | ≤0.0078-0.010 | 0.25-1.0 |
| 9 | ≤0.0078-0.010 | >8 |
| 10 | ≤0.0078-0.010 | >8 |
| 11 | ≤0.0078-0.010 | 0.25-1.0 |
| 12 | ≤0.0078-0.010 | 0.25-1.0 |
| 13 | ≤0.0078-0.010 | 0.25-1.0 |
| 13-Fr-I | ≤0.0078-0.010 | 0.062-0.25 |
| 13-Fr-II | ≤0.0078-0.010 | 0.062-0.25 |
| 14 | 0.010-0.10 | >8 |
| 15(−) | 0.10-1.0 | >8 |
| 15(+) | ≤0.0078-0.010 | 0.25-1.0 |
| 16 | ≤0.0078-0.010 | 0.25-1.0 |
| 17 | ≤0.0078-0.010 | 1.0-4.0 |
| 18 | ≤0.0078-0.010 | >8 |
| 19 | ≤0.0078-0.010 | >8 |
| 20 | ≤0.0078-0.010 | 1.0-4.0 |
| 21 | 0.010-0.10 | 0.25-1.0 |
| 22 | ≤0.0078-0.010 | 0.25-1.0 |
| 23 | ≤0.0078-0.010 | >8 |
| 24 | ≤0.0078-0.010 | >8 |
| 25 | ≤0.0078-0.010 | 0.25-1.0 |
| 26 | ≤0.0078-0.010 | 0.25-1.0 |
| 27 | 0.010-0.10 | >8 |
| 28 | ≤0.0078-0.010 | >8 |
| 29 | 0.010-0.10 | >8 |
| 30 | ≤0.0078-0.010 | 0.25-1.0 |
| 32 | 0.10-1.0 | 0.25-1.0 |
| 33 | 0.010-0.10 | 1.0-4.0 |
| 34 | ≤0.0078-0.010 | 0.25-1.0 |
| 35 | ≤0.0078-0.010 | 0.25-1.0 |
| 36 | ≤0.0078-0.010 | >8 |
| 37 | 0.010-0.10 | >8 |
| 38(−) | 0.10-1.0 | >8 |
| 38(+) | ≤0.0078-0.010 | 0.062-0.25 |
| 39 | 0.010-0.10 | 0.25-1.0 |
| 40 | ≤0.0078-0.010 | 0.25-1.0 |
| 41 | ≤0.0078-0.010 | 0.25-1.0 |
| 42 | ≤0.0078-0.010 | >8 |
| 43 | ≤0.0078-0.010 | 0.25-1.0 |
| 44 | ≤0.0078-0.010 | 1.0-4.0 |
| 45 | ≤0.0078-0.010 | 0.25-1.0 |
| 46 | ≤0.0078-0.010 | >8 |
| 47 | 0.010-0.10 | 0.25-1.0 |
| 48 | 0.010-0.10 | 0.25-1.0 |
| 49 | 0.010-0.10 | 0.062-0.25 |
| 50 | 0.010-0.10 | 0.25-1.0 |
| 51 | ≤0.0078-0.010 | 1.0-4.0 |
| 52 | ≤0.0078-0.010 | 0.062-0.25 |
| 53 | 0.010-0.10 | 0.062-0.25 |
| 54 | 0.010-0.10 | 0.062-0.25 |
| 55 | 0.010-0.10 | 0.062-0.25 |
| 56 | 0.010-0.10 | 0.25-1.0 |
| 57 | 0.010-0.10 | 0.25-1.0 |
| 58 | ≤0.0078-0.010 | 0.062-0.25 |
| 59 | ≤0.0078-0.010 | 0.25-1.0 |
| 60 | ≤0.0078-0.010 | 0.25-1.0 |
| 61 | 0.010-0.10 | 0.25-1.0 |
| 62 | ≤0.0078-0.010 | 0.25-1.0 |
| 63(+) | 0.010-0.10 | 0.062-0.25 |
| 64(+) | 0.010-0.10 | 0.25-1.0 |
| 65 | ≤0.0078-0.010 | 0.25-1.0 |
| 66 | ≤0.0078-0.010 | 0.25-1.0 |
| 67 | ≤0.0078-0.010 | 0.062-0.25 |
| 68 | ≤0.0078-0.010 | 0.25-1.0 |
| 69 | 0.010-0.10 | >8 |
| 70 | 0.010-0.10 | 0.25-1.0 |
| 71 | ≤0.0078-0.010 | 0.25-1.0 |
| 72 | ≤0.0078-0.010 | 0.25-1.0 |
| 73 | ≤0.0078-0.010 | >8 |
| 74 | ≤0.0078-0.010 | >8 |
| 75 | ≤0.0078-0.010 | 0.062-0.25 |
| 76 | ≤0.0078-0.010 | >8 |
| 77 | 0.010-0.10 | 0.25-1.0 |
| 78 | 0.010-0.10 | >8 |
| 79 | ≤0.0078-0.010 | 0.25-1.0 |
| 80 | ≤0.0078-0.010 | >8 |
| 81 | ≤0.0078-0.010 | 0.25-1.0 |
| 82 | 0.010-0.10 | 0.062-0.25 |
| 83 | 0.010-0.10 | 0.25-1.0 |
| 84(+) | >8 | 1.0-4.0 |
| 85(+) | 0.10-1.0 | >8 |
| 86 | ≤0.0078-0.010 | 0.25-1.0 |
| 87 | ≤0.0078-0.010 | 0.062-0.25 |
| 88 | 0.010-0.10 | >8 |
| 89 | 0.010-0.10 | 0.25-1.0 |
| 90 | ≤0.0078-0.010 | >8 |
| 91 | ≤0.0078-0.010 | 0.25-1.0 |
| 92 | ≤0.0078-0.010 | 0.25-1.0 |
| 93 | ≤0.0078-0.010 | 0.25-1.0 |
| 94 | ≤0.0078-0.010 | 0.25-1.0 |
| 94-Fr-I | ≤0.0078-0.010 | 0.25-1.0 |
| 94-Fr-II | ≤0.0078-0.010 | 0.25-1.0 |
| 95 | ≤0.0078-0.010 | 0.25-1.0 |
| 96 | ≤0.0078-0.010 | 0.25-1.0 |
| 97 | ≤0.0078-0.010 | 0.25-1.0 |
| 98 | 0.010-0.10 | >8 |
| 99 | ≤0.0078-0.010 | 0.25-1.0 |
| 100 | ≤0.0078-0.010 | 0.25-1.0 |
| 101 | 0.10-1.0 | >8 |
| 102(−) | 0.10-1.0 | >8 |
| 102(+) | ≤0.0078-0.010 | 0.25-1.0 |
| 103 | ≤0.0078-0.010 | 0.062-0.25 |
| 104 | ≤0.0078-0.010 | 0.25-1.0 |
| 105 | ≤0.0078-0.010 | >8 |
| 106(+) | >8 | >8 |
| 107 | >8 | >8 |
| 108(−) | >8 | >8 |
| 108(+) | ≤0.0078-0.010 | 0.25-1.0 |
| 109(−) | 0.10-1.0 | 1.0-4.0 |
| 109(+) | ≤0.0078-0.010 | 0.25-1.0 |
| 110(−) | >8 | >8 |
| 110(+) | ≤0.0078-0.010 | 0.25-1.0 |
| 111 | ≤0.0078-0.010 | 0.25-1.0 |
| 115 | >8 | >8 |
| 116 | >8 | >8 |
| 117 | >8 | >8 |
| 118 | ≤0.0078-0.010 | 0.25-1.0 |
| 119(−) | 0.10-1.0 | >8 |

-continued

| Example Number | Candida albicans MIC (µg/mL) | Aspergillus fumigatus MIC (µg/mL) |
|---|---|---|
| 119(+) | ≤0.0078-0.010 | 0.25-1.0 |
| 120(−) | 0.010-0.10 | 0.25-1.0 |
| 120(+) | ≤0.0078-0.010 | 0.062-0.25 |
| 121(−) | 0.10-1.0 | >8 |
| 121(+) | ≤0.0078-0.010 | 0.25-1.0 |
| 122(−) | 1.0-8.0 | >8 |
| 122(+) | ≤0.0078-0.010 | 0.25-1.0 |
| 123(−) | 0.010-0.10 | 0.25-1.0 |
| 123(+) | 0.010-0.10 | 0.062-0.25 |
| 124 | 0.010-0.10 | 0.25-1.0 |
| 125 | >8 | >8 |
| 126 | 1.0-8.0 | >8 |
| 127 | 0.10-1.0 | >8 |

Example 132: Hedgehog Signalling Pathway Activity

Hedgehog signaling pathway Gli Reporter-NIH3T3 cells were cultured in DMEM medium with 10% Calf serum, 1% Penn-strep, 500 µg/ml of Geneticin.

To perform the Gli luciferase reporter assay, Gli Reporter—NIH3T3 cells were seeded at 25,000 cells per well into white clear-bottom 96-well microplate in 100 µl of growth medium. Cells were incubated at 37° C., and 5% $CO_2$ for overnight. The next day, remove the medium from wells and add 45 µl of diluted inhibitor in assay medium (Opti-MEM Reduced Serum Medium+0.5% calf serum+1% non-essential amino acids+1 mM Na-pyruvate+10 mM HEPES+1% Pen/Strep) per well. Incubate cells at 37° C. in a $CO_2$ incubator for 2 hours. Then add 5 µl of diluted mShh in assay medium to wells (final [mShh]=1 µg/ml). Add 50 µl of assay medium to cell-free control wells. Cells were treated for 27 hours. After treatment, cells were lysed and luciferase assay was performed using ONE-Step luciferase assay system: add 50 µl of One-Step Luciferase reagent per well and rock at room temperature for ~30 minutes. Luminescence was measured using a luminometer (BioTek Synergy™ 2 microplate reader). Compounds of the present invention are active in blockade of hedgehog signalling.

Results: Hedgehog Inhibitory Activity

| Example Number | Hedgehog $IC_{50}$ (µM) |
|---|---|
| 12 | 0.4 |
| 20 | 0.19 |
| 28 | 0.58 |
| 36 | 0.85 |
| 38 | 0.038 |
| 38(−) | 0.059 |
| 38(+) | 0.12 |
| 63(+) | 0.15 |
| 64(+) | 0.16 |
| 84(+) | 0.46 |
| 85(+) | 0.253 |
| 101 | 0.217 |
| 106(+) | 0.31 |
| 107 | 0.27 |
| 115 | 0.51 |
| 116 | 0.16 |
| 117 | 0.092 |
| 125 | 0.092 |
| 126 | 0.19 |
| 127 | 0.02 |

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A compound of Formula (I), or salt thereof:

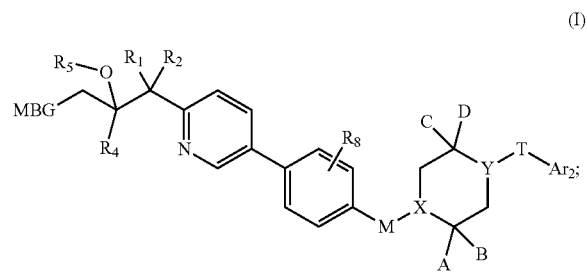

wherein MBG is optionally substituted tetrazolyl, optionally substituted triazolyl, optionally substituted oxazolyl, optionally substituted pyrimidinyl, optionally substituted thiazolyl, or optionally substituted pyrazolyl;

$R_1$ is halo or alkyl;

$R_2$ is halo or alkyl;

or $R_1$, $R_2$, and the carbon atom to which they are attached form an optionally substituted cycloalkyl;

$R_4$ is independently aryl, heteroaryl, cycloalkyl, or arylalkyl, each substituted with 0, 1, 2 or 3 independent $R_6$;

$R_5$ is H, alkyl, phosphato, phosphito, alkoxyphosphato, or —C(O)alkyl optionally substituted with 1 or 2 $NH_2$;

each $R_6$ is independently optionally substituted alkyl, cyano, haloalkyl, alkoxy, halo, or haloalkoxy;

$R_8$ is hydrogen or halo;

M is —$(CH_2)_o$— or —(C=O)—;

o is 0, 1, 2, or 3;

T is —$(CH_2)_s$— or —(C=O)—;

s is 0, 1, 2, or 3;

each X and Y is independently $CR_9$ or N;

A and B are each hydrogen; or A, B, and the carbon to which they are attached form a carbonyl;

C and D are each hydrogen; or C, D, and the carbon to which they are attached form a carbonyl;

$Ar_2$ is aryl, heteroaryl, heterocycloalkyl, each independently substituted with 0, 1, 2, or 3 independent $R_9$, cyano, halo, haloalkyl, $NH_2$, alkoxy, haloalkoxy, optionally substituted arylalkyl,

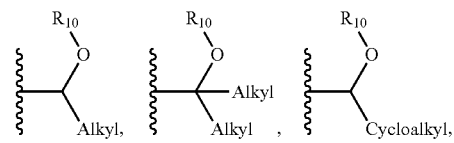

-continued

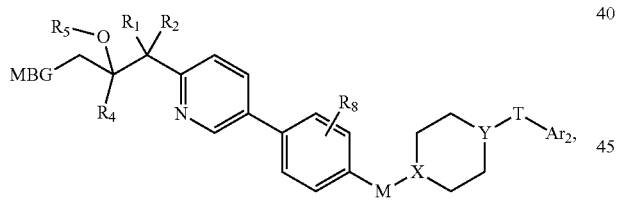

each p is independently 0, 1, 2, or 3;

each $R_9$ is independently optionally substituted alkyl or hydrogen; and each $R_{10}$ is independently H, alkyl, phosphato, phosphito, alkoxyphosphato, or —C(O)alkyl optionally substituted with 1 or 2 independent $NH_2$.

2. The compound of claim 1, according to Formula (II):

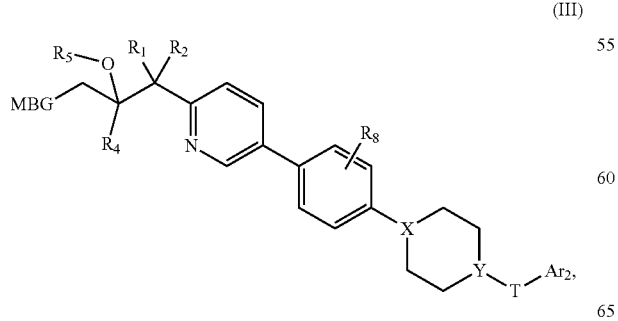
(II)

or salt thereof.

3. The compound of claim 2, according to Formula (III):

(III)

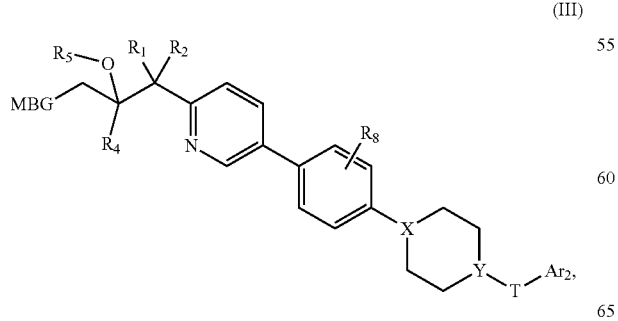

or salt thereof.

4. The compound of claim 3, or salt thereof, wherein $Ar_2$ is:

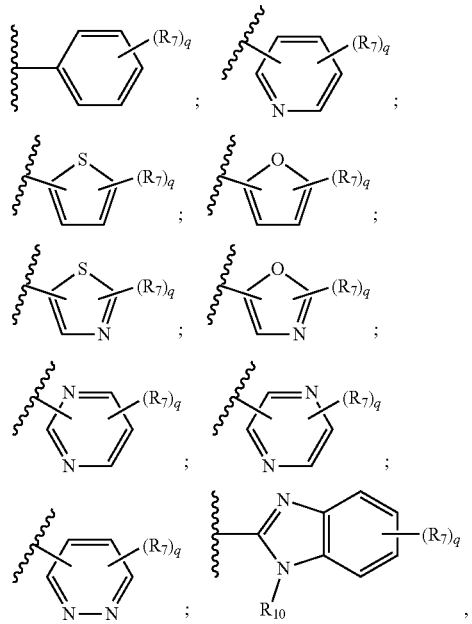

wherein each $R_7$ is independently $R_9$, cyano, halo, haloalkyl, $NH_2$, alkoxy, haloalkoxy, optionally substituted arylalkyl,

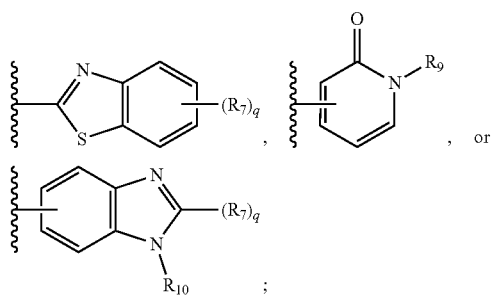

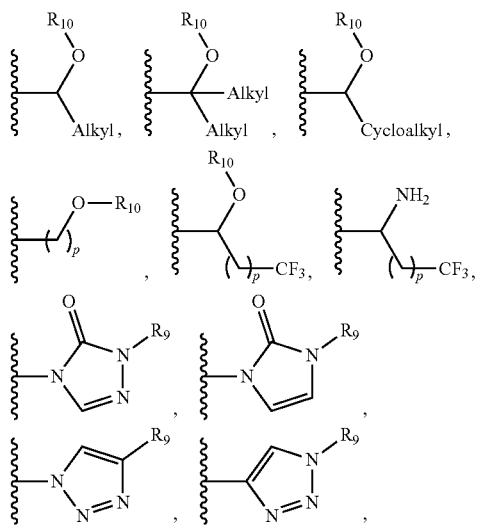

-continued
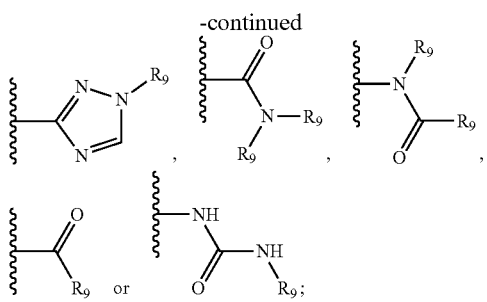
each p is independently 0, 1, 2, or 3;
each q is independently 0, 1, 2, or 3;
each $R_9$ is independently optionally substituted alkyl or hydrogen; and
each $R_{10}$ is independently H, alkyl, phosphato, phosphito, alkoxyphosphato, or —C(O)alkyl optionally substituted with 1 or 2 amino.
5. The compound of claim 3, or salt thereof, wherein $Ar_2$ is:
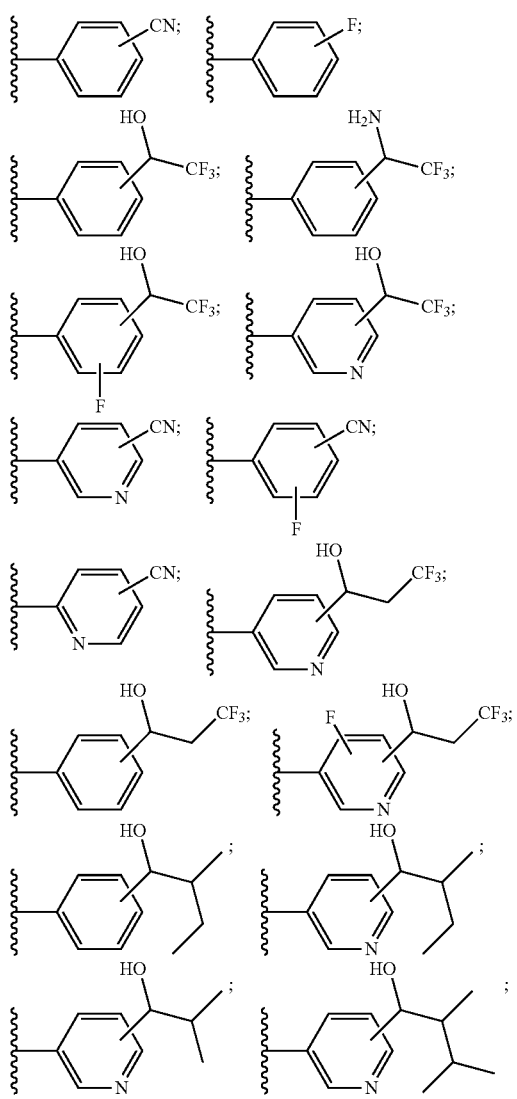
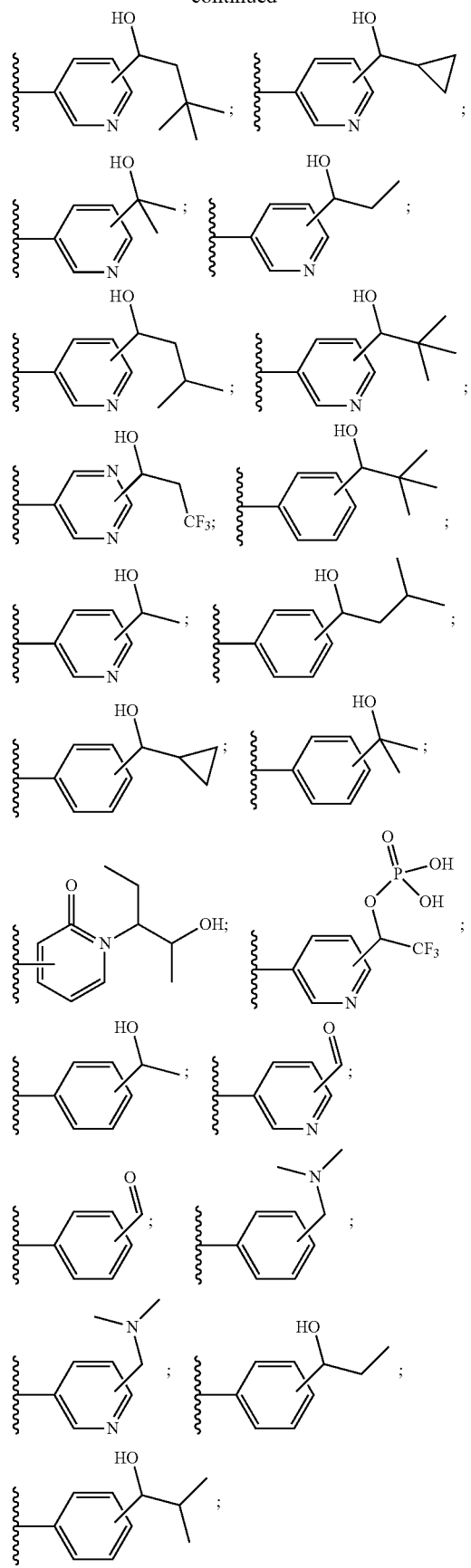

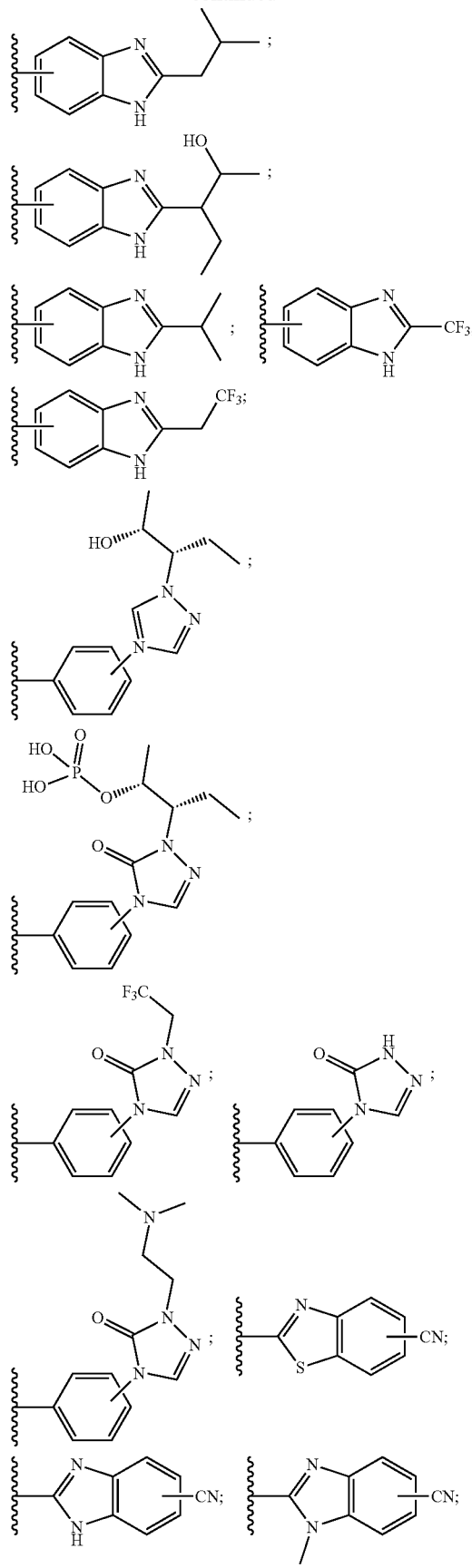
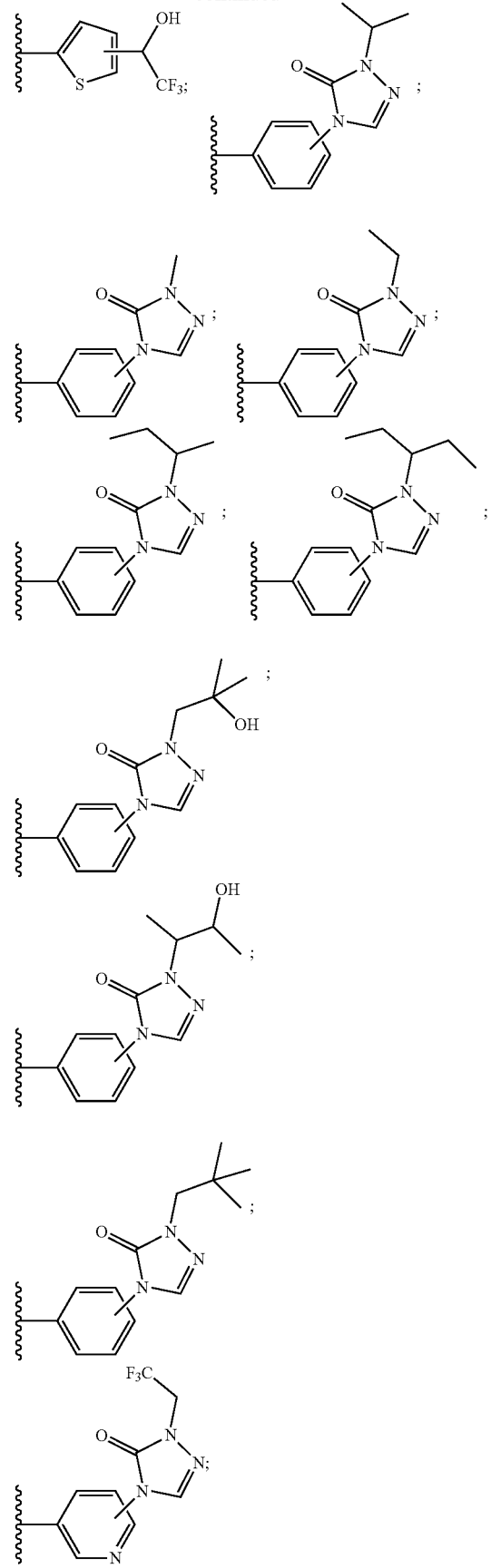

-continued
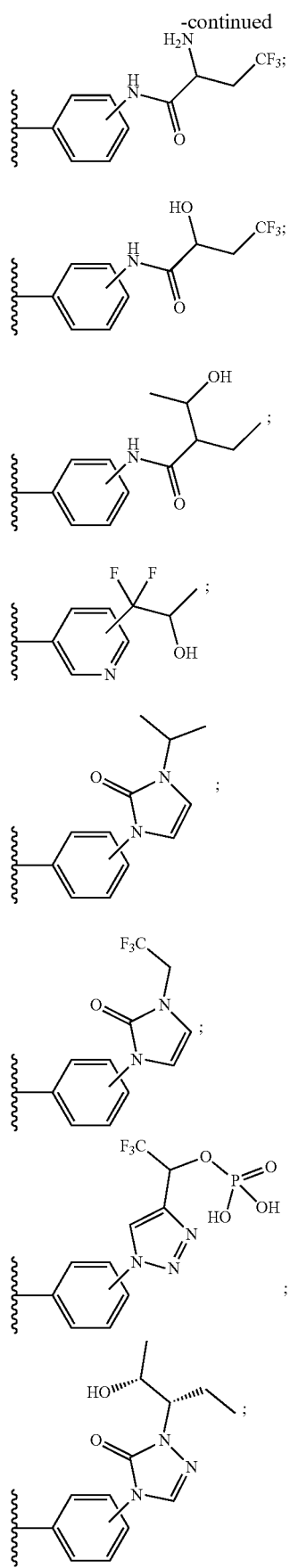
-continued
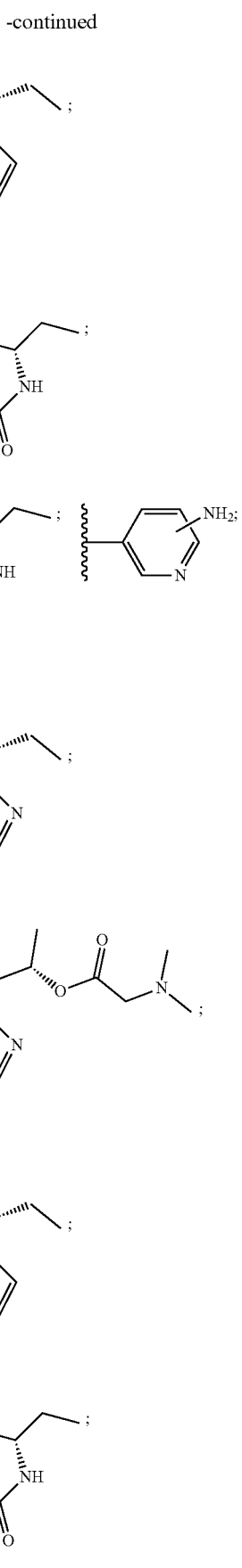

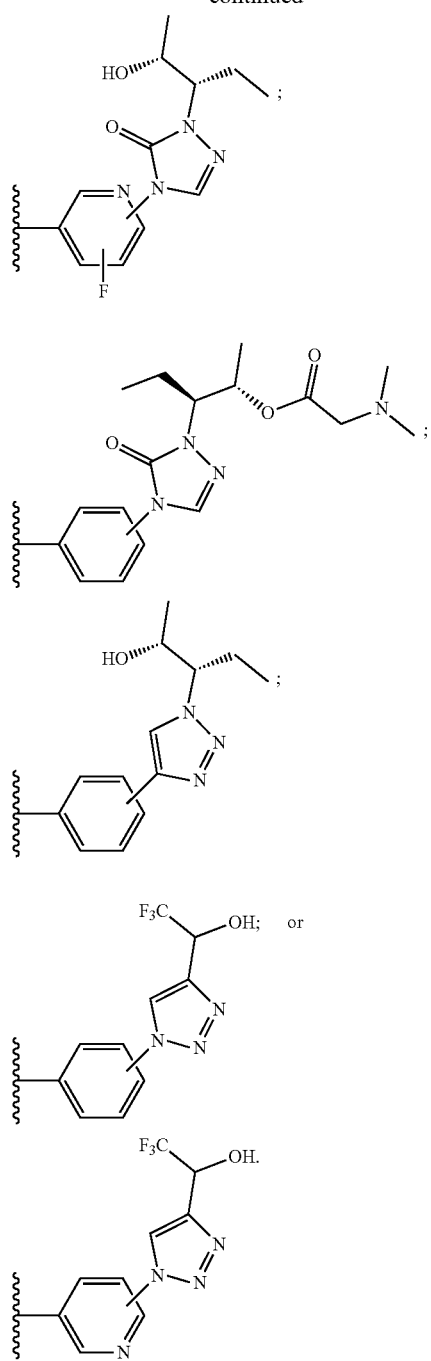
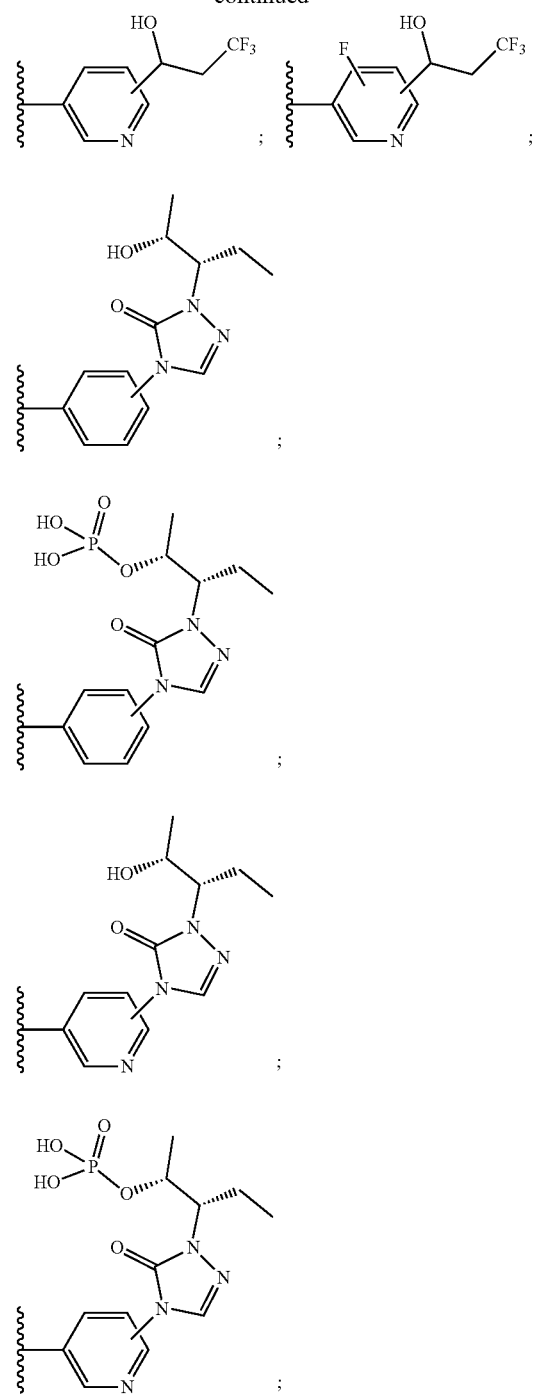
6. The compound of claim 3, or salt thereof, wherein Ar$_2$ is:
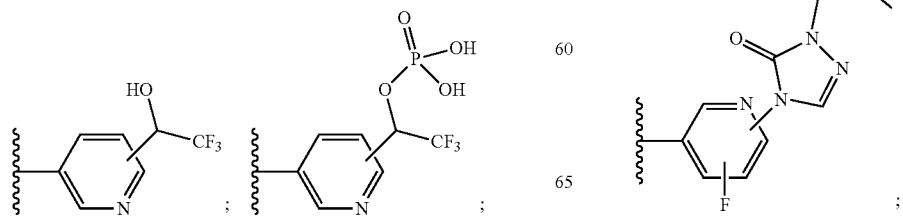

-continued

[chemical structures]

7. The compound of claim 3, or salt thereof, wherein Ar₂ is:

[chemical structures]

579
-continued
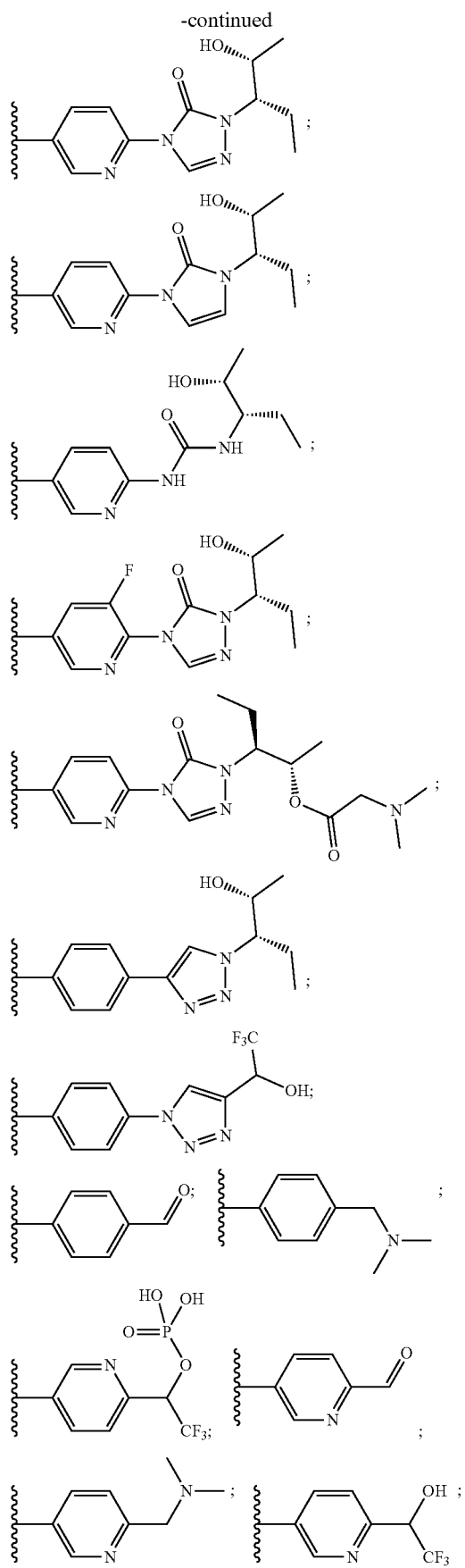
580
-continued
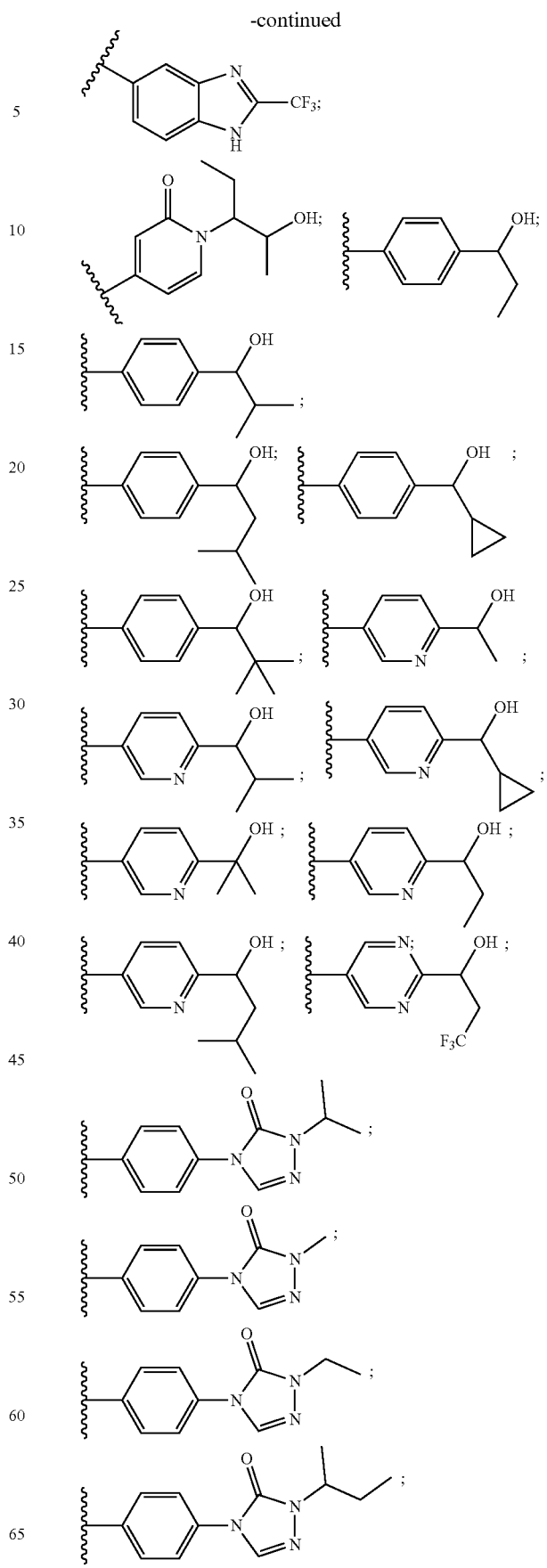

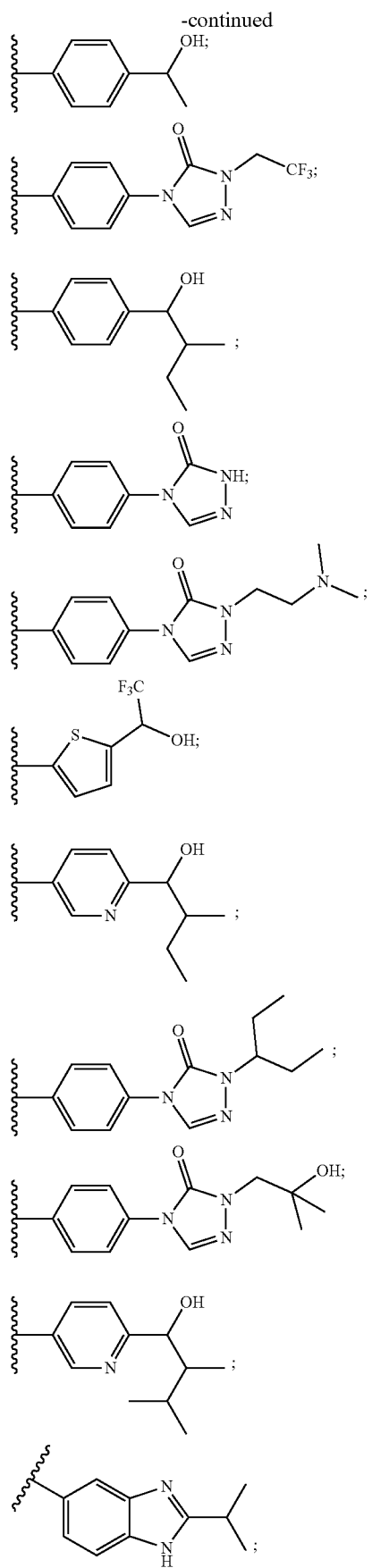
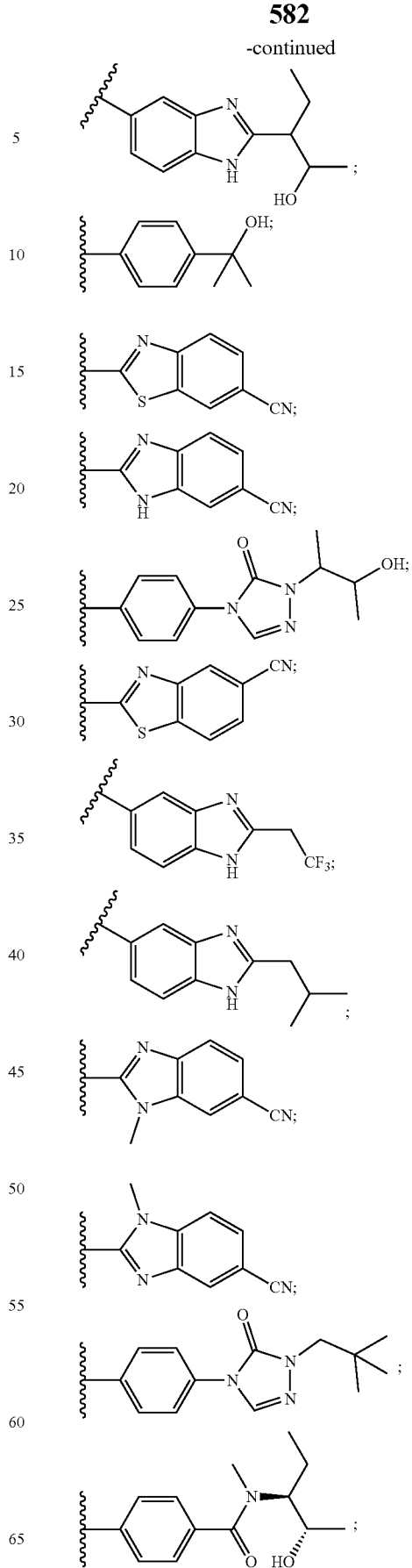

583
-continued
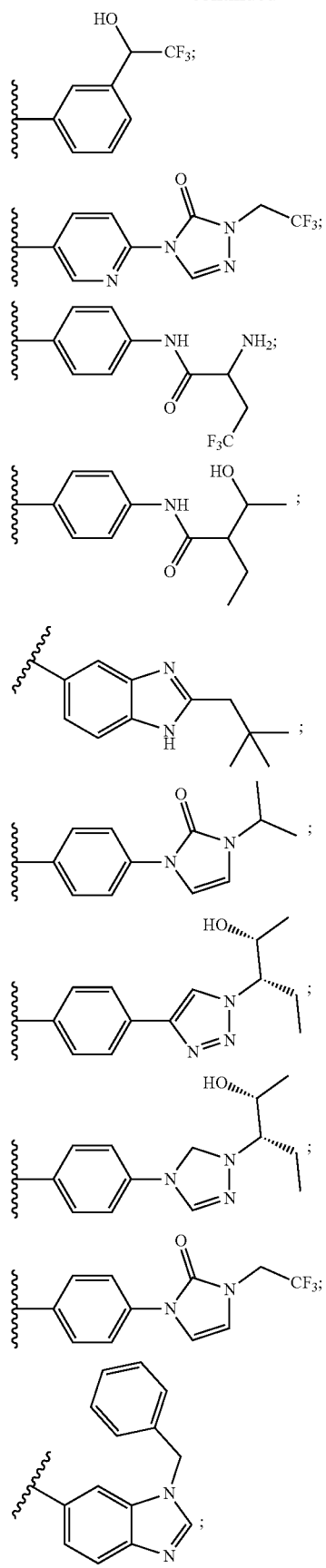
584
-continued
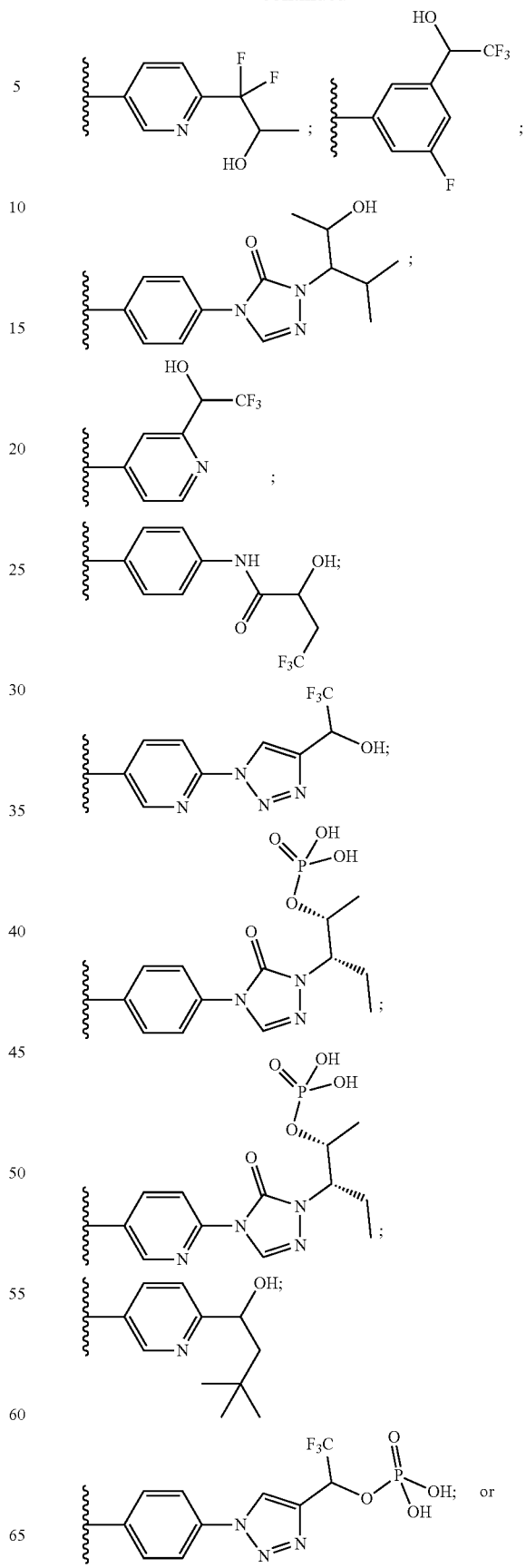

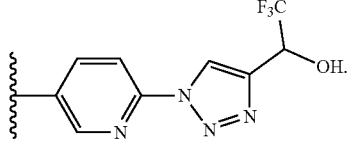

8. The compound of claim 3, or salt thereof, wherein Ar$_2$ is:

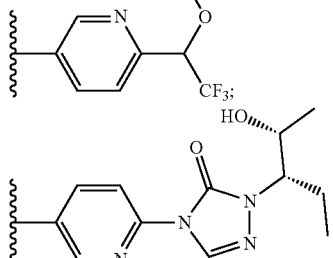

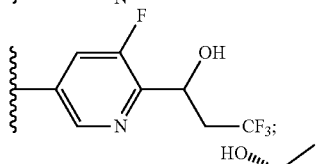

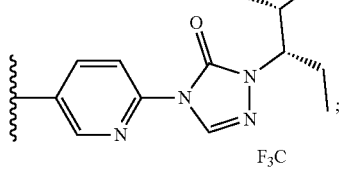

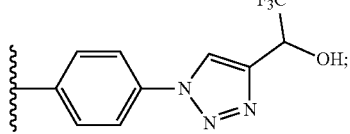

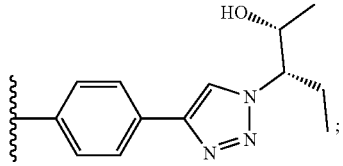

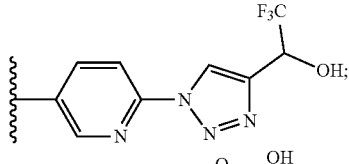

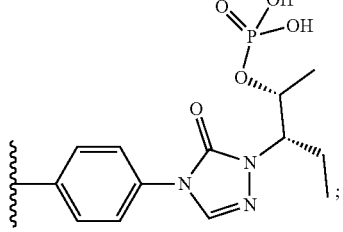

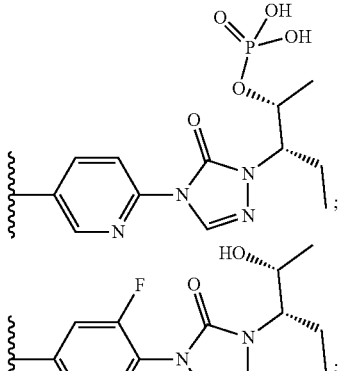

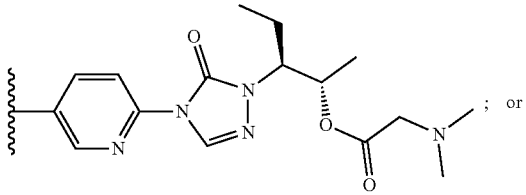

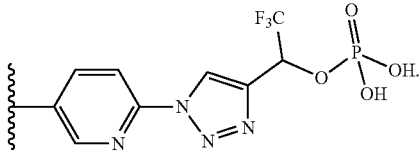

9. The compound of claim 1, or salt thereof, wherein R$_1$ is fluoro.

10. The compound of claim 1, or salt thereof, wherein R$_2$ is fluoro.

11. The compound of claim 1, or salt thereof, wherein R$_1$ and R$_2$ are fluoro.

12. The compound of claim 1, or salt thereof, wherein R$_4$ is phenyl optionally substituted with 0, 1, 2 or 3 independent R$_6$.

13. The compound of claim 1, or salt thereof, wherein R$_4$ is phenyl optionally substituted with 0, 1, 2 or 3 independent halo.

14. The compound of claim 1, or salt thereof, wherein R$_4$ is phenyl optionally substituted with 0, 1, 2 or 3 independent fluoro.

15. The compound of claim 1, or salt thereof, wherein R$_4$ is:

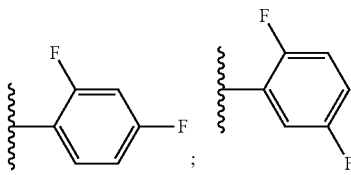

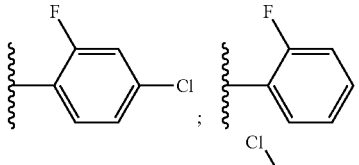

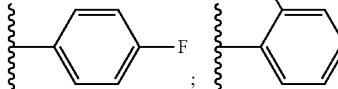

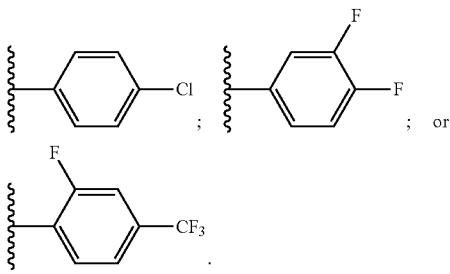

16. The compound of claim 1, or salt thereof, wherein R₄ is

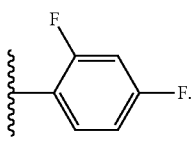 [SMILES: *c1ccc(F)cc1F]

17. The compound of claim 1, or salt thereof, wherein R₄ is

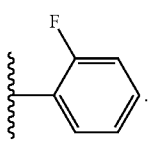

18. The compound of claim 1, or salt thereof, wherein R₄ is

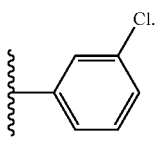 [SMILES: *c1cccc(Cl)c1]

19. The compound of claim 1, or salt thereof, wherein X is N and Y is CH.

20. The compound of claim 1, or salt thereof, wherein X is CH and Y is N.

21. The compound of claim 1, or salt thereof, wherein both X and Y are N.

22. The compound of claim 1, or salt thereof, wherein R₁ is fluoro; R₂ is fluoro; R₄ is

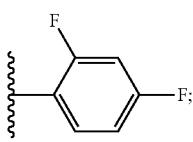 [SMILES: *c1ccc(F)cc1F]

R₅ is hydrogen; and MBG is 1-tetrazolyl.

23. The compound of claim 1, or salt thereof, wherein R₁ is fluoro; R₂ is fluoro; R₄ is

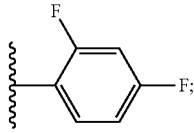 [SMILES: *c1ccc(F)cc1F]

R₅ is hydrogen; X and Y are N; and MBG is 1-tetrazolyl.

24. The compound of claim 1, or salt thereof, wherein R₁ is fluoro; R₂ is fluoro; R₄ is

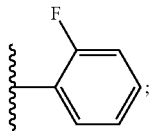

R₅ is hydrogen; and MBG is 1-tetrazolyl.

25. The compound of claim 1, or salt thereof, wherein R₁ is fluoro; R₂ is fluoro; R₄ is

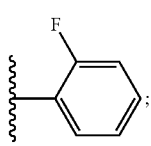 [SMILES: *c1ccccc1F]

R₅ is hydrogen; X and Y are N; and MBG is 1-tetrazolyl.

26. The compound of claim 1, or salt thereof, wherein R₁ is fluoro; R₂ is fluoro; R₄ is

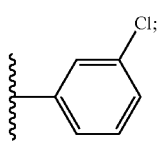 [SMILES: *c1cccc(Cl)c1]

R₅ is hydrogen; and MBG is 1-tetrazolyl.

27. The compound of claim 1, or salt thereof, wherein R₁ is fluoro; R₂ is fluoro; R₄ is

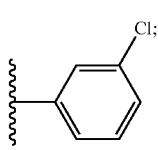

R₅ is hydrogen; X and Y are N; and MBG is 1-tetrazolyl.

28. The compound of claim 1, wherein the compound is:
(R)-4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)benzonitrile (1);
(R)-2-(2,4-difluorophenyl)-1,1-difluoro-1-(5-(4-(4-(4-fluorophenyl)piperazin-1-yl)phenyl)pyridin-2-yl)-3-(1H-tetrazol-1-yl)propan-2-ol (2);
(2R)-2-(2,4-difluorophenyl)-1,1-difluoro-3-(1H-tetrazol-1-yl)-1-(5-(4-(4-(2,2,2-trifluoro-1-hydroxyethyl)phenyl)piperazin-1-yl)phenyl)pyridin-2-yl)propan-2-ol (3);

(2R)-1-(5-(4-(4-(4-(1-amino-2,2,2-trifluoroethyl)phenyl)piperazin-1-yl)phenyl)pyridin-2-yl)-2-(2,4-difluorophenyl)-1,1-difluoro-3-(1H-tetrazol-1-yl)propan-2-ol (4);

(2R)-2-(2,4-difluorophenyl)-1,1-difluoro-1-(5-(4-(4-(3-fluoro-4-(2,2,2-trifluoro-1-hydroxyethyl)phenyl)piperazin-1-yl)phenyl)pyridin-2-yl)-3-(1H-tetrazol-1-yl)propan-2-ol (5);

(2R)-2-(2,4-difluorophenyl)-1,1-difluoro-3-(1H-tetrazol-1-yl)-1-(5-(4-(4-(6-(2,2,2-trifluoro-1-hydroxyethyl)pyridin-3-yl)piperazin-1-yl)phenyl)pyridin-2-yl)propan-2-ol (6);

(R)-5-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)picolinonitrile (7);

(R)-4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-2-fluorobenzonitrile (8);

(R)-4-(4-(4-(6-(2-(2,4-difluorophenyl)-1,1-difluoro-2-hydroxy-3-(1H-tetrazol-1-yl)propyl)pyridin-3-yl)-2-fluorophenyl)piperazin-1-yl)-3-fluorobenzonitrile (9);

(R)-4-(4-(4-(6-(2-(2,4-difluorophenyl)-1,1-difluoro-2-hydroxy-3-(1H-tetrazol-1-yl)propyl)pyridin-3-yl)-2-fluorophenyl)piperazin-1-yl)benzonitrile (10);

(R)-4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-3-fluorobenzonitrile (11);

(R)-6-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)nicotinonitrile (12);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-3,3,3-trifluoropropan-1-ol (13);

(R)-1-(5-(4-(4-(4-aminophenyl)piperazin-1-yl)phenyl)pyridin-2-yl)-2-(2,4-difluorophenyl)-1,1-difluoro-3-(1H-tetrazol-1-yl)propan-2-ol (14);

(−)-2-(2,5-difluorophenyl)-1,1-difluoro-3-(1H-tetrazol-1-yl)-1-(5-(4-(4-(4-(2,2,2-trifluoro-1-hydroxyethyl)phenyl)piperazin-1-yl)phenyl)pyridin-2-yl)propan-2-ol (15(−));

(+)-2-(2,5-difluorophenyl)-1,1-difluoro-3-(1H-tetrazol-1-yl)-1-(5-(4-(4-(4-(2,2,2-trifluoro-1-hydroxyethyl)phenyl)piperazin-1-yl)phenyl)pyridin-2-yl)propan-2-ol (15(+));

(2R)-2-(2,4-difluorophenyl)-1,1-difluoro-3-(4H-1,2,4-triazol-4-yl)-1-(5-(4-(4-(4-(2,2,2-trifluoro-1-hydroxyethyl)phenyl)piperazin-1-yl)phenyl)pyridin-2-yl)propan-2-ol (16);

(R)-4-((4-(4-(6-(2-(2,4-difluorophenyl)-1,1-difluoro-2-hydroxy-3-(1H-tetrazol-1-yl)propyl)pyridin-3-yl)phenyl)piperazin-1-yl)methyl)benzonitrile (17);

(R)-4-(4-(4-(6-(2-(2,4-difluorophenyl)-1,1-difluoro-2-hydroxy-3-(1H-tetrazol-1-yl)propyl)pyridin-3-yl)benzyl)piperazin-1-yl)benzonitrile (18);

(R)-4-(4-(4-(6-(2-(2,4-difluorophenyl)-1,1-difluoro-2-hydroxy-3-(1H-tetrazol-1-yl)propyl)pyridin-3-yl)benzoyl)piperazin-1-yl)benzonitrile (19);

4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (20);

1-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-3-((2S,3S)-2-hydroxypentan-3-yl)urea (21);

(R)-4-(4-(4-(6-(2-(2,4-difluorophenyl)-1,1-difluoro-2-hydroxy-3-(1H-tetrazol-1-yl)propyl)pyridin-3-yl)phenyl)piperidin-1-yl)benzonitrile (22);

(R)-4-(4-(4-(6-(2-(2,4-difluorophenyl)-1,1-difluoro-2-hydroxy-3-(1H-tetrazol-1-yl)propyl)pyridin-3-yl)phenyl)piperazine-1-carbonyl)benzonitrile (23);

(R)-4-(4-(4-(6-(2-(2,4-difluorophenyl)-1,1-difluoro-2-hydroxy-3-(1H-tetrazol-1-yl)propyl)pyridin-3-yl)phenyl)-3-oxopiperazin-1-yl)benzonitrile (24);

(R)-4-(4-(4-(6-(2-(2,4-difluorophenyl)-1,1-difluoro-2-hydroxy-3-(1H-tetrazol-1-yl)propyl)pyridin-3-yl)phenyl)-2-oxopiperazin-1-yl)benzonitrile (25);

(R)-4-(1-(4-(6-(2-(2,4-difluorophenyl)-1,1-difluoro-2-hydroxy-3-(1H-tetrazol-1-yl)propyl)pyridin-3-yl)phenyl)piperidin-4-yl)benzonitrile (26);

(R)-4-(4-(4-(6-(2-(2,4-difluorophenyl)-1,1-difluoro-2-hydroxy-3-(1H-tetrazol-1-yl)propyl)pyridin-3-yl)benzyl)-3-oxopiperazin-1-yl)benzonitrile (27);

(R)-4-((4-(4-(6-(2-(2,4-difluorophenyl)-1,1-difluoro-2-hydroxy-3-(1H-tetrazol-1-yl)propyl)pyridin-3-yl)phenyl)-2-oxopiperazin-1-yl)methyl)benzonitrile (28);

(R)-4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)benzaldehyde (29);

(R)-2-(2,4-difluorophenyl)-1-(5-(4-(4-(4-((dimethylamino)methyl)phenyl)piperazin-1-yl)phenyl)pyridin-2-yl)-1,1-difluoro-3-(1H-tetrazol-1-yl)propan-2-ol (30);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2,2,2-trifluoroethyl dihydrogen phosphate (31);

(R)-5-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)picolinaldehyde (32);

(R)-2-(2,4-difluorophenyl)-1-(5-(4-(4-(6-((dimethylamino)methyl)pyridin-3-yl)piperazin-1-yl)phenyl)pyridin-2-yl)-1,1-difluoro-3-(1H-tetrazol-1-yl)propan-2-ol (33);

(2R)-2-(2,4-difluorophenyl)-1,1-difluoro-3-(1H-tetrazol-1-yl)-1-(5-(4-(4-(5-(2,2,2-trifluoro-1-hydroxyethyl)pyridin-2-yl)piperazin-1-yl)phenyl)pyridin-2-yl)propan-2-ol (34);

(R)-2-(2,4-difluorophenyl)-1,1-difluoro-3-(1H-tetrazol-1-yl)-1-(5-(4-(4-(2-(trifluoromethyl)-1H-benzo[d]imidazol-5-yl)piperazin-1-yl)phenyl)pyridin-2-yl)propan-2-ol (35);

4-(4-(4-(6-(2-cyclopropyl-1,1-difluoro-2-hydroxy-3-(1H-tetrazol-1-yl)propyl)pyridin-3-yl)phenyl)piperazin-1-yl)benzonitrile (36);

4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-1-(2-hydroxypentan-3-yl)pyridin-2(1H)-one (37);

4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38);

(−)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(−));

(+)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(+));

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)propan-1-ol (39);
1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-2-methylpropan-1-ol (40);
1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-3-methylbutan-1-ol (41);
(2R)-1-(5-(4-(4-(4-(cyclopropyl(hydroxy)methyl)phenyl)piperazin-1-yl)phenyl)pyridin-2-yl)-2-(2,4-difluorophenyl)-1,1-difluoro-3-(1H-tetrazol-1-yl)propan-2-ol (42);
1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-2,2-dimethylpropan-1-ol (43);
(2R)-2-(2,4-difluorophenyl)-1,1-difluoro-1-(5-(4-(4-(6-(1-hydroxyethyl)pyridin-3-yl)piperazin-1-yl)phenyl)pyridin-2-yl)-3-(1H-tetrazol-1-yl)propan-2-ol (44);
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2-methylpropan-1-ol (45);
(2R)-1-(5-(4-(4-(6-(cyclopropyl(hydroxy)methyl)pyridin-3-yl)piperazin-1-yl)phenyl)pyridin-2-yl)-2-(2,4-difluorophenyl)-1,1-difluoro-3-(1H-tetrazol-1-yl)propan-2-ol (46);
(R)-2-(2,4-difluorophenyl)-1,1-difluoro-1-(5-(4-(4-(6-(2-hydroxypropan-2-yl)pyridin-3-yl)piperazin-1-yl)phenyl)pyridin-2-yl)-3-(1H-tetrazol-1-yl)propan-2-ol (47);
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)propan-1-ol (48);
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-3-methylbutan-1-ol (49);
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2,2-dimethylpropan-1-ol (50);
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyrimidin-2-yl)-3,3,3-trifluoropropan-1-ol (51);
(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-isopropyl-1H-1,2,4-triazol-5(4H)-one (52);
(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-methyl-1H-1,2,4-triazol-5(4H)-one (53);
(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-ethyl-1H-1,2,4-triazol-5(4H)-one (54);
1-(sec-butyl)-4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,4-triazol-5(4H)-one (55);
(2R)-2-(2,4-difluorophenyl)-1,1-difluoro-1-(5-(4-(4-(4-(1-hydroxyethyl)phenyl)piperazin-1-yl)phenyl)pyridin-2-yl)-3-(1H-tetrazol-1-yl)propan-2-ol (56);
4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-N-((2S,3S)-2-hydroxypentan-3-yl)benzamide (57);
(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-(2,2,2-trifluoroethyl)-1H-1,2,4-triazol-5(4H)-one (58);
1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-2-methylbutan-1-ol (59);
(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,4-triazol-5 (4H)-one (60);
(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-(2-(dimethylamino)ethyl)-1H-1,2,4-triazol-5(4H)-one (61);
(2R)-2-(2,4-difluorophenyl)-1,1-difluoro-3-(1H-tetrazol-1-yl)-1-(5-(4-(4-(5-(2,2,2-trifluoro-1-hydroxyethyl)thiophen-2-yl)piperazin-1-yl)phenyl)pyridin-2-yl)propan-2-ol (62);
(+)-4-(4-(4-(4-(6-(1,1-difluoro-2-(4-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (63(+));
(+)-4-(4-(4-(4-(6-(1,1-difluoro-2-(3-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (64(+));
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2-methylbutan-1-ol (65);
(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-(pentan-3-yl)-1H-1,2,4-triazol-5(4H)-one (66);
(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-(2-hydroxy-2-methylpropyl)-1H-1,2,4-triazol-5(4H)-one (67);
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2,3-dimethylbutan-1-ol (68);
(R)-2-(2,4-difluorophenyl)-1,1-difluoro-1-(5-(4-(4-(2-isopropyl-1H-benzo[d]imidazol-6-yl)piperazin-1-yl)phenyl)pyridin-2-yl)-3-(1H-tetrazol-1-yl)propan-2-ol (69);
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-3-fluoropyridin-2-yl)-3,3,3-trifluoropropan-1-ol (70);
3-(6-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-1H-benzo[d]imidazol-2-yl)pentan-2-ol (71);
(R)-2-(2,4-difluorophenyl)-1,1-difluoro-1-(5-(4-(4-(4-(2-hydroxypropan-2-yl)phenyl)piperazin-1-yl)phenyl)pyridin-2-yl)-3-(1H-tetrazol-1-yl)propan-2-ol (72);
(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)benzo[d]thiazole-6-carbonitrile (73);

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-1H-benzo[d]imidazole-6-carbonitrile (74);

4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1-(3-hydroxybutan-2-yl)-1H-1,2,4-triazol-5(4H)-one (75);

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)benzo[d]thiazole-5-carbonitrile (76);

(R)-2-(2,4-difluorophenyl)-1,1-difluoro-3-(1H-tetrazol-1-yl)-1-(5-(4-(4-(2-(2,2,2-trifluoroethyl)-1H-benzo[d]imidazol-6-yl)piperazin-1-yl)phenyl)pyridin-2-yl)propan-2-ol (77);

(R)-2-(2,4-difluorophenyl)-1,1-difluoro-1-(5-(4-(4-(2-isobutyl-1H-benzo[d]imidazol-6-yl)piperazin-1-yl)phenyl)pyridin-2-yl)-3-(1H-tetrazol-1-yl)propan-2-ol (78);

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-1-methyl-1H-benzo[d]imidazole-6-carbonitrile (79);

(R)-2-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)-1-methyl-1H-benzo[d]imidazole-5-carbonitrile (80);

(R)-4-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-1-neopentyl-1H-1,2,4-triazol-5(4H)-one (81);

4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (82);

4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-N-((2S,3S)-2-hydroxypentan-3-yl)-N-methylbenzamide (83);

(+)-4-(4-(4-(4-(6-(1,1-difluoro-2-(3-fluorophenyl)-2-hydroxy-3-(3-methyl-1H-1,2,4-triazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (84(+));

(+)-4-(4-(4-(4-(6-(1,1-difluoro-2-(3-fluorophenyl)-2-hydroxy-3-(5-methyl-1H-1,2,4-triazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (85(+));

(2R)-2-(2,4-difluorophenyl)-1,1-difluoro-3-(1H-tetrazol-1-yl)-1-(5-(4-(4-(3-(2,2,2-trifluoro-1-hydroxyethyl)phenyl)piperazin-1-yl)phenyl)pyridin-2-yl)propan-2-ol (86);

(R)-4-(5-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-1-(2,2,2-trifluoroethyl)-1H-1,2,4-triazol-5(4H)-one (87);

2-amino-N-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-4,4,4-trifluorobutanamide (88);

N-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-2-ethyl-3-hydroxybutanamide (89);

(R)-2-(2,4-difluorophenyl)-1,1-difluoro-1-(5-(4-(4-(2-neopentyl-1H-benzo[d]imidazol-6-yl)piperazin-1-yl)phenyl)pyridin-2-yl)-3-(1H-tetrazol-1-yl)propan-2-ol (90);

(R)-1-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-3-isopropyl-1H-imidazol-2(3H)-one (91);

(2S,3S)-3-(3-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,4-triazol-1-yl)pentan-2-ol (92);

4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1-(2-hydroxypentan-3-yl)-1H-1,2,4-triazol-5(4H)-one (93);

(2R)-2-(2,4-difluorophenyl)-1,1-difluoro-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (94);

(2S,3S)-3-(4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-1-yl)pentan-2-ol (95);

(R)-1-(4-(4-(4-(6-(2-(2,4-difluorophenyl)-1,1-difluoro-2-hydroxy-3-(1H-tetrazol-1-yl)propyl)pyridin-3-yl)phenyl)piperazin-1-yl)phenyl)-3-(2,2,2-trifluoroethyl)-1H-imidazol-2(3H)-one (96);

1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-3-(2-hydroxypentan-3-yl)-1H-imidazol-2(3H)-one (97);

(R)-1-(5-(4-(4-(1-benzyl-1H-benzo[d]imidazol-6-yl)piperazin-1-yl)phenyl)pyridin-2-yl)-2-(2,4-difluorophenyl)-1,1-difluoro-3-(1H-tetrazol-1-yl)propan-2-ol (98);

(2R)-1-(5-(4-(4-(6-(1,1-difluoro-2-hydroxypropyl)pyridin-3-yl)piperazin-1-yl)phenyl)pyridin-2-yl)-2-(2,4-difluorophenyl)-1,1-difluoro-3-(1H-tetrazol-1-yl)propan-2-ol (99);

(2R)-2-(2,4-difluorophenyl)-1,1-difluoro-1-(5-(4-(4-(3-fluoro-5-(2,2,2-trifluoro-1-hydroxyethyl)phenyl)piperazin-1-yl)phenyl)pyridin-2-yl)-3-(1H-tetrazol-1-yl)propan-2-ol (100);

4-(4-(4-(4-(6-(2-(2,4-difluorophenyl)-1,1-difluoro-2-hydroxy-3-(1H-pyrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (101);

(−)-4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (102(−));

(+)-4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (102(+));

4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1-(2-hydroxy-4-methylpentan-3-yl)-1H-1,2,4-triazol-5(4H)-one (103);

(2R)-2-(2,4-difluorophenyl)-1,1-difluoro-3-(1H-tetrazol-1-yl)-1-(5-(4-(4-(2-(2,2,2-trifluoro-1-hydroxyethyl)pyridin-4-yl)piperazin-1-yl)phenyl)pyridin-2-yl)propan-2-ol (104);

N-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-4,4,4-trifluoro-2-hydroxybutanamide (105);

(+)-4-(4-(4-(4-(6-(1,1-difluoro-2-(2-fluorophenyl)-2-hydroxy-3-(3-(trifluoromethyl)-1H-1,2,4-triazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (106(+));

4-(4-(4-(4-(6-(2-(2,4-difluorophenyl)-1,1-difluoro-2-hydroxy-3-(2H-1,2,3-triazol-2-yl)propyl)pyridin-3-yl)phenyl)piperazin-1-yl)phenyl)-1-((2S,3S)-2-hydroxypentan-3-yl)-1H-1,2,4-triazol-5(4H)-one (107);

(−)-1,1-difluoro-2-(2-fluorophenyl)-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (108(−));

(+)-1,1-difluoro-2-(2-fluorophenyl)-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (108(+));

(−)-4-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (109(−));

(+)-4-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (109(+));

(−)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (110(−));

(+)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (110(+));

(2R)-2-(2,4-difluorophenyl)-1,1-difluoro-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (111);

(2S,3S)-3-(4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-5-oxo-4,5-dihydro-1H-1,2,4-triazol-1-yl)pentan-2-yl dihydrogen phosphate (112);

(2S,3S)-3-(4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl dihydrogen phosphate (113);

(+)-(2S,3S)-3-(4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-5-oxo-4,5-dihydro-1H-1,2,4-triazol-1-yl)pentan-2-yl dihydrogen phosphate (114);

4-(4-(4-(4-(6-(1,1-difluoro-2-(2-fluorophenyl)-2-hydroxy-3-(1H-tetrazol-5-yl)propyl)pyridin-3-yl)phenyl)piperazin-1-yl)phenyl)-1-((2S,3S)-2-hydroxypentan-3-yl)-1H-1,2,4-triazol-5(4H)-one (115);

4-(4-(4-(4-(6-(1,1-difluoro-2-(2-fluorophenyl)-2-hydroxy-3-(2H-1,2,3-triazol-2-yl)propyl)pyridin-3-yl)phenyl)piperazin-1-yl)phenyl)-1-((2S,3S)-2-hydroxypentan-3-yl)-1H-1,2,4-triazol-5(4H)-one (116);

4-(4-(4-(4-(6-(1,1-difluoro-2-(2-fluorophenyl)-2-hydroxy-3-(1H-pyrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (117);

1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-3,3-dimethylbutan-1-ol (118);

(−)-1-(5-(4-(4-(6-(1,1-difluoro-2-(3-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (119(−));

(+)-1-(5-(4-(4-(6-(1,1-difluoro-2-(3-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (119(+));

(−)-1-(5-(4-(4-(6-(2-(2,4-difluorophenyl)-1,1-difluoro-2-hydroxy-3-(1H-1,2,4-triazol-1-yl)propyl)pyridin-3-yl)phenyl)piperazin-1-yl)pyridin-2-yl)-3,3,3-trifluoropropan-1-ol (120(−));

(+)-1-(5-(4-(4-(6-(2-(2,4-difluorophenyl)-1,1-difluoro-2-hydroxy-3-(1H-1,2,4-triazol-1-yl)propyl)pyridin-3-yl)phenyl)piperazin-1-yl)pyridin-2-yl)-3,3,3-trifluoropropan-1-ol (120(+));

(−)-1-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (121(−));

(+)-1-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (121(+));

(−)-1-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (122(−));

(+)-1-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (122(+));

(−)-4-(4-(4-(4-(6-(2-(2,4-difluorophenyl)-1,1-difluoro-2-hydroxy-3-(1H-1,2,4-triazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (123(−));

(+)-4-(4-(4-(4-(6-(2-(2,4-difluorophenyl)-1,1-difluoro-2-hydroxy-3-(1H-1,2,4-triazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (123(+));

4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-3-fluoropyridin-2-yl)-1-((2S,3S)-2-hydroxypentan-3-yl)-1H-1,2,4-triazol-5(4H)-one (124);

4-(4-(4-(4-(6-(2-(3-chlorophenyl)-1,1-difluoro-2-hydroxy-3-(2H-1,2,3-triazol-2-yl)propyl)pyridin-3-yl)phenyl)piperazin-1-yl)phenyl)-1-((2S,3S)-2-hydroxypentan-3-yl)-1H-1,2,4-triazol-5(4H)-one (125);

4-(4-(4-(4-(6-(2-(3-chlorophenyl)-1,1-difluoro-2-hydroxy-3-(1H-pyrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (126);

4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127);

(−)-4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127(−));

(+)-4-(4-(4-(4-(6-(2-(3-chlorophenyl)-1,1-difluoro-2-hydroxy-3-(1H-tetrazol-1-yl)propyl)pyridin-3-yl)phenyl)

piperazin-1-yl)phenyl)-1-((2S,3S)-2-hydroxypentan-3-yl)-1H-1,2,4-triazol-5(4H)-one (127(+));
(+)-(2S,3S)-3-(4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl dihydrogen phosphate (128);
1-(1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-4-yl)-2,2,2-trifluoroethyl dihydrogen phosphate (129);
(2S,3S)-3-(4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl 2-(dimethylamino)acetate (130); or salt thereof.

29. The compound of claim 1, wherein the compound is:
(2R)-2-(2,4-difluorophenyl)-1,1-difluoro-3-(1H-tetrazol-1-yl)-1-(5-(4-(4-(6-(2,2,2-trifluoro-1-hydroxyethyl)pyridin-3-yl)piperazin-1-yl)phenyl)pyridin-2-yl)propan-2-ol (6);
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-3,3,3-trifluoropropan-1-ol (13);
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-2,2,2-trifluoroethyl dihydrogen phosphate (31);
4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38);
(+)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(+));
(+)-4-(4-(4-(4-(6-(1,1-difluoro-2-(4-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (63(+));
(+)-4-(4-(4-(4-(6-(1,1-difluoro-2-(3-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (64(+));
1-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-3-fluoropyridin-2-yl)-3,3,3-trifluoropropan-1-ol (70);
4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (82);
(2R)-2-(2,4-difluorophenyl)-1,1-difluoro-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (94);
(2S,3S)-3-(4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-1-yl)pentan-2-ol (95);
(+)-4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (102(+));
(+)-1,1-difluoro-2-(2-fluorophenyl)-3-(1H-tetrazol-1-yl)-1-(5-(4-(4-(4-(2,2,2-trifluoro-1-hydroxyethyl)-1H-1,2,3-triazol-1-yl)phenyl)piperazin-1-yl)phenyl)pyridin-2-yl)propan-2-ol (108(+));
(+)-4-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-1-((2S,3S)-2-hydroxypentan-3-yl)-1H-1,2,4-triazol-5(4H)-one (109(+));
(+)-1,1-difluoro-2-(2-fluorophenyl)-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (110(+));
(2R)-2-(2,4-difluorophenyl)-1,1-difluoro-3-(1H-tetrazol-1-yl)-1-(5-(4-(4-(6-(4-(2,2,2-trifluoro-1-hydroxyethyl)-1H-1,2,3-triazol-1-yl)pyridin-3-yl)piperazin-1-yl)phenyl)pyridin-2-yl)propan-2-ol (111);
(2S,3S)-3-(4-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-5-oxo-4,5-dihydro-1H-1,2,4-triazol-1-yl)pentan-2-yl dihydrogen phosphate (112);
(2S,3S)-3-(4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl dihydrogen phosphate (113);
(+)-(2S,3S)-3-(4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-5-oxo-4,5-dihydro-1H-1,2,4-triazol-1-yl)pentan-2-yl dihydrogen phosphate (114);
(+)-1-(5-(4-(4-(6-(1,1-difluoro-2-(3-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (119(+));
(+)-1-(5-(4-(4-(6-(1,1-difluoro-2-(4-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (121(+));
(+)-1-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-3,3,3-trifluoropropan-1-ol (122(+));
4-(5-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)-3-fluoropyridin-2-yl)-1-((2S,3S)-2-hydroxypentan-3-yl)-1H-1,2,4-triazol-5(4H)-one (124);
(+)-(2S,3S)-3-(4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl dihydrogen phosphate (128);
1-(1-(4-(4-(4-(6-((R)-2-(2,4-difluorophenyl)-1,1-difluoro-2-hydroxy-3-(1H-tetrazol-1-yl)propyl)pyridin-3-yl)phenyl)piperazin-1-yl)phenyl)-1H-1,2,3-triazol-4-yl)-2,2,2-trifluoroethyl dihydrogen phosphate (129); or
(2S,3S)-3-(4-(5-(4-(4-(6-(1,1-difluoro-2-(2-fluorophenyl)-2-hydroxy-3-(1H-tetrazol-1-yl)propyl)pyridin-3-yl)phenyl)piperazin-1-yl)pyridin-2-yl)-5-oxo-4,5-dihydro-1H-1,2,4-triazol-1-yl)pentan-2-yl 2-(dimethylamino)acetate (130);
or salt thereof.

30. The compound of claim 1, wherein the compound is:
4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38);

(−)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(−));

(+)-4-(4-(4-(4-(6-(1,1-difluoro-2-(2-fluorophenyl)-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (38(+));

4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127);

(−)-4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127(−)); or (+)-4-(4-(4-(4-(6-(2-(3-chlorophenyl)-1,1-difluoro-2-hydroxy-3-(1H-tetrazol-1-yl)propyl)pyridin-3-yl)phenyl)piperazin-1-yl)phenyl)-1-((2S,3S)-2-hydroxypentan-3-yl)-1H-1,2,4-triazol-5(4H)-one (127(+));

or salt thereof.

31. A method of treating a subject suffering from a systemic fungal infection or onychomycosis, comprising administering to the subject an effective amount of a compound of claim 1, or salt thereof.

32. A composition comprising a compound of claim 1, or salt thereof, and a pharmaceutically acceptable carrier.

\* \* \* \* \*